(12) United States Patent
Krill et al.

(10) Patent No.: US 12,377,110 B2
(45) Date of Patent: Aug. 5, 2025

(54) FOSPROPOFOL METHODS AND COMPOSITIONS

(71) Applicant: Epalex Corporation, Mountain View, CA (US)

(72) Inventors: Steven L. Krill, San Clemente, CA (US); Feng-Jing Chen, Irvine, CA (US); Michael A. Rogawski, Sacramento, CA (US); Edward Brendan Magrab, Far Hills, NJ (US); Allen H. Heller, Woodbridge, CT (US)

(73) Assignee: EPALEX CORPORATION, Mountain View, CA (US)

( * ) Notice: Subject to any disclaimer, the term of this patent is extended or adjusted under 35 U.S.C. 154(b) by 192 days.

(21) Appl. No.: 18/169,296

(22) Filed: Feb. 15, 2023

(65) Prior Publication Data

US 2023/0277567 A1    Sep. 7, 2023

Related U.S. Application Data

(60) Continuation of application No. 17/686,738, filed on Mar. 4, 2022, now Pat. No. 11,628,178, which is a continuation of application No. 17/562,605, filed on Dec. 27, 2021, now abandoned, which is a continuation-in-part of application No. 17/465,966, filed on Sep. 3, 2021, and a continuation-in-part of application No. 17/466,016, filed on Sep. 3, 2021, now Pat. No. 11,439,653, and a continuation-in-part of application No. 17/387,059, filed on Jul. 28, 2021, now Pat. No. 11,478,490, said application No. 17/465,966 is a division of application No. 17/217,656, filed on Mar. 30, 2021, now Pat. No. 11,207,334, said application No. 17/387,059 is a continuation-in-part of application No. 17/217,656, filed on Mar. 30, 2021, now Pat. No. 11,207,334, said application No. 17/466,016 is a continuation of application No. 17/217,656, filed on Mar. 30, 2021, now Pat. No. 11,207,334, said application No. 17/562,605 is a continuation-in-part of application No. 17/168,365, filed on Feb. 5, 2021, now Pat. No. 11,547,714, and a continuation-in-part of application No. 17/066,957, filed on Oct. 9, 2020, now abandoned, and a continuation-in-part of application No. 16/831,035, filed on Mar. 26, 2020, now abandoned.

(60) Provisional application No. 62/970,324, filed on Feb. 5, 2020, provisional application No. 62/914,051, filed on Oct. 11, 2019, provisional application No. 62/824,182, filed on Mar. 26, 2019.

(51) Int. Cl.
*A61K 31/661*     (2006.01)
*A61K 9/00*       (2006.01)
*A61K 9/20*       (2006.01)
*A61K 47/12*      (2006.01)

(52) U.S. Cl.
CPC .......... *A61K 31/661* (2013.01); *A61K 9/0053* (2013.01); *A61K 9/2013* (2013.01); *A61K 47/12* (2013.01)

(58) Field of Classification Search
CPC ................................................ A61K 31/661
See application file for complete search history.

(56) References Cited

U.S. PATENT DOCUMENTS

| | | | |
|---|---|---|---|
| 6,383,471 B1 | 5/2002 | Chen et al. |
| 7,230,003 B2 | 6/2007 | Gallop et al. |
| 7,241,807 B2 | 7/2007 | Xu et al. |
| 7,538,092 B2 | 5/2009 | Orlando et al. |
| 7,550,155 B2 | 6/2009 | Zhang et al. |
| 7,645,792 B2 | 1/2010 | Xu et al. |
| 8,354,454 B2 | 1/2013 | Mills et al. |
| 8,383,687 B2 | 2/2013 | Harris et al. |
| 8,470,861 B2 | 6/2013 | Anders et al. |
| 8,541,400 B2 | 9/2013 | Johnsson et al. |
| 8,962,696 B2 | 2/2015 | Harris et al. |
| 9,023,813 B2 | 5/2015 | Shull |
| 9,272,978 B2 | 3/2016 | Zhang et al. |
| 9,339,553 B2 | 5/2016 | Zhang et al. |
| 9,556,156 B2 | 1/2017 | Dugar et al. |
| 9,643,917 B2 | 5/2017 | Li et al. |
| 9,757,334 B2 | 9/2017 | Lovell et al. |
| 10,239,851 B2 | 3/2019 | Li et al. |
| 10,568,834 B2 | 2/2020 | Garti et al. |
| 11,207,334 B1 | 12/2021 | Krill et al. |

(Continued)

FOREIGN PATENT DOCUMENTS

| CN | 1698588 A | 11/2005 |
|---|---|---|
| CN | 101675917 A | 3/2010 |

(Continued)

OTHER PUBLICATIONS

International Patent Application No. PCT/US2021/065225; Int'l Search Report and the Written Opinion; dated Mar. 15, 2022; 15 pages.

(Continued)

*Primary Examiner* — Rei Tsang Shiao
(74) *Attorney, Agent, or Firm* — BakerHostetler

(57) ABSTRACT

The present disclosure pertains to the use of fospropofol, pharmaceutically acceptable salts of fospropofol, or mixtures thereof. Pharmaceutical compositions comprising fospropofol, pharmaceutically acceptable salts of fospropofol, or mixtures thereof, and methods of treating diseases or disorders, including migraine are also disclosed.

32 Claims, 73 Drawing Sheets

(56) References Cited

U.S. PATENT DOCUMENTS

| | | | |
|---|---|---|---|
| 11,628,178 B2* | 4/2023 | Krill | A61K 31/661 514/130 |
| 2005/0004381 A1 | 1/2005 | Gallop et al. | |
| 2006/0205969 A1 | 9/2006 | Xu et al. | |
| 2007/0135390 A1 | 6/2007 | West et al. | |
| 2007/0202158 A1 | 8/2007 | Slusher et al. | |
| 2007/0259933 A1 | 11/2007 | Virsik et al. | |
| 2008/0161400 A1 | 7/2008 | Virsik et al. | |
| 2008/0214508 A1* | 9/2008 | Slusher | A61P 43/00 514/130 |
| 2008/0306285 A1 | 12/2008 | Hale et al. | |
| 2009/0076141 A1 | 3/2009 | Virsik | |
| 2009/0156562 A1 | 6/2009 | Winch | |
| 2009/0221532 A1 | 9/2009 | Gibiansky et al. | |
| 2009/0286763 A1 | 11/2009 | Xu et al. | |
| 2010/0311698 A1 | 12/2010 | Patel et al. | |
| 2011/0269844 A1 | 11/2011 | LeDonne | |
| 2012/0289470 A1 | 11/2012 | Heit et al. | |
| 2012/0295866 A1 | 11/2012 | Shull et al. | |
| 2012/0316247 A1 | 12/2012 | Xie et al. | |
| 2019/0151458 A1 | 5/2019 | Ciufolini et al. | |
| 2019/0224123 A1 | 7/2019 | Theisinger et al. | |
| 2020/0289404 A1 | 9/2020 | Slusher et al. | |

FOREIGN PATENT DOCUMENTS

| | | |
|---|---|---|
| CN | 101675918 A | 3/2010 |
| CN | 102351895 A | 2/2012 |
| CN | 102382005 A | 3/2012 |
| CN | 103172658 A | 6/2013 |
| CN | 103816542 A | 5/2014 |
| CN | 106138015 A | 11/2016 |
| WO | WO 2000/008033 A1 | 2/2000 |
| WO | WO 2000/048572 A1 | 8/2000 |
| WO | WO 2002/013810 A1 | 2/2002 |
| WO | WO 2003/057153 A2 | 7/2003 |
| WO | WO 2003/086413 A1 | 10/2003 |
| WO | WO 2004/030658 A1 | 4/2004 |
| WO | WO 2004/032971 A1 | 4/2004 |
| WO | WO 2005/044201 A2 | 5/2005 |
| WO | WO 2006/017351 A1 | 2/2006 |
| WO | WO 2006/033911 A2 | 3/2006 |
| WO | WO 2008/157627 A1 | 12/2008 |
| WO | WO 2009/016269 A1 | 2/2009 |
| WO | WO 2011/160267 A1 | 12/2011 |
| WO | WO 2011/160268 A1 | 12/2011 |
| WO | WO 2013/093931 A2 | 6/2013 |
| WO | WO 2017/205632 A1 | 11/2017 |

OTHER PUBLICATIONS

Abdelmalak et al.; "Fospropofol, A New Sedative Anesthetic, and Its Utility in the Perioperative Period"; Current Pharmaceutical Design; vol. 18; 2012; p. 6241-6252.

Meek et al.; "Comparing propofol with placebo for early resolution of acute migraine in adult emergency department patients: A double-blind randomised controlled trial"; Emergency Medicine Australasia; 2020; 8 pages.

Mitra et al.; "Propofol for migraine in the emergency department: A pilot randomised controlled trial"; Emergency Medicine Australasia; vol. 32; 2020; p. 542-547.

Piatka et al.; "Propofol for Treatment of Acute Migraine in the Emergency Department: A Systematic Review"; Academic Emergency Medicine; 2019; 13 pages.

Wei et al.; "Oral Delivery of Propofol with Methoxymethylphosphonic Acid as the Delivery Vehicle"; Journal of Medicinal Chemistry; vol. 60; 2017; p. 8580-8590.

Supplemental Tables S1 and S2 from Wozniak et al.; "Gastrointestinal delivery of propofol from fospropofol: its bioavailability and activity in rodents and human volunteers"; Journal of Translational Medicine; vol. 13; 2015; 3 pages.

Ahmad et al.; "Interactions between opioid drugs and propofol in laboratory models of seizures"; British Journal of Anaesthesia; vol. 74; 1995; p. 311-314.

Alessandri et al.; "Seizures and Sepsis: A Narrative Review"; Journal of Clinical Medicine; vol. 10; 2021; 10 pages.

Al-Hader et al.; "The Comparative Effects of Propofol, Thiopental, and Diazepam, Administered Intravenously, on Pentylenetetrazol Seizure Threshold in The Rabbit"; Life Sciences; vol. 51; 1992; p. 779-786.

"The American Headache Society Position Statement On Integrating New Migraine Treatments Into Clinical Practice"; Headache; vol. 59; 2019; 18 pages.

Bauman et al.; "Seizure Clusters: Morbidity and Mortality"; Frontier in Neurology; vol. 12; Feb. 2021; 5 pages.

Baumgartner et al.; "A survey of the European Reference Network EpiCARE on clinical practice for selected rare epilepsies"; Epilepsia Open; vol. 6; 2021; p. 160-470.

Beghi; "Addressing the burden of epilepsy: Many unmet needs"; Pharmacological Research; vol. 107; 2016; p. 79-84.

Beghi; "The Epidemiology of Epilepsy"; Neuroepidemiology; vol. 54; 2020; p. 185-191.

Begley et al.; "The direct cost of epilepsy in the United States: A systematic review of estimates"; Epilepsia; vol. 56; 2015; p. 1376-1387.

Bengalorkar et al.; "Fospropofol: Clinical Pharmacology"; Journal of Anaesthesiology Clinical Pharmacoloy; vol. 27; 2011; p. 79-83.

Bialer et al.; "Progress report on new antiepileptic drugs: A summary of the Fifteenth Eilat Conference on New Antiepileptic Drugs and Devices (EILAT XV). I. Drugs in preclinical and early clinical development"; Epilepsia; vol. 61; 2020; p. 2340-2364.

Binnie et al.; "Acute effects of lamotrigine (BW430C) in persons with epilepsy"; Epilepsia; vol. 27; 1986; p. 248-254 (abstract only).

Binnie et al.; "Photosensitivity as a model for acute antiepileptic drug studies"; Electroencephalogr Clin Neurophysiol.; vol. 63; Jan. 1986; p. 35-41 (abstract only).

Binnie; "Preliminary evaluation of potential anti-epileptic drugs by single dose electrophysiological and pharmacological studies in patients"; J. Neural Transm.; vol. 72; 1988; p. 259-266 (abstract only).

Bonafede et al.; "Direct and Indirect Healthcare Resource Utilization and Costs Among Migraine Patients in the United States"; Headache; May 2018; p. 700-714.

Bond et al.; "The use of analogue scales in rating subjective feelings"; Br. J. Med. Psychol.; vol. 47; 1974; p. 211-218.

Borgdorff; "Arguments against the role of cortical spreading depression in migraine"; Neurological Research; vol. 40 No. 3; 2018; p. 173-181.

Brodie et al.; "Patterns of treatment response in newly diagnosed epilepsy"; Neurology; vol. 78; 2012; p. 1548-1554.

Brophy et al.; "Guidelines for the Evaluation and Management of Status Epilepticus"; Neurocrit Care; vol. 17; 2012; p. 3-23.

Burch et al.; "The Prevalence and Impact of Migraine and Severe Headache in the United States: Figures and Trends From Government Health Studies"; Headache; vol. 58; 2018; p. 496-505.

Cameron; "Opisthotonos again"; Anaesthesia; vol. 42; 1987; p. 1124.

"Summary Health Statistics: National Health Interview Survey"; https://ftp.cdc.gov/pub/Health_Statistics/NCHS/NHIS/SHS/2018_SHS_Table_A-5.pdf; U.S. Department of Health and Human Services; 2018; 9 pages.

Chernik et al.; "Validity and reliability of the Observer's Assessment of Alertness/Sedation Scale: study with Intravenous Midazolam"; Journal of Clinical Psychopharmacology; vol. 10 No. 4; 1990; p. 244-251.

"Clinical Brief—Examining the Economic Impact and Implications of Epilepsy"; The American Journal of Managed Care; Feb. 2020; 8 pages.

Cohen; "Clinical trial: a dose-response study of fospropofol disodium for moderate sedation during colonoscopy"; Alimentary Pharmacology & Therapeutics; vol. 27; 2008; p. 597-608.

Contreras et al.; "Bioavailability of Oral Propofol in Humans"; Int'l Society for Anaesthetic Pharmacology; 2011; p. 21-23 (abstracts).

(56) References Cited

OTHER PUBLICATIONS

Dalic et al.; "Managing drug-resistant epilepsy: challenges and solutions"; Neuropsychiatric Disease and Treatment; vol. 12; 2016; p. 2605-2616.
De Riu et al.; "Propofol Anticonvulsant Activity in Experimental Epileptic Status"; British Journal of Anaesthesia; vol. 69; 1992; p. 177-181.
Dinis-Oliveria; "Metabolic Profiles of Propofol and Fospropofol: Clinical and Forensic Interpretative Aspects"; BioMed Research Int'l; vol. 2018 Article 6852857; 2018; 16 pages.
Falco-Water; "Epilepsy—Definition, Classification, Pathophysiology, and Epidemiology"; Seminars in Neurology; vol. 40; 2020; p. 617-623.
Farzana et al.; "Parosmia and Dysgeusia after Intravenous Propofol-Based General Anesthesia: A Case Report"; Annals of Cardiac Anaesthesia; vol. 25; 2022; p. 112-115.
Feist et al.; "Prevalence and incidence of epilepsy"; Neurology; vol. 88; 2017; p. 296-303.
Fisher et al.; "Epileptic Seizures and Epilepsy: Definitions Proposed by the International League Against Epilepsy (ILAE) and the International Bureau for Epilepsy (IBE)"; Epilepsia; vol. 46 No. 4; 2005; p. 470-472.
Fisher et al.; "A practical clinical definition of epilepsy"; Epilepsia; vol. 55; 2014; p. 475-482.
Fodale et al.; "Propofol Infusion Syndrome An Overview of a Perplexing Disease"; Drug Safety; vol. 31; 2008; p. 293-303.
French et al.; "Efficacy and Tolerability of the New Antiepileptic Drugs, II: Treatment of Refractory Epilepsy: Report of the TTA and QSS Subcommittees of the American Academy of Neurology and the American Epilepsy Society"; Epilepsia; vol. 45; 2004; p. 410-423.
French et al.; "Inhaled alprazolam rapidly suppresses epileptic activity in photosensitive participants"; Epilepsia; vol. 60; 2019; p. 1602-1609.
French et al.; "Time to Start Calling Things by Their Own Names? The Case for Antiseizure Medicines"; Epilepsia Current; vol. 20; 2020; p. 69-72.
Gan et al.; "Determination of plasma concentrations of propofol associated with 50% reduction in postoperative nausea"; Anesthesiology; vol. 87; 1997; p. 779-784.
Garcia et al.; "General Anesthetic Actions on GABAA Receptors"; Current Neuropharmacology; vol. 8, 2010; p. 2-9.
"Global, regional, and national incidence, prevalence, and years lived with disability for 310 diseases and injuries, 1990-2015: a systematic analysis for the Global Burden of Disease Study 2015"; GBD 2015 Disease and Injury Incidence and Prevalence Collaborators; Lancet; vol. 388; Oct. 2016; p. 1545-1602.
"Global, regional, and national incidence, prevalence, and years lived with disability for 328 diseases and injuries for 195 countries, 1990-2016: a systematic analysis for the Global Burden of Disease Study 2016"; GBD 2016 Disease and Injury Incidence and Prevalence Collaborators; Lancet; vol. 390; Sep. 2017; p. 1211-1259.
"Global, regional, and national burden of epilepsy, 1990-2016: a systematic analysis for the Global Burden of Disease Study 2016"; GBD 2016 Epilepsy Collaborators; Lancet; vol. 18; Apr. 2019; p. 357-375.
"Global, regional, and national incidence, prevalence, and years lived with disability for 354 diseases and injuries for 195 countries and territories, 1990-2017: a systematic analysis for the Global Burden of Disease Study 2017"; GBD 2017 Disease and Injury Incidence and Prevalence Collaborators; Lancet; vol. 392; Nov. 2018; p. 1789-1858.
Hasan; "Evaluation of the Anticonvulsant Effects of Propofol in Pentylenetetrazole kindled Rats"; The FASEB Journal; vol. 31; 2017; p. 813.6 (abstract only).
Hasan et al.; "Comparison between the effects of propofol and midazolam on pentylenetetrazole kindled convulsions in rats"; The FASEB Journal; vol. 33; 2019; p. 665.4 (abstract only).

"Headache Classification Committee of the International Headache Society (IHS)"; The International Classification of Headache Disorders, 3rd edition; Cephalalgia; vol. 38; 2018; 211 pages.
Hiraoka et al.; "Changes in drug plasma concentrations of an extensively bound and highly extracted drug, propofol, in response to altered plasma binding"; Clinical Pharmacology & Therapeutics; vol. 75; 2004; p. 324-330.
Hiraoka et al.; "Kidneys contribute to the extrahepatic clearance of propofol in humans, but not lungs and brain"; British Journal of Clinical Pharmacology; vol. 60; 2005; p. 176-182.
Hoymork et al.; "Why do women wake up faster than men from propofol anaesthesia?"; British Journal of Anaesthesia; vol. 95; 2005; p. 627-633.
Johannessen et al.; "Therapeutic drug monitoring of antiepileptic drugs: current status and future prospects"; Expert Opinion on Drug Metabolism & Toxicology; vol. 16; 2020; p. 227-238.
Kasteleijn-Nolst et al.; "Photosensitive epilepsy: a model to study the effects of antiepileptic drugs. Evaluation of the piracetam analogue, levetiracetam"; Epilepsy Research; vol. 25; 1996; p. 225-230.
Kasteleijn-Nolst et al.; "Evaluation of brivaracetam, a novel SV2A ligand, in the photosensitivity model"; Neurology; vol. 69; 2007; p. 1027-1034.
Katsarava et al.; "Defining the Differences Between Episodic Migraine and Chronic Migraine"; Curr Pain Headache Rep; vol. 16; 2012; p. 86-92.
Kumar et al.; "Intraoperative refractory status epilepticus caused by propofol—a case report-"; Korean Journal of Anesthesiology; vol. 74; 2021; p. 70-72.
Lee et al.; "Diagnosis and Treatment of Status Epilepticus"; Journal of Epilepsy Research; vol. 10; 2020; p. 45-54.
Lingamaneni et al.; "Anesthetic Properties of 4-lodopropofol"; Anesthesiology; vol. 94; Jun. 2001; p. 1050-1057.
Lipton et al.; "Migraine prevalence, disease burden, and the need for preventive therapy"; Neurology; vol. 68; 2007; p. 343-349.
Lipton et al.; "Predicting Inadequate Response to Acute Migraine Medication: Results From the American Migraine Prevalence and Prevention (AMPP) Study"; Headache; vol. 56; 2016; p. 1635-1648.
Lowson et al.; "Anticonvulsant Properties of Propofol and Thiopentone: Comparison Using Two Tests in Laboratory Mice"; British Journal of Anaesthesia; vol. 64; 1990; p. 59-63.
Lu et al.; "Propofol-induced refractory status epilepticus at remission age in benign epilepsy with centrotemporal spikes—A case report and literature review"; Medicine; vol. 98; 2019; 5 pages.
Mahmoud et al.; "Migraine and the risk of cardiovascular and cerebrovascular events: a metaanalysis of 16 cohort studies including 1 152 407 subjects"; BMJ Open; 2018; 10 pages.
Marmura et al.; "The Acute Treatment of Migraine in Adults: The American Headache Society Evidence Assessment of Migraine Pharmacotherapies"; Headache; vol. 55; 2015; p. 3-20.
Mathew et al.; "Intravenous Valproate Sodium (Depacon) Aborts Migraine Rapidly: A Preliminary Report"; Headache; vol. 40; 2000; p. 720-723.
Meyer et al.; "Propofol: Pro- or Anticonvulsant Drug?"; Int'l Anesthesia Research Society; vol. 108; Jun. 2009; p. 1993-1994.
Munakata et al.; "Economic Burden of Transformed Migraine: Results From the American Migraine Prevalence and Prevention (AMPP) Study"; Headache; vol. 49; 2009; p. 498-508.
Ngugi et al.; "Estimation of the burden of active and life-time epilepsy: A meta-analytic approach"; Epilepsia; vol. 51(5); 2010; p. 883-890.
Nicolodi et al.; "Exploration of NMDA Receptors in Migraine: Therapeutic and Theoretic Implications"; Int'l J. Clin. Pharm. Res; vol. 15; 1995; p. 181-189.
Nishikawa et al.; "Inhibitory Influence of GABA on Central Serotonergic Transmission. Involvement of the Habenulo-Raphé Pathways in the GABAergic Inhibition of Ascending Cerebral Serotonergic Neurons"; Brain Research; vol. 331; 1985; p. 81-90.
Oei-Lim et al.; "Pharmacokinetics of propofol during conscious sedation using target-controlled infusion in anxious patients undergoing dental treatment"; British Journal of Anaesthesia; vol. 80; 1998; p. 324-331.

(56) References Cited

OTHER PUBLICATIONS

Ohmori et al.; "The Anticonvulsant Action of Propofol on Epileptiform Activity in Rat Hippocampal Slices"; Anesth Analg; vol. 99; 2004; p. 1095-1101.
Pack et al.; "Epilepsy Overview and Revised Classification of Seizures and Epilepsies"; Continuum Journal; vol. 25; Apr. 2019; p. 306-321.
Penovich; "Acute Repetitive Seizures (ARS) or Cluster Seizures"; https://www.epilepsyfoundationmn.org/2020/01/14/acute-repetitive-seizures-ars-or-cluster-seizures/; Jan. 2021; 4 pages.
Perucca et al.; "30 years of second-generation antiseizure medications: impact and future perspectives"; Lancet Neurology; vol. 19; 2020; 12 pages.
Puledda et al.; "Non-Pharmacological Approaches for Migraine"; Neurotheraputics; vol. 15; 2018; p. 336-345.
Puri G.D; "Target controlled infusion total intravenous anaesthesia and Indian patients: Do we need our own data?"; Indian Journal of Anaesthesia; vol. 62; 2018; p. 245-248.
Rampil; "A primer for EEG signal processing in anesthesia"; Anesthesiology; vol. 89; 1998; p. 980-1002.
Raoof et al.; "In vivo assessment of intestinal, hepatic, and pulmonary first pass metabolism of propofol in the rat"; Pharmaceutical Research; vol. 13; 1996; p. 891-895.
Rogawski, MD; "Common Pathophysiologic Mechanisms in Migraine and Epilepsy"; Arch Neurol; vol. 65 No. 6; Jun. 2008; p. 709-714.
Rohmann et al.; "Migraine, headache, and mortality in women: a cohort study"; The Journal of Headache and Pain; vol. 21:27; 2020; 8 pages.
Rui et al.; "National Hospital Ambulatory Medical Care Survey: 2017 Emergency Department Summary Tables"; CDC National Center for Health Statistics; https://www.cdc.gov/nchs/data/nhamcs/web_tables/2017_ed_web_tables-508.pdf; 2017; accessed Apr. 2020; 37 pages.
Sahinovic et al.; "Clinical Pharmacokinetics and Pharmacodynamics of Propofol"; Clin Pharmacokinet; vol. 57; 2018; p. 1539-1558.
Samra et al.; "Effects of propofol sedation on seizures and intracranially recorded epileptiform activity in patients with partial epilepsy"; Anesthesiology; vol. 82; 1995; p. 843-851.
Schwedt et al.; "Acute treatment of migraine in adults"; Wolters Kluwer; 2021; 36 pages.
Silberstein; "Practice parameter: evidence-based guidelines for migraine headache (an evidence-based review): report of the Quality Standards Subcommittee of the American Academy of Neurology"; Neurology; vol. 55; 2000; p. 754-762.
Silvestri et al.; "Fospropofol Disodium for Sedation in Elderly Patients Undergoing Flexible Bronchoscopy"; J Bronchology Interv Pulmonol.; vol. 18(1); Jan. 2011; p. 15-22.
Simon et al.; "Disposition and pharmacology of propofol glucuronide administered intravenously to animals"; Xenobiotica; vol. 22 No. 11; 1992; p. 1267-1273.
J. R. Sneyd; "Excitatory events associated with propofol anaesthesia: a review"; Journal of the Royal Society of Medicine; vol. 85; May 1992; p. 288-291.
Straube et al.; "Primary headaches during lifespan"; The Journal of Headache and Pain; vol. 20; 2019; 14 pages.
Strzelczyk et al.; "Expanding the Treatment Landscape for Lennox-Gastaut Syndrome: Current and Future Strategies"; CNS Drugs; vol. 35; 2021; p. 61-83.
"Summary Health Statistics: National Health Interview Survey, 2018"; U.S. Dept. of Health and Human Services; 2018; 9 pages.
Trapani et al.; "Propofol in Anesthesia. Mechanism of Action, Structure-Activity Relationships, and Drug Delivery"; Current Medicinal Chemistry; vol. 7; 2000; p. 249-271.
VanHaerents et al.; "Epilepsy Emergencies: Status Epilepticus, Acute Repetitive Seizures, and Autoimmune Encephalitis"; Continuum: Lifelong Learning in Neurology; vol. 25; 2019; p. 454-476.
Vasileiou et al.; "Propofol: A review of its non-anaesthetic effects"; European Journal of Pharmacology; vol. 605; 2009; 8 pages.
Vasquez et al.; "Pediatric refractory and super-refractory status epilepticus"; Seizure; vol. 68; 2019; p. 62-71.
Veselis et al.; "Low-dose Propofol-induced Amnesia Is Not due to a Failure of Encoding"; Anesthesiology; vol. 109; Aug. 2008; p. 213-224.
Wood et al.; "Propofol Infusion for the Treatment of Status Epilepticus"; The Lancet; Feb. 1988; p. 480-481.
"Epilepsy—A public health imperative"; World Health Organization; 2019; 171 pages.
H.F. Yanny; "Propofol infusions for status epilepticus"; Anaesthesia; vol. 43; 1988; p. 514.
Zack et al.; "National and State Estimates of the Numbers of Adults and Children with Active Epilepsy—United States, 2015"; Morbidity and Mortality Weekly Report; vol. 66 No. 31; Aug. 2017; p. 821-825.
Zhang et al.; "Systematic review and meta-analysis of propofol versus barbiturates for controlling refractory status epilepticus"; BMC Neurology; vol. 19; 2019; 11 pages.
Brodie; "Road to refractory epilepsy: The Glasgow story"; Epilepsia; vol. 54 Supplemental 2; 2013; p. 5-8.
Kasteleijin-Nolst Trenite; "Photosensitivity in epilepsy. Electrophysiological and clinical correlates"; Acta Neurol Scan Suppl.; vol. 125; 1989; p. 3-147.
Kasteleijin-Nolst Trenite et al.; "Preliminary assessment of the efficacy of Org 6370 in photosensitive epileptic patients: paradoxical enhancement of photosensitivity and provocation of myoclonic seizures"; Epilpsia; vol. 33(1); 1992; p. 135-141.
Kasteleijin-Nolst Trenite et al.; "Evaluation of carisbamate, a novel antiepileptic drug, in photosensitive patients: An exploratory, placebo-controlled study"; Epilepsy Research; vol. 74; 2007; p. 193-200.
Nishikawa et al.; "Inhibitory Influence of GABA on Central Serotonergic Transmission. Raph6 Nuclei as the Neuroanatomical Site of the GABAergic Inhibition of Cerebral Serotonergic Neurons"; Brain Research; vol. 331; 1985; p. 91-103.
"Initial Investigational New Drug Application—(Fospropofol Disodium) For Oral Administration"; Investigator's Brochure; Version 1.0; Jul. 2020; 69 pages.
"US 21 CFR Part 58. Good Laboratory Practice for Nonclinical Laboratory Studies"; Available at https://www.ecfr.gov/cgi-bin/text-idx?SID=3be49f31878defa85f39ed3b84fcbe1&mc=true&node=se21.1.58_11&rgn=div8; 16 pages.
"Diprivan® (propofol) injectable emulsion, USP"; https://www.accessdata.fda.gov/drugsatfda_docs/label/2017/019627s066lbl.pdf; Fresenius-Kabi; Apr. 2017; 54 pages.
Sheehan et al.; "Comparative Validation of the S-STS, the ISSTPlus, and the C-SSRS for Assessing the Suicidal Thinking and Behavior FDA 2012 Suicidality Categories"; Innov Clin Neurosci.; vol. 11; 2014; p. 32-46.
Sheehan et al.; "Status Update on the Sheehan-Suicidality Tracking Scale (S-STS) 2014"; Innov Clin Neurosci.; vol. 11; 2014; p. 93-140.
"Bioanalytical Method Validation Guidance for Industry"; U.S. Dept. of Health and Human Services; May 2018; Biopharmaceutics; 41 pages.
"E6(R2) Good Clinical Practice: Integrated Addendum to ICH E6(R1) Guidance for Industry"; U.S. Dept. of Health and Human Services; Mar. 2018; 69 pages.
"Lusedra™ (fospropofol disodium) Injection, for intravenous use"; FDA printed label. Revised Oct. 2009. Available at https://www.accessdata.fda.gov/drugsatfda_docs/label/2010/022244s006lbl.pdf; 3 pages.
Aeschbacher et al.; "Propofol in rabbits. 2. Long-term anesthesia."; Laboratory Animal Science; vol. 43(4); Aug. 1993; p. 328-335 (abstract only).
Glen et al.; "Interaction Studies and other investigations of the pharmacology of propofol ('Diprivan')"; Postgrad Med J.; vol. 61 Suppl. 3; 1985; p. 7-14 (abstract only).
Muir et al.; "Respiratory depression and apnea induced by propofol in dogs"; Am J Vet Res.; vol. 59(2); Feb. 1998; p. 157-161 (abstract only).
"IHS Classification ICHD-3"; https://ichd-3.org/evolution-of-ihs-classification-1-3/; International Headache Society; © 2021; accessed Feb. 9, 2023; 3 pages.
U.S. Appl. No. 17/066,957, filed Oct. 9, 2020, Rogawski et al.
U.S. Appl. No. 17/168,365, filed Feb. 5, 2021, Murphy et al.

(56) References Cited

OTHER PUBLICATIONS

U.S. Appl. No. 17/387,059, filed Jul. 28, 2021, Krill et al.
U.S. Appl. No. 17/465,966, filed Sep. 3, 2021, Krill et al.
U.S. Appl. No. 17/562,605, filed Dec. 27, 2021, Krill et al.
Feng et al., "Novel propofol derivatives and implications for anesthesia practice", J. Anaesthesiol Clin Pharmacol., Jan.-Mar. 2017; vol. 33(1), p. 9-15.
Dhir; "Propofol in the treatment of refractory migraine headaches"; Expert Review of Neurotherapeutics; vol. 16 No. 9; 2016; p. 1007-1011.
Harris et al.; "Monitored anesthesia care (MAC) sedation: clinical utility of fospropofol"; Therapeutics and Clinical Risk Management; vol. 5; 2009; p. 949-959.
Ovesen et al.; "Intraluminal pH in the Stomach, Duodenum, and Proximal Jejunum in Normal Subjects and Patients With Exocrine Pancreatic Insufficiency"; Gastroenterology; vol. 90; 1986; p. 958-962.
Wozniak et al.; "Gastrointestinal delivery of propofol from fospropofol: its bioavailability and activity in rodents and human volunteers"; Journal of Translational Medicine; vol. 13; 2015; 13 pages.
Wilson et al.; "The abuse potential of propofol"; Clinical Toxicology; vol. 48; 2010; p. 165-170.
Ward et al.; "Use of intravenous propofol in the treatment of migraine headache"; EMA; 2013; p. 619.
Soleimanpour et al.; "Improvement of refractory migraine headache by propofol: case series"; Int'l Journal of Emergency Medicine; vol. 5; 2012; 4 pages.
Soleimanpour et al.; "Effectiveness of intravenous Dexamethasone versus Propofol for pain relief in the migraine headache: A prospective double blind randomized clinical trial"; BMC Neurology; vol. 12; 2012; 7 pages.
Simmonds et al.; "The Effect of Single-Dose Propofol Injection on Pain and Quality of Life in Chronic Daily Headache: A Randomized, Double-Blind, Controlled Trial"; Int'l Anesthesia Research Society; vol. 109 No. 6; Dec. 2009; p. 1972-1980.
Sheridan et al.; "Low-Dose Propofol for the Abortive Treatment of Pediatric Migraine in the Emergency Department"; Pediatric Emergency Care; vol. 28 No. 12; Dec. 2012; p. 1293-1296.
Sheridan e al.; "Low-Dose Propofol for Pediatric Migraine: a Prospective, Randomized Controlled Trial"; The Journal of Emergency Medicine; vol. 54 No. 5; 2018; p. 600-606.
Schneider et al.; "Propofol dependency after treatment of tension headache"; Addiction Biology; vol. 6; 2001; p. 263-265.
Sato et al.; "Low-dose intravenous propofol as a possible therapeutic option for acute confusional migraine"; American Journal of Emergency Medicine; vol. 35; 2017; 2 pages.
Reinsel et al.; "The P300 event-related potential during propofol sedation: a possible marker for amnesia?"; British Journal of Anesthesia; vol. 74; 1995; 674-680.
Razavi et al.; "Propofol and Alfentanil in Treatment of a Patient with Episodic Cluster Headache"; Anesth Pain Medicine; vol. 4(2); May 2014; 3 pages.
Mosier et al.; "Sedative Dosing of Propofol For Treatment of Migraine Headache In The Emergency Department: A Case Series"; Western Journal of Emergency Medicine; vol. 14 No. 6; Nov. 2013; p. 646-649.
Moshtaghion et al.; "The Efficacy of Propofol vs. Subcutaneous Sumatriptan for Treatment of Acute Migraine Headaches in the Emergency Department: A Double-Blinded Clinical Trial"; World Institute of Pain; 2014; 5 pages.
Mohseni et al.; "Propofol Alleviates Intractable Migraine Headache: A Case Report"; Anesthesiology and Pain Medicine; vol. 2(2); 2012; p. 94-96.
Mendes et al.; "Intravenous Propofol in the Treatment of Refractory Headache"; Headache; vol. 42; 2002; p. 638-641.
Long et al.; "Benign Headache Management in the Emergency Department"; The Journal of Emergency Medicine; vol. 54 No. 4; 2018; p. 458-468.
Krusz et al.; "Intravenous Propofol: Unique Effectiveness in Treating Intractable Migraine"; Headache; vol. 40; Mar. 2000; p. 224-230.
Ferrari et al.; "Oral triptans (serotonin 5-HT1B/1D agonists) in acute migraine treatment: a meta-analysis of 53 trials"; The Lancet; vol. 358; Nov. 2001; p. 1668-1675.
Drummond-Lewis et al.; "Propofol: A New Treatment Strategy for Refractory Migraine Headache"; Pain Medicine; vol. 3 No. 4; 2002; p. 366-369.
Dhir et al.; "Propofol hemisuccinate suppresses cortical spreading depression"; Neuroscience Letters; vol. 514; 2012; p. 67-70.
Dhir et al.; "Seizure Protection by Intrapulmonary Delivery of Propofol Hemisuccinate"; The Journal of Pharmacology and Experimental Therapeutics; vol. 336 No. 1; 2011; p. 215-222.
Bloomstone; "Propofol: A Novel Treatment for Breaking Migraine Headache"; Anesthesiology; vol. 106; 2007; p. 405-406.
Baker; "The Anticonvulsant Effects of Propofol and a Propofol Analog, 2,6-Diisopropyl-4-(1-Hydroxy-2,2,2-Trifluoroethyl)Phenol, in a 6 Hz Partial Seizure Model"; Int'l Anesthesia Research Society; vol. 112 No. 2; Feb. 2011; p. 340-344.
Kurt et al.; "Anxiolytic-Like Profile of Propofol, a General Anesthetic, in the Plus-Maze Test in Mice"; Polish Journal of Pharmacology; vol. 55; 2003; p. 973-977.
Zacny et al.; "Propofol at Conscious Sedation Doses Produces Mild Analgesia to Cold Pressor-Induced Pain in Healthy Volunteers"; Journal of Clinical Anesthesia; vol. 8; 1996; p. 469-474.
Nishiyama et al.; "Intrathecal propofol has analgesic effects on inflammation-induced pain in rats"; Canadian Journal of Anesthesia; vol. 51(9); 2004; p. 899-904.
Bennett et al.; "Postoperative Infections Traced to Contamination of an Intravenous Anesthetic, Propofol"; The New England Journal of Medicine; vol. 333; 1995; p. 147-154.
Pytliak et al.; "Serotonin Receptors—From Molecular Biology to Clinical Applications"; Physiological Research; 2011; 19 pages.
Fechner et al.; "Pharmacokinetics and Clinical Pharmacodynamics of the New Propofol Prodrug GPI 15715 in Volunteers"; Anesthesiology; vol. 99 No. 2; Aug. 2003; p. 303-313.
Mahajan et al.; "Fospropofol"; Journal of Pharmacology and Pharmacotherapeutics; vol. 3 No. 3; Jul.-Sep. 2012; p. 293-296.
Borgeat et al.; "Subhypnotic Doses of Propofol Relieve Pruritus Associated with Liver Disease"; Gastroenterology; vol. 104; Jan. 1993; p. 244-247.
Kam et al.; "Pruritus—itching for a cause and relief?"; Anaesthesia; vol. 51; 1996; p. 1133-1138.
Pain et al.; "Effect of Nonsedative Doses of Propofol on an Innate Anxiogenic Situation in Rats"; Anesthesiology; vol. 90; 1999; p. 191-196.

* cited by examiner

Overlay of Individual and Mean Fospropofol Plasma Concentrations by Cohort (Fasting Conditions) - Linear Scale - PK Set

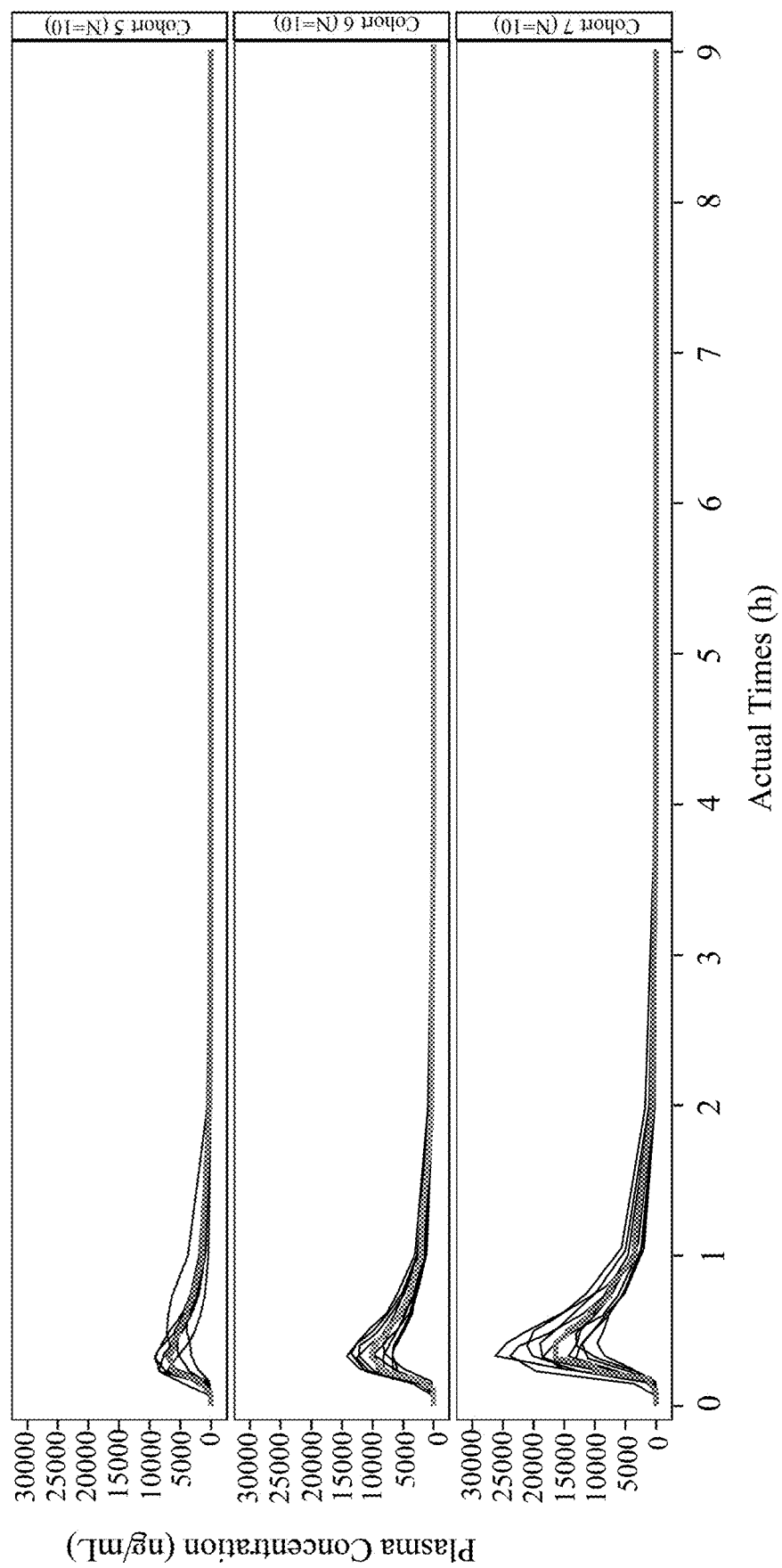
Fig. 4B Overlay of Individual and Mean Fospropofol Plasma Concentrations by Cohort (Fasting Conditions) - Linear Scale - PK Set Overlay of Individual and Mean Fospropofol Plasma Concentrations Food Effect Cohort (Fasting and Fed Conditions) - Linear Scale - PK Set Overlay of Individual and Mean Propofol Plasma Concentrations Food Effect Cohort (Fasting and Fed Conditions) - Linear Scale - PK Set FosDS = Fospropofol disodium Scatterplots with Linear Regression Line for BIS score Against Ln-Transformed Propofol Plasma concentrations by Cohort - PK Set FosDS = Fospropofol disodium p=0.098, R2 = 0.2752 p=0.004, R2 = 0.6295

FOSPROPOFOL METHODS AND COMPOSITIONS

CROSS REFERENCE TO RELATED APPLICATIONS

This application claims the benefit of the following applications:
This application is a continuation of U.S. patent application Ser. No. 17/686,738, filed Mar. 4, 2022, which is:
a continuation of U.S. patent application Ser. No. 17/562,605, filed Dec. 27, 2021, which is:
a continuation-in-part of U.S. patent application Ser. No. 17/387,059, filed Jul. 28, 2021, which is a continuation-in-part of U.S. patent application Ser. No. 17/217,656, filed Mar. 30, 2021;
a continuation-in-part of U.S. patent application Ser. No. 17/465,966, filed Sep. 3, 2021, which is a divisional of U.S. patent application Ser. No. 17/217,656, filed Mar. 30, 2021;
a continuation-in-part of U.S. patent application Ser. No. 17/466,016, filed Sep. 3, 2021, which is a continuation of U.S. patent application Ser. No. 17/217,656, filed Mar. 30, 2021;
a continuation-in-part of U.S. patent application Ser. No. 17/168,365, filed Feb. 5, 2021, which claims the benefit of U.S. Provisional Application No. 62/970,324, filed Feb. 5, 2020;
a continuation-in-part of U.S. patent application Ser. No. 17/066,957, filed Oct. 9, 2020, which claims the benefit of U.S. Provisional Application No. 62/914,051, filed Oct. 11, 2019;
a continuation-in-part of U.S. patent application Ser. No. 16/831,035, filed Mar. 26, 2020, which claims the benefit of U.S. Provisional Application No. 62/824,182, filed Mar. 26, 2019.
The entirety of each of the above aforementioned applications is incorporated by reference herein in its entirety.

TECHNICAL FIELD

The present disclosure pertains to the use of propofol prodrugs, pharmaceutically acceptable salts of propofol prodrugs, or mixtures thereof, to treat disease or disorder, including migraine.

The present disclosure also pertains to the use of fospropofol, pharmaceutically acceptable salts of fospropofol, or mixtures thereof, to treat migraine.

The disclosure also pertains to pharmaceutical compositions for oral administration of fospropofol, or pharmaceutically acceptable salts of fospropofol, well as methods for oral administration of fospropofol.

BACKGROUND

Propofol (2,6-diisopropylphenol) is an intravenous short-acting anesthetic agent that has gained acceptance for inducing and maintaining anesthesia and for procedural sedation. Propofol is a highly lipophilic drug which must be formulated as a suspension with a lipid carrier in aqueous medium. Consequently, propofol derivatives were developed which possessed increased water solubility to simplify formulation. One of these was fospropofol ((2,6-diisopropylphenoxy) methyl dihydrogen phosphate). Fospropofol is a water-soluble, phosphono-O-methyl prodrug of propofol that was approved in the United States as an alternative to propofol for monitored anesthesia care during procedures.

While intravenous administration is useful for anesthesia applications, oral administration of fospropofol would be desirable for other uses. Oral dosing, however, requires a dosage form having adequate bioavailability with minimal subject-to-subject variability. Thus, there is a need for dosage forms of fospropofol that are orally bioavailable with minimal inter-subject variability.

Fospropofol is rapidly metabolized by endothelial alkaline phosphatases to release propofol, phosphate, and formaldehyde. The small amount of formaldehyde is rapidly converted to formate and safely eliminated, similar to the other available phosphate methyl prodrugs such as fosphenytoin.

Migraine is a primary headache disorder characterized by recurrent headaches that may be moderate or severe. Typically, the headaches affect one half of the head, are pulsating in nature, and last from two to 72 hours.

Migraines are called primary headaches because the pain is not caused by another disorder or disease such as a brain tumor or head injury. Symptoms of migraines may include nausea, vomiting, and sensitivity to light, sound, or smell. The pain is generally made worse by physical activity. Some cause pain on just the right side or left side of the head, others result in pain all over. Migraine sufferers may have moderate or severe pain and usually can't participate in normal activities because of the pain. Often when a migraine strikes, people try to find a quiet, dark room.

Many people have an aura with a migraine, typically a short period of visual disturbance that signals that the headache will soon occur. Sufferers have reported seeing flashes or bright spots. Occasionally, an aura can occur with little or no headache following it.

The range of time someone is affected by an attack is often longer than the migraine itself, as there is a pre-monitory, or build-up phase, and a post-drome phase that can last one to two days. Different people have different triggers and different symptoms.

Migraines are believed to be due to a mixture of environmental and genetic factors. Genomics of migraines have been examined and certain gene mutations have been associated with severe migraines, but the etiology is presumably polygenic. Changing hormone levels may also play a role, as migraines affect slightly more boys than girls before puberty and two to three times more women than men after puberty. Catemanial migraine is not uncommon in women associated with the menses.

Migraines are believed to involve the nerves and blood vessels of the brain. However, older ideas that migraines were principally vascular in nature are now considered to be incorrect. Although an exact cause is unknown, brain scans show that migraines may be due to "hyperactivity" in parts of the brain. This activity can spread across the cortex during the course of the migraine, which is known as spreading cortical depression.

Migraines are one of the most common causes of disability. There are about 100 million people with recurrent headaches in the U.S. and about 37 million of these people have migraines. The World Health Organization suggests that 18 percent of women and 7 percent of men in the U.S. suffer from migraines. Globally, approximately 15% of people are affected by migraines. Migraines most often start at puberty and get worse during middle age. In some women, migraines become less common following menopause. Migraine headaches are a common cause of disability in the United States, affecting approximately 27 million American adults, or 17.1% of women and 5.6% of men.

There is often a distinction between a migraine with an aura and a migraine without an aura. The most current terminology defines a classic migraine as a migraine with an aura and non-classic or common migraine as a migraine without aura. Also, there is often a distinction between chronic migraine and episodic migraine. Chronic migraine, which affects 3.2 million Americans (2%), is defined as having at least 15 headache days a month, with at least 8 days of having headaches with migraine features, and for longer than 3 months in duration. Episodic migraine, in contrast, is a condition defined as having fewer headache days or fewer headache days with migraine features per month.

Migraine treatment may also be characterised as acute treatment or prophylactic (i.e., preventative) treatment. In some embodiments, the methods and pharmaceutical compositions disclosed herein are useful for acute treatment of migraine. In some embodiments, the methods and pharmaceutical compositions disclosed herein are useful for acute treatment of migraine with or without aura. In other embodiments, the methods and pharmaceutical compositions disclosed herein are useful for prophylactic treatment of migraine.

Current treatments for migraine are divided into acute, abortive agents (analgesics, triptans, ergots, etc.), and medications that are used chronically to will reduce the frequency and severity of migraine attacks.

Initial recommended treatment is with one of the acute treatments, such as ibuprofen, naproxen sodium or acetaminophen. Caffeine may also be used for treatment. Nausea medications may also be administered.

Triptans and dihydroergotamine (DHE-45) are also commonly used acute treatments. The oral triptans [sumatriptan (Imitrex), naratriptan (Amerge), zolmitriptan (Zomig), rizatriptan (Maxalt), almotriptan (Axert), frovatriptan (Frova), and eletriptan (Relpax)] are thought to be generally effective in only 60 to 70% of patients. Lasmiditan (Reyvow), an oral ditan related to the oral triptans, is used in a similar fashion to the triptans and has similar efficacy. A large percentage of migraine sufferers are either resistant to these medications or they have unacceptable side effects.

Various NSAID drugs other than ibuprofen and naproxen may also be used for acute treatment, such as diclofenac and ketorolac. Opiates are generally ineffective and are contraindicated.

Calcitonin gene related peptide (CGRP) receptor targeted small molecules such as ubrogepant and rimegepant are newer acute treatments but they are generally less effective than the triptans although they are better tolerated.

Many patients require chronic (daily) therapy to prevent migraine attacks. The antidepressant and mood stabilizer Amitriptyline is quite effective in some patients, as are beta-blockers including propranolol and metoprolol, as well certain antiseizure drugs including topiramate, valproate, and gabapentin.

Antibodies that act on CGRP or its receptor are now also widely used as preventives. They include Aimovig® (erenumab), Emgality® (galcanezumab), Ajovy® (fremanezumab), and Vyepti (eptinezumab). Although these agents are effective in many patients, there are many in whom they are ineffective. Furthermore, being recombinant biologicals, they are expensive, and because they are proteins they must be administered by injection, which does not appeal to some patients.

Quilipta™ (atogepant) along with rimegepant are small molecule CGRP receptor antagonists that are used chronically, like CGRP antibodies, as preventives. They are no more effective than the antibodies and many patients continue to experience unacceptable migraine attacks.

Thus, there is a need for additional methods of treating migraine, particularly refractory migraine.

SUMMARY

The present disclosure provides methods and compositions that meet the need for additional migraine treatments, including treatments for refractory migraine.

The disclosure is directed to methods of treating migraine in a patient in need thereof, comprising administering to the patient an effective amount of fospropofol, a pharmaceutically acceptable salt of fospropofol, or mixtures thereof, in one or more doses.

The disclosure is also directed to methods of treating migraine in a patient in need thereof, comprising administering to the patient a composition comprising an effective amount of fospropofol, a pharmaceutically acceptable salt of fospropofol, or mixtures thereof, in one or more doses.

The disclosure is also directed to pharmaceutical compositions comprising fospropofol, a pharmaceutically acceptable salt of fospropofol, or mixtures thereof, and a pharmaceutically acceptable excipient.

The present disclosure provides pharmaceutical dosage forms for oral administration comprising fospropofol or a pharmaceutically acceptable salt of fospropofol, and a pharmaceutically acceptable acid.

The disclosure also provides methods of orally administering fospropofol, or a pharmaceutically acceptable salt thereof, to a subject in need thereof, the method comprising orally co-administering fospropofol, or a pharmaceutically acceptable salt thereof, and a pharmaceutically acceptable acid, to the subject.

The present disclosure provides pharmaceutically acceptable salts of fospropofol, wherein said salt is a disodium salt.

The present disclosure provides pharmaceutically acceptable salts of fospropofol, wherein said salt is a potassium, diethylamine, t-butylamine, ethylene diamine, benzathine, piperazine, ethanolamine, diethanolamine, ammonium, tromethamine, benethamine, histidine, calcium, magnesium, or zinc salt.

The present disclosure also provides pharmaceutical compositions comprising a fospropofol salt of the disclosure and a pharmaceutically acceptable excipient.

The present disclosure also provides methods of treating migraine in a patient in need thereof, comprising administering to the patient an effective amount of a fospropofol salt of the disclosure.

The present disclosure also provides methods and compositions that meet the need for additional migraine treatments, including treatments for refractory migraine.

The disclosure is directed to methods of treating migraine in a patient in need thereof, comprising administering to the patient an effective amount of fospropofol, a pharmaceutically acceptable salt of fospropofol, or mixtures thereof, in one or more doses.

The disclosure is also directed to methods of treating migraine in a patient in need thereof, comprising administering to the patient a composition comprising an effective amount of fospropofol, a pharmaceutically acceptable salt of fospropofol, or mixtures thereof, in one or more doses.

The disclosure is also directed to pharmaceutical compositions comprising fospropofol, a pharmaceutically acceptable salt of fospropofol, or mixtures thereof, and a pharmaceutically acceptable excipient.

BRIEF DESCRIPTION OF THE DRAWINGS

FIGS. 4A and 4B show an Overlay of Individual and Mean Fospropofol Plasma Concentrations by Cohort (Fasting Conditions)—Linear Scale—PK Set—Example A16

DETAILED DESCRIPTION OF ILLUSTRATIVE EMBODIMENTS

Figure 1:
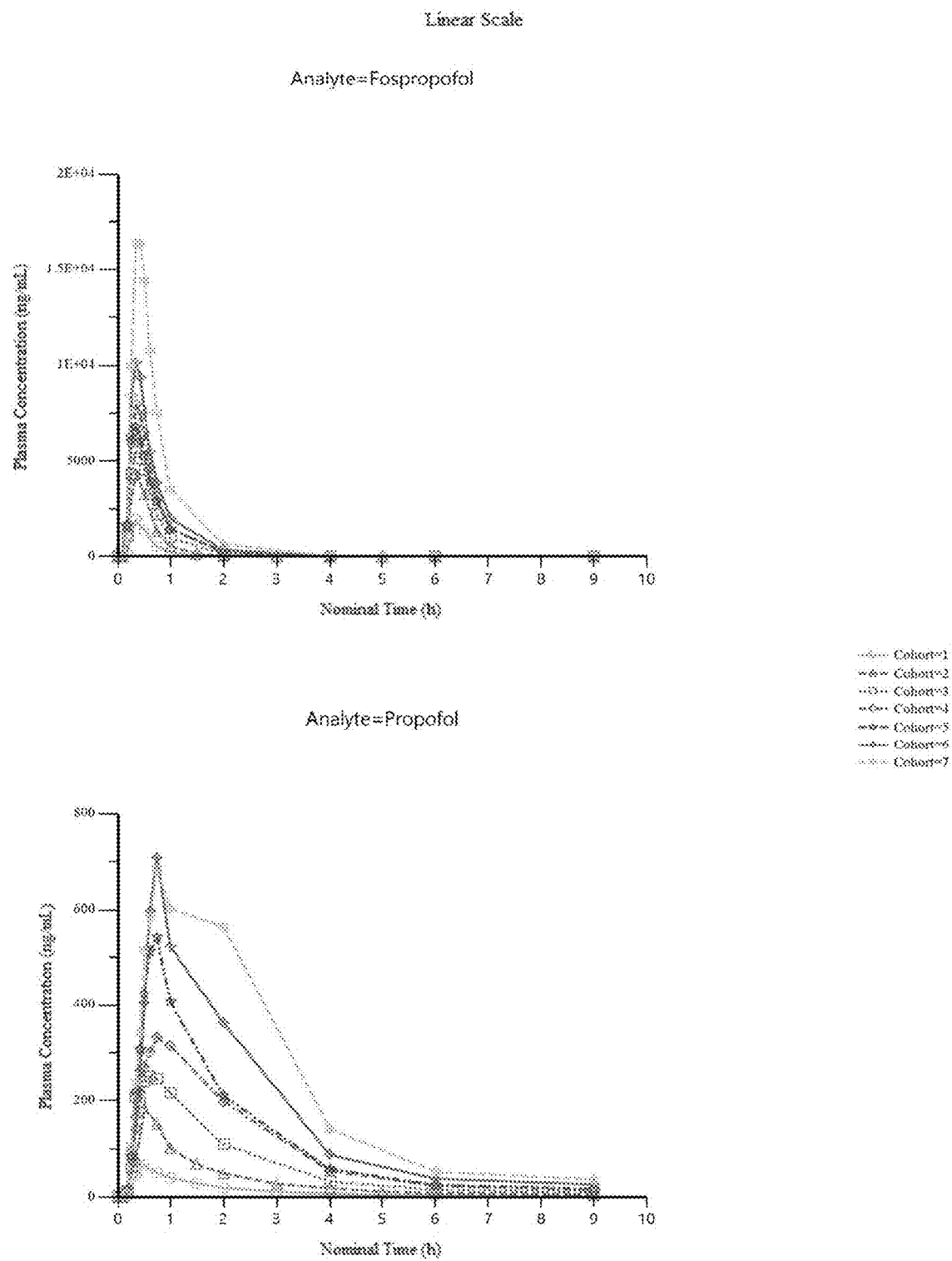
FIG. 1 shows mean concentration vs. time plots for fospropofol and propofol by cohort in Part 1 of Study A16.

The present disclosure may be understood more readily by reference to the following detailed description of desired embodiments and the examples included therein. In the following specification and the claims that follow, reference will be made to a number of terms which have the following meanings.

Unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 to 10" is inclusive of the endpoints, 2 and 10, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one.

Certain features of the disclosure which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the disclosure that are, for brevity, described in the context of a single embodiment, may also be provided separately or in any sub-combination. Finally, while an embodiment may be described as part of a series of steps, each said step may also be considered an independent embodiment in itself, combinable with others.

"Propofol prodrug", as used herein, refers to a molecule which, when administered to a mammal, is converted in vivo to propofol.

As used herein, "propofol" refers to 2,6-diisopropylphenol, which has the structure:

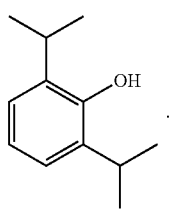

As used herein, "fospropofol" refers to (2,6-diisopropylphenoxy)methyl dihydrogen phosphate, which has the structure:

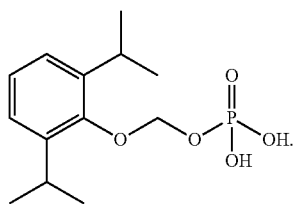 [SMILES: CC(C)c1cccc(C(C)C)c1OCOP(=O)(O)O]

The terms "fospropofol disodium", or "disodium salt of fospropofol" refer to the compound having the structure:

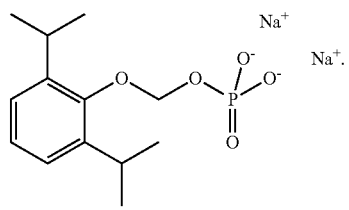 [SMILES: CC(C)c1cccc(C(C)C)c1OCOP(=O)([O-])[O-] ; [Na+]]

The phrase "propofol prodrug, a pharmaceutically acceptable salt of propofol prodrug, or mixtures thereof" is meant to encompass a propofol prodrug alone, a pharmaceutically acceptable salt of propofol alone, mixtures of two or more pharmaceutically acceptable salts of a propofol prodrug, and mixtures of a propofol prodrug and one or more pharmaceutically acceptable salts of a propofol prodrug.

The phrase "fospropofol, a pharmaceutically acceptable salt of fospropofol, or mixtures thereof" is meant to encompass fospropofol alone, a pharmaceutically acceptable salt of fospropofol alone, mixtures of two or more pharmaceutically acceptable salts of fospropofol, and mixtures and fospropofol and one or more pharmaceutically acceptable salts of fospropofol.

As used herein, "pharmaceutically acceptable salt of fospropofol" refers to a salt of fospropofol that is pharmaceutically acceptable and that possesses the desired pharmacologic activity. Such salts are generally non-toxic, and may be inorganic or organic base addition salts. Specifically, such salts include: salts formed when at least one acidic proton present in fospropofol either is replaced by at least one metal ion, e.g., an alkali metal ion, an alkaline earth ion, or an aluminum ion; or by an organic base such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Examples of pharmaceutically acceptable salts of fospropofol include monosodium, monopotassium, disodium, dipotassium salts, diethylamine, t-butyl amine, ethylene diamine, benzathine, piperazine, ethanolamine, diethanolamine, ammonium, tromethamine, benethamine, histidine, calcium, magnesium, and zinc salts. Other exemplary salts include the meglumine, deanol, hydrabamine, 2-diethylaminoethanol, 4-(2-hydroxyethyl)-morpholine, 1-(2hydroxylethyl)-pyrrolidone, or imidazole.

A crystal form may be referred to herein as being characterized by graphical data "as shown in" a Figure. Such data include, for example, powder X-ray diffractograms (XRPD), Differential Scanning Calorimetry (DSC) thermograms, thermogravimetric analysis (TGA) profiles, and dynamic vapor sorption profiles (DVS). As is well-known in the art, the graphical data potentially provides additional technical information to further define the respective solid state form which can not necessarily be described by reference to numerical values or peak positions alone. Thus, the term "substantially as shown in" when referring to graphical data in a Figure herein means a pattern that is not necessarily identical to those depicted herein, but that falls within the limits of experimental error or deviations, when considered by one of ordinary skill in the art. The skilled person would readily be able to compare the graphical data in the Figures herein with graphical data generated for an unknown crystal form and confirm whether the two sets of graphical data are characterizing the same crystal form or two different crystal forms.

The terms "polymorph" or "crystalline form" refer to distinct crystal arrangements of the same chemical composition. The term "form" includes polymorphs, crystalline forms, and non-crystalline (amorphous) solids.

A solid, crystalline form may be referred to herein as "polymorphically pure" or as "substantially free of any other form." As used herein in this context, the expression "substantially free of any other forms" will be understood to mean that the solid form contains about 20% or less, about 10% or less, about 5% or less, about 2% or less, about 1% or less, or 0% of any other forms of the subject compound as measured, for example, by XRPD. Thus, a solid form of a fospropofol salt described herein as substantially free of any other solid forms would be understood to contain greater than about 80% (w/w), greater than about 90% (w/w), greater than about 95% (w/w), greater than about 98% (w/w), greater than about 99% (w/w), or about 100% of the subject solid form of the fospropofol salt. Accordingly, in some embodiments of the disclosure, the described solid forms of fospropofol salts may contain from about 1% to about 20% (w/w), from about 5% to about 20% (w/w), or from about 5% to about 10% (w/w) of one or more other solid forms of fospropofol salts.

As used herein, unless stated otherwise, XRPD peaks reported herein are measured using CuKα radiation, $\lambda=1.5419$ Å.

The terms "subject," or "patient" are used herein to refer to an animal, for example a human, to whom treatment, including prophylactic treatment, with the pharmaceutical compositions or methods according to the present invention, is provided. The terms "subject" or "patient" as used herein refers to human and non-human animals.

As used herein, the term "treating" means reducing or eliminating the signs or symptoms of the condition for which fospropofol is being administered. In some embodiments, as applied to migraine, the term "treating" (or "treatment"), as used herein, refers to preventing, delaying the onset of, reducing the severity of, or eliminating either the patient's migraine or one or more of the patient's migraine symptoms. Migraine symptoms can include pain, nausea/vomitting, photophobia, and phonophobia.

The terms "reducing" or "reducing or eliminating" as used herein both encompass eliminating (i.e., reducing to zero (or none, absent)). Thus, where the term "reducing" is used alone, eliminating may also be encompassed.

The terms "administering" or "administration", as used herein, refer to delivering fospropofol into or onto the patient's body in a manner that results in the presence of propofol in the patient's systemic circulation. Any such method of administering may be used in performing the methods of the present disclosure. In some embodiments of the disclosed methods, the administering is oral, peroral, subcutaneous, intramuscular, intravenous, transmucosal, sublingual, buccal, transdermal, intraintestinal, rectal, or intrapulmonary.

As used herein, the term "orally co-administering" refers to simultaneous administration, or sequential administration in such a manner that the fospropofol, or a pharmaceutically acceptable salt thereof, and the pharmaceutically acceptable acid are present in the subject's stomach at the same time.

The term "migraine," as used herein, refers to a chronic neurovascular disorder characterized by recurrent attacks of often severe headache ("migraine attacks"), typically accompanied by nausea and sensitivity to light and/or sound.

Migraine is a clinical diagnosis, criteria for which would be known and understood by those practicing in the treatment of migraine, and would include, for example, the criteria proposed by the International Headache Society (IHS). See http.//ihs-classification.org/en/.

"Migraine with aura" is migraine characterized by focal neurological symptoms that typically precede, or sometimes accompany, the headache.

"Migraine without aura" is migraine characterized by the absence of focal neurological symptoms that typically precede, or sometimes accompany, the headache.

"Refractory migraine," as used herein, refers to migraine that fails to respond to pharmacologic treatment. Failure to respond in this regard includes, for example, failure of a pharmacological treatment to eliminate migraine pain, as well as failure of a pharmacological treatment to reduce severe or moderate migraine pain to mild migraine pain. Refractory migraine may fail to respond to one or more types of pharmacologic treatment, for example, acute pharmacologic treatment. Examples of pharmacologic treatments to which refractory migraine may fail to respond include nonsteroidal anti-inflammatory agents (e.g. ibuprofen, naproxen sodium diclofenac, ketorolac), CGRP inhibitors (e.g., gepants rimegepant, ubrogepant and atogepant; anti-CGRP or anti-CGRP receptor antibodies), dihydroergatime mesylate, and triptans (e.g., sumatriptan (Imitrex), rizatriptan (Maxalt), almotriptan (Axert), naratriptan (Amerge), zolmitriptan (Zomig), frovatriptan (Frova) and eletriptan (Relpax)).

The term "effective amount" or "therapeutically effective amount", as used herein, refers to an amount sufficient to reduce or eliminate the signs or symptoms of the condition for which fospropofol is being administered. The therapeutically effective amount may be contained in a single dosage form, or may be the cumulative amount contained in multiple dosage forms.

The term "effective amount", as used with respect to methods of treating migraine, refers to an amount sufficient to reduce or eliminate the patient's migraine pain, to eliminate the patient's most bothersome symptom ("MBS"), or to both reduce or eliminate the patient's migraine pain, and to eliminate the patient's MBS. The effective amount may be the amount given in a single dose, or may be the cumulative amount given in multiple doses.

The term "most bothersome symptom" (or "MBS"), is the migraine symptom, other than pain, that is most bothersome to the patient. Examples of MBS include nausea, photophobia, and phonophobia.

The term "bothersome symptom" is a migraine symptom, other than pain, that is bothersome to the patient. Examples include nausea, photophobia, and phonophobia.

As used herein, "photophobia" refers to sensitivity to light.

As used herein, "phonophobia" refers to sensitivity to sound.

As used herein, "hypotention" refers to a fall from baseline blood pressure greater than 20 mm Hg systolic or 20 mm diastolic.

As used herein, the terms "pain relief," "relief from pain," "relief from headache pain," or "headache pain relief" refer to either eliminating pain or reducing severe or moderate pain to mild pain.

As used herein, the term "within" as used to characterize a period of time (e.g., "within 2 hours") includes the specified time point as well as any time points prior to the specified time point. For example, "within 2 hours" includes the time point 2 hours, as well as, for example, 15 minutes, 30 minutes, 1 hour, and 1.5 hours.

As used herein, the term "pulsatile release" refers to a release in which the fospropofol is released from the dosage form in two or more portions, with periods of time between subsequent releases in which little or no drug release takes place. propofolpropofol. A pulsatile release dosage form is prepared by, for example, combining an immediate release portion with a delayed release portion; or combining two or more delayed release portions wherein each portion releases drug at a different time following administration. Examples of dosage forms that provide pulsatile release include capsules containing immediate release granules and delayed release granules; bilayer tablets having an immediate release layer and a delayed-release layer.

The term "modified release" as used herein, refers to a dosage form in which the release of drug is modified relative to an immediate release dosage form.

As used herein, the term "extended release dosage form" refers to a dosage form that releases the encompassed fospropofol over an extended period of time.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, diluent, or release modifier to facilitate administration of an agent and that is compatible therewith.

The term "dose", as used herein, refers to an amount of fospropofol, a pharmaceutically acceptable salt of fospropofol, or mixtures thereof, administered to the patient at a point in time. A dose may be administered in a single dosage form (e.g., tablet, capsule, etc.), or in multiple dosage forms. For example, an 800 mg "dose" of fospropofol may be administered in a single 800 mg tablet, in two 400 mg tablets, or in a 600 mg tablet and a 200 mg capsule. In other aspects, a dose may be administered via a modified release dosage form that releases a first amount of fospropofol, a pharmaceutically acceptable salt of fospropofol, or mixtures thereof, to the patient at a point or period in time, followed by a second amount fospropofol, a pharmaceutically acceptable salt of fospropofol, or mixtures thereof, to the patient at another point or period in time. Thus, a modified-release dosage form provides a single dose that approximates administering multiple separate doses.

The term "Cmax", as used herein, refers to the peak concentration of a compound (e.g., propofol or fospropofol) observed in the patient's plasma following administration of fospropofol, a pharmaceutically acceptable salt of fospropofol, or mixtures thereof. The concentration of propofol in the subject's plasma samples can be determined using standard analytical methods.

The term "mean Cmax", as used herein, refers the mean (arithmetic or geometric) Cmax in a population. The concentration of propofol or of fospropofol in the patient's plasma samples can be determined using standard analytical methods.

The term "plasma concentration", as used herein, refers to the quantity of compound (e.g., propofol or fospropofol) per unit volume of plasma. The term "mean concentration", as used herein, refers to the mean (arithmetic or geometric) plasma concentration in a population.

The term "$AUC_{0-tau}$", (or "AUCt") as used herein, refers to the area under the plasma concentration-time curve from time zero to time t ($AUC_{0-tau}$), where tau is the last time point with measurable concentration of the analyte (i.e., propofol or fospropofol).

The term "$AUC_0$-∞", as used herein, refers to the area under the patient's plasma concentration-time curve from time zero to time infinity ($AUC_0$-∞), where $AUC_{0-\infty}=AUC_{0-tau}+C_{tau}/\lambda z$, $C_{tau}$ is the last measurable drug concentration and $\lambda z$ is the terminal or elimination rate constant calculated according to an appropriate method. Thus, AUC∞ refers to the AUC obtained by extrapolation of $AUC_0$ to ∞.

The term "mean $AUC_0$-∞ c", as used herein, refers to the mean (arithmetic or geometric) $AUC_0$-∞ in a population.

The term "$AUC_{2hr}$", as used herein, refers to the partial AUC at time 2 hr, i.e., the area under the patient's plasma concentration-time curve from time zero to time 2 hours.

The term "mean $AUC_{2hr}$", as used herein, refers to the mean (arithmetic or geometric) $AUC_{2hr}$ in a population.

The term "$AUC_{1hr}$", as used herein, refers to the partial AUC at time 1 hr, i.e., the area under the patient's plasma concentration-time curve from time zero to time 1 hour.

The term "mean $AUC_{1hr}$", as used herein, refers to the mean (arithmetic or geometric) $AUC_{1hr}$ in a population.

The term "$AUC_{4hr}$", as used herein, refers to the partial AUC at time 4 hr, i.e., the area under the patient's plasma concentration-time curve from time zero to time 4 hours.

The term "mean $AUC_{4hr}$", as used herein, refers to the mean (arithmetic or geometric) $AUC_{4hr}$ in a population.

The term "$AUC_{20min}$", as used herein, refers to the partial AUC at time 20 minutes, i.e., the area under the patient's plasma concentration-time curve from time zero to time 20 minutes.

The term "mean $AUC_{20min}$", as used herein, refers to the mean (arithmetic or geometric) $AUC_{20min}$ in a population.

The term "$AUC_{30min}$", as used herein, refers to the partial AUC at time 30 minutes, i.e., the area under the patient's plasma concentration-time curve from time zero to time 30 minutes.

The term "mean $AUC_{30min}$", as used herein, refers to the mean (arithmetic or geometric) $AUC_{30min}$ in a population.

The term "$AUC_{60min}$", as used herein, refers to the partial AUC at time 60 minutes, i.e., the area under the patient's plasma concentration-time curve from time zero to time 60 minutes.

The term "mean $AUC_{60min}$", as used herein, refers to the mean (arithmetic or geometric) $AUC_{60min}$ in a population.

The term "$AUC_{120min}$", as used herein, refers to the partial AUC at time 120 minutes, i.e., the area under the patient's plasma concentration-time curve from time zero to time 120 minutes.

The term "mean $AUC_{120min}$", as used herein, refers to the mean (arithmetic or geometric) $AUC_{120min}$ in a population.

The term "$C_{20}$", as used herein, refers to the concentration of analyte (i.e., propofol or fospropofol) in a patient's plasma at the time point 20 minutes following administration.

The term "mean $C_{20}$", as used herein, refers to the mean (arithmetic or geometric) $C_{20}$ in a population.

The term "$C_{30}$", as used herein, refers to the concentration of analyte (i.e., propofol or fospropofol) in a patient's plasma at the time point 30 minutes following administration.

The term "mean $C_{30}$", as used herein, refers to the mean (arithmetic or geometric) $C_{30}$ in a population.

The term "$C_{60}$", or "$C_{1hr}$", as used herein, refers to the concentration of analyte (i.e., propofol or fospropofol) in a patient's plasma at the time point 60 minutes following administration.

The term "mean $C_{60}$", as used herein, refers to the mean (arithmetic or geometric) $C_{60}$ in a population.

The term "$C_{120}$", or "$C_{2hr}$", as used herein, refers to the concentration of analyte (i.e., propofol or fospropofol) in patient's plasma at the time point 120 minutes (i.e., 2 hours) following administration.

The term "mean $C_{120}$" (or "mean $C_{2hr}$") as used herein, refers to the mean (arithmetic or geometric) $C_{120}$ (or "mean $C_{2hr}$") in a population.

The term "Tmax" as used herein, refers to the time interval from the administration of the first dose to the time at which Cmax occurs.

The term median Tmax refers to the median Tmax observed in a population.

The term "plasma concentration", as used herein, refers to the quantity of compound (e.g., propofol or fospropofol) per unit volume of plasma.

The term "mean concentration", as used herein, refers to the mean (arithmetic or geometric) plasma concentration in a population.

Two treatments (e.g. 2 formulations, male vs. female, etc.) are not different from one another (i.e., are "bioequivalent") if the 90% confidence interval of the ratio of a log-transformed exposure measure (AUC and/or $C_{max}$) falls completely within the range 80-125%.

If a pharmacokinetic parameter set forth herein (e.g., Ctau, Cmax, AUCtau, etc.) does not specify either "plasma" or "mean", then the term includes either plasma or mean.

Methods of Treating Migraine

In some aspects, the present disclosure is directed to methods of treating migraine in a patient in need thereof, comprising administering to said patient an effective amount of fospropofol, a pharmaceutically acceptable salt of fospropofol, or mixtures thereof, in one or more doses.

In other aspects, the present disclosure is directed to methods of treating migraine in a patient in need thereof, comprising administering to said patient a composition comprising an effective amount of fospropofol, a pharmaceutically acceptable salt of fospropofol, or mixtures thereof, in one or more doses.

In some aspects, the methods of the disclosure are directed to treating migraine.

In some embodiments, the patient's migraine is migraine with aura.

In other embodiments, the patient's migraine is migraine without aura.

In other embodiments, the patient's migraine is cluster headache.

In other embodiments, the patient's migraine is intractable migraine.

In some embodiments of the disclosed methods, the patient's migraine is refractory migraine.

Refractory migraine may fail to respond to one or more types of pharmacologic treatment. Examples of pharmacologic treatment to which refractory migraine may fail to respond include CGRP inhibitors (e.g., gepants, anti-CGRP antibodies), and triptans (e.g., sumatriptan (Imitrex), rizatriptan (Maxalt), almotriptan (Axert), naratriptan (Amerge), zolmitriptan (Zomig), frovatriptan (Frova) and eletriptan (Relpax)).

In some embodiments of the disclosed methods, the patient's refractory migraine may fail to respond to CGRP inhibitors, and is referred to as CGRP inhibitor-refractory migraine.

In some embodiments, the patient's CGRP-inhibitor refractory migraine fails to respond to gepant treatment, and is referred to as gepant-refractory migraine. In other embodiments, the patient's CGRP-inhibitor refractory migraine fails to respond to anti-CGRP antibodies, and is referred to as anti-CGRP antibody-refractory migraine.

In other embodiments of the disclosed methods, the patient's refractory migraine may fail to respond to triptans, and is referred to as triptan-refractory migraine.

In other embodiments of the disclosed methods, the patient's refractory migraine may fail to respond to NSAIDs and is referred to as NSAID-refractory migraine.

In other embodiments of the disclosed methods, the patient's refractory migraine may fail to respond to dihydroegotamine (DHE) and is referred to as DHE-refractory migraine.

In some aspects, the methods of the disclosure are directed to treating migraine in a patient in need thereof. The methods of the disclosure, therefore, are performed on patients suffering from migraine.

In some embodiments, the patient is a mammal.
In other embodiments, the patient is a human.
In some embodiments, the patient is female.
In other embodiments, the patient is male.
In some embodiments, the patient is 18 years of age or older.
In other embodiments, the patient is between 6 and 17 years of age.

In some embodiments, the patient was diagnosed with migraine at least one year prior to being administered forpropofol in accordance with the disclosed methods.

In some aspects, the methods of the disclosure comprise administering to the patient an effective amount of a propofol prodrug, a pharmaceutically acceptable salt of a propofol prodrug, or mixtures thereof.

Examples of propofol prodrugs can be found in, for example, U.S. Pat. No. 6,204,257; Kumpulainen, Hanna, et al. "Synthesis, in vitro and in vivo characterization of novel ethyl dioxy phosphate prodrug of propofol." *European journal of pharmaceutical sciences* 34.2-3 (2008): 110-1.17; and Baker, Max T., Mohamed Naguib, and David C. Warltier. "Propofol: the challenges of formulation." The *Journal of the American Society of Anesthesiologists* 103.4 (2005): 860-876.

In some aspects, the methods of the disclosure comprise administering to the patient an effective amount of fospropofol, a pharmaceutically acceptable salt of fospropofol, or mixtures thereof.

In other embodiments, the methods of the disclosure comprise administering to the patient an effective amount of a propofol prodrug, a pharmaceutically acceptable salt of a propofol prodrug, or mixtures thereof, wherein the propofol prodrug is sodium 2-(2-(2,6-diisopropylphenoxy)-2-oxoethoxy)acetate; (Azepan-1-ylcarbamoylmethyl)carbamic acid 2,6-diisopropylphenyl ester hydrochloride; (E)-3-(2,6-diisopropylphenoxy)acrylic acid; (O-[2-carboxyethyl]-propofol), (S)-2-amino-3-(2,6-diisopropylphenoxycarbonyloxy)-propanoic acid; (S)-2-amino-3-(2,6-diisopropylphenoxycarbonyloxy)-propanoic acid mesylate salt; (S)-2-amino-3-(2,6-diisopropylphenoxycarbonyloxy)-propanoic acid hydrochloride; {1-[3-(2,6-diisopropylphenoxy)-3-oxo-2(R)-fluoro-1-propyl]} phosphate monoester dipotassium salt; {1-[4-(2,6-diisopropylphenoxy)-4-oxo-2(R)-trifluoromethyl-1-butyl]} phosphate monoester dilithium salt; {1-[4-(2,6-diisopropylphenoxy)-4-oxo-3-(R)-3-trifluoromethyl-1-butyl]}phosphate monoester dilithium salt; {1-[4-(2,6-diisopropylphenoxy)-4-oxo-3-(R,S)-3-fluoro-1-butyl]} phosphate monoester dipotassium salt; {1-[4-(2,6-diisopropylphenoxy)-4-oxo-3-(S)-3-fluoro-1-butyl]} phosphate monoester disodium salt; {1-[6-(2,6-diisopropylphenoxy)-

6-oxo-5-(S)-difluoromethyl-1-hexyl]}phosphate diarginine salt; 1-((((2,6-diisopropylphenoxy)carbonyl)oxy)methyl)-3-(dimethylcarbamoyl)pyridin-1-ium iodide; 1-((((2,6-diisopropylphenoxy)carbonyl)oxy)methyl)-3-(hydroxycarbamoyl)pyridin-1-ium iodide; 1-((((2,6-diisopropylphenoxy)carbonyl)oxy)methyl)-3-(methoxycarbonyl)pyridin-1-ium iodide; 1-((((2,6-diisopropylphenoxy)carbonyl)oxy)methyl)-3-(methoxycarbonyl)pyridin-1-ium methanesulfonate; 1-((((2,6-diisopropylphenoxy)carbonyl) oxy)methyl)-3-(methylcarbamoyl)pyridin-1-ium tetrafluoroborate; 1-((((2,6-diisopropylphenoxy)carbonyl)oxy)methyl)-3-(methylcarbamoyl)pyridin-1-ium nitrate; 1-((((2, 6-diisopropylphenoxy)carbonyl)oxy)methyl)-3-(methylcarbamoyl)pyridin-1-ium chloride; 1-((((2,6-diisopropylphenoxy)carbonyl)oxy)methyl)-4-formyl-3-hydroxy-5-(hydroxymethyl)-2-methylpyridin-1-imidoxide; 1-(((2,6-diisopropylphenoxy)carbonyl)oxy)-N-((((2,6-diisopropylphenoxy)carbonyl)oxy)methyl)-N,N-dimethyl-methanaminium iodide; 1-(((2,6-diisopropylphenoxy)carbonyloxy)methyl)-3-(dimethylcarbamoyl)pyridinium mesylate; 1-(((2,6-diisopropylphenoxy)carbonyloxy)methyl)-3-(methylcarbamoyl)pyridinium mesylate; 1-(((2,6-diisopropylphenoxy)carbonyloxy)methyl)-3-(methylcarbamoyl)pyridinium iodide; 1-((2',6'-diisopropylphenoxy)carbonylamino)ethyl-2,3,4,6-tetra-O-acetyl-β-D-glucopyrano side; 1-((2',6'-diisopropylphenoxy)carbonylamino)ethyl-β-D-glucopyranoside; 1-((2',6'-diisopropylphenoxy)carbonyloxy)ethyl-2,3,4,6-tetra-O-acetyl-β-D-glucopyranoside; 1-((2',6'-diisopropylphenoxy)carbonyloxy)ethyl-2,3,4,6-tetra-O-acetyl-α-D-glucopyranoside; 1-((2',6'-diisopropylphenoxy)carbonyloxy)ethyl-hepta-O-acetyl-β-D-maltose; 1-((2',6'-diisopropylphenoxy)carbonyloxy)ethyl-α-D-glucopyranoside; 1-((2',6'-diisopropylphenoxy)carbonyloxy)ethyl-β-D-maltose; 1-((2',6'-diisopropylphenoxy)carbonyloxy)ethyl-β-n-glucopyranoside; 1-((2',6'-diisopropylphenoxy)carbonyloxy)propyl-2,3,4,6-tetra-O-acetyl-β-D-glucopyranoside; 1-((2',6'-diisopropylphenoxy)carbonyloxy)propyl-2,3,4,6-tetra-O-acetyl-α-D-glucopyranoside; 1-((2',6'-diisopropylphenoxy)carbonyloxy)propyl-hepta-O-acetyl-β-D-maltose; 1-((2',6'-diisopropylphenoxy)carbonyloxy)propyl-α-D-glucopyranoside; 1-((2',6'-diisopropylphenoxy)carbonyloxy)propyl-β-D-glucopyranoside; 1-((2',6'-diisopropylphenoxy)carbonyloxy)propyl-β-D-maltose; 1-Amino-2-[2,6-(diisopropyl)phenoxycarbonyloxy]ethane; 2-[2,6-(Diisopropyl)phenoxycarbonyloxy]ethyl (2S)-2-amino-3-hydroxypropionamide; 2-(((2,6-diisopropylphenoxy)carbonyl)oxy)-N-((((2,6-diisopropylphenoxy)carbonyl)oxy)methyl)-N,N-dimethylethan-1-aminiumiodide; 2-(((2,6-diisopropylphenoxy)carbonyl)oxy)-N,N,N-trimethylethan-1-aminium iodide; 2-(((2,6-diisopropylphenoxy)carbonyl)oxy)-N,N,N-trimethylethan-1-aminium methanesulfonate; 2-(2,6-diisopropylphenoxy)-2-hydroxyethylphosphate; 2-(2,6-diisopropylphenoxy)-3,4,5-trihydroxy tetrahydropyran-6-yl, dihydrogenphosphate; 2-(2,6-diisopropylphenxoy)-3,4,5-trihydroxytetrahydropyran-6-yl dihydrogen phosphate arginine; 2,6-(diisopropyl)phenyl 1-[((2S)-2-amino-(3R)-3-hydroxybutyryl)aminomethyl]-1-cyclohexane acetate; 2,6-(diisopropyl)phenyl 1-[((2S)-2-amino-3-hydroxypropionyl)aminomethyl]-1-cyclohexane acetate; 2,6-(diisopropyl)phenyl 1-[((2S)-2-amino-3-methylbutyryl)aminomethyl]-1-cyclohexane acetate; 2,6-(diisopropyl)phenyl 4-[(2S)-2,3-diaminopropionylamino]-3,3-dimethylbutanoate; 2,6-(diisopropyl)phenyl 4-[(2S)-2,6-diaminohexanoylamino]-3,3-dimethylbutanoate; 2,6-(Diisopropyl)phenyl 4-[(2S)-2-amino-(3R)-3-hydroxylbutyryl]aminobutanoate; 2,6-(diisopropyl)phenyl 4-[(2S)-2-amino-(3R)-3-hydroxybutyryl]amino-3,3-dimethylbutanoate; 2,6-(diisopropyl)phenyl 4-[(2S)-2-amino-(3R)-3-hydroxylbutyryl]aminobutanoate; 2,6-(diisopropyl)phenyl 4-[(2S)-2-amino-(4-hydroxyphenyl)propionylamino]-3,3-dimethylbutanoate; 2,6-(Diisopropyl)phenyl 4-[(2S)-2-amino-(indol-3-yl)propionylamino]-3,3-dimethylbutanoate; 2,6-(Diisopropyl)phenyl 4-[(2S)-2-amino-3-carbamoylpropionylamino]butanoate; 2,6-(Diisopropyl)phenyl 4-[(2S)-2-amino-3-hydroxypropionylamino]butanoate; 2,6-(diisopropyl)phenyl 4-[(2S)-2-amino-3-carbamoylpropionylamino]-3,3-dimethylbutanoate; 2,6-(diisopropyl)phenyl 4-[(2S)-2-amino-3-carbamoylpropionylamino]butanoate; 2,6-(diisopropyl)phenyl 4-[(2S)-2-amino-3-carboxypropionylamino]-3,3-dimethylbutanoate; 2,6-(diisopropyl)phenyl 4-[(2S)-2-amino-3-hydroxypropionylamino]-3,3-dimethylbutanoate; 2,6-(diisopropyl)phenyl 4-[(2S)-2-amino-3-hydroxypropionylamino]butanoate; 2,6-(Diisopropyl)phenyl 4-[(2S)-2-amino-3-hydroxypropionylamino]-3,3-dimethylbutanoate; 2,6-(diisopropyl)phenyl 4-[(2S)-2-amino-3-methylbutyrylamino]-3,3-dimethylbutanoate; 2,6-(diisopropyl)phenyl 4-[(2S)-2-amino-3-methylbutyrylamino]butanoate; 2,6-(diisopropyl)phenyl 4-[(2S)-2-amino-4-carboxybutyrylamino]-3,3-dimethylbutanoate; 2,6-(diisopropyl)phenyl 4-[(2S)-2-amino-4-carboxylbutyrylamino]butanoate; 2,6-(diisopropyl)phenyl 4-[(2S)-2-aminopropionylamino]-3,3-dimethylbutanoate; 2,6-(diisopropyl)phenyl 4-[(2S)-pyrrolidin-2-ylcarbonylamino]-3,3-dimethylbutanoate; 2,6-(diisopropyl)phenyl 4-[(2S)-pyrrolidin-2-ylcarbonylamino]butanoate; 2,6-(Diisopropyl)phenyl 4-[(2S)-pyrrolidin-2-ylcarbonylamino]-3,3-dimethylbutanoate; 2,6-(diisopropyl)phenyl 4-[aminomethylcarbonylamino]-3,3-dimethylbutanoate; 2,6-(Diisopropyl)phenyl 1-[((2S)-2-amino-(3R)-3-hydroxybutyryl)aminomethyl]-1-cyclohexane acetate; 2,6-(Diisopropyl)phenyl 1-[((2S)-2-amino-3-hydroxypropionyl)aminomethyl]-1-cyclohexane acetate; 2,6-(Diisopropyl)phenyl 1-[((2S)-2-amino-3-methylbutyryl)aminomethyl]-1-cyclohexane acetate; 2,6-diisopropylphenyl 4-((2-(2-methylpyrazolidin-1-yl)ethyl)amino)-4-oxobutanoate; 2,6-diisopropylphenyl 4-((2-(4,5-dihydro-1H-pyrazol-1-yl)ethyl)amino)-4-oxobutanoate; 2,6-diisopropylphenyl 4-((2-(4-ethylpiperazin-1-yl)ethyl)amino)-4-oxobutanoate; 2,6-diisopropylphenyl 4-((2-(4-methylpiperazin-1-yl)ethyl)amino)-4-oxobutanoate; 2,6-diisopropylphenyl 4-((2-morpholinoethyl)amino)-4-oxobutanoate; 2,6-Diisopropylphenyl 4-(2-(Tert-Butoxycarbonylamino)Propanoyloxy)Butanoate; 2,6-Diisopropylphenyl 4-(2-Aminoacetoxy) Butanoate Trifluoroacetic Acid Salt; 2,6-Diisopropylphenyl 4-(2-Aminopropanoyloxy)ButanoateHydrochloride; 2,6-Diisopropylphenyl 4-Hydroxybutanoate; 2,6-diisopropylphenyl 4-oxo-4-((2-(piperazin-1-yl)ethyl)amino)butanoate; 2,6-diisopropylphenyl 4-oxo-4-((2-(piperidin-1-yl)ethyl)amino)butanoate; 2,6-diisopropylphenyl 4-oxo-4-((2-(pyrazolidin-1-yl)ethyl)amino)butanoate; 2,6-diisopropylphenyl 4-oxo-4-((2-(pyrrolidin-1-yl)ethyl)amino)butanoate; 2,6-diisopropylphenyl 4-oxo-4-((2-thiomorpholinoethyl)amino)butanoate; 2-[2,6-(diisopropyl)phenoxycarbonylamino]ethyl (2S)-2-amino-3-carboxypropionamide; 2-[2,6-(diisopropyl)phenoxycarbonylamino]ethyl (2S)-2-amino-3-hydroxypropionamide; 2-[2,6-(diisopropyl)phenoxycarbonylamino]ethyl (2S)-2-amino-3-methylbutanoylamide; 2-[2,6-(diisopropyl)phenoxycarbonyloxy]ethyl (2S)-2,6-diaminohexanoylamide; 2-[2,6-(diisopropyl)phenoxycarbonyloxy]ethyl (2S)-2-amino-(4-hydroxyphenyl)propionamide; 2-[2,6-(Diisopropyl)phenoxycarbonyloxy]ethyl (2S)-2-amino-(4-hydroxyphenyl)propionamide; 2-[2,6-(diisopropyl)phenoxycarbonyloxy]ethyl (2S)-2-amino-3-carbamoylpropionate; 2-[2,6-(diisopropyl)phenoxycarbonyloxy]ethyl(2S)-2-amino-3-carbamoylpropionamide; 2-[2,6-(Diisopropyl) phenoxycarbonyloxy]ethanol; 1-Amino-2-[2,6-(diisopropyl) phenoxycarbonyloxy]ethane; 2-[2,6-(diisopropyl)phenoxycarbonyloxy]ethyl (2S)-2-amino-3-hydroxypropionate; 2-[2,6-(diisopropyl)phenoxycarbonyloxy]ethyl (2S)-2-amino-3-hydroxypropionamide; 2-[2,6-(diisopropyl)phenoxycarbonyloxy]ethyl glycinamide; 2-amino-3-(2,6-diisopropylphenoxycarbonyloxy)-propanoic acid mesylate; 2-amino-3-methyl-3-(2,6-diisopropyl-phenoxycarbonyloxy)-propanoic acid; 3-(((((2,6-diisopropylphenoxy)carbonyl) oxy)methyl)carbamoyl)-1-methylpyridin-1-ium iodide; 3-((2,6-diisopropylphenoxy)carbonyl)-1-((((2,6-diisopropylphenoxy)carbonyl)oxy)methyl)pyridin-1-ium methanesulfonate; 3-{[2-[2,6-Bis(isopropyl)phenoxycarbonyl]-benzoyl]amino}-propanoic acid; 3-{[2-[2,6-Bis(isopropyl)phenoxycarbonyloxy]-benzoyl]amino}-propanoic acid; 3-carbamoyl-1-((((2,6-diisopropyl-phenoxy)carbonyl)oxy)methyl)pyridin-1-ium iodide; 3-carbamoyl-1-(((2,6-diisopropylphenoxy)carbonyloxy)methyl)pyridinium mesylate; 3-carboxy-1-((((2,6-diisopropylphenoxy)carbonyl)oxy)methyl)pyridin-1-ium iodide; 3-carboxy-1-((((2,6-diisopropylphenoxy)carbonyl)oxy)methyl)pyridin-1-ium methanesulfonate; 4-[(2S)-2-amino-(3R)-3-hydroxybutyryl]amino-3,3-dimethylbutanoate; 4-[(2S)-2-amino-3-carbamoylpropionylamino]-3,3-dimethylbutanoate; 4-[(2S)-2-amino-4-carboxybutyrylamino]-3,3-dimethylbutanoate; 4-[(2S)-2-aminopropionylamino]-3,3-dimethylbutanoate; 2,6-(Diisopropyl)phenyl 4-[aminomethylcarbonylamino]-3,3-dimethylbutanoate; 2,6-(Diisopropyl)phenyl; arginine 2-(2,6-diisopropylphenoxy)-2-hydroxy ethylphosphate; arginine 2-(2,6-diisopropylphenoxy)-3,4,5-trihydroxy tetrahydropyran-6-yl dihydrogen phosphate; Boc-Asp(OPropofol)-OBzl; Boc-Asp(OPropofol)-OH; Boc-Glu(OPropofol)-OBzl; Boc-Glu(OPropofol)-OH; di[propofol 5-carboxyl-2(S)-fluorohexanoate] zinc salt; di[propofol 5-carboxyl-2-(S)-fluorohexanoate] zinc salt; di[propofol 7-carboxyl-2(R,S)-fluorocaprylate] calcium salt; di[propofol 7-carboxyl-2-(R,S)-fluorocaprylate] calcium salt; disodium lauryl-iminodipropionate2-(2,6-diisopropylphenoxy)tetrahydropyran-6-yl dihydrogen phosphate; disodium lauryl-iminodipropionate-2-(2,6-diisopropylphenoxy)tetrahydropyran-6-yl dihydrogenphosphate; H-Abu-Asp(OPropofol)-OH; H-Abu-Thr(γ-OC(O)OPropofol)-OH Hydrochloride; H-Aib-OCH$_2$OPropofol; H-Ala-Asn-OPropofol; H-Ala-Asp(OCH$_2$OPropofol)-OH; H-Ala-Asp(OPropofol)-OH; H-Ala-Cys(β-SC(O)OPropofol)-OH; H-Ala-Glu(OPropofol)-OH; H-Ala-OPropofol Hydrochloride; H-Ala-Phe-OPropofol; H-Ala-Ser(β-OC(O)OPropofol)-OH; H-Ala-Thr(β-OC(O)OPropofol)-OH; H-Ala-Thr(γ-OC(O)OPropofol)-OH Hydrochloride; H-Ala-Tyr-OPropofol; H-Arg-Asp(OPropofol)-OH; H-Arg-Phe-OPropofol; H-Arg-Thr(γ-OC(O)OPropofol)-OH Tris-Hydrochloride; H-Asn-Asp(OCH$_2$OPropofol)-OH; H-Asn-Asp(OPropofol)-OH; H-Asn-D-Thr(γ-OC(O)OPropofol)-OH; H-Asn-Glu(OPropofol)-OH; H-Asn-OPropofol Hydrochloride; H-Asn-Thr(β-OC(O)OPropofol)-OH; H-Asn-Thr(γ-OC(O)OPropofol)-OH Hydrochloride; H-Asn-Tyr-OPropofol; H-Asp(OCH$_2$OPropofol)-Arg-OH; H-Asp(OCH$_2$OPropofol)-Asp-OH; H-Asp(OCH$_2$OPropofol)-Lys-OH; H-Asp(OCH$_2$OPropofol)-OH; H-Asp(OCH$_2$OPropofol)-Ser-OH; H-Asp(OPropofol)-Ala-OH; H-Asp(OPropofol)-Asp-OH; H-Asp(OPropofol)-Gln-OH; H-Asp(OPropofol)-Glu-OH; H-Asp(OPropofol)-Gly-OH; H-Asp(OPropofol)-Ile-OH; H-Asp(OPropofol)-Leu-OH; H-Asp(OPropofol)-Met-OH; H-Asp(OPropofol)-OBzl; H-Asp(OPropofol)-OH; H-Asp(OPropofol)-O-Trityl; H-Asp(OPropofol)-Phe-OH; H-Asp(OPropofol)-Pro-OH; H-Asp(OPropofol)-Ser-OH; H-Asp(OPropofol)-Val-OH; H-Asp-Ala-OPropofol; H-Asp-Asn-OPropofol; H-Asp-Asp(OCH$_2$OPropofol)-OH; H-Asp-Asp(OPropofol)-OH; H-Asp-OCH$_2$OPropofol; H-Asp-Phe-OPropofol; H-Asp-Ser(β-OC(O)OPropofol)-OH; H-Asp-Tyr-OPropofol; H-Cys-Asp(OPropofol)-OH; H-Dap(β-NHC(O)OPropofol)-Ala-OH; H-Dap-Ala-OPropofol; H-Dap-Asn-OPropofol; H-Dap-Thr(γ-OC(O)OPropofol)-OH Bis-Hydrochloride; H-Dap-Tyr-OPropofol; H-D-Asn-Thr(γ-OC(O)OPropofol)-OH; H-D-Lys-Thr(γ-OC(O)OPropofol)-OH Bis-Hydrochloride; H-D-Ser-Thr(γ-OC(O)OPropofol)-OH Hydrochloride; H-Gln-Asn-OPropofol; H-Gln-Asp(OCH$_2$OPropofol)-OH; H-Gln-OPropofol Hydrochloride; H-Gln-Phe-OPropofol; H-Glu(OPropofol)-Ala-OH; H-Glu(OPropofol)-Arg-OH; H-Glu(OPropofol)-Asp-OH; H-Glu(OPropofol)-Gln-OH; H-Glu(OPropofol)-Glu-OH; H-Glu(OPropofol)-Gly-OH; H-Glu(OPropofol)-Ile-OH; H-Glu(OPropofol)-Leu-OH; H-Glu(OPropofol)-Lys-OH; H-Glu(OPropofol)-Met-OH; H-Glu(OPropofol)-OBzl; H-Glu(OPropofol)-OH; H-Glu(OPropofol)-Phe-OH; H-Glu(OPropofol)-Ser-OH; H-Glu(OPropofol)-Val-OH; H-Glu-Asp(OCH$_2$OPropofol)-OH; H-Glu-Phe-OPropofol; H-Glu-Tyr-OPropofol; H-Gly-Asn-OPropofol; H-Gly-Asp(OCH$_2$OPropofol)-OH; H-Gly-OPropofol Hydrochloride; H-Gly-Phe-OPropofol; H-Gly-Thr(γ-OC(O)OPropofol)-OH; H-Gly-Tyr-OPropofol; H-His-Asp(OCH$_2$OPropofol)-OH; H-His-OPropofol; H-His-Phe-OPropofol; H-His-Thr(γ-OC(O)OPropofol)-OHBis-Hydrochloride; H-Leu-Asp(OPropofol)-OH; H-Leu-D-Thr(γ-OC(O)OPropofol)-OH; H-Leu-Glu(OPropofol)-OH; H-Leu-Thr(γ-OC(O)OPropofol)-OH Hydrochloride; H-Lys-Asp(OPropofol)-OH; H-Lys-Cys(β-SC(O)OPropofol)-OH; H-Lys-Glu(OPropofol)-OH; H-Lys-OPropofol Hydrochloride; H-Lys-Ser(β-OC(O)OPropofol)-OH; H-Lys-Thr(p OC(O)OPropofol)-OH; H-Lys-Thr(γ-OC(O)OPropofol)-OH Bis-Hydrochloride; H-Lys-Tyr-OPropofol; H-Met-Asp(OPropofol)-OH; H-Met-OPropofol; H-Met-Thr(γ-OC(O)OPropofol)-OHHydrochloride; H-NVal-Asp(OPropofol)-OH; H-Orn-Asp(OPropofol)-OH; H-Orn-Thr(γ-OC(O)OPropofol)-OHBis-Hydrochloride; H-Phe-Asp(OPropofol)-OH; H-Phe-OPropofol; H-Pro-OPropofol Hydrochloride; H-Pro-Phe-OPropofol; H-Pro-Thr(γ-OC(O)OPropofol)-OH Hydrochloride; H-Pro-Tyr-OPropofol; H-Sar-Asp(OPropofol)-OH; H-Ser-Asn-OPropofol; H-Ser-Asp(OCH$_2$OPropofol)-OH; H-Ser-Cys(β-SC(O)OPropofol)-OH; H-Ser-D-Thr(γ-OC(O)OPropofol)-OH; H-Ser-OPropofol; H-Ser-Phe-OPropofol; H-Ser-Ser(β-OC(O)OPropofol)-OH; H-Ser-Thr(β-OC(O)OPropofol)-OH; H-Ser-Thr(γOC(O)OPropofol)-OH Hydrochloride; H-Ser-Tyr-OPropofol; H-Thr-Asp(OCH$_2$OPropofol)-OH; H-Thr-OPropofol Hydrochloride; H-Thr-Phe-OPropofol; H-Trp-Asp(OCH$_2$OPropofol)-OH; H-Trp-Phe-OPropofol; H-Tyr-Asn-OPropofol; H-Tyr-Asp(OCH$_2$OPropofol)-OH; H-Tyr-Asp(OPropofol)-OH; H-Tyr-OPropofol Hydrochloride; H-Tyr-Phe-OPropofol; H-Tyr-Ser(β-OC(O)OPropofol)-OH; H-Val-Ala-OPropofol; H-Val-Asn-OPropofol; H-Val-OCH$_2$OPropofol; H-Val-OPropofol; H-Val-Phe-OPropofol; H-Val-Ser-OPropofol; H-Val-Thr(β-OC(O)OPropofol)-OH; H-Val-Thr(γ-OC(O)OPropofol)-OH Hydrochloride H-Val-Tyr-OPropofol; 2,6-(Diisopropyl)phenyl hydroxybutyrate disodium phosphate; 2,6-(Diisopropyl)phenyl hydroxyvalerate phosphate disodium salt; H-β-Ala-Asp(OPropofol)-OH; H—O-Ala-Thr(β-OC(O)OPropofol)-OH Hydrochloride; 1-Amino-2-[2,6-(diisopropyl)phenoxycarbonyloxy]ethane; N-(2-Dibutylaminoethyl)-succinamic acid 2,6-diisopropyl-phenyl ester; N-(2-Dibutylaminoethyl)-succinamic acid 2,6-diisopropyl-phenyl ester hydrochloride;

N-(2-Diethylamino-ethyl)-succinamic acid 2,6-diisopropylphenyl ester Hydrochloride; N-(2-Diethylammoethyl)-succinamic acid 2,6-diisopropylphenyl ester; N-(2-Diisopropylaminoethyl)-succinamic acid 2,6-diisopropyl-phenyl ester; N-(2-Diisopropylamino-ethyl)-succinamic acid 2,6-diisopropylphenyl ester Hydrochloride; N-(2-Dimethylaminoethyl)-succinamic acid 2,6-diisopropyl-phenyl ester Hydrochloride; N-(2-Dimethylaminoethyl)-succinamic acid 2,6-diisopropyl-phenyl ester; N-(2-Morpholin-4-yl-ethyl)-succinamic acid 2,6-diisopropylphenyl ester; N-(2-Morpholin-4-yl-ethyl)-succinamic acid 2,6-diisopropylphenyl ester Hydrochloride; N-(2-Piperidin-1-yl-ethyl)-succinamic acid 2,6-diisopropylphenyl ester; N-(2-Piperidin-1-yl-ethyl)-succinamic acid 2,6-diisopropylphenyl ester hydrochloride; N-(2-Pyrrolidin-1-yl-ethyl)-succinamic acid 2,6-diisopropylphenyl ester; N-(2-Pyrrolidin-1-yl-ethyl)-succinamic acid 2,6-diisopropylphenyl ester hydrochloride; O-[t-butoxycarbonyl]-propofol); propofol 2-carboxyl-2(S)-fluoropropionate sodium salt; propofol 3-(N,N-diethyl) amino-2-(R,S)-fluoropropionate hydrochloride; propofol 3-(N-isopropyl)amino-2-(R,S)-2-monofluoromethylpropionate methanesulfonate; propofol 3-(N-isopropyl)amino-2 (R,S)-2-monofluoromethylpropionate methanesulfonate; propofol 3-(pyrrolidin-1-yl)-2-(S)-trifluoromethyl propionate hydrochloride; propofol 3-(pyrrolidin-1-yl)-2-(S)-trifluoromethylpropionate hydrochloride; propofol 3-carboxyl-2(R)-fluorobutyrate sodium salt; propofol 3-N-isopropylamino-2-(R,S)-fluoropropionate hydrochloride; propofol 3-N-methyl-N-cyclohexylamino-2-(R,S)-fluoropropionate hydrochloride; propofol 3-N-methyl-N-cyclohexylamino-2-(R,S)-fluoropropionate hydrochloride; propofol 3-phosphoryl-2-(R,S)-fluoropropionate zinc salt; propofol 4-(aziridin-1-yl)-2-(S)-2-fluorobutyrate hydrochloride; propofol 4-(N,N-dimethyl)amino-2-(R)-2-trifluoromethylbutyrate hydrochloride; propofol 4-(N,N-dimethyl) amino-2-(R)-fluorobutyrate hydrochloride; propofol 4-(N, N-dimethyl)amino-2-(R)-trifluoromethylbutyrate hydrochloride; propofol 4-(N,N-dimethyl)amino-2-(R,S)-fluorobutyrate hydrochloride; propofol 4-(N-cyclopropyl-N-methyl)amino-2-(R)-difluoromethylbutyratehydrochloride; propofol 4-(N-methyl-N-benzyl)amino-2-(R,S)-trifluoromethylbutyrate hydrochloride; propofol 4-(N-methyl-N-ethyl) amino-2-(R,S)-2-fluorobutyrate hydrochloride; propofol 4-(N-methyl-N-isopropyl)amino-2-(R,S)-fluorobutyrate methanesulfonate; propofol 4-(pyrrolidin-1-yl)-2-(R)-2-fluorobutyrate hydrochloride; propofol 4-carboxyl-2-(R)-2-trifluoromethylvalerate lithium salt; propofol 4-carboxyl-2 (R)-fluorobutyrate sodium salt; propofol 4-carboxyl-2-(R, S)-difluoromethylvalerate potassium salt; propofol 4-carboxyl-2(R,S)-fluorovalerate sodium salt; propofol 4-carboxyl-2-(S)-fluorovalerate potassium salt; propofol 4-carboxyl-2-(S)-fluorovalerate potassium salt; propofol 4-carboxyl-2-(S)-trifluoromethylbutyrate ammonium salt; propofol 4-N-(aziridin-1-yl)-2(S)-2-fluorobutyrate hydrochloride; propofol 4-N-methyl-N-benzylamino-2-(R)-fluorobutyrate hydrochloride; propofol 4-phosphoryl-2-(R)-fluorobutyrate disodium salt; propofol 4-phosphoryl-2-(R, S)-fluorobutyrate calcium salt; propofol 5-(N-methyl-N-benzyl)amino-2-(S)-2-fluorovalerate hydrochloride; propofol 5-carboxyl-2(R,S)-difluoromethylvalerate potassium salt; propofol 5-N-cyclopentylamino-2,2-difluorovalerate hydrochloride; propofol 5-phosphoryl-2-(S)-fluorovalerate zinc salt; propofol 6-(N,N-dimethyl)amino-2-(R)-fluorovaleratehydrochloride; Propofol Hemisuccinate; propofol hydroxybutyrate; propofol hydroxyvalerate; propofol 6-(N,N-dimethyl)amino-2-(R)-fluorovaleratehydrochloride; propofol-2-(R)-fluoropropionate monoester sodium salt; propofol-2-(R,S)-fluorobutyrate monoester sodium salt; propofol-2-(R,S)-fluoropentanoate monoester sodium salt; (S)-2-amino-3-(2,6-diisopropylphenoxycarbonyloxy)-propanoic acid mesylate; Sodium 4-(2,6-Diisopropylphenoxy)-4-Oxobutyl Phosphate; 2-(2,6-diisopropylphenoxy)-tetrahydropyran-6-yl dihydrogen phosphate arginine; tri[propofol 3-phosphoryl-2-(R,S)-2-monofluoromethylpropionate] dialuminum salt; tri[propofol 8-carboxyl-2-(R,S)-monofluoromethylpelargonate] aluminum salt; Succinic Acid Mono-Propofol Ester; Propofol to Maltotrionic Acid; Propofol to Glucuronic Acid; Propofol to Gluconic Acid; Propofol to Modified Glucose; BOC-protected 1-deoxy-1-hydrazinoglucitol; 2-amino-3-methyl-3-(2,6-diisopropylphenoxycarbonyloxy)-propanoic acid; 2-amino-3-(2,6-diisopropyl-phenoxycarbonyloxy)-propanoic acid; 1-(2,6-diisopropylphenoxy)ethyl dihydrogen phosphate; Mono (propofol) phosphate; Di(propofol) phosphate; Carboxylic hemiesters of propofol; hemisuccinate ester of propofol; hemiglutarate ester of propofol; hemiadipate ester of propofol.; (2',6'-Diisopropylphenyl 4-(2-trimethylammoniumethyloxy) phosphonobutyrate); (2',6'-Diisopropylphenyl 3-ortho (O-trimethylammonium ethylphosphonooxy)-1-propionate); (4-(2,6-diisopropylphenoxy)-4-oxobutanoyl) glycine; 4-(4-(2,6-diisopropylphenoxy)-4-oxobutanamido) butanoic acid; HX0507; HX0969w; HX0892; HX0891; propofol methoxymethylphosphonic prodrug; propofol hemiglutarate; propofol hemiadipate; monopropofol phosphate; dipropofol phosphate; 1-(((2,6-diisopropylphenoxy) carbonyloxy)methyl)-3-(dimethylcarbamoyl)pyridinium mesylate; 1-(((2,6-diisopropylphenoxy)carbonyloxy) methyl)-3-(methylcarbamoyl)pyridinium mesylate; 3-carbamoyl-1-(((2,6-diisopropylphenoxy)carbonyloxy)methyl) pyridinium mesylate; 1-(((2,6-diisopropylphenoxy) carbonyloxy)methyl)-3-(methylcarbamoyl)pyridinium iodide; 1-((((2,6-diisopropylphenoxy)carbonyl)oxy) methyl)-3-(dimethylcarbamoyl)pyridin-1-ium methanesulfonate; 1-((((2,6-diisopropylphenoxy)carbonyl)oxy) methyl)-3-(dimethylcarbamoyl)pyridin-1-ium iodide; 1-((((2,6-diisopropylphenoxy)carbonyl)oxy)methyl)-3-(methoxycarbonyl)pyridin-1-ium iodide; 3-carboxy-1-((((2, 6-diisopropylphenoxy)carbonyl)oxy)methyl)pyridin-1-ium iodide; 2-(((2,6-diisopropylphenoxy)carbonyl)oxy)-N,N,N-trimethylethan-1-aminiumiodide; 2-(((2,6-diisopropylphenoxy)carbonyl)oxy)-N,N-dimethylethan-1-aminium chloride; 1-((((2,6-diisopropylphenoxy)carbonyl)oxy)methyl)-3-(hydroxycarbamoyl)pyridin-1-ium iodide; 3-(((((2,6-diisopropylphenoxy)carbonyl)oxy)methyl)carbamoyl)-1-methylpyridin-1-ium iodide; 1-(((2,6-diisopropylphenoxy) carbonyl)oxy)-N-((((2,6-diisopropylphenoxy)carbonyl)oxy) methyl)-N,N-dimethylmethanaminiumiodide; 2-(((2,6-diisopropylphenoxy)carbonyl)oxy)-N-((((2,6-diisopropylphenoxy)carbonyl)oxy)methyl)-N,N-dimethylethan-1-aminiumiodide; 1-((((2,6-diisopropylphenoxy)carbonyl) oxy)methyl)-4-formyl-3-hydroxy-5-(hydroxymethyl)-2-methylpyridin-1-ium iodide; 3-((2,6-diisopropylphenoxy) carbonyl)-1-((((2,6-diisopropylphenoxy)carbonyl)oxy) methyl)pyridin-1-ium methanesulfonate; 2-(((2,6-diisopropylphenoxy)carbonyl)oxy)-N,N,N-trimethylethan-1-aminium methanesulfonate; 3-carbamoyl-1-((((2,6-diisopropylphenoxy)carbonyl)oxy)methy)pyridin-1-ium bromide; 3-carbamoyl-1-((((2,6-diisopropylphenoxy)carbonyl)oxy)methyl)pyridin-1-ium chloride; 1-((((2,6-diisopropylphenoxy)carbonyl)oxy)methyl)-3-(methylcarbamoyl) pyridin-1-ium tetrafluoroborate; 1-((((2,6-diisopropylphenoxy)carbonyl)oxy)methyl)-3-(methylcarbamoyl) pyridin-1-ium nitrate; 1-((((2,6-diisopropylphenoxy)carbonyl)oxy)methyl)-3-(methylcarbamoyl)pyridin-1-ium chloride; 1-((((2,6-diisopropylphenoxy)carbonyl)oxy)methyl)-3-(methoxycarbonyl)pyridin-1-ium methanesulfonate; or 3-carboxy-1-((((2,6-diisopropylphenoxy)carbonyl)oxy)methyl)pyridin-1-ium methanesulfonate.

In some embodiments, the administering is oral.
In some embodiments, the administering is peroral.
In other embodiments, the administering is subcutaneous.
In other embodiments, the administering is intramuscular.
In other embodiments, the administering is intravenous.
In other embodiments, the administering is rectal.

In the methods of the disclosure, the patient is administered an effective amount of fospropofol, a pharmaceutically acceptable salt of fospropofol, or mixtures thereof.

In some embodiments of the methods of the disclosure, the patient is administered an effective amount of fospropofol.

In other embodiments, the patient is administered an effective amount of a pharmaceutically acceptable salt of fospropofol.

In some embodiments of the methods, the pharmaceutically acceptable salt of fospropofol is the disodium salt, i.e., fospropofol disodium, having the structure:

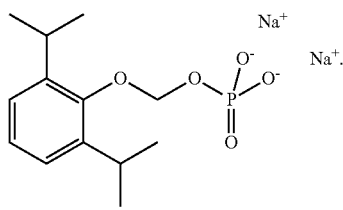 [SMILES: CC(C)c1cccc(C(C)C)c1OCOP(=O)([O-])[O-] ; [Na+]]

In some embodiments, the patient is administered an effective amount of a mixture of fospropofol and a pharmaceutically acceptable salt thereof. Thus, in some embodiments, the patient is administered an effective amount of fospropofol and fospropofol disodium.

In other embodiments, the patient is administered an effective amount of a mixture of pharmaceutically acceptable salts. In some embodiments, the patient is administered an effective amount of a mixture of fospropofol disodium and a second pharmaceutically acceptable fospropofol salt.

In some aspects of the methods of the disclosure, the patient is administered an effective amount of fospropofol, a pharmaceutically acceptable salt of fospropofol, or mixtures thereof.

In some embodiments, the effective amount of fospropofol, a pharmaceutically acceptable salt of fospropofol, or mixtures thereof, is an amount of 50-4800 mg (on a fospropofol basis), for example, an amount that is about (i.e., the specified number±10%) any one of 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, 2050 mg, 3100 mg, 3150 mg, 3200 mg, 3250 mg, 3300 mg, 3350 mg, 3400 mg, 3450 mg, 3500 mg, 3550 mg, 3600 mg, 3650 mg, 3700 mg, 3750 mg, 3800 mg, 3850 mg, 3900 mg, 3950 mg, 4000 mg, 4050 mg, 4100 mg, 4150 mg, 4200 mg, 4250 mg, 4300 mg, 4350 mg, 4400 mg, 4450 mg, 4500 mg, 4550 mg, 4600 mg, 4650 mg, 4700 mg, 4750 mg, or 4800 mg.

In some embodiments, the effective amount of fospropofol, a pharmaceutically acceptable salt of fospropofol, or mixtures thereof, is an amount of 50-1000 mg (on a fospropofol basis), for example, an amount that is about (i.e., the specified number±10%) any one of 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg.

In some embodiments, the effective amount of fospropofol, a pharmaceutically acceptable salt of fospropofol, or mixtures thereof, is an amount of 50-750 mg (on a fospropofol basis), for example, an amount that is about (i.e., the specified number±10%) any one of 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, or 750 mg.

In some embodiments, the effective amount of fospropofol, a pharmaceutically acceptable salt of fospropofol, or mixtures thereof, is an amount of 75-1500 mg (on a fospropofol basis), for example, an amount that is about (i.e., the specified number±10%) any one of 75 mg, 150 mg, 225 mg, 300 mg, 375 mg, 450 mg, 525 mg, 600 mg, 675 mg, 750 mg, 825 mg, 900 mg, 975 mg, 1050 mg, 1125 mg, 1200 mg, 1275 mg, 1350 mg, 1425 mg, or 1500 mg.

In some embodiments, the effective amount of fospropofol, a pharmaceutically acceptable salt of fospropofol, or mixtures thereof, is 100-4800 mg (on a fospropofol basis), for example, an amount that is about (i.e., the specified number±10%) any one of 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, 2050 mg, 3100 mg, 3150 mg, 3200 mg, 3250 mg, 3300 mg, 3350 mg, 3400 mg, 3450 mg, 3500 mg, 3550 mg, 3600 mg, 3650 mg, 3700 mg, 3750 mg, 3800 mg, 3850 mg, 3900 mg, 3950 mg, 4000 mg, 4050 mg, 4100 mg, 4150 mg, 4200 mg, 4250 mg, 4300 mg, 4350 mg, 4400 mg, 4450 mg, 4500 mg, 4550 mg, 4600 mg, 4650 mg, 4700 mg, 4750 mg, or 4800 mg.

In some embodiments, the effective amount of fospropofol, a pharmaceutically acceptable salt of fospropofol, or mixtures thereof, is 100-3600 mg (on a fospropofol basis), for example, an amount that is about (i.e., the specified number±10%) any one of 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, 2050 mg, 3100 mg, 3150 mg, 3200 mg, 3250 mg, 3300 mg, 3350 mg, 3400 mg, 3450 mg, 3500 mg, 3550 mg, or 3600 mg.

In some embodiments, the effective amount of fospropofol, a pharmaceutically acceptable salt of fospropofol, or mixtures thereof, is 100-3200 mg (on a fospropofol basis), for example, an amount that is about (i.e., the specified number±10%) any one of 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, 2050 mg, 3100 mg, 3150 mg, or 3200 mg.

In some embodiments, the effective amount of fospropofol, a pharmaceutically acceptable salt of fospropofol, or mixtures thereof, is 200-2400 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, or 2400 mg.

In some embodiments, the effective amount of fospropofol, a pharmaceutically acceptable salt of fospropofol, or mixtures thereof, is 200-2300 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, or 2300 mg.

In some embodiments, the effective amount of fospropofol, a pharmaceutically acceptable salt of fospropofol, or mixtures thereof, is 200-2200 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, or 2200 mg.

In some embodiments, the effective amount of fospropofol, a pharmaceutically acceptable salt of fospropofol, or mixtures thereof, is 200-2100 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, or 2100 mg.

In some embodiments, the effective amount of fospropofol, a pharmaceutically acceptable salt of fospropofol, or mixtures thereof, is 200-2000 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg.

In some embodiments, the effective amount of fospropofol, a pharmaceutically acceptable salt of fospropofol, or mixtures thereof, is 200-1900 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, or 1900 mg.

In some embodiments, the effective amount of fospropofol, a pharmaceutically acceptable salt of fospropofol, or mixtures thereof, is 200-1800 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, or 1800 mg.

In some embodiments, the effective amount of fospropofol, a pharmaceutically acceptable salt of fospropofol, or mixtures thereof, is 200-1700 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, or 1700 mg.

In some embodiments, the effective amount of fospropofol, a pharmaceutically acceptable salt of fospropofol, or mixtures thereof, is 200-1600 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, or 1600 mg.

In some embodiments, the effective amount of fospropofol, a pharmaceutically acceptable salt of fospropofol, or mixtures thereof, is 200-1600 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, or 1600 mg.

In some embodiments, the effective amount of fospropofol, a pharmaceutically acceptable salt of fospropofol, or mixtures thereof, is 200-1500 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, or 1500 mg.

In some embodiments, the effective amount of fospropofol, a pharmaceutically acceptable salt of fospropofol, or mixtures thereof, is 200-1400 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, or 1400 mg.

In some embodiments, the effective amount of fospropofol, a pharmaceutically acceptable salt of fospropofol, or mixtures thereof, is 200-1300 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, or 1300 mg.

In some embodiments, the effective amount of fospropofol, a pharmaceutically acceptable salt of fospropofol, or mixtures thereof, is 200-1200 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, or 1200 mg.

In some embodiments, the effective amount of fospropofol, a pharmaceutically acceptable salt of fospropofol, or mixtures thereof, is 200-1100 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, or 1100 mg.

In some embodiments, the effective amount of fospropofol, a pharmaceutically acceptable salt of fospropofol, or mixtures thereof, is 200-1000 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg.

In some embodiments, the effective amount of fospropofol, a pharmaceutically acceptable salt of fospropofol, or mixtures thereof, is 200-900 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, or 900 mg.

In some embodiments, the effective amount of fospropofol, a pharmaceutically acceptable salt of fospropofol, or mixtures thereof, is 200-800 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, or 800 mg.

In some embodiments, the effective amount of fospropofol, a pharmaceutically acceptable salt of fospropofol, or mixtures thereof, is 200-700 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, or 700 mg.

In some embodiments, the effective amount of fospropofol, a pharmaceutically acceptable salt of fospropofol, or mixtures thereof, is 200-600 mg (on a fospropofol basis), for example, an amount that is about (i.e., the specified number±10%) any one of 200 mg, 250 mg, 300 mg, 350 mg, 400 mg, 450 mg, 500 mg, 550 mg, or 600 mg.

In some embodiments, the effective amount of fospropofol, a pharmaceutically acceptable salt of fospropofol, or mixtures thereof, is 200-500 mg (on a fospropofol basis), for example, an amount that is about (i.e., the specified number±10%) any one of 200 mg, 250 mg, 300 mg, 350 mg, 400 mg, 450 mg, or 500 mg.

In some embodiments, the effective amount of fospropofol, a pharmaceutically acceptable salt of fospropofol, or mixtures thereof, is 200-400 mg (on a fospropofol basis), for example, an amount that is about (i.e., the specified number±10%) any one of 200 mg, 250 mg, 300 mg, 350 mg, or 400 mg.

In some embodiments, the effective amount of fospropofol, a pharmaceutically acceptable salt of fospropofol, or mixtures thereof, is 200-300 mg (on a fospropofol basis), for example, an amount that is about (i.e., the specified number±10%) any one of 200 mg, 250 mg, or 300 mg.

In some embodiments, the effective amount of fospropofol, a pharmaceutically acceptable salt of fospropofol, or mixtures thereof, is 400-2400 mg (on a fospropofol basis), for example, an amount that is about (i.e., the specified number±10%) any one of 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, or 2400 mg.

In some embodiments, the effective amount of fospropofol, a pharmaceutically acceptable salt of fospropofol, or mixtures thereof, is 400-2000 mg (on a fospropofol basis), for example, an amount that is about (i.e., the specified number±10%) any one of 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg.

In some embodiments, the effective amount of fospropofol, a pharmaceutically acceptable salt of fospropofol, or mixtures thereof, is 400-1600 mg (on a fospropofol basis), for example, an amount that is about (i.e., the specified number±10%) any one of 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, or 1600 mg.

In some embodiments, the effective amount of fospropofol, a pharmaceutically acceptable salt of fospropofol, or mixtures thereof, is 400-1200 mg (on a fospropofol basis), for example, an amount that is about (i.e., the specified number±10%) any one of 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, or 1200 mg.

In some embodiments, the effective amount of fospropofol, a pharmaceutically acceptable salt of fospropofol, or mixtures thereof, is 400-1200 mg (on a fospropofol basis), for example, an amount that is about (i.e., the specified number±10%) any one of 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, or 1200 mg.

In some embodiments, the effective amount of fospropofol, a pharmaceutically acceptable salt of fospropofol, or mixtures thereof, is 400-1000 mg (on a fospropofol basis), for example, an amount that is about (i.e., the specified number±10%) any one of 400 mg, 450 mg, 500 mg, 550 mg, 600 mg, 650 mg, 700 mg, 750 mg, 800 mg, 850 mg, 900 mg, 950 mg, or 1000 mg.

In some embodiments, the effective amount of fospropofol, a pharmaceutically acceptable salt of fospropofol, or mixtures thereof, is 400-800 mg (on a fospropofol basis), for example, an amount that is about (i.e., the specified number±10%) any one of 400 mg, 450 mg, 500 mg, 550 mg, 600 mg, 650 mg, 700 mg, 750 mg, or 800 mg.

In some embodiments, the effective amount of fospropofol, a pharmaceutically acceptable salt of fospropofol, or mixtures thereof, is 400-600 mg (on a fospropofol basis), for example, an amount that is about (i.e., the specified number±10%) any one of 400 mg, 450 mg, 500 mg, 550 mg, or 600 mg.

In some embodiments, the effective amount of fospropofol, a pharmaceutically acceptable salt of fospropofol, or mixtures thereof, is 600-1200 mg (on a fospropofol basis), for example, an amount that is about (i.e., the specified number±10%) any one of 600 mg, 650 mg, 700 mg, 750 mg, 800 mg, 850 mg, 900 mg, 950 mg, 1000 mg, 1050 mg, 1100 mg, 1150 mg, or 1200 mg.

In some embodiments, the effective amount of fospropofol, a pharmaceutically acceptable salt of fospropofol, or mixtures thereof, is 800-1200 mg (on a fospropofol basis), for example, an amount that is about (i.e., the specified number±10%) any one of 800 mg, 850 mg, 900 mg, 950 mg, 1000 mg, 1050 mg, 1100 mg, 1150 mg, or 1200 mg.

In some embodiments, the effective amount of fospropofol, a pharmaceutically acceptable salt of fospropofol, or mixtures thereof, is 1000-2000 mg (on a fospropofol basis), for example, an amount that is about (i.e., the specified number±10%) any one of 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg.

In some embodiments, the effective amount of fospropofol, a pharmaceutically acceptable salt of fospropofol, or mixtures thereof, is 1000-1600 mg (on a fospropofol basis), for example, an amount that is about (i.e., the specified number±10%) any one of 1000 mg, 1050 mg, 1100 mg, 1150 mg, 1200 mg, 1250 mg, 1300 mg, 1350 mg, 1400 mg, 1450 mg, 1500 mg, 1550 mg, or 1600 mg.

In some embodiments, the effective amount of fospropofol, a pharmaceutically acceptable salt of fospropofol, or mixtures thereof, is 1200-2000 mg (on a fospropofol basis), for example, an amount that is about (i.e., the specified number±10%) any one of 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg.

In some embodiments, the effective amount of fospropofol, a pharmaceutically acceptable salt of fospropofol, or mixtures thereof, is 1200-1800 mg (on a fospropofol basis), for example, an amount that is about (i.e., the specified number±10%) any one of 1200 mg, 1250 mg, 1300 mg, 1350 mg, 1400 mg, 1450 mg, 1500 mg, 1550 mg, 1600 mg, 1650 mg, 1700 mg, 1750 mg, or 1800 mg.

In some embodiments, the effective amount of fospropofol, a pharmaceutically acceptable salt of fospropofol, or mixtures thereof, is 1600-2400 mg (on a fospropofol basis), for example, an amount that is about (i.e., the specified number±10%) any one of 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, or 2400 mg.

In some embodiments, the effective amount of fospropofol, a pharmaceutically acceptable salt of fospropofol, or mixtures thereof, is 1800-2400 mg (on a fospropofol basis), for example, an amount that is about (i.e., the specified number±10%) any one of 1800 mg, 1850 mg, 1900 mg, 1950 mg, 2000 mg, 2050 mg, 2100 mg, 2150 mg, 2200 mg, 2250 mg, 2300 mg, 2350 mg, or 2400 mg.

In some embodiments, the effective amount of fospropofol, a pharmaceutically acceptable salt of fospropofol, or mixtures thereof, is 2000-2400 mg (on a fospropofol basis), for example, an amount that is about (i.e., the specified number±10%) any one of 2000 mg, 2050 mg, 2100 mg, 2150 mg, 2200 mg, 2250 mg, 2300 mg, 2350 mg, or 2400 mg.

In some embodiments, the effective amount of fospropofol, a pharmaceutically acceptable salt of fospropofol, or mixtures thereof, is 400 mg (on a fospropofol basis).

In some embodiments, the effective amount of fospropofol, a pharmaceutically acceptable salt of fospropofol, or mixtures thereof, is 500 mg (on a fospropofol basis).

In some embodiments, the effective amount of fospropofol, a pharmaceutically acceptable salt of fospropofol, or mixtures thereof, is 600 mg (on a fospropofol basis).

In some embodiments, the effective amount of fospropofol, a pharmaceutically acceptable salt of fospropofol, or mixtures thereof, is 700 mg (on a fospropofol basis).

In some embodiments, the effective amount of fospropofol, a pharmaceutically acceptable salt of fospropofol, or mixtures thereof, is 800 mg (on a fospropofol basis).

In some embodiments, the effective amount of fospropofol, a pharmaceutically acceptable salt of fospropofol, or mixtures thereof, is 900 mg (on a fospropofol basis).

In some embodiments, the effective amount of fospropofol, a pharmaceutically acceptable salt of fospropofol, or mixtures thereof, is 1000 mg (on a fospropofol basis).

In some embodiments, the effective amount of fospropofol, a pharmaceutically acceptable salt of fospropofol, or mixtures thereof, is about 1 mg/kg to about 80 mg/kg, for example, an amount that is about (i.e., the specified number±10%) any one of 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 51 mg/kg, 52 mg/kg, 53 mg/kg, 54 mg/kg, 55 mg/kg, 56 mg/kg, 57 mg/kg, 58 mg/kg, 59 mg/kg, 60 mg/kg, 61 mg/kg, 62 mg/kg, 63 mg/kg, 64 mg/kg, 65 mg/kg, 66 mg/kg, 67 mg/kg, 68 mg/kg, 69 mg/kg, 70 mg/kg, 71 mg/kg, 72 mg/kg, 73 mg/kg, 74 mg/kg, 75 mg/kg, 76 mg/kg, 77 mg/kg, 78 mg/kg, 79 mg/kg, or 80 mg/kg.

In some embodiments, the effective amount of fospropofol, a pharmaceutically acceptable salt of fospropofol, or mixtures thereof, is about 7 mg/kg to 15 mg/kg, for example, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, or 15.0 mg/kg.

In the methods of the disclosure, an effective amount of fospropofol, a pharmaceutically acceptable salt of fospropofol, or mixtures thereof, is administered in one or more doses.

In some embodiments of the disclosed methods, an effective amount of fospropofol, a pharmaceutically acceptable salt of fospropofol, or mixtures thereof, is administered in one dose.

In some embodiments of the disclosed methods, an effective amount of fospropofol, a pharmaceutically acceptable salt of fospropofol, or mixtures thereof, is administered in more than one dose.

In some embodiments of the disclosed methods, an effective amount of fospropofol, a pharmaceutically acceptable salt of fospropofol, or mixtures thereof, is administered in two or more doses.

In some embodiments, an effective amount of fospropofol, a pharmaceutically acceptable salt of fospropofol, or mixtures thereof, is administered in two doses.

In other embodiments, an effective amount of fospropofol, a pharmaceutically acceptable salt of fospropofol, or mixtures thereof, is administered in more than two doses.

In other embodiments, an effective amount of fospropofol, a pharmaceutically acceptable salt of fospropofol, or mixtures thereof, is administered in three doses.

In other embodiments, an effective amount of fospropofol, a pharmaceutically acceptable salt of fospropofol, or mixtures thereof, is administered in more than three doses.

In other embodiments, an effective amount of fospropofol, a pharmaceutically acceptable salt of fospropofol, or mixtures thereof, is administered in four doses.

In other embodiments, an effective amount of fospropofol, a pharmaceutically acceptable salt of fospropofol, or mixtures thereof, is administered in more than four doses.

In some embodiments of the disclosed methods in which an effective amount of fospropofol, a pharmaceutically acceptable salt of fospropofol, or mixtures thereof, is administered in two or more doses, two doses, or more than two doses, the time interval between administration of the first dose and administration of the second dose is about 5-120 minutes, for example, a time interval that is about (i.e., the specified number±10%) any one of 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, or 120 minutes.

In some embodiments in which the dose is administered intravenously, the time interval between administration of the first dose and administration of the second dose is about 5-15 minutes, for example, a time interval that is about (i.e., the specified number±10%) any one of 5 minutes, 10 minutes, or 15 minutes. In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 5-105 minutes, for example, a time interval that is about (i.e., the specified number±10%) any one of 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, minutes, 85 minutes, 90 minutes, 95 minutes, or 105 minutes.

In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 5-30 minutes, for example, a time interval that is about (i.e., the specified number±10%) any one of 5 minutes, 10 minutes, 15 minutes, 20 minutes, or 30 minutes.

In some embodiments in which the dose is administered perorally, the time interval between administration of the first dose and administration of the second dose is about 5-30 minutes, for example, a time interval that is about (i.e., the specified number±10%) any one of 5 minutes, 10 minutes, 15 minutes, 20 minutes, or 30 minutes. In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 30 minutes.

In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 30-90 minutes, for example, a time interval that is about (i.e., the specified number±10%) any one of 30 minutes, 45 minutes, 60 minutes, 75 minutes, or 90 minutes.

In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 30-75 minutes, for example, a time interval that is about (i.e., the specified number±10%) any one of 30 minutes, 45 minutes, 60 minutes, or 75 minutes.

In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 30-60 minutes, for example, a time interval that is about (i.e., the specified number±10%) any one of 30 minutes, 45 minutes, or 60 minutes.

In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 30-45 minutes, for example, a time interval that is about (i.e., the specified number±10%) any one of 30 minutes, or 45 minutes.

In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 1-24 hours, for example, a time interval that is about (i.e., the specified number±10%) any one of 1 hour, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 10.5 hours, 11 hours, 11.5 hours, 12 hours, 12.5 hours, 13 hours, 13.5 hours, 14 hours, 14.5 hours, 15 hours, 15.5 hours, 16 hours, 16.5 hours, 17 hours, 17.5 hours, 18 hours, 18.5 hours, 19 hours, 19.5 hours, 20 hours, 20.5 hours, 21 hours, 21.5 hours, 22 hours, 22.5 hours, 23 hours, 23.5 hours, or 24 hours.

In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 1-4 hours, for example, a time interval that is about (i.e., the specified number±10%) any one of 1 hour, 2 hours, 2.5 hours, 3 hours, 3.5 hours, or 4 hours.

In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 4-8 hours, for example, a time interval that is about (i.e., the specified number±10%) any one of 4 hours, 4.5 hours, 5 hours, 5.5 hours, 6 hours, 6.5 hours, 7 hours, 7.5 hours, or 8 hours.

In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 8-12 hours, for example, a time interval that is about (i.e., the specified number±10%) any one of 8 hours, 8.5 hours, 9 hours, 9.5 hours, 10 hours, 10.5 hours, 11 hours, 11.5 hours, or 12 hours.

In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 12-16 hours, for example, a time interval that is about (i.e., the specified number±10%) any one of 12 hours, 12.5 hours, 13 hours, 13.5 hours, 14 hours, 14.5 hours, 15 hours, 15.5 hours, or 16 hours.

In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 16-20 hours, for example, a time interval that is about (i.e., the specified number±10%) any one of 16 hours, 16.5 hours, 17 hours, 17.5 hours, 18 hours, 18.5 hours, 19 hours, 19.5 hours, or 20 hours.

In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 20-24 hours, for example, a time interval that is about (i.e., the specified number±10%) any one of 20 hours, 20.5 hours, 21 hours, 21.5 hours, 22 hours, 22.5 hours, 23 hours, 23.5 hours, or 24 hours.

In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 24-48 hours, for example, a time interval that is about (i.e., the specified number±10%) any one of 24 hours, 24.5 hours, 25 hours, 25.5 hours, 26 hours, 26.5 hours, 27 hours, 27.5 hours, or 28 hours, 28.5 hours, 29 hours, 29.5 hours, 30 hours, 30.5 hours, 31 hours, 31.5 hours, 32 hours, 32.5 hours, 33 hours, 33.5 hours, 34 hours, 34.5 hours, 35 hours, 35.5 hours, 36 hours, 36.5 hours, 37 hours, 37.5 hours, 38 hours, 38.5 hours, 39 hours, 39.5 hours, 40 hours, 40.5 hours, 41 hours, 41.5 hours, 42 hours, 42.5 hours, 43 hours, 43.5 hours, 44 hours, 44.5 hours, 45 hours, 45.5 hours, 46 hours, 46.5 hours, 47 hours, 47.5 hours, or 48 hours.

In some embodiments of the disclosed methods in which the effective amount of fospropofol, a pharmaceutically acceptable salt of fospropofol, or mixtures thereof, is administered in two or more doses, two doses, or more than two doses, the first dose provides 10-100% (by weight on a fospropofol basis) of the effective amount of fospropofol, a pharmaceutically acceptable salt of fospropofol, or mixtures thereof, for example, a percentage that is about (i.e., the specified number±10%) one of 10%, 15%, 20%, 25%, 30%, 35% 40%, 45%, 50%, 55%, 60%, 65%, 70%, 75%, 80%, 85%, 90%, 95%, or 100%.

In other embodiments of the disclosed methods in which the effective amount of fospropofol, a pharmaceutically acceptable salt of fospropofol, or mixtures thereof, is administered in two or more doses, two doses, or more than two doses, the first dose provides 20-100% (by weight on a fospropofol basis) of the effective amount of fospropofol, a pharmaceutically acceptable salt of fospropofol, or mixtures thereof, for example, a percentage that is about (i.e., the specified number±10%) one of 20%, 25%, 30%, 35% 40%, 45%, 50%, 55%, 60%, 65%, 70%, 75%, 80%, 85%, 90%, 95%, or 100%.

In other embodiments of the disclosed methods in which the effective amount of fospropofol, a pharmaceutically acceptable salt of fospropofol, or mixtures thereof, is administered in two or more doses, two doses, or more than two doses, the first dose provides 30-100% (by weight on a fospropofol basis) of the effective amount of fospropofol, a pharmaceutically acceptable salt of fospropofol, or mixtures thereof, for example, a percentage that is about (i.e., the specified number±10%) one of 30%, 35% 40%, 45%, 50%, 55%, 60%, 65%, 70%, 75%, 80%, 85%, 90%, 95%, or 100%.

In other embodiments of the disclosed methods in which the effective amount of fospropofol, a pharmaceutically acceptable salt of fospropofol, or mixtures thereof, is administered in two or more doses, two doses, or more than two doses, the first dose provides 40-100% (by weight on a fospropofol basis) of the effective amount of fospropofol, a pharmaceutically acceptable salt of fospropofol, or mixtures thereof, for example, a percentage that is about (i.e., the specified number±10%) one of 40%, 45%, 50%, 55%, 60%, 65%, 70%, 75%, 80%, 85%, 90%, 95%, or 100%.

In other embodiments of the disclosed methods in which the effective amount of fospropofol, a pharmaceutically acceptable salt of fospropofol, or mixtures thereof, is administered in two or more doses, two doses, or more than two doses, the first dose provides 50-100% (by weight on a fospropofol basis) of the effective amount of fospropofol, a pharmaceutically acceptable salt of fospropofol, or mixtures thereof, for example, a percentage that is about (i.e., the specified number±10%) one of 50%, 55%, 60%, 65%, 70%, 75%, 80%, 85%, 90%, 95%, or 100%.

In other embodiments of the disclosed methods in which the effective amount of fospropofol, a pharmaceutically acceptable salt of fospropofol, or mixtures thereof, is administered in two or more doses, two doses, or more than two doses, the first dose provides 60-100% (by weight on a fospropofol basis) of the effective amount of fospropofol, a pharmaceutically acceptable salt of fospropofol, or mixtures thereof, for example, a percentage that is about (i.e., the specified number±10%) one of 60%, 65%, 70%, 75%, 80%, 85%, 90%, 95%, or 100%.

In other embodiments of the disclosed methods in which the effective amount of fospropofol, a pharmaceutically acceptable salt of fospropofol, or mixtures thereof, is administered in two or more doses, two doses, or more than two doses, the first dose provides 70-100% (by weight on a fospropofol basis) of the effective amount of fospropofol, a pharmaceutically acceptable salt of fospropofol, or mixtures thereof, for example, a percentage that is about (i.e., the specified number±10%) one of 70%, 75%, 80%, 85%, 90%, 95%, or 100%.

In other embodiments of the disclosed methods in which the effective amount of fospropofol, a pharmaceutically acceptable salt of fospropofol, or mixtures thereof, is administered in two or more doses, two doses, or more than two doses, the first dose provides 80-100% (by weight on a fospropofol basis) of the effective amount of fospropofol, a pharmaceutically acceptable salt of fospropofol, or mixtures thereof, for example, a percentage that is about (i.e., the specified number±10%) one of 80%, 85%, 90%, 95%, or 100%.

In other embodiments of the disclosed methods in which the effective amount of fospropofol, a pharmaceutically acceptable salt of fospropofol, or mixtures thereof, is administered in two or more doses, two doses, or more than two doses, the first dose provides 90-100% (by weight on a fospropofol basis) of the effective amount of fospropofol, a pharmaceutically acceptable salt of fospropofol, or mixtures thereof, for example, a percentage that is about (i.e., the specified number±10%) one of 90%, 95%, or 100%.

In some embodiments of the disclosed methods in which the effective amount of fospropofol, a pharmaceutically acceptable salt of fospropofol, or mixtures thereof, is administered in two or more doses, two doses, or more than two doses, the first dose provides 10-90% (by weight on a fospropofol basis) of the effective amount of fospropofol, a pharmaceutically acceptable salt of fospropofol, or mixtures thereof, for example, a percentage that is about (i.e., the specified number±10%) one of 10%, 15%, 20%, 25%, 30%, 35% 40%, 45%, 50%, 55%, 60%, 65%, 70%, 75%, 80%, 85%, or 90%.

In some embodiments of the disclosed methods in which the effective amount of fospropofol, a pharmaceutically acceptable salt of fospropofol, or mixtures thereof, is administered in two or more doses, two doses, or more than two doses, the first dose provides 10-80% (by weight on a fospropofol basis) of the effective amount of fospropofol, a pharmaceutically acceptable salt of fospropofol, or mixtures thereof, for example, a percentage that is about (i.e., the specified number±10%) one of 10%, 15%, 20%, 25%, 30%, 35% 40%, 45%, 50%, 55%, 60%, 65%, 70%, 75%, or 80%.

In some embodiments of the disclosed methods in which the effective amount of fospropofol, a pharmaceutically acceptable salt of fospropofol, or mixtures thereof, is administered in two or more doses, two doses, or more than two doses, the first dose provides 10-70% (by weight on a fospropofol basis) of the effective amount of fospropofol, a pharmaceutically acceptable salt of fospropofol, or mixtures thereof, for example, a percentage that is about (i.e., the specified number±10%) one of 10%, 15%, 20%, 25%, 30%, 35% 40%, 45%, 50%, 55%, 60%, 65%, or 70%.

In some embodiments of the disclosed methods in which the effective amount of fospropofol, a pharmaceutically acceptable salt of fospropofol, or mixtures thereof, is administered in two or more doses, two doses, or more than two doses, the first dose provides 10-60% (by weight on a fospropofol basis) of the effective amount of fospropofol, a pharmaceutically acceptable salt of fospropofol, or mixtures thereof, for example, a percentage that is about (i.e., the specified number±10%) one of 10%, 15%, 20%, 25%, 30%, 35% 40%, 45%, 50%, 55%, or 60%.

In some embodiments of the disclosed methods in which the effective amount of fospropofol, a pharmaceutically acceptable salt of fospropofol, or mixtures thereof, is administered in two or more doses, two doses, or more than two doses, the first dose provides 10-50% (by weight on a fospropofol basis) of the effective amount of fospropofol, a pharmaceutically acceptable salt of fospropofol, or mixtures thereof, for example, a percentage that is about (i.e., the specified number±10%) one of 10%, 15%, 20%, 25%, 30%, 35% 40%, 45%, or 50%.

In some embodiments of the disclosed methods in which the effective amount of fospropofol, a pharmaceutically acceptable salt of fospropofol, or mixtures thereof, is administered in two or more doses, two doses, or more than two doses, the first dose provides 10-40% (by weight on a fospropofol basis) of the effective amount of fospropofol, a pharmaceutically acceptable salt of fospropofol, or mixtures thereof, for example, a percentage that is about (i.e., the specified number±10%) one of 10%, 15%, 20%, 25%, 30%, 35%, or 40%.

In some embodiments of the disclosed methods in which the effective amount of fospropofol, a pharmaceutically acceptable salt of fospropofol, or mixtures thereof, is administered in two or more doses, two doses, or more than two doses, the first dose provides 10-30% (by weight on a fospropofol basis) of the effective amount of fospropofol, a pharmaceutically acceptable salt of fospropofol, or mixtures thereof, for example, a percentage that is about (i.e., the specified number±10%) one of 10%, 15%, 20%, 25%, or 30%.

In some embodiments of the disclosed methods in which the effective amount of fospropofol, a pharmaceutically acceptable salt of fospropofol, or mixtures thereof, is administered in two or more doses, two doses, or more than two doses, the first dose provides 10-20% (by weight on a fospropofol basis) of the effective amount of fospropofol, a pharmaceutically acceptable salt of fospropofol, or mixtures thereof, for example, a percentage that is about (i.e., the specified number±10%) one of 10%, 15%, or 20%.

In some embodiments of the disclosed methods in which the effective amount of fospropofol, a pharmaceutically acceptable salt of fospropofol, or mixtures thereof, is administered in two or more doses, two doses, or more than two doses, the first dose provides a percentage that is about (i.e., the specified number±10%) one of 10%, 15%, 20%, 25%, 30%, 35% 40%, 45%, 50%, 55%, 60%, 65%, 70%, 75%, 80%, 85%, 90%, 95%, or 100% of the effective amount of fospropofol, or a pharmaceutically acceptable salt thereof.

In some embodiments of the disclosed methods in which the effective amount of fospropofol, a pharmaceutically acceptable salt of fospropofol, or mixtures thereof, is administered in more than two doses, the time interval between administration of the second dose and administration of the third dose is about 5-120 minutes, for example, a time interval that is about (i.e., the specified number±10%) any one of 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes or 120 minutes.

In other embodiments of the disclosed methods in which the effective amount of fospropofol, a pharmaceutically acceptable salt of fospropofol, or mixtures thereof, is administered in more than two doses, the time interval between administration of the second dose and administration of the third dose is about 5-105 minutes, for example, a time interval that is about (i.e., the specified number±10%) any one of 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, or 105 minutes.

In other embodiments of the disclosed methods in which the effective amount of fospropofol, a pharmaceutically acceptable salt of fospropofol, or mixtures thereof, is administered in two or more doses, two doses, or more than two doses, the time interval between administration of the first dose and administration of the second dose is about 30 minutes.

In other embodiments of the disclosed methods in which the effective amount of fospropofol, a pharmaceutically acceptable salt of fospropofol, or mixtures thereof, is administered in more than two doses, the time interval between administration of the second dose and administration of the third dose is about 30-90 minutes, for example, a time interval that is about (i.e., the specified number±10%) any one of 30 minutes, 45 minutes, 60 minutes, 75 minutes, or 90 minutes.

In other embodiments of the disclosed methods in which the effective amount of fospropofol, a pharmaceutically acceptable salt of fospropofol, or mixtures thereof, is administered in more than two doses, the time interval between administration of the second dose and administration of the third dose is about 30-75 minutes, for example, a time interval that is about (i.e., the specified number±10%) any one of 30 minutes, 45 minutes, 60 minutes, or 75 minutes.

In other embodiments of the disclosed methods in which the effective amount of fospropofol, a pharmaceutically acceptable salt of fospropofol, or mixtures thereof, is administered in more than two doses, the time interval between administration of the second dose and administration of the third dose is about 30-60 minutes, for example, a time interval that is about (i.e., the specified number±10%) any one of 30 minutes, 45 minutes, or 60 minutes.

In other embodiments of the disclosed methods in which the effective amount of fospropofol, a pharmaceutically acceptable salt of fospropofol, or mixtures thereof, is administered in more than two doses, the time interval between administration of the second dose and administration of the third dose is about 30-45 minutes, for example, a time interval that is about (i.e., the specified number±10%) any one of 30 minutes, or 45 minutes.

In other embodiments of the disclosed methods in which the effective amount of fospropofol, a pharmaceutically acceptable salt of fospropofol, or mixtures thereof, is administered in more than two doses, the time interval between administration of the second dose and administration of the third dose is about 1-24 hours, for example, a time interval that is about (i.e., the specified number±10%) any one of 1 hour, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 10.5 hours, 11 hours, 11.5 hours, 12 hours, 12.5 hours, 13 hours, 13.5 hours, 14 hours, 14.5 hours, 15 hours, 15.5 hours, 16 hours, 16.5 hours, 17 hours, 17.5 hours, 18 hours, 18.5 hours, 19 hours, 19.5 hours, 20 hours, 20.5 hours, 21 hours, 21.5 hours, 22 hours, 22.5 hours, 23 hours, 23.5 hours, or 24 hours.

In other embodiments of the disclosed methods in which the effective amount of fospropofol, a pharmaceutically acceptable salt of fospropofol, or mixtures thereof, is administered in more than two doses, the time interval between administration of the second dose and administration of the third dose is about 1-4 hours, for example, a time interval that is about (i.e., the specified number±10%) any one of 1 hour, 2 hours, 2.5 hours, 3 hours, 3.5 hours, or 4 hours.

In other embodiments of the disclosed methods in which the effective amount of fospropofol, a pharmaceutically acceptable salt of fospropofol, or mixtures thereof, is administered in more than two doses, the time interval between administration of the second dose and administration of the third dose is about 4-8 hours, for example, a time interval that is about (i.e., the specified number±10%) any one of 4 hours, 4.5 hours, 5 hours, 5.5 hours, 6 hours, 6.5 hours, 7 hours, 7.5 hours, or 8 hours.

In other embodiments of the disclosed methods in which the effective amount of fospropofol, a pharmaceutically acceptable salt of fospropofol, or mixtures thereof, is administered in more than two doses, the time interval between administration of the second dose and administration of the third dose is about 8-12 hours, for example, a time interval that is about (i.e., the specified number±10%) any one of 8 hours, 8.5 hours, 9 hours, 9.5 hours, 10 hours, 10.5 hours, 11 hours, 11.5 hours, or 12 hours.

In other embodiments of the disclosed methods in which the effective amount of fospropofol, a pharmaceutically acceptable salt of fospropofol, or mixtures thereof, is administered in more than two doses, the time interval between administration of the second dose and administration of the third dose is about 12-16 hours, for example, a time interval that is about (i.e., the specified number±10%) any one of 12 hours, 12.5 hours, 13 hours, 13.5 hours, 14 hours, 14.5 hours, 15 hours, 15.5 hours, or 16 hours.

In other embodiments of the disclosed methods in which the effective amount of fospropofol, a pharmaceutically acceptable salt of fospropofol, or mixtures thereof, is administered in more than two doses, the time interval between administration of the second dose and administration of the third dose is about 16-20 hours, for example, a time interval that is about (i.e., the specified number±10%) any one of 16 hours, 16.5 hours, 17 hours, 17.5 hours, 18 hours, 18.5 hours, 19 hours, 19.5 hours, or 20 hours.

In other embodiments of the disclosed methods in which the effective amount of fospropofol, a pharmaceutically acceptable salt of fospropofol, or mixtures thereof, is administered in more than two doses, the time interval between administration of the second dose and administration of the third dose is about 20-24 hours, for example, a time interval that is about (i.e., the specified number±10%) any one of 20 hours, 20.5 hours, 21 hours, 21.5 hours, 22 hours, 22.5 hours, 23 hours, 23.5 hours, or 24 hours.

In some embodiments of the disclosed methods in which the effective amount of fospropofol, a pharmaceutically acceptable salt of fospropofol, or mixtures thereof, is administered in more than two doses, the first dose provides 10-80% (by weight on a fospropofol basis) of the effective amount of fospropofol, a pharmaceutically acceptable salt of fospropofol, or mixtures thereof, for example, a percentage that is about (i.e., the specified number±10%) any one of 10%, 15%, 20%, 25%, 30%, 35% 40%, 45%, 50%, 55%, 60%, 65%, 70%, 75%, or 80%.

In other embodiments of the disclosed methods in which the effective amount of fospropofol, a pharmaceutically acceptable salt of fospropofol, or mixtures thereof, is administered in more than two doses, the first dose provides 20-80% (by weight on a fospropofol basis) of the effective amount of fospropofol, a pharmaceutically acceptable salt of fospropofol, or mixtures thereof, for example, a percentage that is about (i.e., the specified number±10%) any one of 20%, 25%, 30%, 35% 40%, 45%, 50%, 55%, 60%, 65%, 70%, 75%, or 80%.

In other embodiments of the disclosed methods in which the effective amount of fospropofol, a pharmaceutically acceptable salt of fospropofol, or mixtures thereof, is administered in more than two doses, the first dose provides 30-80% (by weight on a fospropofol basis) of the effective amount of fospropofol, a pharmaceutically acceptable salt of fospropofol, or mixtures thereof, for example, a percentage that is about (i.e., the specified number±10%) any one of 30%, 35% 40%, 45%, 50%, 55%, 60%, 65%, 70%, 75%, or 80%.

In other embodiments of the disclosed methods in which the effective amount of fospropofol, a pharmaceutically acceptable salt of fospropofol, or mixtures thereof, is administered in more than two doses, the first dose provides 40-80% (by weight on a fospropofol basis) of the effective amount of fospropofol, a pharmaceutically acceptable salt of fospropofol, or mixtures thereof, for example, a percentage that is about (i.e., the specified number±10%) any one of 40%, 45%, 50%, 55%, 60%, 65%, 70%, 75%, or 80%.

In other embodiments of the disclosed methods in which the effective amount of fospropofol, a pharmaceutically acceptable salt of fospropofol, or mixtures thereof, is administered in more than two doses, the first dose provides 50-80% (by weight on a fospropofol basis) of the effective amount of fospropofol, a pharmaceutically acceptable salt of fospropofol, or mixtures thereof, for example, a percentage that is about (i.e., the specified number±10%) any one of 50%, 55%, 60%, 65%, 70%, 75%, or 80%.

In other embodiments of the disclosed methods in which the effective amount of fospropofol, a pharmaceutically acceptable salt of fospropofol, or mixtures thereof, is administered in more than two doses, the first dose provides 60-80% (by weight on a fospropofol basis) of the effective amount of fospropofol, a pharmaceutically acceptable salt of fospropofol, or mixtures thereof, for example, a percentage that is about (i.e., the specified number±10%) any one of 60%, 65%, 70%, 75%, or 80%.

In other embodiments of the disclosed methods in which the effective amount of fospropofol, a pharmaceutically acceptable salt of fospropofol, or mixtures thereof, is administered in more than two doses, the first dose provides 70-80% (by weight on a fospropofol basis) of the effective amount of fospropofol, a pharmaceutically acceptable salt of fospropofol, or mixtures thereof, for example, a percentage that is about (i.e., the specified number±10%) any one of 70%, 75%, 80%.

In some embodiments of the disclosed methods in which the effective amount of fospropofol, a pharmaceutically acceptable salt of fospropofol, or mixtures thereof, is administered in more than two doses, the first dose provides 10-70% (by weight on a fospropofol basis) of the effective amount of fospropofol, a pharmaceutically acceptable salt of fospropofol, or mixtures thereof, for example, a percentage that is about (i.e., the specified number±10%) any one of 10%, 15%, 20%, 25%, 30%, 35% 40%, 45%, 50%, 55%, 60%, 65%, or 70%.

In some embodiments of the disclosed methods in which the effective amount of fospropofol, a pharmaceutically acceptable salt of fospropofol, or mixtures thereof, is administered in more than two doses, the first dose provides 10-60% (by weight on a fospropofol basis) of the effective amount of fospropofol, a pharmaceutically acceptable salt of fospropofol, or mixtures thereof, for example, a percentage that is about (i.e., the specified number±10%) any one of 10%, 15%, 20%, 25%, 30%, 35% 40%, 45%, 50%, 55%, or 60%.

In some embodiments of the disclosed methods in which the effective amount of fospropofol, a pharmaceutically acceptable salt of fospropofol, or mixtures thereof, is administered in more than two doses, the first dose provides 10-50% (by weight on a fospropofol basis) of the effective amount of fospropofol, a pharmaceutically acceptable salt of fospropofol, or mixtures thereof, for example, a percentage that is about (i.e., the specified number±10%) any one of 10%, 15%, 20%, 25%, 30%, 35% 40%, 45%, or 50%.

In some embodiments of the disclosed methods in which the effective amount of fospropofol, a pharmaceutically acceptable salt of fospropofol, or mixtures thereof, is administered in more than two doses, the first dose provides 10-40% (by weight on a fospropofol basis) of the effective amount of fospropofol, a pharmaceutically acceptable salt of fospropofol, or mixtures thereof, for example, a percentage that is about (i.e., the specified number±10%) any one of 10%, 15%, 20%, 25%, 30%, 35%, or 40%.

In some embodiments of the disclosed methods in which the effective amount of fospropofol, a pharmaceutically acceptable salt of fospropofol, or mixtures thereof, is administered in more than two doses, the first dose provides 10-30% (by weight on a fospropofol basis) of the effective amount of fospropofol, a pharmaceutically acceptable salt of fospropofol, or mixtures thereof, for example, a percentage that is about (i.e., the specified number±10%) any one of 10%, 15%, 20%, 25%, or 30%.

In some embodiments of the disclosed methods in which the effective amount of fospropofol, a pharmaceutically acceptable salt of fospropofol, or mixtures thereof, is administered in more than two doses, the first dose provides 10-20% (by weight on a fospropofol basis) of the effective amount of fospropofol, a pharmaceutically acceptable salt of fospropofol, or mixtures thereof, for example, a percentage that is about (i.e., the specified number±10%) any one of 10%, 15%, or 20%.

In some embodiments of the disclosed methods in which the effective amount of fospropofol, a pharmaceutically acceptable salt of fospropofol, or mixtures thereof, is administered in more than two doses, the first dose provides a percentage that is about (i.e., the specified number±10%) any one of 10%, 15%, 20%, 25%, 30%, 35% 40%, 45%, 50%, 55%, 60%, 65%, 70%, 75%, or 80% (by weight on a fospropofol basis) of the effective amount of fospropofol, or a pharmaceutically acceptable salt thereof.

In some embodiments of the disclosed methods in which the effective amount of fospropofol, a pharmaceutically acceptable salt of fospropofol, or mixtures thereof, is administered in more than two doses, the second dose provides 10-60% (by weight on a fospropofol basis) of the effective amount of fospropofol, a pharmaceutically acceptable salt of fospropofol, or mixtures thereof, for example, a percentage that is about (i.e., the specified number±10%) any one of 10%, 15%, 20%, 25%, 30%, 35% 40%, 45%, 50%, 55%, or 60%.

In other embodiments of the disclosed methods in which the effective amount of fospropofol, a pharmaceutically acceptable salt of fospropofol, or mixtures thereof, is administered in more than two doses, the second dose provides 20-60% (by weight on a fospropofol basis) of the effective amount of fospropofol, a pharmaceutically acceptable salt of fospropofol, or mixtures thereof, for example, a percentage that is about (i.e., the specified number±10%) any one of 20%, 25%, 30%, 35% 40%, 45%, 50%, 55%, or 60%.

In other embodiments of the disclosed methods in which the effective amount of fospropofol, a pharmaceutically acceptable salt of fospropofol, or mixtures thereof, is administered in more than two doses, the second dose provides 30-60% (by weight on a fospropofol basis) of the effective amount of fospropofol, a pharmaceutically acceptable salt of fospropofol, or mixtures thereof, for example, a percentage that is about (i.e., the specified number±10%) any one of 30%, 35% 40%, 45%, 50%, 55%, or 60%.

In other embodiments of the disclosed methods in which the effective amount of fospropofol, a pharmaceutically acceptable salt of fospropofol, or mixtures thereof, is administered in more than two doses, the second dose provides 40-60% (by weight on a fospropofol basis) of the effective amount of fospropofol, a pharmaceutically acceptable salt of fospropofol, or mixtures thereof, for example, a percentage that is about (i.e., the specified number±10%) any one of 40%, 45%, 50%, 55%, or 60%.

In other embodiments of the disclosed methods in which the effective amount of fospropofol, a pharmaceutically acceptable salt of fospropofol, or mixtures thereof, is administered in more than two doses, the second dose provides 50-60% (by weight on a fospropofol basis) of the effective amount of fospropofol, a pharmaceutically acceptable salt of fospropofol, or mixtures thereof, for example, a percentage that is about (i.e., the specified number±10%) any one of 50%, 55%, or 60%.

In some aspects of the methods of the disclosure, administering an effective amount of fospropofol, a pharmaceutically acceptable salt of fospropofol, or mixtures thereof, in one or more doses, results in a plasma Cmax or mean Cmax of propofol of at least 200-4000 ng/mL, for example, a Cmax or mean Cmax that is about (i.e., the specified number±10%) any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3050 ng/mL, 3100 ng/mL, 3150 ng/mL, 3200 ng/mL, 3250 ng/mL, 3300 ng/mL, 3350 ng/mL, 3400 ng/mL, 3450 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, or 4000 ng/mL.

In some aspects of the methods of the disclosure, administering an effective amount of fospropofol, a pharmaceutically acceptable salt of fospropofol, or mixtures thereof, in one or more doses, results in a plasma Cmax or mean Cmax of propofol of at least 200-1600 ng/mL, for example, a Cmax or mean Cmax that is about (i.e., the specified number±10%) any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, or 1600 ng/mL.

In some embodiments, administering an effective amount of fospropofol, a pharmaceutically acceptable salt of fospropofol, or mixtures thereof, in one or more doses results in a plasma Cmax or mean Cmax of propofol of at least 200-1200 ng/mL, for example, a Cmax or mean Cmax that is about (i.e., the specified number±10%) any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1050 ng/mL, 1100 ng/mL, 1150 ng/mL, or 1200 ng/mL.

In some embodiments, administering an effective amount of fospropofol, a pharmaceutically acceptable salt of fospropofol, or mixtures thereof, in one or more doses results in a plasma Cmax or mean Cmax of propofol of at least 200-1000 ng/mL, for example, a Cmax or mean Cmax that is about (i.e., the specified number±10%) any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, or 1000 ng/mL.

In some embodiments, administering an effective amount of fospropofol, a pharmaceutically acceptable salt of fospropofol, or mixtures thereof, in one or more doses results in a plasma Cmax or mean Cmax of propofol of at least 200-800 ng/mL, for example, a Cmax or mean Cmax that is about (i.e., the specified number±10%) any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, or 800 ng/mL.

In some embodiments, administering an effective amount of fospropofol, a pharmaceutically acceptable salt of fospropofol, or mixtures thereof, in one or more doses results in a plasma Cmax or mean Cmax of propofol of at least 200-600 ng/mL, for example, a Cmax or mean Cmax that is about (i.e., the specified number±10%) any one of 200 ng/mL, 250 ng/mL, 300 ng/mL, 350 ng/mL, 400 ng/mL, 450 ng/mL, 500 ng/mL, 550 ng/mL, or 600 ng/mL.

In some embodiments, administering an effective amount of fospropofol, a pharmaceutically acceptable salt of fospropofol, or mixtures thereof, in one or more doses results in a plasma Cmax or mean Cmax of propofol of at least 200-400 ng/mL, for example, a Cmax or mean Cmax that is about (i.e., the specified number±10%) any one of 200 ng/mL, 250 ng/mL, 300 ng/mL, 350 ng/mL, or 400 ng/mL.

In some embodiments, administering an effective amount of fospropofol, a pharmaceutically acceptable salt of fospropofol, or mixtures thereof, in one or more doses results in a plasma Cmax or mean Cmax of propofol of at least 50-500 ng/mL, for example, a Cmax or mean Cmax that is about (i.e., the specified number±10%) any one of 50 ng/mL, 100 ng/mL, 150 ng/mL, 200 ng/mL, 250 ng/mL, 300 ng/mL, 350 ng/mL, 400 ng/mL, 450 ng/mL, or 500 ng/mL.

In some embodiments, administering an effective amount of fospropofol, a pharmaceutically acceptable salt of fospropofol, or mixtures thereof, in one or more doses results in a plasma Cmax or mean Cmax of propofol of no greater than 5000 ng/mL.

In some embodiments, administering an effective amount of fospropofol, a pharmaceutically acceptable salt of fospropofol, or mixtures thereof, in one or more doses results in a plasma Cmax or mean Cmax of propofol of no greater than 4000 ng/mL.

In some embodiments, administering an effective amount of fospropofol, a pharmaceutically acceptable salt of fospropofol, or mixtures thereof, in one or more doses results in a plasma Cmax or mean Cmax of propofol of no greater than 3000 ng/mL.

In some embodiments, administering an effective amount of fospropofol, a pharmaceutically acceptable salt of fospropofol, or mixtures thereof, in one or more doses results in a plasma Cmax or mean Cmax of propofol of no greater than 2000 ng/mL.

In some embodiments, administering an effective amount of fospropofol, a pharmaceutically acceptable salt of fospropofol, or mixtures thereof, in one or more doses results in a plasma Cmax or mean Cmax of propofol of no greater than 1600 ng/mL.

In other embodiments, administering an effective amount of fospropofol, a pharmaceutically acceptable salt of fospropofol, or mixtures thereof, in one or more doses results in a plasma Cmax or mean Cmax of propofol of no greater than 1200 ng/mL.

In other embodiments, administering an effective amount of fospropofol, a pharmaceutically acceptable salt of fospropofol, or mixtures thereof, in one or more doses results in a plasma Cmax or mean Cmax of propofol of no greater than 1000 ng/mL.

In other embodiments, administering an effective amount of fospropofol, a pharmaceutically acceptable salt of fospropofol, or mixtures thereof, in one or more doses results in a plasma Cmax or mean Cmax of propofol of no greater than 800 ng/mL.

In other embodiments, administering an effective amount of fospropofol, a pharmaceutically acceptable salt of fospropofol, or mixtures thereof, in one or more doses results in a plasma Cmax or mean Cmax of propofol of no greater than 600 ng/mL.

In other embodiments, administering an effective amount of fospropofol, a pharmaceutically acceptable salt of fospropofol, or mixtures thereof, in one or more doses results in a plasma Cmax or mean Cmax of propofol of no greater than 500 ng/mL.

In other embodiments, administering an effective amount of fospropofol, a pharmaceutically acceptable salt of fospropofol, or mixtures thereof, in one or more doses results in a plasma Cmax or mean Cmax of propofol of no greater than 400 ng/mL.

In other embodiments, administering an effective amount of fospropofol, a pharmaceutically acceptable salt of fospropofol, or mixtures thereof, in one or more doses results in a plasma Cmax or mean Cmax of propofol of no greater than 200 ng/mL.

In other embodiments, administering an effective amount of fospropofol, a pharmaceutically acceptable salt of fospropofol, or mixtures thereof, in one or more doses results in a plasma Cmax or mean Cmax of propofol of no greater than 100 ng/mL.

In some aspects of the methods of the disclosure, administering an effective amount of fospropofol, a pharmaceutically acceptable salt of fospropofol, or mixtures thereof, in one or more doses, results in a plasma Cmax or mean Cmax of fospropofol of at least 800-18000 ng/mL, for example, a Cmax or mean Cmax that is about (i.e., the specified number±10%) any one of 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 1950 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, 4000 ng/mL, 4050 ng/mL, 4100 ng/mL, 4150 ng/mL, 4200 ng/mL, 4250 ng/mL, 4300 ng/mL, 4350 ng/mL, 4400 ng/mL, 4450 ng/mL, 4500 ng/mL, 4550 ng/mL, 4600 ng/mL, 4650 ng/mL, 4700 ng/mL, 4750 ng/mL, 4800 ng/mL, 4850 ng/mL, 4900 ng/mL, 4950 ng/mL, 5000 ng/mL, 5050 ng/mL, 5100 ng/mL, 5150 ng/mL, 5200 ng/mL, 5250 ng/mL, 5300 ng/mL, 5350 ng/mL, 5400 ng/mL, 5450 ng/mL, 5500 ng/mL, 5550 ng/mL, 5600 ng/mL, 5650 ng/mL, 5700 ng/mL, 5750 ng/mL, 5800 ng/mL, 5850 ng/mL, 5900 ng/mL, 5950 ng/mL, 6000 ng/mL, 6050 ng/mL, 6100 ng/mL, 6150 ng/mL, 6200 ng/mL, 6250 ng/mL, 6300 ng/mL, 6350 ng/mL, 6400 ng/mL, 6450 ng/mL, 6500 ng/mL, 6550 ng/mL, 6600 ng/mL, 6650 ng/mL, 6700 ng/mL, 6750 ng/mL, 6800 ng/mL, 6850 ng/mL, 6900 ng/mL, 6950 ng/mL, 7000 ng/mL, 7050 ng/mL, 7100 ng/mL, 7150 ng/mL, 7200 ng/mL, 7250 ng/mL, 7300 ng/mL, 7350 ng/mL, 7400 ng/mL, 7450 ng/mL, 7500 ng/mL, 7550 ng/mL, 7600 ng/mL, 7650 ng/mL, 7700 ng/mL, 7750 ng/mL, 7800 ng/mL, 7850 ng/mL, 7900 ng/mL, 7950 ng/mL, 8000 ng/mL, 8050 ng/mL, 8100 ng/mL, 8150 ng/mL, 8200 ng/mL, 8250 ng/mL, 8300 ng/mL, 8350 ng/mL, 8400 ng/mL, 8450 ng/mL, 8500 ng/mL, 8550 ng/mL, 8600 ng/mL, 8650 ng/mL, 8700 ng/mL, 8750 ng/mL, 800 ng/mL, 8850 ng/mL, 8900 ng/mL, 8950 ng/mL, 9000 ng/mL, 9050 ng/mL, 9100 ng/mL, 9150 ng/mL, 9200 ng/mL, 9250 ng/mL, 9300 ng/mL, 9350 ng/mL, 9400 ng/mL, 9450 ng/mL, 9500 ng/mL, 9550 ng/mL, 9600 ng/mL, 9650 ng/mL, 9700 ng/mL, 9750 ng/mL, 9000 ng/mL, 9950 ng/mL, 9900 ng/mL, 9950 ng/mL, 10000 ng/mL, 10050 ng/mL, 10100 ng/mL, 10150 ng/mL, 10200 ng/mL, 10250 ng/mL, 10300 ng/mL, 10350 ng/mL, 10400 ng/mL, 10450 ng/mL, 10500 ng/mL, 10550 ng/mL, 10600 ng/mL, 10650 ng/mL, 10700 ng/mL, 10750 ng/mL, 1000 ng/mL, 101050 ng/mL, 10900 ng/mL, 10950 ng/mL, 11000 ng/mL, 11050 ng/mL, 11100 ng/mL, 11150 ng/mL, 11200 ng/mL, 11250 ng/mL, 11300 ng/mL, 11350 ng/mL, 11400 ng/mL, 11450 ng/mL, 11500 ng/mL, 11550 ng/mL, 11600 ng/mL, 11650 ng/mL, 11700 ng/mL, 11750 ng/mL, 1100 ng/mL, 111150 ng/mL, 11900 ng/mL, 11950 ng/mL, 12000 ng/mL, 12050 ng/mL, 12100 ng/mL, 12150 ng/mL, 12200 ng/mL, 12250 ng/mL, 12300 ng/mL, 12350 ng/mL, 12400 ng/mL, 12450 ng/mL, 12500 ng/mL, 12550 ng/mL, 12600 ng/mL, 12650 ng/mL, 12700 ng/mL, 12750 ng/mL, 1200 ng/mL, 121250 ng/mL, 12900 ng/mL, 12950 ng/mL, 13000 ng/mL, 13050 ng/mL, 13100 ng/mL, 13150 ng/mL, 13200 ng/mL, 13250 ng/mL, 13300 ng/mL, 13350 ng/mL, 13400 ng/mL, 13450 ng/mL, 13500 ng/mL, 13550 ng/mL, 13600 ng/mL, 13650 ng/mL, 13700 ng/mL, 13750 ng/mL, 1300 ng/mL, 131350 ng/mL, 13900 ng/mL, 13950 ng/mL, 14000 ng/mL, 14050 ng/mL, 14100 ng/mL, 14150 ng/mL, 14200 ng/mL, 14250 ng/mL, 14300 ng/mL, 14350 ng/mL, 14400 ng/mL, 14450 ng/mL, 14500 ng/mL, 14550 ng/mL, 14600 ng/mL, 14650 ng/mL, 14700 ng/mL, 14750 ng/mL, 1400 ng/mL, 141450 ng/mL, 14900 ng/mL, 14950 ng/mL, 15000 ng/mL, 15050 ng/mL, 15100 ng/mL, 15150 ng/mL, 15200 ng/mL, 15250 ng/mL, 15300 ng/mL, 15350 ng/mL, 15400 ng/mL, 15450 ng/mL, 15500 ng/mL, 15550 ng/mL, 15600 ng/mL, 15650 ng/mL, 15700 ng/mL, 15750 ng/mL, 1500 ng/mL, 151550 ng/mL, 15900 ng/mL, 15950 ng/mL, 16000 ng/mL, 16050 ng/mL, 16100 ng/mL, 16150 ng/mL, 16200 ng/mL, 16250 ng/mL, 16300 ng/mL, 16350 ng/mL, 16400 ng/mL, 16450 ng/mL, 16500 ng/mL, 16550 ng/mL, 16600 ng/mL, 16650 ng/mL, 16700 ng/mL, 16750 ng/mL, 1600 ng/mL, 161650 ng/mL, 16900 ng/mL, 16950 ng/mL, 17000 ng/mL, 17050 ng/mL, 17100 ng/mL, 17150 ng/mL, 17200 ng/mL, 17250 ng/mL, 17300 ng/mL, 17350 ng/mL, 17400 ng/mL, 17450 ng/mL, 17500 ng/mL, 17550 ng/mL, 17600 ng/mL, 17650 ng/mL, 17700 ng/mL, 17750 ng/mL, 1700 ng/mL, 171750 ng/mL, 17900 ng/mL, 17950 ng/mL, or 18000 ng/mL.

In some aspects of the methods of the disclosure, administering an effective amount of fospropofol, a pharmaceutically acceptable salt of fospropofol, or mixtures thereof, in one or more doses, results in a plasma Cmax or mean Cmax of fospropofol of at least 2000-10000 ng/mL, for example, a Cmax or mean Cmax that is about (i.e., the specified number±10%) any one of 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, 4000 ng/mL, 4050 ng/mL, 4100 ng/mL, 4150 ng/mL, 4200 ng/mL, 4250 ng/mL, 4300 ng/mL, 4350 ng/mL, 4400 ng/mL, 4450 ng/mL, 4500 ng/mL, 4550 ng/mL, 4600 ng/mL, 4650 ng/mL, 4700 ng/mL, 4750 ng/mL, 4800 ng/mL, 4850 ng/mL, 4900 ng/mL, 4950 ng/mL, 5000 ng/mL, 5050 ng/mL, 5100 ng/mL, 5150 ng/mL, 5200 ng/mL, 5250 ng/mL, 5300 ng/mL, 5350 ng/mL, 5400 ng/mL, 5450 ng/mL, 5500 ng/mL, 5550 ng/mL, 5600 ng/mL, 5650 ng/mL, 5700 ng/mL, 5750 ng/mL, 5800 ng/mL, 5850 ng/mL, 5900 ng/mL, 5950 ng/mL, 6000 ng/mL, 6050 ng/mL, 6100 ng/mL, 6150 ng/mL, 6200 ng/mL, 6250 ng/mL, 6300 ng/mL, 6350 ng/mL, 6400 ng/mL, 6450 ng/mL, 6500 ng/mL, 6550 ng/mL, 6600 ng/mL, 6650 ng/mL, 6700 ng/mL, 6750 ng/mL, 6800 ng/mL, 6850 ng/mL, 6900 ng/mL, 6950 ng/mL, 7000 ng/mL, 7050 ng/mL, 7100 ng/mL, 7150 ng/mL, 7200 ng/mL, 7250 ng/mL, 7300 ng/mL, 7350 ng/mL, 7400 ng/mL, 7450 ng/mL, 7500 ng/mL, 7550 ng/mL, 7600 ng/mL, 7650 ng/mL, 7700 ng/mL, 7750 ng/mL, 7800 ng/mL, 7850 ng/mL, 7900 ng/mL, 7950 ng/mL, 8000 ng/mL, 8050 ng/mL, 8100 ng/mL, 8150 ng/mL, 8200 ng/mL, 8250 ng/mL, 8300 ng/mL, 8350 ng/mL, 8400 ng/mL, 8450 ng/mL, 8500 ng/mL, 8550 ng/mL, 8600 ng/mL, 8650 ng/mL, 8700 ng/mL, 8750 ng/mL, 800 ng/mL, 8850 ng/mL, 8900 ng/mL, 8950 ng/mL, 9000 ng/mL, 9050 ng/mL, 9100 ng/mL, 9150 ng/mL, 9200 ng/mL, 9250 ng/mL, 9300 ng/mL, 9350 ng/mL, 9400 ng/mL, 9450 ng/mL, 9500 ng/mL, 9550 ng/mL, 9600 ng/mL, 9650 ng/mL, 9700 ng/mL, 9750 ng/mL, 9000 ng/mL, 9950 ng/mL, 9900 ng/mL, 9950 ng/mL, or 10000 ng/mL.

In some aspects of the methods of the disclosure, administering an effective amount of fospropofol, a pharmaceutically acceptable salt of fospropofol, or mixtures thereof, in one or more doses, results in a plasma Cmax or mean Cmax of fospropofol that is a value that is 80% to 125% of (or bioequivalent to) 800-18000 ng/mL, for example, a Cmax or mean Cmax that is a value that is 80% to 125% of (or bioequivalent to) any one of 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 1950 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, 4000 ng/mL, 4050 ng/mL, 4100 ng/mL, 4150 ng/mL, 4200 ng/mL, 4250 ng/mL, 4300 ng/mL, 4350 ng/mL, 4400 ng/mL, 4450 ng/mL, 4500 ng/mL, 4550 ng/mL, 4600 ng/mL, 4650 ng/mL, 4700 ng/mL, 4750 ng/mL, 4800 ng/mL, 4850 ng/mL, 4900 ng/mL, 4950 ng/mL, 5000 ng/mL, 5050 ng/mL, 5100 ng/mL, 5150 ng/mL, 5200 ng/mL, 5250 ng/mL, 5300 ng/mL, 5350 ng/mL, 5400 ng/mL, 5450 ng/mL, 5500 ng/mL, 5550 ng/mL, 5600 ng/mL, 5650 ng/mL, 5700 ng/mL, 5750 ng/mL, 5800 ng/mL, 5850 ng/mL, 5900 ng/mL, 5950 ng/mL, 6000 ng/mL, 6050 ng/mL, 6100 ng/mL, 6150 ng/mL, 6200 ng/mL, 6250 ng/mL, 6300 ng/mL, 6350 ng/mL, 6400 ng/mL, 6450 ng/mL, 6500 ng/mL, 6550 ng/mL, 6600 ng/mL, 6650 ng/mL, 6700 ng/mL, 6750 ng/mL, 6800 ng/mL, 6850 ng/mL, 6900 ng/mL, 6950 ng/mL, 7000 ng/mL, 7050 ng/mL, 7100 ng/mL, 7150 ng/mL, 7200 ng/mL, 7250 ng/mL, 7300 ng/mL, 7350 ng/mL, 7400 ng/mL, 7450 ng/mL, 7500 ng/mL, 7550 ng/mL, 7600 ng/mL, 7650 ng/mL, 7700 ng/mL, 7750 ng/mL, 7800 ng/mL, 7850 ng/mL, 7900 ng/mL, 7950 ng/mL, 8000 ng/mL, 8050 ng/mL, 8100 ng/mL, 8150 ng/mL, 8200 ng/mL, 8250 ng/mL, 8300 ng/mL, 8350 ng/mL, 8400 ng/mL, 8450 ng/mL, 8500 ng/mL, 8550 ng/mL, 8600 ng/mL, 8650 ng/mL, 8700 ng/mL, 8750 ng/mL, 800 ng/mL, 8850 ng/mL, 8900 ng/mL, 8950 ng/mL, 9000 ng/mL, 9050 ng/mL, 9100 ng/mL, 9150 ng/mL, 9200 ng/mL, 9250 ng/mL, 9300 ng/mL, 9350 ng/mL, 9400 ng/mL, 9450 ng/mL, 9500 ng/mL, 9550 ng/mL, 9600 ng/mL, 9650 ng/mL, 9700 ng/mL, 9750 ng/mL, 9000 ng/mL, 9950 ng/mL, 9900 ng/mL, 9950 ng/mL, 10000 ng/mL, 10050 ng/mL, 10100 ng/mL, 10150 ng/mL, 10200 ng/mL, 10250 ng/mL, 10300 ng/mL, 10350 ng/mL, 10400 ng/mL, 10450 ng/mL, 10500 ng/mL, 10550 ng/mL, 10600 ng/mL, 10650 ng/mL, 10700 ng/mL, 10750 ng/mL, 1000 ng/mL, 101050 ng/mL, 10900 ng/mL, 10950 ng/mL, 11000 ng/mL, 11050 ng/mL, 11100 ng/mL, 11150 ng/mL, 11200 ng/mL, 11250 ng/mL, 11300 ng/mL, 11350 ng/mL, 11400 ng/mL, 11450 ng/mL, 11500 ng/mL, 11550 ng/mL, 11600 ng/mL, 11650 ng/mL, 11700 ng/mL, 11750 ng/mL, 1100 ng/mL, 111150 ng/mL, 11900 ng/mL, 11950 ng/mL, 12000 ng/mL, 12050 ng/mL, 12100 ng/mL, 12150 ng/mL, 12200 ng/mL, 12250 ng/mL, 12300 ng/mL, 12350 ng/mL, 12400 ng/mL, 12450 ng/mL, 12500 ng/mL, 12550 ng/mL, 12600 ng/mL, 12650 ng/mL, 12700 ng/mL, 12750 ng/mL, 1200 ng/mL, 121250 ng/mL, 12900 ng/mL, 12950 ng/mL, 13000 ng/mL, 13050 ng/mL, 13100 ng/mL, 13150 ng/mL, 13200 ng/mL, 13250 ng/mL, 13300 ng/mL, 13350 ng/mL, 13400 ng/mL, 13450 ng/mL, 13500 ng/mL, 13550 ng/mL, 13600 ng/mL, 13650 ng/mL, 13700 ng/mL, 13750 ng/mL, 1300 ng/mL, 131350 ng/mL, 13900 ng/mL, 13950 ng/mL, 14000 ng/mL, 14050 ng/mL, 14100 ng/mL, 14150 ng/mL, 14200 ng/mL, 14250 ng/mL, 14300 ng/mL, 14350 ng/mL, 14400 ng/mL, 14450 ng/mL, 14500 ng/mL, 14550 ng/mL, 14600 ng/mL, 14650 ng/mL, 14700 ng/mL, 14750 ng/mL, 1400 ng/mL, 141450 ng/mL, 14900 ng/mL, 14950 ng/mL, 15000 ng/mL, 15050 ng/mL, 15100 ng/mL, 15150 ng/mL, 15200 ng/mL, 15250 ng/mL, 15300 ng/mL, 15350 ng/mL, 15400 ng/mL, 15450 ng/mL, 15500 ng/mL, 15550 ng/mL, 15600 ng/mL, 15650 ng/mL, 15700 ng/mL, 15750 ng/mL, 1500 ng/mL, 151550 ng/mL, 15900 ng/mL, 15950 ng/mL, 16000 ng/mL, 16050 ng/mL, 16100 ng/mL, 16150 ng/mL, 16200 ng/mL, 16250 ng/mL, 16300 ng/mL, 16350 ng/mL, 16400 ng/mL, 16450 ng/mL, 16500 ng/mL, 16550 ng/mL, 16600 ng/mL, 16650 ng/mL, 16700 ng/mL, 16750 ng/mL, 1600 ng/mL, 161650 ng/mL, 16900 ng/mL, 16950 ng/mL, 17000 ng/mL, 17050 ng/mL, 17100 ng/mL, 17150 ng/mL, 17200 ng/mL, 17250 ng/mL, 17300 ng/mL, 17350 ng/mL, 17400 ng/mL, 17450 ng/mL, 17500 ng/mL, 17550 ng/mL, 17600 ng/mL, 17650 ng/mL, 17700 ng/mL, 17750 ng/mL, 1700 ng/mL, 171750 ng/mL, 17900 ng/mL, 17950 ng/mL, or 18000 ng/mL.

In some aspects of the methods of the disclosure, administering an effective amount of fospropofol, a pharmaceutically acceptable salt of fospropofol, or mixtures thereof, in one or more doses, results in a plasma Cmax or mean Cmax of fospropofol that is a value that is 80% to 125% of (or bioequivalent to) 2000-10000 ng/mL, for example, a Cmax or mean Cmax that is a value that is 80% to 125% of (or bioequivalent to) any one of 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, 4000 ng/mL, 4050 ng/mL, 4100 ng/mL, 4150 ng/mL, 4200 ng/mL, 4250 ng/mL, 4300 ng/mL, 4350 ng/mL, 4400 ng/mL, 4450 ng/mL, 4500 ng/mL, 4550 ng/mL, 4600 ng/mL, 4650 ng/mL, 4700 ng/mL, 4750 ng/mL, 4800 ng/mL, 4850 ng/mL, 4900 ng/mL, 4950 ng/mL, 5000 ng/mL, 5050 ng/mL, 5100 ng/mL, 5150 ng/mL, 5200 ng/mL, 5250 ng/mL, 5300 ng/mL, 5350 ng/mL, 5400 ng/mL, 5450 ng/mL, 5500 ng/mL, 5550 ng/mL, 5600 ng/mL, 5650 ng/mL, 5700 ng/mL, 5750 ng/mL, 5800 ng/mL, 5850 ng/mL, 5900 ng/mL, 5950 ng/mL, 6000 ng/mL, 6050 ng/mL, 6100 ng/mL, 6150 ng/mL, 6200 ng/mL, 6250 ng/mL, 6300 ng/mL, 6350 ng/mL, 6400 ng/mL, 6450 ng/mL, 6500 ng/mL, 6550 ng/mL, 6600 ng/mL, 6650 ng/mL, 6700 ng/mL, 6750 ng/mL, 6800 ng/mL, 6850 ng/mL, 6900 ng/mL, 6950 ng/mL, 7000 ng/mL, 7050 ng/mL, 7100 ng/mL, 7150 ng/mL, 7200 ng/mL, 7250 ng/mL, 7300 ng/mL, 7350 ng/mL, 7400 ng/mL, 7450 ng/mL, 7500 ng/mL, 7550 ng/mL, 7600 ng/mL, 7650 ng/mL, 7700 ng/mL, 7750 ng/mL, 7800 ng/mL, 7850 ng/mL, 7900 ng/mL, 7950 ng/mL, 8000 ng/mL, 8050 ng/mL, 8100 ng/mL, 8150 ng/mL, 8200 ng/mL, 8250 ng/mL, 8300 ng/mL, 8350 ng/mL, 8400 ng/mL, 8450 ng/mL, 8500 ng/mL, 8550 ng/mL, 8600 ng/mL, 8650 ng/mL, 8700 ng/mL, 8750 ng/mL, 800 ng/mL, 8850 ng/mL, 8900 ng/mL, 8950 ng/mL, 9000 ng/mL, 9050 ng/mL, 9100 ng/mL, 9150 ng/mL, 9200 ng/mL, 9250 ng/mL, 9300 ng/mL, 9350 ng/mL, 9400 ng/mL, 9450 ng/mL, 9500 ng/mL, 9550 ng/mL, 9600 ng/mL, 9650 ng/mL, 9700 ng/mL, 9750 ng/mL, 9000 ng/mL, 9950 ng/mL, 9900 ng/mL, 9950 ng/mL, or 10000 ng/mL.

In some embodiments, administering an effective amount of fospropofol, a pharmaceutically acceptable salt of fospropofol, or mixtures thereof, in one or more doses results in a plasma Cmax or mean Cmax of fospropofol of no greater than 15000 ng/mL.

In some embodiments, administering an effective amount of fospropofol, a pharmaceutically acceptable salt of fospropofol, or mixtures thereof, in one or more doses results in a plasma Cmax or mean Cmax of fospropofol of no greater than 14000 ng/mL.

In some embodiments, administering an effective amount of fospropofol, a pharmaceutically acceptable salt of fospropofol, or mixtures thereof, in one or more doses results in a plasma Cmax or mean Cmax of fospropofol of no greater than 13000 ng/mL.

In some embodiments, administering an effective amount of fospropofol, a pharmaceutically acceptable salt of fospropofol, or mixtures thereof, in one or more doses results in a plasma Cmax or mean Cmax of fospropofol of no greater than 12000 ng/mL.

In some embodiments, administering an effective amount of fospropofol, a pharmaceutically acceptable salt of fospropofol, or mixtures thereof, in one or more doses results in a plasma Cmax or mean Cmax of fospropofol of no greater than 11000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no greater than 10000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no greater than 9000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no greater than 8000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no greater than 7000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no greater than 6000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no greater than 5000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no greater than 4000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no greater than 3000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no greater than 2000 ng/mL.

In some embodiments, administering an effective amount of fospropofol, a pharmaceutically acceptable salt of fospropofol, or mixtures thereof, in one or more doses results in a plasma Cmax or mean Cmax of fospropofol of no less than 14000 ng/mL.

In some embodiments, administering an effective amount of fospropofol, a pharmaceutically acceptable salt of fospropofol, or mixtures thereof, in one or more doses results in a plasma Cmax or mean Cmax of fospropofol of no less than 13000 ng/mL.

In some embodiments, administering an effective amount of fospropofol, a pharmaceutically acceptable salt of fospropofol, or mixtures thereof, in one or more doses results in a plasma Cmax or mean Cmax of fospropofol of no less than 12000 ng/mL.

In some embodiments, administering an effective amount of fospropofol, a pharmaceutically acceptable salt of fospropofol, or mixtures thereof, in one or more doses results in a plasma Cmax or mean Cmax of fospropofol of no less than 11000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no less than 10000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no less than 9000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no less than 8000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no less than 7000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no less than 6000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no less than 5000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no less than 4000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no less than 3000 ng/mL.

In other embodiments, administering an effective amount of fospropofol, a pharmaceutically acceptable salt of fospropofol, or mixtures thereof, in one or more doses results in a plasma Cmax or mean Cmax of fospropofol of no less than 2000 ng/mL.

In some embodiments, administering an effective amount of fospropofol, a pharmaceutically acceptable salt of fospropofol, or mixtures thereof, in one or more doses results in a plasma Cmax or mean Cmax of fospropofol of no less than 1500 ng/mL.

In some embodiments, administering an effective amount of fospropofol, a pharmaceutically acceptable salt of fospropofol, or mixtures thereof, in one or more doses results in a plasma Cmax or mean Cmax of fospropofol of no less than 1200 ng/mL.

In some embodiments, administering an effective amount of fospropofol, a pharmaceutically acceptable salt of fospropofol, or mixtures thereof, in one or more doses results in a plasma Cmax or mean Cmax of fospropofol of no less than 1000 ng/mL.

In some embodiments, administering an effective amount of fospropofol, a pharmaceutically acceptable salt of fospropofol, or mixtures thereof, in one or more doses results in a plasma Cmax or mean Cmax of fospropofol of no less than 800 ng/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no greater than 3200 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no greater than 2400 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no greater than 1600 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no greater than 800 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no greater than 600 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no greater than 400 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no greater than 300 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no greater than 200 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no greater than 100 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no greater than 50 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no less than 3200 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no less than 2400 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no less than 1600 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no less than 800 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no less than 600 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no less than 400 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no less than 300 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no less than 200 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no less than 100 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol of no less than 50 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no greater than 8000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no greater than 7000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no greater than 6000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no greater than 5000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no greater than 4500 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no greater than 4000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no greater than 3000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no greater than 2000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no greater than 1000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no less than 8000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no less than 7000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no less than 6000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no less than 5000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no less than 4500 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no less than 4000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no less than 3000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no less than 2000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of fospropofol of no less than 1000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of propofol of no greater than 300 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of propofol of no greater than 200 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of propofol of no greater than 150 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of propofol of no greater than 100 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of propofol of no greater than 50 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of propofol of no greater than 30 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of propofol of no greater than 20 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of propofol of no less than 300 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of propofol of no less than 200 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of propofol of no less than 150 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of propofol of no less than 100 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of propofol of no less than 50 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of propofol of no less than 30 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of propofol of no less than 20 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no greater than 7000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no greater than 6000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no greater than 5000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no greater than 4000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no greater than 3500 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no greater than 3000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no greater than 2000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no greater than 1000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no greater than 800 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no greater than 700 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no less than 7000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no less than 6000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no less than 5000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no less than 4000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no less than 3500 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no less than 3000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no less than 2000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no less than 1000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no less than 800 ng hr/mL.

In some aspects of the methods of the disclosure, administering an effective amount of fospropofol, a pharmaceutically acceptable salt of fospropofol, or mixtures thereof, in one or more doses, results in a plasma $AUC_{1hr}$ or mean $AUC_{1hr}$ of fospropofol of no less than 700 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no greater than 800 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no greater than 700 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no greater than 600 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no greater than 500 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no greater than 400 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no greater than 300 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no greater than 200 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no greater than 100 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no less than 800 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no less than 700 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no less than 600 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no less than 500 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no less than 400 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no less than 300 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no less than 200 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of propofol of no less than 100 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no greater than 12000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no greater than 8000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no greater than 7000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no greater than 6000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no greater than 5000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no greater than 4000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no greater than 3000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no greater than 2000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no greater than 1000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no less than 12000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no less than 8000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no less than 7000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no less than 6000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no less than 5000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no less than 4000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no less than 3000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no less than 2000 ng hr/mL.

In some aspects of the methods of the disclosure, administering an effective amount of fospropofol, a pharmaceutically acceptable salt of fospropofol, or mixtures thereof, in one or more doses, results in a plasma $AUC_{4hr}$ or mean $AUC_{4hr}$ of fospropofol of no less than 1000 ng hr/mL.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{60min}$ ratio on a mean concentration vs. time curve that is less than 0.1.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{60min}$ ratio on a mean concentration vs. time curve that is less than 0.2.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{60min}$ ratio on a mean concentration vs. time curve that is less than 0.29.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{60min}$ ratio on a mean concentration vs. time curve that is less than 0.3.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{60min}$ ratio on a mean concentration vs. time curve that is less than 0.4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{60min}$ ratio on a mean concentration vs. time curve that is at least 0.1.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{60min}$ ratio on a mean concentration vs. time curve that is at least 0.2.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{60min}$ ratio on a mean concentration vs. time curve that is at least 0.29.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{60min}$ ratio on a mean concentration vs. time curve that is at least 0.3.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{60min}$ ratio on a mean concentration vs. time curve that is at least 0.4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{120min}$ ratio on a mean concentration vs. time curve that is less than 0.1.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{120min}$ ratio on a mean concentration vs. time curve that is less than 0.2.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{120min}$ ratio on a mean concentration vs. time curve that is less than 0.23.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{120min}$ ratio on a mean concentration vs. time curve that is less than 0.3.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{120min}$ ratio on a mean concentration vs. time curve that is at least 0.1.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{120min}$ ratio on a mean concentration vs. time curve that is at least 0.2.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{120min}$ ratio on a mean concentration vs. time curve that is at least 0.23.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{20min}$/mean $AUC_{120min}$ ratio on a mean concentration vs. time curve that is at least 0.3.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{60min}$ ratio on a mean concentration vs. time curve that is less than 0.3.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{60min}$ ratio on a mean concentration vs. time curve that is less than 0.4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{60min}$ ratio on a mean concentration vs. time curve that is less than 0.5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{60min}$ ratio on a mean concentration vs. time curve that is less than 0.6.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{60min}$ ratio on a mean concentration vs. time curve that is less than 0.68.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{60min}$ ratio on a mean concentration vs. time curve that is less than 0.7.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{60min}$ ratio on a mean concentration vs. time curve that is less than 0.8.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{60min}$ ratio on a mean concentration vs. time curve that is at least 0.3.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{60min}$ ratio on a mean concentration vs. time curve that is at least 0.4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{60min}$ ratio on a mean concentration vs. time curve that is at least 0.5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{60min}$ ratio on a mean concentration vs. time curve that is at least 0.6.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{60min}$ ratio on a mean concentration vs. time curve that is at least 0.68.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{60min}$ ratio on a mean concentration vs. time curve that is at least 0.7.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{60min}$ ratio on a mean concentration vs. time curve that is at least 0.8.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{120min}$ ratio on a mean concentration vs. time curve that is less than 0.3.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{120min}$ ratio on a mean concentration vs. time curve that is less than 0.4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{120min}$ ratio on a mean concentration vs. time curve that is less than 0.5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{120min}$ ratio on a mean concentration vs. time curve that is less than 0.55.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{120min}$ ratio on a mean concentration vs. time curve that is less than 0.6.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{120min}$ ratio on a mean concentration vs. time curve that is at least 0.3.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{120min}$ ratio on a mean concentration vs. time curve that is at least 0.4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{120min}$ ratio on a mean concentration vs. time curve that is at least 0.5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{120min}$ ratio on a mean concentration vs. time curve that is at least 0.55.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{30min}$/mean $AUC_{120min}$ ratio on a mean concentration vs. time curve that is at least 0.6.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{2hr}$ ratio on a mean concentration vs. time curve that is less than 1.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{2hr}$ ratio on a mean concentration vs. time curve that is less than 0.9.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{2hr}$ ratio on a mean concentration vs. time curve that is less than 0.8.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{2hr}$ ratio on a mean concentration vs. time curve that is less than 0.7.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{2hr}$ ratio on a mean concentration vs. time curve that is less than 0.6.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{2hr}$ ratio on a mean concentration vs. time curve that is less than 0.5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{2hr}$ ratio on a mean concentration vs. time curve that is less than 0.4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{2hr}$ ratio on a mean concentration vs. time curve that is at least 1.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{2hr}$ ratio on a mean concentration vs. time curve that is at least 0.9.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{2hr}$ ratio on a mean concentration vs. time curve that is at least 0.8.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{2hr}$ ratio on a mean concentration vs. time curve that is at least 0.7.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{2hr}$ ratio on a mean concentration vs. time curve that is at least 0.6.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{2hr}$ ratio on a mean concentration vs. time curve that is at least 0.5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{2hr}$ ratio on a mean concentration vs. time curve that is at least 0.4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{4hr}$ ratio on a mean concentration vs. time curve that is less than 0.9.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{4hr}$ ratio on a mean concentration vs. time curve that is less than 0.8.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{4hr}$ ratio on a mean concentration vs. time curve that is less than 0.7.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{4hr}$ ratio on a mean concentration vs. time curve that is less than 0.6.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{4hr}$ ratio on a mean concentration vs. time curve that is less than 0.5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{4hr}$ ratio on a mean concentration vs. time curve that is less than 0.4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{4hr}$ ratio on a mean concentration vs. time curve that is less than 0.3.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{4hr}$ ratio on a mean concentration vs. time curve that is at least 0.9.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{4hr}$ ratio on a mean concentration vs. time curve that is at least 0.8.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{4hr}$ ratio on a mean concentration vs. time curve that is at least 0.7.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{4hr}$ ratio on a mean concentration vs. time curve that is at least 0.6.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{4hr}$ ratio on a mean concentration vs. time curve that is at least 0.5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{4hr}$ ratio on a mean concentration vs. time curve that is at least 0.4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{1hr}$/mean $AUC_{4hr}$ ratio on a mean concentration vs. time curve that is at least 0.3.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{2hr}$/mean $AUC_{4hr}$ ratio on a mean concentration vs. time curve that is less than 1.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean$AUC_{2hr}$/mean $AUC_{4hr}$ ratio on a mean concentration vs. time curve that is less than 0.9.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean$AUC_{2hr}$/mean $AUC_{4hr}$ ratio on a mean concentration vs. time curve that is less than 0.8.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{2hr}$/mean $AUC_{4hr}$ ratio on a mean concentration vs. time curve that is less than 0.7.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{2hr}$/mean $AUC_{4hr}$ ratio on a mean concentration vs. time curve that is less than 0.6.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean$AUC_{2hr}$/mean $AUC_{4hr}$ ratio on a mean concentration vs. time curve that is less than 0.5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{2hr}$/mean $AUC_{4hr}$ ratio on a mean concentration vs. time curve that is less than 0.4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{2hr}$/mean $AUC_{4hr}$ ratio on a mean concentration vs. time curve that is at least 1.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{2hr}$/mean $AUC_{4hr}$ ratio on a mean concentration vs. time curve that is at least 0.9.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{2hr}$/mean $AUC_{4hr}$ ratio on a mean concentration vs. time curve that is at least 0.8.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{2hr}$/mean $AUC_{4hr}$ ratio on a mean concentration vs. time curve that is at least 0.7.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{2hr}$/mean $AUC_{4hr}$ ratio on a mean concentration vs. time curve that is at least 0.6.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{2hr}$/mean $AUC_{4hr}$ ratio on a mean concentration vs. time curve that is at least 0.5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $AUC_{2hr}$/mean $AUC_{4hr}$ ratio on a mean concentration vs. time curve that is at least 0.4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{60}$ ratio that is less than 5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{60}$ ratio that is less than 4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{60}$ ratio that is less than 3.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{60}$ ratio that is less than 2.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{60}$ ratio that is at least 5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{60}$ ratio that is at least 4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{60}$ ratio that is at least 3.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{60}$ ratio that is at least 2.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{120}$ ratio that is less than 80.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{120}$ ratio that is less than 76.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{120}$ ratio that is less than 70.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{120}$ ratio that is less than 60.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{120}$ ratio that is less than 50.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{120}$ ratio that is at least 80.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{120}$ ratio that is at least 76.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{120}$ ratio that is at least 70.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{120}$ ratio that is at least 60.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{20}$/mean $C_{120}$ ratio that is at least 50.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{60}$ ratio that is less than 3.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{60}$ ratio that is less than 2.5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{60}$ ratio that is less than 2.4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{60}$ ratio that is less than 2.0.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{60}$ ratio that is less than 1.5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{60}$ ratio that is less than 1.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{60}$ ratio that is at least 3.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{60}$ ratio that is at least 2.5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{60}$ ratio that is at least 2.4.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{60}$ ratio that is at least 2.0.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{60}$ ratio that is at least 1.5.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{60}$ ratio that is at least 1.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{120}$ ratio that is less than 40.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{120}$ ratio that is less than 36.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{120}$ ratio that is less than 35.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{120}$ ratio that is less than 30.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{120}$ ratio that is less than 25.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{120}$ ratio that is less than 20.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{120}$ ratio that is less than 15.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{120}$ ratio that is at least 40.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{120}$ ratio that is at least 36.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{120}$ ratio that is at least 35.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{120}$ ratio that is at least 30.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{120}$ ratio that is at least 25.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{120}$ ratio that is at least 20.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{30}$/mean $C_{120}$ ratio that is at least 15.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{1hr}$/mean $C_{4hr}$ ratio that is less than 8.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{1hr}$/mean $C_{4hr}$ ratio that is at least 8.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{2hr}$/mean $C_{4hr}$ ratio that is less than 6.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{2hr}$/mean $C_{4hr}$ ratio that is at least 6.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{1hr}$/mean $C_{2hr}$ ratio that is less than 11.

In some aspects of the methods of the disclosure, administering an effective amount of fospropofol, a pharmaceutically acceptable salt of fospropofol, or mixtures thereof, in one or more doses, results in a plasma propofol or a plasma fospropofol mean $C_{1hr}$/mean $C_{2hr}$ ratio that is at least 11.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol or of fospropofol no greater than 40-80% of $AUC_0$-∞ or mean $AUC_0$-∞.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol or of fospropofol no greater than 40% of $AUC_0$-∞ or mean $AUC_0$-∞.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol or of fospropofol no greater than 50% of $AUC_0$-∞ or mean $AUC_0$-∞.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol or of fospropofol no greater than 60% of $AUC_0$-∞ or mean $AUC_0$-∞.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol or of fospropofol no greater than 70% of $AUC_0$-∞ or mean $AUC_0$-∞.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol or of fospropofol no greater than 80% of $AUC_0$-∞ or mean $AUC_0$-∞.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol or of fospropofol no less than 40-80% of $AUC_0$-∞ or mean $AUC_0$-∞.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol or of fospropofol no less than 40% of $AUC_0$-∞ or mean $AUC_0$-∞.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol or of fospropofol no less than 50% of $AUC_0$-∞ or mean $AUC_0$-∞.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol or of fospropofol no less than 60% of $AUC_0$-∞ or mean $AUC_0$-∞.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol or of fospropofol no less than 70% of $AUC_0$-∞ or mean $AUC_0$-∞.

In some aspects of the methods of the disclosure, administering an effective amount of fospropofol, a pharmaceutically acceptable salt of fospropofol, or mixtures thereof, in one or more doses, results in a plasma $AUC_{2hr}$ or mean $AUC_{2hr}$ of propofol or of fospropofol no less than 80% of $AUC_0$-∞ or mean $AUC_0$-∞.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 100-1600 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 100-1200 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 100-1000 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 100-800 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 100-600 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 100-400 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 100-200 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 200-1600 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 200-1200 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 200-1000 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 200-800 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 200-600 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 200-400 ng/mL for at least 30 minutes. In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 30-300 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 40-1700 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 40-1500 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 40-1300 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 40-1100 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 40-900 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 40-700 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 40-500 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 100-1700 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 100-1500 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 100-1300 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 100-1100 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 100-900 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 100-700 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 100-500 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 200-1700 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 200-1500 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 200-1300 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 200-1100 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 200-900 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 200-700 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 200-500 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 100-1600 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 100-1200 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 100-1000 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 100-800 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 100-600 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 100-400 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 100-200 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 200-1600 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 200-1200 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 200-1000 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 200-800 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 200-600 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol of 200-400 ng/mL for at least 60 minutes. In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 40-1700 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 40-1500 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 40-1300 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 40-1100 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 40-900 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 40-700 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 40-500 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 100-1700 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 100-1500 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 100-1300 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 100-1100 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 100-900 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 100-700 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 100-500 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 200-1700 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 200-1500 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 200-1300 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 200-1100 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 200-900 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 200-700 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of fospropofol of 200-500 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 100-1600 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 100-1200 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 100-1000 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 100-800 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 100-600 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 100-400 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 100-200 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 200-1600 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 200-1200 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 200-1000 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 200-800 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 200-600 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 200-400 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 100-1600 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 100-1200 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 100-1000 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 100-800 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 100-600 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 100-400 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 100-200 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 200-1600 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 200-1200 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 200-1000 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 200-800 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 200-600 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of 200-400 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 30 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 40 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 50 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 100 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 150 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 180 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 200 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 300 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 400 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 500 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 600 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 700 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 800 ng/mL for at least 30 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 30 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 40 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 50 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 75 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 100 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 150 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 200 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 300 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 400 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 500 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 600 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 700 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 800 ng/mL for at least 60 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 30 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 40 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 50 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 75 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 100 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 150 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 200 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 300 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 400 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 500 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 600 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 700 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 800 ng/mL for at least 90 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 5 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 15 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 25 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 50 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 100 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 200 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 300 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 400 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 500 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 600 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 700 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol, or of fospropofol, of at least 800 ng/mL for at least 120 minutes.

In some aspects of the methods of the disclosure, administering an effective amount of fospropofol, a pharmaceutically acceptable salt of fospropofol, or mixtures thereof, in one or more doses, results in a plasma concentration or mean concentration of propofol or of fospropofol at a time point 0.5-6 hr after Tmax or median Tmax that is 50-90% of the corresponding plasma Cmax or mean Cmax of propofol or of fospropofol.

As used in these aspects, the term "the corresponding" means that the parameter corresponds to the analyte of interest. Thus, for example, if one is considering the plasma concentration of propofol, then the corresponding Tmax is that of propofol, and the corresponding Cmax is that of propofol.

In some aspects of the methods of the disclosure, administering an effective amount of fospropofol, a pharmaceutically acceptable salt of fospropofol, or mixtures thereof, in one or more doses, results in a plasma concentration or mean concentration of propofol or of fospropofol 30 minutes after the corresponding Tmax or median Tmax that is 50-90% of the corresponding plasma Cmax or mean Cmax of propofol or of fospropofol.

In some aspects of the methods of the disclosure, administering an effective amount of fospropofol, a pharmaceutically acceptable salt of fospropofol, or mixtures thereof, in one or more doses, results in a plasma concentration or mean concentration of propofol or of fospropofol 30 minutes after the corresponding Tmax or median Tmax that is about (i.e., the specified number±10%) 90% of the corresponding plasma Cmax or mean Cmax of propofol or of fospropofol.

In some aspects of the methods of the disclosure, administering an effective amount of fospropofol, a pharmaceutically acceptable salt of fospropofol, or mixtures thereof, in one or more doses, results in a plasma concentration or mean concentration of propofol or of fospropofol at the time point 30 minutes after the corresponding Tmax or median Tmax that is about (i.e., the specified number±10%) 80% of the corresponding plasma Cmax or mean Cmax of propofol or of fospropofol.

In some aspects of the methods of the disclosure, administering an effective amount of fospropofol, a pharmaceutically acceptable salt of fospropofol, or mixtures thereof, in one or more doses, results in a plasma concentration or mean concentration of propofol or of fospropofol at the time point 30 minutes after the corresponding Tmax or median Tmax that is about (i.e., the specified number±10%) 70% of the corresponding plasma Cmax or mean Cmax of propofol or of fospropofol.

In some aspects of the methods of the disclosure, administering an effective amount of fospropofol, a pharmaceutically acceptable salt of fospropofol, or mixtures thereof, in one or more doses, results in a plasma concentration or mean concentration of propofol or of fospropofol at the time point 30 minutes after the corresponding Tmax or median Tmax that is about (i.e., the specified number±10%) 60% of the corresponding plasma Cmax or mean Cmax of propofol or of fospropofol.

In some aspects of the methods of the disclosure, administering an effective amount of fospropofol, a pharmaceutically acceptable salt of fospropofol, or mixtures thereof, in one or more doses, results in a plasma concentration or mean concentration of propofol or of fospropofol at the time point 30 minutes after the corresponding Tmax or median Tmax that is about (i.e., the specified number±10%) 50% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 1 hr after the corresponding Tmax or median Tmax that is 50-90% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol at the time point 1 hr after the corresponding Tmax or median Tmax that is about (i.e., the specified number±10%) 90% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 1 hr after the corresponding Tmax or median Tmax that is about (i.e., the specified number±10%) 80% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 1 hr after the corresponding Tmax or median Tmax that is about (i.e., the specified number±10%) 70% of plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 1 hr after the corresponding Tmax or median Tmax that is about (i.e., the specified number±10%) 60% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 1 hr after the corresponding Tmax or median Tmax that is about (i.e., the specified number±10%) 50% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 1.5 hr the corresponding after Tmax or median Tmax that is 50-90% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 1.5 hr after the corresponding Tmax or median Tmax that is about (i.e., the specified number±10%) 90% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 1.5 hr after the corresponding Tmax or median Tmax that is about (i.e., the specified number±10%) 80% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 1.5 hr after the corresponding Tmax or median Tmax that is about (i.e., the specified number±10%) 70% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 1.5 hr after the corresponding Tmax or median Tmax that is about (i.e., the specified number±10%) 60% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 1.5 hr after the corresponding Tmax or median Tmax that is about (i.e., the specified number±10%) 50% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 2 hr after the corresponding Tmax or median Tmax that is 50-90% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 2 hr after the corresponding Tmax or median Tmax that is about (i.e., the specified number±10%) 90% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 2 hr after the corresponding Tmax or median Tmax that is about (i.e., the specified number±10%) 80% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 2 hr after the corresponding Tmax or median Tmax that is about (i.e., the specified number±10%) 70% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 2 hr after the corresponding Tmax or median Tmax that is about (i.e., the specified number±10%) 60% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 2 hr after the corresponding Tmax or median Tmax that is about (i.e., the specified number±10%) 50% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 3 hr after the corresponding Tmax or median Tmax that is 50-90% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 3 hr after the corresponding Tmax or median Tmax that is about (i.e., the specified number±10%) 90% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 3 hr after the corresponding Tmax or median Tmax that is about (i.e., the specified number±10%) 80% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 3 hr after the corresponding Tmax or median Tmax that is about (i.e., the specified number±10%) 70% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 3 hr after the corresponding Tmax or median Tmax that is about (i.e., the specified number±10%) 60% of the corresponding plasma Cmax or mean Cmax of propofol or of fospropofol.

In some embodiments, administering an effective amount of fospropofol, a pharmaceutically acceptable salt of fospropofol, or mixtures thereof, in one or more doses, results in a plasma concentration or mean concentration of propofol or of fospropofol at the time point 3 hr after the corresponding Tmax or median Tmax that is about (i.e., the specified number±10%) 50% of the corresponding plasma Cmax or mean Cmax of propofol or of fospropofol.

In some aspects of the methods of the disclosure, administering an effective amount of fospropofol, a pharmaceutically acceptable salt of fospropofol, or mixtures thereof, in one or more doses, results in a propofol or a fospropofol Tmax or median Tmax of 0.1 hr-2 hour.

In some aspects of the methods of the disclosure, administering an effective amount of fospropofol, a pharmaceutically acceptable salt of fospropofol, or mixtures thereof, in one or more doses, results in a propofol or a fospropofol Tmax or median Tmax of 20 min-4 hours.

In some aspects of the methods of the disclosure, administering an effective amount of fospropofol, a pharmaceutically acceptable salt of fospropofol, or mixtures thereof, in one or more doses, results in a propofol or a fospropofol Tmax or median Tmax of 30 min-4 hours.

In some aspects of the methods of the disclosure, administering an effective amount of fospropofol, a pharmaceutically acceptable salt of fospropofol, or mixtures thereof, in one or more doses, results in a propofol or a fospropofol Tmax or median Tmax of 60 min-4 hours.

In some aspects of the methods of the disclosure, administering an effective amount of fospropofol, a pharmaceutically acceptable salt of fospropofol, or mixtures thereof, in one or more doses, results in a Tmax or median Tmax for propofol of 0.6 hr-4 hours.

In some aspects of the methods of the disclosure, administering an effective amount of fospropofol, a pharmaceutically acceptable salt of fospropofol, or mixtures thereof, in one or more doses, results in a Tmax or median Tmax for propofol of 1 hr-2 hours.

In some aspects of the methods of the disclosure, administering an effective amount of fospropofol, a pharmaceutically acceptable salt of fospropofol, or mixtures thereof, in one or more doses, results in a Tmax or median Tmax for fospropofol of 0.1 hr-0.7 hours.

In some aspects of the methods of the disclosure, administering an effective amount of fospropofol, a pharmaceutically acceptable salt of fospropofol, or mixtures thereof, in one or more doses, results in a Tmax or median Tmax for fospropofol of 0.2 hr-0.5 hours. In some embodiments, administering an effective amount of fospropofol, a pharmaceutically acceptable salt of fospropofol, or mixtures thereof, in one or more doses, results in a propofol or a fospropofol Tmax or median Tmax of about (i.e., the specified number±10%) 20 min.

In some embodiments, administering an effective amount of fospropofol, a pharmaceutically acceptable salt of fospropofol, or mixtures thereof, in one or more doses, results in a propofol or a fospropofol Tmax or median Tmax of about (i.e., the specified number±10%) 30 min.

In some embodiments, administering an effective amount of fospropofol, a pharmaceutically acceptable salt of fospropofol, or mixtures thereof, in one or more doses, results in a propofol or a fospropofol Tmax or median Tmax of about (i.e., the specified number±10%) 45 min.

In some embodiments, administering an effective amount of fospropofol, a pharmaceutically acceptable salt of fospropofol, or mixtures thereof, in one or more doses, results in a propofol or a fospropofol Tmax or median Tmax of about (i.e., the specified number±10%) 1 hr.

In some embodiments, administering an effective amount of fospropofol, a pharmaceutically acceptable salt of fospropofol, or mixtures thereof, in one or more doses, results in a propofol or a fospropofol Tmax or median Tmax of about (i.e., the specified number±10%) 1.5 hr.

In some embodiments, administering an effective amount of fospropofol, a pharmaceutically acceptable salt of fospropofol, or mixtures thereof, in one or more doses, results in a propofol or a fospropofol Tmax or median Tmax of about (i.e., the specified number±10%) 2.0 hr.

In some embodiments, administering an effective amount of fospropofol, a pharmaceutically acceptable salt of fospropofol, or mixtures thereof, in one or more doses, results in a propofol or a fospropofol Tmax or median Tmax of about (i.e., the specified number±10%) 2.5 hr.

In some embodiments, administering an effective amount of fospropofol, a pharmaceutically acceptable salt of fospropofol, or mixtures thereof, in one or more doses, results in a propofol or a fospropofol Tmax or median Tmax of about (i.e., the specified number±10%) 3.0 hr.

In some embodiments, administering an effective amount of fospropofol, a pharmaceutically acceptable salt of fospropofol, or mixtures thereof, in one or more doses, results in a propofol or a fospropofol Tmax or median Tmax of about (i.e., the specified number±10%) 3.5 hr.

In some embodiments, administering an effective amount of fospropofol, a pharmaceutically acceptable salt of fospropofol, or mixtures thereof, in one or more doses, results in a propofol or a fospropofol Tmax or median Tmax of about (i.e., the specified number±10%) 4.0 hr.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the mean plasma Cmax for fospropofol has a coefficient of variation that is less than 55%, such as, for example, less than any one of 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 5%, 14%, 13%, 12%, 11%, 10%, 9%, 8%, 7%, 6%, or 5%.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the mean plasma Tmax for fospropofol has a coefficient of variation that is less than 39%, such as, for example, less than any one of 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5%.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the mean plasma $AUC_{1hr}$ for fospropofol has a coefficient of variation that is less than 58%, such as, for example, less than any one of 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5%.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the mean plasma $AUC_{2hr}$ for fospropofol has a coefficient of variation that is less than 57%, such as, for example, less than any one of 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 1%, 14%, 13%, 12%, 11%, 10%, 9%, 8%, 7%, 6%, or 5%.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the mean plasma $AUC_{4hr}$ for fospropofol has a coefficient of variation that is less than 58%, such as, for example, less than any one of 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5%.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the mean plasma Cmax for propofol has a coefficient of variation that is less than 68%, such as, for example, less than any one of 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5%.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the mean plasma Tmax for propofol has a coefficient of variation that is less than 69%, such as, for example, less than any one of 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44% 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5%.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the mean plasma $AUC_{1hr}$ for propofol has a coefficient of variation that is less than 71%, such as, for example, less than any one of 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 7%, 16%, 15%, 14%, 13%, 12%, 11%, 10%, 9%, 8%, 7%, 6%, or 5%.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the mean plasma $AUC_{2hr}$ for propofol has a coefficient of variation that is less than 65%, such as, for example, less than any one of 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5%.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the mean plasma $AUC_{4hr}$ for propofol has a coefficient of variation that is less than 56%, such as, for example, less than any one of 56%, 55%, 54%, 53%, 52%, 51%, 50%, 49%, 48%, 47% 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5%.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the plasma fospropofol mean $AUC_{0-9hrs}$ per mg of fospropofol (or a pharmaceutically acceptable salt of fospropofol) administered is at least 3.0 ng*h/mL, such as, for example, at least any one of 3.0 ng*h/mL/mg, 3.1 ng*h/mL/mg, 3.2 ng*h/mL/mg, 3.3 ng*h/mL/mg, 3.4 ng*h/mL/mg, 3.5 ng*h/mL/mg, 3.6 ng*h/mL/mg, 3.7 ng*h/mL/mg, 3.8 ng*h/mL/mg, 3.9 ng*h/mL/mg, 4.0 ng*h/mL/mg, 4.1 ng*h/mL/mg, 4.2 ng*h/mL/mg, 4.3 ng*h/mL/mg, 4.4 ng*h/mL/mg, 4.5 ng*h/mL/mg, 4.6 ng*h/mL/mg, 4.7 ng*h/mL/mg, 4.8 ng*h/mL/mg, 4.9 ng*h/mL/mg, 5.0 ng*h/mL/mg, 5.1 ng*h/mL/mg, 5.2 ng*h/mL/mg, 5.3 ng*h/mL/mg, 5.4 ng*h/mL/mg, 5.5 ng*h/mL/mg, 5.6 ng*h/mL/mg, 5.7 ng*h/mL/mg, 5.8 ng*h/mL/mg, 5.9 ng*h/mL/mg, 6.0 ng*h/mL/mg, 6.1 ng*h/mL/mg, 6.2 ng*h/mL/mg, 6.3 ng*h/mL/mg, 6.4 ng*h/mL/mg, 6.5 ng*h/mL/mg, 6.6 ng*h/mL/mg, 6.7 ng*h/mL/mg, 6.8 ng*h/mL/mg, 6.9 ng*h/mL/mg, 7.0 ng*h/mL/mg, 7.1 ng*h/mL/mg, 7.2 ng*h/mL/mg, 7.3 ng*h/mL/mg, 7.4 ng*h/mL/mg, 7.5 ng*h/mL/mg, 7.6 ng*h/mL/mg, 7.7 ng*h/mL/mg, 7.8 ng*h/mL/mg, 7.9 ng*h/mL/mg, 8.0 ng*h/mL/mg, 8.1 ng*h/mL/mg, 8.2 ng*h/mL/mg, 8.3 ng*h/mL/mg, 8.4 ng*h/mL/mg, 8.5 ng*h/mL/mg, 8.6 ng*h/mL/mg, 8.7 ng*h/mL/mg, 8.8 ng*h/mL/mg, 8.9 ng*h/mL/mg, or 9.0 ng*h/mL/mg.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the plasma fospropofol mean $AUC_{0-\infty}$ per mg of fospropofol (or a pharmaceutically acceptable salt of fospropofol) administered is at least 3.0 ng*h/mL, such as, for example, at least any one of 3.0 ng*h/mL/mg, 3.1 ng*h/mL/mg, 3.2 ng*h/mL/mg, 3.3 ng*h/mL/mg, 3.4 ng*h/mL/mg, 3.5 ng*h/mL/mg, 3.6 ng*h/mL/mg, 3.7 ng*h/mL/mg, 3.8 ng*h/mL/mg, 3.9 ng*h/mL/mg, 4.0 ng*h/mL/mg, 4.1 ng*h/mL/mg, 4.2 ng*h/mL/mg, 4.3 ng*h/mL/mg, 4.4 ng*h/mL/mg, 4.5 ng*h/mL/mg, 4.6 ng*h/mL/mg, 4.7 ng*h/mL/mg, 4.8 ng*h/mL/mg, 4.9 ng*h/mL/mg, 5.0 ng*h/mL/mg, 5.1 ng*h/mL/mg, 5.2 ng*h/mL/mg, 5.3 ng*h/mL/mg, 5.4 ng*h/mL/mg, 5.5 ng*h/mL/mg, 5.6 ng*h/mL/mg, 5.7 ng*h/mL/mg, 5.8 ng*h/mL/mg, 5.9 ng*h/mL/mg, 6.0 ng*h/mL/mg, 6.1 ng*h/mL/mg, 6.2 ng*h/mL/mg, 6.3 ng*h/mL/mg, 6.4 ng*h/mL/mg, 6.5 ng*h/mL/mg, 6.6 ng*h/mL/mg, 6.7 ng*h/mL/mg, 6.8 ng*h/mL/mg, 6.9 ng*h/mL/mg, 7.0 ng*h/mL/mg, 7.1 ng*h/mL/mg, 7.2 ng*h/mL/mg, 7.3 ng*h/mL/mg, 7.4 ng*h/mL/mg, 7.5 ng*h/mL/mg, 7.6 ng*h/mL/mg, 7.7 ng*h/mL/mg, 7.8 ng*h/mL/mg, 7.9 ng*h/mL/mg, 8.0 ng*h/mL/mg, 8.1 ng*h/mL/mg, 8.2 ng*h/mL/mg, 8.3 ng*h/mL/mg, 8.4 ng*h/mL/mg, 8.5 ng*h/mL/mg, 8.6 ng*h/mL/mg, 8.7 ng*h/mL/mg, 8.8 ng*h/mL/mg, 8.9 ng*h/mL/mg, or 9.0 ng*h/mL/mg.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the plasma fospropofol mean $C_{max}$ per mg of fospropofol (or a pharmaceutically acceptable salt of fospropofol) administered is at least 5.0 ng/mL/mg, such as, for example, at least any one of 5.0 ng/mL/mg, 5.1 ng/mL/mg, 5.2 ng/mL/mg, 5.3 ng/mL/mg, 5.4 ng/mL/mg, 5.5 ng/mL/mg, 5.6 ng/mL/mg, 5.7 ng/mL/mg, 5.8 ng/mL/mg, 5.9 ng/mL/mg, 6.0 ng/mL/mg, 6.1 ng/mL/mg, 6.2 ng/mL/mg, 6.3 ng/mL/mg, 6.4 ng/mL/mg, 6.5 ng/mL/mg, 6.6 ng/mL/mg, 6.7 ng/mL/mg, 6.8 ng/mL/mg, 6.9 ng/mL/mg, 7.0 ng/mL/mg, 7.1 ng/mL/mg, 7.2 ng/mL/mg, 7.3 ng/mL/mg, 7.4 ng/mL/mg, 7.5 ng/mL/mg, 7.6 ng/mL/mg, 7.7 ng/mL/mg, 7.8 ng/mL/mg, 7.9 ng/mL/mg, 8.0 ng/mL/mg, 8.1 ng/mL/mg, 8.2 ng/mL/mg, 8.3 ng/mL/mg, 8.4 ng/mL/mg, 8.5 ng/mL/mg, 8.6 ng/mL/mg, 8.7 ng/mL/mg, 8.8 ng/mL/mg, 8.9 ng/mL/mg, 9.0 ng/mL/mg, 9.1 ng/mL/mg, 9.2 ng/mL/mg, 9.3 ng/mL/mg, 9.4 ng/mL/mg, 9.5 ng/mL/mg, 9.6 ng/mL/mg, 9.7 ng/mL/mg, 9.8 ng/mL/mg, 9.9 ng/mL/mg, 10.0 ng/mL/mg, 10.1 ng/mL/mg, 10.2 ng/mL/mg, 10.3 ng/mL/mg, 10.4 ng/mL/mg, 10.5 ng/mL/mg, 10.6 ng/mL/mg, 10.7 ng/mL/mg, 10.8 ng/mL/mg, 10.9 ng/mL/mg, 11.0 ng/mL/mg, 11.1 ng/mL/mg, 11.2 ng/mL/mg, 11.3 ng/mL/mg, 11.4 ng/mL/mg, 11.5 ng/mL/mg, 11.6 ng/mL/mg, 11.7 ng/mL/mg, 11.8 ng/mL/mg, 11.9 ng/mL/mg, 12.0 ng/mL/mg, 12.1 ng/mL/mg, 12.2 ng/mL/mg, 12.3 ng/mL/mg, 12.4 ng/mL/mg, 12.5 ng/mL/mg, 12.6 ng/mL/mg, 12.7 ng/mL/mg, 12.8 ng/mL/mg, 12.9 ng/mL/mg, 13.0 ng/mL/mg, 13.1 ng/mL/mg, 13.2 ng/mL/mg, 13.3 ng/mL/mg, 13.4 ng/mL/mg, 13.5 ng/mL/mg, 13.6 ng/mL/mg, 13.7 ng/mL/mg, 13.8 ng/mL/mg, 13.9 ng/mL/mg, 14.0 ng/mL/mg, 14.1 ng/mL/mg, 14.2 ng/mL/mg, 14.3 ng/mL/mg, 14.4 ng/mL/mg, 14.5 ng/mL/mg, 14.6 ng/mL/mg, 14.7 ng/mL/mg, 14.8 ng/mL/mg, 14.9 ng/mL/mg, 15.0 ng/mL/mg, 15.1 ng/mL/mg, 15.2 ng/mL/mg, 15.3 ng/mL/mg, 15.4 ng/mL/mg, 15.5 ng/mL/mg, 15.6 ng/mL/mg, 15.7 ng/mL/mg, 15.8 ng/mL/mg, 15.9 ng/mL/mg, 16.0 ng/mL/mg, 16.1 ng/mL/mg, 16.2 ng/mL/mg, 16.3 ng/mL/mg, 16.4 ng/mL/mg, 16.5 ng/mL/mg, 16.6 ng/mL/mg, 16.7 ng/mL/mg, 16.8 ng/mL/mg, 16.9 ng/mL/mg, or 17.0 ng/mL/mg.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the plasma propofol mean $AUC_{0-9}$ hr per mg of fospropofol (or a pharmaceutically acceptable salt of fospropofol) administered is at least 0.5 ng*h/mL/mg, such as, for example, at least any one of 0.5 ng*h/mL/mg, 0.55 ng*h/mL/mg, 0.6 ng*h/mL/mg, 0.65 ng*h/mL/mg, 0.7 ng*h/mL/mg, 0.75 ng*h/mL/mg, 0.8 ng*h/mL/mg, 0.85 ng*h/mL/mg, 0.9 ng*h/mL/mg, 0.95 ng*h/mL/mg, 1.0 ng*h/mL/mg, 1.05 ng*h/mL/mg, 1.10 ng*h/mL/mg, 1.15 ng*h/mL/mg, 1.2 ng*h/mL/mg, 1.25 ng*h/mL/mg, 1.3 ng*h/mL/mg, 1.35 ng*h/mL/mg, 1.4 ng*h/mL/mg, 1.45 ng*h/mL/mg, 1.5 ng*h/mL/mg, 1.55 ng*h/mL/mg, 1.6 ng*h/mL/mg, 1.65 ng*h/mL/mg, or 1.7 ng*h/mL/mg.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the plasma propofol mean $AUC_{0-\infty}$ per mg of fospropofol (or a pharmaceutically acceptable salt of fospropofol) administered is at least 0.5 ng*h/mL/mg, such as, for example, at least any one of 0.5 ng*h/mL/mg, 0.55 ng*h/mL/mg, 0.6 ng*h/mL/mg, 0.65 ng*h/mL/mg, 0.7 ng*h/mL/mg, 0.75 ng*h/mL/mg, 0.8 ng*h/mL/mg, 0.85 ng*h/mL/mg, 0.9 ng*h/mL/mg, 0.95 ng*h/mL/mg, 1.0 ng*h/mL/mg, 1.05 ng*h/mL/mg, 1.10 ng*h/mL/mg, 1.15 ng*h/mL/mg, 1.2 ng*h/mL/mg, 1.25 ng*h/mL/mg, 1.3 ng*h/mL/mg, 1.35 ng*h/mL/mg, 1.4 ng*h/mL/mg, 1.45 ng*h/mL/mg, 1.5 ng*h/mL/mg, 1.55 ng*h/mL/mg, 1.6 ng*h/mL/mg, 1.65 ng*h/mL/mg, or 1.7 ng*h/mL/mg.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein the plasma propofol mean $C_{max}$ per mg of fospropofol (or a pharmaceutically acceptable salt of fospropofol) administered is at least 0.3 ng/mL/mg, such as, for example, at least any one of 0.3 ng/mL/mg, 0.35 ng/mL/mg, 0.4 ng/mL/mg, 0.45 ng/mL/mg, 0.5 ng/mL/mg, 0.55 ng/mL/mg, 0.6 ng/mL/mg, 0.65 ng/mL/mg, 0.7 ng/mL/mg, 0.75 ng/mL/mg, 0.8 ng/mL/mg, 0.85 ng/mL/mg, or 0.9 ng/mL/mg.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 1 hour of the administration at least 1%, at least 2%, at least 3% at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20% of the patients are headache free without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 2 hours of the administration at least 5%, at least 10%, at least 15% at least 20%, at least 25%, at least 30%, at least 35%, at least 40%, at least 45%, or at least 50%, of the patients are headache free without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 4 hours of the at least 20%, at least 25%, at least 30%, at least 35% at least 40%, at least 45%, at least 50%, at least 55%, at least 60%, at least 65%, at least 70%, or at least 75%, of the patients are headache free without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 24 hours of the administration at least 50%, at least 55%, at least 60%, at least 65%, at least 70%, or at least 75%, at least 80%, at least 85%, at least 90%, or at least 95%, of the patients are headache free without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 48 hours of the administration at least 50%, at least 55%, at least 60%, at least 65%, at least 70%, or at least 75%, at least 80%, at least 85%, at least 90%, or at least 95%, of the patients are headache free without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 1 hour of the administration at least 1%, at least 2%, at least 3% at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20%, of the patients have experienced headache pain relief without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 1 hours of the administration at least 20%, at least 25%, at least 30%, at least 35% at least 40%, at least 45%, at least 50%, at least 55%, at least 60%, at least 65%, at least 70%, or at least 75%, of the patients have experienced headache pain relief without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 2 hours of the administration at least 50%, at least 55%, at least 60%, at least 65%, at least 70%, or at least 75%, at least 80%, at least 85%, at least 90%, or at least 95%, of the patients have experienced headache pain relief without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 4 hours of the administration at least 50%, at least 55%, at least 60%, at least 65%, at least 70%, or at least 75%, at least 80%, at least 85%, at least 90%, or at least 95%, of the patients have experienced headache pain relief without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 24 hours of the administration up to at least 50%, at least 55%, at least 60%, at least 65%, at least 70%, or at least 75%, at least 80%, at least 85%, at least 90%, or at least 95% of the patients have experienced headache pain relief without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 48 hours of the administration at least 50%, at least 55%, at least 60%, at least 65%, at least 70%, or at least 75%, at least 80%, at least 85%, at least 90%, or at least 95%, of the patients have experienced headache pain relief without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 1 hour of the administration at least 20%, at least 25%, at least 30%, at least 35% at least 40%, at least 45%, at least 50%, at least 55%, at least 60%, at least 65%, at least 70%, or at least 75%, of the patients are free of their most bothersome symptom (MBS) without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 2 hours of the administration at least 20%, at least 25%, at least 30%, at least 35% at least 40%, at least 45%, at least 50%, at least 55%, at least 60%, at least 65%, at least 70%, at least 75%, or at least 80%, of the patients are free of their most bothersome symptom (MBS) without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 4 hours of the administration at least 20%, at least 25%, at least 30%, at least 35% at least 40%, at least 45%, at least 50%, at least 55%, at least 60%, at least 65%, at least 70%, at least 75%, or at least 80%, of the patients are free of their most bothersome symptom (MBS) without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 24 hours of the administration up to 80%, such as, for example, up to 80%, up to 75%, up to 70%, up to 65%, up to 60%, up to 55%, up to 50%, up to 45%, up to 40%, up to 35%, or up to 30%, of the patients are free of their most bothersome symptom (MBS) without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 48 hours of the administration at least 20%, at least 25%, at least 30%, at least 35% at least 40%, at least 45%, at least 50%, at least 55%, at least 60%, at least 65%, at least 70%, at least 75%, or at least 80%, of the patients are free of their most bothersome symptom (MBS) without being administered a rescue medication.

In some embodiments of these methods, the MBS is nausea, photophobia, or phonophobia.

In some embodiments, the MBS is nausea.
In some embodiments, the MBS is photophobia.
In some embodiments, the MBS is phonophobia.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 1 hour of the administration at least 20%, at least 25%, at least 30%, at least 35% at least 40%, at least 45%, at least 50%, at least 55%, at least 60%, at least 65%, at least 70%, or at least 75%, of the patients are free of a bothersome symptom without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 2 hours of the administration at least 20%, at least 25%, at least 30%, at least 35% at least 40%, at least 45%, at least 50%, at least 55%, at least 60%, at least 65%, at least 70%, at least 75%, or at least 80%, of the patients are free of a bothersome symptom without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 4 hours of the administration at least 20%, at least 25%, at least 30%, at least 35% at least 40%, at least 45%, at least 50%, at least 55%, at least 60%, at least 65%, at least 70%, at least 75%, or at least 80%, of the patients are free of a bothersome symptom without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 24 hours of the administration up to 80%, such as, for example, up to 80%, up to 75%, up to 70%, up to 65%, up to 60%, up to 55%, up to 50%, up to 45%, up to 40%, up to 35%, or up to 30%, of the patients are free of a bothersome symptom without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 48 hours of the administration at least 20%, at least 25%, at least 30%, at least 35% at least 40%, at least 45%, at least 50%, at least 55%, at least 60%, at least 65%, at least 70%, at least 75%, or at least 80%, of the patients are free of a bothersome symptom without being administered a rescue medication.

In some embodiments of these methods, the bothersome symptom is nausea, photophobia, or phonophobia.

In some embodiments, the bothersome symptom is nausea.

In some embodiments, the bothersome symptom is photophobia.

In some embodiments, the bothersome symptom is phonophobia.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 1 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had nausea at administration are free of their nausea without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 2 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had nausea at administration are free of their nausea without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 4 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had nausea at administration are free of their nausea without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 24 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had nausea at administration are free of their nausea without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 48 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had nausea at administration are free of their nausea without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 1 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had photophobia at administration are free of their photophobia without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 2 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had photophobia at administration are free of their photophobia without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 4 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95% of the patients whom had photophobia at administration are free of their photophobia without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 24 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had photophobia at administration are free of their photophobia without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 48 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had photophobia at administration are free of their photophobia without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 1 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had phonophobia at administration are free of their phonophobia without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 2 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had phonophobia at administration are free of their phonophobia without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 4 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had phonophobia at administration are free of their phonophobia without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 24 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had phonophobia at administration are free of their phonophobia without being administered a rescue medication.

In some aspects, the methods are directed to treating migraine in a population of patients in need thereof, wherein the method comprises administering to the population an effective amount of fospropofol, a pharmaceutically acceptable salt of fospropofol, or mixtures thereof, wherein within 48 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had phonophobia at administration are free of their phonophobia without being administered a rescue medication.

In some embodiments of the methods of treating migraine in a patient in need thereof, wherein the methods comprise administering to the patient an effective amount of fospropofol, a pharmaceutically acceptable salt of fospropofol, or mixtures thereof, at 1 hour after the administration the subject is headache free.

In other embodiments of the methods of treating migraine in a patient in need thereof, wherein the methods comprise administering to the patient an effective amount of fospropofol, a pharmaceutically acceptable salt of fospropofol, or mixtures thereof, at 1 hour after the administration the subject has experienced headache pain relief.

In some embodiments of the methods of treating migraine in a patient in need thereof, wherein the methods comprise administering to the patient an effective amount of fospropofol, a pharmaceutically acceptable salt of fospropofol, or mixtures thereof, at 2 hour after the administration the subject is headache free.

In other embodiments of the methods of treating migraine in a patient in need thereof, wherein the methods comprise administering to the patient an effective amount of fospropofol, a pharmaceutically acceptable salt of fospropofol, or mixtures thereof, at 2 hour after the administration the subject has experienced headache pain relief.

In some embodiments of the methods of treating migraine in a patient in need thereof, wherein the methods comprise administering to the patient an effective amount of fospropofol, a pharmaceutically acceptable salt of fospropofol, or mixtures thereof, at 4 hour after the administration the subject is headache free.

In other embodiments of the methods of treating migraine in a patient in need thereof, wherein the methods comprise administering to the patient an effective amount of fospropofol, a pharmaceutically acceptable salt of fospropofol, or mixtures thereof, at 4 hour after the administration the subject has experienced headache pain relief.

In some aspects, the methods are directed to treating migraine in a population of patients in need thereof, wherein the method comprises administering to the population an effective amount of fospropofol, a pharmaceutically acceptable salt of fospropofol, or mixtures thereof, sooner than 115 minutes after onset of migraine.

In some aspects, the methods are directed to treating migraine in a population of patients in need thereof, wherein fospropofol, a pharmaceutically acceptable salt of fospropofol, or mixtures thereof, is administered sooner than 115 minutes after onset of migraine and the Cmax of propofol is increased compared to administration after 115 minutes.

In some aspects, the methods are directed to increasing the Cmax of propofol and treating migraine in a population of patients in need thereof with fospropofol, a pharmaceutically acceptable salt of fospropofol, or mixtures thereof, wherein the fospropofol, a pharmaceutically acceptable salt of fospropofol, or mixtures thereof is administered sooner than 115 minutes after onset of migraine.

In some aspects, the methods are directed to treating migraine in a population of patients in need thereof, wherein fospropofol, a pharmaceutically acceptable salt of fospropofol, or mixtures thereof, is administered as an acidified pharmaceutical dosage form and the Cmax of propofol does not decrease if the time to treatment from migraine onset is delayed.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma fospropofol $AUC_{1hr}$ or the patient population has a mean $AUC_{1hr}$ of at least 1000 ng*h/mL, such as, for example, at least 1000 ng*h/mL, at least 1050 ng*h/mL, at least 1100 ng*h/mL, at least 1150 ng*h/mL, at least 1200 ng*h/mL, at least 1250 ng*h/mL, at least 1300 ng*h/mL, at least 1350 ng*h/mL, at least 1400 ng*h/mL, at least 1450 ng*h/mL, at least 1500 ng*h/mL, at least 1550 ng*h/mL, at least 1600 ng*h/mL, at least 1650 ng*h/mL, at least 1700 ng*h/mL, at least 1750 ng*h/mL, at least 1800 ng*h/mL, at least 1850 ng*h/mL, at least 1900 ng*h/mL, at least 1950 ng*h/mL, at least 2000 ng*h/mL, at least 2050 ng*h/mL, at least 2100 ng*h/mL, at least 2150 ng*h/mL, at least 2200 ng*h/mL, at least 2250 ng*h/mL, at least 2300 ng*h/mL, at least 2350 ng*h/mL, at least 2400 ng*h/mL, at least 2450 ng*h/mL, at least 2500 ng*h/mL, at least 2550 ng*h/mL, at least 2600 ng*h/mL, at least 2650 ng*h/mL, at least 2700 ng*h/mL, at least 2750 ng*h/mL, at least 2800 ng*h/mL, at least 2850 ng*h/mL, at least 2900 ng*h/mL, at least 2950 ng*h/mL, at least 3000 ng*h/mL, at least 3050 ng*h/mL, at least 3100 ng*h/mL, at least 3150 ng*h/mL, at least 3200 ng*h/mL, at least 3250 ng*h/mL, at least 3300 ng*h/mL, at least 3350 ng*h/mL, at least 3400 ng*h/mL, at least 3450 ng*h/mL, at least 3500 ng*h/mL, at least 3550 ng*h/mL, at least 3600 ng*h/mL, at least 3650 ng*h/mL, at least 3700 ng*h/mL, at least 3750 ng*h/mL, at least 3800 ng*h/mL, at least 3850 ng*h/mL, at least 3900 ng*h/mL, at least 3950 ng*h/mL, at least 4000 ng*h/mL, at least 4050 ng*h/mL, at least 4100 ng*h/mL, at least 4150 ng*h/mL, at least 4200 ng*h/mL, at least 4250 ng*h/mL, at least 4300 ng*h/mL, at least 4350 ng*h/mL, at least 4400 ng*h/mL, at least 4450 ng*h/mL, at least 4500 ng*h/mL, at least 4550 ng*h/mL, at least 4600 ng*h/mL, at least 4650 ng*h/mL, at least 4700 ng*h/mL, at least 4750 ng*h/mL, at least 4800 ng*h/mL, at least 4850 ng*h/mL, at least 4900 ng*h/mL, at least 4950 ng*h/mL, at least 5000 ng*h/mL, at least 5050 ng*h/mL, at least 5100 ng*h/mL, at least 5150 ng*h/mL, at least 5200 ng*h/mL, at least 5250 ng*h/mL, at least 5300 ng*h/mL, at least 5350 ng*h/mL, at least 5400 ng*h/mL, at least 5450 ng*h/mL, at least 5500 ng*h/mL, at least 5550 ng*h/mL, at least 5600 ng*h/mL, at least 5650 ng*h/mL, at least 5700 ng*h/mL, at least 5750 ng*h/mL, at least 5800 ng*h/mL, at least 5850 ng*h/mL, at least 5900 ng*h/mL, at least 5950 ng*h/mL, at least 6000 ng*h/mL, at least 6050 ng*h/mL, at least 6100 ng*h/mL, at least 6150 ng*h/mL, at least 6200 ng*h/mL, at least 6250 ng*h/mL, at least 6300 ng*h/mL, at least 6350 ng*h/mL, at least 6400 ng*h/mL, at least 6450 ng*h/mL, at least 6500 ng*h/mL, at least 6550 ng*h/mL, at least 6600 ng*h/mL, at least 6650 ng*h/mL, at least 6700 ng*h/mL, at least 6750 ng*h/mL, at least 6800 ng*h/mL, at least 6850 ng*h/mL, at least 6900 ng*h/mL, at least 6950 ng*h/mL, at least 7000 ng*h/mL, at least 7050 ng*h/mL, at least 7100 ng*h/mL, at least 7150 ng*h/mL, at least 7200 ng*h/mL, at least 7250 ng*h/mL, at least 7300 ng*h/mL, at least 7350 ng*h/mL, at least 7400 ng*h/mL, at least 7450 ng*h/mL, at least 7500 ng*h/mL, at least 7550 ng*h/mL, at least 7600 ng*h/mL, at least 7650 ng*h/mL, at least 7700 ng*h/mL, at least 7750 ng*h/mL, at least 7800 ng*h/mL, at least 7850 ng*h/mL, at least 7900 ng*h/mL, at least 7950 ng*h/mL, at least 8000 ng*h/mL, at least 8050 ng*h/mL, at least 8100 ng*h/mL, at least 8150 ng*h/mL, at least 8200 ng*h/mL, at least 8250 ng*h/mL, at least 8300 ng*h/mL, at least 8350 ng*h/mL, at least 8400 ng*h/mL, at least 8450 ng*h/mL, at least 8500 ng*h/mL, at least 8550 ng*h/mL, at least 8600 ng*h/mL, at least 8650 ng*h/mL, at least 8700 ng*h/mL, at least 8750 ng*h/mL, at least 8800 ng*h/mL, at least 8850 ng*h/mL, at least 8900 ng*h/mL, at least 8950 ng*h/mL, at least 9000 ng*h/mL, at least 9050 ng*h/mL, at least 9100 ng*h/mL, at least 9150 ng*h/mL, at least 9200 ng*h/mL, at least 9250 ng*h/mL, at least 9300 ng*h/mL, at least 9350 ng*h/mL, at least 9400 ng*h/mL, at least 9450 ng*h/mL, at least 9500 ng*h/mL, at least 9550 ng*h/mL, at least 9600 ng*h/mL, at least 9650 ng*h/mL, at least 9700 ng*h/mL, at least 9750 ng*h/mL, at least 9800 ng*h/mL, at least 9850 ng*h/mL, at least 9900 ng*h/mL, at least 9950 ng*h/mL, or at least 10000 ng*h/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma fospropofol $AUC_{1hr}$ or the patient population has a mean $AUC_{1hr}$ as set forth herein and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma fospropofol $AUC_{1hr}$ or the patient population has a mean $AUC_{1hr}$ of at least 6000 ng*h/mL and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma fospropofol $AUC_{1hr}$ or the patient population has a mean $AUC_{1hr}$ as set forth herein and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma fospropofol $AUC_{1hr}$ or the patient population has a mean $AUC_{1hr}$ of at least 2000 ng*h/mL and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma fospropofol $AUC_{1hr}$ or the patient population has a mean AUC1 hr as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma fospropofol $AUC_{1hr}$ or the patient population has a mean $AUC_{1hr}$ of at least 3000 ng*h/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has a plasma fospropofol concentration ($C_{1hr}$) or the patient population has a mean $C_{1hr}$ of at least 500 ng/mL, such as, for example, at least 500 ng/mL, at least 550 ng/mL, at least 600 ng/mL, at least 650 ng/mL, at least 700 ng/mL, at least 750 ng/mL, at least 800 ng/mL, at least 850 ng/mL, at least 900 ng/mL, at least 950 ng/mL, 1000 ng/mL, such as, for example, at least 1000 ng/mL, at least 1050 ng/mL, at least 1100 ng/mL, at least 1150 ng/mL, at least 1200 ng/mL, at least 1250 ng/mL, at least 1300 ng/mL, at least 1350 ng/mL, at least 1400 ng/mL, at least 1450 ng/mL, at least 1500 ng/mL, at least 1550 ng/mL, at least 1600 ng/mL, at least 1650 ng/mL, at least 1700 ng/mL, at least 1750 ng/mL, at least 1800 ng/mL, at least 1850 ng/mL, at least 1900 ng/mL, at least 1950 ng/mL, at least 2000 ng/mL, at least 2050 ng/mL, at least 2100 ng/mL, at least 2150 ng/mL, at least 2200 ng/mL, at least 2250 ng/mL, at least 2300 ng/mL, at least 2350 ng/mL, at least 2400 ng/mL, at least 2450 ng/mL, at least 2500 ng/mL, at least 2550 ng/mL, at least 2600 ng/mL, at least 2650 ng/mL, at least 2700 ng/mL, at least 2750 ng/mL, at least 2800 ng/mL, at least 2850 ng/mL, at least 2900 ng/mL, at least 2950 ng/mL, at least 3000 ng/mL, at least 3050 ng/mL, at least 3100 ng/mL, at least 3150 ng/mL, at least 3200 ng/mL, at least 3250 ng/mL, at least 3300 ng/mL, at least 3350 ng/mL, at least 3400 ng/mL, at least 3450 ng/mL, at least 3500 ng/mL, at least 3550 ng/mL, at least 3600 ng/mL, at least 3650 ng/mL, at least 3700 ng/mL, at least 3750 ng/mL, at least 3800 ng/mL, at least 3850 ng/mL, at least 3900 ng/mL, at least 3950 ng/mL, at least 4000 ng/mL, at least 4050 ng/mL, at least 4100 ng/mL, at least 4150 ng/mL, at least 4200 ng/mL, at least 4250 ng/mL, at least 4300 ng/mL, at least 4350 ng/mL, at least 4400 ng/mL, at least 4450 ng/mL, at least 4500 ng/mL, at least 4550 ng/mL, at least 4600 ng/mL, at least 4650 ng/mL, at least 4700 ng/mL, at least 4750 ng/mL, at least 4800 ng/mL, at least 4850 ng/mL, at least 4900 ng/mL, at least 4950 ng/mL, or at least 5000 ng/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has a plasma fospropofol concentration ($C_{1hr}$) or the patient population has a mean $C_{1hr}$ as set forth herein and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma fospropofol concentration ($C_{1hr}$) or the patient population has a mean $C_{1hr}$ of at least 2000 ng/mL and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma fospropofol concentration ($C_{1hr}$) or the patient population has a mean $C_{1hr}$ as set forth herein and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma fospropofol concentration ($C_{1hr}$) or the patient population has a mean $C_{1hr}$ of at least 1000 ng/mL and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma fospropofol concentration ($C_{1hr}$) or the patient population has a mean $C_{1hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma fospropofol concentration ($C_{1hr}$) or the patient population has a mean $C_{1hr}$ of at least 1000 ng/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma fospropofol $AUC_{2hr}$ or the patient population has a mean $AUC_{2hr}$ of at least 1000 ng*h/mL, such as, for example, at least 1000 ng*h/mL, at least 1050 ng*h/mL, at least 1100 ng*h/mL, at least 1150 ng*h/mL, at least 1200 ng*h/mL, at least 1250 ng*h/mL, at least 1300 ng*h/mL, at least 1350 ng*h/mL, at least 1400 ng*h/mL, at least 1450 ng*h/mL, at least 1500 ng*h/mL, at least 1550 ng*h/mL, at least 1600 ng*h/mL, at least 1650 ng*h/mL, at least 1700 ng*h/mL, at least 1750 ng*h/mL, at least 1800 ng*h/mL, at least 1850 ng*h/mL, at least 1900 ng*h/mL, at least 1950 ng*h/mL, at least 2000 ng*h/mL, at least 2050 ng*h/mL, at least 2100 ng*h/mL, at least 2150 ng*h/mL, at least 2200 ng*h/mL, at least 2250 ng*h/mL, at least 2300 ng*h/mL, at least 2350 ng*h/mL, at least 2400 ng*h/mL, at least 2450 ng*h/mL, at least 2500 ng*h/mL, at least 2550 ng*h/mL, at least 2600 ng*h/mL, at least 2650 ng*h/mL, at least 2700 ng*h/mL, at least 2750 ng*h/mL, at least 2800 ng*h/mL, at least 2850 ng*h/mL, at least 2900 ng*h/mL, at least 2950 ng*h/mL, at least 3000 ng*h/mL, at least 3050 ng*h/mL, at least 3100 ng*h/mL, at least 3150 ng*h/mL, at least 3200 ng*h/mL, at least 3250 ng*h/mL, at least 3300 ng*h/mL, at least 3350 ng*h/mL, at least 3400 ng*h/mL, at least 3450 ng*h/mL, at least 3500 ng*h/mL, at least 3550 ng*h/mL, at least 3600 ng*h/mL, at least 3650 ng*h/mL, at least 3700 ng*h/mL, at least 3750 ng*h/mL, at least 3800 ng*h/mL, at least 3850 ng*h/mL, at least 3900 ng*h/mL, at least 3950 ng*h/mL, at least 4000 ng*h/mL, at least 4050 ng*h/mL, at least 4100 ng*h/mL, at least 4150 ng*h/mL, at least 4200 ng*h/mL, at least 4250 ng*h/mL, at least 4300 ng*h/mL, at least 4350 ng*h/mL, at least 4400 ng*h/mL, at least 4450 ng*h/mL, at least 4500 ng*h/mL, at least 4550 ng*h/mL, at least 4600 ng*h/mL, at least 4650 ng*h/mL, at least 4700 ng*h/mL, at least 4750 ng*h/mL, at least 4800 ng*h/mL, at least 4850 ng*h/mL, at least 4900 ng*h/mL, at least 4950 ng*h/mL, at least 5000 ng*h/mL, at least 5050 ng*h/mL, at least 5100 ng*h/mL, at least 5150 ng*h/mL, at least 5200 ng*h/mL, at least 5250 ng*h/mL, at least 5300 ng*h/mL, at least 5350 ng*h/mL, at least 5400 ng*h/mL, at least 5450 ng*h/mL, at least 5500 ng*h/mL, at least 5550 ng*h/mL, at least 5600 ng*h/mL, at least 5650 ng*h/mL, at least 5700 ng*h/mL, at least 5750 ng*h/mL, at least 5800 ng*h/mL, at least 5850 ng*h/mL, at least 5900 ng*h/mL, at least 5950 ng*h/mL, at least 6000 ng*h/mL, at least 6050 ng*h/mL, at least 6100 ng*h/mL, at least 6150 ng*h/mL, at least 6200 ng*h/mL, at least 6250 ng*h/mL, at least 6300 ng*h/mL, at least 6350 ng*h/mL, at least 6400 ng*h/mL, at least 6450 ng*h/mL, at least 6500 ng*h/mL, at least 6550 ng*h/mL, at least 6600 ng*h/mL, at least 6650 ng*h/mL, at least 6700 ng*h/mL, at least 6750 ng*h/mL, at least 6800 ng*h/mL, at least 6850 ng*h/mL, at least 6900 ng*h/mL, at least 6950 ng*h/mL, at least 7000 ng*h/mL, at least 7050 ng*h/mL, at least 7100 ng*h/mL, at least 7150 ng*h/mL, at least 7200 ng*h/mL, at least 7250 ng*h/mL, at least 7300 ng*h/mL, at least 7350 ng*h/mL, at least 7400 ng*h/mL, at least 7450 ng*h/mL, at least 7500 ng*h/mL, at least 7550 ng*h/mL, at least 7600 ng*h/mL, at least 7650 ng*h/mL, at least 7700 ng*h/mL, at least 7750 ng*h/mL, at least 7800 ng*h/mL, at least 7850 ng*h/mL, at least 7900 ng*h/mL, at least 7950 ng*h/mL, at least 8000 ng*h/mL, at least 8050 ng*h/mL, at least 8100 ng*h/mL, at least 8150 ng*h/mL, at least 8200 ng*h/mL, at least 8250 ng*h/mL, at least 8300 ng*h/mL, at least 8350 ng*h/mL, at least 8400 ng*h/mL, at least 8450 ng*h/mL, at least 8500 ng*h/mL, at least 8550 ng*h/mL, at least 8600 ng*h/mL, at least 8650 ng*h/mL, at least 8700 ng*h/mL, at least 8750 ng*h/mL, at least 8800 ng*h/mL, at least 8850 ng*h/mL, at least 8900 ng*h/mL, at least 8950 ng*h/mL, at least 9000 ng*h/mL, at least 9050 ng*h/mL, at least 9100 ng*h/mL, at least 9150 ng*h/mL, at least 9200 ng*h/mL, at least 9250 ng*h/mL, at least 9300 ng*h/mL, at least 9350 ng*h/mL, at least 9400 ng*h/mL, at least 9450 ng*h/mL, at least 9500 ng*h/mL, at least 9550 ng*h/mL, at least 9600 ng*h/mL, at least 9650 ng*h/mL, at least 9700 ng*h/mL, at least 9750 ng*h/mL, at least 9800 ng*h/mL, at least 9850 ng*h/mL, at least 9900 ng*h/mL, at least 9950 ng*h/mL, or at least 10000 ng*h/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma fospropofol $AUC_{2hr}$ or the patient population has a mean $AUC_{2hr}$ as set forth herein and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma fospropofol $AUC_{2hr}$ or the patient population has a mean $AUC_{2hr}$ of at least 3000 ng*h/mL and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma fospropofol $AUC_{2hr}$ or the patient population has a mean $AUC_{2hr}$ as set forth herein and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma fospropofol $AUC_{2hr}$ or the patient population has a mean $AUC_{2hr}$ of at least 1000 ng*h/mL and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma fospropofol $AUC_{2hr}$ or the patient population has a mean $AUC_{2hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma fospropofol $AUC_{2hr}$ or the patient population has a mean $AUC_{2hr}$ of at least 1000 ng*h/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hour after the administration the patient has plasma fospropofol concentration ($C_{2hr}$) or the patient population has a mean $C_{2hr}$ of at least 25 ng/mL, such as, for example, at least 25 ng/mL, at least 50 ng/mL, at least 75 ng/mL, at least 100 ng/mL, at least 125 ng/mL, at least 150 ng/mL, at least 175 ng/mL, at least 200 ng/mL, at least 225 ng/mL, at least 250 ng/mL, 275 ng/mL, at least 300 ng/mL, at least 325 ng/mL, at least 350 ng/mL, at least 400 ng/mL, at least 425 ng/mL, at least 450 ng/mL, at least 475 ng/mL, at least 500 ng/mL, at least 525 ng/mL, at least 550 ng/mL, at least 575 ng/mL, at least 600 ng/mL, at least 625 ng/mL, at least 650 ng/mL, at least 675 ng/mL, at least 700 ng/mL, at least 725 ng/mL, at least 750 ng/mL, at least 775 ng/mL, at least 800 ng/mL, at least 825 ng/mL, at least 850 ng/mL, at least 875 ng/mL, at least 900 ng/mL, at least 925 ng/mL, at least 950 ng/mL, at least 975 ng/mL, at least 1000 ng/mL, at least 1100 ng/mL, at least 1125 ng/mL, at least 1150 ng/mL, at least 1175 ng/mL, at least 1200 ng/mL, at least 1225 ng/mL, at least 1250 ng/mL, 1275 ng/mL, at least 1300 ng/mL, at least 1325 ng/mL, at least 1350 ng/mL, at least 1400 ng/mL, at least 1425 ng/mL, at least 1450 ng/mL, at least 1475 ng/mL, at least 1500 ng/mL, at least 1525 ng/mL, at least 1550 ng/mL, at least 1575 ng/mL, at least 1600 ng/mL, at least 1625 ng/mL, at least 1650 ng/mL, at least 1675 ng/mL, at least 1700 ng/mL, at least 1725 ng/mL, at least 1750 ng/mL, at least 1775 ng/mL, at least 1800 ng/mL, at least 1825 ng/mL, at least 1850 ng/mL, at least 1875 ng/mL, at least 1900 ng/mL, at least 1925 ng/mL, at least 1950 ng/mL, at least 1975 ng/mL, or at least 2000 ng/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has a plasma fospropofol concentration ($C_{2hr}$) or the patient population has a mean $C_{2hr}$ as set forth herein and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hour after the administration the patient has plasma fospropofol concentration ($C_{2hr}$) or the patient population has a mean $C_{2hr}$ of at least 100 ng/mL and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma fospropofol concentration ($C_{2hr}$) or the patient population has a mean $C_{2hr}$ as set forth herein and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma fospropofol concentration ($C_{2hr}$) or the patient population has a mean $C_{2hr}$ of at least 40 ng/mL and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma fospropofol concentration ($C_{2hr}$) or the patient population has a mean $C_{2hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma fospropofol concentration ($C_{2hr}$) or the patient population has a mean $C_{2hr}$ of at least 50 ng/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient is headache free, has experienced a reduction in headache pain, is no longer experiencing a most bothersome symptom, or is no longer experiencing a bothersome symptom, and the plasma Cmax or the patient population mean Cmax of propofol is at least any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3050 ng/mL, 3100 ng/mL, 3150 ng/mL, 3200 ng/mL, 3250 ng/mL, 3300 ng/mL, 3350 ng/mL, 3400 ng/mL, 3450 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, or 4000 ng/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient is headache free, has experienced a reduction in headache pain, is no longer experiencing a most bothersome symptom, or is no longer experiencing a bothersome symptom and the plasma Cmax or the patient population mean Cmax of fospropofol (or a pharmaceutically acceptable salt of fospropofol) is at least any one of 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 1950 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, 4000 ng/mL, 4050 ng/mL, 4100 ng/mL, 4150 ng/mL, 4200 ng/mL, 4250 ng/mL, 4300 ng/mL, 4350 ng/mL, 4400 ng/mL, 4450 ng/mL, 4500 ng/mL, 4550 ng/mL, 4600 ng/mL, 4650 ng/mL, 4700 ng/mL, 4750 ng/mL, 4800 ng/mL, 4850 ng/mL, 4900 ng/mL, 4950 ng/mL, 5000 ng/mL, 5050 ng/mL, 5100 ng/mL, 5150 ng/mL, 5200 ng/mL, 5250 ng/mL, 5300 ng/mL, 5350 ng/mL, 5400 ng/mL, 5450 ng/mL, 5500 ng/mL, 5550 ng/mL, 5600 ng/mL, 5650 ng/mL, 5700 ng/mL, 5750 ng/mL, 5800 ng/mL, 5850 ng/mL, 5900 ng/mL, 5950 ng/mL, 6000 ng/mL, 6050 ng/mL, 6100 ng/mL, 6150 ng/mL, 6200 ng/mL, 6250 ng/mL, 6300 ng/mL, 6350 ng/mL, 6400 ng/mL, 6450 ng/mL, 6500 ng/mL, 6550 ng/mL, 6600 ng/mL, 6650 ng/mL, 6700 ng/mL, 6750 ng/mL, 6800 ng/mL, 6850 ng/mL, 6900 ng/mL, 6950 ng/mL, 7000 ng/mL, 7050 ng/mL, 7100 ng/mL, 7150 ng/mL, 7200 ng/mL, 7250 ng/mL, 7300 ng/mL, 7350 ng/mL, 7400 ng/mL, 7450 ng/mL, 7500 ng/mL, 7550 ng/mL, 7600 ng/mL, 7650 ng/mL, 7700 ng/mL, 7750 ng/mL, 7800 ng/mL, 7850 ng/mL, 7900 ng/mL, 7950 ng/mL, 8000 ng/mL, 8050 ng/mL, 8100 ng/mL, 8150 ng/mL, 8200 ng/mL, 8250 ng/mL, 8300 ng/mL, 8350 ng/mL, 8400 ng/mL, 8450 ng/mL, 8500 ng/mL, 8550 ng/mL, 8600 ng/mL, 8650 ng/mL, 8700 ng/mL, 8750 ng/mL, 800 ng/mL, 8850 ng/mL, 8900 ng/mL, 8950 ng/mL, 9000 ng/mL, 9050 ng/mL, 9100 ng/mL, 9150 ng/mL, 9200 ng/mL, 9250 ng/mL, 9300 ng/mL, 9350 ng/mL, 9400 ng/mL, 9450 ng/mL, 9500 ng/mL, 9550 ng/mL, 9600 ng/mL, 9650 ng/mL, 9700 ng/mL, 9750 ng/mL, 9000 ng/mL, 9950 ng/mL, 9900 ng/mL, 9950 ng/mL, 10000 ng/mL, 10050 ng/mL, 10100 ng/mL, 10150 ng/mL, 10200 ng/mL, 10250 ng/mL, 10300 ng/mL, 10350 ng/mL, 10400 ng/mL, 10450 ng/mL, 10500 ng/mL, 10550 ng/mL, 10600 ng/mL, 10650 ng/mL, 10700 ng/mL, 10750 ng/mL, 1000 ng/mL, 101050 ng/mL, 10900 ng/mL, 10950 ng/mL, 11000 ng/mL, 11050 ng/mL, 11100 ng/mL, 11150 ng/mL, 11200 ng/mL, 11250 ng/mL, 11300 ng/mL, 11350 ng/mL, 11400 ng/mL, 11450 ng/mL, 11500 ng/mL, 11550 ng/mL, 11600 ng/mL, 11650 ng/mL, 11700 ng/mL, 11750 ng/mL, 1100 ng/mL, 111150 ng/mL, 11900 ng/mL, 11950 ng/mL, 12000 ng/mL, 12050 ng/mL, 12100 ng/mL, 12150 ng/mL, 12200 ng/mL, 12250 ng/mL, 12300 ng/mL, 12350 ng/mL, 12400 ng/mL, 12450 ng/mL, 12500 ng/mL, 12550 ng/mL, 12600 ng/mL, 12650 ng/mL, 12700 ng/mL, 12750 ng/mL, 1200 ng/mL, 121250 ng/mL, 12900 ng/mL, 12950 ng/mL, 13000 ng/mL, 13050 ng/mL, 13100 ng/mL, 13150 ng/mL, 13200 ng/mL, 13250 ng/mL, 13300 ng/mL, 13350 ng/mL, 13400 ng/mL, 13450 ng/mL, 13500 ng/mL, 13550 ng/mL, 13600 ng/mL, 13650 ng/mL, 13700 ng/mL, 13750 ng/mL, 1300 ng/mL, 131350 ng/mL, 13900 ng/mL, 13950 ng/mL, 14000 ng/mL, 14050 ng/mL, 14100 ng/mL, 14150 ng/mL, 14200 ng/mL, 14250 ng/mL, 14300 ng/mL, 14350 ng/mL, 14400 ng/mL, 14450 ng/mL, 14500 ng/mL, 14550 ng/mL, 14600 ng/mL, 14650 ng/mL, 14700 ng/mL, 14750 ng/mL, 1400 ng/mL, 141450 ng/mL, 14900 ng/mL, 14950 ng/mL, 15000 ng/mL, 15050 ng/mL, 15100 ng/mL, 15150 ng/mL, 15200 ng/mL, 15250 ng/mL, 15300 ng/mL, 15350 ng/mL, 15400 ng/mL, 15450 ng/mL, 15500 ng/mL, 15550 ng/mL, 15600 ng/mL, 15650 ng/mL, 15700 ng/mL, 15750 ng/mL, 1500 ng/mL, 151550 ng/mL, 15900 ng/mL, 15950 ng/mL, 16000 ng/mL, 16050 ng/mL, 16100 ng/mL, 16150 ng/mL, 16200 ng/mL, 16250 ng/mL, 16300 ng/mL, 16350 ng/mL, 16400 ng/mL, 16450 ng/mL, 16500 ng/mL, 16550 ng/mL, 16600 ng/mL, 16650 ng/mL, 16700 ng/mL, 16750 ng/mL, 1600 ng/mL, 161650 ng/mL, 16900 ng/mL, 16950 ng/mL, 17000 ng/mL, 17050 ng/mL, 17100 ng/mL, 17150 ng/mL, 17200 ng/mL, 17250 ng/mL, 17300 ng/mL, 17350 ng/mL, 17400 ng/mL, 17450 ng/mL, 17500 ng/mL, 17550 ng/mL, 17600 ng/mL, 17650 ng/mL, 17700 ng/mL, 17750 ng/mL, 1700 ng/mL, 171750 ng/mL, 17900 ng/mL, 17950 ng/mL, or 18000 ng/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient is headache free, has experienced a reduction in headache pain, is no longer experiencing a most bothersome symptom, or is no longer experiencing a bothersome symptom and the propofol plasma $AUC_{0-\infty}$ per mg of fospropofol (or a pharmaceutically acceptable salt of fospropofol) administered or the propofol patient population mean $AUC_{0-\infty}$ per mg of fospropofol (or a pharmaceutically acceptable salt of fospropofol) administered is, at least any one of 0.5 ng*h/mL/mg, 0.55 ng*h/mL/mg, 0.6 ng*h/mL/mg, 0.65 ng*h/mL/mg, 0.7 ng*h/mL/mg, 0.75 ng*h/mL/mg, 0.8 ng*h/mL/mg, 0.85 ng*h/mL/mg, 0.9 ng*h/mL/mg, 0.95 ng*h/mL/mg, 1.0 ng*h/mL/mg, 1.05 ng*h/mL/mg, 1.10 ng*h/mL/mg, 1.15 ng*h/mL/mg, 1.2 ng*h/mL/mg, 1.25 ng*h/mL/mg, 1.3 ng*h/mL/mg, 1.35 ng*h/mL/mg, 1.4 ng*h/mL/mg, 1.45 ng*h/mL/mg, 1.5 ng*h/mL/mg, 1.55 ng*h/mL/mg, 1.6 ng*h/mL/mg, 1.65 ng*h/mL/mg, or 1.7 ng*h/mL/mg.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient is headache free, has experienced a reduction in headache pain, is no longer experiencing a most bothersome symptom, or is no longer experiencing a bothersome symptom and the fospropofol plasma $AUC_{0-\infty}$ per mg of fospropofol (or a pharmaceutically acceptable salt of fospropofol) administered or the fospropofol patient population mean $AUC_{0-\infty}$ per mg of fospropofol (or a pharmaceutically acceptable salt of fospropofol) administered is at least 3.0 ng*h/mL, such as, for example, at least any one of 3.0 ng*h/mL/mg, 3.1 ng*h/mL/mg, 3.2 ng*h/mL/mg, 3.3 ng*h/mL/mg, 3.4 ng*h/mL/mg, 3.5 ng*h/mL/mg, 3.6 ng*h/mL/mg, 3.7 ng*h/mL/mg, 3.8 ng*h/mL/mg, 3.9 ng*h/mL/mg, 4.0 ng*h/mL/mg, 4.1 ng*h/mL/mg, 4.2 ng*h/mL/mg, 4.3 ng*h/mL/mg, 4.4 ng*h/mL/mg, 4.5 ng*h/mL/mg, 4.6 ng*h/mL/mg, 4.7 ng*h/mL/mg, 4.8 ng*h/mL/mg, 4.9 ng*h/mL/mg, 5.0 ng*h/mL/mg, 5.1 ng*h/mL/mg, 5.2 ng*h/mL/mg, 5.3 ng*h/mL/mg, 5.4 ng*h/mL/mg, 5.5 ng*h/mL/mg, 5.6 ng*h/mL/mg, 5.7 ng*h/mL/mg, 5.8 ng*h/mL/mg, 5.9 ng*h/mL/mg, 6.0 ng*h/mL/mg, 6.1 ng*h/mL/mg, 6.2 ng*h/mL/mg, 6.3 ng*h/mL/mg, 6.4 ng*h/mL/mg, 6.5 ng*h/mL/mg, 6.6 ng*h/mL/mg, 6.7 ng*h/mL/mg, 6.8 ng*h/mL/mg, 6.9 ng*h/mL/mg, 7.0 ng*h/mL/mg, 7.1 ng*h/mL/mg, 7.2 ng*h/mL/mg, 7.3 ng*h/mL/mg, 7.4 ng*h/mL/mg, 7.5 ng*h/mL/mg, 7.6 ng*h/mL/mg, 7.7 ng*h/mL/mg, 7.8 ng*h/mL/mg, 7.9 ng*h/mL/mg, 8.0 ng*h/mL/mg, 8.1 ng*h/mL/mg, 8.2 ng*h/mL/mg, 8.3 ng*h/mL/mg, 8.4 ng*h/mL/mg, 8.5 ng*h/mL/mg, 8.6 ng*h/mL/mg, 8.7 ng*h/mL/mg, 8.8 ng*h/mL/mg, 8.9 ng*h/mL/mg, or 9.0 ng*h/mL/mg.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient is headache free, has experienced a reduction in headache pain, is no longer experiencing a most bothersome symptom, or is no longer experiencing a bothersome symptom, and the plasma Cmax or the patient population mean Cmax of propofol is at least any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3050 ng/mL, 3100 ng/mL, 3150 ng/mL, 3200 ng/mL, 3250 ng/mL, 3300 ng/mL, 3350 ng/mL, 3400 ng/mL, 3450 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, or 4000 ng/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient is headache free, has experienced a reduction in headache pain, is no longer experiencing a most bothersome symptom, or is no longer experiencing a bothersome symptom and the plasma Cmax or the patient population mean Cmax of fospropofol (or a pharmaceutically acceptable salt of fospropofol) is at least any one of 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 1950 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, 4000 ng/mL, 4050 ng/mL, 4100 ng/mL, 4150 ng/mL, 4200 ng/mL, 4250 ng/mL, 4300 ng/mL, 4350 ng/mL, 4400 ng/mL, 4450 ng/mL, 4500 ng/mL, 4550 ng/mL, 4600 ng/mL, 4650 ng/mL, 4700 ng/mL, 4750 ng/mL, 4800 ng/mL, 4850 ng/mL, 4900 ng/mL, 4950 ng/mL, 5000 ng/mL, 5050 ng/mL, 5100 ng/mL, 5150 ng/mL, 5200 ng/mL, 5250 ng/mL, 5300 ng/mL, 5350 ng/mL, 5400 ng/mL, 5450 ng/mL, 5500 ng/mL, 5550 ng/mL, 5600 ng/mL, 5650 ng/mL, 5700 ng/mL, 5750 ng/mL, 5800 ng/mL, 5850 ng/mL, 5900 ng/mL, 5950 ng/mL, 6000 ng/mL, 6050 ng/mL, 6100 ng/mL, 6150 ng/mL, 6200 ng/mL, 6250 ng/mL, 6300 ng/mL, 6350 ng/mL, 6400 ng/mL, 6450 ng/mL, 6500 ng/mL, 6550 ng/mL, 6600 ng/mL, 6650 ng/mL, 6700 ng/mL, 6750 ng/mL, 6800 ng/mL, 6850 ng/mL, 6900 ng/mL, 6950 ng/mL, 7000 ng/mL, 7050 ng/mL, 7100 ng/mL, 7150 ng/mL, 7200 ng/mL, 7250 ng/mL, 7300 ng/mL, 7350 ng/mL, 7400 ng/mL, 7450 ng/mL, 7500 ng/mL, 7550 ng/mL, 7600 ng/mL, 7650 ng/mL, 7700 ng/mL, 7750 ng/mL, 7800 ng/mL, 7850 ng/mL, 7900 ng/mL, 7950 ng/mL, 8000 ng/mL, 8050 ng/mL, 8100 ng/mL, 8150 ng/mL, 8200 ng/mL, 8250 ng/mL, 8300 ng/mL, 8350 ng/mL, 8400 ng/mL, 8450 ng/mL, 8500 ng/mL, 8550 ng/mL, 8600 ng/mL, 8650 ng/mL, 8700 ng/mL, 8750 ng/mL, 800 ng/mL, 8850 ng/mL, 8900 ng/mL, 8950 ng/mL, 9000 ng/mL, 9050 ng/mL, 9100 ng/mL, 9150 ng/mL, 9200 ng/mL, 9250 ng/mL, 9300 ng/mL, 9350 ng/mL, 9400 ng/mL, 9450 ng/mL, 9500 ng/mL, 9550 ng/mL, 9600 ng/mL, 9650 ng/mL, 9700 ng/mL, 9750 ng/mL, 9000 ng/mL, 9950 ng/mL, 9900 ng/mL, 9950 ng/mL, 10000 ng/mL, 10050 ng/mL, 10100 ng/mL, 10150 ng/mL, 10200 ng/mL, 10250 ng/mL, 10300 ng/mL, 10350 ng/mL, 10400 ng/mL, 10450 ng/mL, 10500 ng/mL, 10550 ng/mL, 10600 ng/mL, 10650 ng/mL, 10700 ng/mL, 10750 ng/mL, 1000 ng/mL, 101050 ng/mL, 10900 ng/mL, 10950 ng/mL, 11000 ng/mL, 11050 ng/mL, 11100 ng/mL, 11150 ng/mL, 11200 ng/mL, 11250 ng/mL, 11300 ng/mL, 11350 ng/mL, 11400 ng/mL, 11450 ng/mL, 11500 ng/mL, 11550 ng/mL, 11600 ng/mL, 11650 ng/mL, 11700 ng/mL, 11750 ng/mL, 1100 ng/mL, 111150 ng/mL, 11900 ng/mL, 11950 ng/mL, 12000 ng/mL, 12050 ng/mL, 12100 ng/mL, 12150 ng/mL, 12200 ng/mL, 12250 ng/mL, 12300 ng/mL, 12350 ng/mL, 12400 ng/mL, 12450 ng/mL, 12500 ng/mL, 12550 ng/mL, 12600 ng/mL, 12650 ng/mL, 12700 ng/mL, 12750 ng/mL, 1200 ng/mL, 121250 ng/mL, 12900 ng/mL, 12950 ng/mL, 13000 ng/mL, 13050 ng/mL, 13100 ng/mL, 13150 ng/mL, 13200 ng/mL, 13250 ng/mL, 13300 ng/mL, 13350 ng/mL, 13400 ng/mL, 13450 ng/mL, 13500 ng/mL, 13550 ng/mL, 13600 ng/mL, 13650 ng/mL, 13700 ng/mL, 13750 ng/mL, 1300 ng/mL, 131350 ng/mL, 13900 ng/mL, 13950 ng/mL, 14000 ng/mL, 14050 ng/mL, 14100 ng/mL, 14150 ng/mL, 14200 ng/mL, 14250 ng/mL, 14300 ng/mL, 14350 ng/mL, 14400 ng/mL, 14450 ng/mL, 14500 ng/mL, 14550 ng/mL, 14600 ng/mL, 14650 ng/mL, 14700 ng/mL, 14750 ng/mL, 1400 ng/mL, 141450 ng/mL, 14900 ng/mL, 14950 ng/mL, 15000 ng/mL, 15050 ng/mL, 15100 ng/mL, 15150 ng/mL, 15200 ng/mL, 15250 ng/mL, 15300 ng/mL, 15350 ng/mL, 15400 ng/mL, 15450 ng/mL, 15500 ng/mL, 15550 ng/mL, 15600 ng/mL, 15650 ng/mL, 15700 ng/mL, 15750 ng/mL, 1500 ng/mL, 151550 ng/mL, 15900 ng/mL, 15950 ng/mL, 16000 ng/mL, 16050 ng/mL, 16100 ng/mL, 16150 ng/mL, 16200 ng/mL, 16250 ng/mL, 16300 ng/mL, 16350 ng/mL, 16400 ng/mL, 16450 ng/mL, 16500 ng/mL, 16550 ng/mL, 16600 ng/mL, 16650 ng/mL, 16700 ng/mL, 16750 ng/mL, 1600 ng/mL, 161650 ng/mL, 16900 ng/mL, 16950 ng/mL, 17000 ng/mL, 17050 ng/mL, 17100 ng/mL, 17150 ng/mL, 17200 ng/mL, 17250 ng/mL, 17300 ng/mL, 17350 ng/mL, 17400 ng/mL, 17450 ng/mL, 17500 ng/mL, 17550 ng/mL, 17600 ng/mL, 17650 ng/mL, 17700 ng/mL, 17750 ng/mL, 1700 ng/mL, 171750 ng/mL, 17900 ng/mL, 17950 ng/mL, or 18000 ng/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient is headache free, has experienced a reduction in headache pain, is no longer experiencing a most bothersome symptom, or is no longer experiencing a bothersome symptom and the propofol plasma $AUC_{0-\infty}$ per mg of fospropofol (or a pharmaceutically acceptable salt of fospropofol) administered or the propofol patient population mean $AUC_{0-\infty}$ per mg of fospropofol (or a pharmaceutically acceptable salt of fospropofol) administered is, at least any one of 0.5 ng*h/mL/mg, 0.55 ng*h/mL/mg, 0.6 ng*h/mL/mg, 0.65 ng*h/mL/mg, 0.7 ng*h/mL/mg, 0.75 ng*h/mL/mg, 0.8 ng*h/mL/mg, 0.85 ng*h/mL/mg, 0.9 ng*h/mL/mg, 0.95 ng*h/mL/mg, 1.0 ng*h/mL/mg, 1.05 ng*h/mL/mg, 1.10 ng*h/mL/mg, 1.15 ng*h/mL/mg, 1.2 ng*h/mL/mg, 1.25 ng*h/mL/mg, 1.3 ng*h/mL/mg, 1.35 ng*h/mL/mg, 1.4 ng*h/mL/mg, 1.45 ng*h/mL/mg, 1.5 ng*h/mL/mg, 1.55 ng*h/mL/mg, 1.6 ng*h/mL/mg, 1.65 ng*h/mL/mg, or 1.7 ng*h/mL/mg.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient is headache free, has experienced a reduction in headache pain, is no longer experiencing a most bothersome symptom, or is no longer experiencing a bothersome symptom and the fospropofol plasma $AUC_{0-\infty}$ per mg of fospropofol (or a pharmaceutically acceptable salt of fospropofol) administered or the fospropofol patient population mean $AUC_{0-\infty}$ per mg of fospropofol (or a pharmaceutically acceptable salt of fospropofol) administered is at least 3.0 ng*h/mL, such as, for example, at least any one of 3.0 ng*h/mL/mg, 3.1 ng*h/mL/mg, 3.2 ng*h/mL/mg, 3.3 ng*h/mL/mg, 3.4 ng*h/mL/mg, 3.5 ng*h/mL/mg, 3.6 ng*h/mL/mg, 3.7 ng*h/mL/mg, 3.8 ng*h/mL/mg, 3.9 ng*h/mL/mg, 4.0 ng*h/mL/mg, 4.1 ng*h/mL/mg, 4.2 ng*h/mL/mg, 4.3 ng*h/mL/mg, 4.4 ng*h/mL/mg, 4.5 ng*h/mL/mg, 4.6 ng*h/mL/mg, 4.7 ng*h/mL/mg, 4.8 ng*h/mL/mg, 4.9 ng*h/mL/mg, 5.0 ng*h/mL/mg, 5.1 ng*h/mL/mg, 5.2 ng*h/mL/mg, 5.3 ng*h/mL/mg, 5.4 ng*h/mL/mg, 5.5 ng*h/mL/mg, 5.6 ng*h/mL/mg, 5.7 ng*h/mL/mg, 5.8 ng*h/mL/mg, 5.9 ng*h/mL/mg, 6.0 ng*h/mL/mg, 6.1 ng*h/mL/mg, 6.2 ng*h/mL/mg, 6.3 ng*h/mL/mg, 6.4 ng*h/mL/mg, 6.5 ng*h/mL/mg, 6.6 ng*h/mL/mg, 6.7 ng*h/mL/mg, 6.8 ng*h/mL/mg, 6.9 ng*h/mL/mg, 7.0 ng*h/mL/mg, 7.1 ng*h/mL/mg, 7.2 ng*h/mL/mg, 7.3 ng*h/mL/mg, 7.4 ng*h/mL/mg, 7.5 ng*h/mL/mg, 7.6 ng*h/mL/mg, 7.7 ng*h/mL/mg, 7.8 ng*h/mL/mg, 7.9 ng*h/mL/mg, 8.0 ng*h/mL/mg, 8.1 ng*h/mL/mg, 8.2 ng*h/mL/mg, 8.3 ng*h/mL/mg, 8.4 ng*h/mL/mg, 8.5 ng*h/mL/mg, 8.6 ng*h/mL/mg, 8.7 ng*h/mL/mg, 8.8 ng*h/mL/mg, 8.9 ng*h/mL/mg, or 9.0 ng*h/mL/mg.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient is headache free, has experienced a reduction in headache pain, is no longer experiencing a most bothersome symptom, or is no longer experiencing a bothersome symptom, and the plasma Cmax or the patient population mean Cmax of propofol is at least any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3050 ng/mL, 3100 ng/mL, 3150 ng/mL, 3200 ng/mL, 3250 ng/mL, 3300 ng/mL, 3350 ng/mL, 3400 ng/mL, 3450 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, or 4000 ng/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient is headache free, has experienced a reduction in headache pain, is no longer experiencing a most bothersome symptom, or is no longer experiencing a bothersome symptom and the plasma Cmax or the patient population mean Cmax of fospropofol (or a pharmaceutically acceptable salt of fospropofol) is at least any one of 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 1950 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, 4000 ng/mL, 4050 ng/mL, 4100 ng/mL, 4150 ng/mL, 4200 ng/mL, 4250 ng/mL, 4300 ng/mL, 4350 ng/mL, 4400 ng/mL, 4450 ng/mL, 4500 ng/mL, 4550 ng/mL, 4600 ng/mL, 4650 ng/mL, 4700 ng/mL, 4750 ng/mL, 4800 ng/mL, 4850 ng/mL, 4900 ng/mL, 4950 ng/mL, 5000 ng/mL, 5050 ng/mL, 5100 ng/mL, 5150 ng/mL, 5200 ng/mL, 5250 ng/mL, 5300 ng/mL, 5350 ng/mL, 5400 ng/mL, 5450 ng/mL, 5500 ng/mL, 5550 ng/mL, 5600 ng/mL, 5650 ng/mL, 5700 ng/mL, 5750 ng/mL, 5800 ng/mL, 5850 ng/mL, 5900 ng/mL, 5950 ng/mL, 6000 ng/mL, 6050 ng/mL, 6100 ng/mL, 6150 ng/mL, 6200 ng/mL, 6250 ng/mL, 6300 ng/mL, 6350 ng/mL, 6400 ng/mL, 6450 ng/mL, 6500 ng/mL, 6550 ng/mL, 6600 ng/mL, 6650 ng/mL, 6700 ng/mL, 6750 ng/mL, 6800 ng/mL, 6850 ng/mL, 6900 ng/mL, 6950 ng/mL, 7000 ng/mL, 7050 ng/mL, 7100 ng/mL, 7150 ng/mL, 7200 ng/mL, 7250 ng/mL, 7300 ng/mL, 7350 ng/mL, 7400 ng/mL, 7450 ng/mL, 7500 ng/mL, 7550 ng/mL, 7600 ng/mL, 7650 ng/mL, 7700 ng/mL, 7750 ng/mL, 7800 ng/mL, 7850 ng/mL, 7900 ng/mL, 7950 ng/mL, 8000 ng/mL, 8050 ng/mL, 8100 ng/mL, 8150 ng/mL, 8200 ng/mL, 8250 ng/mL, 8300 ng/mL, 8350 ng/mL, 8400 ng/mL, 8450 ng/mL, 8500 ng/mL, 8550 ng/mL, 8600 ng/mL, 8650 ng/mL, 8700 ng/mL, 8750 ng/mL, 800 ng/mL, 8850 ng/mL, 8900 ng/mL, 8950 ng/mL, 9000 ng/mL, 9050 ng/mL, 9100 ng/mL, 9150 ng/mL, 9200 ng/mL, 9250 ng/mL, 9300 ng/mL, 9350 ng/mL, 9400 ng/mL, 9450 ng/mL, 9500 ng/mL, 9550 ng/mL, 9600 ng/mL, 9650 ng/mL, 9700 ng/mL, 9750 ng/mL, 9000 ng/mL, 9950 ng/mL, 9900 ng/mL, 9950 ng/mL, 10000 ng/mL, 10050 ng/mL, 10100 ng/mL, 10150 ng/mL, 10200 ng/mL, 10250 ng/mL, 10300 ng/mL, 10350 ng/mL, 10400 ng/mL, 10450 ng/mL, 10500 ng/mL, 10550 ng/mL, 10600 ng/mL, 10650 ng/mL, 10700 ng/mL, 10750 ng/mL, 1000 ng/mL, 101050 ng/mL, 10900 ng/mL, 10950 ng/mL, 11000 ng/mL, 11050 ng/mL, 11100 ng/mL, 11150 ng/mL, 11200 ng/mL, 11250 ng/mL, 11300 ng/mL, 11350 ng/mL, 11400 ng/mL, 11450 ng/mL, 11500 ng/mL, 11550 ng/mL, 11600 ng/mL, 11650 ng/mL, 11700 ng/mL, 11750 ng/mL, 1100 ng/mL, 111150 ng/mL, 11900 ng/mL, 11950 ng/mL, 12000 ng/mL, 12050 ng/mL, 12100 ng/mL, 12150 ng/mL, 12200 ng/mL, 12250 ng/mL, 12300 ng/mL, 12350 ng/mL, 12400 ng/mL, 12450 ng/mL, 12500 ng/mL, 12550 ng/mL, 12600 ng/mL, 12650 ng/mL, 12700 ng/mL, 12750 ng/mL, 1200 ng/mL, 121250 ng/mL, 12900 ng/mL, 12950 ng/mL, 13000 ng/mL, 13050 ng/mL, 13100 ng/mL, 13150 ng/mL, 13200 ng/mL, 13250 ng/mL, 13300 ng/mL, 13350 ng/mL, 13400 ng/mL, 13450 ng/mL, 13500 ng/mL, 13550 ng/mL, 13600 ng/mL, 13650 ng/mL, 13700 ng/mL, 13750 ng/mL, 1300 ng/mL, 131350 ng/mL, 13900 ng/mL, 13950 ng/mL, 14000 ng/mL, 14050 ng/mL, 14100 ng/mL, 14150 ng/mL, 14200 ng/mL, 14250 ng/mL, 14300 ng/mL, 14350 ng/mL, 14400 ng/mL, 14450 ng/mL, 14500 ng/mL, 14550 ng/mL, 14600 ng/mL, 14650 ng/mL, 14700 ng/mL, 14750 ng/mL, 1400 ng/mL, 141450 ng/mL, 14900 ng/mL, 14950 ng/mL, 15000 ng/mL, 15050 ng/mL, 15100 ng/mL, 15150 ng/mL, 15200 ng/mL, 15250 ng/mL, 15300 ng/mL, 15350 ng/mL, 15400 ng/mL, 15450 ng/mL, 15500 ng/mL, 15550 ng/mL, 15600 ng/mL, 15650 ng/mL, 15700 ng/mL, 15750 ng/mL, 1500 ng/mL, 151550 ng/mL, 15900 ng/mL, 15950 ng/mL, 16000 ng/mL, 16050 ng/mL, 16100 ng/mL, 16150 ng/mL, 16200 ng/mL, 16250 ng/mL, 16300 ng/mL, 16350 ng/mL, 16400 ng/mL, 16450 ng/mL, 16500 ng/mL, 16550 ng/mL, 16600 ng/mL, 16650 ng/mL, 16700 ng/mL, 16750 ng/mL, 1600 ng/mL, 161650 ng/mL, 16900 ng/mL, 16950 ng/mL, 17000 ng/mL, 17050 ng/mL, 17100 ng/mL, 17150 ng/mL, 17200 ng/mL, 17250 ng/mL, 17300 ng/mL, 17350 ng/mL, 17400 ng/mL, 17450 ng/mL, 17500 ng/mL, 17550 ng/mL, 17600 ng/mL, 17650 ng/mL, 17700 ng/mL, 17750 ng/mL, 17700 ng/mL, 171750 ng/mL, 17900 ng/mL, 17950 ng/mL, or 18000 ng/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient is headache free, has experienced a reduction in headache pain, is no longer experiencing a most bothersome symptom, or is no longer experiencing a bothersome symptom and the propofol plasma $AUC_{0-\infty}$ per mg of fospropofol (or a pharmaceutically acceptable salt of fospropofol) administered or the propofol patient population mean $AUC_{0-\infty}$ per mg of fospropofol (or a pharmaceutically acceptable salt of fospropofol) administered is, at least any one of 0.5 ng*h/mL/mg, 0.55 ng*h/mL/mg, 0.6 ng*h/mL/mg, 0.65 ng*h/mL/mg, 0.7 ng*h/mL/mg, 0.75 ng*h/mL/mg, 0.8 ng*h/mL/mg, 0.85 ng*h/mL/mg, 0.9 ng*h/mL/mg, 0.95 ng*h/mL/mg, 1.0 ng*h/mL/mg, 1.05 ng*h/mL/mg, 1.10 ng*h/mL/mg, 1.15 ng*h/mL/mg, 1.2 ng*h/mL/mg, 1.25 ng*h/mL/mg, 1.3 ng*h/mL/mg, 1.35 ng*h/mL/mg, 1.4 ng*h/mL/mg, 1.45 ng*h/mL/mg, 1.5 ng*h/mL/mg, 1.55 ng*h/mL/mg, 1.6 ng*h/mL/mg, 1.65 ng*h/mL/mg, or 1.7 ng*h/mL/mg.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient is headache free, has experienced a reduction in headache pain, is no longer experiencing a most bothersome symptom, or is no longer experiencing a bothersome symptom and the fospropofol plasma $AUC_{0-\infty}$ per mg of fospropofol (or a pharmaceutically acceptable salt of fospropofol) administered or the fospropofol patient population mean $AUC_{0-\infty}$ per mg of fospropofol (or a pharmaceutically acceptable salt of fospropofol) administered is at least 3.0 ng*h/mL, such as, for example, at least any one of 3.0 ng*h/mL/mg, 3.1 ng*h/mL/mg, 3.2 ng*h/mL/mg, 3.3 ng*h/mL/mg, 3.4 ng*h/mL/mg, 3.5 ng*h/mL/mg, 3.6 ng*h/mL/mg, 3.7 ng*h/mL/mg, 3.8 ng*h/mL/mg, 3.9 ng*h/mL/mg, 4.0 ng*h/mL/mg, 4.1 ng*h/mL/mg, 4.2 ng*h/mL/mg, 4.3 ng*h/mL/mg, 4.4 ng*h/mL/mg, 4.5 ng*h/mL/mg, 4.6 ng*h/mL/mg, 4.7 ng*h/mL/mg, 4.8 ng*h/mL/mg, 4.9 ng*h/mL/mg, 5.0 ng*h/mL/mg, 5.1 ng*h/mL/mg, 5.2 ng*h/mL/mg, 5.3 ng*h/mL/mg, 5.4 ng*h/mL/mg, 5.5 ng*h/mL/mg, 5.6 ng*h/mL/mg, 5.7 ng*h/mL/mg, 5.8 ng*h/mL/mg, 5.9 ng*h/mL/mg, 6.0 ng*h/mL/mg, 6.1 ng*h/mL/mg, 6.2 ng*h/mL/mg, 6.3 ng*h/mL/mg, 6.4 ng*h/mL/mg, 6.5 ng*h/mL/mg, 6.6 ng*h/mL/mg, 6.7 ng*h/mL/mg, 6.8 ng*h/mL/mg, 6.9 ng*h/mL/mg, 7.0 ng*h/mL/mg, 7.1 ng*h/mL/mg, 7.2 ng*h/mL/mg, 7.3 ng*h/mL/mg, 7.4 ng*h/mL/mg, 7.5 ng*h/mL/mg, 7.6 ng*h/mL/mg, 7.7 ng*h/mL/mg, 7.8 ng*h/mL/mg, 7.9 ng*h/mL/mg, 8.0 ng*h/mL/mg, 8.1 ng*h/mL/mg, 8.2 ng*h/mL/mg, 8.3 ng*h/mL/mg, 8.4 ng*h/mL/mg, 8.5 ng*h/mL/mg, 8.6 ng*h/mL/mg, 8.7 ng*h/mL/mg, 8.8 ng*h/mL/mg, 8.9 ng*h/mL/mg, or 9.0 ng*h/mL/mg.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma fospropofol $AUC_{4hr}$ or the patient population has a mean $AUC_{4hr}$ of at least 1000 ng*h/mL, such as, for example, at least 1000 ng*h/mL, at least 1050 ng*h/mL, at least 1100 ng*h/mL, at least 1150 ng*h/mL, at least 1200 ng*h/mL, at least 1250 ng*h/mL, at least 1300 ng*h/mL, at least 1350 ng*h/mL, at least 1400 ng*h/mL, at least 1450 ng*h/mL, at least 1500 ng*h/mL, at least 1550 ng*h/mL, at least 1600 ng*h/mL, at least 1650 ng*h/mL, at least 1700 ng*h/mL, at least 1750 ng*h/mL, at least 1800 ng*h/mL, at least 1850 ng*h/mL, at least 1900 ng*h/mL, at least 1950 ng*h/mL, at least 2000 ng*h/mL, at least 2050 ng*h/mL, at least 2100 ng*h/mL, at least 2150 ng*h/mL, at least 2200 ng*h/mL, at least 2250 ng*h/mL, at least 2300 ng*h/mL, at least 2350 ng*h/mL, at least 2400 ng*h/mL, at least 2450 ng*h/mL, at least 2500 ng*h/mL, at least 2550 ng*h/mL, at least 2600 ng*h/mL, at least 2650 ng*h/mL, at least 2700 ng*h/mL, at least 2750 ng*h/mL, at least 2800 ng*h/mL, at least 2850 ng*h/mL, at least 2900 ng*h/mL, at least 2950 ng*h/mL, at least 3000 ng*h/mL, at least 3050 ng*h/mL, at least 3100 ng*h/mL, at least 3150 ng*h/mL, at least 3200 ng*h/mL, at least 3250 ng*h/mL, at least 3300 ng*h/mL, at least 3350 ng*h/mL, at least 3400 ng*h/mL, at least 3450 ng*h/mL, at least 3500 ng*h/mL, at least 3550 ng*h/mL, at least 3600 ng*h/mL, at least 3650 ng*h/mL, at least 3700 ng*h/mL, at least 3750 ng*h/mL, at least 3800 ng*h/mL, at least 3850 ng*h/mL, at least 3900 ng*h/mL, at least 3950 ng*h/mL, at least 4000 ng*h/mL, at least 4050 ng*h/mL, at least 4100 ng*h/mL, at least 4150 ng*h/mL, at least 4200 ng*h/mL, at least 4250 ng*h/mL, at least 4300 ng*h/mL, at least 4350 ng*h/mL, at least 4400 ng*h/mL, at least 4450 ng*h/mL, at least 4500 ng*h/mL, at least 4550 ng*h/mL, at least 4600 ng*h/mL, at least 4650 ng*h/mL, at least 4700 ng*h/mL, at least 4750 ng*h/mL, at least 4800 ng*h/mL, at least 4850 ng*h/mL, at least 4900 ng*h/mL, at least 4950 ng*h/mL, at least 5000 ng*h/mL, at least 5050 ng*h/mL, at least 5100 ng*h/mL, at least 5150 ng*h/mL, at least 5200 ng*h/mL, at least 5250 ng*h/mL, at least 5300 ng*h/mL, at least 5350 ng*h/mL, at least 5400 ng*h/mL, at least 5450 ng*h/mL, at least 5500 ng*h/mL, at least 5550 ng*h/mL, at least 5600 ng*h/mL, at least 5650 ng*h/mL, at least 5700 ng*h/mL, at least 5750 ng*h/mL, at least 5800 ng*h/mL, at least 5850 ng*h/mL, at least 5900 ng*h/mL, at least 5950 ng*h/mL, at least 6000 ng*h/mL, at least 6050 ng*h/mL, at least 6100 ng*h/mL, at least 6150 ng*h/mL, at least 6200 ng*h/mL, at least 6250 ng*h/mL, at least 6300 ng*h/mL, at least 6350 ng*h/mL, at least 6400 ng*h/mL, at least 6450 ng*h/mL, at least 6500 ng*h/mL, at least 6550 ng*h/mL, at least 6600 ng*h/mL, at least 6650 ng*h/mL, at least 6700 ng*h/mL, at least 6750 ng*h/mL, at least 6800 ng*h/mL, at least 6850 ng*h/mL, at least 6900 ng*h/mL, at least 6950 ng*h/mL, at least 7000 ng*h/mL, at least 7050 ng*h/mL, at least 7100 ng*h/mL, at least 7150 ng*h/mL, at least 7200 ng*h/mL, at least 7250 ng*h/mL, at least 7300 ng*h/mL, at least 7350 ng*h/mL, at least 7400 ng*h/mL, at least 7450 ng*h/mL, at least 7500 ng*h/mL, at least 7550 ng*h/mL, at least 7600 ng*h/mL, at least 7650 ng*h/mL, at least 7700 ng*h/mL, at least 7750 ng*h/mL, at least 7800 ng*h/mL, at least 7850 ng*h/mL, at least 7900 ng*h/mL, at least 7950 ng*h/mL, at least 8000 ng*h/mL, at least 8050 ng*h/mL, at least 8100 ng*h/mL, at least 8150 ng*h/mL, at least 8200 ng*h/mL, at least 8250 ng*h/mL, at least 8300 ng*h/mL, at least 8350 ng*h/mL, at least 8400 ng*h/mL, at least 8450 ng*h/mL, at least 8500 ng*h/mL, at least 8550 ng*h/mL, at least 8600 ng*h/mL, at least 8650 ng*h/mL, at least 8700 ng*h/mL, at least 8750 ng*h/mL, at least 8800 ng*h/mL, at least 8850 ng*h/mL, at least 8900 ng*h/mL, at least 8950 ng*h/mL, at least 9000 ng*h/mL, at least 9050 ng*h/mL, at least 9100 ng*h/mL, at least 9150 ng*h/mL, at least 9200 ng*h/mL, at least 9250 ng*h/mL, at least 9300 ng*h/mL, at least 9350 ng*h/mL, at least 9400 ng*h/mL, at least 9450 ng*h/mL, at least 9500 ng*h/mL, at least 9550 ng*h/mL, at least 9600 ng*h/mL, at least 9650 ng*h/mL, at least 9700 ng*h/mL, at least 9750 ng*h/mL, at least 9800 ng*h/mL, at least 9850 ng*h/mL, at least 9900 ng*h/mL, at least 9950 ng*h/mL, or at least 10000 ng*h/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma fospropofol $AUC_{4hr}$ or the patient population has a mean $AUC_{4hr}$ as set forth herein and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma fospropofol $AUC_{4hr}$ or the patient population has a mean $AUC_{4hr}$ of at least 1000 ng*h/mL and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma fospropofol $AUC_{4hr}$ or the patient population has a mean $AUC_{4hr}$ as set forth herein and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma fospropofol $AUC_{4hr}$ or the patient population has a mean $AUC_{4hr}$ of at least 1000 ng*h/mL and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma fospropofol $AUC_{4hr}$ or the patient population has a mean $AUC_{4hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma fospropofol $AUC_{4hr}$ or the patient population has a mean $AUC_{4hr}$ of at least 1000 ng*h/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hour after the administration the patient has plasma fospropofol concentration ($C_{4hr}$) or the patient population has a mean $C_{4hr}$ of 0 ng/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has a plasma fospropofol concentration ($C_{4hr}$) or the patient population has a mean $C_{4hr}$ as set forth herein and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma fospropofol concentration ($C_{4hr}$) or the patient population has a mean $C_{4hr}$ of 0 ng/mL and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma fospropofol concentration ($C_{4hr}$) or the patient population has a mean $C_{4hr}$ as set forth herein and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma fospropofol concentration ($C_{4hr}$) or the patient population has a mean $C_{4hr}$ of 0 ng/mL and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma fospropofol concentration ($C_{4hr}$) or the patient population has a mean $C_{4hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma fospropofol concentration ($C_{4hr}$) or the patient population has a mean $C_{4hr}$ of 0 ng/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma propofol $AUC_{1hr}$ or the patient population has a mean $AUC_{1hr}$ of at least at least 25 ng*h/mL, such as, for example, at least 25 ng*h/mL, at least 50 ng*h/mL, at least 75 ng*h/mL, at least 100 ng*h/mL, at least 125 ng*h/mL, at least 150 ng*h/mL, at least 175 ng*h/mL, at least 200 ng*h/mL, at least 225 ng*h/mL, at least 250 ng*h/mL, 275 ng*h/mL, at least 300 ng*h/mL, at least 325 ng*h/mL, at least 350 ng*h/mL, at least 400 ng*h/mL, at least 425 ng*h/mL, at least 450 ng*h/mL, at least 475 ng*h/mL, at least 500 ng*h/mL, at least 525 ng*h/mL, at least 550 ng*h/mL, at least 575 ng*h/mL, at least 600 ng*h/mL, at least 625 ng*h/mL, at least 650 ng*h/mL, at least 675 ng*h/mL, at least 700 ng*h/mL, at least 725 ng*h/mL, at least 750 ng*h/mL, at least 775 ng*h/mL, at least 800 ng*h/mL, at least 825 ng*h/mL, at least 850 ng*h/mL, at least 875 ng*h/mL, at least 900 ng*h/mL, at least 925 ng*h/mL, at least 950 ng*h/mL, at least 975 ng*h/mL, or at least 1000 ng*h/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma propofol $AUC_{1hr}$ or the patient population has a mean $AUC_{1hr}$ as set forth herein and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma propofol $AUC_{1hr}$ or the patient population has a mean $AUC_{1hr}$ of at least 250 ng*h/mL and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma propofol $AUC_{1hr}$ or the patient population has a mean $AUC_{1hr}$ as set forth herein and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma propofol $AUC_{1hr}$ or the patient population has a mean $AUC_{1hr}$ of at least 50 ng*h/mL and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma propofol $AUC_{1hr}$ or the patient population has a mean $AUC_{1hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma propofol $AUC_{1hr}$ or the patient population has a mean $AUC_{1hr}$ of at least 50 ng*h/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma propofol concentration ($C_{1hr}$) or the patient population has a mean $C_{1hr}$ of at least 25 ng/mL, such as, for example, at least 25 ng/mL, at least 50 ng/mL, at least 75 ng/mL, at least 100 ng/mL, at least 125 ng/mL, at least 150 ng/mL, at least 175 ng/mL, at least 200 ng/mL, at least 225 ng/mL, at least 250 ng/mL, 275 ng/mL, at least 300 ng/mL, at least 325 ng/mL, at least 350 ng/mL, at least 400 ng/mL, at least 425 ng/mL, at least 450 ng/mL, at least 475 ng/mL, at least 500 ng/mL, at least 525 ng/mL, at least 550 ng/mL, at least 575 ng/mL, at least 600 ng/mL, at least 625 ng/mL, at least 650 ng/mL, at least 675 ng/mL, at least 700 ng/mL, at least 725 ng/mL, at least 750 ng/mL, at least 775 ng/mL, at least 800 ng/mL, at least 825 ng/mL, at least 850 ng/mL, at least 875 ng/mL, at least 900 ng/mL, at least 925 ng/mL, at least 950 ng/mL, at least 975 ng/mL, or at least 1000 ng/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has a plasma propofol concentration ($C_{1hr}$) or the patient population has a mean $C_{1hr}$ as set forth herein and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma propofol concentration ($C_{1hr}$) or the patient population has a mean $C_{1hr}$ of at least 500 ng/mL and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma propofol concentration ($C_{1hr}$) or the patient population has a mean $C_{1hr}$ as set forth herein and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma propofol concentration ($C_{1hr}$) or the patient population has a mean $C_{1hr}$ of at least 90 ng/mL and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma propofol concentration ($C_{1hr}$) or the patient population has a mean $C_{1hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 1 hour after the administration the patient has plasma propofol concentration ($C_{1hr}$) or the patient population has a mean $C_{1hr}$ of at least 90 ng/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma propofol $AUC_{2hr}$ or the patient population has a mean $AUC_{2hr}$ of at least at least 25 ng*h/mL, such as, for example, at least 25 ng*h/mL, at least 50 ng*h/mL, at least 75 ng*h/mL, at least 100 ng*h/mL, at least 125 ng*h/mL, at least 150 ng*h/mL, at least 175 ng*h/mL, at least 200 ng*h/mL, at least 225 ng*h/mL, at least 250 ng*h/mL, 275 ng*h/mL, at least 300 ng*h/mL, at least 325 ng*h/mL, at least 350 ng*h/mL, at least 400 ng*h/mL, at least 425 ng*h/mL, at least 450 ng*h/mL, at least 475 ng*h/mL, at least 500 ng*h/mL, at least 525 ng*h/mL, at least 550 ng*h/mL, at least 575 ng*h/mL, at least 600 ng*h/mL, at least 625 ng*h/mL, at least 650 ng*h/mL, at least 675 ng*h/mL, at least 700 ng*h/mL, at least 725 ng*h/mL, at least 750 ng*h/mL, at least 775 ng*h/mL, at least 800 ng*h/mL, at least 825 ng*h/mL, at least 850 ng*h/mL, at least 875 ng*h/mL, at least 900 ng*h/mL, at least 925 ng*h/mL, at least 950 ng*h/mL, at least 975 ng*h/mL, or at least 1000 ng*h/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma propofol $AUC_{2hr}$ or the patient population has a mean $AUC_{2hr}$ as set forth herein and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma propofol $AUC_{2hr}$ or the patient population has a mean $AUC_{2hr}$ of at least 100 ng*h/mL and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma propofol $AUC_{2hr}$ or the patient population has a mean $AUC_{2hr}$ as set forth herein and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma propofol $AUC_{2hr}$ or the patient population has a mean $AUC_{2hr}$ of at least 90 ng*h/mL and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma propofol $AUC_{2hr}$ or the patient population has a mean $AUC_{2hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma propofol $AUC_{2hr}$ or the patient population has a mean $AUC_{2hr}$ of at least 40 ng*h/mL and the patient is no longer experiencing its most bothersome symptom (MBS).

In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma propofol concentration ($C_{2hr}$) or the patient population has a mean $C_{2hr}$ of at least 25 ng/mL, such as, for example, at least 25 ng/mL, at least 50 ng/mL, at least 75 ng/mL, at least 100 ng/mL, at least 125 ng/mL, at least 150 ng/mL, at least 175 ng/mL, at least 200 ng/mL, at least 225 ng/mL, at least 250 ng/mL, 275 ng/mL, at least 300 ng/mL, at least 325 ng/mL, at least 350 ng/mL, at least 400 ng/mL, at least 425 ng/mL, at least 450 ng/mL, at least 475 ng/mL, at least 500 ng/mL, at least 525 ng/mL, at least 550 ng/mL, at least 575 ng/mL, at least 600 ng/mL, at least 625 ng/mL, at least 650 ng/mL, at least 675 ng/mL, at least 700 ng/mL, at least 725 ng/mL, at least 750 ng/mL, at least 775 ng/mL, at least 800 ng/mL, at least 825 ng/mL, at least 850 ng/mL, at least 875 ng/mL, at least 900 ng/mL, at least 925 ng/mL, at least 950 ng/mL, at least 975 ng/mL, or at least 1000 ng/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hour after the administration the patient has a plasma propofol concentration ($C_{2hr}$) or the patient population has a mean $C_{2hr}$ as set forth herein and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma propofol concentration ($C_{2hr}$) or the patient population has a mean $C_{2hr}$ of at least 40 ng/mL and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hour after the administration the patient has plasma propofol concentration ($C_{2hr}$) or the patient population has a mean $C_{2hr}$ as set forth herein and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma propofol concentration ($C_{2hr}$) or the patient population has a mean $C_{2hr}$ of at least 40 ng/mL and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma propofol concentration ($C_{2hr}$) or the patient population has a mean $C_{2hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 2 hours after the administration the patient has plasma propofol concentration ($C_{2hr}$) or the patient population has a mean $C_{2hr}$ of at least 20 ng/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma propofol $AUC_{4hr}$ or the patient population has a mean $AUC_{4hr}$ of at least at least 25 ng*h/mL, such as, for example, at least 25 ng*h/mL, at least 50 ng*h/mL, at least 75 ng*h/mL, at least 100 ng*h/mL, at least 125 ng*h/mL, at least 150 ng*h/mL, at least 175 ng*h/mL, at least 200 ng*h/mL, at least 225 ng*h/mL, at least 250 ng*h/mL, 275 ng*h/mL, at least 300 ng*h/mL, at least 325 ng*h/mL, at least 350 ng*h/mL, at least 400 ng*h/mL, at least 425 ng*h/mL, at least 450 ng*h/mL, at least 475 ng*h/mL, at least 500 ng*h/mL, at least 525 ng*h/mL, at least 550 ng*h/mL, at least 575 ng*h/mL, at least 600 ng*h/mL, at least 625 ng*h/mL, at least 650 ng*h/mL, at least 675 ng*h/mL, at least 700 ng*h/mL, at least 725 ng*h/mL, at least 750 ng*h/mL, at least 775 ng*h/mL, at least 800 ng*h/mL, at least 825 ng*h/mL, at least 850 ng*h/mL, at least 875 ng*h/mL, at least 900 ng*h/mL, at least 925 ng*h/mL, at least 950 ng*h/mL, at least 975 ng*h/mL, or at least 1000 ng*h/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma propofol $AUC_{4hr}$ or the patient population has a mean $AUC_{4hr}$ as set forth herein and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma propofol $AUC_{4hr}$ or the patient population has a mean $AUC_{4hr}$ of at least 150 ng*h/mL and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma propofol $AUC_{4hr}$ or the patient population has a mean $AUC_{4hr}$ as set forth herein and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma propofol $AUC_{4hr}$ or the patient population has a mean $AUC_{4hr}$ of at least 150 ng*h/mL and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma propofol $AUC_{4hr}$ or the patient population has a mean $AUC_{4hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma propofol $AUC_{4hr}$ or the patient population has a mean $AUC_{4hr}$ of at least 100 ng*h/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hour after the administration the patient has plasma propofol concentration ($C_{4hr}$) or the patient population has a mean $C_{4hr}$ of at least 5 ng/mL, such as, for example, at least 5 ng/mL, at least 10 ng/mL, at least 15 ng/mL, at least 20 ng/mL, at least 25 ng/mL, at least 50 ng/mL, at least 75 ng/mL, at least 100 ng/mL, at least 125 ng/mL, at least 150 ng/mL, at least 175 ng/mL, at least 200 ng/mL, at least 225 ng/mL, at least 250 ng/mL, 275 ng/mL, at least 300 ng/mL, at least 325 ng/mL, at least 350 ng/mL, at least 400 ng/mL, at least 425 ng/mL, at least 450 ng/mL, at least 475 ng/mL, at least 500 ng/mL, at least 525 ng/mL, at least 550 ng/mL, at least 575 ng/mL, at least 600 ng/mL, at least 625 ng/mL, at least 650 ng/mL, at least 675 ng/mL, at least 700 ng/mL, at least 725 ng/mL, at least 750 ng/mL, at least 775 ng/mL, at least 800 ng/mL, at least 825 ng/mL, at least 850 ng/mL, at least 875 ng/mL, at least 900 ng/mL, at least 925 ng/mL, at least 950 ng/mL, at least 975 ng/mL, or at least 1000 ng/mL.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has a plasma propofol concentration ($C_{4hr}$) or the patient population has a mean $C_{4hr}$ as set forth herein and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma propofol concentration ($C_{4hr}$) or the patient population has a mean $C_{4hr}$ of at least 10 ng/mL and the patient is headache free.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma propofol concentration ($C_{4hr}$) or the patient population has a mean $C_{4hr}$ as set forth herein and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma propofol concentration ($C_{4hr}$) or the patient population has a mean $C_{4hr}$ of at least 10 ng/mL and the patient has experienced a reduction in headache pain.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma propofol concentration ($C_{4hr}$) or the patient population has a mean $C_{4hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) an effective amount of fospropofol, a pharmaceutically acceptable salt of fospropofol, or mixtures thereof, wherein at 4 hours after the administration the patient has plasma propofol concentration ($C_{4hr}$) or the patient population has a mean $C_{4hr}$ of at least 10 ng/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the methods described herein are directed to treating a disease or disorder in a subject in need thereof.

In some embodiments of the disclosed methods of treating a disease or disorder, the disease or disorder is migraine, acute repetitive seizures, seizure clusters, neuropathic pain, postherpetic neuralgia, traumatic brain injury, Alzheimer's disease, epilepsy, anxiety, fragile X syndrome, post-traumatic stress disorder, lysosomal storage disorders (Niemann-Pick type C disease), depression (including postpartum depression), premenstrual dysphoric disorder, alcohol craving, or smoking cessation.

In some embodiments of the disclosed methods of treating a disease or disorder, the disease or disorder is migraine.

In some aspects, the disclosure is directed to methods of treating migraine.

In some embodiments, the subject's migraine is migraine with aura.

In other embodiments, the subject's migraine is migraine without aura.

In other embodiments, the subject's migraine is cluster headache.

In other embodiments, the subject's migraine is intractable migraine.

In some embodiments, the patient's migraine is refractory migraine. In some embodiments of the disclosed methods, the subject's refractory migraine may fail to respond to CGRP inhibitors, and is referred to as CGRP inhibitor-refractory migraine.

In some embodiments, the subject's CGRP-inhibitor refractory migraine fails to respond to gepant treatment, and is referred to as gepant-refractory migraine. In other embodiments, the subject's CGRP-inhibitor refractory migraine fails to respond to anti-CGRP antibodies, and is referred to as anti-CGRP antibody-refractory migraine.

In other embodiments, the subject's refractory migraine may fail to respond to triptans, and is referred to as triptan-refractory migraine.

In other embodiments, the subject's refractory migraine may fail to respond to NSAIDs and is referred to as NSAID-refractory migraine.

In other embodiments, the subject's refractory migraine may fail to respond to dihydroegotamine (DHE) and is referred to as DHE-refractory migraine.

In some embodiments of the methods of the disclosure, the fospropofol, a pharmaceutically acceptable salt of fospropofol, or mixtures thereof, may be administered in combination with other drugs that are used to treat migraine.

In some embodiments of the disclosed methods of treating a disease or disorder, the disease or disorder is epilepsy.

In some embodiments of the disclosed methods of treating a disease or disorder, the disease or disorder is tremor. In some embodiments, the tremor is essential tremor or Parkinsonian tremor (tremor in persons with Parkinson's disease). In other embodiments, the tremor is orthostatic tremor, primary writing tremor, cerebellar tremor, rubral tremor, neuropathic tremor or dystonic tremor.

In some embodiments of the methods of the disclosure, administering an effective amount of fospropofol, a pharmaceutically acceptable salt of fospropofol, or mixtures thereof, in one or more doses, results in a reduction of the patient's migraine pain.

In some embodiments, the reduction of the patient's migraine pain is demonstrated by change in the patient's rating of the severity of the pain following administration of fospropofol, or a pharmaceutically acceptable salt thereof.

In some embodiments, the reduction of the patient's migraine pain is demonstrated by change in the patient's rating of the pain from severe prior to administration of fospropofol, to no pain following administration of fospropofol, or a pharmaceutically acceptable salt thereof.

In some embodiments, the reduction of the patient's migraine pain is demonstrated by change in the patient's rating of the pain from severe prior to administration of fospropofol, to mild following administration of fospropofol, or a pharmaceutically acceptable salt thereof.

In some embodiments, the reduction of the patient's migraine pain is demonstrated by change in the patient's rating of the pain from severe prior to administration of fospropofol, to moderate following administration of fospropofol, or a pharmaceutically acceptable salt thereof.

In some embodiments, the reduction of the patient's migraine pain is demonstrated by change in the patient's rating of the pain from moderate prior to administration of fospropofol, a pharmaceutically acceptable salt of fospropofol, or mixtures thereof, to no pain following administration of fospropofol.

In some embodiments, the reduction of the patient's migraine pain is demonstrated by change in the patient's rating of the pain from moderate prior to administration of fospropofol, a pharmaceutically acceptable salt of fospropofol, or mixtures thereof, to mild following administration of fospropofol.

In some embodiments, the reduction of the patient's migraine pain is demonstrated by change in the patient's rating of the pain from mild prior to administration of fospropofol, a pharmaceutically acceptable salt of fospropofol, or mixtures thereof, to no pain following administration of fospropofol.

In some embodiments, the reduction of the patient's migraine pain is demonstrated by a reduction of three points in a 4 point Likert scale. The term "Likert scale" as used herein, refers generally to a questionnaire-based rating scale in which the patient is asked to rate the severity of the pain on a scale of, for example, 0-3, wherein 0=none, 1=mild, 2=moderate, 3=severe.

In other embodiments, the reduction of the patient's migraine pain is demonstrated by a reduction of at least two points in a 4 point Likert scale.

In other embodiments, the reduction of the patient's migraine pain is demonstrated by a reduction of at least one point in a 4 point Likert scale.

In some embodiments, administering an effective amount of fospropofol, a pharmaceutically acceptable salt of fospropofol, or mixtures thereof, in one or more doses, results in a reduction of the patient's migraine pain from severe to moderate on a 4-point Likert scale in which the 4 points are None, Mild, Moderate, Severe.

In some embodiments, administering an effective amount of fospropofol, a pharmaceutically acceptable salt of fospropofol, or mixtures thereof, in one or more doses, results in a reduction of the patient's migraine pain from severe to mild on a 4-point Likert scale in which the 4 points are None, Mild, Moderate, Severe.

In some embodiments, administering an effective amount of fospropofol, a pharmaceutically acceptable salt of fospropofol, or mixtures thereof, in one or more doses, results in a reduction of the patient's migraine pain from severe to none on a 4-point Likert scale in which the 4 points are None, Mild, Moderate, Severe.

In some embodiments, administering an effective amount of fospropofol, a pharmaceutically acceptable salt of fospropofol, or mixtures thereof, in one or more doses, results in a reduction of the patient's migraine pain from moderate to mild on a 4-point Likert scale in which the 4 points are None, Mild, Moderate, Severe.

In some embodiments, administering an effective amount of fospropofol, a pharmaceutically acceptable salt of fospropofol, or mixtures thereof, in one or more doses, results in a reduction of the patient's migraine pain from moderate to none on a 4-point Likert scale in which the 4 points are None, Mild, Moderate, Severe.

In some embodiments, administering an effective amount of fospropofol, a pharmaceutically acceptable salt of fospropofol, or mixtures thereof, in one or more doses, results in a reduction of the patient's migraine pain from mild to none on a 4-point Likert scale in which the 4 points are None, Mild, Moderate, Severe.

In some embodiments of the disclosed methods, administering an effective amount of fospropofol, a pharmaceutically acceptable salt of fospropofol, or mixtures thereof, in one or more doses, results in a reduction in the patient's headache pain, and the elimination of the patient's bothersome symptom, within 2 hours.

In some embodiments of the disclosed methods, administering an effective amount of fospropofol, a pharmaceutically acceptable salt of fospropofol, or mixtures thereof, in one or more doses, results in a reduction in the patient's headache pain, and the elimination of the patient's most bothersome symptom, within 2 hours.

In some embodiments of the disclosed methods, administering an effective amount of fospropofol, a pharmaceutically acceptable salt of fospropofol, or mixtures thereof, in one or more doses, results in a reduction in the patient's headache pain, and the elimination of the patient's nausea, within 2 hours.

In some embodiments of the disclosed methods, administering an effective amount of fospropofol, a pharmaceutically acceptable salt of fospropofol, or mixtures thereof, in one or more doses, results in a reduction in the patient's headache pain, and the elimination of the patient's photophobia, within 2 hours.

In some embodiments of the disclosed methods, administering an effective amount of fospropofol, a pharmaceutically acceptable salt of fospropofol, or mixtures thereof, in one or more doses, results in a reduction in the patient's headache pain, and the elimination of the patient's phonophobia, within 2 hours.

In other embodiments of the disclosed methods, administering an effective amount of fospropofol, a pharmaceutically acceptable salt of fospropofol, or mixtures thereof, in one or more doses, results in an elimination of the patient's headache pain, and the elimination of the patient's most bothersome symptom, within 2 hours.

In other embodiments of the disclosed methods, administering an effective amount of fospropofol, a pharmaceutically acceptable salt of fospropofol, or mixtures thereof, in one or more doses, results in an elimination of the patient's headache pain, and the elimination of the patient's most bothersome symptom, within 2 hours.

In other embodiments of the disclosed methods, administering an effective amount of fospropofol, a pharmaceutically acceptable salt of fospropofol, or mixtures thereof, in one or more doses, results in an elimination of the patient's headache pain, and the elimination of the patient's nausea, within 2 hours.

In other embodiments of the disclosed methods, administering an effective amount of fospropofol, a pharmaceutically acceptable salt of fospropofol, or mixtures thereof, in one or more doses, results in an elimination of the patient's headache pain, and the elimination of the patient's photophobia, within 2 hours.

In other embodiments of the disclosed methods, administering an effective amount of fospropofol, a pharmaceutically acceptable salt of fospropofol, or mixtures thereof, in one or more doses, results in an elimination of the patient's headache pain, and the elimination of the patient's phonophobia, within 2 hours.

In some aspects of the disclosed methods, the reduction in the patient's migraine pain occurs within 5-240 minutes, for example, 10-240 minutes of administration of fospropofol, or a pharmaceutically acceptable salt thereof.

In some embodiments, the reduction in the patient's migraine pain occurs within 5-15 minutes, for example, 10-15 minutes of administration of fospropofol, or a pharmaceutically acceptable salt thereof.

In some embodiments, the reduction in the patient's migraine pain occurs within 5-30 minutes, for example, 10-30 minutes of administration of fospropofol, or a pharmaceutically acceptable salt thereof.

In some embodiments, the reduction in the patient's migraine pain occurs within 5-60 minutes, for example, 10-60 minutes of administration of fospropofol, or a pharmaceutically acceptable salt thereof.

In some embodiments, the reduction in the patient's migraine pain occurs within 5-120 minutes, for example, 10-120 minutes of administration of fospropofol, or a pharmaceutically acceptable salt thereof.

In some embodiments, the reduction in the patient's migraine pain occurs within 120 minutes of administration of fospropofol, or a pharmaceutically acceptable salt thereof.

In some embodiments, the reduction in the patient's migraine pain occurs within 30 minutes of administration of fospropofol, or a pharmaceutically acceptable salt thereof.

In some embodiments, the reduction in the patient's migraine pain occurs within 60 minutes of administration of fospropofol, or a pharmaceutically acceptable salt thereof.

In some embodiments, the reduction in the patient's migraine pain occurs within 90 minutes of administration of fospropofol, or a pharmaceutically acceptable salt thereof.

In some embodiments, the reduction in the patient's migraine pain occurs within 120 minutes of administration of fospropofol, or a pharmaceutically acceptable salt thereof.

In some embodiments, the reduction in the patient's migraine pain occurs within 3 hour of administration of fospropofol, or a pharmaceutically acceptable salt thereof.

In some embodiments, the reduction in the patient's migraine pain occurs within 4 hours of administration of fospropofol, or a pharmaceutically acceptable salt thereof.

In some embodiments, the reduction in the patient's migraine pain occurs within 6 hours of administration of fospropofol, or a pharmaceutically acceptable salt thereof.

In some embodiments, the reduction in the patient's migraine pain occurs within 12 hours of administration of fospropofol, or a pharmaceutically acceptable salt thereof.

In some embodiments, the reduction in the patient's migraine pain occurs within 24 hours of administration of fospropofol, or a pharmaceutically acceptable salt thereof.

In some embodiments, the reduction in the patient's migraine pain occurs within 48 hours of administration of fospropofol, or a pharmaceutically acceptable salt thereof.

In some aspects of the disclosed methods, a patient whose migraine pain was eliminated following administration of fospropofol, a pharmaceutically acceptable salt of fospropofol, or mixtures thereof, remains free of migraine pain for at least 12 hours.

In some aspects of the disclosed methods, a patient whose migraine pain was eliminated following administration of fospropofol, a pharmaceutically acceptable salt of fospropofol, or mixtures thereof, remains free of migraine pain for at least 24 hours.

In some embodiments, a patient whose migraine pain was eliminated following administration of fospropofol, a pharmaceutically acceptable salt of fospropofol, or mixtures thereof, remains free of migraine pain for at least 48 hours.

In some embodiments, a patient whose migraine pain was eliminated following administration of fospropofol, a pharmaceutically acceptable salt of fospropofol, or mixtures thereof, remains free of migraine pain for at least 72 hours.

In some aspects of the disclosed methods, administration of an effective amount of fospropofol, a pharmaceutically acceptable salt of fospropofol, or mixtures thereof, to a patient whose migraine symptoms include nausea/vomitting results in elimination of the patient's nausea/vomitting.

In some embodiments, the elimination of the patient's nausea/vomitting occurs within 30 minutes of administration of fospropofol, or a pharmaceutically acceptable salt thereof.

In some embodiments, the elimination of the patient's nausea/vomitting occurs within 60 minutes of administration of fospropofol, or a pharmaceutically acceptable salt thereof.

In some embodiments, the elimination of the patient's nausea/vomitting occurs within 90 minutes of administration of fospropofol, or a pharmaceutically acceptable salt thereof.

In some embodiments, the elimination of the patient's nausea/vomitting occurs within 120 minutes of administration of fospropofol, or a pharmaceutically acceptable salt thereof.

In some embodiments, the elimination of the patient's nausea/vomitting occurs within 3 hour of administration of fospropofol, or a pharmaceutically acceptable salt thereof.

In some embodiments, the elimination of the patient's nausea/vomitting occurs within 4 hours of administration of fospropofol, or a pharmaceutically acceptable salt thereof.

In some embodiments, the elimination of the patient's nausea/vomitting occurs within 6 hours of administration of fospropofol, or a pharmaceutically acceptable salt thereof.

In some embodiments, the elimination of the patient's nausea/vomitting occurs within 12 hours of administration of fospropofol, or a pharmaceutically acceptable salt thereof.

In some embodiments, the elimination of the patient's nausea/vomitting occurs within 24 hours of administration of fospropofol, or a pharmaceutically acceptable salt thereof.

In some embodiments, the elimination of the patient's nausea/vomitting occurs within 48 hours of administration of fospropofol, or a pharmaceutically acceptable salt thereof.

In some embodiments, administration of an effective amount of fospropofol, a pharmaceutically acceptable salt of fospropofol, or mixtures thereof, to a patient whose migraine symptoms include nausea/vomitting results in reduction of nausea/vomitting of at least 50% from baseline as measured by the patient's rating.

In some embodiments, administration of an effective amount of fospropofol, a pharmaceutically acceptable salt of fospropofol, or mixtures thereof, to a patient whose migraine symptoms include nausea/vomitting results in reduction of nausea/vomitting of at least 93% from baseline as measured by the patient's rating.

In some embodiments, administration of an effective amount of fospropofol, a pharmaceutically acceptable salt of fospropofol, or mixtures thereof, to a patient whose migraine symptoms include nausea/vomitting results in reduction of nausea/vomitting of less than 90% from baseline as measured by the patient's rating.

In some aspects of the disclosed methods, administration of an effective amount of fospropofol, a pharmaceutically acceptable salt of fospropofol, or mixtures thereof, to a patient whose migraine symptoms include photophobia results in elimination of the patient's photophobia. In some embodiments, the elimination of the patient's photophobia occurs within 30 minutes of administration of fospropofol, or a pharmaceutically acceptable salt thereof.

In some embodiments, the elimination of the patient's photophobia occurs within 60 minutes of administration of fospropofol, or a pharmaceutically acceptable salt thereof.

In some embodiments, the elimination of the patient's photophobia occurs within 90 minutes of administration of fospropofol, or a pharmaceutically acceptable salt thereof.

In some embodiments, the elimination of the patient's photophobia occurs within 120 minutes of administration of fospropofol, or a pharmaceutically acceptable salt thereof.

In some embodiments, the elimination of the patient's photophobia occurs within 3 hour of administration of fospropofol, or a pharmaceutically acceptable salt thereof.

In some embodiments, the elimination of the patient's photophobia occurs within 4 hours of administration of fospropofol, or a pharmaceutically acceptable salt thereof.

In some embodiments, the elimination of the patient's photophobia occurs within 6 hours of administration of fospropofol, or a pharmaceutically acceptable salt thereof.

In some embodiments, the elimination of the patient's photophobia occurs within 12 hours of administration of fospropofol, or a pharmaceutically acceptable salt thereof.

In some embodiments, the elimination of the patient's photophobia occurs within 24 hours of administration of fospropofol, or a pharmaceutically acceptable salt thereof.

In some embodiments, the elimination of the patient's photophobia occurs within 48 hours of administration of fospropofol, or a pharmaceutically acceptable salt thereof.

In some embodiments, administration of an effective amount of fospropofol, a pharmaceutically acceptable salt of fospropofol, or mixtures thereof, to a patient whose migraine symptoms include photophobia results in reduction of photophobia of at least 50% as measured by the patient's rating.

In some embodiments, administration of an effective amount of fospropofol, a pharmaceutically acceptable salt of fospropofol, or mixtures thereof, to a patient whose migraine symptoms include photophobia results in reduction of photophobia of at least 80% as measured by the patient's rating.

In some embodiments, administration of an effective amount of fospropofol, a pharmaceutically acceptable salt of fospropofol, or mixtures thereof, to a patient whose migraine symptoms include photophobia results in reduction of photophobia of less than 75% as measured by the patient's rating.

In some aspects of the disclosed methods, administration of an effective amount of fospropofol, a pharmaceutically acceptable salt of fospropofol, or mixtures thereof, to a patient whose migraine symptoms include phonophobia results in elimination of the patient's phonophobia.

In some embodiments, the elimination of the patient's phonophobia occurs within 30 minutes of administration of fospropofol, or a pharmaceutically acceptable salt thereof.

In some embodiments, the elimination of the patient's phonophobia occurs within 60 minutes of administration of fospropofol, or a pharmaceutically acceptable salt thereof.

In some embodiments, the elimination of the patient's phonophobia occurs within 90 minutes of administration of fospropofol, or a pharmaceutically acceptable salt thereof.

In some embodiments, the elimination of the patient's phonophobia occurs within 120 minutes of administration of fospropofol, or a pharmaceutically acceptable salt thereof.

In some embodiments, the elimination of the patient's phonophobia occurs within 3 hour of administration of fospropofol, or a pharmaceutically acceptable salt thereof.

In some embodiments, the elimination of the patient's phonophobia occurs within 4 hours of administration of fospropofol, or a pharmaceutically acceptable salt thereof.

In some embodiments, the elimination of the patient's phonophobia occurs within 6 hours of administration of fospropofol, or a pharmaceutically acceptable salt thereof.

In some embodiments, the elimination of the patient's phonophobia occurs within 12 hours of administration of fospropofol, or a pharmaceutically acceptable salt thereof.

In some embodiments, the elimination of the patient's phonophobia occurs within 24 hours of administration of fospropofol, or a pharmaceutically acceptable salt thereof.

In some embodiments, the elimination of the patient's phonophobia occurs within 48 hours of administration of fospropofol, or a pharmaceutically acceptable salt thereof.

In some embodiments, administration of an effective amount of fospropofol, a pharmaceutically acceptable salt of fospropofol, or mixtures thereof, to a patient whose migraine symptoms include phonophobia results in reduction of phonophobia of at least 50% as measured by the patient's rating.

In some embodiments, administration of an effective amount of fospropofol, a pharmaceutically acceptable salt of fospropofol, or mixtures thereof, to a patient whose migraine symptoms include phonophobia results in reduction of phonophobia of at least 80% as measured by the patient's rating.

In some embodiments, administration of an effective amount of fospropofol, a pharmaceutically acceptable salt of fospropofol, or mixtures thereof, to a patient whose migraine symptoms include phonophobia results in reduction of phonophobia of less than 75% as measured by the patient's rating.

In some embodiments of the disclosed methods, administering to the patient an effective amount of fospropofol, a pharmaceutically acceptable salt of fospropofol, or mixtures thereof, in one or more doses, results in no clinically meaningful risk of apnea.

In some embodiments of the disclosed methods, administering to the patient an effective amount of fospropofol, a pharmaceutically acceptable salt of fospropofol, or mixtures thereof, in one or more doses, results in no clinically meaningful risk of hypoxemia In some embodiments of the disclosed methods, administering to the patient an effective amount of fospropofol, a pharmaceutically acceptable salt of fospropofol, or mixtures thereof, in one or more doses, results in a risk of hypotension of less than 2%. In some embodiments, administering to the patient an effective amount of fospropofol, a pharmaceutically acceptable salt of fospropofol, or mixtures thereof, in one or more doses, results in a risk of hypotension of less than 10%.

In some embodiments, administering to the patient an effective amount of fospropofol, a pharmaceutically acceptable salt of fospropofol, or mixtures thereof, in one or more doses, results in a risk of hypotension of greater than 5%.

In some embodiments of the disclosed methods, administering to the patient an effective amount of fospropofol, a pharmaceutically acceptable salt of fospropofol, or mixtures thereof, in one or more doses, results in no clinically meaningful risk of developing unresponsiveness to vigorous tactile or painful stimulation as assessed using the Modified Observer's Assessment of Alertness (OAA/S) Scale.

In some embodiments of the disclosed methods, administering to the patient an effective amount of fospropofol, a pharmaceutically acceptable salt of fospropofol, or mixtures thereof, in one or more doses, results in a risk of paresthesia of less than 20%.

In some embodiments of the disclosed methods, administering to the patient an effective amount of fospropofol, a pharmaceutically acceptable salt of fospropofol, or mixtures thereof, in one or more doses, results in a risk of paresthesia of less than 40%.

In some embodiments of the disclosed methods, administering to the patient an effective amount of fospropofol, a pharmaceutically acceptable salt of fospropofol, or mixtures thereof, in one or more doses, results in a risk of paresthesia of less than 60%.

In some embodiments of the disclosed methods, administering to the patient an effective amount of fospropofol, a pharmaceutically acceptable salt of fospropofol, or mixtures thereof, in one or more doses, results in a risk of paresthesia of less than 80%.

In some embodiments of the disclosed methods, administering to the patient an effective amount of fospropofol, a pharmaceutically acceptable salt of fospropofol, or mixtures thereof, in one or more doses, results in a risk of developing cough of less than 10%.

In some embodiments of the disclosed methods, administering to the patient an effective amount of fospropofol, a pharmaceutically acceptable salt of fospropofol, or mixtures thereof, in one or more doses, results in a risk of pruritus of less than 10%.

In some embodiments of the disclosed methods, administering to the patient an effective amount of fospropofol, a pharmaceutically acceptable salt of fospropofol, or mixtures thereof, in one or more doses, results in a risk of euphoria of less than 25%.

In some embodiments of the disclosed methods, administering to the patient an effective amount of fospropofol, a pharmaceutically acceptable salt of fospropofol, or mixtures thereof, in one or more doses, results in a risk of seeking behavior of less than 5%.

In some embodiments of the disclosed methods, administering to the patient an effective amount of fospropofol, a pharmaceutically acceptable salt of fospropofol, or mixtures thereof, in one or more doses, results in a risk of excessive somnolence of less than 15%.

In some embodiments of the disclosed methods, administering to the patient an effective amount of fospropofol, a pharmaceutically acceptable salt of fospropofol, or mixtures thereof, in one or more doses, results in a risk of excessive somnolence less than 20%.

In some embodiments of the disclosed methods, administering to the patient an effective amount of fospropofol, a pharmaceutically acceptable salt of fospropofol, or mixtures thereof, in one or more doses, results in a risk of chest tightness of less than 2%.

In some embodiments, administering to the patient an effective amount of fospropofol, a pharmaceutically acceptable salt of fospropofol, or mixtures thereof, in one or more doses, results in no clinically meaningful risk of chest tightness.

In some embodiments of the disclosed methods, administering to the patient an effective amount of fospropofol, a pharmaceutically acceptable salt of fospropofol, or mixtures thereof, in one or more doses, results in a risk of chest tightness greater than 5%.

Pharmaceutical Compositions

In some aspects, the disclosure is directed to pharmaceutical compositions comprising fospropofol, a pharmaceutically acceptable salt of fospropofol, or mixtures thereof, and a pharmaceutically acceptable excipient.

In some embodiments, the pharmaceutical composition is a solid.

In other embodiments, the pharmaceutical composition is a liquid.

In other embodiments, the pharmaceutical composition is a suspension.

In other embodiments, the pharmaceutical composition is a paste.

The pharmaceutical compositions of the present disclosure may take any physical form suitable for the mode of administration.

In some embodiments, the physical form of the pharmaceutical composition is a capsule (gelatin or non-gelatin), enteric capsules, cachets, tablets, beads, or powders.

In some embodiments, the physical form of the pharmaceutical composition is coated beads.

In other embodiments, the physical form of the pharmaceutical composition is tablets.

In some embodiments, the physical form of the pharmaceutical composition is coated tablets.

In some embodiments, the physical form of the pharmaceutical composition is enteric coated tablets.

In some embodiments, the physical form of the pharmaceutical composition is multilayer tablets.

In some embodiments, the physical form of the pharmaceutical composition is multilayer coated tablets.

In some embodiments, the physical form of the pharmaceutical composition is coated multilayer uncoated tablets.

In some embodiments, the physical form of the pharmaceutical composition is a tablet within a tablet.

In some embodiments, the physical form of the pharmaceutical composition is a capsule.

In some embodiments, the physical form of the pharmaceutical composition is a capsule containing pellets or beads.

In some embodiments, the physical form of the pharmaceutical composition is a capsule containing pellets or beads, wherein the pellets or beads are heterogenous with respect to release of fospropofol.

In some embodiments, the physical form of the pharmaceutical composition is a capsule containing tablets, wherein the tablets are heterogenous with respect to release of fospropofol.

In other embodiments, the physical form of the pharmaceutical composition is a gel, water soluble jellies, creams, lotions, suspensions, foams, powders, slurries, ointments, solutions, oils, pastes, suppositories, sprays, or emulsions.

In some embodiments, the physical form of the pharmaceutical composition is a controlled release dosage form. As used herein, the term "controlled release dosage form" refers to a dosage form that releases the encompassed fospropofol over an extended period of time.

In some embodiments, the physical form of the pharmaceutical composition is a modified-release dosage form.

In some aspects, the pharmaceutical compositions of the disclosure comprises a pharmaceutically acceptable excipient.

In some embodiments, the pharmaceutically acceptable excipient may be water, glycols, oils, alcohols, flavoring agents, preservatives, coloring agents, starches, sugars, micro-crystalline cellulose, surfactants, polymers, diluents, granulating agents, lubricants, binders, fillers, and disintegrants.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, dicalcium phosphate, hydroxypropyl methyl cellulose, microcrystalline cellulose, and mixtures thereof.

Fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, dicalcium phosphate, pre-gelatinized starch, and mixtures thereof.

Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof.

In some embodiments, the solid pharmaceutical dosage form is uncoated or coated to delay disintegration and absorption in the gastrointestinal tract. For example, a time delay material such as glyceryl monostearate or glyceryl distearate can be employed.

Surfactant which can be used to form pharmaceutical compositions and dosage forms of the invention include, but are not limited to, hydrophilic surfactants, lipophilic surfactants, ionic surfactants, and mixtures thereof.

Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof, lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof, polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-lOoleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof.

Solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, S-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Release modifiers may include coatings or matrix materials.

Release modifying coatings include but are not limited to polymer coating materials, such as cellulose acetate phthalate, cellulose acetate trimaletate, hydroxy propyl methylcellulose phthalate, polyvinyl acetate phthalate, ammonio methacrylate copolymers such as those sold under the Trade Mark Eudragit® RS and RL, poly acrylic acid and poly acrylate and methacrylate copolymers such as those sold under the Trade Mark Eudragite S and L, polyvinyl acetaldiethylamino acetate, hydroxypropyl methylcellulose acetate succinate, shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, gelatin, starch, and cellulose based cross-linked polymers—in which the degree of crosslinking is low so as to facilitate adsorption of water and expansion of the polymer matrix, hydoxypropyl cellulose, hydroxypropyl methylcellulose, polyvinylpyrrolidone, crosslinked starch, microcrystalline cellulose, chitin, aminoacryl-methacrylate copolymer (Eudragit® RS-PM, Rohm & Haas), pullulan, collagen, casein, agar, gum arabic, sodium carboxymethyl cellulose, (swellable hydrophilic polymers) poly(hydroxyalkyl methacrylate) (m. wt. ~5 k-5,000 k), polyvinylpyrrolidone (m. wt. ~10 k-360 k), anionic and cationic hydrogels, polyvinyl alcohol having a low acetate residual, a swellable mixture of agar and carboxymethyl cellulose, copolymers of maleic anhydride and styrene, ethylene, propylene or isobutylene, pectin (m. wt. ~30 k-300 k), polysaccharides such as agar, acacia, karaya, tragacanth, algins and guar, polyacrylamides, Polyox® polyethylene oxides (m. wt. ~100 k-5,000 k), AquaKeep® acrylate polymers, diesters of polyglucan, crosslinked polyvinyl alcohol and poly N-vinyl-2-pyrrolidone, sodium starch glucolate (e.g. Explotab®;

Edward Mandell C. Ltd.); hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, polyethylene oxides (e.g. Polyox®, Union Carbide), methyl ethyl cellulose, ethylhydroxy ethylcellulose, cellulose acetate, cellulose butyrate, cellulose propionate, gelatin, collagen, starch, maltodextrin, pullulan, polyvinyl pyrrolidone, polyvinyl alcohol, polyvinyl acetate, glycerol fatty acid esters, polyacrylamide, polyacrylic acid, copolymers of methacrylic acid or methacrylic acid (e.g. Eudragit®, Rohm and Haas), other acrylic acid derivatives, sorbitan esters, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof. As will be appreciated by the person skilled in the art, excipients such as plasticisers, lubricants, solvents and the like may be added to the coating. Suitable plasticisers include for example acetylated monoglycerides; butyl phthalyl butyl glycolate; dibutyl tartrate; diethyl phthalate; dimethyl phthalate; ethyl phthalyl ethyl glycolate; glycerin; propylene glycol; triacetin; citrate; tripropioin; diacetin; dibutyl phthalate; acetyl monoglyceride; polyethylene glycols; castor oil; triethyl citrate; polyhydric alcohols, glycerol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-1-octyl phthalate, di-1-decyl phthalate, di-n-undecyl phthalate, di-n-tridecylphthalate, tri-2-ethylhexyltrimellitate, di-2-ethylhexyl adipate, di-2-ethylhexyl sebacate, di-2-ethylhexyl azelate, dibutyl sebacate.

Release-modifying matrix materials include hydrophilic polymers, hydrophobic polymers and mixtures thereof, dicalcium phosphate, microcrystalline cellulose, sodium carboxymethylcellulose, hydroxyalkylcelluloses such as hydroxypropylmethylcellulose and hydroxypropylcellulose, polyethylene oxide, alkylcelluloses such as methylcellulose and ethylcellulose, polyethylene glycol, polyvinylpyrrolidone, cellulose acetate, cellulose acetate butyrate, cellulose acetate phthalate, cellulose acetate trimellitate, polyvinylacetate phthalate, polyalkylmethacrylates, polyvinyl acetate, Poly(2-hydroxy ethyl methacrylate), Poly(N-vinyl pyrrolidone), Poly(methyl methacrylate), Poly(vinyl alcohol), Poly (acrylic acid), Polyacrylamide, Poly(ethylene-co-vinyl acetate), Poly(ethylene glycol), Poly(methacrylic acid), Polylactides (PLA), Polyglycolides (PGA), Poly(lactide-co-glycolides) (PLGA), Polyanhydrides, and Polyorthoesters, and mixture thereof.

In some aspects, pharmaceutical compositions of the disclosure comprise an effective amount of fospropofol, a pharmaceutically acceptable salt of fospropofol, or mixtures thereof.

In some embodiments of the pharmaceutical compositions of the disclosure comprise an effective amount of fospropofol.

In other embodiments, the pharmaceutical compositions of the disclosure comprise an effective amount of a pharmaceutically acceptable salt of fospropofol.

In some embodiments, pharmaceutical compositions of the disclosure comprise fospropofol disodium.

In some embodiments, the pharmaceutical compositions of the disclosure comprise an effective amount of a mixture of fospropofol and a pharmaceutically acceptable salt thereof. Thus, in some embodiments, the pharmaceutical compositions of the disclosure comprise an effective amount of fospropofol and fospropofol disodium.

In other embodiments, the pharmaceutical compositions of the disclosure comprise an effective amount of a mixture of pharmaceutically acceptable salts. In some embodiments, the pharmaceutical compositions of the disclosure comprise an effective amount of a mixture of fospropofol disodium and a second pharmaceutically acceptable fospropofol salt.

In some aspects, the pharmaceutical compositions of the disclosure comprise an effective amount of fospropofol, a pharmaceutically acceptable salt of phospropofol, or mixtures thereof.

In some embodiments, the pharmaceutical compositions of the disclosure comprise fospropofol, a pharmaceutically acceptable salt of fospropofol, or mixtures thereof, in an amount of 50-4800 mg (on a fospropofol basis), for example, an amount that is about (i.e., the specified number±10%) any one of 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, 2050 mg, 3100 mg, 3150 mg, 3200 mg, 3250 mg, 3300 mg, 3350 mg, 3400 mg, 3450 mg, 3500 mg, 3550 mg, 3600 mg, 3650 mg, 3700 mg, 3750 mg, 3800 mg, 3850 mg, 3900 mg, 3950 mg, 4000 mg, 4050 mg, 4100 mg, 4150 mg, 4200 mg, 4250 mg, 4300 mg, 4350 mg, 4400 mg, 4450 mg, 4500 mg, 4550 mg, 4600 mg, 4650 mg, 4700 mg, 4750 mg, or 4800 mg.

In some embodiments, the pharmaceutical compositions of the disclosure comprise fospropofol, a pharmaceutically acceptable salt of fospropofol, or mixtures thereof, in an amount of 50-1000 mg (on a fospropofol basis), for example, an amount that is about (i.e., the specified number±10%) any one of 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg.

In some embodiments, the pharmaceutical compositions of the disclosure comprise fospropofol, a pharmaceutically acceptable salt of fospropofol, or mixtures thereof, in an amount of 50-750 mg (on a fospropofol basis), for example, an amount that is about (i.e., the specified number±10%) any one of 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, or 750 mg.

In some embodiments, the pharmaceutical compositions of the disclosure comprise fospropofol, a pharmaceutically acceptable salt of fospropofol, or mixtures thereof, in an amount of 75-1500 mg (on a fospropofol basis), for example, an amount that is about (i.e., the specified number±10%) any one of 75 mg, 150 mg, 225 mg, 300 mg, 375 mg, 450 mg, 525 mg, 600 mg, 675 mg, 750 mg, 825 mg, 900 mg, 975 mg, 1050 mg, 1125 mg, 1200 mg, 1275 mg, 1350 mg, 1425 mg, or 1500 mg.

In some embodiments, the pharmaceutical compositions of the disclosure comprise fospropofol, a pharmaceutically acceptable salt of fospropofol, or mixtures thereof, in an amount of 100-4800 mg (on a fospropofol basis), for example, an amount that is about (i.e., the specified number±10%) any one of 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, 2050 mg, 3100 mg, 3150 mg, 3200 mg, 3250 mg, 3300 mg, 3350 mg, 3400 mg, 3450 mg, 3500 mg, 3550 mg, 3600 mg, 3650 mg, 3700 mg, 3750 mg, 3800 mg, 3850 mg, 3900 mg, 3950 mg, 4000 mg, 4050 mg, 4100 mg, 4150 mg, 4200 mg, 4250 mg, 4300 mg, 4350 mg, 4400 mg, 4450 mg, 4500 mg, 4550 mg, 4600 mg, 4650 mg, 4700 mg, 4750 mg, or 4800 mg.

In some embodiments, the pharmaceutical compositions of the disclosure comprise fospropofol, a pharmaceutically acceptable salt of fospropofol, or mixtures thereof, in an amount of 100-3600 mg (on a fospropofol basis), for example, an amount that is about (i.e., the specified number±10%) any one of 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, 2050 mg, 3100 mg, 3150 mg, 3200 mg, 3250 mg, 3300 mg, 3350 mg, 3400 mg, 3450 mg, 3500 mg, 3550 mg, or 3600 mg.

In some embodiments, the pharmaceutical compositions of the disclosure comprise fospropofol, a pharmaceutically acceptable salt of fospropofol, or mixtures thereof, in an amount of 100-3200 mg (on a fospropofol basis), for example, an amount that is about (i.e., the specified number±10%) any one of 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, 2050 mg, 3100 mg, 3150 mg, or 3200 mg.

In some embodiments, the pharmaceutical compositions of the disclosure comprise fospropofol, a pharmaceutically acceptable salt of fospropofol, or mixtures thereof, in an amount of 200-2400 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, or 2400 mg.

In some embodiments, the pharmaceutical compositions of the disclosure comprise fospropofol, a pharmaceutically acceptable salt of fospropofol, or mixtures thereof, in an amount of 200-2300 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, or 2300 mg.

In some embodiments, the pharmaceutical compositions of the disclosure comprise fospropofol, a pharmaceutically acceptable salt of fospropofol, or mixtures thereof, in an amount of 200-2200 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, or 2200 mg.

In some embodiments, the pharmaceutical compositions of the disclosure comprise fospropofol, a pharmaceutically acceptable salt of fospropofol, or mixtures thereof, in an amount of 200-2100 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, or 2100 mg.

In some embodiments, the pharmaceutical compositions of the disclosure comprise fospropofol, a pharmaceutically acceptable salt of fospropofol, or mixtures thereof, in an amount of 200-2000 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg.

In some embodiments, the pharmaceutical compositions of the disclosure comprise fospropofol, a pharmaceutically acceptable salt of fospropofol, or mixtures thereof, in an amount of 200-1900 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, or 1900 mg.

In some embodiments, the pharmaceutical compositions of the disclosure comprise fospropofol, a pharmaceutically acceptable salt of fospropofol, or mixtures thereof, in an amount of 200-1800 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, or 1800 mg.

In some embodiments, the pharmaceutical compositions of the disclosure comprise fospropofol, a pharmaceutically acceptable salt of fospropofol, or mixtures thereof, in an amount of 200-1700 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, or 1700 mg.

In some embodiments, the pharmaceutical compositions of the disclosure comprise fospropofol, a pharmaceutically acceptable salt of fospropofol, or mixtures thereof, in an amount of 200-1600 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, or 1600 mg.

In some embodiments, the pharmaceutical compositions of the disclosure comprise fospropofol, a pharmaceutically acceptable salt of fospropofol, or mixtures thereof, in an amount of 200-1600 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, or 1600 mg.

In some embodiments, the pharmaceutical compositions of the disclosure comprise fospropofol, a pharmaceutically acceptable salt of fospropofol, or mixtures thereof, in an amount of 200-1500 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, or 1500 mg.

In some embodiments, the pharmaceutical compositions of the disclosure comprise fospropofol, a pharmaceutically acceptable salt of fospropofol, or mixtures thereof, in an amount of 200-1400 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, or 1400 mg.

In some embodiments, the pharmaceutical compositions of the disclosure comprise fospropofol, a pharmaceutically acceptable salt of fospropofol, or mixtures thereof, in an amount of 200-1300 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, or 1300 mg.

In some embodiments, the pharmaceutical compositions of the disclosure comprise fospropofol, a pharmaceutically acceptable salt of fospropofol, or mixtures thereof, in an amount of 200-1200 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, or 1200 mg.

In some embodiments, the pharmaceutical compositions of the disclosure comprise fospropofol, a pharmaceutically acceptable salt of fospropofol, or mixtures thereof, in an amount of 200-1100 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, or 1100 mg.

In some embodiments, the pharmaceutical compositions of the disclosure comprise fospropofol, a pharmaceutically acceptable salt of fospropofol, or mixtures thereof, in an amount of 200-1000 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg.

In some embodiments, the pharmaceutical compositions of the disclosure comprise fospropofol, a pharmaceutically acceptable salt of fospropofol, or mixtures thereof, in an amount of 200-900 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, 800 mg, 850 mg, or 900 mg.

In some embodiments, the pharmaceutical compositions of the disclosure comprise fospropofol, a pharmaceutically acceptable salt of fospropofol, or mixtures thereof, in an amount of 200-800 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, 700 mg, 750 mg, or 800 mg.

In some embodiments, the pharmaceutical compositions of the disclosure comprise fospropofol, a pharmaceutically acceptable salt of fospropofol, or mixtures thereof, in an amount of 200-700 mg (on a fospropofol basis), for example, an amount that is about (i.e., the specified number±10%) any one of 200 mg, 250 mg, 300 mg, 350 mg, 400 mg, 450 mg, 500 mg, 550 mg, 600 mg, 650 mg, or 700 mg.

In some embodiments, the pharmaceutical compositions of the disclosure comprise fospropofol, a pharmaceutically acceptable salt of fospropofol, or mixtures thereof, in an amount of 200-600 mg (on a fospropofol basis), for example, an amount that is about (i.e., the specified number±10%) any one of 200 mg, 250 mg, 300 mg, 350 mg, 400 mg, 450 mg, 500 mg, 550 mg, or 600 mg.

In some embodiments, the pharmaceutical compositions of the disclosure comprise fospropofol, a pharmaceutically acceptable salt of fospropofol, or mixtures thereof, in an amount of 200-500 mg (on a fospropofol basis), for example, an amount that is about (i.e., the specified number±10%) any one of 200 mg, 250 mg, 300 mg, 350 mg, 400 mg, 450 mg, or 500 mg.

In some embodiments, the pharmaceutical compositions of the disclosure comprise fospropofol, a pharmaceutically acceptable salt of fospropofol, or mixtures thereof, in an amount of 200-400 mg (on a fospropofol basis), for example, an amount that is about (i.e., the specified number±10%) any one of 200 mg, 250 mg, 300 mg, 350 mg, or 400 mg.

In some embodiments, the pharmaceutical compositions of the disclosure comprise fospropofol, a pharmaceutically acceptable salt of fospropofol, or mixtures thereof, in an amount of 200-300 mg (on a fospropofol basis), for example, an amount that is about (i.e., the specified number±10%) any one of 200 mg, 250 mg, or 300 mg.

In some embodiments, the pharmaceutical compositions of the disclosure comprise fospropofol, a pharmaceutically acceptable salt of fospropofol, or mixtures thereof, in an amount of 400-2400 mg (on a fospropofol basis), for example, an amount that is about (i.e., the specified number±10%) any one of 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, or 2400 mg.

In some embodiments, the effective amount of fospropofol, a pharmaceutically acceptable salt of fospropofol, or mixtures thereof, is In some embodiments, the pharmaceutical compositions of the disclosure comprise fospropofol, a pharmaceutically acceptable salt of fospropofol, or mixtures thereof, in an amount of 400-2000 mg (on a fospropofol basis), for example, an amount that is about (i.e., the specified number±10%) any one of 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg.

In some embodiments, the pharmaceutical compositions of the disclosure comprise fospropofol, a pharmaceutically acceptable salt of fospropofol, or mixtures thereof, in an amount of 400-1600 mg (on a fospropofol basis), for example, an amount that is about (i.e., the specified number±10%) any one of 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, or 1600 mg.

In some embodiments, the pharmaceutical compositions of the disclosure comprise fospropofol, a pharmaceutically acceptable salt of fospropofol, or mixtures thereof, in an amount of 400-1200 mg (on a fospropofol basis), for example, an amount that is about (i.e., the specified number±10%) any one of 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, or 1200 mg.

In some embodiments, the pharmaceutical compositions of the disclosure comprise fospropofol, a pharmaceutically acceptable salt of fospropofol, or mixtures thereof, in an amount of 400-1200 mg (on a fospropofol basis), for example, an amount that is about (i.e., the specified number±10%) any one of 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, or 1200 mg.

In some embodiments, the pharmaceutical compositions of the disclosure comprise fospropofol, a pharmaceutically acceptable salt of fospropofol, or mixtures thereof, in an amount of 400-1000 mg (on a fospropofol basis), for example, an amount that is about (i.e., the specified number±10%) any one of 400 mg, 450 mg, 500 mg, 550 mg, 600 mg, 650 mg, 700 mg, 750 mg, 800 mg, 850 mg, 900 mg, 950 mg, or 1000 mg.

In some embodiments, the pharmaceutical compositions of the disclosure comprise fospropofol, a pharmaceutically acceptable salt of fospropofol, or mixtures thereof, in an amount of 400-800 mg (on a fospropofol basis), for example, an amount that is about (i.e., the specified number±10%) any one of 400 mg, 450 mg, 500 mg, 550 mg, 600 mg, 650 mg, 700 mg, 750 mg, or 800 mg.

In some embodiments, the pharmaceutical compositions of the disclosure comprise fospropofol, a pharmaceutically acceptable salt of fospropofol, or mixtures thereof, in an amount of 400-600 mg (on a fospropofol basis), for example, an amount that is about (i.e., the specified number±10%) any one of 400 mg, 450 mg, 500 mg, 550 mg, or 600 mg.

In some embodiments, the pharmaceutical compositions of the disclosure comprise fospropofol, a pharmaceutically acceptable salt of fospropofol, or mixtures thereof, in an amount of 600-1200 mg (on a fospropofol basis), for example, an amount that is about (i.e., the specified number±10%) any one of 600 mg, 650 mg, 700 mg, 750 mg, 800 mg, 850 mg, 900 mg, 950 mg, 1000 mg, 1050 mg, 1100 mg, 1150 mg, or 1200 mg.

In some embodiments, the pharmaceutical compositions of the disclosure comprise fospropofol, a pharmaceutically acceptable salt of fospropofol, or mixtures thereof, in an amount of 800-1200 mg (on a fospropofol basis), for example, an amount that is about (i.e., the specified number±10%) any one of 800 mg, 850 mg, 900 mg, 950 mg, 1000 mg, 1050 mg, 1100 mg, 1150 mg, or 1200 mg.

In some embodiments, the pharmaceutical compositions of the disclosure comprise fospropofol, a pharmaceutically acceptable salt of fospropofol, or mixtures thereof, in an amount of 1000-2000 mg (on a fospropofol basis), for example, an amount that is about (i.e., the specified number±10%) any one of 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg.

In some embodiments, the pharmaceutical compositions of the disclosure comprise fospropofol, a pharmaceutically acceptable salt of fospropofol, or mixtures thereof, in an amount of 1000-1600 mg (on a fospropofol basis) delivered perorally, for example, an amount that is about (i.e., the specified number±10%) any one of 1000 mg, 1050 mg, 1100 mg, 1150 mg, 1200 mg, 1250 mg, 1300 mg, 1350 mg, 1400 mg, 1450 mg, 1500 mg, 1550 mg, or 1600 mg.

In some embodiments, the pharmaceutical compositions of the disclosure comprise fospropofol, a pharmaceutically acceptable salt of fospropofol, or mixtures thereof, in an amount of 1200-2000 mg (on a fospropofol basis), for example, an amount that is about (i.e., the specified number±10%) any one of 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg.

In some embodiments, the pharmaceutical compositions of the disclosure comprise fospropofol, a pharmaceutically acceptable salt of fospropofol, or mixtures thereof, in an amount of 1200-1800 mg (on a fospropofol basis), for example, an amount that is about (i.e., the specified number±10%) any one of 1200 mg, 1250 mg, 1300 mg, 1350 mg, 1400 mg, 1450 mg, 1500 mg, 1550 mg, 1600 mg, 1650 mg, 1700 mg, 1750 mg, or 1800 mg.

In some embodiments, the pharmaceutical compositions of the disclosure comprise fospropofol, a pharmaceutically acceptable salt of fospropofol, or mixtures thereof, in an amount of 1600-2400 mg (on a fospropofol basis), for example, an amount that is about (i.e., the specified number±10%) any one of 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, or 2400 mg.

In some embodiments, the pharmaceutical compositions of the disclosure comprise fospropofol, a pharmaceutically acceptable salt of fospropofol, or mixtures thereof, in an amount of 1800-2400 mg (on a fospropofol basis), for example, an amount that is about (i.e., the specified number±10%) any one of 1800 mg, 1850 mg, 1900 mg, 1950 mg, 2000 mg, 2050 mg, 2100 mg, 2150 mg, 2200 mg, 2250 mg, 2300 mg, 2350 mg, or 2400 mg.

In some embodiments, the pharmaceutical compositions of the disclosure comprise fospropofol, a pharmaceutically acceptable salt of fospropofol, or mixtures thereof, in an amount of 2000-2400 mg (on a fospropofol basis), for example, an amount that is about (i.e., the specified number±10%) any one of 2000 mg, 2050 mg, 2100 mg, 2150 mg, 2200 mg, 2250 mg, 2300 mg, 2350 mg, or 2400 mg.

In some embodiments, the pharmaceutical compositions of the disclosure comprise fospropofol, a pharmaceutically acceptable salt of fospropofol, or mixtures thereof, in an amount of 50 mg (on a fospropofol basis).

In some embodiments, the pharmaceutical compositions of the disclosure comprise fospropofol, a pharmaceutically acceptable salt of fospropofol, or mixtures thereof, in an amount of 100 mg (on a fospropofol basis).

In some embodiments, the pharmaceutical compositions of the disclosure comprise fospropofol, a pharmaceutically acceptable salt of fospropofol, or mixtures thereof, in an amount of 125 mg (on a fospropofol basis).

In some embodiments, the pharmaceutical compositions of the disclosure comprise fospropofol, a pharmaceutically acceptable salt of fospropofol, or mixtures thereof, in an amount of 150 mg (on a fospropofol basis).

In some embodiments, the pharmaceutical compositions of the disclosure comprise fospropofol, a pharmaceutically acceptable salt of fospropofol, or mixtures thereof, in an amount of 175 mg (on a fospropofol basis).

In some embodiments, the pharmaceutical compositions of the disclosure comprise fospropofol, a pharmaceutically acceptable salt of fospropofol, or mixtures thereof, in an amount of 200 mg (on a fospropofol basis).

In some embodiments, the pharmaceutical compositions of the disclosure comprise fospropofol, a pharmaceutically acceptable salt of fospropofol, or mixtures thereof, in an amount of 225 mg (on a fospropofol basis).

In some embodiments, the pharmaceutical compositions of the disclosure comprise fospropofol, a pharmaceutically acceptable salt of fospropofol, or mixtures thereof, in an amount of 250 mg (on a fospropofol basis).

In some embodiments, the pharmaceutical compositions of the disclosure comprise fospropofol, a pharmaceutically acceptable salt of fospropofol, or mixtures thereof, in an amount of 275 mg (on a fospropofol basis).

In some embodiments, the pharmaceutical compositions of the disclosure comprise fospropofol, a pharmaceutically acceptable salt of fospropofol, or mixtures thereof, in an amount of 300 mg (on a fospropofol basis).

In some embodiments, the pharmaceutical compositions of the disclosure comprise fospropofol, a pharmaceutically acceptable salt of fospropofol, or mixtures thereof, in an amount of 325 mg (on a fospropofol basis).

In some embodiments, the pharmaceutical compositions of the disclosure comprise fospropofol, a pharmaceutically acceptable salt of fospropofol, or mixtures thereof, in an amount of 350 mg (on a fospropofol basis).

In some embodiments, the pharmaceutical compositions of the disclosure comprise fospropofol, a pharmaceutically acceptable salt of fospropofol, or mixtures thereof, in an amount of 375 mg (on a fospropofol basis).

In some embodiments, the pharmaceutical compositions of the disclosure comprise fospropofol, a pharmaceutically acceptable salt of fospropofol, or mixtures thereof, in an amount of 400 mg (on a fospropofol basis).

In some embodiments, the pharmaceutical compositions of the disclosure comprise fospropofol, a pharmaceutically acceptable salt of fospropofol, or mixtures thereof, in an amount of 425 mg (on a fospropofol basis).

In some embodiments, the pharmaceutical compositions of the disclosure comprise fospropofol, a pharmaceutically acceptable salt of fospropofol, or mixtures thereof, in an amount of 450 mg (on a fospropofol basis).

In some embodiments, the pharmaceutical compositions of the disclosure comprise fospropofol, a pharmaceutically acceptable salt of fospropofol, or mixtures thereof, in an amount of 475 mg (on a fospropofol basis).

In some embodiments, the pharmaceutical compositions of the disclosure comprise fospropofol, a pharmaceutically acceptable salt of fospropofol, or mixtures thereof, in an amount of 500 mg (on a fospropofol basis).

In some embodiments, the pharmaceutical compositions of the disclosure comprise fospropofol, a pharmaceutically acceptable salt of fospropofol, or mixtures thereof, in an amount of 525 mg (on a fospropofol basis).

In some embodiments, the pharmaceutical compositions of the disclosure comprise fospropofol, a pharmaceutically acceptable salt of fospropofol, or mixtures thereof, in an amount of 550 mg (on a fospropofol basis).

In some embodiments, the pharmaceutical compositions of the disclosure comprise fospropofol, a pharmaceutically acceptable salt of fospropofol, or mixtures thereof, in an amount of 575 mg (on a fospropofol basis).

In some embodiments, the pharmaceutical compositions of the disclosure comprise fospropofol, a pharmaceutically acceptable salt of fospropofol, or mixtures thereof, in an amount of 600 mg (on a fospropofol basis).

In some embodiments, the pharmaceutical compositions of the disclosure comprise fospropofol, a pharmaceutically acceptable salt of fospropofol, or mixtures thereof, in an amount of 625 mg (on a fospropofol basis).

In some embodiments, the pharmaceutical compositions of the disclosure comprise fospropofol, a pharmaceutically acceptable salt of fospropofol, or mixtures thereof, in an amount of 650 mg (on a fospropofol basis).

In some embodiments, the pharmaceutical compositions of the disclosure comprise fospropofol, a pharmaceutically acceptable salt of fospropofol, or mixtures thereof, in an amount of 675 mg (on a fospropofol basis).

In some embodiments, the pharmaceutical compositions of the disclosure comprise fospropofol, a pharmaceutically acceptable salt of fospropofol, or mixtures thereof, in an amount of 700 mg (on a fospropofol basis).

In some embodiments, the pharmaceutical compositions of the disclosure comprise fospropofol, a pharmaceutically acceptable salt of fospropofol, or mixtures thereof, in an amount of 725 mg (on a fospropofol basis).

In some embodiments, the pharmaceutical compositions of the disclosure comprise fospropofol, a pharmaceutically acceptable salt of fospropofol, or mixtures thereof, in an amount of 750 mg (on a fospropofol basis).

In some embodiments, the pharmaceutical compositions of the disclosure comprise fospropofol, a pharmaceutically acceptable salt of fospropofol, or mixtures thereof, in an amount of 775 mg (on a fospropofol basis).

In some embodiments, the pharmaceutical compositions of the disclosure comprise fospropofol, a pharmaceutically acceptable salt of fospropofol, or mixtures thereof, in an amount of 800 mg (on a fospropofol basis).

In some embodiments, the pharmaceutical compositions of the disclosure comprise fospropofol, a pharmaceutically acceptable salt of fospropofol, or mixtures thereof, in an amount of 825 mg (on a fospropofol basis).

In some embodiments, the pharmaceutical compositions of the disclosure comprise fospropofol, a pharmaceutically acceptable salt of fospropofol, or mixtures thereof, in an amount of 850 mg (on a fospropofol basis).

In some embodiments, the pharmaceutical compositions of the disclosure comprise fospropofol, a pharmaceutically acceptable salt of fospropofol, or mixtures thereof, in an amount of 875 mg (on a fospropofol basis).

In some embodiments, the pharmaceutical compositions of the disclosure comprise fospropofol, a pharmaceutically acceptable salt of fospropofol, or mixtures thereof, in an amount of 900 mg (on a fospropofol basis).

In some embodiments, the pharmaceutical compositions of the disclosure comprise fospropofol, a pharmaceutically acceptable salt of fospropofol, or mixtures thereof, in an amount of 925 mg (on a fospropofol basis).

In some embodiments, the pharmaceutical compositions of the disclosure comprise fospropofol, a pharmaceutically acceptable salt of fospropofol, or mixtures thereof, in an amount of 950 mg (on a fospropofol basis).

In some embodiments, the pharmaceutical compositions of the disclosure comprise fospropofol, a pharmaceutically acceptable salt of fospropofol, or mixtures thereof, in an amount of 975 mg (on a fospropofol basis).

In some embodiments, the pharmaceutical compositions of the disclosure comprise fospropofol, a pharmaceutically acceptable salt of fospropofol, or mixtures thereof, in an amount of 1000 mg (on a fospropofol basis).

In some aspects of the disclosure, the pharmaceutical compositions of the disclosure have specific release characteristics.

In some embodiments, the pharmaceutical compositions of the disclosure, 20% to 80% by weight of the pharmaceutical composition dissolves within 30 minutes when suspended in 0.1 N HCL.

In some embodiments, the pharmaceutical compositions of the disclosure, 20% to 80% by weight of said solid pharmaceutical composition dissolves within 30 minutes when suspended in pH 4.5 buffer.

The pharmaceutical compositions of the disclosure may be used in performing the methods of treatment of the disclosure.

In some aspects, the pharmaceutical compositions of the disclosure, when administered to a patient, produce specific pharmacokinetic profiles.

In some embodiments, the pharmaceutical compositions of the disclosure, when administered to a patient in one or more doses, results in a plasma Cmax or mean Cmax of propofol of at least 200-4000 ng/mL, for example, a Cmax or mean Cmax that is about (i.e., the specified number±10%) any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3050 ng/mL, 3100 ng/mL, 3150 ng/mL, 3200 ng/mL, 3250 ng/mL, 3300 ng/mL, 3350 ng/mL, 3400 ng/mL, 3450 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, or 4000 ng/mL.

In some embodiments, the pharmaceutical compositions of the disclosure, when administered to a patient in one or more doses, results in a plasma Cmax or mean Cmax of propofol of at least 200-1600 ng/mL, for example, a Cmax or mean Cmax that is about (i.e., the specified number±10%) any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, or 1600 ng/mL.

In some embodiments, the pharmaceutical compositions of the disclosure, when administered to a patient in one or more doses, results in a plasma Cmax or mean Cmax of propofol of at least 200-1200 ng/mL, for example, a Cmax or mean Cmax that is about (i.e., the specified number±10%) any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1050 ng/mL, 1100 ng/mL, 1150 ng/mL, or 1200 ng/mL.

In some embodiments, the pharmaceutical compositions of the disclosure, when administered to a patient in one or more doses, results in a plasma Cmax or mean Cmax of propofol of at least 200-1000 ng/mL, for example, a Cmax or mean Cmax that is about (i.e., the specified number±10%) any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, or 1000 ng/mL.

In some embodiments, the pharmaceutical compositions of the disclosure, when administered to a patient in one or more doses, results in a plasma Cmax or mean Cmax of propofol of at least 200-800 ng/mL, for example, a Cmax or mean Cmax that is about (i.e., the specified number±10%) any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, or 800 ng/mL.

In some embodiments, the pharmaceutical compositions of the disclosure, when administered to a patient in one or more doses, results in a plasma Cmax or mean Cmax of propofol of at least 200-600 ng/mL, for example, a Cmax or mean Cmax that is about (i.e., the specified number±10%) any one of 200 ng/mL, 250 ng/mL, 300 ng/mL, 350 ng/mL, 400 ng/mL, 450 ng/mL, 500 ng/mL, 550 ng/mL, or 600 ng/mL.

In some embodiments, the pharmaceutical compositions of the disclosure, when administered to a patient in one or more doses, results in a plasma Cmax or mean Cmax of propofol of at least 200-400 ng/mL, for example, a Cmax or mean Cmax that is about (i.e., the specified number±10%) any one of 200 ng/mL, 250 ng/mL, 300 ng/mL, 350 ng/mL, or 400 ng/mL.

In some embodiments, the pharmaceutical compositions of the disclosure, when administered to a patient in one or more doses, results in a plasma Cmax or mean Cmax of propofol of at least 50-500 ng/mL, for example, a Cmax or mean Cmax that is about (i.e., the specified number±10%)

any one of 50 ng/mL, 100 ng/mL, 150 ng/mL, 200 ng/mL, 250 ng/mL, 300 ng/mL, 350 ng/mL, 400 ng/mL, 450 ng/mL, or 500 ng/mL.

In some embodiments, the pharmaceutical compositions of the disclosure, when administered to a patient in one or more doses, results in a plasma Cmax or mean Cmax of propofol of no greater than 5000 ng/mL.

In some embodiments, the pharmaceutical compositions of the disclosure, when administered to a patient in one or more doses, results in a plasma Cmax or mean Cmax of propofol of no greater than 4000 ng/mL.

In some embodiments, the pharmaceutical compositions of the disclosure, when administered to a patient in one or more doses, results in a plasma Cmax or mean Cmax of propofol of no greater than 3000 ng/mL.

In some embodiments, the pharmaceutical compositions of the disclosure, when administered to a patient in one or more doses, results in a plasma Cmax or mean Cmax of propofol of no greater than 2000 ng/mL.

In some embodiments, the pharmaceutical compositions of the disclosure, when administered to a patient in one or more doses, results in a plasma Cmax of propofol of no greater than 1600 ng/mL.

In some embodiments, the pharmaceutical compositions of the disclosure, when administered to a patient in one or more doses, results in a plasma Cmax or mean Cmax of propofol of no greater than 1200 ng/mL.

In some embodiments, the pharmaceutical compositions of the disclosure, when administered to a patient in one or more doses, results in a plasma Cmax of propofol of no greater than 1000 ng/mL.

In some embodiments, the pharmaceutical compositions of the disclosure, when administered to a patient in one or more doses, results in a plasma Cmax or mean Cmax of propofol of no greater than 800 ng/mL.

In some embodiments, the pharmaceutical compositions of the disclosure, when administered to a patient in one or more doses, results in a plasma Cmax or mean Cmax of propofol of no greater than 600 ng/mL.

In some embodiments, the pharmaceutical compositions of the disclosure, when administered to a patient in one or more doses, results in a plasma Cmax or mean Cmax of propofol of no greater than 500 ng/mL.

In some embodiments, the pharmaceutical compositions of the disclosure, when administered to a patient in one or more doses, results in a plasma Cmax or mean Cmax of propofol of no greater than 400 ng/mL.

In some embodiments, the pharmaceutical compositions of the disclosure, when administered to a patient in one or more doses, results in a plasma Cmax or mean Cmax of propofol of no greater than 200 ng/mL.

In some embodiments, the pharmaceutical compositions of the disclosure, when administered to a patient in one or more doses, results in a plasma Cmax or mean Cmax of propofol of no greater than 100 ng/mL.

In some embodiments, the pharmaceutical compositions of the disclosure, when administered to a patient in one or more doses, results in a plasma Cmax or mean Cmax of fospropofol of at least 800-18000 ng/mL, for example, a Cmax or mean Cmax that is about (i.e., the specified number±10%) any one of 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 1950 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, 4000 ng/mL, 4050 ng/mL, 4100 ng/mL, 4150 ng/mL, 4200 ng/mL, 4250 ng/mL, 4300 ng/mL, 4350 ng/mL, 4400 ng/mL, 4450 ng/mL, 4500 ng/mL, 4550 ng/mL, 4600 ng/mL, 4650 ng/mL, 4700 ng/mL, 4750 ng/mL, 4800 ng/mL, 4850 ng/mL, 4900 ng/mL, 4950 ng/mL, 5000 ng/mL, 5050 ng/mL, 5100 ng/mL, 5150 ng/mL, 5200 ng/mL, 5250 ng/mL, 5300 ng/mL, 5350 ng/mL, 5400 ng/mL, 5450 ng/mL, 5500 ng/mL, 5550 ng/mL, 5600 ng/mL, 5650 ng/mL, 5700 ng/mL, 5750 ng/mL, 5800 ng/mL, 5850 ng/mL, 5900 ng/mL, 5950 ng/mL, 6000 ng/mL, 6050 ng/mL, 6100 ng/mL, 6150 ng/mL, 6200 ng/mL, 6250 ng/mL, 6300 ng/mL, 6350 ng/mL, 6400 ng/mL, 6450 ng/mL, 6500 ng/mL, 6550 ng/mL, 6600 ng/mL, 6650 ng/mL, 6700 ng/mL, 6750 ng/mL, 6800 ng/mL, 6850 ng/mL, 6900 ng/mL, 6950 ng/mL, 7000 ng/mL, 7050 ng/mL, 7100 ng/mL, 7150 ng/mL, 7200 ng/mL, 7250 ng/mL, 7300 ng/mL, 7350 ng/mL, 7400 ng/mL, 7450 ng/mL, 7500 ng/mL, 7550 ng/mL, 7600 ng/mL, 7650 ng/mL, 7700 ng/mL, 7750 ng/mL, 7800 ng/mL, 7850 ng/mL, 7900 ng/mL, 7950 ng/mL, 8000 ng/mL, 8050 ng/mL, 8100 ng/mL, 8150 ng/mL, 8200 ng/mL, 8250 ng/mL, 8300 ng/mL, 8350 ng/mL, 8400 ng/mL, 8450 ng/mL, 8500 ng/mL, 8550 ng/mL, 8600 ng/mL, 8650 ng/mL, 8700 ng/mL, 8750 ng/mL, 800 ng/mL, 8850 ng/mL, 8900 ng/mL, 8950 ng/mL, 9000 ng/mL, 9050 ng/mL, 9100 ng/mL, 9150 ng/mL, 9200 ng/mL, 9250 ng/mL, 9300 ng/mL, 9350 ng/mL, 9400 ng/mL, 9450 ng/mL, 9500 ng/mL, 9550 ng/mL, 9600 ng/mL, 9650 ng/mL, 9700 ng/mL, 9750 ng/mL, 9000 ng/mL, 9950 ng/mL, 9900 ng/mL, 9950 ng/mL, 10000 ng/mL, 10050 ng/mL, 10100 ng/mL, 10150 ng/mL, 10200 ng/mL, 10250 ng/mL, 10300 ng/mL, 10350 ng/mL, 10400 ng/mL, 10450 ng/mL, 10500 ng/mL, 10550 ng/mL, 10600 ng/mL, 10650 ng/mL, 10700 ng/mL, 10750 ng/mL, 1000 ng/mL, 101050 ng/mL, 10900 ng/mL, 10950 ng/mL, 11000 ng/mL, 11050 ng/mL, 11100 ng/mL, 11150 ng/mL, 11200 ng/mL, 11250 ng/mL, 11300 ng/mL, 11350 ng/mL, 11400 ng/mL, 11450 ng/mL, 11500 ng/mL, 11550 ng/mL, 11600 ng/mL, 11650 ng/mL, 11700 ng/mL, 11750 ng/mL, 1100 ng/mL, 111150 ng/mL, 11900 ng/mL, 11950 ng/mL, 12000 ng/mL, 12050 ng/mL, 12100 ng/mL, 12150 ng/mL, 12200 ng/mL, 12250 ng/mL, 12300 ng/mL, 12350 ng/mL, 12400 ng/mL, 12450 ng/mL, 12500 ng/mL, 12550 ng/mL, 12600 ng/mL, 12650 ng/mL, 12700 ng/mL, 12750 ng/mL, 1200 ng/mL, 121250 ng/mL, 12900 ng/mL, 12950 ng/mL, 13000 ng/mL, 13050 ng/mL, 13100 ng/mL, 13150 ng/mL, 13200 ng/mL, 13250 ng/mL, 13300 ng/mL, 13350 ng/mL, 13400 ng/mL, 13450 ng/mL, 13500 ng/mL, 13550 ng/mL, 13600 ng/mL, 13650 ng/mL, 13700 ng/mL, 13750 ng/mL, 1300 ng/mL, 131350 ng/mL, 13900 ng/mL, 13950 ng/mL, 14000 ng/mL, 14050 ng/mL, 14100 ng/mL, 14150 ng/mL, 14200 ng/mL, 14250 ng/mL, 14300 ng/mL, 14350 ng/mL, 14400 ng/mL, 14450 ng/mL, 14500 ng/mL, 14550 ng/mL, 14600 ng/mL, 14650 ng/mL, 14700 ng/mL, 14750 ng/mL, 1400 ng/mL, 141450 ng/mL, 14900 ng/mL, 14950 ng/mL, 15000 ng/mL, 15050 ng/mL, 15100 ng/mL, 15150 ng/mL, 15200 ng/mL, 15250 ng/mL, 15300 ng/mL, 15350 ng/mL, 15400 ng/mL, 15450 ng/mL, 15500 ng/mL, 15550 ng/mL, 15600 ng/mL, 15650 ng/mL, 15700 ng/mL, 15750 ng/mL, 1500 ng/mL, 151550 ng/mL, 15900 ng/mL, 15950 ng/mL, 16000 ng/mL, 16050 ng/mL, 16100 ng/mL, 16150 ng/mL, 16200 ng/mL, 16250 ng/mL, 16300 ng/mL, 16350 ng/mL, 16400 ng/mL, 16450 ng/mL, 16500 ng/mL, 16550 ng/mL, 16600 ng/mL, 16650 ng/mL, 16700 ng/mL, 16750 ng/mL, 1600 ng/mL, 161650 ng/mL, 16900 ng/mL, 16950 ng/mL, 17000 ng/mL, 17050 ng/mL, 17100 ng/mL, 17150 ng/mL, 17200 ng/mL, 17250 ng/mL, 17300 ng/mL, 17350 ng/mL, 17400 ng/mL, 17450 ng/mL, 17500 ng/mL, 17550 ng/mL, 17600 ng/mL, 17650 ng/mL, 17700 ng/mL, 17750 ng/mL, 1700 ng/mL, 171750 ng/mL, 17900 ng/mL, 17950 ng/mL, or 18000 ng/mL.

In some embodiments, the pharmaceutical compositions of the disclosure, when administered to a patient in one or more doses, results in a plasma Cmax or mean Cmax of fospropofol of at least 2000-10000 ng/mL, for example, a Cmax or mean Cmax that is about (i.e., the specified number±10%) any one of 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, 4000 ng/mL, 4050 ng/mL, 4100 ng/mL, 4150 ng/mL, 4200 ng/mL, 4250 ng/mL, 4300 ng/mL, 4350 ng/mL, 4400 ng/mL, 4450 ng/mL, 4500 ng/mL, 4550 ng/mL, 4600 ng/mL, 4650 ng/mL, 4700 ng/mL, 4750 ng/mL, 4800 ng/mL, 4850 ng/mL, 4900 ng/mL, 4950 ng/mL, 5000 ng/mL, 5050 ng/mL, 5100 ng/mL, 5150 ng/mL, 5200 ng/mL, 5250 ng/mL, 5300 ng/mL, 5350 ng/mL, 5400 ng/mL, 5450 ng/mL, 5500 ng/mL, 5550 ng/mL, 5600 ng/mL, 5650 ng/mL, 5700 ng/mL, 5750 ng/mL, 5800 ng/mL, 5850 ng/mL, 5900 ng/mL, 5950 ng/mL, 6000 ng/mL, 6050 ng/mL, 6100 ng/mL, 6150 ng/mL, 6200 ng/mL, 6250 ng/mL, 6300 ng/mL, 6350 ng/mL, 6400 ng/mL, 6450 ng/mL, 6500 ng/mL, 6550 ng/mL, 6600 ng/mL, 6650 ng/mL, 6700 ng/mL, 6750 ng/mL, 6800 ng/mL, 6850 ng/mL, 6900 ng/mL, 6950 ng/mL, 7000 ng/mL, 7050 ng/mL, 7100 ng/mL, 7150 ng/mL, 7200 ng/mL, 7250 ng/mL, 7300 ng/mL, 7350 ng/mL, 7400 ng/mL, 7450 ng/mL, 7500 ng/mL, 7550 ng/mL, 7600 ng/mL, 7650 ng/mL, 7700 ng/mL, 7750 ng/mL, 7800 ng/mL, 7850 ng/mL, 7900 ng/mL, 7950 ng/mL, 8000 ng/mL, 8050 ng/mL, 8100 ng/mL, 8150 ng/mL, 8200 ng/mL, 8250 ng/mL, 8300 ng/mL, 8350 ng/mL, 8400 ng/mL, 8450 ng/mL, 8500 ng/mL, 8550 ng/mL, 8600 ng/mL, 8650 ng/mL, 8700 ng/mL, 8750 ng/mL, 800 ng/mL, 8850 ng/mL, 8900 ng/mL, 8950 ng/mL, 9000 ng/mL, 9050 ng/mL, 9100 ng/mL, 9150 ng/mL, 9200 ng/mL, 9250 ng/mL, 9300 ng/mL, 9350 ng/mL, 9400 ng/mL, 9450 ng/mL, 9500 ng/mL, 9550 ng/mL, 9600 ng/mL, 9650 ng/mL, 9700 ng/mL, 9750 ng/mL, 9000 ng/mL, 9950 ng/mL, 9900 ng/mL, 9950 ng/mL, or 10000 ng/mL.

In some embodiments, the pharmaceutical compositions of the disclosure, when administered to a patient in one or more doses, results in a plasma Cmax or mean Cmax of fospropofol that is a value that is 80% to 125% of (or bioequivalent to) 800-18000 ng/mL, for example, a Cmax or mean Cmax that is a value that is 80% to 125% of (or bioequivalent to) any one of 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 1950 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, 4000 ng/mL, 4050 ng/mL, 4100 ng/mL, 4150 ng/mL, 4200 ng/mL, 4250 ng/mL, 4300 ng/mL, 4350 ng/mL, 4400 ng/mL, 4450 ng/mL, 4500 ng/mL, 4550 ng/mL, 4600 ng/mL, 4650 ng/mL, 4700 ng/mL, 4750 ng/mL, 4800 ng/mL, 4850 ng/mL, 4900 ng/mL, 4950 ng/mL, 5000 ng/mL, 5050 ng/mL, 5100 ng/mL, 5150 ng/mL, 5200 ng/mL, 5250 ng/mL, 5300 ng/mL, 5350 ng/mL, 5400 ng/mL, 5450 ng/mL, 5500 ng/mL, 5550 ng/mL, 5600 ng/mL, 5650 ng/mL, 5700 ng/mL, 5750 ng/mL, 5800 ng/mL, 5850 ng/mL, 5900 ng/mL, 5950 ng/mL, 6000 ng/mL, 6050 ng/mL, 6100 ng/mL, 6150 ng/mL, 6200 ng/mL, 6250 ng/mL, 6300 ng/mL, 6350 ng/mL, 6400 ng/mL, 6450 ng/mL, 6500 ng/mL, 6550 ng/mL, 6600 ng/mL, 6650 ng/mL, 6700 ng/mL, 6750 ng/mL, 6800 ng/mL, 6850 ng/mL, 6900 ng/mL, 6950 ng/mL, 7000 ng/mL, 7050 ng/mL, 7100 ng/mL, 7150 ng/mL, 7200 ng/mL, 7250 ng/mL, 7300 ng/mL, 7350 ng/mL, 7400 ng/mL, 7450 ng/mL, 7500 ng/mL, 7550 ng/mL, 7600 ng/mL, 7650 ng/mL, 7700 ng/mL, 7750 ng/mL, 7800 ng/mL, 7850 ng/mL, 7900 ng/mL, 7950 ng/mL, 8000 ng/mL, 8050 ng/mL, 8100 ng/mL, 8150 ng/mL, 8200 ng/mL, 8250 ng/mL, 8300 ng/mL, 8350 ng/mL, 8400 ng/mL, 8450 ng/mL, 8500 ng/mL, 8550 ng/mL, 8600 ng/mL, 8650 ng/mL, 8700 ng/mL, 8750 ng/mL, 800 ng/mL, 8850 ng/mL, 8900 ng/mL, 8950 ng/mL, 9000 ng/mL, 9050 ng/mL, 9100 ng/mL, 9150 ng/mL, 9200 ng/mL, 9250 ng/mL, 9300 ng/mL, 9350 ng/mL, 9400 ng/mL, 9450 ng/mL, 9500 ng/mL, 9550 ng/mL, 9600 ng/mL, 9650 ng/mL, 9700 ng/mL, 9750 ng/mL, 9000 ng/mL, 9950 ng/mL, 9900 ng/mL, 9950 ng/mL, 10000 ng/mL, 10050 ng/mL, 10100 ng/mL, 10150 ng/mL, 10200 ng/mL, 10250 ng/mL, 10300 ng/mL, 10350 ng/mL, 10400 ng/mL, 10450 ng/mL, 10500 ng/mL, 10550 ng/mL, 10600 ng/mL, 10650 ng/mL, 10700 ng/mL, 10750 ng/mL, 1000 ng/mL, 101050 ng/mL, 10900 ng/mL, 10950 ng/mL, 11000 ng/mL, 11050 ng/mL, 11100 ng/mL, 11150 ng/mL, 11200 ng/mL, 11250 ng/mL, 11300 ng/mL, 11350 ng/mL, 11400 ng/mL, 11450 ng/mL, 11500 ng/mL, 11550 ng/mL, 11600 ng/mL, 11650 ng/mL, 11700 ng/mL, 11750 ng/mL, 1100 ng/mL, 111150 ng/mL, 11900 ng/mL, 11950 ng/mL, 12000 ng/mL, 12050 ng/mL, 12100 ng/mL, 12150 ng/mL, 12200 ng/mL, 12250 ng/mL, 12300 ng/mL, 12350 ng/mL, 12400 ng/mL, 12450 ng/mL, 12500 ng/mL, 12550 ng/mL, 12600 ng/mL, 12650 ng/mL, 12700 ng/mL, 12750 ng/mL, 1200 ng/mL, 121250 ng/mL, 12900 ng/mL, 12950 ng/mL, 13000 ng/mL, 13050 ng/mL, 13100 ng/mL, 13150 ng/mL, 13200 ng/mL, 13250 ng/mL, 13300 ng/mL, 13350 ng/mL, 13400 ng/mL, 13450 ng/mL, 13500 ng/mL, 13550 ng/mL, 13600 ng/mL, 13650 ng/mL, 13700 ng/mL, 13750 ng/mL, 1300 ng/mL, 131350 ng/mL, 13900 ng/mL, 13950 ng/mL, 14000 ng/mL, 14050 ng/mL, 14100 ng/mL, 14150 ng/mL, 14200 ng/mL, 14250 ng/mL, 14300 ng/mL, 14350 ng/mL, 14400 ng/mL, 14450 ng/mL, 14500 ng/mL, 14550 ng/mL, 14600 ng/mL, 14650 ng/mL, 14700 ng/mL, 14750 ng/mL, 1400 ng/mL, 141450 ng/mL, 14900 ng/mL, 14950 ng/mL, 15000 ng/mL, 15050 ng/mL, 15100 ng/mL, 15150 ng/mL, 15200 ng/mL, 15250 ng/mL, 15300 ng/mL, 15350 ng/mL, 15400 ng/mL, 15450 ng/mL, 15500 ng/mL, 15550 ng/mL, 15600 ng/mL, 15650 ng/mL, 15700 ng/mL, 15750 ng/mL, 1500 ng/mL, 151550 ng/mL, 15900 ng/mL, 15950 ng/mL, 16000 ng/mL, 16050 ng/mL, 16100 ng/mL, 16150 ng/mL, 16200 ng/mL, 16250 ng/mL, 16300 ng/mL, 16350 ng/mL, 16400 ng/mL, 16450 ng/mL, 16500 ng/mL, 16550 ng/mL, 16600 ng/mL, 16650 ng/mL, 16700 ng/mL, 16750 ng/mL, 1600 ng/mL, 161650 ng/mL, 16900 ng/mL, 16950 ng/mL, 17000 ng/mL, 17050 ng/mL, 17100 ng/mL, 17150 ng/mL, 17200 ng/mL, 17250 ng/mL, 17300 ng/mL, 17350 ng/mL, 17400 ng/mL, 17450 ng/mL, 17500 ng/mL, 17550 ng/mL, 17600 ng/mL, 17650 ng/mL, 17700 ng/mL, 17750 ng/mL, 1700 ng/mL, 171750 ng/mL, 17900 ng/mL, 17950 ng/mL, or 18000 ng/mL.

In some embodiments, the pharmaceutical compositions of the disclosure, when administered to a patient in one or more doses, results in a plasma Cmax or mean Cmax of fospropofol that is a value that is 80% to 125% of (or bioequivalent to) 2000-10000 ng/mL, for example, a Cmax or mean Cmax that is a value that is 80% to 125% of (or bioequivalent to) any one of 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, 4000 ng/mL, 4050 ng/mL, 4100 ng/mL, 4150 ng/mL, 4200 ng/mL, 4250 ng/mL, 4300 ng/mL, 4350 ng/mL, 4400 ng/mL, 4450 ng/mL, 4500 ng/mL, 4550 ng/mL, 4600 ng/mL, 4650 ng/mL, 4700 ng/mL, 4750 ng/mL, 4800 ng/mL, 4850 ng/mL, 4900 ng/mL, 4950 ng/mL, 5000 ng/mL, 5050 ng/mL, 5100 ng/mL, 5150 ng/mL, 5200 ng/mL, 5250 ng/mL, 5300 ng/mL, 5350 ng/mL, 5400 ng/mL, 5450 ng/mL, 5500 ng/mL, 5550 ng/mL, 5600 ng/mL, 5650 ng/mL, 5700 ng/mL, 5750 ng/mL, 5800 ng/mL, 5850 ng/mL, 5900 ng/mL, 5950 ng/mL, 6000 ng/mL, 6050 ng/mL, 6100 ng/mL, 6150 ng/mL, 6200 ng/mL, 6250 ng/mL, 6300 ng/mL, 6350 ng/mL, 6400 ng/mL, 6450 ng/mL, 6500 ng/mL, 6550 ng/mL, 6600 ng/mL, 6650 ng/mL, 6700 ng/mL, 6750 ng/mL, 6800 ng/mL, 6850 ng/mL, 6900 ng/mL, 6950 ng/mL, 7000 ng/mL, 7050 ng/mL, 7100 ng/mL, 7150 ng/mL, 7200 ng/mL, 7250 ng/mL, 7300 ng/mL, 7350 ng/mL, 7400 ng/mL, 7450 ng/mL, 7500 ng/mL, 7550 ng/mL, 7600 ng/mL, 7650 ng/mL, 7700 ng/mL, 7750 ng/mL, 7800 ng/mL, 7850 ng/mL, 7900 ng/mL, 7950 ng/mL, 8000 ng/mL, 8050 ng/mL, 8100 ng/mL, 8150 ng/mL, 8200 ng/mL, 8250 ng/mL, 8300 ng/mL, 8350 ng/mL, 8400 ng/mL, 8450 ng/mL, 8500 ng/mL, 8550 ng/mL, 8600 ng/mL, 8650 ng/mL, 8700 ng/mL, 8750 ng/mL, 800 ng/mL, 8850 ng/mL, 8900 ng/mL, 8950 ng/mL, 9000 ng/mL, 9050 ng/mL, 9100 ng/mL, 9150 ng/mL, 9200 ng/mL, 9250 ng/mL, 9300 ng/mL, 9350 ng/mL, 9400 ng/mL, 9450 ng/mL, 9500 ng/mL, 9550 ng/mL, 9600 ng/mL, 9650 ng/mL, 9700 ng/mL, 9750 ng/mL, 9000 ng/mL, 9950 ng/mL, 9900 ng/mL, 9950 ng/mL, or 10000 ng/mL.

In some embodiments, the pharmaceutical compositions of the disclosure, when administered to a patient in one or more doses, results in a plasma Cmax or mean Cmax of fospropofol of no greater than 15000 ng/mL.

In some embodiments, the pharmaceutical compositions of the disclosure, when administered to a patient in one or more doses, results in a plasma Cmax or mean Cmax of fospropofol of no greater than 14000 ng/mL.

In some embodiments, the pharmaceutical compositions of the disclosure, when administered to a patient in one or more doses, results in a plasma Cmax or mean Cmax of fospropofol of no greater than 13000 ng/mL.

In some embodiments, the pharmaceutical compositions of the disclosure, when administered to a patient in one or more doses, results in a plasma Cmax or mean Cmax of fospropofol of no greater than 12000 ng/mL.

In some embodiments, the pharmaceutical compositions of the disclosure, when administered to a patient in one or more doses, results in a plasma Cmax or mean Cmax of fospropofol of no greater than 11000 ng/mL.

In some embodiments, the pharmaceutical compositions of the disclosure, when administered to a patient in one or more doses, results in a plasma Cmax or mean Cmax of fospropofol of no greater than 10000 ng/mL.

In some embodiments, the pharmaceutical compositions of the disclosure, when administered to a patient in one or more doses, results in a plasma Cmax or mean Cmax of fospropofol of no greater than 9000 ng/mL.

In some embodiments, the pharmaceutical compositions of the disclosure, when administered to a patient in one or more doses, results in a plasma Cmax or mean Cmax of fospropofol of no greater than 8000 ng/mL.

In some embodiments, the pharmaceutical compositions of the disclosure, when administered to a patient in one or more doses, results in a plasma Cmax or mean Cmax of fospropofol of no greater than 7000 ng/mL.

In some embodiments, the pharmaceutical compositions of the disclosure, when administered to a patient in one or more doses, results in a plasma Cmax or mean Cmax of fospropofol of no greater than 6000 ng/mL.

In some embodiments, the pharmaceutical compositions of the disclosure, when administered to a patient in one or more doses, results in a plasma Cmax or mean Cmax of fospropofol of no greater than 5000 ng/mL.

In some embodiments, the pharmaceutical compositions of the disclosure, when administered to a patient in one or more doses, results in a plasma Cmax or mean Cmax of fospropofol of no greater than 4000 ng/mL.

In some embodiments, the pharmaceutical compositions of the disclosure, when administered to a patient in one or more doses, results in a plasma Cmax or mean Cmax of fospropofol of no greater than 3000 ng/mL.

In some embodiments, the pharmaceutical compositions of the disclosure, when administered to a patient in one or more doses, results in a plasma Cmax or mean Cmax of fospropofol of no greater than 2000 ng/mL.

In some embodiments, the pharmaceutical compositions of the disclosure, when administered to a patient in one or more doses, results in a plasma $AUC_{2hr}$ or mean $AUC_{2hr}$ of propofol of no greater than 3200 ng hr/mL.

In some embodiments, the pharmaceutical compositions of the disclosure, when administered to a patient in one or more doses, results in a plasma $AUC_{2hr}$ or mean $AUC_{2hr}$ of propofol of no greater than 2400 ng hr/mL.

In some embodiments, the pharmaceutical compositions of the disclosure, when administered to a patient in one or more doses, results in a plasma $AUC_{2hr}$ or mean $AUC_{2hr}$ of propofol of no greater than 1600 ng hr/mL.

In some embodiments, the pharmaceutical compositions of the disclosure, when administered to a patient in one or more doses, results in a plasma $AUC_{2hr}$ or mean $AUC_{2hr}$ of propofol of no greater than 800 ng hr/mL.

In some embodiments, the pharmaceutical compositions of the disclosure, when administered to a patient in one or more doses, results in a plasma $AUC_{2hr}$ or mean $AUC_{2hr}$ of propofol of no greater than 600 ng hr/mL.

In some embodiments, the pharmaceutical compositions of the disclosure, when administered to a patient in one or more doses, results in a plasma $AUC_{2hr}$ or mean $AUC_{2hr}$ of propofol of no greater than 400 ng hr/mL.

In some embodiments, the pharmaceutical compositions of the disclosure, when administered to a patient in one or more doses, results in a plasma $AUC_{2hr}$ or mean $AUC_{2hr}$ of propofol of no greater than 300 ng hr/mL.

In some embodiments, the pharmaceutical compositions of the disclosure, when administered to a patient in one or more doses, results in a plasma $AUC_{2hr}$ or mean $AUC_{2hr}$ of propofol of no greater than 200 ng hr/mL.

In some embodiments, the pharmaceutical compositions of the disclosure, when administered to a patient in one or more doses, results in a plasma $AUC_{2hr}$ or mean $AUC_{2hr}$ of propofol of no greater than 100 ng hr/mL.

In some embodiments, the pharmaceutical compositions of the disclosure, when administered to a patient in one or more doses, results in a plasma $AUC_{2hr}$ or mean $AUC_{2hr}$ of propofol of no greater than 50 ng hr/mL.

In some embodiments, the pharmaceutical compositions of the disclosure, when administered to a patient in one or more doses, results in a plasma $AUC_{2hr}$ or mean $AUC_{2hr}$ of propofol of no less than 3200 ng hr/mL.

In some embodiments, the pharmaceutical compositions of the disclosure, when administered to a patient in one or more doses, results in a plasma $AUC_{2hr}$ or mean $AUC_{2hr}$ of propofol of no less than 2400 ng hr/mL.

In some embodiments, the pharmaceutical compositions of the disclosure, when administered to a patient in one or more doses, results in a plasma $AUC_{2hr}$ or mean $AUC_{2hr}$ of propofol of no less than 1600 ng hr/mL.

In some embodiments, the pharmaceutical compositions of the disclosure, when administered to a patient in one or more doses, results in a plasma $AUC_{2hr}$ or mean $AUC_{2hr}$ of propofol of no less than 800 ng hr/mL.

In some embodiments, the pharmaceutical compositions of the disclosure, when administered to a patient in one or more doses, results in a plasma $AUC_{2hr}$ or mean $AUC_{2hr}$ of propofol of no less than 600 ng hr/mL.

In some embodiments, the pharmaceutical compositions of the disclosure, when administered to a patient in one or more doses, results in a plasma $AUC_{2hr}$ or mean $AUC_{2hr}$ of propofol of no less than 400 ng hr/mL.

In some embodiments, the pharmaceutical compositions of the disclosure, when administered to a patient in one or more doses, results in a plasma $AUC_{2hr}$ or mean $AUC_{2hr}$ of propofol of no less than 300 ng hr/mL.

In some embodiments, the pharmaceutical compositions of the disclosure, when administered to a patient in one or more doses, results in a plasma $AUC_{2hr}$ or mean $AUC_{2hr}$ of propofol of no less than 200 ng hr/mL.

In some embodiments, the pharmaceutical compositions of the disclosure, when administered to a patient in one or more doses, results in a plasma $AUC_{2hr}$ or mean $AUC_{2hr}$ of propofol of no less than 100 ng hr/mL.

In some embodiments, the pharmaceutical compositions of the disclosure, when administered to a patient in one or more doses, results in a plasma $AUC_{2hr}$ or mean $AUC_{2hr}$ of propofol of no less than 50 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no greater than 8000 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no greater than 7000 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no greater than 6000 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no greater than 5000 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no greater than 4500 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no greater than 4000 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no greater than 3000 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no greater than 2000 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no greater than 1000 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no less than 8000 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no less than 7000 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no less than 6000 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no less than 5000 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no less than 4500 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no less than 4000 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no less than 3000 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no less than 2000 ng hr/mL.

In some embodiments, the pharmaceutical compositions of the disclosure, when administered to a patient in one or more doses, results in a plasma $AUC_{2hr}$ or mean $AUC_{2hr}$ of fospropofol of no less than 1000 ng hr/mL.

In some embodiments, the pharmaceutical compositions of the disclosure, when administered to a patient in one or more doses, results in a plasma $AUC_{1hr}$ or mean $AUC_{1hr}$ of propofol of no greater than 300 ng hr/mL.

In some embodiments, the pharmaceutical compositions of the disclosure, when administered to a patient in one or more doses, results in a plasma $AUC_{1hr}$ or mean $AUC_{1hr}$ of propofol of no greater than 200 ng hr/mL.

In some embodiments, the pharmaceutical compositions of the disclosure, when administered to a patient in one or more doses, results in a plasma $AUC_{1hr}$ or mean $AUC_{1hr}$ of propofol of no greater than 150 ng hr/mL.

In some embodiments, the pharmaceutical compositions of the disclosure, when administered to a patient in one or more doses, results in a plasma $AUC_{1hr}$ or mean $AUC_{1hr}$ of propofol of no greater than 100 ng hr/mL.

In some embodiments, the pharmaceutical compositions of the disclosure, when administered to a patient in one or more doses, results in a plasma $AUC_{1hr}$ or mean $AUC_{1hr}$ of propofol of no greater than 50 ng hr/mL.

In some embodiments, the pharmaceutical compositions of the disclosure, when administered to a patient in one or more doses, results in a plasma $AUC_{1hr}$ or mean $AUC_{1hr}$ of propofol of no greater than 30 ng hr/mL.

In some embodiments, the pharmaceutical compositions of the disclosure, when administered to a patient in one or more doses, results in a plasma $AUC_{1hr}$ or mean $AUC_{1hr}$ of propofol of no greater than 20 ng hr/mL.

In some embodiments, the pharmaceutical compositions of the disclosure, when administered to a patient in one or more doses, results in a plasma $AUC_{1hr}$ or mean $AUC_{1hr}$ of propofol of no less than 300 ng hr/mL.

In some embodiments, the pharmaceutical compositions of the disclosure, when administered to a patient in one or more doses, results in a plasma $AUC_{1hr}$ or mean $AUC_{1hr}$ of propofol of no less than 200 ng hr/mL.

In some embodiments, the pharmaceutical compositions of the disclosure, when administered to a patient in one or more doses, results in a plasma $AUC_{1hr}$ or mean $AUC_{1hr}$ of propofol of no less than 150 ng hr/mL.

In some embodiments, the pharmaceutical compositions of the disclosure, when administered to a patient in one or more doses, results in a plasma $AUC_{1hr}$ or mean $AUC_{1hr}$ of propofol of no less than 100 ng hr/mL.

In some embodiments, the pharmaceutical compositions of the disclosure, when administered to a patient in one or more doses, results in a plasma $AUC_{1hr}$ or mean $AUC_{1hr}$ of propofol of no less than 50 ng hr/mL.

In some embodiments, the pharmaceutical compositions of the disclosure, when administered to a patient in one or more doses, results in a plasma $AUC_{1hr}$ or mean $AUC_{1hr}$ of propofol of no less than 30 ng hr/mL.

In some embodiments, the pharmaceutical compositions of the disclosure, when administered to a patient in one or more doses, results in a plasma $AUC_{1hr}$ or mean $AUC_{1hr}$ of propofol of no less than 20 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no greater than 7000 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no greater than 6000 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no greater than 5000 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no greater than 4000 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no greater than 3500 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no greater than 3000 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no greater than 2000 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no greater than 1000 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no greater than 800 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no greater than 700 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no less than 7000 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no less than 6000 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no less than 5000 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no less than 4000 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no less than 3500 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no less than 3000 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no less than 2000 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no less than 1000 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no less than 800 ng hr/mL.

In some embodiments, the pharmaceutical compositions of the disclosure, when administered to a patient in one or more doses, results in a plasma $AUC_{1hr}$ or mean $AUC_{1hr}$ of fospropofol of no less than 700 ng hr/mL.

In some embodiments, the pharmaceutical compositions of the disclosure, when administered to a patient in one or more doses, results in a plasma $AUC_{4hr}$ or mean $AUC_{4hr}$ of propofol of no greater than 800 ng hr/mL.

In some embodiments, the pharmaceutical compositions of the disclosure, when administered to a patient in one or more doses, results in a plasma $AUC_{4hr}$ or mean $AUC_{4hr}$ of propofol of no greater than 700 ng hr/mL.

In some embodiments, the pharmaceutical compositions of the disclosure, when administered to a patient in one or more doses, results in a plasma $AUC_{4hr}$ or mean $AUC_{4hr}$ of propofol of no greater than 600 ng hr/mL.

In some embodiments, the pharmaceutical compositions of the disclosure, when administered to a patient in one or more doses, results in a plasma $AUC_{4hr}$ or mean $AUC_{4hr}$ of propofol of no greater than 500 ng hr/mL.

In some embodiments, the pharmaceutical compositions of the disclosure, when administered to a patient in one or more doses, results in a plasma $AUC_{4hr}$ or mean $AUC_{4hr}$ of propofol of no greater than 400 ng hr/mL.

In some embodiments, the pharmaceutical compositions of the disclosure, when administered to a patient in one or more doses, results in a plasma $AUC_{4hr}$ or mean $AUC_{4hr}$ of propofol of no greater than 300 ng hr/mL.

In some embodiments, the pharmaceutical compositions of the disclosure, when administered to a patient in one or more doses, results in a plasma $AUC_{4hr}$ or mean $AUC_{4hr}$ of propofol of no greater than 200 ng hr/mL.

In some embodiments, the pharmaceutical compositions of the disclosure, when administered to a patient in one or more doses, results in a plasma $AUC_{4hr}$ or mean $AUC_{4hr}$ of propofol of no greater than 100 ng hr/mL.

In some embodiments, the pharmaceutical compositions of the disclosure, when administered to a patient in one or more doses, results in a plasma $AUC_{4hr}$ or mean $AUC_{4hr}$ of propofol of no less than 800 ng hr/mL.

In some embodiments, the pharmaceutical compositions of the disclosure, when administered to a patient in one or more doses, results in a plasma $AUC_{4hr}$ or mean $AUC_{4hr}$ of propofol of no less than 700 ng hr/mL.

In some embodiments, the pharmaceutical compositions of the disclosure, when administered to a patient in one or more doses, results in a plasma $AUC_{4hr}$ or mean $AUC_{4hr}$ of propofol of no less than 600 ng hr/mL.

In some embodiments, the pharmaceutical compositions of the disclosure, when administered to a patient in one or more doses, results in a plasma $AUC_{4hr}$ or mean $AUC_{4hr}$ of propofol of no less than 500 ng hr/mL.

In some embodiments, the pharmaceutical compositions of the disclosure, when administered to a patient in one or more doses, results in a plasma $AUC_{4hr}$ or mean $AUC_{4hr}$ of propofol of no less than 400 ng hr/mL.

In some embodiments, the pharmaceutical compositions of the disclosure, when administered to a patient in one or more doses, results in a plasma $AUC_{4hr}$ or mean $AUC_{4hr}$ of propofol of no less than 300 ng hr/mL.

In some embodiments, the pharmaceutical compositions of the disclosure, when administered to a patient in one or more doses, results in a plasma $AUC_{4hr}$ or mean $AUC_{4hr}$ of propofol of no less than 200 ng hr/mL.

In some embodiments, the pharmaceutical compositions of the disclosure, when administered to a patient in one or more doses, results in a plasma $AUC_{4hr}$ or mean $AUC_{4hr}$ of propofol of no less than 100 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no greater than 12000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no greater than 8000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no greater than 7000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no greater than 6000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no greater than 5000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no greater than 4000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no greater than 3000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no greater than 2000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no greater than 1000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no less than 12000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no less than 8000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no less than 7000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no less than 6000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no less than 5000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no less than 4000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no less than 3000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no less than 2000 ng hr/mL.

In some embodiments, the pharmaceutical compositions of the disclosure, when administered to a patient in one or more doses, results in a plasma $AUC_{4hr}$ or mean $AUC_{4hr}$ of fospropofol of no less than 1000 ng hr/mL.

In some embodiments, the pharmaceutical compositions of the disclosure, when administered to a patient in one or more doses, results in a plasma $AUC_{2hr}$ or mean $AUC_{2hr}$ of propofol or of fospropofol no greater than 40-80% of the corresponding $AUC_0$-$\infty$ or mean $AUC_0$-$\infty$.

In some embodiments, the pharmaceutical compositions of the disclosure, when administered to a patient in one or more doses, results in a plasma $AUC_{2hr}$ or mean $AUC_{2hr}$ of propofol or of fospropofol no greater than 40% of the corresponding $AUC_0$-$\infty$ or mean $AUC_0$-$\infty$.

In some embodiments, the pharmaceutical compositions of the disclosure, when administered to a patient in one or more doses, results in a plasma $AUC_{2hr}$ or mean $AUC_{2hr}$ of propofol or of fospropofol no greater than 50% of the corresponding $AUC_0$-$\infty$ or mean $AUC_0$-$\infty$.

In some embodiments, the pharmaceutical compositions of the disclosure, when administered to a patient in one or more doses, results in a plasma $AUC_{2hr}$ or mean $AUC_{2hr}$ of propofol or of fospropofol no greater than 60% of the corresponding $AUC_0$-$\infty$ or mean $AUC_0$-$\infty$.

In some embodiments, the pharmaceutical compositions of the disclosure, when administered to a patient in one or more doses, results in a plasma $AUC_{2hr}$ or mean $AUC_{2hr}$ of propofol or of fospropofol no greater than 70% of the corresponding $AUC_0$-$\infty$ or mean $AUC_0$-$\infty$.

In some embodiments, the pharmaceutical compositions of the disclosure, when administered to a patient in one or more doses, results in a plasma $AUC_{2hr}$ or mean $AUC_{2hr}$ of propofol or of fospropofol no greater than 80% of the corresponding $AUC_0$-$\infty$ or mean $AUC_0$-$\infty$.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{60min}$ ratio on a mean concentration vs. time curve that is less than 0.1.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{60min}$ ratio on a mean concentration vs. time curve that is less than 0.2.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{60min}$ ratio on a mean concentration vs. time curve that is less than 0.29.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{60min}$ ratio on a mean concentration vs. time curve that is less than 0.3.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{60min}$ ratio on a mean concentration vs. time curve that is less than 0.4.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{60min}$ ratio on a mean concentration vs. time curve that is at least 0.1.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{60min}$ ratio on a mean concentration vs. time curve that is at least 0.2.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{60min}$ ratio on a mean concentration vs. time curve that is at least 0.29.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{60min}$ ratio on a mean concentration vs. time curve that is at least 0.3.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{60min}$ ratio on a mean concentration vs. time curve that is at least 0.4.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{120min}$ ratio on a mean concentration vs. time curve that is less than 0.1.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{120min}$ ratio on a mean concentration vs. time curve that is less than 0.2.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{120min}$ ratio on a mean concentration vs. time curve that is less than 0.23.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{120min}$ ratio on a mean concentration vs. time curve that is less than 0.3.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{120min}$ ratio on a mean concentration vs. time curve that is at least 0.1.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{120min}$ ratio on a mean concentration vs. time curve that is at least 0.2.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{120min}$ ratio on a mean concentration vs. time curve that is at least 0.23.

In some aspects of the methods of the disclosure, the pharmaceutical compositions of the disclosure, when administered to a patient in one or more doses, results in a plasma propofol or a plasma fospropofol mean $AUC_{20min}$/mean $AUC_{120min}$ ratio on a mean concentration vs. time curve that is at least 0.3.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is less than 0.3.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is less than 0.4.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is less than 0.5.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is less than 0.6.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is less than 0.68.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is less than 0.7.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is less than 0.8.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is less than 0.9.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is less than 1.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is at least 0.3.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is at least 0.4.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is at least 0.5.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is at least 0.6.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is at least 0.68.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is at least 0.7.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{60min}$ ratio on a mean concentration vs. time curve that is at least 0.8.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{120min}$ ratio on a mean concentration vs. time curve that is less than 0.3.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{120min}$ ratio on a mean concentration vs. time curve that is less than 0.4.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{120min}$ ratio on a mean concentration vs. time curve that is less than 0.5.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{120min}$ ratio on a mean concentration vs. time curve that is less than 0.55.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{120min}$ ratio on a mean concentration vs. time curve that is less than 0.6.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{120min}$ ratio on a mean concentration vs. time curve that is less than 0.7.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{120min}$ ratio on a mean concentration vs. time curve that is less than 0.8.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{120min}$ ratio on a mean concentration vs. time curve that is less than 0.9.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{120min}$ ratio on a mean concentration vs. time curve that is less than 1.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{120min}$ ratio on a mean concentration vs. time curve that is at least 0.3.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{120min}$ ratio on a mean concentration vs. time curve that is at least 0.4.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{120min}$ ratio on a mean concentration vs. time curve that is at least 0.5.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{120min}$ ratio on a mean concentration vs. time curve that is at least 0.55.

In some aspects of the methods of the disclosure, the pharmaceutical compositions of the disclosure, when administered to a patient in one or more doses, results in a plasma propofol or a plasma fospropofol mean $AUC_{30min}$/mean $AUC_{120min}$ ratio on a mean concentration vs. time curve that is at least 0.6.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{2hr}$ ratio on a mean concentration vs. time curve that is less than 1.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{2hr}$ ratio on a mean concentration vs. time curve that is less than 0.9.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{2hr}$ ratio on a mean concentration vs. time curve that is less than 0.8.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{2hr}$ ratio on a mean concentration vs. time curve that is less than 0.7.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{2hr}$ ratio on a mean concentration vs. time curve that is less than 0.6.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{2hr}$ ratio on a mean concentration vs. time curve that is less than 0.5.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{2hr}$ ratio on a mean concentration vs. time curve that is less than 0.4.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{2hr}$ ratio on a mean concentration vs. time curve that is at least 1.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{2hr}$ ratio on a mean concentration vs. time curve that is at least 0.9.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{2hr}$ ratio on a mean concentration vs. time curve that is at least 0.8.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{2hr}$ ratio on a mean concentration vs. time curve that is at least 0.7.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{2hr}$ ratio on a mean concentration vs. time curve that is at least 0.6.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{2hr}$ ratio on a mean concentration vs. time curve that is at least 0.5.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{2hr}$ ratio on a mean concentration vs. time curve that is at least 0.4.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{4hr}$ ratio on a mean concentration vs. time curve that is less than 0.9.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{4hr}$ ratio on a mean concentration vs. time curve that is less than 0.8.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{4hr}$ ratio on a mean concentration vs. time curve that is less than 0.7.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{4hr}$ ratio on a mean concentration vs. time curve that is less than 0.6.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{4hr}$ ratio on a mean concentration vs. time curve that is less than 0.5.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{4hr}$ ratio on a mean concentration vs. time curve that is less than 0.4.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{4hr}$ ratio on a mean concentration vs. time curve that is less than 0.3.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{4hr}$ ratio on a mean concentration vs. time curve that is at least 0.9.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{4hr}$ ratio on a mean concentration vs. time curve that is at least 0.8.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{4hr}$ ratio on a mean concentration vs. time curve that is at least 0.7.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{4hr}$ ratio on a mean concentration vs. time curve that is at least 0.6.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{4hr}$ ratio on a mean concentration vs. time curve that is at least 0.5.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{4hr}$ ratio on a mean concentration vs. time curve that is at least 0.4.

In some aspects of the methods of the disclosure, the pharmaceutical compositions of the disclosure, when administered to a patient in one or more doses, results in a plasma propofol or a plasma fospropofol mean $AUC_{1hr}$/mean $AUC_{4hr}$ ratio on a mean concentration vs. time curve that is at least 0.3.

In some aspects of the methods of the disclosure, the pharmaceutical compositions of the disclosure, when administered to a patient in one or more doses, results in a plasma propofol or a plasma fospropofol mean $AUC_{2hr}$/mean $AUC_{4hr}$ ratio on a mean concentration vs. time curve that is less than 1.

In some aspects of the methods of the disclosure, the pharmaceutical compositions of the disclosure, when administered to a patient in one or more doses, results in a plasma propofol or a plasma fospropofol mean $AUC_{2hr}$/mean $AUC_{4hr}$ ratio on a mean concentration vs. time curve that is less than 0.9.

In some aspects of the methods of the disclosure, the pharmaceutical compositions of the disclosure, when administered to a patient in one or more doses, results in a plasma propofol or a plasma fospropofol mean $AUC_{2hr}$/mean $AUC_{4hr}$ ratio on a mean concentration vs. time curve that is less than 0.8.

In some aspects of the methods of the disclosure, the pharmaceutical compositions of the disclosure, when administered to a patient in one or more doses, results in a plasma propofol or a plasma fospropofol mean $AUC_{2hr}$/mean $AUC_{4hr}$ ratio on a mean concentration vs. time curve that is less than 0.7.

In some aspects of the methods of the disclosure, the pharmaceutical compositions of the disclosure, when administered to a patient in one or more doses, results in a plasma propofol or a plasma fospropofol mean $AUC_{2hr}$/mean $AUC_{4hr}$ ratio on a mean concentration vs. time curve that is less than 0.6.

In some aspects of the methods of the disclosure, the pharmaceutical compositions of the disclosure, when administered to a patient in one or more doses, results in a plasma propofol or a plasma fospropofol mean $AUC_{2hr}$/mean $AUC_{4hr}$ ratio on a mean concentration vs. time curve that is less than 0.5.

In some aspects of the methods of the disclosure, the pharmaceutical compositions of the disclosure, when administered to a patient in one or more doses, results in a plasma propofol or a plasma fospropofol mean $AUC_{2hr}$/mean $AUC_{4hr}$ ratio on a mean concentration vs. time curve that is less than 0.4.

In some aspects of the methods of the disclosure, the pharmaceutical compositions of the disclosure, when administered to a patient in one or more doses, results in a plasma propofol or a plasma fospropofol mean $AUC_{2hr}$/mean $AUC_{4hr}$ ratio on a mean concentration vs. time curve that is at least 1.

In some aspects of the methods of the disclosure, the pharmaceutical compositions of the disclosure, when administered to a patient in one or more doses, results in a plasma propofol or a plasma fospropofol mean $AUC_{2hr}$/mean $AUC_{4hr}$ ratio on a mean concentration vs. time curve that is at least 0.9.

In some aspects of the methods of the disclosure, the pharmaceutical compositions of the disclosure, when administered to a patient in one or more doses, results in a plasma propofol or a plasma fospropofol mean $AUC_{2hr}$/mean $AUC_{4hr}$ ratio on a mean concentration vs. time curve that is at least 0.8.

In some aspects of the methods of the disclosure, the pharmaceutical compositions of the disclosure, when administered to a patient in one or more doses, results in a plasma propofol or a plasma fospropofol mean $AUC_{2hr}$/mean $AUC_{4hr}$ ratio on a mean concentration vs. time curve that is at least 0.7.

In some aspects of the methods of the disclosure, the pharmaceutical compositions of the disclosure, when administered to a patient in one or more doses, results in a plasma propofol or a plasma fospropofol mean $AUC_{2hr}$/mean $AUC_{4hr}$ ratio on a mean concentration vs. time curve that is at least 0.6.

In some aspects of the methods of the disclosure, the pharmaceutical compositions of the disclosure, when administered to a patient in one or more doses, results in a plasma propofol or a plasma fospropofol mean $AUC_{2hr}$/mean $AUC_{4hr}$ ratio on a mean concentration vs. time curve that is at least 0.5.

In some aspects of the methods of the disclosure, the pharmaceutical compositions of the disclosure, when administered to a patient in one or more doses, results in a plasma propofol or a plasma fospropofol mean $AUC_{2hr}$/mean $AUC_{4hr}$ ratio on a mean concentration vs. time curve that is at least 0.4.

In some aspects of the methods of the disclosure, the pharmaceutical compositions of the disclosure, when administered to a patient in one or more doses, results in a plasma propofol or a plasma fospropofol mean $C_{20}$/mean $C_{60}$ ratio is less than 5.

In some aspects of the methods of the disclosure, the pharmaceutical compositions of the disclosure, when administered to a patient in one or more doses, results in a plasma propofol or a plasma fospropofol mean $C_{20}$/mean $C_{60}$ ratio is less than 4.

In some aspects of the methods of the disclosure, the pharmaceutical compositions of the disclosure, when administered to a patient in one or more doses, results in a plasma propofol or a plasma fospropofol mean $C_{20}$/mean $C_{60}$ ratio is less than 3.

In some aspects of the methods of the disclosure, the pharmaceutical compositions of the disclosure, when administered to a patient in one or more doses, results in a plasma propofol or a plasma fospropofol mean $C_{20}$/mean $C_{60}$ ratio is less than 2.

In some aspects of the methods of the disclosure, the pharmaceutical compositions of the disclosure, when administered to a patient in one or more doses, results in a plasma propofol or a plasma fospropofol mean $C_{20}$/mean $C_{60}$ ratio that is at least 5.

In some aspects of the methods of the disclosure, the pharmaceutical compositions of the disclosure, when administered to a patient in one or more doses, results in a plasma propofol or a plasma fospropofol mean $C_{20}$/mean $C_{60}$ ratio that is at least 4.

In some aspects of the methods of the disclosure, the pharmaceutical compositions of the disclosure, when administered to a patient in one or more doses, results in a plasma propofol or a plasma fospropofol mean $C_{20}$/mean $C_{60}$ ratio that is at least 3.

In some aspects of the methods of the disclosure, the pharmaceutical compositions of the disclosure, when administered to a patient in one or more doses, results in a plasma propofol or a plasma fospropofol mean $C_{20}$/mean $C_{60}$ ratio that is at least 2.

In some aspects of the methods of the disclosure, the pharmaceutical compositions of the disclosure, when administered to a patient in one or more doses, results in a plasma propofol or a plasma fospropofol mean $C_{20}$/mean $C_{120}$ ratio is less than 80.

In some aspects of the methods of the disclosure, the pharmaceutical compositions of the disclosure, when administered to a patient in one or more doses, results in a plasma propofol or a plasma fospropofol mean $C_{20}$/mean $C_{120}$ ratio is less than 76.

In some aspects of the methods of the disclosure, the pharmaceutical compositions of the disclosure, when administered to a patient in one or more doses, results in a plasma propofol or a plasma fospropofol mean $C_{20}$/mean $C_{120}$ ratio is less than 70.

In some aspects of the methods of the disclosure, the pharmaceutical compositions of the disclosure, when administered to a patient in one or more doses, results in a plasma propofol or a plasma fospropofol mean $C_{20}$/mean $C_{120}$ ratio is less than 60.

In some aspects of the methods of the disclosure, the pharmaceutical compositions of the disclosure, when administered to a patient in one or more doses, results in a plasma propofol or a plasma fospropofol mean $C_{20}$/mean $C_{120}$ ratio is less than 50.

In some aspects of the methods of the disclosure, the pharmaceutical compositions of the disclosure, when administered to a patient in one or more doses, results in a plasma propofol or a plasma fospropofol mean $C_{20}$/mean $C_{120}$ ratio that is at least 80.

In some aspects of the methods of the disclosure, the pharmaceutical compositions of the disclosure, when administered to a patient in one or more doses, results in a plasma propofol or a plasma fospropofol mean $C_{20}$/mean $C_{120}$ ratio that is at least 76.

In some aspects of the methods of the disclosure, the pharmaceutical compositions of the disclosure, when administered to a patient in one or more doses, results in a plasma propofol or a plasma fospropofol mean $C_{20}$/mean $C_{120}$ ratio that is at least 70.

In some aspects of the methods of the disclosure, the pharmaceutical compositions of the disclosure, when administered to a patient in one or more doses, results in a plasma propofol or a plasma fospropofol mean $C_{20}$/mean $C_{120}$ ratio that is at least 60.

In some aspects of the methods of the disclosure, the pharmaceutical compositions of the disclosure, when administered to a patient in one or more doses, results in a plasma propofol or a plasma fospropofol mean $C_{20}$/mean $C_{120}$ ratio that is at least 50.

In some aspects of the methods of the disclosure, the pharmaceutical compositions of the disclosure, when administered to a patient in one or more doses, results in a plasma propofol or a plasma fospropofol mean $C_{30}$/mean $C_{60}$ ratio is less than 2.5.

In some aspects of the methods of the disclosure, the pharmaceutical compositions of the disclosure, when administered to a patient in one or more doses, results in a plasma propofol or a plasma fospropofol mean $C_{30}$/mean $C_{60}$ ratio is less than 2.4.

In some aspects of the methods of the disclosure, the pharmaceutical compositions of the disclosure, when administered to a patient in one or more doses, results in a plasma propofol or a plasma fospropofol mean $C_{30}$/mean $C_{60}$ ratio is less than 2.0.

In some aspects of the methods of the disclosure, the pharmaceutical compositions of the disclosure, when administered to a patient in one or more doses, results in a plasma propofol or a plasma fospropofol mean $C_{30}$/mean $C_{60}$ ratio is less than 1.5.

In some aspects of the methods of the disclosure, the pharmaceutical compositions of the disclosure, when administered to a patient in one or more doses, results in a plasma propofol or a plasma fospropofol mean $C_{30}$/mean $C_{60}$ ratio is less than 1.

In some aspects of the methods of the disclosure, the pharmaceutical compositions of the disclosure, when administered to a patient in one or more doses, results in a plasma propofol or a plasma fospropofol mean $C_{30}$/mean $C_{60}$ ratio that is at least 3.

In some aspects of the methods of the disclosure, the pharmaceutical compositions of the disclosure, when administered to a patient in one or more doses, results in a plasma propofol or a plasma fospropofol mean $C_{30}$/mean $C_{60}$ ratio that is at least 2.5.

In some aspects of the methods of the disclosure, the pharmaceutical compositions of the disclosure, when administered to a patient in one or more doses, results in a plasma propofol or a plasma fospropofol mean $C_{30}$/mean $C_{60}$ ratio that is at least 2.4.

In some aspects of the methods of the disclosure, the pharmaceutical compositions of the disclosure, when administered to a patient in one or more doses, results in a plasma propofol or a plasma fospropofol mean $C_{30}$/mean $C_{60}$ ratio that is at least 2.0.

In some aspects of the methods of the disclosure, the pharmaceutical compositions of the disclosure, when administered to a patient in one or more doses, results in a plasma propofol or a plasma fospropofol mean $C_{30}$/mean $C_{60}$ ratio that is at least 1.5.

In some aspects of the methods of the disclosure, the pharmaceutical compositions of the disclosure, when administered to a patient in one or more doses, results in a plasma propofol or a plasma fospropofol mean $C_{30}$/mean $C_{60}$ ratio that is at least 1.

In some aspects of the methods of the disclosure, the pharmaceutical compositions of the disclosure, when administered to a patient in one or more doses, results in a plasma propofol or a plasma fospropofol mean $C_{30}$/mean $C_{120}$ ratio is less than 40.

In some aspects of the methods of the disclosure, the pharmaceutical compositions of the disclosure, when administered to a patient in one or more doses, results in a plasma propofol or a plasma fospropofol mean $C_{30}$/mean $C_{120}$ ratio is less than 36.

In some aspects of the methods of the disclosure, the pharmaceutical compositions of the disclosure, when administered to a patient in one or more doses, results in a plasma propofol or a plasma fospropofol mean $C_{30}$/mean $C_{120}$ ratio is less than 35.

In some aspects of the methods of the disclosure, the pharmaceutical compositions of the disclosure, when administered to a patient in one or more doses, results in a plasma propofol or a plasma fospropofol mean $C_{30}$/mean $C_{120}$ ratio is less than 30.

In some aspects of the methods of the disclosure, the pharmaceutical compositions of the disclosure, when administered to a patient in one or more doses, results in a plasma propofol or a plasma fospropofol mean $C_{30}$/mean $C_{120}$ ratio is less than 25.

In some aspects of the methods of the disclosure, the pharmaceutical compositions of the disclosure, when administered to a patient in one or more doses, results in a plasma propofol or a plasma fospropofol mean $C_{30}$/mean $C_{120}$ ratio is less than 20.

In some aspects of the methods of the disclosure, the pharmaceutical compositions of the disclosure, when administered to a patient in one or more doses, results in a plasma propofol or a plasma fospropofol mean $C_{30}$/mean $C_{120}$ ratio is less than 15.

In some aspects of the methods of the disclosure, the pharmaceutical compositions of the disclosure, when administered to a patient in one or more doses, results in a plasma propofol or a plasma fospropofol mean $C_{30}$/mean $C_{120}$ ratio that is at least 40.

In some aspects of the methods of the disclosure, the pharmaceutical compositions of the disclosure, when administered to a patient in one or more doses, results in a plasma propofol or a plasma fospropofol mean $C_{30}$/mean $C_{120}$ ratio that is at least 36.

In some aspects of the methods of the disclosure, the pharmaceutical compositions of the disclosure, when administered to a patient in one or more doses, results in a plasma propofol or a plasma fospropofol mean $C_{30}$/mean $C_{120}$ ratio that is at least 35.

In some aspects of the methods of the disclosure, the pharmaceutical compositions of the disclosure, when administered to a patient in one or more doses, results in a plasma propofol or a plasma fospropofol mean $C_{30}$/mean $C_{120}$ ratio that is at least 30.

In some aspects of the methods of the disclosure, the pharmaceutical compositions of the disclosure, when administered to a patient in one or more doses, results in a plasma propofol or a plasma fospropofol mean $C_{30}$/mean $C_{120}$ ratio that is at least 25.

In some aspects of the methods of the disclosure, the pharmaceutical compositions of the disclosure, when administered to a patient in one or more doses, results in a plasma propofol or a plasma fospropofol mean $C_{30}$/mean $C_{120}$ ratio that is at least 20.

In some aspects of the methods of the disclosure, the pharmaceutical compositions of the disclosure, when administered to a patient in one or more doses, results in a plasma propofol or a plasma fospropofol mean $C_{30}$/mean $C_{120}$ ratio that is at least 15.

In some aspects of the methods of the disclosure, the pharmaceutical compositions of the disclosure, when administered to a patient in one or more doses, results in a plasma propofol or a plasma fospropofol mean $C_{1hr}$/mean $C_{2hr}$ ratio that is less than 3.

In some aspects of the methods of the disclosure, the pharmaceutical compositions of the disclosure, when administered to a patient in one or more doses, results in a plasma propofol or a plasma fospropofol mean $C_{1hr}$/mean $C_{2hr}$ ratio that is at least 3.

In some aspects of the methods of the disclosure, the pharmaceutical compositions of the disclosure, when administered to a patient in one or more doses, results in a plasma propofol or a plasma fospropofol mean $C_{1hr}$/mean $C_{4hr}$ ratio that is less than 8.

In some aspects of the methods of the disclosure, the pharmaceutical compositions of the disclosure, when administered to a patient in one or more doses, results in a plasma propofol or a plasma fospropofol mean $C_{1hr}$/mean $C_{4hr}$ ratio that is at least 8.

In some aspects of the methods of the disclosure, the pharmaceutical compositions of the disclosure, when administered to a patient in one or more doses, results in a plasma propofol or a plasma fospropofol mean $C_{2hr}$/mean $C_{4hr}$ ratio that is less than 6.

In some aspects of the methods of the disclosure, the pharmaceutical compositions of the disclosure, when administered to a patient in one or more doses, results in a plasma propofol or a plasma fospropofol mean $C_{2hr}$/mean $C_{4hr}$ ratio that is at least 6.

In some aspects of the methods of the disclosure, the pharmaceutical compositions of the disclosure, when administered to a patient in one or more doses, results in a plasma propofol or a plasma fospropofol mean $C_{1hr}$/mean $C_{2hr}$ ratio that is less than 11.

In some aspects of the methods of the disclosure, the pharmaceutical compositions of the disclosure, when administered to a patient in one or more doses, results in a plasma propofol or a plasma fospropofol mean $C_{1hr}$/mean $C_{2hr}$ ratio that is at least 11.

In some aspects of the methods of the disclosure, the pharmaceutical compositions of the disclosure, when administered to a patient in one or more doses, results in a plasma $AUC_{2hr}$ or mean $AUC_{2hr}$ of propofol or of fospropofol no greater than 40-80% of the corresponding $AUC_0$-$\infty$ or mean $AUC_0$-$\infty$.

In some aspects of the methods of the disclosure, the pharmaceutical compositions of the disclosure, when administered to a patient in one or more doses, results in a plasma $AUC_{2hr}$ or mean $AUC_{2hr}$ of propofol or of fospropofol no greater than 40% of the corresponding $AUC_0$-$\infty$ or mean $AUC_0$-$\infty$.

In some aspects of the methods of the disclosure, the pharmaceutical compositions of the disclosure, when administered to a patient in one or more doses, results in a plasma $AUC_{2hr}$ or mean $AUC_{2hr}$ of propofol or of fospropofol no greater than 50% of the corresponding $AUC_0$-$\infty$ or mean $AUC_0$-$\infty$.

In some aspects of the methods of the disclosure, the pharmaceutical compositions of the disclosure, when administered to a patient in one or more doses, results in a plasma $AUC_{2hr}$ or mean $AUC_{2hr}$ of propofol or of fospropofol no greater than 60% of the corresponding $AUC_0$-$\infty$ or mean $AUC_0$-$\infty$.

In some aspects of the methods of the disclosure, the pharmaceutical compositions of the disclosure, when administered to a patient in one or more doses, results in a plasma $AUC_{2hr}$ or mean $AUC_{2hr}$ of propofol or of fospropofol no greater than 70% of the corresponding $AUC_0$-$\infty$ or mean $AUC_0$-$\infty$.

In some aspects of the methods of the disclosure, the pharmaceutical compositions of the disclosure, when administered to a patient in one or more doses, results in a plasma $AUC_{2hr}$ or mean $AUC_{2hr}$ of propofol or of fospropofol no greater than 80% of the corresponding $AUC_0$-$\infty$ or mean $AUC_0$-$\infty$.

In some aspects of the methods of the disclosure, the pharmaceutical compositions of the disclosure, when administered to a patient in one or more doses, results in a plasma $AUC_{2hr}$ or mean $AUC_{2hr}$ of propofol or of fospropofol no less than 40-80% of $AUC_0$-$\infty$ or mean $AUC_0$-$\infty$.

In some aspects of the methods of the disclosure, the pharmaceutical compositions of the disclosure, when administered to a patient in one or more doses, results in a plasma $AUC_{2hr}$ or mean $AUC_{2hr}$ of propofol or of fospropofol no less than 40% of $AUC_{0-\infty}$ or mean $AUC_0$-$\infty$.

In some aspects of the methods of the disclosure, the pharmaceutical compositions of the disclosure, when administered to a patient in one or more doses, results in a plasma $AUC_{2hr}$ or mean $AUC_{2hr}$ of propofol or of fospropofol no less than 50% of $AUC_{0-\infty}$ or mean $AUC_0$-$\infty$.

In some aspects of the methods of the disclosure, the pharmaceutical compositions of the disclosure, when administered to a patient in one or more doses, results in a plasma $AUC_{2hr}$ or mean $AUC_{2hr}$ of propofol or of fospropofol no less than 60% of $AUC_{0-\infty}$ or mean $AUC_0$-$\infty$.

In some aspects of the methods of the disclosure, the pharmaceutical compositions of the disclosure, when administered to a patient in one or more doses, results in a plasma $AUC_{2hr}$ or mean $AUC_{2hr}$ of propofol or of fospropofol no less than 70% of $AUC_{0-\infty}$ or mean $AUC_0$-$\infty$.

In some aspects of the methods of the disclosure, the pharmaceutical compositions of the disclosure, when administered to a patient in one or more doses, results in a plasma $AUC_{2hr}$ or mean $AUC_{2hr}$ of propofol or of fospropofol no less than 80% of $AUC_{0-\infty}$ or mean $AUC_0$-$\infty$.

In some embodiments, the pharmaceutical compositions of the disclosure, when administered to a patient in one or more doses, results in a plasma concentration or mean concentration of propofol or of fospropofol of 100-1600 ng/mL for at least 30 minutes.

In some embodiments, the pharmaceutical compositions of the disclosure, when administered to a patient in one or more doses, results in a plasma concentration or mean concentration of propofol or of fospropofol of 100-1200 ng/mL for at least 30 minutes.

In some embodiments, the pharmaceutical compositions of the disclosure, when administered to a patient in one or more doses, results in a plasma concentration or mean concentration of propofol or of fospropofol of 100-1000 ng/mL for at least 30 minutes.

In some embodiments, the pharmaceutical compositions of the disclosure, when administered to a patient in one or more doses, results in a plasma concentration or mean concentration of propofol or of fospropofol of 100-800 ng/mL for at least 30 minutes.

In some embodiments, the pharmaceutical compositions of the disclosure, when administered to a patient in one or more doses, results in a plasma concentration or mean concentration of propofol or of fospropofol of 100-600 ng/mL for at least 30 minutes.

In some embodiments, the pharmaceutical compositions of the disclosure, when administered to a patient in one or more doses, results in a plasma concentration or mean concentration of propofol or of fospropofol of 100-400 ng/mL for at least 30 minutes.

In some embodiments, the pharmaceutical compositions of the disclosure, when administered to a patient in one or more doses, results in a plasma concentration or mean concentration of propofol or of fospropofol of 100-200 ng/mL for at least 30 minutes.

In some embodiments, the pharmaceutical compositions of the disclosure, when administered to a patient in one or more doses, results in a plasma concentration or mean concentration of propofol or of fospropofol of 200-1600 ng/mL for at least 30 minutes.

In some embodiments, the pharmaceutical compositions of the disclosure, when administered to a patient in one or more doses, results in a plasma concentration or mean concentration of propofol or of fospropofol of 200-1200 ng/mL for at least 30 minutes.

In some embodiments, the pharmaceutical compositions of the disclosure, when administered to a patient in one or more doses, results in a plasma concentration or mean concentration of propofol or of fospropofol of 200-1000 ng/mL for at least 30 minutes.

In some embodiments, the pharmaceutical compositions of the disclosure, when administered to a patient in one or more doses, results in a plasma concentration or mean concentration of propofol or of fospropofol of 200-800 ng/mL for at least 30 minutes.

In some embodiments, the pharmaceutical compositions of the disclosure, when administered to a patient in one or more doses, results in a plasma concentration or mean concentration of propofol or of fospropofol of 200-600 ng/mL for at least 30 minutes.

In some embodiments, the pharmaceutical compositions of the disclosure, when administered to a patient in one or more doses, results in a plasma concentration or mean concentration of propofol or of fospropofol of 200-400 ng/mL for at least 30 minutes.

In some embodiments, the pharmaceutical compositions of the disclosure, when administered to a patient in one or more doses, results in a plasma concentration or mean concentration of propofol or of fospropofol of 30-300 ng/mL for at least 30 minutes.

In some embodiments, the pharmaceutical compositions of the disclosure, when administered to a patient in one or more doses, results in a plasma concentration or mean concentration of propofol or of fospropofol of 40-1700 ng/mL for at least 30 minutes.

In some aspects of the methods of the disclosure, the pharmaceutical compositions of the disclosure, when administered to a patient in one or more doses, results in a plasma concentration or mean concentration of fospropofol of 30-300 ng/mL for at least 30 minutes.

In some aspects of the methods of the disclosure, the pharmaceutical compositions of the disclosure, when administered to a patient in one or more doses, results in a plasma concentration or mean concentration of fospropofol of 40-1700 ng/mL for at least 30 minutes.

In some aspects of the methods of the disclosure, the pharmaceutical compositions of the disclosure, when administered to a patient in one or more doses, results in a plasma concentration or mean concentration of fospropofol of 40-1500 ng/mL for at least 30 minutes.

In some aspects of the methods of the disclosure, the pharmaceutical compositions of the disclosure, when administered to a patient in one or more doses, results in a plasma concentration or mean concentration of fospropofol of 40-1300 ng/mL for at least 30 minutes.

In some aspects of the methods of the disclosure, the pharmaceutical compositions of the disclosure, when administered to a patient in one or more doses, results in a plasma concentration or mean concentration of fospropofol of 40-1100 ng/mL for at least 30 minutes.

In some aspects of the methods of the disclosure, the pharmaceutical compositions of the disclosure, when administered to a patient in one or more doses, results in a plasma concentration or mean concentration of fospropofol of 40-900 ng/mL for at least 30 minutes.

In some aspects of the methods of the disclosure, the pharmaceutical compositions of the disclosure, when administered to a patient in one or more doses, results in a plasma concentration or mean concentration of fospropofol of 40-700 ng/mL for at least 30 minutes.

In some aspects of the methods of the disclosure, the pharmaceutical compositions of the disclosure, when administered to a patient in one or more doses, results in a plasma concentration or mean concentration of fospropofol of 40-500 ng/mL for at least 30 minutes.

In some aspects of the methods of the disclosure, the pharmaceutical compositions of the disclosure, when administered to a patient in one or more doses, results in a plasma concentration or mean concentration of fospropofol of 100-1700 ng/mL for at least 30 minutes.

In some aspects of the methods of the disclosure, the pharmaceutical compositions of the disclosure, when administered to a patient in one or more doses, results in a plasma concentration or mean concentration of fospropofol of 100-1500 ng/mL for at least 30 minutes.

In some aspects of the methods of the disclosure, the pharmaceutical compositions of the disclosure, when administered to a patient in one or more doses, results in a plasma concentration or mean concentration of fospropofol of 100-1300 ng/mL for at least 30 minutes.

In some aspects of the methods of the disclosure, the pharmaceutical compositions of the disclosure, when administered to a patient in one or more doses, results in a plasma concentration or mean concentration of fospropofol of 100-1100 ng/mL for at least 30 minutes.

In some aspects of the methods of the disclosure, the pharmaceutical compositions of the disclosure, when administered to a patient in one or more doses, results in a plasma concentration or mean concentration of fospropofol of 100-900 ng/mL for at least 30 minutes.

In some aspects of the methods of the disclosure, the pharmaceutical compositions of the disclosure, when administered to a patient in one or more doses, results in a plasma concentration or mean concentration of fospropofol of 100-700 ng/mL for at least 30 minutes.

In some aspects of the methods of the disclosure, the pharmaceutical compositions of the disclosure, when administered to a patient in one or more doses, results in a plasma concentration or mean concentration of fospropofol of 100-500 ng/mL for at least 30 minutes.

In some aspects of the methods of the disclosure, the pharmaceutical compositions of the disclosure, when administered to a patient in one or more doses, results in a plasma concentration or mean concentration of fospropofol of 200-1700 ng/mL for at least 30 minutes.

In some aspects of the methods of the disclosure, the pharmaceutical compositions of the disclosure, when administered to a patient in one or more doses, results in a plasma concentration or mean concentration of fospropofol of 200-1500 ng/mL for at least 30 minutes.

In some aspects of the methods of the disclosure, the pharmaceutical compositions of the disclosure, when administered to a patient in one or more doses, results in a plasma concentration or mean concentration of fospropofol of 200-1300 ng/mL for at least 30 minutes.

In some aspects of the methods of the disclosure, the pharmaceutical compositions of the disclosure, when administered to a patient in one or more doses, results in a plasma concentration or mean concentration of fospropofol of 200-1100 ng/mL for at least 30 minutes.

In some aspects of the methods of the disclosure, the pharmaceutical compositions of the disclosure, when administered to a patient in one or more doses, results in a plasma concentration or mean concentration of fospropofol of 200-900 ng/mL for at least 30 minutes.

In some aspects of the methods of the disclosure, the pharmaceutical compositions of the disclosure, when administered to a patient in one or more doses, results in a plasma concentration or mean concentration of fospropofol of 200-700 ng/mL for at least 30 minutes.

In some aspects of the methods of the disclosure, the pharmaceutical compositions of the disclosure, when administered to a patient in one or more doses, results in a plasma concentration or mean concentration of fospropofol of 200-500 ng/mL for at least 30 minutes.

In some embodiments, the pharmaceutical compositions of the disclosure, when administered to a patient in one or more doses, results in a plasma concentration or mean concentration of propofol or of fospropofol of 100-1600 ng/mL for at least 60 minutes.

In some embodiments, the pharmaceutical compositions of the disclosure, when administered to a patient in one or more doses, results in a plasma concentration or mean concentration of propofol or of fospropofol of 100-1200 ng/mL for at least 60 minutes.

In some embodiments, the pharmaceutical compositions of the disclosure, when administered to a patient in one or more doses, results in a plasma concentration or mean concentration of propofol or of fospropofol of 100-1000 ng/mL for at least 60 minutes.

In some embodiments, the pharmaceutical compositions of the disclosure, when administered to a patient in one or more doses, results in a plasma concentration or mean concentration of propofol or of fospropofol of 100-800 ng/mL for at least 60 minutes.

In some embodiments, the pharmaceutical compositions of the disclosure, when administered to a patient in one or more doses, results in a plasma concentration or mean concentration of propofol or of fospropofol of 100-600 ng/mL for at least 60 minutes.

In some embodiments, the pharmaceutical compositions of the disclosure, when administered to a patient in one or more doses, results in a plasma concentration or mean concentration of propofol or of fospropofol of 100-400 ng/mL for at least 60 minutes.

In some embodiments, the pharmaceutical compositions of the disclosure, when administered to a patient in one or more doses, results in a plasma concentration or mean concentration of propofol or of fospropofol of 100-200 ng/mL for at least 60 minutes.

In some embodiments, the pharmaceutical compositions of the disclosure, when administered to a patient in one or more doses, results in a plasma concentration or mean concentration of propofol or of fospropofol of 200-1600 ng/mL for at least 60 minutes.

In some embodiments, the pharmaceutical compositions of the disclosure, when administered to a patient in one or more doses, results in a plasma concentration or mean concentration of propofol or of fospropofol of 200-1200 ng/mL for at least 60 minutes.

In some embodiments, the pharmaceutical compositions of the disclosure, when administered to a patient in one or more doses, results in a plasma concentration or mean concentration of propofol or of fospropofol of 200-1000 ng/mL for at least 60 minutes.

In some embodiments, the pharmaceutical compositions of the disclosure, when administered to a patient in one or more doses, results in a plasma concentration or mean concentration of propofol or of fospropofol of 200-800 ng/mL for at least 60 minutes.

In some embodiments, the pharmaceutical compositions of the disclosure, when administered to a patient in one or more doses, results in a plasma concentration or mean concentration of propofol or of fospropofol of 200-600 ng/mL for at least 60 minutes.

In some embodiments, the pharmaceutical compositions of the disclosure, when administered to a patient in one or more doses, results in a plasma concentration or mean concentration of propofol or of fospropofol of 200-400 ng/mL for at least 60 minutes.

In some aspects of the methods of the disclosure, the pharmaceutical compositions of the disclosure, when administered to a patient in one or more doses, results in a plasma concentration or mean concentration of fospropofol of 40-1700 ng/mL for at least 60 minutes.

In some aspects of the methods of the disclosure, the pharmaceutical compositions of the disclosure, when administered to a patient in one or more doses, results in a plasma concentration or mean concentration of fospropofol of 40-1500 ng/mL for at least 60 minutes.

In some aspects of the methods of the disclosure, the pharmaceutical compositions of the disclosure, when administered to a patient in one or more doses, results in a plasma concentration or mean concentration of fospropofol of 40-1300 ng/mL for at least 60 minutes.

In some aspects of the methods of the disclosure, the pharmaceutical compositions of the disclosure, when administered to a patient in one or more doses, results in a plasma concentration or mean concentration of fospropofol of 40-1100 ng/mL for at least 60 minutes.

In some aspects of the methods of the disclosure, the pharmaceutical compositions of the disclosure, when administered to a patient in one or more doses, results in a plasma concentration or mean concentration of fospropofol of 40-900 ng/mL for at least 60 minutes.

In some aspects of the methods of the disclosure, the pharmaceutical compositions of the disclosure, when administered to a patient in one or more doses, results in a plasma concentration or mean concentration of fospropofol of 40-700 ng/mL for at least 60 minutes.

In some aspects of the methods of the disclosure, the pharmaceutical compositions of the disclosure, when administered to a patient in one or more doses, results in a plasma concentration or mean concentration of fospropofol of 40-500 ng/mL for at least 60 minutes.

In some aspects of the methods of the disclosure, the pharmaceutical compositions of the disclosure, when administered to a patient in one or more doses, results in a plasma concentration or mean concentration of fospropofol of 100-1700 ng/mL for at least 60 minutes.

In some aspects of the methods of the disclosure, the pharmaceutical compositions of the disclosure, when administered to a patient in one or more doses, results in a plasma concentration or mean concentration of fospropofol of 100-1500 ng/mL for at least 60 minutes.

In some aspects of the methods of the disclosure, the pharmaceutical compositions of the disclosure, when administered to a patient in one or more doses, results in a plasma concentration or mean concentration of fospropofol of 100-1300 ng/mL for at least 60 minutes.

In some aspects of the methods of the disclosure, the pharmaceutical compositions of the disclosure, when administered to a patient in one or more doses, results in a plasma concentration or mean concentration of fospropofol of 100-1100 ng/mL for at least 60 minutes.

In some aspects of the methods of the disclosure, the pharmaceutical compositions of the disclosure, when administered to a patient in one or more doses, results in a plasma concentration or mean concentration of fospropofol of 100-900 ng/mL for at least 60 minutes.

In some aspects of the methods of the disclosure, the pharmaceutical compositions of the disclosure, when administered to a patient in one or more doses, results in a plasma concentration or mean concentration of fospropofol of 100-700 ng/mL for at least 60 minutes.

In some aspects of the methods of the disclosure, the pharmaceutical compositions of the disclosure, when administered to a patient in one or more doses, results in a plasma concentration or mean concentration of fospropofol of 100-500 ng/mL for at least 60 minutes.

In some aspects of the methods of the disclosure, the pharmaceutical compositions of the disclosure, when administered to a patient in one or more doses, results in a plasma concentration or mean concentration of fospropofol of 200-1700 ng/mL for at least 60 minutes.

In some aspects of the methods of the disclosure, the pharmaceutical compositions of the disclosure, when administered to a patient in one or more doses, results in a plasma concentration or mean concentration of fospropofol of 200-1500 ng/mL for at least 60 minutes.

In some aspects of the methods of the disclosure, the pharmaceutical compositions of the disclosure, when administered to a patient in one or more doses, results in a plasma concentration or mean concentration of fospropofol of 200-1300 ng/mL for at least 60 minutes.

In some aspects of the methods of the disclosure, the pharmaceutical compositions of the disclosure, when administered to a patient in one or more doses, results in a plasma concentration or mean concentration of fospropofol of 200-1100 ng/mL for at least 60 minutes.

In some aspects of the methods of the disclosure, the pharmaceutical compositions of the disclosure, when administered to a patient in one or more doses, results in a plasma concentration or mean concentration of fospropofol of 200-900 ng/mL for at least 60 minutes.

In some aspects of the methods of the disclosure, the pharmaceutical compositions of the disclosure, when administered to a patient in one or more doses, results in a plasma concentration or mean concentration of fospropofol of 200-700 ng/mL for at least 60 minutes.

In some aspects of the methods of the disclosure, the pharmaceutical compositions of the disclosure, when administered to a patient in one or more doses, results in a plasma concentration or mean concentration of fospropofol of 200-500 ng/mL for at least 60 minutes.

In some embodiments, the pharmaceutical compositions of the disclosure, when administered to a patient in one or more doses, results in a plasma concentration or mean concentration of propofol or of fospropofol of 100-1600 ng/mL for at least 90 minutes.

In some embodiments, the pharmaceutical compositions of the disclosure, when administered to a patient in one or more doses, results in a plasma concentration or mean concentration of propofol or of fospropofol of 100-1200 ng/mL for at least 90 minutes.

In some embodiments, the pharmaceutical compositions of the disclosure, when administered to a patient in one or more doses, results in a plasma concentration or mean concentration of propofol or of fospropofol of 100-1000 ng/mL for at least 90 minutes.

In some embodiments, the pharmaceutical compositions of the disclosure, when administered to a patient in one or more doses, results in a plasma concentration or mean concentration of propofol or of fospropofol of 100-800 ng/mL for at least 90 minutes.

In some embodiments, the pharmaceutical compositions of the disclosure, when administered to a patient in one or more doses, results in a plasma concentration or mean concentration of propofol or of fospropofol of 100-600 ng/mL for at least 90 minutes.

In some embodiments, the pharmaceutical compositions of the disclosure, when administered to a patient in one or more doses, results in a plasma concentration or mean concentration of propofol or of fospropofol of 100-400 ng/mL for at least 90 minutes.

In some embodiments, the pharmaceutical compositions of the disclosure, when administered to a patient in one or more doses, results in a plasma concentration or mean concentration of propofol or of fospropofol of 100-200 ng/mL for at least 90 minutes.

In some embodiments, the pharmaceutical compositions of the disclosure, when administered to a patient in one or more doses, results in a plasma concentration or mean concentration of propofol or of fospropofol of 200-1600 ng/mL for at least 90 minutes.

In some embodiments, the pharmaceutical compositions of the disclosure, when administered to a patient in one or more doses, results in a plasma concentration or mean concentration of propofol or of fospropofol of 200-1200 ng/mL for at least 90 minutes.

In some embodiments, the pharmaceutical compositions of the disclosure, when administered to a patient in one or more doses, results in a plasma concentration or mean concentration of propofol or of fospropofol of 200-1000 ng/mL for at least 90 minutes.

In some embodiments, the pharmaceutical compositions of the disclosure, when administered to a patient in one or more doses, results in a plasma concentration or mean concentration of propofol or of fospropofol of 200-800 ng/mL for at least 90 minutes.

In some embodiments, the pharmaceutical compositions of the disclosure, when administered to a patient in one or more doses, results in a plasma concentration or mean concentration of propofol or of fospropofol of 200-600 ng/mL for at least 90 minutes.

In some embodiments, the pharmaceutical compositions of the disclosure, when administered to a patient in one or more doses, results in a plasma concentration or mean concentration of propofol or of fospropofol of 200-400 ng/mL for at least 90 minutes.

In some embodiments, the pharmaceutical compositions of the disclosure, when administered to a patient in one or more doses, results in a plasma concentration or mean concentration of propofol or of fospropofol of 100-1600 ng/mL for at least 120 minutes.

In some embodiments, the pharmaceutical compositions of the disclosure, when administered to a patient in one or more doses, results in a plasma concentration or mean concentration of propofol or of fospropofol of 100-1200 ng/mL for at least 120 minutes.

In some embodiments, the pharmaceutical compositions of the disclosure, when administered to a patient in one or more doses, results in a plasma concentration or mean concentration of propofol or of fospropofol of 100-1000 ng/mL for at least 120 minutes.

In some embodiments, the pharmaceutical compositions of the disclosure, when administered to a patient in one or more doses, results in a plasma concentration or mean concentration of propofol or of fospropofol of 100-800 ng/mL for at least 120 minutes.

In some embodiments, the pharmaceutical compositions of the disclosure, when administered to a patient in one or more doses, results in a plasma concentration or mean concentration of propofol or of fospropofol of 100-600 ng/mL for at least 120 minutes.

In some embodiments, the pharmaceutical compositions of the disclosure, when administered to a patient in one or more doses, results in a plasma concentration or mean concentration of propofol or of fospropofol of 100-400 ng/mL for at least 120 minutes.

In some embodiments, the pharmaceutical compositions of the disclosure, when administered to a patient in one or more doses, results in a plasma concentration or mean concentration of propofol or of fospropofol of 100-200 ng/mL for at least 120 minutes.

In some embodiments, the pharmaceutical compositions of the disclosure, when administered to a patient in one or more doses, results in a plasma concentration or mean concentration of propofol or of fospropofol of 200-1600 ng/mL for at least 120 minutes.

In some embodiments, the pharmaceutical compositions of the disclosure, when administered to a patient in one or more doses, results in a plasma concentration or mean concentration of propofol or of fospropofol of 200-1200 ng/mL for at least 120 minutes.

In some embodiments, the pharmaceutical compositions of the disclosure, when administered to a patient in one or more doses, results in a plasma concentration or mean concentration of propofol or of fospropofol of 200-1000 ng/mL for at least 120 minutes.

In some embodiments, the pharmaceutical compositions of the disclosure, when administered to a patient in one or more doses, results in a plasma concentration or mean concentration of propofol or of fospropofol of 200-800 ng/mL for at least 120 minutes.

In some embodiments, the pharmaceutical compositions of the disclosure, when administered to a patient in one or more doses, results in a plasma concentration or mean concentration of propofol or of fospropofol of 200-600 ng/mL for at least 120 minutes.

In some embodiments, the pharmaceutical compositions of the disclosure, when administered to a patient in one or more doses, results in a plasma concentration or mean concentration of propofol or of fospropofol of 200-400 ng/mL for at least 120 minutes.

In some aspects of the methods of the disclosure, the pharmaceutical compositions of the disclosure, when administered to a patient in one or more doses, results in a plasma concentration or mean concentration of propofol, or of fospropofol, of at least 30 ng/mL for at least 30 minutes.

In some aspects of the methods of the disclosure, the pharmaceutical compositions of the disclosure, when administered to a patient in one or more doses, results in a plasma concentration or mean concentration of propofol, or of fospropofol, of at least 40 ng/mL for at least 30 minutes.

In some aspects of the methods of the disclosure, the pharmaceutical compositions of the disclosure, when administered to a patient in one or more doses, results in a plasma concentration or mean concentration of propofol or of fospropofol of at least 50 ng/mL for at least 30 minutes.

In some aspects of the methods of the disclosure, the pharmaceutical compositions of the disclosure, when administered to a patient in one or more doses, results in a plasma concentration or mean concentration of propofol or of fospropofol of at least 100 ng/mL for at least 30 minutes.

In some aspects of the methods of the disclosure, the pharmaceutical compositions of the disclosure, when administered to a patient in one or more doses, results in a plasma concentration or mean concentration of propofol, or of fospropofol, of at least 150 ng/mL for at least 30 minutes.

In some aspects of the methods of the disclosure, the pharmaceutical compositions of the disclosure, when administered to a patient in one or more doses, results in a plasma concentration or mean concentration of propofol or of fospropofol of at least 180 ng/mL for at least 30 minutes.

In some aspects of the methods of the disclosure, the pharmaceutical compositions of the disclosure, when administered to a patient in one or more doses, results in a plasma concentration or mean concentration of propofol or of fospropofol of at least 200 ng/mL for at least 30 minutes.

In some aspects of the methods of the disclosure, the pharmaceutical compositions of the disclosure, when administered to a patient in one or more doses, results in a plasma concentration or mean concentration of propofol or of fospropofol of at least 300 ng/mL for at least 30 minutes.

In some aspects of the methods of the disclosure, the pharmaceutical compositions of the disclosure, when administered to a patient in one or more doses, results in a plasma concentration or mean concentration of propofol or of fospropofol of at least 400 ng/mL for at least 30 minutes.

In some aspects of the methods of the disclosure, the pharmaceutical compositions of the disclosure, when administered to a patient in one or more doses, results in a plasma concentration or mean concentration of propofol or of fospropofol of at least 500 ng/mL for at least 30 minutes.

In some aspects of the methods of the disclosure, the pharmaceutical compositions of the disclosure, when administered to a patient in one or more doses, results in a plasma concentration or mean concentration of propofol or of fospropofol of at least 600 ng/mL for at least 30 minutes.

In some aspects of the methods of the disclosure, the pharmaceutical compositions of the disclosure, when administered to a patient in one or more doses, results in a plasma concentration or mean concentration of propofol or of fospropofol of at least 700 ng/mL for at least 30 minutes.

In some aspects of the methods of the disclosure, the pharmaceutical compositions of the disclosure, when administered to a patient in one or more doses, results in a plasma concentration or mean concentration of propofol or of fospropofol of at least 800 ng/mL for at least 30 minutes.

In some aspects of the methods of the disclosure, the pharmaceutical compositions of the disclosure, when administered to a patient in one or more doses, results in a plasma concentration or mean concentration of propofol, or of fospropofol, of at least 30 ng/mL for at least 60 minutes.

In some aspects of the methods of the disclosure, the pharmaceutical compositions of the disclosure, when administered to a patient in one or more doses, results in a plasma concentration or mean concentration of propofol, or of fospropofol, of at least 40 ng/mL for at least 60 minutes.

In some aspects of the methods of the disclosure, the pharmaceutical compositions of the disclosure, when administered to a patient in one or more doses, results in a plasma concentration or mean concentration of propofol or of fospropofol of at least 50 ng/mL for at least 60 minutes.

In some aspects of the methods of the disclosure, the pharmaceutical compositions of the disclosure, when administered to a patient in one or more doses, results in a plasma concentration or mean concentration of propofol or of fospropofol of at least 75 ng/mL for at least 60 minutes.

In some aspects of the methods of the disclosure, the pharmaceutical compositions of the disclosure, when administered to a patient in one or more doses, results in a plasma concentration or mean concentration of propofol or of fospropofol of at least 100 ng/mL for at least 60 minutes.

In some aspects of the methods of the disclosure, the pharmaceutical compositions of the disclosure, when administered to a patient in one or more doses, results in a plasma concentration or mean concentration of propofol, or of fospropofol, of at least 150 ng/mL for at least 60 minutes.

In some aspects of the methods of the disclosure, the pharmaceutical compositions of the disclosure, when administered to a patient in one or more doses, results in a plasma concentration or mean concentration of propofol or of fospropofol of at least 200 ng/mL for at least 60 minutes.

In some aspects of the methods of the disclosure, the pharmaceutical compositions of the disclosure, when administered to a patient in one or more doses, results in a plasma concentration or mean concentration of propofol or of fospropofol of at least 300 ng/mL for at least 60 minutes.

In some aspects of the methods of the disclosure, the pharmaceutical compositions of the disclosure, when administered to a patient in one or more doses, results in a plasma concentration or mean concentration of propofol or of fospropofol of at least 400 ng/mL for at least 60 minutes.

In some aspects of the methods of the disclosure, the pharmaceutical compositions of the disclosure, when administered to a patient in one or more doses, results in a plasma concentration or mean concentration of propofol or of fospropofol of at least 500 ng/mL for at least 60 minutes.

In some aspects of the methods of the disclosure, the pharmaceutical compositions of the disclosure, when administered to a patient in one or more doses, results in a plasma concentration or mean concentration of propofol or of fospropofol of at least 600 ng/mL for at least 60 minutes.

In some aspects of the methods of the disclosure, the pharmaceutical compositions of the disclosure, when administered to a patient in one or more doses, results in a plasma concentration or mean concentration of propofol or of fospropofol of at least 700 ng/mL for at least 60 minutes.

In some aspects of the methods of the disclosure, the pharmaceutical compositions of the disclosure, when administered to a patient in one or more doses, results in a plasma concentration or mean concentration of propofol or of fospropofol of at least 800 ng/mL for at least 60 minutes.

In some aspects of the methods of the disclosure, the pharmaceutical compositions of the disclosure, when administered to a patient in one or more doses, results in a plasma concentration or mean concentration of propofol, or of fospropofol, of at least 30 ng/mL for at least 90 minutes.

In some aspects of the methods of the disclosure, the pharmaceutical compositions of the disclosure, when administered to a patient in one or more doses, results in a plasma concentration or mean concentration of propofol, or of fospropofol, of at least 40 ng/mL for at least 90 minutes.

In some aspects of the methods of the disclosure, the pharmaceutical compositions of the disclosure, when administered to a patient in one or more doses, results in a plasma concentration or mean concentration of propofol, or of fospropofol, of at least 50 ng/mL for at least 90 minutes.

In some aspects of the methods of the disclosure, the pharmaceutical compositions of the disclosure, when administered to a patient in one or more doses, results in a plasma concentration or mean concentration of propofol, or of fospropofol, of at least 75 ng/mL for at least 90 minutes.

In some aspects of the methods of the disclosure, the pharmaceutical compositions of the disclosure, when administered to a patient in one or more doses, results in a plasma concentration or mean concentration of propofol, or of fospropofol, of at least 100 ng/mL for at least 90 minutes.

In some aspects of the methods of the disclosure, the pharmaceutical compositions of the disclosure, when administered to a patient in one or more doses, results in a plasma concentration or mean concentration of propofol, or of fospropofol, of at least 150 ng/mL for at least 90 minutes.

In some aspects of the methods of the disclosure, the pharmaceutical compositions of the disclosure, when administered to a patient in one or more doses, results in a plasma concentration or mean concentration of propofol, or of fospropofol, of at least 200 ng/mL for at least 90 minutes.

In some aspects of the methods of the disclosure, the pharmaceutical compositions of the disclosure, when administered to a patient in one or more doses, results in a plasma concentration or mean concentration of propofol, or of fospropofol, of at least 300 ng/mL for at least 90 minutes.

In some aspects of the methods of the disclosure, the pharmaceutical compositions of the disclosure, when administered to a patient in one or more doses, results in a plasma concentration or mean concentration of propofol, or of fospropofol, of at least 400 ng/mL for at least 90 minutes.

In some aspects of the methods of the disclosure, the pharmaceutical compositions of the disclosure, when administered to a patient in one or more doses, results in a plasma concentration or mean concentration of propofol, or of fospropofol, of at least 500 ng/mL for at least 90 minutes.

In some aspects of the methods of the disclosure, the pharmaceutical compositions of the disclosure, when administered to a patient in one or more doses, results in a plasma concentration or mean concentration of propofol, or of fospropofol, of at least 600 ng/mL for at least 90 minutes.

In some aspects of the methods of the disclosure, the pharmaceutical compositions of the disclosure, when administered to a patient in one or more doses, results in a plasma concentration or mean concentration of propofol, or of fospropofol, of at least 700 ng/mL for at least 90 minutes.

In some aspects of the methods of the disclosure, the pharmaceutical compositions of the disclosure, when administered to a patient in one or more doses, results in a plasma concentration or mean concentration of propofol, or of fospropofol, of at least 800 ng/mL for at least 90 minutes.

In some aspects of the methods of the disclosure, the pharmaceutical compositions of the disclosure, when administered to a patient in one or more doses, results in a plasma concentration or mean concentration of propofol or of fospropofol of at least 5 ng/mL for at least 120 minutes.

In some aspects of the methods of the disclosure, the pharmaceutical compositions of the disclosure, when administered to a patient in one or more doses, results in a plasma concentration or mean concentration of propofol or of fospropofol of at least 15 ng/mL for at least 120 minutes.

In some aspects of the methods of the disclosure, the pharmaceutical compositions of the disclosure, when administered to a patient in one or more doses, results in a plasma concentration or mean concentration of propofol or of fospropofol of at least 25 ng/mL for at least 120 minutes.

In some aspects of the methods of the disclosure, the pharmaceutical compositions of the disclosure, when administered to a patient in one or more doses, results in a plasma concentration or mean concentration of propofol or of fospropofol of at least 50 ng/mL for at least 120 minutes.

In some aspects of the methods of the disclosure, the pharmaceutical compositions of the disclosure, when administered to a patient in one or more doses, results in a plasma concentration or mean concentration of propofol or of fospropofol of at least 100 ng/mL for at least 120 minutes.

In some aspects of the methods of the disclosure, the pharmaceutical compositions of the disclosure, when administered to a patient in one or more doses, results in a plasma concentration or mean concentration of propofol or of fospropofol of at least 200 ng/mL for at least 120 minutes.

In some aspects of the methods of the disclosure, the pharmaceutical compositions of the disclosure, when administered to a patient in one or more doses, results in a plasma concentration or mean concentration of propofol or of fospropofol of at least 300 ng/mL for at least 120 minutes.

In some aspects of the methods of the disclosure, the pharmaceutical compositions of the disclosure, when administered to a patient in one or more doses, results in a plasma concentration or mean concentration of propofol or of fospropofol of at least 400 ng/mL for at least 120 minutes.

In some aspects of the methods of the disclosure, the pharmaceutical compositions of the disclosure, when administered to a patient in one or more doses, results in a plasma concentration or mean concentration of propofol or of fospropofol of at least 500 ng/mL for at least 120 minutes.

In some aspects of the methods of the disclosure, the pharmaceutical compositions of the disclosure, when administered to a patient in one or more doses, results in a plasma concentration or mean concentration of propofol or of fospropofol of at least 600 ng/mL for at least 120 minutes.

In some aspects of the methods of the disclosure, the pharmaceutical compositions of the disclosure, when administered to a patient in one or more doses, results in a plasma concentration or mean concentration of propofol or of fospropofol of at least 700 ng/mL for at least 120 minutes.

In some aspects of the methods of the disclosure, the pharmaceutical compositions of the disclosure, when administered to a patient in one or more doses, results in a plasma concentration or mean concentration of propofol or of fospropofol of at least 800 ng/mL for at least 120 minutes.

In some embodiments, the pharmaceutical compositions of the disclosure, when administered to a patient in one or more doses, results in a plasma concentration or mean concentration of propofol or of fospropofol at a time point 0.5-6 hr after the corresponding Tmax or median Tmax that is 50-90% of the corresponding plasma Cmax or mean Cmax.

In some embodiments, the pharmaceutical compositions of the disclosure, when administered to a patient in one or more doses, results in a plasma concentration or mean concentration of propofol or of fospropofol 30 minutes after the corresponding Tmax or median Tmax that is 50-90% of the corresponding plasma Cmax or mean Cmax.

In some embodiments, the pharmaceutical compositions of the disclosure, when administered to a patient in one or more doses, results in a plasma concentration or mean concentration of propofol or of fospropofol 30 minutes after the corresponding Tmax or median Tmax that is about (i.e., the specified number±10%) 90% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 30 minutes after the corresponding Tmax or median Tmax that is about (i.e., the specified number±10%) 80% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 30 minutes after the corresponding Tmax or median Tmax that is about (i.e., the specified number±10%) 70% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 30 minutes after the corresponding Tmax or median Tmax that is about (i.e., the specified number±10%) 60% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 30 minutes after the corresponding Tmax or median Tmax that is about (i.e., the specified number±10%) 50% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 1 hr after the corresponding Tmax or median Tmax that is 50-90% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 1 hr after the corresponding Tmax or median Tmax that is about (i.e., the specified number±10%) 90% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 1 hr after the corresponding Tmax or median Tmax that is about (i.e., the specified number±10%) 80% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 1 hr after the corresponding Tmax or median Tmax that is about (i.e., the specified number±10%) 70% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 1 hr after the corresponding Tmax or median Tmax that is about (i.e., the specified number±10%) 60% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 1 hr after the corresponding Tmax or median Tmax that is about (i.e., the specified number±10%) 50% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 1.5 hr after the corresponding Tmax or median Tmax that is 50-90% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 1.5 hr after the corresponding Tmax or median Tmax that is about (i.e., the specified number±10%) 90% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 1.5 hr after the corresponding Tmax or median Tmax that is about (i.e., the specified number±10%) 80% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 1.5 hr after the corresponding Tmax or median Tmax that is about (i.e., the specified number±10%) 70% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 1.5 hr after the corresponding Tmax or median Tmax that is about (i.e., the specified number±10%) 60% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 1.5 hr after the corresponding Tmax or median Tmax that is about (i.e., the specified number±10%) 50% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 2 hr after the corresponding Tmax or median Tmax that is 50-90% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 2 hr after the corresponding Tmax or median Tmax that is about (i.e., the specified number±10%) 90% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 2 hr after the corresponding Tmax or median Tmax that is about (i.e., the specified number±10%) 80% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 2 hr after the corresponding Tmax or median Tmax that is about (i.e., the specified number±10%) 70% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 2 hr after the corresponding Tmax or median Tmax that is about (i.e., the specified number±10%) 60% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 2 hr after the corresponding Tmax or median Tmax that is about (i.e., the specified number±10%) 50% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 3 hr after the corresponding Tmax or median Tmax that is 50-90% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 3 hr after the corresponding Tmax or median Tmax that is about 90% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 3 hr after the corresponding Tmax or median Tmax that is about (i.e., the specified number±10%) 80% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 3 hr after the corresponding Tmax or median Tmax that is about (i.e., the specified number±10%) 70% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 3 hr after the corresponding Tmax or median Tmax that is about (i.e., the specified number±10%) 60% of the corresponding plasma Cmax or mean Cmax.

In some embodiments, the pharmaceutical compositions of the disclosure, when administered to a patient in one or more doses, results in a plasma concentration or mean concentration of propofol or of fospropofol at the time point 3 hr after the corresponding Tmax or median Tmax that is about (i.e., the specified number±10%) 50% of the corresponding plasma Cmax or mean Cmax.

In some aspects of the methods of the disclosure, the pharmaceutical compositions of the disclosure, when administered to a patient in one or more doses, results in a propofol or fospropofol Tmax or median Tmax of 0.1 hr-2 hour.

In some aspects of the methods of the disclosure, the pharmaceutical compositions of the disclosure, when administered to a patient in one or more doses, results in a propofol or fospropofol Tmax or median Tmax of 20 min-4 hours.

In some aspects of the methods of the disclosure, the pharmaceutical compositions of the disclosure, when administered to a patient in one or more doses, results in a propofol or fospropofol Tmax or median Tmax of 30 min-4 hours.

In some aspects of the methods of the disclosure, the pharmaceutical compositions of the disclosure, when administered to a patient in one or more doses, results in a propofol or fospropofol Tmax or median Tmax of 60 min-4 hours.

In some aspects of the methods of the disclosure, the pharmaceutical compositions of the disclosure, when administered to a patient in one or more doses, results in a Tmax or median Tmax for propofol of 0.6 hr-4 hours.

In some aspects of the methods of the disclosure, the pharmaceutical compositions of the disclosure, when administered to a patient in one or more doses, results in a Tmax or median Tmax for propofol of 1 hr-2 hours.

In some aspects of the methods of the disclosure, the pharmaceutical compositions of the disclosure, when administered to a patient in one or more doses, results in a Tmax or median Tmax for fospropofol of 0.1 hr-0.7 hours.

In some aspects of the methods of the disclosure, the pharmaceutical compositions of the disclosure, when administered to a patient in one or more doses, results in a Tmax or median Tmax for fospropofol of 0.2 hr-0.5 hours.

In some embodiments, the pharmaceutical compositions of the disclosure, when administered to a patient in one or more doses, results in a Tmax or median Tmax for propofol or for fospropofol of about (i.e., the specified number±10%) 20 min.

In some embodiments, the pharmaceutical compositions of the disclosure, when administered to a patient in one or more doses, results in a Tmax or median Tmax for propofol or for fospropofol of about (i.e., the specified number±10%) 30 min.

In some embodiments, the pharmaceutical compositions of the disclosure, when administered to a patient in one or more doses, results in a Tmax or median Tmax for propofol or for fospropofol of about (i.e., the specified number±10%) 45 min.

In some embodiments, the pharmaceutical compositions of the disclosure, when administered to a patient in one or more doses, results in a Tmax or median Tmax for propofol or for fospropofol of about (i.e., the specified number±10%) 1 hr.

In some embodiments, the pharmaceutical compositions of the disclosure, when administered to a patient in one or more doses, results in a Tmax or median Tmax for propofol or for fospropofol of about (i.e., the specified number±10%) 1.5 hr.

In some embodiments, the pharmaceutical compositions of the disclosure, when administered to a patient in one or more doses, results in a Tmax or median Tmax for propofol or for fospropofol of about (i.e., the specified number±10%) 2.0 hr.

In some embodiments, the pharmaceutical compositions of the disclosure, when administered to a patient in one or more doses, results in a Tmax or median Tmax for propofol or for fospropofol of about (i.e., the specified number±10%) 2.5 hr.

In some embodiments, the pharmaceutical compositions of the disclosure, when administered to a patient in one or more doses, results in a Tmax or median Tmax for propofol or for fospropofol of about (i.e., the specified number±10%) 3.0 hr.

In some embodiments, the pharmaceutical compositions of the disclosure, when administered to a patient in one or more doses, results in a Tmax or median Tmax for propofol or for fospropofol of about (i.e., the specified number±10%) 3.5 hr.

In some embodiments, the pharmaceutical compositions of the disclosure, when administered to a patient in one or more doses, results in a Tmax or median Tmax for propofol or for fospropofol of about (i.e., the specified number±10%) 4.0 hr.

In some embodiments, the pharmaceutical compositions of the disclosure, when administered to a patient in one or more doses, produces a pulsatile release of forpropofol, a pharmaceutically acceptable salt of fospropofol, or mixtures thereof.

In some aspects, the methods are directed to treating migraine in a population of patients in need thereof, wherein the method comprises administering to the population a pharmaceutical composition of the disclosure, wherein the mean plasma Cmax for fospropofol has a coefficient of variation that is less than 55%, such as, for example, less than any one of 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10% 9%, 8%, 7%, 6%, or 5%.

In some aspects, the methods are directed to treating migraine in a population of patients in need thereof, wherein the method comprises administering to the population a pharmaceutical composition of the disclosure, wherein the mean plasma Tmax for fospropofol has a coefficient of variation that is less than 39%, such as, for example, less than any one of 39%, 38%, 37%, 36%, 35%, 34%, 33%, 32%, 31%, 30%, 29%, 28%, 27%, 26%, 25%, 24%, 23%, 22%, 21%, 20%, 9%, 8%, 17%, 16%, 15%, 14%, 13%, 12%, 11%, 10% 9%, 8%, 7%, 6%, or 5%.

In some aspects, the methods are directed to treating migraine in a population of patients in need thereof, wherein the method comprises administering to the population a pharmaceutical composition of the disclosure, wherein the mean plasma $AUC_{1hr}$ for fospropofol has a coefficient of variation that is less than 58%, such as, for example, less than any one of 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5%.

In some aspects, the methods are directed to treating migraine in a population of patients in need thereof, wherein the method comprises administering to the population a pharmaceutical composition of the disclosure, wherein the mean plasma $AUC_{2hr}$ for fospropofol has a coefficient of variation that is less than 57%, such as, for example, less than any one of 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5%.

In some aspects, the methods are directed to treating migraine in a population of patients in need thereof, wherein the method comprises administering to the population a pharmaceutical composition of the disclosure, wherein the mean plasma $AUC_{4hr}$ for fospropofol has a coefficient of variation that is less than 58%, such as, for example, less than any one of 58%, 57%, 56%, 55%, 54%, 53%, 52%, 51%, 50%, 49%, 48%, 47%, 46%, 45% 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5%.

In some aspects, the methods are directed to treating migraine in a population of patients in need thereof, wherein the method comprises administering to the population a pharmaceutical composition of the disclosure, wherein the mean plasma Cmax for propofol has a coefficient of variation that is less than 68%, such as, for example, less than any one of 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5%.

In some aspects, the methods are directed to treating migraine in a population of patients in need thereof, wherein the method comprises administering to the population a pharmaceutical composition of the disclosure, wherein the mean plasma Tmax for propofol has a coefficient of variation that is less than 69%, such as, for example, less than any one of 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7% 6%, or 5%.

In some aspects, the methods are directed to treating migraine in a population of patients in need thereof, wherein the method comprises administering to the population a pharmaceutical composition of the disclosure, wherein the mean plasma $AUC_{1hr}$ for propofol has a coefficient of variation that is less than 71%, such as, for example, less than any one of 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5%.

In some aspects, the methods are directed to treating migraine in a population of patients in need thereof, wherein the method comprises administering to the population a pharmaceutical composition of the disclosure, wherein the mean plasma $AUC_{2hr}$ for propofol has a coefficient of variation that is less than 65%, such as, for example, less than any one of 65%, 64%, 63%, 62%, 61%, 60%, 59%, 58%, 57%, 56%, 55%, 54%, 53%, 52%, 51%, 50%, 49%, 48%, 47%, 46%, 45% 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 4%, 3%, 12%, 11%, 10%, 9%, 8%, 7%, 6%, or 5%.

In some aspects, the methods are directed to treating migraine in a population of patients in need thereof, wherein the method comprises administering to the population a pharmaceutical composition of the disclosure, wherein the mean plasma $AUC_{4hr}$ for propofol has a coefficient of variation that is less than 56%, such as, for example, less than any one of 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5%.

In some aspects, the methods are directed to treating migraine in a population of patients in need thereof, wherein the method comprises administering to the population a pharmaceutical composition of the disclosure, wherein the plasma fospropofol mean $AUC_{0-9hrs}$ per mg of fospropofol (or a pharmaceutically acceptable salt of fospropofol) administered is at least 3.0 ng*h/mL, such as, for example, at least any one of 3.0 ng*h/mL/mg, 3.1 ng*h/mL/mg, 3.2 ng*h/mL/mg, 3.3 ng*h/mL/mg, 3.4 ng*h/mL/mg, 3.5 ng*h/mL/mg, 3.6 ng*h/mL/mg, 3.7 ng*h/mL/mg, 3.8 ng*h/mL/mg, 3.9 ng*h/mL/mg, 4.0 ng*h/mL/mg, 4.1 ng*h/mL/mg, 4.2 ng*h/mL/mg, 4.3 ng*h/mL/mg, 4.4 ng*h/mL/mg, 4.5 ng*h/mL/mg, 4.6 ng*h/mL/mg, 4.7 ng*h/mL/mg, 4.8 ng*h/mL/mg, 4.9 ng*h/mL/mg, 5.0 ng*h/mL/mg, 5.1 ng*h/mL/mg, 5.2 ng*h/mL/mg, 5.3 ng*h/mL/mg, 5.4 ng*h/mL/mg, 5.5 ng*h/mL/mg, 5.6 ng*h/mL/mg, 5.7 ng*h/mL/mg, 5.8 ng*h/mL/mg, 5.9 ng*h/mL/mg, 6.0 ng*h/mL/mg, 6.1 ng*h/mL/mg, 6.2 ng*h/mL/mg, 6.3 ng*h/mL/mg, 6.4 ng*h/mL/mg, 6.5 ng*h/mL/mg, 6.6 ng*h/mL/mg, 6.7 ng*h/mL/mg, 6.8 ng*h/mL/mg, 6.9 ng*h/mL/mg, 7.0 ng*h/mL/mg, 7.1 ng*h/mL/mg, 7.2 ng*h/mL/mg, 7.3 ng*h/mL/mg, 7.4 ng*h/mL/mg, 7.5 ng*h/mL/mg, 7.6 ng*h/mL/mg, 7.7 ng*h/mL/mg, 7.8 ng*h/mL/mg, 7.9 ng*h/mL/mg, 8.0 ng*h/mL/mg, 8.1 ng*h/mL/mg, 8.2 ng*h/mL/mg, 8.3 ng*h/mL/mg, 8.4 ng*h/mL/mg, 8.5 ng*h/mL/mg, 8.6 ng*h/mL/mg, 8.7 ng*h/mL/mg, 8.8 ng*h/mL/mg, 8.9 ng*h/mL/mg, or 9.0 ng*h/mL/mg.

In some aspects, the methods are directed to treating migraine in a population of patients in need thereof, wherein the method comprises administering to the population a pharmaceutical composition of the disclosure, wherein the plasma fospropofol mean $AUC_{0-\infty}$ per mg of fospropofol (or a pharmaceutically acceptable salt of fospropofol) administered is at least 3.0 ng*h/mL, such as, for example, at least any one of 3.0 ng*h/mL/mg, 3.1 ng*h/mL/mg, 3.2 ng*h/mL/mg, 3.3 ng*h/mL/mg, 3.4 ng*h/mL/mg, 3.5 ng*h/mL/mg, 3.6 ng*h/mL/mg, 3.7 ng*h/mL/mg, 3.8 ng*h/mL/mg, 3.9 ng*h/mL/mg, 4.0 ng*h/mL/mg, 4.1 ng*h/mL/mg, 4.2 ng*h/mL/mg, 4.3 ng*h/mL/mg, 4.4 ng*h/mL/mg, 4.5 ng*h/mL/mg, 4.6 ng*h/mL/mg, 4.7 ng*h/mL/mg, 4.8 ng*h/mL/mg, 4.9 ng*h/mL/mg, 5.0 ng*h/mL/mg, 5.1 ng*h/mL/mg, 5.2 ng*h/mL/mg, 5.3 ng*h/mL/mg, 5.4 ng*h/mL/mg, 5.5 ng*h/mL/mg, 5.6 ng*h/mL/mg, 5.7 ng*h/mL/mg, 5.8 ng*h/mL/mg, 5.9 ng*h/mL/mg, 6.0 ng*h/mL/mg, 6.1 ng*h/mL/mg, 6.2 ng*h/mL/mg, 6.3 ng*h/mL/mg, 6.4 ng*h/mL/mg, 6.5 ng*h/mL/mg, 6.6 ng*h/mL/mg, 6.7 ng*h/mL/mg, 6.8 ng*h/mL/mg, 6.9 ng*h/mL/mg, 7.0 ng*h/mL/mg, 7.1 ng*h/mL/mg, 7.2 ng*h/mL/mg, 7.3 ng*h/mL/mg, 7.4 ng*h/mL/mg, 7.5 ng*h/mL/mg, 7.6 ng*h/mL/mg, 7.7 ng*h/mL/mg, 7.8 ng*h/mL/mg, 7.9 ng*h/mL/mg, 8.0 ng*h/mL/mg, 8.1 ng*h/mL/mg, 8.2 ng*h/mL/mg, 8.3 ng*h/mL/mg, 8.4 ng*h/mL/mg, 8.5 ng*h/mL/mg, 8.6 ng*h/mL/mg, 8.7 ng*h/mL/mg, 8.8 ng*h/mL/mg, 8.9 ng*h/mL/mg, or 9.0 ng*h/mL/mg.

In some aspects, the methods are directed to treating migraine in a population of patients in need thereof, wherein the method comprises administering to the population a pharmaceutical composition of the disclosure, wherein the plasma fospropofol mean $C_{max}$ per mg of fospropofol (or a pharmaceutically acceptable salt of fospropofol) administered is at least 5.0 ng/mL/mg, such as, for example, at least any one of 5.0 ng/mL/mg, 5.1 ng/mL/mg, 5.2 ng/mL/mg, 5.3 ng/mL/mg, 5.4 ng/mL/mg, 5.5 ng/mL/mg, 5.6 ng/mL/mg, 5.7 ng/mL/mg, 5.8 ng/mL/mg, 5.9 ng/mL/mg, 6.0 ng/mL/mg, 6.1 ng/mL/mg, 6.2 ng/mL/mg, 6.3 ng/mL/mg, 6.4 ng/mL/mg, 6.5 ng/mL/mg, 6.6 ng/mL/mg, 6.7 ng/mL/mg, 6.8 ng/mL/mg, 6.9 ng/mL/mg, 7.0 ng/mL/mg, 7.1 ng/mL/mg, 7.2 ng/mL/mg, 7.3 ng/mL/mg, 7.4 ng/mL/mg, 7.5 ng/mL/mg, 7.6 ng/mL/mg, 7.7 ng/mL/mg, 7.8 ng/mL/mg, 7.9 ng/mL/mg, 8.0 ng/mL/mg, 8.1 ng/mL/mg, 8.2 ng/mL/mg, 8.3 ng/mL/mg, 8.4 ng/mL/mg, 8.5 ng/mL/mg, 8.6 ng/mL/mg, 8.7 ng/mL/mg, 8.8 ng/mL/mg, 8.9 ng/mL/mg, 9.0 ng/mL/mg, 9.1 ng/mL/mg, 9.2 ng/mL/mg, 9.3 ng/mL/mg, 9.4 ng/mL/mg, 9.5 ng/mL/mg, 9.6 ng/mL/mg, 9.7 ng/mL/mg, 9.8 ng/mL/mg, 9.9 ng/mL/mg, 10.0 ng/mL/mg, 10.1 ng/mL/mg, 10.2 ng/mL/mg, 10.3 ng/mL/mg, 10.4 ng/mL/mg, 10.5 ng/mL/mg, 10.6 ng/mL/mg, 10.7 ng/mL/mg, 10.8 ng/mL/mg, 10.9 ng/mL/mg, 11.0 ng/mL/mg, 11.1 ng/mL/mg, 11.2 ng/mL/mg, 11.3 ng/mL/mg, 11.4 ng/mL/mg, 11.5 ng/mL/mg, 11.6 ng/mL/mg, 11.7 ng/mL/mg, 11.8 ng/mL/mg, 11.9 ng/mL/mg, 12.0 ng/mL/mg, 12.1 ng/mL/mg, 12.2 ng/mL/mg, 12.3 ng/mL/mg, 12.4 ng/mL/mg, 12.5 ng/mL/mg, 12.6 ng/mL/mg, 12.7 ng/mL/mg, 12.8 ng/mL/mg, 12.9 ng/mL/mg, 13.0 ng/mL/mg, 13.1 ng/mL/mg, 13.2 ng/mL/mg, 13.3 ng/mL/mg, 13.4 ng/mL/mg, 13.5 ng/mL/mg, 13.6 ng/mL/mg, 13.7 ng/mL/mg, 13.8 ng/mL/mg, 13.9 ng/mL/mg, 14.0 ng/mL/mg, 14.1 ng/mL/mg, 14.2 ng/mL/mg, 14.3 ng/mL/mg, 14.4 ng/mL/mg, 14.5 ng/mL/mg, 14.6 ng/mL/mg, 14.7 ng/mL/mg, 14.8 ng/mL/mg, 14.9 ng/mL/mg, 15.0 ng/mL/mg, 15.1 ng/mL/mg, 15.2 ng/mL/mg, 15.3 ng/mL/mg, 15.4 ng/mL/mg, 15.5 ng/mL/mg, 15.6 ng/mL/mg, 15.7 ng/mL/mg, 15.8 ng/mL/mg, 15.9 ng/mL/mg, 16.0 ng/mL/mg, 16.1 ng/mL/mg, 16.2 ng/mL/mg, 16.3 ng/mL/mg, 16.4 ng/mL/mg, 16.5 ng/mL/mg, 16.6 ng/mL/mg, 16.7 ng/mL/mg, 16.8 ng/mL/mg, 16.9 ng/mL/mg, or 17.0 ng/mL/mg.

In some aspects, the methods are directed to treating migraine in a population of patients in need thereof, wherein the method comprises administering to the population a pharmaceutical composition of the disclosure, wherein the plasma propofol mean $AUC_{0-9}$ hr per mg of fospropofol (or a pharmaceutically acceptable salt of fospropofol) administered is at least 0.5 ng*h/mL/mg, such as, for example, at least any one of 0.5 ng*h/mL/mg, 0.55 ng*h/mL/mg, 0.6 ng*h/mL/mg, 0.65 ng*h/mL/mg, 0.7 ng*h/mL/mg, 0.75 ng*h/mL/mg, 0.8 ng*h/mL/mg, 0.85 ng*h/mL/mg, 0.9 ng*h/mL/mg, 0.95 ng*h/mL/mg, 1.0 ng*h/mL/mg, 1.05 ng*h/mL/mg, 1.10 ng*h/mL/mg, 1.15 ng*h/mL/mg, 1.2 ng*h/mL/mg, 1.25 ng*h/mL/mg, 1.3 ng*h/mL/mg, 1.35 ng*h/mL/mg, 1.4 ng*h/mL/mg, 1.45 ng*h/mL/mg, 1.5 ng*h/mL/mg, 1.55 ng*h/mL/mg, 1.6 ng*h/mL/mg, 1.65 ng*h/mL/mg, or 1.7 ng*h/mL/mg.

In some aspects, the methods are directed to treating migraine in a population of patients in need thereof, wherein the method comprises administering to the population a pharmaceutical composition of the disclosure, wherein the plasma propofol mean $AUC_{0-\infty}$ per mg of fospropofol (or a pharmaceutically acceptable salt of fospropofol) administered is at least 0.5 ng*h/mL/mg, such as, for example, at least any one of 0.5 ng*h/mL/mg, 0.55 ng*h/mL/mg, 0.6 ng*h/mL/mg, 0.65 ng*h/mL/mg, 0.7 ng*h/mL/mg, 0.75 ng*h/mL/mg, 0.8 ng*h/mL/mg, 0.85 ng*h/mL/mg, 0.9 ng*h/mL/mg, 0.95 ng*h/mL/mg, 1.0 ng*h/mL/mg, 1.05 ng*h/mL/mg, 1.10 ng*h/mL/mg, 1.15 ng*h/mL/mg, 1.2 ng*h/mL/mg, 1.25 ng*h/mL/mg, 1.3 ng*h/mL/mg, 1.35 ng*h/mL/mg, 1.4 ng*h/mL/mg, 1.45 ng*h/mL/mg, 1.5 ng*h/mL/mg, 1.55 ng*h/mL/mg, 1.6 ng*h/mL/mg, 1.65 ng*h/mL/mg, or 1.7 ng*h/mL/mg.

In some aspects, the methods are directed to treating migraine in a population of patients in need thereof, wherein the method comprises administering to the population a pharmaceutical composition of the disclosure, wherein the plasma propofol mean $C_{max}$ per mg of fospropofol (or a pharmaceutically acceptable salt of fospropofol) administered is at least 0.3 ng/mL/mg, such as, for example, at least any one of 0.3 ng/mL/mg, 0.35 ng/mL/mg, 0.4 ng/mL/mg, 0.45 ng/mL/mg, 0.5 ng/mL/mg, 0.55 ng/mL/mg, 0.6 ng/mL/mg, 0.65 ng/mL/mg, 0.7 ng/mL/mg, 0.75 ng/mL/mg, 0.8 ng/mL/mg, 0.85 ng/mL/mg, or 0.9 ng/mL/mg.

In some aspects, the methods are directed to treating migraine in a population of patients in need thereof, wherein the method comprises administering to the population a pharmaceutical composition of the disclosure, wherein within 1 hour of the administration at least 1%, at least 2%, at least 3% at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20% of the patients are headache free without being administered a rescue medication.

In some aspects, the methods are directed to treating migraine in a population of patients in need thereof, wherein the method comprises administering to the population a pharmaceutical composition of the disclosure, wherein within 2 hours of the administration at least 5%, at least 10%, at least 15% at least 20%, at least 25%, at least 30%, at least 35%, at least 40%, at least 45%, or at least 50%, of the patients are headache free without being administered a rescue medication.

In some aspects, the methods are directed to treating migraine in a population of patients in need thereof, wherein the method comprises administering to the population a pharmaceutical composition of the disclosure, wherein within 4 hours of the at least 20%, at least 25%, at least 30%, at least 35% at least 40%, at least 45%, at least 50%, at least 55%, at least 60%, at least 65%, at least 70%, or at least 75%, of the patients are headache free without being administered a rescue medication.

In some aspects, the methods are directed to treating migraine in a population of patients in need thereof, wherein the method comprises administering to the population a pharmaceutical composition of the disclosure, wherein within 24 hours of the administration at least 50%, at least 55%, at least 60%, at least 65%, at least 70%, or at least 75%, at least 80%, at least 85%, at least 90%, or at least 95%, of the patients are headache free without being administered a rescue medication.

In some aspects, the methods are directed to treating migraine in a population of patients in need thereof, wherein the method comprises administering to the population a pharmaceutical composition of the disclosure, wherein within 48 hours of the administration at least 50%, at least 55%, at least 60%, at least 65%, at least 70%, or at least 75%, at least 80%, at least 85%, at least 90%, or at least 95%, of the patients are headache free without being administered a rescue medication.

In some aspects, the methods are directed to treating migraine in a population of patients in need thereof, wherein the method comprises administering to the population a pharmaceutical composition of the disclosure, wherein within 1 hour of the administration at least 1%, at least 2%, at least 3% at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20%, of the patients have experienced headache pain relief without being administered a rescue medication.

In some aspects, the methods are directed to treating migraine in a population of patients in need thereof, wherein the method comprises administering to the population a pharmaceutical composition of the disclosure, wherein within 1 hours of the administration at least 20%, at least 25%, at least 30%, at least 35% at least 40%, at least 45%, at least 50%, at least 55%, at least 60%, at least 65%, at least 70%, or at least 75%, of the patients have experienced headache pain relief without being administered a rescue medication.

In some aspects, the methods are directed to treating migraine in a population of patients in need thereof, wherein the method comprises administering to the population a pharmaceutical composition of the disclosure, wherein within 2 hours of the administration at least 50%, at least 55%, at least 60%, at least 65%, at least 70%, or at least 75%, at least 80%, at least 85%, at least 90%, or at least 95%, of the patients have experienced headache pain relief without being administered a rescue medication.

In some aspects, the methods are directed to treating migraine in a population of patients in need thereof, wherein the method comprises administering to the population a pharmaceutical composition of the disclosure, wherein within 4 hours of the administration at least 50%, at least 55%, at least 60%, at least 65%, at least 70%, or at least 75%, at least 80%, at least 85%, at least 90%, or at least 95%, of the patients have experienced headache pain relief without being administered a rescue medication.

In some aspects, the methods are directed to treating migraine in a population of patients in need thereof, wherein the method comprises administering to the population a pharmaceutical composition of the disclosure, wherein within 24 hours of the administration up to at least 50%, at least 55%, at least 60%, at least 65%, at least 70%, or at least 75%, at least 80%, at least 85%, at least 90%, or at least 95% of the patients have experienced headache pain relief without being administered a rescue medication.

In some aspects, the methods are directed to treating migraine in a population of patients in need thereof, wherein the method comprises administering to the population a pharmaceutical composition of the disclosure, wherein within 48 hours of the administration at least 50%, at least 55%, at least 60%, at least 65%, at least 70%, or at least 75%, at least 80%, at least 85%, at least 90%, or at least 95%, of the patients have experienced headache pain relief without being administered a rescue medication.

In some aspects, the methods are directed to treating migraine in a population of patients in need thereof, wherein the method comprises administering to the population a pharmaceutical composition of the disclosure, wherein within 1 hour of the administration at least 20%, at least 25%, at least 30%, at least 35% at least 40%, at least 45%, at least 50%, at least 55%, at least 60%, at least 65%, at least 70%, or at least 75%, of the patients are free of their most bothersome symptom (MBS) without being administered a rescue medication.

In some aspects, the methods are directed to treating migraine in a population of patients in need thereof, wherein the method comprises administering to the population a pharmaceutical composition of the disclosure, wherein within 2 hours of the administration at least 20%, at least 25%, at least 30%, at least 35% at least 40%, at least 45%, at least 50%, at least 55%, at least 60%, at least 65%, at least 70%, at least 75%, or at least 80%, of the patients are free of their most bothersome symptom (MBS) without being administered a rescue medication.

In some aspects, the methods are directed to treating migraine in a population of patients in need thereof, wherein the method comprises administering to the population a pharmaceutical composition of the disclosure, wherein within 4 hours of the administration at least 20%, at least 25%, at least 30%, at least 35% at least 40%, at least 45%, at least 50%, at least 55%, at least 60%, at least 65%, at least 70%, at least 75%, or at least 80%, of the patients are free of their most bothersome symptom (MBS) without being administered a rescue medication.

In some aspects, the methods are directed to treating migraine in a population of patients in need thereof, wherein the method comprises administering to the population a pharmaceutical composition of the disclosure, wherein within 24 hours of the administration up to 80%, such as, for example, up to 80%, up to 75%, up to 70%, up to 65%, up to 60%, up to 55%, up to 50%, up to 45%, up to 40%, up to 35%, or up to 30%, of the patients are free of their most bothersome symptom (MBS) without being administered a rescue medication.

In some aspects, the methods are directed to treating migraine in a population of patients in need thereof, wherein the method comprises administering to the population a pharmaceutical composition of the disclosure, wherein within 48 hours of the administration at least 20%, at least 25%, at least 30%, at least 35% at least 40%, at least 45%, at least 50%, at least 55%, at least 60%, at least 65%, at least 70%, at least 75%, or at least 80%, of the patients are free of their most bothersome symptom (MBS) without being administered a rescue medication.

In some embodiments of these methods, the MBS is nausea, photophobia, or phonophobia.

In some embodiments, the MBS is nausea.

In some embodiments, the MBS is photophobia.

In some embodiments, the MBS is phonophobia.

In some aspects, the methods are directed to treating migraine in a population of patients in need thereof, wherein the method comprises administering to the population a pharmaceutical composition of the disclosure, wherein within 1 hour of the administration at least 20%, at least 25%, at least 30%, at least 35% at least 40%, at least 45%, at least 50%, at least 55%, at least 60%, at least 65%, at least 70%, or at least 75%, of the patients are free of a bothersome symptom without being administered a rescue medication.

In some aspects, the methods are directed to treating migraine in a population of patients in need thereof, wherein the method comprises administering to the population a pharmaceutical composition of the disclosure, wherein within 2 hours of the administration at least 20%, at least 25%, at least 30%, at least 35% at least 40%, at least 45%, at least 50%, at least 55%, at least 60%, at least 65%, at least 70%, at least 75%, or at least 80%, of the patients are free of a bothersome symptom without being administered a rescue medication.

In some aspects, the methods are directed to treating migraine in a population of patients in need thereof, wherein the method comprises administering to the population a pharmaceutical composition of the disclosure, wherein within 4 hours of the administration at least 20%, at least 25%, at least 30%, at least 35% at least 40%, at least 45%, at least 50%, at least 55%, at least 60%, at least 65%, at least 70%, at least 75%, or at least 80%, of the patients are free of a bothersome symptom without being administered a rescue medication.

In some aspects, the methods are directed to treating migraine in a population of patients in need thereof, wherein the method comprises administering to the population a pharmaceutical composition of the disclosure, wherein within 24 hours of the administration up to 80%, such as, for example, up to 80%, up to 75%, up to 70%, up to 65%, up to 60%, up to 55%, up to 50%, up to 45%, up to 40%, up to 35%, or up to 30%, of the patients are free of a bothersome symptom without being administered a rescue medication.

In some aspects, the methods are directed to treating migraine in a population of patients in need thereof, wherein the method comprises administering to the population a pharmaceutical composition of the disclosure, wherein within 48 hours of the administration at least 20%, at least 25%, at least 30%, at least 35% at least 40%, at least 45%, at least 50%, at least 55%, at least 60%, at least 65%, at least 70%, at least 75%, or at least 80%, of the patients are free of a bothersome symptom without being administered a rescue medication.

In some embodiments of these methods, the bothersome symptom is nausea, photophobia, or phonophobia.

In some embodiments, the bothersome symptom is nausea.

In some embodiments, the bothersome symptom is photophobia.

In some embodiments, the bothersome symptom is phonophobia.

In some aspects, the methods are directed to treating migraine in a population of patients in need thereof, wherein the method comprises administering to the population a pharmaceutical composition of the disclosure, wherein within 1 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had nausea at administration are free of their nausea without being administered a rescue medication.

In some aspects, the methods are directed to treating migraine in a population of patients in need thereof, wherein the method comprises administering to the population a pharmaceutical composition of the disclosure, wherein within 2 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had nausea at administration are free of their nausea without being administered a rescue medication.

In some aspects, the methods are directed to treating migraine in a population of patients in need thereof, wherein the method comprises administering to the population a pharmaceutical composition of the disclosure, wherein within 4 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had nausea at administration are free of their nausea without being administered a rescue medication.

In some aspects, the methods are directed to treating migraine in a population of patients in need thereof, wherein the method comprises administering to the population a pharmaceutical composition of the disclosure, wherein within 24 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had nausea at administration are free of their nausea without being administered a rescue medication.

In some aspects, the methods are directed to treating migraine in a population of patients in need thereof, wherein the method comprises administering to the population a pharmaceutical composition of the disclosure, wherein within 48 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had nausea at administration are free of their nausea without being administered a rescue medication.

In some aspects, the methods are directed to treating migraine in a population of patients in need thereof, wherein the method comprises administering to the population a pharmaceutical composition of the disclosure, wherein within 1 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had photophobia at administration are free of their photophobia without being administered a rescue medication.

In some aspects, the methods are directed to treating migraine in a population of patients in need thereof, wherein the method comprises administering to the population a pharmaceutical composition of the disclosure, wherein within 2 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had photophobia at administration are free of their photophobia without being administered a rescue medication.

In some aspects, the methods are directed to treating migraine in a population of patients in need thereof, wherein the method comprises administering to the population a pharmaceutical composition of the disclosure, wherein within 4 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95% of the patients whom had photophobia at administration are free of their photophobia without being administered a rescue medication.

In some aspects, the methods are directed to treating migraine in a population of patients in need thereof, wherein the method comprises administering to the population a pharmaceutical composition of the disclosure, wherein within 24 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had photophobia at administration are free of their photophobia without being administered a rescue medication.

In some aspects, the methods are directed to treating migraine in a population of patients in need thereof, wherein the method comprises administering to the population a pharmaceutical composition of the disclosure, wherein within 48 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had photophobia at administration are free of their photophobia without being administered a rescue medication.

In some aspects, the methods are directed to treating migraine in a population of patients in need thereof, wherein the method comprises administering to the population a pharmaceutical composition of the disclosure, wherein within 1 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had phonophobia at administration are free of their phonophobia without being administered a rescue medication.

In some aspects, the methods are directed to treating migraine in a population of patients in need thereof, wherein the method comprises administering to the population a pharmaceutical composition of the disclosure, wherein within 2 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had phonophobia at administration are free of their phonophobia without being administered a rescue medication.

In some aspects, the methods are directed to treating migraine in a population of patients in need thereof, wherein the method comprises administering to the population a pharmaceutical composition of the disclosure, wherein within 4 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had phonophobia at administration are free of their phonophobia without being administered a rescue medication.

In some aspects, the methods are directed to treating migraine in a population of patients in need thereof, wherein the method comprises administering to the population a pharmaceutical composition of the disclosure, wherein within 24 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had phonophobia at administration are free of their phonophobia without being administered a rescue medication.

In some aspects, the methods are directed to treating migraine in a population of patients in need thereof, wherein the method comprises administering to the population a pharmaceutical composition of the disclosure, wherein within 48 hours of the administration at least 20%, at least 25%, at least 30%, at least 35% at least 40%, at least 45%, at least 50%, at least 55%, at least 60%, at least 65%, at least 70%, at least 75%, at least 80%, at least 85%, or at least 95%, of the patients whom had phonophobia at administration are free of their phonophobia without being administered a rescue medication.

In some embodiments of the methods of treating migraine in a patient in need thereof, wherein the methods comprise administering to the patient a pharmaceutical composition of the disclosure, at 1 hour after the administration the subject is headache free.

In other embodiments of the methods of treating migraine in a patient in need thereof, wherein the methods comprise administering to the patient a pharmaceutical composition of the disclosure, at 1 hour after the administration the subject has experienced headache pain relief.

In some aspects, the methods are directed to treating migraine in a population of patients in need thereof, wherein the method comprises administering to the population a pharmaceutical composition of the disclosure sooner than 115 minutes after onset of migraine.

In some aspects, the methods are directed to treating migraine in a population of patients in need thereof, wherein a pharmaceutical composition of the disclosure is administered sooner than 115 minutes after onset of migraine and the Cmax of propofol is increased compared to administration after 115 minutes.

In some aspects, the methods are directed to increasing the Cmax of propofol and treating migraine in a population of patients in need thereof with fospropofol, a pharmaceutically acceptable salt of fospropofol, or mixtures thereof, wherein a pharmaceutical composition of the disclosure is administered sooner than 115 minutes after onset of migraine.

In some aspects, the methods are directed to treating migraine in a population of patients in need thereof, wherein a pharmaceutical composition of the disclosure is administered as an acidified pharmaceutical dosage form and the Cmax of propofol does not decrease if the time to treatment from migraine onset is delayed.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma fospropofol $AUC_{1hr}$ or the patient population has a mean $AUC_{1hr}$ of at least 1000 ng*h/mL, such as, for example, at least 1000 ng*h/mL, at least 1050 ng*h/mL, at least 1100 ng*h/mL, at least 1150 ng*h/mL, at least 1200 ng*h/mL, at least 1250 ng*h/mL, at least 1300 ng*h/mL, at least 1350 ng*h/mL, at least 1400 ng*h/mL, at least 1450 ng*h/mL, at least 1500 ng*h/mL, at least 1550 ng*h/mL, at least 1600 ng*h/mL, at least 1650 ng*h/mL, at least 1700 ng*h/mL, at least 1750 ng*h/mL, at least 1800 ng*h/mL, at least 1850 ng*h/mL, at least 1900 ng*h/mL, at least 1950 ng*h/mL, at least 2000 ng*h/mL, at least 2050 ng*h/mL, at least 2100 ng*h/mL, at least 2150 ng*h/mL, at least 2200 ng*h/mL, at least 2250 ng*h/mL, at least 2300 ng*h/mL, at least 2350 ng*h/mL, at least 2400 ng*h/mL, at least 2450 ng*h/mL, at least 2500 ng*h/mL, at least 2550 ng*h/mL, at least 2600 ng*h/mL, at least 2650 ng*h/mL, at least 2700 ng*h/mL, at least 2750 ng*h/mL, at least 2800 ng*h/mL, at least 2850 ng*h/mL, at least 2900 ng*h/mL, at least 2950 ng*h/mL, at least 3000 ng*h/mL, at least 3050 ng*h/mL, at least 3100 ng*h/mL, at least 3150 ng*h/mL, at least 3200 ng*h/mL, at least 3250 ng*h/mL, at least 3300 ng*h/mL, at least 3350 ng*h/mL, at least 3400 ng*h/mL, at least 3450 ng*h/mL, at least 3500 ng*h/mL, at least 3550 ng*h/mL, at least 3600 ng*h/mL, at least 3650 ng*h/mL, at least 3700 ng*h/mL, at least 3750 ng*h/mL, at least 3800 ng*h/mL, at least 3850 ng*h/mL, at least 3900 ng*h/mL, at least 3950 ng*h/mL, at least 4000 ng*h/mL, at least 4050 ng*h/mL, at least 4100 ng*h/mL, at least 4150 ng*h/mL, at least 4200 ng*h/mL, at least 4250 ng*h/mL, at least 4300 ng*h/mL, at least 4350 ng*h/mL, at least 4400 ng*h/mL, at least 4450 ng*h/mL, at least 4500 ng*h/mL, at least 4550 ng*h/mL, at least 4600 ng*h/mL, at least 4650 ng*h/mL, at least 4700 ng*h/mL, at least 4750 ng*h/mL, at least 4800 ng*h/mL, at least 4850 ng*h/mL, at least 4900 ng*h/mL, at least 4950 ng*h/mL, at least 5000 ng*h/mL, at least 5050 ng*h/mL, at least 5100 ng*h/mL, at least 5150 ng*h/mL, at least 5200 ng*h/mL, at least 5250 ng*h/mL, at least 5300 ng*h/mL, at least 5350 ng*h/mL, at least 5400 ng*h/mL, at least 5450 ng*h/mL, at least 5500 ng*h/mL, at least 5550 ng*h/mL, at least 5600 ng*h/mL, at least 5650 ng*h/mL, at least 5700 ng*h/mL, at least 5750 ng*h/mL, at least 5800 ng*h/mL, at least 5850 ng*h/mL, at least 5900 ng*h/mL, at least 5950 ng*h/mL, at least 6000 ng*h/mL, at least 6050 ng*h/mL, at least 6100 ng*h/mL, at least 6150 ng*h/mL, at least 6200 ng*h/mL, at least 6250 ng*h/mL, at least 6300 ng*h/mL, at least 6350 ng*h/mL, at least 6400 ng*h/mL, at least 6450 ng*h/mL, at least 6500 ng*h/mL, at least 6550 ng*h/mL, at least 6600 ng*h/mL, at least 6650 ng*h/mL, at least 6700 ng*h/mL, at least 6750 ng*h/mL, at least 6800 ng*h/mL, at least 6850 ng*h/mL, at least 6900 ng*h/mL, at least 6950 ng*h/mL, at least 7000 ng*h/mL, at least 7050 ng*h/mL, at least 7100 ng*h/mL, at least 7150 ng*h/mL, at least 7200 ng*h/mL, at least 7250 ng*h/mL, at least 7300 ng*h/mL, at least 7350 ng*h/mL, at least 7400 ng*h/mL, at least 7450 ng*h/mL, at least 7500 ng*h/mL, at least 7550 ng*h/mL, at least 7600 ng*h/mL, at least 7650 ng*h/mL, at least 7700 ng*h/mL, at least 7750 ng*h/mL, at least 7800 ng*h/mL, at least 7850 ng*h/mL, at least 7900 ng*h/mL, at least 7950 ng*h/mL, at least 8000 ng*h/mL, at least 8050 ng*h/mL, at least 8100 ng*h/mL, at least 8150 ng*h/mL, at least 8200 ng*h/mL, at least 8250 ng*h/mL, at least 8300 ng*h/mL, at least 8350 ng*h/mL, at least 8400 ng*h/mL, at least 8450 ng*h/mL, at least 8500 ng*h/mL, at least 8550 ng*h/mL, at least 8600 ng*h/mL, at least 8650 ng*h/mL, at least 8700 ng*h/mL, at least 8750 ng*h/mL, at least 8800 ng*h/mL, at least 8850 ng*h/mL, at least 8900 ng*h/mL, at least 8950 ng*h/mL, at least 9000 ng*h/mL, at least 9050 ng*h/mL, at least 9100 ng*h/mL, at least 9150 ng*h/mL, at least 9200 ng*h/mL, at least 9250 ng*h/mL, at least 9300 ng*h/mL, at least 9350 ng*h/mL, at least 9400 ng*h/mL, at least 9450 ng*h/mL, at least 9500 ng*h/mL, at least 9550 ng*h/mL, at least 9600 ng*h/mL, at least 9650 ng*h/mL, at least 9700 ng*h/mL, at least 9750 ng*h/mL, at least 9800 ng*h/mL, at least 9850 ng*h/mL, at least 9900 ng*h/mL, at least 9950 ng*h/mL, or at least 10000 ng*h/mL.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma fospropofol $AUC_{1hr}$ or the patient population has a mean $AUC_{1hr}$ as set forth herein and the patient is headache free.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma fospropofol $AUC_{1hr}$ or the patient population has a mean $AUC_{1hr}$ of at least 6000 ng*h/mL and the patient is headache free.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma fospropofol $AUC_{1hr}$ or the patient population has a mean $AUC_{1hr}$ as set forth herein and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma fospropofol $AUC_{1hr}$ or the patient population has a mean $AUC_{1hr}$ of at least 2000 ng*h/mL and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma fospropofol $AUC_{1hr}$ or the patient population has a mean $AUC_{1hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma fospropofol $AUC_{1hr}$ or the patient population has a mean $AUC_{1hr}$ of at least 3000 ng*h/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has a plasma fospropofol concentration ($C_{1hr}$) or the patient population has a mean $C_{1hr}$ of at least 500 ng/mL, such as, for example, at least 500 ng/mL, at least 550 ng/mL, at least 600 ng/mL, at least 650 ng/mL, at least 700 ng/mL, at least 750 ng/mL, at least 800 ng/mL, at least 850 ng/mL, at least 900 ng/mL, at least 950 ng/mL, 1000 ng/mL, such as, for example, at least 1000 ng/mL, at least 1050 ng/mL, at least 1100 ng/mL, at least 1150 ng/mL, at least 1200 ng/mL, at least 1250 ng/mL, at least 1300 ng/mL, at least 1350 ng/mL, at least 1400 ng/mL, at least 1450 ng/mL, at least 1500 ng/mL, at least 1550 ng/mL, at least 1600 ng/mL, at least 1650 ng/mL, at least 1700 ng/mL, at least 1750 ng/mL, at least 1800 ng/mL, at least 1850 ng/mL, at least 1900 ng/mL, at least 1950 ng/mL, at least 2000 ng/mL, at least 2050 ng/mL, at least 2100 ng/mL, at least 2150 ng/mL, at least 2200 ng/mL, at least 2250 ng/mL, at least 2300 ng/mL, at least 2350 ng/mL, at least 2400 ng/mL, at least 2450 ng/mL, at least 2500 ng/mL, at least 2550 ng/mL, at least 2600 ng/mL, at least 2650 ng/mL, at least 2700 ng/mL, at least 2750 ng/mL, at least 2800 ng/mL, at least 2850 ng/mL, at least 2900 ng/mL, at least 2950 ng/mL, at least 3000 ng/mL, at least 3050 ng/mL, at least 3100 ng/mL, at least 3150 ng/mL, at least 3200 ng/mL, at least 3250 ng/mL, at least 3300 ng/mL, at least 3350 ng/mL, at least 3400 ng/mL, at least 3450 ng/mL, at least 3500 ng/mL, at least 3550 ng/mL, at least 3600 ng/mL, at least 3650 ng/mL, at least 3700 ng/mL, at least 3750 ng/mL, at least 3800 ng/mL, at least 3850 ng/mL, at least 3900 ng/mL, at least 3950 ng/mL, at least 4000 ng/mL, at least 4050 ng/mL, at least 4100 ng/mL, at least 4150 ng/mL, at least 4200 ng/mL, at least 4250 ng/mL, at least 4300 ng/mL, at least 4350 ng/mL, at least 4400 ng/mL, at least 4450 ng/mL, at least 4500 ng/mL, at least 4550 ng/mL, at least 4600 ng/mL, at least 4650 ng/mL, at least 4700 ng/mL, at least 4750 ng/mL, at least 4800 ng/mL, at least 4850 ng/mL, at least 4900 ng/mL, at least 4950 ng/mL, or at least 5000 ng/mL.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has a plasma fospropofol concentration ($C_{1hr}$) or the patient population has a mean $C_{1hr}$ as set forth herein and the patient is headache free.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma fospropofol concentration ($C_{1hr}$) or the patient population has a mean $C_{1hr}$ of at least 2000 ng/mL and the patient is headache free.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma fospropofol concentration ($C_{1hr}$) or the patient population has a mean $C_{1hr}$ as set forth herein and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma fospropofol concentration ($C_{1hr}$) or the patient population has a mean $C_{1hr}$ of at least 1000 ng/mL and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma fospropofol concentration ($C_{1hr}$) or the patient population has a mean $C_{1hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma fospropofol concentration ($C_{1hr}$) or the patient population has a mean $C_{1hr}$ of at least 1000 ng/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

Fospro—2 Hours

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma fospropofol $AUC_{2hr}$ or the patient population has a mean $AUC_{2hr}$ of at least 1000 ng*h/mL, such as, for example, at least 1000 ng*h/mL, at least 1050 ng*h/mL, at least 1100 ng*h/mL, at least 1150 ng*h/mL, at least 1200 ng*h/mL, at least 1250 ng*h/mL, at least 1300 ng*h/mL, at least 1350 ng*h/mL, at least 1400 ng*h/mL, at least 1450 ng*h/mL, at least 1500 ng*h/mL, at least 1550 ng*h/mL, at least 1600 ng*h/mL, at least 1650 ng*h/mL, at least 1700 ng*h/mL, at least 1750 ng*h/mL, at least 1800 ng*h/mL, at least 1850 ng*h/mL, at least 1900 ng*h/mL, at least 1950 ng*h/mL, at least 2000 ng*h/mL, at least 2050 ng*h/mL, at least 2100 ng*h/mL, at least 2150 ng*h/mL, at least 2200 ng*h/mL, at least 2250 ng*h/mL, at least 2300 ng*h/mL, at least 2350 ng*h/mL, at least 2400 ng*h/mL, at least 2450 ng*h/mL, at least 2500 ng*h/mL, at least 2550 ng*h/mL, at least 2600 ng*h/mL, at least 2650 ng*h/mL, at least 2700 ng*h/mL, at least 2750 ng*h/mL, at least 2800 ng*h/mL, at least 2850 ng*h/mL, at least 2900 ng*h/mL, at least 2950 ng*h/mL, at least 3000 ng*h/mL, at least 3050 ng*h/mL, at least 3100 ng*h/mL, at least 3150 ng*h/mL, at least 3200 ng*h/mL, at least 3250 ng*h/mL, at least 3300 ng*h/mL, at least 3350 ng*h/mL, at least 3400 ng*h/mL, at least 3450 ng*h/mL, at least 3500 ng*h/mL, at least 3550 ng*h/mL, at least 3600 ng*h/mL, at least 3650 ng*h/mL, at least 3700 ng*h/mL, at least 3750 ng*h/mL, at least 3800 ng*h/mL, at least 3850 ng*h/mL, at least 3900 ng*h/mL, at least 3950 ng*h/mL, at least 4000 ng*h/mL, at least 4050 ng*h/mL, at least 4100 ng*h/mL, at least 4150 ng*h/mL, at least 4200 ng*h/mL, at least 4250 ng*h/mL, at least 4300 ng*h/mL, at least 4350 ng*h/mL, at least 4400 ng*h/mL, at least 4450 ng*h/mL, at least 4500 ng*h/mL, at least 4550 ng*h/mL, at least 4600 ng*h/mL, at least 4650 ng*h/mL, at least 4700 ng*h/mL, at least 4750 ng*h/mL, at least 4800 ng*h/mL, at least 4850 ng*h/mL, at least 4900 ng*h/mL, at least 4950 ng*h/mL, at least 5000 ng*h/mL, at least 5050 ng*h/mL, at least 5100 ng*h/mL, at least 5150 ng*h/mL, at least 5200 ng*h/mL, at least 5250 ng*h/mL, at least 5300 ng*h/mL, at least 5350 ng*h/mL, at least 5400 ng*h/mL, at least 5450 ng*h/mL, at least 5500 ng*h/mL, at least 5550 ng*h/mL, at least 5600 ng*h/mL, at least 5650 ng*h/mL, at least 5700 ng*h/mL, at least 5750 ng*h/mL, at least 5800 ng*h/mL, at least 5850 ng*h/mL, at least 5900 ng*h/mL, at least 5950 ng*h/mL, at least 6000 ng*h/mL, at least 6050 ng*h/mL, at least 6100 ng*h/mL, at least 6150 ng*h/mL, at least 6200 ng*h/mL, at least 6250 ng*h/mL, at least 6300 ng*h/mL, at least 6350 ng*h/mL, at least 6400 ng*h/mL, at least 6450 ng*h/mL, at least 6500 ng*h/mL, at least 6550 ng*h/mL, at least 6600 ng*h/mL, at least 6650 ng*h/mL, at least 6700 ng*h/mL, at least 6750 ng*h/mL, at least 6800 ng*h/mL, at least 6850 ng*h/mL, at least 6900 ng*h/mL, at least 6950 ng*h/mL, at least 7000 ng*h/mL, at least 7050 ng*h/mL, at least 7100 ng*h/mL, at least 7150 ng*h/mL, at least 7200 ng*h/mL, at least 7250 ng*h/mL, at least 7300 ng*h/mL, at least 7350 ng*h/mL, at least 7400 ng*h/mL, at least 7450 ng*h/mL, at least 7500 ng*h/mL, at least 7550 ng*h/mL, at least 7600 ng*h/mL, at least 7650 ng*h/mL, at least 7700 ng*h/mL, at least 7750 ng*h/mL, at least 7800 ng*h/mL, at least 7850 ng*h/mL, at least 7900 ng*h/mL, at least 7950 ng*h/mL, at least 8000 ng*h/mL, at least 8050 ng*h/mL, at least 8100 ng*h/mL, at least 8150 ng*h/mL, at least 8200 ng*h/mL, at least 8250 ng*h/mL, at least 8300 ng*h/mL, at least 8350 ng*h/mL, at least 8400 ng*h/mL, at least 8450 ng*h/mL, at least 8500 ng*h/mL, at least 8550 ng*h/mL, at least 8600 ng*h/mL, at least 8650 ng*h/mL, at least 8700 ng*h/mL, at least 8750 ng*h/mL, at least 8800 ng*h/mL, at least 8850 ng*h/mL, at least 8900 ng*h/mL, at least 8950 ng*h/mL, at least 9000 ng*h/mL, at least 9050 ng*h/mL, at least 9100 ng*h/mL, at least 9150 ng*h/mL, at least 9200 ng*h/mL, at least 9250 ng*h/mL, at least 9300 ng*h/mL, at least 9350 ng*h/mL, at least 9400 ng*h/mL, at least 9450 ng*h/mL, at least 9500 ng*h/mL, at least 9550 ng*h/mL, at least 9600 ng*h/mL, at least 9650 ng*h/mL, at least 9700 ng*h/mL, at least 9750 ng*h/mL, at least 9800 ng*h/mL, at least 9850 ng*h/mL, at least 9900 ng*h/mL, at least 9950 ng*h/mL, or at least 10000 ng*h/mL.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma fospropofol $AUC_{2hr}$ or the patient population has a mean $AUC_{2hr}$ as set forth herein and the patient is headache free.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma fospropofol $AUC_{2hr}$ or the patient population has a mean $AUC_{2hr}$ of at least 3000 ng*h/mL and the patient is headache free.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma fospropofol $AUC_{2hr}$ or the patient population has a mean $AUC_{2hr}$ as set forth herein and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma fospropofol $AUC_{2hr}$ or the patient population has a mean $AUC_{2hr}$ of at least 1000 ng*h/mL and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma fospropofol $AUC_{2hr}$ or the patient population has a mean $AUC_{2hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma fospropofol $AUC_{2hr}$ or the patient population has a mean $AUC_{2hr}$ of at least 1000 ng*h/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 2 hour after the administration the patient has plasma fospropofol concentration ($C_{2hr}$) or the patient population has a mean $C_{2hr}$ of at least 25 ng/mL, such as, for example, at least 25 ng/mL, at least 50 ng/mL, at least 75 ng/mL, at least 100 ng/mL, at least 125 ng/mL, at least 150 ng/mL, at least 175 ng/mL, at least 200 ng/mL, at least 225 ng/mL, at least 250 ng/mL, 275 ng/mL, at least 300 ng/mL, at least 325 ng/mL, at least 350 ng/mL, at least 400 ng/mL, at least 425 ng/mL, at least 450 ng/mL, at least 475 ng/mL, at least 500 ng/mL, at least 525 ng/mL, at least 550 ng/mL, at least 575 ng/mL, at least 600 ng/mL, at least 625 ng/mL, at least 650 ng/mL, at least 675 ng/mL, at least 700 ng/mL, at least 725 ng/mL, at least 750 ng/mL, at least 775 ng/mL, at least 800 ng/mL, at least 825 ng/mL, at least 850 ng/mL, at least 875 ng/mL, at least 900 ng/mL, at least 925 ng/mL, at least 950 ng/mL, at least 975 ng/mL, at least 1000 ng/mL, at least 1100 ng/mL, at least 1125 ng/mL, at least 1150 ng/mL, at least 1175 ng/mL, at least 1200 ng/mL, at least 1225 ng/mL, at least 1250 ng/mL, 1275 ng/mL, at least 1300 ng/mL, at least 1325 ng/mL, at least 1350 ng/mL, at least 1400 ng/mL, at least 1425 ng/mL, at least 1450 ng/mL, at least 1475 ng/mL, at least 1500 ng/mL, at least 1525 ng/mL, at least 1550 ng/mL, at least 1575 ng/mL, at least 1600 ng/mL, at least 1625 ng/mL, at least 1650 ng/mL, at least 1675 ng/mL, at least 1700 ng/mL, at least 1725 ng/mL, at least 1750 ng/mL, at least 1775 ng/mL, at least 1800 ng/mL, at least 1825 ng/mL, at least 1850 ng/mL, at least 1875 ng/mL, at least 1900 ng/mL, at least 1925 ng/mL, at least 1950 ng/mL, at least 1975 ng/mL, or at least 2000 ng/mL.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has a plasma fospropofol concentration ($C_{2hr}$) or the patient population has a mean $C_{2hr}$ as set forth herein and the patient is headache free.

In some aspects, the disclosure is directed to methods of treating migraine in a patient or patient population in need thereof, wherein the methods comprise administering to the patient(s) a pharmaceutical composition of the disclosure, wherein at 2 hour after the administration the patient has plasma fospropofol concentration ($C_{2hr}$) or the patient population has a mean $C_{2hr}$ of at least 100 ng/mL and the patient is headache free.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma fospropofol concentration ($C_{2hr}$) or the patient population has a mean $C_{2hr}$ as set forth herein and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma fospropofol concentration ($C_{2hr}$) or the patient population has a mean $C_{2hr}$ of at least 40 ng/mL and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma fospropofol concentration ($C_{2hr}$) or the patient population has a mean $C_{2hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma fospropofol concentration ($C_{2hr}$) or the patient population has a mean $C_{2hr}$ of at least 50 ng/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient is headache free, has experienced a reduction in headache pain, is no longer experiencing a most bothersome symptom, or is no longer experiencing a bothersome symptom, and the plasma Cmax or the patient population mean Cmax of propofol is at least any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3050 ng/mL, 3100 ng/mL, 3150 ng/mL, 3200 ng/mL, 3250 ng/mL, 3300 ng/mL, 3350 ng/mL, 3400 ng/mL, 3450 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, or 4000 ng/mL.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient is headache free, has experienced a reduction in headache pain, is no longer experiencing a most bothersome symptom, or is no longer experiencing a bothersome symptom and the plasma Cmax or the patient population mean Cmax of fospropofol (or a pharmaceutically acceptable salt of fospropofol) is at least any one of 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 1950 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, 4000 ng/mL, 4050 ng/mL, 4100 ng/mL, 4150 ng/mL, 4200 ng/mL, 4250 ng/mL, 4300 ng/mL, 4350 ng/mL, 4400 ng/mL, 4450 ng/mL, 4500 ng/mL, 4550 ng/mL, 4600 ng/mL, 4650 ng/mL, 4700 ng/mL, 4750 ng/mL, 4800 ng/mL, 4850 ng/mL, 4900 ng/mL, 4950 ng/mL, 5000 ng/mL, 5050 ng/mL, 5100 ng/mL, 5150 ng/mL, 5200 ng/mL, 5250 ng/mL, 5300 ng/mL, 5350 ng/mL, 5400 ng/mL, 5450 ng/mL, 5500 ng/mL, 5550 ng/mL, 5600 ng/mL, 5650 ng/mL, 5700 ng/mL, 5750 ng/mL, 5800 ng/mL, 5850 ng/mL, 5900 ng/mL, 5950 ng/mL, 6000 ng/mL, 6050 ng/mL, 6100 ng/mL, 6150 ng/mL, 6200 ng/mL, 6250 ng/mL, 6300 ng/mL, 6350 ng/mL, 6400 ng/mL, 6450 ng/mL, 6500 ng/mL, 6550 ng/mL, 6600 ng/mL, 6650 ng/mL, 6700 ng/mL, 6750 ng/mL, 6800 ng/mL, 6850 ng/mL, 6900 ng/mL, 6950 ng/mL, 7000 ng/mL, 7050 ng/mL, 7100 ng/mL, 7150 ng/mL, 7200 ng/mL, 7250 ng/mL, 7300 ng/mL, 7350 ng/mL, 7400 ng/mL, 7450 ng/mL, 7500 ng/mL, 7550 ng/mL, 7600 ng/mL, 7650 ng/mL, 7700 ng/mL, 7750 ng/mL, 7800 ng/mL, 7850 ng/mL, 7900 ng/mL, 7950 ng/mL, 8000 ng/mL, 8050 ng/mL, 8100 ng/mL, 8150 ng/mL, 8200 ng/mL, 8250 ng/mL, 8300 ng/mL, 8350 ng/mL, 8400 ng/mL, 8450 ng/mL, 8500 ng/mL, 8550 ng/mL, 8600 ng/mL, 8650 ng/mL, 8700 ng/mL, 8750 ng/mL, 800 ng/mL, 8850 ng/mL, 8900 ng/mL, 8950 ng/mL, 9000 ng/mL, 9050 ng/mL, 9100 ng/mL, 9150 ng/mL, 9200 ng/mL, 9250 ng/mL, 9300 ng/mL, 9350 ng/mL, 9400 ng/mL, 9450 ng/mL, 9500 ng/mL, 9550 ng/mL, 9600 ng/mL, 9650 ng/mL, 9700 ng/mL, 9750 ng/mL, 9000 ng/mL, 9950 ng/mL, 9900 ng/mL, 9950 ng/mL, 10000 ng/mL, 10050 ng/mL, 10100 ng/mL, 10150 ng/mL, 10200 ng/mL, 10250 ng/mL, 10300 ng/mL, 10350 ng/mL, 10400 ng/mL, 10450 ng/mL, 10500 ng/mL, 10550 ng/mL, 10600 ng/mL, 10650 ng/mL, 10700 ng/mL, 10750 ng/mL, 1000 ng/mL, 101050 ng/mL, 10900 ng/mL, 10950 ng/mL, 11000 ng/mL, 11050 ng/mL, 11100 ng/mL, 11150 ng/mL, 11200 ng/mL, 11250 ng/mL, 11300 ng/mL, 11350 ng/mL, 11400 ng/mL, 11450 ng/mL, 11500 ng/mL, 11550 ng/mL, 11600 ng/mL, 11650 ng/mL, 11700 ng/mL, 11750 ng/mL, 1100 ng/mL, 111150 ng/mL, 11900 ng/mL, 11950 ng/mL, 12000 ng/mL, 12050 ng/mL, 12100 ng/mL, 12150 ng/mL, 12200 ng/mL, 12250 ng/mL, 12300 ng/mL, 12350 ng/mL, 12400 ng/mL, 12450 ng/mL, 12500 ng/mL, 12550 ng/mL, 12600 ng/mL, 12650 ng/mL, 12700 ng/mL, 12750 ng/mL, 1200 ng/mL, 121250 ng/mL, 12900 ng/mL, 12950 ng/mL, 13000 ng/mL, 13050 ng/mL, 13100 ng/mL, 13150 ng/mL, 13200 ng/mL, 13250 ng/mL, 13300 ng/mL, 13350 ng/mL, 13400 ng/mL, 13450 ng/mL, 13500 ng/mL, 13550 ng/mL, 13600 ng/mL, 13650 ng/mL, 13700 ng/mL, 13750 ng/mL, 1300 ng/mL, 131350 ng/mL, 13900 ng/mL, 13950 ng/mL, 14000 ng/mL, 14050 ng/mL, 14100 ng/mL, 14150 ng/mL, 14200 ng/mL, 14250 ng/mL, 14300 ng/mL, 14350 ng/mL, 14400 ng/mL, 14450 ng/mL, 14500 ng/mL, 14550 ng/mL, 14600 ng/mL, 14650 ng/mL, 14700 ng/mL, 14750 ng/mL, 1400 ng/mL, 141450 ng/mL, 14900 ng/mL, 14950 ng/mL, 15000 ng/mL, 15050 ng/mL, 15100 ng/mL, 15150 ng/mL, 15200 ng/mL, 15250 ng/mL, 15300 ng/mL, 15350 ng/mL, 15400 ng/mL, 15450 ng/mL, 15500 ng/mL, 15550 ng/mL, 15600 ng/mL, 15650 ng/mL, 15700 ng/mL, 15750 ng/mL, 1500 ng/mL, 151550 ng/mL, 15900 ng/mL, 15950 ng/mL, 16000 ng/mL, 16050 ng/mL, 16100 ng/mL, 16150 ng/mL, 16200 ng/mL, 16250 ng/mL, 16300 ng/mL, 16350 ng/mL, 16400 ng/mL, 16450 ng/mL, 16500 ng/mL, 16550 ng/mL, 16600 ng/mL, 16650 ng/mL, 16700 ng/mL, 16750 ng/mL, 1600 ng/mL, 161650 ng/mL, 16900 ng/mL, 16950 ng/mL, 17000 ng/mL, 17050 ng/mL, 17100 ng/mL, 17150 ng/mL, 17200 ng/mL, 17250 ng/mL, 17300 ng/mL, 17350 ng/mL, 17400 ng/mL, 17450 ng/mL, 17500 ng/mL, 17550 ng/mL, 17600 ng/mL, 17650 ng/mL, 17700 ng/mL, 17750 ng/mL, 1700 ng/mL, 171750 ng/mL, 17900 ng/mL, 17950 ng/mL, or 18000 ng/mL.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient is headache free, has experienced a reduction in headache pain, is no longer experiencing a most bothersome symptom, or is no longer experiencing a bothersome symptom and the propofol plasma $AUC_{0-\infty}$ per mg of fospropofol (or a pharmaceutically acceptable salt of fospropofol) administered or the propofol patient population mean $AUC_{0-\infty}$ per mg of fospropofol (or a pharmaceutically acceptable salt of fospropofol) administered is, at least any one of 0.5 ng*h/mL/mg, 0.55 ng*h/mL/mg, 0.6 ng*h/mL/mg, 0.65 ng*h/mL/mg, 0.7 ng*h/mL/mg, 0.75 ng*h/mL/mg, 0.8 ng*h/mL/mg, 0.85 ng*h/mL/mg, 0.9 ng*h/mL/mg, 0.95 ng*h/mL/mg, 1.0 ng*h/mL/mg, 1.05 ng*h/mL/mg, 1.10 ng*h/mL/mg, 1.15 ng*h/mL/mg, 1.2 ng*h/mL/mg, 1.25 ng*h/mL/mg, 1.3 ng*h/mL/mg, 1.35 ng*h/mL/mg, 1.4 ng*h/mL/mg, 1.45 ng*h/mL/mg, 1.5 ng*h/mL/mg, 1.55 ng*h/mL/mg, 1.6 ng*h/mL/mg, 1.65 ng*h/mL/mg, or 1.7 ng*h/mL/mg.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient is headache free, has experienced a reduction in headache pain, is no longer experiencing a most bothersome symptom, or is no longer experiencing a bothersome symptom and the fospropofol plasma $AUC_{0-\infty}$ per mg of fospropofol (or a pharmaceutically acceptable salt of fospropofol) administered or the fospropofol patient population mean $AUC_{0-\infty}$ per mg of fospropofol (or a pharmaceutically acceptable salt of fospropofol) administered is at least 3.0 ng*h/mL, such as, for example, at least any one of 3.0 ng*h/mL/mg, 3.1 ng*h/mL/mg, 3.2 ng*h/mL/mg, 3.3 ng*h/mL/mg, 3.4 ng*h/mL/mg, 3.5 ng*h/mL/mg, 3.6 ng*h/mL/mg, 3.7 ng*h/mL/mg, 3.8 ng*h/mL/mg, 3.9 ng*h/mL/mg, 4.0 ng*h/mL/mg, 4.1 ng*h/mL/mg, 4.2 ng*h/mL/mg, 4.3 ng*h/mL/mg, 4.4 ng*h/mL/mg, 4.5 ng*h/mL/mg, 4.6 ng*h/mL/mg, 4.7 ng*h/mL/mg, 4.8 ng*h/mL/mg, 4.9 ng*h/mL/mg, 5.0 ng*h/mL/mg, 5.1 ng*h/mL/mg, 5.2 ng*h/mL/mg, 5.3 ng*h/mL/mg, 5.4 ng*h/mL/mg, 5.5 ng*h/mL/mg, 5.6 ng*h/mL/mg, 5.7 ng*h/mL/mg, 5.8 ng*h/mL/mg, 5.9 ng*h/mL/mg, 6.0 ng*h/mL/mg, 6.1 ng*h/mL/mg, 6.2 ng*h/mL/mg, 6.3 ng*h/mL/mg, 6.4 ng*h/mL/mg, 6.5 ng*h/mL/mg, 6.6 ng*h/mL/mg, 6.7 ng*h/mL/mg, 6.8 ng*h/mL/mg, 6.9 ng*h/mL/mg, 7.0 ng*h/mL/mg, 7.1 ng*h/mL/mg, 7.2 ng*h/mL/mg, 7.3 ng*h/mL/mg, 7.4 ng*h/mL/mg, 7.5 ng*h/mL/mg, 7.6 ng*h/mL/mg, 7.7 ng*h/mL/mg, 7.8 ng*h/mL/mg, 7.9 ng*h/mL/mg, 8.0 ng*h/mL/mg, 8.1 ng*h/mL/mg, 8.2 ng*h/mL/mg, 8.3 ng*h/mL/mg, 8.4 ng*h/mL/mg, 8.5 ng*h/mL/mg, 8.6 ng*h/mL/mg, 8.7 ng*h/mL/mg, 8.8 ng*h/mL/mg, 8.9 ng*h/mL/mg, or 9.0 ng*h/mL/mg.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient is headache free, has experienced a reduction in headache pain, is no longer experiencing a most bothersome symptom, or is no longer experiencing a bothersome symptom, and the plasma Cmax or the patient population mean Cmax of propofol is at least any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3050 ng/mL, 3100 ng/mL, 3150 ng/mL, 3200 ng/mL, 3250 ng/mL, 3300 ng/mL, 3350 ng/mL, 3400 ng/mL, 3450 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, or 4000 ng/mL.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient is headache free, has experienced a reduction in headache pain, is no longer experiencing a most bothersome symptom, or is no longer experiencing a bothersome symptom and the plasma Cmax or the patient population mean Cmax of fospropofol (or a pharmaceutically acceptable salt of fospropofol) is at least any one of 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 1950 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, 4000 ng/mL, 4050 ng/mL, 4100 ng/mL, 4150 ng/mL, 4200 ng/mL, 4250 ng/mL, 4300 ng/mL, 4350 ng/mL, 4400 ng/mL, 4450 ng/mL, 4500 ng/mL, 4550 ng/mL, 4600 ng/mL, 4650 ng/mL, 4700 ng/mL, 4750 ng/mL, 4800 ng/mL, 4850 ng/mL, 4900 ng/mL, 4950 ng/mL, 5000 ng/mL, 5050 ng/mL, 5100 ng/mL, 5150 ng/mL, 5200 ng/mL, 5250 ng/mL, 5300 ng/mL, 5350 ng/mL, 5400 ng/mL, 5450 ng/mL, 5500 ng/mL, 5550 ng/mL, 5600 ng/mL, 5650 ng/mL, 5700 ng/mL, 5750 ng/mL, 5800 ng/mL, 5850 ng/mL, 5900 ng/mL, 5950 ng/mL, 6000 ng/mL, 6050 ng/mL, 6100 ng/mL, 6150 ng/mL, 6200 ng/mL, 6250 ng/mL, 6300 ng/mL, 6350 ng/mL, 6400 ng/mL, 6450 ng/mL, 6500 ng/mL, 6550 ng/mL, 6600 ng/mL, 6650 ng/mL, 6700 ng/mL, 6750 ng/mL, 6800 ng/mL, 6850 ng/mL, 6900 ng/mL, 6950 ng/mL, 7000 ng/mL, 7050 ng/mL, 7100 ng/mL, 7150 ng/mL, 7200 ng/mL, 7250 ng/mL, 7300 ng/mL, 7350 ng/mL, 7400 ng/mL, 7450 ng/mL, 7500 ng/mL, 7550 ng/mL, 7600 ng/mL, 7650 ng/mL, 7700 ng/mL, 7750 ng/mL, 7800 ng/mL, 7850 ng/mL, 7900 ng/mL, 7950 ng/mL, 8000 ng/mL, 8050 ng/mL, 8100 ng/mL, 8150 ng/mL, 8200 ng/mL, 8250 ng/mL, 8300 ng/mL, 8350 ng/mL, 8400 ng/mL, 8450 ng/mL, 8500 ng/mL, 8550 ng/mL, 8600 ng/mL, 8650 ng/mL, 8700 ng/mL, 8750 ng/mL, 800 ng/mL, 8850 ng/mL, 8900 ng/mL, 8950 ng/mL, 9000 ng/mL, 9050 ng/mL, 9100 ng/mL, 9150 ng/mL, 9200 ng/mL, 9250 ng/mL, 9300 ng/mL, 9350 ng/mL, 9400 ng/mL, 9450 ng/mL, 9500 ng/mL, 9550 ng/mL, 9600 ng/mL, 9650 ng/mL, 9700 ng/mL, 9750 ng/mL, 9000 ng/mL, 9950 ng/mL, 9900 ng/mL, 9950 ng/mL, 10000 ng/mL, 10050 ng/mL, 10100 ng/mL, 10150 ng/mL, 10200 ng/mL, 10250 ng/mL, 10300 ng/mL, 10350 ng/mL, 10400 ng/mL, 10450 ng/mL, 10500 ng/mL, 10550 ng/mL, 10600 ng/mL, 10650 ng/mL, 10700 ng/mL, 10750 ng/mL, 1000 ng/mL, 101050 ng/mL, 10900 ng/mL, 10950 ng/mL, 11000 ng/mL, 11050 ng/mL, 11100 ng/mL, 11150 ng/mL, 11200 ng/mL, 11250 ng/mL, 11300 ng/mL, 11350 ng/mL, 11400 ng/mL, 11450 ng/mL, 11500 ng/mL, 11550 ng/mL, 11600 ng/mL, 11650 ng/mL, 11700 ng/mL, 11750 ng/mL, 1100 ng/mL, 111150 ng/mL, 11900 ng/mL, 11950 ng/mL, 12000 ng/mL, 12050 ng/mL, 12100 ng/mL, 12150 ng/mL, 12200 ng/mL, 12250 ng/mL, 12300 ng/mL, 12350 ng/mL, 12400 ng/mL, 12450 ng/mL, 12500 ng/mL, 12550 ng/mL, 12600 ng/mL, 12650 ng/mL, 12700 ng/mL, 12750 ng/mL, 1200 ng/mL, 121250 ng/mL, 12900 ng/mL, 12950 ng/mL, 13000 ng/mL, 13050 ng/mL, 13100 ng/mL, 13150 ng/mL, 13200 ng/mL, 13250 ng/mL, 13300 ng/mL, 13350 ng/mL, 13400 ng/mL, 13450 ng/mL, 13500 ng/mL, 13550 ng/mL, 13600 ng/mL, 13650 ng/mL, 13700 ng/mL, 13750 ng/mL, 1300 ng/mL, 131350 ng/mL, 13900 ng/mL, 13950 ng/mL, 14000 ng/mL, 14050 ng/mL, 14100 ng/mL, 14150 ng/mL, 14200 ng/mL, 14250 ng/mL, 14300 ng/mL, 14350 ng/mL, 14400 ng/mL, 14450 ng/mL, 14500 ng/mL, 14550 ng/mL, 14600 ng/mL, 14650 ng/mL, 14700 ng/mL, 14750 ng/mL, 1400 ng/mL, 141450 ng/mL, 14900 ng/mL, 14950 ng/mL, 15000 ng/mL, 15050 ng/mL, 15100 ng/mL, 15150 ng/mL, 15200 ng/mL, 15250 ng/mL, 15300 ng/mL, 15350 ng/mL, 15400 ng/mL, 15450 ng/mL, 15500 ng/mL, 15550 ng/mL, 15600 ng/mL, 15650 ng/mL, 15700 ng/mL, 15750 ng/mL, 1500 ng/mL, 151550 ng/mL, 15900 ng/mL, 15950 ng/mL, 16000 ng/mL, 16050 ng/mL, 16100 ng/mL, 16150 ng/mL, 16200 ng/mL, 16250 ng/mL, 16300 ng/mL, 16350 ng/mL, 16400 ng/mL, 16450 ng/mL, 16500 ng/mL, 16550 ng/mL, 16600 ng/mL, 16650 ng/mL, 16700 ng/mL, 16750 ng/mL, 1600 ng/mL, 161650 ng/mL, 16900 ng/mL, 16950 ng/mL, 17000 ng/mL, 17050 ng/mL, 17100 ng/mL, 17150 ng/mL, 17200 ng/mL, 17250 ng/mL, 17300 ng/mL, 17350 ng/mL, 17400 ng/mL, 17450 ng/mL, 17500 ng/mL, 17550 ng/mL, 17600 ng/mL, 17650 ng/mL, 17700 ng/mL, 17750 ng/mL, 1700 ng/mL, 171750 ng/mL, 17900 ng/mL, 17950 ng/mL, or 18000 ng/mL.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient is headache free, has experienced a reduction in headache pain, is no longer experiencing a most bothersome symptom, or is no longer experiencing a bothersome symptom and the propofol plasma $AUC_{0-\infty}$ per mg of fospropofol (or a pharmaceutically acceptable salt of fospropofol) administered or the propofol patient population mean $AUC_{0-\infty}$ per mg of fospropofol (or a pharmaceutically acceptable salt of fospropofol) administered is, at least any one of 0.5 ng*h/mL/mg, 0.55 ng*h/mL/mg, 0.6 ng*h/mL/mg, 0.65 ng*h/mL/mg, 0.7 ng*h/mL/mg, 0.75 ng*h/mL/mg, 0.8 ng*h/mL/mg, 0.85 ng*h/mL/mg, 0.9 ng*h/mL/mg, 0.95 ng*h/mL/mg, 1.0 ng*h/mL/mg, 1.05 ng*h/mL/mg, 1.10 ng*h/mL/mg, 1.15 ng*h/mL/mg, 1.2 ng*h/mL/mg, 1.25 ng*h/mL/mg, 1.3 ng*h/mL/mg, 1.35 ng*h/mL/mg, 1.4 ng*h/mL/mg, 1.45 ng*h/mL/mg, 1.5 ng*h/mL/mg, 1.55 ng*h/mL/mg, 1.6 ng*h/mL/mg, 1.65 ng*h/mL/mg, or 1.7 ng*h/mL/mg.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient is headache free, has experienced a reduction in headache pain, is no longer experiencing a most bothersome symptom, or is no longer experiencing a bothersome symptom and the fospropofol plasma $AUC_{0-\infty}$ per mg of fospropofol (or a pharmaceutically acceptable salt of fospropofol) administered or the fospropofol patient population mean $AUC_{0-\infty}$ per mg of fospropofol (or a pharmaceutically acceptable salt of fospropofol) administered is at least 3.0 ng*h/mL, such as, for example, at least any one of 3.0 ng*h/mL/mg, 3.1 ng*h/mL/mg, 3.2 ng*h/mL/mg, 3.3 ng*h/mL/mg, 3.4 ng*h/mL/mg, 3.5 ng*h/mL/mg, 3.6 ng*h/mL/mg, 3.7 ng*h/mL/mg, 3.8 ng*h/mL/mg, 3.9 ng*h/mL/mg, 4.0 ng*h/mL/mg, 4.1 ng*h/mL/mg, 4.2 ng*h/mL/mg, 4.3 ng*h/mL/mg, 4.4 ng*h/mL/mg, 4.5 ng*h/mL/mg, 4.6 ng*h/mL/mg, 4.7 ng*h/mL/mg, 4.8 ng*h/mL/mg, 4.9 ng*h/mL/mg, 5.0 ng*h/mL/mg, 5.1 ng*h/mL/mg, 5.2 ng*h/mL/mg, 5.3 ng*h/mL/mg, 5.4 ng*h/mL/mg, 5.5 ng*h/mL/mg, 5.6 ng*h/mL/mg, 5.7 ng*h/mL/mg, 5.8 ng*h/mL/mg, 5.9 ng*h/mL/mg, 6.0 ng*h/mL/mg, 6.1 ng*h/mL/mg, 6.2 ng*h/mL/mg, 6.3 ng*h/mL/mg, 6.4 ng*h/mL/mg, 6.5 ng*h/mL/mg, 6.6 ng*h/mL/mg, 6.7 ng*h/mL/mg, 6.8 ng*h/mL/mg, 6.9 ng*h/mL/mg, 7.0 ng*h/mL/mg, 7.1 ng*h/mL/mg, 7.2 ng*h/mL/mg, 7.3 ng*h/mL/mg, 7.4 ng*h/mL/mg, 7.5 ng*h/mL/mg, 7.6 ng*h/mL/mg, 7.7 ng*h/mL/mg, 7.8 ng*h/mL/mg, 7.9 ng*h/mL/mg, 8.0 ng*h/mL/mg, 8.1 ng*h/mL/mg, 8.2 ng*h/mL/mg, 8.3 ng*h/mL/mg, 8.4 ng*h/mL/mg, 8.5 ng*h/mL/mg, 8.6 ng*h/mL/mg, 8.7 ng*h/mL/mg, 8.8 ng*h/mL/mg, 8.9 ng*h/mL/mg, or 9.0 ng*h/mL/mg.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient is headache free, has experienced a reduction in headache pain, is no longer experiencing a most bothersome symptom, or is no longer experiencing a bothersome symptom, and the plasma Cmax or the patient population mean Cmax of propofol is at least any one of 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3050 ng/mL, 3100 ng/mL, 3150 ng/mL, 3200 ng/mL, 3250 ng/mL, 3300 ng/mL, 3350 ng/mL, 3400 ng/mL, 3450 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, or 4000 ng/mL.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient is headache free, has experienced a reduction in headache pain, is no longer experiencing a most bothersome symptom, or is no longer experiencing a bothersome symptom and the plasma Cmax or the patient population mean Cmax of fospropofol (or a pharmaceutically acceptable salt of fospropofol) is at least any one of 800 ng/mL, 850 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1350 ng/mL, 1400 ng/mL, 1450 ng/mL, 1500 ng/mL, 1550 ng/mL, 1600 ng/mL, 1650 ng/mL, 1700 ng/mL, 1750 ng/mL, 1800 ng/mL, 1850 ng/mL, 1900 ng/mL, 1950 ng/mL, 2000 ng/mL, 2050 ng/mL, 2100 ng/mL, 2150 ng/mL, 2200 ng/mL, 2250 ng/mL, 2300 ng/mL, 2350 ng/mL, 2400 ng/mL, 2450 ng/mL, 2500 ng/mL, 2550 ng/mL, 2600 ng/mL, 2650 ng/mL, 2700 ng/mL, 2750 ng/mL, 2800 ng/mL, 2850 ng/mL, 2900 ng/mL, 2950 ng/mL, 3000 ng/mL, 3500 ng/mL, 3550 ng/mL, 3600 ng/mL, 3650 ng/mL, 3700 ng/mL, 3750 ng/mL, 3800 ng/mL, 3850 ng/mL, 3900 ng/mL, 3950 ng/mL, 4000 ng/mL, 4050 ng/mL, 4100 ng/mL, 4150 ng/mL, 4200 ng/mL, 4250 ng/mL, 4300 ng/mL, 4350 ng/mL, 4400 ng/mL, 4450 ng/mL, 4500 ng/mL, 4550 ng/mL, 4600 ng/mL, 4650 ng/mL, 4700 ng/mL, 4750 ng/mL, 4800 ng/mL, 4850 ng/mL, 4900 ng/mL, 4950 ng/mL, 5000 ng/mL, 5050 ng/mL, 5100 ng/mL, 5150 ng/mL, 5200 ng/mL, 5250 ng/mL, 5300 ng/mL, 5350 ng/mL, 5400 ng/mL, 5450 ng/mL, 5500 ng/mL, 5550 ng/mL, 5600 ng/mL, 5650 ng/mL, 5700 ng/mL, 5750 ng/mL, 5800 ng/mL, 5850 ng/mL, 5900 ng/mL, 5950 ng/mL, 6000 ng/mL, 6050 ng/mL, 6100 ng/mL, 6150 ng/mL, 6200 ng/mL, 6250 ng/mL, 6300 ng/mL, 6350 ng/mL, 6400 ng/mL, 6450 ng/mL, 6500 ng/mL, 6550 ng/mL, 6600 ng/mL, 6650 ng/mL, 6700 ng/mL, 6750 ng/mL, 6800 ng/mL, 6850 ng/mL, 6900 ng/mL, 6950 ng/mL, 7000 ng/mL, 7050 ng/mL, 7100 ng/mL, 7150 ng/mL, 7200 ng/mL, 7250 ng/mL, 7300 ng/mL, 7350 ng/mL, 7400 ng/mL, 7450 ng/mL, 7500 ng/mL, 7550 ng/mL, 7600 ng/mL, 7650 ng/mL, 7700 ng/mL, 7750 ng/mL, 7800 ng/mL, 7850 ng/mL, 7900 ng/mL, 7950 ng/mL, 8000 ng/mL, 8050 ng/mL, 8100 ng/mL, 8150 ng/mL, 8200 ng/mL, 8250 ng/mL, 8300 ng/mL, 8350 ng/mL, 8400 ng/mL, 8450 ng/mL, 8500 ng/mL, 8550 ng/mL, 8600 ng/mL, 8650 ng/mL, 8700 ng/mL, 8750 ng/mL, 800 ng/mL, 8850 ng/mL, 8900 ng/mL, 8950 ng/mL, 9000 ng/mL, 9050 ng/mL, 9100 ng/mL, 9150 ng/mL, 9200 ng/mL, 9250 ng/mL, 9300 ng/mL, 9350 ng/mL, 9400 ng/mL, 9450 ng/mL, 9500 ng/mL, 9550 ng/mL, 9600 ng/mL, 9650 ng/mL, 9700 ng/mL, 9750 ng/mL, 9000 ng/mL, 9950 ng/mL, 9900 ng/mL, 9950 ng/mL, 10000 ng/mL, 10050 ng/mL, 10100 ng/mL, 10150 ng/mL, 10200 ng/mL, 10250 ng/mL, 10300 ng/mL, 10350 ng/mL, 10400 ng/mL, 10450 ng/mL, 10500 ng/mL, 10550 ng/mL, 10600 ng/mL, 10650 ng/mL, 10700 ng/mL, 10750 ng/mL, 1000 ng/mL, 101050 ng/mL, 10900 ng/mL, 10950 ng/mL, 11000 ng/mL, 11050 ng/mL, 11100 ng/mL, 11150 ng/mL, 11200 ng/mL, 11250 ng/mL, 11300 ng/mL, 11350 ng/mL, 11400 ng/mL, 11450 ng/mL, 11500 ng/mL, 11550 ng/mL, 11600 ng/mL, 11650 ng/mL, 11700 ng/mL, 11750 ng/mL, 1100 ng/mL, 111150 ng/mL, 11900 ng/mL, 11950 ng/mL, 12000 ng/mL, 12050 ng/mL, 12100 ng/mL, 12150 ng/mL, 12200 ng/mL, 12250 ng/mL, 12300 ng/mL, 12350 ng/mL, 12400 ng/mL, 12450 ng/mL, 12500 ng/mL, 12550 ng/mL, 12600 ng/mL, 12650 ng/mL, 12700 ng/mL, 12750 ng/mL, 1200 ng/mL, 121250 ng/mL, 12900 ng/mL, 12950 ng/mL, 13000 ng/mL, 13050 ng/mL, 13100 ng/mL, 13150 ng/mL, 13200 ng/mL, 13250 ng/mL, 13300 ng/mL, 13350 ng/mL, 13400 ng/mL, 13450 ng/mL, 13500 ng/mL, 13550 ng/mL, 13600 ng/mL, 13650 ng/mL, 13700 ng/mL, 13750 ng/mL, 1300 ng/mL, 131350 ng/mL, 13900 ng/mL, 13950 ng/mL, 14000 ng/mL, 14050 ng/mL, 14100 ng/mL, 14150 ng/mL, 14200 ng/mL, 14250 ng/mL, 14300 ng/mL, 14350 ng/mL, 14400 ng/mL, 14450 ng/mL, 14500 ng/mL, 14550 ng/mL, 14600 ng/mL, 14650 ng/mL, 14700 ng/mL, 14750 ng/mL, 1400 ng/mL, 141450 ng/mL, 14900 ng/mL, 14950 ng/mL, 15000 ng/mL, 15050 ng/mL, 15100 ng/mL, 15150 ng/mL, 15200 ng/mL, 15250 ng/mL, 15300 ng/mL, 15350 ng/mL, 15400 ng/mL, 15450 ng/mL, 15500 ng/mL, 15550 ng/mL, 15600 ng/mL, 15650 ng/mL, 15700 ng/mL, 15750 ng/mL, 1500 ng/mL, 151550 ng/mL, 15900 ng/mL, 15950 ng/mL, 16000 ng/mL, 16050 ng/mL, 16100 ng/mL, 16150 ng/mL, 16200 ng/mL, 16250 ng/mL, 16300 ng/mL, 16350 ng/mL, 16400 ng/mL, 16450 ng/mL, 16500 ng/mL, 16550 ng/mL, 16600 ng/mL, 16650 ng/mL, 16700 ng/mL, 16750 ng/mL, 1600 ng/mL, 161650 ng/mL, 16900 ng/mL, 16950 ng/mL, 17000 ng/mL, 17050 ng/mL, 17100 ng/mL, 17150 ng/mL, 17200 ng/mL, 17250 ng/mL, 17300 ng/mL, 17350 ng/mL, 17400 ng/mL, 17450 ng/mL, 17500 ng/mL, 17550 ng/mL, 17600 ng/mL, 17650 ng/mL, 17700 ng/mL, 17750 ng/mL, 1700 ng/mL, 171750 ng/mL, 17900 ng/mL, 17950 ng/mL, or 18000 ng/mL.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient is headache free, has experienced a reduction in headache pain, is no longer experiencing a most bothersome symptom, or is no longer experiencing a bothersome symptom and the propofol plasma $AUC_{0-\infty}$ per mg of fospropofol (or a pharmaceutically acceptable salt of fospropofol) administered or the propofol patient population mean $AUC_{0-\infty}$ per mg of fospropofol (or a pharmaceutically acceptable salt of fospropofol) administered is, at least any one of 0.5 ng*h/mL/mg, 0.55 ng*h/mL/mg, 0.6 ng*h/mL/mg, 0.65 ng*h/mL/mg, 0.7 ng*h/mL/mg, 0.75 ng*h/mL/mg, 0.8 ng*h/mL/mg, 0.85 ng*h/mL/mg, 0.9 ng*h/mL/mg, 0.95 ng*h/mL/mg, 1.0 ng*h/mL/mg, 1.05 ng*h/mL/mg, 1.10 ng*h/mL/mg, 1.15 ng*h/mL/mg, 1.2 ng*h/mL/mg, 1.25 ng*h/mL/mg, 1.3 ng*h/mL/mg, 1.35 ng*h/mL/mg, 1.4 ng*h/mL/mg, 1.45 ng*h/mL/mg, 1.5 ng*h/mL/mg, 1.55 ng*h/mL/mg, 1.6 ng*h/mL/mg, 1.65 ng*h/mL/mg, or 1.7 ng*h/mL/mg.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient is headache free, has experienced a reduction in headache pain, is no longer experiencing a most bothersome symptom, or is no longer experiencing a bothersome symptom and the fospropofol plasma $AUC_{0-\infty}$ per mg of fospropofol (or a pharmaceutically acceptable salt of fospropofol) administered or the fospropofol patient population mean $AUC_{0-\infty}$ per mg of fospropofol (or a pharmaceutically acceptable salt of fospropofol) administered is at least 3.0 ng*h/mL, such as, for example, at least any one of 3.0 ng*h/mL/mg, 3.1 ng*h/mL/mg, 3.2 ng*h/mL/mg, 3.3 ng*h/mL/mg, 3.4 ng*h/mL/mg, 3.5 ng*h/mL/mg, 3.6 ng*h/mL/mg, 3.7 ng*h/mL/mg, 3.8 ng*h/mL/mg, 3.9 ng*h/mL/mg, 4.0 ng*h/mL/mg, 4.1 ng*h/mL/mg, 4.2 ng*h/mL/mg, 4.3 ng*h/mL/mg, 4.4 ng*h/mL/mg, 4.5 ng*h/mL/mg, 4.6 ng*h/mL/mg, 4.7 ng*h/mL/mg, 4.8 ng*h/mL/mg, 4.9 ng*h/mL/mg, 5.0 ng*h/mL/mg, 5.1 ng*h/mL/mg, 5.2 ng*h/mL/mg, 5.3 ng*h/mL/mg, 5.4 ng*h/mL/mg, 5.5 ng*h/mL/mg, 5.6 ng*h/mL/mg, 5.7 ng*h/mL/mg, 5.8 ng*h/mL/mg, 5.9 ng*h/mL/mg, 6.0 ng*h/mL/mg, 6.1 ng*h/mL/mg, 6.2 ng*h/mL/mg, 6.3 ng*h/mL/mg, 6.4 ng*h/mL/mg, 6.5 ng*h/mL/mg, 6.6 ng*h/mL/mg, 6.7 ng*h/mL/mg, 6.8 ng*h/mL/mg, 6.9 ng*h/mL/mg, 7.0 ng*h/mL/mg, 7.1 ng*h/mL/mg, 7.2 ng*h/mL/mg, 7.3 ng*h/mL/mg, 7.4 ng*h/mL/mg, 7.5 ng*h/mL/mg, 7.6 ng*h/mL/mg, 7.7 ng*h/mL/mg, 7.8 ng*h/mL/mg, 7.9 ng*h/mL/mg, 8.0 ng*h/mL/mg, 8.1 ng*h/mL/mg, 8.2 ng*h/mL/mg, 8.3 ng*h/mL/mg, 8.4 ng*h/mL/mg, 8.5 ng*h/mL/mg, 8.6 ng*h/mL/mg, 8.7 ng*h/mL/mg, 8.8 ng*h/mL/mg, 8.9 ng*h/mL/mg, or 9.0 ng*h/mL/mg.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma fospropofol $AUC_{4hr}$ or the patient population has a mean $AUC_{4hr}$ of at least 1000 ng*h/mL, such as, for example, at least 1000 ng*h/mL, at least 1050 ng*h/mL, at least 1100 ng*h/mL, at least 1150 ng*h/mL, at least 1200 ng*h/mL, at least 1250 ng*h/mL, at least 1300 ng*h/mL, at least 1350 ng*h/mL, at least 1400 ng*h/mL, at least 1450 ng*h/mL, at least 1500 ng*h/mL, at least 1550 ng*h/mL, at least 1600 ng*h/mL, at least 1650 ng*h/mL, at least 1700 ng*h/mL, at least 1750 ng*h/mL, at least 1800 ng*h/mL, at least 1850 ng*h/mL, at least 1900 ng*h/mL, at least 1950 ng*h/mL, at least 2000 ng*h/mL, at least 2050 ng*h/mL, at least 2100 ng*h/mL, at least 2150 ng*h/mL, at least 2200 ng*h/mL, at least 2250 ng*h/mL, at least 2300 ng*h/mL, at least 2350 ng*h/mL, at least 2400 ng*h/mL, at least 2450 ng*h/mL, at least 2500 ng*h/mL, at least 2550 ng*h/mL, at least 2600 ng*h/mL, at least 2650 ng*h/mL, at least 2700 ng*h/mL, at least 2750 ng*h/mL, at least 2800 ng*h/mL, at least 2850 ng*h/mL, at least 2900 ng*h/mL, at least 2950 ng*h/mL, at least 3000 ng*h/mL, at least 3050 ng*h/mL, at least 3100 ng*h/mL, at least 3150 ng*h/mL, at least 3200 ng*h/mL, at least 3250 ng*h/mL, at least 3300 ng*h/mL, at least 3350 ng*h/mL, at least 3400 ng*h/mL, at least 3450 ng*h/mL, at least 3500 ng*h/mL, at least 3550 ng*h/mL, at least 3600 ng*h/mL, at least 3650 ng*h/mL, at least 3700 ng*h/mL, at least 3750 ng*h/mL, at least 3800 ng*h/mL, at least 3850 ng*h/mL, at least 3900 ng*h/mL, at least 3950 ng*h/mL, at least 4000 ng*h/mL, at least 4050 ng*h/mL, at least 4100 ng*h/mL, at least 4150 ng*h/mL, at least 4200 ng*h/mL, at least 4250 ng*h/mL, at least 4300 ng*h/mL, at least 4350 ng*h/mL, at least 4400 ng*h/mL, at least 4450 ng*h/mL, at least 4500 ng*h/mL, at least 4550 ng*h/mL, at least 4600 ng*h/mL, at least 4650 ng*h/mL, at least 4700 ng*h/mL, at least 4750 ng*h/mL, at least 4800 ng*h/mL, at least 4850 ng*h/mL, at least 4900 ng*h/mL, at least 4950 ng*h/mL, at least 5000 ng*h/mL, at least 5050 ng*h/mL, at least 5100 ng*h/mL, at least 5150 ng*h/mL, at least 5200 ng*h/mL, at least 5250 ng*h/mL, at least 5300 ng*h/mL, at least 5350 ng*h/mL, at least 5400 ng*h/mL, at least 5450 ng*h/mL, at least 5500 ng*h/mL, at least 5550 ng*h/mL, at least 5600 ng*h/mL, at least 5650 ng*h/mL, at least 5700 ng*h/mL, at least 5750 ng*h/mL, at least 5800 ng*h/mL, at least 5850 ng*h/mL, at least 5900 ng*h/mL, at least 5950 ng*h/mL, at least 6000 ng*h/mL, at least 6050 ng*h/mL, at least 6100 ng*h/mL, at least 6150 ng*h/mL, at least 6200 ng*h/mL, at least 6250 ng*h/mL, at least 6300 ng*h/mL, at least 6350 ng*h/mL, at least 6400 ng*h/mL, at least 6450 ng*h/mL, at least 6500 ng*h/mL, at least 6550 ng*h/mL, at least 6600 ng*h/mL, at least 6650 ng*h/mL, at least 6700 ng*h/mL, at least 6750 ng*h/mL, at least 6800 ng*h/mL, at least 6850 ng*h/mL, at least 6900 ng*h/mL, at least 6950 ng*h/mL, at least 7000 ng*h/mL, at least 7050 ng*h/mL, at least 7100 ng*h/mL, at least 7150 ng*h/mL, at least 7200 ng*h/mL, at least 7250 ng*h/mL, at least 7300 ng*h/mL, at least 7350 ng*h/mL, at least 7400 ng*h/mL, at least 7450 ng*h/mL, at least 7500 ng*h/mL, at least 7550 ng*h/mL, at least 7600 ng*h/mL, at least 7650 ng*h/mL, at least 7700 ng*h/mL, at least 7750 ng*h/mL, at least 7800 ng*h/mL, at least 7850 ng*h/mL, at least 7900 ng*h/mL, at least 7950 ng*h/mL, at least 8000 ng*h/mL, at least 8050 ng*h/mL, at least 8100 ng*h/mL, at least 8150 ng*h/mL, at least 8200 ng*h/mL, at least 8250 ng*h/mL, at least 8300 ng*h/mL, at least 8350 ng*h/mL, at least 8400 ng*h/mL, at least 8450 ng*h/mL, at least 8500 ng*h/mL, at least 8550 ng*h/mL, at least 8600 ng*h/mL, at least 8650 ng*h/mL, at least 8700 ng*h/mL, at least 8750 ng*h/mL, at least 8800 ng*h/mL, at least 8850 ng*h/mL, at least 8900 ng*h/mL, at least 8950 ng*h/mL, at least 9000 ng*h/mL, at least 9050 ng*h/mL, at least 9100 ng*h/mL, at least 9150 ng*h/mL, at least 9200 ng*h/mL, at least 9250 ng*h/mL, at least 9300 ng*h/mL, at least 9350 ng*h/mL, at least 9400 ng*h/mL, at least 9450 ng*h/mL, at least 9500 ng*h/mL, at least 9550 ng*h/mL, at least 9600 ng*h/mL, at least 9650 ng*h/mL, at least 9700 ng*h/mL, at least 9750 ng*h/mL, at least 9800 ng*h/mL, at least 9850 ng*h/mL, at least 9900 ng*h/mL, at least 9950 ng*h/mL, or at least 10000 ng*h/mL.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma fospropofol $AUC_{4hr}$ or the patient population has a mean $AUC_{4hr}$ as set forth herein and the patient is headache free.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma fospropofol $AUC_{4hr}$ or the patient population has a mean $AUC_{4hr}$ of at least 1000 ng*h/mL and the patient is headache free.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma fospropofol $AUC_{4hr}$ or the patient population has a mean $AUC_{4hr}$ as set forth herein and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma fospropofol $AUC_{4hr}$ or the patient population has a mean $AUC_{4hr}$ of at least 1000 ng*h/mL and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma fospropofol $AUC_{4hr}$ or the patient population has a mean $AUC_{4hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma fospropofol $AUC_{4hr}$ or the patient population has a mean $AUC_{4hr}$ of at least 1000 ng*h/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 4 hour after the administration the patient has plasma fospropofol concentration ($C_{4hr}$) or the patient population has a mean $C_{4hr}$ of 0 ng/mL.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has a plasma fospropofol concentration ($C_{4hr}$) or the patient population has a mean $C_{4hr}$ as set forth herein and the patient is headache free.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma fospropofol concentration ($C_{4hr}$) or the patient population has a mean $C_{4hr}$ of 0 ng/mL and the patient is headache free.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma fospropofol concentration ($C_{4hr}$) or the patient population has a mean $C_{4hr}$ as set forth herein and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma fospropofol concentration ($C_{4hr}$) or the patient population has a mean $C_{4hr}$ of 0 ng/mL and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma fospropofol concentration ($C_{4hr}$) or the patient population has a mean $C_{4hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma fospropofol concentration ($C_{4hr}$) or the patient population has a mean $C_{4hr}$ of 0 ng/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma propofol $AUC_{1hr}$ or the patient population has a mean $AUC_{1hr}$ of at least at least 25 ng*h/mL, such as, for example, at least 25 ng*h/mL, at least 50 ng*h/mL, at least 75 ng*h/mL, at least 100 ng*h/mL, at least 125 ng*h/mL, at least 150 ng*h/mL, at least 175 ng*h/mL, at least 200 ng*h/mL, at least 225 ng*h/mL, at least 250 ng*h/mL, 275 ng*h/mL, at least 300 ng*h/mL, at least 325 ng*h/mL, at least 350 ng*h/mL, at least 400 ng*h/mL, at least 425 ng*h/mL, at least 450 ng*h/mL, at least 475 ng*h/mL, at least 500 ng*h/mL, at least 525 ng*h/mL, at least 550 ng*h/mL, at least 575 ng*h/mL, at least 600 ng*h/mL, at least 625 ng*h/mL, at least 650 ng*h/mL, at least 675 ng*h/mL, at least 700 ng*h/mL, at least 725 ng*h/mL, at least 750 ng*h/mL, at least 775 ng*h/mL, at least 800 ng*h/mL, at least 825 ng*h/mL, at least 850 ng*h/mL, at least 875 ng*h/mL, at least 900 ng*h/mL, at least 925 ng*h/mL, at least 950 ng*h/mL, at least 975 ng*h/mL, or at least 1000 ng*h/mL.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma propofol $AUC_{1hr}$ or the patient population has a mean $AUC_{1hr}$ as set forth herein and the patient is headache free.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma propofol $AUC_{1hr}$ or the patient population has a mean $AUC_{1hr}$ of at least 250 ng*h/mL and the patient is headache free.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma propofol $AUC_{1hr}$ or the patient population has a mean $AUC_{1hr}$ as set forth herein and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma propofol $AUC_{1hr}$ or the patient population has a mean $AUC_{1hr}$ of at least 50 ng*h/mL and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma propofol $AUC_{1hr}$ or the patient population has a mean $AUC_{1hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma propofol $AUC_{1hr}$ or the patient population has a mean $AUC_{1hr}$ of at least 50 ng*h/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma propofol concentration ($C_{1hr}$) or the patient population has a mean $C_{1hr}$ of at least 25 ng/mL, such as, for example, at least 25 ng/mL, at least 50 ng/mL, at least 75 ng/mL, at least 100 ng/mL, at least 125 ng/mL, at least 150 ng/mL, at least 175 ng/mL, at least 200 ng/mL, at least 225 ng/mL, at least 250 ng/mL, 275 ng/mL, at least 300 ng/mL, at least 325 ng/mL, at least 350 ng/mL, at least 400 ng/mL, at least 425 ng/mL, at least 450 ng/mL, at least 475 ng/mL, at least 500 ng/mL, at least 525 ng/mL, at least 550 ng/mL, at least 575 ng/mL, at least 600 ng/mL, at least 625 ng/mL, at least 650 ng/mL, at least 675 ng/mL, at least 700 ng/mL, at least 725 ng/mL, at least 750 ng/mL, at least 775 ng/mL, at least 800 ng/mL, at least 825 ng/mL, at least 850 ng/mL, at least 875 ng/mL, at least 900 ng/mL, at least 925 ng/mL, at least 950 ng/mL, at least 975 ng/mL, or at least 1000 ng/mL.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has a plasma propofol concentration ($C_{1hr}$) or the patient population has a mean $C_{1hr}$ as set forth herein and the patient is headache free.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma propofol concentration ($C_{1hr}$) or the patient population has a mean $C_{1hr}$ of at least 500 ng/mL and the patient is headache free.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma propofol concentration ($C_{1hr}$) or the patient population has a mean $C_{1hr}$ as set forth herein and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma propofol concentration ($C_{1hr}$) or the patient population has a mean $C_{1hr}$ of at least 90 ng/mL and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma propofol concentration ($C_{1hr}$) or the patient population has a mean $C_{1hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 1 hour after the administration the patient has plasma propofol concentration ($C_{1hr}$) or the patient population has a mean $C_{1hr}$ of at least 90 ng/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma propofol $AUC_{2hr}$ or the patient population has a mean $AUC_{2hr}$ of at least at least 25 ng*h/mL, such as, for example, at least 25 ng*h/mL, at least 50 ng*h/mL, at least 75 ng*h/mL, at least 100 ng*h/mL, at least 125 ng*h/mL, at least 150 ng*h/mL, at least 175 ng*h/mL, at least 200 ng*h/mL, at least 225 ng*h/mL, at least 250 ng*h/mL, 275 ng*h/mL, at least 300 ng*h/mL, at least 325 ng*h/mL, at least 350 ng*h/mL, at least 400 ng*h/mL, at least 425 ng*h/mL, at least 450 ng*h/mL, at least 475 ng*h/mL, at least 500 ng*h/mL, at least 525 ng*h/mL, at least 550 ng*h/mL, at least 575 ng*h/mL, at least 600 ng*h/mL, at least 625 ng*h/mL, at least 650 ng*h/mL, at least 675 ng*h/mL, at least 700 ng*h/mL, at least 725 ng*h/mL, at least 750 ng*h/mL, at least 775 ng*h/mL, at least 800 ng*h/mL, at least 825 ng*h/mL, at least 850 ng*h/mL, at least 875 ng*h/mL, at least 900 ng*h/mL, at least 925 ng*h/mL, at least 950 ng*h/mL, at least 975 ng*h/mL, or at least 1000 ng*h/mL.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma propofol AUC$_{2hr}$ or the patient population has a mean AUC$_{2hr}$ as set forth herein and the patient is headache free.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma propofol AUC$_{2hr}$ or the patient population has a mean AUC$_{2hr}$ of at least 100 ng*h/mL and the patient is headache free.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma propofol AUC$_{2hr}$ or the patient population has a mean AUC$_{2hr}$ as set forth herein and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma propofol AUC$_{2hr}$ or the patient population has a mean AUC$_{2hr}$ of at least 90 ng*h/mL and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma propofol AUC$_{2hr}$ or the patient population has a mean AUC$_{2hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma propofol AUC$_{2hr}$ or the patient population has a mean AUC$_{2hr}$ of at least 40 ng*h/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma propofol concentration ($C_{2hr}$) or the patient population has a mean $C_{2hr}$ of at least 25 ng/mL, such as, for example, at least 25 ng/mL, at least 50 ng/mL, at least 75 ng/mL, at least 100 ng/mL, at least 125 ng/mL, at least 150 ng/mL, at least 175 ng/mL, at least 200 ng/mL, at least 225 ng/mL, at least 250 ng/mL, 275 ng/mL, at least 300 ng/mL, at least 325 ng/mL, at least 350 ng/mL, at least 400 ng/mL, at least 425 ng/mL, at least 450 ng/mL, at least 475 ng/mL, at least 500 ng/mL, at least 525 ng/mL, at least 550 ng/mL, at least 575 ng/mL, at least 600 ng/mL, at least 625 ng/mL, at least 650 ng/mL, at least 675 ng/mL, at least 700 ng/mL, at least 725 ng/mL, at least 750 ng/mL, at least 775 ng/mL, at least 800 ng/mL, at least 825 ng/mL, at least 850 ng/mL, at least 875 ng/mL, at least 900 ng/mL, at least 925 ng/mL, at least 950 ng/mL, at least 975 ng/mL, or at least 1000 ng/mL.

In some aspects, the disclosure is directed to methods of treating migraine in a patient or patient population in need thereof, wherein the methods comprise administering to the patient(s) a pharmaceutical composition of the disclosure, wherein at 2 hour after the administration the patient has a plasma propofol concentration ($C_{2hr}$) or the patient population has a mean $C_{2hr}$ as set forth herein and the patient is headache free.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma propofol concentration ($C_{2hr}$) or the patient population has a mean $C_{2hr}$ of at least 40 ng/mL and the patient is headache free.

In some aspects, the disclosure is directed to methods of treating migraine in a patient or patient population in need thereof, wherein the methods comprise administering to the patient(s) a pharmaceutical composition of the disclosure, wherein at 2 hour after the administration the patient has plasma propofol concentration ($C_{2hr}$) or the patient population has a mean $C_{2hr}$ as set forth herein and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma propofol concentration ($C_{2hr}$) or the patient population has a mean $C_{2hr}$ of at least 40 ng/mL and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma propofol concentration ($C_{2hr}$) or the patient population has a mean $C_{2hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 2 hours after the administration the patient has plasma propofol concentration ($C_{2hr}$) or the patient population has a mean $C_{2hr}$ of at least 20 ng/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma propofol $AUC_{4hr}$ or the patient population has a mean $AUC_{4hr}$ of at least at least 25 ng*h/mL, such as, for example, at least 25 ng*h/mL, at least 50 ng*h/mL, at least 75 ng*h/mL, at least 100 ng*h/mL, at least 125 ng*h/mL, at least 150 ng*h/mL, at least 175 ng*h/mL, at least 200 ng*h/mL, at least 225 ng*h/mL, at least 250 ng*h/mL, 275 ng*h/mL, at least 300 ng*h/mL, at least 325 ng*h/mL, at least 350 ng*h/mL, at least 400 ng*h/mL, at least 425 ng*h/mL, at least 450 ng*h/mL, at least 475 ng*h/mL, at least 500 ng*h/mL, at least 525 ng*h/mL, at least 550 ng*h/mL, at least 575 ng*h/mL, at least 600 ng*h/mL, at least 625 ng*h/mL, at least 650 ng*h/mL, at least 675 ng*h/mL, at least 700 ng*h/mL, at least 725 ng*h/mL, at least 750 ng*h/mL, at least 775 ng*h/mL, at least 800 ng*h/mL, at least 825 ng*h/mL, at least 850 ng*h/mL, at least 875 ng*h/mL, at least 900 ng*h/mL, at least 925 ng*h/mL, at least 950 ng*h/mL, at least 975 ng*h/mL, or at least 1000 ng*h/mL.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma propofol $AUC_{4hr}$ or the patient population has a mean $AUC_{4hr}$ as set forth herein and the patient is headache free.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma propofol $AUC_{4hr}$ or the patient population has a mean $AUC_{4hr}$ of at least 150 ng*h/mL and the patient is headache free.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma propofol $AUC_{4hr}$ or the patient population has a mean $AUC_{4hr}$ as set forth herein and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma propofol $AUC_{4hr}$ or the patient population has a mean $AUC_{4hr}$ of at least 150 ng*h/mL and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma propofol $AUC_{4hr}$ or the patient population has a mean $AUC_{4hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma propofol $AUC_{4hr}$ or the patient population has a mean $AUC_{4hr}$ of at least 100 ng*h/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 4 hour after the administration the patient has plasma propofol concentration ($C_{4hr}$) or the patient population has a mean $C_{4hr}$ of at least 5 ng/mL, such as, for example, at least 5 ng/mL, at least 10 ng/mL, at least 15 ng/mL, at least 20 ng/mL, at least 25 ng/mL, at least 50 ng/mL, at least 75 ng/mL, at least 100 ng/mL, at least 125 ng/mL, at least 150 ng/mL, at least 175 ng/mL, at least 200 ng/mL, at least 225 ng/mL, at least 250 ng/mL, 275 ng/mL, at least 300 ng/mL, at least 325 ng/mL, at least 350 ng/mL, at least 400 ng/mL, at least 425 ng/mL, at least 450 ng/mL, at least 475 ng/mL, at least 500 ng/mL, at least 525 ng/mL, at least 550 ng/mL, at least 575 ng/mL, at least 600 ng/mL, at least 625 ng/mL, at least 650 ng/mL, at least 675 ng/mL, at least 700 ng/mL, at least 725 ng/mL, at least 750 ng/mL, at least 775 ng/mL, at least 800 ng/mL, at least 825 ng/mL, at least 850 ng/mL, at least 875 ng/mL, at least 900 ng/mL, at least 925 ng/mL, at least 950 ng/mL, at least 975 ng/mL, or at least 1000 ng/mL.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has a plasma propofol concentration ($C_{4hr}$) or the patient population has a mean $C_{4hr}$ as set forth herein and the patient is headache free.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma propofol concentration ($C_{4hr}$) or the patient population has a mean $C_{4hr}$ of at least 10 ng/mL and the patient is headache free.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma propofol concentration ($C_{4hr}$) or the patient population has a mean $C_{4hr}$ as set forth herein and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma propofol concentration ($C_{4hr}$) or the patient population has a mean $C_{4hr}$ of at least 10 ng/mL and the patient has experienced a reduction in headache pain.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma propofol concentration ($C_{4hr}$) or the patient population has a mean $C_{4hr}$ as set forth herein and the patient is no longer experiencing its most bothersome symptom. In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

In some aspects, the disclosure is directed to methods of treating migraine in a patient or patient population in need thereof, wherein the methods comprise administering to the patient(s) a pharmaceutical composition of the disclosure, wherein at 4 hours after the administration the patient has plasma propofol concentration ($C_{4hr}$) or the patient population has a mean $C_{4hr}$ of at least 10 ng/mL and the patient is no longer experiencing its most bothersome symptom (MBS). In some embodiments, the MBS is nausea, photophobia, or phonophobia. In some embodiments, the MBS is nausea, photophobia, or phonophobia. In some embodiments, the MBS is nausea. In some embodiments, the MBS is photophobia. In some embodiments, the MBS is phonophobia.

Acidified Pharmaceutical Dosage Forms

In some aspects, the pharmaceutical compositions of the disclosure are pharmaceutical dosage forms for oral administration comprising fospropofol or a pharmaceutically acceptable salt thereof, and a pharmaceutically acceptable acid. Such pharmaceutical compositions may be referred to herein as "acidified pharmaceutical dosage forms."

In some embodiments, the methods of treatment disclosed herein are performed using the acidified pharmaceutical dosage forms.

In some embodiments, the acidified pharmaceutical dosage forms comprise fospropofol:

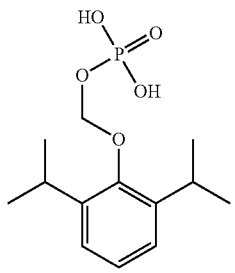

In other embodiments, the acidified pharmaceutical dosage forms comprise a pharmaceutically acceptable salt of fospropofol.

In some embodiments, the pharmaceutically acceptable salt of fospropofol is a potassium, diethylamine, t-butylamine, ethylene diamine, benzathine, piperazine, ethanolamine, diethanolamine, ammonium, tromethamine, benethamine, histidine, calcium, magnesium, or zinc salt.

In some embodiments, the acidified pharmaceutical dosage forms comprise fospropofol disodium:

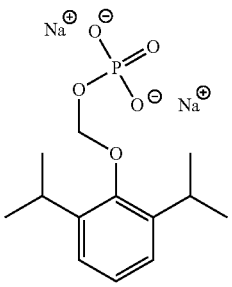

Fospropofol Disodium

The acidified pharmaceutical dosage forms of the disclosure including a pharmaceutically acceptable salt of fospropofol comprise a pharmaceutically acceptable acid. Pharmaceutically acceptable acids are known in the art. Exemplary pharmaceutically acceptable acids include all applicable stereoisomers including diastereomers, enantiomers and mixtures thereof, for example, 1-hydroxy-2-naphthoic acid, 2,2-dichloroacetic acid, 2-hydroxethane-sulfonic acid, 4-acetamidobenzoic acid, 4-aminosalicyclic acid, acetic acid, aceturic acid, Acid hydrolyzed proteins, Acid Modified Starch, Aconitic Acid, adipic acid, alginic acid, a-oxo-glutaric acid, benzenesulfonic acid, benzoic acid, butyric acid, camphor-10-sulfonic acid, camphoric acid, capric acid, caproic acid, caprylic acid, carbonic acid, Cholic acid, cinnamic acid, citric acid, cyclamic acid, D(-)-Lactic acid, Desoxycholic acid, D-glucaric acid, D-gluco-heptonic acid, D-glucuronic acid, Di(tert-butyl)naphthalene-disulfonic acid, Di(tert-butyl)naphthalenesulfonic acid, DL-lactic acid, DL-mandelic acid, DL-tartaric acid, tartaric acid, dodecylsulfuric acid, Erythorbic Acid (D-isoascorbic acid), ethane-1,2-disulfonic acid, ethanesulfonic acid, formic acid, fumaric acid, galactaric acid, gentisic acid, glutaric acid, glycerophosphoric acid, Glycocholic acid, glycolic acid, hexanedioic acid, hippuric acid, hydrobromic acid, Hydrochloric acid, Iron naphthenate, iron salts, iron salts, isobutyric acid, L(+)-lactic acid, L(+)-potassium acid tartrate, tartaric acid, L(+)-tartaric acid, Lactic acid, lactobionic acid, L-ascorbic acid, ascorbic acid, L-aspartic acid, lauric acid, L-glutamic acid, L-Glutamic acid hydrochloride, Linoleic acid, L-Malic acid, L-pyroglutamic acid, L-tartaric acid, maleic acid, malic acid, malonic acid, methanesulfonic acid, monobasic potassium phosphate, monobasic sodium phosphate, naphthalene-1,5-disulfonic acid, naphthalene-2-sulfonic acid, naphthenic acids, Niacin (nicotinic acid), nicotinic acid, nitric acid, octanoic acid, oleic acid, orotic acid, oxalic acid, palmitic acid, pamoic acid, Pectin low acid, Pectinic acid, phosphoric acid, propanoic acid, Propionic acid, p-toluenesulfonic acid, pyruvic acid, saccharin, salicylic acid, sebacic acid, Sodium acid pyrophosphate, Sodium aluminum phosphate, sodium metabisulfite, Sorbic acid, stearic acid, succinic acid, sulfuric acid, tall oil fatty acids, Tannic acid (hydrolyzable gallotannins), Taurocholic acid, thiocyanic acid, Thiodipropionic acid, trifluoroacetic acid, undec-10-enoic acid, orange juice, apple juice, grapefruit juice, as well as combinations thereof. As used herein, a "pharmaceutically acceptable acid" preferably refers to an acid that is on the FDA published inactive ingredient database (ID) for approved drug products or the generally recognized as safe (GRAS) database for use in food. In some embodiments, the pharmaceutically acceptable acid is a polyacid such as hyaluronic acid, polyacrylic acid (e.g., Carbomers), polyaspartic acid, polyglutamic acid or mixtures thereof.

In some embodiments, the pharmaceutically acceptable acid is ascorbic acid, citric acid, malic acid, tartaric acid, succinic acid, fumaric acid, maleic acid, lactic acid, monobasic sodium phosphate, monobasic potassium phosphate, or sodium metabisulfite.

In other embodiments, the pharmaceutically acceptable acid is ascorbic acid, citric acid, malic acid, or tartaric acid, or all applicable stereoisomers including diastereomers, enantiomers and mixtures thereof.

In some embodiments, the pharmaceutically acceptable acid is ascorbic acid. As used herein, the term "ascorbic acid" refers to DL-ascorbic acid, L-ascorbic acid, D-ascorbic acid, or mixtures thereof. In some embodiments, the ascorbic acid is DL-ascorbic acid. In other embodiments, the ascorbic acid is L-ascorbic acid. In other embodiments, the ascorbic acid is D-ascorbic acid.

In some embodiments, the pharmaceutically acceptable acid is tartaric acid. As used herein, the term "tartaric acid" refers to DL-tartaric acid, L-tartaric acid, D-tartaric acid, meso-tartaric acid, or mixtures thereof. In some embodiments, the tartaric acid is DL-tartaric acid. In other embodiments, the tartaric acid is L-tartaric acid. In other embodiments, the tartaric acid is D-tartaric acid.

In some embodiments, the pharmaceutically acceptable acid is malic acid. As used herein, the term "malic acid" refers to DL-malic acid, L-malic acid, D-malic acid, or mixtures thereof. In some embodiments, the malic acid is DL-malic acid. In other embodiments, the malic acid is L-malic acid. In other embodiments, the malic acid is D-malic acid.

In some embodiments, the pharmaceutically acceptable acid is citric acid.

In some embodiments, the pharmaceutically acceptable acid is fumaric acid, i.e., the trans isomer of butenedioic acid. In some embodiments, the pharmaceutically acceptable acid is maleic acid, i.e., the cis isomer of butenedioic acid. In some embodiments, the pharmaceutically acceptable acid is a mixture of the cis isomer of butenedioic acid and the trans isomer of butenedioic acid. An exemplary composition comprising fumaric acid comprises 384.2 mg fospropofol disodium hydrate (equivalent to 300 mg fospropofol disodium), 28.2 mg of polyplasdone XL, 2.8 mg of magnesium stearate, and 150.0 mg of fumaric acid. Another exemplary composition comprising fumaric acid comprises 127.8 mg fospropofol disodium hydrate (equivalent to 100 mg fospropofol disodium), 14.7 mg of polyplasdone XL, 1.46 mg of magnesium stearate, and 150.0 mg of fumaric acid.

In some embodiments in which the acidified pharmaceutical dosage forms of the disclosure comprise fospropofol in acid form, i.e.,

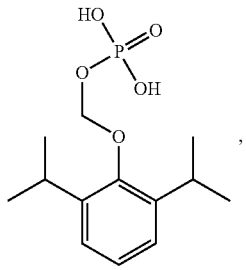 [SMILES: CC(C)c1cccc(C(C)C)c1OCOP(=O)(O)O]

the dosage forms do not include an additional pharmaceutically acceptable acid because in such embodiments, the fospropofol acid itself provides the acidity to achieve oral bioavailability and/or reduced inter-subject variability.

In some aspects, the acidified pharmaceutical dosage forms further comprise a pharmaceutically acceptable excipient. In such aspects, the pharmaceutically acceptable excipient is present in addition to the pharmaceutically acceptable acid. Examples of pharmaceutically acceptable excipients were disclosed previously herein.

In some embodiments, the fospropofol (or pharmaceutically acceptable salt thereof) and the pharmaceutically acceptable acid can be present in the same unit dosage form. In other embodiments, all or a portion of the pharmaceutically acceptable acid can be administered separately from the unit dosage form comprising the fospropofol (or pharmaceutically acceptable salt thereof).

In some aspects, the acidified pharmaceutical dosage forms are those that when dissolved in water, contain an amount of pharmaceutically acceptable acid necessary to drive the ionic equilibrium of the aqueous solution towards a pH lower than 7 and preferably ≤4.5.

In some aspects, the acidified pharmaceutical dosage forms are those wherein dissolving an amount of the dosage form containing a therapeutically effective amount of fospropofol, or a pharmaceutically acceptable salt thereof, in 300 mL of water at 25° C., results in a solution having a pH of less than or equal to 6.3, such as, for example, a pH of less than or equal to 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, or 1.0.

In some embodiments, a therapeutically effective amount of fospropofol, or a pharmaceutically acceptable salt of fospropofol, is 10-4800 mg (on a fospropofol basis), for example, an amount that is about (i.e., the specified number±10%) any one of 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, 2050 mg, 3100 mg, 3150 mg, 3200 mg, 3250 mg, 3300 mg, 3350 mg, 3400 mg, 3450 mg, 3500 mg, 3550 mg, 3600 mg, 3650 mg, 3700 mg, 3750 mg, 3800 mg, 3850 mg, 3900 mg, 3950 mg, 4000 mg, 4050 mg, 4100 mg, 4150 mg, 4200 mg, 4250 mg, 4300 mg, 4350 mg, 4400 mg, 4450 mg, 4500 mg, 4550 mg, 4600 mg, 4650 mg, 4700 mg, 4750 mg, or 4800 mg.

In other embodiments, a therapeutically effective amount of fospropofol, or a pharmaceutically acceptable salt of fospropofol, is about 1 mg/kg to about 80 mg/kg (on a fospropofol basis), for example, an amount that is about (i.e., the specified number±10%) any one of 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 51 mg/kg, 52 mg/kg, 53 mg/kg, 54 mg/kg, 55 mg/kg, 56 mg/kg, 57 mg/kg, 58 mg/kg, 59 mg/kg, 60 mg/kg, 61 mg/kg, 62 mg/kg, 63 mg/kg, 64 mg/kg, 65 mg/kg, 66 mg/kg, 67 mg/kg, 68 mg/kg, 69 mg/kg, 70 mg/kg, 71 mg/kg, 72 mg/kg, 73 mg/kg, 74 mg/kg, 75 mg/kg, 76 mg/kg, 77 mg/kg, 78 mg/kg, 79 mg/kg, or 80 mg/kg.

In some embodiments, the acidified pharmaceutical dosage forms are those wherein dissolving an amount of the dosage form containing a therapeutically effective amount of fospropofol, or a pharmaceutically acceptable salt thereof, in 300 mL of water at 25° C., results in a solution having a pH of less than or equal to 4.5.

In other embodiments, the acidified pharmaceutical dosage forms are those wherein dissolving an amount of the dosage form containing a therapeutically effective amount of fospropofol, or a pharmaceutically acceptable salt thereof, in 300 mL of water at 25° C., results in a solution having a pH of less than or equal to 4.2.

In other embodiments, the acidified pharmaceutical dosage forms are those wherein dissolving an amount of the dosage form containing a therapeutically effective amount of fospropofol, or a pharmaceutically acceptable salt thereof, in 300 mL of water at 25° C., results in a solution having a pH of less than or equal to 4.0.

In some aspects, the acidified pharmaceutical dosage forms are those releasing the active ingredient (e.g., the fospropofol or the fospropofol salt) immediately or in modified or extended-release manner.

In some aspects, the acidified pharmaceutical dosage forms are those wherein dissolution of an amount of the dosage form containing a therapeutically effective amount of fospropofol, or a pharmaceutically acceptable salt thereof, in 300 mL of 0.1 N HCl at 37° C., results in at least 30% (e.g., 30%, 35%, 40%, 45%, 50%, 55%, 60%, 65%, 70%, 75%, 80%, 85%, 90%, 95%, 98%, or 99% or greater than 99%) of the fospropofol or pharmaceutically acceptable salt thereof (on a fospropofol basis) in the dosage form being released from the dosage form within 60 minutes or less (e.g., within 60 minutes, 55 minutes, 50 minutes, 45 minutes, 40 minutes, 35 minutes, 30 minutes, 25 minutes, 20 minutes, 15 minutes, 10 minutes, or within 5 minutes.

In some embodiments, the acidified pharmaceutical dosage forms are those wherein dissolution of an amount of the dosage form containing a therapeutically effective amount of fospropofol, or a pharmaceutically acceptable salt thereof, in 300 mL of 0.1 N HCl at 37° C. results in at least 30% of the fospropofol or pharmaceutically acceptable salt thereof (on a fospropofol basis) in the dosage form being released from the dosage form within 30 minutes.

In some embodiments, the acidified pharmaceutical dosage forms are those wherein dissolution of an amount of the dosage form containing a therapeutically effective amount of fospropofol, or a pharmaceutically acceptable salt thereof, in 300 mL of 0.1 N HCl at 37° C. results in at least 50% of the fospropofol or pharmaceutically acceptable salt thereof (on a fospropofol basis) in the dosage form being released from the dosage form within 60 minutes.

In other embodiments, the acidified pharmaceutical dosage forms are those wherein dissolution of an amount of the dosage form containing a therapeutically effective amount of fospropofol, or a pharmaceutically acceptable salt thereof, in 300 mL of 0.1 N HCl at 37° C. results in at least 90% of the fospropofol or pharmaceutically acceptable salt thereof (on a fospropofol basis) in the dosage form being released from the dosage form within 30 minutes.

In some aspects, the acidified pharmaceutical dosage forms are those wherein the mole ratio of fospropofol, or a pharmaceutically acceptable salt thereof, to pharmaceutically acceptable acid is 3:1 or less, such as, for example, 0.2:1, 0.25:1, 0.3:1, 0.35:1, 0.4:1, 0.45:1, 0.5:1, 0.55:1, 0.6:1, 0.65:1, 0.7:1, 0.75:1, 0.8:1, 0.85:1, 0.9:1, 0.95:1, 1:1, 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, or 3:1.

The acidified pharmaceutical dosage forms may be tablets, capsules, caplets, softgels, sterile aqueous or organic solutions, reconstitutable powders, elixirs, liquids, colloidal or other types of suspensions, emulsions, beads, beadlets, granules, microparticles, nanoparticles, and combinations thereof.

In some embodiments, the acidified pharmaceutical dosage forms is a tablet, capsule, or softgel.

In some aspects, the disclosure is directed to methods of administering fospropofol or a pharmaceutically acceptable salt thereof to a subject in need thereof, the method comprising orally administering fospropofol, or a pharmaceutically acceptable salt thereof, and a pharmaceutically acceptable acid, to the subject.

In some embodiments, the disclosure is directed to methods of administering fospropofol or a pharmaceutically acceptable salt thereof to a subject in need thereof, comprising orally administering to the subject an acidified pharmaceutical dosage forms.

In other embodiments of the disclosed methods, the subject is orally co-administered fospropofol (or a pharmaceutically acceptable salt thereof) and a pharmaceutically acceptable acid.

In some embodiments of the disclosed methods, the fospropofol (or pharmaceutically acceptable salt thereof) and the pharmaceutically acceptable acid are administered in the same unit dosage form (i.e., the fospropofol or pharmaceutically acceptable salt thereof are present in the same dosage form together with the pharmaceutically acceptable acid).

In other embodiments, all or a portion of the pharmaceutically acceptable acid is administered separately from the dosage form comprising the fospropofol (or pharmaceutically acceptable salt thereof).

In some embodiments, the methods are for orally administering fospropofol.

In other embodiments, the methods are for orally administering a pharmaceutically acceptable salt of fospropofol.

In other embodiments, the methods are for orally administering fospropofol disodium.

In some embodiments of the disclosed methods, the pharmaceutically acceptable acid used in the methods of the disclosure is 1-hydroxy-2-naphthoic acid, 2,2-dichloroacetic acid, 2-hydroxethanesulfonic acid, 4-acetamidobenzoic acid, 4-aminosalicyclic acid, acetic acid, aceturic acid, Acid hydrolyzed proteins, Acid Modified Starch, Aconitic Acid, adipic acid, alginic acid, a-oxo-glutaric acid, benzenesulfonic acid, benzoic acid, butyric acid, camphor-10-sulfonic acid, camphoric acid, capric acid, caproic acid, caprylic acid, carbonic acid, Cholic acid, cinnamic acid, citric acid, cyclamic acid, D(-)-Lactic acid, Desoxycholic acid, D-glucaric acid, D-glucoheptonic acid, D-glucuronic acid, Di(tert-butyl)naphthalenedisulfonic acid, Di(tert-butyl)naphthalenesulfonic acid, DL-lactic acid, DL-mandelic acid, DL-tartaric acid, tartaric acid, dodecylsulfuric acid, Erythorbic acid (D-isoascorbic acid), ethane-1,2-disulfonic acid, ethanesulfonic acid, formic acid, fumaric acid, galactaric acid, gentisic acid, glutaric acid, glycerophosphoric acid, Glycocholic acid, glycolic acid, hexanedioic acid, hippuric acid, hydrobromic acid, Hydrochloric acid, Iron naphthenate, iron salts, iron salts, isobutyric acid, L(+)-lactic acid, L(+)-potassium acid tartrate, L(+)-tartaric acid, Lactic acid, lactobionic acid, L-ascorbic acid, ascorbic acid, L-aspartic acid, lauric acid, L-glutamic acid, L-Glutamic acid hydrochloride, Linoleic acid, L-Malic acid, L-pyroglutamic acid, L-tartaric acid, maleic acid, malic acid, malonic acid, methanesulfonic acid, monobasic potassium phosphate, monobasic sodium phosphate, naphthalene-1,5-disulfonic acid, naphthalene-2-sulfonic acid, naphthenic acids, Niacin (nicotinic acid), nicotinic acid, nitric acid, octanoic acid, oleic acid, orotic acid, oxalic acid, palmitic acid, pamoic acid, Pectin low acid, Pectinic acid, phosphoric acid, propanoic acid, Propionic acid, p-toluenesulfonic acid, pyruvic acid, saccharin, salicylic acid, sebacic acid, Sodium acid pyrophosphate, Sodium aluminum phosphate, sodium metabisulfite, Sorbic acid, stearic acid, succinic acid, sulfuric acid, tall oil fatty acids, Tannic acid (hydrolyzable gallotannins), Taurocholic acid, thiocyanic acid, Thiodipropionic acid, trifluoroacetic acid, undec-10-enoicacid, orange juice, apple juice, grapefruit juice, or a combination thereof.

In some embodiments, the pharmaceutically acceptable acid used in the methods of the disclosure is ascorbic acid. In some embodiments, the ascorbic acid is DL-ascorbic acid. In other embodiments, the ascorbic acid is L-ascorbic acid. In other embodiments, the ascorbic acid is D-ascorbic acid.

In other embodiments, the pharmaceutically acceptable acid used in the methods of the disclosure is tartaric acid. In some embodiments, the tartaric acid is DL-tartaric acid. In other embodiments, the tartaric acid is L-tartaric acid. In other embodiments, the tartaric acid is D-tartaric acid.

In some embodiments, the pharmaceutically acceptable acid used in the methods of the disclosure is citric acid.

In some embodiments, the pharmaceutically acceptable acid used in the methods of the disclosure is malic acid. In some embodiments, the malic acid is DL-malic acid. In other embodiments, the malic acid is L-malic acid. In other embodiments, the malic acid is D-malic acid.

In some methods of the disclosure, the administration of fospropofol (or a pharmaceutically acceptable salt thereof) and a pharmaceutically acceptable acid results in a propofol Cmax that is greater than the propofol Cmax resulting from administering fospropofol, or a pharmaceutically acceptable salt thereof, without co-administration of the pharmaceutically acceptable acid.

In some embodiments of such methods, the administration of fospropofol (or a pharmaceutically acceptable salt thereof) and a pharmaceutically acceptable acid comprises administering a pharmaceutical dosage form as described herein, such as, for example, an acidified pharmaceutical dosage form described herein.

In some embodiments of the methods of the disclosure, the administration of fospropofol (or a pharmaceutically acceptable salt thereof) and a pharmaceutically acceptable acid results in a propofol Cmax that is at least 1.2 times greater than a propofol Cmax resulting from administering fospropofol, or a pharmaceutically acceptable salt thereof, without administration of the pharmaceutically acceptable acid, such as for example, at least 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4 times greater.

In some embodiments of the methods of the disclosure, the propofol Cmax is 1.2 times greater than a propofol Cmax resulting from administering fospropofol, or a pharmaceutically acceptable salt thereof without administration of the pharmaceutically acceptable acid.

In some embodiments of the methods of the disclosure, the propofol Cmax is at least 1.5 times greater than a propofol Cmax resulting from administering fospropofol, or a pharmaceutically acceptable salt thereof, without administration of the pharmaceutically acceptable acid.

In some embodiments of the methods of the disclosure, the propofol Cmax is at least 2 times greater than a propofol Cmax resulting from administering fospropofol, or a pharmaceutically acceptable salt thereof, without administration of the pharmaceutically acceptable acid.

In some embodiments of the methods of the disclosure, the propofol Cmax is at least 2.5 times greater than a propofol Cmax resulting from administering fospropofol, or a pharmaceutically acceptable salt thereof, without administration of the pharmaceutically acceptable acid.

In some embodiments of the methods of the disclosure, the propofol Cmax is 3 times greater than a propofol Cmax resulting from administering fospropofol, or a pharmaceutically acceptable salt thereof, without administration of the pharmaceutically acceptable acid.

In some methods of the disclosure, the administration of fospropofol (or a pharmaceutically acceptable salt thereof) and a pharmaceutically acceptable acid results in a propofol AUC that is greater than a propofol AUC resulting from administering fospropofol, or a pharmaceutically acceptable salt thereof, without administration of the pharmaceutically acceptable acid.

In some embodiments, the AUC is AUCt.

In other embodiments, the AUC is AUC∞.

In some embodiments of such methods, the administration of fospropofol (or a pharmaceutically acceptable salt thereof) and a pharmaceutically acceptable acid comprises administering a pharmaceutical dosage form as described herein, such as, for example, an acidified pharmaceutical dosage form as described herein.

In some embodiments of the methods of the disclosure, the propofol AUC∞ is at least 1.5 times greater than a propofol AUC∞ resulting from administering fospropofol, or a pharmaceutically acceptable salt thereof, without administration of the pharmaceutically acceptable acid, such as for example, at least 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4 times greater.

In some embodiments of the methods of the disclosure, the propofol AUC∞ is 1.5 times greater than a propofol AUC∞ resulting from administering fospropofol, or a pharmaceutically acceptable salt thereof, without administration of the pharmaceutically acceptable acid.

In some embodiments of the methods of the disclosure, the propofol AUC∞ is at least 1.6 times greater than a propofol AUC∞ resulting from administering fospropofol, or a pharmaceutically acceptable salt thereof, without administration of the pharmaceutically acceptable acid.

In some embodiments of the methods of the disclosure, the propofol AUC∞ is at least 2 times greater than a propofol AUC∞ resulting from administering fospropofol, or a pharmaceutically acceptable salt thereof, without administration of the pharmaceutically acceptable acid.

In some embodiments of the methods of the disclosure, the propofol AUC∞ is at least 2.5 times greater than a propofol AUC∞ resulting from administering fospropofol, or a pharmaceutically acceptable salt thereof, without administration of the pharmaceutically acceptable acid.

In some embodiments of the methods of the disclosure, the propofol AUC∞ is at least 3 times greater than a propofol AUC∞ resulting from administering fospropofol, or a pharmaceutically acceptable salt thereof, without administration of the pharmaceutically acceptable acid.

In some aspects, the methods of the disclosure result in plasma concentrations of fospropofol or propofol that exhibit a food effect. The term "food effect," as used herein, means that the extent and/or rate of drug absorption depends on whether the subject is fed or fasted at the time that the drug is administered.

The term "fed" as used herein, means that means that the subject has eaten food within one hour of less of ingesting the fospropofol or a pharmaceutically acceptable salt thereof. For example, following an overnight fast of at least 10 hours, the subject starts a meal 30 minutes before administration of the drug product, and eats the meal within 30 minutes or less. The fospropofol or a pharmaceutically acceptable salt thereof is taken with 240 mL (8 fl. oz.) of water. Additional water is allowed ad lib except for 1 hour before and 1 hour after drug administration. No food is allowed for at least 4 hours after the close.

In the context of a food effect study, fasted conditions may be as follows: Following an overnight fast of at least 10 hours, investigators should administer the drug product to study subjects with 240 mL (i.e., 8 fluid ounces) of water. Additional water is permitted ad lib except for the period 1 hour before to 1 hour after administration of the drug product. The study subjects should not consume food for at least 4 hours after the close. Subjects should receive standardized meals scheduled at the same time throughout the study.

The term "fasted" as used herein, means that the subject has not eaten food within one hour of less of ingesting the fospropofol or a pharmaceutically acceptable salt thereof. For example, following an overnight fast of at least 10 hours, fospropofol or a pharmaceutically acceptable salt thereof is administered with 240 mL (i.e., 8 fluid ounces) of water. Additional water is permitted ad lib except for the period 1 hour before to 1 hour after administration of the drug product. the subject does not consume food for at least 4 hours after the close.

In the context of a food effect study, fed conditions may be as follows: Following an overnight fast of at least 10 hours, the study should start the recommended meal 30 minutes before administration of the drug product. Trial subjects should eat this meal in 30 minutes or less. the study subjects should take the drug product with 240 mL (8 fl. oz.) of water. Additional water is allowed ad lib except for 1 hour before and 1 hour after drug administration. No food is allowed for at least 4 hours after the close.

In some embodiments, administration of fospropofol (or a pharmaceutically acceptable salt thereof) and a pharmaceutically acceptable acid results in plasma fospropofol Cmax (fed):Cmax (fasted) ratio that is about 0.3-1.5, for example, about 0.3, 0.4, 0.5, 0.6, 0.7, 0.8, 0.9, 1.0, 1.1, 1.2, 1.3, 1.4, or 1.5.

In some embodiments, administration of fospropofol (or a pharmaceutically acceptable salt thereof) and a pharmaceutically acceptable acid results in plasma fospropofol Cmax (fed):Cmax (fasted) ratio that is 0.3 or greater, such as, for example, 0.3, 0.35, 0.4, 0.45, 0.5, 0.55, 0.6, 0.65, 0.7, 0.75, 0.8, 0.85, 0.9, 0.95, 1.0, 1.05, 1.1, 1.15, 1.2, 1.25, 1.3, 1.35, 1.4, 1.45, 1.5, and the like.

In some embodiments, administration of fospropofol (or a pharmaceutically acceptable salt thereof) and a pharmaceutically acceptable acid results in plasma fospropofol Cmax (fed):Cmax (fasted) ratio that is about 0.18-1.5, for example, about 0.18, 0.2, 0.25, 0.3, 0.4, 0.5, 0.6, 0.7, 0.8, 0.9, 1.0, 1.1, 1.2, 1.3, 1.4, or 1.5.

In some embodiments, administration of fospropofol (or a pharmaceutically acceptable salt thereof) and a pharmaceutically acceptable acid results in plasma fospropofol Cmax (fed):Cmax (fasted) ratio that is 0.18 or greater, such as, for example, 0.18, 0.2, 0.25, 0.3, 0.35, 0.4, 0.45, 0.5, 0.55, 0.6, 0.65, 0.7, 0.75, 0.8, 0.85, 0.9, 0.95, 1.0, 1.05, 1.1, 1.15, 1.2, 1.25, 1.3, 1.35, 1.4, 1.45, 1.5, and the like.

In some embodiments, administration of fospropofol (or a pharmaceutically acceptable salt thereof) and a pharmaceutically acceptable acid results in plasma fospropofol Cmax (fed):Cmax (fasted) ratio that is 0.3 or greater, such as, for example, 0.3 or greater, 0.35 or greater, 0.4 or greater, 0.45 or greater, 0.5 or greater, 0.55 or greater, 0.6 or greater, 0.65 or greater, 0.7 or greater, 0.75 or greater, 0.8 or greater, 0.85 or greater, 0.9 or greater, 0.95 or greater, 1.0 or greater, 1.05 or greater, 1.1 or greater, 1.15 or greater, 1.2 or greater, 1.25 or greater, 1.3 or greater, 1.35 or greater, 1.4 or greater, 1.45 or greater, 1.5 or greater, and the like.

In some embodiments, administration of fospropofol (or a pharmaceutically acceptable salt thereof) and a pharmaceutically acceptable acid results in plasma fospropofol Cmax (fed) that is at least 30% of the corresponding plasma fospropofol Cmax (fasted) such as, for example, 30%, 35%, 40%, 45%, 50%, 55%, 60%, 65%, 70%, 75%, 80%, 85%, 90%, 95% 100%, 105%, 110%, 115%, 120%, 125%, 130%, 135%, 140%, 145%, 150%, and the like.

In some embodiments, administration of fospropofol (or a pharmaceutically acceptable salt thereof) and a pharmaceutically acceptable acid results in plasma fospropofol Cmax (fed) that is at least 30% of the corresponding plasma fospropofol Cmax (fasted) such as, for example, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 105%, at least 110%, at least 115%, at least 120%, at least 125%, at least 130%, at least 135%, at least 140%, at least 145%, at least 150%, and the like.

As used herein, the term "Cmax (fasted)", refers to the peak concentration in the plasma a following administration of fospropofol or a pharmaceutically acceptable salt thereof to a subject that is fasted. As used herein, the term "Cmax (fed)", refers to the peak concentration in the plasma following administration of fospropofol or a pharmaceutically acceptable salt thereof to a subject that is fed. The peak concentration of forpropofol in the subject's plasma samples can be determined using an appropriate pharmacokinetic model applied to a plasma concentration vs. time profile determined using standard analytical methods. Appropriate pharmacokinetic models for determining Cmax are known to those of ordinary skill in the art.

In some embodiments of the disclosed methods, the Cmax (fed):Cmax (fasted) ratio is calculated using the arithmetic mean of the individual Cmax (fed) values calculated in a population of subjects and the arithmetic mean of the individual Cmax (fasted) values calculated in a population of subjects.

In some embodiments, administration of acidified pharmaceutical dosage forms of the disclosure results in plasma fospropofol Cmax (fed):Cmax (fasted) ratio that is about 0.3-1.5, for example, about 0.3, 0.4, 0.5, 0.6, 0.7, 0.8, 0.9, 1.0, 1.1, 1.2, 1.3, 1.4, or 1.5.

In some embodiments, administration of acidified pharmaceutical dosage forms of the disclosure results in plasma fospropofol Cmax (fed):Cmax (fasted) ratio that is 0.3 or greater, such as, for example, 0.3, 0.35, 0.4, 0.45, 0.5, 0.55, 0.6, 0.65, 0.7, 0.75, 0.8, 0.85, 0.9, 0.95, 1.0, 1.05, 1.1, 1.15, 1.2, 1.25, 1.3, 1.35, 1.4, 1.45, 1.5, and the like.

In some embodiments, administration of acidified pharmaceutical dosage forms of the disclosure results in plasma fospropofol Cmax (fed):Cmax (fasted) ratio that is about 0.18-1.5, for example, about 0.18, 0.2, 0.25, 0.3, 0.4, 0.5, 0.6, 0.7, 0.8, 0.9, 1.0, 1.1, 1.2, 1.3, 1.4, or 1.5.

In some embodiments, administration of acidified pharmaceutical dosage forms of the disclosure results in plasma fospropofol Cmax (fed):Cmax (fasted) ratio that is 0.18 or greater, such as, for example, 0.18, 0.20, 0.25, 0.3, 0.35, 0.4, 0.45, 0.5, 0.55, 0.6, 0.65, 0.7, 0.75, 0.8, 0.85, 0.9, 0.95, 1.0, 1.05, 1.1, 1.15, 1.2, 1.25, 1.3, 1.35, 1.4, 1.45, 1.5, and the like.

In some embodiments, administration of acidified pharmaceutical dosage forms of the disclosure results in plasma fospropofol Cmax (fed):Cmax (fasted) ratio that is 0.3 or greater, such as, for example, 0.3 or greater, 0.35 or greater, 0.4 or greater, 0.45 or greater, 0.5 or greater, 0.55 or greater, 0.6 or greater, 0.65 or greater, 0.7 or greater, 0.75 or greater, 0.8 or greater, 0.85 or greater, 0.9 or greater, 0.95 or greater, 1.0 or greater, 1.05 or greater, 1.1 or greater, 1.15 or greater, 1.2 or greater, 1.25 or greater, 1.3 or greater, 1.35 or greater, 1.4 or greater, 1.45 or greater, 1.5 or greater, and the like.

In some embodiments, administration of acidified pharmaceutical dosage forms of the disclosure results in plasma fospropofol Cmax (fed) that is at least 30% of the corresponding plasma fospropofol Cmax (fasted) such as, for example, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, and the like.

In some embodiments, administration of acidified pharmaceutical dosage forms of the disclosure results in plasma fospropofol Cmax (fed) that is at least 30% of the corresponding plasma fospropofol Cmax (fasted) such as, for example, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 105%, at least 110%, at least 115%, at least 120%, at least 125%, at least 130%, at least 135%, at least 140%, at least 145%, at least 150%, and the like.

In some embodiments of the methods of the disclosure, the ratio of the plasma fospropofol Cmax (fed):Cmax (fasted) resulting from administration of fospropofol (or a pharmaceutically acceptable salt thereof) and a pharmaceutically acceptable acid is greater than the ratio of plasma fospropofol Cmax (fed):Cmax (fasted) resulting from administration of fospropofol (or a pharmaceutically acceptable salt thereof) without the pharmaceutically acceptable acid.

In some embodiments, the ratio of the plasma fospropofol Cmax (fed):Cmax (fasted) resulting from administration of fospropofol (or a pharmaceutically acceptable salt thereof) and a pharmaceutically acceptable acid is at least 1.25 times greater, at least 1.5 times greater, at least 2 times greater, at least 2.5 times greater, at least 3 times greater, at least 3.5 times greater, at least 4 times greater, at least 4.5 times greater, at least 5 times greater, at least 5.5 times greater, at least 6 times greater, at least 6.5 times greater, at least 7 times greater, at least 7.5 times greater, at least 8 times greater, at least 8.5 times greater, at least 9 times greater, at least 9.5 times greater, or at least 10 times greater than the ratio of plasma fospropofol Cmax (fed):Cmax (fasted) resulting from administration of fospropofol (or a pharmaceutically acceptable salt thereof) without the pharmaceutically acceptable acid.

In some embodiments, the ratio of the plasma fospropofol Cmax (fed):Cmax (fasted) resulting from administration of fospropofol (or a pharmaceutically acceptable salt thereof) and a pharmaceutically acceptable acid is at least 5 times greater or at least 6 times greater than the ratio of plasma fospropofol Cmax (fed):Cmax (fasted) resulting from administration of a fospropofol (or a pharmaceutically acceptable salt thereof) composition without the pharmaceutically acceptable acid.

In some embodiments, the ratio of the plasma fospropofol Cmax (fed):Cmax (fasted) resulting from administering fospropofol (or a pharmaceutically acceptable salt thereof) and a pharmaceutically acceptable acid is at least 125%, at least 150%, at least 200%, at least 250%, at least 300%, at least 350%, at least 400%, or at least 450%, at least 500%, at least 550%, at least 600%, at least 650%, at least 700%, at least 750%, at least 800%, at least 850%, at least 900%, at least 950%, or at least 1000%, of the ratio of plasma fospropofol Cmax (fed):Cmax (fasted) resulting from administering a fospropofol (or a pharmaceutically acceptable salt thereof) composition without a pharmaceutically acceptable acid.

In some embodiments, the ratio of the plasma fospropofol Cmax (fed):Cmax (fasted) resulting from administration of the acidified pharmaceutical dosage forms of the disclosure is at least 1.25 times greater, at least 1.5 times greater, at least 2 times greater, at least 2.5 times greater, at least 3 times greater, at least 3.5 times greater, at least 4 times greater, at least 4.5 times greater, at least 5 times greater, at least 5.5 times greater, at least 6 times greater, at least 6.5 times greater, at least 7 times greater, at least 7.5 times greater, at least 8 times greater, at least 8.5 times greater, at least 9 times greater, at least 9.5 times greater, or at least 10 times greater than the ratio of plasma fospropofol Cmax (fed):Cmax (fasted) resulting from administration of a fospropofol (or a pharmaceutically acceptable salt thereof) composition without the pharmaceutically acceptable acid.

In some embodiments, the ratio of the plasma fospropofol Cmax (fed):Cmax (fasted) resulting from administration of the acidified pharmaceutical dosage forms of the disclosure at least 5 times greater or at least 6 times greater than the ratio of plasma fospropofol Cmax (fed):Cmax (fasted) resulting from administration of a fospropofol (or a pharmaceutically acceptable salt thereof) composition without the pharmaceutically acceptable acid.

In some embodiments, the ratio of the plasma fospropofol Cmax (fed):Cmax (fasted) resulting from administration of the acidified pharmaceutical dosage forms of the disclosure is at least 125%, at least 150%, at least 200%, at least 250%, at least 300%, at least 350%, at least 400%, or at least 450%, at least 500%, at least 550%, at least 600%, at least 650%, at least 700%, at least 750%, at least 800%, at least 850%, at least 900%, at least 950%, or at least 1000%, of the ratio of plasma fospropofol Cmax (fed):Cmax (fasted) resulting from administering a fospropofol (or a pharmaceutically acceptable salt thereof) composition without a pharmaceutically acceptable acid.

In some embodiments, administering fospropofol (or a pharmaceutically acceptable salt thereof) and a pharmaceutically acceptable acid results in plasma fospropofol AUC∞ (fed):AUC∞ (fasted) ratio that is about 0.4 to 1.0, for example about 0.4, 0.45, 0.5, 0.55, 0.6, 0.65, 0.7, 0.75, 0.8, 0.85, 0.9, 0.95, and 1.0.

In some embodiments, administering fospropofol (or a pharmaceutically acceptable salt thereof) and a pharmaceutically acceptable acid results in plasma fospropofol AUC∞ (fed):AUC∞ (fasted) ratio that is 0.4 or greater, such as, for example, 0.4, 0.45, 0.5, 0.55, 0.6, 0.65, 0.7, 0.75, 0.8, 0.85, 0.9, 0.95, 1.0, 1.05, 1.10, 1.15, 1.20, and the like.

In some embodiments, administering fospropofol (or a pharmaceutically acceptable salt thereof) and a pharmaceutically acceptable acid results in plasma fospropofol AUC∞ (fed):AUC∞ (fasted) ratio that is about 0.3 to 1.0, for example about 0.3, 0.35, 0.4, 0.45, 0.5, 0.55, 0.6, 0.65, 0.7, 0.75, 0.8, 0.85, 0.9, 0.95, and 1.0.

In some embodiments, administering fospropofol (or a pharmaceutically acceptable salt thereof) and a pharmaceutically acceptable acid results in plasma fospropofol AUC∞ (fed):AUC∞ (fasted) ratio that is 0.3 or greater, such as, for example, 0.3, 0.35, 0.4, 0.45, 0.5, 0.55, 0.6, 0.65, 0.7, 0.75, 0.8, 0.85, 0.9, 0.95, 1.0, 1.05, 1.10, 1.15, 1.20, and the like.

In some embodiments, administering fospropofol (or a pharmaceutically acceptable salt thereof) and a pharmaceutically acceptable acid results in plasma fospropofol AUC∞ (fed):AUC∞ (fasted) ratio that is 0.4 or greater, such as, for example, 0.4 or greater, 0.45 or greater, 0.5 or greater, 0.55 or greater, 0.6 or greater, 0.65 or greater, 0.7 or greater, 0.75 or greater, 0.8 or greater, 0.85 or greater, 0.9 or greater, 0.95 or greater, 1.0 or greater, 1.05 or greater, 1.10 or greater, 1.15 or greater, 1.20 or greater, and the like.

In some embodiments, administering fospropofol (or a pharmaceutically acceptable salt thereof) and a pharmaceutically acceptable acid results in plasma fospropofol AUC∞ (fed):AUC∞ (fasted) ratio that is 0.3 or greater, such as, for example, 0.3 or greater, 0.35 or greater, 0.4 or greater, 0.45 or greater, 0.5 or greater, 0.55 or greater, 0.6 or greater, 0.65 or greater, 0.7 or greater, 0.75 or greater, 0.8 or greater, 0.85 or greater, 0.9 or greater, 0.95 or greater, 1.0 or greater, 1.05 or greater, 1.10 or greater, 1.15 or greater, 1.20 or greater, and the like.

In some embodiments, administration of fospropofol (or a pharmaceutically acceptable salt thereof) and a pharmaceutically acceptable acid results in plasma fospropofol AUC∞ (fed) that is at least 40% of the corresponding plasma fospropofol AUC∞ (fasted) such as, for example, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, and the like.

In some embodiments, administration of fospropofol (or a pharmaceutically acceptable salt thereof) and a pharmaceutically acceptable acid results in plasma fospropofol AUC∞ (fed) that is at least 40% of the corresponding plasma fospropofol AUC∞ (fasted) such as, for example, at least 40%, at least 45%, at least 50%, at least 55%, at least 60%, at least 65%, at least 70%, at least 75%, at least 80%, at least 85%, at least 90%, at least 95%, at least 100%, at least 105%, at least 110%, at least 115%, at least 120%, at least 125%, at least 130%, at least 135%, at least 140%, at least 145%, at least 150%, and the like.

As used herein, the term "AUC∞ (fasted)", refers to the area under the plasma concentration-time curve from extrapolation of $AUC_0$ to ∞ following administration of fospropofol or a pharmaceutically acceptable salt thereof to a subject that is fasted. As used herein, the term "AUC∞ (fed)", refers to the area under the plasma concentration-time curve from extrapolation of $AUC_0$ to ∞ following administration of fospropofol or a pharmaceutically acceptable salt thereof to a subject that is fed. Methods for determining concentration-time curves and AUC are known to those of ordinary skill in the art.

In some embodiments of the disclosed methods, the AUC∞ (fed):AUC∞ (fasted) ratio is calculated using the arithmetic mean of the individual AUC∞ (fed) values calculated in a population of subjects and the arithmetic mean of the individual AUC∞ (fasted) values calculated in a population of subjects.

In some embodiments, administering the acidified pharmaceutical dosage forms of the disclosure results in plasma fospropofol AUC∞ (fed):AUC∞ (fasted) ratio that is about 0.4 to 1.0, for example about 0.4, 0.45, 0.5, 0.55, 0.6, 0.65, 0.7, 0.75, 0.8, 0.85, 0.9, 0.95, and 1.0.

In some embodiments, administering the acidified pharmaceutical dosage forms of the disclosure results in plasma fospropofol AUC∞ (fasted):AUC∞ (fed) ratio that is 0.4 or greater, such as, for example, 0.4, 0.45, 0.5, 0.55, 0.6, 0.65, 0.7, 0.75, 0.8, 0.85, 0.9, 0.95, 1.0, 1.05, 1.10, 1.15, 1.20, and the like.

In some embodiments, administering the acidified pharmaceutical dosage forms of the disclosure results in plasma fospropofol AUC∞ (fed):AUC∞ (fasted) ratio that is about 0.3 to 1.0, for example about 0.3, 0.35, 0.4, 0.45, 0.5, 0.55, 0.6, 0.65, 0.7, 0.75, 0.8, 0.85, 0.9, 0.95, and 1.0.

In some embodiments, administering the acidified pharmaceutical dosage forms of the disclosure results in plasma fospropofol AUC∞ (fasted):AUC∞ (fed) ratio that is 0.3 or greater, such as, for example, 0.3, 0.35, 0.4, 0.45, 0.5, 0.55, 0.6, 0.65, 0.7, 0.75, 0.8, 0.85, 0.9, 0.95, 1.0, 1.05, 1.10, 1.15, 1.20, and the like.

In some embodiments, administering the acidified pharmaceutical dosage forms of the disclosure results in plasma fospropofol AUC∞ (fasted):AUC∞ (fed) ratio that is 0.4 or greater, such as, for example, 0.4 or greater, 0.45 or greater, 0.5 or greater, 0.55 or greater, 0.6 or greater, 0.65 or greater, 0.7 or greater, 0.75 or greater, 0.8 or greater, 0.85 or greater, 0.9 or greater, 0.95 or greater, 1.0 or greater, 1.05 or greater, 1.10 or greater, 1.15 or greater, 1.20 or greater, and the like.

In some embodiments, administering the acidified pharmaceutical dosage forms of the disclosure results in plasma fospropofol AUC∞ (fasted):AUC∞ (fed) ratio that is 0.3 or greater, such as, for example, 0.3 or greater, 0.35 or greater, 0.4 or greater, 0.45 or greater, 0.5 or greater, 0.55 or greater, 0.6 or greater, 0.65 or greater, 0.7 or greater, 0.75 or greater, 0.8 or greater, 0.85 or greater, 0.9 or greater, 0.95 or greater, 1.0 or greater, 1.05 or greater, 1.10 or greater, 1.15 or greater, 1.20 or greater, and the like.

In some embodiments, administering the acidified pharmaceutical dosage forms of the disclosure results in plasma fospropofol AUC∞ (fed) that is at least 40% of the corresponding plasma fospropofol AUC∞ (fasted) such as, for example, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, and the like.

In some embodiments, administering the acidified pharmaceutical dosage forms of the disclosure results in plasma fospropofol AUC∞ (fed) that is at least 40% of the corresponding plasma fospropofol AUC∞ (fasted) such as, for example, at least 40%, at least 45%, at least 50%, at least 55%, at least 60%, at least 65%, at least 70%, at least 75%, at least 80%, at least 85%, at least 90%, at least 95%, at least 100%, at least 105%, at least 110%, at least 115%, at least 120%, at least 125%, at least 130%, at least 135%, at least 140%, at least 145%, at least 150%, and the like.

In some embodiments, the ratio of the plasma fospropofol AUC∞ (fed):AUC∞ (fasted) resulting from administering fospropofol (or a pharmaceutically acceptable salt thereof) and a pharmaceutically acceptable acid is greater than the ratio of plasma fospropofol AUC∞ (fed):AUC∞ (fasted) resulting from administering fospropofol (or a pharmaceutically acceptable salt thereof) without the pharmaceutically acceptable acid.

In some embodiments, the ratio of the plasma fospropofol AUC∞ (fed):AUC∞ (fasted) resulting from administering fospropofol (or a pharmaceutically acceptable salt thereof) and a pharmaceutically acceptable acid is at least 1.5 time greater, at least 2 times greater, at least 2.5 times greater, at least 3 times greater, at least 3.5 times greater, at least 4 times greater, or at least 4.5 times greater than the ratio of plasma fospropofol AUC∞ (fed):AUC∞ (fasted) resulting from administering fospropofol (or a pharmaceutically acceptable salt thereof) without the pharmaceutically acceptable acid.

In some embodiments, the ratio of the plasma fospropofol AUC∞ (fed):AUC∞ (fasted) resulting from administering fospropofol (or a pharmaceutically acceptable salt thereof) and a pharmaceutically acceptable acid is at least 2 times greater or at least 2.5 times greater than the ratio of plasma fospropofol AUC∞ (fed):AUC∞ (fasted) resulting from administering fospropofol (or a pharmaceutically acceptable salt thereof) without the pharmaceutically acceptable acid.

In some embodiments, the ratio of the plasma fospropofol AUC∞ (fed):AUC∞ (fasted) resulting from administering fospropofol (or a pharmaceutically acceptable salt thereof) and a pharmaceutically acceptable acid is at least 150%, at least 200%, at least 250%, at least 300%, at least 350%, at least 400%, or at least 450% of the ratio of plasma fospropofol AUC∞ (fed):AUC∞ (fasted) resulting from administering a fospropofol (or a pharmaceutically acceptable salt thereof) composition without a pharmaceutically acceptable acid.

In some embodiments, the ratio of the plasma fospropofol AUC∞ (fed):AUC∞ (fasted) resulting from administering the acidified pharmaceutical dosage forms of the disclosure is greater than the ratio of plasma fospropofol AUC∞ (fed):AUC∞ (fasted) resulting from administering a fospropofol (or a pharmaceutically acceptable salt thereof) composition without a pharmaceutically acceptable acid.

In some embodiments, the ratio of the plasma fospropofol AUC∞ (fed):AUC∞ (fasted) resulting from administering the acidified pharmaceutical dosage forms of the disclosure is at least 1.5 time greater, at least 2 times greater, at least 2.5 times greater, at least 3 times greater, at least 3.5 times greater, at least 4 times greater, or at least 4.5 times greater than the ratio of plasma fospropofol AUC∞ (fed):AUC∞ (fasted) resulting from administering a fospropofol (or a pharmaceutically acceptable salt thereof) composition without a pharmaceutically acceptable acid.

In some embodiments, the ratio of the plasma fospropofol AUC∞ (fed):AUC∞ (fasted) resulting from administering the acidified pharmaceutical dosage forms of the disclosure is at least 2 times greater or at least 2.5 times greater than the ratio of plasma fospropofol AUC∞ (fed):AUC∞ (fasted) resulting from administering fospropofol (or a pharmaceutically acceptable salt thereof) composition without a pharmaceutically acceptable acid.

In some embodiments, the ratio of the plasma fospropofol AUC∞ (fed):AUC∞ (fasted) resulting from administering the acidified pharmaceutical dosage forms of the disclosure is at least 150%, at least 200%, at least 250%, at least 300%, at least 350%, at least 400%, or at least 450% of the ratio of plasma fospropofol AUC∞ (fed):AUC∞ (fasted) resulting from administering a fospropofol (or a pharmaceutically acceptable salt thereof) composition without a pharmaceutically acceptable acid.

In some embodiments, administering fospropofol (or a pharmaceutically acceptable salt thereof) and a pharmaceutically acceptable acid results in a plasma total fospropofol AUC∞ (fed):AUC∞ (fasted) ratio that is about 0.4 to 1.0, for example about 0.4, 0.45, 0.5, 0.55, 0.6, 0.65, 0.7, 0.75, 0.8, 0.85, 0.9, 0.95, and 1.0.

In some embodiments, administering fospropofol (or a pharmaceutically acceptable salt thereof) and a pharmaceutically acceptable acid results in a plasma total fospropofol AUC∞ (fed):AUC∞ (fasted) ratio that is 0.4 or greater, such as, for example, 0.4, 0.45, 0.5, 0.55, 0.6, 0.65, 0.7, 0.75, 0.8, 0.85, 0.9, 0.95, 1.0, 1.05, 1.10, 1.15, 1.20, and the like.

In some embodiments, administering fospropofol (or a pharmaceutically acceptable salt thereof) and a pharmaceutically acceptable acid results in a plasma total fospropofol AUC∞ (fed):AUC∞ (fasted) ratio that is about 0.3 to 1.0, for example about 0.3, 0.35, 0.4, 0.45, 0.5, 0.55, 0.6, 0.65, 0.7, 0.75, 0.8, 0.85, 0.9, 0.95, and 1.0.

In some embodiments, administering fospropofol (or a pharmaceutically acceptable salt thereof) and a pharmaceutically acceptable acid results in a plasma total fospropofol AUC∞ (fed):AUC∞ (fasted) ratio that is 0.3 or greater, such as, for example, 0.3, 0.35, 0.4, 0.45, 0.5, 0.55, 0.6, 0.65, 0.7, 0.75, 0.8, 0.85, 0.9, 0.95, 1.0, 1.05, 1.10, 1.15, 1.20, and the like.

In some embodiments, administering fospropofol (or a pharmaceutically acceptable salt thereof) and a pharmaceutically acceptable acid results in a plasma total fospropofol AUC∞ (fed):AUC∞ (fasted) ratio that is 0.4 or greater, such as, for example, 0.4 or greater, 0.45 or greater, 0.5 or greater, 0.55 or greater, 0.6 or greater, 0.65 or greater, 0.7 or greater, 0.75 or greater, 0.8 or greater, 0.85 or greater, 0.9 or greater, 0.95 or greater, 1.0 or greater, 1.05 or greater, 1.10 or greater, 1.15 or greater, 1.20 or greater, and the like.

In some embodiments, administering fospropofol (or a pharmaceutically acceptable salt thereof) and a pharmaceutically acceptable acid results in a plasma total fospropofol AUC∞ (fed):AUC∞ (fasted) ratio that is 0.3 or greater, such as, for example, 0.3 or greater, 0.35 or greater, 0.4 or greater, 0.45 or greater, 0.5 or greater, 0.55 or greater, 0.6 or greater, 0.65 or greater, 0.7 or greater, 0.75 or greater, 0.8 or greater, 0.85 or greater, 0.9 or greater, 0.95 or greater, 1.0 or greater, 1.05 or greater, 1.10 or greater, 1.15 or greater, 1.20 or greater, and the like.

In some embodiments, administration of fospropofol (or a pharmaceutically acceptable salt thereof) and a pharmaceutically acceptable acid results in plasma total fospropofol AUC∞ (fed) that is at least 40% of the corresponding plasma total fospropofol AUC∞ (fasted) such as, for example, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, and the like.

In some embodiments, administration of fospropofol (or a pharmaceutically acceptable salt thereof) and a pharmaceutically acceptable acid results in plasma total fospropofol AUC∞ (fed) that is at least 40% of the corresponding plasma total fospropofol AUC∞ (fasted) such as, for example, at least 40%, at least 45%, at least 50%, at least 55%, at least 60%, at least 65%, at least 70%, at least 75%, at least 80%, at least 85%, at least 90%, at least 95%, at least 100%, at least 105%, at least 110%, at least 115%, at least 120%, at least 125%, at least 130%, at least 135%, at least 140%, at least 145%, at least 150%, and the like.

As used here, the term "plasma total fospropofol AUC∞ (fasted)", refers to the sum of the AUC∞ (fasted) for fospropofol and the AUC∞ (fasted) for propofol, following administration of fospropofol or a pharmaceutically acceptable salt thereof to a subject that is fasted. As used here, the term "plasma total fospropofol AUC∞ (fed)", refers to the sum of the AUC∞ (fed) for fospropofol and the AUC∞ (fed)

for propofol, following administration of fospropofol or a pharmaceutically acceptable salt thereof to a subject that is fed. Methods for determining concentration-time curves and AUC are known to those of ordinary skill in the art.

In some embodiments of the disclosed methods, the plasma total fospropofol AUC∞ (fed):AUC∞ (fasted) ratio is calculated using the arithmetic mean of the individual AUC∞ (fed) values calculated in a population of subjects and the arithmetic mean of the individual AUC∞ (fasted) values calculated in a population of subjects.

In some embodiments, administering the acidified pharmaceutical dosage forms of the disclosure results in plasma total fospropofol AUC∞ (fasted):AUC∞ (fed) ratio that is about 0.4 to 1.0, for example about 0.4, 0.45, 0.5, 0.55, 0.6, 0.65, 0.7, 0.75, 0.8, 0.85, 0.9, 0.95, and 1.0.

In some embodiments, administering the compositions of the disclosure results in plasma total fospropofol AUC∞ (fasted):AUC∞ (fed) ratio that is 0.4 or greater, such as, for example, 0.4, 0.45, 0.5, 0.55, 0.6, 0.65, 0.7, 0.75, 0.8, 0.85, 0.9, 0.95, 1.0, 1.05, 1.10, 1.15, 1.20, and the like.

In some embodiments, administering the acidified pharmaceutical dosage forms of the disclosure results in plasma total fospropofol AUC∞ (fasted):AUC∞ (fed) ratio that is about 0.3 to 1.0, for example about 0.3, 0.35, 0.4, 0.45, 0.5, 0.55, 0.6, 0.65, 0.7, 0.75, 0.8, 0.85, 0.9, 0.95, and 1.0.

In some embodiments, administering the compositions of the disclosure results in plasma total fospropofol AUC∞ (fasted):AUC∞ (fed) ratio that is 0.3 or greater, such as, for example, 0.3, 0.35, 0.4, 0.45, 0.5, 0.55, 0.6, 0.65, 0.7, 0.75, 0.8, 0.85, 0.9, 0.95, 1.0, 1.05, 1.10, 1.15, 1.20, and the like.

In some embodiments, administering the acidified pharmaceutical dosage forms of the disclosure results in plasma total fospropofol AUC∞ (fasted):AUC∞ (fed) ratio that is 0.4 or greater, such as, for example, 0.4 or greater, 0.45 or greater, 0.5 or greater, 0.55 or greater, 0.6 or greater, 0.65 or greater, 0.7 or greater, 0.75 or greater, 0.8 or greater, 0.85 or greater, 0.9 or greater, 0.95 or greater, 1.0 or greater, 1.05 or greater, 1.10 or greater, 1.15 or greater, 1.20 or greater, and the like.

In some embodiments, administering the acidified pharmaceutical dosage forms of the disclosure results in plasma total fospropofol AUC∞ (fasted):AUC∞ (fed) ratio that is 0.3 or greater, such as, for example, 0.3 or greater, 0.35 or greater, 0.4 or greater, 0.45 or greater, 0.5 or greater, 0.55 or greater, 0.6 or greater, 0.65 or greater, 0.7 or greater, 0.75 or greater, 0.8 or greater, 0.85 or greater, 0.9 or greater, 0.95 or greater, 1.0 or greater, 1.05 or greater, 1.10 or greater, 1.15 or greater, 1.20 or greater, and the like.

In some embodiments, administering the acidified pharmaceutical dosage forms of the disclosure results in plasma total fospropofol AUC∞ (fed) that is at least 40% of the corresponding plasma total fospropofol AUC∞ (fasted) such as, for example, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, and the like.

In some embodiments, administering the acidified pharmaceutical dosage forms of the disclosure results in plasma total fospropofol AUC∞ (fed) that is at least 30% of the corresponding plasma total fospropofol AUC∞ (fasted) such as, for example, 30%. 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, and the like.

In some embodiments, administering the acidified pharmaceutical dosage forms of the disclosure results in plasma total fospropofol AUC∞ (fed) that is at least 40% of the corresponding plasma total fospropofol AUC∞ (fasted) such as, for example, at least 40%, at least 45%, at least 50%, at least 55%, at least 60%, at least 65%, at least 70%, at least 75%, at least 80%, at least 85%, at least 90%, at least 95%, at least 100%, at least 105%, at least 110%, at least 115%, at least 120%, at least 125%, at least 130%, at least 135%, at least 140%, at least 145%, at least 150%, and the like.

In some embodiments, the ratio of the plasma total fospropofol AUC∞ (fed):AUC∞ (fasted) resulting from administering fospropofol (or a pharmaceutically acceptable salt thereof) and a pharmaceutically acceptable acid is greater than the ratio of plasma total fospropofol AUC∞ (fed):AUC∞ (fasted) resulting from administering fospropofol (or a pharmaceutically acceptable salt thereof) without the pharmaceutically acceptable acid.

In some embodiments, the ratio of the plasma total fospropofol AUC∞ (fed):AUC∞ (fasted) resulting from administering fospropofol (or a pharmaceutically acceptable salt thereof) and a pharmaceutically acceptable acid is at least 1.5 time greater, at least 2 times greater, at least 2.5 times greater, at least 3 times greater, at least 3.5 times greater, at least 4 times greater, or at least 4.5 times greater than the ratio of plasma total fospropofol AUC∞ (fed): AUC∞ (fasted) resulting from administering fospropofol (or a pharmaceutically acceptable salt thereof) without the pharmaceutically acceptable acid.

In some embodiments, the ratio of the plasma total fospropofol AUC∞ (fed):AUC∞ (fasted) resulting from administering fospropofol (or a pharmaceutically acceptable salt thereof) and a pharmaceutically acceptable acid is at least 2 times greater or at least 2.5 times greater than the ratio of plasma total fospropofol AUC∞ (fed):AUC∞ (fasted) resulting from administering fospropofol (or a pharmaceutically acceptable salt thereof) without the pharmaceutically acceptable acid.

In some embodiments, the ratio of the plasma total fospropofol AUC∞ (fed):AUC∞ (fasted) resulting from administering fospropofol (or a pharmaceutically acceptable salt thereof) and a pharmaceutically acceptable acid is at least 150%, at least 200%, at least 250%, at least 300%, at least 350%, at least 400%, or at least 450% of the ratio of plasma total fospropofol AUC∞ (fed):AUC∞ (fasted) resulting from administering a fospropofol (or a pharmaceutically acceptable salt thereof) composition without a pharmaceutically acceptable acid.

In some embodiments, the ratio of the plasma total fospropofol AUC∞ (fed):AUC∞ (fasted) resulting from administering the acidified pharmaceutical dosage forms of the disclosure is greater than the ratio of plasma total fospropofol AUC∞ (fed):AUC∞ (fasted) resulting from administering a fospropofol (or a pharmaceutically acceptable salt thereof) composition without a pharmaceutically acceptable acid.

In some embodiments, the ratio of the plasma total fospropofol AUC∞ (fed):AUC∞ (fasted) resulting from administering the acidified pharmaceutical dosage forms of the disclosure is at least 1.5 time greater, at least 2 times greater, at least 2.5 times greater, at least 3 times greater, at least 3.5 times greater, at least 4 times greater, or at least 4.5 times greater than the ratio of plasma total fospropofol AUC∞ (fed):AUC∞ (fasted) resulting from administering a fospropofol (or a pharmaceutically acceptable salt thereof) composition without a pharmaceutically acceptable acid.

In some embodiments, the ratio of the plasma total fospropofol AUC∞ (fed):AUC∞ (fasted) resulting from administering the acidified pharmaceutical dosage forms of the disclosure is at least 2 times greater or at least 2.5 times greater than the ratio of plasma total fospropofol AUC∞ (fed):AUC∞ (fasted) resulting from administering fospropofol (or a pharmaceutically acceptable salt thereof) composition without a pharmaceutically acceptable acid.

In some embodiments, the ratio of the plasma total fospropofol AUC∞ (fed):AUC∞ (fasted) resulting from administering the acidified pharmaceutical dosage forms of the disclosure is at least 150%, at least 200%, at least 250%, at least 300%, at least 350%, at least 400%, or at least 450% of the ratio of plasma total fospropofol AUC∞ (fed):AUC∞ (fasted) resulting from administering a fospropofol (or a pharmaceutically acceptable salt thereof) composition without a pharmaceutically acceptable acid.

In some embodiments of the disclosed methods, the subject has been administered an agent that reduces stomach pH.

In some embodiments of the methods disclosed herein, the subject is a human.

In some embodiments of the methods disclosed herein, the subject is experiencing hypochlorhydria or achlorhydria prior to the administration of a dosage form as described herein. In some embodiments, the subject is diagnosed with hypochlorhydria or achlorhydria prior to the administration. In other embodiments of the methods disclosed herein, the subject is suspected of having hypochlorhydria or achlorhydria prior to the administration.

In some embodiments of the methods disclosed herein, the subject has been administered a proton pump inhibitor (PPI) prior to the administration of a dosage form as described herein. Exemplary proton pump inhibitors include Omeprazole (Prilosec), Esomeprazole (Nexium), Lansoprazole (Prevacid), Rabeprazole (AcipHex), Pantoprazole (Protonix), Dexlansoprazole (Dexilant), and Zegerid (omeprazole with sodium bicarbonate).

In some embodiments, the methods described herein are directed to treating a disease or disorder comprising orally administering to a subject a pharmaceutical dosage form described herein.

In other embodiments, the methods described herein are directed to treating a disease or disorder comprising orally administering fospropofol, or a pharmaceutically acceptable salt thereof, and a pharmaceutically acceptable acid, to a subject.

Fospropofol Salts

The present disclosure also relates to pharmaceutically acceptable salts of fospropofol, processes for preparation thereof, pharmaceutical compositions comprising those salt forms, and methods of treatment using those salt forms.

In some embodiments, the methods of treatment disclosed herein are performed using one or more of the pharmaceutically acceptable salts of fospropofol disclosed herein.

In other embodiments, the pharmaceutical compositions disclosed herein comprise one or more of the pharmaceutically acceptable salts of fospropofol disclosed herein.

The fospropofol salts according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

In some aspects, the present disclosure pertains to pharmaceutically acceptable salts of fospropofol. In some embodiments, the pharmaceutically acceptable salts of fospropofol are the potassium, diethylamine, t-butyl amine, ethylene diamine, benzathine, piperazine, ethanolamine, diethanolamine, ammonium, tromethamine, benethamine, histidine, calcium, magnesium, or zinc salts.

In some embodiments, the pharmaceutically acceptable salt of fospropofol is the potassium salt.

Figure 34:
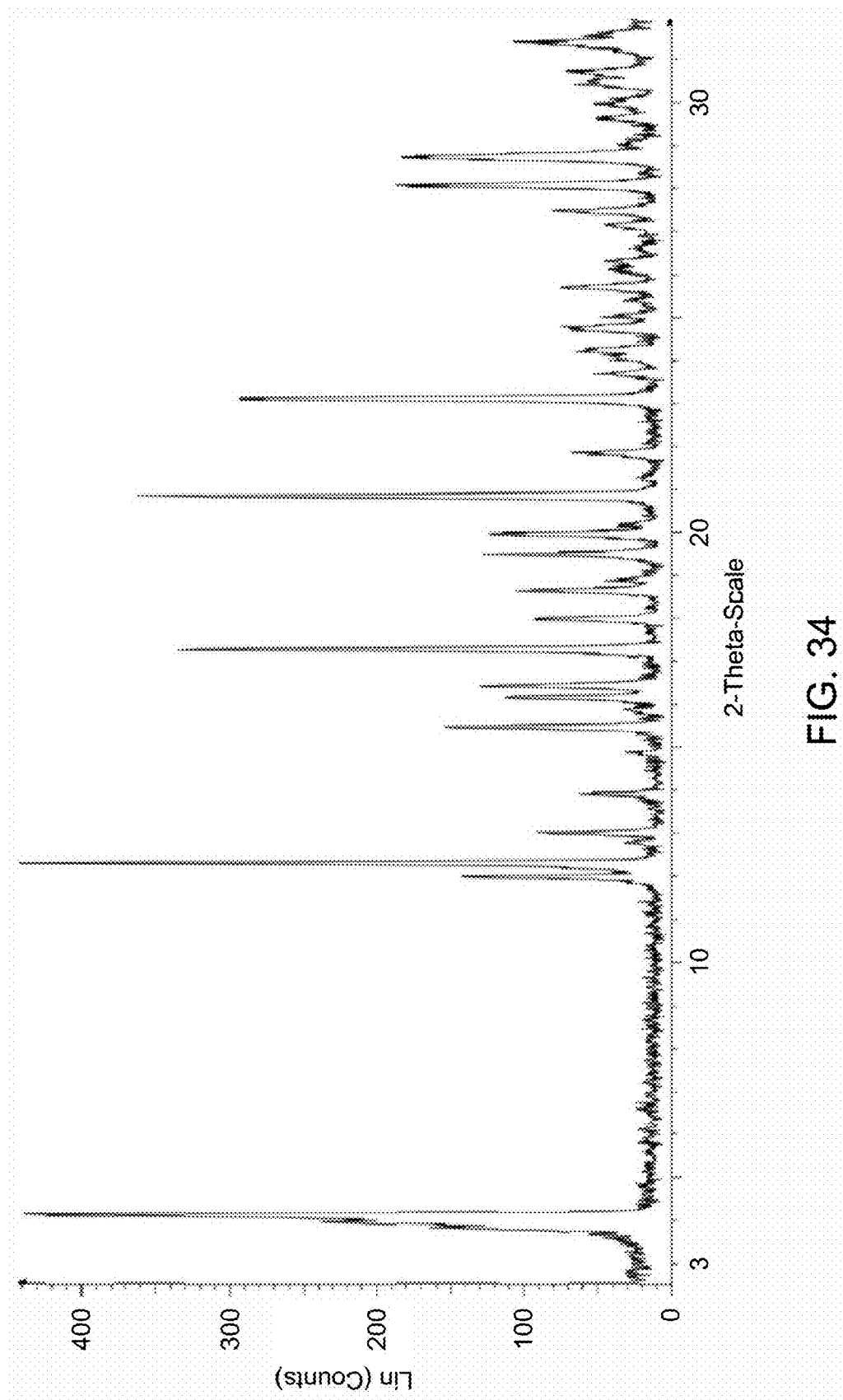
FIG. 34 shows an X-ray powder diffractogram (XRPD) of a potassium salt of fospropofol.

In some embodiments, the fospropofol potassium salt has an XRPD substantially as shown in FIG. 34. The XRPD of the potassium salt of fospropofol shown in FIG. 34 comprises reflection angles (degrees 2-theta±0.2 degrees 2-theta), and relative intensities as shown in Table 1:

TABLE 1

| XRPD Data for Potassium salt of Fospropofol | |
|---|---|
| Angle (degrees 2-theta ± 0.2 degrees 2-theta) | Relative Intensity |
| 4.1 | 99.1 |
| 12.0 | 31.9 |
| 12.3 | 100.0 |
| 13.0 | 20.5 |
| 13.9 | 13.7 |
| 14.9 | 6.9 |
| 15.5 | 34.6 |
| 15.9 | 7.6 |
| 16.2 | 25.5 |
| 16.4 | 29.8 |
| 17.3 | 62.3 |
| 18.0 | 21.1 |
| 18.7 | 21.4 |
| 18.9 | 10.3 |
| 19.5 | 28.8 |
| 20.0 | 27.7 |
| 20.9 | 48.4 |
| 21.8 | 11.0 |
| 23.1 | 66.4 |
| 23.7 | 8.5 |
| 24.0 | 9.4 |
| 24.2 | 12.6 |
| 24.8 | 13.0 |
| 25.0 | 10.5 |
| 25.7 | 15.5 |
| 26.1 | 9.1 |
| 26.3 | 9.4 |
| 27.1 | 8.8 |
| 27.5 | 15.1 |
| 28.1 | 39.6 |
| 28.7 | 37.1 |
| 29.1 | 6.7 |
| 29.6 | 8.3 |
| 30.0 | 12.2 |
| 30.4 | 14.8 |
| 30.7 | 16.0 |
| 31.4 | 24.4 |

In some embodiments of the present disclosure, the potassium salt of fospropofol is characterized by an XRPD pattern comprising a peak at one of the angles listed in Table 1. In other aspects, the potassium salt of fospropofol is characterized by an XRPD pattern comprising more than one peak at one of the angles listed in Table 1 above. In other aspects, the potassium salt of fospropofol is characterized by an XRPD pattern comprising two peaks selected from the angles listed in Table 1 above. In other aspects, the potassium salt of fospropofol is characterized by an XRPD pattern comprising three peaks selected from the angles listed in Table 1 above. In other aspects, the potassium salt of fospropofol is characterized by an XRPD pattern comprising four peaks selected from the angles listed in Table 1 above. In other aspects, the potassium salt of fospropofol is characterized by an XRPD pattern comprising five peaks selected from the angles listed in Table 1 above. In other aspects, the potassium salt of fospropofol is characterized by an XRPD pattern comprising six peaks selected from the angles listed in Table 1 above. In other aspects, the potassium salt of fospropofol is characterized by an XRPD pattern comprising seven peaks selected from the angles listed in Table 1 above. In other aspects, the potassium salt of fospropofol is characterized by an XRPD pattern comprising eight peaks selected from the angles listed in Table 1 above. In other aspects, the potassium salt of fospropofol is characterized by an XRPD pattern comprising nine peaks selected from the angles listed in Table 1 above. In other aspects, the potassium salt of fospropofol is characterized by an XRPD pattern comprising ten peaks selected from the angles listed in Table 1 above. In other aspects, the potassium salt of fospropofol is characterized by an XRPD pattern comprising more than ten peaks selected from the angles listed in Table 1 above.

In some embodiments, the potassium salt of fospropofol is characterized by an XRPD pattern comprising a peak at 12.3, 17.3, and 20.9 degrees±0.2 degrees 2-theta. In other embodiments, the potassium salt of fospropofol is characterized by an XRPD pattern comprising peaks at 12.3, 17.3, 20.9, and 23.1 degrees±0.2 degrees 2-theta. In other embodiments, the potassium salt of fospropofol is characterized by an XRPD pattern comprising peaks at 12.3, 17.3, 20.9, 23.1, 28.1, and 28.7 degrees±0.2 degree 2-theta. In yet other embodiments, the potassium salt of fospropofol is characterized by an XRPD pattern comprising peaks at 12.3, 15.5, 16.2, 16.4, 17.3, 18.0, 18.7, 19.5, 20.0, 20.9, 23.1, 28.1, and 28.7 degrees±0.2 degree 2-theta.

In some embodiments of the present disclosure, the potassium salt of fospropofol is characterized by an XRPD pattern comprising peaks at three or more of 12.3, 15.5, 16.2, 16.4, 17.3, 18.0, 18.7, 19.5, 20.0, 20.9, 23.1, 28.1, and 28.7 degrees±0.2 degrees 2-theta. In some embodiments of the present disclosure, the potassium salt of fospropofol is characterized by an XRPD pattern comprising peaks at four or more of 12.3, 15.5, 16.2, 16.4, 17.3, 18.0, 18.7, 19.5, 20.0, 20.9, 23.1, 28.1, and 28.7 degrees±0.2 degrees 2-theta. In some embodiments of the present disclosure, the potassium salt of fospropofol is characterized by an XRPD pattern comprising peaks at five or more of 12.3, 15.5, 16.2, 16.4, 17.3, 18.0, 18.7, 19.5, 20.0, 20.9, 23.1, 28.1, and 28.7 degrees 0.2 degrees 2-theta. In some embodiments of the present disclosure, the potassium salt of fospropofol is characterized by an XRPD pattern comprising peaks at six or more of 12.3, 15.5, 16.2, 16.4, 17.3, 18.0, 18.7, 19.5, 20.0, 20.9, 23.1, 28.1, and 28.7 degrees±0.2 degrees 2-theta. In some embodiments of the present disclosure, the potassium salt of fospropofol is characterized by an XRPD pattern comprising peaks at seven or more of 12.3, 15.5, 16.2, 16.4, 17.3, 18.0, 18.7, 19.5, 20.0, 20.9, 23.1, 28.1, and 28.7 degrees±0.2 degrees 2-theta.

Figure 35:
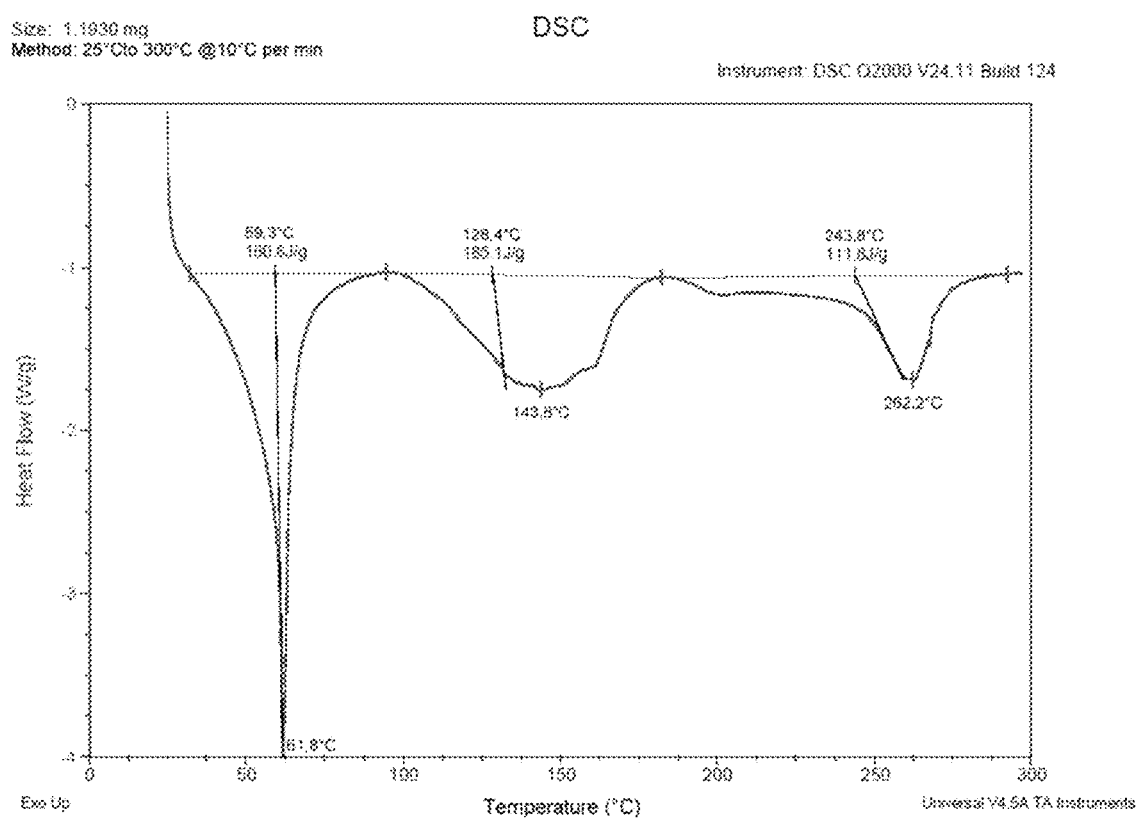
FIG. 35 shows a differential scanning calorimetry (DSC) profile of a potassium salt of fospropofol.

The potassium salt of fospropofol can be characterized by a DSC thermogram substantially as shown in FIG. 35. As FIG. 35 shows, the potassium salt of fospropofol produced endothermic peaks at 61.8° C., 143.8° C., and 262.2° C. when heated at a rate of 10° C./min. In some embodiments of the present disclosure, the potassium salt of fospropofol is characterized by a DSC thermogram comprising an endothermic peak at about 62° C. In some embodiments of the present disclosure, the potassium salt of fospropofol is characterized by a DSC thermogram comprising an endothermic peak at about 144° C. In some embodiments of the present disclosure, the potassium salt of fospropofol is characterized by a DSC thermogram comprising an endothermic peak at about 262° C.

In some embodiments of the present disclosure, the potassium salt of fospropofol is characterized by an XRPD pattern comprising peaks at 12.3, 17.3, and 20.9 degrees±0.2 degrees 2-theta, and a DSC thermogram comprising an endothermic peak at about 62° C., 144° C., or 262° C. when heated at a rate of 10° C./min.

In some embodiments, the pharmaceutically acceptable salt of fospropofol is the diethylamine salt.

Figure 36:
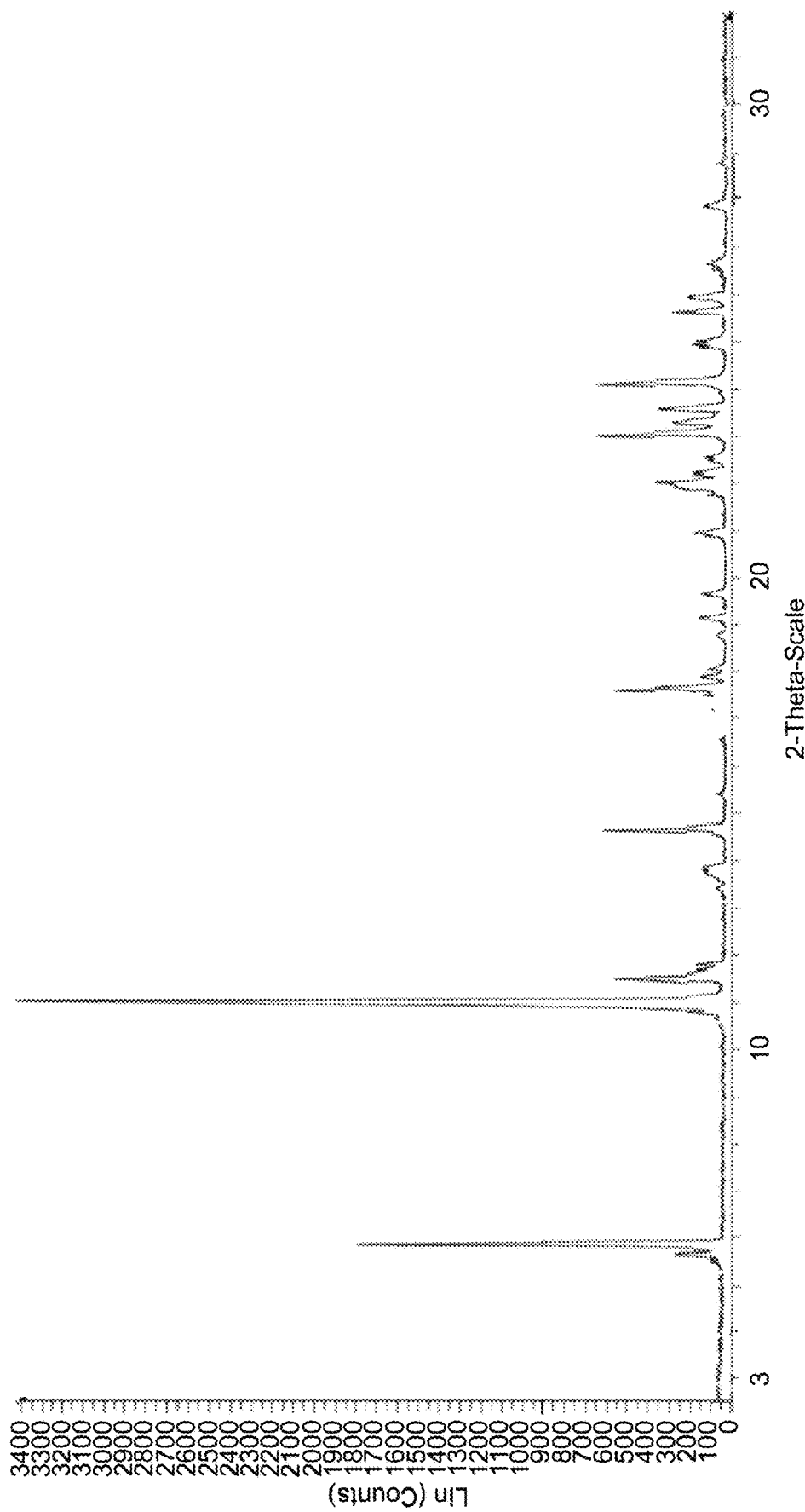
FIG. 36 shows an X-ray powder diffractogram (XRPD) of a diethylamine salt of fospropofol (Form II).

In other embodiments, the diethylamine salt of fospropofol (Form II) has an XRPD substantially as shown in FIG. 36. The XRPD of the diethylamine salt of fospropofol shown in FIG. 36 comprises reflection angles (degrees 2-theta±0.2 degrees 2-theta), and relative intensities as shown in Table 2A:

TABLE 2A

XRPD Data for Form II Diethylamine salt of Fospropofol

| Angle (degrees 2-theta ± 0.2 degrees 2-theta) | Relative Intensity |
| --- | --- |
| 5.6 | 7.7 |
| 5.8 | 52.5 |
| 11.0 | 100.0 |
| 11.5 | 16.6 |
| 11.7 | 5.1 |
| 13.7 | 3.9 |
| 14.6 | 18.3 |
| 17.6 | 16.9 |
| 17.8 | 4.3 |
| 18.0 | 3.4 |
| 18.7 | 2.2 |
| 19.1 | 4.5 |
| 19.6 | 4.3 |
| 20.9 | 5.3 |
| 22.0 | 10.7 |
| 22.2 | 5.6 |
| 22.5 | 3.4 |
| 23.0 | 18.6 |
| 23.2 | 8.4 |
| 23.5 | 10.4 |
| 24.1 | 18.9 |
| 24.9 | 5.7 |
| 25.6 | 8.5 |
| 25.9 | 6.2 |

In some embodiments of the present disclosure, the diethylamine salt of fospropofol is characterized by an XRPD pattern comprising a peak at one of the angles listed in Table 2A. In other aspects, the diethylamine salt of fospropofol is characterized by an XRPD pattern comprising more than one peak at one of the angles listed in Table 2A above. In other aspects, the diethylamine salt of fospropofol is characterized by an XRPD pattern comprising two peaks selected from the angles listed in Table 2A above. In other aspects, the diethylamine salt of fospropofol is characterized by an XRPD pattern comprising three peaks selected from the angles listed in Table 2A above. In other aspects, the diethylamine salt of fospropofol is characterized by an XRPD pattern comprising four peaks selected from the angles listed in Table 2A above. In other aspects, the diethylamine salt of fospropofol is characterized by an XRPD pattern comprising five peaks selected from the angles listed in Table 2A above. In other aspects, the diethylamine salt of fospropofol is characterized by an XRPD pattern comprising six peaks selected from the angles listed in Table 2A above. In other aspects, the diethylamine salt of fospropofol is characterized by an XRPD pattern comprising seven peaks selected from the angles listed in Table 2A above. In other aspects, the diethylamine salt of fospropofol is characterized by an XRPD pattern comprising eight peaks selected from the angles listed in Table 2A above. In other aspects, the diethylamine salt of fospropofol is characterized by an XRPD pattern comprising nine peaks selected from the angles listed in Table 2A above. In other aspects, the diethylamine salt of fospropofol is characterized by an XRPD pattern comprising ten peaks selected from the angles listed in Table 2A above. In other aspects, the diethylamine salt of fospropofol is characterized by an XRPD pattern comprising more than ten peaks selected from the angles listed in Table 2A above.

In some embodiments, the diethylamine salt of fospropofol is characterized by an XRPD pattern comprising a peaks at 5.8 and 11.0 degrees±0.2 degrees 2-theta. In other embodiments, the diethylamine salt of fospropofol is characterized by an XRPD pattern comprising peaks at 5.8, 11.0, and 11.5 degrees±0.2 degrees 2-theta. In other embodiments, the diethylamine salt of fospropofol is characterized by an XRPD pattern comprising peaks at 5.8, 11.0, 11.5, 14.6, and 17.6 degrees±0.2 degree 2-theta. In yet other embodiments, the diethylamine salt of fospropofol is characterized by an XRPD pattern comprising peaks at 5.8, 11.0, 11.5, 14.6, 17.6, 22.0, 23.0, and 24.1 degrees±0.2 degree 2-theta.

In some embodiments of the present disclosure, the diethylamine salt of fospropofol is characterized by an XRPD pattern comprising peaks at two or more of 5.8, 11.0, 11.5, 14.6, 17.6, 22.0, 23.0, and 24.1 degrees±0.2 degrees 2-theta. In some embodiments of the present disclosure, the diethylamine salt of fospropofol is characterized by an XRPD pattern comprising peaks at three or more of 5.8, 11.0, 11.5, 14.6, 17.6, 22.0, 23.0, and 24.1 degrees±0.2 degrees 2-theta. In some embodiments of the present disclosure, the diethylamine salt of fospropofol is characterized by an XRPD pattern comprising peaks at four or more of 5.8, 11.0, 11.5, 14.6, 17.6, 22.0, 23.0, and 24.1 degrees±0.2 degrees 2-theta. In some embodiments of the present disclosure, the diethylamine salt of fospropofol is characterized by an XRPD pattern comprising peaks at five or more of 5.8, 11.0, 11.5, 14.6, 17.6, 22.0, 23.0, and 24.1 degrees±0.2 degrees 2-theta.

Figure 37:
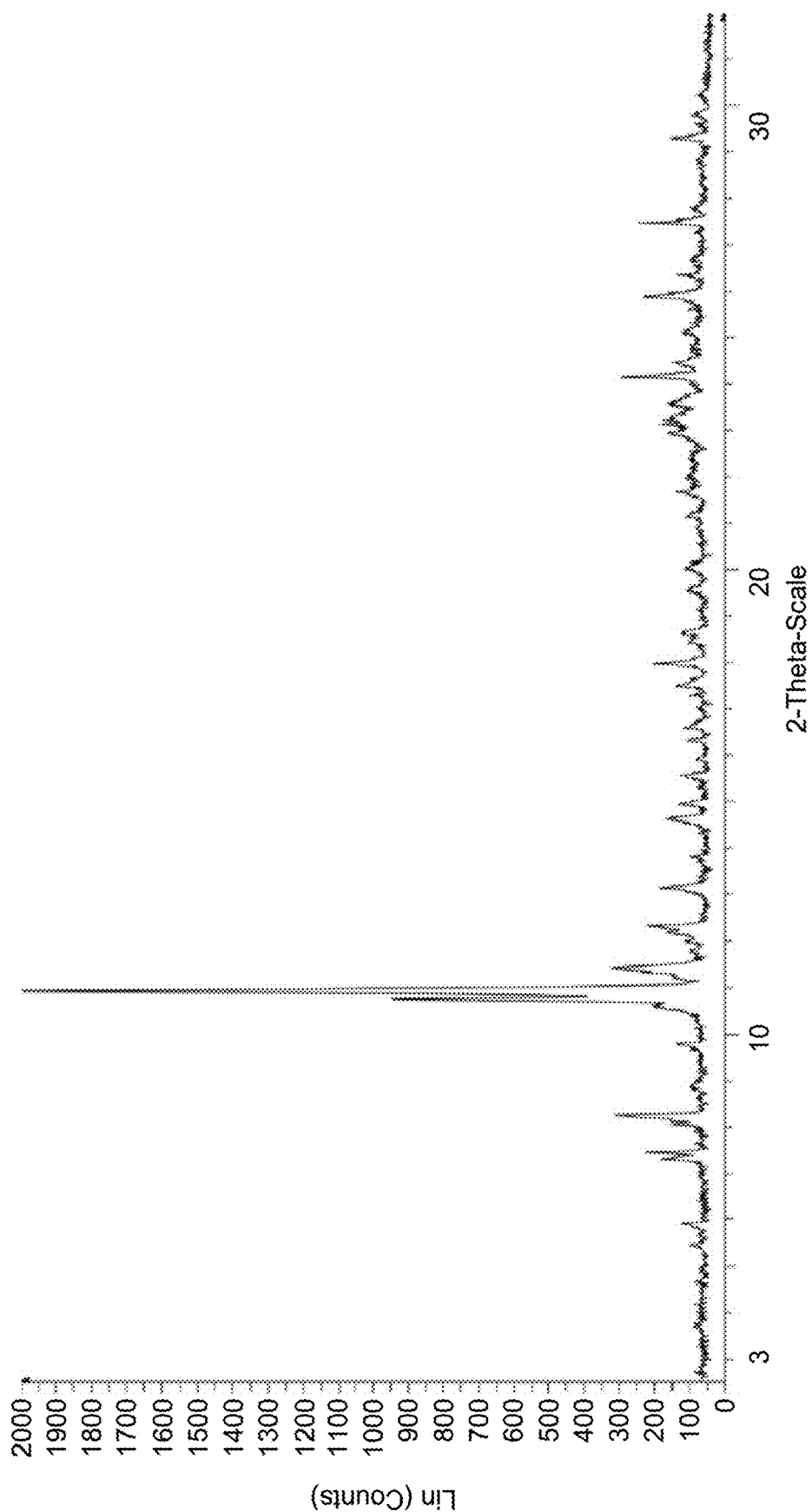
FIG. 37 shows an X-ray powder diffractogram (XRPD) of a diethylamine salt of fospropofol (Form I).

In some embodiments, the diethylamine salt of fospropofol (Form I) has an XRPD substantially as shown in FIG. 37. The XRPD of the diethylamine salt of fospropofol shown in FIG. 37 comprises reflection angles (degrees 2-theta±0.2 degrees 2-theta and relative intensities as shown in Table 2:

TABLE 2

XRPD Data for Form I Diethylamine salt of Fospropofol

| Angle (degrees 2-theta ± 0.2 degrees 2-theta) | Relative Intensity |
|---|---|
| 5.9 | 6.2 |
| 7.3 | 9.2 |
| 7.4 | 11.4 |
| 8.2 | 15.7 |
| 9.8 | 7.1 |
| 10.6 | 10.0 |
| 10.7 | 47.1 |
| 10.9 | 100.0 |
| 11.4 | 16.3 |
| 12.2 | 8.5 |
| 12.3 | 10.9 |
| 13.1 | 9.1 |
| 14.6 | 8.2 |
| 14.9 | 6.5 |
| 15.6 | 6.5 |
| 16.3 | 5.2 |
| 16.6 | 6.2 |
| 17.5 | 6.8 |
| 18.0 | 9.9 |

TABLE 2-continued

XRPD Data for Form I Diethylamine salt of Fospropofol

| Angle (degrees 2-theta ± 0.2 degrees 2-theta) | Relative Intensity |
|---|---|
| 18.6 | 5.7 |
| 19.6 | 5.4 |
| 20.1 | 5.4 |
| 21.7 | 6.8 |
| 23.0 | 8.5 |
| 23.2 | 9.2 |
| 23.6 | 8.3 |
| 24.2 | 14.5 |
| 25.9 | 11.6 |
| 27.5 | 12.0 |

In some embodiments of the present disclosure, the diethylamine salt of fospropofol is characterized by an XRPD pattern comprising a peak at one of the angles listed in Table 2. In other aspects, the diethylamine salt of fospropofol is characterized by an XRPD pattern comprising more than one peak at one of the angles listed in Table 2 above. In other aspects, the diethylamine salt of fospropofol is characterized by an XRPD pattern comprising two peaks selected from the angles listed in Table 2 above. In other aspects, the diethylamine salt of fospropofol is characterized by an XRPD pattern comprising three peaks selected from the angles listed in Table 2 above. In other aspects, the diethylamine salt of fospropofol is characterized by an XRPD pattern comprising four peaks selected from the angles listed in Table 2 above. In other aspects, the diethylamine salt of fospropofol is characterized by an XRPD pattern comprising five peaks selected from the angles listed in Table 2 above. In other aspects, the diethylamine salt of fospropofol is characterized by an XRPD pattern comprising six peaks selected from the angles listed in Table 2 above. In other aspects, the diethylamine salt of fospropofol is characterized by an XRPD pattern comprising seven peaks selected from the angles listed in Table 2 above. In other aspects, the diethylamine salt of fospropofol is characterized by an XRPD pattern comprising eight peaks selected from the angles listed in Table 2 above. In other aspects, the diethylamine salt of fospropofol is characterized by an XRPD pattern comprising nine peaks selected from the angles listed in Table 2 above. In other aspects, the diethylamine salt of fospropofol is characterized by an XRPD pattern comprising ten peaks selected from the angles listed in Table 2 above. In other aspects, the diethylamine salt of fospropofol is characterized by an XRPD pattern comprising more than ten peaks selected from the angles listed in Table 2 above.

In some embodiments, the diethylamine salt of fospropofol is characterized by an XRPD pattern comprising a peak at 10.9 and 11.4 degrees±0.2 degrees 2-theta. In other embodiments, the diethylamine salt of fospropofol is characterized by an XRPD pattern comprising peaks at 10.9, 11.4, and 14.6 degrees±0.2 degrees 2-theta. In other embodiments, the diethylamine salt of fospropofol is characterized by an XRPD pattern comprising peaks at 10.9, 11.4, 14.6, and 24.2 degrees±0.2 degree 2-theta. In yet other embodiments, the diethylamine salt of fospropofol is characterized by an XRPD pattern comprising peaks at 10.9, 11.4, 14.6, 24.2, 25.9, and 27.5 degrees±0.2 degree 2-theta.

In some embodiments of the present disclosure, the diethylamine salt of fospropofol is characterized by an XRPD pattern comprising peaks at two or more of 10.9, 11.4, 14.6, 24.2, 25.9, and 27.5 degrees±0.2 degrees 2-theta. In some embodiments of the present disclosure, the diethylamine salt of fospropofol is characterized by an XRPD pattern comprising peaks at three or more of 10.9, 11.4, 14.6, 24.2, 25.9, and 27.5 degrees±0.2 degrees 2-theta. In some embodiments of the present disclosure, the diethylamine salt of fospropofol is characterized by an XRPD pattern comprising peaks at four or more of 10.9, 11.4, 14.6, 24.2, 25.9, and 27.5 degrees±0.2 degrees 2-theta. In some embodiments of the present disclosure, the diethylamine salt of fospropofol is characterized by an XRPD pattern comprising peaks at five or more of 10.9, 11.4, 14.6, 24.2, 25.9, and 27.5 degrees±0.2 degrees 2-theta.

Figure 38:
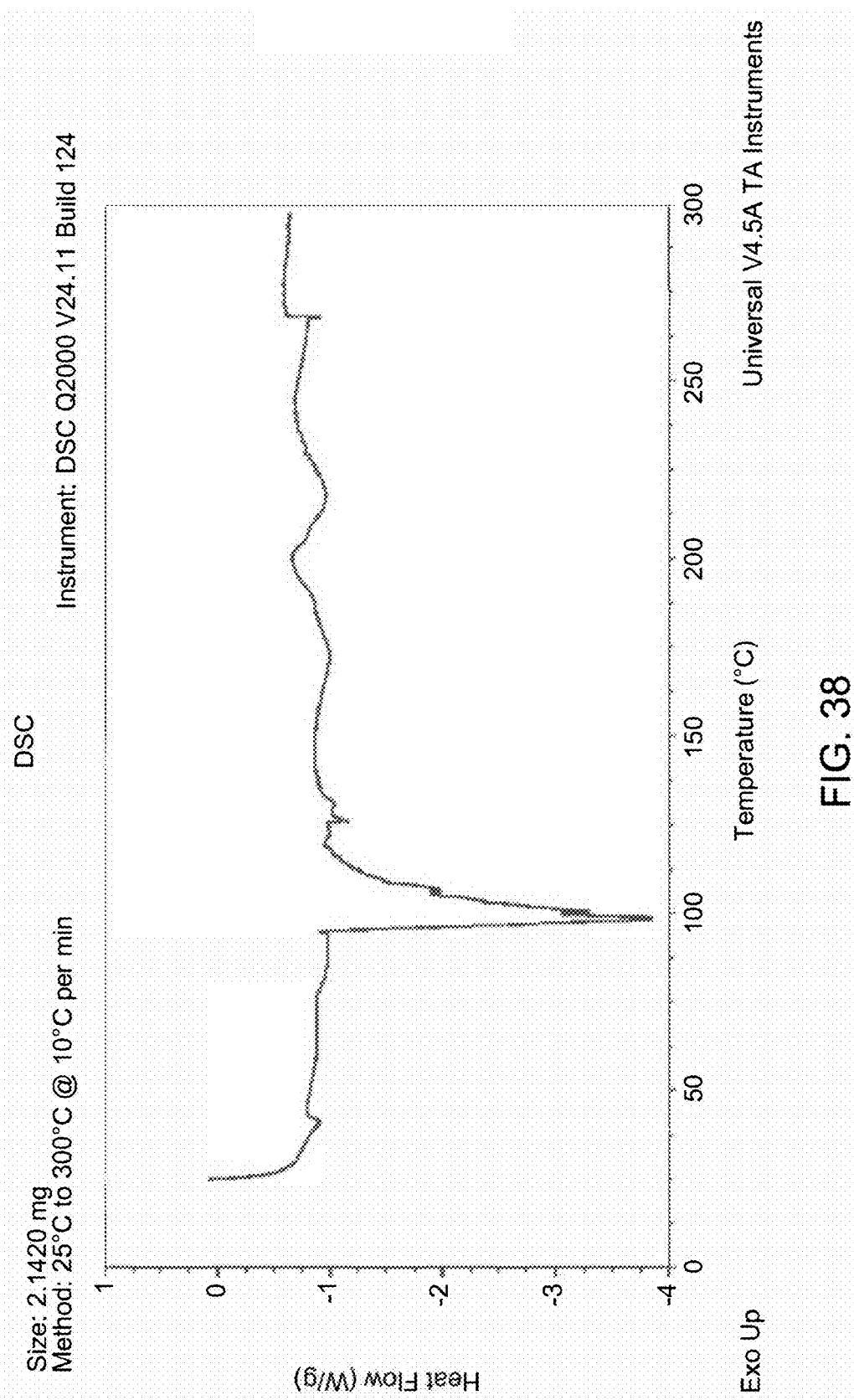
FIG. 38 shows a differential scanning calorimetry (DSC) profile of the diethylamine salt of fospropofol (Form I).

The Form I diethylamine salt of fospropofol can be characterized by a DSC thermogram substantially as shown in FIG. 38. As FIG. 38 shows, the diethylamine salt of fospropofol produced endothermic peaks at about 98° C. when heated at a rate of 10° C./min. In some embodiments of the present disclosure, the diethylamine salt of fospropofol is characterized by a DSC thermogram comprising an endothermic peak at about 98° C.

In some embodiments of the present disclosure, the diethylamine salt of fospropofol is characterized by an XRPD pattern comprising peaks at one or more of 10.9, 11.4, 14.6, 24.2, 25.9, and 27.5 degrees±0.2 degrees 2-theta, and a DSC thermogram comprising an endothermic peak at about 98° C. when heated at a rate of 10° C./min.

Figure 39:
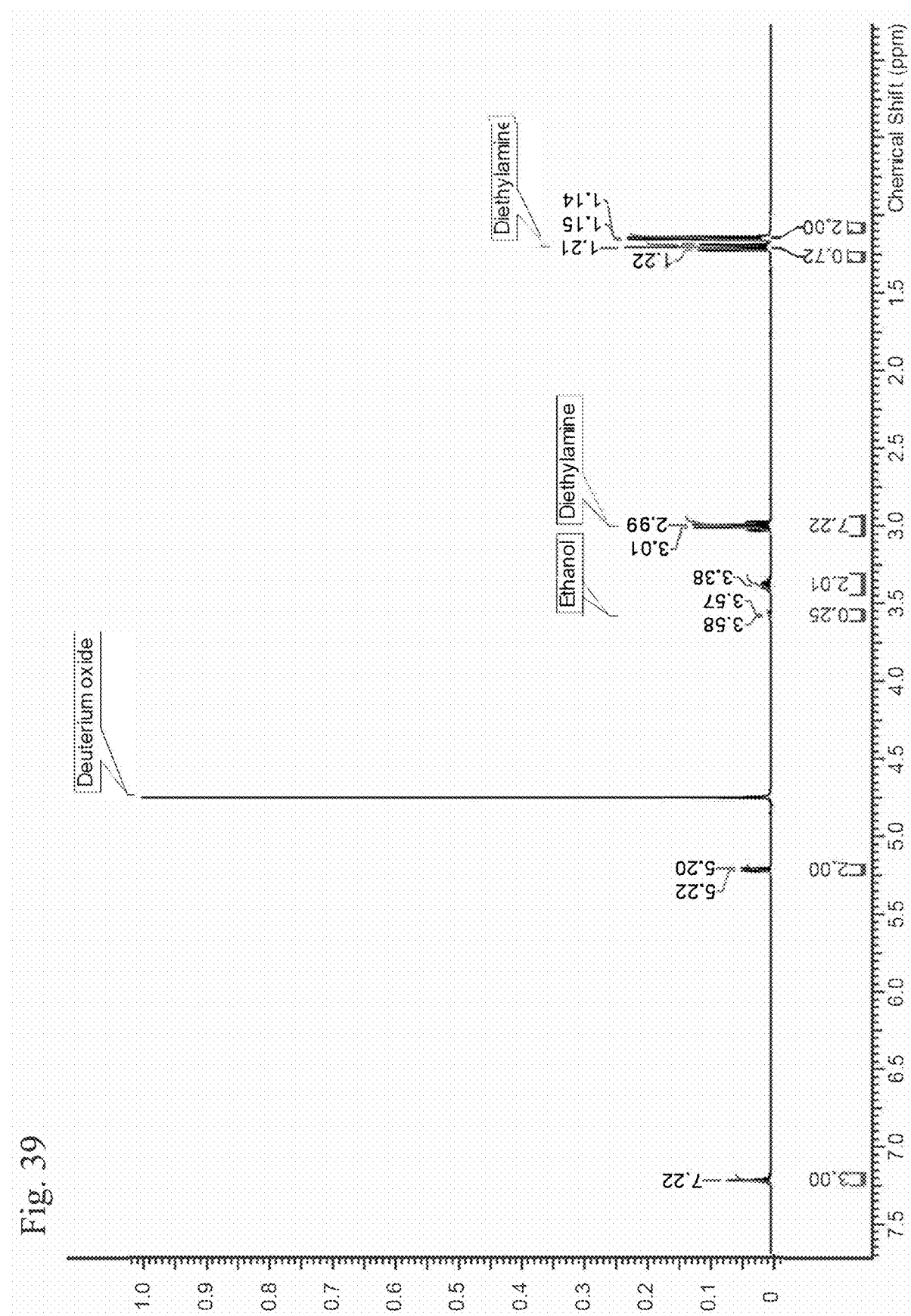
FIG. 39 shows a nuclear magnetic resonance (NMR) spectrum of a diethylamine salt of fospropofol (Form I).

The Form I diethylamine salt of fospropofol can be characterized by an NMR spectrum substantially as shown in FIG. 39.

In some embodiments, the pharmaceutically acceptable salt of fospropofol is the t-butylamine salt.

Figure 40:
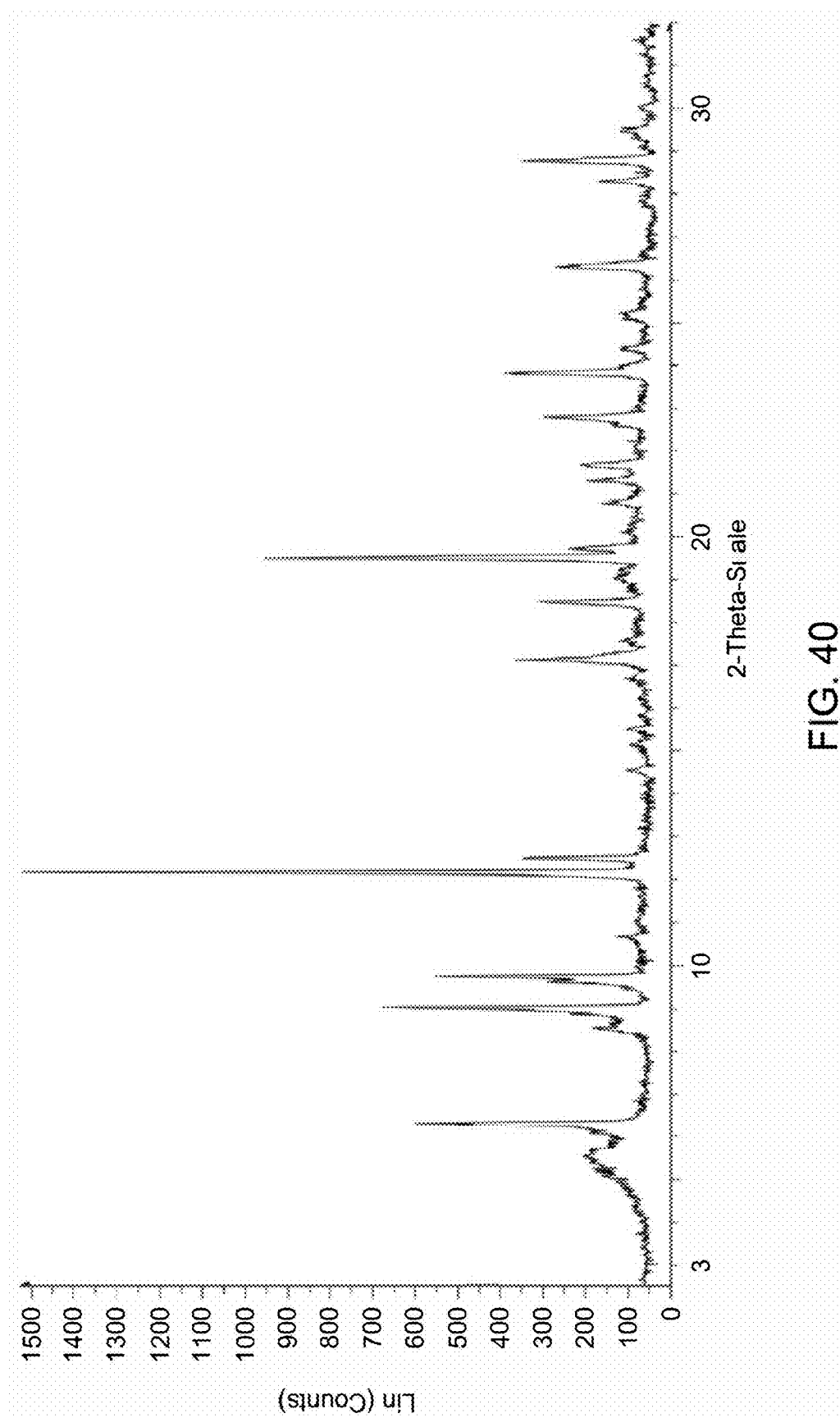
FIG. 40 shows an X-ray powder diffractogram (XRPD) of a t-butylamine salt of fospropofol.

In some embodiments, the t-butylamine salt of fospropofol has an XRPD substantially as shown in FIG. 40. The XRPD of the t-butylamine salt of fospropofol shown in FIG. 40 comprises reflection angles (degrees 2-theta±0.2 degrees 2-theta), and relative intensities as shown in Table 3:

TABLE 3

XRPD Data for t-butylamine salt of Fospropofol

| Angle (degrees 2-theta ± 0.2 degrees 2-theta) | Relative Intensity |
| --- | --- |
| 6.3 | 39.4 |
| 8.5 | 12.2 |
| 9.0 | 44.6 |
| 9.6 | 19.1 |
| 9.7 | 36.3 |
| 10.7 | 8.5 |
| 12.2 | 100.0 |
| 12.5 | 23.0 |
| 17.1 | 23.8 |
| 18.5 | 20.7 |
| 19.5 | 62.3 |
| 19.7 | 15.9 |
| 20.8 | 10.5 |
| 21.3 | 13.1 |
| 21.7 | 14.0 |
| 22.8 | 19.6 |
| 23.9 | 25.5 |
| 24.4 | 7.4 |
| 25.2 | 7.7 |
| 26.4 | 17.7 |
| 28.3 | 11.4 |
| 28.8 | 22.8 |
| 29.5 | 7.6 |

In some embodiments of the present disclosure, the t-butylamine salt of fospropofol is characterized by an XRPD pattern comprising a peak at one of the angles listed in Table 3. In other aspects, the t-butylamine salt of fospropofol is characterized by an XRPD pattern comprising more than one peak at one of the angles listed in Table 3 above. In other aspects, the t-butylamine salt of fospropofol is characterized by an XRPD pattern comprising two peaks selected from the angles listed in Table 3 above. In other aspects, the t-butylamine salt of fospropofol is characterized by an XRPD pattern comprising three peaks selected from the angles listed in Table 3 above. In other aspects, the t-butylamine salt of fospropofol is characterized by an XRPD pattern comprising four peaks selected from the angles listed in Table 3 above. In other aspects, the t-butylamine salt of fospropofol is characterized by an XRPD pattern comprising five peaks selected from the angles listed in Table 3 above. In other aspects, the t-butylamine salt of fospropofol is characterized by an XRPD pattern comprising six peaks selected from the angles listed in Table 3 above. In other aspects, the t-butylamine salt of fospropofol is characterized by an XRPD pattern comprising seven peaks selected from the angles listed in Table 3 above. In other aspects, the t-butylamine salt of fospropofol is characterized by an XRPD pattern comprising eight peaks selected from the angles listed in Table 3 above. In other aspects, the t-butylamine salt of fospropofol is characterized by an XRPD pattern comprising nine peaks selected from the angles listed in Table 3 above. In other aspects, the t-butylamine salt of fospropofol is characterized by an XRPD pattern comprising ten peaks selected from the angles listed in Table 3 above. In other aspects, the t-butylamine salt of fospropofol is characterized by an XRPD pattern comprising more than ten peaks selected from the angles listed in Table 3 above.

In some embodiments, the t-butylamine salt of fospropofol is characterized by an XRPD pattern comprising a peak at 12.2 degrees±0.2 degrees 2-theta. In other embodiments, the t-butylamine salt of fospropofol is characterized by an XRPD pattern comprising peaks at 9.0, 9.6, and 12.2 degrees±0.2 degrees 2-theta. In other embodiments, the t-butylamine salt of fospropofol is characterized by an XRPD pattern comprising peaks at 9.0, 9.6, 12.2, 17.1, and 19.5 degrees±0.2 degree 2-theta. In yet other embodiments, the t-butylamine salt of fospropofol is characterized by an XRPD pattern comprising peaks at 9.0, 9.6, 12.2, 17.1, 19.5, 21.3, 21.7, 23.9, 26.4, 28.3, and 28.8 degrees±0.2 degree 2-theta.

In some embodiments of the present disclosure, the t-butylamine salt of fospropofol is characterized by an XRPD pattern comprising peaks at three or more of 9.0, 9.6, 12.2, 17.1, 19.5, 21.3, 21.7, 23.9, 26.4, 28.3, and 28.8 degrees±0.2 degrees 2-theta. In some embodiments of the present disclosure, the t-butylamine salt of fospropofol is characterized by an XRPD pattern comprising peaks at four or more of 9.0, 9.6, 12.2, 17.1, 19.5, 21.3, 21.7, 23.9, 26.4, 28.3, and 28.8 degrees±0.2 degrees 2-theta. In some embodiments of the present disclosure, the t-butylamine salt of fospropofol is characterized by an XRPD pattern comprising peaks at five or more of 9.0, 9.6, 12.2, 17.1, 19.5, 21.3, 21.7, 23.9, 26.4, 28.3, and 28.8 degrees±0.2 degrees 2-theta. In some embodiments of the present disclosure, the t-butylamine salt of fospropofol is characterized by an XRPD pattern comprising peaks at six or more of 9.0, 9.6, 12.2, 17.1, 19.5, 21.3, 21.7, 23.9, 26.4, 28.3, and 28.8 degrees±0.2 degrees 2-theta. In some embodiments of the present disclosure, the t-butylamine salt of fospropofol is characterized by an XRPD pattern comprising peaks at seven or more of 9.0, 9.6, 12.2, 17.1, 19.5, 21.3, 21.7, 23.9, 26.4, 28.3, and 28.8 degrees±0.2 degrees 2-theta.

Figure 41:
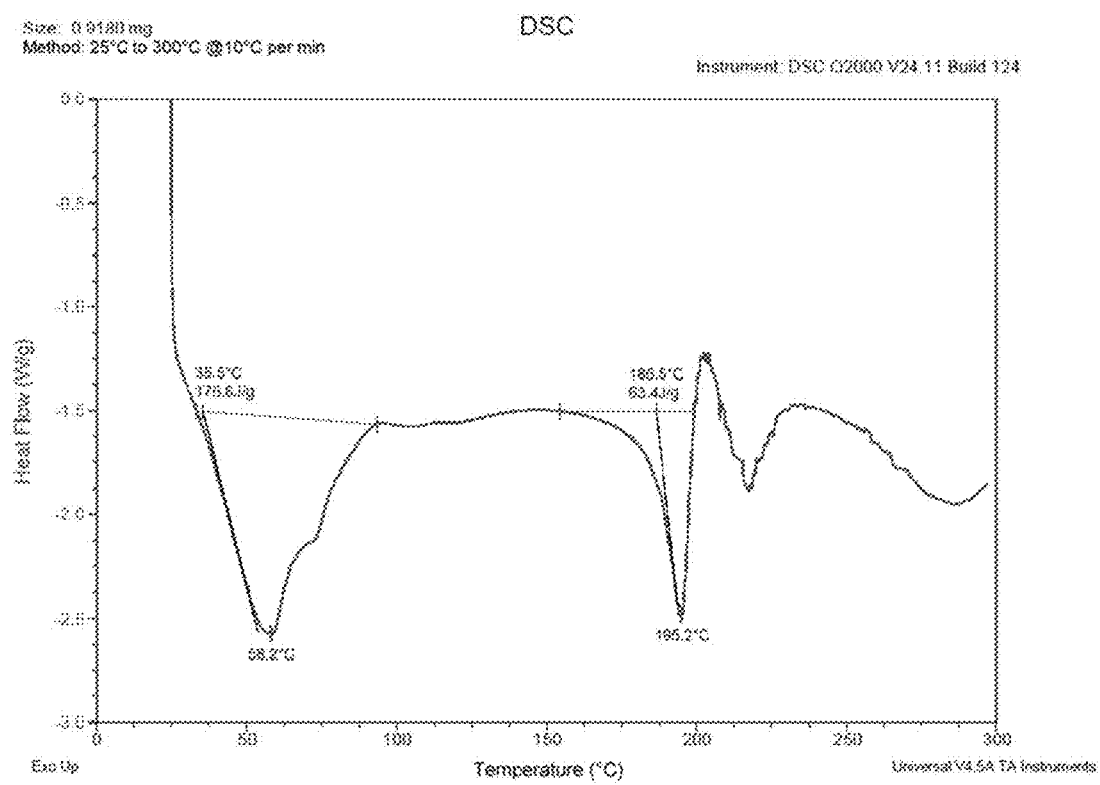
FIG. 41 shows a differential scanning calorimetry (DSC) profile of a t-butylamine salt of fospropofol.

The t-butylamine salt of fospropofol can be characterized by a DSC thermogram substantially as shown in FIG. 41. As FIG. 41 shows, the t-butylamine salt of fospropofol produced endothermic peaks at about 58.2° C. and 195.2° C. when heated at a rate of 10° C./min. In some embodiments of the present disclosure, the t-butylamine salt of fospropofol is characterized by a DSC thermogram comprising an endothermic peak at about 58° C., or at about 195° C.

In some embodiments of the present disclosure, the t-butylamine salt of fospropofol is characterized by an XRPD pattern comprising peaks at one or more of 9.0, 9.6, 12.2, 17.1, 19.5, 21.3, 21.7, 23.9, 26.4, 28.3, and 28.8 degrees±0.2 degrees 2-theta, and a DSC thermogram comprising an endothermic peak at about 58° C., or at about 195° C. when heated at a rate of 10° C./min.

Figure 42:
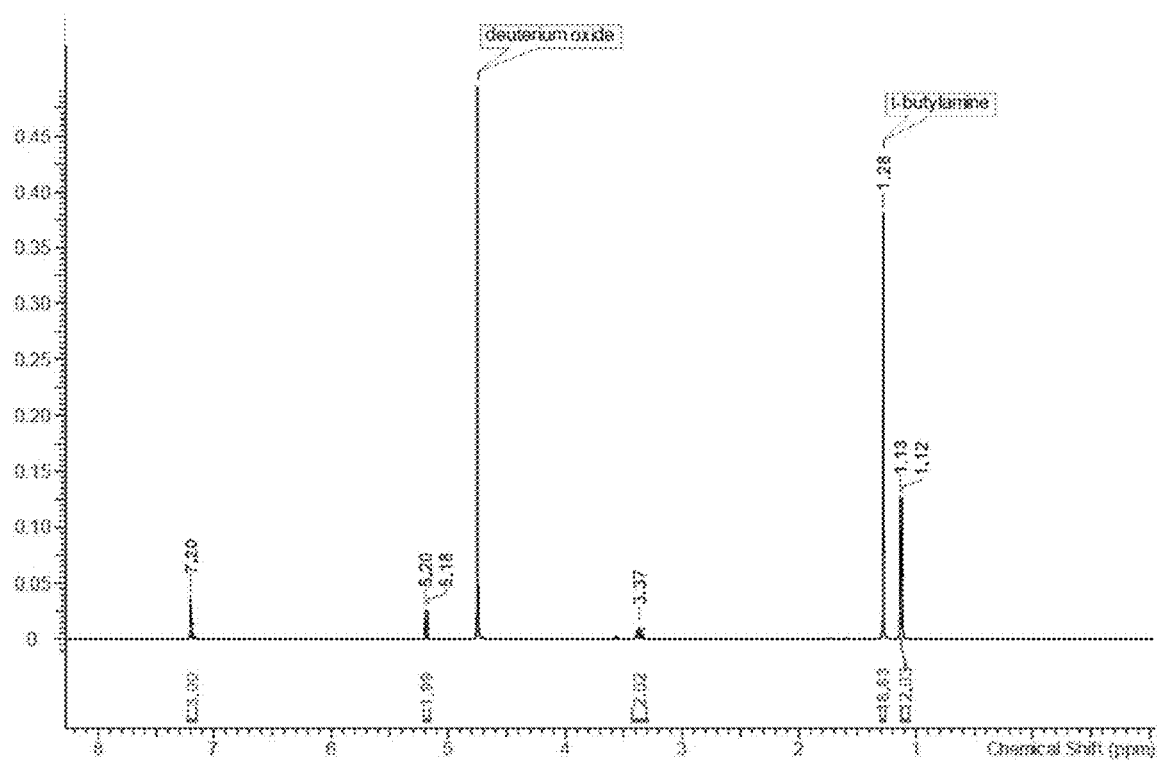
FIG. 42 shows a nuclear magnetic resonance (NMR) spectrum of a t-butylamine salt of fospropofol.

The t-butylamine salt of fospropofol can be characterized by an NMR spectrum substantially as shown in FIG. 42.

In some embodiments, the pharmaceutically acceptable salt of fospropofol is the ethylene diamine salt.

Figure 43:
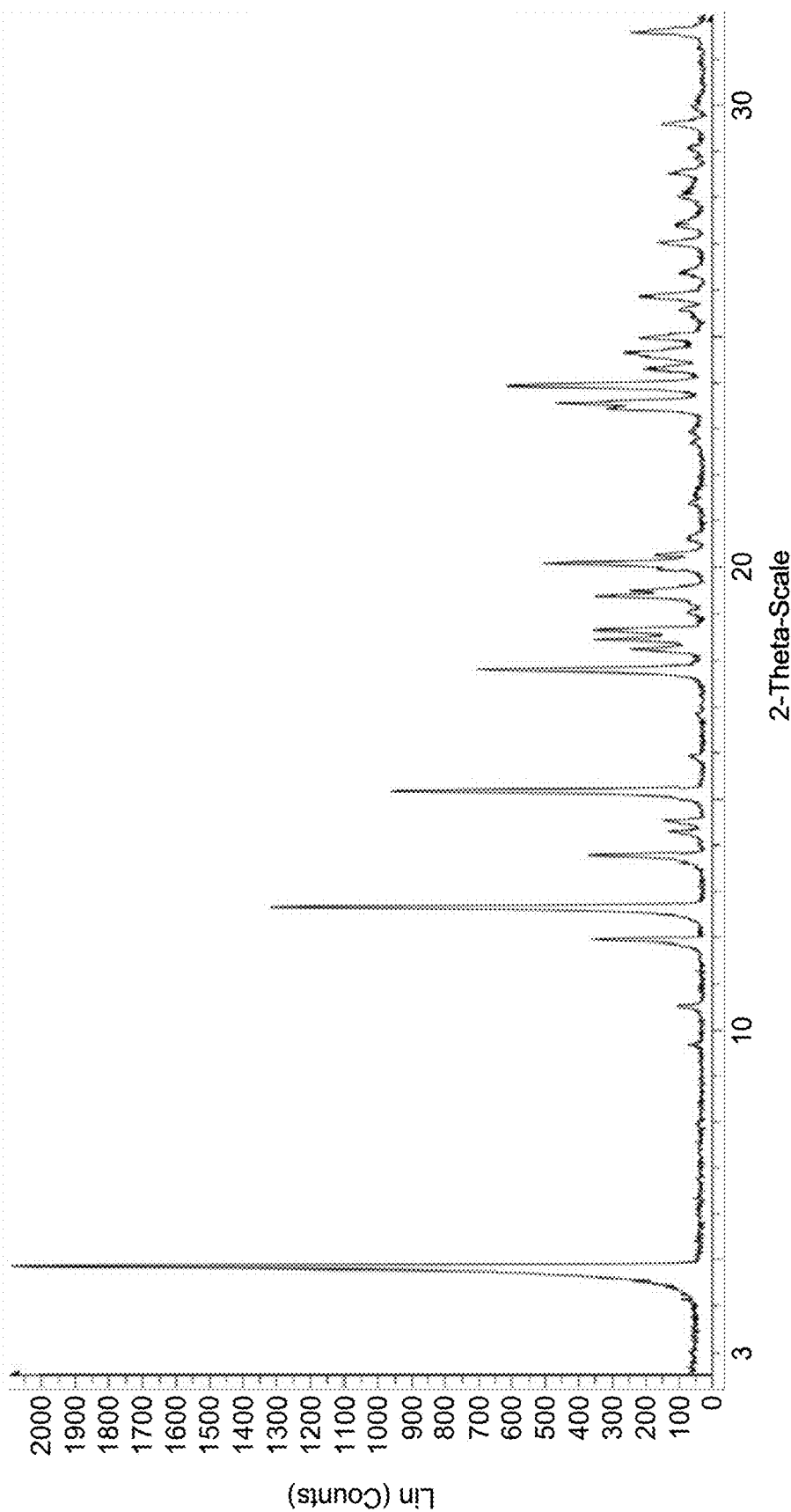
FIG. 43 shows an X-ray powder diffractogram (XRPD) of an ethylene diamine salt of fospropofol.

In some embodiments, the ethylene diamine salt of fospropofol has an XRPD substantially as shown in FIG. 43. The XRPD of the ethylene diamine salt of fospropofol shown in FIG. 43 comprises reflection angles (degrees 2-theta±0.2 degrees 2-theta), and relative intensities as shown in Table 4:

TABLE 4

XRPD Data for ethylene diamine salt of Fospropofol

| Angle (degrees 2-theta ± 0.2 degrees 2-theta) | Relative Intensity |
| --- | --- |
| 4.8 | 100.0 |
| 10.5 | 5.4 |
| 11.9 | 17.4 |
| 12.6 | 63.1 |
| 13.7 | 18.2 |
| 14.3 | 6.6 |
| 14.5 | 7.4 |
| 15.1 | 45.8 |
| 17.8 | 34.0 |
| 18.2 | 11.9 |
| 18.4 | 17.1 |
| 18.6 | 17.3 |
| 19.4 | 16.8 |
| 19.5 | 12.0 |
| 20.1 | 24.4 |
| 20.3 | 8.3 |
| 23.4 | 15.1 |
| 23.6 | 22.5 |
| 23.9 | 29.5 |
| 24.3 | 10.2 |
| 24.7 | 12.8 |
| 25.0 | 10.6 |
| 25.6 | 4.9 |
| 25.9 | 10.6 |
| 26.4 | 4.9 |
| 27.0 | 8.0 |
| 27.4 | 5.6 |
| 28.0 | 5.2 |
| 28.5 | 6.5 |
| 29.6 | 7.4 |
| 31.6 | 11.6 |

In some embodiments of the present disclosure, the ethylene diamine salt of fospropofol is characterized by an XRPD pattern comprising a peak at one of the angles listed in Table 4. In other aspects, the ethylene diamine salt of fospropofol is characterized by an XRPD pattern comprising more than one peak at one of the angles listed in Table 4 above. In other aspects, the ethylene diamine salt of fospropofol is characterized by an XRPD pattern comprising two peaks selected from the angles listed in Table 4 above. In other aspects, the ethylene diamine salt of fospropofol is characterized by an XRPD pattern comprising three peaks selected from the angles listed in Table 4 above. In other aspects, the ethylene diamine salt of fospropofol is characterized by an XRPD pattern comprising four peaks selected from the angles listed in Table 4 above. In other aspects, the ethylene diamine salt of fospropofol is characterized by an XRPD pattern comprising five peaks selected from the angles listed in Table 4 above. In other aspects, the ethylene diamine salt of fospropofol is characterized by an XRPD pattern comprising six peaks selected from the angles listed in Table 4 above. In other aspects, the ethylene diamine salt of fospropofol is characterized by an XRPD pattern comprising seven peaks selected from the angles listed in Table 4 above. In other aspects, the ethylene diamine salt of fospropofol is characterized by an XRPD pattern comprising eight peaks selected from the angles listed in Table 4 above. In other aspects, the ethylene diamine salt of fospropofol is characterized by an XRPD pattern comprising nine peaks selected from the angles listed in Table 4 above. In other aspects, the ethylene diamine salt of fospropofol is characterized by an XRPD pattern comprising ten peaks selected from the angles listed in Table 4 above. In other aspects, the ethylene diamine salt of fospropofol is characterized by an XRPD pattern comprising more than ten peaks selected from the angles listed in Table 4 above.

In some embodiments, the ethylene diamine salt of fospropofol is characterized by an XRPD pattern comprising a peak at 12.6 degrees±0.2 degrees 2-theta. In other embodiments, the ethylene diamine salt of fospropofol is characterized by an XRPD pattern comprising peaks at 11.9, 12.6, and 13.7 degrees±0.2 degrees 2-theta. In other embodiments, the ethylene diamine salt of fospropofol is characterized by an XRPD pattern comprising peaks at 11.9, 12.6, 13.7, 15.1, 17.8, and 20.1 degrees±0.2 degree 2-theta. In yet other embodiments, the ethylene diamine salt of fospropofol is characterized by an XRPD pattern comprising peaks at 11.9, 12.6, 13.7, 15.1, 17.8, 20.1, 23.6, and 23.9 degrees±0.2 degree 2-theta.

In some embodiments of the present disclosure, the ethylene diamine salt of fospropofol is characterized by an XRPD pattern comprising peaks at three or more of 11.9, 12.6, 13.7, 15.1, 17.8, 20.1, 23.6, and 23.9 degrees±0.2 degrees 2-theta. In some embodiments of the present disclosure, the ethylene diamine salt of fospropofol is characterized by an XRPD pattern comprising peaks at four or more of 11.9, 12.6, 13.7, 15.1, 17.8, 20.1, 23.6, and 23.9 degrees±0.2 degrees 2-theta. In some embodiments of the present disclosure, the ethylene diamine salt of fospropofol is characterized by an XRPD pattern comprising peaks at five or more of 11.9, 12.6, 13.7, 15.1, 17.8, 20.1, 23.6, and 23.9 degrees±0.2 degrees 2-theta. In some embodiments of the present disclosure, the ethylene diamine salt of fospropofol is characterized by an XRPD pattern comprising peaks at six or more of 11.9, 12.6, 13.7, 15.1, 17.8, 20.1, 23.6, and 23.9 degrees±0.2 degrees 2-theta. In some embodiments of the present disclosure, the ethylene diamine salt of fospropofol is characterized by an XRPD pattern comprising peaks at seven or more of 11.9, 12.6, 13.7, 15.1, 17.8, 20.1, 23.6, and 23.9 degrees±0.2 degrees 2-theta.

Figure 44:
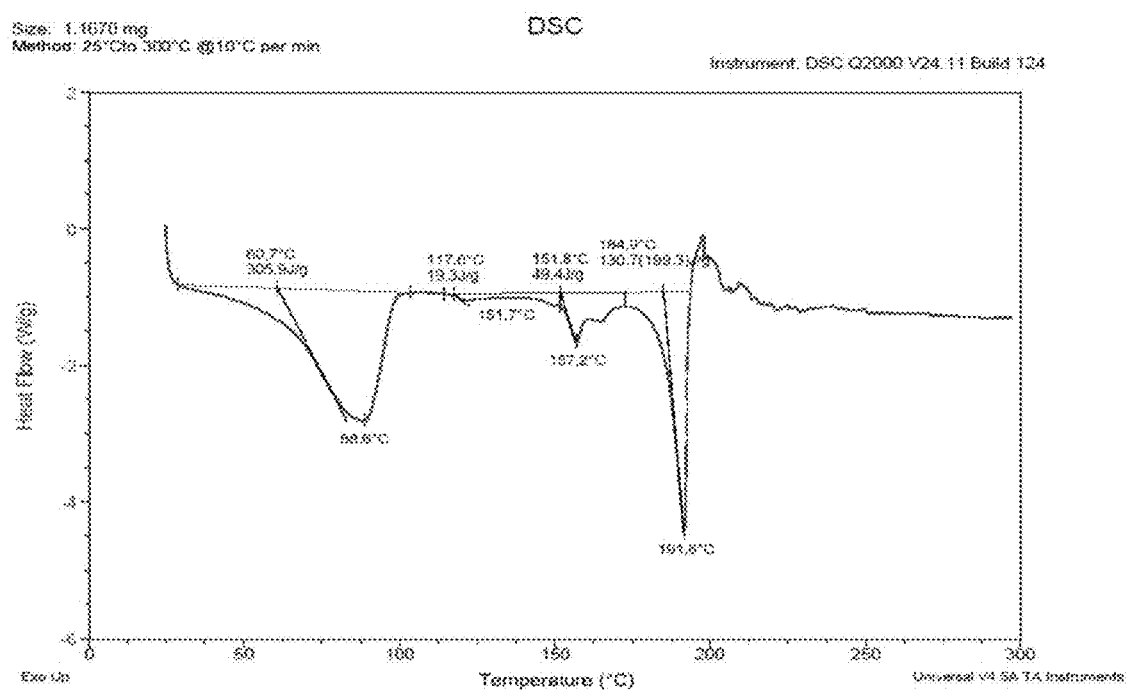
FIG. 44 shows a differential scanning calorimetry (DSC) profile of an ethylene diamine salt of fospropofol.

The ethylene diamine salt of fospropofol can be characterized by a DSC thermogram substantially as shown in FIG. 44. As FIG. 44 shows, the ethylene diamine salt of fospropofol produced endothermic peaks at about 88.6° C. and 191.6° C. when heated at a rate of 10° C./min. In some embodiments of the present disclosure, the ethylene diamine salt of fospropofol is characterized by a DSC thermogram comprising an endothermic peak at about 89° C., or at about 192° C.

In some embodiments of the present disclosure, the ethylene diamine salt of fospropofol is characterized by an XRPD pattern comprising peaks at one or more of 11.9, 12.6, 13.7, 15.1, 17.8, 20.1, 23.6, and 23.9 degrees±0.2 degrees 2-theta, and a DSC thermogram comprising an endothermic peak at about 89° C., or at about 192° C., when heated at a rate of 10° C./min.

Figure 45:
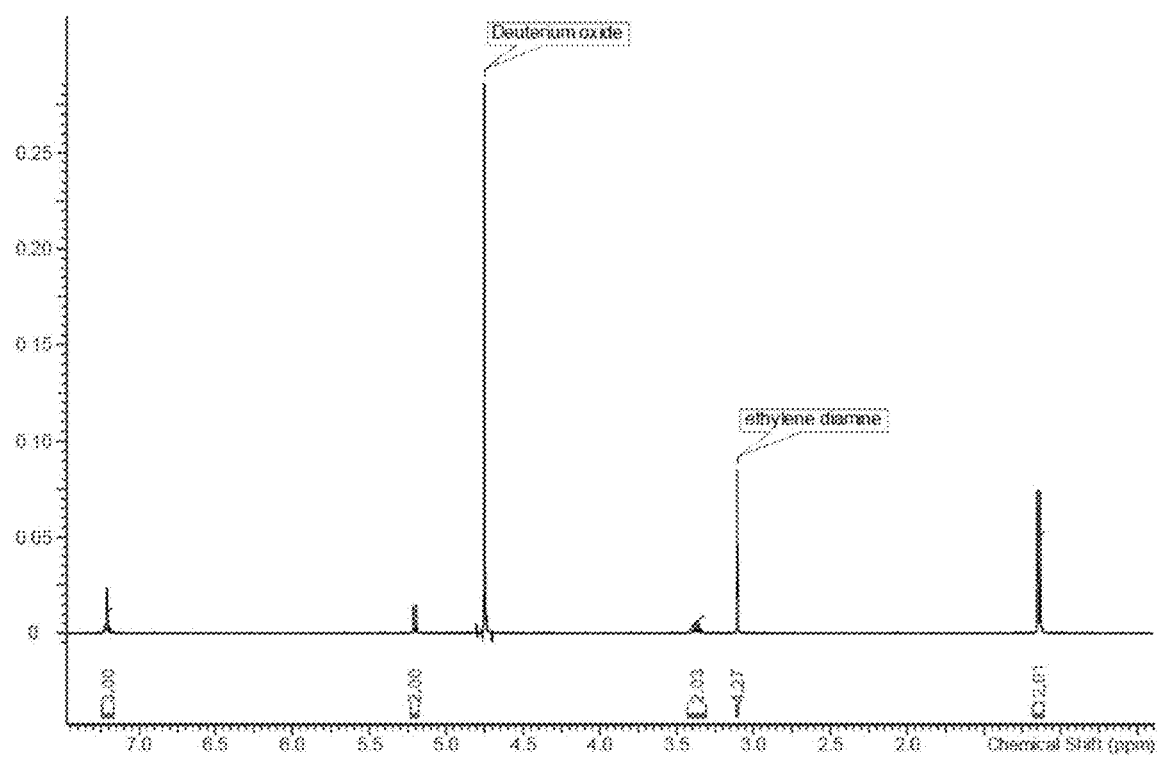
FIG. 45 shows a nuclear magnetic resonance (NMR) spectrum of an ethylene diamine salt of fospropofol.

The ethylene diamine salt of fospropofol can be characterized by an NMR spectrum substantially as shown in FIG. 45.

In some embodiments, the pharmaceutically acceptable salt of fospropofol is the benzathine (i.e., $N^1,N^2$-dibenzylethane-1,2-diamine)salt.

Figure 46:
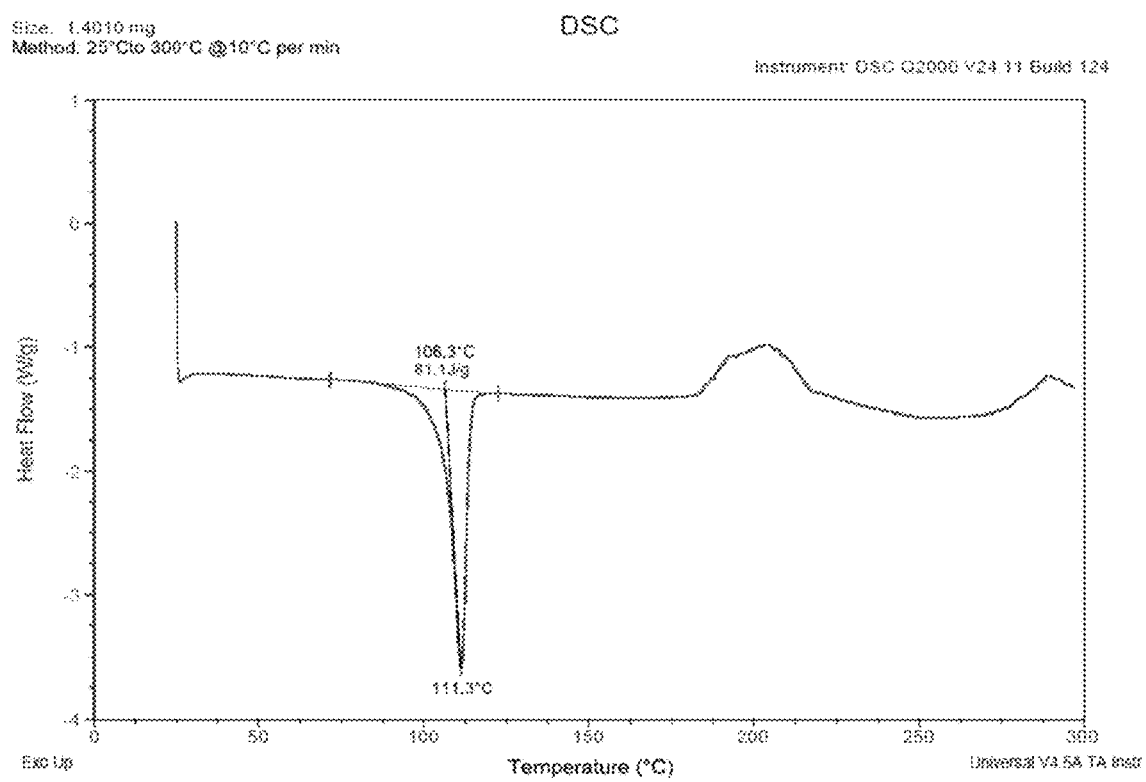
FIG. 46 shows a differential scanning calorimetry (DSC) profile of the benzathine salt of fospropofol.

The benzathine salt of fospropofol can be characterized by a DSC thermogram substantially as shown in FIG. 46. As FIG. 46 shows, the benzathine salt of fospropofol produced endothermic peak at about 111.3° C. when heated at a rate of 10° C./min. In some embodiments of the present disclosure, the benzathine salt of fospropofol is characterized by a DSC thermogram comprising an endothermic peak at about 111° C.

Figure 47:
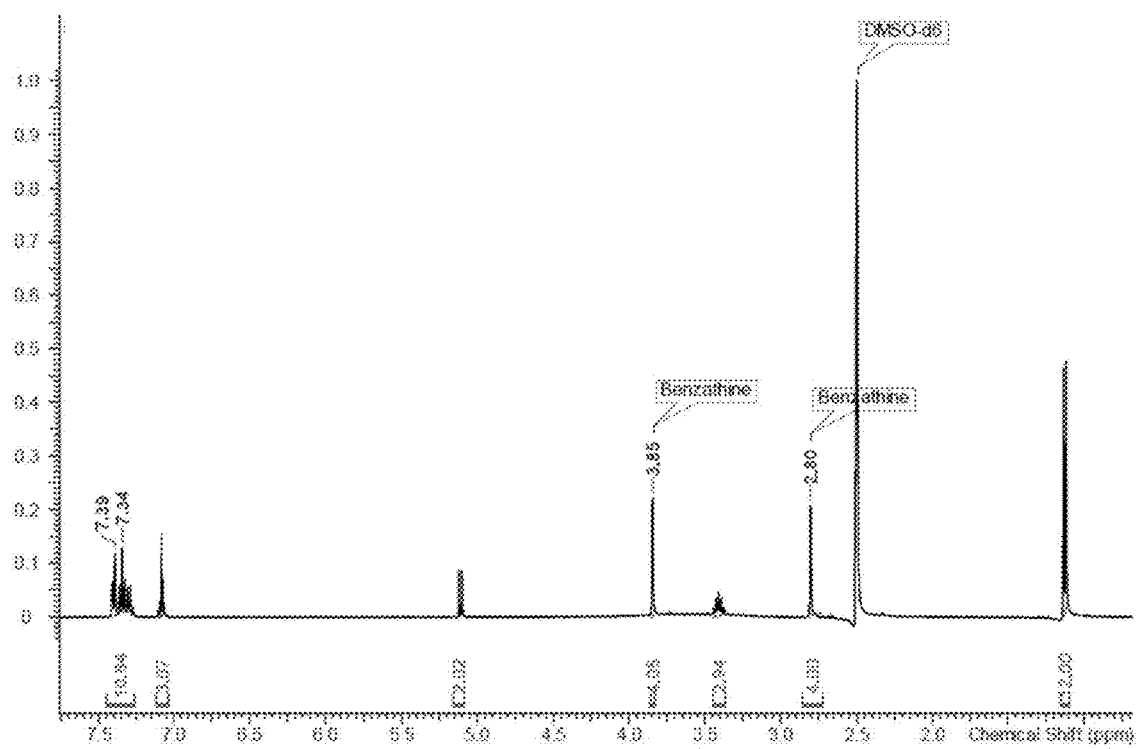
FIG. 47 shows a nuclear magnetic resonance (NMR) spectrum of the benzathine salt of fospropofol.

The benzathine salt of fospropofol can be characterized by an NMR spectrum substantially as shown in FIG. 47.

In some embodiments, the pharmaceutically acceptable salt of fospropofol is the piperazine salt.

Figure 48:
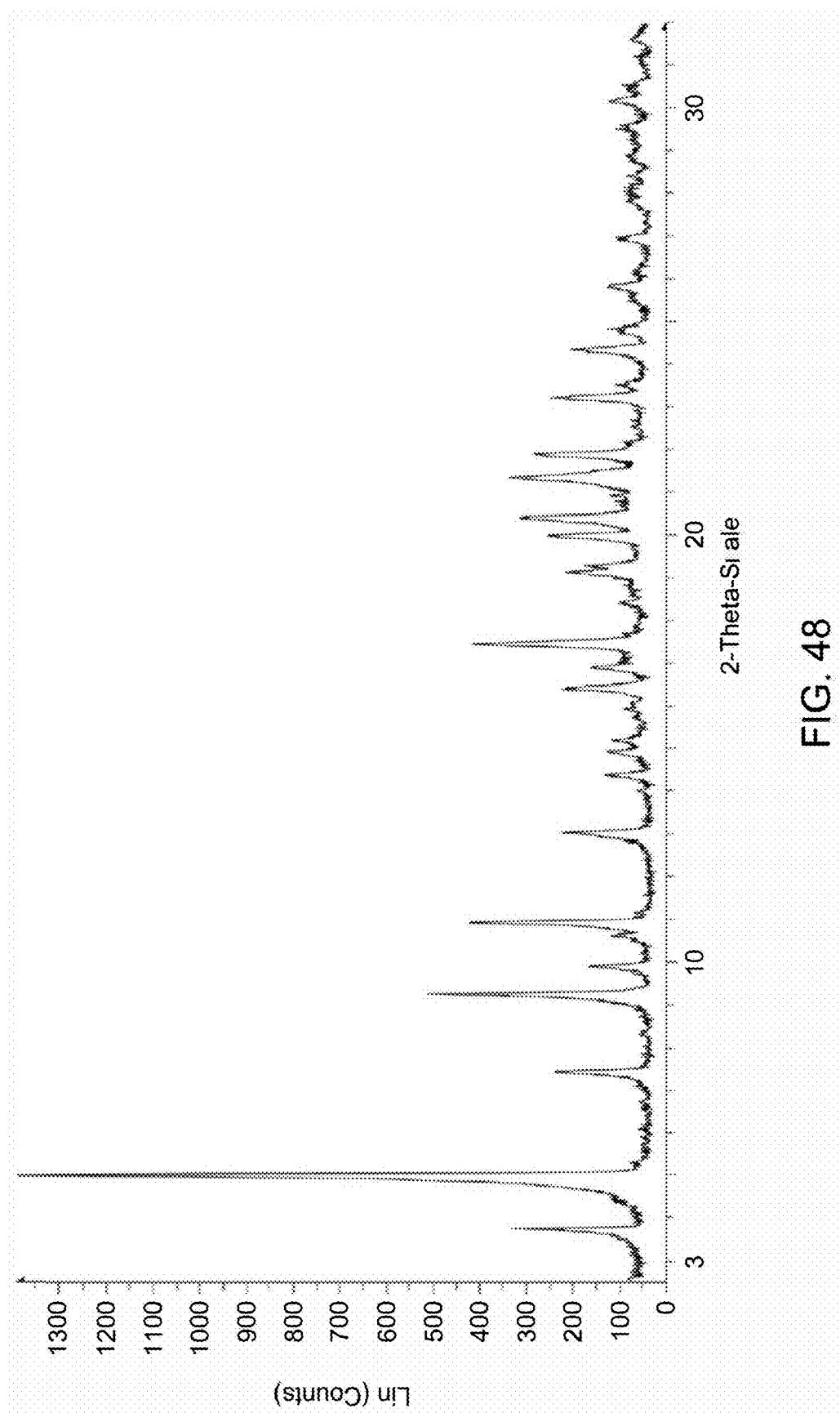
FIG. 48 shows an X-ray powder diffractogram (XRPD) of a piperazine salt of fospropofol.

In some embodiments, the piperazine salt of fospropofol has an XRPD substantially as shown in FIG. 48. The XRPD of the piperazine salt of fospropofol shown in FIG. 48 comprises reflection angles (degrees 2-theta±0.2 degrees 2-theta), and relative intensities as shown in Table 6:

TABLE 6

XRPD Data for piperazine salt of Fospropofol

| Angle (degrees 2-theta ± 0.2 degrees 2-theta) | Relative Intensity |
| --- | --- |
| 3.7 | 23.9 |
| 4.9 | 100.0 |
| 7.4 | 17.3 |
| 9.2 | 36.8 |
| 9.9 | 12.2 |
| 10.6 | 8.5 |
| 10.9 | 30.4 |
| 13.0 | 16.3 |
| 14.4 | 9.6 |
| 14.9 | 9.2 |
| 15.2 | 8.3 |
| 16.3 | 16.2 |
| 16.9 | 11.6 |
| 17.4 | 30.0 |
| 19.1 | 15.4 |
| 19.3 | 12.2 |
| 20.0 | 18.2 |
| 20.4 | 22.5 |
| 21.3 | 24.3 |
| 21.9 | 20.3 |
| 23.2 | 18.0 |
| 24.3 | 14.3 |
| 24.8 | 9.1 |
| 25.8 | 8.8 |
| 26.9 | 7.6 |

In some embodiments of the present disclosure, the piperazine salt of fospropofol is characterized by an XRPD pattern comprising a peak at one of the angles listed in Table 6. In other aspects, the piperazine salt of fospropofol is characterized by an XRPD pattern comprising more than one peak at one of the angles listed in Table 6 above. In other aspects, the piperazine salt of fospropofol is characterized by an XRPD pattern comprising two peaks selected from the angles listed in Table 6 above. In other aspects, the piperazine salt of fospropofol is characterized by an XRPD pattern comprising three peaks selected from the angles listed in Table 6 above. In other aspects, the piperazine salt of fospropofol is characterized by an XRPD pattern comprising four peaks selected from the angles listed in Table 6 above. In other aspects, the piperazine salt of fospropofol is characterized by an XRPD pattern comprising five peaks selected from the angles listed in Table 6 above. In other aspects, the piperazine salt of fospropofol is characterized by an XRPD pattern comprising six peaks selected from the angles listed in Table 6 above. In other aspects, the piperazine salt of fospropofol is characterized by an XRPD pattern comprising seven peaks selected from the angles listed in Table 6 above. In other aspects, the piperazine salt of fospropofol is characterized by an XRPD pattern comprising eight peaks selected from the angles listed in Table 6 above. In other aspects, the piperazine salt of fospropofol is characterized by an XRPD pattern comprising nine peaks selected from the angles listed in Table 6 above. In other aspects, the piperazine salt of fospropofol is characterized by an XRPD pattern comprising ten peaks selected from the angles listed in Table 6 above. In other aspects, the piperazine salt of fospropofol is characterized by an XRPD pattern comprising more than ten peaks selected from the angles listed in Table 6 above.

In some embodiments, the piperazine salt of fospropofol is characterized by an XRPD pattern comprising a peak at 4.9, 9.2, and 10.9 degrees±0.2 degrees 2-theta. In other embodiments, the piperazine salt of fospropofol is characterized by an XRPD pattern comprising peaks at 4.9, 9.2, 10.9, 13.0, 16.3, and 17.4 degrees±0.2 degrees 2-theta. In other embodiments, the piperazine salt of fospropofol is characterized by an XRPD pattern comprising peaks at 20.0, 20.4, 21.3, 21.9, 23.2, and 24.3 degrees±0.2 degree 2-theta. In yet other embodiments, the piperazine salt of fospropofol is characterized by an XRPD pattern comprising peaks at 4.9, 9.2, 10.9, 13.0, 16.3, 17.4, 20.0, 20.4, 21.3, 21.9, 23.2, and 24.3 degrees±0.2 degree 2-theta.

In some embodiments of the present disclosure, the piperazine salt of fospropofol is characterized by an XRPD pattern comprising peaks at three or more of 4.9, 9.2, 10.9, 13.0, 16.3, 17.4, 20.0, 20.4, 21.3, 21.9, 23.2, and 24.3 degrees±0.2 degrees 2-theta. In some embodiments of the present disclosure, the piperazine salt of fospropofol is characterized by an XRPD pattern comprising peaks at four or more of 4.9, 9.2, 10.9, 13.0, 16.3, 17.4, 20.0, 20.4, 21.3, 21.9, 23.2, and 24.3 degrees±0.2 degrees 2-theta. In some embodiments of the present disclosure, the piperazine salt of fospropofol is characterized by an XRPD pattern comprising peaks at five or more of 4.9, 9.2, 10.9, 13.0, 16.3, 17.4, 20.0, 20.4, 21.3, 21.9, 23.2, and 24.3 degrees±0.2 degrees 2-theta. In some embodiments of the present disclosure, the piperazine salt of fospropofol is characterized by an XRPD pattern comprising peaks at six or more of 4.9, 9.2, 10.9, 13.0, 16.3, 17.4, 20.0, 20.4, 21.3, 21.9, 23.2, and 24.3 degrees±0.2 degrees 2-theta. In some embodiments of the present disclosure, the piperazine salt of fospropofol is characterized by an XRPD pattern comprising peaks at seven or more of 4.9, 9.2, 10.9, 13.0, 16.3, 17.4, 20.0, 20.4, 21.3, 21.9, 23.2, and 24.3 degrees±0.2 degrees 2-theta.

Figure 49:
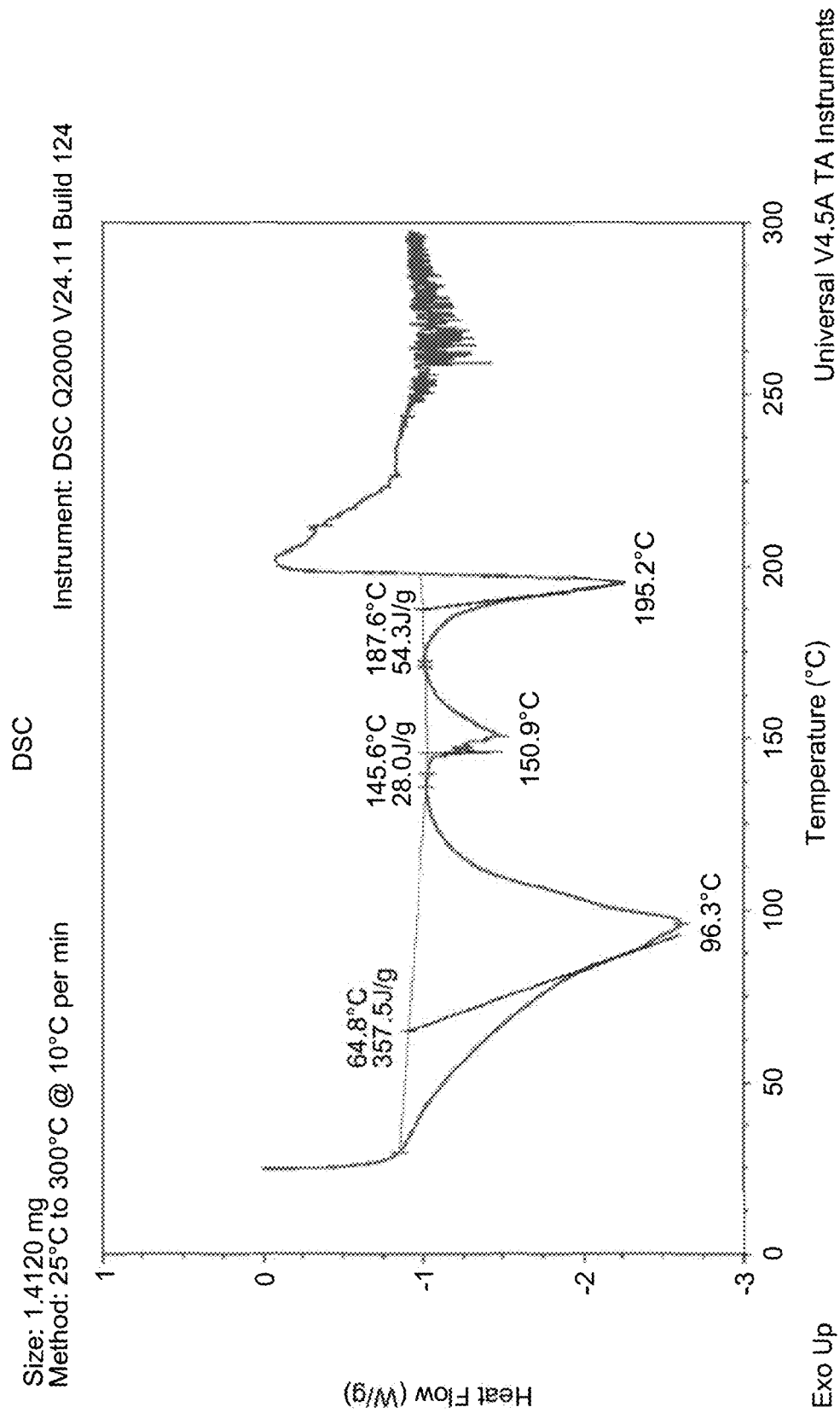
FIG. 49 shows a differential scanning calorimetry (DSC) profile of a piperazine salt of fospropofol.

The piperazine salt of fospropofol can be characterized by a DSC thermogram substantially as shown in FIG. 49. As FIG. 49 shows, the piperazine salt of fospropofol produced endothermic peak at 96.3° C., 150.9° C., and 195.2° C. when heated at a rate of 10° C./min. In some embodiments of the present disclosure, the piperazine salt of fospropofol is characterized by a DSC thermogram comprising an endothermic peak at about 96° C., 151° C., or 195° C. when heated at a rate of 10° C./min.

In some embodiments of the present disclosure, the piperazine salt of fospropofol is characterized by an XRPD pattern comprising peaks at one or more of 4.9, 9.2, 10.9, 13.0, 16.3, 17.4, 20.0, 20.4, 21.3, 21.9, 23.2, and 24.3 degrees±0.2 degrees 2-theta, and a DSC thermogram comprising an endothermic peak at about 96° C., 151° C., or 195° C. when heated at a rate of 10° C./min.

Figure 50:
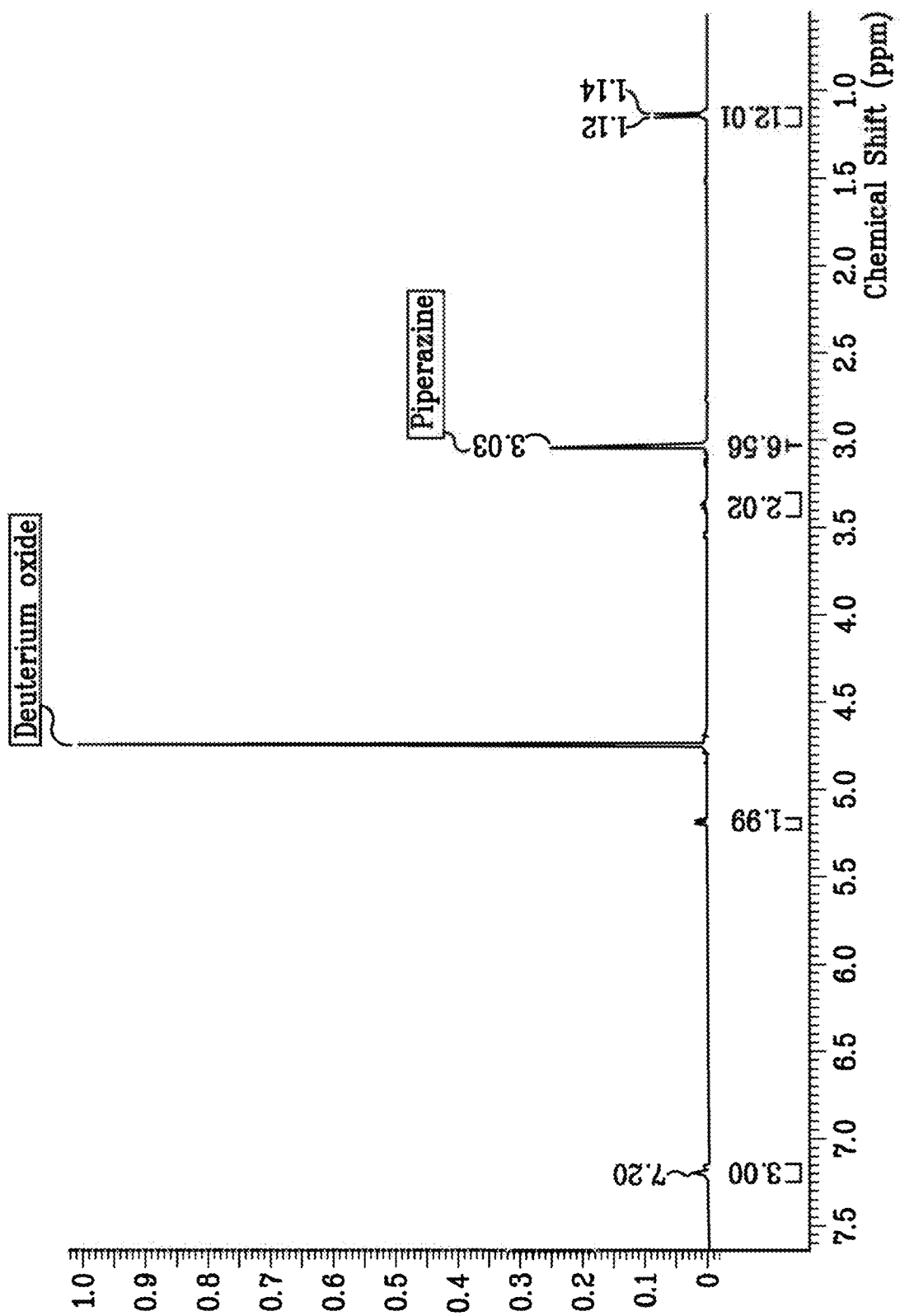
FIG. 50 shows a nuclear magnetic resonance (NMR) spectrum of a piperazine salt of fospropofol.

The piperazine salt of fospropofol can be characterized by an NMR spectrum substantially as shown in FIG. 50.

In some embodiments, the pharmaceutically acceptable salt of fospropofol is the ethanolamine salt.

Figure 51:
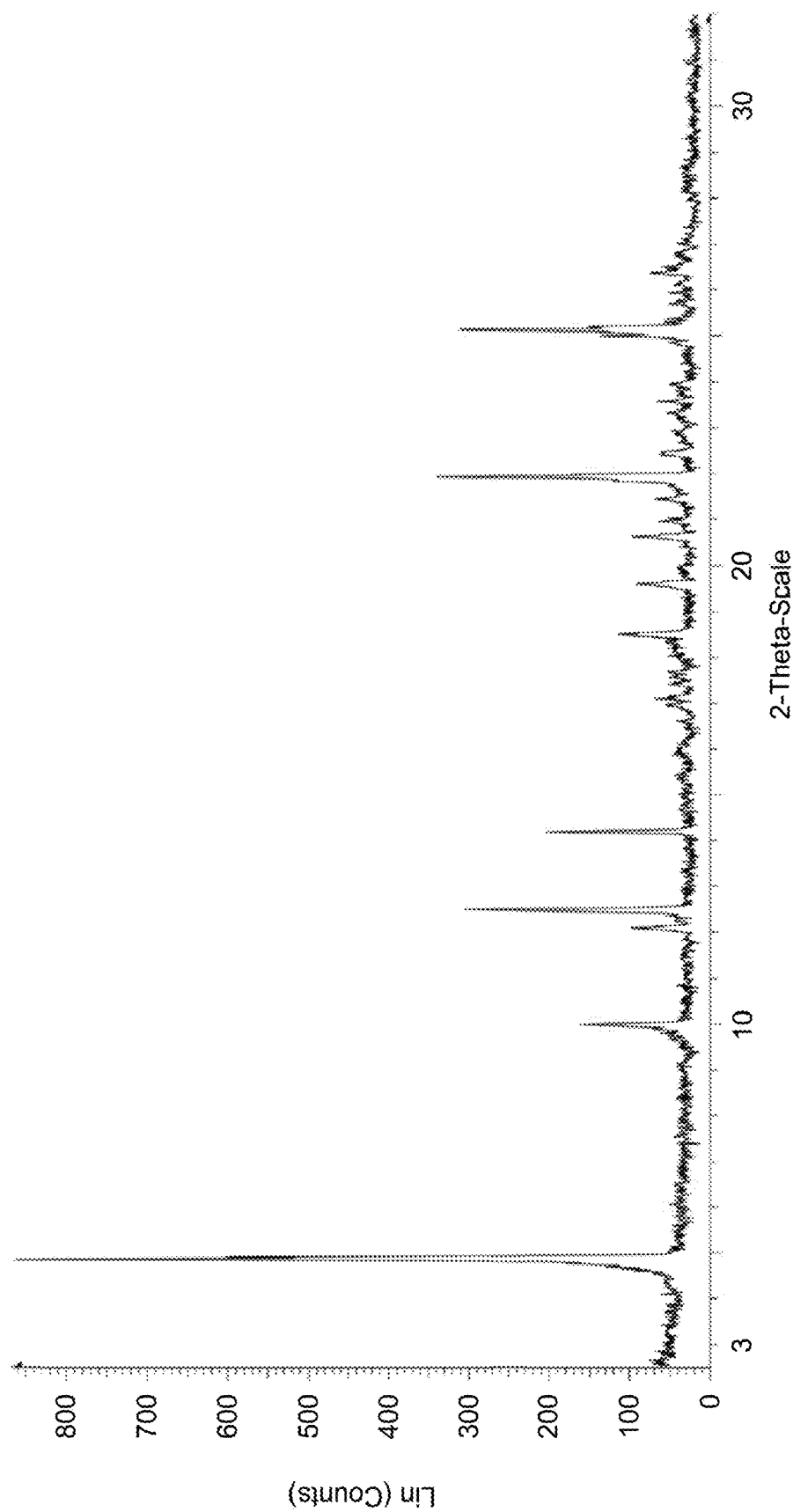
FIG. 51 shows an X-ray powder diffractogram (XRPD) of an ethanolamine salt of fospropofol (Form II).

In some embodiments, the ethanolamine salt of fospropofol (Form II) has an XRPD substantially as shown in FIG. 51. The XRPD of the Form II ethanolamine salt of fospropofol shown in FIG. 51 comprises reflection angles (degrees 2-theta±0.2 degrees 2-theta), and relative intensities as shown in Table 7A:

TABLE 7A

XRPD Data for Form II ethanolamine salt of Fospropofol

| Angle (degrees 2-theta ± 0.2 degrees 2-theta) | Relative Intensity |
|---|---|
| 4.8 | 100.0 |
| 10.0 | 19.0 |
| 12.1 | 11.9 |
| 12.5 | 35.5 |
| 14.2 | 24.1 |
| 18.5 | 13.1 |
| 19.6 | 10.6 |
| 20.6 | 11.6 |
| 21.9 | 39.5 |
| 25.1 | 35.6 |

In some embodiments of the present disclosure, the ethanolamine salt of fospropofol is characterized by an XRPD pattern comprising a peak at one of the angles listed in Table 7A. In other aspects, the ethanolamine salt of fospropofol is characterized by an XRPD pattern comprising more than one peak at one of the angles listed in Table 7A above. In other aspects, the ethanolamine salt of fospropofol is characterized by an XRPD pattern comprising two peaks selected from the angles listed in Table 7A above. In other aspects, the ethanolamine salt of fospropofol is characterized by an XRPD pattern comprising three peaks selected from the angles listed in Table 7A above. In other aspects, the ethanolamine salt of fospropofol is characterized by an XRPD pattern comprising four peaks selected from the angles listed in Table 7A above. In other aspects, the ethanolamine salt of fospropofol is characterized by an XRPD pattern comprising five peaks selected from the angles listed in Table 7A above. In other aspects, the ethanolamine salt of fospropofol is characterized by an XRPD pattern comprising six peaks selected from the angles listed in Table 7A above. In other aspects, the ethanolamine salt of fospropofol is characterized by an XRPD pattern comprising seven peaks selected from the angles listed in Table 7A above. In other aspects, the ethanolamine salt of fospropofol is characterized by an XRPD pattern comprising eight peaks selected from the angles listed in Table 7A above. In other aspects, the ethanolamine salt of fospropofol is characterized by an XRPD pattern comprising nine peaks selected from the angles listed in Table 7A above. In other aspects, the ethanolamine salt of fospropofol is characterized by an XRPD pattern comprising ten peaks selected from the angles listed in Table 7A above. In other aspects, the ethanolamine salt of fospropofol is characterized by an XRPD pattern comprising more than ten peaks selected from the angles listed in Table 7A above.

In some embodiments, the ethanolamine salt of fospropofol is characterized by an XRPD pattern comprising a peaks at 12.5, and 14.2 degrees degrees±0.2 degrees 2-theta. In other embodiments, the ethanolamine salt of fospropofol is characterized by an XRPD pattern comprising peaks at 12.5, 14.2, and 21.9 degrees±0.2 degrees 2-theta. In other embodiments, the ethanolamine salt of fospropofol is characterized by an XRPD pattern comprising peaks at 12.5, 14.2, 21.9, and 25.1 degrees±0.2 degree 2-theta. In yet other embodiments, the ethanolamine salt of fospropofol is characterized by an XRPD pattern comprising peaks at 4.8, 12.5, 14.2, 21.9, and 25.1 degrees±0.2 degree 2-theta.

In some embodiments of the present disclosure, the ethanolamine salt of fospropofol is characterized by an XRPD pattern comprising peaks at two or more of 4.8, 12.5, 14.2, 21.9, and 25.1 degrees degrees±0.2 degrees 2-theta. In some embodiments of the present disclosure, the ethanolamine salt of fospropofol is characterized by an XRPD pattern comprising peaks at three or more of 4.8, 12.5, 14.2, 21.9, and 25.1 degrees±0.2 degrees 2-theta. In some embodiments of the present disclosure, the ethanolamine salt of fospropofol is characterized by an XRPD pattern comprising peaks at four or more of 4.8, 12.5, 14.2, 21.9, and 25.1 degrees±0.2 degrees 2-theta.

Figure 52:
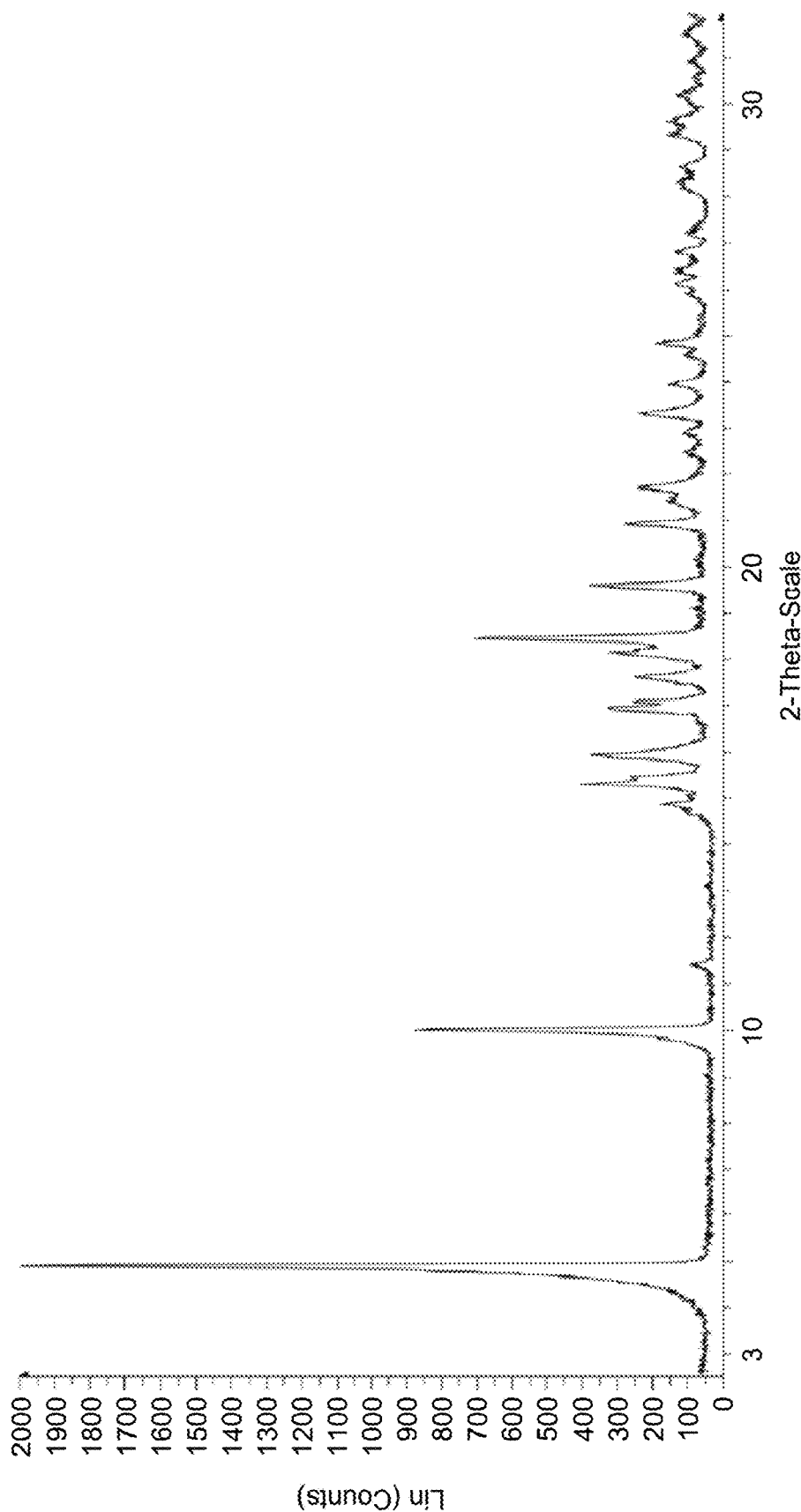
FIG. 52 shows an X-ray powder diffractogram (XRPD) of an ethanolamine salt of fospropofol (Form I).

In other embodiments, the ethanolamine salt of fospropofol (Form I) has an XRPD substantially as shown in FIG. 52. The XRPD of the Form I ethanolamine salt of fospropofol shown in FIG. 52 comprises reflection angles (degrees 2-theta±0.2 degrees 2-theta), and relative intensities as shown in Table 7:

TABLE 7

XRPD Data for Form I ethanolamine salt of Fospropofol

| Angle (degrees 2-theta ± 0.2 degrees 2-theta) | Relative Intensity |
|---|---|
| 4.8 | 100.0 |
| 10.0 | 44.4 |
| 11.4 | 4.9 |
| 14.8 | 9.0 |
| 15.3 | 20.1 |
| 15.5 | 13.0 |
| 15.9 | 19.0 |
| 17.0 | 16.0 |
| 17.1 | 12.7 |
| 17.6 | 12.5 |
| 18.2 | 16.5 |
| 18.5 | 35.5 |
| 19.6 | 19.3 |
| 20.9 | 14.2 |
| 21.4 | 8.0 |
| 21.7 | 12.2 |
| 22.5 | 6.0 |
| 22.9 | 6.2 |
| 23.3 | 12.3 |
| 24.0 | 7.7 |
| 24.6 | 5.7 |
| 24.9 | 9.6 |

In some embodiments of the present disclosure, the ethanolamine salt of fospropofol is characterized by an XRPD pattern comprising a peak at one of the angles listed in Table 7. In other aspects, the ethanolamine salt of fospropofol is characterized by an XRPD pattern comprising more than one peak at one of the angles listed in Table 7 above. In other aspects, the ethanolamine salt of fospropofol is characterized by an XRPD pattern comprising two peaks selected from the angles listed in Table 7 above. In other aspects, the ethanolamine salt of fospropofol is characterized by an XRPD pattern comprising three peaks selected from the angles listed in Table 7 above. In other aspects, the ethanolamine salt of fospropofol is characterized by an XRPD pattern comprising four peaks selected from the angles listed in Table 7 above. In other aspects, the ethanolamine salt of fospropofol is characterized by an XRPD pattern comprising five peaks selected from the angles listed in Table 7 above. In other aspects, the ethanolamine salt of fospropofol is characterized by an XRPD pattern comprising six peaks selected from the angles listed in Table 7 above. In other aspects, the ethanolamine salt of fospropofol is characterized by an XRPD pattern comprising seven peaks selected from the angles listed in Table 7 above. In other aspects, the ethanolamine salt of fospropofol is characterized by an XRPD pattern comprising eight peaks selected from the angles listed in Table 7 above. In other aspects, the ethanolamine salt of fospropofol is characterized by an XRPD pattern comprising nine peaks selected from the angles listed in Table 7 above. In other aspects, the ethanolamine salt of fospropofol is characterized by an XRPD pattern comprising ten peaks selected from the angles listed in Table 7 above. In other aspects, the ethanolamine salt of fospropofol is characterized by an XRPD pattern comprising more than ten peaks selected from the angles listed in Table 7 above.

In some embodiments, the ethanolamine salt of fospropofol is characterized by an XRPD pattern comprising a peak at 10.0 degrees±0.2 degrees 2-theta. In other embodiments, the ethanolamine salt of fospropofol is characterized by an XRPD pattern comprising peaks at 10.0, 18.5, 19.6, and 20.9 degrees±0.2 degrees 2-theta. In other embodiments, the ethanolamine salt of fospropofol is characterized by an XRPD pattern comprising peaks at 10.0, 17.0, 18.5, 19.6, and 20.9 degrees±0.2 degree 2-theta. In yet other embodiments, the ethanolamine salt of fospropofol is characterized by an XRPD pattern comprising peaks at 10.0, 15.3, 15.9, 17.0, 18.5, 19.6, and 20.9 degrees±0.2 degree 2-theta.

In some embodiments of the present disclosure, the ethanolamine salt of fospropofol is characterized by an XRPD pattern comprising peaks at two or more of 10.0, 15.3, 15.9, 17.0, 18.5, 19.6, and 20.9 degrees±0.2 degrees 2-theta. In some embodiments of the present disclosure, the ethanolamine salt of fospropofol is characterized by an XRPD pattern comprising peaks at three or more of 10.0, 15.3, 15.9, 17.0, 18.5, 19.6, and 20.9 degrees±0.2 degrees 2-theta. In some embodiments of the present disclosure, the ethanolamine salt of fospropofol is characterized by an XRPD pattern comprising peaks at four or more of 10.0, 15.3, 15.9, 17.0, 18.5, 19.6, and 20.9 degrees±0.2 degrees 2-theta. In some embodiments of the present disclosure, the ethanolamine salt of fospropofol is characterized by an XRPD pattern comprising peaks at five or more of 10.0, 15.3, 15.9, 17.0, 18.5, 19.6, and 20.9 degrees±0.2 degrees 2-theta.

Figure 53:
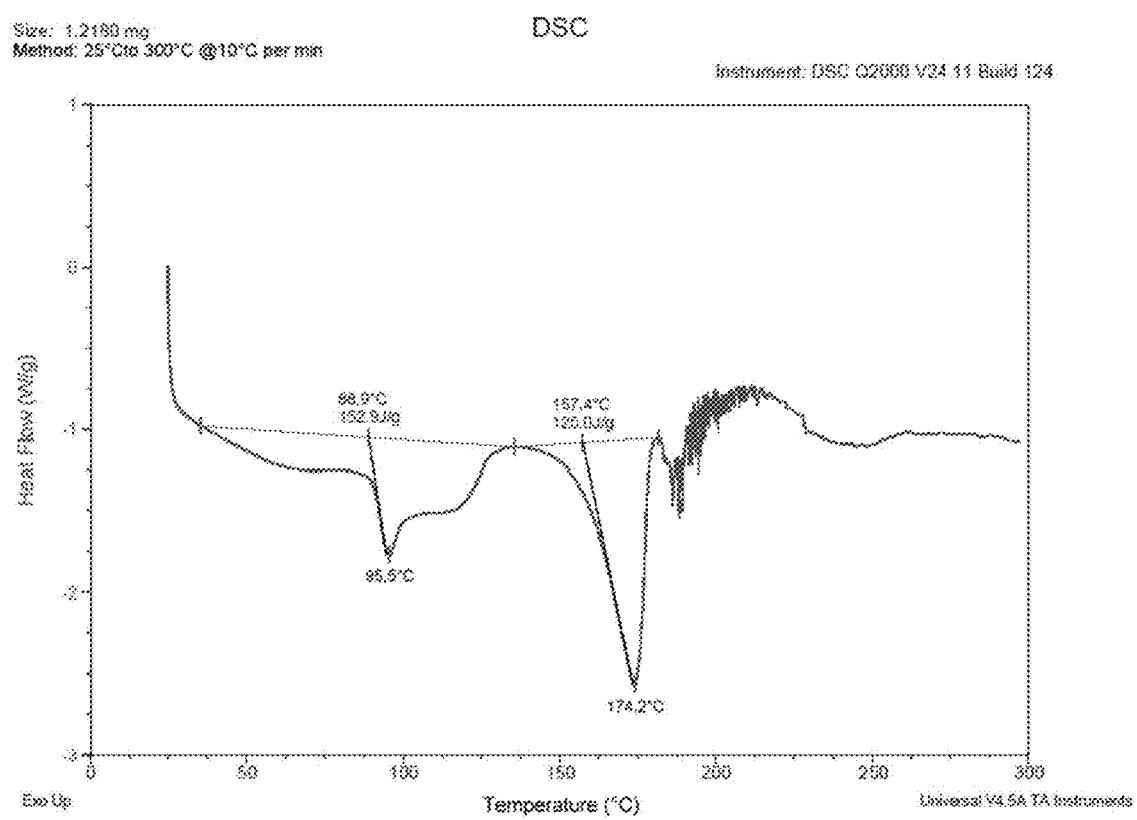
FIG. 53 shows a differential scanning calorimetry (DSC) profile of an ethanolamine salt of fospropofol (Form I).

The Form I ethanolamine salt of fospropofol can be characterized by a DSC thermogram substantially as shown in FIG. 53. As FIG. 53 shows, the ethanolamine salt of fospropofol produced endothermic peak at 95.5° C. and 174.2° C. when heated at a rate of 10° C./min. In some embodiments of the present disclosure, the ethanolamine salt of fospropofol is characterized by a DSC thermogram comprising an endothermic peak at about 96° C., or about 174° C. when heated at a rate of 10° C./min.

In some embodiments of the present disclosure, the Form I ethanolamine salt of fospropofol is characterized by an XRPD pattern comprising peaks at one or more of 10.0, 15.3, 15.9, 17.0, 18.5, 19.6, and 20.9 degrees±0.2 degrees 2-theta, and a DSC thermogram comprising an endothermic peak at about 96° C., or about 174° C. when heated at a rate of 10° C./min.

Figure 54:
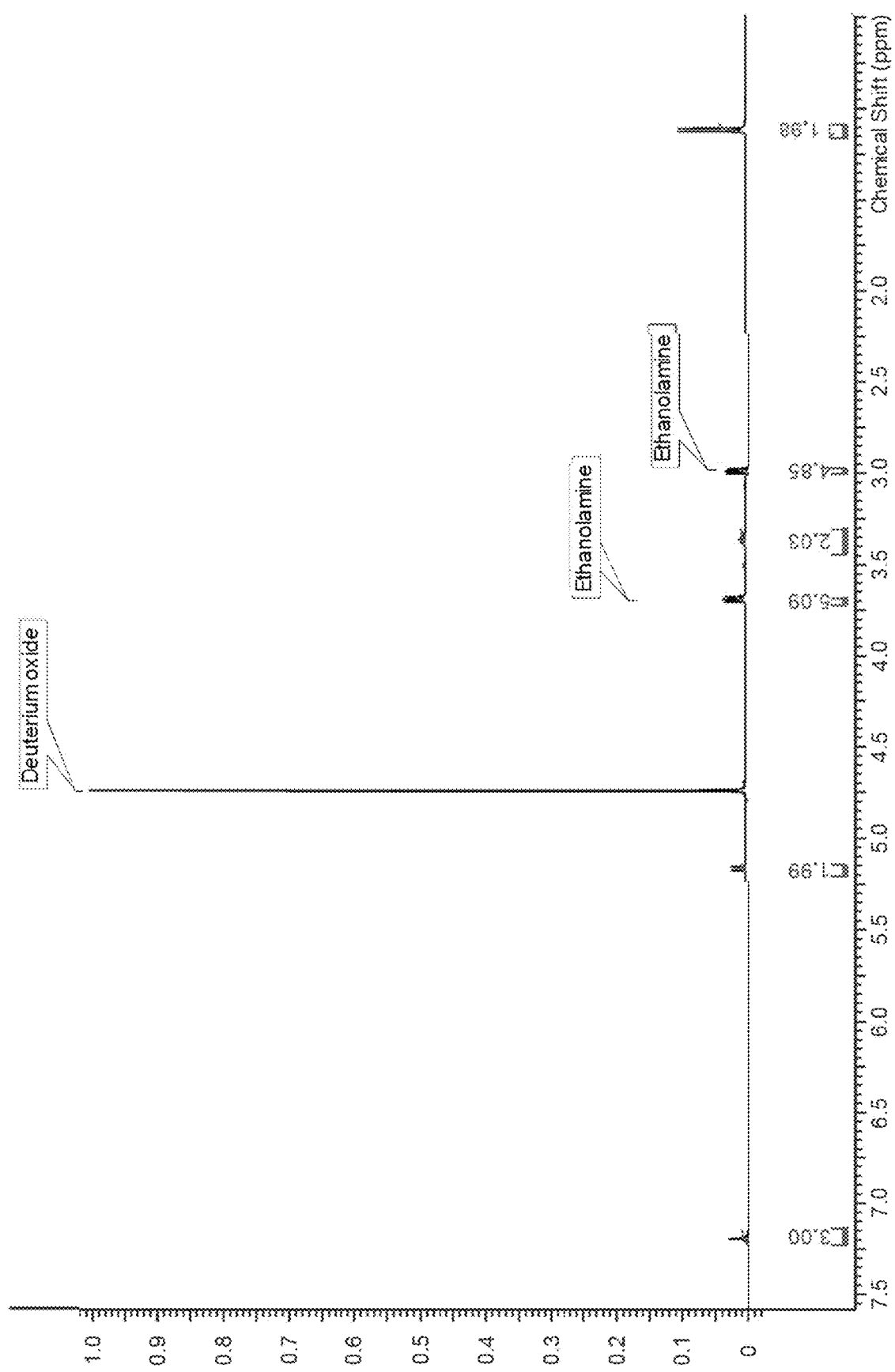
FIG. 54 shows a nuclear magnetic resonance (NMR) spectrum of an ethanolamine salt of fospropofol (Form I).

The Form I ethanolamine salt of fospropofol can be characterized by an NMR spectrum substantially as shown in FIG. 54.

In some embodiments, the pharmaceutically acceptable salt of fospropofol is the diethanolamine salt.

Figure 55:
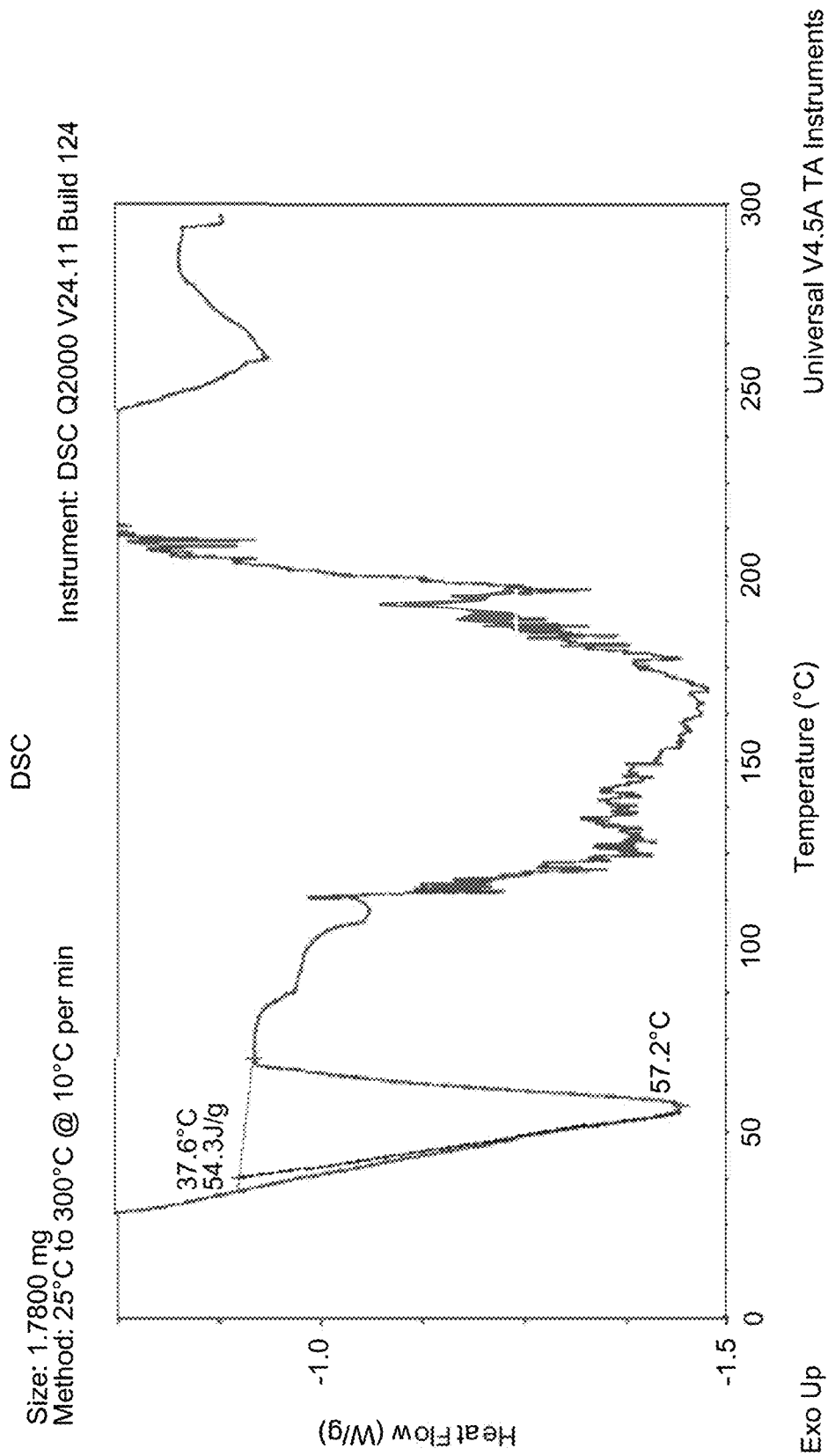
FIG. 55 shows differential scanning calorimetry (DSC) profile of a diethanolamine salt of fospropofol.

The diethanolamine salt of fospropofol can be characterized by a DSC thermogram substantially as shown in FIG. 55. As FIG. 55 shows, the diethanolamine salt of fospropofol produced endothermic peak at 57.2° C. when heated at a rate of 10° C./min. In some embodiments of the present disclosure, the diethanolamine salt of fospropofol is characterized by a DSC thermogram comprising an endothermic peak at about 57° C. when heated at a rate of 10° C./min.

Figure 56:
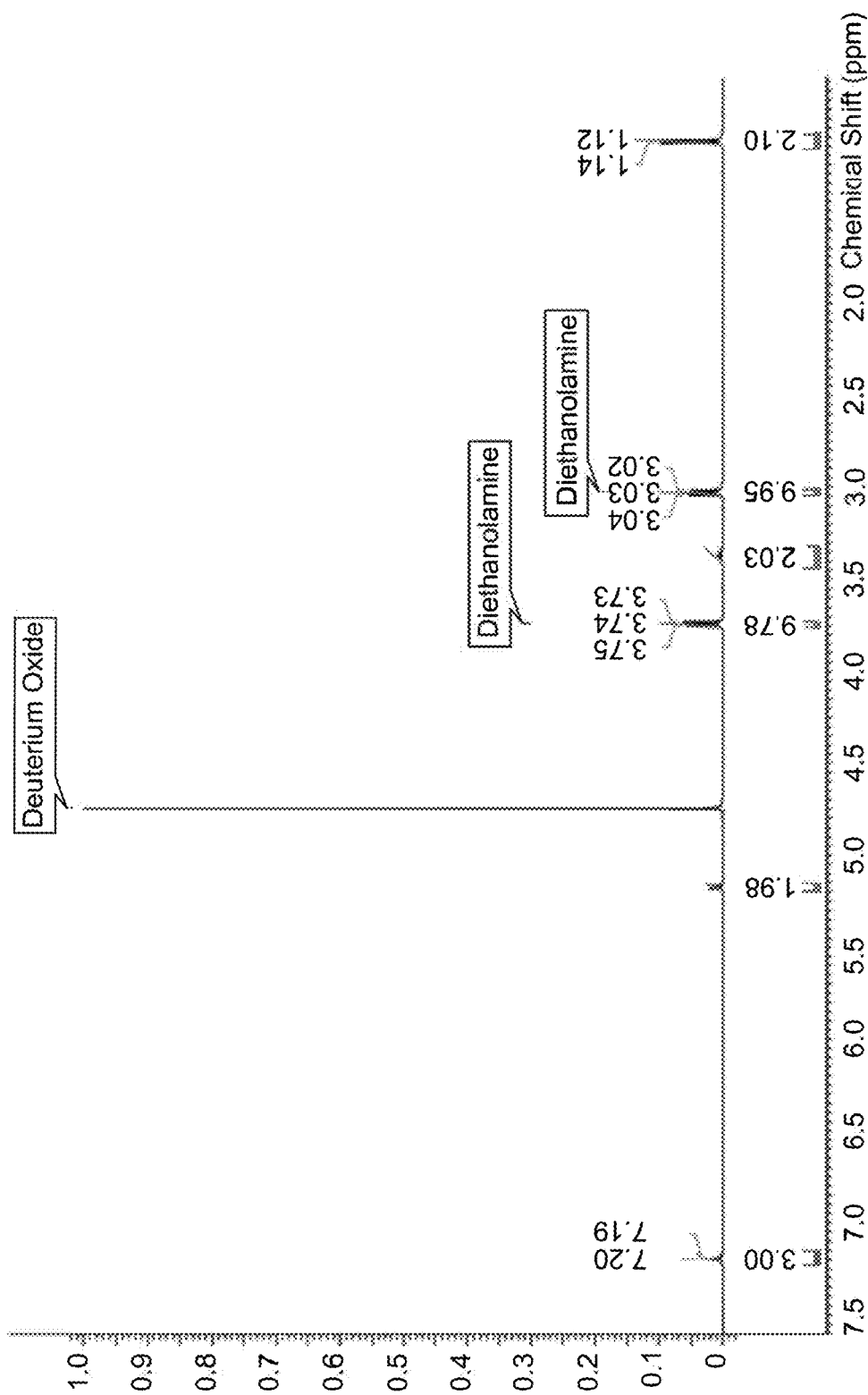
FIG. 56 shows a nuclear magnetic resonance (NMR) spectrum of a diethanolamine salt of fospropofol.

The diethanolamine salt of fospropofol can be characterized by an NMR spectrum substantially as shown in FIG. 56.

In some embodiments, the pharmaceutically acceptable salt of fospropofol is the ammonium salt.

Figure 57:
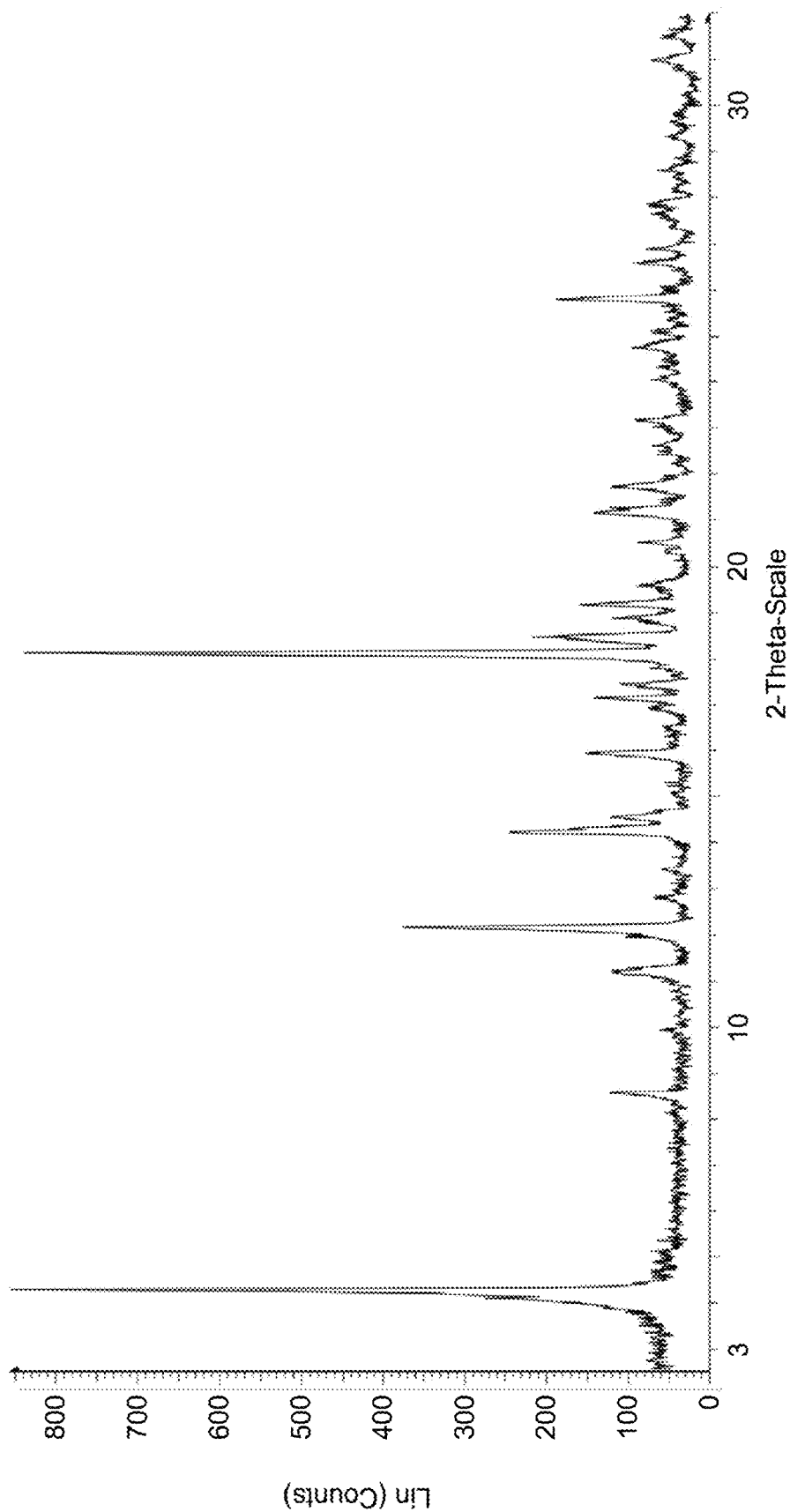
FIG. 57 shows an X-ray powder diffractogram (XRPD) of an ammonium salt of fospropofol.

In some embodiments, the ammonium salt of fospropofol has an XRPD substantially as shown in FIG. 57. The XRPD of the ammonium salt of fospropofol shown in FIG. 57 comprises reflection angles (degrees 2-theta±0.2 degrees 2-theta), and relative intensities as shown in Table 9:

TABLE 9

XRPD Data for ammonium salt of Fospropofol

| Angle (degrees 2-theta ± 0.2 degrees 2-theta) | Relative Intensity |
|---|---|
| 4.3 | 100.0 |
| 8.6 | 14.7 |
| 11.2 | 14.2 |
| 12.2 | 43.7 |
| 14.2 | 28.7 |
| 14.5 | 14.0 |
| 15.9 | 18.1 |
| 16.9 | 9.0 |
| 17.1 | 16.8 |
| 17.5 | 12.8 |
| 18.1 | 98.5 |
| 18.5 | 25.9 |
| 18.9 | 14.2 |
| 19.2 | 18.8 |
| 19.6 | 10.5 |
| 20.5 | 10.2 |
| 21.1 | 16.5 |
| 21.8 | 14.0 |
| 22.6 | 8.3 |
| 23.2 | 11.0 |
| 24.1 | 8.5 |
| 24.8 | 11.3 |
| 25.8 | 21.6 |
| 26.6 | 10.3 |
| 26.9 | 9.0 |

In some embodiments of the present disclosure, the ammonium salt of fospropofol is characterized by an XRPD pattern comprising a peak at one of the angles listed in Table 9. In other aspects, the ammonium salt of fospropofol is characterized by an XRPD pattern comprising more than one peak at one of the angles listed in Table 9 above. In other aspects, the ammonium salt of fospropofol is characterized by an XRPD pattern comprising two peaks selected from the angles listed in Table 9 above. In other aspects, the ammonium salt of fospropofol is characterized by an XRPD pattern comprising three peaks selected from the angles listed in Table 9 above. In other aspects, the ammonium salt of fospropofol is characterized by an XRPD pattern comprising four peaks selected from the angles listed in Table 9 above. In other aspects, the ammonium salt of fospropofol is characterized by an XRPD pattern comprising five peaks selected from the angles listed in Table 9 above. In other aspects, the ammonium salt of fospropofol is characterized by an XRPD pattern comprising six peaks selected from the angles listed in Table 9 above. In other aspects, the ammonium salt of fospropofol is characterized by an XRPD pattern comprising seven peaks selected from the angles listed in Table 9 above. In other aspects, the ammonium salt of fospropofol is characterized by an XRPD pattern comprising eight peaks selected from the angles listed in Table 9 above. In other aspects, the ammonium salt of fospropofol is characterized by an XRPD pattern comprising nine peaks selected from the angles listed in Table 9 above. In other aspects, the ammonium salt of fospropofol is characterized by an XRPD pattern comprising ten peaks selected from the angles listed in Table 9 above. In other aspects, the ammonium salt of fospropofol is characterized by an XRPD pattern comprising more than ten peaks selected from the angles listed in Table 9 above.

In some embodiments, the ammonium salt of fospropofol is characterized by an XRPD pattern comprising a peak at 18.1 degrees±0.2 degrees 2-theta. In other embodiments, the ammonium salt of fospropofol is characterized by an XRPD pattern comprising peaks at 18.1, 18.5, 19.2, 21.1, 21.8, and 25.8 degrees±0.2 degrees 2-theta. In other embodiments, the ammonium salt of fospropofol is characterized by an XRPD pattern comprising peaks at 12.2, 14.2, 15.9, 18.1, 18.5, and 19.2 degrees±0.2 degree 2-theta. In yet other embodiments, the ammonium salt of fospropofol is characterized by an XRPD pattern comprising peaks at 12.2, 14.2, 15.9, 18.1, 18.5, 19.2, 21.1, 21.8, and 25.8 degrees±0.2 degree 2-theta.

In some embodiments of the present disclosure, the ammonium salt of fospropofol is characterized by an XRPD pattern comprising peaks at three or more of 12.2, 14.2, 15.9, 18.1, 18.5, 19.2, 21.1, 21.8, and 25.8 degrees±0.2 degrees 2-theta. In some embodiments of the present disclosure, the ammonium salt of fospropofol is characterized by an XRPD pattern comprising peaks at four or more of 12.2, 14.2, 15.9, 18.1, 18.5, 19.2, 21.1, 21.8, and 25.8 degrees±0.2 degrees 2-theta. In some embodiments of the present disclosure, the ammonium salt of fospropofol is characterized by an XRPD pattern comprising peaks at five or more of 12.2, 14.2, 15.9, 18.1, 18.5, 19.2, 21.1, 21.8, and 25.8 degrees±0.2 degrees 2-theta. In some embodiments of the present disclosure, the ammonium salt of fospropofol is characterized by an XRPD pattern comprising peaks at six or more of 12.2, 14.2, 15.9, 18.1, 18.5, 19.2, 21.1, 21.8, and 25.8 degrees±0.2 degrees 2-theta. In some embodiments of the present disclosure, the ammonium salt of fospropofol is characterized by an XRPD pattern comprising peaks at seven or more of 12.2, 14.2, 15.9, 18.1, 18.5, 19.2, 21.1, 21.8, and 25.8 degrees±0.2 degrees 2-theta.

Figure 58:
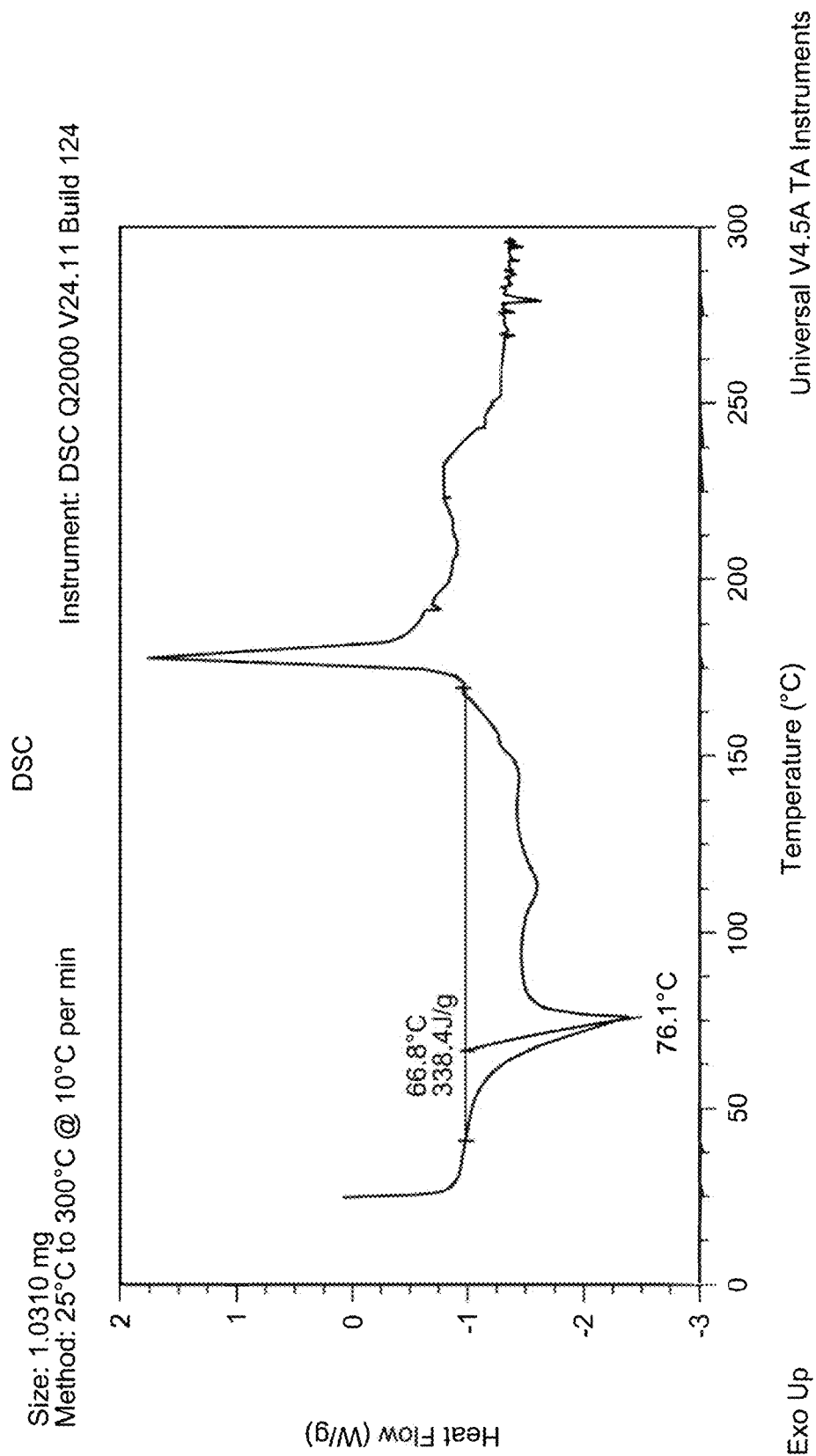
FIG. 58 shows a differential scanning calorimetry (DSC) profile of the ammonium salt of fospropofol.

The ammonium salt of fospropofol can be characterized by a DSC thermogram substantially as shown in FIG. 58. As FIG. 58 shows, the ammonium salt of fospropofol produced endothermic peak at 76.1° C. when heated at a rate of 10° C./min. In some embodiments of the present disclosure, the ammonium salt of fospropofol is characterized by a DSC thermogram comprising an endothermic peak at about 76° C. when heated at a rate of 10° C./min.

In some embodiments of the present disclosure, the ammonium salt of fospropofol is characterized by an XRPD pattern comprising peaks at 12.2, 14.2, 15.9, 18.1, 18.5, 19.2, 21.1, 21.8, and 25.8 degrees±0.2 degrees 2-theta, and a DSC thermogram comprising an endothermic peak at about 76° C. when heated at a rate of 10° C./min.

In some embodiments, the pharmaceutically acceptable salt of fospropofol is the tromethamine (i.e., 2-amino-2-(hydroxymethyl)propane-1,3-diol)salt.

Figure 59:
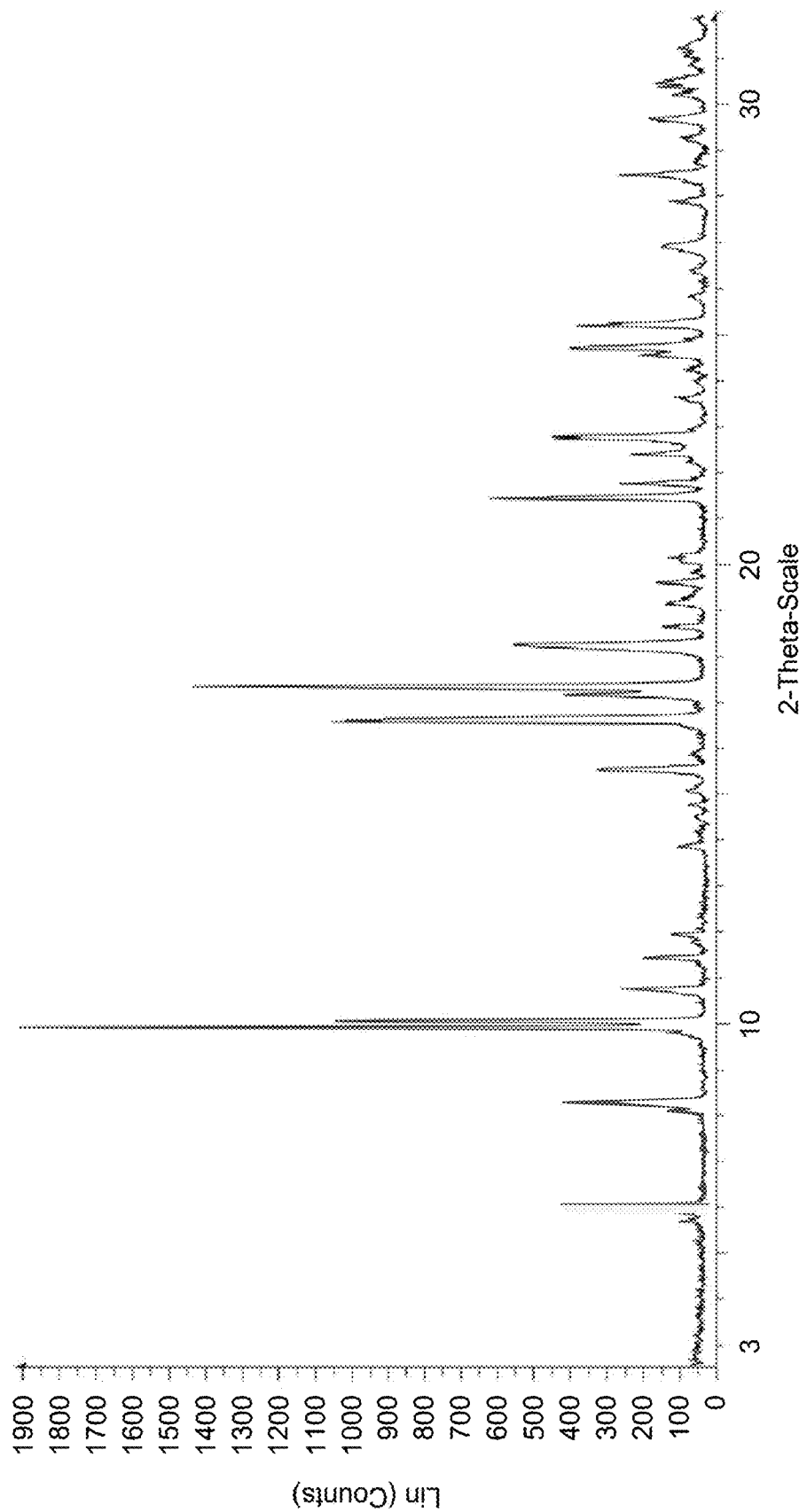
FIG. 59 shows an X-ray powder diffractogram (XRPD) of a tromethamine salt of fospropofol.

In some embodiments, the tromethamine salt of fospropofol has an XRPD substantially as shown in FIG. 59. The XRPD of the tromethamine salt of fospropofol shown in FIG. 59 comprises reflection angles (degrees 2-theta±0.2 degrees 2-theta), and relative intensities as shown in Table 10:

TABLE 10

XRPD Data for tromethamine salt of Fospropofol

| Angle (degrees 2-theta ± 0.2 degrees 2-theta) | Relative Intensity |
|---|---|
| 5.9 | 13.4 |
| 6.0 | 19.9 |
| 8.3 | 22.3 |
| 9.9 | 100.0 |
| 10.0 | 55.0 |
| 10.7 | 13.9 |
| 11.4 | 10.5 |
| 11.9 | 6.3 |
| 13.8 | 5.7 |
| 15.5 | 17.0 |
| 16.6 | 55.5 |
| 17.2 | 21.6 |
| 17.3 | 75.0 |
| 18.3 | 28.7 |
| 18.6 | 7.9 |
| 19.2 | 7.1 |
| 19.6 | 9.0 |
| 20.1 | 7.0 |
| 21.4 | 32.9 |
| 21.8 | 14.2 |
| 22.4 | 12.2 |
| 22.7 | 23.0 |
| 23.7 | 6.2 |
| 24.6 | 10.8 |
| 24.7 | 20.9 |
| 25.2 | 19.9 |
| 26.9 | 7.4 |
| 27.9 | 6.5 |
| 28.5 | 14.2 |
| 29.3 | 5.1 |
| 29.7 | 10.2 |

In some embodiments of the present disclosure, the tromethamine salt of fospropofol is characterized by an XRPD pattern comprising a peak at one of the angles listed in Table 10. In other aspects, the tromethamine salt of fospropofol is characterized by an XRPD pattern comprising more than one peak at one of the angles listed in Table 10 above. In other aspects, the tromethamine salt of fospropofol is characterized by an XRPD pattern comprising two peaks selected from the angles listed in Table 10 above. In other aspects, the tromethamine salt of fospropofol is characterized by an XRPD pattern comprising three peaks selected from the angles listed in Table 10 above. In other aspects, the tromethamine salt of fospropofol is characterized by an XRPD pattern comprising four peaks selected from the angles listed in Table 10 above. In other aspects, the tromethamine salt of fospropofol is characterized by an XRPD pattern comprising five peaks selected from the angles listed in Table 10 above. In other aspects, the tromethamine salt of fospropofol is characterized by an XRPD pattern comprising six peaks selected from the angles listed in Table 10 above. In other aspects, the tromethamine salt of fospropofol is characterized by an XRPD pattern comprising seven peaks selected from the angles listed in Table 10 above. In other aspects, the tromethamine salt of fospropofol is characterized by an XRPD pattern comprising eight peaks selected from the angles listed in Table 10 above. In other aspects, the tromethamine salt of fospropofol is characterized by an XRPD pattern comprising nine peaks selected from the angles listed in Table 10 above. In other aspects, the tromethamine salt of fospropofol is characterized by an XRPD pattern comprising ten peaks selected from the angles listed in Table 10 above. In other aspects, the tromethamine salt of fospropofol is characterized by an XRPD pattern comprising more than ten peaks selected from the angles listed in Table 10 above.

In some embodiments, the tromethamine salt of fospropofol is characterized by an XRPD pattern comprising a peak at 10.0, 16.6, and 17.3 degrees±0.2 degrees 2-theta. In other embodiments, the tromethamine salt of fospropofol is characterized by an XRPD pattern comprising peaks at 10.0, 10.7, 16.6, 17.3, and 18.3 degrees 0.2 degrees 2-theta. In other embodiments, the tromethamine salt of fospropofol is characterized by an XRPD pattern comprising peaks at 10.0, 16.6, 17.3, 18.3, 24.7, and 25.2 degrees±0.2 degree 2-theta. In yet other embodiments, the tromethamine salt of fospropofol is characterized by an XRPD pattern comprising peaks at 6.0, 10.0, 10.7, 16.6, 17.3, 18.3, 24.7, and 25.2 degrees 0.2 degree 2-theta.

In some embodiments of the present disclosure, the tromethamine salt of fospropofol is characterized by an XRPD pattern comprising peaks at three or more of 6.0, 10.0, 10.7, 16.6, 17.3, 18.3, 24.7, and 25.2 degrees±0.2 degrees 2-theta. In some embodiments of the present disclosure, the tromethamine salt of fospropofol is characterized by an XRPD pattern comprising peaks at four or more of 6.0, 10.0, 10.7, 16.6, 17.3, 18.3, 24.7, and 25.2 degrees±0.2 degrees 2-theta. In some embodiments of the present disclosure, the tromethamine salt of fospropofol is characterized by an XRPD pattern comprising peaks at five or more of 6.0, 10.0, 10.7, 16.6, 17.3, 18.3, 24.7, and 25.2 degrees±0.2 degrees 2-theta. In some embodiments of the present disclosure, the tromethamine salt of fospropofol is characterized by an XRPD pattern comprising peaks at six or more of 6.0, 10.0, 10.7, 16.6, 17.3, 18.3, 24.7, and 25.2 degrees±0.2 degrees 2-theta. In some embodiments of the present disclosure, the tromethamine salt of fospropofol is characterized by an XRPD pattern comprising peaks at seven or more of 6.0, 10.0, 10.7, 16.6, 17.3, 18.3, 24.7, and 25.2 degrees±0.2 degrees 2-theta.

Figure 60:
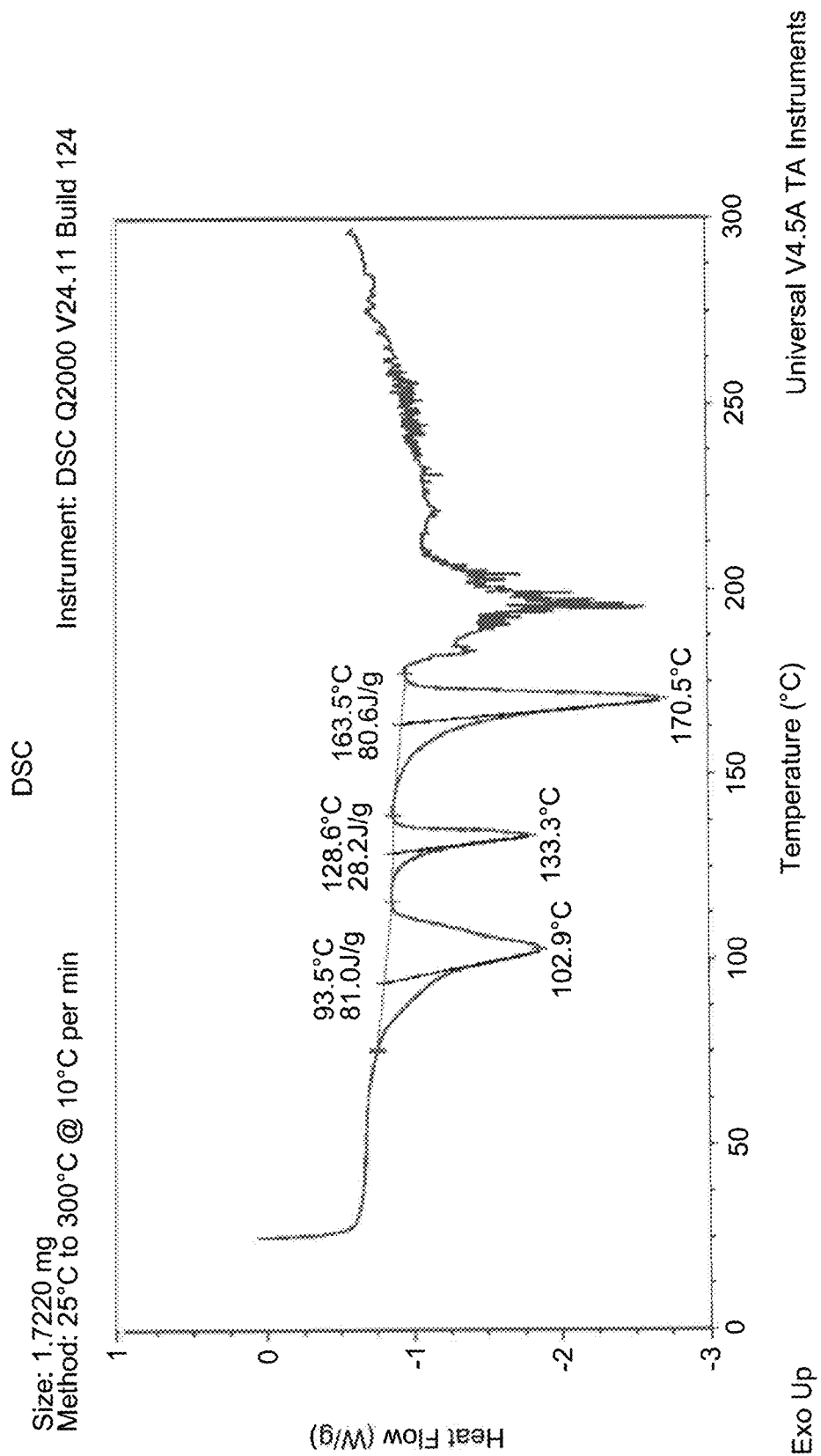
FIG. 60 shows a differential scanning calorimetry (DSC) profile of a tromethamine salt of fospropofol.

The tromethamine salt of fospropofol can be characterized by a DSC thermogram substantially as shown in FIG. 60. As FIG. 60 shows, the tromethamine salt of fospropofol produced endothermic peaks at 102.9° C., 133.3° C., and 170.5° C. when heated at a rate of 10° C./min. In some embodiments of the present disclosure, the tromethamine salt of fospropofol is characterized by a DSC thermogram comprising an endothermic peak at about 103° C., about 133° C., or about 171° C. when heated at a rate of 10° C./min.

In some embodiments of the present disclosure, the tromethamine salt of fospropofol is characterized by an XRPD pattern comprising peaks at one or more of 6.0, 10.0, 10.7, 16.6, 17.3, 18.3, 24.7, and 25.2 degrees±0.2 degrees 2-theta, and a DSC thermogram comprising an endothermic peak at about 103° C., about 133° C., or about 171° C. when heated at a rate of 10° C./min.

Figure 61:
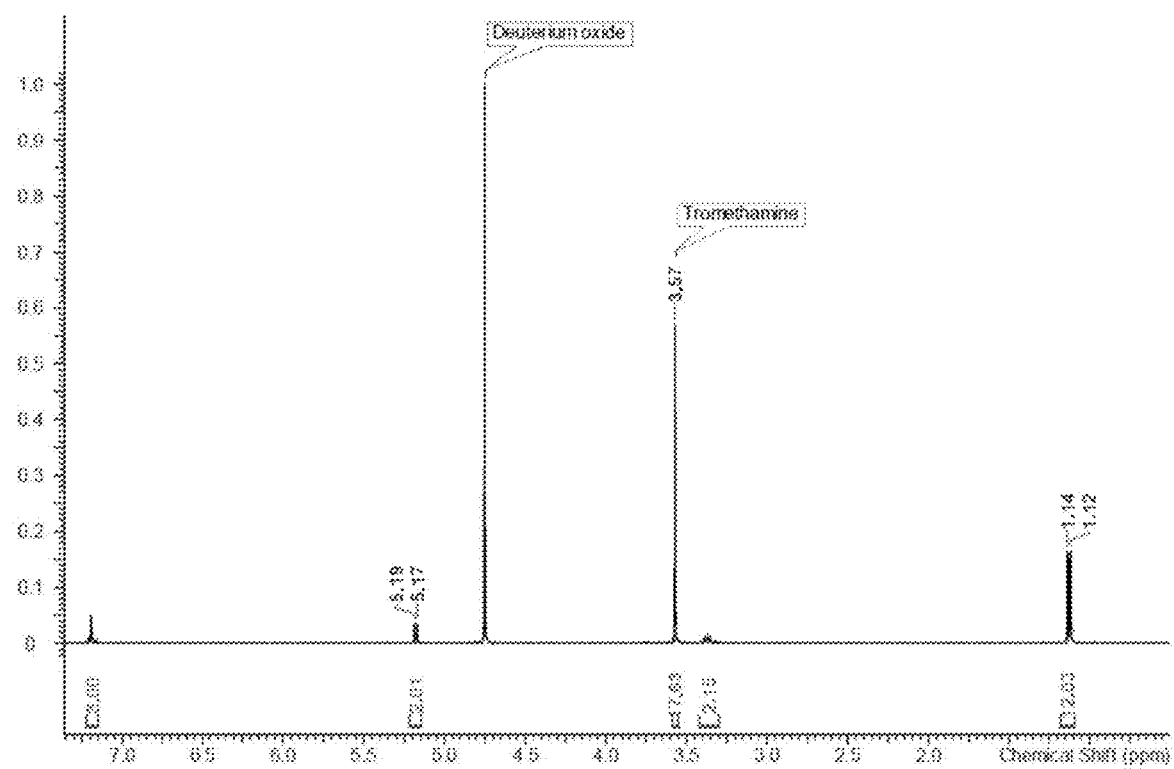
FIG. 61 shows a nuclear magnetic resonance (NMR) spectrum of a tromethamine salt of fospropofol.

In some embodiments, the tromethamine salt of fospropofol can be characterized by an NMR spectrum substantially as shown in FIG. 61.

In some embodiments, the pharmaceutically acceptable salt of fospropofol is the benethamine (i.e., N-benzyl-2-phenylethananine) salt.

Figure 62:
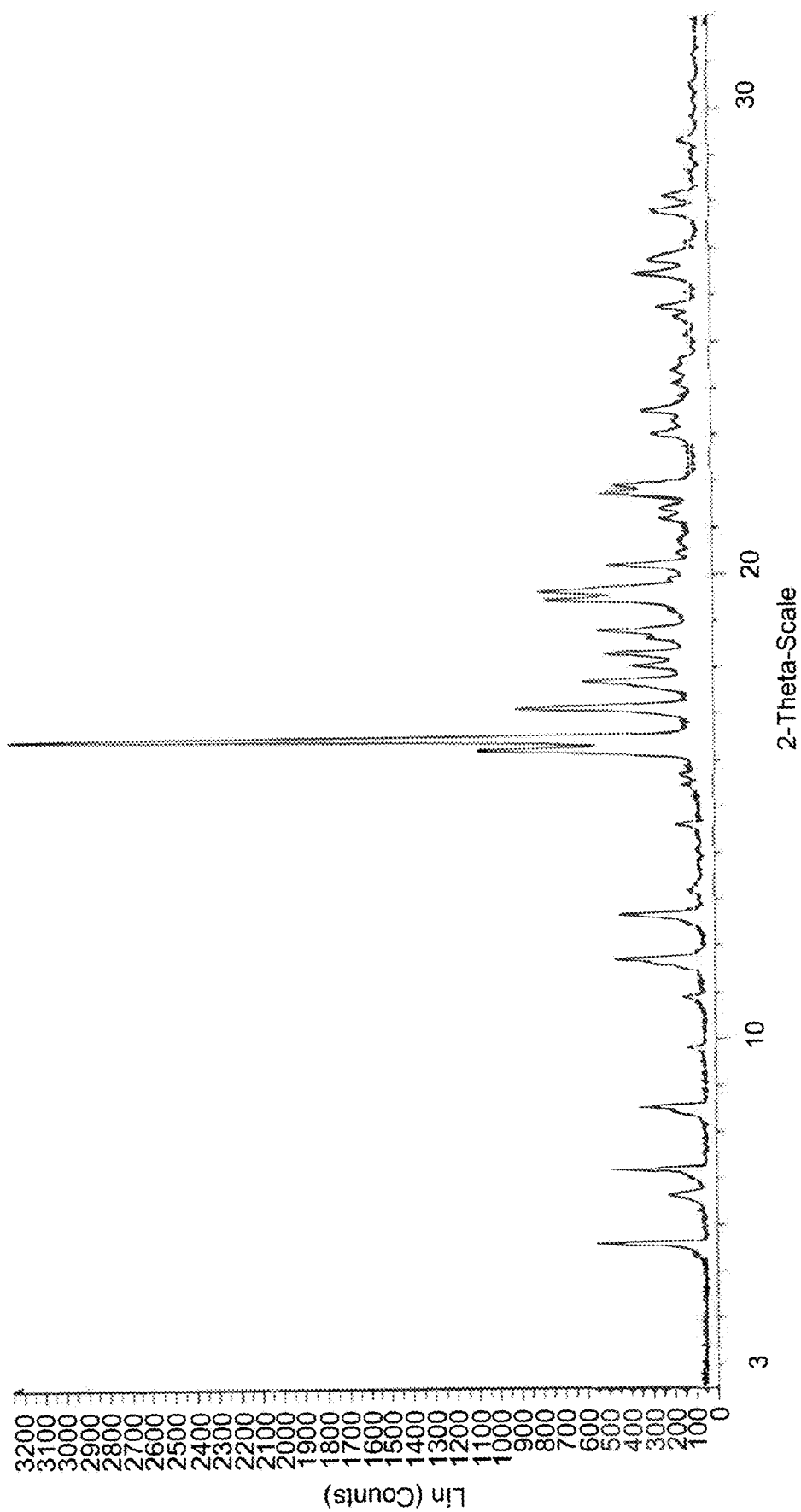
FIG. 62 shows an X-ray powder diffractogram (XRPD) of a benethamine salt of fospropofol.

In some embodiments, the benethamine salt of fospropofol has an XRPD substantially as shown in FIG. 62. The XRPD of the benethamine salt of fospropofol shown in FIG. 62 comprises reflection angles (degrees 2-theta±0.2 degrees 2-theta), and relative intensities as shown in Table 11:

TABLE 11

XRPD Data for benethamine salt of Fospropofol

| Angle (degrees 2-theta ± 0.2 degrees 2-theta) | Relative Intensity |
|---|---|
| 5.5 | 17.0 |
| 6.6 | 6.9 |
| 7.2 | 15.3 |
| 8.5 | 10.9 |
| 9.8 | 4.1 |
| 10.9 | 4.8 |
| 11.7 | 14.5 |
| 12.6 | 13.6 |
| 14.6 | 5.3 |
| 16.2 | 33.5 |
| 16.4 | 100.0 |
| 17.1 | 28.1 |
| 17.7 | 18.4 |
| 18.0 | 12.0 |
| 18.3 | 15.4 |
| 18.8 | 16.2 |
| 19.5 | 23.5 |
| 19.6 | 24.4 |
| 20.2 | 14.8 |
| 21.2 | 7.4 |
| 21.4 | 7.3 |
| 21.7 | 15.7 |
| 21.9 | 14.0 |
| 23.0 | 8.5 |
| 23.5 | 9.9 |
| 25.5 | 4.8 |
| 25.8 | 7.4 |
| 26.5 | 11.0 |
| 26.7 | 8.5 |
| 27.8 | 8.3 |
| 28.1 | 6.5 |

In some embodiments of the present disclosure, the benethamine salt of fospropofol is characterized by an XRPD pattern comprising a peak at one of the angles listed in Table 11. In other aspects, the benethamine salt of fospropofol is characterized by an XRPD pattern comprising more than one peak at one of the angles listed in Table 11 above. In other aspects, the benethamine salt of fospropofol is characterized by an XRPD pattern comprising two peaks selected from the angles listed in Table 11 above. In other aspects, the benethamine salt of fospropofol is characterized by an XRPD pattern comprising three peaks selected from the angles listed in Table 11 above. In other aspects, the benethamine salt of fospropofol is characterized by an XRPD pattern comprising four peaks selected from the angles listed in Table 11 above. In other aspects, the benethamine salt of fospropofol is characterized by an XRPD pattern comprising five peaks selected from the angles listed in Table 11 above. In other aspects, the benethamine salt of fospropofol is characterized by an XRPD pattern comprising six peaks selected from the angles listed in Table 11 above. In other aspects, the benethamine salt of fospropofol is characterized by an XRPD pattern comprising seven peaks selected from the angles listed in Table 11 above. In other aspects, the benethamine salt of fospropofol is characterized by an XRPD pattern comprising eight peaks selected from the angles listed in Table 11 above.

In other aspects, the benethamine salt of fospropofol is characterized by an XRPD pattern comprising nine peaks selected from the angles listed in Table 11 above. In other aspects, the benethamine salt of fospropofol is characterized by an XRPD pattern comprising ten peaks selected from the angles listed in Table 11 above. In other aspects, the benethamine salt of fospropofol is characterized by an XRPD pattern comprising more than ten peaks selected from the angles listed in Table 11 above.

In some embodiments, the benethamine salt of fospropofol is characterized by an XRPD pattern comprising a peak at 16.4 degrees±0.2 degrees 2-theta. In other embodiments, the benethamine salt of fospropofol is characterized by an XRPD pattern comprising peaks at 8.5, 11.7, 12.6, and 16.4 degrees±0.2 degrees 2-theta. In other embodiments, the benethamine salt of fospropofol is characterized by an XRPD pattern comprising peaks at 5.5, 7.2, 8.5, 11.7, 12.6, and 16.4 degrees±0.2 degree 2-theta. In yet other embodiments, the benethamine salt of fospropofol is characterized by an XRPD pattern comprising peaks at 5.5, 7.2, 8.5, 11.7, 12.6, 16.4, 17.7, and 19.6 degrees±0.2 degree 2-theta.

In some embodiments of the present disclosure, the benethamine salt of fospropofol is characterized by an XRPD pattern comprising peaks at three or more of 5.5, 7.2, 8.5, 11.7, 12.6, 16.4, 17.7, and 19.6 degrees±0.2 degrees 2-theta. In some embodiments of the present disclosure, the benethamine salt of fospropofol is characterized by an XRPD pattern comprising peaks at four or more of 5.5, 7.2, 8.5, 11.7, 12.6, 16.4, 17.7, and 19.6 degrees±0.2 degrees 2-theta. In some embodiments of the present disclosure, the benethamine salt of fospropofol is characterized by an XRPD pattern comprising peaks at five or more of 5.5, 7.2, 8.5, 11.7, 12.6, 16.4, 17.7, and 19.6 degrees±0.2 degrees 2-theta. In some embodiments of the present disclosure, the benethamine salt of fospropofol is characterized by an XRPD pattern comprising peaks at six or more of 5.5, 7.2, 8.5, 11.7, 12.6, 16.4, 17.7, and 19.6 degrees±0.2 degrees 2-theta.

Figure 63:
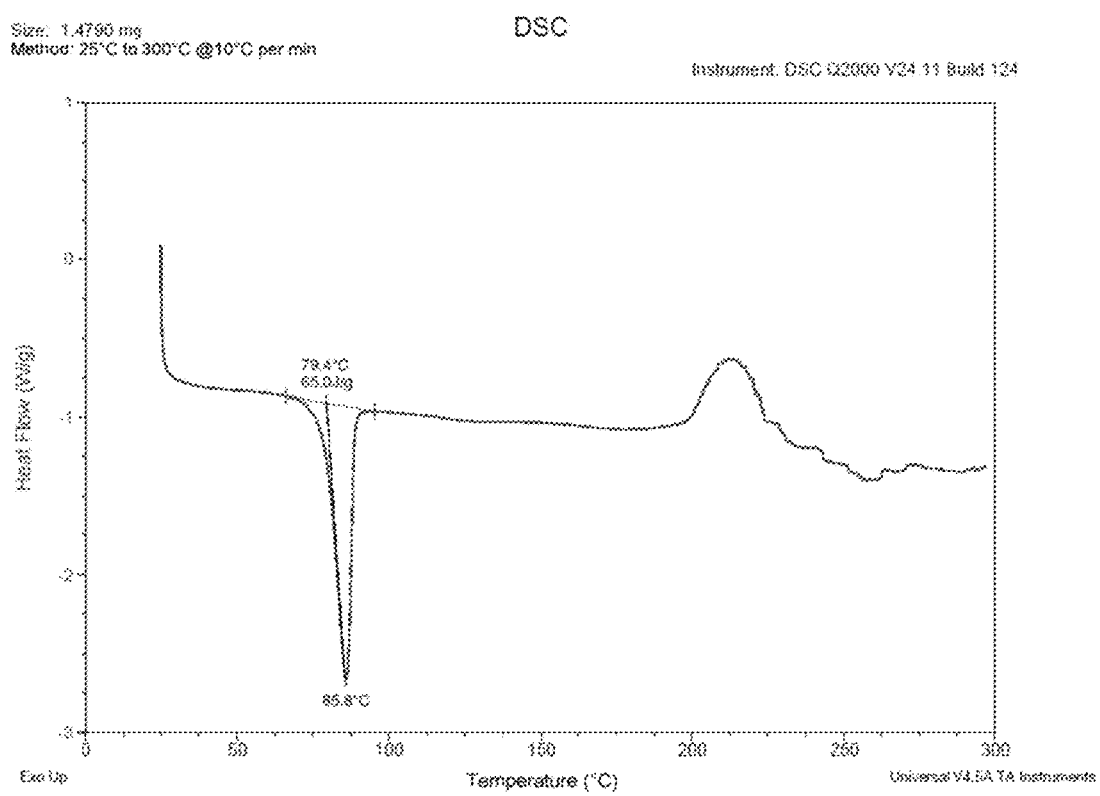
FIG. 63 shows a differential scanning calorimetry (DSC) profile of a benethamine salt of fospropofol.

The benethamine salt of fospropofol can be characterized by a DSC thermogram substantially as shown in FIG. 63. As FIG. 63 shows, the benethamine salt of fospropofol produced endothermic peaks at 85.8° C. when heated at a rate of 10° C./min. In some embodiments of the present disclosure, the benethamine salt of fospropofol is characterized by a DSC thermogram comprising an endothermic peak at about 86° C. when heated at a rate of 10° C./min.

In some embodiments of the present disclosure, the benethamine salt of fospropofol is characterized by an XRPD pattern comprising peaks at one or more of 5.5, 7.2, 8.5, 11.7, 12.6, 16.4, 17.7, and 19.6 degrees±0.2 degrees 2-theta, and a DSC thermogram comprising an endothermic peak at about 86° C. when heated at a rate of 10° C./min.

Figure 64:
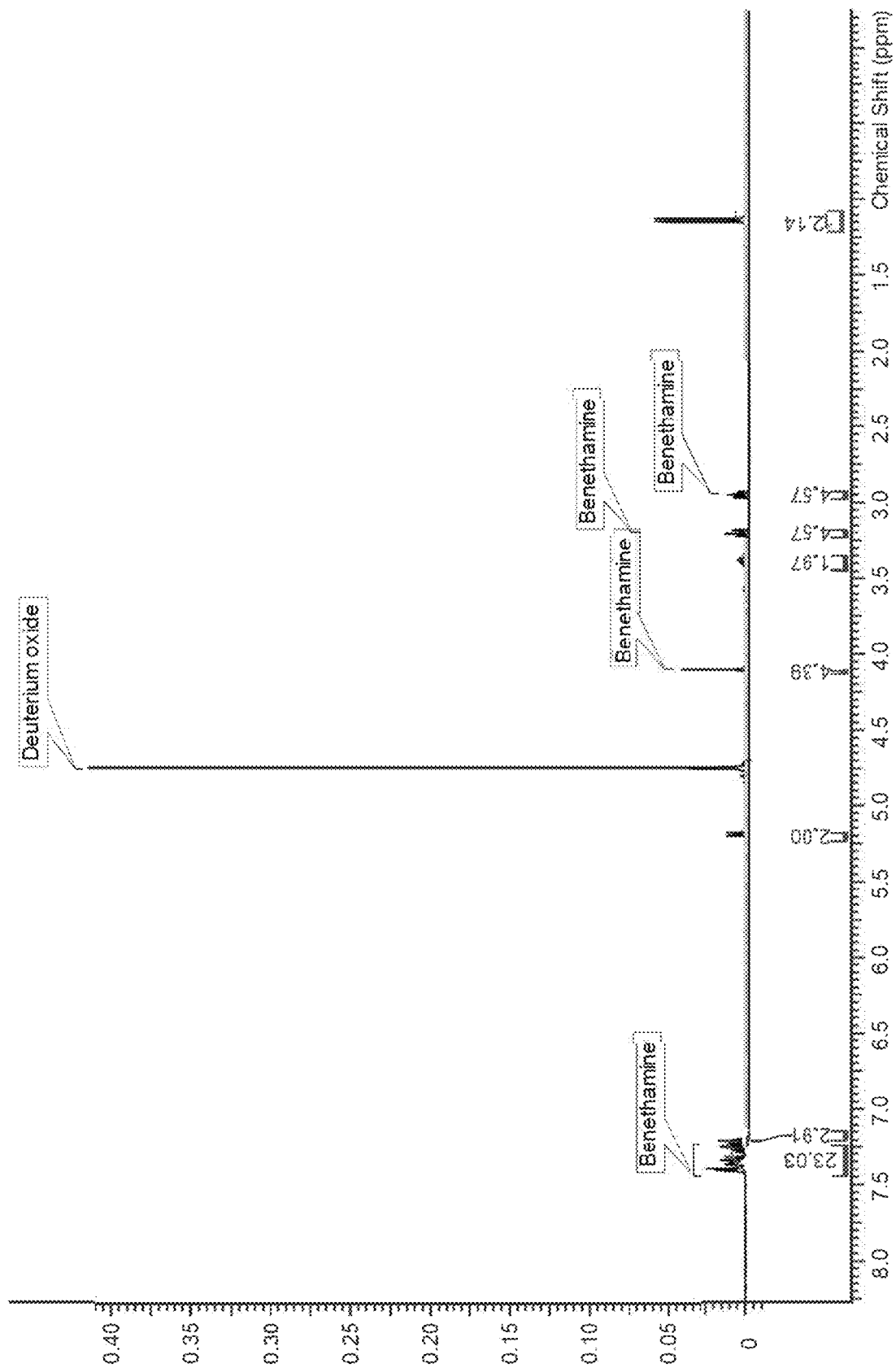
FIG. 64 shows a nuclear magnetic resonance (NMR) spectrum of a benethamine salt of fospropofol.

In some embodiments, the benethamine salt of fospropofol can be characterized by an NMR spectrum substantially as shown in FIG. 64.

In some embodiments, the pharmaceutically acceptable salt of fospropofol is the histidine salt.

Figure 65:
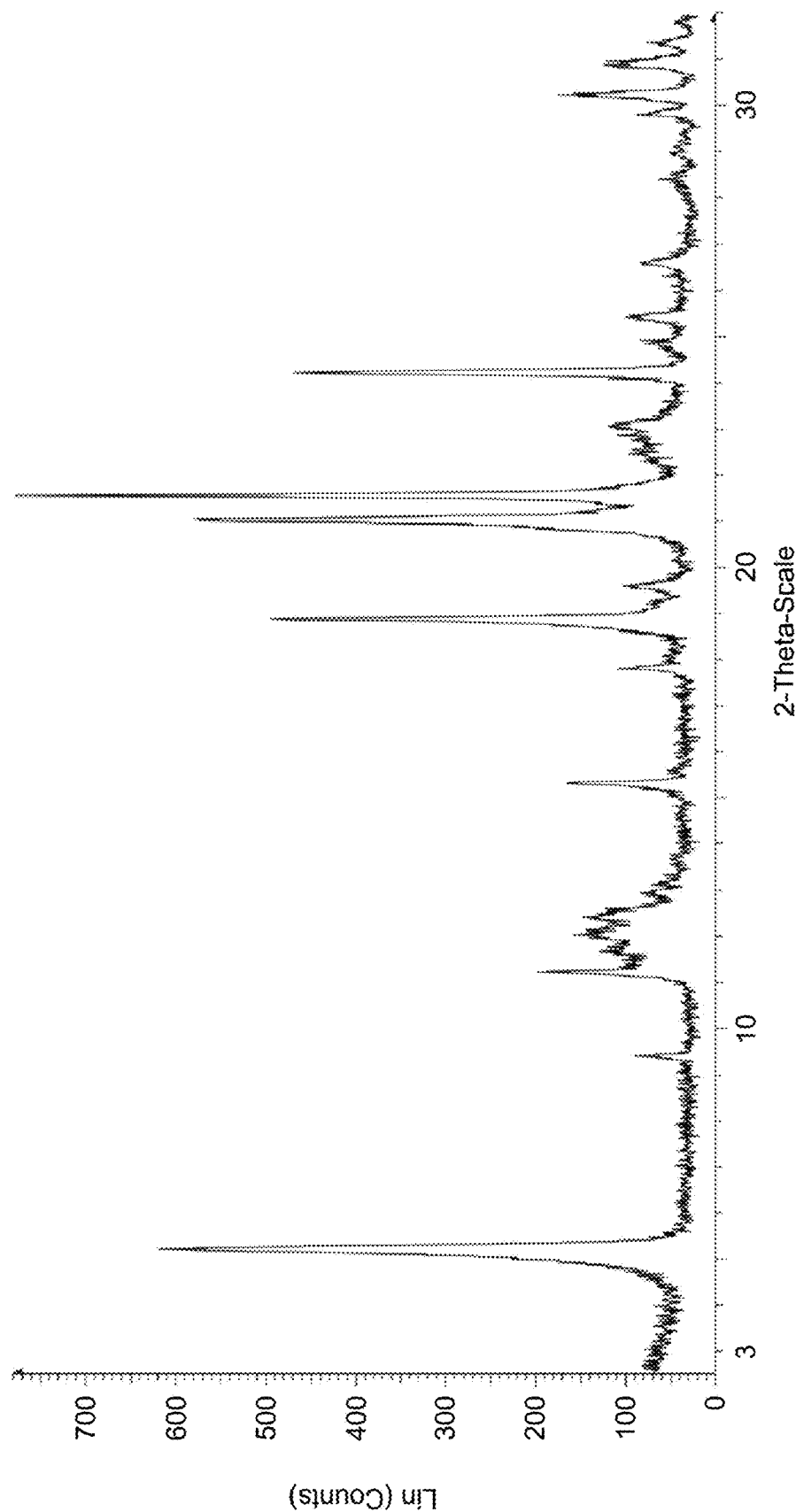
FIG. 65 shows an X-ray powder diffractogram (XRPD) of a histidine salt of fospropofol.

In some embodiments, the histidine salt of fospropofol has an XRPD substantially as shown in FIG. 65. The XRPD of the histidine salt of fospropofol shown in FIG. 65 comprises reflection angles (degrees 2-theta±0.2 degrees 2-theta), and relative intensities as shown in Table 12:

TABLE 12

XRPD Data for histidine salt of Fospropofol

| Angle (degrees 2-theta ± 0.2 degrees 2-theta) | Relative Intensity |
|---|---|
| 5.2 | 79.7 |
| 9.4 | 11.6 |
| 11.2 | 25.7 |
| 11.7 | 16.3 |
| 12.0 | 20.3 |
| 12.4 | 19.0 |
| 15.3 | 20.8 |
| 17.8 | 14.3 |
| 18.9 | 63.5 |
| 19.6 | 13.1 |
| 21.1 | 74.3 |
| 21.5 | 100.0 |
| 23.1 | 15.3 |
| 24.2 | 60.4 |
| 25.4 | 12.9 |
| 26.6 | 10.3 |
| 29.8 | 11.7 |
| 30.2 | 22.3 |
| 30.9 | 15.9 |
| 31.4 | 10.0 |

In some embodiments of the present disclosure, the histidine salt of fospropofol is characterized by an XRPD pattern comprising a peak at one of the angles listed in Table 12. In other aspects, the histidine salt of fospropofol is characterized by an XRPD pattern comprising more than one peak at one of the angles listed in Table 12 above. In other aspects, the histidine salt of fospropofol is characterized by an XRPD pattern comprising two peaks selected from the angles listed in Table 12 above. In other aspects, the histidine salt of fospropofol is characterized by an XRPD pattern comprising three peaks selected from the angles listed in Table 12 above. In other aspects, the histidine salt of fospropofol is characterized by an XRPD pattern comprising four peaks selected from the angles listed in Table 12 above. In other aspects, the histidine salt of fospropofol is characterized by an XRPD pattern comprising five peaks selected from the angles listed in Table 12 above. In other aspects, the histidine salt of fospropofol is characterized by an XRPD pattern comprising six peaks selected from the angles listed in Table 12 above. In other aspects, the histidine salt of fospropofol is characterized by an XRPD pattern comprising seven peaks selected from the angles listed in Table 12 above. In other aspects, the histidine salt of fospropofol is characterized by an XRPD pattern comprising eight peaks selected from the angles listed in Table 12 above. In other aspects, the histidine salt of fospropofol is characterized by an XRPD pattern comprising nine peaks selected from the angles listed in Table 12 above. In other aspects, the histidine salt of fospropofol is characterized by an XRPD pattern comprising ten peaks selected from the angles listed in Table 12 above. In other aspects, the histidine salt of fospropofol is characterized by an XRPD pattern comprising more than ten peaks selected from the angles listed in Table 12 above.

In some embodiments, the histidine salt of fospropofol is characterized by an XRPD pattern comprising a peak at 11.2, 15.3, and 18.9 degrees±0.2 degrees 2-theta. In other embodiments, the histidine salt of fospropofol is characterized by an XRPD pattern comprising peaks at 18.9, 21.1, 21.5, and 24.2 degrees±0.2 degrees 2-theta. In other embodiments, the histidine salt of fospropofol is characterized by an XRPD pattern comprising peaks at 18.9, 21.1, 21.5, 24.2, and 30.2 degrees±0.2 degree 2-theta. In yet other embodiments, the histidine salt of fospropofol is characterized by an XRPD pattern comprising peaks at 11.2, 15.3, 18.9, 21.1, 21.5, 24.2, and 30.2 degrees±0.2 degree 2-theta.

In some embodiments of the present disclosure, the histidine salt of fospropofol is characterized by an XRPD pattern comprising peaks at three or more of 11.2, 15.3, 18.9, 21.1, 21.5, 24.2, and 30.2 degrees±0.2 degrees 2-theta. In some embodiments of the present disclosure, the histidine salt of fospropofol is characterized by an XRPD pattern comprising peaks at four or more of 11.2, 15.3, 18.9, 21.1, 21.5, 24.2, and 30.2 degrees±0.2 degrees 2-theta. In some embodiments of the present disclosure, the histidine salt of fospropofol is characterized by an XRPD pattern comprising peaks at five or more of 11.2, 15.3, 18.9, 21.1, 21.5, 24.2, and 30.2 degrees±0.2 degrees 2-theta. In some embodiments of the present disclosure, the histidine salt of fospropofol is characterized by an XRPD pattern comprising peaks at six or more of 11.2, 15.3, 18.9, 21.1, 21.5, 24.2, and 30.2 degrees 10.2 degrees 2-theta.

Figure 66:
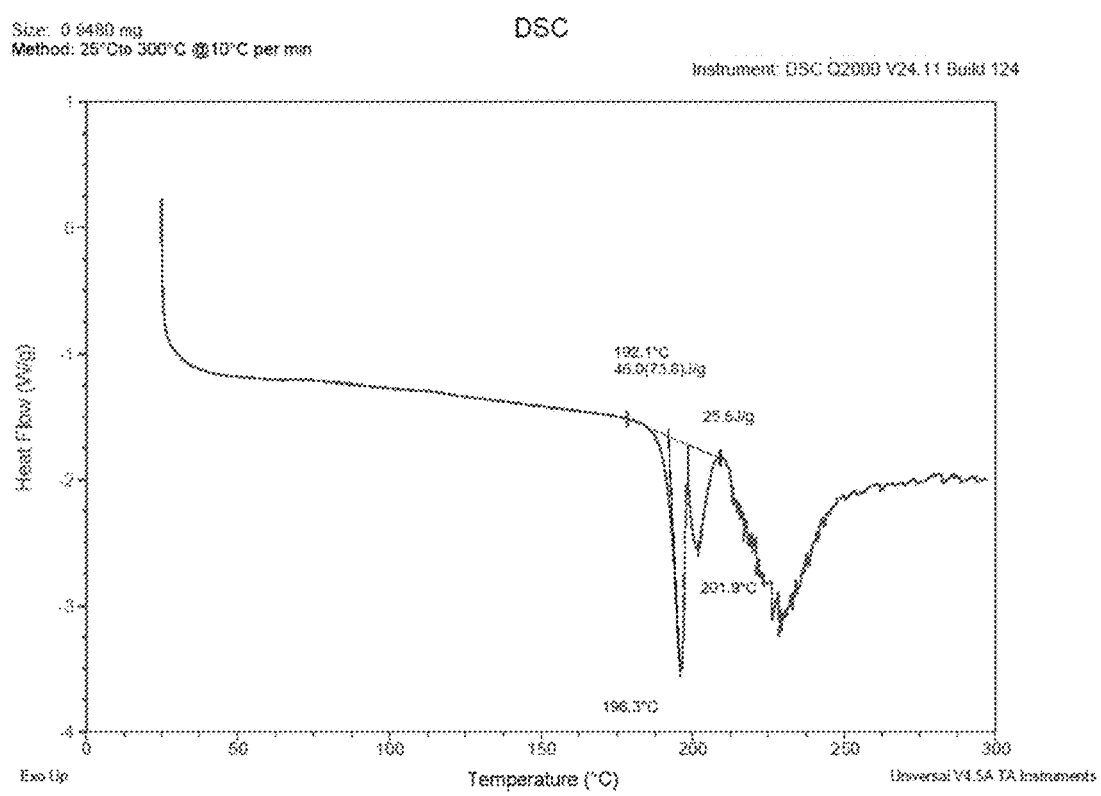
FIG. 66 shows a differential scanning calorimetry (DSC) profile of a histidine salt of fospropofol.

The histidine salt of fospropofol can be characterized by a DSC thermogram substantially as shown in FIG. 66. As FIG. 66 shows, the histidine salt of fospropofol produced endothermic peaks at 196.3° C. and 201.9° C. when heated at a rate of 10° C./min. In some embodiments of the present disclosure, the histidine salt of fospropofol is characterized by a DSC thermogram comprising an endothermic peak at about 196° C. or 202° C. when heated at a rate of 10° C./min.

In some embodiments of the present disclosure, the histidine salt of fospropofol is characterized by an XRPD pattern comprising peaks at one or more of 11.2, 15.3, 18.9, 21.1, 21.5, 24.2, and 30.2 degrees±0.2 degrees 2-theta, and a DSC thermogram comprising an endothermic peak at about 196° C. or 202° C. when heated at a rate of 10° C./min.

Figure 67:
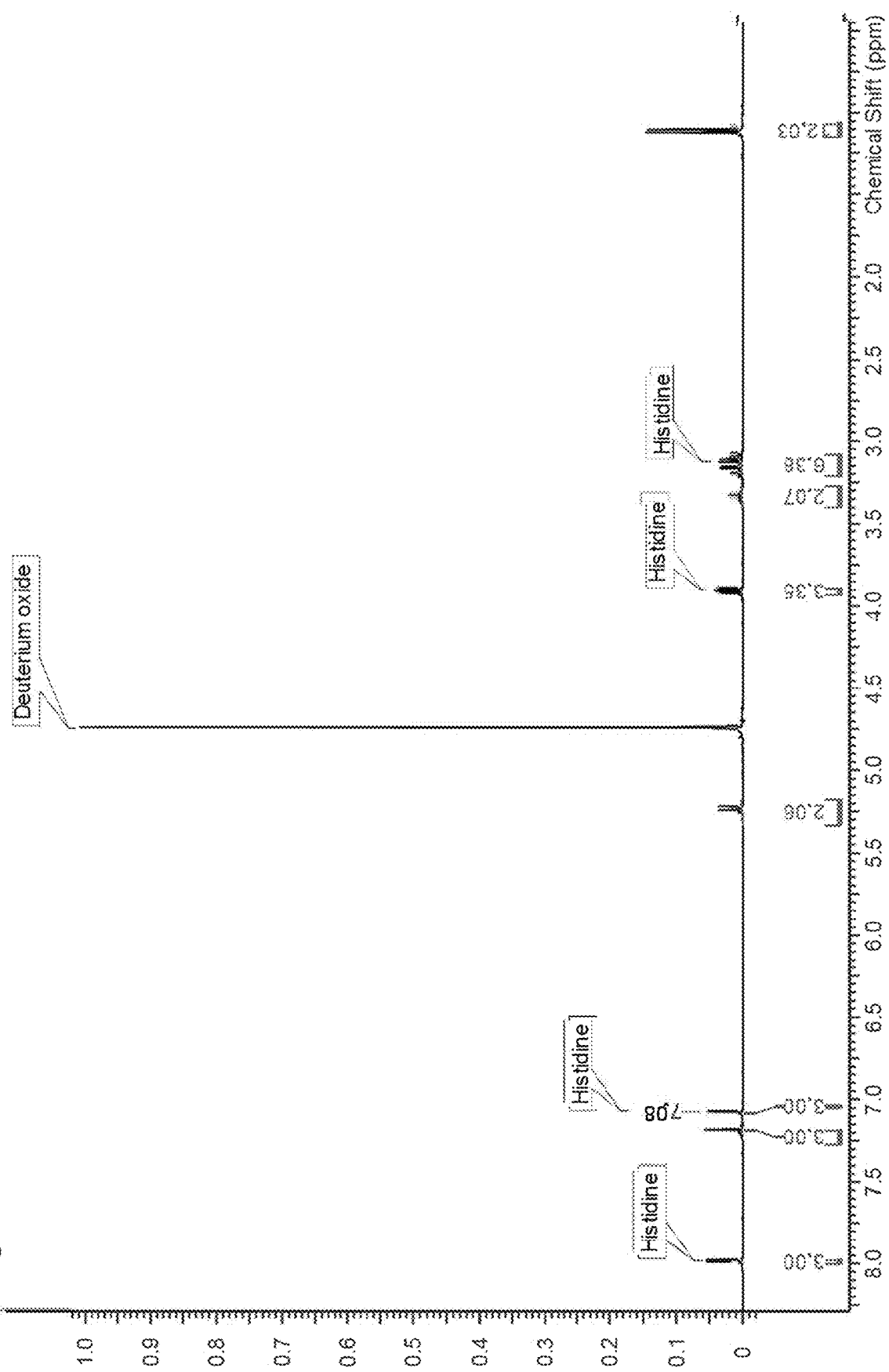
FIG. 67 shows a nuclear magnetic resonance (NMR) spectrum of a histidine salt of fospropofol.

In some embodiments, the histidine salt of fospropofol can be characterized by an NMR spectrum substantially as shown in FIG. 67.

In some embodiments, the pharmaceutically acceptable salt of fospropofol is the calcium salt.

Figure 68:
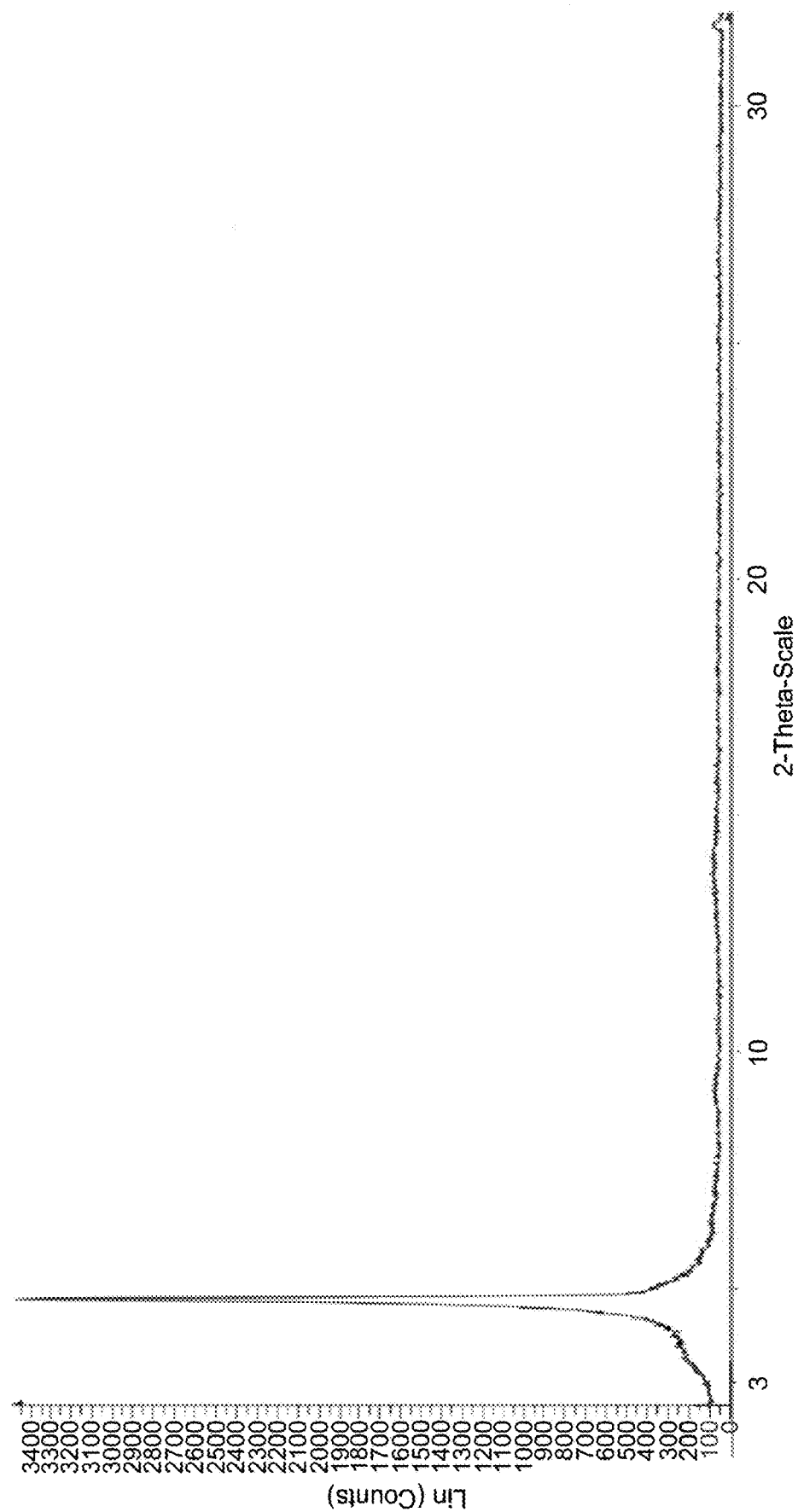
FIG. 68 shows an X-ray powder diffractogram (XRPD) of a calcium salt of fospropofol (Form I).

In some embodiments, the calcium salt of fospropofol (Form I) has an XRPD substantially as shown in FIG. 68. The Form I calcium salt of fospropofol has a single peak at 4.7 degrees 2-theta±0.2 degrees 2-theta.

Figure 69:
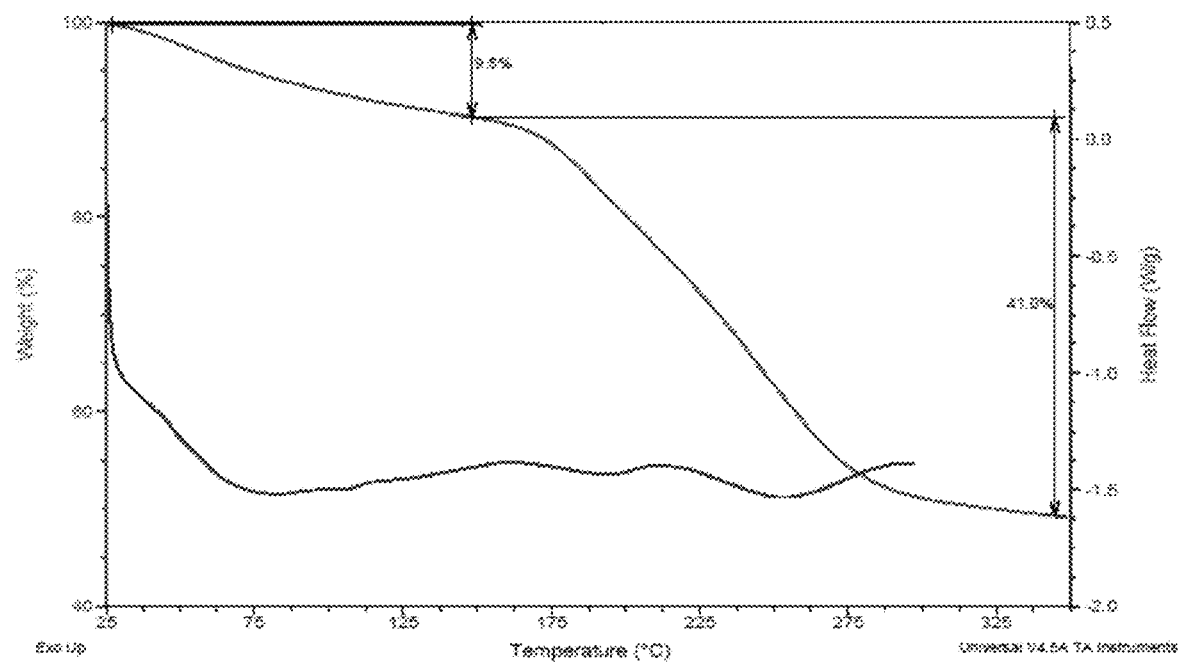
FIG. 69 shows a thermogravimetric analysis (TGA) profile of a calcium salt of fospropofol (Form I).

In some embodiments, the Form I calcium salt of fospropofol can be characterized by a DSC thermogram substantially as shown in FIG. 69.

In other embodiments, the Form I calcium salt of fospropofol can be characterized by a TGA profile substantially as shown in FIG. 69. As FIG. 69 shows, the Form I calcium salt of fospropofol lost about 9.5% of its weight upon heating to 125° C., and about 41% of its weight upon heating to 325° C. a rate of 10° C./min.

Figure 70:
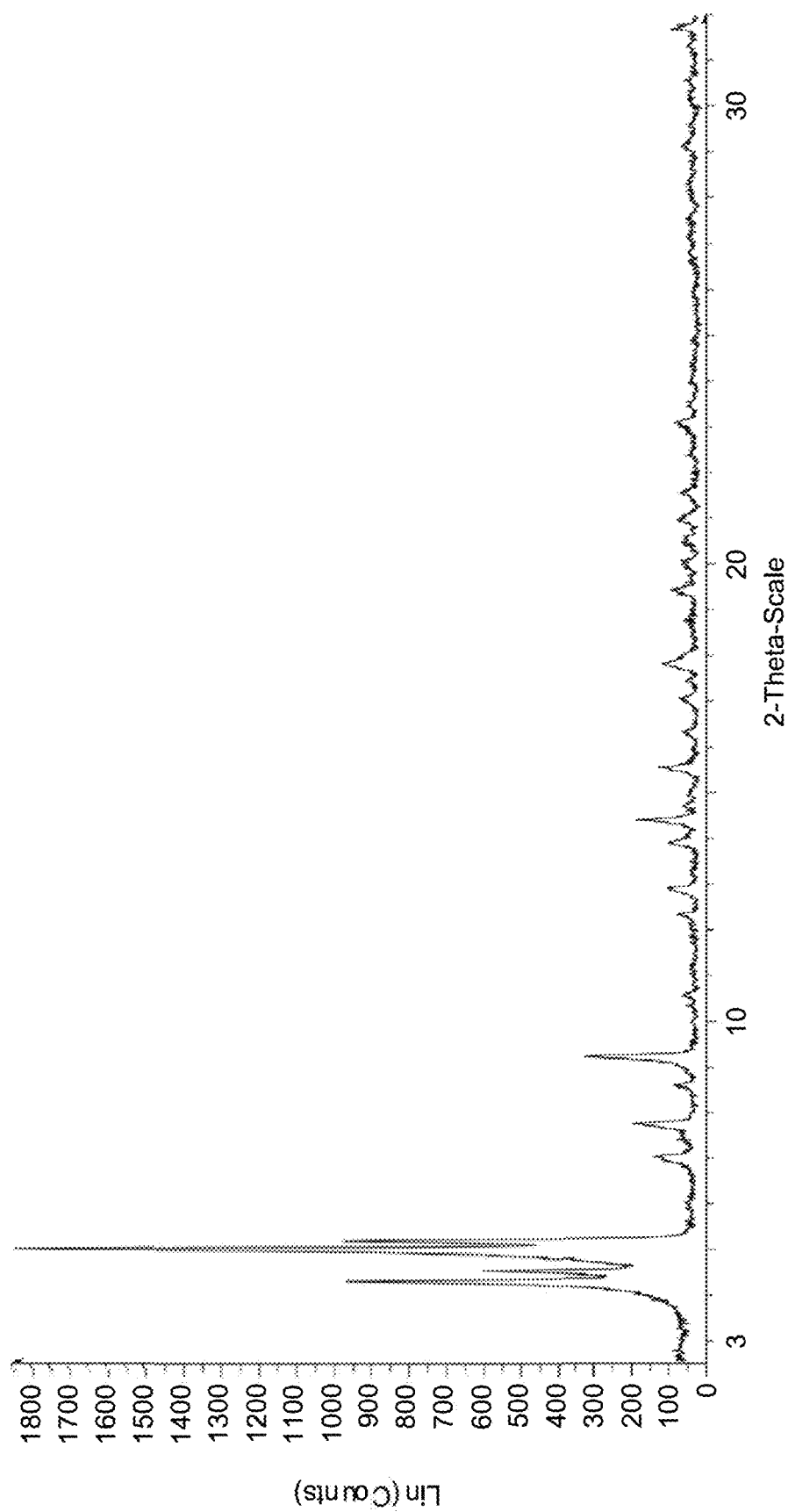
FIG. 70 shows an X-ray powder diffractogram (XRPD) of a calcium salt of fospropofol (Form II).

In other embodiments, the calcium salt of fospropofol (Form II) has an XRPD substantially as shown in FIG. 70. The XRPD of the Form II calcium salt of fospropofol shown in FIG. 70 comprises reflection angles (degrees 2-theta±0.2 degrees 2-theta), and relative intensities as shown in Table 13A:

TABLE 13A

XRPD Data for Form II calcium salt of Fospropofol

| Angle (degrees 2-theta ± 0.2 degrees 2-theta) | Relative Intensity |
| --- | --- |
| 4.3 | 52.7 |
| 4.5 | 32.0 |

TABLE 13A-continued

XRPD Data for Form II calcium salt of Fospropofol

| Angle (degrees 2-theta ± 0.2 degrees 2-theta) | Relative Intensity |
| --- | --- |
| 5.0 | 100.0 |
| 5.1 | 52.9 |
| 7.0 | 7.7 |
| 7.7 | 11.1 |
| 8.6 | 4.8 |
| 9.2 | 17.6 |
| 12.3 | 4.3 |
| 12.9 | 5.9 |
| 13.9 | 5.3 |
| 14.4 | 10.5 |
| 15.6 | 7.1 |
| 16.3 | 3.4 |
| 17.1 | 3.9 |
| 17.8 | 6.5 |
| 19.4 | 4.6 |
| 20.0 | 3.9 |
| 20.5 | 3.2 |
| 21.0 | 4.2 |
| 21.5 | 4.0 |

In some embodiments of the present disclosure, the calcium salt of fospropofol is characterized by an XRPD pattern comprising a peak at one of the angles listed in Table 13A. In other aspects, the calcium salt of fospropofol is characterized by an XRPD pattern comprising more than one peak at one of the angles listed in Table 13A above. In other aspects, the calcium salt of fospropofol is characterized by an XRPD pattern comprising two peaks selected from the angles listed in Table 13A above. In other aspects, the calcium salt of fospropofol is characterized by an XRPD pattern comprising three peaks selected from the angles listed in Table 13A above. In other aspects, the calcium salt of fospropofol is characterized by an XRPD pattern comprising four peaks selected from the angles listed in Table 13A above. In other aspects, the calcium salt of fospropofol is characterized by an XRPD pattern comprising five peaks selected from the angles listed in Table 13A above. In other aspects, the calcium salt of fospropofol is characterized by an XRPD pattern comprising six peaks selected from the angles listed in Table 13A above. In other aspects, the calcium salt of fospropofol is characterized by an XRPD pattern comprising seven peaks selected from the angles listed in Table 13A above. In other aspects, the calcium salt of fospropofol is characterized by an XRPD pattern comprising eight peaks selected from the angles listed in Table 13A above. In other aspects, the calcium salt of fospropofol is characterized by an XRPD pattern comprising nine peaks selected from the angles listed in Table 13A above. In other aspects, the calcium salt of fospropofol is characterized by an XRPD pattern comprising ten peaks selected from the angles listed in Table 13A above. In other aspects, the calcium salt of fospropofol is characterized by an XRPD pattern comprising more than ten peaks selected from the angles listed in Table 13A above.

In some embodiments, the calcium salt of fospropofol is characterized by an XRPD pattern comprising a peak at 5.1, 7.0, 7.7, 8.6, 9.2, and 14.4 degrees±0.2 degrees 2-theta. In other embodiments, the calcium salt of fospropofol is characterized by an XRPD pattern comprising peaks at 5.0, 5.1, 7.0, 7.7, 8.6, and 9.2 degrees±0.2 degrees 2-theta. In other embodiments, the calcium salt of fospropofol is characterized by an XRPD pattern comprising peaks at 5.0, 5.1, 7.0, 7.7, 8.6, 9.2, and 14.4 degrees±0.2 degree 2-theta. In yet other embodiments, the calcium salt of fospropofol is characterized by an XRPD pattern comprising peaks at 4.3, 4.5, 5.0, 5.1, 7.0, 7.7, 8.6, 9.2, and 14.4 degrees±0.2 degree 2-theta.

In some embodiments of the present disclosure, the calcium salt of fospropofol is characterized by an XRPD pattern comprising peaks at three or more of 4.3, 4.5, 5.0, 5.1, 7.0, 7.7, 8.6, 9.2, and 14.4 degrees±0.2 degrees 2-theta. In some embodiments of the present disclosure, the calcium salt of fospropofol is characterized by an XRPD pattern comprising peaks at four or more of 4.3, 4.5, 5.0, 5.1, 7.0, 7.7, 8.6, 9.2, and 14.4 degrees 0.2 degrees 2-theta. In some embodiments of the present disclosure, the calcium salt of fospropofol is characterized by an XRPD pattern comprising peaks at five or more of 4.3, 4.5, 5.0, 5.1, 7.0, 7.7, 8.6, 9.2, and 14.4 degrees±0.2 degrees 2-theta. In some embodiments of the present disclosure, the calcium salt of fospropofol is characterized by an XRPD pattern comprising peaks at six or more of 4.3, 4.5, 5.0, 5.1, 7.0, 7.7, 8.6, 9.2, and 14.4 degrees±0.2 degrees 2-theta.

Figure 71:
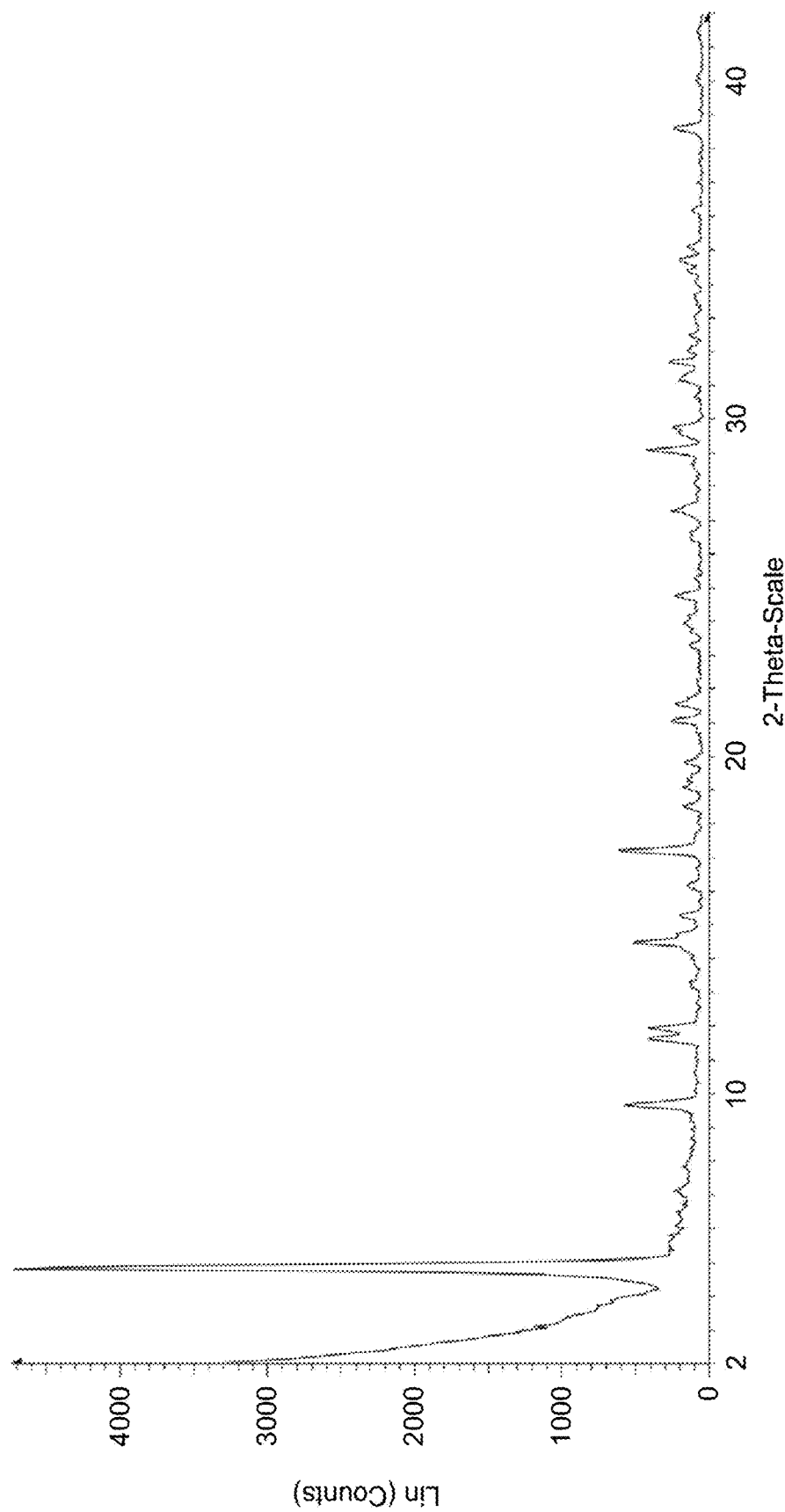
FIG. 71 shows an X-ray powder diffractogram (XRPD) of a calcium salt of fospropofol (Form III).

In yet other embodiments, the calcium salt of fospropofol (Form III) has an XRPD substantially as shown in FIG. 71. The XRPD of the Form III calcium salt of fospropofol shown in FIG. 71 comprises reflection angles (degrees 2-theta±0.2 degrees 2-theta), and relative intensities as shown in Table 13:

TABLE 13

XRPD Data for Form III calcium salt of Fospropofol

| Angle (degrees 2-theta ± 0.2 degrees 2-theta) | Relative Intensity |
| --- | --- |
| 4.8 | 100.0 |
| 9.7 | 12.0 |
| 11.6 | 9.3 |
| 11.9 | 8.8 |
| 13.2 | 2.9 |
| 14.5 | 11.3 |
| 15.3 | 4.0 |
| 16.1 | 3.2 |
| 17.2 | 13.0 |
| 18.3 | 3.7 |
| 19.1 | 3.2 |
| 19.3 | 3.4 |
| 19.8 | 3.9 |
| 21.1 | 5.4 |
| 21.6 | 4.8 |
| 23.3 | 2.6 |
| 24.0 | 3.5 |
| 24.8 | 4.9 |
| 26.5 | 2.6 |
| 27.3 | 5.2 |
| 29.1 | 9.3 |
| 29.6 | 4.6 |
| 29.8 | 5.7 |
| 31.2 | 4.2 |
| 31.7 | 5.9 |
| 34.5 | 3.1 |
| 34.8 | 4.3 |
| 35.1 | 3.2 |
| 38.6 | 5.1 |

In some embodiments of the present disclosure, the calcium salt of fospropofol is characterized by an XRPD pattern comprising a peak at one of the angles listed in Table 13. In other aspects, the calcium salt of fospropofol is characterized by an XRPD pattern comprising more than one peak at one of the angles listed in Table 13 above. In other aspects, the calcium salt of fospropofol is characterized by an XRPD pattern comprising two peaks selected from the angles listed in Table 13 above. In other aspects, the calcium salt of fospropofol is characterized by an XRPD pattern comprising three peaks selected from the angles listed in Table 13 above. In other aspects, the calcium salt of fospropofol is characterized by an XRPD pattern comprising four peaks selected from the angles listed in Table 13 above. In other aspects, the calcium salt of fospropofol is characterized by an XRPD pattern comprising five peaks selected from the angles listed in Table 13 above. In other aspects, the calcium salt of fospropofol is characterized by an XRPD pattern comprising six peaks selected from the angles listed in Table 13 above. In other aspects, the calcium salt of fospropofol is characterized by an XRPD pattern comprising seven peaks selected from the angles listed in Table 13 above. In other aspects, the calcium salt of fospropofol is characterized by an XRPD pattern comprising eight peaks selected from the angles listed in Table 13 above. In other aspects, the calcium salt of fospropofol is characterized by an XRPD pattern comprising nine peaks selected from the angles listed in Table 13 above. In other aspects, the calcium salt of fospropofol is characterized by an XRPD pattern comprising ten peaks selected from the angles listed in Table 13 above. In other aspects, the calcium salt of fospropofol is characterized by an XRPD pattern comprising more than ten peaks selected from the angles listed in Table 13 above.

In some embodiments, the calcium salt of fospropofol is characterized by an XRPD pattern comprising a peak at 4.8, and 9.7 degrees±0.2 degrees 2-theta. In other embodiments, the calcium salt of fospropofol is characterized by an XRPD pattern comprising peaks at 9.7, 11.6, 11.9, 14.5, and 17.2 degrees' 0.2 degrees 2-theta. In other embodiments, the calcium salt of fospropofol is characterized by an XRPD pattern comprising peaks at 11.6, 11.9, 14.5, and 17.2 degrees' 0.2 degree 2-theta. In yet other embodiments, the calcium salt of fospropofol is characterized by an XRPD pattern comprising peaks at 4.8, 9.7, 11.6, 11.9, 14.5, 17.2, and 29.1 degrees 0.2 degree 2-theta.

In some embodiments of the present disclosure, the calcium salt of fospropofol is characterized by an XRPD pattern comprising peaks at three or more of 4.8, 9.7, 11.6, 11.9, 14.5, 17.2, and 29.1 degrees±0.2 degrees 2-theta. In some embodiments of the present disclosure, the calcium salt of fospropofol is characterized by an XRPD pattern comprising peaks at four or more of 4.8, 9.7, 11.6, 11.9, 14.5, 17.2, and 29.1 degrees' 0.2 degrees 2-theta. In some embodiments of the present disclosure, the calcium salt of fospropofol is characterized by an XRPD pattern comprising peaks at five or more of 4.8, 9.7, 11.6, 11.9, 14.5, 17.2, and 29.1 degrees±0.2 degrees 2-theta. In some embodiments of the present disclosure, the calcium salt of fospropofol is characterized by an XRPD pattern comprising peaks at six or more of 4.8, 9.7, 11.6, 11.9, 14.5, 17.2, and 29.1 degrees' 0.2 degrees 2-theta.

In some embodiments, the pharmaceutically acceptable salt of fospropofol is the magnesium salt.

Figure 72:
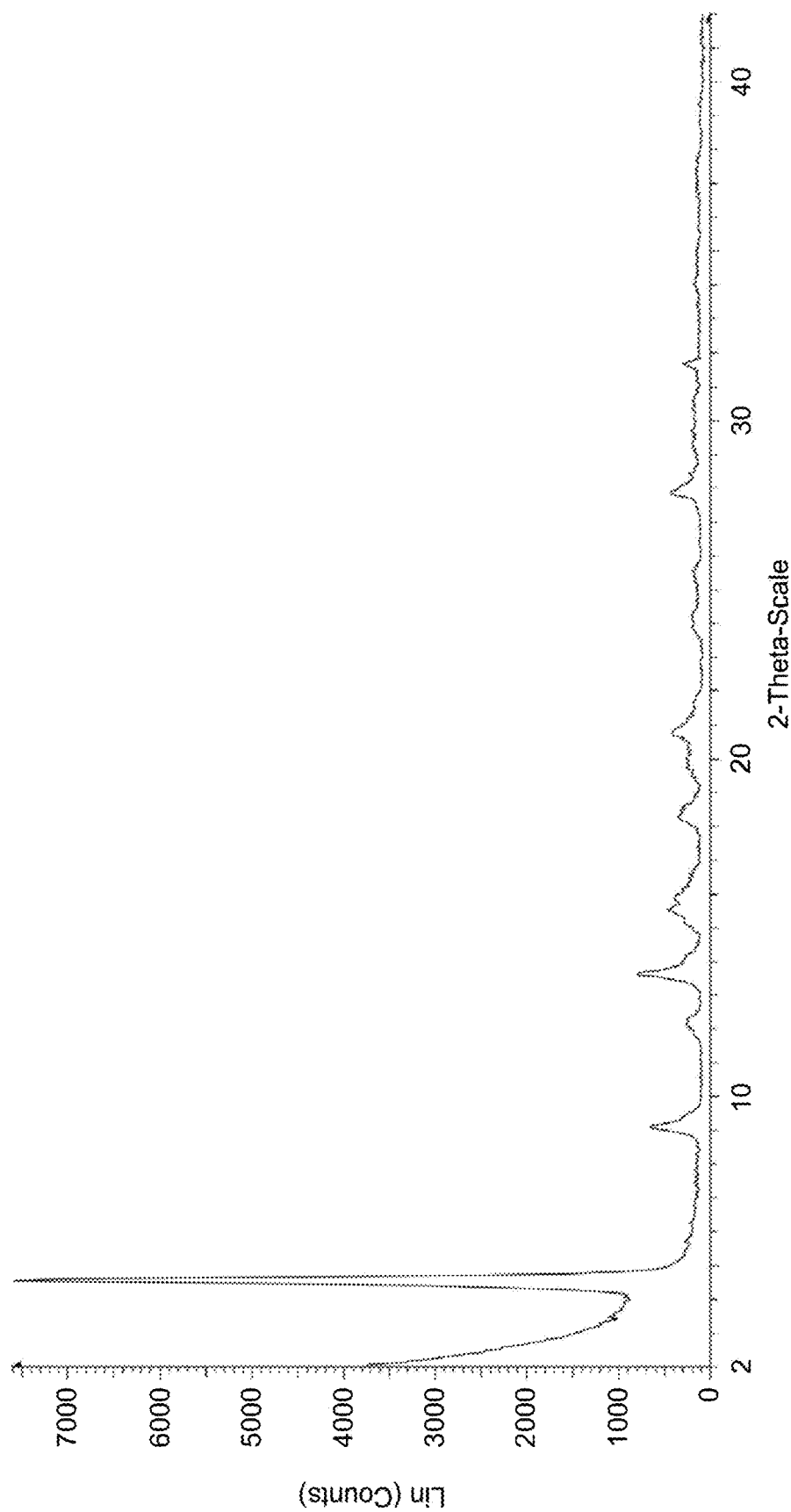
FIG. 72 shows an X-ray powder diffractogram (XRPD) of a magnesium salt of fospropofol.

In some embodiments, the magnesium salt of fospropofol has an XRPD substantially as shown in FIG. 72. The XRPD of the magnesium salt of fospropofol shown in FIG. 72 comprises reflection angles (degrees 2-theta±0.2 degrees 2-theta), and relative intensities as shown in Table 14:

TABLE 14

XRPD Data for magnesium salt of Fospropofol

| Angle (degrees 2-theta ± 0.2 degrees 2-theta) | Relative Intensity |
| --- | --- |
| 4.5 | 100.0 |
| 9.1 | 8.8 |

TABLE 14-continued

XRPD Data for magnesium salt of Fospropofol

| Angle (degrees 2-theta ± 0.2 degrees 2-theta) | Relative Intensity |
|---|---|
| 12.2 | 3.5 |
| 13.6 | 10.3 |
| 15.5 | 6.2 |
| 18.3 | 4.8 |
| 20.8 | 5.9 |
| 24.1 | 3.2 |
| 27.9 | 5.9 |
| 31.7 | 3.9 |

In some embodiments of the present disclosure, the magnesium salt of fospropofol is characterized by an XRPD pattern comprising a peak at one of the angles listed in Table 14. In other aspects, the magnesium salt of fospropofol is characterized by an XRPD pattern comprising more than one peak at one of the angles listed in Table 14 above. In other aspects, the magnesium salt of fospropofol is characterized by an XRPD pattern comprising two peaks selected from the angles listed in Table 14 above. In other aspects, the magnesium salt of fospropofol is characterized by an XRPD pattern comprising three peaks selected from the angles listed in Table 14 above. In other aspects, the magnesium salt of fospropofol is characterized by an XRPD pattern comprising four peaks selected from the angles listed in Table 14 above. In other aspects, the magnesium salt of fospropofol is characterized by an XRPD pattern comprising five peaks selected from the angles listed in Table 14 above. In other aspects, the magnesium salt of fospropofol is characterized by an XRPD pattern comprising six peaks selected from the angles listed in Table 14 above. In other aspects, the magnesium salt of fospropofol is characterized by an XRPD pattern comprising seven peaks selected from the angles listed in Table 14 above. In other aspects, the magnesium salt of fospropofol is characterized by an XRPD pattern comprising eight peaks selected from the angles listed in Table 14 above. In other aspects, the magnesium salt of fospropofol is characterized by an XRPD pattern comprising nine peaks selected from the angles listed in Table 14 above. In other aspects, the magnesium salt of fospropofol is characterized by an XRPD pattern comprising ten peaks selected from the angles listed in Table 14 above. In other aspects, the magnesium salt of fospropofol is characterized by an XRPD pattern comprising more than ten peaks selected from the angles listed in Table 14 above.

In some embodiments, the magnesium salt of fospropofol is characterized by an XRPD pattern comprising a peak at 4.5 degrees±0.2 degrees 2-theta. In other embodiments, the magnesium salt of fospropofol is characterized by an XRPD pattern comprising peaks at 4.5, 9.1, and 13.6 degrees±0.2 degrees 2-theta. In other embodiments, the magnesium salt of fospropofol is characterized by an XRPD pattern comprising peaks at 4.5, 9.1, 13.6, and 20.8 degrees±0.2 degree 2-theta. In yet other embodiments, the magnesium salt of fospropofol is characterized by an XRPD pattern comprising peaks at 4.5, 9.1, 13.6, 20.8, and 27.9 degrees±0.2 degree 2-theta.

In some embodiments of the present disclosure, the magnesium salt of fospropofol is characterized by an XRPD pattern comprising peaks at two or more of 4.5, 9.1, 13.6, 20.8, and 27.9 degrees±0.2 degrees 2-theta. In some embodiments of the present disclosure, the magnesium salt of fospropofol is characterized by an XRPD pattern comprising peaks at three or more of 4.5, 9.1, 13.6, 20.8, and 27.9 degrees±0.2 degrees 2-theta. In some embodiments of the present disclosure, the magnesium salt of fospropofol is characterized by an XRPD pattern comprising peaks at four or more of 4.5, 9.1, 13.6, 20.8, and 27.9 degrees±0.2 degrees 2-theta.

Figure 73:
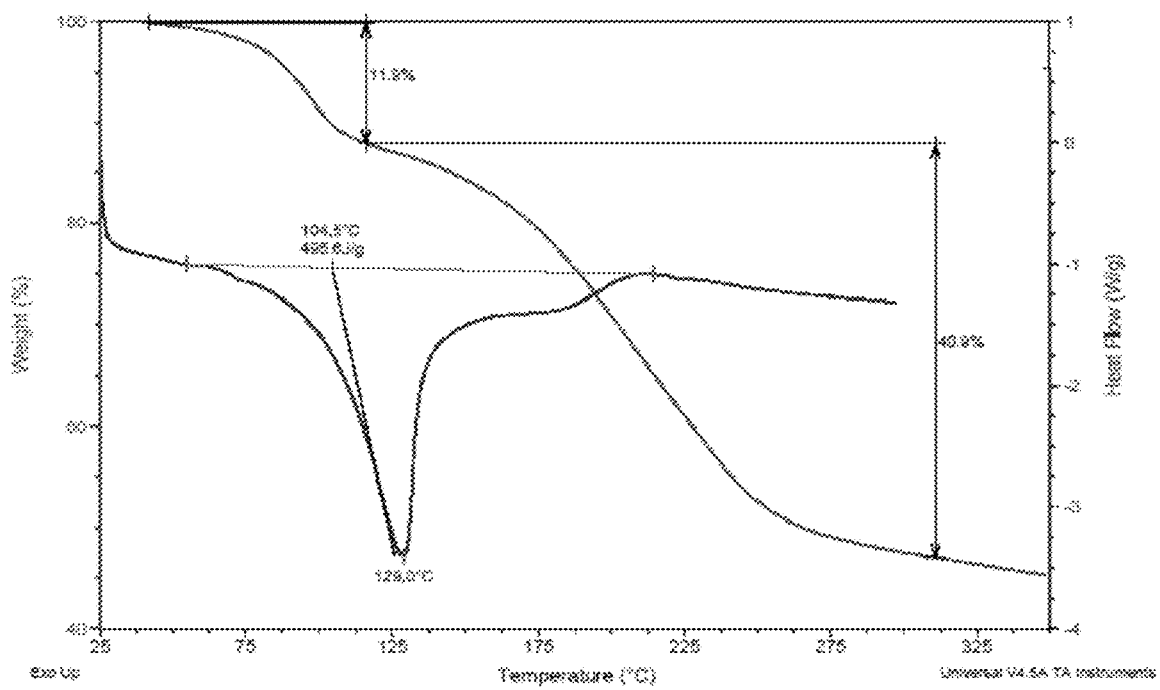
FIG. 73 shows a differential scanning calorimetry (DSC) profile and a thermogravimetric analysis profile (TGA) of a magnesium salt of fospropofol.

In some embodiments, the magnesium salt of fospropofol can be characterized by a DSC thermogram substantially as shown in FIG. 73. As FIG. 73 shows, the magnesium salt of fospropofol produced an endothermic peak at 129.0° C. when heated at a rate of 10° C./min. In some embodiments of the present disclosure, the magnesium salt of fospropofol is characterized by a DSC thermogram comprising an endothermic peak at about 129° C. when heated at a rate of 10° C./min.

In other embodiments, the magnesium salt of fospropofol can be characterized by a TGA profile substantially as shown in FIG. 73. As FIG. 73 shows, the magnesium salt of fospropofol lost about 12% of its weight upon heating to 125° C., and about 41% of its weight upon heating to 325° C. a rate of 10° C./min.

In some embodiments of the present disclosure, the magnesium salt of fospropofol is characterized by an XRPD pattern comprising peaks at 4.5, 9.1, 13.6, 20.8, and 27.9 degrees±0.2 degrees 2-theta, and a DSC thermogram comprising an endothermic peak at about 129° C. when heated at a rate of 10° C./min.

In some embodiments, the pharmaceutically acceptable salt of fospropofol is the zinc salt.

Figure 74:
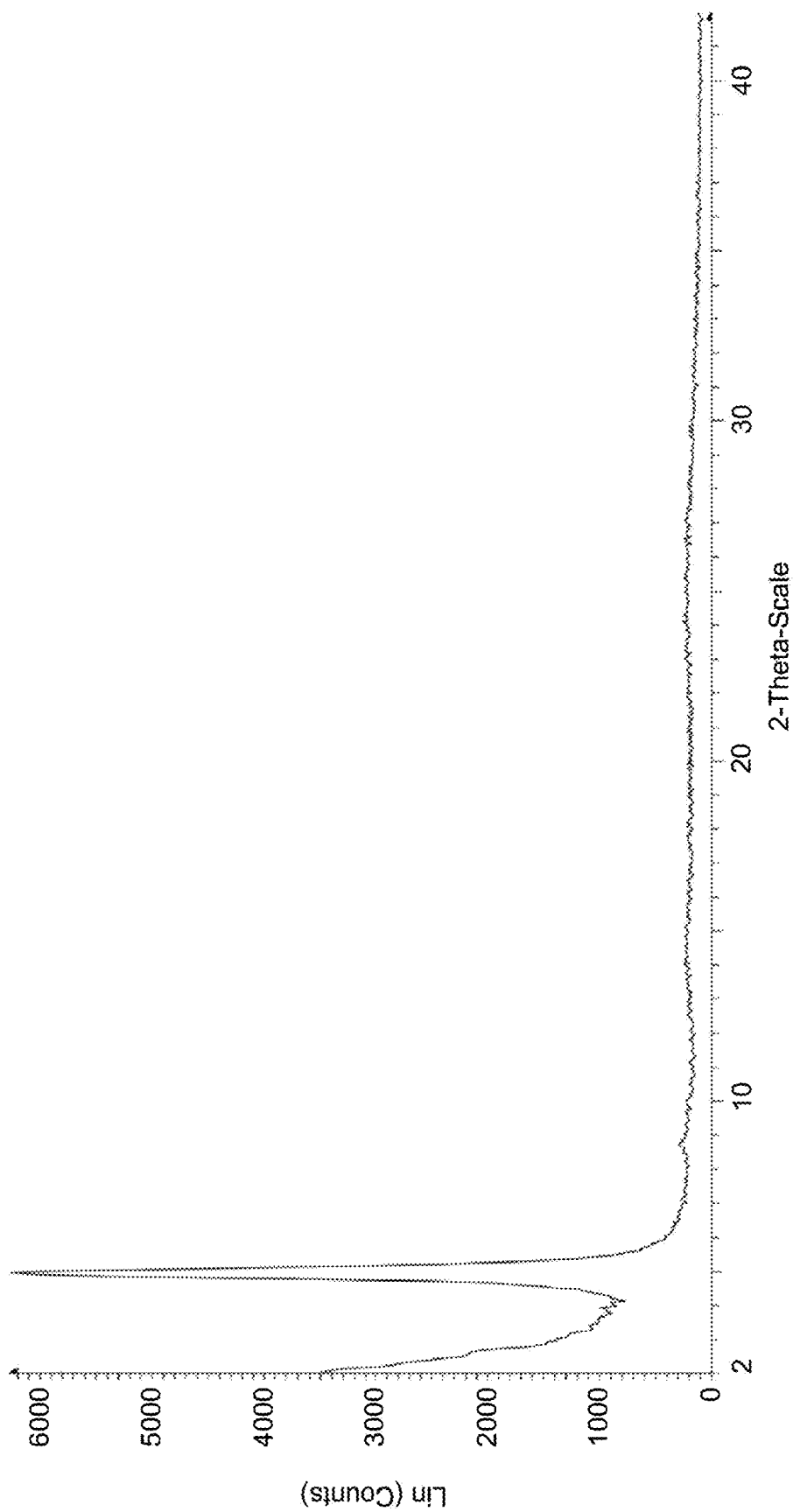
FIG. 74 shows an X-ray powder diffractogram (XRPD) of a zinc salt of fospropofol (Form II).

In some embodiments, the zinc salt of fospropofol (Form II) has an XRPD substantially as shown in FIG. 74. Form II of the zinc salt has a single peak at 4.9 degrees 2-theta±0.2 degrees 2-theta.

Figure 75:
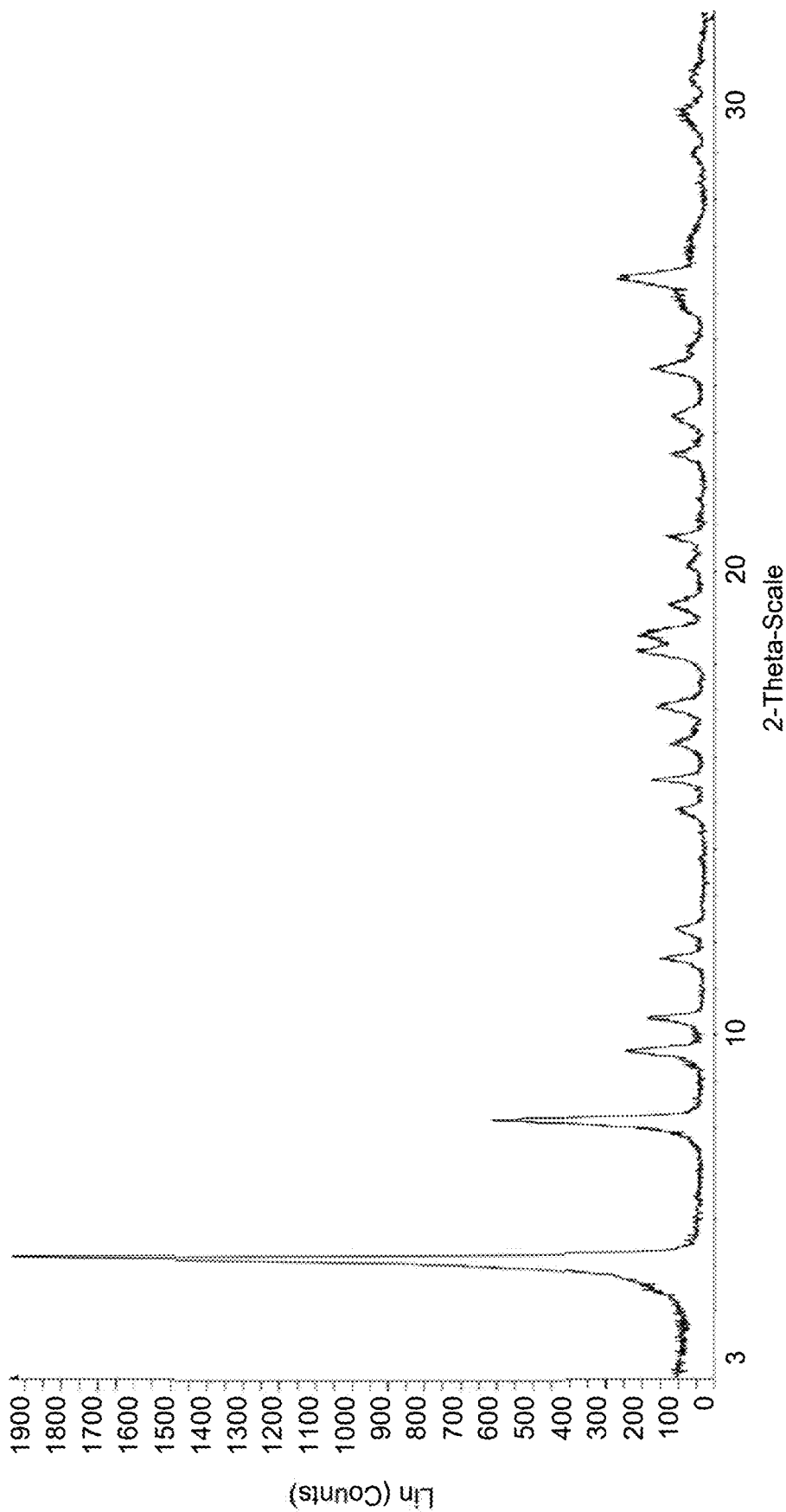
FIG. 75 shows an X-ray powder diffractogram (XRPD) of a zinc salt of fospropofol (Form I).

In some embodiments, the zinc salt of fospropofol (Form I) has an XRPD substantially as shown in FIG. 75. The XRPD of the Form I zinc salt of fospropofol shown in FIG. 75 comprises reflection angles (degrees 2-theta±0.2 degrees 2-theta), and relative intensities as shown in Table 15:

TABLE 15

XRPD Data for Form I zinc salt of Fospropofol

| Angle (degrees 2-theta ± 0.2 degrees 2-theta) | Relative Intensity |
|---|---|
| 5.1 | 100.0 |
| 8.1 | 32.0 |
| 9.6 | 12.5 |
| 10.3 | 9.7 |
| 11.6 | 7.5 |
| 12.2 | 5.7 |
| 14.8 | 5.7 |
| 15.5 | 9.2 |
| 16.2 | 6.3 |
| 17.0 | 8.2 |
| 18.2 | 10.9 |
| 18.6 | 10.5 |
| 19.2 | 6.0 |
| 20.1 | 4.3 |
| 20.7 | 6.5 |
| 22.5 | 5.7 |
| 23.3 | 6.2 |
| 24.3 | 8.9 |
| 26.3 | 13.8 |

In some embodiments of the present disclosure, the Form I zinc salt of fospropofol is characterized by an XRPD pattern comprising a peak at one of the angles listed in Table 15. In other aspects, the zinc salt of fospropofol is characterized by an XRPD pattern comprising more than one peak at one of the angles listed in Table 15 above. In other aspects, the zinc salt of fospropofol is characterized by an XRPD pattern comprising two peaks selected from the angles listed in Table 15 above. In other aspects, the zinc salt of fospropofol is characterized by an XRPD pattern comprising three peaks selected from the angles listed in Table 15 above. In other aspects, the zinc salt of fospropofol is characterized by an XRPD pattern comprising four peaks selected from the angles listed in Table 15 above. In other aspects, the zinc salt of fospropofol is characterized by an XRPD pattern comprising five peaks selected from the angles listed in Table 15 above. In other aspects, the zinc salt of fospropofol is characterized by an XRPD pattern comprising six peaks selected from the angles listed in Table 15 above. In other aspects, the zinc salt of fospropofol is characterized by an XRPD pattern comprising seven peaks selected from the angles listed in Table 15 above. In other aspects, the zinc salt of fospropofol is characterized by an XRPD pattern comprising eight peaks selected from the angles listed in Table 15 above. In other aspects, the zinc salt of fospropofol is characterized by an XRPD pattern comprising nine peaks selected from the angles listed in Table 15 above. In other aspects, the zinc salt of fospropofol is characterized by an XRPD pattern comprising ten peaks selected from the angles listed in Table 15 above. In other aspects, the zinc salt of fospropofol is characterized by an XRPD pattern comprising more than ten peaks selected from the angles listed in Table 15 above.

In some embodiments, the Form I zinc salt of fospropofol is characterized by an XRPD pattern comprising a peak at 8.1, 9.6, and 10.3 degrees±0.2 degrees 2-theta. In other embodiments, the zinc salt of fospropofol is characterized by an XRPD pattern comprising peaks at 18.2, 18.6, and 26.3 degrees±0.2 degrees 2-theta. In other embodiments, the zinc salt of fospropofol is characterized by an XRPD pattern comprising peaks at 8.1, 9.6, 10.3, 11.6, and 12.2 degrees±0.2 degree 2-theta. In yet other embodiments, the zinc salt of fospropofol is characterized by an XRPD pattern comprising peaks at 5.1, 8.1, 9.6, 10.3, 11.6, 12.2, 18.2, 18.6, and 26.3 degrees 0.2 degree 2-theta.

In some embodiments of the present disclosure, the Form I zinc salt of fospropofol is characterized by an XRPD pattern comprising peaks at three or more of 5.1, 8.1, 9.6, 10.3, 11.6, 12.2, 18.2, 18.6, and 26.3 degrees 0.2 degrees 2-theta. In some embodiments of the present disclosure, the zinc salt of fospropofol is characterized by an XRPD pattern comprising peaks at four or more of 5.1, 8.1, 9.6, 10.3, 11.6, 12.2, 18.2, 18.6, and 26.3 degrees±0.2 degrees 2-theta. In some embodiments of the present disclosure, the zinc salt of fospropofol is characterized by an XRPD pattern comprising peaks at five or more of 5.1, 8.1, 9.6, 10.3, 11.6, 12.2, 18.2, 18.6, and 26.3 degrees±0.2 degrees 2-theta. In some embodiments of the present disclosure, the zinc salt of fospropofol is characterized by an XRPD pattern comprising peaks at six or more of 5.1, 8.1, 9.6, 10.3, 11.6, 12.2, 18.2, 18.6, and 26.3 degrees±0.2 degrees 2-theta. In some embodiments of the present disclosure, the zinc salt of fospropofol is characterized by an XRPD pattern comprising peaks at seven or more of 5.1, 8.1, 9.6, 10.3, 11.6, 12.2, 18.2, 18.6, and 26.3 degrees±0.2 degrees 2-theta.

Figure 76:
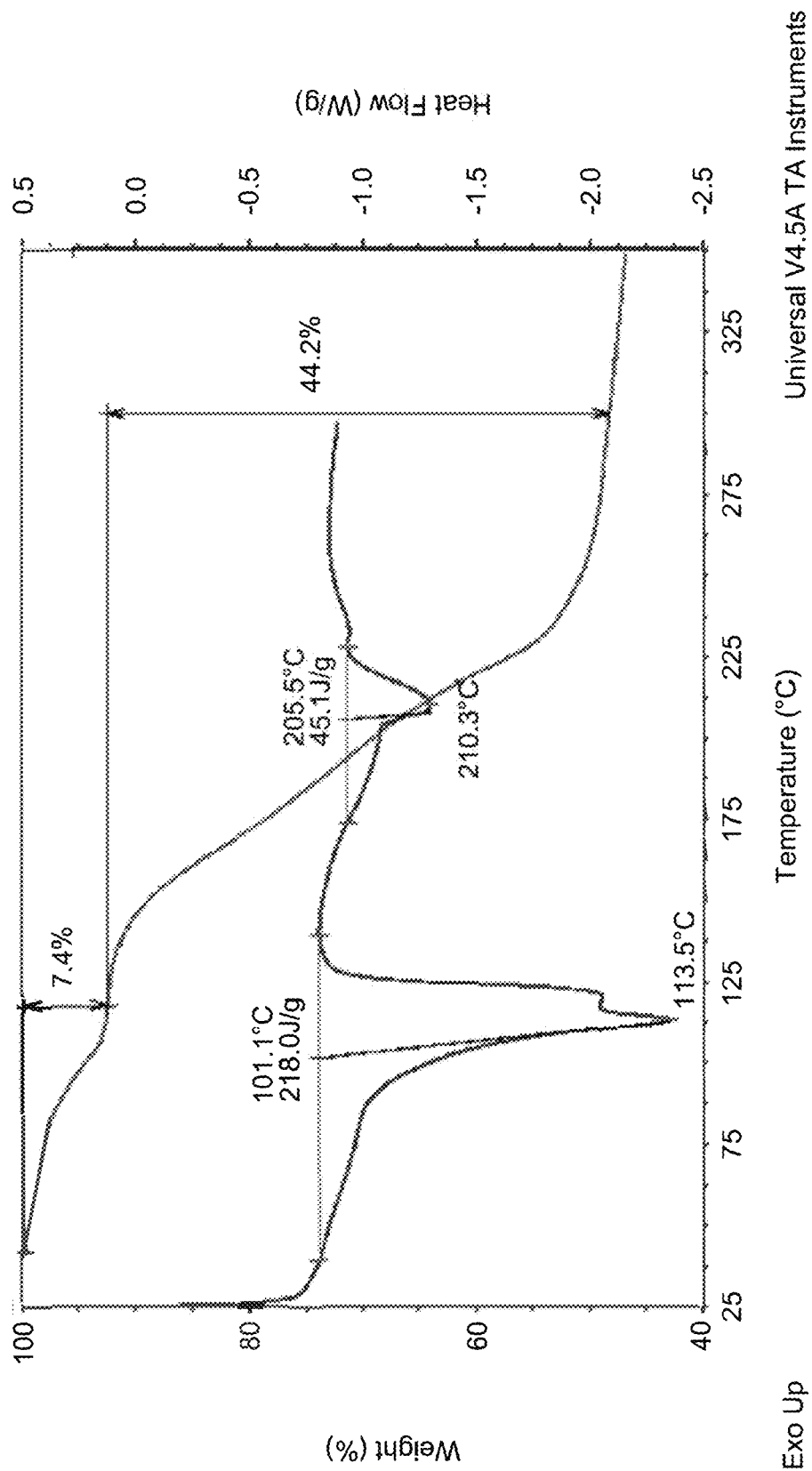
FIG. 76 shows a differential scanning calorimetry (DSC) profile and a thermogravimetric analysis profile (TGA) of a zinc salt of fospropofol (Form I).

The Form I zinc salt of fospropofol can be characterized by a DSC thermogram substantially as shown in FIG. 76. As FIG. 76 shows, the zinc salt of fospropofol produced an endothermic peaks at 113.5° C. and 210.3° C. when heated at a rate of 10° C./min. In some embodiments of the present disclosure, the zinc salt of fospropofol is characterized by a DSC thermogram comprising endothermic peaks at about 114° C. or about 210° C. when heated at a rate of 10° C./min.

In other embodiments, the Form I zinc salt of fospropofol can be characterized by a TGA profile substantially as shown in FIG. 76. As FIG. 76 shows, the magnesium salt of fospropofol lost about 7.4% of its weight upon heating to 125° C., and about 44% of its weight upon heating to 325° C. a rate of 10° C./min.

In some embodiments of the present disclosure, the Form I zinc salt of fospropofol is characterized by an XRPD pattern comprising peaks at 5.1, 8.1, 9.6, 10.3, 11.6, 12.2, 18.2, 18.6, and 26.3 degrees±0.2 degrees 2-theta, and a DSC thermogram comprising endothermic peaks at 114° C. and 210° C. when heated at a rate of 10° C./min.

Methods of Using Fospropofol Salts

The pharmaceutically acceptable salt of fospropofol may be used in the methods of treatment disclosed herein.

In some aspects, the present disclosure is directed to methods of treating migraine in a patient in need thereof, comprising administering to said patient an effective amount of a pharmaceutically acceptable salt of fospropofol wherein the pharmaceutically acceptable salt is a potassium, diethyl amine, t-butyl amine, ethylene diamine, benzathine, piperazine, ethanolamine, diethanolamine, ammonium, tromethamine, benethamine, histidine, calcium, magnesium, or zinc salt.

In some embodiments, the patient's migraine is migraine with aura. Migraine with aura is characterized by focal neurological symptoms that typically precede, or sometimes accompany, the headache.

In other embodiments, the patient's migraine is migraine without aura. Migraine without aura is characterized by the absence of focal neurological symptoms that typically precede, or sometimes accompany, the headache.

In other embodiments, the patient's migraine is cluster headache.

In other embodiments, the patient's migraine is intractable migraine.

In some embodiments of the disclosed methods, the patient's migraine is refractory migraine.

Refractory migraine may fail to respond one or more types of pharmacologic treatment. Examples of pharmacologic treatment to which refractory migraine may fail to respond include CGRP inhibitors (e.g., gepants, including ubrogepant and rimegepant; anti-CGRP antibodies such as Aimovig® (erenumab); Emgality® (galcanezumab); and Ajovy® (fremanezumab); triptans (e.g., sumatriptan (Imitrex), rizatriptan (Maxalt), almotriptan (Axert), naratriptan (Amerge), zolmitriptan (Zomig), frovatriptan (Frova) and eletriptan (Relpax)), antidepressant (e.g., amitriptyline), antiseizure drugs (e.g., topirimate, valproate, and gabapentin), and NSAIDs (e.g., ibuprofen, naprozen sodium, diclofenac and ketorolac).

In some embodiments of the disclosed methods, the patient's refractory migraine may fail to respond to CGRP inhibitors, and is referred to as CGRP inhibitor-refractory migraine.

In some embodiments, the patient's CGRP-inhibitor refractory migraine fails to respond to gepant treatment, and is referred to as gepant-refractory migraine. In other embodiments, the patient's CGRP-inhibitor refractory migraine fails to respond to anti-CGRP antibodies, and is referred to as anti-CGRP antibody-refractory migraine.

In other embodiments of the disclosed methods, the patient's refractory migraine may fail to respond to triptans, and is referred to as triptan-refractory migraine.

In other embodiments of the disclosed methods, the patient's refractory migraine may fail to respond to NSAIDs and is referred to as NSAID-refractory migraine.

In other embodiments of the disclosed methods, the patient's refractory migraine may fail to respond to dihydroegotamine (DHE) and is referred to as DHE-refractory migraine.

In other embodiments, the patient's migraine is catemanial migraine.

In other embodiments, the patient's migraine is menstrual migraine.

In some aspects, the methods of the disclosure are directed to treating migraine in a patient in need thereof. The methods of the disclosure, therefore, are performed on patients suffering from migraine.

In some embodiments, the patient is a mammal.

In other embodiments, the patient is a human.

In some embodiments, the patient is female.

In other embodiments, the patient is male.

In some embodiments, the patient is 18 years of age or older.

In other embodiments, the patient is between 6 and 17 years of age.

In other embodiments, the patient is less than 6 years of age.

In some embodiments, the patient was diagnosed with migraine at least one year prior to being administered forpropofol in accordance with the disclosed methods.

In some embodiments, the administering is oral.

In some embodiments, the administering is peroral.

In other embodiments, the administering is subcutaneous.

In other embodiments, the administering is intramuscular.

In other embodiments, the administering is intravenous.

In other embodiments, the administering is rectal.

Pharmaceutical Compositions of the Fospropofol Salts

In some aspects, the disclosure is directed to pharmaceutical compositions comprising a pharmaceutically acceptable salt of fospropofol wherein the pharmaceutically acceptable salt is a potassium, diethyl amine, t-butyl amine, ethylene diamine, benzathine, piperazine, ethanolamine, diethanolamine, ammonium, tromethamine, benethamine, histidine, calcium, magnesium, or zinc salt, or mixtures thereof, and a pharmaceutically acceptable excipient.

In some embodiments, the pharmaceutical composition is a solid.

In other embodiments, the pharmaceutical composition is a liquid.

In other embodiments, the pharmaceutical composition is a suspension.

The pharmaceutical compositions of the present disclosure may take any physical form suitable for the mode of administration.

In some embodiments, the physical form of the pharmaceutical composition is a capsule (gelatin or non-gelatin), enteric capsules, cachets, tablets, beads, or powders.

In some embodiments, the physical form of the pharmaceutical composition is coated beads.

In other embodiments, the physical form of the pharmaceutical composition is tablets.

In some embodiments, the physical form of the pharmaceutical composition is coated tablets.

In some embodiments, the physical form of the pharmaceutical composition is enteric coated tablets.

In some embodiments, the physical form of the pharmaceutical composition is multilayer tablets.

In some embodiments, the physical form of the pharmaceutical composition is multilayer coated tablets.

In some embodiments, the physical form of the pharmaceutical composition is coated multilayer uncoated tablets.

In some embodiments, the physical form of the pharmaceutical composition is a tablet within a tablet.

In some embodiments, the physical form of the pharmaceutical composition is a capsule.

In some embodiments, the physical form of the pharmaceutical composition is a capsule containing pellets or beads.

In some embodiments, the physical form of the pharmaceutical composition is a capsule containing pellets or beads, wherein the pellets or beads are heterogenous with respect to release of fospropofol.

In some embodiments, the physical form of the pharmaceutical composition is a capsule containing tablets, wherein the tablets are heterogenous with respect to release of fospropofol.

In other embodiments, the physical form of the pharmaceutical composition is a gel, water soluble jellies, creams, lotions, suspensions, foams, powders, slurries, ointments, solutions, oils, pastes, suppositories, sprays, or emulsions.

In some embodiments, the physical form of the pharmaceutical composition is a modified release dosage form.

In some aspects, the pharmaceutical compositions of the disclosure comprises a pharmaceutically acceptable excipient. Pharmaceutically acceptable excipients for use in pharmaceutical compositions have been described previously herein.

EXAMPLES

Example A1

A randomized, double blind, placebo-controlled, ascending single-close, safety-tolerability, pharmacokinetic, and efficacy study of PO fospropofol administered to young healthy male and female volunteers for the acute treatment of moderate or severe migraine headache is conducted as follows.

This study will assess the safety-tolerability, pharmacokinetics, and efficacy (pain relief) of ascending single oral (PO) doses of fospropofol administered to healthy young male and female volunteers for the acute treatment of moderate or severe migraine headache.

The study will also assess the efficacy for relief of associated symptoms (nausea, photophobia, phonophobia) of ascending single oral doses of fospropofol administered to healthy young male and female volunteers for the acute treatment of moderate to severe migraine headache.

Inclusion criteria: Male and female volunteers, age 18-65 years inclusive with an established diagnosis of migraine, with or without aura, according to IHS criteria. The age at the time of initial migraine diagnosis≤50 yo, and the time since initial diagnosis of migraine>one year. The estimated frequency of migraine episodes classified as moderate or severe is at least one per month on average over the past year. Subjects with coexisting headache other than migraine are eligible provided that these headaches are distinguishable from the subject's migraine headaches. No relevant contraindication to use of fospropofol or propofol according to FDA approved labeling. Concomitant medications intended to reduce the frequency of migraine are permitted provided that the close is stable for at least 3 months prior to enrolment and estimated headache frequency meets the criterion above. If concomitant medications intended to reduce the frequency of migraine are discontinued prior to the study, these medications must be discontinued at least one month prior to enrolment. Patients will also have an absence of any clinically significant medical condition that, in the opinion of the investigator or the Sponsor, may be potentially associated with an increased risk from participation in the study.

Exclusion criteria: Subjects with any medical condition (e.g., sleep apnea) which, in the opinion of the investigator or the Sponsor, may be potentially associated with an increased risk from the administration of study drug. Subjects with a contraindication to use of fospropofol or propofol according to FDA approved labeling. Subjects with any medical condition, which, in the opinion of the investigator or the Sponsor, may be potentially associated with an increased risk from participation in the study. Subjects who require concomitant medications, the use of which, in the opinion of the investigator or the Sponsor, may be potentially associated with an increased risk from participation in the study. Subjects unable or unwilling to provide informed consent. Women of childbearing potential must be on adequate, reliable contraception.

Five separate cohorts of 12 subjects are scheduled to receive ascending single PO doses of fospropofol or placebo under double-blind conditions in five stages corresponding to planned doses of 200 mg, 600 mg, 800 mg, 1000 mg, and 1200 mg. Each cohort will participate in each stage (10 to receive fospropofol and 2 to receive placebo). Assuming the completion of five stages, the total number of subjects participating is 60 (50 to receive fospropofol and 10 to receive placebo).

Two subjects within each cohort are randomly assigned to receive placebo.

Following each stage, the decision whether to progress to the next close is based on a review of safety, tolerability and pharmacokinetic (PK) data from the preceding stage by the Safety Committee, as described below.

The Safety Committee may approve close escalation according to the close levels planned in the protocol, may recommend against close escalation, may recommend study of an intermediate close level other than the close levels planned in the protocol, or may recommend that additional data be gathered at a close level already studied.

- Treatment A—200 mg Fospropofol administered as 1 capsule containing 200 mg fospropofol
- Treatment B—600 mg Fospropofol administered as 3 capsules, each containing 200 mg fospropofol
- Treatment C—800 mg Fospropofol administered as 4 capsules, each containing 200 mg fospropofol
- Treatment D—1000 mg Fospropofol administered as 5 capsules, each containing 200 mg fospropofol
- Treatment E—1200 mg Fospropofol administered as 5 capsules, each containing 200 mg fospropofol
- Treatment P—Placebo capsule—matching the appearance of the capsule containing 200 mg of fospropofol; Number of placebo capsules to depend on the closing stage.

Within each separate cohort of 12 subjects, 10 subjects will receive single ascending PO doses of fospropofol at the close levels below. Two of the 12 subjects in each cohort will be randomly assigned to receive placebo.

| Level | Planned dose (mg) |
|---|---|
| 1 | 200 |
| 2 | 600 |
| 3 | 800 |
| 4 | 1000 |
| 5 | 1200 |

1200 mg is the maximum planned close. The close escalation will be stopped if there is any evidence of tolerability issues. Thus, the highest close administered may be lower than 1200 mg.

Following completion of each close level, PK data collected until 9 hours post-close, and safety, tolerability data will be evaluated by a Safety Committee before proceeding to the next close. Depending on safety and tolerability as well as available PK data, the close escalation may be modified such that intermediate close levels are administered.

The Safety Committee will include at least the Qualified Investigator (QI), one medically qualified Sponsor representative, and an independent third-party physician. Adjustments to the currently outlined closes and/or closing regimen may be implemented by the Safety Committee, but the close to be administered at a given close level will not exceed the close currently outlined in the protocol.

Minutes of the safety review committee meeting will be prepared and signed by all voting participants. The minutes of the safety review committee meetings (including the decisions to escalate the close, determination of the next close level, increase in the safety monitoring, rationale for the decisions and supportive data) will be shared with the Independent ethics committee(s) [IEC(s)]/Institutional review board(s) [IRB(s)] overseeing the concerned study part.

The subject's blood will be sampled pre-close (within 15 min of closing) and post-close: 5, 10, 20, 30, 45, 90 minutes and 2, 4, 6, and 9 hours post-close. Plasma samples will be assayed for fospropofol and propofol using validated analytical method(s) according to the principles of Good Laboratory Practice.

The following parameters will be calculated with fospropofol and propofol plasma concentrations: AUC0-30 min, AUC0-2 h, AUC0-t, AUC0-inf, Cmax, Residual area, Tmax, T½ el, Kel, Cl/F, Vd/F, and Vd/F/kg.

Subject's will assess headache pain utilizing a 4-point Likert Scale to be assessed at baseline (within 15 min of closing), and post-close at 15 min, 30 min, 1 h, 1.5 h, 2 h, 4 h, 6 h, 8 h, 10 h (in clinic) and following discharge (by diary) at 24 h and 48 h post-closing. Subjects will be asked to record by patient diary any recurrence or worsening of headache pain, and time of onset or worsening. (Note that a qualifying headache must be of at least moderate severity.)

Subjects will assess presence/absence of the most bothersome associated symptom for the presenting headache at baseline (within 15 min of closing), and post-close at 15 min, 30 min, 1 h, 1.5 h, 2 h, 4 h, 6 h, 8 h, 10 h (in clinic) and following discharge (by diary) at 24 h and 48 h post-closing. Subjects will be asked to record by patient diary any recurrence or worsening of the most bothersome symptom, and time of onset or worsening.

Subject's will assess the presence/absence of nausea/vomiting, photophobia, and/or phonophobia at baseline (within 15 min of closing), and post-close at 15 min, 30 min, 1 h, 1.5 h, 2 h, 4 h, 6 h, 8 h, 10 h (in clinic) and following discharge (by diary) at 12 h, 24 h and 48 h post-closing.

Subjects will be asked to record by patient diary any recurrence or worsening of the most bothersome symptom, and time of onset or worsening.

Subjects will be instructed to report any adverse events directly to the investigators or clinic staff. Subjects will be instructed to record in the patient diary any adverse events emerging following discharge. All subjects will have telephone access to the investigator or investigator staff to report any urgent concerns in the course of the study.

In order to detect the possible emergence of any clinically significant cardiac arrhythmia or other abnormality cardiac telemetry will be monitored from pre-close until 10 hours post-close. Volunteers with any clinically significant ECG abnormality at baseline (pre-close) will be excluded.

Blood pressure (BP), heart rate (HR), respiratory rate (RR), and pulse oximetry will be recorded within 15 min pre-close and at approximately 30 min, and 1, 1.5, 2, 2.5, 3, 4, 5, 6, 8, and 10 hours after closing.

Modified Observer's Assessment of Alertness/Sedation (OAA/S) score within 15 min pre-close and at approximately 15 min, 30 min, and 1, 1.5, 2, 2.5, 3, 4, 5, 6, 8, and 10 hours after closing will be assessed.

Hematology, biochemistry, and urinalysis will be assessed at screening and end of study participation.

Alcohol breath test, urine cotinine determination, and urine drug screen will be assessed at check-in.

A physical examination will be conducted at screening and end of study. An abbreviated physical exam will be conducted at clinic check-in.

Subjects will be monitored throughout the study by clinic staff for adverse events. A physician will be on site for each drug administration and until 10 hours post-close, and available on call for the remainder of the study.

This study will demonstrate that fospropofol, administered perorally, is safe and effective in treating migraine.

Example A2

Randomized, double blind, parallel group, comparative evaluation of the safety-tolerability, pharmacokinetics, and efficacy of 3 close regimens (2 administrations separated by 30 min) of PO fospropofol administered to young healthy male and female volunteers for the acute treatment of moderate or severe migraine headache is conducted as follows.

This study will assess the safety-tolerability, pharmacokinetics, and efficacy (pain relief), in a similar population as in Example 1, of three close regimens (a, b, and c), each comprising 2 PO (peroral) administrations: an initial close followed by a second close administered 30 min later. The amount of the initial close D1 will 400 mg. The amount of the second close D2 will vary according to regimen a, b, and c. The amount of the second close D2 will be D2a=100 mg; D2b=200 mg; and D2c=400 mg.

The study will also assess the efficacy for relief of associated symptoms (nausea, photophobia, phonophobia) of three close regimens (a, b, and c) of fospropofol, each comprising 2 PO administrations: an initial close followed by a second close administered 30 min later.

Inclusion criteria: Male and female volunteers, age 18-65 years inclusive with an established diagnosis of migraine, with or without aura, according to IHS criteria. The age at the time of initial migraine diagnosis≤50 yo, and the time since initial diagnosis of migraine>one year. The estimated frequency of migraine episodes classified as moderate or severe is at least one per month on average over the past year. Subjects with coexisting headache other than migraine are eligible provided that these headaches are distinguishable from the subject's migraine headaches. No relevant contraindication to use of fospropofol or propofol according to FDA approved labeling. Concomitant medications intended to reduce the frequency of migraine are permitted provided that the close is stable for at least 3 months prior to enrolment and estimated headache frequency meets the criterion above. If concomitant medications intended to reduce the frequency of migraine are discontinued prior to the study, these medications must be discontinued at least one month prior to enrolment. Patients will also have an absence of any clinically significant medical condition that, in the opinion of the investigator or the Sponsor, may be potentially associated with an increased risk from participation in the study.

Exclusion criteria: Subjects with any medical condition (e.g., sleep apnea) which, in the opinion of the investigator or the Sponsor, may be potentially associated with an increased risk from the administration of study drug. Subjects with a contraindication to use of fospropofol or propofol according to FDA approved labeling. Subjects with any medical condition, which, in the opinion of the investigator or the Sponsor, may be potentially associated with an increased risk from participation in the study. Subjects who require concomitant medications, the use of which, in the opinion of the investigator or the Sponsor, may be potentially associated with an increased risk from participation in the study. Subjects unable or unwilling to provide informed consent. Women of childbearing potential must be on adequate, reliable contraception.

Randomized, double blind, parallel group, comparative evaluation of the safety-tolerability, pharmacokinetics, and efficacy of 3 close regimens (2 administrations separated by 30 min) of PO fospropofol administered to young healthy male and female volunteers for the acute treatment of moderate or severe migraine headache.

A separate cohort of 36 subjects will be randomized to receive one of 3 regimens (N=12/group) under double-blind conditions, each regimen comprising 2 PO administrations: an initial close (same mg amount for all treatment groups) followed by a second close (mg amount depending on the assigned regimen) administered 30 min later. Double-blinding will be preserved by administering an appropriate number of active and placebo capsules for the second close.

The subject's blood will be sampled pre-close (within 15 min of closing) and post-close: 5, 10, 20, 30, 45, 90 minutes and 2, 4, 6, and 9 hours post-close. Plasma samples will be assayed for fospropofol and propofol using validated analytical method(s) according to the principles of Good Laboratory Practice.

The following parameters will be calculated with fospropofol and propofol plasma concentrations: $AUC_{0-30\,min}$, $AUC_{0-2\,h}$, $AUC_{0-t}$, $AUC_{0-inf}$, $C_{max}$, Residual area, $T_{max}$, $T_{1/2}$ el, Kel, Cl/F, Vd/F, and Vd/F/kg.

Subject's will assess headache pain utilizing a 4-point Likert Scale to be assessed at baseline (within 15 min of closing), and post-close at 15 min, 30 min, 1 h, 1.5 h, 2 h, 4 h, 6 h, 8 h, 10 h (in clinic) and following discharge (by diary) at 24 h and 48 h post-closing. Subjects will be asked to record by patient diary any recurrence or worsening of headache pain, and time of onset or worsening. (Note that a qualifying headache must be of at least moderate severity.)

Subjects will assess presence/absence of the most bothersome associated symptom for the presenting headache at baseline (within 15 min of closing), and post-close at 15 min, 30 min, 1 h, 1.5 h, 2 h, 4 h, 6 h, 8 h, 10 h (in clinic) and following discharge (by diary) at 24 h and 48 h post-closing. Subjects will be asked to record by patient diary any recurrence or worsening of the most bothersome symptom, and time of onset or worsening.

Subject's will assess the presence/absence of nausea/vomiting, photophobia, and/or phonophobia at baseline (within 15 min of closing), and post-close at 15 min, 30 min, 1 h, 1.5 h, 2 h, 4 h, 6 h, 8 h, 10 h (in clinic) and following discharge (by diary) at 12 h, 24 h and 48 h post-closing. Subjects will be asked to record by patient diary any recurrence or worsening of the most bothersome symptom, and time of onset or worsening.

Subjects will be instructed to report any adverse events directly to the investigators or clinic staff. Subjects will be instructed to record in the patient diary any adverse events emerging following discharge. All subjects will have telephone access to the investigator or investigator staff to report any urgent concerns in the course of the study.

In order to detect the possible emergence of any clinically significant cardiac arrhythmia or other abnormality cardiac telemetry will be monitored from pre-close until 10 hours post-close. Volunteers with any clinically significant ECG abnormality at baseline (pre-close) will be excluded.

Blood pressure (BP), heart rate (HR), respiratory rate (RR), and pulse oximetry will be recorded within 15 min pre-close and at approximately 30 min, and 1, 1.5, 2, 2.5, 3, 4, 5, 6, 8, and 10 hours after closing.

Modified Observer's Assessment of Alertness/Sedation (OAA/S) score within 15 min pre-close and at approximately 15 min, 30 min, and 1, 1.5, 2, 2.5, 3, 4, 5, 6, 8, and 10 hours after closing will be assessed.

Hematology, biochemistry, and urinalysis will be assessed at screening and end of study participation.

Alcohol breath test, urine cotinine determination, and urine drug screen will be assessed at check-in.

A physical examination will be conducted at screening and end of study. An abbreviated physical exam will be conducted at clinic check-in.

Subjects will be monitored throughout the study by clinic staff for adverse events. A physician will be on site for each drug administration and until 10 hours post-close, and available on call for the remainder of the study.

This study will demonstrate that fospropofol, administered perorally, is safe and effective in treating migraine.

Example A3

Randomized, double blind, parallel group, comparative evaluation of the safety-tolerability, pharmacokinetics, and efficacy of 3 close regimens (2 administrations separated by 30 min) of PO fospropofol administered to young healthy male and female volunteers for the acute treatment of moderate or severe migraine headache is conducted as follows.

This study will assess the safety-tolerability, pharmacokinetics, and efficacy (pain relief), in a similar population as in Example 1, of three close regimens (a, b, and c), each comprising 2 PO (peroral) administrations: an initial close followed by a second close administered 30 min later. The amount of the initial close D1 will 600 mg. The amount of the second close D2 will vary according to regimen a, b, and c. The amount of the second close D2 will be D2a=150 mg; D2b=300 mg; and D2c=600 mg.

The study will also assess the efficacy for relief of associated symptoms (nausea, photophobia, phonophobia) of three close regimens (a, b, and c) of fospropofol, each comprising 2 PO administrations: an initial close followed by a second close administered 30 min later.

Inclusion criteria: Male and female volunteers, age 18-65 years inclusive with an established diagnosis of migraine, with or without aura, according to IHS criteria. The age at the time of initial migraine diagnosis≤50 yo, and the time since initial diagnosis of migraine>one year. The estimated frequency of migraine episodes classified as moderate or severe is at least one per month on average over the past year. Subjects with coexisting headache other than migraine are eligible provided that these headaches are distinguishable from the subject's migraine headaches. No relevant contraindication to use of fospropofol or propofol according to FDA approved labeling. Concomitant medications intended to reduce the frequency of migraine are permitted provided that the close is stable for at least 3 months prior to enrolment and estimated headache frequency meets the criterion above. If concomitant medications intended to reduce the frequency of migraine are discontinued prior to the study, these medications must be discontinued at least one month prior to enrolment. Patients will also have an absence of any clinically significant medical condition that, in the opinion of the investigator or the Sponsor, may be potentially associated with an increased risk from participation in the study.

Exclusion criteria: Subjects with any medical condition (e.g., sleep apnea) which, in the opinion of the investigator or the Sponsor, may be potentially associated with an increased risk from the administration of study drug. Subjects with a contraindication to use of fospropofol or propofol according to FDA approved labeling. Subjects with any medical condition, which, in the opinion of the investigator or the Sponsor, may be potentially associated with an increased risk from participation in the study. Subjects who require concomitant medications, the use of which, in the opinion of the investigator or the Sponsor, may be potentially associated with an increased risk from participation in the study. Subjects unable or unwilling to provide informed consent. Women of childbearing potential must be on adequate, reliable contraception.

Randomized, double blind, parallel group, comparative evaluation of the safety-tolerability, pharmacokinetics, and efficacy of 3 close regimens (2 administrations separated by 30 min) of PO fospropofol administered to young healthy male and female volunteers for the acute treatment of moderate or severe migraine headache.

A separate cohort of 36 subjects will be randomized to receive one of 3 regimens (N=12/group) under double-blind conditions, each regimen comprising 2 PO administrations: an initial close (same mg amount for all treatment groups) followed by a second close (mg amount depending on the assigned regimen) administered 30 min later. Double-blinding will be preserved by administering an appropriate number of active and placebo capsules for the second close.

The subject's blood will be sampled pre-close (within 15 min of closing) and post-close: 5, 10, 20, 30, 45, 90 minutes and 2, 4, 6, and 9 hours post-close. Plasma samples will be assayed for fospropofol and propofol using validated analytical method(s) according to the principles of Good Laboratory Practice.

The following parameters will be calculated with fospropofol and propofol plasma concentrations: AUC0-30 min, AUC0-2 h, AUC0-t, AUC0-inf, Cmax, Residual area, Tmax, T½ el, Kel, Cl/F, Vd/F, and Vd/F/kg.

Subject's will assess headache pain utilizing a 4-point Likert Scale to be assessed at baseline (within 15 min of closing), and post-close at 15 min, 30 min, 1 h, 1.5 h, 2 h, 4 h, 6 h, 8 h, 10 h (in clinic) and following discharge (by diary) at 24 h and 48 h post-closing. Subjects will be asked to record by patient diary any recurrence or worsening of headache pain, and time of onset or worsening. (Note that a qualifying headache must be of at least moderate severity.)

Subjects will assess presence/absence of the most bothersome associated symptom for the presenting headache at baseline (within 15 min of closing), and post-close at 15 min, 30 min, 1 h, 1.5 h, 2 h, 4 h, 6 h, 8 h, 10 h (in clinic) and following discharge (by diary) at 24 h and 48 h post-closing. Subjects will be asked to record by patient diary any recurrence or worsening of the most bothersome symptom, and time of onset or worsening.

Subject's will assess the presence/absence of nausea/vomiting, photophobia, and/or phonophobia at baseline (within 15 min of closing), and post-close at 15 min, 30 min, 1 h, 1.5 h, 2 h, 4 h, 6 h, 8 h, 10 h (in clinic) and following discharge (by diary) at 12 h, 24 h and 48 h post-closing. Subjects will be asked to record by patient diary any recurrence or worsening of the most bothersome symptom, and time of onset or worsening.

Subjects will be instructed to report any adverse events directly to the investigators or clinic staff. Subjects will be instructed to record in the patient diary any adverse events emerging following discharge. All subjects will have telephone access to the investigator or investigator staff to report any urgent concerns in the course of the study.

In order to detect the possible emergence of any clinically significant cardiac arrhythmia or other abnormality cardiac telemetry will be monitored from pre-close until 10 hours post-close. Volunteers with any clinically significant ECG abnormality at baseline (pre-close) will be excluded.

Blood pressure (BP), heart rate (HR), respiratory rate (RR), and pulse oximetry will be recorded within 15 min pre-close and at approximately 30 min, and 1, 1.5, 2, 2.5, 3, 4, 5, 6, 8, and 10 hours after closing.

Modified Observer's Assessment of Alertness/Sedation (OAA/S) score within 15 min pre-close and at approximately 15 min, 30 min, and 1, 1.5, 2, 2.5, 3, 4, 5, 6, 8, and 10 hours after closing will be assessed.

Hematology, biochemistry, and urinalysis will be assessed at screening and end of study participation.

Alcohol breath test, urine cotinine determination, and urine drug screen will be assessed at check-in.

A physical examination will be conducted at screening and end of study. An abbreviated physical exam will be conducted at clinic check-in.

Subjects will be monitored throughout the study by clinic staff for adverse events. A physician will be on site for each drug administration and until 10 hours post-close, and available on call for the remainder of the study.

This study will demonstrate that fospropofol, administered perorally, is safe and effective in treating migraine.

Example A4

A "fospropofol tablet within a tablet" can be prepared as follows.

The core tablet contains fospropofol (200 mg; 20% by wt. dosage form), microcrystalline cellulose (100 mg; 10% by wt. of dosage form), pregelatinized starch (e.g., Starch 1500) (97.5 mg; 9.75% by weight of dosage form), magnesium stearate (2.5 mg; 0.25% by wt. of dosage form).

The outer layer, which surrounds the core tablet, contains fospropofol disodium (400 mg; 40% by wt. of dosage form), microcrystalline cellulose (100 mg; 10% wt. of dosage form), pregelatinized starch (e.g., Starch 1500) (97.5 mg; 9.75% by wt. of dosage form), magnesium stearate (2.5 mg; 0.25% by wt. of dosage form).

This is a modified-release dosage form. The outer layer dissolves rapidly in the stomach. The core tablet dissolves slowly in the stomach, and further dissolves in the intestines.

Example A5

A "fospropofol bilayer tablet" can be prepared as follows.

One layer contains fospropofol (200 mg; 20% by wt. of bilayer tablet), microcrystalline cellulose (100 mg; 10% by wt. of bilayer tablet), pregelatinized starch (e.g., Starch 1500) (97.5 mg; 9.75% by wt. of bilayer tablet), magnesium stearate (2.5 mg; 0.25% by wt. of bilayer tablet).

The other layer contains fospropofol disodium (400 mg; 40% by wt. of bilayer tablet), microcrystalline cellulose (100 mg; 10% by wt. of bilayer tablet), pregelatinized starch (e.g., Starch 1500) (97.5 mg; 9.75% by wt. of bilayer tablet), magnesium stearate (2.5 mg; 0.25% by wt. of bilayer tablet).

This is a modified-release dosage form. One layer dissolves rapidly in the stomach. The other layer dissolves slowly in the stomach, and further dissolves in the intestines.

Example A6

A fospropofol dosage form with immediate release and delayed release components can be prepared as follows.

The delayed release component contains fospropofol disodium (200 mg; 20% by wt. of final dosage form), microcrystalline cellulose (100 mg; 10% by wt. of final dosage form), pregelatinized starch (e.g., Starch 1500) (17.5 mg; 1.75% by wt. of final dosage form), HMPC (80 mg; 8% by wt. of final dosage form), magnesium stearate (2.5 mg; 0.25% by wt. of final dosage form).

The immediate release component contains fospropofol disodium (400 mg; 40% by wt. of final dosage form), microcrystalline cellulose (100 mg; 10% by wt. of final dosage form), pregelatinized starch (e.g., Starch 1500) (97.5 mg; 9.75% by wt. of final dosage form), and magnesium stearate (2.5 mg; 0.25% by wt. of final dosage form).

This is a modified-release dosage form. The delayed release component granules and the immediate release component granules may be combined and pressed into a tablet, or may be combined in a capsule.

Example A7

A Fospropofol Dosage form with immediate release and enteric coated components can be prepared as follows.

The enteric coated component contains fospropofol disodium (200 mg; 20% by wt. of final dosage form), microcrystalline cellulose (100 mg; 10% by wt. of final dosage form), pregelatinized starch (e.g., Starch 1500) (47.5 mg; 4.75% by wt. of final dosage form), magnesium stearate (2.5 mg; 0.25% by wt. of final dosage form), Eudragit L (50 mg; 5% by wt. of final dosage form).

The immediate release component contains fospropofol disodium (400 mg; 40% by wt. of final dosage form), microcrystalline cellulose (100 mg; 10% by wt. of final dosage form), pregelatinized starch (e.g., Starch 1500) (97.5 mg; 9.75% by wt. of final dosage form), and magnesium stearate (2.5 mg; 0.25% by wt. of final dosage form).

This is a modified-release dosage form. The enteric coated component granules and the immediate release component granules or beads may be combined and pressed into a tablet, or may be combined in a capsule.

Example A8

Randomized, double blind, parallel group, comparative evaluation of the safety-tolerability, pharmacokinetics, and efficacy of 3 dosage forms of PO fospropofol administered to young healthy male and female volunteers for the acute treatment of moderate or severe migraine headache is conducted as follows.

This study will assess the safety-tolerability, pharmacokinetics, and efficacy (pain relief), in a similar population as in Example 1, of a single administration of one of three dosage forms (the dosage forms of Examples 5, 6, and 7).

The study will also assess the efficacy for relief of associated symptoms (nausea, photophobia, phonophobia) of a single administration of one of three dosage forms (the dosage forms of Examples 5, 6, and 7).

Inclusion criteria: Male and female volunteers, age 18-65 years inclusive with an established diagnosis of migraine, with or without aura, according to IHS criteria. The age at the time of initial migraine diagnosis≤50 yo, and the time since initial diagnosis of migraine>one year. The estimated frequency of migraine episodes classified as moderate or severe is at least one per month on average over the past year. Subjects with coexisting headache other than migraine are eligible provided that these headaches are distinguishable from the subject's migraine headaches. No relevant contraindication to use of fospropofol or propofol according to FDA approved labeling. Concomitant medications intended to reduce the frequency of migraine are permitted provided that the close is stable for at least 3 months prior to enrolment and estimated headache frequency meets the criterion above. If concomitant medications intended to reduce the frequency of migraine are discontinued prior to the study, these medications must be discontinued at least one month prior to enrolment. Patients will also have an absence of any clinically significant medical condition that, in the opinion of the investigator or the Sponsor, may be potentially associated with an increased risk from participation in the study.

Exclusion criteria: Subjects with any medical condition (e.g., sleep apnea) which, in the opinion of the investigator or the Sponsor, may be potentially associated with an increased risk from the administration of study drug. Subjects with a contraindication to use of fospropofol or propofol according to FDA approved labeling. Subjects with any medical condition, which, in the opinion of the investigator or the Sponsor, may be potentially associated with an increased risk from participation in the study. Subjects who require concomitant medications, the use of which, in the opinion of the investigator or the Sponsor, may be potentially associated with an increased risk from participation in the study. Subjects unable or unwilling to provide informed consent. Women of childbearing potential must be on adequate, reliable contraception.

A separate cohort of 36 subjects will be randomized to receive one of 3 regimens (N=12/group) under double-blind conditions, each regimen comprising a single administration of one of the dosage forms of Example 5, 6, or 7. Double-blinding will be preserved by administering an appropriate number of active and placebo capsules for the second close.

The subject's blood will be sampled pre-close (within 15 min of closing) and post-close: 5, 10, 20, 30, 45, 90 minutes and 2, 4, 6, and 9 hours post-close. Plasma samples will be assayed for fospropofol and propofol using validated analytical method(s) according to the principles of Good Laboratory Practice.

The following parameters will be calculated with fospropofol and propofol plasma concentrations: AUC0-30 min, AUC0-2 h, AUC0-t, AUC0-inf, Cmax, Residual area, Tmax, T½ el, Kel, Cl/F, Vd/F, and Vd/F/kg.

Subject's will assess headache pain utilizing a 4-point Likert Scale to be assessed at baseline (within 15 min of closing), and post-close at 15 min, 30 min, 1 h, 1.5 h, 2 h, 4 h, 6 h, 8 h, 10 h (in clinic) and following discharge (by diary) at 24 h and 48 h post-closing. Subjects will be asked to record by patient diary any recurrence or worsening of headache pain, and time of onset or worsening. (Note that a qualifying headache must be of at least moderate severity.)

Subjects will assess presence/absence of the most bothersome associated symptom for the presenting headache at baseline (within 15 min of closing), and post-close at 15 min, 30 min, 1 h, 1.5 h, 2 h, 4 h, 6 h, 8 h, 10 h (in clinic) and following discharge (by diary) at 24 h and 48 h post-closing. Subjects will be asked to record by patient diary any recurrence or worsening of the most bothersome symptom, and time of onset or worsening.

Subject's will assess the presence/absence of nausea/vomiting, photophobia, and/or phonophobia at baseline (within 15 min of closing), and post-close at 15 min, 30 min, 1 h, 1.5 h, 2 h, 4 h, 6 h, 8 h, 10 h (in clinic) and following discharge (by diary) at 12 h, 24 h and 48 h post-closing. Subjects will be asked to record by patient diary any recurrence or worsening of the most bothersome symptom, and time of onset or worsening.

Subjects will be instructed to report any adverse events directly to the investigators or clinic staff. Subjects will be instructed to record in the patient diary any adverse events emerging following discharge. All subjects will have telephone access to the investigator or investigator staff to report any urgent concerns in the course of the study.

In order to detect the possible emergence of any clinically significant cardiac arrhythmia or other abnormality cardiac telemetry will be monitored from pre-close until 10 hours post-close. Volunteers with any clinically significant ECG abnormality at baseline (pre-close) will be excluded.

Blood pressure (BP), heart rate (HR), respiratory rate (RR), and pulse oximetry will be recorded within 15 min pre-close and at approximately 30 min, and 1, 1.5, 2, 2.5, 3, 4, 5, 6, 8, and 10 hours after closing.

Modified Observer's Assessment of Alertness/Sedation (OAA/S) score within 15 min pre-close and at approximately 15 min, 30 min, and 1, 1.5, 2, 2.5, 3, 4, 5, 6, 8, and 10 hours after closing will be assessed.

Hematology, biochemistry, and urinalysis will be assessed at screening and end of study participation.

Alcohol breath test, urine cotinine determination, and urine drug screen will be assessed at check-in.

A physical examination will be conducted at screening and end of study. An abbreviated physical exam will be conducted at clinic check-in.

Subjects will be monitored throughout the study by clinic staff for adverse events. A physician will be on site for each drug administration and until 10 hours post-close, and available on call for the remainder of the study.

This study will demonstrate that each of the dosage forms of Examples 5, 6, or 7, is safe and effective in treating migraine.

Example A9

Safety-tolerability and pharmacokinetics (PK) of single ascending oral (PO) doses of fospropofol disodium in healthy adult male and female volunteers.

Study Drug: Fospropofol Disodium
Study Phase and Type: Phase 1—Single Ascending Dose (SAD)

Study Design: Single center, Phase 1, randomized, modified double-blind, SAD, safety-tolerability and pharmacokinetic (PK) study of Fospropofol Disodium in healthy male and female volunteers under fasting conditions. The study is characterized as modified double-blind because treatment assignment will be unblinded for review of safety-tolerability and propofol PK following each closing stage.

The study will investigate a maximum of 5 ascending close levels as needed. Separate cohorts of 12 subjects at each close level will be randomized to receive either Fospropofol Disodium. (10 subjects) or matching placebo (2 subjects).

A separate cohort of 12 subjects will receive a single dose of Fospropofol (Fospropofol Disodium) administered PO at the highest well-tolerated close following a standardized high fat meal.

Subjects: Up to 72 healthy adult male and female subjects, ≥18 and ≤65 years of age with a body mass index (BMI) within 18.5-29.9 kg/m$^2$, inclusive. Females of childbearing potential must be using reliable contraception.

Each subject will receive a single dose of Fospropofol Disodium or a single dose of placebo. Each cohort of 12 subjects will include at least seven female subjects.

Subjects will not be permitted to participate in more than one dose level. Subjects who withdraw or are withdrawn from the study after closing will not be replaced.

Screening Procedures: Demographic data, medical and medication histories, physical examination, body measurements, electrocardiogram (ECG), vital signs (blood pressure [BP], heart rate [HR], respiratory rate [RR], pulse oximetry [PO], and oral temperature [OT]), hematology, blood chemistry, human immunodeficiency virus (HIV), hepatitis B and C tests, urinalysis, urine drug screen, alcohol breath test, urine cotinine test, Serum pregnancy test (women of child-bearing potential). Screening to occur within 30 days of clinic admission.

Confinements and Washout: At each close level, 12 subjects will be confined to the study site for at least 14 hours before closing.

At each close level, subjects will be confined until at least 10 hours post-close.

Because separate cohorts will participate at each stage, washout is not applicable.

Study Drug and Dosage Form: Staring close 200 mg.

Fospropofol Disodium to be administered as an appropriate number of powder filled capsules, each capsule containing 200 mg of fospropofol disodium.

Placebo to be administered as an appropriate number of matched powder filled capsules, each capsule containing a suitable placebo.

Study Drug Administration: In the SAD portion of the study each cohort of 12 subjects will receive single ascending oral doses of Fospropofol Disodium under fasting conditions (10 subjects) or matching placebo (2 subjects) at the planned close levels. On admission to the clinic, subjects who meet inclusion/exclusion criteria will be assigned treatment (Fospropofol Disodium or placebo) according to the randomization schedule. The site will be informed as to which medication to be dispensed to each particular subject at the time of the subject's randomization.

No food will be allowed from at least 10 hours before closing until at least 4 hours after closing.

Fospropofol Disodium will be administered with 240 mL of water at ambient temperature. Except for water administered with study drug, no fluids will be allowed from before closing until 1 hour post-close.

Following completion of each close level, pharmacokinetic (PK) data for propofol collected until 9 hours post-close, and safety and tolerability data with treatment assignment (i.e., unblinded) collected until the clinic check-out (approximately 10 hours post-close) will be evaluated by a Safety Committee before proceeding to the next close. Successive cohorts will be closed at weekly intervals.

A separate cohort of 12 subjects will be randomized to receive either Fospropofol Disodium. (10 subjects) or matching placebo (2 subjects). Fospropofol Disodium will be administered at the highest well-tolerated close. Following an overnight fast of at least 10 hours, subjects will start a standardized high fat meal 30 minutes prior to administration of study drug. Study subjects will be requested to complete this meal within 30 minutes; however, study drug will be administered 30 minutes after start of the meal. Study drug will be administered with 240 mL (8 fluid ounces) of water. No food will be allowed for at least 4 hours post-close. Except for administration in fed condition, study procedures for the food effect cohort will be identical to the procedures in the SAD cohorts.

Inclusion Criteria Male or female, non-smoker (no use of tobacco products within 3 months prior to screening), ≥18 and ≤55 years of age, with BMI ≥18.0 and ≤29.9 kg/m$^2$ and body weight≥50.0 kg Healthy as defined by:

The absence of clinically significant illness and surgery within 4 weeks prior to closing. Subjects vomiting within 24 hours pre-close will be carefully evaluated. Inclusion pre-closing is at the discretion of the center PI.

The absence of clinically significant history of neurological (other than migraine), endocrine, cardiovascular, pulmonary, hematological, immunologic, psychiatric, gastrointestinal, renal, hepatic, and metabolic disease.

The absence of clinically significant history of sleep apnea

Clinical laboratory values within the laboratory acceptable range unless values are deemed by the PI/Sub-Investigator as "Not Clinically Significant".

Ability to comprehend the nature of the study, as assessed by the PI/Sub-Investigator. Capable of giving written informed consent. Able to communicate effectively with clinic staff.

Ability to fast for at least 10 hours and consume standard meals.

Availability to volunteer for the entire study duration and willing to adhere to all protocol requirements.

Female subjects must agree not to be nursing at any time during the study and until 30 days after the study follow-up visit.

Female subjects must fulfill at least one of the following:

Be surgically sterile for a minimum of 6 months;

Post-menopausal for a minimum of 1 year;

Agree to avoid pregnancy and use medically acceptable method of contraception from at least 30 days prior to administration of study drug until 30 days after the study follow-up visit.

Medically acceptable methods of contraception include hormonal contraception, hormonal or non-hormonal intrauterine device, or double barrier method (simultaneous use of male condom with intravaginally applied spermicide and diaphragm or cervical cap). Complete abstinence alone can be used as a method of contraception.

Exclusion Criteria Subjects to whom any of the following applies will be excluded:

Any clinically significant abnormality at physical examination, clinically significant abnormal laboratory test results or positive serologic test for hepatitis B, hepatitis C, or HIV found during medical screening. (Subjects with positive serology for hepatitis C and negative HCV RNA are eligible at the discretion of the principal investigator.)

Positive urine drug screen, alcohol breath test, urine cotinine test at screening (or at clinic check-in)

Positive serum pregnancy test (women of child-bearing potential) at screening (or positive urine pregnancy test at clinic check-in).

History of severe allergic reactions (e.g. anaphylactic reactions, angioedema), hypersensitivity or idiosyncratic reaction to fospropofol, propofol, Fospropofol Disodium excipients or related substances.

Individuals having undergone any major surgery within 6 months prior to the start of the study, unless deemed otherwise by the PI.

Clinically significant ECG abnormalities (e.g., QTcF>450 msec in males or ≥470 msec in females) or vital sign abnormalities (systolic blood pressure lower than 95 or over 145 mmHg, diastolic blood pressure lower than 55 or over 95 mmHg, or heart rate less than 50 or over 100 bpm) at screening.

Oxygen saturation by oximetry less than 93% at screening

History of significant alcohol abuse within one year prior to screening or regular use of alcohol within six months prior to the screening visit (more than fourteen units of alcohol per week [1 unit=150 mL of wine, 360 mL of beer, or 45 mL of 40% alcohol]).

History of significant drug abuse within one year prior to screening or use of hard drugs (such as cocaine, phencyclidine [PCP], crack, opioid derivatives including heroin, and amphetamine derivatives) within 1 year prior to screening.

Participation in an interventional clinical research study involving the administration of an investigational or marketed drug or device within 30 days prior to administration of study drug or administration of a biological product in the context of a clinical research study within 90 days prior to administration of study drug. Concomitant participation in an investigational study involving no drug or device administration is permitted provided obligations associated with the concomitant participation are not expected to interfere with procedures and obligations of the present study.

Use of medication other than topical products without significant systemic absorption:

Prescription medication within 14 days prior to the first closing;

Over-the-counter products and natural health products (including herbal remedies such as St. John's wort, homeopathic and traditional medicines, probiotics, food supplements such as vitamins, minerals, amino acids, essential fatty acids, and protein supplements used in sports) within 7 days prior to the first closing, with the exception of the occasional use of acetaminophen(up to 2 g daily);

A depot injection or an implant of any drug within 3 months prior to the first closing.

Donation of plasma within 7 days prior to closing. Donation or loss of blood (excluding volume drawn at screening) of 50 mL to 499 mL of blood within 30 days, or more than 499 mL within 56 days prior to the first closing.

Hemoglobin≤135 g/L for men or ≤120 g/L for women at screening.

Intolerance to and/or difficulty with blood sampling through venipuncture.

Abnormal diet patterns (for any reason) during the four weeks preceding the study, including fasting, high protein diets etc.

Employee or immediate relative of an employee of Epalex Corporation, its affiliates or partners.

Study Restrictions: Subjects will be asked to refrain from using products that may potentially affect their safety and/or the PK of the study drug. Main study restrictions include:

Prescription medication from 14 days prior to closing until after the last PK blood sample collection of the study;

Over-the-counter products from 14 days prior to closing until after the last PK blood sample collection of the study;

Natural health products from 14 days pre-close until after the last PK blood sample collection;

Food containing poppy seeds within 24 hours prior to admission of each period;

Alcohol-based products from 48 hours prior to closing until after the last PK blood sample collection (of each close level or period).

For safety reasons, subjects will be required to remain seated or semi-reclined and avoid sleeping for the first 1 hour before and 4 hours after drug administration.

PK Sampling Time Points: A total of 14 blood samples (for analysis of both fospropofol and propofol) will be collected (in each close level or period): Pre-close (within 10 min of closing) and post-close: 5, 10, 20, 30, 45, 60, 90 minutes and 2, 3, 4, 5, 6, and 9 hours post-close.

Total Blood Volume Total blood volume per subject will not exceed a maximum of 200 mL including screening.

Safety Monitoring: Medical surveillance and AE monitoring:

Subjects will be monitored throughout the study by Clinic staff for AEs.

Continuous cardiac telemetry and pulse oximetry:

In order to ensure the absence of any clinically significant cardiac arrhythmia or other abnormality at baseline (pre-close), cardiac telemetry will be performed from approximately 10 hours pre-close until closing. Cardiac telemetry will be continued until 9 hours post-close to monitor for any cardiac effects of study drug. Volunteers with any clinically significant ECG abnormality at baseline (pre-close) will be excluded. Pulse oximetry will be continuously monitored over the same time course.

Vital signs:

BP, HR, RR, and Pulse Oximetry (PO) will be recorded pre-close within 10 min of closing and at approximately 5, 10, 20, 30, 45, 60, 90 2, 2.5, 3, 4, 6, and 9 hours after closing. Pulse oximetry will be continuously monitored.

Level of Alertness

Level of sedation will be assessed using the Modified Observer's Assessment of Alertness/Sedation (MOAA/S) Score. See Chernik DA, Gillings D, Laine H, et al. Validity and reliability of the Observer's Assessment of Alertness/Sedation Scale: study with intravenous midazolam. J Clin Psychopharmacol 1990 Aug. 10(4):244-51.

| Responsiveness | Score |
| --- | --- |
| Responds readily to name spoken in normal tone | 5 (alert) |
| Lethargic response to name spoken in normal tone | 4 |
| Responds only after name is called loudly and/or repeatedly | 3 |
| Responds only after mild prodding or shaking | 2 |
| Responds only after painful trapezius squeeze | 1 |
| Does not respond to painful trapezius squeeze | 0 |

Sedation (MOAA/S score) will be recorded within 15 min pre-close, at 15 min post-close and at approximately 15 min intervals until 3 hours after closing, and at 30 min intervals thereafter until 9 hours post-close provided that the subject has demonstrated at least three consecutive MOAA/S scores of 5 immediately prior to the 3 hour timepoint. A subject who has not demonstrated three consecutive MOAA/S scores of 5 immediately prior to the 3 hour timepoint will continue with MOAA/S assessments at 15 min intervals until he or she demonstrates three consecutive MOAA/S scores of 5, with MOAA/S scores recorded at 30 min interval thereafter until 8 hours post-close. See Cohen LB. Clinical trial: a close-response study of fospropofol disodium for moderate sedation during colonoscopy. 2008; Aliment Pharmacol Ther 27, 597-608.

In addition, the bispectral (BIS) index (a commercially available EEG-derived measure of anesthesia and sedation, Coviden, Mansfield, MA, USA) will be continuously assessed from 15 min pre-close until ~8 h post close using the commercially available BIS complete 2-channel monitor. The device uses a, disposable (single patient use), pre-gelled 4 electrode array that is applied directly to the patient's forehead, and the procedure is minimally invasive. See https://www.medtronic.com/covidien/en-us/products/brain-monitoring/bis-complete-2-channel-monitor.html.

12-lead ECG:

12-lead ECG will be performed on Day 1 before closing.

Laboratory assessments:

Hematology, biochemistry, and urinalysis at check-in.

Alcohol breath test, urine cotinine test, and urine drug screen at check-in.

Physical examination:

Brief physical examination: at check-in and check-out.

Check-out/Early Termination Procedures: The following procedures will be done at each clinic check-out or for early termination (when applicable): hematology, blood chemistry, urinalysis, physical examination, vital signs, 12-lead ECG, oral temperature, AE monitoring, urine pregnancy test for women of child-bearing potential.

Analytical Method: Fospropofol and propofol will be analyzed in plasma samples using a validated method. Additional plasma samples may be drawn and stored for possible future bioanalysis of other analytes.

Pharmacokinetic Parameters: The following pharmacokinetic parameters will be calculated for both fospropofol and propofol plasma concentrations: $AUC_{0-t}$, $AUC_{0-inf}$, $C_{max}$, Residual area, $T_{max}$, $T_{1/2el}$, $K_{el}$, Cl/F, Vd/F, and Vd/F/kg Statistical Analyses: Statistical analyses will be performed for the safety, tolerability and PK data Laboratory Assessments Hematology: Hematology will be drawn at screening, before closing at each close level (at check-in or in the morning of Day −1), and at checkout, including the following: complete blood count with differential, hemoglobin, and hematocrit.

Biochemistry: Blood chemistry will be drawn at screening, before closing at each close level (at check-in or in the morning of Day −1), and at check-out, including the following: albumin, alkaline phosphatase, aspartate aminotransferase, alanine aminotransferase, urea, calcium, chloride, glucose, phosphorus, potassium, creatinine, sodium, total bilirubin, and total protein.

Serology: Hepatitis B (HBs Ag), Hepatitis C (HCV) antibody, and HIV antigen and antibody detection will be drawn at screening.

Urinalysis: Urine for Urinalysis at screening, before closing at each close level (at check-in or in the morning of Day −1), and at check-out, including the following: macroscopic examination, pH, specific gravity, protein, glucose, ketones, bilirubin, occult blood, nitrite, urobilinogen, and leukocytes. Unless otherwise specified, microscopic examination will be performed on abnormal findings.

Drug, Cotinine, and Alcohol Screen: A urine drug screen (amphetamines, methamphetamines, barbiturates, benzodiazepines, tetrahydrocannabinol, cocaine, opiates, PCP, MDMA, methadone), a urine cotinine test, and an alcohol breath test will be performed at screening and at each check-in.

Pregnancy Tests: For women of child bearing potential: A serum pregnancy test will be performed at screening. A urine pregnancy test will be performed before closing at each close level (at check-in or in the morning of Day −1) and at early termination, where applicable.

Example A10

Safety-tolerability, pharmacokinetics, and efficacy of single ascending oral doses of fospropofol disodium administered to healthy adult male and female volunteers for the acute treatment of moderate to severe migraine headache.

Study Drug: Fospropofol Disodium

Study Phase and Type: Phase 2a—Single Ascending Dose (SAD) in adults with migraine Study Design: Multi-center, Phase 2a, placebo controlled, modified double-blind, SAD, safety-tolerability, pharmacokinetic (PK), and efficacy study of Fospropofol Disodium in adult males and females for the acute treatment of moderate to severe migraine headache.

The study design is characterized as modified double-blind because treatment assignment will be unblinded for review of safety-tolerability, propofol PK, and efficacy following each closing stage.

The study will evaluate 3 ascending close levels (in 3 stages) with close levels to be selected on the basis of the prior Phase 1 healthy volunteer study. Separate cohorts of 24 subjects will be randomized to receive ascending doses of Fospropofol Disodium or matching placebo (18 of 24 subjects to receive Fospropofol Disodium and 6 of 24 subjects to receive placebo at each close level). During each closing stage subjects and investigators will be blinded to the treatment assignment. Following each closing stage, safety-tolerability, pharmacokinetic, and efficacy assessments will be reviewed with treatment assignment unblinded. Depending on results reviewed following Stage 1 and following Stage 2, close escalation may stop and/or the close levels for subsequent stages may be modified to levels lower than those specified in the protocol. (It is possible that a close level already studied will be repeated with a subsequent cohort to provide additional information at that close level.) In no case will closes exceed the highest close level specified in the protocol.

Subjects: Up to 76 adult males and females≥18 and ≤55 years of age with a body mass index (BMI) within 18.0-35.0 kg/m² inclusive and body weight≥50 kg. Females of childbearing potential must be using reliable contraception or totally abstain from intercourse.

Separate cohorts of 24 subjects will receive Fospropofol Disodium (18 subjects) or placebo (6) at each of three ascending close levels). Each cohort of 24 to be balanced on gender 12:12, 13:11, or 14:10 with no fewer than 12 females.

Subjects who withdraw or are withdrawn from the study after closing, for reasons other than safety and tolerability, may be replaced after consultation with the Safety Review Committee.

Screening Procedures: Demographic data, medical and medication histories including drug allergies, physical examination, body measurements, electrocardiogram (ECG), vital signs (blood pressure [BP], heart rate [HR], respiratory rate [RR], pulse oximetry [PO], and oral temperature [OT]), hematology, blood chemistry, human immunodeficiency virus (HIV), hepatitis B and C tests, urinalysis, urine drug screen, alcohol breath test, urine cotinine test, Serum pregnancy test (women of child-bearing potential). Screening to occur within 30 days of clinic admission. [Subjects who do not present with a qualifying headache within 30 days of screening may have a second screening visit within 45 days of the first screening at the discretion of the investigator. Second screening visit may be abbreviated to updated history and serum pregnancy test for women of childbearing potential. A subject who does not present with a qualifying headache within 30 days of the second screening will be classified as a screening failure.]

Migraine History: Confirm migraine diagnosis according to ICHD criteria, age of onset, estimated frequency of migraine episodes, including frequency of episodes classified as moderate or severe, history of migraine-associated symptoms (nausea/vomiting, photophobia, phonophobia), characteristic features of episodes including aura (if any), nature of pain, associated symptoms; history of headache types other than migraine, history of medications (if any) used for treatment of acute migraine (past and current); history of medications (if any) used for the purpose of migraine prophylaxis (past and current). Identification of an appropriate "rescue" treatment (See Rescue Treatment below)

Confinement in clinic: Subjects will arrive at the study clinic during the course of a migraine headache of at least moderate severity (in the subject's judgment). Subjects will be confined to the study site for 1 to 2 hours before closing and confined until at least 9 hours following a single dose of study drug.

Study Drug and Dosage Form: Three close levels.
  Fospropofol disodium to be administered as an appropriate number of powder filled capsules, each capsule containing 200 mg of fospropofol disodium (Epalex Corporation, USA).
  Placebo to be administered as an equivalent number of identical capsules containing placebo.

Study Drug Administration: Each cohort of 24 subjects will receive a single oral dose of either Fospropofol disodium (N=18) or matching placebo (N=6) at one of three close levels. Fospropofol disodium administered as capsules containing 200 mg.
  Subjects will receive a single dose of Fospropofol disodium or placebo
  Study drug will be administered with 240 mL of water at ambient temperature. Except for water administered with study drug, no fluids will be allowed from 1 hour before closing until 1 hour post-close.
  There will be at least 7 days between closing of each close level. Following completion of each close level, pharmacokinetic (PK) data for propofol collected until 9 hours post-close, safety and tolerability data collected until the clinic check-out (approximately 10 hours post-close), and the efficacy data collected until 9 hours post-close will be evaluated by a Safety Committee before proceeding to the next close.

Inclusion Criteria Male or female, non-smoker (no use of tobacco products within 3 months prior to screening), ≥18 and ≤55 years of age, with BMI ≥18.0 and ≤35.0 kg/m² and body weight≥50.0 kg
  Generally healthy (other than migraine) as defined by:
  The absence of clinically significant illness and surgery within 4 weeks prior to closing. Subjects vomiting within 24 hours pre-close will be carefully evaluated. Inclusion pre-closing is at the discretion of the center PI.
  The absence of clinically significant history of neurological (other than migraine), endocrine, cardiovascular, pulmonary, hematological, immunologic, psychiatric, gastrointestinal, renal, hepatic, and metabolic disease.
  The absence of clinically significant history of sleep apnea
  Subject has at least 1 year history of migraines (with or without aura), consistent with a diagnosis according to the International Classification of Headache Disorder, 3rd Edition, Beta version including the following:
  Migraine attacks present for more than 1 year with age of onset prior to 50 years of age
  Migraine attacks last, 4 to 72 hours if untreated, on average, in the 3 months prior to screening visit
  Two to eight (2-8) moderate or severe migraine attacks per month in the 3 months prior to the screening visit. The migraine, for which the patient receives treatment during the study, must have at least one of the associated symptoms: nausea, photophobia, phonophobia, or migraine with aura Subjects on prophylactic migraine medication are permitted to remain on therapy provided they have been on a stable dose for at least 3 months prior to screening visit and the close is not expected to change during the course of the study Clinical laboratory values within the laboratory acceptable range unless values are deemed by the PI/Sub-Investigator as "Not Clinically Significant".

Ability to comprehend the nature of the study, as assessed by the PI/Sub-Investigator. Capable of giving written informed consent. Able to communicate effectively with clinic staff.

Availability to volunteer for the entire study duration and willing to adhere to all protocol requirements.

Female subjects must agree not to be nursing at any time during the study and until 30 days after the study follow-up visit.

Female subjects must fulfill at least one of the following:

Be surgically sterile for a minimum of 6 months;

Post-menopausal for a minimum of 1 year;

Agree to avoid pregnancy and use medically acceptable method of contraception from at least 30 days prior to administration of study drug until 30 days after the study follow-up visit.

Medically acceptable methods of contraception include hormonal contraception, hormonal or non-hormonal intrauterine device, or double barrier method (simultaneous use of male condom with intravaginally applied spermicide and diaphragm or cervical cap). Complete abstinence alone can be used as a method of contraception.

Subjects with coexisting history of headache other than migraine are eligible provided that these headaches are distinguishable from the subject's migraine headaches No contraindication to use of fospropofol according to FDA approved labeling Concomitant medications taken for the purpose of migraine prophylaxis are permitted provided that the dose of these medications is stable for at least 3 months prior to administration of study drug and estimated headache frequency at screening meets the criterion above If concomitant medications intended to reduce the frequency of migraine are discontinued prior to the study, these medications must be discontinued at least one month prior to receiving study drug Absence of any medical condition that, in the opinion of the investigator or the Sponsor, may be potentially associated with an increased risk from study drug or participation in the study.

Subject must be willing to avoid the use of analgesics or any acute migraine medication(s) for 24 hours prior to receiving study drug.

Subject must be willing to forgo rescue treatment (defined below) for at least 2 hours after initiation of treatment with study drug.

Exclusion Criteria Subjects to whom any of the following applies will be excluded:

Patient has basilar migraine or hemiplegic migraine

Patient is taking narcotic (opiate) medication

Patient uses an opiate as first line acute treatment for migraine attacks

History of ergotamine, triptan, or any acute therapy intake on ≥10 days per month on a regular basis for ≥3 months History of simple analgesic intake on ≥10 days per month for ≥3 months History of use of opioid or combination medication intake or butalbital containing analgesic greater than 5 days per month for ≥3 months Very frequent chronic tension type headaches for 15 or more days per month (or unable to distinguish between tension-type headaches and migraine)

Patient has major depression, other pain syndromes that might interfere with study assessments, psychiatric conditions, dementia, or significant neurological disorders (other than migraine)

Any clinically significant abnormality at physical examination, clinically significant abnormal laboratory test results or positive serologic test for hepatitis B, hepatitis C, or HIV found during medical screening. (Subjects with positive serology for hepatitis C and negative HCV RNA are eligible at the discretion of the principal investigator.)

Positive urine drug screen (unless consistent with an ongoing prescription drug as documented by the center investigator), positive alcohol breath test, urine cotinine test at screening or at clinic check-in Positive serum pregnancy test (women of child-bearing potential) at screening (or positive urine pregnancy test at clinic check-in).

History of severe allergic reactions (e.g. anaphylactic reactions, angioedema), hypersensitivity or idiosyncratic reaction to fospropofol, propofol, Fospropofol Disodium excipients or related substances.

Individuals having undergone any major surgery within 6 months prior to the start of the study, unless deemed otherwise by the PI.

Clinically significant ECG abnormalities (e.g., QTcF≥450 msec in males or ≥470 msec in females) or persistent (3 determinations) vital sign abnormalities at screening (systolic blood pressure lower than 90 or over 145 mmHg, diastolic blood pressure lower than 55 or over 95 mmHg, or heart rate less than 50 or over 100 bpm). Vital signs to be taken in a seated position and may be repeated up to a total of three determinations.

Oxygen saturation by oximetry less than 93% at screening

History of significant alcohol abuse within one year prior to screening or regular use of alcohol within six months prior to the screening visit (more than fourteen units of alcohol per week [1 unit=150 mL of wine, 360 mL of beer, or 45 mL of 40% alcohol]).

History of significant drug abuse within one year prior to screening or use of hard drugs (such as cocaine, phencyclidine [PCP], crack, opioid derivatives including heroin, and amphetamine derivatives) within 1 year prior to screening.

Participation in an interventional clinical research study involving the administration of an investigational or marketed drug or device within 30 days prior to administration of study drug or administration of a biological product in the context of a clinical research study within 90 days prior to administration of study drug. Concomitant participation in an investigational study involving no drug or device administration is permitted provided obligations associated with the concomitant participation are not expected to interfere with procedures and obligations of the present study.

Any medical condition (other than migraine) requiring ongoing, more than occasional, use of analgesic drugs. (Occasional use of acetaminophen, aspirin, or NSAID, or topical products without significant systemic absorption is not an exclusion).

Any medical condition requiring ongoing treatment with sedative-hypnotic drugs (e.g., benzodiazepines, barbiturates)

Donation of plasma within 7 days prior to closing. Donation or loss of blood (excluding volume drawn at screening) of 50 mL to 499 mL of blood within 30 days, or more than 499 mL within 56 days prior to the first closing.

Hemoglobin≤135 g/L for men or ≤120 g/L for women at screening.

Intolerance to and/or difficulty with blood sampling through venipuncture.

Abnormal diet patterns (for any reason) during the four weeks preceding the study, including fasting, high protein diets etc.

Employee or immediate relative of an employee of Epalex Corporation, its affiliates or partners.

Study Restrictions: Subjects will be asked to refrain from using products that may potentially affect their safety, the PK profile of the study drug, and/or assessments of efficacy. Main study restrictions include the following:

Analgesic drugs, e.g., opiates alone or in a combination product from screening until the end-of-study follow-up visit. Occasional use of acetaminophen, aspirin, or an NSAID will be permitted; however, a subject will not be eligible to receive study drug if he/she has taken an analgesic (including over the counter) in the preceding 24 hours. Analgesics (except as rescue) are not permitted from 24 hours prior to clinic admission until the end-of-study follow-up visit.

Marijuana products including THC and CBD are not permitted from screening until the end-of-study follow-low-up visit.

Sedative-hypnotic drugs, prescription or OTC, (e.g., benzodiazepines, barbiturates, sleeping aids, Fiorinal) from screening until the end-of-study follow-up visit.

Triptans, e.g., sumatriptan, Imitrex (except as rescue, where applicable) are not permitted from screening until the end-of-study follow-up visit.

Ergotamine or combination drugs, containing ergotamine e.g. cafergot (except as rescue, where applicable) from screening until the end-of-study follow-up visit.

Metoclopramide, e.g. Reglan (except as rescue, where applicable) from screening until the end-of-study follow-up visit.

Alcohol-based products are permitted; however, a subject will not be eligible to receive study drug if he/she has taken any alcohol-based product in the preceding 24 hours. Alcohol-based products are not permitted from 24 hours prior to clinic admission until the end-of-study follow-up visit.

Prescription and OTC medications that are medically necessary (except analgesics, sedative-hypnotics, and drugs intended for treatment of acute migraine, as described above) are permitted. The center principal investigator (PI) will review, record, and approve at screening the concomitant medications expected to be continued over the course of study. In case of questions as to the suitability of a concomitant medication, investigators are encouraged to consult with the Sponsor.

For safety reasons, subjects will be required to remain seated or semi-reclined and avoid sleeping for the first 1 hour before and 4 hours after administration of study drug.

PK Sampling Time Points: A total of 14 blood samples (for analysis of both fospropofol and propofol) will be collected (in each close level or period): Pre-close (within 10 min of closing) and post-close: 5, 10, 20, 30, 45, 60, 90 minutes and 2, 3, 4, 5, 6, and 9 hours post-close.

Subject Safety Monitoring: Medical surveillance and AE monitoring:

Subjects will be monitored throughout the study by Clinic staff for AEs.

Continuous cardiac telemetry and pulse oximetry:

To detect any clinically significant cardiac arrhythmia or other abnormality at baseline (pre-close), cardiac telemetry will be performed for at least 30 minutes prior to closing and continued until approximately 9 hours post-close to monitor for any cardiac effects of study drug. Subjects with any clinically significant ECG abnormality at baseline (pre-close) will be excluded. Pulse oximetry will be monitored over the same time course.

Vital signs:

BP, HR, RR, and Pulse Oximetry (PO) will be recorded pre-close within 10 min of closing and at approximately 5, 10, 20, 30, 45, 60, 90 2, 2.5, 3, 4, 6, and 9 hours after closing.

Level of Alertness

Level of sedation will be assessed using the Modified Observer's Assessment of Alertness/Sedation (MOAA/S) Score. See Chernik D A, Gillings D, Laine H, et al. Validity and reliability of the Observer's Assessment of Alertness/Sedation Scale: study with intravenous midazolam. J Clin Psychopharmacol 1990 Aug. 10(4):244-51.

| Responsiveness | Score |
|---|---|
| Responds readily to name spoken in normal tone | 5 (alert) |
| Lethargic response to name spoken in normal tone | 4 |
| Responds only after name is called loudly and/or repeatedly | 3 |
| Responds only after mild prodding or shaking | 2 |
| Responds only after painful trapezius squeeze | 1 |
| Does not respond to painful trapezius squeeze | 0 |

Sedation (MOAA/S score) will be recorded within 10 min pre-close and at approximately 5 min intervals until 3 hours after closing, and at 15 min intervals thereafter until 9 hours post-close provided that the subject has demonstrated at least three consecutive MOAA/S scores of 5 immediately prior to the 3 hour timepoint. A subject who has not demonstrated three consecutive MOAA/S scores of 5 immediately prior to the 3 hour timepoint will continue with MOAA/S assessments at 5 min intervals until he or she demonstrates three consecutive MOAA/S scores of 5, with MOAA/S scores recorded at 15 min intervals thereafter until 9 hours post-close. See Cohen LB.

Clinical trial: a close-response study of fospropofol disodium for moderate sedation during colonoscopy. 2008; Aliment Pharmacol Ther 27, 597-608.

12-lead ECG:
12-lead ECG will be performed at Clinic check-in (Day 1, before closing) and at Clinic checkout.

Laboratory assessments:
Hematology, biochemistry, and urinalysis at clinic check-in and at the follow-up (final) visit to be scheduled between 48 h and 96 h after administration of study drug.
Alcohol breath test, urine cotinine test, and urine drug screen at check-in.
For women of child-bearing potential, urine pregnancy test at check-in; serum pregnancy test at follow-up (final) visit scheduled between 48 h and 96 h after administration of study drug [A serum pregnancy test will be obtained at screening.]

Physical examination:
Complete physical exam (PE) at screening, brief PE at clinic check-in and clinic checkout; complete PE at follow-up (final) visit scheduled between 48 h and 96 h after administration of study drug Clinic Check-in Food will not be permitted from the time of clinic check-in until 4 hours after closing of study drug. Fluids will not be permitted from one hour before until one hour after administration of study drug (except for water (240 mL) administered with study drug.) Water will be permitted ad lib at all other times.
Abbreviated physical exam, alcohol breath test, and urine drug screen at check-in. Urine pregnancy test (women of child-bearing potential)
Record time and nature of last meal or food intake
Record concomitant medications and all medications taken in the 24 hours prior to check-in.
Record characteristics of the presenting headache and associated symptoms including, but not limited to the following:
Characteristics of the presenting headache (i.e., throbbing, unilateral or bilateral, aggravated by exercise).
Subject's assessment of headache pain at admission to clinic on a 4-point Likert Scale, (i.e., 0=none, 1=mild, 2=moderate, 3=severe) for the presenting headache.
Most bothersome associated symptom for the presenting headache (e.g., nausea/vomiting, photophobia, phonophobia)
Presence of associated symptoms, nausea, vomiting, photophobia, phonophobia (Yes/No) at clinic admission Efficacy Measures: Subject's assessment of headache pain—4-point Likert Scale (Severe, Moderate, Mild, No pain) to be assessed at baseline prior to closing (within 10 min of closing), and post-close at 5 min, 15 min, 30 min, 45 min, 1 h, 1.5 h, 2 h, 3 h, 4 h, 6 h, 8 h, and at clinic discharge, and following discharge (by diary) at 12, 24 h and 48 h post-closing. Headache qualifying for treatment with study drug must be of at least moderate severity at baseline (pre-close and within 10 min of closing study drug). Subjects will be asked to announce while in clinic the time that no headache pain is first noted, or, after discharge, if applicable, to record the time that no headache pain is first noted in the patient diary. Subjects will also be asked to announce in clinic and/or record by patient diary after discharge from clinic any recurrence or worsening of headache pain, and time of onset of worsening.
Subject's assessment of presence/absence of most bothersome symptom (MBS)—subjects to be questioned as to presence or absence of the most bothersome symptom associated with presenting headache (identified at clinic admission) at the same time points as the assessment of headache pain [baseline prior to closing (within 10 min of closing), and post-close at 5 min, 15 min, 30 min, 45 min, 1 h, 1.5 h, 2 h, 3 h, 4 h, 6 h, 8 h, and at clinic discharge, and following discharge (by diary) at 12, 24 h and 48 h post-closing.]
Subjects will also be asked to announce while in clinic the time that disappearance of the most bothersome symptom is first noted, or, after discharge, if applicable, to record the time that no headache pain is first noted in the patient diary. Subjects will also be asked to announce in clinic and/or record by patient diary after discharge from clinic any recurrence of the most bothersome symptom, and time of onset of recurrence.
Subject assessment of presence/absence of migraine-associated symptoms (other than MBS): nausea/vomiting, photophobia, and/or phonophobia at baseline (within 15 min of closing), and post-close at 5 min, 15 min, 30 min, 45 min, 1 h, 1.5 h, 2 h, 3 h, 4 h, 6 h, 8 h, and at clinic discharge, and following discharge (by diary) at 12, 24 h and 48 h post-closing. Subjects will also be asked to announce while in clinic the time that disappearance of migraine-associated symptoms is first noted, or, after discharge, if applicable, to record the time that disappearance of the associated symptom is first noted in the patient diary. Subjects will also be asked to announce in clinic and/or record by patient diary after discharge from clinic any recurrence of a migraine-associated symptom, and time of onset of recurrence.
While in clinic subjects will be instructed to report any adverse events directly to the investigators or clinic staff. Subjects will be instructed to record in the patient diary any adverse events emerging following discharge. All subjects will have telephone access to the investigator or investigator staff to report any urgent concerns in the course of the study.

Rescue Treatment Rescue treatment (acute treatment for migraine pain) may be administered at any time at the investigator's discretion. Subjects and investigators will be encouraged to avoid administration of rescue treatment earlier than 2 hours after administration of study drug. Rescue treatment may include an analgesic and/or acute migraine medication(s). Selection of rescue for each subject may be guided by history of treatment effective for the subject in the past. In general, the investigator and subject will have agreed on the appropriate rescue therapy for the subject at screening. In identifying an appropriate rescue therapy, the additive cardiorespiratory effects of narcotic analgesics and sedative hypnotic agents when administered concomitantly with fospropofol should be considered.

Clinic Check-out: The following procedures will be carried out at clinic check-out: physical examination, vital signs, 12-lead ECG, oral temperature, AE monitoring. Distribute diary for subjects to record and grade any ongoing headache pain, and any ongoing migraine-associated symptoms (present/absent), and/or any recurrence or worsening of pain or migraine-associated symptoms. Schedule follow-up visit.

Follow-up Visit/End of Study Participation The following procedures will be carried out at a follow-up end of study visit to be scheduled 48 to 96 hours after administration of study drug: hematology, blood chemistry, urinalysis, AE monitoring, serum pregnancy test for women of child-bearing potential Analytical Fospropofol and propofol will be analyzed in plasma samples Method: using a validated method. Additional plasma samples may be drawn and stored for possible future bioanalysis of other analytes.

Pharmacokinetic Parameters: The following pharmacokinetic parameters will be calculated for both fospropofol and propofol plasma concentrations: $AUC_{0-t}$, $AUC_{0-inf}$, $C_{max}$, Residual area, $T_{max}$, $T_{1/2el}$, $K_{el}$, Cl/F, Vd/F, and Vd/F/kg Statistical Analyses: Statistical analyses will be performed with the safety, tolerability, efficacy, and PK data.

Laboratory Assessments—Example A10

Hematology: Hematology will be drawn at screening, at clinic check-in, and at the follow-up (final) visit. Hematology will include complete blood count with differential, hemoglobin, and hematocrit.

Chemistry: Blood chemistry will be drawn at screening, at clinic check-in, and at the follow-up (final) visit. Blood chemistry will include albumin, alkaline phosphatase, aspartate aminotransferase, alanine aminotransferase, urea, calcium, chloride, glucose, phosphorus, potassium, creatinine, sodium, total bilirubin, and total protein.

Serology: Hepatitis B (HBs Ag), Hepatitis C (HCV) antibody, and HIV antigen and antibody detection will be drawn at screening.

Urinalysis: Urine for Urinalysis will be taken at screening, at clinic check-in, and at the follow-up (final) visit. Urinalysis will include macroscopic examination, pH, specific gravity, protein, glucose, ketones, bilirubin, occult blood, nitrite, urobilinogen, and leukocytes. Unless otherwise specified, microscopic examination will be performed on abnormal findings.

Drug, Cotinine, and Alcohol Screen: A urine drug screen (amphetamines, methamphetamines, barbiturates, benzodiazepines, tetrahydrocannabinol, cocaine, opiates, PCP, MDMA, methadone), a urine cotinine test, and an alcohol breath test will be performed at screening and at clinic check-in.

Pregnancy Tests: For women of child bearing potential: A serum pregnancy test will be performed at screening. A urine pregnancy test will be performed at clinic check-in. A serum pregnancy test will be performed at the follow-up (final) visit, and at early termination, where applicable.

Example A11

Safety-tolerability, pharmacokinetics, and efficacy of single pulsed ascending oral doses of fospropofol disodium administered to adult males and females for the acute treatment of moderate to severe migraine headache.

Study Drug: Fospropofol disodium

Study Phase and Type: Phase 2a—Single Pulsed Ascending Dose (SAD) in adults with migraine Study Design: Multi-center, Phase 2a, placebo controlled, modified double-blind, Single Pulsed Ascending Dose, safety-tolerability, pharmacokinetic (PK), and efficacy study of Fospropofol disodium in adult males and females for the acute treatment of moderate to severe migraine headache. The study is characterized as modified double-blind because treatment assignment will be unblinded for review of safety-tolerability, propofol PK, and efficacy following each closing stage.

The study will evaluate 3 ascending close levels of a pulsed close (in 3 stages) with close levels to be selected on the basis of the prior Phase 2a SAD study in subjects with acute migraine (Study Fospropofol Disodium-02A). Separate cohorts of 16 subjects will be randomized to receive a fixed dose (all subjects) followed by ascending pulsed doses of Fospropofol disodium or matching placebo (12 of 16 subjects to receive a pulsed dose of Fospropofol disodium and 4 of 16 subjects to receive a pulsed dose of placebo at each close level). During each closing stage subjects and investigators will be blinded to the treatment assignment.

Subjects: Up to 52 adult males and females≥18 and ≤55 years of age with a body mass index (BMI) within 18.0-35.0 kg/m² inclusive and body weight≥50 kg. Females of childbearing potential must be using reliable contraception or totally abstain from intercourse. Three separate cohorts of 16 subjects will receive a fixed dose of Fospropofol Disodium followed by a second "pulsed" dose of EP-102 30 minutes later (12 subjects) or a second "pulsed" dose of placebo 30 minutes (4 subjects) at each of three ascending close levels. Each cohort of 16 to be balanced on gender 8:8 or 9:7 with no fewer than 8 females.

Subjects who withdraw or are withdrawn from the study after closing, for reasons other than safety and tolerability, may be replaced after consultation with the Safety Review Committee.

Screening Procedures: Demographic data, medical and medication histories including drug allergies, physical examination, body measurements, electrocardiogram (ECG), vital signs (blood pressure [BP], heart rate [HR], respiratory rate [RR], pulse oximetry [PO], and oral temperature [OT]), hematology, blood chemistry, human immunodeficiency virus (HIV), hepatitis B and C tests, urinalysis, urine drug screen, alcohol breath test, urine cotinine test, Serum pregnancy test (women of child-bearing potential). Screening to occur within 30 days of clinic admission. [Subjects who do not present with a qualifying headache within 30 days of screening may have a second screening visit within 45 days of the first screening at the discretion of the investigator. Second screening visit may be abbreviated to updated history and serum pregnancy test for women of childbearing potential. A subject who does not present with a qualifying headache within 30 days of the second screening will be classified as a screening failure.]

Migraine History: Confirm migraine diagnosis according to ICHD criteria, age of onset, estimated frequency of migraine episodes, including frequency of episodes classified as moderate or severe, history of migraine-associated symptoms (nausea/vomiting, photophobia, phonophobia), characteristic features of episodes including aura (if any), nature of pain, associated symptoms; history of headache types other than migraine, history of medications (if any) used for treatment of acute migraine (past and current); history of medications (if any) used for the purpose of migraine prophylaxis (past and current). Identification of an appropriate "rescue" treatment (See Rescue Treatment below)

Confinement in clinic: Subjects will arrive at the study clinic during the course of a migraine headache of at least moderate severity (in the subject's judgment). Subjects will be confined to the study site for 1 to 2 hours before closing and confined until at least 9 hours following the initial dose of study drug.

Study Drug and Dosage Form: Fixed dose for the initial close (all stages) and three ascending active close levels for the second (pulsed) close Fospropofol disodium to be administered as an appropriate number of powder filled capsules, each capsule containing 200 mg of fospropofol disodium and/or 100 mg of fospropofol disodium (Epalex Corporation, USA).

Placebo to be administered (second "pulsed" close) as an equivalent number of identical capsules containing placebo.

Study Drug Administration: Each cohort of 16 subjects will receive the same single fixed oral dose of Fospropofol disodium (N=16) as the initial close. After 30 minutes, subjects will receive a second "pulsed" dose of Fospropofol disodium (N=12) or matching placebo (N=4). The amount of the second "pulsed" close will increase at each stage (ascending close design). Fospropofol disodium will be administered as capsules containing 200 mg and/or 100 mg of fospropofol disodium (Fospropofol disodium) to achieve the planned close.

Study drug (each of the two administrations) will be administered with 240 mL of water at ambient temperature. Except for water administered with study drug, no fluids will be allowed from 1 hour before closing until 1 hour post-close.

There will be at least 7 days between closing of each close level. Following completion of each close level, pharmacokinetic (PK) data for propofol collected until 9 hours post-close (where time post-close refers to the time interval from the initial close), safety and tolerability data collected until the clinic check-out (approximately 10 hours post-close), and the efficacy data collected until 9 hours post-close will be evaluated by a Safety Committee before proceeding to the next close.

Inclusion Criteria Male or female, non-smoker (no use of tobacco products within 3 months prior to screening), ≥18 and ≤55 years of age, with BMI ≥18.0 and ≤32.0 kg/m$^2$ and body weight≥50.0 kg Generally healthy (other than migraine) as defined by:

The absence of clinically significant illness and surgery within 4 weeks prior to closing. Subjects vomiting within 24 hours pre-close will be carefully evaluated. Inclusion pre-closing is at the discretion of the center PI.

The absence of clinically significant history of neurological (other than migraine), endocrine, cardiovascular, pulmonary, hematological, immunologic, psychiatric, gastrointestinal, renal, hepatic, and metabolic disease.

The absence of clinically significant history of sleep apnea

Subject has at least 1 year history of migraines (with or without aura), consistent with a diagnosis according to the International Classification of Headache Disorder, 3rd Edition, Beta version including the following: Migraine attacks present for more than 1 year with age of onset prior to 50 years of age Migraine attacks last, 4 to 72 hours if untreated, on average, in the 3 months prior to screening visit Two to eight (2-8) moderate or severe migraine attacks per month in the 3 months prior to the screening visit. The migraine, for which the patient receives treatment during the study, must have at least one of the associated symptoms: nausea, photophobia, phonophobia, or migraine with aura Subjects on prophylactic migraine medication are permitted to remain on therapy provided they have been on a stable dose for at least 3 months prior to screening visit and the close is not expected to change during the course of the study Clinical laboratory values within the laboratory acceptable range unless values are deemed by the PI/Sub-Investigator as "Not Clinically Significant".

Ability to comprehend the nature of the study, as assessed by the PI/Sub-Investigator. Capable of giving written informed consent. Able to communicate effectively with clinic staff.

Availability to volunteer for the entire study duration and willing to adhere to all protocol requirements.

Female subjects must agree not to be nursing at any time during the study and until 30 days after the study follow-up visit.

Female subjects must fulfill at least one of the following:

Be surgically sterile for a minimum of 6 months;

Post-menopausal for a minimum of 1 year;

Agree to avoid pregnancy and use medically acceptable method of contraception from at least 30 days prior to the study until 30 days after the study follow-up visit.

Medically acceptable methods of contraception include hormonal contraception, hormonal or non-hormonal intrauterine device, or double barrier method (simultaneous use of male condom with intravaginally applied spermicide and diaphragm or cervical cap). Complete abstinence alone can be used as a method of contraception.

Subjects with coexisting history of headache other than migraine are eligible provided that these headaches are distinguishable from the subject's migraine headaches No contraindication to use of fospropofol according to FDA approved labeling Concomitant medications taken for the purpose of migraine prophylaxis are permitted provided that the dose of these medications is stable for at least 3 months prior to administration of study drug and estimated headache frequency at screening meets the criterion above If concomitant medications intended to reduce the frequency of migraine are discontinued prior to the study, these medications must be discontinued at least one month prior to receiving study drug Absence of any medical condition that, in the opinion of the investigator or the Sponsor, may be potentially associated with an increased risk from study drug or participation in the study.

Subject must be willing to avoid the use of analgesics or any acute migraine medication(s) for 24 hours prior to receiving study drug.

Subject must be willing to forgo rescue treatment (defined below) for 2 hours after initiation of treatment with study drug.

Exclusion Criteria Subjects to whom any of the following applies will be excluded:

Patient has basilar migraine or hemiplegic migraine

Patient is taking narcotic (opiate) medication

Patient uses an opiate as first line acute treatment for migraine attacks

History of ergotamine, triptan, or any acute therapy intake on ≥10 days per month on a regular basis for ≥3 months History of simple analgesic intake on ≥10 days per month for ≥3 months History of use of opioid or combination medication intake or butalbital containing analgesic greater than 5 days per month for >3 months Very frequent chronic tension type headaches for 15 or more days per month (or unable to distinguish between tension-type headaches and migraine)

Patient has major depression, other pain syndromes that might interfere with study assessments, psychiatric conditions, dementia, or significant neurological disorders (other than migraine)

Any clinically significant abnormality at physical examination, clinically significant abnormal laboratory test results or positive serologic test for hepatitis B, hepatitis C, or HIV found during medical screening. (Subjects with positive serology for hepatitis C and negative HCV RNA are eligible at the discretion of the principal investigator.)

Positive urine drug screen (unless consistent with an ongoing prescription drug as documented by the center investigator), positive alcohol breath test, urine cotinine test at screening or at clinic check-in Positive serum pregnancy test (women of child-bearing potential) at screening (or positive urine pregnancy test at clinic check-in).

History of severe allergic reactions (e.g. anaphylactic reactions, angioedema), hypersensitivity or idiosyncratic reaction to fospropofol, propofol, Fospropofol Disodium excipients or related substances.

Individuals having undergone any major surgery within 6 months prior to the start of the study, unless deemed otherwise by the PI.

Clinically significant ECG abnormalities (e.g., QTcF≥450 msec in males or ≥470 msec in females) or persistent (3 determinations) vital sign abnormalities at screening (systolic blood pressure lower than 90 or over 145 mmHg, diastolic blood pressure lower than 55 or over 95 mmHg, or heart rate less than 50 or over 100 bpm). Vital signs to be taken in a seated position and may be repeated up to a total of three determinations.

Oxygen saturation by oximetry less than 93% at screening

History of significant alcohol abuse within one year prior to screening or regular use of alcohol within six months prior to the screening visit (more than fourteen units of alcohol per week [1 unit=150 mL of wine, 360 mL of beer, or 45 mL of 40% alcohol]).

History of significant drug abuse within one year prior to screening or use of hard drugs (such as cocaine, phencyclidine [PCP], crack, opioid derivatives including heroin, and amphetamine derivatives) within 1 year prior to screening.

Participation in an interventional clinical research study involving the administration of an investigational or marketed drug or device within 30 days prior to administration of study drug or administration of a biological product in the context of a clinical research study within 90 days prior to administration of study drug. Concomitant participation in an investigational study involving no drug or device administration is permitted provided obligations associated with the concomitant participation are not expected to interfere with procedures and obligations of the present study.

Any medical condition (other than migraine) requiring ongoing, more than occasional, use of analgesic drugs. (Occasional use of acetaminophen, aspirin, or NSAID, or topical products without significant systemic absorption is not an exclusion).

Any medical condition requiring ongoing treatment with sedative-hypnotic drugs (e.g., benzodiazepines, barbiturates)

Donation of plasma within 7 days prior to closing. Donation or loss of blood (excluding volume drawn at screening) of 50 mL to 499 mL of blood within 30 days, or more than 499 mL within 56 days prior to the first closing.

Hemoglobin≤135 g/L for men or ≤120 g/L for women at screening.

Intolerance to and/or difficulty with blood sampling through venipuncture.

Abnormal diet patterns (for any reason) during the four weeks preceding the study, including fasting, high protein diets etc.

Employee or immediate relative of an employee of Epalex Corporation, its affiliates or partners Study Restrictions: Analgesic drugs, e.g., opiates alone or in a combination product from screening until the end-of-study follow-up visit. Occasional use of acetaminophen, aspirin, or an NSAID will be permitted; however, a subject will not be eligible to receive study drug if he/she has taken any analgesic (including over the counter) in the preceding 24 hours. Analgesics (except as rescue) are not permitted from 24 hours prior to clinic admission until the end-of-study follow-up visit.

Marijuana products including THC and CBD are not permitted from screening until the end-of-study follow-up visit.

Sedative-hypnotic drugs, prescription or OTC, (e.g., benzodiazepines, barbiturates, sleeping aids, Fiorinal) from screening until the end-of-study follow-up visit.

Triptans, e.g., sumatriptan, Imitrex (except as rescue, where applicable) are not permitted from screening until the end-of-study follow-up visit.

Ergotamine or combination drugs, containing ergotamine e.g. cafergot (except as rescue, where applicable) from screening until the end-of-study follow-up visit.

Metoclopramide, e.g. Reglan (except as rescue, where applicable) from screening until the end-of-study follow-up visit.

Alcohol-based products are permitted; however, a subject will not be eligible to receive study drug if he/she has taken any alcohol based product in the preceding 24 hours. Alcohol-based products are not permitted from 24 hours prior to clinic admission until the end-of-study follow-up visit.

Prescription and OTC medications that are medically necessary (except analgesics, sedative-hypnotics, and drugs intended for treatment of acute migraine, as described above) are permitted. The center principal investigator (PI) will review, record, and approve at screening the concomitant medications expected to be continued over the course of study. In case of questions as to the suitability of a concomitant medication, investigators are encouraged to consult with the Sponsor.

For safety reasons, subjects will be required to remain seated or semi-reclined and avoid sleeping for the first 1 hour before and 4 hours after drug administration.

PK Sampling Time Points: A total of 14 blood samples (for analysis of both fospropofol and propofol) will be collected (in each close level or period): Pre-close (within 10 min of closing) and post-close: 5, 10, 20, 30, 45, 60, 90 minutes and 2, 3, 4, 5, 6, and 9 hours post-close.

Subject Safety Monitoring: Medical surveillance and AE monitoring:
  Subjects will be monitored throughout the study by Clinic staff for AEs.
  Continuous cardiac telemetry and pulse oximetry:
  To detect any clinically significant cardiac arrhythmia or other abnormality at baseline (pre-close), cardiac telemetry will be performed for at least 30 minutes prior to closing and continued until approximately 9 hours post-close to monitor for any cardiac effects of study drug. Subjects with any clinically significant ECG abnormality at baseline (pre-close) will be excluded. Pulse oximetry will be monitored over the same time course.
  Vital signs:
  BP, HR, RR, and Pulse Oximetry (PO) will be recorded pre-close within 10 min of closing and at approximately 5, 10, 20, 30, 45, 60, 90 2, 2.5, 3, 4, 6, and 9 hours after closing.
  Level of Alertness
  Level of sedation will be assessed using the Modified Observer's Assessment of Alertness/Sedation (MOAA/S) Score. See Chernik D A, Gillings D, Laine H, et al. Validity and reliability of the Observer's Assessment of Alertness/Sedation Scale: study with intravenous midazolam. J Clin Psychopharmacol 1990 Aug. 10(4):244-51.

| Responsiveness | Score |
| --- | --- |
| Responds readily to name spoken in normal tone | 5 (alert) |
| Lethargic response to name spoken in normal tone | 4 |
| Responds only after name is called loudly and/or repeatedly | 3 |
| Responds only after mild prodding or shaking | 2 |
| Responds only after painful trapezius squeeze | 1 |
| Does not respond to painful trapezius squeeze | 0 |

Sedation (MOAA/S score) will be recorded within 10 min pre-close and at approximately 5 min intervals until 3 hours after closing, and at 15 min intervals thereafter until 9 hours post-close provided that the subject has demonstrated at least three consecutive MOAA/S scores of 5 immediately prior to the 3 hour timepoint. A subject who has not demonstrated three consecutive MOAA/S scores of 5 immediately prior to the 3 hour timepoint will continue with MOAA/S assessments at 5 min intervals until he or she demonstrates three consecutive MOAA/S scores of 5, with MOAA/S scores recorded at 15 min interval thereafter until 9 hours post-close. See Cohen LB. Clinical trial: a close-response study of fospropofol disodium for moderate sedation during colonoscopy. 2008; Aliment Pharmacol Ther 27, 597-608.

12-lead ECG:
  12-lead ECG will be performed at Clinic check-in (Day 1 before closing) and at Clinic checkout.
Laboratory assessments:
  Hematology, biochemistry, and urinalysis at clinic check-in and at follow-up (final) visit scheduled between 48 h and 96 h after administration of study drug.
  Alcohol breath test, urine cotinine test, and urine drug screen at check-in.
  For women of child-bearing potential, urine pregnancy test at check-in; serum pregnancy test at follow-up (final) visit scheduled between 48 h and 96 h after administration of study drug [A serum pregnancy test will be obtained at screening.]
Physical examination:
  Complete physical exam (PE) at screening, brief PE at clinic check-in and clinic checkout; complete PE at follow-up (final) visit scheduled between 48 h and 96 h after administration of study drug
Clinic Check-in Food will not be permitted from the time of clinic check-in until 4 hours after the initial closing of study drug. Fluids will not be permitted from one hour before the initial close until one hour after administration of the second (pulsed close) of study drug (except for water (240 mL) administered with study drug.) Water will be permitted ad lib at all other times.
  Abbreviated physical exam, alcohol breath test, and urine drug screen at check-in. Urine pregnancy test (women of child-bearing potential)
  Record time and nature of last meal or food intake
  Record concomitant medications and all medications taken in the 24 hours prior to check-in.
  Record characteristics of the presenting headache and associated symptoms including, but not limited to the following:
  Characteristics of the presenting headache (i.e., throbbing, unilateral or bilateral, aggravated by exercise).
  Subject's assessment of headache pain at admission to clinic on a 4-point Likert Scale, (i.e., 0=none, 1=mild, 2=moderate, 3=severe) for the presenting headache.
  Most bothersome associated symptom for the presenting headache (e.g., nausea/vomiting, photophobia, phonophobia)
  Presence of associated symptoms, nausea, vomiting, photophobia, phonophobia (Yes/No) at clinic admission
Efficacy Measures: Note: Pre-close and post-close times are with reference to the initial dose of study drug.
  Subject's assessment of headache pain—4-point Likert Scale (Severe, Moderate, Mild, No pain) to be assessed at baseline prior to closing (within 10 min of closing), and post-close at 5 min, 15 min, 30 min, 45 min, 1 h, 1.5 h, 2 h, 3 h, 4 h, 6 h, 8 h, and at clinic discharge, and following discharge (by diary) at 12, 24 h and 48 h post-closing.
  Headache qualifying for treatment with study drug must be of at least moderate severity at baseline (pre-close and within 10 min of closing study drug).

Subjects will be asked to announce while in clinic the time that no headache pain is first noted, or, after discharge, if applicable, to record the time that no headache pain is first noted in the patient diary. Subjects will also be asked to announce in clinic and/or record by patient diary after discharge from clinic any recurrence or worsening of headache pain, and time of onset of worsening.

Subject's assessment of presence/absence of most bothersome symptom (MBS)—subjects to be questioned as to presence or absence of the most bothersome symptom associated with presenting headache (identified at clinic admission) at the same time points as the assessment of headache pain [baseline prior to closing (within 10 min of closing), and post-close at 5 min, 15 min, 30 min, 45 min, 1 h, 1.5 h, 2 h, 3 h, 4 h, 6 h, 8 h, and at clinic discharge, and following discharge (by diary) at 12, 24 h and 48 h post-closing.] Subjects will also be asked to announce while in clinic the time that disappearance of the most bothersome symptom is first noted, or, after discharge, if applicable, to record the time that no headache pain is first noted in the patient diary. Subjects will also be asked to announce in clinic and/or record by patient diary after discharge from clinic any recurrence of the most bothersome symptom, and time of onset of recurrence.

Subject assessment of presence/absence of migraine-associated symptoms (other than MBS): nausea/vomiting, photophobia, and/or phonophobia at baseline (within 15 min of closing), and post-close at 5 min, 15 min, 30 min, 45 min, 1 h, 1.5 h, 2 h, 3 h, 4 h, 6 h, 8 h, and at clinic discharge, and following discharge (by diary) at 12, 24 h and 48 h post-closing. Subjects will also be asked to announce while in clinic the time that disappearance of migraine-associated symptoms is first noted, or, after discharge, if applicable, to record the time that disappearance of the associated symptom is first noted in the patient diary. Subjects will also be asked to announce in clinic and/or record by patient diary after discharge from clinic any recurrence of a migraine-associated symptom, and time of onset of recurrence.

While in clinic subjects will be instructed to report any adverse events directly to the investigators or clinic staff. Subjects will be instructed to record in the patient diary any adverse events emerging following discharge. All subjects will have telephone access to the investigator or investigator staff to report any urgent concerns in the course of the study.

Rescue Treatment Rescue treatment (acute treatment for migraine pain) may be administered at any time at the investigator's discretion. Subjects and investigators will be encouraged to avoid administration of rescue treatment earlier than 2 hours after initial administration of study drug. Rescue treatment may include an analgesic and/or acute migraine medication(s). Selection of rescue for each subject may be guided by history of treatment effective for the subject in the past. In general, the investigator and subject will have agreed on the appropriate rescue therapy for the subject at screening. In identifying an appropriate rescue therapy, the additive cardiorespiratory effects of narcotic analgesics and sedative hypnotic agents when administered concomitantly with fospropofol should be considered.

Clinic Check-out: The following procedures will be carried out at clinic check-out: physical examination, vital signs, 12-lead ECG, oral temperature, AE monitoring. Distribute diary for subjects to record and grade any ongoing headache pain, and any ongoing migraine-associated symptoms (present/absent), and/or any recurrence or worsening of pain or migraine-associated symptoms. Schedule follow-up visit.

Follow-up Visit/End of Study Participation The following procedures will be carried out at a follow-up end of study visit to be scheduled 48 to 96 hours after administration of study drug: hematology, blood chemistry, urinalysis, AE monitoring, serum pregnancy test for women of child-bearing potential Analytical Fospropofol and propofol will be analyzed in plasma samples using Method: a validated method. Additional plasma samples may be drawn and stored for possible future bioanalysis of other analytes.

Pharmaco-kinetic Parameters: The following pharmacokinetic parameters will be calculated for both fospropofol and propofol plasma concentrations: $AUC_{0-t}$, $AUC_{0-inf}$, $C_{max}$, Residual area, $T_{max}$, $T_{1/2el}$, $K_{el}$, Cl/F, Vd/F, and Vd/F/kg Statistical Analyses: Statistical analyses will be performed with the safety, tolerability, efficacy, and PK data.

Laboratory Assessments—Example A11

Hematology: Hematology will be drawn at screening, at clinic check-in, and at the follow-up (final) visit. Hematology will include complete blood count with differential, hemoglobin, and hematocrit.

Chemistry: Blood chemistry will be drawn at screening, at clinic check-in, and at the follow-up (final) visit. Blood chemistry will include albumin, alkaline phosphatase, aspartate aminotransferase, alanine aminotransferase, urea, calcium, chloride, glucose, phosphorus, potassium, creatinine, sodium, total bilirubin, and total protein.

Serology: Hepatitis B (HBs Ag), Hepatitis C (HCV) antibody, and HIV antigen and antibody detection will be drawn at screening.

Urinalysis: Urine for Urinalysis will be taken at screening, at clinic check-in, and at the follow-up (final) visit. Urinalysis will include macroscopic examination, pH, specific gravity, protein, glucose, ketones, bilirubin, occult blood, nitrite, urobilinogen, and leukocytes. Unless otherwise specified, microscopic examination will be performed on abnormal findings.

Drug, Cotinine, and Alcohol Screen: A urine drug screen (amphetamines, methamphetamines, barbiturates, benzodiazepines, tetrahydrocannabinol, cocaine, opiates, PCP, MDMA, methadone), a urine cotinine test, and an alcohol breath test will be performed at screening and at clinic check-in.

Pregnancy Tests: For women of child bearing potential: A serum pregnancy test will be performed at screening. A urine pregnancy test will be performed at clinic check-in. A serum pregnancy test will be performed at the follow-up (final) visit, and at early termination, where applicable.

Example A12

Safety-tolerability, pharmacokinetics, and efficacy of single ascending oral doses of fospropofol disodium administered to healthy adult male and female volunteers for the acute treatment of moderate to severe migraine headache.

Study Drug: Fospropofol Disodium

Study Phase and Type: Phase 2a—Single Ascending Dose (SAD) in adults with migraine Study Design: Multi-center, Phase 2a, placebo controlled, modified double-blind, SAD, safety-tolerability, pharmacokinetic (PK), and efficacy study of Fospropofol Disodium in adult males and females for the acute treatment of moderate to severe migraine headache. The study design is characterized as modified double-blind because treatment assignment will be unblinded for review of safety-tolerability, propofol PK, and efficacy following each closing stage.

The study will evaluate 3 ascending close levels (in 3 stages) with close levels to be selected on the basis of the prior Phase 1 healthy volunteer study. Separate cohorts of 12-500 subjects will be randomized to receive ascending doses of Fospropofol Disodium or matching placebo (9-375 subjects to receive Fospropofol Disodium and 3-125 subjects to receive placebo at each close level). During each closing stage subjects and investigators will be blinded to the treatment assignment. Following each closing stage, safety-tolerability, pharmacokinetic, and efficacy assessments will be reviewed with treatment assignment unblinded. Depending on results reviewed following Stage 1 and following Stage 2, close escalation may stop and/or the close levels for subsequent stages may be modified to levels lower than those specified in the protocol. (It is possible that a close level already studied will be repeated with a subsequent cohort to provide additional information at that close level.) In no case will closes exceed the highest close level specified in the protocol.

Subjects: Up to 500 adult males and females≥18 and ≤55 years of age with a body mass index (BMI) within 18.0-35.0 kg/m² inclusive and body weight≥50 kg. Females of childbearing potential must be using reliable contraception or totally abstain from intercourse.

Separate cohorts of 12-500 subjects will receive Fospropofol Disodium (9-375 subjects) or placebo (4-125) at each of three ascending close levels). Each cohort of 12-500 to be balanced on gender 1:1, 1.3:1.1, or 1.4:1.0 with no fewer than 50% females.

Subjects who withdraw or are withdrawn from the study after closing, for reasons other than safety and tolerability, may be replaced after consultation with the Safety Review Committee.

Screening Procedures: Demographic data, medical and medication histories including drug allergies, physical examination, body measurements, electrocardiogram (ECG), vital signs (blood pressure [BP], heart rate [HR], respiratory rate [RR], pulse oximetry [PO], and oral temperature [OT]), hematology, blood chemistry, human immunodeficiency virus (HIV), hepatitis B and C tests, urinalysis, urine drug screen, alcohol breath test, urine cotinine test, Serum pregnancy test (women of child-bearing potential). Screening to occur within 30 days of clinic admission. [Subjects who do not present with a qualifying headache within 30 days of screening may have a second screening visit within 45 days of the first screening at the discretion of the investigator. Second screening visit may be abbreviated to updated history and serum pregnancy test for women of childbearing potential. A subject who does not present with a qualifying headache within 30 days of the second screening will be classified as a screening failure.]

Migraine History: Confirm migraine diagnosis according to ICHD criteria, age of onset, estimated frequency of migraine episodes, including frequency of episodes classified as moderate or severe, history of migraine-associated symptoms (nausea/vomiting, photophobia, phonophobia), characteristic features of episodes including aura (if any), nature of pain, associated symptoms; history of headache types other than migraine, history of medications (if any) used for treatment of acute migraine (past and current); history of medications (if any) used for the purpose of migraine prophylaxis (past and current). Identification of an appropriate "rescue" treatment (See Rescue Treatment below)

Confinement in clinic: Subjects will arrive at the study clinic during the course of a migraine headache of at least moderate severity (in the subject's judgment). Subjects will be confined to the study site for 1 to 2 hours before closing and confined until at least 9 hours following a single dose of study drug.

Study Drug and Dosage Form: Three close levels: Selected from within the range 200 mg-3600 mg.

Fospropofol Disodium to be administered as an appropriate number of powder filled capsules, each capsule containing 200 mg of fospropofol disodium (Epalex Corporation, USA).

Placebo to be administered as an equivalent number of identical capsules containing placebo.

Study Drug Administration: Each cohort of 12-500 subjects will receive a single oral dose of either Fospropofol Disodium (N=9-375) or matching placebo (N=3-125) at one of three close levels. Fospropofol Disodium administered as capsules containing 200 mg.

Subjects will receive a single dose of Fospropofol Disodium or placebo.

Study drug will be administered with 240 mL of water at ambient temperature. Except for water administered with study drug, no fluids will be allowed from 1 hour before closing until 1 hour post-close.

There will be at least 7 days between closing of each close level. Following completion of each close level, pharmacokinetic (PK) data for propofol collected until 9 hours post-close, safety and tolerability data collected until the clinic check-out (approximately 10 hours post-close), and the efficacy data collected until 9 hours post-close will be evaluated by a Safety Committee before proceeding to the next close.

Inclusion Criteria Male or female, non-smoker (no use of tobacco products within 3 months prior to screening), ≥18 and ≤55 years of age, with BMI ≥18.0 and ≤35.0 kg/m² and body weight≥50.0 kg Generally healthy (other than migraine) as defined by:

The absence of clinically significant illness and surgery within 4 weeks prior to closing. Subjects vomiting within 24 hours pre-close will be carefully evaluated. Inclusion pre-closing is at the discretion of the center PI.

The absence of clinically significant history of neurological (other than migraine), endocrine, cardiovascular, pulmonary, hematological, immunologic, psychiatric, gastrointestinal, renal, hepatic, and metabolic disease.

The absence of clinically significant history of sleep apnea

Subject has at least 1 year history of migraines (with or without aura), consistent with a diagnosis according to the International Classification of Headache Disorder, 3rd Edition, Beta version including the following:

Migraine attacks present for more than 1 year with age of onset prior to 50 years of age Migraine attacks last, 4 to 72 hours if untreated, on average, in the 3 months prior to screening visit Two to eight (2-8) moderate or severe migraine attacks per month in the 3 months prior to the screening visit. The migraine, for which the patient receives treatment during the study, must have at least one of the associated symptoms: nausea, photophobia, phonophobia, or migraine with aura Subjects on prophylactic migraine medication are permitted to remain on therapy provided they have been on a stable dose for at least 3 months prior to screening visit and the close is not expected to change during the course of the study Clinical laboratory values within the laboratory acceptable range unless values are deemed by the PI/Sub-Investigator as "Not Clinically Significant".

Ability to comprehend the nature of the study, as assessed by the PI/Sub-Investigator. Capable of giving written informed consent. Able to communicate effectively with clinic staff.

Availability to volunteer for the entire study duration and willing to adhere to all protocol requirements.

Female subjects must agree not to be nursing at any time during the study and until 30 days after the study follow-up visit.

Female subjects must fulfill at least one of the following:

Be surgically sterile for a minimum of 6 months;

Post-menopausal for a minimum of 1 year;

Agree to avoid pregnancy and use medically acceptable method of contraception from at least 30 days prior to administration of study drug until 30 days after the study follow-up visit.

Medically acceptable methods of contraception include hormonal contraception, hormonal or non-hormonal intrauterine device, or double barrier method (simultaneous use of male condom with intravaginally applied spermicide and diaphragm or cervical cap). Complete abstinence alone can be used as a method of contraception.

Subjects with coexisting history of headache other than migraine are eligible provided that these headaches are distinguishable from the subject's migraine headaches No contraindication to use of fospropofol according to FDA approved labeling Concomitant medications taken for the purpose of migraine prophylaxis are permitted provided that the dose of these medications is stable for at least 3 months prior to administration of study drug and estimated headache frequency at screening meets the criterion above If concomitant medications intended to reduce the frequency of migraine are discontinued prior to the study, these medications must be discontinued at least one month prior to receiving study drug Absence of any medical condition that, in the opinion of the investigator or the Sponsor, may be potentially associated with an increased risk from study drug or participation in the study.

Subject must be willing to avoid the use of analgesics or any acute migraine medication(s) for 24 hours prior to receiving study drug.

Subject must be willing to forgo rescue treatment (defined below) for at least 2 hours after initiation of treatment with study drug.

Exclusion Criteria Subjects to whom any of the following applies will be excluded:

Patient has basilar migraine or hemiplegic migraine

Patient is taking narcotic (opiate) medication

Patient uses an opiate as first line acute treatment for migraine attacks

History of ergotamine, triptan, or any acute therapy intake on ≥10 days per month on a regular basis for ≥3 months History of simple analgesic intake on ≥10 days per month for ≥3 months History of use of opioid or combination medication intake or butalbital containing analgesic greater than 5 days per month for ≥3 months Very frequent chronic tension type headaches for 15 or more days per month (or unable to distinguish between tension-type headaches and migraine)

Patient has major depression, other pain syndromes that might interfere with study assessments, psychiatric conditions, dementia, or significant neurological disorders (other than migraine)

Any clinically significant abnormality at physical examination, clinically significant abnormal laboratory test results or positive serologic test for hepatitis B, hepatitis C, or HIV found during medical screening. (Subjects with positive serology for hepatitis C and negative HCV RNA are eligible at the discretion of the principal investigator.)

Positive urine drug screen (unless consistent with an ongoing prescription drug as documented by the center investigator), positive alcohol breath test, urine cotinine test at screening or at clinic check-in Positive serum pregnancy test (women of child-bearing potential) at screening (or positive urine pregnancy test at clinic check-in).

History of severe allergic reactions (e.g. anaphylactic reactions, angioedema), hypersensitivity or idiosyncratic reaction to fospropofol, propofol, Fospropofol Disodium excipients or related substances.

Individuals having undergone any major surgery within 6 months prior to the start of the study, unless deemed otherwise by the PI.

Clinically significant ECG abnormalities (e.g., QTcF≥450 msec in males or ≥470 msec in females) or persistent (3 determinations) vital sign abnormalities at screening (systolic blood pressure lower than 90 or over 145 mmHg, diastolic blood pressure lower than 55 or over 95 mmHg, or heart rate less than 50 or over 100 bpm).

Vital signs to be taken in a seated position and may be repeated up to a total of three determinations.

Oxygen saturation by oximetry less than 93% at screening

History of significant alcohol abuse within one year prior to screening or regular use of alcohol within six months prior to the screening visit (more than fourteen units of alcohol per week [1 unit=150 mL of wine, 360 mL of beer, or 45 mL of 40% alcohol]).

History of significant drug abuse within one year prior to screening or use of hard drugs (such as cocaine, phencyclidine [PCP], crack, opioid derivatives including heroin, and amphetamine derivatives) within 1 year prior to screening.

Participation in an interventional clinical research study involving the administration of an investigational or marketed drug or device within 30 days prior to administration of study drug or administration of a biological product in the context of a clinical research study within 90 days prior to administration of study drug. Concomitant participation in an investigational study involving no drug or device administration is permitted provided obligations associated with the concomitant participation are not expected to interfere with procedures and obligations of the present study.

Any medical condition (other than migraine) requiring ongoing, more than occasional, use of analgesic drugs. (Occasional use of acetaminophen, aspirin, or NSAID, or topical products without significant systemic absorption is not an exclusion).

Any medical condition requiring ongoing treatment with sedative-hypnotic drugs (e.g., benzodiazepines, barbiturates)

Donation of plasma within 7 days prior to closing. Donation or loss of blood (excluding volume drawn at screening) of 50 mL to 499 mL of blood within 30 days, or more than 499 mL within 56 days prior to the first closing.

Hemoglobin≤135 g/L for men or ≤120 g/L for women at screening.

Intolerance to and/or difficulty with blood sampling through venipuncture.

Abnormal diet patterns (for any reason) during the four weeks preceding the study, including fasting, high protein diets etc.

Employee or immediate relative of an employee of Epalex Corporation, its affiliates or partners.

Study Restrictions: Subjects will be asked to refrain from using products that may potentially affect their safety, the PK profile of the study drug, and/or assessments of efficacy. Main study restrictions include the following:

Analgesic drugs, e.g., opiates alone or in a combination product from screening until the end-of-study follow-up visit. Occasional use of acetaminophen, aspirin, or an NSAID will be permitted; however, a subject will not be eligible to receive study drug if he/she has taken any analgesic (including over the counter) in the preceding 24 hours. Analgesics (except as rescue) are not permitted from 24 hours prior to clinic admission until the end-of-study follow-up visit.

Marijuana products including THC and CBD are not permitted from screening until the end-of-study follow-up visit.

Sedative-hypnotic drugs, prescription or OTC, (e.g., benzodiazepines, barbiturates, sleeping aids, Fiorinal) from screening until the end-of-study follow-up visit.

Triptans, e.g., sumatriptan, Imitrex (except as rescue, where applicable) are not permitted from screening until the end-of-study follow-up visit.

Ergotamine or combination drugs, containing ergotamine e.g. cafergot (except as rescue, where applicable) from screening until the end-of-study follow-up visit.

Metoclopramide, e.g. Reglan (except as rescue, where applicable) from screening until the end-of-study follow-up visit.

Alcohol-based products are permitted; however, a subject will not be eligible to receive study drug if he/she has taken any alcohol-based product in the preceding 24 hours. Alcohol-based products are not permitted from 24 hours prior to clinic admission until the end-of-study follow-up visit.

Prescription and OTC medications that are medically necessary (except analgesics, sedative-hypnotics, and drugs intended for treatment of acute migraine, as described above) are permitted. The center principal investigator (PI) will review, record, and approve at screening the concomitant medications expected to be continued over the course of study. In case of questions as to the suitability of a concomitant medication, investigators are encouraged to consult with the Sponsor.

For safety reasons, subjects will be required to remain seated or semi-reclined and avoid sleeping for the first 1 hour before and 4 hours after administration of study drug.

PK Sampling Time Points: A total of 14 blood samples (for analysis of both fospropofol and propofol) will be collected (in each close level or period): Pre-close (within 10 min of closing) and post-close: 5, 10, 20, 30, 45, 60, 90 minutes and 2, 3, 4, 5, 6, and 9 hours post-close.

Subject Safety Monitoring: Medical surveillance and AE monitoring:

Subjects will be monitored throughout the study by Clinic staff for AEs.

Continuous cardiac telemetry and pulse oximetry:

To detect any clinically significant cardiac arrhythmia or other abnormality at baseline (pre-close), cardiac telemetry will be performed for at least 30 minutes prior to closing and continued until approximately 9 hours post-close to monitor for any cardiac effects of study drug. Subjects with any clinically significant ECG abnormality at baseline (pre-close) will be excluded. Pulse oximetry will be monitored over the same time course.

Vital signs:

BP, HR, RR, and Pulse Oximetry (PO) will be recorded pre-close within 10 min of closing and at approximately 5, 10, 20, 30, 45, 60, 90 2, 2.5, 3, 4, 6, and 9 hours after closing.

Level of Alertness

Level of sedation will be assessed using the Modified Observer's Assessment of Alertness/Sedation (MOAA/S) Score. See Chernik D A, Gillings D, Laine H, et al. Validity and reliability of the Observer's Assessment of Alertness/Sedation Scale: study with intravenous midazolam. J Clin Psychopharmacol 1990 Aug. 10(4):244-51.

| Responsiveness | Score |
| --- | --- |
| Responds readily to name spoken in normal tone | 5 (alert) |
| Lethargic response to name spoken in normal tone | 4 |
| Responds only after name is called loudly and/or repeatedly | 3 |
| Responds only after mild prodding or shaking | 2 |
| Responds only after painful trapezius squeeze | 1 |
| Does not respond to painful trapezius squeeze | 0 |

Sedation (MOAA/S score) will be recorded within 10 min pre-close and at approximately 5 min intervals until 3 hours after closing, and at 15 min intervals thereafter until 9 hours post-close provided that the subject has demonstrated at least three consecutive MOAA/S scores of 5 immediately prior to the 3 hour timepoint. A subject who has not demonstrated three consecutive MOAA/S scores of 5 immediately prior to the 3 hour timepoint will continue with MOAA/S assessments at 5 min intervals until he or she demonstrates three consecutive MOAA/S scores of 5, with MOAA/S scores recorded at 15 min intervals thereafter until 9 hours post-close. See Cohen LB. Clinical trial: a close-response study of fospropofol disodium for moderate sedation during colonoscopy. 2008; Aliment Pharmacol Ther 27, 597-608.

12-lead ECG:

12-lead ECG will be performed at Clinic check-in (Day 1, before closing) and at Clinic checkout.

Laboratory assessments:

Hematology, biochemistry, and urinalysis at clinic check-in and at the follow-up (final) visit to be scheduled between 48 h and 96 h after administration of study drug.

Alcohol breath test, urine cotinine test, and urine drug screen at check-in.

For women of child-bearing potential, urine pregnancy test at check-in; serum pregnancy test at follow-up (final) visit scheduled between 48 h and 96 h after administration of study drug [A serum pregnancy test will be obtained at screening.]

Physical examination:

Complete physical exam (PE) at screening, brief PE at clinic check-in and clinic checkout; complete PE at follow-up (final) visit scheduled between 48 h and 96 h after administration of study drug Clinic Check-in Food will not be permitted from the time of clinic check-in until 4 hours after closing of study drug. Fluids will not be permitted from one hour before until one hour after administration of study drug (except for water (240 mL) administered with study drug.) Water will be permitted ad lib at all other times.

Abbreviated physical exam, alcohol breath test, and urine drug screen at check-in. Urine pregnancy test (women of child-bearing potential)

Record time and nature of last meal or food intake

Record concomitant medications and all medications taken in the 24 hours prior to check-in.

Record characteristics of the presenting headache and associated symptoms including, but not limited to the following:

Characteristics of the presenting headache (i.e., throbbing, unilateral or bilateral, aggravated by exercise).

Subject's assessment of headache pain at admission to clinic on a 4-point Likert Scale, (i.e., 0=none, 1=mild, 2=moderate, 3=severe) for the presenting headache.

Most bothersome associated symptom for the presenting headache (e.g., nausea/vomiting, photophobia, phonophobia)

Presence of associated symptoms, nausea, vomiting, photophobia, phonophobia (Yes/No) at clinic admission Efficacy Measures: Subject's assessment of headache pain—4-point Likert Scale (Severe, Moderate, Mild, No pain) to be assessed at baseline prior to closing (within 10 min of closing), and post-close at 5 min, 15 min, 30 min, 45 min, 1 h, 1.5 h, 2 h, 3 h, 4 h, 6 h, 8 h, and at clinic discharge, and following discharge (by diary) at 12, 24 h and 48 h post-closing. Headache qualifying for treatment with study drug must be of at least moderate severity at baseline (pre-close and within 10 min of closing study drug). Subjects will be asked to announce while in clinic the time that no headache pain is first noted, or, after discharge, if applicable, to record the time that no headache pain is first noted in the patient diary. Subjects will also be asked to announce in clinic and/or record by patient diary after discharge from clinic any recurrence or worsening of headache pain, and time of onset of worsening.

Subject's assessment of presence/absence of most bothersome symptom (MBS)—subjects to be questioned as to presence or absence of the most bothersome symptom associated with presenting headache (identified at clinic admission) at the same time points as the assessment of headache pain [baseline prior to closing (within 10 min of closing), and post-close at 5 min, 15 min, 30 min, 45 min, 1 h, 1.5 h, 2 h, 3 h, 4 h, 6 h, 8 h, and at clinic discharge, and following discharge (by diary) at 12, 24 h and 48 h post-closing.] Subjects will also be asked to announce while in clinic the time that disappearance of the most bothersome symptom is first noted, or, after discharge, if applicable, to record the time that no headache pain is first noted in the patient diary. Subjects will also be asked to announce in clinic and/or record by patient diary after discharge from clinic any recurrence of the most bothersome symptom, and time of onset of recurrence.

Subject assessment of presence/absence of migraine-associated symptoms (other than MBS): nausea/vomiting, photophobia, and/or phonophobia at baseline (within 15 min of closing), and post-close at 5 min, 15 min, 30 min, 45 min, 1 h, 1.5 h, 2 h, 3 h, 4 h, 6 h, 8 h, and at clinic discharge, and following discharge (by diary) at 12, 24 h and 48 h post-closing. Subjects will also be asked to announce while in clinic the time that disappearance of migraine-associated symptoms is first noted, or, after discharge, if applicable, to record the time that disappearance of the associated symptom is first noted in the patient diary. Subjects will also be asked to announce in clinic and/or record by patient diary after discharge from clinic any recurrence of a migraine-associated symptom, and time of onset of recurrence.

While in clinic subjects will be instructed to report any adverse events directly to the investigators or clinic staff. Subjects will be instructed to record in the patient diary any adverse events emerging following discharge. All subjects will have telephone access to the investigator or investigator staff to report any urgent concerns in the course of the study.

Rescue Treatment Rescue treatment (acute treatment for migraine pain) may be administered at any time at the investigator's discretion. Subjects and investigators will be encouraged to avoid administration of rescue treatment earlier than 2 hours after administration of study drug. Rescue treatment may include an analgesic and/or acute migraine medication(s). Selection of rescue for each subject may be guided by history of treatment effective for the subject in the past. In general, the investigator and subject will have agreed on the appropriate rescue therapy for the subject at screening. In identifying an appropriate rescue therapy, the additive cardiorespiratory effects of narcotic analgesics and sedative hypnotic agents when administered concomitantly with fospropofol should be considered.

Clinic Check-out: The following procedures will be carried out at clinic check-out: physical examination, vital signs, 12-lead ECG, oral temperature, AE monitoring. Distribute diary for subjects to record and grade any ongoing headache pain, and any ongoing migraine-associated symptoms (present/absent), and/or any recurrence or worsening of pain or migraine-associated symptoms. Schedule follow-up visit.

Follow-up Visit/End of Study Participation The following procedures will be carried out at a follow-up end of study visit to be scheduled 48 to 96 hours after administration of study drug: hematology, blood chemistry, urinalysis, AE monitoring, serum pregnancy test for women of child-bearing potential Analytical Method: Fospropofol and propofol will be analyzed in plasma samples using a validated method. Additional plasma samples may be drawn and stored for possible future bioanalysis of other analytes.

Pharmacokinetic Parameters: The following pharmacokinetic parameters will be calculated for both fospropofol and propofol plasma concentrations: $AUC_{0-t}$, $AUC_{0-inf}$, $C_{max}$, Residual area, $T_{max}$, $T_{1/2el}$, $K_{el}$, Cl/F, Vd/F, and Vd/F/kg.

Statistical Analyses: Statistical analyses will be performed with the safety, tolerability, efficacy, and PK data Laboratory Assessments—Example A12

Hematology: Hematology will be drawn at screening, at clinic check-in, and at the follow-up (final) visit. Hematology will include complete blood count with differential, hemoglobin, and hematocrit.

Chemistry: Blood chemistry will be drawn at screening, at clinic check-in, and at the follow-up (final) visit. Blood chemistry will include albumin, alkaline phosphatase, aspartate aminotransferase, alanine aminotransferase, urea, calcium, chloride, glucose, phosphorus, potassium, creatinine, sodium, total bilirubin, and total protein.

Serology: Hepatitis B (HBs Ag), Hepatitis C (HCV) antibody, and HIV antigen and antibody detection will be drawn at screening.

Urinalysis: Urine for Urinalysis will be taken at screening, at clinic check-in, and at the follow-up (final) visit. Urinalysis will include macroscopic examination, pH, specific gravity, protein, glucose, ketones, bilirubin, occult blood, nitrite, urobilinogen, and leukocytes. Unless otherwise specified, microscopic examination will be performed on abnormal findings.

Drug, Cotinine, and Alcohol Screen: A urine drug screen (amphetamines, methamphetamines, barbiturates, benzodiazepines, tetrahydrocannabinol, cocaine, opiates, PCP, MDMA, methadone), a urine cotinine test, and an alcohol breath test will be performed at screening and at clinic check-in.

Pregnancy Tests: For women of child bearing potential: A serum pregnancy test will be performed at screening. A urine pregnancy test will be performed at clinic check-in. A serum pregnancy test will be performed at the follow-up (final) visit, and at early termination, where applicable.

Example A13

Safety-tolerability, pharmacokinetics, and efficacy of single pulsed ascending oral doses of Fospropofol Disodium administered to adult males and females for the acute treatment of moderate to severe migraine headache.

Study Drug: Fospropofol Disodium

Study Phase and Type: Phase 2a—Single Pulsed Ascending Dose (SAD) in adults with migraine Study Design: Multi-center, Phase 2a, placebo controlled, modified double-blind, Single Pulsed Ascending Dose, safety-tolerability, pharmacokinetic (PK), and efficacy study of Fospropofol Disodium in adult males and females for the acute treatment of moderate to severe migraine headache. The study is characterized as modified double-blind because treatment assignment will be unblinded for review of safety-tolerability, propofol PK, and efficacy following each closing stage.

The study will evaluate 3 ascending close levels of a pulsed close (in 3 stages) with close levels to be selected on the basis of the prior Phase 2a SAD study in subjects with acute migraine (Study Fospropofol Disodium). Separate cohorts of 12-500 subjects will be randomized to receive a fixed dose (all subjects) followed by ascending pulsed doses of Fospropofol Disodium or matching placebo (9-375 subjects to receive a pulsed dose of Fospropofol Disodium and 3-125 subjects to receive a pulsed dose of placebo at each close level). During each closing stage subjects and investigators will be blinded to the treatment assignment.

Subjects: Up to 500 adult males and females≥18 and ≤55 years of age with a body mass index (BMI) within 18.0-35.0 kg/m² inclusive and body weight≥50 kg. Females of childbearing potential must be using reliable contraception or totally abstain from intercourse.

Three separate cohorts of up to 160 subjects will receive a fixed dose of Fospropofol Disodium followed by a second "pulsed" dose of Fospropofol Disodium 30 minutes later (up to 120 subjects) or a second "pulsed" dose of placebo 30 minutes (up to 40 subjects) at each of three ascending close levels. Each cohort of up to 160 to be balanced on gender 1:1 or 1.3:1 with no fewer than 50% females.

Subjects who withdraw or are withdrawn from the study after closing, for reasons other than safety and tolerability, may be replaced after consultation with the Safety Review Committee.

Screening Procedures: Demographic data, medical and medication histories including drug allergies, physical examination, body measurements, electrocardiogram (ECG), vital signs (blood pressure [BP], heart rate [HR], respiratory rate [RR], pulse oximetry [PO], and oral temperature [OT]), hematology, blood chemistry, human immunodeficiency virus (HIV), hepatitis B and C tests, urinalysis, urine drug screen, alcohol breath test, urine cotinine test, Serum pregnancy test (women of child-bearing potential). Screening to occur within 30 days of clinic admission. [Subjects who do not present with a qualifying headache within 30 days of screening may have a second screening visit within 45 days of the first screening at the discretion of the investigator. Second screening visit may be abbreviated to updated history and serum pregnancy test for women of childbearing potential. A subject who does not present with a qualifying headache within 30 days of the second screening will be classified as a screening failure.]

Migraine History: Confirm migraine diagnosis according to ICHD criteria, age of onset, estimated frequency of migraine episodes, including frequency of episodes classified as moderate or severe, history of migraine-associated symptoms (nausea/vomiting, photophobia, phonophobia), characteristic features of episodes including aura (if any), nature of pain, associated symptoms; history of headache types other than migraine, history of medications (if any) used for treatment of acute migraine (past and current); history of medications (if any) used for the purpose of migraine prophylaxis (past and current). Identification of an appropriate "rescue" treatment (See Rescue Treatment below)

Confinement in clinic: Subjects will arrive at the study clinic during the course of a migraine headache of at least moderate severity (in the subject's judgment). Subjects will be confined to the study site for 1 to 2 hours before closing and confined until at least 9 hours following the initial dose of study drug.

Study Drug and Dosage Form: Fixed dose for the initial close (all stages) and three ascending active close levels for the second (pulsed) close Fospropofol Disodium to be administered as an appropriate number of powder filled capsules, each capsule containing 200 mg of fospropofol disodium and/or 100 mg of fospropofol disodium (Epalex Corporation, USA).

Placebo to be administered (second "pulsed" close) as an equivalent number of identical capsules containing placebo.

Study Drug Administration: Each cohort of up to 160 subjects will receive the same single fixed oral dose selected from 100-3600 mg of Fospropofol Disodium (N=160) as the initial close. After 30 minutes, subjects will receive a second "pulsed" dose of Fospropofol Disodium (N=up to 120) or matching placebo (N=up to 40). The amount of the second "pulsed" close will increase at each stage (ascending close design). Fospropofol Disodium will be administered as capsules containing 200 mg and/or 100 mg of fospropofol disodium (Fospropofol Disodium) to achieve the planned close.

Study drug (each of the two administrations) will be administered with 240 mL of water at ambient temperature. Except for water administered with study drug, no fluids will be allowed from 1 hour before closing until 1 hour post-close.

There will be at least 7 days between closing of each close level. Following completion of each close level, pharmacokinetic (PK) data for propofol collected until 9 hours post-close (where time post-close refers to the time interval from the initial close), safety and tolerability data collected until the clinic check-out (approximately 10 hours post-close), and the efficacy data collected until 9 hours post-close will be evaluated by a Safety Committee before proceeding to the next close.

Inclusion Criteria Male or female, non-smoker (no use of tobacco products within 3 months prior to screening), ≥18 and ≤55 years of age, with BMI ≥18.0 and ≤32.0 kg/m² and body weight≥50.0 kg Generally healthy (other than migraine) as defined by:

The absence of clinically significant illness and surgery within 4 weeks prior to closing. Subjects vomiting within 24 hours pre-close will be carefully evaluated. Inclusion pre-closing is at the discretion of the center PI.

The absence of clinically significant history of neurological (other than migraine), endocrine, cardiovascular, pulmonary, hematological, immunologic, psychiatric, gastrointestinal, renal, hepatic, and metabolic disease.

The absence of clinically significant history of sleep apnea

Subject has at least 1 year history of migraines (with or without aura), consistent with a diagnosis according to the International Classification of Headache Disorder, 3rd Edition, Beta version including the following:

Migraine attacks present for more than 1 year with age of onset prior to 50 years of age Migraine attacks last, 4 to 72 hours if untreated, on average, in the 3 months prior to screening visit Two to eight (2-8) moderate or severe migraine attacks per month in the 3 months prior to the screening visit. The migraine, for which the patient receives treatment during the study, must have at least one of the associated symptoms: nausea, photophobia, phonophobia, or migraine with aura Subjects on prophylactic migraine medication are permitted to remain on therapy provided they have been on a stable dose for at least 3 months prior to screening visit and the close is not expected to change during the course of the study Clinical laboratory values within the laboratory acceptable range unless values are deemed by the PI/Sub-Investigator as "Not Clinically Significant".

Ability to comprehend the nature of the study, as assessed by the PI/Sub-Investigator. Capable of giving written informed consent. Able to communicate effectively with clinic staff.

Availability to volunteer for the entire study duration and willing to adhere to all protocol requirements.

Female subjects must agree not to be nursing at any time during the study and until 30 days after the study follow-up visit.

Female subjects must fulfill at least one of the following:

Be surgically sterile for a minimum of 6 months;

Post-menopausal for a minimum of 1 year;

Agree to avoid pregnancy and use medically acceptable method of contraception from at least 30 days prior to the study until 30 days after the study follow-up visit.

Medically acceptable methods of contraception include hormonal contraception, hormonal or non-hormonal intrauterine device, or double barrier method (simultaneous use of male condom with intravaginally applied spermicide and diaphragm or cervical cap). Complete abstinence alone can be used as a method of contraception.

Subjects with coexisting history of headache other than migraine are eligible provided that these headaches are distinguishable from the subject's migraine headaches No contraindication to use of fospropofol according to FDA approved labeling Concomitant medications taken for the purpose of migraine prophylaxis are permitted provided that the dose of these medications is stable for at least 3 months prior to administration of study drug and estimated headache frequency at screening meets the criterion above If concomitant medications intended to reduce the frequency of migraine are discontinued prior to the study, these medications must be discontinued at least one month prior to receiving study drug Absence of any medical condition that, in the opinion of the investigator or the Sponsor, may be potentially associated with an increased risk from study drug or participation in the study.

Subject must be willing to avoid the use of analgesics or any acute migraine medication(s) for 24 hours prior to receiving study drug.

Subject must be willing to forgo rescue treatment (defined below) for 2 hours after initiation of treatment with study drug.

Exclusion Criteria Subjects to whom any of the following applies will be excluded:

Patient has basilar migraine or hemiplegic migraine

Patient is taking narcotic (opiate) medication

Patient uses an opiate as first line acute treatment for migraine attacks

History of ergotamine, triptan, or any acute therapy intake on ≥10 days per month on a regular basis for ≥3 months History of simple analgesic intake on ≥10 days per month for ≥3 months History of use of opioid or combination medication intake or butalbital containing analgesic greater than 5 days per month for >3 months Very frequent chronic tension type headaches for 15 or more days per month (or unable to distinguish between tension-type headaches and migraine)

Patient has major depression, other pain syndromes that might interfere with study assessments, psychiatric conditions, dementia, or significant neurological disorders (other than migraine)

Any clinically significant abnormality at physical examination, clinically significant abnormal laboratory test results or positive serologic test for hepatitis B, hepatitis C, or HIV found during medical screening. (Subjects with positive serology for hepatitis C and negative HCV RNA are eligible at the discretion of the principal investigator.)

Positive urine drug screen (unless consistent with an ongoing prescription drug as documented by the center investigator), positive alcohol breath test, urine cotinine test at screening or at clinic check-in Positive serum pregnancy test (women of child-bearing potential) at screening (or positive urine pregnancy test at clinic check-in).

History of severe allergic reactions (e.g. anaphylactic reactions, angioedema), hypersensitivity or idiosyncratic reaction to fospropofol, propofol, Fospropofol Disodium excipients or related substances.

Individuals having undergone any major surgery within 6 months prior to the start of the study, unless deemed otherwise by the PI.

Clinically significant ECG abnormalities (e.g., QTcF>450 msec in males or >470 msec in females) or persistent (3 determinations) vital sign abnormalities at screening (systolic blood pressure lower than 90 or over 145 mmHg, diastolic blood pressure lower than 55 or over 95 mmHg, or heart rate less than 50 or over 100 bpm). Vital signs to be taken in a seated position and may be repeated up to a total of three determinations.

Oxygen saturation by oximetry less than 93% at screening

History of significant alcohol abuse within one year prior to screening or regular use of alcohol within six months prior to the screening visit (more than fourteen units of alcohol per week [1 unit=150 mL of wine, 360 mL of beer, or 45 mL of 40% alcohol]).

History of significant drug abuse within one year prior to screening or use of hard drugs (such as cocaine, phencyclidine [PCP], crack, opioid derivatives including heroin, and amphetamine derivatives) within 1 year prior to screening.

Participation in an interventional clinical research study involving the administration of an investigational or marketed drug or device within 30 days prior to administration of study drug or administration of a biological product in the context of a clinical research study within 90 days prior to administration of study drug. Concomitant participation in an investigational study involving no drug or device administration is permitted provided obligations associated with the concomitant participation are not expected to interfere with procedures and obligations of the present study.

Any medical condition (other than migraine) requiring ongoing, more than occasional, use of analgesic drugs. (Occasional use of acetaminophen, aspirin, or NSAID, or topical products without significant systemic absorption is not an exclusion).

Any medical condition requiring ongoing treatment with sedative-hypnotic drugs (e.g., benzodiazepines, barbiturates)

Donation of plasma within 7 days prior to closing. Donation or loss of blood (excluding volume drawn at screening) of 50 mL to 499 mL of blood within 30 days, or more than 499 mL within 56 days prior to the first closing.

Hemoglobin<135 g/L for men or <120 g/L for women at screening.

Intolerance to and/or difficulty with blood sampling through venipuncture.

Abnormal diet patterns (for any reason) during the four weeks preceding the study, including fasting, high protein diets etc.

Employee or immediate relative of an employee of Epalex Corporation, its affiliates or partners.

Study Restrictions: Analgesic drugs, e.g., opiates alone or in a combination product from screening until the end-of-study follow-up visit. Occasional use of acetaminophen, aspirin, or an NSAID will be permitted; however, a subject will not be eligible to receive study drug if he/she has taken an analgesic (including over the counter) in the preceding 24 hours. Analgesics (except as rescue) are not permitted from 24 hours prior to clinic admission until the end-of-study follow-up visit.

Marijuana products including THC and CBD are not permitted from screening until the end-of-study follow-up visit.

Sedative-hypnotic drugs, prescription or OTC, (e.g., benzodiazepines, barbiturates, sleeping aids, Fiorinal) from screening until the end-of-study follow-up visit.

Triptans, e.g., sumatriptan, Imitrex (except as rescue, where applicable) are not permitted from screening until the end-of-study follow-up visit.

Ergotamine or combination drugs, containing ergotamine e.g. cafergot (except as rescue, where applicable) from screening until the end-of-study follow-up visit.

Metoclopramide, e.g. Reglan (except as rescue, where applicable) from screening until the end-of-study follow-up visit.

Alcohol-based products are permitted; however, a subject will not be eligible to receive study drug if he/she has taken any alcohol based product in the preceding 24 hours. Alcohol-based products are not permitted from 24 hours prior to clinic admission until the end-of-study follow-up visit.

Prescription and OTC medications that are medically necessary (except analgesics, sedative-hypnotics, and drugs intended for treatment of acute migraine, as described above) are permitted. The center principal investigator (PI) will review, record, and approve at screening the concomitant medications expected to be continued over the course of study. In case of questions as to the suitability of a concomitant medication, investigators are encouraged to consult with the Sponsor.

For safety reasons, subjects will be required to remain seated or semi-reclined and avoid sleeping for the first 1 hour before and 4 hours after drug administration.

PK Sampling Time Points: A total of 14 blood samples (for analysis of both fospropofol and propofol) will be collected (in each close level or period): Pre-close (within 10 min of closing) and post-close: 5, 10, 20, 30, 45, 60, 90 minutes and 2, 3, 4, 5, 6, and 9 hours post-close.

Subject Safety Monitoring: Medical surveillance and AE monitoring:

Subjects will be monitored throughout the study by Clinic staff for AEs.

Continuous cardiac telemetry and pulse oximetry:

To detect any clinically significant cardiac arrhythmia or other abnormality at baseline (pre-close), cardiac telemetry will be performed for at least 30 minutes prior to closing and continued until approximately 9 hours post-close to monitor for any cardiac effects of study drug. Subjects with any clinically significant ECG abnormality at baseline (pre-close) will be excluded. Pulse oximetry will be monitored over the same time course.

Vital signs:

BP, HR, RR, and Pulse Oximetry (PO) will be recorded pre-close within 10 min of closing and at approximately 5, 10, 20, 30, 45, 60, 90 2, 2.5, 3, 4, 6, and 9 hours after closing.

Level of Alertness

Level of sedation will be assessed using the Modified Observer's Assessment of Alertness/Sedation (MOAA/S) Score. See Chernik DA, Gillings D, Laine H, et al. Validity and reliability of the Observer's Assessment of Alertness/Sedation Scale: study with intravenous midazolam. J Clin Psychopharmacol 1990 Aug. 10(4):244-51.

| Responsiveness | Score |
| --- | --- |
| Responds readily to name spoken in normal tone | 5 (alert) |
| Lethargic response to name spoken in normal tone | 4 |
| Responds only after name is called loudly and/or repeatedly | 3 |
| Responds only after mild prodding or shaking | 2 |
| Responds only after painful trapezius squeeze | 1 |
| Does not respond to painful trapezius squeeze | 0 |

Sedation (MOAA/S score) will be recorded within 10 min pre-close and at approximately 5 min intervals until 3 hours after closing, and at 15 min intervals thereafter until 9 hours post-close provided that the subject has demonstrated at least three consecutive MOAA/S scores of 5 immediately prior to the 3 hour timepoint. A subject who has not demonstrated three consecutive MOAA/S scores of 5 immediately prior to the 3 hour timepoint will continue with MOAA/S assessments at 5 min intervals until he or she demonstrates three consecutive MOAA/S scores of 5, with MOAA/S scores recorded at 15 min interval thereafter until 9 hours post-close. See Cohen LB. Clinical trial: a close-response study of fospropofol disodium for moderate sedation during colonoscopy. 2008; Aliment Pharmacol Ther 27, 597-608.

12-lead ECG:

12-lead ECG will be performed at Clinic check-in (Day 1 before closing) and at Clinic checkout.

Laboratory assessments:

Hematology, biochemistry, and urinalysis at clinic check-in and at follow-up (final) visit scheduled between 48 h and 96 h after administration of study drug.

Alcohol breath test, urine cotinine test, and urine drug screen at check-in.

For women of child-bearing potential, urine pregnancy test at check-in; serum pregnancy test at follow-up (final) visit scheduled between 48 h and 96 h after administration of study drug [A serum pregnancy test will be obtained at screening.]

Physical examination:

Complete physical exam (PE) at screening, brief PE at clinic check-in and clinic checkout; complete PE at follow-up (final) visit scheduled between 48 h and 96 h after administration of study drug Clinic Check-in Food will not be permitted from the time of clinic check-in until 4 hours after the initial closing of study drug. Fluids will not be permitted from one hour before the initial close until one hour after administration of the second (pulsed close) of study drug (except for water (240 mL) administered with study drug.) Water will be permitted ad lib at all other times.

Abbreviated physical exam, alcohol breath test, and urine drug screen at check-in. Urine pregnancy test (women of child-bearing potential)

Record time and nature of last meal or food intake

Record concomitant medications and all medications taken in the 24 hours prior to check-in.

Record characteristics of the presenting headache and associated symptoms including, but not limited to the following:

Characteristics of the presenting headache (i.e., throbbing, unilateral or bilateral, aggravated by exercise).

Subject's assessment of headache pain at admission to clinic on a 4-point Likert Scale, (i.e., 0=none, 1=mild, 2=moderate, 3=severe) for the presenting headache.

Most bothersome associated symptom for the presenting headache (e.g., nausea/vomiting, photophobia, phonophobia)

Presence of associated symptoms, nausea, vomiting, photophobia, phonophobia (Yes/No) at clinic admission Efficacy Measures: Note: Pre-close and post-close times are with reference to the initial dose of study drug.

Subject's assessment of headache pain—4-point Likert Scale (Severe, Moderate, Mild, No pain) to be assessed at baseline prior to closing (within 10 min of closing), and post-close at 5 min, 15 min, 30 min, 45 min, 1 h, 1.5 h, 2 h, 3 h, 4 h, 6 h, 8 h, and at clinic discharge, and following discharge (by diary) at 12, 24 h and 48 h post-closing. Headache qualifying for treatment with study drug must be of at least moderate severity at baseline (pre-close and within 10 min of closing study drug). Subjects will be asked to announce while in clinic the time that no headache pain is first noted, or, after discharge, if applicable, to record the time that no headache pain is first noted in the patient diary. Subjects will also be asked to announce in clinic and/or record by patient diary after discharge from clinic any recurrence or worsening of headache pain, and time of onset of worsening.

Subject's assessment of presence/absence of most bothersome symptom (MBS)—subjects to be questioned as to presence or absence of the most bothersome symptom associated with presenting headache (identified at clinic admission) at the same time points as the assessment of headache pain [baseline prior to closing (within 10 min of closing), and post-close at 5 min, 15 min, 30 min, 45 min, 1 h, 1.5 h, 2 h, 3 h, 4 h, 6 h, 8 h, and at clinic discharge, and following discharge (by diary) at 12, 24 h and 48 h post-closing.] Subjects will also be asked to announce while in clinic the time that disappearance of the most bothersome symptom is first noted, or, after discharge, if applicable, to record the time that no headache pain is first noted in the patient diary. Subjects will also be asked to announce in clinic and/or record by patient diary after discharge from clinic any recurrence of the most bothersome symptom, and time of onset of recurrence.

Subject assessment of presence/absence of migraine-associated symptoms (other than MBS): nausea/vomiting, photophobia, and/or phonophobia at baseline (within 15 min of closing), and post-close at 5 min, 15 min, 30 min, 45 min, 1 h, 1.5 h, 2 h, 3 h, 4 h, 6 h, 8 h, and at clinic discharge, and following discharge (by diary) at 12, 24 h and 48 h post-closing. Subjects will also be asked to announce while in clinic the time that disappearance of migraine-associated symptoms is first noted, or, after discharge, if applicable, to record the time that disappearance of the associated symptom is first noted in the patient diary. Subjects will also be asked to announce in clinic and/or record by patient diary after discharge from clinic any recurrence of a migraine-associated symptom, and time of onset of recurrence.

While in clinic subjects will be instructed to report any adverse events directly to the investigators or clinic staff. Subjects will be instructed to record in the patient diary any adverse events emerging following discharge. All subjects will have telephone access to the investigator or investigator staff to report any urgent concerns in the course of the study.

Rescue Treatment Rescue treatment (acute treatment for migraine pain) may be administered at any time at the investigator's discretion. Subjects and investigators will be encouraged to avoid administration of rescue treatment earlier than 2 hours after initial administration of study drug. Rescue treatment may include an analgesic and/or acute migraine medication(s). Selection of rescue for each subject may be guided by history of treatment effective for the subject in the past. In general, the investigator and subject will have agreed on the appropriate rescue therapy for the subject at screening. In identifying an appropriate rescue therapy, the additive cardiorespiratory effects of narcotic analgesics and sedative hypnotic agents when administered concomitantly with fospropofol should be considered.

Clinic Check-out: The following procedures will be carried out at clinic check-out: physical examination, vital signs, 12-lead ECG, oral temperature, AE monitoring. Distribute diary for subjects to record and grade any ongoing headache pain, and any ongoing migraine-associated symptoms (present/absent), and/or any recurrence or worsening of pain or migraine-associated symptoms. Schedule follow-up visit.

Follow-up Visit/End of Study Participation The following procedures will be carried out at a follow-up end of study visit to be scheduled 48 to 96 hours after administration of study drug: hematology, blood chemistry, urinalysis, AE monitoring, serum pregnancy test for women of child-bearing potential Analytical Method: Fospropofol and propofol will be analyzed in plasma samples using a validated method. Additional plasma samples may be drawn and stored for possible future bioanalysis of other analytes.

Pharmaco-kinetic Parameters: The following pharmacokinetic parameters will be calculated for both fospropofol and propofol plasma concentrations: $AUC_{0-t}$, $AUC_{0-inf}$, $C_{max}$, Residual area, $T_{max}$, $T_{1/2el}$, $K_{el}$, Cl/F, Vd/F, and Vd/F/kg.

Statistical Analyses: Statistical analyses will be performed with the safety, tolerability, efficacy, and PK data Laboratory Assessments—Example A13

Hematology: Hematology will be drawn at screening, at clinic check-in, and at the follow-up (final) visit. Hematology will include complete blood count with differential, hemoglobin, and hematocrit.

Chemistry: Blood chemistry will be drawn at screening, at clinic check-in, and at the follow-up (final) visit. Blood chemistry will include albumin, alkaline phosphatase, aspartate aminotransferase, alanine aminotransferase, urea, calcium, chloride, glucose, phosphorus, potassium, creatinine, sodium, total bilirubin, and total protein.

Serology: Hepatitis B (HBs Ag), Hepatitis C (HCV) antibody, and HIV antigen and antibody detection will be drawn at screening.

Urinalysis: Urine for Urinalysis will be taken at screening, at clinic check-in, and at the follow-up (final) visit. Urinalysis will include macroscopic examination, pH, specific gravity, protein, glucose, ketones, bilirubin, occult blood, nitrite, urobilinogen, and leukocytes. Unless otherwise specified, microscopic examination will be performed on abnormal findings.

Drug, Cotinine, and Alcohol Screen: A urine drug screen (amphetamines, methamphetamines, barbiturates, benzodiazepines, tetrahydrocannabinol, cocaine, opiates, PCP, MDMA, methadone), a urine cotinine test, and an alcohol breath test will be performed at screening and at clinic check-in.

Pregnancy Tests: For women of child bearing potential: A serum pregnancy test will be performed at screening. A urine pregnancy test will be performed at clinic check-in. A serum pregnancy test will be performed at the follow-up (final) visit, and at early termination, where applicable.

Example A14

Open-label exploratory study to describe the pharmacokinetics, safety-tolerability, and clinical outcome following a single oral dose of fospropofol disodium administered to adult women and men experiencing moderate to severe migraine headache.

Study Drug: Fospropofol Disodium

Study Phase and Type: Phase 1b—Open-label exploratory single-close administration to adults with moderate to severe migraine headache Study Design: Phase 1b, multi-center, open-label, single-close, exploratory study to describe PK, safety-tolerability, and clinical outcome following a single oral dose of fospropofol disodium administered to adult women and men experiencing moderate to severe migraine headache.

The study is intended to evaluate one dose level (the maximum well-tolerated close to be selected on the basis of the prior Phase 1 healthy volunteer study).

Subjects: Up to 150 subjects with a diagnosis of episodic migraine will be enrolled. An interim analysis including PK, safety-tolerability, clinical outcome data will be carried out after completion of 50 subjects. Following the interim analysis, the administered dose may be modified, including but not limited to a change in the closing regimen up or down or using a divided close (2 administrations separated in time).

The study will enroll adult women and men≥18 and ≤55 years of age with a body mass index (BMI) within 18.0-29.9 kg/m² inclusive, and body weight>50 kg. Women of childbearing potential must be using reliable contraception or totally abstain from intercourse.

The overall study population enrolled must comprise at least 50% women.

This is a single-close study. Subjects who withdraw or are withdrawn from the study after closing will not be replaced.

Screening Procedures: Demographic data, medical and medication histories including drug allergies, physical examination, body measurements, electrocardiogram (ECG), vital signs (blood pressure [BP], heart rate [HR], respiratory rate [RR], pulse oximetry [PO], and oral temperature [OT]), hematology, blood chemistry, human immunodeficiency virus (HIV), hepatitis B and C tests, urinalysis, urine drug screen, alcohol breath test, urine cotinine test, Serum pregnancy test (women of child-bearing potential). Screening to occur within 30 days of clinic admission. [Subjects who do not present with a qualifying headache within 30 days of screening may have a second screening visit within 45 days of the first screening at the discretion of the investigator. Second screening visit may be abbreviated to updated history and serum pregnancy test for women of childbearing potential. A subject who does not present with a qualifying headache within 75 days of the first screening will be classified as a screening failure.]

Migraine History: Confirm migraine diagnosis according to ICHD criteria; age of onset, estimated frequency of migraine episodes, including frequency of episodes classified as moderate or severe, history of migraine-associated symptoms (nausea/vomiting, photophobia, phonophobia), characteristic features of episodes including aura (if any), nature of pain, associated symptoms; history of headache types other than migraine, history of medications (if any) used for treatment of acute migraine (past and current); history of medications (if any) used for the purpose of migraine prophylaxis (past and current). Identification of an appropriate "rescue" treatment (See Rescue Treatment below)

Note that potential subjects on concomitant drugs for migraine prophylaxis are excluded. A list of concomitant medications requiring exclusion will be provided. Subjects maintained on a continuing regimen of a drug intended for migraine prophylaxis will not be eligible. Subjects maintained on a continuing regimen of a drug prescribed for a purpose other than migraine prophylaxis but with a potential prophylactic effect on migraine, e.g., beta blockers, tricyclic antidepressants will not be eligible. Subjects in these categories may be enrolled if the disqualifying drug is discontinued at least one month before enrolment and the subject meets all other eligibility criteria (e.g. headache frequency, etc., at the time of enrolment Confinement in clinic: Subjects will arrive at the study clinic during the course of a migraine headache. To qualify for treatment with study drug, headache must be of at least moderate severity (in the subject's judgment) at the time of treatment. Subjects will be confined to the study site for up to 2 hours before closing and confined until at least 9 hours following a single dose of study drug.

Study Drug and Dosage Form: One close level.

Fospropofol disodium to be administered as an appropriate number of powder-filled capsules, each capsule containing 200 mg of fospropofol disodium (Epalex Corporation, USA).

Study Drug Administration: Each subject will receive a single oral dose of Fospropofol disodium at a single dose level selected from within the range 200 mg to 3200 mg. Fospropofol disodium will be administered as an appropriate number of capsules containing 200 mg of fospropofol disodium.

Subjects will receive a single dose of fospropofol disodium administered as the appropriate number of capsules containing 200 mg of fospropofol disodium.

The dose of fospropofol disodium will be reduced if there are safety concerns or evidence of clinically significant tolerability issues. In no case will the total close to a subject exceed the highest close level specified in the protocol.

Study drug will be administered with 240 mL of water at ambient temperature. Except for water administered with study drug, no fluids will be allowed from 30 min before closing until 1 hour post-close.

Inclusion Criteria Male or female, non-smoker (no use of tobacco products within 3 months prior to screening), ≥18 and ≤55 years of age, with BMI≥18.0 and ≤29.9.0 kg/m² and body weight≥50.0 kg Generally healthy (other than migraine) as defined by:

The absence of clinically significant illness and surgery within 4 weeks prior to closing. Subjects vomiting within 24 hours pre-close will be carefully evaluated. Inclusion pre-closing is at the discretion of the center PI.

The absence of clinically significant history of neurological (other than migraine), endocrine, cardiovascular, pulmonary, hematological, immunologic, psychiatric, gastrointestinal, renal, hepatic, and metabolic disease.

The absence of clinically significant history of sleep apnea

Subject has at least a one-year history of migraine (with or without aura), consistent with a diagnosis according to the International Classification of Headache Disorder, 3rd Edition, including the following:

Migraine attacks present for more than 1 year with age of onset prior to 50 years of age Migraine attacks last, 4 to 72 hours if untreated, on average, in the 3 months prior to screening visit Two to eight (2-8) moderate or severe migraine attacks per month in the 3 months prior to the screening visit. The migraine, for which the patient receives treatment during the study, must have at least one of the associated symptoms: nausea, photophobia, phonophobia, or migraine with aura Subjects on prophylactic migraine medication are not eligible.

Subjects maintained on a continuing regimen of a drug prescribed for a purpose other than migraine prophylaxis but with a potential prophylactic effect on migraine, e.g., beta blockers, tricyclic antidepressants will not be eligible. (A list of these drugs will be provided). Subjects in these categories may be enrolled if the disqualifying drug is discontinued at least one month before enrolment and the subject meets all other eligibility criteria (e.g. headache frequency, etc., at the time of enrolment.)

Clinical laboratory values within the laboratory acceptable range unless values are deemed by the PI/Sub-Investigator as "Not Clinically Significant".

Ability to comprehend the nature of the study, as assessed by the PI/Sub-Investigator. Capable of giving written informed consent. Able to communicate effectively with clinic staff.

Availability to volunteer for the entire study duration and willing to adhere to all protocol requirements.

Female subjects must agree not to be nursing at any time during the study and until 30 days after the study follow-up visit.

Female subjects must fulfill at least one of the following:

Be surgically sterile for a minimum of 6 months;

Post-menopausal for a minimum of 1 year;

Agree to avoid pregnancy and use medically acceptable method of contraception from at least 30 days prior to administration of study drug until 30 days after the study follow-up visit.

Medically acceptable methods of contraception include hormonal contraception, hormonal or non-hormonal intrauterine device, or double barrier method (simultaneous use of male condom with intravaginally applied spermicide and diaphragm or cervical cap). Complete abstinence alone can be used as a method of contraception.

Subjects with coexisting history of headache other than migraine are eligible provided that these headaches are distinguishable from the subject's migraine headaches No contraindication to use of fospropofol according to FDA approved labeling If concomitant medications intended to reduce the frequency of migraine are discontinued prior to the study, these medications must be discontinued at least one month prior to receiving study drug Absence of any medical condition that, in the opinion of the investigator or the Sponsor, may be potentially associated with an increased risk from study drug or participation in the study.

Subject must be willing to avoid the use of analgesics or any acute migraine medication(s) for 24 hours prior to receiving study drug.

Subject must be willing to forgo rescue treatment (defined below) for at least 2 hours after initiation of treatment with study drug.

Exclusion Criteria Subjects to whom any of the following applies will be excluded:

Patient has basilar migraine or hemiplegic migraine

Patient is taking narcotic (opiate) medication

Patient uses an opiate as first line acute treatment for migraine attacks

History of ergotamine, triptan, or any acute therapy intake on ≥10 days per month on a regular basis for ≥3 months History of simple analgesic intake on ≥10 days per month for ≥3 months History of use of opioid or combination medication intake or butalbital containing analgesic greater than 5 days per month for ≥3 months Very frequent chronic tension type headaches for 15 or more days per month (or unable to distinguish between tension-type headaches and migraine)

Patient has major depression, other pain syndromes that might interfere with study assessments, psychiatric conditions, dementia, or significant neurological disorders (other than migraine)

Any clinically significant abnormality at physical examination, clinically significant abnormal laboratory test results or positive serologic test for hepatitis B, hepatitis C, or HIV found during medical screening. (Subjects with positive serology for hepatitis C and negative HCV RNA are eligible at the discretion of the principal investigator.)

Positive urine drug screen (unless consistent with an ongoing prescription drug as documented by the center investigator), positive alcohol breath test, urine cotinine test at screening or at clinic check-in Positive serum pregnancy test (women of child-bearing potential) at screening (or positive urine pregnancy test at clinic check-in).

History of severe allergic reactions (e.g. anaphylactic reactions, angioedema), hypersensitivity or idiosyncratic reaction to fospropofol, propofol, fospropofol disodium excipients or related substances.

Individuals having undergone any major surgery within 6 months prior to the start of the study, unless deemed otherwise by the PI.

Clinically significant ECG abnormalities (e.g., QTcF>450 msec in males or >470 msec in females) or persistent (3 determinations) vital sign abnormalities at screening (systolic blood pressure lower than 90 or over 145 mmHg, diastolic blood pressure lower than 55 or over 95 mmHg, or heart rate less than 50 or over 100 bpm). Vital signs to be taken in a seated position and may be repeated up to a total of three determinations.

Oxygen saturation by oximetry less than 93% at screening

History of significant alcohol abuse within one year prior to screening or regular use of alcohol within six months prior to the screening visit (more than fourteen units of alcohol per week [1 unit=150 mL of wine, 360 mL of beer, or 45 mL of 40% alcohol]).

History of significant drug abuse within one year prior to screening or use of hard drugs (such as cocaine, phencyclidine [PCP], crack, opioid derivatives including heroin, and amphetamine derivatives) within 1 year prior to screening.

Participation in an interventional clinical research study involving the administration of an investigational or marketed drug or device within 30 days prior to administration of study drug or administration of a biological product in the context of a clinical research study within 90 days prior to administration of study drug. Concomitant participation in an investigational study involving no drug or device administration is permitted provided obligations associated with the concomitant participation are not expected to interfere with procedures and obligations of the present study.

Any medical condition (other than migraine) requiring ongoing, more than occasional, use of analgesic drugs. (Occasional use of acetaminophen, aspirin, or NSAID, or topical products without significant systemic absorption is not an exclusion).

Any medical condition requiring ongoing treatment with sedative-hypnotic drugs (e.g., benzodiazepines, barbiturates)

Donation of plasma within 7 days prior to closing. Donation or loss of blood (excluding volume drawn at screening) of 50 mL to 499 mL of blood within 30 days, or more than 499 mL within 56 days prior to the first closing.

Hemoglobin≤135 g/L for men or ≤120 g/L for women at screening.

Intolerance to and/or difficulty with blood sampling through venipuncture.

Abnormal diet patterns (for any reason) during the four weeks preceding the study, including fasting, high protein diets etc.

Employee or immediate relative of an employee of Epalex Corporation, its affiliates or partners Study Restrictions: Subjects will be asked to refrain from using products that may potentially affect their safety, the PK profile of the study drug, and/or assessments of clinical outcome. Main study restrictions include the following:

Occasional use of analgesic drugs, e.g., opiates alone or in a combination product, acetaminophen, aspirin, or an NSAID will be permitted; however, a subject will not be eligible to receive study drug if he/she has taken any analgesic (including over the counter) in the preceding 24 hours. Analgesics (except as rescue) are not permitted from 24 hours prior to clinic admission until the end-of-study follow-up visit.

Marijuana products including THC and CBD are not permitted from screening until the end-of-study follow-up visit.

Sedative-hypnotic drugs, prescription or OTC, (e.g., benzodiazepines, barbiturates, sleeping aids, Fiorinal) from screening until the end-of-study follow-up visit.

Use of triptans, e.g., sumatriptan, Imitrex is permitted. However, a subject will not be eligible to receive study drug if he/she has taken any triptan in the preceding 24 hours. Triptans (except as rescue) are not permitted from 24 hours prior to clinic admission until the end-of-study follow-up visit.

Ergotamine or combination drugs, containing ergotamine e.g. cafergot are permitted. However, a subject will not be eligible to receive study drug if he/she has taken an drug containing ergotamine in the preceding 24 hours. Ergotamine or combination drugs containing ergotamine (except as rescue) are not permitted from 24 hours prior to clinic admission until the end-of-study follow-up visit.

Metoclopramide, e.g. Reglan is permitted. However, a subject will not be eligible to receive study drug if he/she has taken metoclopramide, or an drug containing metoclopramide in the preceding 24 hours.

Alcohol-based products are permitted; however, a subject will not be eligible to receive study drug if he/she has taken any alcohol-based product in the preceding 24 hours. Alcohol-based products are not permitted from 24 hours prior to clinic admission until the end-of-study follow-up visit.

Prescription and OTC medications that are medically necessary (except sedative-hypnotics) are permitted on a case-by-case basis. The center principal investigator (PI) will review, record, and approve at screening the concomitant medications expected to be continued over the course of study. In case of questions as to the suitability of a concomitant medication, investigators are encouraged to consult with the Sponsor.

For safety reasons, subjects will be required to remain seated or semi-reclined for the first 1 hour before and 4 hours after administration of study drug. Subjects may ambulate to the rest room at the discretion of the investigator, but must be accompanied by study staff while walking to and from the rest room. Subjects will be permitted to sleep ad lib until 4 hours after administration except for the 2 hour assessments of headache pain and associated migraine symptoms. The clinic staff should attempt to record these assessments in all subjects.

PK Sampling Time Points: A total of 14 blood samples (for analysis of both fospropofol and propofol) will be collected (in each close level or period): Pre-close (within 10 min of closing) and post-close: 5, 10, 20, 30, 45, 60, 90 minutes and 2, 3, 4, 5, 6, and 9 hours post-close.

Subject Safety Monitoring: Medical surveillance and AE monitoring:

Subjects will be monitored throughout the study by Clinic staff for AEs.

Continuous pulse oximetry: Pulse oximetry will be monitored for at least 30 minutes prior to closing and continued until approximately 9 hours post-close to monitor oxygen saturation.

Vital signs:

BP, HR, RR, and Pulse Oximetry (PO) will be recorded pre-close within 10 min of closing and at approximately 5, 10, 20, 30, 45, 60, 90 2, 2.5, 3, 4, 6, and 9 hours after closing.

Level of Alertness

Level of sedation will be assessed using the Modified Observer's Assessment of Alertness/Sedation (MOAA/S) Score. See Chernik D A, Gillings D, Laine H, et al. Validity and reliability of the Observer's Assessment of Alertness/Sedation Scale: study with intravenous midazolam. J Clin Psychopharmacol 1990 Aug. 10(4):244-51.

| Responsiveness | Score |
|---|---|
| Responds readily to name spoken in normal tone | 5 (alert) |
| Lethargic response to name spoken in normal tone | 4 |
| Responds only after name is called loudly and/or repeatedly | 3 |
| Responds only after mild prodding or shaking | 2 |
| Responds only after painful trapezius squeeze | 1 |
| Does not respond to painful trapezius squeeze | 0 |

Sedation (MOAA/S score) will be recorded within 30 min pre-close and at approximately 15 min intervals until 4 hours after closing, and at 30 min intervals thereafter until 9 hours post-close provided that the subject has demonstrated at least three consecutive MOAA/S scores of 5 immediately prior to the 4 hour timepoint. A subject who has not demonstrated three consecutive MOAA/S scores of 5 immediately prior to the 4 hour timepoint will continue with MOAA/S assessments at 15 min intervals until he or she demonstrates three consecutive MOAA/S scores of 5, with MOAA/S scores recorded at 30 min intervals thereafter until 9 hours post-close. See Cohen LB. Clinical trial: a close-response study of fospropofol disodium for moderate sedation during colonoscopy. 2008; Aliment Pharmacol Ther 27, 597-608.

12-lead ECG:
12-lead ECG will be performed at Clinic check-in (Day 1, before closing) and at Clinic checkout.

Laboratory assessments:
Hematology, biochemistry, and urinalysis at clinic check-in and at the follow-up (final) visit to be scheduled between 48 h and 96 h after administration of study drug.

Alcohol breath test, urine cotinine test, and urine drug screen at check-in.

For women of child-bearing potential, urine pregnancy test at check-in; serum pregnancy test at follow-up (final) visit scheduled between 48 h and 96 h after administration of study drug [A serum pregnancy test will be obtained at screening.]

Physical examination:
Complete physical exam (PE) at screening, brief PE at clinic check-in and clinic checkout; complete PE at follow-up (final) visit scheduled between 48 h and 96 h after administration of study drug.

Clinic Check-in Food will not be permitted from the time of clinic check-in until 4 hours after closing of study drug. Fluids will not be permitted from 30 min before until one hour after administration of study drug (except for water (240 mL) administered with study drug.) Water will be permitted ad lib at all other times.

Abbreviated physical exam, alcohol breath test, and urine drug screen at check-in. Urine pregnancy test (women of child-bearing potential).

Record time and nature of last meal or food intake

Record concomitant medications and all medications taken in the 24 hours prior to check-in.

Record characteristics of the presenting headache and associated symptoms including, but not limited to the following:

Characteristics of the presenting headache (i.e., throbbing, unilateral or bilateral, aggravated by exercise).

Subject's assessment of headache pain at admission to clinic on a 4-point Likert Scale, (i.e., 0=none, 1=mild, 2=moderate, 3=severe) for the presenting headache.

Most bothersome associated symptom for the presenting headache (e.g., nausea/vomiting, photophobia, phonophobia) Presence of associated symptoms, nausea, vomiting, photophobia, phonophobia (Yes/No) at clinic admission.

Clinical Outcome Measures: Subject's assessment of headache pain—4-point Likert Scale (Severe, Moderate, Mild, No pain) to be assessed at baseline prior to closing (within 10 min of closing), and post-close at 5 min, 15 min, 30 min, 45 min, 1 h, 1.5 h, 2 h, 3 h, 4 h, 6 h, 8 h, and at clinic discharge, and following discharge (by telephone interviews) at 12, 24 h and 48 h post-closing. Headache qualifying for treatment with study drug must be of at least moderate severity at baseline (pre-close and within 10 min of closing study drug). Subjects will be asked to announce while in clinic the time that no headache pain is first noted, or, after discharge, if applicable, to report the time that no headache pain is first noted in the patient diary. Subjects will also be asked to announce in clinic and/or report at phone interviews after discharge from clinic any recurrence or worsening of headache pain, and time of onset of worsening.

Subject's assessment of presence/absence of most bothersome symptom (MBS)—subjects to be questioned as to presence or absence of the most bothersome symptom associated with presenting headache (identified at clinic admission) at the same time points as the assessment of headache pain [baseline prior to closing (within 10 min of closing), and post-close at 5 min, 15 min, 30 min, 45 min, 1 h, 1.5 h, 2 h, 3 h, 4 h, 6 h, 8 h, and at clinic discharge, and following discharge (by telephone interviews) at 12, 24 h and 48 h post-closing.] Subjects will also be asked to announce while in clinic the time that disappearance of the most bothersome symptom is first noted, or, after discharge, if applicable, to report the time that no headache pain is first noted at the telephone interviews. Subjects will also be asked to announce in clinic and/or report at the telephone interviews after discharge from clinic any recurrence of the most bothersome symptom, and time of onset of recurrence.

Subject assessment of presence/absence of migraine-associated symptoms (other than MBS): nausea/vomiting, photophobia, and/or phonophobia at baseline (within 15 min of closing), and post-close at 5 min, 15 min, 30 min, 45 min, 1 h, 1.5 h, 2 h, 3 h, 4 h, 6 h, 8 h, and at clinic discharge, and following discharge (by diary) at 12, 24 h and 48 h post-closing. Subjects will also be asked to announce while in clinic the time that disappearance of migraine-associated symptoms is first noted, or, after discharge, if applicable, to report at telephone interviews the time that disappearance of the associated symptom is first noted. Subjects will also be asked to announce in clinic and/or report by telephone interviews after discharge from clinic any recurrence of a migraine-associated symptom, and time of onset of recurrence.

While in clinic subjects will be instructed to report any adverse events directly to the investigators or clinic staff. Subjects will be instructed to report at telephone interviews any adverse events emerging following discharge. All subjects will have telephone access to the investigator or investigator staff to report any urgent concerns in the course of the study.

Rescue Treatment Rescue treatment (acute treatment for migraine pain) may be administered at any time at the investigator's discretion. Subjects and investigators will be encouraged to avoid administration of rescue treatment earlier than 2 hours after administration of study drug. Rescue treatment may include an analgesic and/or acute migraine medication(s). Selection of rescue for each subject may be guided by history of treatment effective for the subject in the past. In general, the investigator and subject will have agreed on the appropriate rescue therapy for the subject at screening. In identifying an appropriate rescue therapy, the additive cardiorespiratory effects of narcotic analgesics and sedative hypnotic agents when administered concomitantly with fospropofol should be considered.

Clinic Check-out: The following procedures will be carried out at clinic check-out: physical examination, vital signs, 12-lead ECG, oral temperature, AE monitoring. Arrange telephone interviews for subjects to report and grade any ongoing headache pain, and any ongoing migraine-associated symptoms (present/absent), and/or any recurrence or worsening of pain or migraine-associated symptoms. Schedule follow-up visit.

Follow-up Visit/End of Study Participation The following procedures will be carried out at a follow-up end of study visit to be scheduled 48 to 96 hours after administration of study drug: hematology, blood chemistry, urinalysis, AE monitoring, serum pregnancy test for women of child-bearing potential.

Analytical Fospropofol and propofol will be analyzed in plasma samples Method: using a validated method. Additional plasma samples may be drawn and stored for possible future bioanalysis of other analytes.

Pharmacokinetic Parameters: The following pharmacokinetic parameters will be calculated for both fospropofol and propofol plasma concentrations: $AUC_{0-t}$, $AUC_{0-inf}$, $C_{max}$, Residual area, $T_{max}$, $T_{1/2el}$, $K_{el}$, Cl/F, Vd/F, and Vd/F/kg.

Statistical Analyses: Descriptive analyses will be performed with the PK, safety, tolerability, and clinical outcome data at the interim analysis (N=50 completed subjects) and at end of study.

Laboratory Assessments—Example A14

Hematology: Hematology will be drawn at screening, at clinic check-in, and at the follow-up (final) visit. Hematology will include complete blood count with differential, hemoglobin, and hematocrit.

Chemistry: Blood chemistry will be drawn at screening, at clinic check-in, and at the follow-up (final) visit. Blood chemistry will include albumin, alkaline phosphatase, aspartate aminotransferase, alanine aminotransferase, urea, calcium, chloride, glucose, phosphorus, potassium, creatinine, sodium, total bilirubin, and total protein.

Serology: Hepatitis B (HBs Ag), Hepatitis C (HCV) antibody, and HIV antigen and antibody detection will be drawn at screening.

Urinalysis: Urine for Urinalysis will be taken at screening, at clinic check-in, and at the follow-up (final) visit. Urinalysis will include macroscopic examination, pH, specific gravity, protein, glucose, ketones, bilirubin, occult blood, nitrite, urobilinogen, and leukocytes. Unless otherwise specified, microscopic examination will be performed on abnormal findings.

Drug, Cotinine, and Alcohol Screen: A urine drug screen (amphetamines, methamphetamines, barbiturates, benzodiazepines, tetrahydrocannabinol, cocaine, opiates, PCP, MDMA, methadone), a urine cotinine test, and an alcohol breath test will be performed at screening and at clinic check-in.

Pregnancy Tests: For women of child bearing potential: A serum pregnancy test will be performed at screening. A urine pregnancy test will be performed at clinic check-in. A serum pregnancy test will be performed at the follow-up (final) visit, and at early termination, where applicable.

Example A15—Animal Studies

Study No. 15-1

The purpose of Study No. 15-1 (non-GLP) was to determine the maximum tolerated close (MTD) of fospropofol when administered by oral gavage to Sprague-Dawley rats (Phase 1) and to evaluate the potential toxicity of fospropofol in Sprague-Dawley rats when administered once daily by oral gavage for 7 days (Phase 2). In addition, the toxicokinetic (TK) profiles of fospropofol and propofol were determined. Oral gavage administration of fospropofol disodium to Sprague-Dawley rats at single fospropofol close levels up to 300 mg/kg or once daily for 7 consecutive days at fospropofol close levels of 150 and 250 mg/kg/day was well tolerated at all closes. Although one 150 mg/kg/day TK female was found dead on Day 7 at approximately 30 minutes postdose, the cause of death was considered related to the pharmacodynamic effects of fospropofol. Based on these results, the MTD was considered to be 250 mg/kg/day (1500 mg/m²/day).

Study No. 15-2

The purpose of Study No. 15-2 (non-GLP) was to determine the MTD of fospropofol when administered by oral gavage to Beagle dogs (Phase 1) and to evaluate the potential toxicity of fospropofol in Beagle dogs when administered once daily by oral gavage for 7 days (Phase 2), as well as to determine the TK profiles of fospropofol and propofol. Administration of fospropofol disodium by oral gavage to Beagle dogs at single fospropofol close levels up to 120 mg/kg or at fospropofol close levels of 120 and 160 mg/kg/day once daily for 7 days was tolerated at all closes with no mortality or adverse findings. Based on these results, the MTD was considered to be 160 mg/kg/day (3200 mg/m²/day).

Study No. 15-3

The purpose of Study No. 15-3 (GLP) was to determine the potential toxicity of fospropofol in Sprague-Dawley rats when administered once daily by oral gavage for 14 days. Administration of fospropofol disodium by once daily oral gavage to Sprague-Dawley rats at fospropofol close levels of 0, 50, 100, and 250 mg/kg/day for 14 consecutive days resulted in treatment-related mortalities at 250 mg/kg/day. The cause of death for the three 250 mg/kg/day group main study females found dead could not be determined, but was considered related to the pharmacodynamic effects of fospropofol, based on the time of death relative to the time of close administration, and the clinical signs recorded before death. Clinical observations during the closing period for these animals included labored breathing, prostrate, splayed hindlimbs, uncoordinated movement, decreased activity, and eyes closed. There were no treatment-related gross observations or microscopic findings in any of these animals. Based on these results, the NOAEL was determined to be 100 mg/kg/day (600 mg/m²/day). Systemic exposure to fospropofol and propofol appeared to be dependent on sex, with greater exposure in females. The toxicokinetic results are presented in the tables below.

Fospropofol Exposure

Following daily oral gavage administration of fospropofol disodium to males and females at fospropofol doses of 50, 100, and 250 mg/kg/day, peak plasma concentrations ($C_{max}$) and area under the curve (AUC) through 6 hours after closing ($AUC_{0-6hr}$) increased for fospropofol on Day 1 and Day 14 with increasing close in a greater than close-proportional manner. Systemic exposure ($AUC_{0-6hr}$ values) to fospropofol did not appear to change following repeated administration of fospropofol disodium to male and female rats) Table 15-1.

TABLE 15-1

Fospropofol Toxicokinetic Parameters on Days 1 and 14 Following Daily Oral Gavage Administration of Fospropofol Disodinm (GLP Study 15-3)

| Gender | Dose (mg/kg) | Treatment Day | $C_{max}$ (ng/mL) | $T_{max}$ (hr) | $AUC_{0-6\ hr}$ (hr*ng/mL) |
| --- | --- | --- | --- | --- | --- |
| Male | 50 | 1 | 178 | 0.083 | 97.1 |
| Male | 50 | 14 | 149 | 0.083 | 96.9 |
| Male | 100 | 1 | 930 | 0.083 | 386 |
| Male | 100 | 14 | 1360 | 0.083 | 370 |
| Male | 250 | 1 | 8510 | 0.083 | 3720 |
| Male | 250 | 14 | 5020 | 0.083 | 2130 |
| Female | 50 | 1 | 582 | 0.083 | 166 |
| Female | 50 | 14 | 341 | 0.25 | 160 |
| Female | 100 | 1 | 1630 | 0.083 | 827 |
| Female | 100 | 14 | 2560 | 0.083 | 1170 |
| Female | 250 | 1 | 8400 | 0.083 | 4630 |
| Female | 250 | 14 | 8440 | 0.083 | 3810 |

Fospropofol doses of 50, 100, and 250 mg/kg were administered to male and female Sprague-Dawley rats. Blood (plasma) was collected at alternating time points from 2 cohorts of 3 animals per sex per treatment group at predose and approximately 0.083, 0.25, 0.5, 1, 3, and 6 hours postdose.

Propofol Exposure

Following daily oral gavage administration of fospropofol disodium to males and females, $C_{max}$ and $AUC_{0-6hr}$ values for propofol increased with increasing fospropofol close in an approximately close-proportional manner on Days 1 and 14. Systemic exposure ($AUC_{0-6hr}$ values) to propofol did not appear to change following repeated administration of fospropofol disodium to male rats, but exposure appeared to increase following repeated administration of fospropofol disodium to female rats (Table 15-2).

TABLE 15-2

Propofol Toxicokinetic Parameters on Days 1 and 14 Following Daily Oral Gavage Administration of Fospropofol Disodinm (GLP Study 15-3)

| Gender | Dose (mg/kg) | Treatment Day | $C_{max}$ (ng/mL) | $T_{max}$ (hr) | $AUC_{0-6\ hr}$ (hr*ng/mL) |
| --- | --- | --- | --- | --- | --- |
| Male | 50 | 1 | 140 | 0.5 | 219 |
| Male | 50 | 14 | 301 | 0.25 | 416 |
| Male | 100 | 1 | 503 | 0.25 | 821 |
| Male | 100 | 14 | 641 | 0.25 | 989 |
| Male | 250 | 1 | 1190 | 0.25 | 2140 |
| Male | 250 | 14 | 1430 | 0.29 | 1280 |
| Female | 50 | 1 | 404 | 0.25 | 477 |
| Female | 50 | 14 | 1080 | 0.25 | 1050 |
| Female | 100 | 1 | 781 | 0.25 | 1780 |
| Female | 100 | 14 | 1830 | 0.25 | 3070 |
| Female | 250 | 1 | 2730 | 0.25 | 4160 |
| Female | 250 | 14 | 4440 | 0.5 | 9290 |

Fospropofol doses of 50, 100, and 250 mg/kg were administered to male and female Sprague-Dawley rats. Blood (plasma) was collected at alternating time points from 2 cohorts of 3 animals per sex per treatment group at predose and approximately 0.083, 0.25, 0.5, 1, 3, and 6 hours postdose.

Study No. 15-4

The purpose of Study No. 15-4 (GLP) was to determine the potential toxicity of fospropofol in Beagle dogs when administered once daily by oral gavage for 14 days. Administration of fospropofol disodium once daily by oral gavage to Beagle dogs at fospropofol close levels of 0, 50, 100, and 160 mg/kg/day for 14 consecutive days was well tolerated at all close levels with no adverse findings. Because the treatment-related clinical observations (consistent with the expected transient sedative actions of fospropofol) and effects on hematology and clinical chemistry parameters were considered nonadverse, the NOAEL was determined to be 160 mg/kg/day (3200 mg/m²/day). The toxicokinetic results are presented in the tables below.

Fospropofol Exposure

Following daily oral gavage administration of fospropofol disodium, plasma concentrations of fospropofol increased rapidly. The $T_{max}$ ranged from 0.0833 to 1 hour after closing (Table 15-3). No consistent changes in $T_{max}$ with time, close, or sex were observed. Where accurate determination was possible, apparent individual terminal half-lives varied from 0.3 to 0.6 hours in males and females.

In both males and females, fospropofol $C_{max}$ and $AUC_{0-6hr}$ increased in a manner that was less than close proportional on Days 1 and 14, except in females on Day 14, where the increase was close proportional. Among males, $C_{max}$ and $AUC_{0-6hr}$ did not increase with repeat closing, whereas among females $AUC_{0-6hr}$ appeared to increase with repeat closing at the 100-mg/kg and the 160-mg/kg propofol close levels (Table 15-3). After single and repeated oral gavage administration at propofol close levels of 50, 100, and 160 mg/kg/day for 14 days, no clear sex differences were noted for $C_{max}$ or $AUC_{0-6h}$; however, at 100 and 160 mg/kg/day on Day 14, a slight trend toward a lower exposure was observed in males compared to females.

TABLE 15-3

Fospropofol Toxicokinetic Parameters on Days 1 and 14 Following Daily Oral Gavage Administration of Fospropofol Disodium (GLP Study 15-4)

| Gender | Dose (mg/kg) | Treatment Day | Cmax (ng/mL) | Tmax (hr) | AUC0-6 hr (hr*ng/mL) |
| --- | --- | --- | --- | --- | --- |
| Male | 50 | 1 | 5130 | 0.5-1 | 7710 |
| Male | 50 | 14 | 3300 | 0.5-1 | 4860 |
| Male | 100 | 1 | 9480 | 0.5-1 | 11700 |
| Male | 100 | 14 | 6340 | 0.25-1 | 6340 |
| Male | 160 | 1 | 10000 | 0.25-1 | 13500 |
| Male | 160 | 14 | 6970 | 0.083-1 | 9000 |
| Female | 50 | 1 | 3680 | 0.5-1 | 4710 |
| Female | 50 | 14 | 3770 | 0.5-1 | 5730 |
| Female | 100 | 1 | 10100 | 0.25-0.5 | 11900 |
| Female | 100 | 14 | 9310 | 0.5-1 | 15100 |
| Female | 160 | 1 | 7380 | 0.25-1 | 11200 |
| Female | 160 | 14 | 12700 | 0.25-1 | 16000 |

Fospropofol doses of 50, 100, and 160 mg/kg were administered to male and female Beagle dogs. Blood (plasma) was collected from separate cohorts of 4 animals per sex per treatment group at predose and approximately 0.083, 0.25, 0.5, 1, 3, and 6 hours postdose.

Propofol Exposure

The metabolite propofol was formed with a $T_{max}$ of 0.0833 to 1 hour inmost groups after closing (Table 15-4). No consistent changes in $T_{max}$ with time, close, or sex were observed. Where accurate determination was possible, apparent individual terminal half-lives varied from 0.8 to 1.8 hours in males and from 0.5 to 1.3 hours in females.

Following daily oral gavage administration of fospropofol disodium, propofol $C_{max}$ and $AUC_{0-6hr}$ appeared to increase in both sexes in a manner that was close proportional on Day 1 and more than close proportional on Day 14. At the 160-mg/kg propofol close, after 14 days of closing, $C_{max}$ increased about 7-fold in males and 3-fold in females compared with Day 1; $AUC_{0-6hr}$ after 14 days of closing compared with Day 1 increased over 2-fold in males and over 5-fold in females (Table 15-4). It should be noted that these observations should be interpreted with caution due to relatively high variability of TK parameters among animals within the same close group.

TABLE 15-4

Propofol Toxicokinetic Parameters on Days 1 and 14 Following Daily Oral Gavage Administration of Fospropofol Disodium (GLP Study 15-4)

| Gender | Dose (mg/kg) | Treatment Day | $C_{max}$ (ng/mL) | $T_{max}$ (hr) | AUC0-6 hr (hr*ng/mL) |
|---|---|---|---|---|---|
| Male | 50 | 1 | 156 | 1-3 | 211 |
| Male | 50 | 14 | 184 | 1 | 275 |
| Male | 100 | 1 | 505 | 0.5-1 | 777 |
| Male | 100 | 14 | 764 | 0.5-1 | 1220 |
| Male | 160 | 1 | 399 | 0.0833-1 | 716 |
| Male | 160 | 14 | 2900 | 0.25-1 | 1970 |
| Female | 50 | 1 | 171 | 1 | 269 |
| Female | 50 | 14 | 141 | 1 | 189 |
| Female | 100 | 1 | 414 | 0.5-1 | 672 |
| Female | 100 | 14 | 639 | 1 | 972 |
| Female | 160 | 1 | 447 | 0.0833-1 | 637 |
| Female | 160 | 14 | 1620 | 0.25-1 | 1770 |

Fospropofol doses of 50, 100, and 160 mg/kg were administered to male and female Beagle dogs. Blood (plasma) was collected from separate cohorts of 4 animals per sex per treatment group at predose and approximately 0.083, 0.25, 0.5, 1, 3, and 6 hours postdose.

Summary of Nonclinical Toxicology of Fospropofol Disodium

Pivotal GLP 14-day repeat-close toxicity studies with 7-day recovery periods were conducted in Sprague-Dawley rats (Study No. 15-3) and Beagle dogs (Study No. 15-4). In the rats, daily oral administration of fospropofol disodium for 14 days at fospropofol close levels of 0, 50, 100, and 250 mg/kg/day (0, 300, 600, and 1500 mg/m²/day, respectively) resulted in 4 mortalities at the high dose level. The cause of death for these animals was considered to be related to the known pharmacodynamic effects of high doses of fospropofol, based on the time of death relative to the time of close administration, and the clinical signs recorded before death which included: labored breathing, prostrate, splayed hindlimbs, uncoordinated movement, decreased activity, and eyes closed. Other treatment-related effects included reduced body weight gain at 250 mg/kg/day, and a transient increase in prothrombin time at 250 mg/kg/day. There were no treatment-related histopathology findings in any tissues, including all GIT-related tissues that were evaluated, indicating that there were no local toxicities associated with orally administered fospropofol disodium at fospropofol close levels up to 250 mg/kg/day (the MTD established in this species). The NOAEL was determined to be 100 mg/kg/day (600 mg/m²/day) in male and female Sprague-Dawley rats.

In Beagle dogs, daily oral administration of fospropofol disodium for 14 days at fospropofol close levels of 0, 50, 100, and 160 mg/kg/day (0, 1000, 2000, and 3200 mg/m²/day, respectively) resulted in no mortalities. As in the rat, CNS-related clinical signs were observed which were consistent with the established pharmacodynamic effects of fospropofol. There were no toxicologically significant changes in body weights, cardiovascular evaluations (ECGs, including QTc), ophthalmology, clinical pathology (hematology, coagulation, clinical chemistry, and urinalysis), and absolute or relative organ weights. No gross necropsy findings were observed at main or recovery sacrifices, and there were no treatment-related histopathological findings in any tissues, including all GIT-related tissues. As for the rat, the absence of histopathology findings in the GIT indicated that there were no local toxicities associated with orally administered fospropofol disodium at fospropofol close levels up to 160 mg/kg/day in the dog (the MTD established in this species). The NOAEL was determined to be 160 mg/kg/day (3200 mg/m²/d) in male and female Beagle dogs.

Overall, no new treatment-related adverse findings were observed in the oral fospropofol toxicology studies that would limit the use of fospropofol disodium in healthy volunteer or migraine patient populations.

Example A16

Part 1: PK of Single Ascending Doses of Fospropofol Disodium (200 to 2000 mg)

Part 1 of Study A16 was a double-blind, randomized, placebo-controlled study to investigate the safety-tolerability and PK of oral administration of single ascending doses of fospropofol disodium to healthy adult male and female volunteers.

Subjects were healthy adults (age 18-55 years inclusive, BMI 18-29.9 kg/m²). Separate cohorts of 12 subjects each were randomized to receive fospropofol disodium at doses of 200, 400, 800, 1000, 1200, 1600, or 2000 mg (n=10 per cohort) or matching placebo (n=2 per cohort).

Subjects were admitted to the clinical unit for an overnight fast (Day -1), administered study drug on Day 1, and remained in the clinical unit until Day 2.

Fospropofol disodium was formulated as powder in an HPMC capsule, each capsule containing 200 mg of fospropofol disodium (weight adjusted for water content). Placebo was administered as an appropriate number of matching capsules.

Blood samples were collected for analysis of fospropofol and propofol at preclose and at 5, 10, 20, 30, 45 minutes, and 1, 1.5, 2, 4, 6 and 9 hours postclose (Cohorts 1-2). Based on PK results from the early cohorts, sampling times were optimized beginning with Cohort 3 (800 mg) to preclose, 5, 10, 15, 20, 25, 30, 37, and 45, minutes and 1, 2, 4, 6, and 9 hours after closing.

The following pharmacokinetic parameters were determined for fospropofol and propofol from plasma:area under the curve from time of closing to last measured time point ($AUC_{0-t}$), area under the curve from time of closing extrapolated to infinity ($AUC_{0-inf}$), residual area, maximum plasma concentration ($C_{max}$), time to maximum concentration ($T_{max}$), $t_{1/2}$, apparent clearance (Cl/F), and apparent volume of distribution ($V_d/F$).

Pharmacokinetic parameters are summarized in Table 16-1 and Table 16-2. Mean concentration vs. time plots for fospropofol and propofol by cohort are shown in FIG. 1.

Table 16-1 and FIG. 1 indicate that the median $T_{max}$ for fospropofol occurred at approximately 20 minutes, with fospropofol concentrations falling substantially (to less than 10% of $C_{max}$) by 2 hours after closing.

Table 16-2 and FIG. 1 indicate that the median $T_{max}$ for propofol was close-related, ranging from 30 minutes after the 200-mg dose to 45 minutes after doses of 1600 or 2000 mg, with propofol concentrations falling substantially (to less than 25% of $C_{max}$) by 4 hours after closing.

TABLE 16-1

Study A16 Part 1: PK Parameters for Fospropofol After Oral Administration of Fospropofol Disodium

| Dose (mg) | $AUC_{0-T}$ (ng · h/mL) | $AUC_{0-\infty}$ (ng · h/mL) | $C_{max}$ (ng/mL) | $T_{max}$ (h) | $t_{1/2}$ (h) | CL/F (L/h) |
|---|---|---|---|---|---|---|
| 200 | 856 (435) | 882 (432) | 1977 (758) | 0.33 (0.33-0.50) | 0.21 (0.05) | 277 (127) |
| 400 | 2202 (958) | 2231 (960) | 4460 (1811) | 0.33 (0.17-0.50) | 0.24 (0.07) | 211 (96) |
| 800 | 3288 (906) | 3356 (921) | 6041 (1854) | 0.33 (0.24-0.50) | 0.27 (0.07) | 254 (64) |
| 1000 | 4702 (1634) | 4845 (1759) | 8243 (2332) | 0.33 (0.25-0.42) | 0.29 (0.08) | 229 (74) |
| 1200 | 4399 (1425) | 4502 (1410) | 7110 (1613) | 0.33 (0.25-0.50) | 0.34 (0.07) | 288 (82) |
| 1600 | 6094 (1589) | 6305 (6305) | 10233 (2763) | 0.33 (0.25-0.42) | 0.35 (0.11) | 270 (70) |
| 2000 | 10821 (3866) | 10970 (3859) | 17088 (5487) | 0.38 (0.33-0.50) | 0.37 (0.13) | 204 (72) |

Values are means (SD), or median (range) for $T_{max}$
n = 10 subjects in each dose cohort.

TABLE 16-1A

PK Parameters for Fospropofol After oral Administration of Fospropofol Disodium on a per mg basis

| Dose (mg FOSPDiNa) | $AUC_{0-T}$/mg FOSP DiNa (ng · h/mL)/mg | $AUC_{0-\infty/mg\ FOSP\ DiNa}$ (ng · h/mL)/mg | $C_{max}$/mg FOSP DiNa (ng/mL)/mg |
|---|---|---|---|
| 200 | 4.28 | 4.41 | 9.89 |
| 400 | 5.51 | 5.58 | 11.15 |
| 800 | 4.11 | 4.20 | 7.55 |
| 1000 | 4.70 | 4.85 | 8.24 |
| 1200 | 3.67 | 3.75 | 5.93 |
| 1600 | 3.81 | 3.94 | 6.40 |
| 2000 | 5.41 | 5.49 | 8.54 |

TABLE 16-2

Study A16 Part 1: PK Parameters for Propofol After Oral Administration of Fospropofol Disodium

| Dose (mg) | $AUC_{0-T}$ (ng · h/mL) | $AUC_{0-\infty}$ (ng · h/mL) | $C_{max}$ (ng/mL) | $T_{max}$ (h) | $t_{1/2}$ (h) | CL/F (L/h) |
|---|---|---|---|---|---|---|
| 200 | 103.4 (34) | 118 (38) | 69 (44) | 0.50 (0.50-1.0) | 3.80 (2.75) | 1889 (706) |
| 400 | 276 (89) | 298 (95) | 201 (128) | 0.50 (0.50-1.0) | 2.94 (1.18) | 1658 (1200) |
| 800 | 551 (213) | 577 (215) | 362 (376) | 0.62 (0.33-1.0) | 1.94 (0.61) | 1561 (564) |
| 1000[a] | 846 (280) | 887 (286) | 403 (122) | 0.75 (0.40-2.0) | 2.02 (0.47) | 1213 (311) |
| 1200 | 1011 (275) | 1010 (257) | 641 (292) | 0.62 (0.42-2.0) | 2.06 (0.94) | 1260 (326) |
| 1600 | 1475 (595) | 1602 (590) | 748 (331) | 0.75 (0.75-2.0) | 2.95 (1.87) | 1182 (623) |
| 2000 | 2004 (627) | 2253 (536) | 806 (409) | 0.75 (0.50-2.00) | 1.96 (0.46) | 933 (237) |

Values are means (SD), or median (range) for $T_{max}$
[a] n = 10 subjects in each dose cohort, except the 1000-mg cohort for propofol (n = 9)

TABLE 16-1A

PK Parameters for Fospropofol After Oral Administration of Fospropofol Disodium on a per mg basis

| Dose (mg FOSPDiNa) | $AUC_{0-T}$/mg FOSP DiNa (ng · h/mL)/mg | $AUC_{0-\infty/mg\ FOSP\ DiNA}$ (ng · h/mL)/mg | $C_{max}$/mg FOSP DiNA (ng/mL)/mg |
|---|---|---|---|
| 200 | 0.52 | 0.59 | 0.35 |
| 400 | 0.69 | 0.75 | 0.50 |
| 800 | 0.69 | 0.72 | 0.45 |
| 1000 | 0.85 | 0.89 | 0.40 |
| 1200 | 0.84 | 0.84 | 0.53 |
| 1600 | 0.92 | 1.00 | 0.47 |
| 2000 | 1.00 | 1.13 | 0.40 |

Dose proportionality assessment using the power model indicated that the PK parameters for fospropofol ($AUC_{0-2h}$, $AUC_{0-T}$, $AUC_{0-\infty}$, and $C_{max}$) were close proportional over the close range from 200 mg to 2000 mg.

The PK parameters for propofol ($AUC_{0-2h}$ and $C_{max}$) were close proportional over the close range from 200 mg to 2000 mg, whereas $AUC_{0-T}$ and $AUC_{0-\infty}$, values for propofol increased with close in a slightly greater than close-proportional manner. Based on the power model, $C_{max}$ and $AUC_{0-\infty}$, values for propofol were close proportional over the close range from 200 mg to 1200 mg, whereas $AUC_{0-T}$ values increased with close in a slightly greater than close-proportional manner.

Within each cohort, the coefficient of variation (CV) around the mean $C_{max}$ for propofol was greater than the CV around the mean $C_{max}$ for fospropofol. The CV around the mean $C_{max}$ for propofol ranged from 30% to 99% across the cohorts. Contributing to the wider variability in propofol $C_{max}$ was the presence of occasional "outlier" values for the propofol $C_{max}$ that were more than 2 standard deviations above the mean for the respective close cohort (Table 16-3).

TABLE 16-3

Study A16 Part 1: Variability in $C_{max}$ Values for Propofol After Oral Administration of Fospropofol Disodium

| | $C_{max}$ | | | | |
|---|---|---|---|---|---|
| Dose (mg) | Mean (SD) (ng/mL) | Minimum (ng/mL) | Maximum (ng/mL) | Maximum value: SDs above the mean | CV (%) |
| 200 | 69 (44) | 35.08 | 191.02 | 2.74 | 64 |
| 400 | 201 (128) | 33.47 | 498.55 | 2.32 | 63 |
| 800 | 362 (376) | 127.49 | 1352.75 | 2.64 | 99 |
| 1000[a] | 403 (122) | 266.72 | 681.00 | 2.28 | 30 |
| 1200 | 641 (292) | 193.37 | 1188.45 | 1.87 | 46 |
| 1600 | 748 (331) | 228.54 | 1171.27 | 1.28 | 44 |
| 2000 | 806 (409) | 199.53 | 1615.57 | 1.98 | 51 |

Values are means (SD), or median (range) for $T_{max}$.
[a] n = 10 subjects in each dose cohort, except the 1000-mg cohort for propofol (n = 9).

Table 16-3 illustrates that the highest observed $C_{max}$ values within the 200, 400, 800, and 1000 mg cohorts were greater than 2 standard deviations above the mean for that cohort. The highest observed $C_{max}$ values in the 200, 400, 800, and 1000 mg cohorts were more than 2 times the mean $C_{max}$ value for the respective cohort. In the 800-mg cohort, the highest observed $C_{max}$ value was 1352.75 ng/mL, a value approximately 3.7-fold higher than mean value of $C_{max}$ (362 ng/mL) for the 800 mg cohort. Analyses to explore the role of subject-related factors potentially predictive of unusually high $C_{max}$ values, e.g., weight, BMI, sex, age, serum alkaline phosphatase did not identify any predictive factor.

TABLE 16-4

Propofol exposure by subject (800 mg Cohort).

| Subject No. | Cmax ng/mL | Tmax hr | AUC1 ng · h/mL | AUC2 ng · h/mL | AUC4 ng · h/mL | Female |
|---|---|---|---|---|---|---|
| 301 | 157.83 | 3 | 98.10 | 237.31 | 397.29 | 1 |
| 303 | 204.51 | 3 | 97.97 | 244.69 | 359.96 | 1 |
| 304 | 279.41 | 1 | 153.18 | 259.05 | 337.29 | 0 |
| 305 | 255.22 | 1.5 | 124.03 | 334.03 | 614.19 | 1 |
| 307 | 399.94 | 1.5 | 193.54 | 372.18 | 523.43 | 1 |
| 308 | 1352.75 | 0.5 | 480.16 | 743.01 | 922.96 | 1 |
| 309 | 227.29 | 1.5 | 111.55 | 227.07 | 321.62 | 0 |
| 310 | 264.22 | 1.5 | 171.46 | 340.01 | 460.08 | 0 |
| 311 | 127.49 | 2 | 79.38 | 158.72 | 227.73 | 0 |
| 312 | 351.47 | 2 | 190.10 | 411.20 | 572.00 | 1 |
| Mean | 362.01 | 1.75 | 169.95 | 332.73 | 473.66 | |
| SD | 357.55 | 0.79 | 116.21 | 163.24 | 198.58 | |
| CV (%) | 98.8% | 45.2% | 68.4% | 49.1% | 41.9% | |

TABLE 16-5

Propofol exposure by subject (800 mg Cohort) omitting data from Subject 308, who demonstrated very high outlier exposure.

| Subject No. | Cmax ng/mL | Tmax hr | AUC1 ng · h/mL | AUC2 ng · h/mL | AUC4 ng · h/mL | Female |
|---|---|---|---|---|---|---|
| 301 | 157.83 | 3 | 98.10 | 237.31 | 397.29 | 1 |
| 303 | 204.51 | 3 | 97.97 | 244.69 | 359.96 | 1 |
| 304 | 279.41 | 1 | 153.18 | 259.05 | 337.29 | 0 |
| 305 | 255.22 | 1.5 | 124.03 | 334.03 | 614.19 | 1 |
| 307 | 399.94 | 1.5 | 193.54 | 372.18 | 523.43 | 1 |
| 308 | | | | | | 1 |
| 309 | 227.29 | 1.5 | 111.55 | 227.07 | 321.62 | 0 |
| 310 | 264.22 | 1.5 | 171.46 | 340.01 | 460.08 | 0 |
| 311 | 127.49 | 2 | 79.38 | 158.72 | 227.73 | 0 |
| 312 | 351.47 | 2 | 190.10 | 411.20 | 572.00 | 1 |
| Mean | 251.93 | 1.89 | 135.48 | 287.14 | 423.73 | |
| SD | 86.55 | 0.70 | 42.75 | 81.23 | 127.77 | |
| CV (%) | 34.4% | 36.9% | 31.6% | 28.3% | 30.2% | |

TABLE 16-6

Propofol exposure by subject (800 mg Cohort) omitting data from Subject 308, females only.

| Subject No. | Cmax | Tmax | Auc1 | Auc2 | Auc4 | Female |
|---|---|---|---|---|---|---|
| 301 | 157.83 | 3 | 98.10 | 237.31 | 397.29 | 1 |
| 303 | 204.51 | 3 | 97.97 | 244.69 | 359.96 | 1 |
| 304 | | | | | | 0 |
| 305 | 255.22 | 2 | 124.03 | 334.03 | 614.19 | 1 |
| 307 | 399.94 | 2 | 193.54 | 372.18 | 523.43 | 1 |
| 308 | | | | | | 1 |
| 309 | | | | | | 0 |
| 310 | | | | | | 0 |
| 311 | | | | | | 0 |
| 312 | 351.47 | 2 | 190.10 | 411.20 | 572.00 | 1 |
| Mean | 273.79 | 2.20 | 140.75 | 319.88 | 493.37 | |

TABLE 16-6-continued

Propofol exposure by subject (800 mg Cohort) omitting data from Subject 308, females only.

| Subject No. | Cmax | Tmax | Auc1 | Auc2 | Auc4 | Female |
|---|---|---|---|---|---|---|
| SD | 100.67 | 0.76 | 47.83 | 77.05 | 110.36 | |
| CV (%) | 36.8% | 34.5% | 34.0% | 24.1% | 22.4% | |

TABLE 16-7

Fospropofol Exposure by subject.

| Subject No. | Cmax ng/mL | Tmax hr | AUC1 ng · h/mL | AUC2 ng · h/mL | AUC4 ng · h/mL | Female |
|---|---|---|---|---|---|---|
| 301 | 7942.73 | 0.25 | 2690.24 | 2988.84 | 3040.44 | 1 |
| 303 | 5546.32 | 0.33 | 2805.69 | 3782.78 | 4067.25 | 1 |
| 304 | 5265.38 | 0.25 | 2328.26 | 2497.80 | 2497.80 | 0 |
| 305 | 9361.51 | 0.33 | 3662.37 | 4416.94 | 4632.93 | 1 |
| 307 | 8555.93 | 0.50 | 4155.53 | 5002.09 | 5157.89 | 1 |
| 308 | 4964.97 | 0.33 | 2717.73 | 2909.41 | 2981.03 | 1 |
| 309 | 4768.77 | 0.42 | 2698.85 | 3555.61 | 3676.43 | 0 |
| 310 | 5211.25 | 0.25 | 2441.52 | 2661.24 | 2661.24 | 0 |
| 311 | 4763.18 | 0.25 | 2010.86 | 2308.48 | 2367.38 | 0 |
| 312 | 4031.53 | 0.50 | 2257.18 | 3141.45 | 3313.27 | 1 |
| Mean | 6041.16 | 0.34 | 2776.82 | 3326.46 | 3439.57 | |
| SD | 1854.40 | 0.10 | 656.02 | 865.72 | 934.21 | |
| CV (%) | 30.7% | 29.2% | 23.6% | 26.0% | 27.2% | |

TABLE 16-8

Fospropofol exposure by patient (females only).

| Subject No. | Cmax | Tmax | Auc1 | Auc2 | Auc4 | Female |
|---|---|---|---|---|---|---|
| 301 | 7942.73 | 0.25 | 2690.24 | 2988.84 | 3040.44 | 1 |
| 303 | 5546.32 | 0.333 | 2805.69 | 3782.78 | 4067.25 | 1 |
| 304 | | | | | | 0 |
| 305 | 9361.51 | 0.333 | 3662.37 | 4416.94 | 4632.93 | 1 |
| 307 | 8555.93 | 0.5 | 4155.53 | 5002.09 | 5157.89 | 1 |
| 308 | 4964.97 | 0.333 | 2717.73 | 2909.41 | 2981.03 | 1 |
| 309 | | | | | | 0 |
| 310 | | | | | | 0 |
| 311 | | | | | | 0 |
| 312 | 4031.53 | 0.5 | 2257.18 | 3141.45 | 3313.27 | 1 |
| Mean | 6733.83 | 0.37 | 3048.12 | 3706.92 | 3865.47 | |
| SD | 2169.22 | 0.10 | 710.67 | 855.43 | 901.99 | |
| CV (%) | 32.2% | 27.3% | 23.3% | 23.1% | 23.3% | |

The preliminary PK data from Study A16, Part 1, indicated that exposure to propofol (both $C_{max}$ and AUC) after oral administration of fospropofol disodium was approximately close proportional over the close range of 200 to 2000 mg. Within each close cohort, the intersubject variability for propofol exposure was greater than for fospropofol. Most of the closing cohorts were characterized by the observation of 1 subject with unusually high propofol exposure. Analyses to explore the role of subject-related factors potentially predictive of unusually high $C_{max}$ values, e.g., weight, BMI, sex, age, serum alkaline phosphatase, did not identify any predictive factor.

Part 2: PK of a Single Dose of 1200 mg Fospropofol Disodium Following a High-Fat Meal Part 2 of Study A16 was a double-blind, placebo-controlled, single-close pilot study to investigate the PK, safety, and tolerability of 1200 mg of fospropofol disodium administered to healthy adult men and women following a high-fat meal.

Subjects were healthy adults (age 18-55 years inclusive, BMI 18-29.9 kg/m²). A separate cohort of 15 subjects was randomly assigned to receive a single oral dose of either fospropofol disodium (n=12) or matching placebo (n=3) within 30 minutes (±1 minute) after the start of a standardized high-fat meal.

Subjects were admitted to the clinical unit for an overnight fast (Day −1), administered study drug on Day 1 within 30 minutes of the start a standardized high-fat meal, and remained in the clinical unit until Day 2.

Fospropofol disodium was formulated as powder in 6 HPMC capsules, each capsule containing 200 mg of fospropofol disodium (weight adjusted for water content). Placebo was administered as 6 matching capsules.

Blood samples were collected for analysis of fospropofol and propofol at preclose, 5, 10, 15, 20, 25, 30, 37, and 45, minutes and 1, 2, 4, 6, and 9 hours after closing.

The following PK parameters were determined for fospropofol and propofol from plasma:area under the curve from time of closing to last measured time point ($AUC_{0-t}$), area under the curve from time of closing extrapolated to infinity ($AUC_{0-inf}$), residual area, maximum plasma concentration ($C_{max}$), time to maximum concentration ($T_{max}$), $t_{1/2}$, apparent clearance (Cl/F), and apparent volume of distribution ($V_d/F$).

Figure 2:
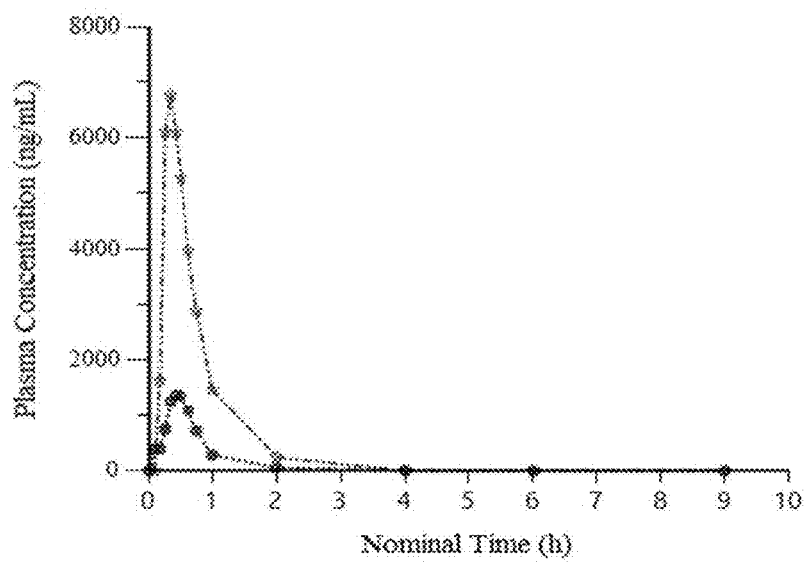
FIG. 2 shows mean concentrations are plotted overtime for fospropofol and propofol by cohort for Part 2 of Study A16.
Figure 2:
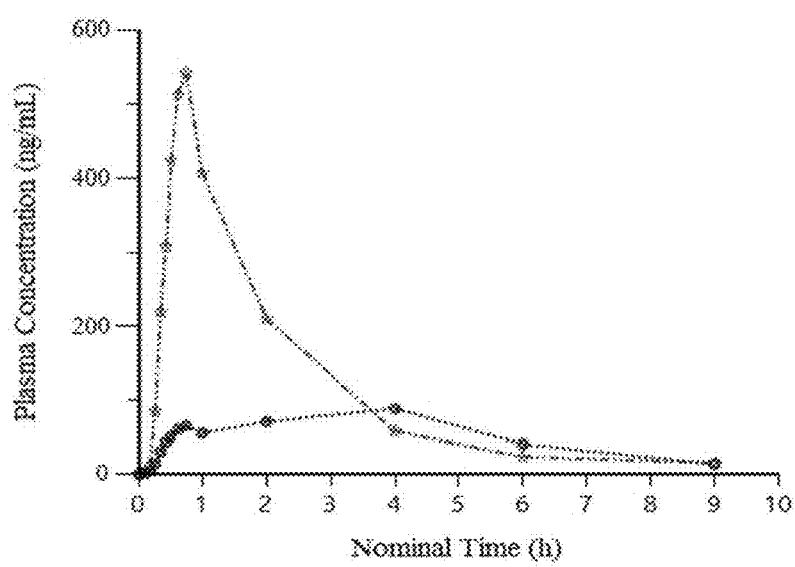
Figure 3:
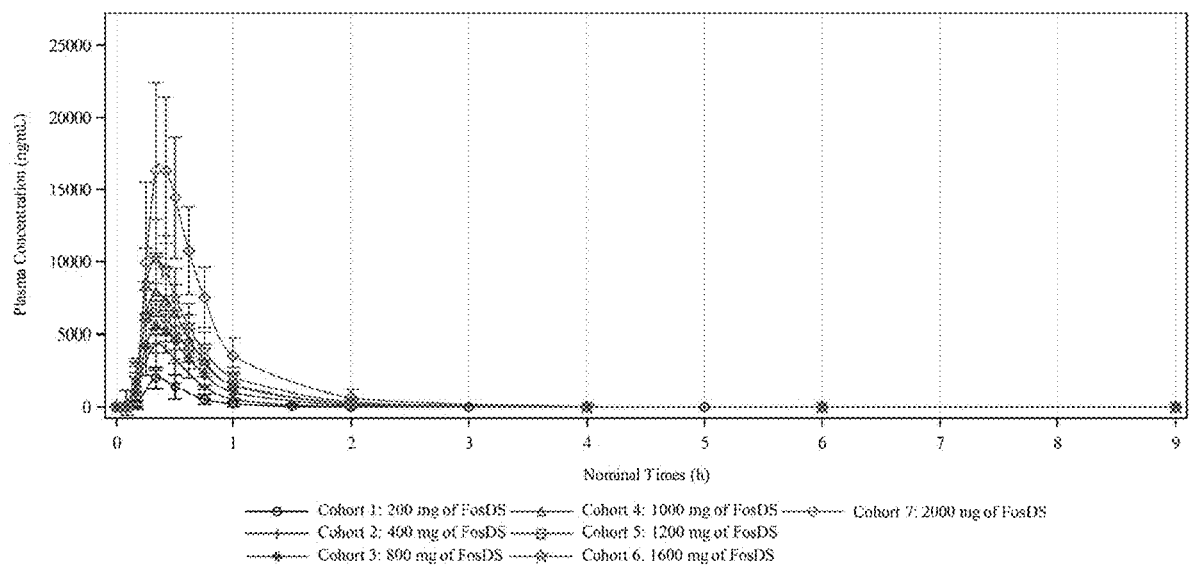
FIG. 3 shows the Mean (±SD) Fospropofol Plasma Concentrations by Cohort (Fasting Conditions)—Linear Scale—PK Set—Example A16
Figure 4A:
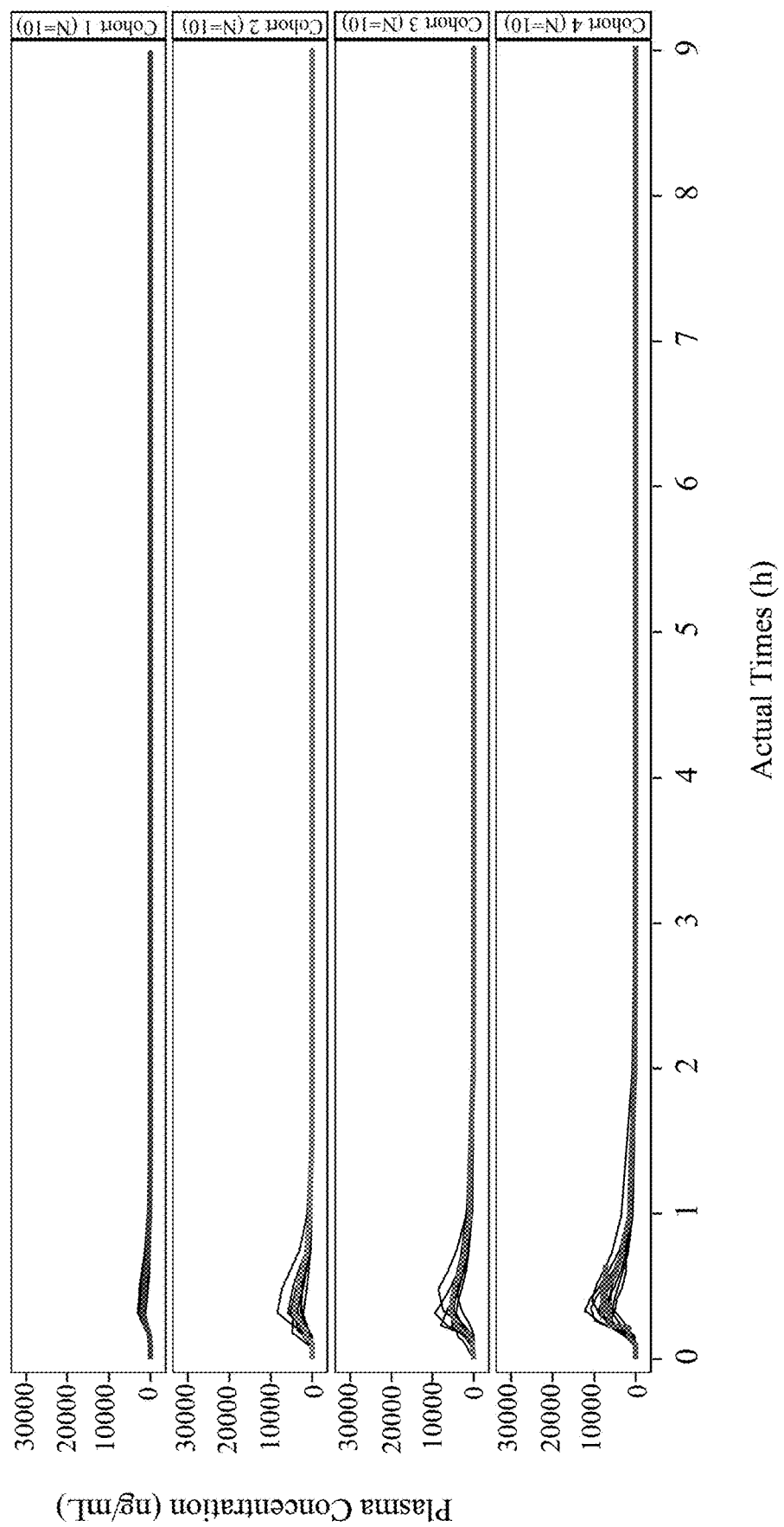
Figure 5:
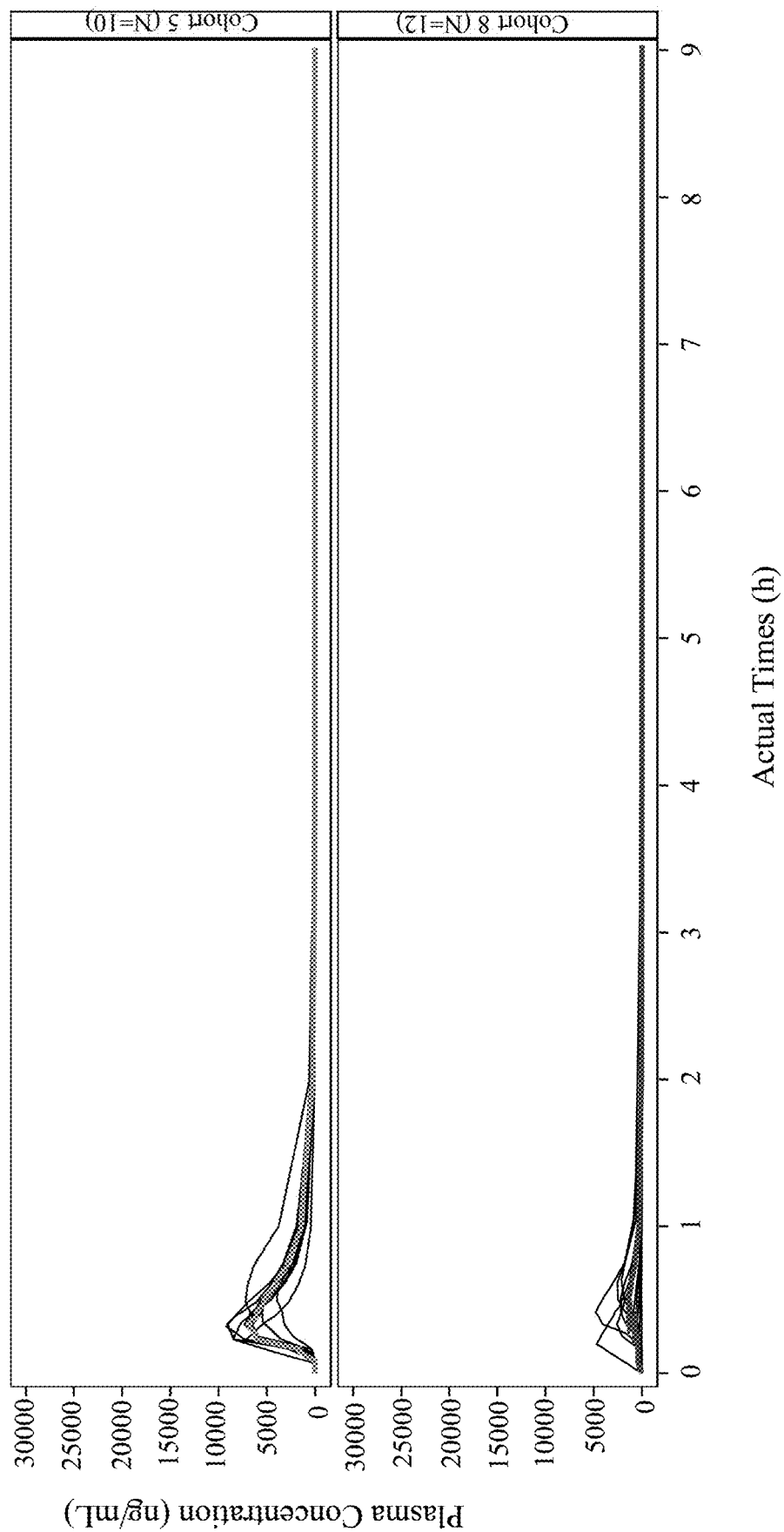
FIG. 5 shows an Overlay of Individual and Mean Fospropofol Plasma Concentrations Food Effect Cohort (Fasting and Fed Conditions)—Linear Scale—Example A16
Figure 6:
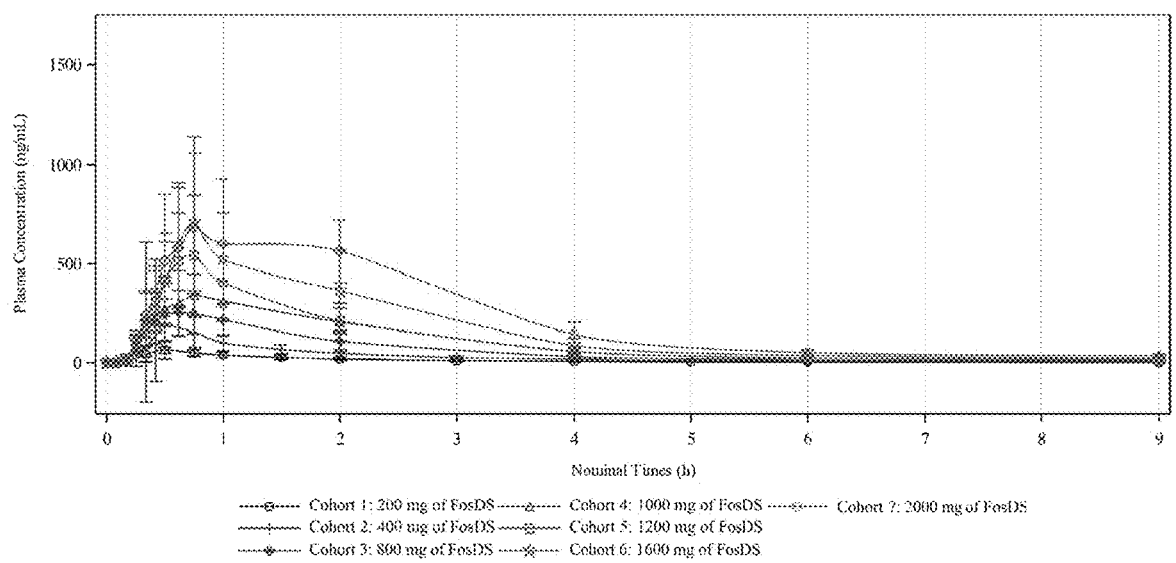
FIG. 6 shows the Mean (±SD) Propofol Plasma Concentrations by Cohort (Fasting Conditions)—Linear Scale—Example A16
Figure 7A:
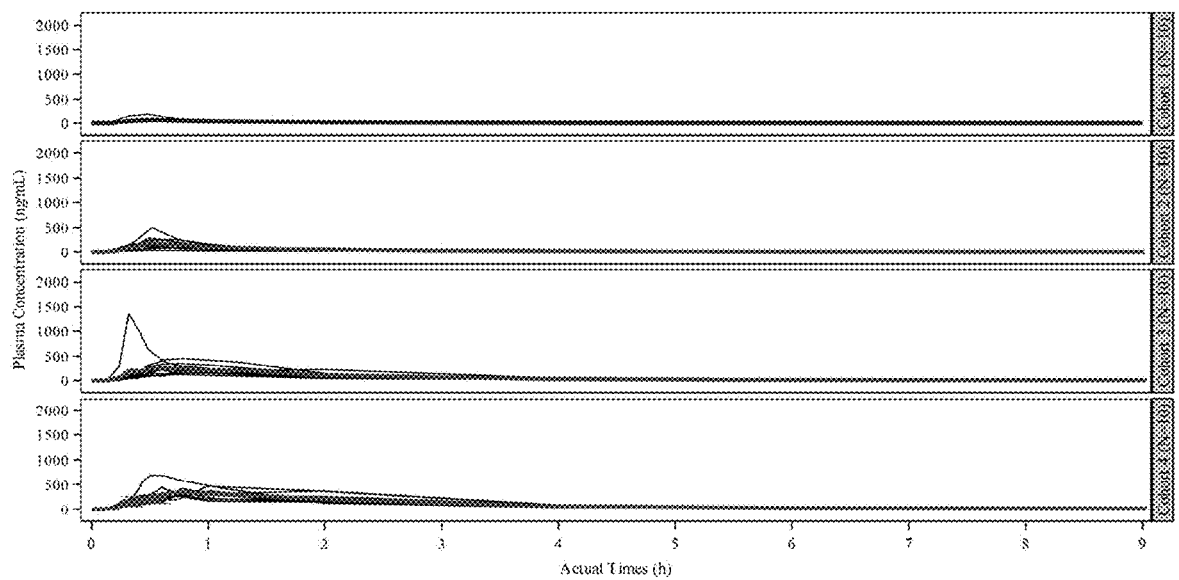
FIGS. 7A and 7B show an Overlay of Individual and Mean Propofol Plasma Concentrations by Cohort (Fasting Conditions)—Linear Scale—Example A16
Figure 7B:
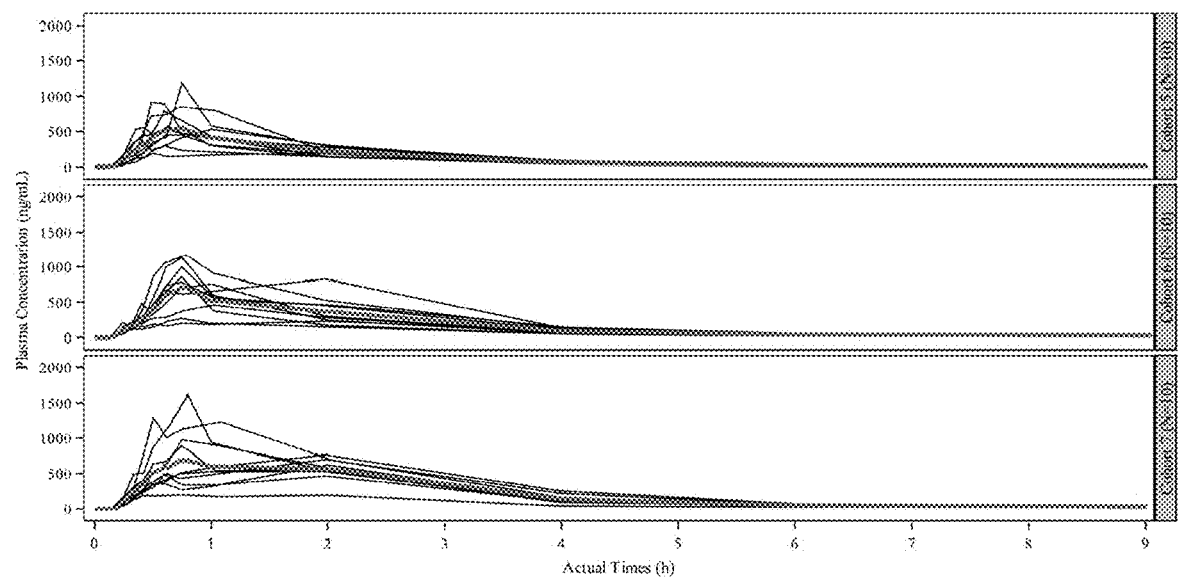
Figure 8:
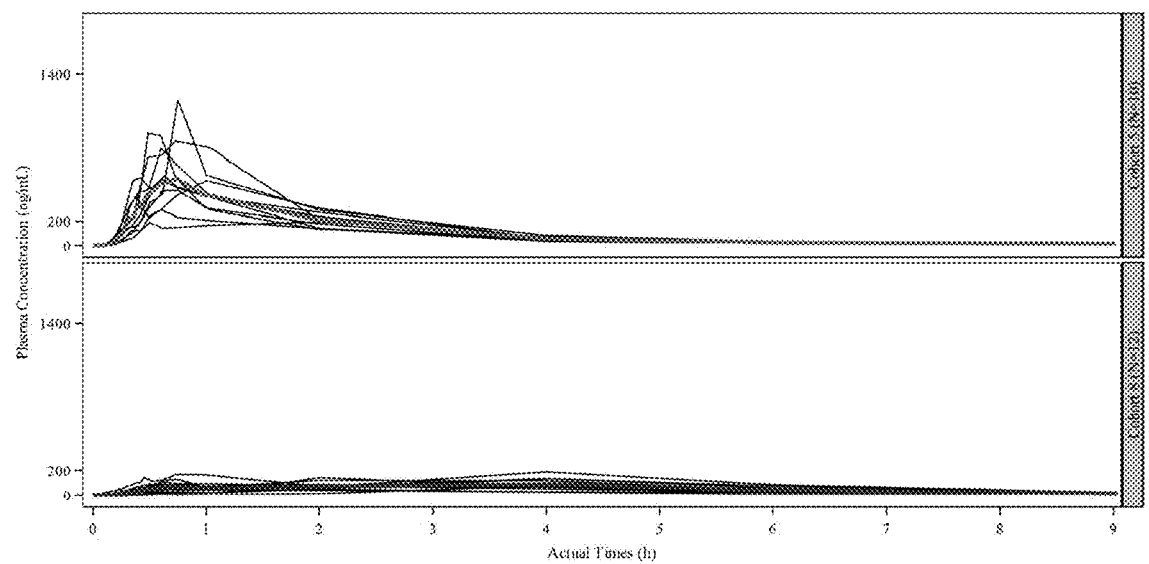
FIG. 8 shows an Overlay of Individual and Mean Propofol Plasma Concentrations Food Effect Cohort (Fasting and Fed Conditions)—Linear Scale—PK Set—Example A16
Figure 9:
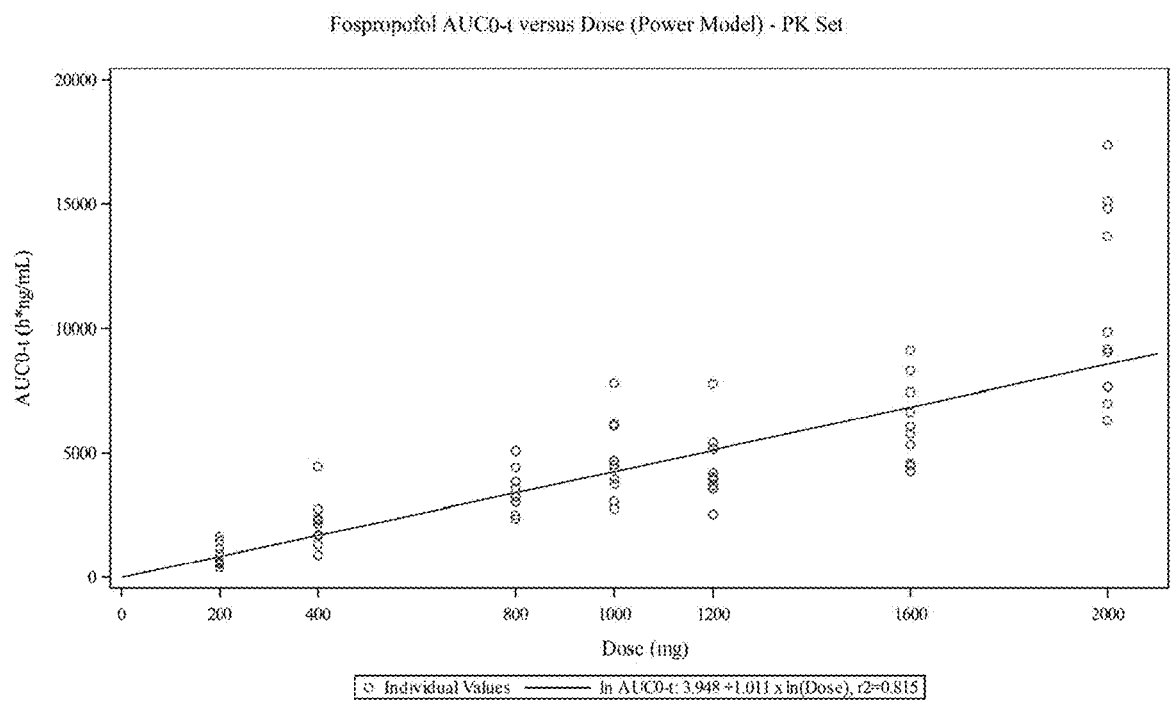
FIG. 9 shows the Fospropofol AUC0-t versus Dose (Power Model)—PK Set—Example A16
Figure 10:
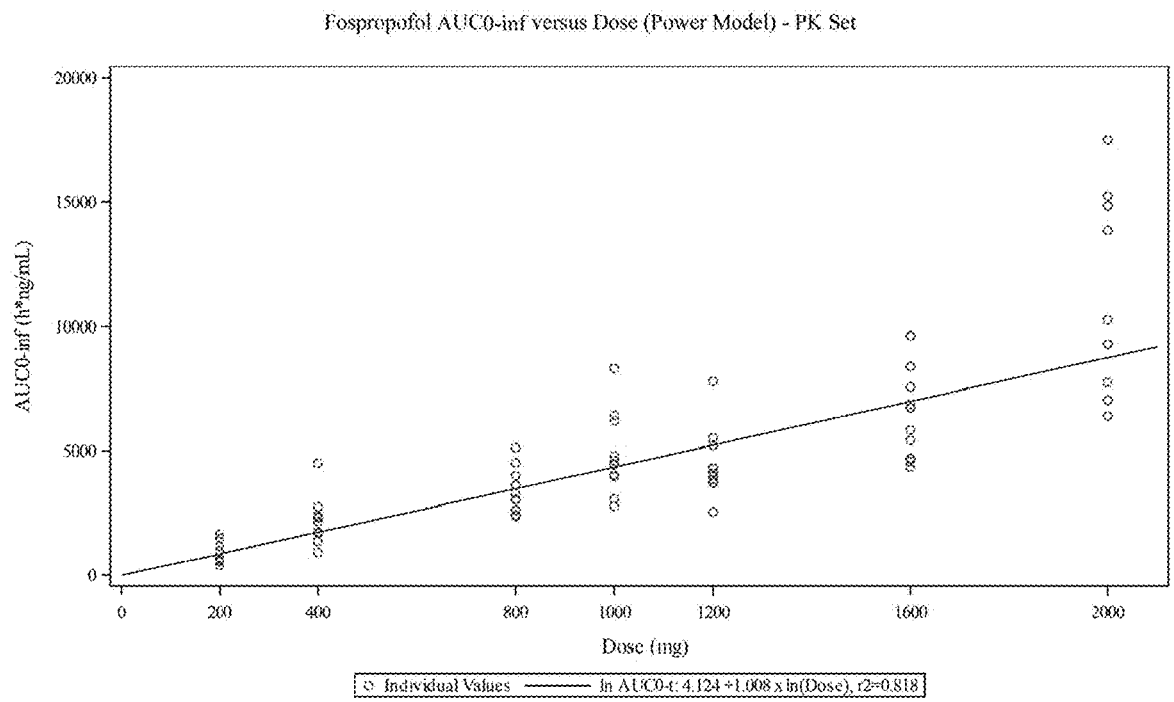
FIG. 10 shows the Fospropofol AUC0-inf versus Dose (Power Model)—PK Set—Example A16
Figure 11:
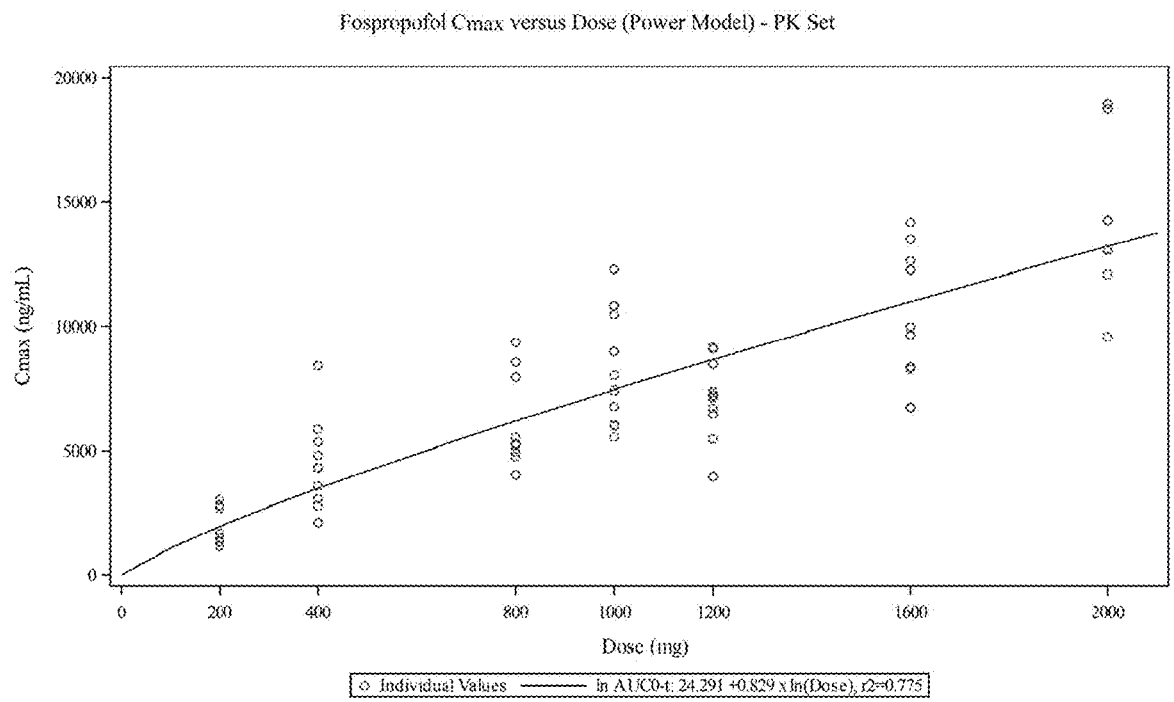
FIG. 11 shows the Fospropofol Cmax versus Dose (Power Model)—PK Set—Example A16
Figure 12:
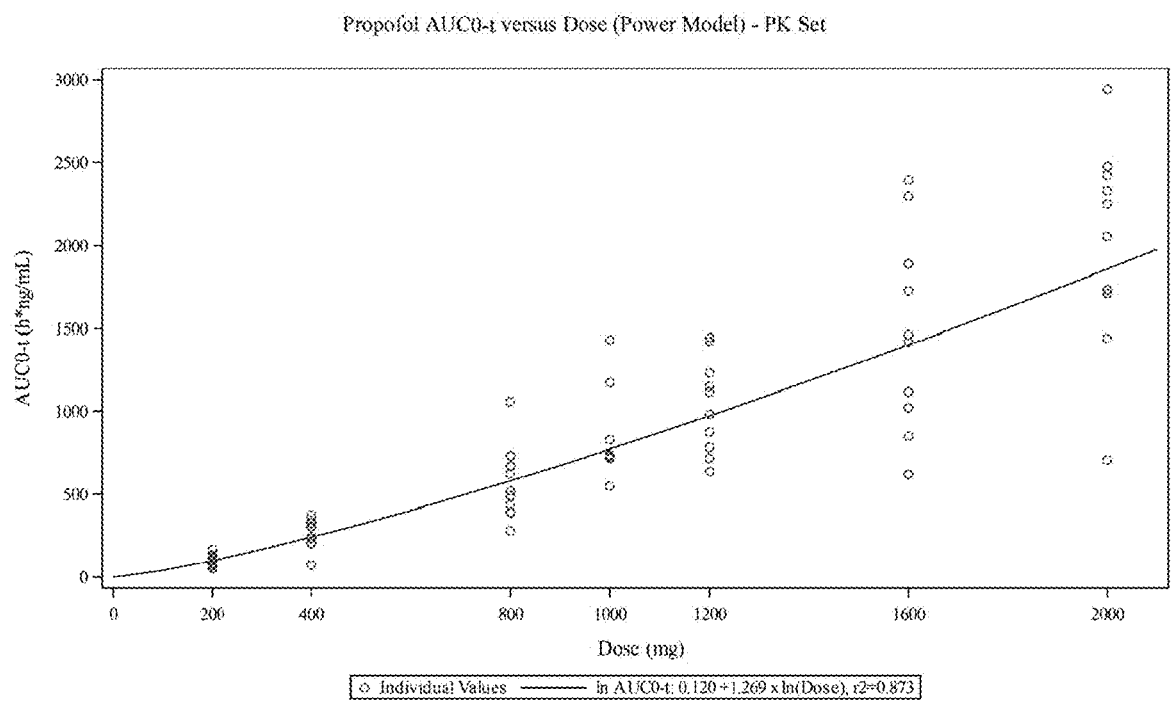
FIG. 12 shows the Propofol AUC0-t versus Dose (Power Model)—PK Set—Example A16
Figure 13:
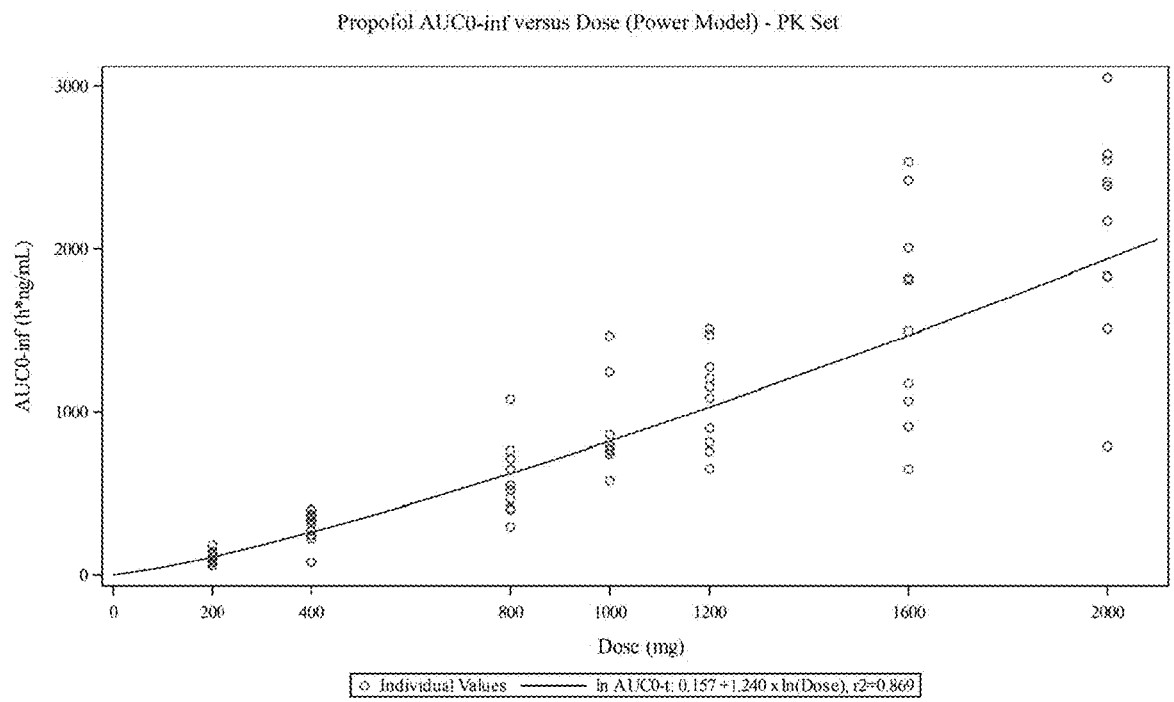
FIG. 13 shows the Propofol AUC0-inf versus Dose (Power Model)—PK Set—Example A16
Figure 14:
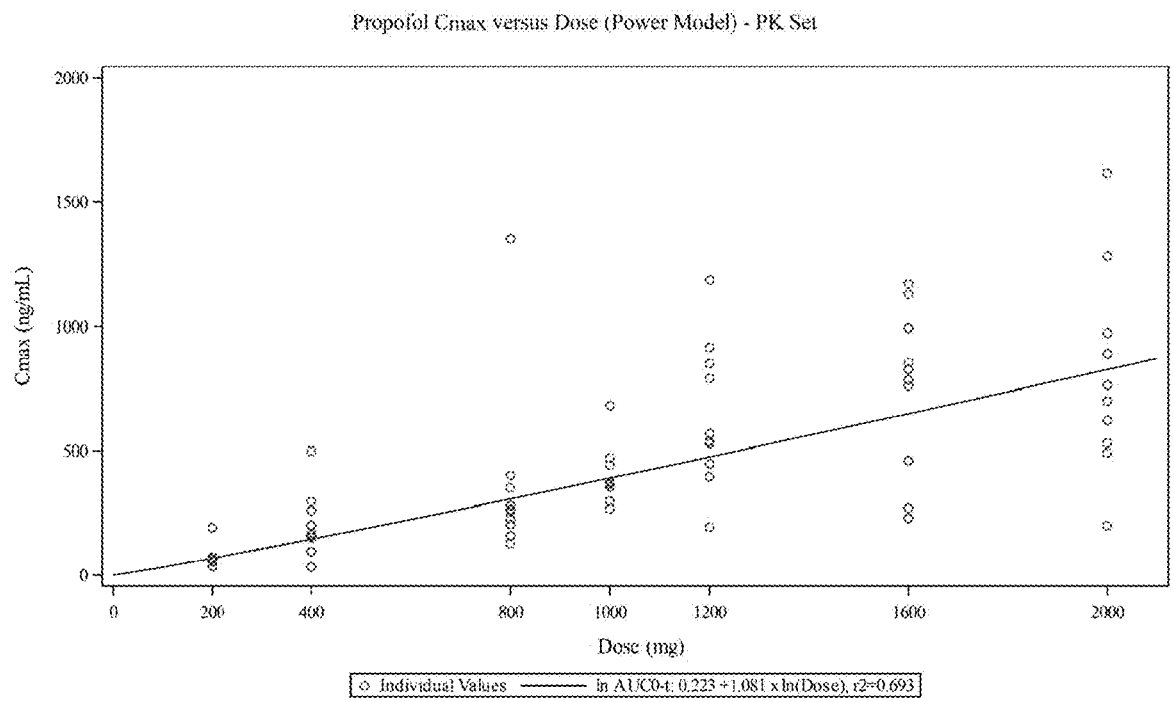
FIG. 14 shows the Propofol Cmax versus Dose (Power Model)—PK Set—Example A16
Figure 15:
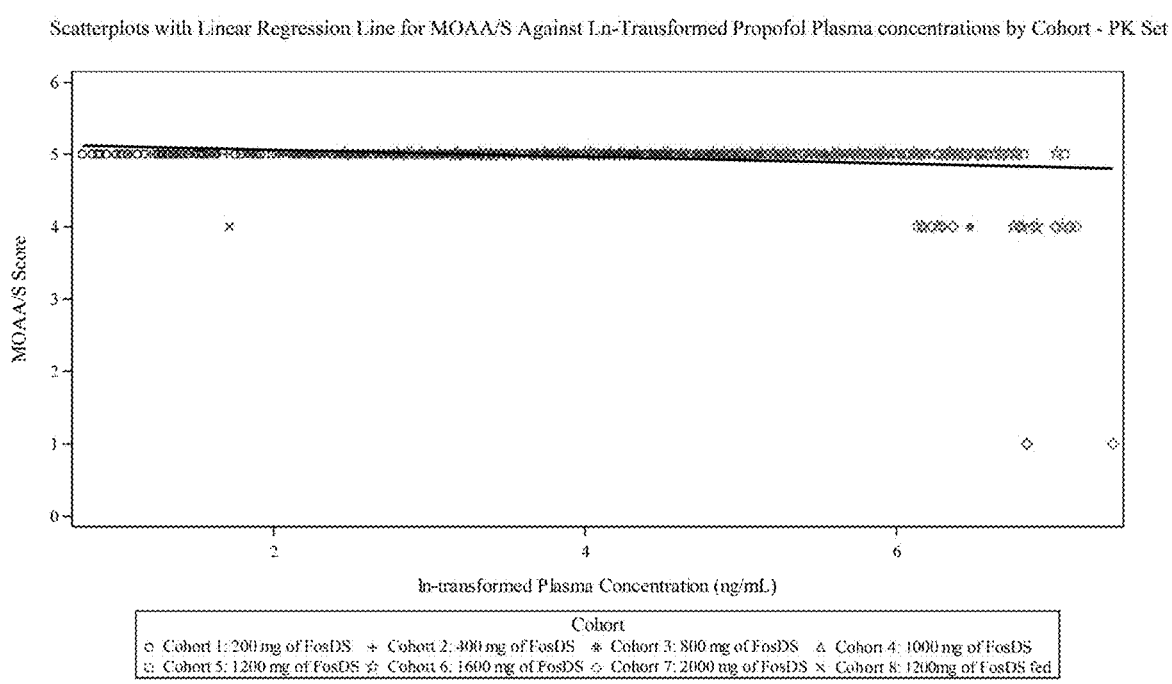
FIG. 15 shows the Scatterplots with Linear Regression Line for MOAA/S Against Ln-Transformed Propofol Plasma concentrations by Cohort—PK Set—Example A16.
Figure 16:
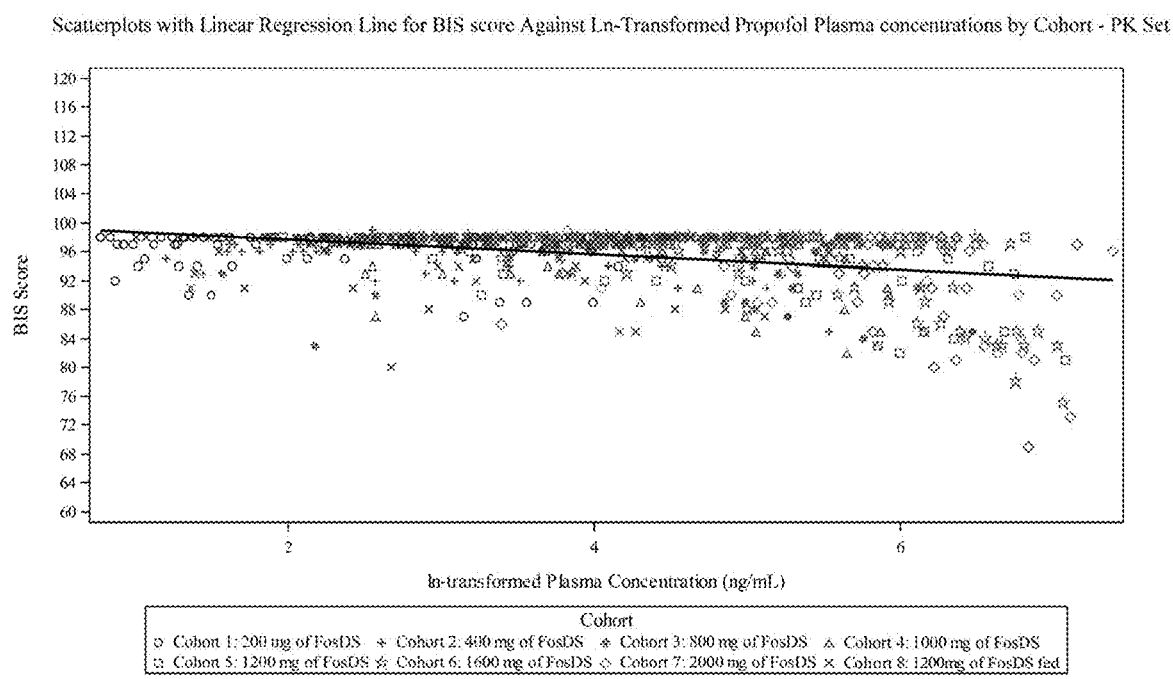
FIG. 16 shows the Scatterplots with Linear Regression Line for BIS score Against Ln-Transformed Propofol Plasma concentrations by Cohort—PK Set—Example A16.

PK parameters from the fed cohort (Cohort 8, 1200 mg) are summarized together with the parameters from the fasted cohort that received 1200 mg (Cohort 5, Part 1) in Table 16-9. Mean concentrations are plotted over time for fospropofol and propofol by cohort in FIG. 2.

Compared with subjects in Part 1 who received 1200 mg of fospropofol disodium under fasting conditions, subjects who received 1200 mg of fospropofol disodium following a high-fat meal showed a significant reduction in exposure (Table 16-9). Mean exposure to fospropofol under fed conditions (both $C_{max}$ and AUC) was approximately 24% of the exposure under fasting conditions, with no appreciable effect on $T_{max}$ (median, 0.333 h). For propofol, the mean AUC following a high-fat meal was approximately 40% of the mean AUC observed under fasting conditions, and the mean $C_{max}$ under fed conditions was approximately 19% of the mean $C_{max}$ observed under fasting conditions. Administration of fospropofol disodium after a high-fat meal delayed the propofol $T_{max}$ from a median value of 0.617 (range, 0.417-2.00) hours under fasting conditions to a median value of 2.00 (range, 0.500-4.00) hours.

Results of the pilot food-effect study indicate that administration of fospropofol disodium 1200 mg within 30 minutes after the start of a high-fat meal is associated with a significant reduction in exposure to both fospropofol and propofol.

Example A17. Study A17

Open-label study to describe the pharmacokinetics, and safety, tolerability, and relief of pain and associated migraine symptoms (nausea/vomiting, photophobia, phonophobia) following a single oral dose of fospropofol administered to adult women and men experiencing moderate to severe migraine headache.

Study Drug Fospropofol Disodium
Study Phase and Type Phase 1b—Open-label, single-close administration to adults with moderate to severe migraine headache
Objectives Primary Objectives
  To describe the pharmacokinetics (PK) of a single oral dose of fospropofol administered to adult women and men experiencing moderate to severe migraine headache.
  To describe safety-tolerability of a single oral dose of fospropofol administered to adult women and men experiencing moderate to severe migraine headache.
Exploratory Objectives
  To assess the clinical course (relief of pain and associated migraine symptoms: nausea/vomiting, photophobia, phonophobia) after a single oral dose of fospropofol administered to adult women and men experiencing moderate to severe migraine headache.
  To explore the influence of covariates on PK and to characterize pharmacokinetic-pharmacodynamic (PK-PD) relationships between plasma propofol concentration and PD assessments (measures of pain, associated migraine symptoms, and sedation).
Study Design This is a Phase 1b, multicenter study with an open-label, single-close design in adult women and men with a history of episodic migraine with or without aura, diagnosed based on the International Classification of Headache Disorders, edition 3 (ICHD-3). (Headache Classification Committee of the International Headache Society (IHS). The International Classification of Headache Disorders, 3rd edition. Cepha-

TABLE 16-9

Study A16: PK Parameters for Fospropofol and Propofol after Oral Administration of fospropofol disodinm 1200 mg in the Fasted (Cohort 5) and Fed (Cohort 8) State

| Analyte/ Condition | $AUC_{0-T}$ (ng · h/mL) | $AUC_{0-\infty}$ (ng · h/mL) | $C_{max}$ (ng/mL) | $T_{max}$ (h) | $t_{1/2}$ (h) | CL/F (L/h) |
|---|---|---|---|---|---|---|
| Fospropofol | | | | | | |
| Fasted (Cohort 5) n = 10 | 4399 (1425) | 4502 (1410) | 7110 (1613) | 0.33 (0.25-0.50) | 0.34 (0.07) | 288 (82) |
| Fed (Cohort 8) n= 12 | 993 (970) | 1076 (1012)[a] | 1792 (1661) | 0.33 (0.08-0.62) | 0.26 (0.15)a | 4122 (4829)[a] |
| Propofol | | | | | | |
| Fasted (Cohort 5) n = 10 | 1011 (275) | 1010 (257) | 641 (292) | 0.62 (0.42-2.0) | 2.06 (0.94) | 1260 (326) |
| Fed (Cohort 8) n= 12 | 478 (174) | 450 (450)[b] | 116 (42) | 2.00 (0.50-4.0) | 2.29 (0.67)[b] | 3111 (1511)[b] |

Values are means (SD), or median (range) for $T_{max}$, of data.
[a]Values based on n = 10/12 subjects because of insufficient data points to estimate elimination phase.
[b]Values based on n = 7/12 subjects because of insufficient data points to estimate elimination phase.

lalgia 2018; 38:1-211) Migraine diagnosis will be confirmed in a virtual (online) interview with a specialist in headache medicine. The study is planned to complete approximately 85 subjects.

Enrolled subjects will be asked to come to the study site for treatment when they experience a qualifying migraine headache. Dosing must occur within 4 hours after onset of the migraine symptoms. If treatment at the study site is not feasible or practicable within 4 hours after onset of migraine symptoms, subjects should use their usual medication for that headache and attempt to visit the clinic for treatment as soon as possible (within 4 hours) after onset of their next migraine headache. Dosing must occur within 60 days after enrollment (see Post-enrollment Period below).

At clinic check-in for treatment, study personnel will verify eligibility for closing regarding the criteria for a qualifying headache and adherence to post-enrollment study restrictions (see Eligibility for Dosing below).

Treatment will consist of a single oral dose of fospropofol disodium. Blood samples will be drawn for assessment of PK parameters for fospropofol and propofol preclose and during a postclose period of 4 hours after closing (see PK Sampling below).

Safety assessments will be performed throughout. Headache pain and associated migraine symptoms will be assessed at 1, 2, and 4 hours after closing and at clinic discharge (check-out).

Persistence or recurrence of migraine pain and other symptoms will be assessed at Day 2 and Day 3 follow-up telephone interviews.

Participants are considered to have completed the study if they have been closed with fospropofol disodium within 60 days after enrollment and if they have completed all procedures listed in the Schedule of Events for Day 1, the virtual (online) interview with the specialist in headache medicine, and the follow-up telephone interviews on Days 2 and 3.

Justification for Dose Selection of the dose for this study is based on the results of the prior Phase 1a study in healthy volunteers (Study A16).

Safety Committee A Safety Review Committee will be established to review periodic summaries of safety data from this study and to provide consultation as outlined in the Safety Committee Charter.

Subject Selection The study is planned to complete approximately 85 subjects. Because the prevalence of migraine headaches is higher in women than in men, efforts will be made to enroll at least 50% women.

Subjects must meet the general inclusion and exclusion criteria listed below (Inclusion Criteria and Exclusion Criteria) at screening to be enrolled in the study. To be eligible for fospropofol disodium treatment after onset of a migraine headache, enrolled subjects must meet criteria specific to the presenting headache at clinic check-in (see Qualifying Headache below) and adhere to study restrictions specific to the period between enrollment and clinic check-in (see Post-enrollment Restrictions below).

Inclusion Criteria Subjects must meet all of the following criteria at screening to be enrolled in the study:

1. Written informed consent approved by the Institutional Review Board (IRB) given before any study-related procedures are performed 2. Male or female, ≥18 and ≤55 years of age at the time of signed informed consent, with a body mass index (BMI) ≥18.0 and 29.9 kg/m² and body weight≥50.0 kg for men and ≥45.0 kg for women.

3. History of episodic migraine (Katsarava Z, Buse D C, Manack A N, et al (2012). Defining the differences between episodic migraine and chronic migraine. Current pain and headache reports, 16(1):86-92) consistent with a diagnosis of migraine with or without aura according to the ICHD-3 criteria, plus the following:
   a) Migraine attacks present for ≥1 year with age of onset≤50 years.
   b) History of 2 to 8 migraine attacks with moderate or severe pain per month (at least 8 hours in duration if untreated or any duration if treated) in each of the 3 months prior to the screening visit.

4. Subjects who are treated with drugs intended for migraine prophylaxis or drugs prescribed for a purpose other than migraine prophylaxis but with a potential prophylactic effect on migraine are eligible if they have been on a stable regimen for at least 3 months and meet other inclusion/exclusion criteria.

5. Female subjects must fulfill at least one of the following:
   a) Surgically sterile, defined as women who have had a tubal ligation, hysterectomy, or bilateral oophorectomy at least 6 months prior to screening.
   b) Post-menopausal, defined as absence of menses for at least 12 months prior to screening.
   c) Women who are sexually active and at risk for pregnancy must agree to avoid pregnancy and use a medically acceptable method of contraception from at least 30 days prior to screening until 30 days after study drug administration.
   Medically acceptable methods of contraception include hormonal contraception, hormonal or non-hormonal intrauterine device, double barrier method (simultaneous use of male condom with intravaginally applied spermicide and diaphragm or cervical cap), or male partner vasectomy at least 6 months previously. Complete abstinence alone can be used as a method of contraception.

6. Male subjects who are not vasectomized for at least 6 months, and who are sexually active with a non-sterile female partner (see definitions of surgically sterile and post-menopausal above) must be willing to use one of the following acceptable contraceptive methods throughout the study and for 90 days after the study drug administration (Complete abstinence alone can be used as a method of contraception):
   a) Simultaneous use of male condom and, for the female partner, intrauterine contraceptive device with or without hormone release (placed at least 4 weeks previously)
   b) Simultaneous use of male condom and, for the female partner, hormonal contraception
   c) Simultaneous use of male condom and, for the female partner, intravaginally applied spermicide with diaphragm or cervical cap 7. Able to comprehend the nature of the study, capable of giving written informed consent, and able to communicate effectively with clinic staff (as assessed by the investigator)

8. Available to volunteer for the entire study duration and willing to adhere to all protocol requirements, including the post-enrollment restrictions (see Post-enrollment Restrictions below)
9. Agrees not to post any information related to the study on any website or social media site (e.g., Facebook, Twitter, LinkedIn, Google+, etc.) until the entire trial has been completed
10. Willing to forgo rescue medicine for at least 2 hours after initiation of treatment with study drug (see In-Clinic Rescue Medicine)

Exclusion Criteria Subjects to whom any of the following criteria apply at screening will be excluded:
1. History of hemiplegic migraine (at any time in the past).
2. History of headaches of any type occurring on ≥15 days/month during any of the 3 months prior to screening.
3. If subject has coexisting history of tension-type headaches and migraine, inability to distinguish between tension-type headaches and migraine.
4. In the investigator's judgment, overuse of medication for migraine or other conditions, defined as use of any of the following in any of the 3 months prior to screening:
   a) Narcotics (opioids)≥5 days/month(Opioids are allowed as second-line treatment as long as they were used ≤5 days/month), or
   b) Sedative-hypnotic drugs, (e.g., benzodiazepines, barbiturates, sleeping aids, combination analgesic medications containing butalbital)≥8 days/month, or
   c) Triptans (e.g., sumatriptan, naratriptan, almotriptan, etc.) or ergotamine≥8 days/month, or
   d) Simple analgesics (e.g., aspirin, NSAIDs, acetaminophen, caffeinated analgesic combinations)≥12 days/month (Occasional use of topical products without significant systemic absorption is permitted.)
   e) Anti-emetics, diphenhydramine≥10 days/month.
   f) Gepants: calcitonin gene-related peptide (CGRP) receptor antagonists (e.g., ubrogepant, rimegepant) ≥10 days/month.
   g) Ditans (lasmiditan)≥10 days/month.
   h) Herbal supplements and natural health products used for acute treatment of migraine≥10 days/month.
5. History of any of the following:
   a) Clinically significant history of endocrine, cardiovascular, pulmonary, hematologic, immunologic, gastrointestinal, renal, hepatic, or metabolic disease; or psychiatric conditions, major depression, dementia, or significant neurological disorders other than migraine that in the investigator's judgment would interfere with the study, or
   b) Active malignancy of any type or a history of malignancy within the last 5 years (except basal cell carcinoma of the skin that has been excised at least 12 weeks prior to study start), or
   c) Major surgery within 6 months prior to screening, unless the investigator deems the subject eligible (minor surgery performed 4 or more weeks prior to screening would not be a reason for exclusion), or
   d) Pain syndrome other than migraine that in the investigator's judgment would interfere with the study, or
   e) Diagnosis of sleep apnea, or
   f) Any other medical condition that, in the opinion of the investigator or the Sponsor, may be potentially associated with an increased risk to the subject from study drug or to participation in the study.
6. Positive serologic test for hepatitis B, hepatitis C, or HIV at screening. (Reflex HCV RNA testing will be performed for any positive hepatitis C screening test. If the results of reflex testing are negative, the subject may be deemed eligible for the study.)
7. Subjects who have any of the following at screening:
   a) Clinically significant abnormality at physical examination (in the judgment of the investigator), or
   b) Clinically significant ECG abnormalities (in the judgment of the investigator), or
   c) Vital sign abnormalities (systolic blood pressure [BP]≤90 mmHg or ≥145 mmHg, diastolic blood pressure≤55 mmHg or ≥95 mmHg, or heart rate [HR]≤50 bpm or ≥110 bpm), or
   d) Oxygen saturation by oximetry (SpO$_2$)≤93%, or
   e) Hemoglobin≤135 g/L for men or ≤120 g/L for women
   f) Clinically significant abnormal laboratory test results (out of the study laboratory's acceptable range, unless out-of-range values are deemed by the investigator to be not clinically significant).
8. Subjects with a history of any of the following:
   a) Significant alcohol abuse within 1 year prior to screening or regular use of alcohol within 6 months prior to screening (more than 14 units of alcohol per week [1 unit=150 mL of wine, 360 mL of beer, or 45 mL of 40% alcohol]), or
   b) Significant drug abuse or use of cocaine, phencyclidine [PCP], crack, opioid derivatives including heroin, or amphetamine derivatives, or similar drugs within 1 year prior to screening, or significant use of marijuana or tetrahydrocannabinol [THC]-containing products that in the investigator's judgment is medically significant in that it would impact the safety of the subject or the interpretation of the study results.
   c) Use of tobacco or nicotine products within 3 months prior to screening.
9. Subjects who have any of the following at screening:
   a) A positive alcohol breath test or
   b) A positive urine drug screen (unless consistent with an ongoing prescription drug as documented by the investigator) (Note that detectable levels of marijuana (THC or metabolites) in the urine drug screen are not exclusionary if in the investigator's documented opinion the positive test does not signal a clinical condition that would impact the safety of the subject or interpretation of the study results) or
   c) A positive urine cotinine test
10. Women who are pregnant (have a positive urine pregnancy test at screening) or who are lactating
11. Subjects who have a history of severe allergic reactions (e.g., anaphylactic reactions, angioedema), hypersensitivity, or idiosyncratic reaction to fospropofol, propofol, or related substances.
12. Subjects who have participated in an interventional clinical research study involving:
    a) Administration of an investigational or marketed drug or device within 30 days prior to closing with fospropofol disodium, or
    b) Administration of a biological product in the context of a clinical research study within 90 days prior to closing with fospropofol disodium
    (Concomitant participation in an investigational study involving no drug or device administration is permitted, provided obligations associated with the concomitant participation are not expected to interfere with procedures and obligations of the present study.)
13. Subjects who have intolerance to and/or difficulty with blood sampling through venipuncture
14. Employees or immediate families (defined as spouse, significant-other, parent, child, or sibling, whether adopted or biologic) of an employee of Epalex Corporation, its affiliates, or partners; investigator or study center personnel directly affiliated with this study and/or their immediate families.
15. Subjects who have a condition or are in a situation that in the investigator's opinion may put the subject at significant risk, may confound the study results, or may interfere significantly with the subject's participation in the study.
16. Score of >0 on the Sheehan Suicidality Tracking Scale (S-STS) for a recall period of 30 days prior to screening.

Eligibility for Dosing: Qualifying Headache To qualify for treatment with study drug, the presenting headache must meet the following criteria:
  1. Headache onset (assessed at phone call notifying clinic staff of headache onset)
   a) Subject was free of migraine symptoms for at least 48 hours before the start of symptoms of the migraine headache to be treated (and did not take medications for the acute treatment of migraine during this period).
   b) Time between onset of the symptoms of the migraine headache to be treated and estimated time of treatment must be less than 4 hours.
  2. At clinic check-in
   a) Time between onset of the symptoms of the migraine headache to be treated and actual time treatment must be less than 4 hours.
   b) Moderate or severe pain intensity (2 or 3 on a 4-point Likert scale where 0=none, 1=mild, 2=moderate, 3=severe).
   c) Has at least 1 of the following characteristics: unilateral location, throbbing (pulsating), or aggravated by routine physical activity.
   d) Associated with at least 1 of the following symptoms: nausea/vomiting, photophobia, or phonophobia.
  3. Within 10 minutes before closing
   a) Moderate or severe pain intensity (2 or 3 on a 4-point Likert scale where 0=none, 1=mild, 2=moderate, 3=severe).
   b) Presence of at least 1 symptom (nausea/vomiting, photophobia, or phonophobia).

Eligibility for Dosing: Post-Restrictions The following restrictions specific to the period after enrollment must be met for treatment of a migraine with enrollment Study fospropofol disodium to occur.
Medications Permitted with Restrictions
If the subject experiences a migraine headache where study treatment is not feasible or practicable, the following medications for acute migraine treatment are allowed after enrollment, as agreed with the investigator at screening, provided the following restrictions to prevent overuse are met and provided the subject has not taken them within 48 hours prior to clinic check-in (see Point 3 under Restricted and prohibited substances or products below):
  1. Narcotics (opioids) as second-line treatment only: No more than 4 days/month or in the 30 days prior to closing.
  2. Sedative-hypnotic drugs, (e.g., benzodiazepines, barbiturates, sleeping aids, combination drugs containing butalbital):No more than 7 days/month or in the 30 days prior to closing.
  3. Triptans (e.g., sumatriptan, naratriptan, almotriptan, etc.) or ergotamine: No more than 7 days/month or in the 30 days prior to closing.
  4. Analgesics, alone or in a combination product (e.g., aspirin, NSAIDs, acetaminophen, caffeinated analgesic combinations): No more than 11 days/month or in the 30 days prior to closing.
  5. Anti-emetics, diphenhydramine. No more than 9 days/month or in the 30 days prior to closing.
  6. Gepants: CGRP receptor antagonists (e.g., ubrogepant, rimegepant). No more than 9 days/month or in the 30 days prior to closing.
  7. Ditans: lasmiditan. No more than 9 days/month or in the 30 days prior to closing.
  8. Herbal supplements and natural health products used for acute treatment of migraine. No more than 9 days/month or in the 30 days prior to closing.

Restricted and prohibited substances or products
  1. Alcohol-based products are to be restricted as follows:
   a) No more than 14 units of alcohol per week [1 unit=150 mL of wine, 360 mL of beer, or 45 mL of 40% alcohol])
   b) Fospropofol disodium closing is not to be performed if subject consumed alcohol within 24 hours prior to clinic check-in (Alcohol breath test must be negative at check-in)
  2. The following products are not permitted at any time during study participation (from enrollment until after study completion [after the Day 3 telephone call]):
   a) Cocaine, phencyclidine [PCP], crack, opioid derivatives including heroin, amphetamine derivatives, or similar drugs, and marijuana or tetrahydrocannabinol [THC]-containing products. Urine drug screen must be negative at check-in. (Foods containing poppy seeds should be avoided during study participation because they may interfere with results of the urine drug screen.) Note that detectable levels of marijuana (THC or metabolites) in the urine drug screen at check-in are not exclusionary for closing if in the investigator's documented opinion the positive test does not signal a clinical condition that would impact the safety of the subject or interpretation of the study results and documents that the subject affirms that they have not used any marijuana or THC-containing product within the 48 hours prior to the onset of migraine symptoms
   b) Any tobacco or nicotine products (Urine cotinine test must be negative at check-in.)
  3. Fospropofol disodium closing is not to be performed if the subject has taken any of these medications within 48 hours prior to clinic check-in:
   a) Narcotics (opioids), sedative-hypnotic drugs, (e.g., benzodiazepines, barbiturates, sleeping aids, combination drugs containing butalbital).
   b) Triptans (e.g., sumatriptan, naratriptan, almotriptan, etc.) or ergotamine.
   c) Analgesics, alone or in a combination product (e.g., aspirin, NSAIDs, or acetaminophen).

d) Anti-emetics, diphenhydramine.
e) Gepants: CGRP receptor antagonists (e.g., ubrogepant, rimegepant).
f) Ditans: lasmiditan.
g) Herbal supplements and natural health products used to treat migraine.
h) Marijuana or THC-containing products Other Restrictions Dosing is not to be performed if any of the following conditions apply.
1. Events within 30 days prior to clinic check-in:
a) Significant illness or any surgical procedure
b) Subject donated plasma or blood
2. Any vaccination (e.g., COVID-19 vaccination, influenza) within 10 days prior to clinic check-in.
3. Tension-type headaches occurring on ≥15 days in any month since enrollment.
4. Clinically significant abnormalities at physical examination or in ECG, vital signs, $SpO_2$, hemoglobin, or other laboratory results (as defined under Exclusion Criteria for screening, Point 7). At clinic check-in, elevations in BP and/or pulse attributable to headache pain or other migraine symptoms may be accepted according to the investigator's judgment.
5. Positive urine pregnancy test at clinic check-in.
6. Abnormal diet patterns (for any reason) during the 4 weeks preceding clinic check-in, including fasting, high protein diets etc.
7. Subject has a response on the S-STS greater than zero to any question other than Question 2 and a response greater than 1 on Question 2. (Subjects with a response of 1 to Question 2 will be discontinued at the discretion of the investigator.)
8. Conditions or situations arising since clinic enrollment that in the investigator's opinion, may put the subject at significant risk or may confound the study results.

Permitted Throughout the Study
1. Standard migraine prophylactic medications and other medications with a prophylactic effect on migraines are permitted as prescribed, provided that no changes in close are made during the study. Prophylactic medications may not be started during the study.
2. Hormonal contraception and routine use of over-the-counter (OTC) multivitamins for general health are permitted throughout the study.
3. Other prescription medications and OTC medicines are permitted if medically necessary as agreed with the investigator on a case-by-case basis at screening.
4. Herbal supplements and health products are permitted if agreed with the investigator on a case-by-case basis at screening.

In-Clinic Rescue Medicine Rescue medicine may be administered in the clinic at the discretion of the investigator at any time after fospropofol disodium closing if additional medication for acute treatment of migraine pain is necessary. However, investigators and subjects will be encouraged to avoid administration of rescue medication earlier than 2 hours after fospropofol disodium closing.
In general, the investigator and subject will agree at screening on the appropriate rescue therapy for the subject. Subjects must supply their own rescue medication at clinic check-in.
Selection of in-clinic rescue medication for each subject may be guided by treatment that was effective for the subject in the past. First-line rescue therapy may include an analgesic and/or acute migraine medication and will not include narcotics. If necessary, a second-line rescue therapy may be agreed upon at the investigator's discretion.
The following products may be agreed upon between subject and investigator at screening to be used as rescue medication if required in the clinic after closing with fospropofol disodium:
1. Analgesics, alone or in a combination product, including acetaminophen, aspirin, or NSAIDs.
2. Triptans (e.g., sumatriptan, naratriptan, almotriptan).
3. Gepants (CGRP antagonists, e.g., ubrogepant, rimegepant).
4. Ditans (lasmiditan).
Because of the potential for additive cardiorespiratory effects when narcotic analgesics and sedative-hypnotic agents (e.g., opiates, benzodiazepines, barbiturates, sleeping aids, combination drugs containing butalbital) are administered concomitantly with fospropofol disodium, these medications are not recommended as rescue therapy after fospropofol disodium closing. Prescription anti-emetics, including metoclopramide, prochlorperazine, chlorpromazine, as well as OTC drugs sometimes helpful for nausea, such as dimenhydrate, meclizine, and diphenhydramine, are associated with sedation and should be avoided as rescue treatment until at least 4 hours after treatment with fospropofol disodium.

Study Drug and Dosage Form Fospropofol disodium is formulated for oral administration in an appropriate number of powder-filled hydroxypropyl methylcellulose (HPMC) capsules. Each HPMC capsule contains 200 mg of fospropofol disodium (uncorrected for sodium content) and no inactive ingredients. It is possible that capsules containing smaller amounts of fospropofol disodium (i.e., 100 mg) may also be used.

Dose Level/Dose Adjustment Initially, all subjects will receive 1 oral dose of 800 mg of fospropofol disodium. After completion of 10 subjects, and depending on tolerability and PK results, the close may be modified for the remaining subjects, for example by reducing the dose for all subjects or for a subset of subjects with low body weight or by increasing the dose for all subjects or for a subset of subjects with high body weight. Any upward close adjustment (for all or for a subset of subjects) will require unanimous approval by the Safety Committee. A divided close may also be considered, for example in which the close would be divided into 2 administrations separated in time during the same study visit. It is also possible that the Sponsor at its initiative, or if recommended by the Safety Committee, may reduce the close at any time during the study.

Administration of Study Drug Dosing must occur within 4 hours after onset of migraine symptoms.
The study drug will be administered with water at ambient temperature in the amount of approximately 240 mL [8 oz]. Except for water administered with the study drug, fluids will not be permitted from closing until 1 hour after closing (see Study Restrictions). Fluids will be permitted ad lib thereafter.
As a safety precaution, subjects will be required to remain seated or semi-reclined for 15 minutes before and for 4 hours after administration of study drug. During the 4 hours after closing, subjects may ambulate to the restroom at the discretion of the investigator but must be accompanied by study staff while walking to and from the restroom.

Subjects will be permitted to sleep ad lib (in a semi-reclined position) after administration of study drug but are to be awakened for the assessments of headache pain and associated migraine symptoms at 1, 2, and 4 hours after closing.

Screening Procedures Screening procedures will comprise written informed consent and review of inclusion/exclusion criteria, including demographic data; body measurements (height, weight); medical and migraine history; medication history (including drug allergies); 12-lead ECG; pulse oximetry; vital signs (BP, HR, RR, temperature), safety laboratory assessments (hematology, blood chemistry, HIV, hepatitis B and C tests, urinalysis, urine drug screen, alcohol breath test, urine cotinine test, urine pregnancy test for women); complete physical examination, and the Sheehan Suicidality Tracking Scale.

Migraine history will be obtained by subject interview and will include age of onset and time since first attack; estimated frequency of migraine episodes during the prior 3 months, including frequency of episodes classified as moderate or severe; history of migraine-associated symptoms (nausea/vomiting, photophobia, phonophobia, or other symptoms); most bothersome symptom (nausea/vomiting, photophobia, or phonophobia); characteristic features of episodes (unilateral vs bilateral location, pulsating quality, pain intensity, aggravation by or causing avoidance of routine physical activity); presence and features of aura, if any; and history of headache types other than migraine and subject's ability to distinguish between migraine and tension-type headaches.

A virtual (online) interview will be conducted with the subject by a specialist in headache medicine to confirm the migraine diagnosis according to ICHD-3 criteria. See Headache Classification Committee of the International Headache Society (IHS). The International Classification of Headache Disorders, 3rd edition. Cephalalgia 2018; 38:1-211.

Medication history will be obtained by interview and will include history of migraine-related medications during the 3 months prior to screening. Migraine-related medications include medications (if any) used for first- and/or second-line treatment of acute migraine and medications used for migraine prophylaxis or that have prophylactic effect on migraine. History of other medications will be recorded for the 30 days prior to screening.

Medications expected to be used during the course of study will be reviewed, recorded, and approved at screening by the investigator (consultation with Sponsor will be available as needed). Such medications include migraine medicine to be used if treatment at the study site is not feasible within 4 hours after symptom onset (see Post-enrollment Period below).

The investigator and subject are to agree at screening on an appropriate rescue medication to be used if needed in clinic after fospropofol disodium closing (see Rescue Medication).

Subjects who give written informed consent and meet inclusion/exclusion criteria will be enrolled in the study. Enrolled subjects will receive instructions regarding identification of a qualifying headache as well as restrictions and procedures for the post-enrollment period.

Post-enrollment Period Enrolled subjects will be asked to come to the study site for treatment with study drug as soon as possible when they experience migraine symptoms, as closing must occur within 4 hours after symptom onset. If treatment at the study site is not feasible or practicable within 4 hours after the onset of migraine symptoms, subjects should use their usual headache medication as agreed at screening and within the parameters noted in the post-enrollment restrictions. This situation may arise, for example, if the onset of symptoms occurs outside of study site hours, or if family or work circumstances make it impracticable for the subject to reach the site for treatment within the 4-hour time frame. In such cases, the subject should attempt to visit the clinic for treatment as soon as possible (within 4 hours) after onset of their next migraine headache.

Clinic admission for treatment of a qualifying headache is to occur within 60 days after enrollment. Clinic staff are to remain in contact with subjects as needed to address any barriers that may prevent subjects from presenting for treatment.

If an enrolled subject is not treated with fospropofol disodium for a qualifying headache within 60 days after enrollment, this situation is to be classified as "failure to close." If possible, reasons for failure to close within 60 days should be ascertained and recorded using the following checklist of potential issues: lack of moderate to severe headaches, work circumstances, family circumstances, lack of adherence to post-enrollment restrictions, or other reasons.

Headache Onset Because closing must be performed within 4 hours after the onset of migraine symptoms, subjects will be instructed to notify staff by calling the study site as soon as possible when migraine symptoms start.

A comprehensive review of eligibility for closing will be performed only at clinic check-in. However, preliminary eligibility for fospropofol disodium closing should be determined during the call to prevent an unnecessary trip to the clinic. Therefore, subjects will be asked about the start time of the migraine symptoms, whether they had migraine symptoms during the 2 days before onset of this migraine, whether they took medications or products that are prohibited during the 48 hours before treatment, and whether they had any recent medical events that might affect study participation.

Subjects who do not meet the preliminary eligibility criteria for closing for the current headache are to be instructed to take their usual headache medicine and to call again as soon as possible after onset of their next migraine headache.

Clinic Check-in The study staff is to perform the following procedures at clinic check-in:
1. Take custody of agreed rescue medication.
2. Assess the presenting headache and associated symptoms
3. Perform safety assessments:
a) 12-lead ECG.
b) Pulse oximetry and vital signs.
c) Safety laboratory assessments, including urine drug, cotinine, and pregnancy tests and alcohol breath test.
d) Abbreviated physical examination.

e) Sheehan Suicidality Tracking Scale (recall period since screening)
4. Record subject's recollection of medications taken since screening on concomitant medication log.
5. Record time and nature of last meal or food intake, including beverages.
6. Review adherence to post-enrollment study restrictions.
7. Assess qualifying headache and associated symptoms within 10 minutes prior to closing.

Confinement in Clinic Subjects will be confined to the study site for approximately 5 hours after closing of the study drug. The duration of confinement may be extended for safety reasons at the discretion of the investigator.

Clinic Check-out and Early Termination The following procedures will be carried out at clinic check-out or for early termination (when applicable): safety laboratory assessments (hematology, blood chemistry, urinalysis, serum pregnancy test), vital signs (BP, HR, RR, temperature), pulse oximetry, 12-lead ECG, headache assessment, abbreviated physical examination, adverse events (AEs).

Transportation from the clinic to the subject's home will be arranged, and subjects will be instructed not to drive or operate heavy machinery for 24 hours after closing. Subjects will be instructed that, if they have a persistent headache or a new headache after discharge, they are permitted to take their usual medication, as long as it is in accordance with post-enrollment study restrictions, and that they will be asked during the follow-up telephone interviews about persistence or recurrence of headache pain and symptoms and whether they took medication and when.

Arrangements for the follow-up telephone interviews will be made.

Follow-up Telephone Interviews Follow-up telephone interviews will be scheduled on Day 2 (between 24 and 32 hours after closing) and on Day 3 (between 48 and 56 hours after closing) for subjects to report and grade any ongoing migraine headache pain, ongoing migraine-associated symptoms (present/absent), recurrence or worsening of pain or migraine-associated symptoms, medication taken, and occurrence of any AEs since clinic discharge.

PK Sampling A total of 7 blood samples of 6 mL each will be collected for analysis of fospropofol and propofol PK. The PK samples will be collected at the following time points: preclose (within 120 minutes before closing) and postclose at 10, 20, and 40 minutes and 1, 2, and 4 hours after closing.

In case of a serious adverse event (SAE) or early withdrawal, a PK blood draw should be performed if possible, at or near the time the subject reports the SAE or at the time of withdrawal from the study.

Safety Procedures and Assessments Medical Surveillance and AE Monitoring

Safety data will be evaluated on an ongoing basis by the Safety Review Committee to ensure it is safe to continue study enrollment and treatment.

The investigator is to be on site from approximately 30 minutes prior to each closing until clinic discharge and available on call until the second follow-up telephone interview has been completed.

The study site is to be staffed to assess and manage potential risks that may occur with sedative-hypnotic agents. Subjects are to be continuously monitored for oxygen desaturation using a pulse oximeter with an alarm, and supplemental oxygen should be available. In addition, although these conditions are unlikely to occur at the selected dose of fospropofol disodium, subjects should be monitored for early signs of hypotension, apnea, or airway obstruction from approximately 30 minutes prior to closing of study drug until clinic discharge. This role may be fulfilled by the investigator or designee trained in airway management.

Safety parameters, including laboratory results and ECG, will be evaluated by the investigator in the context of clinical trial safety. Any abnormal measurement is to be repeated if judged necessary by the investigator. Further action to ensure subject safety may be taken at the investigator's discretion. A board-certified cardiology specialist will be available for consultation if an ECG concern should arise in the course of the study.

12-Lead ECG
A 12-lead ECG will be performed at screening, clinic check-in and clinic check-out.

Sleep Status
Subjects will be permitted to sleep ad lib (in a semi-reclined position) after administration of study drug but are to be awakened for the assessments of headache pain and associated migraine symptoms at 1, 2, and 4 hours after closing.

The subject's sleep status will be recorded after closing at 15-minute intervals through hour 4 (assessed as "appears to be sleeping" or "appears to be awake").

Pulse Oximetry
Pulse oximetry will be recorded at screening and continuously monitored on Day 1 from at least 15 minutes prior to closing until discharge from the clinic. The pulse oximeter is to have an alarm set to give both audible and visual notifications when $SPO_2$ drops to 90% or below. If the alarm signals, the subject should be aroused. Nasal oxygen should be considered if SpO2 remains at 90% or lower after stimulation.

$SPO_2$ values will be recorded from the continuous monitor at approximately the same time points as the sleep status assessments (15-minute intervals).

Vital Signs
BP, HR, and RR will be recorded at screening, on Day 1 within 60 minutes before closing, postclose at 30-minute intervals until 4 hours after closing, and at clinic check-out. Temperature will be recorded at screening, on Day 1 within 60 minutes before closing, and at clinic check-out. If vital sign measurement times coincide with blood collection for laboratory tests, vital signs are to be taken within 5 minutes before the blood draw.

BP, HR, RR, temperature, and pulse oximetry will be recorded with the subject in a seated or semi-reclined position. At clinic check-in, elevations in BP or HR attributable to headache pain or other migraine symptoms may be accepted according to the investigator's judgment.

MOAA/S Score
Level of sedation will be assessed using the Modified Observer's Assessment of Alertness/Sedation (MOAA/S) score at 4 hours after closing. If the MOAA/S score is below 5 at 4 hours after closing, and/or there is reason for concern, the duration of confinement may be extended, and safety monitoring may continue at the discretion of the investigator. Cohen LB. Clinical trial: a close-response study of fospropofol disodium for moderate sedation during colonoscopy. Aliment Pharmacol Ther 2008; 27:597-608. Chernik D A, Gillings D, Laine H, et al. Validity and reliability of the Observer's Assessment of Alertness/Sedation Scale: study with intravenous midazolam. J Clin Psychopharmacol 1990; 10:244-251.

Safety Laboratory Assessments

Hematology, serum chemistry, and urinalysis will be assessed at screening, at clinic check-in, and at clinic check-out.

Serologic tests for hepatitis B, hepatitis C, and HIV will be performed at screening.

A urine drug screen, urine cotinine test, and alcohol breath test will be performed at screening and clinic check-in.

For women, a urine pregnancy test will be performed at screening and at clinic check-in. A serum pregnancy test will be performed at clinic check-out for confirmation.

Physical Examination

A complete physical examination will be performed at screening and abbreviated physical examinations will be performed at clinic check-in and check-out.

Sheehan Suicidality Tracking Scale

The Sheehan Suicidality Tracking Scale will be administered at the screening visit, at clinic check-in, and at the Day 3 telephone interview.

Total Blood Volume Drawn Total blood volume drawn per subject will not exceed a maximum of 200 mL, including screening, PK, and safety assessments.

Measures of Clinical Course (Exploratory) Headache pain and associated migraine symptoms (nausea/vomiting, photophobia, and phonophobia) will be recorded as migraine-related events. Headache pain will be rated on a 4-point Likert scale (0=none, 1=mild, 2=moderate, 3=severe). Associated migraine symptoms (nausea/vomiting, photophobia, and phonophobia) will be classified as either present or absent.

Subjects will be asked to respond to questions regarding headache pain and associated symptoms at clinic check-in, within 10 minutes before closing (baseline), at 1, 2, and 4 hours after closing, at clinic check-out, and by telephone interview on Day 2 and Day 3.

Adverse Events Subjects will be instructed to inform clinical personnel of any potential AEs, i.e., untoward medical symptoms and/or events that may arise from arrival at the clinic for check-in until the final follow-up telephone interview.

Treatment-emergent adverse events (TEAEs) are defined as the reported AEs that first occurred or worsened after administration of the study drug. The incidence, seriousness, severity, duration, and relation to study drug of all TEAEs will be recorded.

Some degree of sedation is an expected and potentially therapeutic effect of the study drug. Although sedation, including events described as feeling "drowsy," "sleepy," "relaxed," etc., will be expected, such terms if expressed by the subject will be recorded as AEs, and severity will be rated by the site investigator as mild, moderate, or severe. Because subjects will be encouraged to sleep after closing if desired, sleep itself will not be considered an AE.

Worsening or recurrence of migraine pain or related migraine symptoms (nausea/vomiting, photophobia, phonophobia) during the clinic visit or after discharge through the Day 3 follow-up interview will be recorded as migraine-related events and will not be recorded as AEs.

Analytical Method Fospropofol and propofol concentrations will be analyzed in plasma samples using a validated method.

Statistical Considerations Safety and Tolerability

Safety and tolerability data will be reported using descriptive statistics. Summary statistics for TEAEs will be reported. Changes from baseline values in vital signs, ECG, and clinical laboratory parameters will be reported.

PK

Interim bioanalysis and PK analyses for fospropofol and propofol are to be performed after approximately 10 subjects have been completed, again after approximately 30 subjects are completed, and may be performed at other intervals as well.

Summary statistics will be used to describe the PK profile of both fospropofol and propofol. Summary statistics will include at minimum arithmetic and geometric means for $AUC_{0-t}$, $AUC_{0-inf}$, and $C_{max}$. $T_{max}$ will be characterized by median and range.

Exploratory Analyses

Clinical Course

Summary statistics of the subject's assessment of headache pain (on the Likert scale) at 1, 2, and 4 hours postclose, at clinic discharge, and at follow-up on Days 1 and 2 will be reported.

Summary statistics of headache recurrence or worsening will also be reported.

Summary statistics of the subject's assessment of the most bothersome symptom (presence or absent) at 1, 2, and 4 hours postclose, and at clinic discharge will be reported. Summary statistics of recurrence or worsening of the most bothersome symptom will also be reported.

Summary statistics of the subject's assessment of migraine-associated symptoms other than the most bothersome symptom as applicable (presence or absent) at 1, 2, and 4 hours postclose, and at clinic discharge will be reported. Summary statistics of recurrence or worsening migraine-associated symptoms will also be reported.

Summary statistics will be reported, including but not limited to (1) proportion of subjects reporting no headache pain at 2 hours; (2) proportion of subjects reporting the absence of most bothersome symptom at 2 hours; and (3) proportion of subjects reporting improvement in pain (change from severe/moderate to mild/absent) at 2 hours. All analyses will be exploratory.

Influence of Covariates; PK-PD Relationships

Exploratory analyses will be performed in an effort to characterize the influence of covariates on PK (e.g., relationship between plasma propofol concentrations and gender, age, weight, and BMI) and to characterize PK-PD relationships (e.g., relationship between plasma propofol concentrations and AEs).

Exploratory analyses in an effort to characterize the relationship between plasma propofol concentration (e.g., $C_{max}$ and or partial AUC) and the clinical course of migraine symptoms will also be performed. Details are to be described in the SAP.

Additional statistical analysis may be performed. All analyses will be descriptive or exploratory and not intended to test any specific hypothesis.

Study Assessments

A total of 7 blood samples of 6 mL each will be collected for analysis of fospropofol and propofol PK. The PK samples will be collected at the following time points: preclose (within 120 minutes before closing) and postclose at 10, 20, and 40 minutes and 1, 2, and 4 hours after closing.

The time tolerance window for blood samples collected during the confinement period will be ±1 minute for all samples. Sample collections done outside the predefined time windows will not be considered as protocol deviations since actual postclose sampling times will be used for PK and statistical analyses.

When appropriate, an indwelling i.v. catheter will be used for blood collection to avoid multiple skin punctures. Otherwise, blood samples will be collectedly direct venipuncture.

In case of an SAE or early withdrawal, a PK blood draw should be performed if possible, at or near the time the subject reports the SAE or at the time of withdrawal from the study.

Blood samples for safety laboratory assessments will be drawn at screening, clinic check-in, and clinic discharge.

The total blood volume drawn per subject will not exceed a maximum of 200 mL, including screening.

Safety Procedures and Assessments

Medical Surveillance and AE Monitoring

A 12-lead ECG will be performed at screening, at clinic check-in (within 120 minutes before closing) and at clinic check-out. Corrected QT interval (QTc) will be recorded.

Subjects will be permitted to sleep ad lib (in a semi-reclined position) after administration of study drug but are to be awakened for the assessments of headache pain and associated migraine symptoms at 1, 2, and 4 hours after closing.

The subject's sleep status will be recorded after closing at 15-minute intervals through hour 4 (assessed as "appears to be sleeping" or "appears to be awake").

Pulse oximetry will be recorded at screening and continuously monitored on Day 1 from at least 15 minutes prior to closing until discharge from the clinic. The pulse oximeter is to have an alarm set to give both audible and visual notifications when SpO2 drops to 90% or below. If the alarm signals, the subject should be aroused. Nasal oxygen should be considered if SpO2 remains at 90% or lower after stimulation.

SpO2 values will be recorded from the continuous monitor within 15 minutes before closing, postclose at approximately the same time points as the sleep status assessments (15-minute intervals), and at clinic check-out, with the subject seated or semi-reclined.

Systolic and diastolic BP (mmHg), HR, and RR will be recorded at screening, on Day 1 within 60 minutes before closing, at 30-minute intervals until 4 hours after closing, and at clinic check-out ( ). For consistency with time points where they should be performed before PK blood draws, these assessments should take place within 10 minutes before each designated time point. Temperature (as degrees Fahrenheit) will be recorded at screening, on Day 1 within 60 minutes before closing, and at clinic check-out.

BP, HR, and RR are to be assessed with the subject having been in a seated or semi-reclined position for at least 5 minutes. At clinic check-in, elevations of BP or HR attributable to headache pain or other migraine symptoms may be accepted according to the investigator's judgment.

Level of sedation will be assessed using the MOAA/S score at 4 hours after closing (within 10 minutes before the 4-hour PK blood draw). Cohen LB. Clinical trial: a close-response study of fospropofol disodium for moderate sedation during colonoscopy. Aliment Pharmacol Ther 2008; 27:597-608. Chernik D A, Gillings D, Laine H, et al. Validity and reliability of the Observer's Assessment of Alertness/Sedation Scale: study with intravenous midazolam. J Clin Psychopharmacol 1990; 10:244-251.

If the MOAA/S score is below 5 at 4 hours after closing and/or there is reason for concern, the duration of confinement may be extended, and safety monitoring may continue at the discretion of the investigator.

Safety Laboratory Assessments

Hematology

Hematology samples will be drawn at screening, clinic check-in, and clinic check-out. Hematology will include complete blood count with differential, hemoglobin, and hematocrit.

Serum Chemistry

Serum chemistry samples will be drawn at screening, clinic check-in, and clinic check-out. Serum chemistry assessments will include albumin, alanine aminotransferase, alkaline phosphatase, aspartate aminotransferase, calcium, chloride, carbon dioxide/bicarbonate, creatinine, glucose, phosphate, potassium, sodium, total bilirubin, total protein, and blood urea nitrogen (BUN).

Serology

Hepatitis B (HBs Ag), Hepatitis C (HCV) antibody, and HIV antigen and antibody detection will be performed at screening. (Reflex HCV RNA testing will be performed for any positive hepatitis C screening test. If the results of reflex testing are negative, the subject may be deemed eligible for the study.)

Urinalysis

Urine for urinalysis will be collected at screening, clinic check-in, and clinic check-out. Urinalysis will include macroscopic examination, pH, specific gravity, protein, glucose, ketones, bilirubin, occult blood, nitrite, urobilinogen, and leukocytes. Unless otherwise specified, microscopic examination will be performed on abnormal findings according to standard procedure.

Drug, Cotinine, and Alcohol

A urine drug screen (amphetamines, methamphetamines, barbiturates, benzodiazepines, THC, cocaine, opiates, PCP, 3,4-methylenedioxy-methamphetamine (MDMA), methadone), a urine cotinine test, and an alcohol breath test will be performed at screening and at clinic check-in.

Pregnancy Tests

For women, a urine pregnancy test will be performed at screening and at clinic check-in. A serum pregnancy test will be performed at clinic check-out for confirmation.

Physical Examination

A complete physical examination will be performed at screening, and abbreviated physical examinations will be performed at clinic check-in and check-out.

The complete physical examination at the screening visit will assess any physical abnormalities and will include at a minimum, assessments of the following body systems: general appearance, overall status of the head, ears, eyes, nose, throat (HEENT), neck, abdomen, lymph nodes, skin, cardiovascular/heart, pulmonary, musculoskeletal, and neurological (level of alertness [more detailed mental status not required unless indicated], speech, cranial nerves, motor strength and tone, cerebellar, sensory, deep tendon reflexes, and gait). Investigators should pay special attention to clinical signs related to previous serious illnesses.

Height and weight will also be measured and recorded at the screening visit.

The abbreviated physical examination at check-in and check-out will assess general appearance, HEENT, cardiovascular, pulmonary, and neurological status. The neurological examination is to consist of level of alertness and speech. Abbreviated physical examinations may be limited to recording change/no change from prior examinations, plus focused examination by system as directed by any AEs reported by the subject (where applicable) or any spontaneous symptom/complaint reported by the subject at the time of the examination.

Sheehan Suicidality Tracking Scale

The Sheehan Suicidality Tracking Scale (S-STS) is a prospective suicidality rating scale to be completed by the investigator or his/her designate. The scale includes 16 questions that allow a longitudinal evaluation of treatment-emergent suicidal ideation and treatment-emergent suicidal behaviors. Sheehan D V, Alphs L D, Mao L, et al. Comparative Validation of the S-STS, the ISST-Plus, and the C-SSRS for Assessing the Suicidal Thinking and Behavior FDA 2012 Suicidality Categories. Innov Clin Neurosci 2014; 11:32-46. Sheehan D V, Giddens J M, Sheehan I S. Status Update on the Sheehan-Suicidality Tracking Scale (S-STS) 2014. Innov Clin Neurosci 2014; 11:93-140.

The S-STS will be completed on a paper form at the site and will be administered at the screening visit, at clinic check-in, and at the Day 3 follow-up telephone interview. The recall period at the screening administration will encompass the time period beginning 30 days prior to the screening visit; the recall period at clinic check-in will be the time period since the screening visit; the recall period for completing the S-STS at the Day 3 telephone interview will be the time period since clinic check-in. The total score plus the subject's response to each item will be recorded.

For each administration of the S-STS, the investigator will immediately evaluate a subject with any response greater than zero to determine if that subject is at risk of self-harm or suicide. If this is the case, the investigator must take appropriate measures to ensure the subject's safety and arrange for an appropriate mental health evaluation.

Any subject with a response greater than zero to any question at screening must be excluded.

At clinic check-in, any subject with a response greater than zero to any question other than Question 2 must be discontinued from the study and the event recorded as an AE, not treatment-emergent. Subjects with a response of 1 ("a little") to Question 2 will be discontinued at the discretion of the investigator. Subjects with a response greater than 1 on Question 2 will be discontinued.

In case of any response greater than zero at the Day 3 telephone interview, the investigator will immediately evaluate that subject to determine if that subject is at risk of self-harm or suicide. If this is the case the investigator will take appropriate measures to ensure the subject's safety and arrange for an appropriate mental health evaluation. The event will be recorded as a treatment-emergent AE and reported to Syneos Health Safety and Pharmacovigilance within 24 hours.

Measures of Clinical Course (Exploratory Evaluations)

Headache pain and associated migraine symptoms (nausea/vomiting, photophobia, and phonophobia) will be recorded as migraine-related events.

Headache pain will be rated on a 4-point Likert scale (0=none, 1=mild, 2=moderate, 3=severe). Associated migraine symptoms (nausea/vomiting, photophobia, and phonophobia) will be classified as either present or absent.

Migraine-related events observed during the clinic stay will be recorded starting at the (clock) time of the 10-minute preclose migraine evaluation and will be updated at the protocol-specified migraine assessment times (1 hour, 2 hours, 4 hours after closing, and at clinic check-out.

The course of any migraine-related events that are ongoing at clinic discharge will be followed up at the Day 2 (between 24 and 32 hours after closing) and Day 3 (between 48 and 56 hours after closing) telephone interviews. Any migraine-related event that is newly emergent after clinic discharge will be recorded and followed up until the Day 3 telephone interview. The time course of migraine-related events after discharge from the clinic will be based on the subject's best recollection of events as reported at the telephone interviews.

The assessment of migraine-related events during the clinic stay and at the follow-up telephone interviews should begin with a non-leading question (without specific prompting) such as, "How are you doing?" Any AEs reported by the subject should be recorded.

Structured interview questions are used for assessing headache pain and migraine-related symptoms at screening, headache onset, clinic check-in, within 10 minutes before closing, postclose, and at the follow-up telephone interviews Statistical Considerations Safety and Tolerability Safety and tolerability data will be reported using descriptive statistics. Summary statistics for TEAEs will be reported. Changes from baseline values in vital signs, ECG, and clinical laboratory parameters will be reported.

PK

Interim bioanalysis and PK analyses for fospropofol and propofol are to be performed after approximately 10 subjects have been completed, again after approximately 30 subjects are completed, and may be performed at other intervals as well.

Summary statistics will be used to describe the PK profile of both fospropofol and propofol. Summary statistics will include at minimum arithmetic and geometric means for AUC0-t, AUC0-inf, and Cmax. Tmax will be characterized by median and range.

Exploratory Analyses

Clinical Course

Summary statistics of the subject's assessment of headache pain (on the Likert scale) at clinic check-in, within 10 minutes preclose (baseline), 1, 2, and 4 hours postclose, at clinic discharge, and at follow-up on Days 2 and 3 will be reported. Summary statistics of headache recurrence or worsening will also be reported.

Summary statistics of the subject's assessment of the most bothersome symptom (presence or absence) at 1, 2, and 4 hours postclose, at clinic discharge, and at follow-up on Days 2 and 3 will be reported. Summary statistics of recurrence or worsening of the most bothersome symptom will also be reported.

Summary statistics of the subject's assessment of migraine-associated symptoms other than the most bothersome symptom as applicable (presence or absence) at 1, 2, and 4 hours postclose, at clinic discharge, and at follow-up on Days 2 and 3 will be reported. Summary statistics regarding recurrence or worsening of migraine-associated symptoms will also be reported.

Summary statistics reported will include but not be limited to (1) proportion of subjects reporting no headache pain at 2 hours; (2) proportion of subjects reporting the absence of most bothersome symptom at 2 hours; (3) proportion of subjects reporting improvement in pain (change from severe/moderate to mild/absent) at 2 hours; and (4) durability of responses over 24 and 48 hours regarding freedom from headache pain, absence of most bothersome symptom, and improvement in headache pain. All analyses will be exploratory.

Influence of Covariates; PK-PD Relationships

Exploratory analyses will be performed in an effort to characterize the influence of covariates on PK (e.g., relationship between plasma propofol concentrations and gender, age, weight, and BMI) and to characterize PK-PD relationships (e.g., relationship between plasma propofol concentrations and AEs). Exploratory analyses will also be performed in an effort to characterize the relationship between plasma propofol concentration (e.g., Cmax and or partial AUC) and the clinical course of migraine symptoms.

Analytical Methodology

Samples will be transported to the bioanalytical facility packed on sufficient dry ice to keep them frozen for at least 72 hours.

Fospropofol and propofol concentrations will be analyzed in plasma samples using a validated method.

The bioanalytical work in support to the study will be conducted in compliance with GCP using the SOPs in place in the bioanalytical laboratory of Syneos Health. Those SOPs were written in accordance with the current regulations and guidelines in place for industry, including guidances on Bioanalytical Method Validation, Good Laboratory Practice (GLP) for Nonclinical Laboratory Studies, and Good Clinical Practice (GCP) International Conference on Harmonisation (ICH) E6(R2). US Food and Drug Administration. Bioanalytical Method Validation: Guidance for Industry. 2018. Available at https://www.fda.gov/files/drugs/published/Bioanalytical-Method-Validation-Guidance-for-Industry.pdf. US 21 CFR Part 58. Good Laboratory Practice for Nonclinical Laboratory Studies. Available at https://www.ecfr.gov/cgi-bin/text-idx?SID=3be49f31878d0efa85f39ed3b84fcbel&mc=true&node=se21.1.58_11&rgn=div8. US Food and Drug Administration. E6(R2) Good Clinical Practice: IntegratedAddendum to ICH E6(R1) Guidance for Industry. 2018. Available at https://www.fda.gov/media/93884/download.

Data Handling

All clinical raw data will be recorded promptly, accurately, and legibly, either as e-source data or indelibly on paper. All raw data will be conserved in order to maintain data integrity. The investigator and/or the clinical staff have the responsibility of ensuring the completeness and accuracy of the clinical data.

All laboratory results provided by the biomedical laboratory will be stored in an information management system that is a validated Code of Federal Regulations (CFR) Part 11 compliant application.

Some of the tables below pertain to 12 subjects (N=12) and some pertain to 18 subjects (N=18). The subjects in the N=12 tables are subjects for whom pharmacokinetic data has been obtained. The subjects in the N=18 tables are subjects for whom clinical data has been obtained, and include the subjects of the N-12 tables.

TABLE 17-1

Study A17-Demographic Data

Table 17-1 Migraine Subject Characteristics (N = 12)

| Subject No. | Age | Sex | Height (cm) | Weight (kg) | BMI |
|---|---|---|---|---|---|
| 04-002 | 42.0 | F | 156.2 | 57.2 | 23.44 |
| 04-005 | 46.0 | F | 163.5 | 73.7 | 27.57 |
| 06-001 | 41.0 | F | 172.7 | 56.2 | 18.84 |
| 06-002 | 46.0 | F | 162.0 | 59.8 | 22.79 |
| 06-008 | 42.0 | M | 187.0 | 103.9 | 29.71 |
| 08-001 | 51.0 | F | 163.2 | 78.7 | 29.55 |
| 08-002 | 25.0 | F | 167.4 | 82.6 | 29.48 |
| 10-001 | 45.0 | F | 156.0 | 60.6 | 24.90 |
| 11-002 | 29.0 | F | 158.8 | 54.8 | 21.73 |
| 12-003 | 41.0 | F | 154.8 | 62.8 | 26.21 |
| 12-005 | 19.0 | F | 158.5 | 68.9 | 27.43 |
| 12-008 | 23.0 | F | 164.6 | 57.3 | 21.15 |

TABLE 17-1A

Summary of Demographic Characteristics of Subjects Treated

| | N = 18 |
|---|---|
| Age (years) | |
| n | 18 |
| Mean (SD) | 38.7 (9.9) |
| Median | 41 |
| Min, Max | 19, 53 |
| Age group (years), n (%) | |
| 18-35 | 6 (33.3) |
| 36-45 | 7 (38.9) |
| >45 | 5 (27.8) |
| Sex, n (%) | |
| Male | 4 (22.2) |
| Female | 14 (77.8) |
| Race, n (%) | |
| White | 11 (61.1) |
| Black or African American | 4 (22.2) |
| Asian | 1 (5.6) |
| Mixed (Black/White or Black/American Indian or Alaska Native) | 2 (11.1) |
| Ethnicity, n (%) | |
| Hispanic or Latino | 3 (16.7) |
| Not Hispanic or Latino | 15 (83.3) |

Note:
Percentages are calculated as n/N*100. Age was derived using date of birth.

TABLE 17-1B

Body Weight and BMI of Subjects Treated

| | N = 18 |
|---|---|
| Weight (kg) | |
| n | 18 |
| Mean (SD) | 64.3 (8.2) |
| Median | 60.6 |
| Min, Max | 54, 82.6 |

TABLE 17-1B-continued

Body Weight and BMI of Subjects Treated

N = 18

| BMI (kg/m2) | |
|---|---|
| n | 18 |
| Mean (SD) | 25.0 (3.3) |
| Median | 24.8 |
| Min, Max | 18.8, 29.71 |

Note:
BMI = Body Mass Index;
n = number of subjects;
Min = minimum;
Max = maximum;
SD = Standard Deviation.
Percentages are calculated as n/N*100.

TABLE 17-2A

Co-primary Measures: Freedom from Migraine Headache Pain and Freedom from Most Bothersome Symptom (MBS) at 2 Hours Postdose in Subjects Treated (N = 18)

| | (N = 18) n (%) |
|---|---|
| Freedom from migraine headache pain at 2 hours [1] | |
| Yes | 4 (22.2) |
| No | 14 (77.8) |
| Freedom from MBS at 2 hours [2] | |
| Yes | 12 (66.7) |
| No | 6 (33.3) |

TABLE 17-2

Efficacy Results with Propofol Pharmacokinetics (N = 12)

| | Pre-Dose | | Time 1 hr | | | |
|---|---|---|---|---|---|---|
| Subject No. | Headache Pain level | MBS Type | Conc. 1 hr ng/hr | AUC 1 hr ng · h/mL | Headache Pain level | MBS (Y/N) |
| 4002 | Severe | Photophobia | 22 | 21.34 | Severe | Yes |
| 4005 | Severe | Photophobia | 103.760 | 59.39 | Mild | Yes |
| 6001 | Moderate | Phonophobia | 302.040 | 187.95 | Mild | No |
| 6002 [a] | Severe | Nausea | 513.450 | 285.41 | None | Yes |
| 6008 | Severe | Photophobia | 0.000 | 0.00 | Moderate | Yes |
| 8001 | Moderate | Photophobia | 92.380 | 52.07 | Moderate | Yes |
| 8002 | Severe | Photophobia | 114.690 | 199.02 | Moderate | Yes |
| 10001 | Moderate | Photophobia | 347.810 | 177.94 | Mild | Yes |
| 11002 [a] | Moderate | Photophobia | 95.340 | 60.99 | Mild | No |
| 12003 | Moderate | Photophobia | 158.790 | 114.22 | Moderate | Yes |
| 12005 | Severe | Nausea | 55.810 | 33.03 | Moderate | Yes |
| 12008 | Severe | Photophobia | 163.550 | 130.59 | Mild | No |

| | Time | | | | | | |
|---|---|---|---|---|---|---|---|
| | 2 hr | | | | 4 hr | | |
| Subject No. | Conc. 2 hr ng/hr | AUC 2 hr ng · h/mL | Headache Pain level | MBS (Y/N) | Conc. 4 hr ng/hr | AUC 4 hr ng · h/mL | Headache Pain level | MBS (Y/N) |
| 4002 | 25.07 | 44.87 | Moderate | No | 79.02 | 148.96 | Moderate | No |
| 4005 | 40.53 | 131.54 | None | No | 13.07 | 185.14 | None | No |
| 6001 | 248.05 | 462.99 | Mild | No | 46.65 | 757.69 | Mild | No |
| 6002 [a] | 94.42 | 589.35 | None | No | 27.44 | 711.21 | None | No |
| 6008 | 0 | 0.00 | Mild | No | 3.96 | 3.96 | None | No |
| 8001 | 108.65 | 152.58 | Moderate | Yes | 47.39 | 308.62 | Mild | No |
| 8002 | 63.28 | 288.01 | Mild | Yes | 27.40 | 378.69 | None | No |
| 10001 | 255.33 | 479.51 | Moderate | Yes | 68.21 | 803.05 | None | Yes |
| 11002 [a] | 89.48 | 153.40 | Mild | No | 24.41 | 267.29 | Mild | No |
| 12003 | 159.75 | 273.49 | Mild | Yes | 41.17 | 474.41 | Mild [b] | Yes [b] |
| 12005 | 75.78 | 98.83 | Mild | No | 36.55 | 211.16 | None | No |
| 12008 | 233.85 | 329.29 | None | No | 97.84 | 660.98 | None | No |

TABLE 17-2A-continued

Co-primary Measures: Freedom from Migraine Headache Pain and Freedom from Most Bothersome Symptom (MBS) at 2 Hours Postdose in Subjects Treated (N = 18)

| | (N = 18) n (%) |
|---|---|
| Freedom from both migraine headache pain and MBS at 2 hours | |
| Yes | 4 (22.2) |
| No | 14 (77.8) |

[1] Freedom from migraine headache pain at 2 hours is defined as reduction in headache severity from moderate or severe pain within 10 minutes before dosing to no pain at 2 hours postdose. A subject is not counted as being pain free if he or she received in-clinic rescue medication at or before the 2-hour assessment.
[2] Freedom from MBS at 2 hours is defined as absence of the migraine related symptom (nausea/vomiting, phonophobia, or photophobia) that was identified within 10 minutes predose as the most bothersome symptom. A subject is not counted as being MBS free if he or she received in-clinic rescue medication at or before the 2-hour assessment.

TABLE 17-2C

Most Bothersome Symptom (MBS) by Time Point in Subjects Treated

| | | N = 18 n (%)[1] | | |
|---|---|---|---|---|
| Time point | | No rescue[2] | Rescue[3] | Total |
| Within 10 min predose | MBS identified[4] | 18 (100) | 0 | 18 (100) |
| 1 hr post dose | MBS free | 7 (38.9) | 0 | 7 (38.9) |
| | MBS present | 11 (61.1) | 0 | 11 (61.1) |
| 2 h post dose | MBS free | 12 (66.7) | 0 | 12 (66.7) |
| | MBS present | 6 (333) | 0 | 6 (33.3) |
| 4 h post dose | MBS free | 14 (77.8) | 2 (11.1) | 16 (88.9) |
| | MBS present | 0 | 2 (11.1) | 2 (11.1) |
| Discharge | MBS free | 13 (72.2) | 3 (16.7) | 16 (88.9) |
| | MBS present | 0 | 0 | |
| | Data missing | 0 | 2 (11.1) | 2 (11.1) |

TABLE 17-2B

Severity of Migraine Headache Pain by Assessment Time Point in Subjects Treated

| Time point | Severity of headache pain | N = 18 n (%)[1] | | |
|---|---|---|---|---|
| | | No rescue[2] | Rescue[3] | Total |
| Within 10 min predose | Pain free | 0 | ... | 0 |
| | Mild pain | 0 | ... | 0 |
| | Moderate pain | 8 (44.4) | ... | 8 (44.4) |
| | Severe pain | 10 (55.6) | ... | 10 (55.6) |
| 1 hr postdose | Pain free | 1 (5.6) | 0 | 1 (5.6) |
| | Mild pain | 9 (50.0) | 0 | 9 (50.0) |
| | Moderate pain | 6 (33.3) | 0 | 6 (33.3) |
| | Severe pain | 2 (11.1) | 0 | 2 (11.1) |
| 2 h postdose | Pain free | 4 (22.2) | 0 | 4 (22.2) |
| | Mild pain | 11 (61.1) | 0 | 11 (61.1) |
| | Moderate pain | 3 (16.7) | 0 | 3 (16.7) |
| | Severe pain | 0 | 0 | 0 |
| 4 h postdose | Pain free | 10 (55.6) | 2 (11.1) | 12 (66.7) |
| | Mild pain | 4 (22.2) | 1 (5.6) | 5 (27.8) |
| | Moderate pain | 1 (5.6) | 0 | 1 (5.6) |
| | Severe pain | 0 | 0 | 0 |
| Discharge | Pain free | 12 (66.7) | 2 (11.1) | 14 (77.8) |
| | Mild pain | 2 (11.1) | 1 (5-6) | 3 (16.7) |
| | Moderate pain | 0 | 0 | 0 |
| | Severe pain | 0 | 0 | 0 |
| | Missing data | 1 (5.6) | 0 | 1 (5.6) |
| 24 h postdose (D2)[4] | Pain free | 13 (72.2) | 0 | 13 (72.2) |
| | Mild pain | 3 (16.7) | 0 | 3 (16.7) |
| | Moderate pain | 1 (11.1) | 1 (11.1) | 2 (22.2) |
| | Severe pain | 0 | 0 | 0 |
| 48 h postdose (D3)[5] | Pain free | 15 (83.3) | 0 | 15 (83.3) |
| | Mild pain | 0 | 1 (11.1) | 1 (11.1) |
| | Moderate pain | 0 | 2 (22.2) | 2 (22.2) |
| | Severe pain | 0 | 0 | 0 |

[1] Percentages are calculated as n/N *100.
[2] Subjects who did not receive in-clinic rescue medication pain between administration of study drug and the specified postdose assessment time point or subjects who did not take medication for acute migraine during the specified follow-up period.
[3] Subjects who received in-clinic rescue medication for headache pain between administration of study drug and the specified assessment time point or who took medication for acute migraine during the specified follow-up period.
[4] Events during the period between discharge and the 24-hour follow-up phone call, including headache pain present at clinic discharge lasting for at least part of the 24-hour period after discharge or any episode of headache pain between discharge and the 24-hour interview, regardless of duration. Severity is defined as the worst pain during the period from discharge to the 24-hour interview.
[5] Events during the period between the 24-hour follow-up phone call and the 48-hour follow-up phone call, including any headache pain present at the 24-hour follow-up phone call and lasting for at least part of the period between the 24-hour and 48-hour follow-up phone calls. Severity is defined as the worst pain during the period from discharge to the 24-hour interview.

TABLE 17-2C-continued

Most Bothersome Symptom (MBS) by Time Point in Subjects Treated

|  |  | N = 18 n (%) [1] | |  |
| --- | --- | --- | --- | --- |
| Time point |  | No rescue [2] | Rescue [3] | Total |
| 24 h postdose (Day 2) [5] | MBS free | 13 (72.2) | 2 (11.1) | 15 (83.3) |
|  | MBS present | 0 | 0 |  |
|  | Data missing | 0 | 3 (16.7) | 3 (16.7) |
| 48 h postdose (Day 3) [6] | MBS free | 12 (66.7) | 2 (11.1) | 14 (77.8) |
|  | MBS present | 0 | 0 |  |
|  | Data missing | 0 | 4 (22.2) | 4 (22.2) |

[1] Percentages are calculated as n/N *100.
[2] Subjects who did not receive in-clinic rescue medication for headache pain between administration of study drug and the specified postdose assessment time point or subjects who did not take medication for acute migraine during the specified follow-up period.
[3] Subjects who received in-clinic rescue medication for headache pain between administration of study drug and the specified assessment time point or who took medication for acute migraine during the specified follow-up period.
[4] Each subject's individual most bothersome symptom (nausea/vomiting, photophobia, or phonophobia) was identified within 10 minutes before dosing with fospropofol disodium.
[5] Events during the period between discharge and the 24-hour follow-up phone call, including MBS present at clinic discharge lasting for at least part of the 24-hour period after discharge or any MBS episode between discharge and the 24-hour interview, regardless of duration.
[6] Events during the period between the 24-hour follow-up phone call and the 48-hour follow-up phone call, including any MBS present at the 24-hour follow-up phone call and lasting for at least part of the period between the 24-hour and 48-hour follow-up phone calls.

TABLE 17-2D

Sustained Headache Pain Freedom and Sustained Pain Relief From 2 to 24 Hours and From 2 to 48 Hours After Dosing in Subjects Treated

|  | N = 18 n (%) | |
| --- | --- | --- |
|  | 2-24 hours postdose | 2-48 hours postdose |
| Sustained headache pain freedom [1] |  |  |
| Yes | 4 (22.2) | 3 (16.7) |
| No | 14 (77.8) | 15 (83.3) |
| Sustained headache pain relief [2] |  |  |
| Yes | 12 (66.7) | 11 (61.1) |
| No | 6 (33.3) | 7 (38.9) |
| Sustained MBS-free response [3] |  |  |
| Yes | 10 (55.6) | 9 (50) |
| No | 8 (44.4) | 9 (50) |

[1] Sustained headache pain freedom is defined as pain freedom at each assessment from 2 to 24 hours postdose (Day 2 Follow-up) or from 2 to 48 hours postdose (Day 3 Follow-up) with no use of in-clinic rescue medication or medication for acute treatment of migraine after clinic discharge.
[2] Sustained headache pain relief is defined as reduction in headache severity from moderate or severe pain to mild or no headache at each assessment from 2 to 24 hours postdose (Day 2 Follow-up) or from 2 to 48 hours postdose (Day 3 Follow-up) with no use of in-clinic rescue medication or medication for acute treatment of migraine after clinic discharge.
[3] A sustained MBS-free response is defined as freedom from the subject's individual most bothersome symptom (identified predose) at each assessment from 2 to 24 hours postdose (Day 2 Follow-up) or from 2 to 48 hours postdose (Day 3 Follow-up) with no use of in-clinic rescue medication or medication for acute treatment of migraine after clinic discharge.

TABLE 17-3

Propofol Pharmacokinetics (N = 12)

| Subject No. | Cmax ng/mL | Tmax hr | AUC1 ng · h/mL | AUC2 ng · h/mL | AUC4 ng · h/mL | Female |
| --- | --- | --- | --- | --- | --- | --- |
| 4002 | 79.02 | 4 | 21.34 | 44.87 | 148.96 | 1 |
| 4005 | 103.76 | 1 | 59.39 | 131.54 | 185.14 | 1 |
| 6001 | 302.04 | 1 | 187.95 | 462.99 | 757.69 | 1 |
| 6002 | 513.45 | 1 | 285.41 | 589.35 | 711.21 | 1 |
| 6008 | 3.86 | 4 | 0.00 | 0.00 | 3.96 | 0 |
| 8001 | 108.65 | 2 | 52.07 | 152.58 | 308.62 | 1 |
| 8002 | 368.56 | 0.667 | 199.02 | 288.01 | 378.69 | 1 |
| 10001 | 347.81 | 1 | 177.94 | 479.51 | 803.05 | 1 |
| 11002 | 105.27 | 0.667 | 60.99 | 153.40 | 267.29 | 1 |
| 12003 | 159.75 | 2 | 114.22 | 273.49 | 474.41 | 1 |
| 12005 | 75.78 | 2 | 33.03 | 98.83 | 211.16 | 1 |
| 12008 | 239.5 | 0.667 | 130.59 | 329.29 | 660.98 | 1 |
| Mean | 200.62 | 1.67 | 110.16 | 250.32 | 409.26 |  |
| SD | 152.92 | 1.21 | 87.40 | 186.30 | 267.64 |  |
| CV (%) | 76.2% | 72.4% | 79.3% | 74.4% | 65.4% |  |

TABLE 17-4

Propofol Pharmacokinetics - (excluding as an outlier data from Subject 6008 who exhibited zero or negligible propofol plasma levels)

| Subject No. | Cmax ng/mL | Tmax hr | AUC1 ng · h/mL | AUC2 ng · h/mL | AUC4 ng · h/mL | Female |
| --- | --- | --- | --- | --- | --- | --- |
| 4002 | 79.02 | 4 | 21.34 | 44.87 | 148.96 | 1 |
| 4005 | 103.76 | 1 | 59.39 | 131.54 | 185.14 | 1 |
| 6001 | 302.04 | 1 | 187.95 | 462.99 | 757.69 | 1 |
| 6002 | 513.45 | 1 | 285.41 | 589.35 | 711.21 | 1 |
| 6008 |  |  |  |  |  | 0 |
| 8001 | 108.65 | 2 | 52.07 | 152.58 | 308.62 | 1 |
| 8002 | 368.56 | 0.667 | 199.02 | 288.01 | 378.69 | 1 |
| 10001 | 347.81 | 1 | 177.94 | 479.51 | 803.05 | 1 |
| 11002 | 105.27 | 0.667 | 60.99 | 153.40 | 267.29 | 1 |
| 12003 | 159.75 | 2 | 114.22 | 273.49 | 474.41 | 1 |
| 12005 | 75.78 | 2 | 33.03 | 98.83 | 211.16 | 1 |
| 12008 | 239.5 | 0.667 | 130.59 | 329.29 | 660.98 | 1 |
| Mean | 218.51 | 1.45 | 120.18 | 273.08 | 446.11 |  |
| SD | 146.62 | 1.00 | 84.14 | 177.03 | 246.73 |  |
| CV (%) | 67.1% | 68.9% | 70.0% | 64.8% | 55.3% |  |

TABLE 17-5

Ratio of Mean Propofol Pharmacokinetics-Migraine subjects vs. Healthy Volunteers (Study A17 vs. Study A16 (800 mg Cohort from A16, excluding subject 308)).
Ratio of mean values in migraine subjects to healthy volunteers

| Cmax | Tmax | Auc1 | Auc2 | Auc4 |
| --- | --- | --- | --- | --- |
| 87% | 77% | 89% | 95% | 106% |

TABLE 17-6

Ratio of Mean Propofol Pharmacokinetics - Migraine subjects vs. Healthy Volunteers - Females (Study A17 vs. Study A16 (800 mg Cohort from A16, females only).
Ratio of mean values in migraine subjects (all female) to female healthy volunteers

| Cmax | Tmax | Auc1 | Auc2 | Auc4 |
| --- | --- | --- | --- | --- |
| 80% | 66% | 85% | 85% | 91% |

TABLE 17-7

Efficacy Results with Fospropofol Pharmacokinetics (N = 12)

| Subject No. | Pre-Dose Headache Pain level | Pre-Dose MBS Type | Time 1 hr Conc. 1 hr ng/hr | Time 1 hr AUC 1 hr ng · h/mL | Headache Pain level | MBS (Y/N) |
|---|---|---|---|---|---|---|
| 4002 | Severe | Photophobia | 327.410 | 723.61 | Severe | Yes |
| 4005 | Severe | Photophobia | 1146.030 | 2418.57 | Mild | Yes |
| 6001 | Moderate | Phonophobia | 2525.100 | 5268.76 | Mild | No |
| 6002 [a] | Severe | Nausea | 2369.220 | 6456.6 | None | Yes |
| 6008 | Severe | Photophobia | 0.00 | 0.00 | Moderate | Yes |
| 8001 | Moderate | Photophobia | 1791.790 | 2684.78 | Moderate | Yes |
| 8002 | Severe | Photophobia | 162.560 | 1315.43 | Moderate | Yes |
| 10001 | Moderate | Photophobia | 1697.140 | 3262.09 | Mild | Yes |
| 11002 [a] | Moderate | Photophobia | 1302.040 | 3522.27 | Mild | No |
| 12003 | Moderate | Photophobia | 1818.430 | 5673.87 | Moderate | Yes |
| 12005 | Severe | Nausea | 741.150 | 1193.95 | Moderate | Yes |
| 12008 | Severe | Photophobia | 3342.040 | 4461.52 | Mild | No |

| Subject No. | Time 2 hr Conc. 2 hr ng/hr | Time 2 hr AUC 2 hr ng · h/mL | Headache Pain level | MBS (Y/N) | Time 4 hr Conc. 4 hr ng/hr | Time 4 hr AUC 4 hr ng · h/mL | Headache Pain level | MBS (Y/N) |
|---|---|---|---|---|---|---|---|---|
| 4002 | 240.76 | 1007.69 | Moderate | No | 0.00 | 1248.45 | Moderate | No |
| 4005 | 107.28 | 3045.22 | None | No | 0.00 | 3152.5 | None | No |
| 6001 | 399.27 | 6730.95 | Mild | No | 0.00 | 7130.22 | Mild | No |
| 6002 [a] | 230.24 | 7756.33 | None | No | 0.00 | 7986.57 | None | No |
| 6008 | 0.00 | 0.00 | Mild | No | 0.00 | 0.00 | None | No |
| 8001 | 170.91 | 3666.13 | Moderate | Yes | 0.00 | 3837.04 | Mild | No |
| 8002 | 48.78 | 1421.1 | Mild | Yes | 0.00 | 1469.88 | None | No |
| 10001 | 128.44 | 4174.88 | Moderate | Yes | 0.00 | 4303.32 | None | Yes |
| 11002 [a] | 427.36 | 4386.97 | Mild | No | 0.00 | 4814.33 | Mild | No |
| 12003 | 239.76 | 6702.97 | Mild | Yes | 0.00 | 6942.73 | Mild [b] | Yes [b] |
| 12005 | 91.97 | 1610.51 | Mild | No | 0.00 | 1702.48 | None | No |
| 12008 | 1626.55 | 6945.81 | None | No | 0.00 | 8572.36 | None | No |

TABLE 17-8

Fospropofol Pharmacokinetics (N = 12)

| Subject No. | Cmax ng/mL | Tmax hr | AUC1 ng · h/mL | AUC2 ng · h/mL | AUC4 ng · h/mL | Female |
|---|---|---|---|---|---|---|
| 4002 | 1419.1 | 0.333 | 723.61 | 1007.69 | 1248.45 | 1 |
| 4005 | 4507.39 | 0.333 | 2418.57 | 3045.22 | 3152.5 | 1 |
| 6001 | 11463.93 | 0.333 | 5268.76 | 6730.95 | 7130.22 | 1 |
| 6002 | 10001.18 | 0.167 | 6456.6 | 7756.33 | 7986.57 | 1 |
| 6008 | 0 | . | 0 | 0 | 0 | 0 |
| 8001 | 5163.62 | 0.333 | 2684.78 | 3666.13 | 3837.04 | 1 |
| 8002 | 3285.03 | 0.333 | 1315.43 | 1421.1 | 1469.88 | 1 |
| 10001 | 5036.79 | 0.167 | 3262.09 | 4174.88 | 4303.32 | 1 |
| 11002 | 7527.26 | 0.333 | 3522.27 | 4386.97 | 4814.33 | 1 |
| 12003 | 10597.13 | 0.333 | 5673.87 | 6702.97 | 6942.73 | 1 |
| 12005 | 2219.93 | 0.667 | 1193.95 | 1610.51 | 1702.48 | 1 |
| 12008 | 8307.86 | 0.333 | 4461.52 | 6945.81 | 8572.36 | 1 |
| Mean | 5794.10 | 0.33 | 3081.79 | 3954.05 | 4263.32 | |
| SD | 3773.68 | 0.13 | 2074.98 | 2629.28 | 2879.02 | |
| CV (%) | 65.1% | 38.7% | 67.3% | 66.5% | 67.5% | |

TABLE 17-9

Fospropofol Pharmacokinetics (Fospropofol plasma concentrations in Subject 6008 were zero (below limit of quantitation) at all time points)

| Subject No. | Cmax ng/mL | Tmax hr | AUC1 ng · h/mL | AUC2 ng · h/mL | AUC4 ng · h/mL | Female |
|---|---|---|---|---|---|---|
| 4002 | 1419.1 | 0.333 | 723.61 | 1007.69 | 1248.45 | 1 |
| 4005 | 4507.39 | 0.333 | 2418.57 | 3045.22 | 3152.5 | 1 |
| 6001 | 11463.93 | 0.333 | 5268.76 | 6730.95 | 7130.22 | 1 |
| 6002 | 10001.18 | 0.167 | 6456.6 | 7756.33 | 7986.57 | 1 |
| 6008 | | | | | | 0 |
| 8001 | 5163.62 | 0.333 | 2684.78 | 3666.13 | 3837.04 | 1 |
| 8002 | 3285.03 | 0.333 | 1315.43 | 1421.1 | 1469.88 | 1 |
| 10001 | 5036.79 | 0.167 | 3262.09 | 4174.88 | 4303.32 | 1 |
| 11002 | 7527.26 | 0.333 | 3522.27 | 4386.97 | 4814.33 | 1 |
| 12003 | 10597.13 | 0.333 | 5673.87 | 6702.97 | 6942.73 | 1 |
| 12005 | 2219.93 | 0.667 | 1193.95 | 1610.51 | 1702.48 | 1 |
| 12008 | 8307.86 | 0.333 | 4461.52 | 6945.81 | 8572.36 | 1 |
| Mean | 6320.84 | 0.33 | 3361.95 | 4313.51 | 4650.90 | |
| SD | 3464.45 | 0.13 | 1923.55 | 2428.76 | 2671.10 | |
| CV (%) | 54.8% | 38.7% | 57.2% | 56.3% | 57.4% | |

TABLE 17-10

Ratio of Mean Fospropofol Pharmacokinetics - Migraine
subjects vs. Healthy Volunteers (Study A17 vs. A16).

Ratio of mean values in migraine subjects (Study A17) to healthy
volunteers (800 mg Cohort from A16, excluding subject 308)

| Cmax | Tmax | Auc1 | Auc2 | Auc4 |
|------|------|------|------|------|
| 105% | 98%  | 121% | 130% | 135% |

TABLE 17-11

Ratio of Mean Fospropofol Pharmacokinetics - Migraine
subjects vs. Healthy Volunteers (Study A17 vs. A16).

Ratio of mean values in migraine subjects (all female; from A17)
to female healthy volunteers (800 mg Cohort from A16,
excluding subject 308)

| Cmax | Tmax | Auc1 | Auc2 | Auc4 |
|------|------|------|------|------|
| 94%  | 89%  | 110% | 116% | 120% |

Systemic Exposure to Propofol after Administration of Fospropofol Disodium Turn to Subjects with Migraine is Inversely Related to Time to Treatment Fospropofol Disodium, 800 mg, was administered orally under medical supervision to 12 adult subjects in the course of a migraine episode (within 4 hours of the reported onset of migraine symptoms). Subjects reported time of onset of migraine symptoms and the time interval between onset of symptoms and treatment with Fospropofol Disodium (time-to-treatment) was recorded. Plasma concentrations of fospropofol and propofol were measured preclose and at intervals until 4 hours after closing. The potential influence of a variety of covariates on systemic exposure (maximal plasma concentration [Cmax] and area under the plasma concentration curve at 1, 2, and 4 hours [AUC1, AUC2, AUC4]) for both fospropofol and propofol was examined. One of 12 migraine subjects who exhibited negligible plasma concentrations for both fospropofol and propofol was excluded from analysis. Values for Cmax and AUCs were log-transformed. Time to treatment among the migraine subjects ranged from 115 to 230 minutes.

Figure 17:
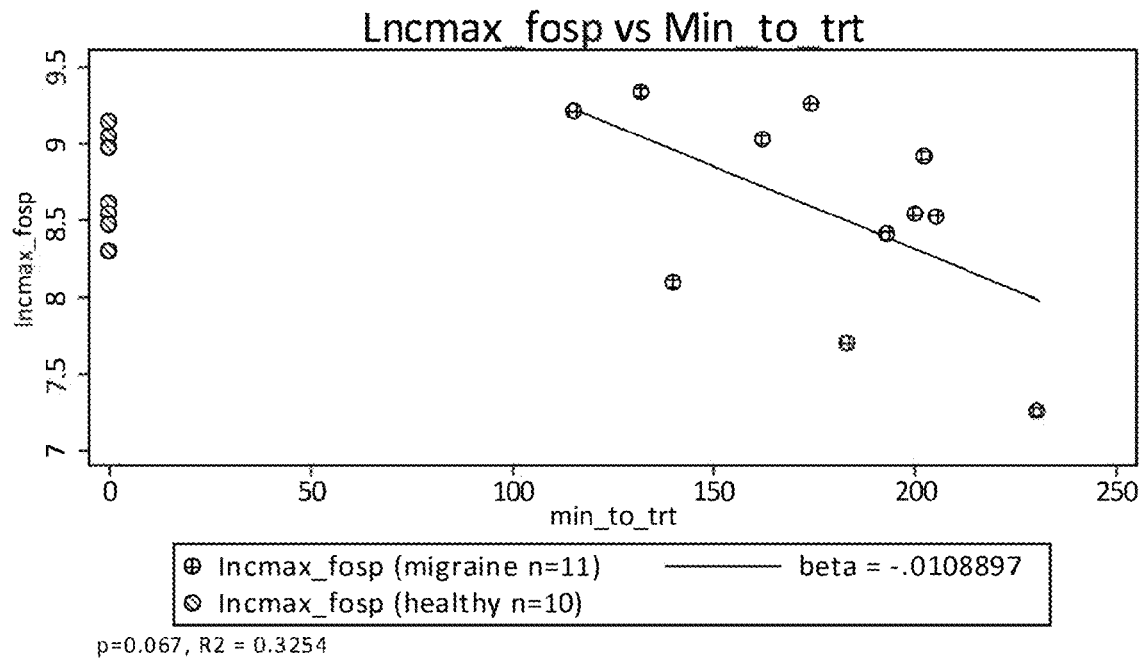
FIG. 17 shows Linear regression of log Cmax fospropofol on Time to Treatment. Among the migraine subjects there is a trend toward an inverse linear association between log Cmax fospropofol and time-to-treatment, $p=0.067$. Values for healthy volunteers are shown on the left.
Figure 18:
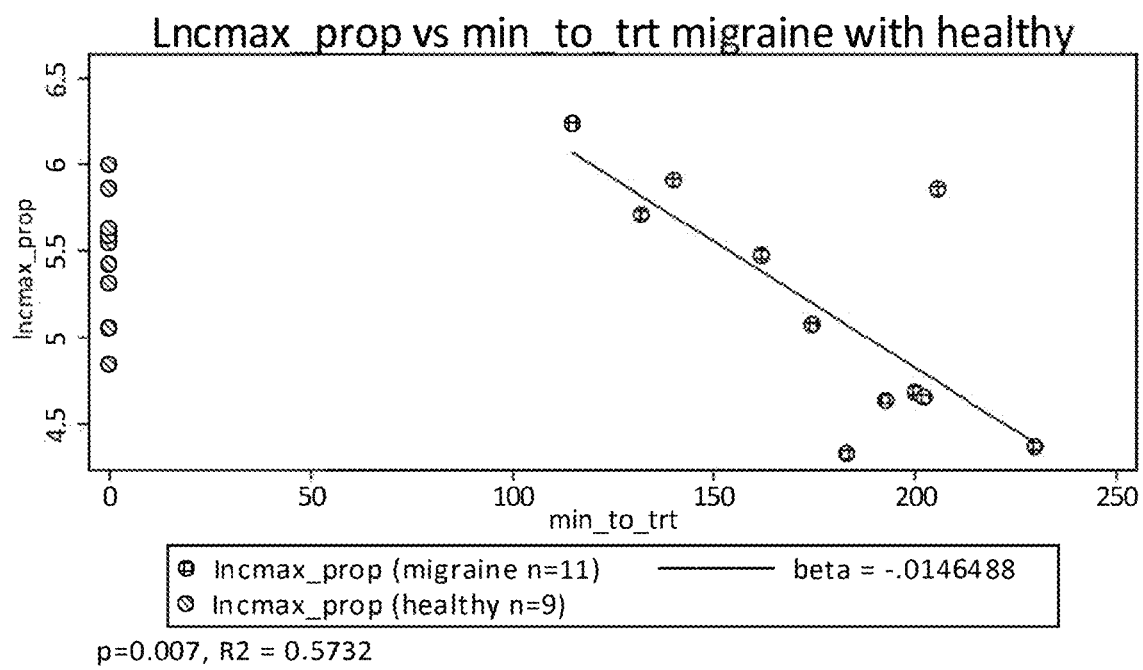
FIG. 18 shows Linear regression of log Cmax propofol on Time-to Treatment. Among the migraine subjects there is a statistically significant inverse linear association between log Cmax propofol and time-to-treatment, $p=0.007$. Values for healthy volunteers are shown on the left.
Figure 19:
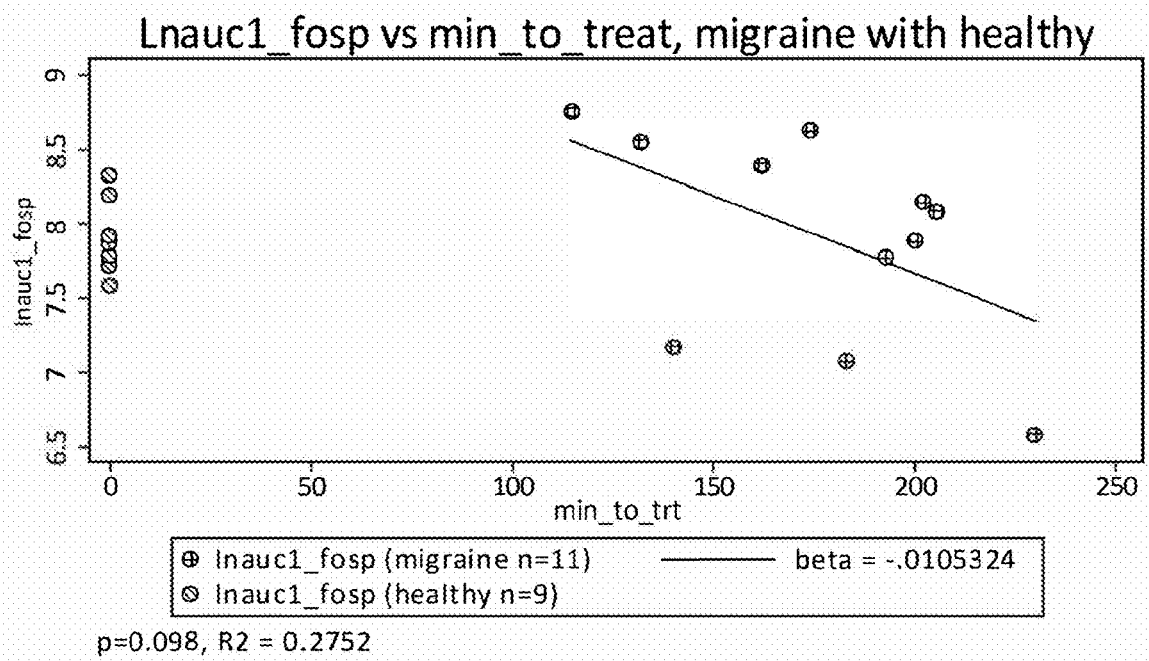
FIG. 19 shows Linear regression of log AUC1 fospropofol on Time-to-Treatment. Among the migraine subjects there is a trend toward an inverse linear association between log AUC1 fospropofol and time-to-treatment, $p=0.098$. Values for healthy volunteers are shown on the left.
Figure 20:
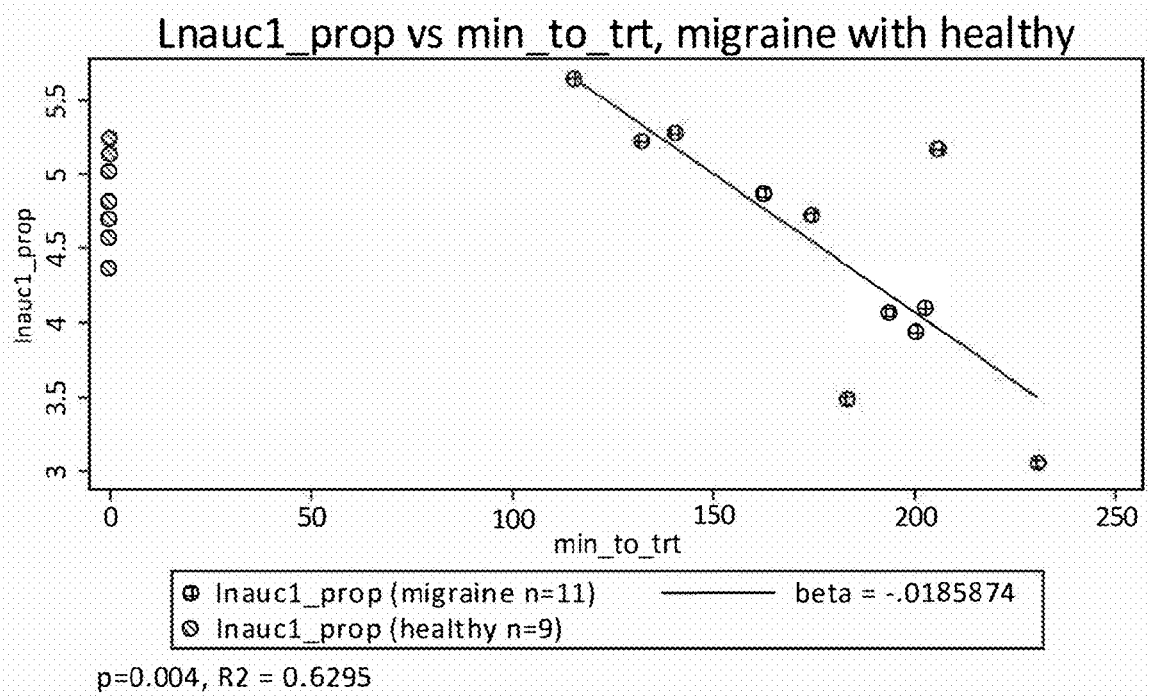
FIG. 20 shows Linear regression of log AUC1 propofol on Time-to-Treatment. Among the migraine subjects there is a statistically significant inverse linear association between log AUC1 propofol and time-to-treatment, $p=0.004$. Values for healthy Volunteers are shown on the left.
Figure 21:
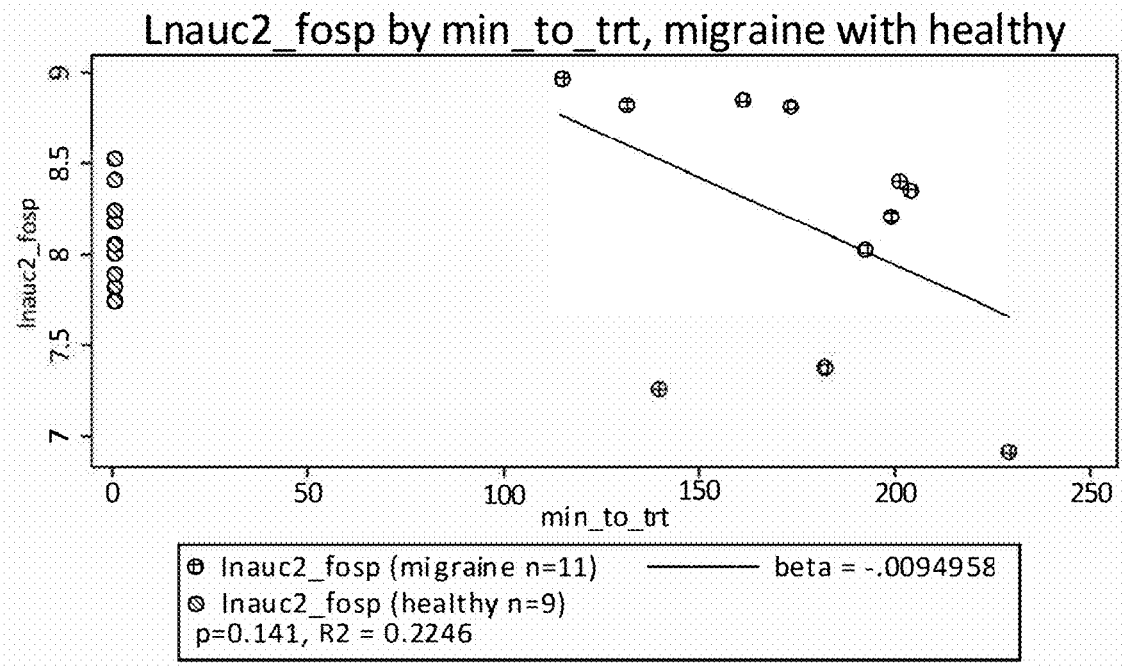
FIG. 21 shows Linear regression of log AUC2 fospropofol on Time-to-Treatment. Among the migraine subjects there is a trend toward an inverse linear association between log AUC2 fospropofol and time-to-treatment, $p=0.141$. Values for healthy volunteers are shown on the left.
Figure 22:
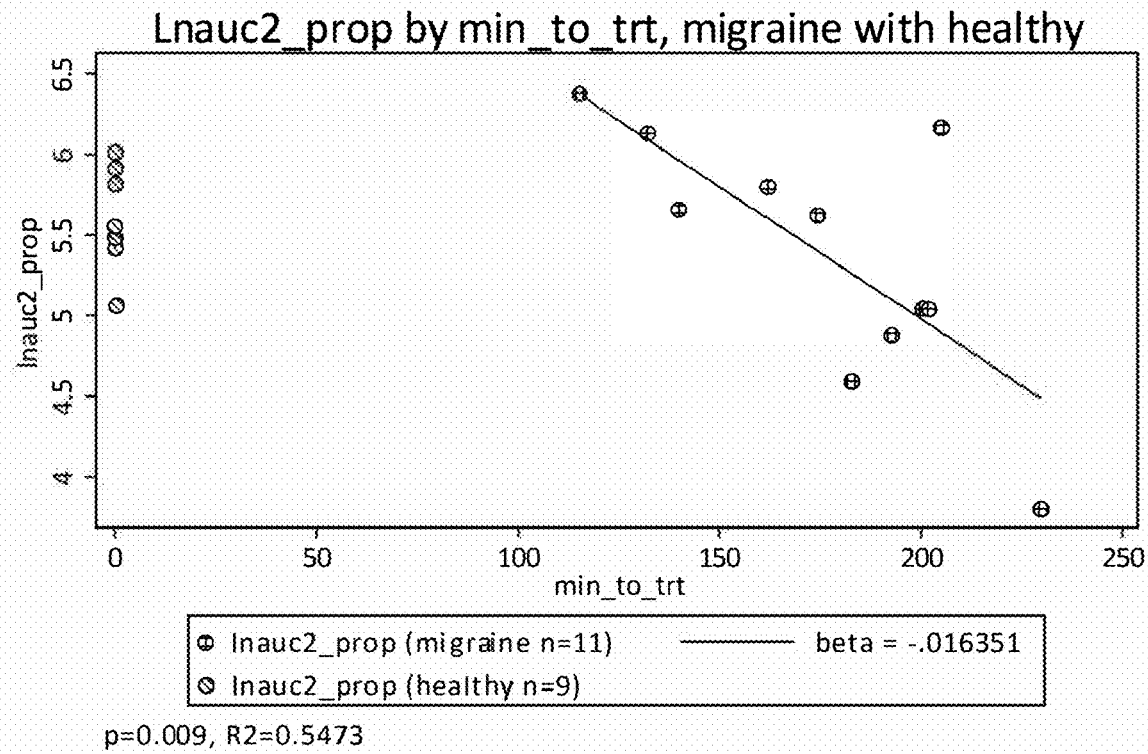
FIG. 22 shows Linear regression of log AUC2 propofol on Time-to-Treatment. Among the migraine subjects there is a statistically significant inverse linear association between log AUC2 propofol and time-to-treatment, $p=0.009$. Values for healthy volunteers are shown on the left.
Figure 23:
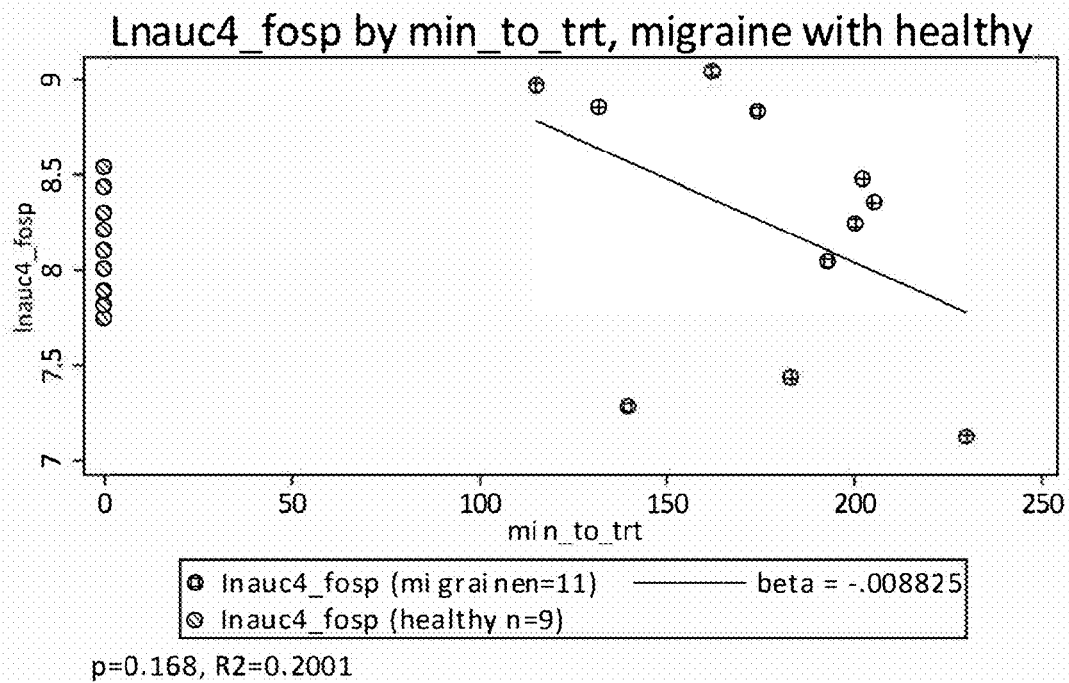
FIG. 23 shows Linear regression of log AUC4 fospropofol on Time-to-Treatment. Among the migraine subjects there is a trend toward an inverse linear association between log AUC4 fospropofol and time-to-treatment, $p=0.168$. Values for healthy volunteers are shown on the left.
Figure 24:
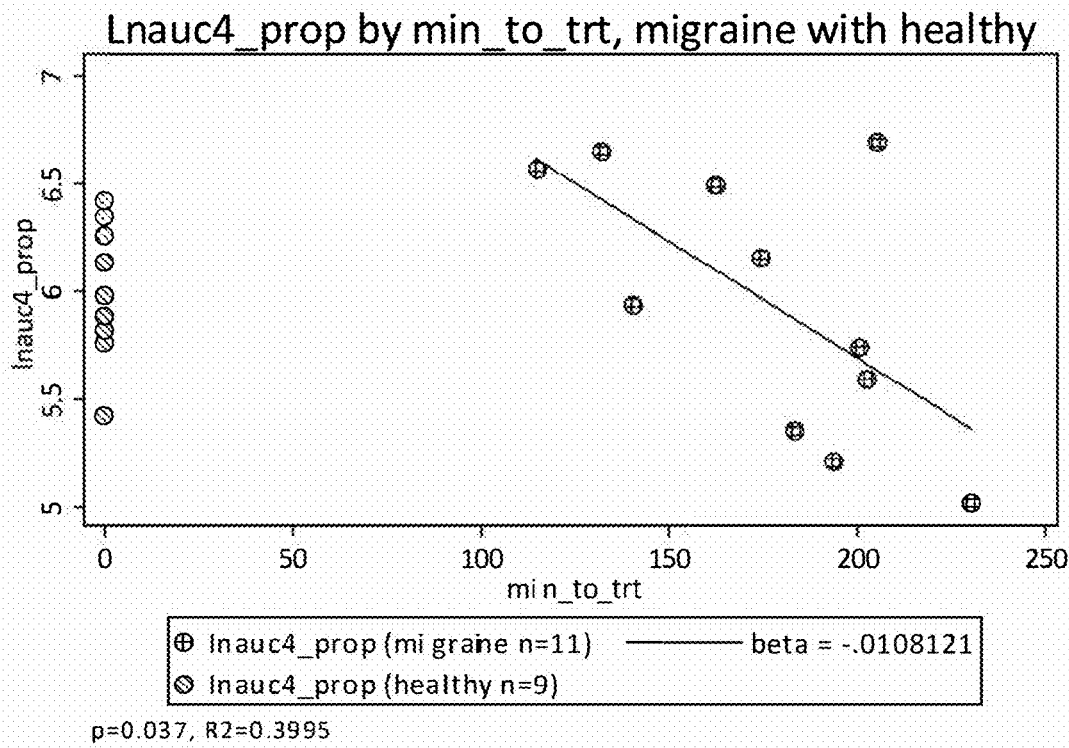
FIG. 24 shows Linear regression of log AUC4 propofol on Time-to-Treatment. Among the migraine subjects there is a statistically significant inverse linear association between log AUC4 propofol and time-to-treatment, $p=0.037$. Values for healthy volunteers are shown on the left.

Among the 11 migraine subjects in the analysis (all female), there was a statistically significant inverse association between time-to-treatment and log propofol Cmax (p=0.007), log propofol AUC1 (p=0.004), log propofol AUC2 (p=0.009), and log propofol AUC4 [FIGS. 18, 20, 22, 24]. A similar trend (not statistically significant) toward an inverse association between time-to-treatment and fospropofol exposure was observed for log fospropofol Cmax (p=0.067) and log fospropofol AUC1 (p=0.98) [FIGS. 17 and 19]. The statistically significant inverse association between propofol exposure and time-to-treatment was unchanged after adjustment for other covariates including age, weight, BMI, and reported time since last meal. Time-to-treatment accounted for ~57%, 63%, 55%, and 40% of the variability in propofol log Cmax, propofol log AUC1, propofol log AUC2, and propofol log AUC4, respectively [FIGS. 18, 20, 22, 24]. Beta coefficients from the linear regressions [FIGS. 18, 20, 22, 24] indicate that over the observed time-to-treatment interval, geometric mean [GM] propofol $C_{max}$ decreased by 1.45% per minute of delay in time-to-treatment (58.5% per hour); GM propofol AUC1 decreased by 1.84% per minute (67.2% per hour); GM propofol AUC2 decreased by 1.62% per minute (62.5% per hour); and GM propofol AUC4 decreased by 1.08% per minute (47.7% per hour).

Figure 25:
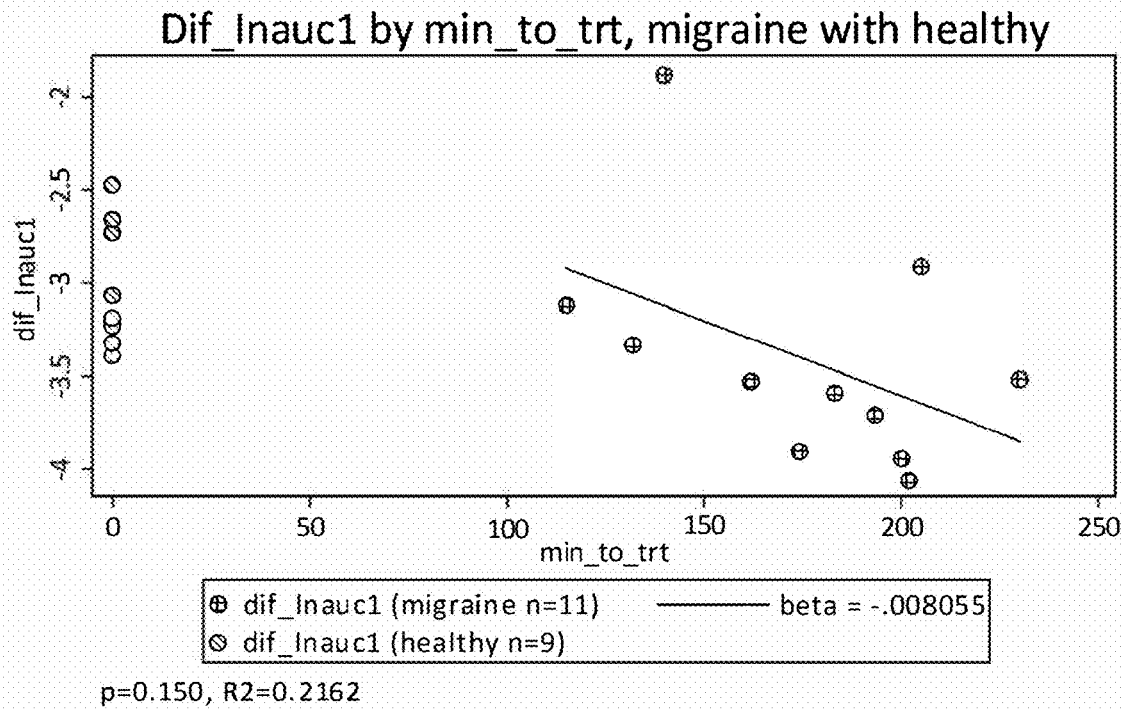
FIG. 25 shows Linear regression of log of the ratio of AUC1 propofol to AUC1 fospropofol on Time-to-Treatment. Among the migraine subjects there is a trend toward an inverse linear association between log of the ratio AUC1 propofol to AUC1 fospropofol and time-to-treatment, $p=0.150$. Values for healthy volunteers are shown on the left. The distribution of the log of the ratio AUC1 propofol to AUC1 fospropofol was statistically different between migraine subjects and healthy volunteers, $p=0.0367$.
Figure 26:
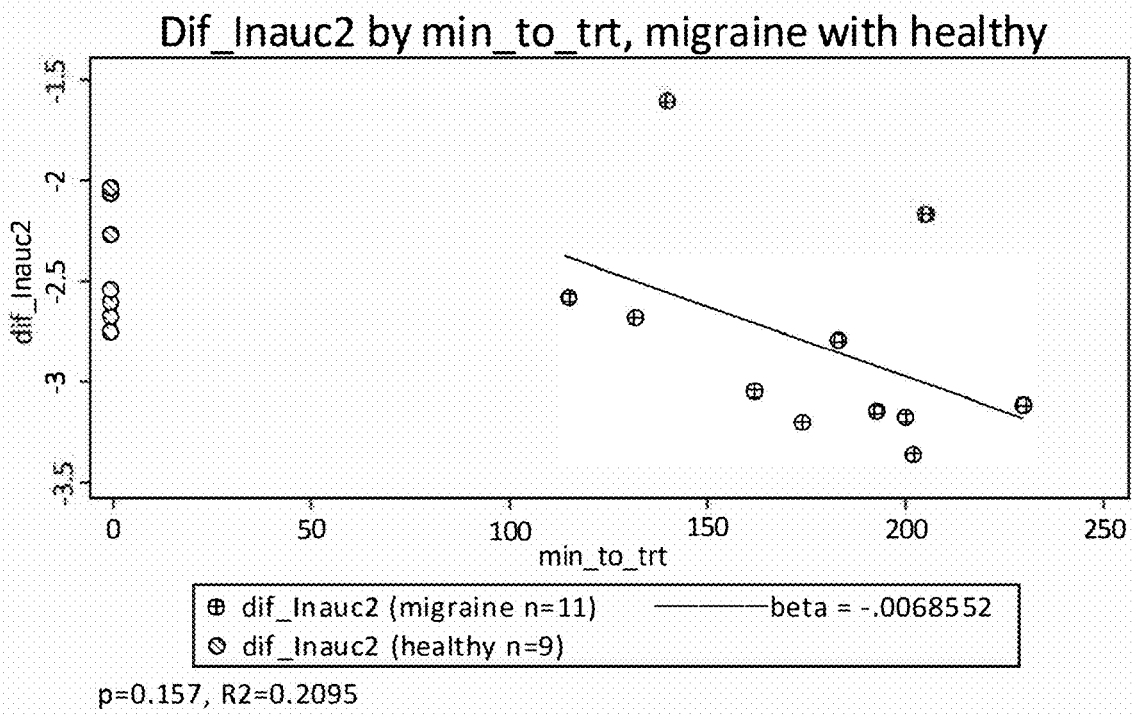
FIG. 26 shows Linear regression of log of the ratio of AUC2 propofol to AUC2 fospropofol on Time-to-Treatment. Among the migraine subjects there is a trend toward an inverse linear association between log of the ratio AUC1 propofol to AUC1 fospropofol and time-to-treatment, $p=0.157$. Values for healthy volunteers are shown on the left.

To explore whether the bioavailability of propofol relative to fospropofol was inversely associated with time to treatment, the log of the ratio of AUC1 propofol to AUC1 fospropofol and the log of the ratio of AUC2 propofol to AUC2 fospropofol were used as approximate indicators of the relative bioavailability at 1 and 2 hours after closing [FIGS. 25 and 26]. There was a trend (not statistically significant) toward an inverse association of time-to-treatment with the log of the ratio of AUC1 propofol to AUC1 fospropofol (p=0.141) and the log of the ratio of AUC2 propofol to AUC2 fospropofol (p=0.157) [FIGS. 25 and 26]. A comparison of the log of the ratio of AUC1 propofol to AUC1 fospropofol between the 11 migraine subjects and 9 healthy volunteers who received Fospropofol Disodium, 800 mg indicated that the distribution of the log of the ratio of AUC1 propofol to AUC1 fospropofol was different between migraine subjects and healthy volunteers, p=0.0367 (Wilcoxon rank-sum test).

TABLE 17-12A

All TEAEs by SOC and PT in Subjects Treated (N = 18)

| MedDRA ® System Organ Class<br>MedDRA ® Preferred Term | N = 18<br>n (%) E |
|---|---|
| Number of subjects with at least 1 TEAE, n (%) | 6 (33.3) |
| Number of TEAEs, E | 9 |
| Nervous system disorders | 3 (16.7) 4 [1] |
| Somnolence | 1 (5.6) 1 |
| Paraesthesia [2] | 2 (11.1) 2 |
| Dysgeusia | 1 (5.6) 1 |
| Reproductive system and breast disorders | 1 (5.6) 2 |
| Genital paraesthesia [2] | 1 (5.6) 2 |
| Skin and subcutaneous tissue disorders | 1 (5.6) 1 |
| Pruritus [2] | 1 (5.6) 1 |
| Gastrointestinal disorders | 2 (11.1) 2 |
| Nausea | 1 (7.7) 1 |
| Dry mouth | 1 (7.7) 1 |

E = number of TEAEs; N = number of subjects dosed; n (%): number and percent of subjects with TEAE; MedDRA ® = Medical Dictionary for Regulatory Activities, Version 24.0; TEAEs = treatment-emergent adverse events.
Each subject could only contribute once to each of the incidence rates, regardless of the number of occurrences; the highest severity is presented.
[1] One subject had paraesthesia, dysgeusia, and dry mouth.
[2] Paresthesia and pruritus are known adverse reactions associated with intravenous fospropofol. (Prescribing information for LUSEDRA ™ [fospropofol disodium] Injection, for intravenous use. Revised October 2009. Available at https://www.accessdata.fda.gov/drugsatfda_docs/label/2010/022244s006lbl.pdf)

TABLE 17-12B

Severity of TEAEs by SOC and PT in Subjects Treated (N = 18)

| MedDRA ® System Organ Class<br>MedDRA ® Preferred Term | N = 18<br>n (%) | | |
|---|---|---|---|
| | Mild | Moderate | Severe |
| Number of subjects with at least 1 TEAE | 3 | 3[1] | 1[1] |
| Number of TEAEs, E | 5 | 3 | 1 |
| Nervous system disorders | 3 | 1 | 0 |
| Somnolence | 1 | 0 | 0 |
| Paraesthesia | 1 | 1 | 0 |
| Dysgeusia | 1 | | |
| Reproductive system and breast disorders | 0 | 1[1] | 1[1] |
| Genital paraesthesia | 0 | 1[1] | 1[1] |
| Number of subjects with at least 1 TEAE | 3 | 3[1] | 1[1] |
| Skin and subcutaneous tissue disorders | 1 | 0 | 0 |
| Pruritus | 1 | 0 | 0 |
| Gastrointestinal disorders | 1 | 1 | 0 |

TABLE 17-12B-continued

Severity of TEAEs by SOC and PT in Subjects Treated (N = 18)

| MedDRA ® System Organ Class<br>MedDRA ® Preferred Term | N = 18<br>n (%) | | |
|---|---|---|---|
| | Mild | Moderate | Severe |
| Nausea | 0 | 1 | 0 |
| Dry mouth | 1 | 0 | 0 |

MedDRA ® = Medical Dictionary for Regulatory Activities, Version 24.0; TEAEs = treatment-emergent adverse events.
[1]Two AEs in the same subject (Genital paraesthesia initially rated severe and subsequently moderate)

TABLE 17-12C

Relation of TEAEs to Study Drug by SOC and PT in Subjects Treated (N = 18)

| MedDRA ® System Organ Class<br>MedDRA ® Preferred Term | N = 18<br>n (%) | |
|---|---|---|
| | Possibly<br>related | Probably<br>related |
| Number of TEAEs, E | 2 | 7 |
| Nervous system disorders | 0 | 4 |
| Somnolence | 0 | 1 |
| Paraesthesia[1] | 0 | 2 |
| Dysgeusia | 0 | 1 |
| Reproductive system and breast disorders | 0 | 2 |
| Genital paraesthesia[1] | 0 | 2 |
| Skin and subcutaneous tissue disorders | 1 | 0 |
| Pruritus[1] | 1 | 0 |
| Gastrointestinal disorders | 1 | 1 |
| Nausea | 1 | |
| Dry mouth | 0 | 1 |

MedDRA ® = Medical Dictionary for Regulatory Activities, Version 24.0; TEAEs = treatment-emergent adverse events.
[1]Paresthesia and pruritus are known adverse reactions associated with intravenous fospropofol. (Prescribing information for LUSEDRA ™ [fospropofol disodium] Injection, for intravenous use. Revised October 2009. Available at https://www.accessdata.fda.gov/drugsatfda_docs/label/2010/022244s006lbl.pdf)

Example 18. Study A18

Single-Dose, Open-Label, PK and Safety-Tolerability 2-Sequence, 3-Period Crossover Study of FOSPROPOFOL DISODIUM TABLETS (200-mg strength) Compared to the FOSPROPOFOL DISODIUM CAPSULE (200-mg strength) in Healthy Male and Female Adults Under Fasting Conditions with Evaluation of the Tablet Food Effect Study Drugs Fospropofol Disodium capsule (200-mg strength), Fospropofol Disodium tablet (200-mg strength)

Study Phase and Type Phase 1
  Part 1: Open-label, single-close pilot study (Single 200-mg tablet)
  Part 2: Open-label, randomized 2-sequence, 3-period, 3-treatment crossover. Treatments Fospropofol Disodium 200-mg capsules fasted [4 capsules]; Fospropofol Disodium tablets 200 mg fasted [number of tablets TBD]; Fospropofol Disodium tablets 200 mg after a high fat meal [number of tablets TBD—same as (B)] (D) Optional Fospropofol Disodium tablets 200 mg after a moderate fat meal [number of tablets TBD—same as (B) and (C)]

Objectives Primary Objectives
  To assess the safety-tolerability and pharmacokinetics (PK) of fospropofol and propofol following a single 200 mg dose of the Fospropofol Disodium tablet administered under fasting conditions to healthy adult male and female volunteers.

To assess the safety-tolerability and comparative pharmacokinetics (PK) including PK variability of fospropofol and propofol following single doses of Fospropofol Disodium administered orally (p.o.) to healthy adult male and female volunteers as (A) Fospropofol Disodium 200 mg capsules fasted [four capsules] (B) Fospropofol Disodium tablets 200 mg fasted [number of tablets TBD] (C) Fospropofol Disodium tablets 200 mg after a high fat meal [number of tablets TBD—same as (B)](D) Optional: Fospropofol Disodium tablets 200 mg after a moderate fat meal [number of tablets TBD—same as (B) and (C)]

Study Design A single-center, Phase 1 PK and safety-tolerability study in 2 parts.
  Part 1 is a pilot study of the PK profile (fospropofol and propofol) after a single dose of the 200 mg Fospropofol Disodium tablet.
  Part 1 will comprise a cohort of 12 healthy adult male and female subjects (at least 50% women). The sample size of 12 subjects is judged sufficient as a pilot study to assess exposure to propofol with the novel tablet formulation and the timing of the maximal plasma concentration for each analyte. Subjects participating in Part 1 will not be permitted to participate in Part 2 of the study.
  Although the PK of the Fospropofol Disodium 200 mg capsule has been well characterized in study A16 after single doses ranging from 200 to 2000 mg, the Fospropofol Disodium 200 mg tablet has not been studied in humans. The PK data after administration of the 200 mg tablet from Part 1 will be used to determine the close (number of 200 mg tablets) to be administered in Part 2 of the study and will also inform the PK sampling schedule to be used in Part 2.
  Part 2 is a randomized, 2-sequence, single-close crossover comparison of Fospropofol Disodium 200-mg tablets vs Fospropofol Disodium 200-mg capsules under fasting conditions, with a third visit for half of the subjects chosen at random to receive a single dose of Fospropofol Disodium 200-mg tablets administered after a high-fat meal. Depending on results after the high-fat meal, a single dose of Fospropofol Disodium 200-mg tablets may be administered after a moderate-fat meal. The PK profile will be determined for fospropofol and propofol after all visits.
  Part 2 will comprise a separate cohort of 18-24 subjects (at least 50% women). Fospropofol Disodium 200-mg capsule administration will consist of 4 capsules (800 mg). The number of Fospropofol Disodium 200-mg tablets will depend on the propofol exposure observed after administration of the 200-mg tablet in Part 1.
  A total of 18-24 subjects will complete the first 2 periods. It is not required that all 24 subjects enter the clinic as a single cohort. For example, it may be preferable for these subjects to be admitted to the clinic as two cohorts of 12.
  Following the second period, half of the subjects (9-12 subjects) who completed Visits 1 and 2 (selected at random), will participate in a third visit at which the same dose of Fospropofol Disodium 200-mg tablets will be administered after a high-fat meal.
  Depending on the results of PK analysis of samples from these subjects, the remaining subjects (9-12 subjects) will receive the same dose of Fospropofol Disodium 200-mg tablets after a moderate-fat meal.

The number of tablets to be administered in Part 2 will be determined based on the PK results after administration of the 200-mg tablet in Part 1, with the goal of selecting the number of 200 mg tablets to be that provide a predicted mean maximal propofol concentration (mean propofol $C_{max}$) similar or somewhat higher (but not lower) than the mean propofol $C_{max}$ observed in Study A16 following an 800-mg dose (4 Fospropofol Disodium 200-mg capsules) administered to healthy adults under fasting conditions. For purposes of this prediction, propofol PK will be assumed to be close-proportional.

Rationale for Dose Selection Part 1:

Part 1 will investigate the PK of fospropofol and propofol after a single tablet of Fospropofol Disodium 200 mg in a cohort of 12 subjects (including at least 6 women).

Extensive Phase 1 single ascending close study was conducted with the Fospropofol Disodium 200-mg capsule. A total of 70 healthy adult men and women received single doses ranging from 200 mg [1 capsule] to 2000 mg [10 capsules]. After a single 200-mg capsule, propofol $C_{max}$ (arithmetic mean, n=10) was 69.43 ng/mL, and propofol $C_{max}$ (geometric mean, n=10) was 61.68 ng/mL. Propofol $AUC_{0-inf}$ (arithmetic mean, n=10) was 118.08 h*ng/mL, and propofol $AUC_{0-inf}$ (geometric mean, n=10) was 112.08 h*ng/mL.

PK studies in dogs using an experimental 600 mg tablet acidified with acetic acid or 3 200 mg capsules under fasted conditions (fasted dogs pretreated with pentagastrin) indicated that propofol $C_{max}$ (arithmetic mean) was approximately 44% higher with tablet closing compared to capsule closing and $AUC_{0-inf}$ was approximately doubled with tablet closing compared to capsule closing. If the enhanced performance of an acidified tablet in man is similar to that in the dog, the predicted propofol $C_{max}$ (arithmetic mean) in man following a 200 mg acidified tablet would be approximately 100 ng/mL and the predicted $AUC_{0-inf}$ (arithmetic mean) would be approximately 236 h*ng/mL. Propofol exposures of this magnitude were observed in Study A16 after a capsule dose of 400 mg and these exposures were well-tolerated.

The expected propofol $C_{max}$ in humans following a 200-mg tablet is well below 1.7 pg/mL (1700 ng/mL), a typical propofol concentration for conscious sedation, and far below the propofol plasma concentrations (greater than 2 pg/mL [2000 ng/mL]) associated with loss of consciousness or respiratory depression. Oei-Lim V L, White M, Kalkman C J, Engbers F H, Makkes P C, Ooms W G. Pharmacokinetics of propofol during conscious sedation using target-controlled infusion in anxious patients undergoing dental treatment. Br J Anaesth 1998; 80:324-31.

Part 2:

The tablet close (number of 200 mg tablets) to be used in Part 2 will be selected to provide a predicted mean propofol $C_{max}$ similar or somewhat higher (but not lower) than the mean propofol $C_{max}$ observed in Study A16 following an 800-mg dose (4 Fospropofol Disodium 200-mg capsules).

After a single dose of 800 mg Fospropofol disodium in Epalex study Study A16 (administered as four 200 mg capsules) propofol $C_{max}$ (arithmetic mean, n=10) was 362.01 ng/mL (range 259.72 to 1352.75 ng/mL). Propofol $AUC_{0-inf}$ (arithmetic mean, n=10) was 558.93 h*ng/mL (range 535.00 to 1077.32 ng/mL). These exposures were well-tolerated. These propofol plasma concentrations are below 1.7 pg/mL (1700 ng/mL), a typical propofol concentration for conscious sedation, and below the propofol plasma concentrations (greater than 2 pg/mL [2000 ng/mL]) associated with loss of consciousness or respiratory depression. Thus, it can be expected that the propofol exposures in Study A18 are well separated from anesthetic exposures associated with respiratory depression. Puri GD. Target controlled infusion total intravenous anaesthesia and Indian patients: Do we need our own data? Indian J Anaesth 2018; 62:245-8.

Sentinel Subjects Because there is no clinical experience with the Fospropofol Disodium 200 mg tablet, 2 sentinel subjects will be employed in Part 1 and 4 Sentinel subjects will be employed in Part 2 of the study.

In Part 1, sentinel closing will be implemented as follows: The 2 sentinel subjects will be closed on the same day. If the close is judged safe and well-tolerated upon clinical safety review by the PI, closing of the remaining 10 subjects in the cohort can occur (no sooner than 20 hours after sentinel closing).

In Part 2, sentinel closing will be used in the first treatment period for subjects receiving Fospropofol Disodium tablets under fasting conditions and in the first treatment period for subjects receiving Fospropofol Disodium tablets after a meal. For each condition, the 2 sentinel subjects will be closed on the same day. Thus, the first set of 2 sentinel subjects will receive Fospropofol Disodium tablets 200 mg fasted [number of tablets TBD], and the second set of 2 sentinel subjects will receive Fospropofol Disodium tablets 200 mg after a high fat meal [the same number of tablets administered in the fasting condition]. For each of these conditions, if the close is judged safe and well-tolerated upon clinical safety review by the PI, closing of the remaining subjects for that condition can occur (no sooner than 20 hours after sentinel closing).

Study Population The total number of subjects to be treated in Part 1 of the study is 12; The total number of subjects to be treated in Part 2 of the study is 18-24. Thus, a total of 30-36 healthy adult male and female subjects (≥18 and ≤55 years of age, with a BMI≥18.5 and 29.9 kg/m²) will be treated over the course of the study.

Subjects who withdraw or are withdrawn from the study before closing may be replaced. Subjects who withdraw or are withdrawn from the study after receiving study drug will not be replaced.

Screening Procedures Screening is to occur within 30 days before administration of study medication. Screening procedures will include demographic data, medical and medication histories, complete physical examination, body measurements, electrocardiogram (ECG), vital signs (blood pressure [BP], heart rate [HR], respiratory rate [RR], pulse oximetry [PO], and oral temperature), hematology, blood chemistry, human immunodeficiency virus (HIV), hepatitis B and C tests, urinalysis, urine drug screen, alcohol breath test, urine cotinine test, and urine pregnancy test for women.

Confinement and Washout For Part 1 of the study, all 12 subjects will be confined to the study site for at least 14 hours before closing and for at least 10 hours after closing. However, the duration of confinement and frequency of monitoring may be increased for safety reasons.

In Part 1 when sentinel subjects are used, 4 sentinel candidates will be confined to the study site for at least 14 hours before sentinel closing. Of these, 2 subjects will be randomly selected as sentinels and 2 will serve as standby sentinels. Preclose safety monitoring procedures will be the same for sentinel standbys as for chosen sentinels. The 2 standby subjects not selected as sentinels will continue confinement in the clinic and will be closed with the remaining 8 subjects, no sooner than 20 hours after closing of the sentinels (without need for repeating check-in procedures). Thus, the total confinement period for the sentinel standby subjects may last approximately 20-24 hours longer than for the sentinel subjects.

In Part 2 of the study a total of 18-24 subjects will be randomized to one of 2 treatment sequences. Each subject will receive the tablets and the capsules according to the assigned treatment sequence. The same procedures for sentinel subjects used in Part 1 will also be followed in Part 2.

Study Drug and Dosage Form The Fospropofol Disodium capsule 200 mg nominal close is formulated for oral administration in hydroxypropyl methylcellulose (HPMC) capsules. Each HPMC capsule contains 200 mg of fospropofol disodium corrected for water and no inactive ingredients.

The Fospropofol Disodium tablet 200 mg strength is formulated for oral administration in a tablet. Each tablet contains 200 mg of fospropofol free acid provided as 230.5 mg of fospropofol disodium corrected for water. The tablet is acidified with citric acid or with tartaric acid.

Study Drug The sequence randomization(assignment to one of two sequences) Administration will be performed according to a schedule generated using validated computer software.

Study Part 1

In Part 1 of the study, a single dose of the Fospropofol Disodium tablet 200 mg strength will be administered to 12 subjects. Two sentinel subjects will be closed and observed for 20 hours before the remaining 10 subjects are treated. No food will be allowed from at least 10 hours before closing until at least 4 hours after closing.

Study Part 2

In Part 2, the crossover portion of the study, 24 subjects will be randomized to one of two treatment sequences. The sequence randomization will be performed according to a schedule generated by the CRO using validated proprietary computer software.

In the first period of Part 2, the 2 sentinel subjects assigned to receive 200-mg Fospropofol Disodium tablets under fasting conditions (number of tablets TBD) will be closed and observed for 20 hours before the remaining subjects are treated.

In the third period of Part 2, the 2 sentinel subjects assigned to receive 200-mg Fospropofol Disodium tablets after a high-fat meal (the same number of tablets as in the fasting condition [TBD]) will be closed and observed for 20 hours before the remaining the subjects are treated.

For closing in all conditions, the study drug will be administered with water at ambient temperature in the amount of approximately 240 mL [8 oz]. Except for water administered with study drug, no fluids will be allowed from 1 hour before closing until 1 hour after closing.

For safety reasons, subjects will be required to remain seated or semi-reclined and avoid sleeping for 1 hour before and for the first 4 hours after drug administration.

Washout Not applicable to Part 1. Part 2 will employ a washout period of at least 1 week between closing days.

Inclusion Criteria Subjects must meet all of the following criteria to be included in the study:

1. Male or female
a) Nonsmoker (no use of tobacco products within 3 months prior to screening),
b) ≥18 and ≤55 years of age
c) BMI≥18.0 and 29.9 kg/m$^2$
d) body weight≥50.0 kg for male and ≥45.0 for female subjects.

2. Healthy as defined by:
e) The absence of clinically significant illness and surgery within 4 weeks prior to closing. Subjects with a history of vomiting will be carefully evaluated. Inclusion of such subjects is at the discretion of the PI.
f) The absence of clinically significant history of neurological (other than migraine), endocrine, cardiovascular, pulmonary, hematological, immunologic, psychiatric, gastrointestinal, renal, hepatic, and metabolic disease.
g) The absence of clinically significant history of sleep apnea 3. Ability to comprehend the nature of the study, as assessed by the PI or delegate. Capable of giving written informed consent.
Able to communicate effectively with clinic staff.

4. Ability to fast for at least 14 hours and consume standard meals during the study.

5. Availability to volunteer for the entire study duration and willing to adhere to all protocol requirements.

6. Female subjects must agree not to be nursing at any time during the study and until 30 days after study drug administration.

7. Female subjects must fulfill at least one of the following:
a) Surgically sterile, defined as women who have had a tubal ligation, hysterectomy, or bilateral oophorectomy at least 6 months prior to drug administration.
b) Post-menopausal, defined as absence of menses for at least 12 months prior to drug administration.
c) Women who are sexually active and at risk for pregnancy must agree to avoid pregnancy and use medically acceptable method of contraception from at least 30 days prior to administration of study drug until 30 days after study drug administration.
Medically acceptable methods of contraception include hormonal contraception, hormonal or non-hormonal intrauterine device, double barrier method (simultaneous use of male condom with intravaginally applied spermicide and diaphragm or cervical cap), or male partner vasectomy at least 6 months previously. Complete abstinence alone can be used as a method of contraception.

8. Male subjects who are not vasectomized for at least 6 months, and who are sexually active with a non-sterile female partner (see definitions of surgically sterile and post-menopausal above) must be willing to use one of the following acceptable contraceptive methods throughout the study and for 90 days after the study drug administration:
   a) Simultaneous use of male condom and, for the female partner, intrauterine contraceptive device with or without hormone release (placed at least 4 weeks previously).
   b) Simultaneous use of male condom and, for the female partner, hormonal contraception.
   c) Simultaneous use of male condom and, for the female partner, intravaginally applied spermicide with diaphragm or cervical cap.

Exclusion Criteria Subjects to whom any of the following applies will be excluded:
1. Any clinically significant abnormality at physical examination, clinically significant abnormal laboratory test results or positive serologic test for hepatitis B, hepatitis C, or HIV found during medical screening. (Subjects with positive serology for hepatitis C and negative HCV RNA are eligible at the discretion of the PI.)
2. Positive urine drug screen, alcohol breath test, urine cotinine test at screening (or at clinic check-in)
3. For women, positive urine pregnancy test at screening or positive serum pregnancy test at clinic check-in.
4. History of severe allergic reactions (e.g. anaphylactic reactions, angioedema), hypersensitivity or idiosyncratic reaction to fospropofol, propofol, excipients or related substances.
5. Individuals having undergone any major surgery within 6 months prior to the start of the study, unless deemed otherwise by the PI.
6. Clinically significant ECG abnormalities (e.g., QTcF>450 msec in males or ≥470 msec in females) or vital sign abnormalities (systolic BP lower than 95 or over 140 mmHg, diastolic BP lower than 55 or over 90 mmHg, or HR less than 50 or over 100 bpm) at screening.
7. Oxygen saturation by oximetry less than 93% at screening
8. History of significant alcohol abuse within 1 year prior to screening or regular use of alcohol of more than 14 units of alcohol per week (1 unit=150 mL of wine, 360 mL of beer, or 45 mL of 40% alcohol) within 6 months prior to the screening visit.
9. History of significant drug abuse within one year prior to screening or use of hard drugs (such as cocaine, phencyclidine [PCP], crack, opioid derivatives including heroin, and amphetamine derivatives) within 1 year prior to screening.
10. Participation in an interventional clinical research study involving the administration of an investigational or marketed drug or device within 30 days prior to administration of study drug or administration of a biological product in the context of a clinical research study within 90 days prior to administration of study drug. Concomitant participation in an investigational study involving no drug or device administration is permitted provided obligations associated with the concomitant participation are not expected to interfere with procedures and obligations of the present study.
11. Use of medication other than topical products without significant systemic absorption:
   a) prescription medication (excluding hormonal contraception) within 14 days prior to the first closing;
   b) over-the-counter products and natural health products (including herbal remedies such as St. John's wort, homeopathic and traditional medicines, probiotics, food supplements such as vitamins, minerals, amino acids, essential fatty acids, and protein supplements used in sports) within 7 days prior to the first closing, with the exception of the occasional use of acetaminophen (up to 2 g daily);
   c) a depot injection or an implant of any drug within 3 months prior to the first closing, excluding hormonal contraception.
12. Donation of plasma within 7 days prior to closing. Donation or loss of blood (excluding volume drawn at screening) of 50 mL to 499 mL of blood within 30 days, or more than 499 mL within 56 days prior to the first closing.
13. Hemoglobin<128 g/L (<12.8 g/dL) for men or 115 g/L (<11.5 g/dL) for women at screening.
14. Intolerance to and/or difficulty with blood sampling through venipuncture.
15. Abnormal diet patterns (for any reason) during the 4 weeks preceding the study, including fasting, high protein diets etc.
16. Employee or immediate relative of an employee of Epalex Corporation, or its affiliates or partners.

Study Restrictions Subjects will be asked to refrain from using products that may potentially affect their safety and/or the PK of the study drug. Main study restrictions include:
   Prescription medication (excluding hormonal contraception) from 14 days prior to closing until after the last PK blood sample collection of the study
   Over-the-counter products from 7 days prior to closing until after the last PK blood sample collection of the study
   Natural health products from 7 days before closing until after the last PK blood sample collection
   Food containing poppy seeds within 24 hours prior to admission
   Alcohol-based products from 48 hours prior to closing until after the last PK blood sample collection
   Subjects will be required to abstain from using soft or hard drugs (including marijuana and tetrahydrocannabinol (THC)-containing products) or any tobacco or nicotine products from screening and throughout the study.

PK Sampling Time Points In Part 1 of the Study a total of 14 blood samples of 6 ml each will be collected for analysis of fospropofol and propofol PK. The PK samples will be collected at the following time points: Preclose (within 120 minutes before closing) and post-close at 5, 10, 20, 30, and 45 minutes and 1, 1.5, 2, 3, 4, 5, 6, and 9 hours after closing.
   In Part 2 of the study a total of 14 blood samples of 6 ml each will be collected for analysis of fospropofol and propofol PK. However, the sampling schedule to be used in Part 2 will be informed by the PK results from Part 1.

Safety Monitoring Medical Surveillance and AE Monitoring
   Subjects will be monitored throughout the study by clinic staff for AEs.

Subjects should be continuously monitored for early signs of hypotension, apnea, airway obstruction, and/or oxygen desaturation. As a precautionary measure, for closing in Part 1, a person trained in airway management and not involved in any critical study procedures will be on site to monitor the subjects from approximately 30 minutes prior to each closing and until 9 hours after administration of the study medication to the last subject.

Additionally, the clinic will be staffed and equipped to manage hypotension, hypoxemia, and airway obstruction and/or apnea, including cardiac dysrhythmias or bradycardia known to occur with sedative-hypnotic agents.

For both Part 1 and Part 2 of the study, the PI or medically qualified delegate will be on site approximately 30 minutes prior to each closing and until 6 hours after administration of the study medication to the last subject, and available on call for the remainder of the study.

Continuous Cardiac Telemetry and Pulse Oximetry

In Part 1 of the study, to ensure the absence of any clinically significant cardiac arrhythmia or other abnormality at baseline (before closing), cardiac telemetry will be performed from at least 10 hours before closing and will be continued for approximately 6 hours after closing (or until clinic discharge, at the Investigator's discretion if necessary for safety reasons) to monitor for any cardiac effects of the study drug. Subjects with any clinically significant ECG abnormality at baseline (before closing) will be excluded.

Pulse oximetry will be continuously monitored over the same time course.

12-lead ECG

A 12-lead ECG will be performed at screening and on Day 1 before closing and at check-out. Corrected QT interval (QTc) will be recorded.

Vital Signs

With the subject in a seated or semi-reclined position, BP, HR, RR will be recorded at screening, preclose (within 120 minutes before closing), and within 5 minutes before the PK blood draws at approximately 10, 20, 30, and 45 minutes and 1, 1.5, 2, 3, 4, 6, and 9 hours after closing, as well as 2.5 hours after closing (no PK draw). Pulse oximetry values will be recorded from the continuous monitor at approximately the same time points.

Level of Alertness and Sedation

Level of sedation will be assessed using the Modified Observer's Assessment of Alertness/Sedation (MOAA/S) Score. Chernik D A, Gillings D, Laine H, et al. Validity and reliability of the Observer's Assessment of Alertness/Sedation Scale: study with intravenous midazolam. J Clin Psychopharmacol 1990 Aug. 10(4):244-51. Sedation (MOAA/S score) will be recorded within 15 minutes before closing, at 15 minutes after closing, at approximately 15-minute intervals until 3 hours after closing, and at approximately 30-minute intervals thereafter until approximately 9 hours after closing, provided that the subject had a score of 5 on at least the 3 consecutive MOAA/S scores immediately prior to the 3-hour timepoint. Subjects who have not demonstrated 3 consecutive MOAA/S scores of 5 immediately prior to the 3-hour timepoint will continue with MOAA/S assessments at 15-minute intervals until they demonstrate 3 consecutive MOAA/S scores of 5, with MOAA/S scores recorded at 30-minute intervals thereafter until approximately 9 hours after closing. Cohen LB. Clinical trial: a close-response study of fospropofol disodium for moderate sedation during colonoscopy. 2008; Aliment Pharmacol Ther 27, 597-608. Subjects who do not have a MOAA/S score of 5 at 9 hours after closing will remain in the clinic until they have reached a MOAA/S score of 5 and are determined by the PI to be awake, alert, and safe to leave (even if the time in the clinic extends beyond 9 hours).

Laboratory Assessments

In Part 1 of the study, Hematology, biochemistry, and urinalysis will be assessed at screening and at check-out.

In Part 2 of the study, Hematology, biochemistry, and urinalysis will be assessed at screening and at check-out at each treatment visit.

Hepatitis B (HBs Ag), Hepatitis C (HCV) antibody, and HIV antigen and antibody detection will be performed at screening.

Alcohol breath test, urine cotinine test, and urine drug screen will be performed at screening and at each clinic check-in. For women, a urine pregnancy test will be performed at screening, and a serum pregnancy test will be performed before closing (at each clinic check-in or in the morning of Day −1).

Physical Examination

A complete physical examination will be performed at screening. A brief physical examination will be performed at check-in and at check-out.

Exploratory Evaluations At 2 hours (±15 minutes) after closing, the PI (or designate) will ask the subject several mental status questions, such as the following: What is your name? Where are you now? What month or season is it? The subject's answers will not be recorded. However, based on the subject's responses, the PI (or designate) will give a subjective assessment as to whether 2 hours after closing the subject would be able to provide a reliable report of hypothetical migraine pain or other symptoms. The assessment will be recorded in the following categorical format:

Yes (In my judgment, if this subject had a migraine headache, in his/her present condition he/she would be able to provide a reliable report of his/her migraine pain or other symptoms.)

No (In my judgment, if this subject had a migraine headache, in his/her present condition he/she would not be able to provide a reliable report of his/her migraine pain or other symptoms.)

Uncertain (In my judgment, if this subject had a migraine headache, in his/her present condition he/she it is not clear whether this subject would be able to provide a reliable report of migraine pain or other symptoms.)

Adverse Events AEs will be evaluated regarding seriousness, severity, and relationship to study drug.

Some degree of sedation is an expected and potentially therapeutic effect of the study drug. Therefore, sedation rated by the PI as mild or moderate will be considered an expected AE.

Check-out/Early Termination Procedures The following procedures will be done at each clinic check-out or for early termination (when applicable): hematology, blood chemistry, urinalysis, brief physical examination, vital signs, pulse oximetry, 12-lead ECG, oral temperature, AE monitoring.

Subjects will be instructed not to drive or operate heavy machinery for 24 hours after closing.

Analytical Method Fospropofol and propofol will be analyzed in plasma samples using validated LC/MS/MS methods. Additional plasma samples may be drawn and stored for possible future bioanalysis of metabolites or other analytes.

Pharmacokinetic Parameters The following PK parameters will be calculated for both fospropofol and propofol plasma concentrations: $AUC_{0-t}$, $AUC_{0-inf}$, $C_{max}$, residual area, $T_{max}$, $t_{1/2el}$, $K_{el}$, Cl/F, Cl/F/kg, Vd/F, and Vd/F/kg.

Statistical Analyses A complete description of the statistical analyses to be performed for the safety, tolerability, and PK data will be presented in a Statistical Analysis Plan (SAP).

Safety and Tolerability

Safety and tolerability data will be reported using descriptive statistics. Summary statistics for treatment-emergent adverse events (TEAEs) will be reported by close. Changes from baseline values in vital signs, ECG, and clinical laboratory parameters will be reported by close.

PK

Interim bioanalysis and PK analyses for propofol are to be performed after completion of Part 1. These results will be used to inform the PK sampling schedule for Part 2.

Summary statistics will be used to describe the PK profile of both fospropofol and propofol for the Fospropofol Disodium 200 mg tablet (Part 1). Summary statistics will be used to describe the PK profile of both fospropofol and propofol for each of the three treatments in Part 2. Summary statistics will include at minimum arithmetic and geometric means for $AUC_0$-t, $AUC_{0-inf}$, $AUC_{0-2h}$, and $C_{max}$. $T_{max}$ will be characterized by median and range.

Pair-wise comparisons among the 3 treatments in Part 2 will be undertaken using log-transformed data to calculate the ratio of geometric means with 90% CI for PK parameters including at minimum Cmax, $AUC_{0-2h}$, AUC(0-T), and AUC(0-inf). Tmax values will be compared using a non-parametric (Wilcoxon) test. (Details to be provided in the SAP.) All inferential statistical analyses will be interpreted, in an exploratory sense only, at an alpha level of 5% for statistical significance.

Example A19—Study A19

Safety-tolerability, Pharmacokinetics, and EEG Photoparoxysmal Response Following Single Doses of Fospropofol Disodium Administered to Photosensitive Adult Subjects With Epilepsy Study Drug Fospropofol Disodium Study Phase and Type Phase 1b Single-center, double-blind, placebo-controlled, randomized 4-sequence, 4-period, 4-treatment, single ascending-close crossover trial Objectives Primary Objectives To describe the safety-tolerability of single oral ascending doses of fospropofol disodium administered orally at 3 close levels compared with placebo in adult photosensitive subjects with epilepsy To describe the pharmacokinetics (PK) of fospropofol and propofol after single ascending doses of fospropofol disodium administered orally at 3 close levels in adult photosensitive subjects with epilepsy Secondary Objectives To evaluate single ascending oral doses of fospropofol disodium at 3 close levels compared with placebo regarding effects on the EEG epileptiform photoparoxysmal response induced by intermittent photic stimulation (IPS) as a measure of potential antiepileptic activity.

To explore the effect of fospropofol disodium on PK of concomitant antiseizure medications (ASMs) as an aid to interpreting safety-tolerability of fospropofol disodium.

Study Design This is a Phase 1b, double-blind, placebo-controlled, randomized 4-sequence, 4-period, 4-treatment, single ascending-close crossover trial in subjects with epilepsy who have a known stable IPS-induced photoparoxysmal response on EEG. Potential subjects will be screened to ensure they have a stable photosensitivity range. After screening, subjects who enter the study will return for 4 treatment visits (Visits 1, 2, 3, and 4), each lasting approximately 1 day (no overnight stays). At each visit, subjects will receive 1 dose of fospropofol disodium at one of 3 close levels (200 mg, 400 mg, or 800 mg) or 1 dose of placebo.

Treatment visits will be separated by a minimum washout period of 7 days (maximum 4 weeks). Thus, the duration of subject participation is expected to range from approximately 4 weeks to a maximum of approximately 16 weeks.

Subjects will be randomly allocated to 1 of 4 treatment sequences (in blocks of 4 subjects) comprising the 3 ascending fospropofol disodium close levels interspersed with a placebo treatment at Visit 1, 2, 3, or 4 (see Randomization below). Patients and examining physicians will be blinded to the position of the placebo visit in the sequence.

To assess the photosensitivity range of the photoparoxysmal response, subjects will be exposed to IPS—i.e., flickering diffuse white light—at a range of frequencies. The individual's photosensitivity range will be determined as the difference between the highest and lowest flash rates that consistently elicit a generalized photoparoxysmal EEG response.

At each treatment visit, the photosensitivity range will be assessed before closing and at 15 and 30 minutes, and 1, 2, 3, 4, and 6 hours after closing. For each of the 3 close levels, the photosensitivity range after treatment with active drug will be compared with the photosensitivity range after placebo administration. During each of the 4 treatment visits (4 in-clinic treatment days), blood samples will be drawn to characterize the PK of fospropofol disodium and propofol, assess levels of ASMs, and to assess laboratory safety parameters.

Depending on responses, additional postclose time points for IPS assessments may be added during Treatment Visit 1, 2, 3, or 4. Subjects may be brought back for 1 or 2 additional visits to evaluate an intermediate fospropofol disodium close level, to revisit a particular close, or to evaluate different PK time points. In such cases, the fospropofol disodium close at any one session will not exceed 800 mg, and the total close given to an individual subject over the course of the entire study will not exceed 2000 mg, which was the highest single dose administered in the Sponsor's previous Phase 1a study in healthy volunteers (Study A16)

Justification for Dose Selection of the closes for this study is based on the results of the Sponsor's prior Phase 1a study in healthy volunteers (Study A16).

The highest close in the present study, 800 mg, was well-tolerated in Study A16. The 800-mg dose was also selected as the close to be used in the ongoing Phase 1b single-close study in subjects with migraine. In the present study, subjects will receive single doses of 200, 400, and 800 mg fospropofol disodium on separate occasions separated by at least 7 days of washout between closes. Based on PK results from Study A16, accumulation of either fospropofol or its propofol metabolite is not expected. In any case, as noted above, the total close received by an individual subject completing all treatments in the current study will not exceed 2000 mg.

Subject Selection Approximately 4 to 8 subjects will be enrolled in an effort to end the study with a minimum of 4 subjects completing all 4 treatment periods (i.e., 4 subjects with evaluable data for placebo and all of the 3 fospropofol disodium close levels).

Inclusion Criteria Subjects must meet all of the following criteria at screening to be enrolled in the study:

1. Written informed consent approved by the Institutional Review Board (IRB) given before any study-related procedures are performed
2. Male or female, ≥18 and ≤60 years of age at the time of signed informed consent
3. Body mass index (BMI)≥18.0 and ≤40.0 kg/m$^2$ and body weight ≥50.0 kg for men and ≥45.0 kg for women. Subjects with BMI up to 45 kg/m$^2$ may be considered at the discretion of the Investigator with agreement of the Sponsor.
4. A diagnosis of epilepsy for which subjects have been treated on a stable regimen of 0-3 concomitant ASMs for at least 30 days before screening.
5. A diagnosis and history of photoparoxysmal response on EEG (confirmed by prescreening, if necessary).
6. At least 3 EEGs performed during the screening visit must have a reproducible IPS-induced photoparoxysmal response on EEG of ≥3 points on a frequency assessment scale in at least 1 eye condition (eyes closing, eyes closed, or eyes open).
7. Subjects in otherwise good health (with the exception of epilepsy), as determined by the Investigator via the medical history, a physical examination, and screening laboratory investigations.
8. Female subjects must fulfill at least one of the following:
   f) Surgically sterile, defined as women who have had a tubal ligation, hysterectomy, or bilateral oophorectomy at least 6 months prior to screening.
   g) Post-menopausal, defined as absence of menses for at least 12 months prior to screening.
   h) Women who are sexually active and at risk for pregnancy must agree to avoid pregnancy and use a medically acceptable method of contraception from at least 30 days prior to screening until 30 days after study drug administration.
   Medically acceptable methods of contraception include hormonal contraception, hormonal or non-hormonal intrauterine device, double barrier method (simultaneous use of male condom with intravaginally applied spermicide and diaphragm or cervical cap), or male partner vasectomy at least 6 months previously. Complete abstinence alone can be used as a method of contraception.
9. Male subjects who are not vasectomized for at least 6 months and who are sexually active with a non-sterile female partner (see definitions of surgically sterile and post-menopausal above) must agree to use one of the following acceptable contraceptive methods throughout the study and for 90 days after the study drug administration Complete abstinence alone can be used as a method of contraception.
   i) Simultaneous use of male condom and, for the female partner, intrauterine contraceptive device with or without hormone release (placed at least 4 weeks previously)
   j) Simultaneous use of male condom and, for the female partner, hormonal contraception
   k) Simultaneous use of male condom and, for the female partner, intravaginally applied spermicide with diaphragm or cervical cap
10. As assessed by the Investigator, able to comprehend the nature of the study, capable of giving written informed consent/assent to participate in the study in accordance with ICH Good Clinical Practice (GCP) guidelines, and able to communicate effectively with clinic staff
11. Agrees to refrain from strenuous exercise the day before screening and during the day prior to each treatment day Exclusion Criteria Subjects are not eligible for this study if one or more of the following conditions exist:

1. History of non-epileptic seizures (e.g., metabolic, structural, or pseudo-seizures).
2. Female subjects who are pregnant (positive serum pregnancy test at screening) or lactating.
3. Individuals of reproductive potential who do not agree to use effective birth control methods (as defined in the inclusion criteria above).
4. An active central nervous system (CNS) infection, demyelinating disease, degenerative neurological disease, or any CNS disease deemed to be progressive during the course of the study that may confound the interpretation of the study results.
5. Clinically significant active liver disease, *porphyria* or with a family history of severe hepatic dysfunction indicated by abnormal liver function tests greater than 3 times the upper limit of normal (AST and ALT).
6. Positive serologic test for hepatitis B, hepatitis C, or HIV at screening. (Reflex HCV RNA testing will be performed for any positive hepatitis C screening test. If the results of reflex testing are negative, the subject may be deemed eligible for the study.)
7. Any clinically significant laboratory abnormality that in the opinion of the Investigator would exclude the subject from the study. Laboratory tests may be repeated at the Investigator's discretion.
8. Any clinically significant psychiatric illness or psychological or behavioral problems that in the opinion of the Investigator would interfere with the subject's ability to participate in the study.
9. History of any of the following:
   l) Significant alcohol abuse within 1 year prior to screening or regular use of alcohol within 6 months prior to screening (more than 14 units of alcohol per week [1 unit=150 mL of wine, 360 mL of beer, or 45 mL of 40% alcohol]), or m) Significant drug abuse or use of cocaine, phencyclidine [PCP], crack, opioid derivatives including heroin, or amphetamine derivatives, or similar drugs within 1 year prior to screening. Use of marijuana or tetrahydrocannabinol [THC]-containing products is permitted unless in the Investigator's opinion such use would impact the safety of the subject or interpretation of the study results. If marijuana is used, use must be consistent throughout the study.

10. Any of the following at screening:
n) A positive alcohol breath test or
o) A positive urine drug screen, unless consistent with an ongoing prescription drug as documented by the Investigator. Detectable levels of marijuana (THC or metabolites) in the urine drug screen are not exclusionary if in the Investigator's documented opinion the positive test does not signal a clinical condition that would impact the safety of the subject or interpretation of the study results.
11. Diagnosis of sleep apnea.
12. Subjects who have participated in any other trials involving an investigational product or device within 30 days before screening.
13. Subjects receiving more than 3 concomitant ASMs for epilepsy.
14. Subjects who have intolerance to and/or difficulty with blood sampling through venipuncture.
15. Employees or immediate families (defined as spouse, significant-other, parent, child, or sibling, whether adopted or biologic) of an employee of Epalex Corporation, its affiliates, or partners; Investigator or study center personnel directly affiliated with this study and/or their immediate families.
16. Score of >0 on the Sheehan Suicidality Tracking Scale (S-STS) for a recall period of 30 days prior to screening.

Study Drug and Dosage Form Fospropofol disodium is formulated for oral administration in an appropriate number of powder-filled hydroxypropyl methylcellulose (HPMC) capsules. Each HPMC capsule contains 200 mg of fospropofol disodium (uncorrected for sodium content) and no inactive ingredients.

Dose Levels Each subject will receive 3 ascending oral doses of fospropofol disodium (200 mg, 400 mg, and 800 mg) on 3 different days, interspersed according to a randomization scheme with 1 day on which they will receive placebo (see Randomization).

Administration of Study Drug Subjects will receive 1 dose of study drug at approximately 8:30 to 9:00 am on each treatment day.

Each close (4 capsules) will be administered with water at ambient temperature in the amount of approximately 240 mL (8 oz). The amount of water may be increased to approximately 355 mL (12 oz) if needed.

Randomization Subjects will be randomly allocated in blocks of 4 subjects to 1 of 4 treatment sequences (A, B, C, or D) according to the scheme shown below:

| Sequence | Treatment Visits | | | |
|---|---|---|---|---|
| | Visit 1 | Visit 2 | Visit 3 | Visit 4 |
| A | Placebo | FOSPROPOFOL DISODIUM 200 mg | FOSPROPOFOL DISODIUM 400 mg | FOSPROPOFOL DISODIUM 800 mg |
| B | FOSPROPOFOL DISODIUM 200 mg | Placebo | FOSPROPOFOL DISODIUM 400 mg | FOSPROPOFOL DISODIUM 800 mg |
| C | FOSPROPOFOL DISODIUM 200 mg | FOSPROPOFOL DISODIUM 400 mg | Placebo | FOSPROPOFOL DISODIUM 800 mg |
| D | FOSPROPOFOL DISODIUM 200 mg | FOSPROPOFOL DISODIUM 400 mg | FOSPROPOFOL DISODIUM 800 mg | Placebo |

Screening Procedures Prescreening
Most potential subjects will have known photosensitivity based on previous evaluation of their photoparoxysmal response on EEG via IPS. If a potential subject has not had an EEG showing a photoparoxysmal response within the past year, or if their ASMs have been adjusted since the last EEG, the subject may be asked to come to the clinic for a 1-hour prescreening EEG with IPS to determine preliminary eligibility for the trial. In this case, the subject would be asked to give written informed consent for the prescreening assessments. If the subject has a reproducible IPS-induced photoparoxysmal response on EEG of ≥3 points they will be scheduled to return for the screening visit.

Screening Visit
The screening visit is to occur within 30 days prior to the first closing visit and consists of obtaining informed consent, confirming that the subject meets all inclusion and exclusion criteria, and collecting baseline assessments.

Screening procedures
Screening procedures will comprise written informed consent and review of inclusion/exclusion criteria, including demographic data; medical history; medication history; full neurological and physical examination; body measurements (height, weight, BMI); 12-lead ECG; laboratory assessments (hematology, blood chemistry, HIV, hepatitis B and C serology, serum pregnancy test for women of childbearing potential; ASM levels; urinalysis, urine drug screen; alcohol breath test); the Sheehan Suicidality Tracking Scale; pulse oximetry and vital signs (BP, HR, RR, temperature).

Medication history will be obtained by interview and will include drug allergies and history of epilepsy-related medications during the month prior to screening.

Baseline IPS Assessment and Determination of Most Sensitive Eye Condition

At the screening IPS assessment, all eye conditions will be assessed (eyes closing, eyes closed, or eyes open). The EEG is to be read by The Epilepsy Study Consortium, and the results must be available before the subject can return for the first treatment visit. At least 3 of the EEGs performed during the screening visit must demonstrate an IPS-induced photoparoxysmal response on EEG, defined as a change of ≥3 points on a frequency assessment scale in at least 1 eye condition. The most sensitive eye condition will be determined after the screening visit by averaging the range over all of the time points.

Treatment Visits (1, 2, 3, and 4) The subject should present to the epilepsy center for treatment visits at approximately 7 am, in time for preclosing procedures to be completed so that closing can occur at approximately 8:30 to 9 am.

The following procedures should be performed before closing (see Schedule of Events):

Urine pregnancy test for all female subjects of childbearing potential.

Drug and alcohol screen.

Sheehan-STS.

Confirm that inclusion/exclusion and study restriction criteria are met.

Place EEG leads for IPS testing of the of the EEG epileptiform photoparoxysmal response.

Start continuous monitoring of pulse oximetry at least 15 minutes before the IPS assessment; record $SPO_2$ values from the continuous monitor within 15 minutes before the IPS assessment.

Assess vital signs within 15 minutes before the IPS assessment.

Assess baseline sedation level with a visual analog scale within 15 minutes before the IPS assessment.

Conduct preclose IPS session in the most sensitive eye condition (determined at screening).

Collect blood samples for preclose EP103/propofol and ASM levels.

Postclose assessments should be performed in the following order (see Table 1):

SpO2 values recorded from the continuous monitor.

Vital signs.

Sedation assessed with the VAS-S.

IPS sessions in the most sensitive eye condition.

Blood samples for PK of EP103 and ASM levels.

AEs.

IPS Assessments IPS assessments will be performed at prescreening (if applicable), at screening, and at each treatment visit. At treatment visits, IPS sessions will be performed in the most sensitive eye condition, as determined at screening.

Prescreening, screening, and preclose IPS assessments will begin at approximately 8:00 to 8:30 am. Postclose IPS assessments will begin at 15 and 30 minutes and at 1, 2, 3, 4, and 6 hours after closing (5 minutes).

Prescreening and Screening

The EEG is to be read by The Epilepsy Study Consortium, and the results must be available before the subject can return for the first treatment visit. At least 3 of the EEGs performed during the screening visit must demonstrate an IPS-induced photoparoxysmal response on EEG, defined as a change of ≥3 points on a frequency assessment scale in at least 1 eye condition. The most sensitive eye condition will be determined after the screening visit by averaging the range over all of the time points.

Postclose

IPS sessions will be repeated in the most sensitive eye condition at 15, and 30 minutes and 1, 2, 3, 4, and 6 hours after closing.

PK Sampling Blood samples will be collected at each treatment visit for analysis of fospropofol and propofol PK, and separate samples will be drawn for assay of concomitant ASM levels.

Blood samples for fospropofol disodium/propofol PK and ASM levels will be drawn immediately after the end of the preclose IPS session (within 30 minutes before closing), at 10 minutes after closing, and immediately after the end of each postclose IPS session (within 10 minutes after the start of the IPS measurement), with the exception that there will be no PK blood draw at 3 hours postclose. In case of a serious adverse event (SAE) or early withdrawal, if possible, a PK blood draw should be collected at or near the time the subject reports the SAE or at the time of withdrawal.

Sample collections done outside the predefined time windows will not be considered as protocol deviations, since actual postclose sampling times will be used for PK and statistical analyses.

The time points of the PK sample collection may be changed, or an additional postclose time point may be added during Treatment Visit 1, 2, 3, or 4 or an additional visit. However, the total number of PK time points (including preclose) will not exceed 9 per visit.

Total Blood Volume Drawn The total amount of blood collected from each subject over the course of this study will not exceed 540 mL and will not exceed 10.5 mL/kg over an 8-week period. In subjects of low body weight, the period between study visits may be extended (to up to 4 weeks) to meet this criterion.

Adverse Events Subjects will be instructed to inform clinical personnel of any potential AEs, i.e., untoward medical symptoms and/or events that may arise from arrival at the clinic for check-in until clinic discharge.

Some degree of sedation is an expected and potentially therapeutic effect of the study drug. Although sedation, including events described as feeling "drowsy," "sleepy," "relaxed," etc., will be expected, such terms if expressed by the subject will be recorded as AEs, and severity will be rated by the site Investigator as mild, moderate, or severe. Because subjects will be allowed to sleep after closing if desired, sleep itself will not be considered an AE.

Stopping Rules The study will be stopped if any 2 subjects experience the same type of worsening (1, 2, or 3 below), or a total of 3 subjects demonstrate any of the following 3 criteria for worsening:

If a subject has a widening of the photosensitivity range by more than 3 points on 2 consecutive occasions after closing as compared to the screening day, the photic stimulation will be terminated, and the subject will be unable to participate in further testing that day.

If a subject experiences a generalized tonic-clonic seizure during any study day, and they have not had a generalized tonic-clonic seizure in the 6 months prior to enrollment, the study will be terminated for that subject. If any subject experiences a generalized tonic-clonic seizure during photic stimulation, the study will be terminated for that subject, and they will not be permitted to participate in further testing.

If in the opinion of the Investigator a subject has evidence of proconvulsive activity on the EEG after administration of the study medication, (e.g. increase in spike-wave activity) then the study will be terminated for that subject and they will not be permitted to participate in further testing that day.

If in the opinion of the Investigator or the Sponsor a subject has evidence of excessive sedation manifest by clinically significant changes in pulse oximetry or changes in vital signs after administration of the study medication, the subject may be permitted to participate in further testing on that day at the discretion of the Investigator. If excessive sedation occurs in any period other than the fourth period, the subject will not proceed to the next period. In such cases, an open-label placebo session(with the subject and the EEG reader blinded) may be substituted for the next planned blinded treatment to ensure that the subject completes the study with at least one IPS under placebo treatment. Any such case will be fully documented in the report and identified in the data analysis.

Analytical Method Fospropofol and propofol concentrations will be analyzed in plasma samples using a validated method.

Statistical Considerations A complete description of the statistical analyses to be performed for the safety, tolerability, and PK data will be presented in a Statistical Analysis Plan (SAP).

Safety and Tolerability

Safety and tolerability data will be reported using descriptive statistics. Summary statistics for TEAEs will be reported. Changes from baseline values in vital signs, ECG, and clinical laboratory parameters will be reported.

PK

Summary statistics will be used to describe the PK profile of both fospropofol and propofol. Summary statistics will include at minimum arithmetic and geometric means for $AUC_{0-t}$, $AUC_{0-inf}$, and $C_{max}$. $T_{max}$ will be characterized by median and range. Exploratory analyses may be performed in an effort to characterize the influence of covariates on PK.

The observed concentrations of concomitant ASMs will be listed and presented as summary statistics. Pharmacokinetic parameters for concomitant ASMs may be calculated, listed, and presented as summary statistics if feasible.

Exploratory analyses may be performed in an effort to characterize the effect, if any, of fospropofol disodium on concentrations of concomitant ASMs. Such analyses could provide useful information as to the potential for drug-drug interactions requiring further evaluation in the subsequent development of fospropofol disodium in the treatment and prevention of epileptic seizures.

Analyses of Photoparoxysmal Response

Descriptive statistics will be presented including the means and standard deviations of photosensitivity range for each subject, for each day. Graphical displays of the data for each subject will allow exploration of inter- and intra-subject variability.

Study Assessments
Intermittent Photic Stimulation Assessments

IPS assessments will be performed at prescreening if applicable, at screening, and at each treatment visit. At treatment visits, IPS sessions will be performed in the most sensitive eye condition, as determined at screening.

Prescreening (if applicable), screening, and preclose IPS assessments will begin at approximately 8:00 to 8:30 am. Postclose IPS assessments will begin at 15 and 30 minutes and at 1, 2, 3, 4, and 6 hours after closing (±5 minutes).

All IPS assessments for screening and during the study will be performed using the systematic protocol designed by Dorothee Kasteleijn. Kasteleijn-Nolst Trenite D G, Marescaux C, Stodieck S, Edelbroek P M, Oosting J. Photosensitive epilepsy: a model to study the effects of antiepileptic drugs. Evaluation of the piracetam analogue, levetiracetam. Epilepsy Res 1996; 25:225-230. The procedure will be as follows:

Photic Stimulator

The IPS will be carried out using the photic stimulator, Grass PS 33, with an un-patterned glass lamp and an intensity of 100 cd/m2/flash.

EEG Measurement with Video Monitoring

IPS session will be recorded with standard 19-21-channel EEG equipment including video monitoring and precise recording of duration and frequency of the flashes (sensor or connection with the photic stimulator).

Electrode Placement:

The international 10-20 system with 2 additional channels, one for eye-movements (to detect changes in eye condition more easily) and one for flash frequencies.

Montage:

A 19-21-channel recording system will be used with a bipolar derivation with emphasis on the parieto-temporal-occipital area (maximum and spreading of EA): The display montage will include T4-T6-02-01-T5-T3 and T4-P4-Pz-P3-T3, apart from 2×4 (8) frontal to occipital leads.

Settings:
  Amplification: 7-10 microV/mm
  High Frequency Filter: 35-70 Hz
  Time constant: 0.3-0.6 sec
  Display speed: 30 mm/sec Methods The lighting will be dimmed but never completely darkened so as to permit observation of the subject, to control ocular fixation, and to note possible clinical ictal phenomena. Subjects will be seated with the photic stimulator at 30-cm distance from the nasion and will be asked to fixate on the center of the lamp.

Throughout the study the flash frequency will be recorded. The eye condition per stimulus for assessment purposes will also be recorded.

In order to enable discrimination between spontaneous and IPS-evoked discharges, at the beginning of the trial day the subject will be assessed for ≥2.5 minutes with eyes open and another 2.5 minutes with eyes closed without any stimulation.

Trains of flashes at constant frequency will be delivered for as close to 4 seconds as possible, and no more than 5 seconds, except when a photoparoxysmal response is elicited, when photic stimulation will be immediately stopped. Intervals between successive flash trains at a given frequency will last for at ≥5 seconds. Determination of the photosensitivity ranges will be assessed with separate trains of flashes of 4-5 seconds duration (or less if generalized epileptic activity occurs).

Flashes will be administered at standard frequencies of 2, 5, 8, 10, 13, 15, 18, 20, 23, 25, 30, 40, 50 and 60 Hz.

At the screening visit, each frequency will be assessed in 3 eye conditions (eyes closing, eyes closed, eyes open), commencing at 2 Hz. As soon as generalized EEG epileptiform activity appears, the stimulation for that particular frequency in a particular eye condition will be instantly terminated. For the other eye conditions, ascending frequencies will be used until generalized epileptiform activity is seen. This will determine the lower threshold frequencies for each eye condition.

Similar assessments will then be carried out starting at 60 Hz and descending through the standard frequencies. Again, the stimulator will be turned off immediately if a generalized response is seen to avoid occurrence of a seizure, and the sequence will be stopped at that point in that specific eye condition. For each eye condition, the upper threshold frequencies are thus determined.

The combination of lower and upper frequencies gives a total of 3 photosensitivity ranges, one per eye condition. If there is any doubt of the interpretation during any of the assessments (for example, blinking during the eyes open condition provoking epileptiform activity), the stimulation in the same eye condition will not be repeated. Photic stimulation will not be carried out between the upper and lower thresholds in order to minimize the risk of inducing a seizure. This method has been found to be the safest, as it prevents elicitation of seizures by avoiding stimulation of the subject at their most sensitive frequencies. The range for each subject will be recorded in the CRF.

Interpretation of Results:

The EEG technician performing the testing will remain blinded throughout the study.

The procedure for determining photosensitivity thresholds described here is interactive and requires immediate decisions by the Investigator during each assessment. The tracings will also be analyzed retrospectively to confirm that the limiting frequencies were the threshold for eliciting a response as defined above.

Blood Sample Collection and Processing

Blood samples will be collected and processed. The total volume of blood drawn from each subject over the course of this study will not exceed 540 mL and will not exceed 10.5 mL/kg over an 8-week period. In subjects of low body weight, the period between study visits may be extended (to up to 4 weeks) to meet this criterion. The maximum total amount of blood drawn includes standard screening and postclose clinical laboratory tests, pharmacokinetic analysis (fospropofol and propofol concentrations), ASM concentrations, and any additional treatment visits for evaluation of intermediate closes, revisiting a particular close, or evaluation of different PK time points.

Sampling for Fospropofol/Propofol PK and ASM Assessment

Blood samples will be collected at each treatment visit for analysis of fospropofol and propofol PK, and separate samples will be drawn for assay of concomitant ASM levels.

Blood samples for fospropofol disodium/propofol PK and ASM levels will be drawn immediately after the end of the preclose IPS session (within 30 minutes before closing), at 10 minutes after closing, and immediately after the end of each postclose IPS session (within 10 minutes after the start of the IPS measurement), with the exception that there will be no PK blood draw at 3 hours postclose. In case of an SAE or early withdrawal, a PK blood draw should be collected, if possible, at or near the time the subject reports the SAE or at the time of withdrawal.

Sample collections done outside the predefined time windows will not be considered as protocol deviations, since actual postclose sampling times will be used for PK and statistical analyses.

The time points of the PK sample collection may be changed, or an additional postclose time point may be added during Treatment Visit 1, 2, 3, or 4 or an additional visit. However, the total number of PK time points (including preclose) will not exceed 9 per visit.

When appropriate, an indwelling i.v. catheter will be used for blood collection to avoid multiple skin punctures. Otherwise, blood samples will be collected by direct venipuncture.

In case of an SAE or early withdrawal, if possible, a PK blood draw should be performed at or near the time the subject reports the SAE or at the time of withdrawal from the study.

Safety Laboratory Assessments

Hematology samples will be drawn at screening and clinic check-out at each treatment visit. Hematology will include complete blood count with differential, hemoglobin, and hematocrit.

Serum chemistry samples will be drawn at screening and clinic check-out at each treatment visit. Serum chemistry assessments will include albumin, alanine aminotransferase, alkaline phosphatase, aspartate aminotransferase, calcium, chloride, carbon dioxide/bicarbonate, creatinine, glucose, phosphate, potassium, sodium, total bilirubin, total protein, and blood urea nitrogen (BUN).

Hepatitis B (HBs Ag), Hepatitis C (HCV) antibody, and HIV antigen and antibody detection will be performed at screening. (Reflex HCV RNA testing will be performed for any positive hepatitis C screening test. If the results of reflex testing are negative, the subject may be deemed eligible for the study.)

Urine for urinalysis will be collected at screening and clinic check-out at each treatment visit. Urinalysis will include macroscopic examination, pH, specific gravity, protein, glucose, ketones, bilirubin, occult blood, nitrite, urobilinogen, and leukocytes. Unless otherwise specified, microscopic examination will be performed on abnormal findings according to standard procedure.

For women, a serum pregnancy test will be performed at screening, and a urine pregnancy test will be performed at clinic check-in at each treatment visit.

A urine drug screen (amphetamines, methamphetamines, barbiturates, benzodiazepines, THC, cocaine, opiates, PCP, 3,4-methylenedioxy-methamphetamine (MDMA), methadone) and an alcohol breath test will be performed at screening and at clinic check-in at each treatment visit.

Other Safety Procedures and Assessments

Medical Surveillance and AE Monitoring

The Investigator is to be on site from approximately 30 minutes prior to each closing until clinic discharge.

The study site is to be staffed to assess and manage potential risks that may occur with sedative-hypnotic agents. Subjects are to be continuously monitored for oxygen desaturation using a pulse oximeter with an alarm, and supplemental oxygen should be available. In addition, although these conditions are unlikely to occur at the selected dose of fospropofol disodium, subjects should be monitored for early signs of hypotension, apnea, or airway obstruction from approximately 30 minutes prior to closing of study drug until clinic discharge. This role may be fulfilled by the Investigator or designee trained in airway management.

Safety parameters, including laboratory results, will be evaluated by the Investigator in the context of clinical trial safety. Any abnormal measurement is to be repeated if judged necessary by the Investigator. Further action to ensure subject safety may be taken at the Investigator's discretion.

Physical Examination

A complete physical and neurological examination will be performed at screening, and abbreviated physical and neurological examinations will be performed at clinic check-out at each treatment visit and at early termination, if applicable.

The complete physical examination at the screening visit will assess any physical abnormalities and will include at a minimum, assessments of the following body systems: general appearance, overall status of the head, ears, eyes, nose, throat (HEENT), neck, abdomen, lymph nodes, skin, cardiovascular/heart, pulmonary, musculoskeletal, and neurological (level of alertness [more detailed mental status not required unless indicated], speech, cranial nerves, motor strength and tone, cerebellar, sensory, deep tendon reflexes, and gait). Investigators should pay special attention to clinical signs related to previous serious illnesses.

Height and weight will also be measured and recorded at the screening visit.

The abbreviated physical examinations will assess general appearance, HEENT, cardiovascular, pulmonary, and neurological status. The neurological examinations are to consist of level of alertness and speech. Abbreviated physical examinations may be limited to recording change/no change from prior examinations, plus focused examination by system as directed by any AEs reported by the subject (where applicable) or any spontaneous symptom/complaint reported by the subject at the time of the examination.

Sheehan Suicidality Tracking Scale

The Sheehan Suicidality Tracking Scale (S-STS) is a prospective suicidality rating scale to be completed by the Investigator or his/her designate. The scale includes 16 questions that allow a longitudinal evaluation of treatment-emergent suicidal ideation and treatment-emergent suicidal behaviors.[25,26] Sheehan D V, Alphs L D, Mao L, et al. Comparative Validation of the S-STS, the ISST-Plus, and the C-SSRS for Assessing the Suicidal Thinking and Behavior FDA 2012 Suicidality Categories. Innov Clin Neurosci 2014; 11:32-46. Sheehan D V, Giddens J M, Sheehan I S. Status Update on the Sheehan-Suicidality Tracking Scale (S-STS) 2014. Innov Clin Neurosci 2014; 11:93-140.

The S-STS will be completed on a paper form at the site and will be administered at the screening visit, at clinic check-in, and at clinic check-out (discharge) for each treatment visit. The recall period at the screening administration will encompass the time period beginning 30 days prior to the screening visit; the recall period at each treatment visit will be the time period since the previous visit. The total score plus the subject's response to each item will be recorded.

At screening, any subject with a response greater than zero to any question must be excluded. At clinic check-in, any subject with a response greater than zero to any question other than Question 2 must be discontinued from the study and the event recorded as an AE, not treatment-emergent. Subjects with a response of 1 ("a little") to Question 2 will be discontinued at the discretion of the Investigator. Subjects with a response greater than 1 on Question 2 will be discontinued.

For each administration of the S-STS, the Investigator will immediately evaluate a subject with any response greater than zero to determine if that subject is at risk of self-harm or suicide. If this is the case, the Investigator must take appropriate measures to ensure the subject's safety and arrange for an appropriate mental health evaluation.

A 12-lead ECG will be performed at screening and at clinic check-out on Treatment Day 4 (or at early termination or check-out of an additional visit, if applicable). Corrected QT interval (QTc) will be recorded.

Pulse oximetry will be recorded at screening and continuously monitored at each treatment visit from at least 15 minutes prior to the preclose IPS assessment until discharge from the clinic. The pulse oximeters to have an alarm set to give both audible and visual notifications when SpO2 drops to 90% or below. If the alarm signals, the subject should be aroused. Nasal oxygen should be considered if SpO2 remains at 90% or lower after stimulation.

At each treatment visit, SpO2 values will be recorded from the continuous monitor within 15 minutes before the preclose IPS assessment, postclose within 10 minutes before each IPS assessment, between IPS assessments at 30-minute intervals (±10 minutes) until 6 hours after closing, and at clinic check-out.

Vital signs (BP, HR, RR, and temperature) are to be assessed at screening and at each treatment visit within 15 minutes before the preclose IPS assessment, postclose within 10 minutes before each IPS assessment, between IPS assessments at 30-minute intervals (±10 minutes) until 6 hours after closing, and at clinic check-out. The subject should be in a seated or semi-reclined position for at least 5 minutes before vital sign assessments. Vital sign assessments may be repeated at the discretion of the Investigator.

Level of sedation will be assessed using a visual analog scale for sedation at screening, and at each treatment visit within 15 minutes before the preclose IPS assessment, postclose within 10 minutes before each IPS assessment, and at clinic check-out. If degree of sedation is a concern, the duration of confinement may be extended, and safety monitoring may continue at the discretion of the Investigator.

The visual analog scale (VAS) for sedation is a distinct 100-millimeter line anchored on the left end at full degree of impairment and on the right end at no degree of impairment, where indication of the degree of impairment perceived at the time of assessment is captured by marking the appropriate position on the line between the anchor points. The measured distance of the mark from the left anchor will be recorded in millimeters Sedation will be measured using a 100-mm linear visual analog scale (VAS). The subject will be given 2 scales, 1 anchored by "Sedated" and "Alert, the other by "Sleepy and "Awake" and asked to "Place a vertical mark on the line indicating your feelings RIGHT NOW". The location of the mark will be measured at a later time and the results will be recorded in mm from the left on the appropriate CRF.

An example of the subject VAS is provided below. The paper scales will be provided to the site, and only originals can be used for subject assessment. Photocopies cannot be provided for subject assessment.

Visual Analog Scale (VAS) for Sedation Assessment

| | |
|---|---|
| Sedated _____ | Alert |
| Sleepy _____ | Awake |

Instructions:
Place a vertical mark on the line indicating your feelings RIGHT NOW.

Analytical Methodology

Samples will be transported to the bioanalytical facility packed on sufficient dry ice to keep them frozen for at least 72 hours.

Safety laboratory values and ASM concentrations will be analyzed using validated methods. Fospropofol and propofol concentrations will be analyzed in plasma samples using a validated method and in accordance with the current regulations and guidelines in place for industry, including guidances on Bioanalytical Method Validation, Good Laboratory Practice (GLP) for Nonclinical Laboratory Studies, and GCP ICH E6(R2). US Food and Drug Administration. Bioanalytical Method Validation: Guidance for Industry. 2018. Available at https://www.fda.gov/files/drugs/published/Bioanalytical-Method-Validation-Guidance-for-Industry.pdf. US 21 CFR Part 58. Good Laboratory Practice for Nonclinical Laboratory Studies. Available at https://www.ecfr.gov/cgi-bin/text-idx?SID=3be49f31878d0efa85f39ed3b84fcbe1&mc=true&node=se21.1.58_11&rgn=div8. US Food and Drug Administration. E6(R2) Good Clinical Practice: IntegratedAddendum to ICH E6(R1) Guidance for Industry. 2018. Available at https://www.fda.gov/media/93884/download.

Statistical Considerations

A complete description of the statistical analyses to be performed for the safety, tolerability, PK, and photoparoxysmal response data will be presented in a Statistical Analysis Plan (SAP).

Safety and Tolerability

Safety and tolerability data will be reported using descriptive statistics. Summary statistics for TEAEs will be reported. Changes from baseline values in vital signs, ECG, and clinical laboratory parameters will be reported.

PK

Summary statistics will be used to describe the PK profile of both fospropofol and propofol. Summary statistics will include at minimum arithmetic and geometric means for $AUC_{0-t}$, $AUC_{0-inf}$, and $C_{max}$. $T_{max}$ will be characterized by median and range. Exploratory analyses may be performed in an effort to characterize the influence of covariates on PK.

The observed concentrations of concomitant ASMs will be listed and presented as summary statistics. Pharmacokinetic parameters for concomitant ASMs may be calculated, listed, and presented as summary statistics if feasible.

Exploratory analyses may be performed in an effort to characterize the effect, if any, of fospropofol disodium on concentrations of concomitant ASMs. Such analyses could provide useful information as to the potential for drug-drug interactions requiring further evaluation in the subsequent development of fospropofol disodium in the treatment and prevention of epileptic seizures.

Photoparoxysmal Response

Descriptive statistics will be presented including the means and standard deviations of photosensitivity range for each subject, for each day. Graphical displays of the data for each subject will allow exploration of inter- and intra-subject variability.

Example A20—Study A20

A Multicenter, Randomized, Double-Blind, Placebo-Controlled, Dose-Finding Study of Fospropofol disodium in the Acute Treatment of Moderate to Severe Migraine Headache Study Drug Fospropofol Disodium Study Phase and Type Phase 2—Multicenter, Randomized, Double-Blind, Placebo-Controlled, Single-close, Dose-Finding Study of FOSPROPOFOL DISODIUM in the Acute Treatment of Moderate to Severe Migraine Headache Objectives Primary Objectives To assess the close response of 2-hour freedom from pain across a range of fospropofol disodium closes.

To assess the close response of 2-hour freedom from the subject's most bothersome symptom (MBS) for the treated headache across a range of fospropofol disodium closes.

To evaluate the safety and tolerability of various doses of fospropofol disodium in the acute treatment of migraine.

Secondary Objectives

To assess the close response of 2-hour pain relief (PR) across a range of fospropofol disodium closes.

To assess the close response of freedom from nausea/vomiting, freedom from photophobia, and freedom from phonophobia (by symptom) at 2 hours post close.

To assess the close response of sustained freedom from pain from 2-24 hours and from 2-48 hours post-close. Sustained freedom from pain is defined as pain free at 2 hours post-close, with no administration of any rescue medication and with no recurrence of headache pain (mild/moderate/severe) during the respective period after closing.

To assess the close response of sustained freedom from the MBS from 2-24 hours and from 2-48 hours post-close. Sustained freedom from the MBS is defined as absence of the MBS at 2 hours post close, with no administration of any rescue medication and with no recurrence of the MBS during the respective period after closing.

To assess the close response of sustained pain relief from 2-24 hours and from 2-48 hours post-close. Sustained pain relief is defined as pain relief at 2 hours post close, with no administration of any rescue medication and with no recurrence of moderate/severe headache pain during the respective period after closing.

To assess the close response of sustained freedom from symptoms (nausea/vomiting, photophobia, or phonophobia), by symptom, from 2-24 hours and from 2-48 hours post-close. Sustained freedom from a symptom is defined as symptom free for that symptom at 2 hours post close, with no administration of any rescue medication and with no recurrence of that symptom during the respective period after closing.

Study Design This is a Phase 2, multicenter, randomized, double-Blind, placebo-controlled, parallel-group, single-close study of fospropofol disodium in the acute treatment of moderate to severe migraine headache in adult women and men with a history of episodic migraine with or without aura, diagnosed based on the International Classification of Headache Disorders, edition 3 (ICHD-3). The migraine diagnosis will be confirmed in a virtual (online) interview with a specialist in headache medicine. The study is planned to complete approximately 1600 subjects.

After screening to confirm eligibility, subjects will be randomized to receive a single dose of either fospropofol disodium at one of 3 close levels or placebo to be self-administered on an outpatient basis when the subject experiences a qualifying migraine headache.

Dosing must occur within 4 hours after onset of the migraine pain.

Dosing must occur within 60 days after randomization.

Subjects will report headache pain (presence and severity) and associated migraine symptoms (present or absent) within 10 minutes before closing, and at 0.5, 1, 1.5, 2, 4, 6, 12, 24, and 48 hours after closing using an electronic diary. Subjects will also report adverse events throughout. Subjects will be permitted to self-administer rescue medication if needed, but they will be strongly encouraged to avoid rescue medication until after 2 hours after closing.

Participants will be considered to have completed the study if they have self-administered study drug within 60 days after randomization and completed all procedures listed in the Schedule of Events including the follow-up clinic visit at Day 6±2 days and the follow-up telephone interview at Day 15±2 days. (The day of treatment is defined as Day 1.)

Justification for Dose Selection of the closes for this study is based on the results of the prior Phase 1a study, Study A16, the prior Phase 1b study, Study A17, and the pharmacokinetic bridging study (tablet to capsule comparison) Study A18.

Safety Committee A Safety Review Committee will be established to review periodic summaries of safety data from this study and to provide consultation as outlined in the Safety Committee Charter. The Safety Review Committee will be blinded to the treatment assignment.

Subject Selection The study is planned to enroll a sufficient number of subjects so as to complete approximately 1600 subjects. Because the prevalence of migraine headaches is higher in women than in men, efforts will be made to enroll at least 50% women.

Subjects must meet the general inclusion and exclusion criteria listed below (Inclusion Criteria and Exclusion Criteria) at screening in order to be randomized in the study. To be eligible for treatment with study, the subject must experience a qualifying headache (see Qualifying Headache below) and adhere to study restrictions specific to the period between randomization and end of study participation (see Post-randomization Study Restrictions below).

Inclusion Criteria Subjects must meet all of the following criteria at screening to be enrolled in the study:

1. Written informed consent approved by the Institutional Review Board (IRB) given before any study-related procedures are performed
2. Male or female, ≥18 and ≤55 years of age at the time of signed informed consent, with a body mass index (BMI) ≥18.0 and ≤35 kg/m² and body weight≥50.0 kg for men and ≥45.0 kg for women.
3. History of episodic migraine consistent with a diagnosis of migraine with or without aura according to the ICHD-3 criteria, plus the following:
    a) Migraine attacks present for ≥1 year with age of onset ≤50 years.
    b) History of 2 to 8 migraine attacks with moderate or severe pain per month (at least 8 hours in duration if untreated or any duration if treated) in each of the 3 months prior to the screening visit.
4. Subjects who are treated with drugs intended for migraine prophylaxis or drugs prescribed for a purpose other than migraine prophylaxis but with a potential prophylactic effect on migraine are eligible if they have been on a stable regimen for at least 3 months prior to screening and meet other inclusion/exclusion criteria.
5. Female subjects must fulfill at least one of the following:
    a) Surgically sterile, defined as women who have had a tubal ligation, hysterectomy, or bilateral oophorectomy at least 6 months prior to screening.
    b) Post-menopausal, defined as absence of menses for at least 12 months prior to screening.
    c) Women who are sexually active and at risk for pregnancy must agree to avoid pregnancy and use a medically acceptable method of contraception from at least 30 days prior to screening until 30 days after study drug administration.
    Medically acceptable methods of contraception include hormonal contraception, hormonal or non-hormonal intrauterine device, double barrier method (simultaneous use of male condom with intravaginally applied spermicide and diaphragm or cervical cap), or male partner vasectomy at least 6 months previously. Complete abstinence alone can be used as a method of contraception.
6. Male subjects who are not vasectomized for at least 6 months, and who are sexually active with a non-sterile female partner (see definitions of surgically sterile and post-menopausal above) must be willing to use one of the following acceptable contraceptive methods throughout the study and for 90 days after the study drug administration (Complete abstinence alone can be used as a method of contraception):
    a) Simultaneous use of male condom and, for the female partner, intrauterine contraceptive device with or without hormone release (placed at least 4 weeks previously)
    b) Simultaneous use of male condom and, for the female partner, hormonal contraception
    c) Simultaneous use of male condom and, for the female partner, intravaginally applied spermicide with diaphragm or cervical cap
7. Able to comprehend the nature of the study, capable of giving written informed consent, and able to communicate effectively with clinic staff (as assessed by the investigator)
8. Available to volunteer for the entire study duration and willing to adhere to all protocol requirements, including the post-randomization restrictions (see Post-Randomization Restrictions below)
9. Agree not to post any information related to the study on any website or social media site (e.g., Facebook, Twitter, LinkedIn, Google+, etc.) until the entire trial has been completed
10. Willing to forgo rescue medicine for at least 2 hours after administration of study drug (see Rescue Medication)

Exclusion Criteria Subjects to whom any of the following criteria apply at screening will be excluded:

1. History of hemiplegic migraine (at any time in the past).
2. History of headaches of any type occurring on ≥15 days/month during any of the 3 months prior to screening.
3. If subject has coexisting history of tension-type headaches and migraine, inability to distinguish between tension-type headaches and migraine.

4. In the investigator's judgment, overuse of medication for migraine or other conditions, defined as use of any of the following in any of the 3 months prior to screening:
   a) Narcotics (opioids)≥5 days/month(Opioids are allowed as second-line treatment as long as they were used ≤5 days/month), or
   b) Sedative-hypnotic drugs, (e.g., benzodiazepines, barbiturates, sleeping aids, combination analgesic medications containing butalbital)≥8 days/month, or
   c) Triptans (e.g., sumatriptan, naratriptan, almotriptan, etc.) or ergotamine≥8 days/month, or
   d) Simple analgesics (e.g., aspirin, NSAIDs, acetaminophen, caffeinated analgesic combinations) ≥12 days/month (Occasional use of topical products without significant systemic absorption is permitted.)
   e) Anti-emetics, diphenhydramine≥10 days/month.
   f) Gepants: calcitonin gene-related peptide (CGRP) receptor antagonists (e.g., ubrogepant, rimegepant)≥10 days/month.
   g) Ditans (lasmiditan)≥10 days/month.
   h) Herbal supplements and natural health products used for acute treatment of migraine≥10 days/month.
5. History of any of the following:
   a) Clinically significant history of endocrine, cardiovascular, pulmonary, hematologic, immunologic, gastrointestinal, renal, hepatic, or metabolic disease; or psychiatric conditions, major depression, dementia, or significant neurological disorders other than migraine that in the investigator's judgment would interfere with the study, or
   b) Active malignancy of any type or a history of malignancy within the last 5 years (except basal cell carcinoma of the skin that has been excised at least 12 weeks prior to study start), or
   c) Major surgery within 6 months prior to screening, unless the investigator deems the subject eligible (minor surgery performed 4 or more weeks prior to screening would not be a reason for exclusion), or
   d) Pain syndrome other than migraine that in the investigator's judgment would interfere with the study, or
   e) Diagnosis of sleep apnea, or
   f) Any other medical condition that, in the opinion of the investigator or the Sponsor, may be potentially associated with an increased risk to the subject from study drug or to participation in the study.
6. Subjects who have any of the following at screening:
   a) Clinically significant abnormality at physical examination (in the judgment of the investigator), or
   b) Clinically significant ECG abnormalities (in the judgment of the investigator), or
   c) Vital sign abnormalities (systolic blood pressure [BP]≤90 mmHg or ≥145 mmHg, diastolic blood pressure ≤55 mmHg or ≥95 mmHg, or heart rate [HR]≤50 bpm or ≥110 bpm), or
   d) Oxygen saturation by oximetry (SpO2)≤93%, or
   e) Hemoglobin≤135 g/L for men or ≤120 g/L for women
   f) Clinically significant abnormal laboratory test results (out of the study laboratory's acceptable range, unless out-of-range values are deemed by the investigator to be not clinically significant).
7. Subjects with a history of any of the following:
   a) Significant alcohol abuse within 1 year prior to screening or regular use of alcohol within 6 months prior to screening (more than 14 units of alcohol per week [1 unit=150 mL of wine, 360 mL of beer, or 45 mL of 40% alcohol]), or
   b) Significant drug abuse or use of cocaine, phencyclidine [PCP], crack, opioid derivatives including heroin, or amphetamine derivatives, or similar drugs within 1 year prior to screening, or significant use of marijuana or tetrahydrocannabinol [THC]-containing products that in the investigator's judgment is medically significant in that it would impact the safety of the subject or the interpretation of the study results.
8. Subjects who have any of the following at screening:
   a) A positive alcohol breath test or
   b) A positive urine drug screen (unless consistent with an ongoing prescription drug as documented by the investigator) (Note that detectable levels of marijuana (THC or metabolites) in the urine drug screen are not exclusionary if in the investigator's documented opinion, the positive test does not signal a clinical condition that would impact the safety of the subject or interpretation of the study results.)
9. Women who are pregnant (have a positive urine pregnancy test at screening) or who are nursing
10. Subjects who have a history of severe allergic reactions (e.g., anaphylactic reactions, angioedema), hypersensitivity, or idiosyncratic reaction to fospropofol, propofol, or related substances.
11. Subjects who have participated in an interventional clinical research study involving:
    a) Administration of an investigational or marketed drug or device within 30 days prior to screening, or
    b) Administration of a biological product in the context of a clinical research study within 90 days prior to screening.
    (Concomitant participation in an investigational study involving no drug, device or other intervention is permitted, provided obligations associated with the concomitant participation are not expected to interfere with procedures and obligations of the present study.)
12. Employees or immediate families (defined as spouse, significant-other, parent, child, or sibling, whether adopted or biologic) of an employee of Epalex Corporation, its affiliates, or partners; investigator or study center personnel directly affiliated with this study and/or their immediate families.
13. Subjects who have a condition or are in a situation that in the investigator's opinion may put the subject at significant risk, may confound the study results, or may interfere significantly with the subject's participation in the study.
14. Score of >0 on the Sheehan Suicidality Tracking Scale (S-STS) for a recall period of 30 days prior to screening.

Eligibility for Dosing: Qualifying Headache To qualify for treatment with study drug, the headache must meet the following criteria:
1. Subject was free of migraine symptoms for at least 48 hours before the start of symptoms of the migraine headache to be treated (and did not take any medications for the acute treatment of migraine during this period).
2. Subject must not have consumed alcohol within 24 hours prior to closing.
3. Subject must not have taken any antacid, proton pump inhibitor, or H2 blocker within 24 hours prior to closing.
4. Time between onset of the pain of the migraine headache to be treated and actual time treatment must be less than 4 hours.
5. Moderate or severe pain intensity (2 or 3 on a 4-point Likert scale where 0=none, 1=mild, 2=moderate, 3=severe) 6. Has at least 1 of the following characteristics: unilateral location, throbbing (pulsating), or aggravated by routine physical activity.
7. Associated with at least 1 of the following symptoms: nausea/vomiting, photophobia, or phonophobia assessed
8. Within 10 minutes before closing:
   a) Moderate or severe pain intensity (2 or 3 on a 4-point Likert scale where 0=none, 1=mild, 2=moderate, 3=severe).
   b) Presence of at least 1 symptom (nausea/vomiting, photophobia, or phonophobia).

Post-randomization Study Restrictions The following restrictions specific to the period after randomization until end of study must be met for treatment of a migraine with fospropofol disodium to occur.

Medications Permitted with Restrictions

If the subject experiences a migraine headache where study treatment is not feasible or practicable, the following medications for acute migraine treatment are allowed after randomization, as agreed with the investigator at screening, provided the following restrictions to prevent overuse are met and provided the subject has not taken them within 48 hours prior to taking study drug (see Point 3 under Restricted and prohibited substances or products below):
   1. Narcotics (opioids) as second-line treatment only: No more than 4 days/month or in the 30 days prior to closing.
   2. Sedative-hypnotic drugs, (e.g., benzodiazepines, barbiturates, sleeping aids, combination drugs containing butalbital):No more than 7 days/month or in the 30 days prior to closing.
   3. Triptans (e.g., sumatriptan, naratriptan, almotriptan, etc.) or ergotamine: No more than 7 days/month or in the 30 days prior to closing.
   4. Analgesics, alone or in a combination product (e.g., aspirin, NSAIDs, acetaminophen, caffeinated analgesic combinations): No more than 11 days/month or in the 30 days prior to closing.
   5. Anti-emetics, diphenhydramine. No more than 9 days/month or in the 30 days prior to closing.
   6. Gepants: CGRP receptor antagonists (e.g., ubrogepant, rimegepant). No more than 9 days/month or in the 30 days prior to closing.
   7. Ditans: lasmiditan. No more than 9 days/month or in the 30 days prior to closing.
   8. Herbal supplements and natural health products used for acute treatment of migraine. No more than 9 days/month or in the 30 days prior to closing.

Restricted and prohibited substances or products
   9. Alcohol-based products are to be restricted as follows:
      a) No more than 14 units of alcohol per week [1 unit=150 mL of wine, 360 mL of beer, or 45 mL of 40% alcohol])
      b) Subject is not to administer study drug they have consumed alcohol within 24 hours prior to closing. (See Eligibility for Dosing: Qualifying Headache.)
   10. The following products are not permitted at any time during study participation (from randomization until study completion [after the Day 15 telephone call]):
      Cocaine, phencyclidine [PCP], crack, opioid derivatives including heroin, amphetamine derivatives, or similar drugs. Urine drug screen must be negative at screening. (Foods containing poppy seeds should be avoided prior to screening because they may interfere with results of the urine drug screen.) Note that detectable levels of marijuana (THC or metabolites) in the urine at screening are not exclusionary if in the investigator's documented opinion, the positive test does not signal a clinical condition that would impact the safety of the subject or interpretation of the study results and documents that the subject affirms that they will not administer study drug if they have used marijuana or any THC-containing product within the 48 hours prior to closing.
   11. FOSPROPOFOL DISODIUM closing is not to be performed if the subject has taken any of these medications within the 48 hours prior do closing with study drug:
      a) Narcotics (opioids), sedative-hypnotic drugs, (e.g., benzodiazepines, barbiturates, sleeping aids, combination drugs containing butalbital).
      b) Triptans (e.g., sumatriptan, naratriptan, almotriptan, etc.) or ergotamine.
      c) Analgesics, alone or in a combination product (e.g., aspirin, NSAIDs, or acetaminophen).
      d) Anti-emetics, diphenhydramine.
      e) Gepants: CGRP receptor antagonists (e.g., ubrogepant, rimegepant).
      f) Ditans: lasmiditan.
      g) Herbal supplements and natural health products used to treat migraine.
      h) Marijuana or THC-containing products
      i) FOSPROPOFOL DISODIUM closing is not to be performed if the subject has taken any of these medications within the 24 hours prior to closing with study drug:
      j) Any antacid
      k) Any proton pump inhibitor
      l) Any H2 blocker Other Restrictions Dosing is not to be performed if any of the following conditions apply.
   1. Events within 30 days prior to clinic check-in:
      a) Significant illness or any surgical procedure
      b) Subject donated plasma or blood
   2. Any vaccination (e.g., COVID-19 vaccination, influenza) within 10 days prior to closing
   3. Headaches occurring on ≥15 days in the month prior to closing with study drug
   4. Abnormal diet patterns (for any reason) during the 4 weeks preceding closing, including fasting, high protein diets etc.

5. Conditions or situations arising since clinic enrollment that in the investigator's opinion, may put the subject at significant risk or may confound the study results.

Permitted Throughout the Study
1. Standard migraine prophylactic medications and other medications with a prophylactic effect on migraines are permitted as prescribed, provided that the regimen (drug, route, close, frequency) has been stable for at least 3 months prior to the screening visit and no changes in the regimen are expected (or made) during study participation. Prophylactic medications may not be started during the study. Examples of permitted prophylactic drugs are beta-blockers, tricyclic antidepressants, topiramate, and valproic acid. Botulinum toxin (approved only for chronic migraine) is prohibited. Nurtec ODT (Rimegepant) approved for acute treatment of migraine as well as prophylaxis is prohibited. Phenytoin, and carbamazepine are prohibited. Among other drugs currently approved for migraine prophylaxis, the following are permitted if the regimen has been stable during the three months prior to screening: Aimovig (erenumab), Ajoy (fremanezumab), Emgality (galcanezumab), Vyepti (eptinezumab).
2. Hormonal contraception and routine use of over-the-counter (OTC) multivitamins for general health are permitted throughout the study.
3. Other prescription medications and OTC medicines are permitted if medically necessary as agreed with the investigator on a case-by-case basis at screening.
4. Herbal supplements and health products are permitted if agreed with the investigator on a case-by-case basis at screening.

Rescue Medication Rescue medication is defined as any treatment for migraine (as agreed between subject and investigator at screening) that is self-administered by the subject in the 48-hour interval following closing with study drug. Rescue medication may be self-administered at any time after closing with study drug if additional medication for acute treatment of migraine pain or associated symptoms is necessary. However, subjects will be strongly encouraged to avoid administration of rescue medication earlier than 2 hours after closing. The subject should record the 2-hour assessments of headache pain, associated symptoms, most bothersome symptom, and assessment of functional disability before taking any rescue treatment. If rescue treatment is needed at any time between 2 hours and 48 hours after closing and near the time of a scheduled assessment, the scheduled assessment be completed before the administration of rescue treatment.

The investigator and subject must agree at screening on the appropriate rescue therapy for the subject. Subjects will supply their own rescue medication and use it according to label. Rescue treatment may be self-administered on more than one occasion after closing but close and frequency must be consistent with product labelling. Any administration of rescue medication including drug, route, quantity, and time of closing must be reported in the electronic diary. Selection of the agreed upon rescue treatment for each subject may be guided by treatment that was effective for the subject in the past. First-line rescue therapy may include an analgesic and/or acute migraine medication and will not include narcotics. If necessary, a second-line rescue therapy may be agreed upon at the investigator's discretion.

The following products may be agreed upon between subject and investigator at screening to be used as rescue medication if required in the clinic after closing with study drug:
1. Analgesics, alone or in a combination product, including acetaminophen, aspirin, or NSAIDs.
2. Triptans (e.g., sumatriptan, naratriptan, almotriptan).
3. Gepants (CGRP antagonists, e.g., ubrogepant (Ubrelvy®), rimegepant (Nurtek®).
4. Ditans (e.g., lasmiditan (Reyvow®)).

Because of the potential for additive cardiorespiratory effects when narcotic analgesics and sedative-hypnotic agents (e.g., opiates, benzodiazepines, barbiturates, sleeping aids, combination drugs containing butalbital) are administered concomitantly with FOSPROPOFOL DISODIUM, these medications are not recommended as rescue therapy after FOSPROPOFOL DISODIUM closing. Prescription antiemetics, including metoclopramide, prochlorperazine, chlorpromazine, as well as OTC drugs sometimes helpful for nausea, such as dimenhydrinate, meclizine, and diphenhydramine, are associated with sedation and should be avoided as rescue treatment until at least 4 hours aftertreatment with FOSPROPOFOL DISODIUM.

Study Drug and Dosage Form FOSPROPOFOL DISODIUM is formulated for oral administration in an appropriate number of tablets. Each tablet contains 200 mg of fospropofol disodium (uncorrected for sodium content) and inactive ingredients. It is possible that tablets containing smaller amounts of FOSPROPOFOL DISODIUM may also be used.

Dose Level Subjects will be randomized 1:1:1:1 to receive one of four double-blind treatments comprising placebo and 3 close levels of FOSPROPOFOL DISODIUM. See Randomization, below.

Administration of Study Drug Dosing must occur within 4 hours after onset of migraine pain.
The study drug will be administered with water at ambient temperature in the amount of approximately 240 mL [8 oz]. Except for water administered with the study drug, fluids will not be permitted from closing until 1 hour after closing (see Study Restrictions). Fluids will be permitted ad lib thereafter.
As a safety precaution, subjects will be instructed to remain seated or semi-reclined for 2 hours after administration of study drug.
Subjects are permitted to sleep (in a semi-reclined position) after administration of study drug but requested to record in the electronic diary assessments of headache pain, associated migraine symptoms, and level of functional disability preclose and at intervals after closing.

Randomization Subjects will be randomly allocated in blocks of 4 subjects to 1 of 4 treatments (A B C, or D) as shown below:

| Treatment Assignment | mg fospropofol disodium | Tablet Strength | Number of Active Tablets | Number of Placebo Tablets |
|---|---|---|---|---|
| A Placebo | 0 | 0 | 0 | 3 |
| B Fospropofol disodium, Dose Level 1 | 200 | 200 | 1 | 2 |
| C Fospropofol disodium, Dose Level 2 | 400 | 200 | 2 | 1 |
| D Fospropofol disodium, Dose Level 3 | 800 | 200 | 4 | 0 |

Placebo tablets will be identical in appearance to the active tablets.

Screening Procedures Screening procedures will comprise written informed consent and review of inclusion/exclusion criteria, including demographic data; body measurements (height, weight); medical and migraine history; medication history (including drug allergies); 12-lead ECG; pulse oximetry; vital signs (BP, HR, RR, temperature), safety laboratory assessments (hematology, blood chemistry, urinalysis, urine drug screen, alcohol breath test, serum pregnancy test for women of child bearing potential; complete physical examination, and the Sheehan Suicidality Tracking Scale.

Migraine history will be obtained by subject interview and will include age of onset and time since first attack; estimated frequency of migraine episodes during the prior 3 months, including frequency of episodes classified as moderate or severe; history of migraine-associated symptoms (nausea/vomiting, photophobia, phonophobia, or other symptoms); the usual most bothersome symptom (nausea/vomiting, photophobia, or phonophobia); characteristic features of episodes (unilateral vs bilateral location, pulsating quality, pain intensity, aggravation by or causing avoidance of routine physical activity); presence and features of aura, if any; and history of headache types other than migraine and subject's ability to distinguish between migraine and tension-type headaches.

Medication history will be obtained by interview and will include history of migraine-related medications during the 3 months prior to screening. Migraine-related medications include medications (if any) used for first- and/or second-line acute treatment of migraine and medications used for migraine prophylaxis or those that have prophylactic effect on migraine. History of other medications will be recorded for the period 30 days prior to screening.

Medications permitted for use during the course of study will be reviewed, recorded, and approved at screening by the investigator (in consultation with the Sponsor as needed or requested). Such medications include acute migraine treatment to be used if treatment with study drug is not feasible within 4 hours after onset of headache pain. Medications used for migraine prophylaxis or those that have prophylactic effect on migraine must have been stable (consistent with respect to drug, route, close, and closing regimen) for at least 3 months prior to screening (see Post-Randomization Study Restrictions).

The investigator and subject are to agree at screening on an appropriate rescue medication(s) to be used if needed after closing with study drug (see Rescue Medication).

Subjects who give written informed consent and meet inclusion/exclusion criteria will be randomized. Randomized subjects will receive instructions regarding restrictions during study participation, identification of a qualifying headache, as well as instructions for administration of study drug and necessary precautions.

Post-randomization Period Randomized subjects will be asked to self-administer study drug as soon as possible when they experience a qualifying migraine, i.e., migraine pain of at least moderate severity together with at least one associated symptom (nausea, photophobia, phonophobia) as closing must occur within 4 hours after onset of migraine pain. If treatment is not feasible or practicable within 4 hours after the onset of migraine pain, subjects should use their usual headache medication as agreed at screening and within the parameters noted in the Post-Randomization Study Restrictions. This situation may arise, for example, if the headache is not a qualifying migraine or if onset of symptoms occurs when family or work circumstances make it impracticable for the subject to self-administer study drug within the 4-hour time frame. In such cases, the subject should attempt to self-administer study drug for the treatment of their next qualifying migraine headache.

Treatment of a qualifying headache is to occur within 60 days after randomization. Clinic staff are to remain in telephone contact with subjects as needed (at least monthly) to identify and address any barriers that may prevent subjects from treating a qualifying headache.

If a randomized subject does not self-administer study drug within 60 days after randomization, this situation is to be classified as "failure to close." If possible, reasons for failure to close within 60 days should be ascertained and recorded using the following checklist of potential issues: lack of moderate to severe headaches, work circumstances, family circumstances, lack of adherence to post-randomization study restrictions, or other reasons.

Prior to Self-administration of Study Drug (Day 1) The subject is to perform the following procedures before self-administration of study drug:
1. Assess the presenting headache and associated symptoms to determine whether it is a qualifying headache (See Eligibility for Dosing, Qualified Headache)
2. Ensure that agreed upon rescue drug(s) is/are available
3. For women of child-bearing potential, perform urine pregnancy test (must be negative before closing)
4. Record time and nature of last meal or food intake, including beverages.
5. Record in the electronic diary pre-close (within 10 minutes prior to closing) severity of qualifying headache pain, presence/absence of associated symptoms (nausea/vomiting, photophobia, and phonophobia), and level of functional disability, and identify and record from among the associated symptoms the most bothersome symptom for the current headache episode.

Following Self-administration of Study Drug (Day 1-Day 3) The subject will be instructed that the study drug may be associated with some degree of sedation. Therefore, the subject should remain seated or semi-reclined for 2 hours after administration of study drug. The subject should refrain from driving or operating heavy equipment for 24 hours after closing.

The subject will record in the electronic diary the assessments as scheduled in the Schedule of Events including severity of headache pain, presence/absence of the most bothersome symptom, presence/absence of the other associated symptoms, and level of functional disability. These assessments will be recorded in the electronic diary at intervals until 48 hours after closing. The quality-of-life assessment will be completed at approximately 24 hours after closing. The subject will record an assessment of satisfaction with study drug at 48 hours. Subjects will record any adverse events in the electronic diary.

Rescue treatment (treatment for migraine self-administered within 2 to 48 hours after closing) as agreed with the investigator at screening may be used at any time after the 2-hour assessment of headache pain, symptoms, and functional disability. The close, route, and frequency of administration must be consistent with the product labelling. Each use of rescue medication (drug, close, route, and time of self-administration) must be recorded in the electronic diary (See Rescue Medication).

As soon as convenient after closing, the subject will contact the study site to schedule the Post-treatment Visit (Visit 2). The post-treatment visit should be scheduled on Day 6±2 days, i.e., on Day 4, 5, 6, 7, or 8 (with the day of closing defined as Day 1).

Post-treatment Visit (Visit 2) Electronic diary entries will be reviewed with the subject. The following procedures will be carried out at Visit 2, the post-treatment visit: Sheehan STS, Safety laboratory assessments (hematology, blood chemistry, urinalysis, serum pregnancy test in women of child-bearing potential), vital signs (BP, HR, RR, temperature), pulse oximetry, 12-lead ECG, headache assessment, physical examination and neurological examination, recording of adverse events (AEs). The subject will complete a work and productivity questionnaire.

Arrangements for the follow-up telephone interviews will be made.

Follow-up Telephone Interview A follow-up telephone interview will be scheduled at approximately 14 days post-treatment for subjects to report and occurrence of any AEs since treatment.

Safety Procedures and Assessments. Medical Surveillance and AE Monitoring

Subjects will record adverse events from the time of randomization until the follow-up telephone interview approximately two weeks after closing (See Overall Schedule of Events) or until discontinuation if the subject withdraws prematurely.

Safety data will be evaluated on an ongoing basis by the Safety Review Committee to ensure it is safe to continue study enrollment and treatment.

Safety parameters, including physical examination, laboratory results and ECG, will be evaluated by the investigator in the context of clinical trial safety. Any abnormal measurement is to be repeated if judged necessary by the investigator.

12-Lead ECG

A 12-lead ECG will be performed at screening (Visit 1) and at the post-treatment visit (Visit 2).

Safety Laboratory Assessments

Hematology, serum chemistry, and urinalysis will be assessed at screening (Visit 1) and at the post-treatment visit (Visit 2).

A urine drug screen and alcohol breath test will be performed at screening (Visit 1). For women of child-bearing potential, a urine pregnancy test will be performed by the subject prior to closing. A serum pregnancy test will be performed at screening and at the post-treatment visit (Visit 2).

Physical Examination

A complete physical examination will be performed at screening (Visit 1) and at the post-treatment visit (Visit 2).

Sheehan Suicidality Tracking Scale

The Sheehan Suicidality Tracking Scale will be administered at the screening visit (Visit 1, and at the and at the post-treatment visit (Visit 2).

Measures of Clinical Course Headache pain and associated migraine symptoms (nausea/vomiting, photophobia, and phonophobia) will be recorded as migraine-related events. Headache pain will be rated on a 4-point Likert scale (0=none, 1=mild, 2=moderate, 3=severe).

Associated migraine symptoms (nausea/vomiting, photophobia, and phonophobia) will be classified as either present or absent.

The subject will record in the electronic diary the assessments as scheduled including severity of headache pain, presence/absence of the most bothersome symptom, presence/absence of the other associated symptoms, and level of functional disability. These assessments will be recorded in the electronic diary at intervals until 48 hours after closing. The quality-of-life assessment will be completed at approximately 24 hours after closing. The subject will record an assessment of satisfaction with study drug at 48 hours. The subject will record in the electronic diary the use of any concomitant medications from the time of closing until 48 hours thereafter. Concomitant medications will be recorded to include identification of the drug, route, close, and time of administration.

The subject will complete a work and productivity questionnaire at the post-treatment visit (Visit 2).

Adverse Events Subjects will be instructed record any potential AEs, i.e., untoward medical symptoms and/or events that may arise from the time of randomization until the follow-up telephone interview (to be conducted approximately 2 weeks after administration of study drug including time of onset, duration, and severity.

Treatment-emergent adverse events (TEAEs) are defined as the reported AEs that first occurred or worsened after administration of the study drug. Adverse events will be reviewed by the investigator at Visit 2 and again at the follow-up telephone interview. The incidence, seriousness, severity, duration, and relation to study drug of all TEAEs will be reviewed and recorded by the investigator.

Some degree of sedation is an expected and potentially therapeutic effect of the study drug. Although sedation, including events described as feeling "drowsy," "sleepy," "relaxed," etc., will be expected, such terms if expressed by the subject will be recorded as AEs, and severity will be rated by the site investigator as mild, moderate, or severe.

Worsening or recurrence of migraine pain or related migraine symptoms (nausea/vomiting, photophobia, phonophobia) from closing until 48 hours after closing will be recorded as migraine-related events and will not be recorded as AEs.

Statistical Considerations A complete description of the statistical analyses to be performed for the safety, tolerability, and clinical course will be presented in a Statistical Analysis Plan (SAP).

Safety and Tolerability

Safety and tolerability data will be reported using descriptive statistics. Summary statistics for TEAEs will be reported. Changes from baseline values on physical examination, and clinical laboratory parameters, and ECG will be reported.

Clinical Course

Summary statistics will be reported by treatment group for the following assessments:
1. Headache pain (on the Likert scale) at all timepoints (See Schedule of Events)
2. Presence/Absence of the most bothersome symptom (MBS) at all timepoints
3. Presence/Absence of each migraine-related symptom (nausea/vomiting, photophobia, or phonophobia), by symptom, at all timepoints
4. Level of functional disability at all timepoints
5. Use of rescue medication at all time points
6. Quality of life assessments (2-24 hours) assessed at 24 hours after closing
7. Assessment of satisfaction with Study Drug assessed at 48 hours after closing
8. Work and productivity loss questionnaire assessed at Visit 2 (Day 6±2 days) where the day of closing is defined as Day 1.

Summary statistics by treatment group will be presented for the following specified outcomes:
(1) Proportion of subjects reporting no headache pain at 2 hours
(2) Proportion of subjects reporting the absence of the most bothersome symptom (MBS) at 2 hours
(3) Proportion of subjects reporting pain relief(change from severe/moderate to mild/absent) at 2 hours.
(4) Proportion of subjects reporting absence of each migraine-related symptom (nausea/vomiting, photophobia, or phonophobia), by symptom, at 2 hours.
(5) Proportion of subjects reporting sustained freedom from headache pain at 24 hours, and at 48 hours.
(6) Proportion of subjects reporting sustained of absence of the MBS at 24 hours, and at 48 hours.
(7) Proportion of subjects reporting pain sustained pain relief at 24 hours, and at 48 hours
(8) Proportion of subjects reporting sustained absence of each migraine-related symptom (nausea/vomiting, photophobia, or phonophobia), by symptom, at 24 hours, and at 48 hours In addition, summary statistics by treatment group will be provided for quality of life (assessed at 24 hours post-close), satisfaction with study drug (assessed at 48 hours post-close), and work and productivity loss (assessed at Visit 2, approximately 2 weeks post-close).

Example B—Acidified Tablets

Example B1: Dissolution and pH Studies

Fospropofol Disodium tablets, 600 mg (label claim; l.c.), were manufactured for dissolution testing and use in a pharmacokinetics study. A total of three tablets for each lot were weighed prior to testing.

TABLE B1

Acidified Tablets - Compositions

| Composition | A1 mg | A1 % w/w | A2 mg | A2 % w/w | A3 mg | A3 % w/w | A4 mg | A4 % w/w |
|---|---|---|---|---|---|---|---|---|
| Fospropofol Disodium hydrate* | 666.9* | 42.96 | 666.9* | 42.96 | 666.9* | 56.43 | 666.9* | 65.18 |
| Polyplasdone XL | 77.6 | 5.00 | 77.6 | 5.00 | 59.1 | 5.00 | 51.2 | 5.00 |
| Magnesium Stearate | 7.8 | 0.50 | 7.8 | 0.50 | 5.9 | 0.50 | 5.1 | 0.50 |
| Citric Acid, monohydrate | 800.0 | 51.54 | | | | | | |
| Ascorbic Acid | | | 800.0 | 51.54 | | | | |
| Tartaric Acid | | | | | 450.0 | 38.07 | | |
| Malic Acid | | | | | | | 300.0 | 29.32 |
| Total | 1552.3 | 100.00 | 1552.3 | 100.00 | 1181.9 | 100.00 | 1023.2 | 100.00 |

*equivalent to 600 mg fospropofol disodium adjusted for water content.

Dissolution studies were performed under the conditions shown in Table B2 (n=3 vessels, 300-mL media volume and a single tablet per vessel). Analyses were performed by HPLC under the conditions shown in Table B3.

TABLE B2

Conditions for Dissolution Studies

| Conditions | Setting |
|---|---|
| Dissolution Medium | 0.1 NHCl de-aerated |
| Apparatus | USP apparatus II (rotating paddles) |
| Vessel Volume | 300 mL |
| Temperature | 37.0° C. ± 0.5° C. |
| Rotation Speed | 50 RPM (200 RPM from 60-75 or 60-90 minutes) |
| Sample Volume | 1.5 mL |
| Sample Times | 5, 10, 15, 20, 25, 30, 40, 45, and 60 minutes with an infinity pull at 75 or 90 minutes |
| In-line Filter | QLA 10 μm Porous (Full Flow) Filters |

TABLE B3

HPLC Instrumental Conditions

| | |
|---|---|
| Instrument | A suitable gradient HPLC system equipped with an inline degasser. |
| Column | Phenomenex Luna C18(2), 50 × 4.6 mm, 3 μm PIN 00B-4251-E0 |
| Detection | UV, 220 nm |
| Column Temperature | 25° C. |
| Sample Temperature | Ambient |
| Flow Rate | 2.0 mL/minute |
| Injection Volume | 10 μL |
| Rim Time | 8 minutes (See gradient table below) |
| Mobile Phase A | 0.1% TFA in HPW |
| Mobile Phase B | 0.1% TFA in ACN |
| Column/Needle Wash | 50:50 ACN:HPW |
| Attenuation | 1000 mAUN (when applicable) |
| Gradient | Time (min), % A, % B |
| | 0.0, 95, 5 |
| | 6.0, 5, 95 |
| | 6.2, 95, 5 |
| | 8.0, 95, 5 |

TABLE B4

A1 (citric acid monohydrate) Dissolution Results for Fospropofol Disodium Tablets, 600 mg, (% of label claim recovery)

| | Pull Point (minutes) | | | | | | | | |
|---|---|---|---|---|---|---|---|---|---|
| Vessel | 5 | 10 | 15 | 20 | 25 | 30 | 40 | 45 | 60 |
| 1 | 10 | 22 | 31 | 42 | 48 | 53 | 61 | 63 | 71 |
| 2 | 10 | 21 | 30 | 38 | 44 | 49 | 55 | 62 | 67 |
| 3 | 12 | 26 | 36 | 44 | 49 | 54 | 62 | 65 | 71 |
| Average | 11 | 23 | 32 | 41 | 47 | 52 | 59 | 63 | 70 |
| SD | 1.2 | 2.6 | 3.2 | 3.1 | 2.6 | 2.6 | 3.8 | 1.5 | 2.3 |
| % RSD | 10.8 | 11.5 | 9.9 | 7.4 | 5.6 | 5.1 | 6.4 | 2.4 | 3.3 |

TABLE B5

A2 (ascorbic acid) Dissolution Results for Fospropofol Disodium Tablets, 600 mg, (% of label claim recovery)

| | Pull Point (minutes) | | | | | | | | |
|---|---|---|---|---|---|---|---|---|---|
| Vessel | 5 | 10 | 15 | 20 | 25 | 30 | 40 | 45 | 60 |
| 1 | 26 | 58 | 76 | 86 | 89 | 90 | 93 | 91 | 92 |
| 2 | 31 | 62 | 78 | 86 | 90 | 91 | 93 | 93 | 93 |
| 3 | 29 | 63 | 78 | 88 | 89 | 91 | 89 | 88 | 91 |
| Average | 29 | 61 | 77 | 87 | 89 | 91 | 92 | 91 | 92 |
| SD | 2.5 | 2.6 | 1.2 | 1.2 | 0.6 | 0.6 | 2.3 | 2.5 | 1.0 |
| % RSD | 8.8 | 4.3 | 1.5 | 1.3 | 0.6 | 0.6 | 2.5 | 2.8 | 1.1 |

TABLE B6

A3 (tartaric acid) Dissolution Results for Fospropofol Disodium Tablets, 600 mg, (% of label claim recovery)

| | Pull Point (minutes) | | | | | | | | |
|---|---|---|---|---|---|---|---|---|---|
| Vessel | 5 | 10 | 15 | 20 | 25 | 30 | 40 | 45 | 60 |
| 1 | 9 | 20 | 28 | 33 | 37 | 41 | 47 | 50 | 54 |
| 2 | 8 | 18 | 27 | 33 | 37 | 40 | 46 | 49 | 56 |
| 3 | 7 | 16 | 24 | 30 | 33 | 37 | 43 | 46 | 52 |
| Average | 8 | 18 | 26 | 32 | 36 | 39 | 45 | 48 | 54 |
| SD | 1.0 | 2.0 | 2.1 | 1.7 | 2.3 | 2.1 | 2.1 | 2.1 | 2.0 |
| % RSD | 12.5 | 11.1 | 7.9 | 5.4 | 6.5 | 5.3 | 4.6 | 4.3 | 3.7 |

TABLE B7

A4 (malic acid) Dissolution Results for Fospropofol Disodium Tablets, 600 mg, (% of label claim recovery)

| | Pull Point (minutes) | | | | | | | | |
|---|---|---|---|---|---|---|---|---|---|
| Vessel | 5 | 10 | 15 | 20 | 25 | 30 | 40 | 45 | 60 |
| 1 | 21 | 48 | 63 | 70 | 76 | 77 | 82 | 82 | 85 |
| 2 | 23 | 48 | 59 | 66 | 74 | 78 | 79 | 81 | 84 |
| 3 | 23 | 49 | 61 | 67 | 70 | 75 | 77 | 79 | 83 |
| Average | 22 | 48 | 61 | 68 | 73 | 77 | 79 | 81 | 84 |
| SD | 1.2 | 0.6 | 2.0 | 2.1 | 3.1 | 1.5 | 2.5 | 1.5 | 1.0 |
| % RSD | 5.2 | 1.2 | 3.3 | 3.1 | 4.2 | 2.0 | 3.2 | 1.9 | 1.2 |

As used herein, the term "label claim" refers the total weight of the fospropofol disodium within the dosage unit.

Figure 27:
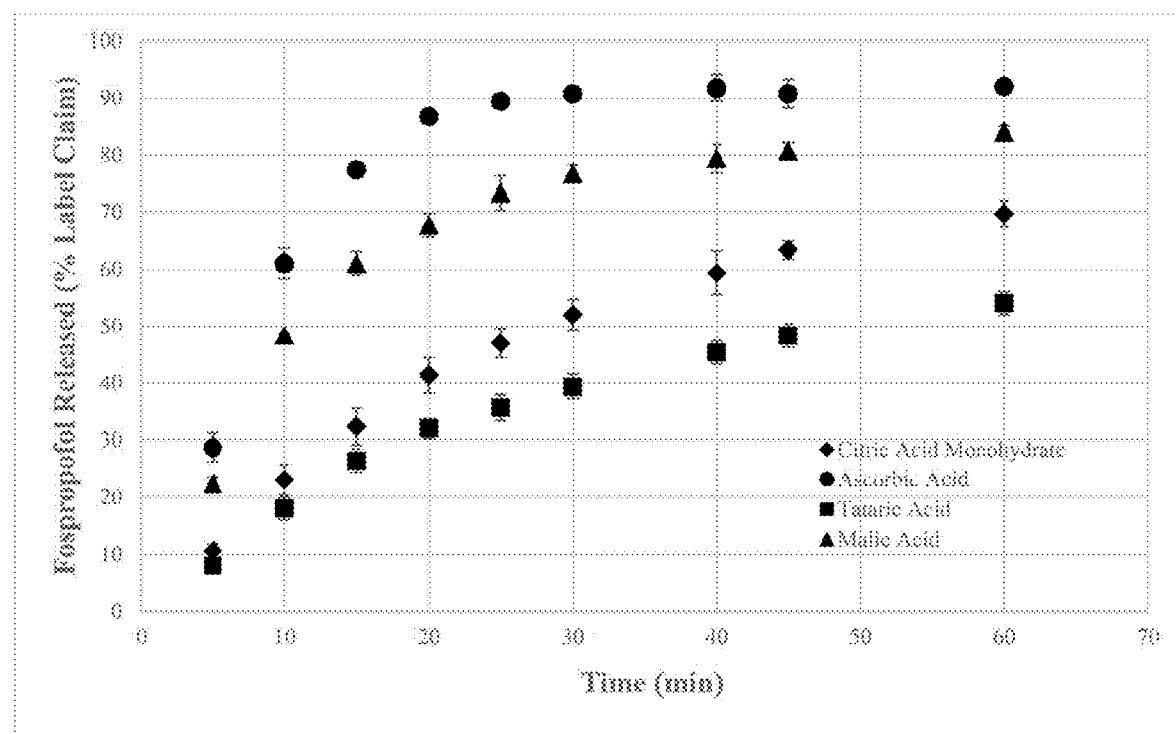
FIG. 27 depicts the dissolution profiles of 600 mg fospropofol disodium salt acidified tablets in 300 mL of 0.1 N HCl at 37° C.

FIG. 27 shows the dissolution profiles of the acidified tablets.

The solution pH values after the acidified tablets were dissolved in 300 mL of water are shown in Table B8.

TABLE B8 pH After Acidified Tablet Dissolved in 300 mL of Water

| Acidifier Excipient | pH |
|---|---|
| Citric Acid | 3.11 |
| Tartaric Acid | 3.13 |
| Malic Acid | 3.94 |
| Ascorbic Acid | 4.10 |

Example B2: Bioavailability Studies

The bioavailability of propofol from the fospropofol-containing dosage forms is assessed in dogs using the following general protocol.

The dogs used in the studies have the following characteristics:

Strain: Beagle
Condition: Purpose-bred, non-naïve
Source: Marshall Farms. North Rose, NY
Number of Males: 6 (plus 1 alternate)
Target Age at the Initiation of Dosing: At least 8 months.
Target Weight at the Initiation of Dosing: 6 to 13 kg All animals used in the studies have documentation of immunization for parvovirus, distemper, adenovirus type 2, parainfluenza, Bordetella, papilloma, and rabies.

Animals are identified with a tattoo or a subcutaneously implanted electronic identification chip.

Each animal is inspected by a clinical veterinarian upon receipt. Animals judged to be in good health are placed immediately in acclimation for at least 10 days.

Animals judged to be suitable for testing are assigned to groups randomly based on body weight stratification into a block design using computer program. Animals are arbitrarily reassigned to a different group at the discretion of the study director based on acclimation data.

The animals are closed as follows:
Dose Route: Tablet; Acidified Tablet
Frequency: Once daily; single administration
    Method: The first day of closing is designated as Day 1 (exception: alternate animals used for replacement after Day 1 assume the day of the animal being replaced).
    Tablet Administration: A single dose of the test article is administered orally via tablet.

Each subject receives 1 (600 mg) tablet. Doses are irrespective of body weight.

In studies wherein the dogs are pretreated with pentagstrin, the pentagastrin is administered intravenously before the dogs are administered the fospropofol-containing tablet.

In a separate study, the dogs are orally administered a solution containing 30 mg/mL fospropofol at a dose of 160 mg/kg in water rather than a tablet.

Bioanalytical Methods:
  Venipuncture from a jugularvein (saphenous or cephalic vein is used, if necessary).
  Target Volume (mL): Approximately 1 mL/time point collected without anesthesia.
  Anticoagulant: Sodium Heparin
  Prior to blood collection, approximately 0.05 mL of 200 mg/mL of sodium orthovanadate (SOV) solution is added to the heparinized blood collection tubes to prevent ex vivo conversion via alkaline phosphatase.
  Special Requirements: After collection, blood collection tubes are kept on wet ice until centrifugation within 30 minutes of collection.
  Processing: Plasma Samples are mixed gently and centrifuged within 30 minutes of collection. The samples are centrifuged at 2-8° C. and the resultant plasma is separated, transferred to duplicate uniquely labeled polypropylene tubes, and kept on wet ice until transferred to storage. Samples are stored in a freezer set to maintain a target of −70° C.
  Bioanalytical samples are analyzed for concentration of test article (fospropofol) and specified metabolites (propofol) using a validated analytical procedure.

Figure 28:
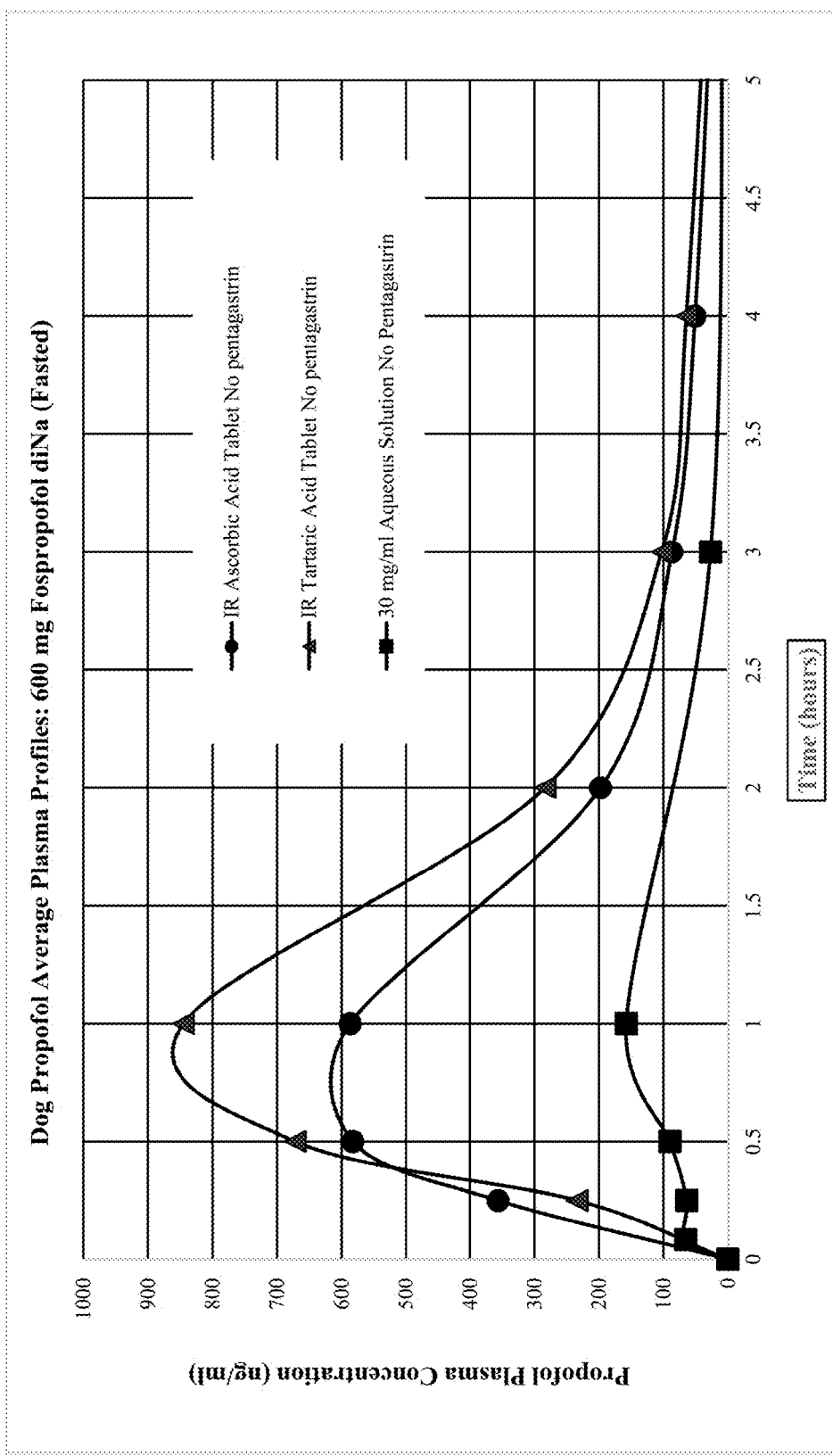
FIG. 28 depicts the dog propofol plasma profile comparison of 600 mg fospropofol disodium tablet with ascorbic acid acidifier (Composition A2) without pentagastrin pretreatment; 600 mg fospropofol disodium tablet with tartaric acid acidifier (Composition A3) without pentagastrin pretreatment; and a 1300 mg fospropofol disodium aqueous solution (30 mg/mL) without pentagastrin pretreatment which propofol plasma concentration is normalized to 600 mg fospropofol disodium. See Example B2.

FIG. 28 shows the propofol plasma profile comparisons of (1) 600 mg fospropofol disodium tablet with ascorbic acid acidifier (Composition A2) with no pentagastrin pretreatment; (2) 600 mg fospropofol disodium tablet with tartaric acid acidifier (Composition A3) with no pentagastrin pretreatment; and (3) 1300 mg fospropofol disodium aqueous solution (30 mg/mL) with no pentagastrin pretreatment.

Figure 29:
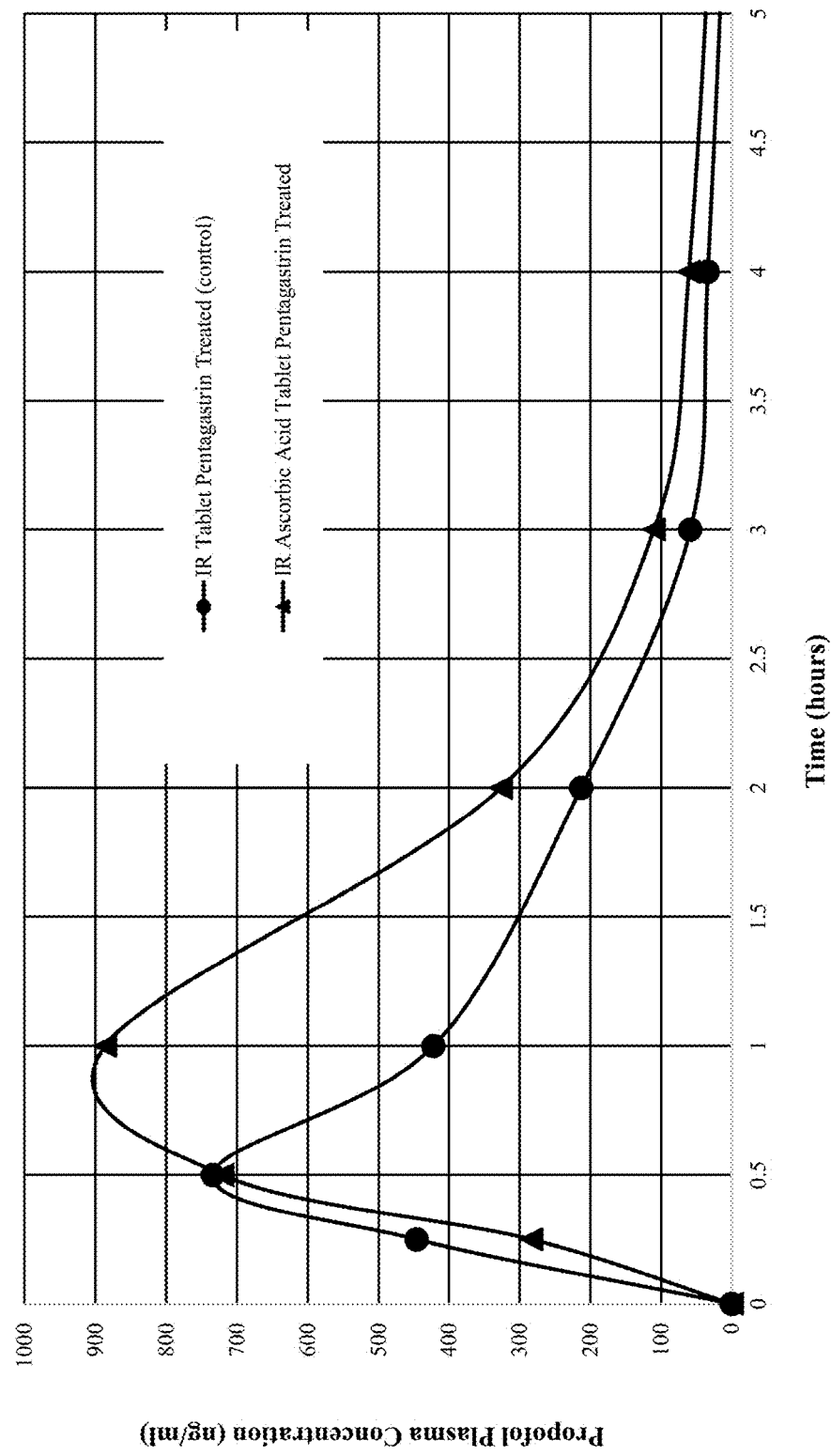
FIG. 29 depicts the dog propofol plasma profile comparison of 600 mg fospropofol disodium tablet with ascorbic acid acidifier (Composition A2) with pentagastrin pretreatment; and 600 mg fospropofol disodium tablet control (i.e., no acidifier) with pentagastrin pretreatment. See Example B2.

FIG. 29 shows the propofol plasma profile comparisons of (1) 600 mg fospropofol disodium tablet with ascorbic acid acidifier (Composition A2) with pentagastrin pretreatment; and (2) 600 mg fospropofol disodium tablet with no acidifier (Control) with pentagastrin pretreatment.

Figure 30:
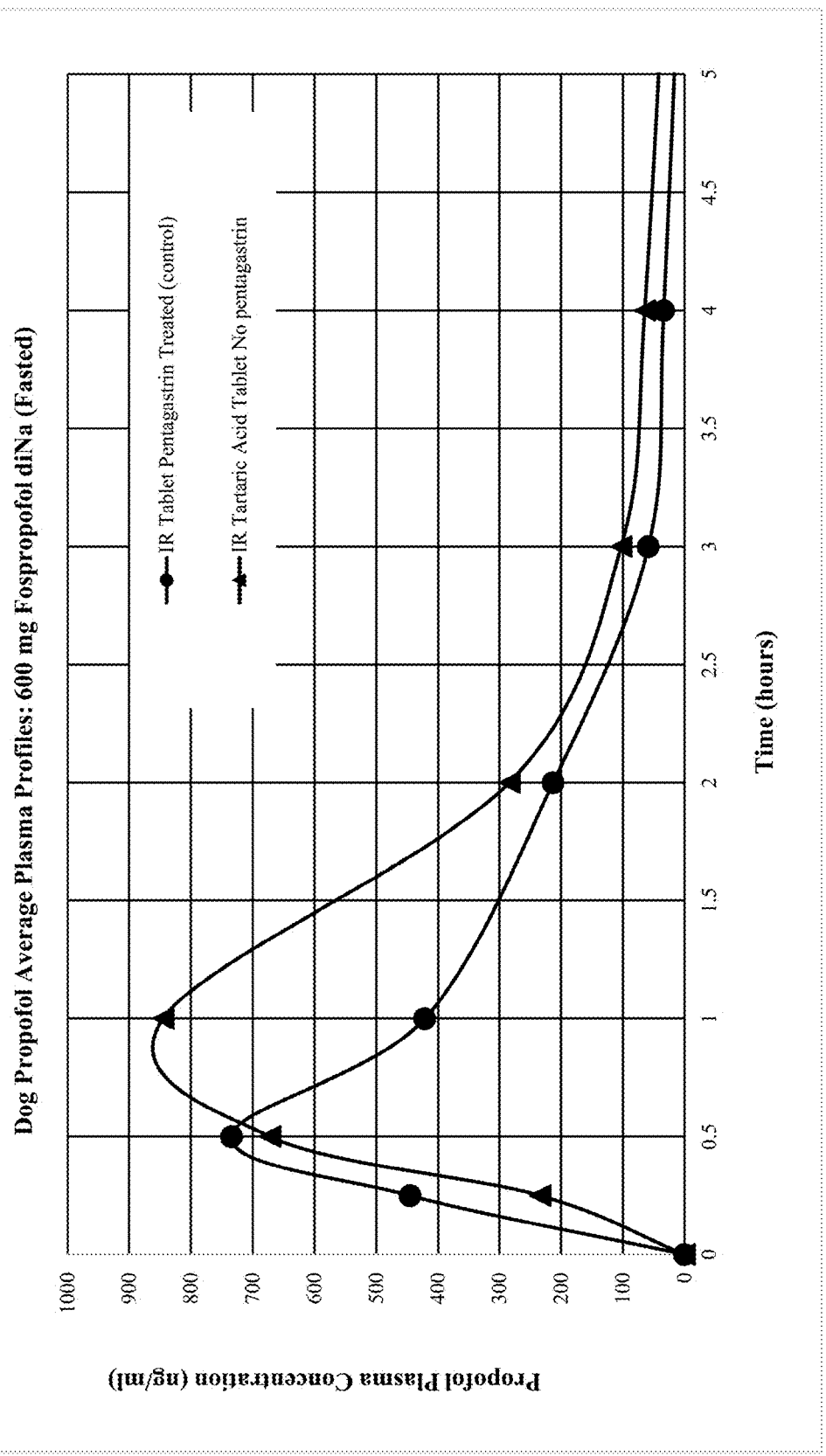
FIG. 30 depicts the propofol plasma profile comparison of 600 mg fospropofol disodium tablet with tartaric acid acidifier (Composition A3) without pentagastrin pretreatment; and 600 mg fospropofol disodium tablet control (i.e., no acidifier) with pentagastrin pretreatment.

FIG. 30 shows the propofol plasma profile comparisons of (1) 600 mg fospropofol disodium tablet with tartaric acid acidifier (Composition A3) with no pentagastrin pretreatment; and (2) 600 mg fospropofol disodium tablet with no acidifier (Control) with pentagastrin pretreatment.

The pharmacokinetic (PK) analysis results are shown in Table B9.

TABLE B9

| PK Results | | |
| --- | --- | --- |
| Cmax (ng/mL) (Propofol) | AUC∞ (ng*hr/mL) (Propofol) | Half-life (h) (Propofol) |
| 1300 mg Fospropofol disodium aqueous solution (30 mg/mL) with no pentagastrin pretreatment (Propofol concentrations in dog plasma from Fospropofol solution in Study Male dogs not pretreated with pentagastrin (from tox study, 160 mg/kg, assume 8.4 kg avg weight) | | |

| | Cmax (ng/mL) (Propofol) | AUC∞ (ng*hr/mL) (Propofol) | Half-life (h) (Propofol) |
| --- | --- | --- | --- |
| Mean | 399.43 | 711.06 | 1.45 |
| SD | 281.70 | 450.13 | 0.58 |
| CV | 71% | 63% | 40% |

TABLE B9-continued

| PK Results | | |
| --- | --- | --- |
| Cmax (ng/mL) (Propofol) | AUC∞ (ng*hr/mL) (Propofol) | Half-life (h) (Propofol) |
| 600 mg Fospropofol disodium tablet with ascorbic acid acidifier (Composition A2) with no pentagastrin pretreatment | | |

| | Cmax (ng/mL) | AUC∞ (ng*hr/mL) | Half-life (h) |
| --- | --- | --- | --- |
| Mean | 714.40 | 1191.91 | 1.48 |
| SD | 295.70 | 506.15 | 0.2 |
| CV | 41% | 42% | 14% |
| 600 mg Fospropofol disodium tablet with tartaric acid acidifier (Composition A3) with no pentagastrin pretreatment | | | |
| Mean | 1107.50 | 1656.87 | 2.93 |
| SD | 685.43 | 998.42 | 3.10 |
| CV | 62% | 60% | 106% |
| 600 mg Fospropofol disodium tablet with control (i.e., no acidifier) with pentagastrin pretreatment | | | |
| Mean | 732.5 | 1002.22 | 1.34 |
| SD | 312.47 | 340.86 | 0.34 |
| CV | 43% | 34% | 26% |
| 600 mg Fospropofol disodinm tablet with ascorbic acid acidifier (Composition A2) with pentagastrin pretreatment | | | |
| Mean | 928.33 | 1623.93 | 3.84 |
| SD | 167.12 | 378.36 | 3.22 |
| CV | 18% | 23% | 84% |

The pharmacokinetic results demonstrate that administering fospropofol together with an acid, such as in the acidified tablets, results in increased propofol Cmax and AUC∞ when compared to the close adjusted exposure seen with the oral solution. See FIG. 28; Table B9. This effect is seen using both ascorbic acid and tartaric acid as the tablet acidifiers.

In addition, the results demonstrate that administration of the acidified tablets with pentagastrin pretreatment results in increased plasma propofol Cmax and AUC∞ compared to the plasma propofol Cmax and AUC∞ observed upon administration of a control tablet(i.e., with no acidifier) with pentagastrin pretreatment. See FIG. 29; Table B9. Pentagastrin pretreatment acidifies the subject's stomach contents to an acidity comparable to that of normal human stomach contents.

In addition, these results demonstrate that co-administration of fospropofol disodium with tartaric acid without pentagastrin pretreatment results in increased plasma propofol Cmax and AUC∞ compared to the plasma propofol Cmax and AUC∞ observed upon administration of a control tablet (i.e., with no acidifier) with pentagastrin pretreatment. See FIG. 30; Table B9.

The experiments described above surprisingly demonstrate that oral administration of fospropofol together with a pharmaceutically acceptable acid increases the plasma propofol Cmax and AUC∞ relative to controls in which fospropofol is orally administered without an acidifier. Moreover, this effect is seen with multiple acids (e.g., ascorbic acid, tartaric acid) and is seen under conditions expected in human subjects. Thus, the disclosed invention solves the problem of providing an oral dosage form that can provide useful propofol pharmacokinetics.

These results also demonstrate that co-administration of fospropofol disodium with a pharmaceutically acceptable acid can result in decreased variability in Cmax and AUC∞ relative to administration without acid.

In a separate study, the food effect upon administering the compositions of the disclosure is examined. Two groups of dogs, one fasted and one fed, are administered either the 600 mg fospropofol acidified composition comprising ascorbic acid (i.e., composition A2) or 600 mg (3×200 mg) of fospropofol control composition (i.e., HMPC capsule; no acidifier). The fasted group is fasted (no food, only water) overnight prior to being administered the fospropofol close. The maximum individual fasting period does not exceed 24 hours. The fasted group is pretreated with pentagastrin. The fed group is given a high calorie meal and the dose of fospropofol is given within an hour of eating the meal. The fed group is not pretreated with pentagastrin.

TABLE B10

Food Effect Study

| Composition | Fospropofol Cmax (ng/mL) | Fospropofol AUC∞ (ng*hr/mL) | Propofol Cmax (ng/mL) | Total Fospropofol (fospropofol + propofol) Mean AUC$_{0-\infty}$ (mol*h/mL) |
|---|---|---|---|---|
| Ascorbic Acid fasted | 21433 | 18986 | 928 | $6.2779 \times 10^{-08}$ |
| Ascorbic Acid fed | 21914 | 13968 | 573 | $4.4435 \times 10^{-08}$ |
| Fed/Fasted ratio | 1.02 | 0.74 | 0.62 | 0.71 |
| Control fasted | 18300 | 15013 | 647 | $4.7778 \times 10^{-08}$ |
| Control fed | 3131 | 4313 | 193 | $1.4223 \times 10^{-08}$ |
| Fed/Fasted ratio | 0.17 | 0.29 | 0.30 | 0.30 |

Figure 31:
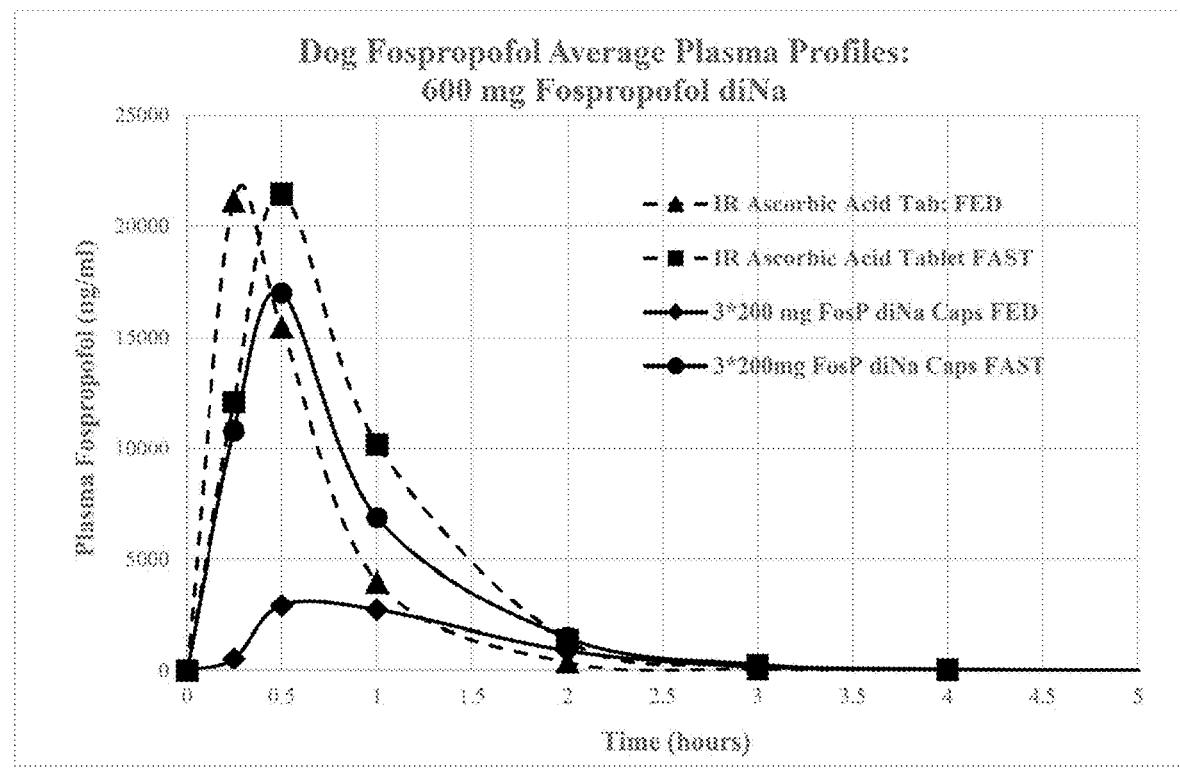
FIG. 31 depicts the fospropofol plasma profiles from 600 mg fospropofol disodium tablet with ascorbic acid acidifier (Composition A2) and 600 mg fospropofol disodium control composition (i.e., HMPC capsules, no acidifier) in fasted and fed dogs.
Figure 32:
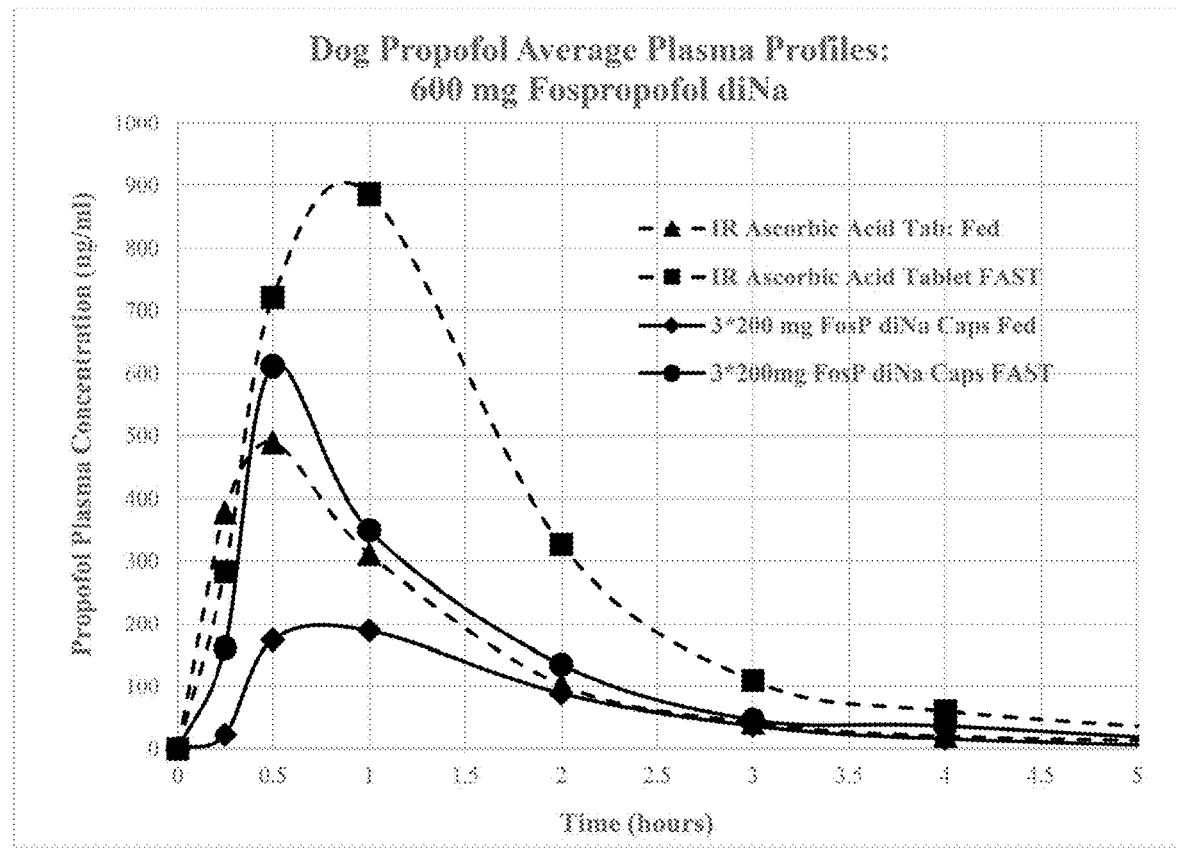
FIG. 32 depicts the propofol plasma profiles from 600 mg fospropofol disodium tablet with ascorbic acid acidifier (Composition A2) and 600 mg fospropofol disodium control composition (i.e., HMPC capsules, no acidifier) in fasted and fed dogs.
Figure 33:
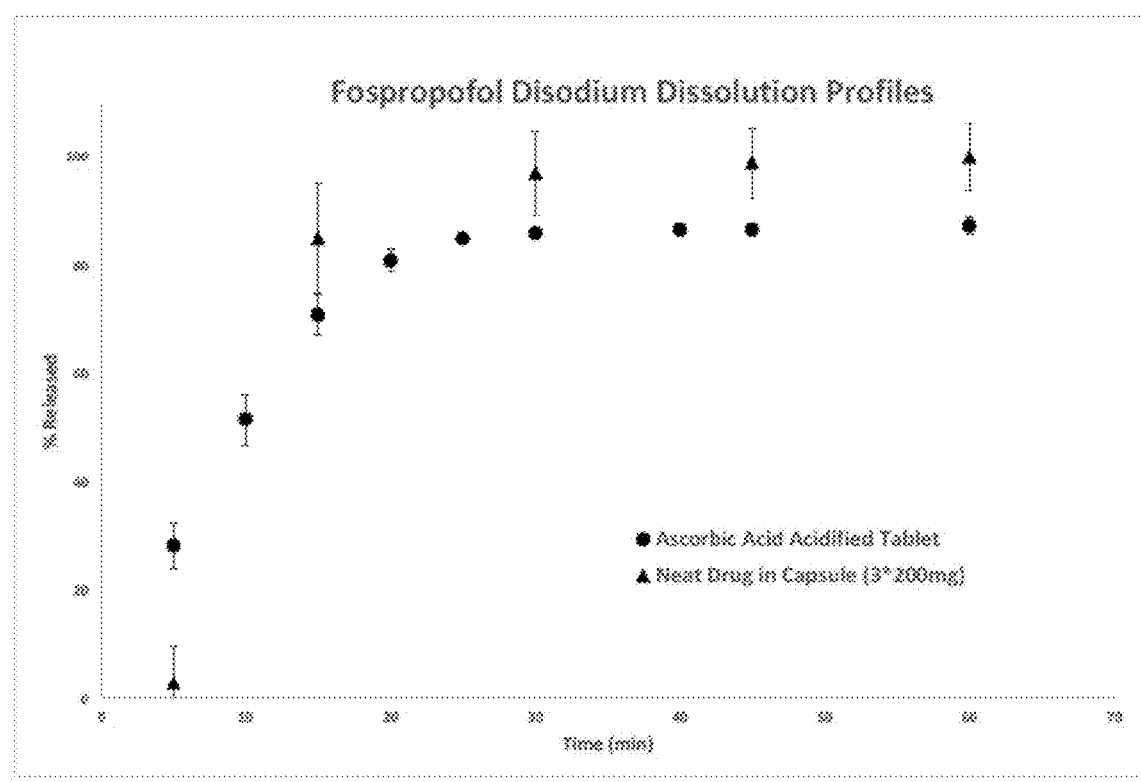
FIG. 33 compares the dissolution profile of the 600 mg fospropofol disodium tablet with ascorbic acid acidifier (Composition A2) and 600 mg (3×200 mg) fospropofol disodium control composition (i.e., HMPC capsules, no acidifier).

These results demonstrate that the acidified compositions demonstrate a food effect and that the food effect differs from that observed with the non-acidified control composition. See FIG. 31; Table B10.

Both the acidified tablet and the control composition exhibit a negative food effect on the bioavailability of fospropofol.

The extent of the food effect is modulated depending on the dosage form.

In the control compositions, the mean fospropofol Cmax (fed) is 17% of the mean fospropofol Cmax (fasted). In the acidified tablet, the mean fospropofol Cmax (fed) is 102% of the mean fospropofol Cmax (fasted).

In the control compositions, the mean total fospropofol Cmax (fed) is 30% of the mean total fospropofol Cmax (fasted). In the acidified tablet, the mean total fospropofol Cmax (fed) is 71% of the mean total fospropofol Cmax (fasted).

In the control compositions, the mean total fospropofol $AUC_{0-\infty}$ (fed) is 30% of the mean total fospropofol $AUC_{0-\infty}$ (fasted). In the acidified tablet, the mean total fospropofol $AUC_{0-\infty}$ (fed) is 71% of the mean total fospropofol $AUC_{0-\infty}$ (fasted).

Example C—Fospropofol Salts

Example C1

Instrumental Methods

XRPD diffractograms were collected on a Bruker D8 diffractometer using Cu Kα radiation (40 kV, 40 mA) and a 0-2θ goniometer fitted with a Ge monochromator. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively.

Samples were run under ambient conditions as flat plate specimens using powder. The sample was prepared on a polished, zero-background (510) silicon wafer by gently pressing onto the flat surface or packed into a cut cavity. The sample was rotated in its own plane. The details of the standard Pharmorphix data collection method are:
 Angular range: 2 to 42° 2θ
 Step size: 0.05° 2θ
 Collection time: 0.5 s/step (total collection time: 6.40 min)

XRPD diffractograms were also collected on a PANalytical Empyrean diffractometer using Cu Kα radiation (45 kV, 40 mA) in transmission geometry. A 0.5° slit, 4 mm mask and 0.04 rad Soller slits with a focusing mirror were used on the incident beam. A PIXcel30 detector, placed on the diffracted beam, was fitted with a receiving slit and 0.04 rad Soller slits. The software used for data collection was X'Pert Data Collector using X'Pert Operator Interface. The data were analysed and presented using Diffrac Plus EVA or HighScore Plus.

Samples were prepared and analysed in either a metal or Millipore 96 well-plate in transmission mode. X-ray transparent film was used between the metal sheets on the metal well-plate and powders (approximately 1-2 mg) were used. The Millipore plate was used to isolate and analyse solids from suspensions by adding a small amount of suspension directly to the plate before filtration under a light vacuum. The scan mode for the metal plate used the gonio scan axis, whereas a 2θ scan was utilised for the Millipore plate. The details of the standard screening data collection method are:
 Angular range: 2.5 to 32.0° 2θ
 Step size: 0.0130° 2θ
 Collection time: 12.75 s/step (total collection time of 2.07 min)

Solution State NMR $^{1}$H NMR and/or $^{13}$C NMR spectra were collected on a Bruker 400 MHz instrument equipped with an auto-sampler and controlled by a DRX400 console. Samples were prepared in DMSO-$d_6$ solvent, unless otherwise stated. Automated experiments were acquired using ICON-NMR configuration within Topspin software, using standard Bruker-loaded experiments ($^{1}$H, $^{13}$C {$^{1}$H}, DEPT135). Off-line analysis was performed using ACD Spectrus Processor.

Differential Scanning Calorimetry (DSC)

DSC data were collected on a TA Instruments Q2000 equipped with a 50 position auto-sampler. Typically, 0.5-3 mg of each sample, in a pin-holed aluminium pan, was heated at 10° C./min from 25° C. to 300° C. A purge of dry nitrogen at 50 ml/min was maintained over the sample. The instrument control software was Advantage for Q Series and Thermal Advantage and the data were analysed using Universal Analysis or TRIOS.

Thermal Gravimetric Analysis

TGA data were collected on a TA Instruments Discovery TGA, equipped with a 25 position auto-sampler. Typically, 5-10 mg of each sample was loaded onto a pre-tared aluminium DSC pan and heated at 10° C./min from ambient temperature to 350° C. A nitrogen purge at 25 ml/min was maintained over the sample. The instrument control software was TRIOS and the data were analysed using TRIOS or Universal Analysis.

Example C2

Preparation of Fospropofol
Procedure 1

Fospropofol disodium (100 mg, ±1 mg) was weighed into 3 HPLC vials and dissolved in water (5 vol. 0.5 ml) at RT. Hydrochloric acid, sulfuric acid or phosphoric acid (2.1 eq.

1 M in THF) was added to the samples and stirred for 5 minutes and no solids were observed. Samples were cooled to 5° C. and still no solids were observed. The sample containing hydrochloric acid was selected to extract the product using DCM (3×extraction with 0.5 ml DCM). The organic layers were collected and concentrated under rotary evaporator at 50° C. resulting in a clear colourless oil. This oil was analysed by 1H NMR, HPLC and scanning ion chromatography.

Procedure 2

Fospropofol disodium (2.0 g) was dissolved in water (5 vol) at RT. Once a clear solution was obtained HCl (2.1 eq., 0.5 Min water) was added and a cloudy solution was formed. The sample was transferred to a separating funnel and DCM (30 ml) added to extract the free acid but instead formed a thick white emulsion with no phase separation. DCM (130 ml) was added to try and increase phase separation and water (100 ml) was added to solubilize any NaCl precipitating out of solution. The thick white emulsion remained so THF was added to disrupt the emulsion, resulting in separation of the aqueous and organic phases both cloudy solutions. The organic layer was collected and the aqueous layer washed with THF:DCM 25:75 (2×40 ml). The organic layer was concentrated under vacuum resulting in a clear oil.

Example C3

The following procedure was used to make the potassium (from KOH), diethylamine, t-butylamine, ethylene diamine, benzathine, piperazine, ethanolamine, diethanolamine, ammonium (from NH$_4$OH), tromethamine, benethamine, and histidine salts.

Fospropofol free acid (25 mg) was dissolved in EtOH (20 vol, 500 l) at RT. The solutions were treated with the corresponding base (2 mol eq., added as a stock solution) at 25° C. After 10 minutes at 25° C., the mixtures were cooled to 5° C. at 0.1° C./min. After 48 hrs at 5° C. solids were filtered, air dried and analysed by XRPD, solutions were allowed to evaporate at RT. Solids formed from evaporation were analysed by XRPD, gums and oils were placed under vacuum for 3 hours. Solids were analysed by XRPD and remaining gums and oils matured at 50° C./RT in 4 hours temperature cycles for 48 hrs.

XRPD was again taken after 7 days storage at 40° C./75% RH. Form II of the diethylamine salt and Form II of the ethanolamine salt were formed by conversion of Form I of the respective salts after 7 days storage at 40° C./75% RH.

Example C4

The following procedures were used to make the calcium (from CaCl$_2$), magnesium (from MgCl$_2$), and zinc (ZnCl$_2$) salts.

Small Scale: Fospropofol disodium (50 mg) was dissolved in water (10 vol, 500 d). The solutions were treated with the corresponding base (1 mol eq., added as a stock solution). Additional ethanol (500 l) was added after the formation of a thick suspension and samples stirred for 1 hour before being filtered and dried in a vacuum oven for 2 hours at 40° C. Form I of the calcium salt and Form I of the zinc salt were produced under these conditions.

Form II of the calcium salt was produced from Form I of the calcium salt after 7 days storage at 40° C./75% RH.

Scale Up: Fospropofol disodium (500 mg) was dissolved in water (10 vol, 5 ml). The solutions were treated with the corresponding base (1 mol eq. CaCl2, MgCl2, or ZnCl2). Additional ethanol* (5 ml) was added after the formation of a thick suspension and samples stirred for 1 hour before being filtered and dried in a vacuum oven for 2 hours at 40° C. *ethanol (5 ml) was added three times for the sample containing the calcium counter ion as thick precipitate continued to stop stirring. This procedure produced Form III of the calcium salt and Form II of the zinc salt. ion chromatography of the product salts indicated that the calcium and magnesium salts each contained 1 eq. of the metal counterion, and the zinc salt contained 2 eq. of the metal counterion.

Example C5

Preparation of Ethylene Diamine Salt

The free acid (500 mg) was dissolved in EtOH (20 vol, 10 ml) at 50° C. The solution was treated with ethylene diamine (2 mol eq.) at 50° C. The sample was cooled to 5° C. at 0.1° C./min. After 48 hrs at 5° C. solids were filtered and dried in a vacuum oven for 2 hours at 40° C.

Example C6—Intrinsic Dissolution Rate at pH 4.5

Intrinsic Dissolution Rate was measure in GI tract buff (pH—4.5 buffer): 2.99 g sodium acetate trihydrate was dissolved in 14.0 ml 2N acetic acid in a 1000 ml volumetric flask, and then made to volume with deionised water.

Data were collected on a Sirius inform instrument fitted with a dual UV DipProbe attachment and Ag/AgCl combination pH electrode. The electrode was calibrated using the four plus parameters derived from a blank titration. The base titrant was standardised by titration with TRIS. 0.5 M HCl and NaOHaqueous solutions were used as the acid and base titrants respectively for the testing. Stirring was facilitated by a dual overhead stirrer to allow thorough mixing within the vessel, and media was introduced via a capillary bundle attached to a dispensing bank comprised of six precision dispensing units. A Peltier heating jacket was used to maintain the temperature of the titration vessel. Discs were introduced to the vessel via the tablet picker housed in the probe arm, after the desired temperature of the media had been reached. Sirius inform Assay Design, Control and Refine software were used to design, run and refine data respectively.

The reference sample was prepared as a 20.1 mM stock solution in water. One MEC data sets were then collected using five additions each of the water stock using 250, 500 and three times 750 µl aliquots, respectively. UV Spectra were then collected after each addition of the water stock to build a multi-point MEC calibration, using a 20 mm path length probe. The MEC data set was then imported into the dissolution data files in order to convert the UV absorbance measured to concentration. The concentration range for UV data collected was 124.8 µM-1.4 mM. MEC data were collected at 37° C. to match the dissolution experiments. Same MEC data was used as for faSSGf IDR experiments due to there being no change in the UV profile at this pH.

Intrinsic Dissolution Rate (IDR): Approximately. 10-20 mg of the sample was compressed in a 3 mm disc recess, under 100 kg for 2 minutes, with greaseproof paper on the compression base, to form nondisintegrating discs. The discs were then plugged with a bung so that only one surface was exposed to the media during analysis and transferred to the Sirius inform dissolution apparatus. Analysis was performed at 37° C. in 36 ml water and 4 ml GI media with the pH set to 4.5, for 1 hour with UV spectra collected every 10 seconds. A stir speed of 100 rpm was used with a 20 mm path length probe. The IDR was calculated based on the surface area of the 3 mm disc recess used (7.07 mm2 surface area). XRPD analysis was performed on all samples, both after compression of the material into the disc recess, and post dissolution analysis to observe any change in form. All analysis was performed using XRPD 2.

X-Ray Powder Diffraction (XRPD2): XRPD diffractograms were collected on a Bruker AXS C2 GADDS diffractometer using Cu Ka radiation (40 kV, 40 mA), an automated XYZ stage, a laser video microscope for auto sample positioning and a Vantec-500 2-dimensional area detector. X-ray optics consists of a single Gobel multilayer mirror coupled with a pinhole collimator of 0.3 mm. The beam divergence, i.e. the effective size of the X-ray beam on the sample, was approximately 4 mm. A 9-9 continuous scan mode was employed with a sample—detector distance of 20 cm which gives an effective 29 range of 1.5°-32.5°. The sample was exposed to the X-ray beam for 120 seconds under ambient conditions. The software used for data collection and analysis was GADDS for Win7/XP and Diffrac Plus EVA respectively.

The results are shown in the Table C1 below.

TABLE C1

| Salt | Average pH | IDR (mg/min/cm$^2$) Duplicate | Average | XRPD Analysis Post Dissolution |
|---|---|---|---|---|
| Sodium | 4.6 | 38.04, 35.67 | 37 | Not Performed |
| Ethylene Diamine (Example 5) | 4.5 | 0.76, 0.78 | 0.77 | Amorphous |
| Calcium (Example 4) | 4.5 | 0.51, 0.37 | 0.44 | Amorphous |
| Magnesium (Example 4) | 4.5 | 0.47, 0.44 | 0.46 | Amorphous |
| Zinc (Example 4) | 4.5 | 0.19, 0.18 | 0.18 | Amorphous |

Example C7—Intrinsic Dissolution Rate at pH 1.9

Intrinsic Dissolution Rate was Determined in Simulated Intestinal Fluid at pH Base Buffer (FaSSGF):

Sodium chloride (2.0 g) and deionized water added to a 1000 ml volumetric flask, pH adjusted to 1.6 with concentrated hydrochloric FaSSGF acid, made up to volume with deionised water.

FaSSGF Media:

Phares SIF (simulated intestinal fluid) powder (0.06 g) was added to a 1 L volumetric flask and made to volume with base buffer.

Data were collected on a Sirius inform instrument fitted with a dual UV Dip Probe attachment and Ag/AgCI combination pH electrode. The electrode was calibrated using the four plus parameters derived from a blank titration. The base titrant was standardised by titration with TRIS. 0.5 M HCl and NaOH aqueous solutions were used as the acid and base titrants respectively for the testing. Stirring was facilitated by a dual overhead stirrer to allow thorough mixing within the vessel, and media was introduced via a capillary bundle attached to a dispensing bank comprised of six precision dispensing units. A Peltier heating jacket was used to maintain the temperature of the titration vessel. Discs were introduced to the vessel via the tablet picker housed in the probe arm, after the desired temperature of the media had been reached. Sirius inform Assay Design, Control and Refine software were used to design, run and refine data respectively.

Molar Extinction Coefficient (MEC): The reference sample was prepared as a 20.1 mM stock solution in water. One MEC data sets were then collected using five additions each of the water stock using 250, 500 and three times 750 µl aliquots, respectively. UV Spectra were then collected after each addition of the water stock to build a multi-point MEC calibration, using a 20 mm path length probe. The MEC data set was then imported into the dissolution data files in order to convert the UV absorbance measured to concentration. The concentration range for UV data collected was 124.8 µM-1.4 mM. MEC data were collected in the dissolution media {faSSGf) and at 37° C. to match the dissolution experiments.

Intrinsic Dissolution Rate (IDR): Ca. 10-20 mg of the sample was compressed in a 3 mm disc recess, under 100 kg for 2 minutes, with greaseproof paper on the compression base, to form nondisintegrating discs. The discs were then plugged with a bung so that only one surface was exposed to the media during analysis and transferred to the Sirius inform dissolution apparatus. Analysis was performed at 37° C. in 40 ml faSSGf media for 1 hour with UV spectra collected every 30 seconds. A stir speed of 100 rpm was used with a 20 mm path length probe. The IDR was calculated based on the surface area of the 3 mm disc recess used (7.07 mm2 surface area). XRPD analysis was performed on all samples, both after compression of the material into the disc recess, and post dissolution analysis to observe any change in form. All analysis was performed using XRPD 2.

X-Ray Powder Diffraction (XRPD2): XRPD diffractograms were collected on a Bruker AXS C2 GADDS diffractometer using Cu Ka radiation (40 kV, 40 mA), an automated XYZ stage, a laser video microscope for auto sample positioning and a Vantec-500 2-dimensional area detector. X-ray optics consists of a single Gobel multilayer mirror coupled with a pinhole collimator of 0.3 mm. The beam divergence, i.e. the effective size of the X-ray beam on the sample, was approximately 4 mm. A 9-9 continuous scan mode was employed with a sample—detector distance of 20 cm which gives an effective 29 range of 1.5°-32.5°. The sample was exposed to the X-ray beam for 120 seconds under ambient conditions. The software used for data collection and analysis was GADDS for Win7/XP and Diffrac Plus EVA respectively.

The results are shown in the Table below.

| Salt | Average pH | IDR (mg/min/cm$^2$) Duplicate | Average | XRPD Analysis Post Dissolution |
|---|---|---|---|---|
| Sodium | 1.8 | 41.5, 44.2 | 43 | Not Performed |
| Ethylene Diamine (Example 5) | 1.6 | 1.16, 1.29 | 1.2 | Amorphous |
| Calcium (Example 4) | 1.8 | 1.15, 1.14 | 1.2 | Amorphous |
| Magnesium (Example 4) | 1.8 | 1.51, 1.67 | 1.6 | Amorphous |
| Zinc (Example 4) | 1.8 | 1.22, 1.31 | 1.3 | Amorphous |

Example C8

A fospropofol calcium salt tablet within a tablet can be prepared as follows. The core tablet contains fospropofol calcium salt (200 mg; 20% by wt. dosage form), microcrystalline cellulose (100 mg; 10% by wt. of dosage form), pregelatinized starch (e.g., Starch 1500) (97.5 mg; 9.75% by weight of dosage form), magnesium stearate (2.5 mg; 0.25% by wt. of dosage form). The outer layer, which surrounds the core tablet, contains fospropofol calcium salt (400 mg; 40% by wt. of dosage form), microcrystalline cellulose (100 mg; 10% wt. of dosage form), pregelatinized starch (e.g., Starch 1500) (97.5 mg; 9.75% by wt. of dosage form), magnesium stearate (2.5 mg; 0.25% by wt. of dosage form). This is a modified-release dosage form. The outer layer dissolves rapidly in the stomach. The core tablet dissolves slowly in the stomach, and further dissolves in the intestines.

Example C9

A fospropofol magnesium salt bilayer tablet can be prepared as follows.

One layer contains fospropofol magnesium salt (200 mg; 20% by wt. of bilayer tablet), microcrystalline cellulose (100 mg; 10% by wt. of bilayer tablet), pregelatinized starch (e.g., Starch 1500) (97.5 mg; 9.75% by wt. of bilayer tablet), magnesium stearate (2.5 mg; 0.25% by wt. of bilayer tablet).

The other layer contains fospropofol magnesium salt (400 mg; 40% by wt. of bilayer tablet), microcrystalline cellulose (100 mg; 10% by wt. of bilayer tablet), pregelatinized starch (e.g., Starch 1500) (97.5 mg; 9.75% by wt. of bilayer tablet), magnesium stearate (2.5 mg; 0.25% by wt. of bilayer tablet).

This is a modified-release dosage form. One layer dissolves rapidly in the stomach. The other layer dissolves slowly in the stomach, and further dissolves in the intestines.

Example C10

A Fospropofol Dosage form with immediate release and delayed release components can be prepared as follows.

The delayed release component contains fospropofol zinc salt (200 mg; 20% by wt. of final dosage form), microcrystalline cellulose (100 mg; 10% by wt. of final dosage form), pregelatinized starch (e.g., Starch 1500) (17.5 mg; 1.75% by wt. of final dosage form), HMPC (80 mg; 8% by wt. of final dosage form), magnesium stearate (2.5 mg; 0.25% by wt. of final dosage form).

The immediate release component contains fospropofol zinc salt (400 mg; 40% by wt. of final dosage form), microcrystalline cellulose (100 mg; 10% by wt. of final dosage form), pregelatinized starch (e.g., Starch 1500) (97.5 mg; 9.75% by wt. of final dosage form), and magnesium stearate (2.5 mg; 0.25% by wt. of final dosage form).

This is a modified-release dosage form. The delayed release component granules and the immediate release component granules may be combined and pressed into a tablet, or may be combined in a capsule.

Example C11

A Fospropofol Dosage form with immediate release and enteric coated components can be prepared as follows.

The enteric coated component contains fospropofol ethylene diamine salt (200 mg; 20% by wt. of final dosage form), microcrystalline cellulose (100 mg; 10% by wt. of final dosage form), pregelatinized starch (e.g., Starch 1500) (47.5 mg; 4.75% by wt. of final dosage form), magnesium stearate (2.5 mg; 0.25% by wt. of final dosage form), Eudragit L (50 mg; 5% by wt. of final dosage form).

The immediate release component contains fospropofol ethylene diamine (400 mg; 40% by wt. of final dosage form), microcrystalline cellulose (100 mg; 10% by wt. of final dosage form), pregelatinized starch (e.g., Starch 1500) (97.5 mg; 9.75% by wt. of final dosage form), and magnesium stearate (2.5 mg; 0.25% by wt. of final dosage form).

This is a modified-release dosage form. The enteric coated component granules and the immediate release component granules or beads may be combined and pressed into a tablet, or may be combined in a capsule.

Example C12

Randomized, double blind, parallel group, comparative evaluation of the safety-tolerability, pharmacokinetics, and efficacy of 3 dosage forms of PO fospropofol salt administered to young healthy male and female volunteers for the acute treatment of moderate or severe migraine headache is conducted as follows.

This study will assess the safety-tolerability, pharmacokinetics, and efficacy (pain relief), in a similar population as in Example C1, of a single administration of one of three dosage forms (the dosage forms of Examples C8, C9, and C10).

The study will also assess the efficacy for relief of associated symptoms (nausea, photophobia, phonophobia) of a single administration of one of three dosage forms (the dosage forms of Examples C8, C9, and C10).

Inclusion criteria: Male and female volunteers, age 18-65 years inclusive with an established diagnosis of migraine, with or without aura, according to IHS criteria. The age at the time of initial migraine diagnosis≤50 yo, and the time since initial diagnosis of migraine>one year. The estimated frequency of migraine episodes classified as moderate or severe is at least one per month on average over the past year. Subjects with coexisting headache other than migraine are eligible provided that these headaches are distinguishable from the subject's migraine headaches. No relevant contraindication to use of fospropofol or propofol according to FDA approved labeling. Concomitant medications intended to reduce the frequency of migraine are permitted provided that the close is stable for at least 3 months prior to enrolment and estimated headache frequency meets the criterion above. If concomitant medications intended to reduce the frequency of migraine are discontinued prior to the study, these medications must be discontinued at least one month prior to enrolment. Patients will also have an absence of any clinically significant medical condition that, in the opinion of the investigator or the Sponsor, may be potentially associated with an increased risk from participation in the study.

Exclusion criteria: Subjects with any medical condition (e.g., sleep apnea) which, in the opinion of the investigator or the Sponsor, may be potentially associated with an increased risk from the administration of study drug. Subjects with a contraindication to use of fospropofol or propofol according to FDA approved labeling. Subjects with any medical condition, which, in the opinion of the investigator or the Sponsor, may be potentially associated with an increased risk from participation in the study. Subjects who require concomitant medications, the use of which, in the opinion of the investigator or the Sponsor, may be potentially associated with an increased risk from participation in the study. Subjects unable or unwilling to provide informed consent. Women of childbearing potential must be on adequate, reliable contraception.

A separate cohort of 36 subjects will be randomized to receive one of 3 regimens (N=12/group) under double-blind conditions, each regimen comprising a single administration of one of the dosage forms of Example C8, C9, or C10.

Double-blinding will be preserved by administering an appropriate number of active and placebo capsules for the second close.

The subject's blood will be sampled pre-close (within 15 min of closing) and post-close: 5, 10, 20, 30, 45, 90 minutes and 2, 4, 6, and 9 hours post-close. Plasma samples will be assayed for fospropofol and propofol using validated analytical method(s) according to the principles of Good Laboratory Practice.

The following parameters will be calculated with fospropofol and propofol plasma concentrations: AUC0-30 min, AUC0-2 h, AUC0-t, AUC0-inf, Cmax, Residual area, Tmax, T½ el, Kel, Cl/F, Vd/F, and Vd/F/kg.

Subject's will assess headache pain utilizing a 4-point Likert Scale to be assessed at baseline (within 15 min of closing), and post-close at 15 min, 30 min, 1 h, 1.5 h, 2 h, 4 h, 6 h, 8 h, 10 h (in clinic) and following discharge (by diary) at 24 h and 48 h post-closing. Subjects will be asked to record by patient diary any recurrence or worsening of headache pain, and time of onset or worsening. (Note that a qualifying headache must be of at least moderate severity.)

Subjects will assess presence/absence of the most bothersome associated symptom for the presenting headache at baseline (within 15 min of closing), and post-close at 15 min, 30 min, 1 h, 1.5 h, 2 h, 4 h, 6 h, 8 h, 10 h (in clinic) and following discharge (by diary) at 24 h and 48 h post-closing. Subjects will be asked to record by patient diary any recurrence or worsening of the most bothersome symptom, and time of onset or worsening.

Subject's will assess the presence/absence of nausea/vomiting, photophobia, and/or phonophobia at baseline (within 15 min of closing), and post-close at 15 min, 30 min, 1 h, 1.5 h, 2 h, 4 h, 6 h, 8 h, 10 h (in clinic) and following discharge (by diary) at 12 h, 24 h and 48 h post-closing. Subjects will be asked to record by patient diary any recurrence or worsening of the most bothersome symptom, and time of onset or worsening.

Subjects will be instructed to report any adverse events directly to the investigators or clinic staff. Subjects will be instructed to record in the patient diary any adverse events emerging following discharge. All subjects will have telephone access to the investigator or investigator staff to report any urgent concerns in the course of the study.

In order to detect the possible emergence of any clinically significant cardiac arrhythmia or other abnormality cardiac telemetry will be monitored from pre-close until 10 hours post-close. Volunteers with any clinically significant ECG abnormality at baseline (pre-close) will be excluded.

Blood pressure (BP), heart rate (HR), respiratory rate (RR), and pulse oximetry will be recorded within 15 min pre-close and at approximately 30 min, and 1, 1.5, 2, 2.5, 3, 4, 5, 6, 8, and 10 hours after closing.

Modified Observer's Assessment of Alertness/Sedation (OAA/S) score within 15 min pre-close and at approximately 15 min, 30 min, and 1, 1.5, 2, 2.5, 3, 4, 5, 6, 8, and 10 hours after closing will be assessed.

Hematology, biochemistry, and urinalysis will be assessed at screening and end of study participation.

Alcohol breath test, urine cotinine determination, and urine drug screen will be assessed at check-in.

A physical examination will be conducted at screening and end of study. An abbreviated physical exam will be conducted at clinic check-in.

Subjects will be monitored throughout the study by clinic staff for adverse events. A physician will be on site for each drug administration and until 10 hours post-close, and available on call for the remainder of the study.

This study will demonstrate that each of the dosage forms of Examples C8, C9, or C10, is safe and effective in treating migraine.

The disclosure is also directed to the following aspects:

Aspect 1. Method of Treating Migraine Aspects A method of treating migraine in a patient in need thereof, comprising administering to said patient an effective amount of fospropofol, a pharmaceutically acceptable salt of fospropofol, or mixtures thereof, in one or more closes.

Aspect 2. The method of aspect 1, wherein said effective amount of fospropofol, a pharmaceutically acceptable salt of fospropofol, or mixtures thereof, is administered orally, perorally, subcutaneously, intramuscularly, intravenously, transmucosally, sublingually, buccally, transdermally, intraintestinally, rectally, or intrapulmonarily.

Aspect 3. The method of aspect 2, wherein said effective amount of fospropofol, a pharmaceutically acceptable salt of fospropofol, or mixtures thereof, is administered perorally.

Aspect 4. The method of aspect 1, wherein said pharmaceutically acceptable salt of fospropofol is fospropofol disodium.

Aspect 5. The method of aspect 1, wherein said effective amount of fospropofol, a pharmaceutically acceptable salt of fospropofol, or mixtures thereof, is 100-4800 mg (on a fospropofol basis).

Aspect 6. The method of aspect 5, wherein said effective amount is 100-3600 mg (on a fospropofol basis).

Aspect 7. The method of aspect 1, wherein said effective amount of fospropofol, a pharmaceutically acceptable salt of fospropofol, or mixtures thereof, is administered in one dose.

Aspect 8. The method of aspect 1, wherein said effective amount of fospropofol, a pharmaceutically acceptable salt of fospropofol, or mixtures thereof, is administered in more than one dose.

Aspect 9. The method of aspect 8, wherein the time interval between administration of the first close and administration of the second close is about 5-120 minutes.

Aspect 10. The method of aspect 8, wherein the first close provides 10-100% (by weight on a fospropofol basis) of the effective amount of fospropofol, a pharmaceutically acceptable salt of fospropofol, or mixtures thereof.

Aspect 11. The method of aspect 1, wherein said administering an effective amount of fospropofol, a pharmaceutically acceptable salt of fospropofol, or mixtures thereof, in one or more closes, results in a plasma Cmax or mean Cmax of propofol of at least 200-1600 ng/mL.

Aspect 12. The method of aspect 1, wherein said administering an effective amount of fospropofol, a pharmaceutically acceptable salt of fospropofol, or mixtures thereof, in one or more closes, results in a plasma Cmax or mean Cmax of propofol of no greater than 5000 ng/mL.

Aspect 13. The method of aspect 1, wherein said administering an effective amount of fospropofol, a pharmaceutically acceptable salt of fospropofol, or mixtures thereof, in one or more closes, results in a plasma $AUC_2$ hr or mean $AUC_2$ hr of propofol of no greater than 3200 ng hr/mL.

Aspect 14. The method of aspect 1, wherein said administering an effective amount of fospropofol, a pharmaceutically acceptable salt of fospropofol, or mixtures thereof, in one or more closes, results in a plasma mean $AUC_{20min}$/mean $AUC_{60min}$ ratio on a mean concentration vs. time curve that is less than 0.29.

Aspect 15. The method of aspect 1, wherein said administering an effective amount of fospropofol, a pharmaceutically acceptable salt of fospropofol, or mixtures thereof, in one or more closes, results in a plasma mean $AUC_{20min}$/mean AUC120 min ratio on a mean concentration vs. time curve that is less than 0.23.

Aspect 16. The method of aspect 1, wherein said administering an effective amount of fospropofol, a pharmaceutically acceptable salt of fospropofol, or mixtures thereof, in one or more closes, results in a plasma mean $AUC_{30min}$/mean $AUC_{60min}$ ratio on a mean concentration vs. time curve that is less than 0.68.

Aspect 17. The method of aspect 1, wherein said administering an effective amount of fospropofol, a pharmaceutically acceptable salt of fospropofol, or mixtures thereof, in one or more closes, results in a plasma mean $AUC_{30min}$/mean AUC120 min ratio on a mean concentration vs. time curve that is less than 0.55.

Aspect 18. The method of aspect 1, wherein said administering an effective amount of fospropofol, a pharmaceutically acceptable salt of fospropofol, or mixtures thereof, in one or more closes, results in a mean $C_{20}$/mean $C_{60}$ ratio is less than 5.

Aspect 19. The method of aspect 1, wherein said administering an effective amount of fospropofol, a pharmaceutically acceptable salt of fospropofol, or mixtures thereof, in one or more closes, results in a mean $C_{20}$/mean $C_{120}$ ratio is less than 76.

Aspect 20. The method of aspect 1, wherein said administering an effective amount of fospropofol, a pharmaceutically acceptable salt of fospropofol, or mixtures thereof, in one or more closes, results in a mean $C_{30}$/mean $C_{60}$ ratio is less than 2.4.

Aspect 21. The method of aspect 1, wherein said administering an effective amount of fospropofol, a pharmaceutically acceptable salt of fospropofol, or mixtures thereof, in one or more closes, results in a mean $C_{30}$/mean $C_{120}$ ratio is less than 36.

Aspect 22. The method of aspect 1, wherein said administering an effective amount of fospropofol, a pharmaceutically acceptable salt of fospropofol, or mixtures thereof, in one or more closes, results in a plasma $AUC_2$ hr or mean $AUC_2$ hr of propofol no greater than 40-80% of $AUC_0$-∞ or mean $AUC_0$-∞.

Aspect 23. The method of aspect 1, wherein said administering an effective amount of fospropofol, a pharmaceutically acceptable salt of fospropofol, or mixtures thereof, in one or more closes, results in a plasma concentration or mean concentration of propofol of 100-1600 ng/mL for at least 30 minutes.

Aspect 24. The method of aspect 1, wherein said administering an effective amount of fospropofol, a pharmaceutically acceptable salt of fospropofol, or mixtures thereof, in one or more closes, results in a plasma concentration or mean concentration of propofol at a time point 0.5-6 hr after Tmax or median Tmax that is 50-90% of plasma Cmax or mean Cmax of propofol.

Aspect 25. The method of aspect 1, wherein said administering an effective amount of fospropofol, a pharmaceutically acceptable salt of fospropofol, or mixtures thereof, in one or more closes, results in a Tmax of 0.1 hr-2 hour.

Aspect 26. The method of aspect 1, wherein said administering an effective amount of fospropofol, a pharmaceutically acceptable salt of fospropofol, or mixtures thereof, in one or more closes, results in a reduction of the patient's migraine pain.

Aspect 27. The method of aspect 1, wherein said administering to the patient an effective amount of fospropofol, a pharmaceutically acceptable salt of fospropofol, or mixtures thereof, in one or more closes, results in no clinically meaningful risk of developing unresponsiveness to vigorous tactile or painful stimulation as assessed by the Modified Observer's Assessment of Alertness (OAA/S) Scale.

Aspect 28. A pharmaceutical composition comprising fospropofol, a pharmaceutically acceptable salt of fospropofol, or mixtures thereof, and a pharmaceutically acceptable excipient.

Aspect 29. The pharmaceutical composition of aspect 28, wherein the pharmaceutical composition is a solid.

Aspect 30. The pharmaceutical composition of aspect 28, wherein the pharmaceutical composition is a capsule (gelatin or non-gelatin), enteric capsule, cachet, tablet, beads, or powder.

Aspect 31. The pharmaceutical composition of aspect 28, comprising fospropofol, a pharmaceutically acceptable salt of fospropofol, or mixtures thereof, in an amount of 100-4800 mg (on a fospropofol basis).

Aspect 32. The pharmaceutical composition of aspect 28, that when administered to a patient in one or more closes, results in a plasma Cmax or mean Cmax of propofol of at least 200-1600 ng/mL.

Aspect 33. The pharmaceutical composition of aspect 28, that when administered to a patient in one or more closes, results in a plasma Cmax or mean Cmax of propofol of no greater than 5000 ng/mL.

Aspect 34. The pharmaceutical composition of aspect 28, that when administered to a patient in one or more closes, results in a plasma $AUC_2$ hr or mean $AUC_2$ hr of propofol of no greater than 3200 ng hr/mL.

Aspect 35. The pharmaceutical composition of aspect 28, that when administered to a patient in one or more closes, results in a plasma $AUC_2$ hr or mean $AUC_2$ hr of propofol no greater than 40-80% of $AUC_0$-∞ or mean $AUC_0$-∞.

Aspect 36. The pharmaceutical composition of aspect 28, that when administered to a patient in one or more closes, results in a plasma concentration or mean concentration of propofol of 100-1600 ng/mL for at least 30 minutes.

Aspect 37. The pharmaceutical composition of aspect 28, that when administered to a patient in one or more closes, results in a mean $C_{20}$/mean $C_{60}$ ratio is less than 5.

Aspect 38. The pharmaceutical composition of aspect 28, that when administered to a patient in one or more closes, results in a mean $C_{20}$/mean $C_{120}$ ratio is less than 76.

Aspect 39. The pharmaceutical composition of aspect 28, that when administered to a patient in one or more closes, results in a plasma concentration or mean concentration of propofol at a time point 0.5-6 hr after Tmax or median Tmax that is 50-90% of plasma Cmax or mean Cmax of propofol.

Propofol Prodrug Aspects:
Aspect 1. A method of treating migraine in a patient in need thereof, comprising administering to said patient an effective amount of a propofol prodrug, a pharmaceutically acceptable salt of a propofol prodrug, or mixtures thereof, in one or more closes.

Aspect 2. The method of aspect 1, wherein said effective amount of a propofol prodrug, a pharmaceutically acceptable salt of a propofol prodrug, or mixtures thereof, is administered orally, perorally, subcutaneously, intramuscularly, intravenously, transmucosally, sublingually, buccally, transdermally, intraintestinally, rectally, or intrapulmonarily.

Aspect 3. The method of aspect 2, wherein said effective amount of a propofol prodrug, a pharmaceutically acceptable salt of a propofol prodrug, or mixtures thereof, is administered perorally.

Aspect 4. The method of aspect 1, wherein said effective amount of a propofol prodrug, a pharmaceutically acceptable salt of a propofol prodrug, or mixtures thereof, is 100-4800 mg (on a propofol prodrug basis or on a propofol basis).

Aspect 5. The method of aspect 4, wherein said effective amount is 100-3600 mg (on a propofol prodrug basis or on a propofol basis).

Aspect 6. The method of aspect 1, wherein said effective amount of a propofol prodrug, a pharmaceutically acceptable salt of a propofol prodrug, or mixtures thereof, is administered in one dose.

Aspect 7. The method of aspect 1, wherein said effective amount of a propofol prodrug, a pharmaceutically acceptable salt of a propofol prodrug, or mixtures thereof, is administered more than one dose.

Aspect 8. The method of aspect 7, wherein the time interval between administration of the first close and administration of the second close is about 5-120 minutes.

Aspect 9. The method of aspect 8, wherein the first close provides 10-100% (by weight on a propofol prodrug basis) of the effective amount of a propofol prodrug, a pharmaceutically acceptable salt of a propofol prodrug, or mixtures thereof.

Aspect 10. The method of aspect 1, wherein said administering an effective amount of a propofol prodrug, a pharmaceutically acceptable salt of a propofol prodrug, or mixtures thereof, in one or more closes, results in a plasma Cmax or mean Cmax of propofol of at least 200-1600 ng/mL.

Aspect 11. The method of aspect 1, wherein said administering an effective amount of a propofol prodrug, a pharmaceutically acceptable salt of a propofol prodrug, or mixtures thereof, in one or more closes, results in a plasma Cmax or mean Cmax of propofol of no greater than 5000 ng/mL.

Aspect 12. The method of aspect 1, wherein said administering an effective amount of a propofol prodrug, a pharmaceutically acceptable salt of a propofol prodrug, or mixtures thereof, in one or more closes, results in a plasma $AUC_2$ hr or mean $AUC_2$ hr of propofol of no greater than 3200 ng hr/mL.

Aspect 13. The method of aspect 1, wherein said administering an effective amount of a propofol prodrug, a pharmaceutically acceptable salt of a propofol prodrug, or mixtures thereof, in one or more closes, results in a plasma mean $AUC_{20min}$/mean $AUC_{60min}$ ratio on a mean concentration vs. time curve that is less than 0.29.

Aspect 14. The method of aspect 1, wherein said administering an effective amount of a propofol prodrug, a pharmaceutically acceptable salt of a propofol prodrug, or mixtures thereof, in one or more closes, results in a plasma mean $AUC_{20min}$/mean $AUC_{120min}$ ratio on a mean concentration vs. time curve that is less than 0.23.

Aspect 15. The method of aspect 1, wherein said administering an effective amount of a propofol prodrug, a pharmaceutically acceptable salt of a propofol prodrug, or mixtures thereof, in one or more closes, results in a plasma mean $AUC_{30min}$/mean $AUC_{60min}$ ratio on a mean concentration vs. time curve that is less than 0.68.

Aspect 16. The method of aspect 1, wherein said administering an effective amount of a propofol prodrug, a pharmaceutically acceptable salt of a propofol prodrug, or mixtures thereof, in one or more closes, results in a plasma mean $AUC_{30min}$/mean $AUC_{120min}$ ratio on a mean concentration vs. time curve that is less than 0.55.

Aspect 17. The method of aspect 1, wherein said administering an effective amount of a propofol prodrug, a pharmaceutically acceptable salt of a propofol prodrug, or mixtures thereof, in one or more closes, results in a mean $C_{20}$/mean $C_{60}$ ratio is less than 5.

Aspect 18. The method of aspect 1, wherein said administering an effective amount of a propofol prodrug, a pharmaceutically acceptable salt of a propofol prodrug, or mixtures thereof, in one or more closes, results in a mean $C_{20}$/mean $C_{120}$ ratio is less than 76.

Aspect 19. The method of aspect 1, wherein said administering an effective amount of a propofol prodrug, a pharmaceutically acceptable salt of a propofol prodrug, or mixtures thereof, in one or more closes, results in a mean $C_{30}$/mean $C_{60}$ ratio is less than 2.4.

Aspect 20. The method of aspect 1, wherein said administering an effective amount of a propofol prodrug, a pharmaceutically acceptable salt of a propofol prodrug, or mixtures thereof, in one or more closes, results in a mean $C_{30}$/mean $C_{120}$ ratio is less than 36.

Aspect 21. The method of aspect 1, wherein said administering an effective amount of a propofol prodrug, a pharmaceutically acceptable salt of a propofol prodrug, or mixtures thereof, in one or more closes, results in a plasma $AUC_2$ hr or mean $AUC_2$ hr of propofol no greater than 40-80% of $AUC_0$-∞ or mean $AUC_0$-∞.

Aspect 22. The method of aspect 1, wherein said administering an effective amount of a propofol prodrug, a pharmaceutically acceptable salt of a propofol prodrug, or mixtures thereof, in one or more closes, results in a plasma concentration or mean concentration of propofol of 100-1600 ng/mL for at least 30 minutes.

Aspect 23. The method of aspect 1, wherein said administering an effective amount of a propofol prodrug, a pharmaceutically acceptable salt of a propofol prodrug, or mixtures thereof, in one or more closes, results in a plasma concentration or mean concentration of propofol at a time point 0.5-6 hr after Tmax or median Tmax that is 50-90% of plasma Cmax or mean Cmax of propofol.

Aspect 24. The method of aspect 1, wherein said administering an effective amount of a propofol prodrug, a pharmaceutically acceptable salt of a propofol prodrug, or mixtures thereof, in one or more closes, results in a Tmax of 0.1 hr-2 hour.

Aspect 25. The method of aspect 1, wherein said administering an effective amount of a propofol prodrug, a pharmaceutically acceptable salt of a propofol prodrug, or mixtures thereof, in one or more closes, results in a reduction of the patient's migraine pain.

Aspect 26. The method of aspect 1, wherein said administering to the patient an effective amount of a propofol prodrug, a pharmaceutically acceptable salt of a propofol prodrug, or mixtures thereof, in one or more closes, results in no clinically meaningful risk of developing unresponsiveness to vigorous tactile or painful stimulation as assessed by the Modified Observer's Assessment of Alertness (OAA/S) Scale.

Aspect 27. A pharmaceutical composition comprising a propofol prodrug, a pharmaceutically acceptable salt of a propofol prodrug, or mixtures thereof, and a pharmaceutically acceptable excipient.

Aspect 28. The pharmaceutical composition of aspect 27, wherein the pharmaceutical composition is a solid.

Aspect 29. The pharmaceutical composition of aspect 27, wherein the pharmaceutical composition is a capsule (gelatin or non-gelatin), enteric capsule, cachet, tablet, beads, or powder.

Aspect 30. The pharmaceutical composition of aspect 27, comprising a propofol prodrug, a pharmaceutically acceptable salt of a propofol prodrug, or mixtures thereof, in an amount of 100-4800 mg (on a propofol prodrug basis or on a propofol basis).

Aspect 31. The pharmaceutical composition of aspect 27, that when administered to a patient in one or more closes, results in a plasma Cmax or mean Cmax of propofol of at least 200-1600 ng/mL.

Aspect 32. The pharmaceutical composition of aspect 27, that when administered to a patient in one or more closes, results in a plasma Cmax or mean Cmax of propofol of no greater than 5000 ng/mL.

Aspect 33. The pharmaceutical composition of aspect 27, that when administered to a patient in one or more closes, results in a plasma $AUC_2$ hr or mean $AUC_2$ hr of propofol of no greater than 3200 ng hr/mL.

Aspect 34. The pharmaceutical composition of aspect 27, that when administered to a patient in one or more closes, results in a plasma $AUC_2$ hr or mean $AUC_2$ hr of propofol no greater than 40-80% of $AUC_0\text{-}\infty$ or mean $AUC_0\text{-}\infty$.

Aspect 35. The pharmaceutical composition of aspect 27, that when administered to a patient in one or more closes, results in a plasma concentration or mean concentration of propofol of 100-1600 ng/mL for at least 30 minutes.

Aspect 36. The pharmaceutical composition of aspect 27, that when administered to a patient in one or more closes, results in a mean $C_{20}$/mean $C_{60}$ ratio is less than 5.

Aspect 37. The pharmaceutical composition of aspect 27, that when administered to a patient in one or more closes, results in a mean $C_{20}$/mean $C_{120}$ ratio is less than 76.

Aspect 38. The pharmaceutical composition of aspect 27, that when administered to a patient in one or more closes, results in a plasma concentration or mean concentration of propofol at a time point 0.5-6 hr after Tmax or median Tmax that is 50-90% of plasma Cmax or mean Cmax of propofol.

Fospropofol Salt Aspects

Aspect 1. A pharmaceutically acceptable salt of fospropofol, wherein said salt is a potassium, diethylamine, t-butylamine, ethylene diamine, benzathine, piperazine, ethanolamine, diethanolamine, ammonium, tromethamine, benethamine, histidine, calcium, magnesium, or zinc salt.

Aspect 2. The pharmaceutically acceptable salt of fospropofol according to aspect 1, wherein said salt is a potassium salt.

Aspect 3. The potassium salt of aspect 2, wherein said salt is characterized by an X-ray powder diffraction pattern substantially as shown in FIG. 34.

Aspect 4. The potassium salt of aspect 2 or aspect 3, wherein said salt is characterized by an X-ray powder diffraction pattern comprising peaks at 12.3, 17.3, and 20.9 degrees±0.2 degrees 2-theta, on the 2-theta scale with lambda=1.54 angstroms (Cu Kα).

Aspect 5. The potassium salt of any one of aspects 2-4, wherein said salt is characterized by an X-ray powder diffraction pattern comprising peaks at three or more of 12.3, 15.5, 16.2, 16.4, 17.3, 18.0, 18.7, 19.5, 20.0, 20.9, 23.1, 28.1, and 28.7 degrees±0.2 degrees 2-theta, on the 2-theta scale with lambda=1.54 angstroms (Cu Kα).

Aspect 6. The potassium salt of any one of aspects 2-5, wherein said salt is characterized by a differential scanning calorimetry (DSC) thermogram substantially as shown in FIG. 35 when heated at a rate of 10° C./min.

Aspect 7. The potassium salt of any one of aspects 2-6, wherein said salt is characterized by a differential scanning calorimetry (DSC) thermogram comprising an endothermic peak at about 62° C., about 144° C., or about 262° C. when heated at a rate of 10° C./min.

Aspect 8. The pharmaceutically acceptable salt of fospropofol according to aspect 1, wherein said salt is a diethylamine salt.

Aspect 9. The diethylamine salt of aspect 8, wherein said salt is the Form II salt characterized by an X-ray powder diffraction pattern substantially as shown in FIG. 36.

Aspect 10. The diethylamine salt of either aspect 8 or aspect 9, wherein said salt is characterized by an X-ray powder diffraction pattern comprising peaks at 5.8 and 11.0 degrees±0.2 degrees 2-theta, on the 2-theta scale with lambda=1.54 angstroms (Cu Kα).

Aspect 11. The diethylamine salt of any one of aspects 8-10, wherein said salt is characterized by an X-ray powder diffraction pattern comprising peaks at two or more of 5.8, 11.0, 11.5, 14.6, 17.6, 22.0, 23.0, and 24.1 degrees±0.2 degrees 2-theta, on the 2-theta scale with lambda=1.54 angstroms (Cu Kα).

Aspect 12. The diethylamine salt of aspect 8, wherein said salt is the Form I salt characterized by an X-ray powder diffraction pattern substantially as shown in FIG. 37.

Aspect 13. The diethylamine salt of either aspect 8 or aspect 12, wherein said salt is characterized by an X-ray powder diffraction pattern comprising peaks at 10.9 and 11.4 degrees±0.2 degrees 2-theta, on the 2-theta scale with lambda=1.54 angstroms (Cu Kα).

Aspect 14. The diethylamine salt of any one of aspects 8, 12, or 13, wherein said salt is characterized by an X-ray powder diffraction pattern comprising peaks at two or more of 10.9, 11.4, 14.6, 24.2, 25.9, and 27.5 degrees±0.2 degrees 2-theta, on the 2-theta scale with lambda=1.54 angstroms (Cu Kα).

Aspect 15. The diethylamine salt of any one of aspects 8, or 12-14, wherein said salt is characterized by a differential scanning calorimetry (DSC) thermogram substantially as shown in FIG. 38 when heated at a rate of 10° C./min.

Aspect 16. The diethylamine salt of any one of aspects 8, or 12-15, wherein said salt is characterized by a differential scanning calorimetry (DSC) thermogram comprising an endothermic peak at about 98° C. when heated at a rate of 10° C./min.

Aspect 17. The pharmaceutically acceptable salt of fospropofol according to aspect 1, wherein said salt is the t-butylamine salt.

Aspect 18. The t-butylamine salt of aspect 17, wherein said salt is characterized by an X-ray powder diffraction pattern substantially as shown in FIG. 40.

Aspect 19. The t-butylamine salt of either aspect 17 or aspect 18, wherein said salt is characterized by an X-ray powder diffraction pattern comprising peak at 12.2 degrees±0.2 degrees 2-theta, on the 2-theta scale with lambda=1.54 angstroms (Cu Kα).

Aspect 20. The t-butylamine salt of any one of aspects 17-19, wherein said salt is characterized by an X-ray powder diffraction pattern comprising peaks at three or more of 9.0, 9.6, 12.2, 17.1, 19.5, 21.3, 21.7, 23.9, 26.4, 28.3, and 28.8 degrees±0.2 degrees 2-theta, on the 2-theta scale with lambda=1.54 angstroms (Cu Kα).

Aspect 21. The t-butylamine salt of any one of aspects 17-20, wherein said salt is characterized by a differential scanning calorimetry (DSC) thermogram substantially as shown in FIG. 41 when heated at a rate of 10° C./min.

Aspect 22. The t-butylamine salt of any one of aspects 17-21, wherein said salt is characterized by a differential scanning calorimetry (DSC) thermogram comprising an endothermic peak at about 58° C., or at about 195° C. when heated at a rate of 10° C./min.

Aspect 23. The pharmaceutically acceptable salt of fospropofol according to aspect 1, wherein said salt is the ethylene diamine salt.

Aspect 24. The ethylene diamine salt of aspect 23, wherein said salt is characterized by an X-ray powder diffraction pattern substantially as shown in FIG. 43.

Aspect 25. The ethylene diamine salt of either aspect 23 or aspect 24, wherein said salt is characterized by an X-ray powder diffraction pattern comprising peak at 12.6 degrees±0.2 degrees 2-theta, on the 2-theta scale with lambda=1.54 angstroms (Cu Kα).

Aspect 26. The ethylene diamine salt of any one of aspects 23-25, wherein said salt is characterized by an X-ray powder diffraction pattern comprising peaks at three or more of 11.9, 12.6, 13.7, 15.1, 17.8, 20.1, 23.6, and 23.9 degrees±0.2 degrees 2-theta, on the 2-theta scale with lambda=1.54 angstroms (Cu Kα).

Aspect 27. The ethylene diamine salt of any one of aspects 23-26, wherein said salt is characterized by a differential scanning calorimetry (DSC) thermogram substantially as shown in FIG. 44 when heated at a rate of 10° C./min.

Aspect 28. The ethylene diamine salt of any one of aspects 23-27, wherein said salt is characterized by a differential scanning calorimetry (DSC) thermogram comprising an endothermic peak at about 89° C. or at about 192° C. when heated at a rate of 10° C./min.

Aspect 29. The pharmaceutically acceptable salt of fospropofol according to aspect 1, wherein said salt is the benzathine salt.

Aspect 30. The benzathine salt of aspect 29, wherein said salt is characterized by a differential scanning calorimetry (DSC) thermogram substantially as shown in FIG. 46 when heated at a rate of 10° C./min.

Aspect 31. The benzathine salt of either aspect 29 or aspect 30, wherein said salt is characterized by a differential scanning calorimetry (DSC) thermogram comprising an endothermic peak at about 111° C. when heated at a rate of 10° C./min.

Aspect 32. The pharmaceutically acceptable salt of fospropofol according to aspect 1, wherein said salt is the piperazine salt.

Aspect 33. The piperazine salt of aspect 32, wherein said salt is characterized by an x-ray powder diffraction pattern substantially as shown in FIG. 48.

Aspect 34. The piperazine salt of either aspect 32 or aspect 33, wherein said salt is characterized by an X-ray powder diffraction pattern comprising peaks at 4.9, 9.2, and 10.9 degrees±0.2 degrees 2-theta, on the 2-theta scale with lambda=1.54 angstroms (Cu Kα).

Aspect 35. The piperazine salt of any one of aspects 32-34, wherein said salt is characterized by an X-ray powder diffraction pattern comprising peaks at three or more of 4.9, 9.2, 10.9, 13.0, 16.3, 17.4, 20.0, 20.4, 21.3, 21.9, 23.2, and 24.3 degrees±0.2 degrees 2-theta, on the 2-theta scale with lambda=1.54 angstroms (Cu Kα).

Aspect 36. The piperazine salt of any one of aspects 32-35, wherein said salt is characterized by a differential scanning calorimetry (DSC) thermogram substantially as shown in FIG. 49 when heated at a rate of 10° C./min.

Aspect 37. The piperazine salt of any one of aspects 32-36, wherein said salt is characterized by a differential scanning calorimetry (DSC) thermogram comprising an endothermic peak at about 96° C., about 151° C., or about 195° C. when heated at a rate of 10° C./min.

Aspect 38. The pharmaceutically acceptable salt of fospropofol according to aspect 1, wherein said salt is the ethanolamine salt.

Aspect 39. The ethanolamine salt of aspect 38, wherein said salt is the Form II salt characterized by an X-ray powder diffraction pattern substantially as shown in FIG. 51.

Aspect 40. The ethanolamine salt of either aspect 38 or aspect 39, wherein said salt is characterized by an X-ray powder diffraction pattern comprising peaks at 12.5, and 14.2 degrees±0.2 degrees 2-theta, on the 2-theta scale with lambda=1.54 angstroms (Cu Kα).

Aspect 41. The ethanolamine salt of any one of aspects 38-40, wherein said salt is characterized by an X-ray powder diffraction pattern comprising peaks at two or more of 4.8, 12.5, 14.2, 21.9, and 25.1 degrees±0.2 degrees 2-theta, on the 2-theta scale with lambda=1.54 angstroms (Cu Kα).

Aspect 42. The ethanolamine salt of aspect 38, wherein said salt is the Form I salt characterized by an X-ray powder diffraction pattern substantially as shown in FIG. 52.

Aspect 43. The ethanolamine salt of either aspect 38 or aspect 42, wherein said salt is characterized by an X-ray powder diffraction pattern comprising peak at 10.0 degrees±0.2 degrees 2-theta, on the 2-theta scale with lambda=1.54 angstroms (Cu Kα).

Aspect 44. The ethanolamine salt of any one of aspects 38, 42, or 43, wherein said salt is characterized by an X-ray powder diffraction pattern comprising peaks at two or more of 10.0, 15.3, 15.9, 17.0, 18.5, 19.6, and 20.9 degrees±0.2 degrees 2-theta, on the 2-theta scale with lambda=1.54 angstroms (Cu Kα).

Aspect 45. The ethanolamine salt of any one of aspects 38, or 42-44, wherein said salt is characterized by a differential scanning calorimetry (DSC) thermogram substantially as shown in FIG. 53 when heated at a rate of 10° C./min.

Aspect 46. The ethanolamine salt of any one of aspects 38, or 42-45, wherein said salt is characterized by a differential scanning calorimetry (DSC) thermogram comprising an endothermic peak at about 96° C., or about 174° C. when heated at a rate of 10° C./min.

Aspect 47. The pharmaceutically acceptable salt of fospropofol according to aspect 1, wherein said salt is the diethanolamine salt.

Aspect 48. The diethanolamine salt of aspect 47, wherein said salt is characterized by a differential scanning calorimetry (DSC) thermogram substantially as shown in FIG. 55 when heated at a rate of 10° C./min.

Aspect 49. The diethanolamine salt of either aspect 47 or aspect 48, wherein said salt is characterized by a differential scanning calorimetry (DSC) thermogram comprising an endothermic peak at about 57° C. when heated at a rate of 10° C./min.

Aspect 50. The pharmaceutically acceptable salt of fospropofol according to aspect 1, wherein said salt is the ammonium salt.

Aspect 51. The ammonium salt of aspect 50, wherein said salt is characterized by an x-ray powder diffraction pattern substantially as shown in FIG. 57.

Aspect 52. The ammonium salt of either aspect 50 or aspect 51, wherein said salt is characterized by an X-ray powder diffraction pattern comprising peak at 18.1 degrees±0.2 degrees 2-theta, on the 2-theta scale with lambda=1.54 angstroms (Cu Kα).

Aspect 53. The ammonium salt of any one of aspects 50-52, wherein said salt is characterized by an X-ray powder diffraction pattern comprising peaks at three or more of 12.2, 14.2, 15.9, 18.1, 18.5, 19.2, 21.1, 21.8, and 25.8 degrees±0.2 degrees 2-theta, on the 2-theta scale with lambda=1.54 angstroms (Cu Kα).

Aspect 54. The ammonium salt of any one of aspects 50-53, wherein said salt is characterized by a differential scanning calorimetry (DSC) thermogram substantially as shown in FIG. 58 when heated at a rate of 10° C./min.

Aspect 55. The ammonium salt of any one of aspects 50-54, wherein said salt is characterized by a differential scanning calorimetry (DSC) thermogram comprising an endothermic peak at about 76° C. when heated at a rate of 10° C./min.

Aspect 56. The pharmaceutically acceptable salt of fospropofol according to aspect 1, wherein said salt is the tromethamine salt.

Aspect 57. The tromethamine salt of aspect 56, wherein said salt is characterized by an x-ray powder diffraction pattern substantially as shown in FIG. 59.

Aspect 58. The tromethamine salt of either aspect 56 or aspect 57, wherein said salt is characterized by an X-ray powder diffraction pattern comprising peaks at 10.0, 16.6, and 17.3 degrees±0.2 degrees 2-theta, on the 2-theta scale with lambda=1.54 angstroms (Cu Kα).

Aspect 59. The tromethamine salt of any one of aspects 56-58, wherein said salt is characterized by an X-ray powder diffraction pattern comprising peaks at three or more of 6.0, 10.0, 10.7, 16.6, 17.3, 18.3, 24.7, and 25.2 degrees±0.2 degrees 2-theta, on the 2-theta scale with lambda=1.54 angstroms (Cu Kα).

Aspect 60. The tromethamine salt of any one of aspects 56-59, wherein said salt is characterized by a differential scanning calorimetry (DSC) thermogram substantially as shown in FIG. 60 when heated at a rate of 10° C./min.

Aspect 61. The tromethamine salt of any one of aspects 56-60, wherein said salt is characterized by a differential scanning calorimetry (DSC) thermogram comprising an endothermic peak at about 103° C., about 133° C., or about 171° C. when heated at a rate of 10° C./min.

Aspect 62. The pharmaceutically acceptable salt of fospropofol according to aspect 1, wherein said salt is the benethamine salt.

Aspect 63. The benethamine salt of aspect 62, wherein said salt is characterized by an x-ray powder diffraction pattern substantially as shown in FIG. 62.

Aspect 64. The benethamine salt of either aspect 62 or aspect 63, wherein said salt is characterized by an X-ray powder diffraction pattern comprising peak at 16.4 degrees±0.2 degrees 2-theta, on the 2-theta scale with lambda=1.54 angstroms (Cu Kα).

Aspect 65. The benethamine salt of any one of aspects 62-64, wherein said salt is characterized by an X-ray powder diffraction pattern comprising peaks at three or more of 5.5, 7.2, 8.5, 11.7, 12.6, 16.4, 17.7, and 19.6 degrees 0.2 degrees 2-theta, on the 2-theta scale with lambda=1.54 angstroms (Cu Kα).

Aspect 66. The benethamine salt of any one of aspects 62-65, wherein said salt is characterized by a differential scanning calorimetry (DSC) thermogram substantially as shown in FIG. 63 when heated at a rate of 10° C./min.

Aspect 67. The benethamine salt of any one of aspects 62-66, wherein said salt is characterized by a differential scanning calorimetry (DSC) thermogram comprising an endothermic peak at about 86° C. when heated at a rate of 10° C./min.

Aspect 68. The pharmaceutically acceptable salt of fospropofol according to aspect 1, wherein said salt is the histidine salt.

Aspect 69. The histidine salt of aspect 68, wherein said salt is characterized by an X-ray powder diffraction pattern substantially as shown in FIG. 65.

Aspect 70. The histidine salt of either aspect 68 or aspect 69, wherein said salt is characterized by an X-ray powder diffraction pattern comprising peaks at 11.2, 15.3, and 18.9 degrees±0.2 degrees 2-theta, on the 2-theta scale with lambda=1.54 angstroms (Cu Kα).

Aspect 71. The histidine salt of any one of aspects 68-70, wherein said salt is characterized by an X-ray powder diffraction pattern comprising peaks at three or more of 11.2, 15.3, 18.9, 21.1, 21.5, 24.2, and 30.2 degrees±0.2 degrees 2-theta, on the 2-theta scale with lambda=1.54 angstroms (Cu Kα).

Aspect 72. The histidine salt of any one of aspects 68-71, wherein said salt is characterized by a differential scanning calorimetry (DSC) thermogram substantially as shown in FIG. 66 when heated at a rate of 10° C./min.

Aspect 73. The histidine salt of any one of aspects 68-72, wherein said salt is characterized by a differential scanning calorimetry (DSC) thermogram comprising an endothermic peak at about 196° C. or at about 202° C. when heated at a rate of 10° C./min.

Aspect 74. The pharmaceutically acceptable salt of fospropofol according to aspect 1, wherein said salt is the calcium salt.

Aspect 75. The calcium salt of aspect 74, wherein said salt is the Form I salt characterized by an X-ray powder diffraction pattern substantially as shown in FIG. 68.

Aspect 76. The calcium salt of either aspect 74 or aspect 75, wherein said salt is characterized by an X-ray powder diffraction pattern comprising a peak at 4.7 degrees±0.2 degrees 2-theta, on the 2-theta scale with lambda=1.54 angstroms (Cu Kα).

Aspect 77. The calcium salt of any one of aspects 74-76, wherein said salt is characterized by a DSC thermogram substantially as shown in FIG. 69, or by a TGA profile substantially as shown in FIG. 69.

Aspect 78. The calcium salt of aspect 74, wherein said salt is the Form II salt characterized by an X-ray powder diffraction pattern substantially as shown in FIG. 70.

Aspect 79. The calcium salt of either aspect 74 or aspect 78, wherein said salt is characterized by an X-ray powder diffraction pattern comprising peaks at 5.1, 7.0, 7.7, 8.6, 9.2, and 14.4 degrees±0.2 degrees 2-theta, on the 2-theta scale with lambda=1.54 angstroms (Cu Kα).

Aspect 80. The calcium salt of any one of aspects 74, 78, or 79, wherein said salt is characterized by an X-ray powder diffraction pattern comprising peaks at three or more of 4.3, 4.5, 5.0, 5.1, 7.0, 7.7, 8.6, 9.2, and 14.4 degrees±0.2 degrees 2-theta, on the 2-theta scale with lambda=1.54 angstroms (Cu Kα).

Aspect 81. The calcium salt of aspect 74, wherein said salt is the Form III salt characterized by an X-ray powder diffraction pattern substantially as shown in FIG. 71.

Aspect 82. The calcium salt of either aspect 74 or aspect 81, wherein said salt is characterized by an X-ray powder diffraction pattern comprising peaks at 4.8, and 9.7 degrees±0.2 degrees 2-theta, on the 2-theta scale with lambda=1.54 angstroms (Cu Kα).

Aspect 83. The calcium salt of any one of aspects 74, 81, or 82, wherein said salt is characterized by an X-ray powder diffraction pattern comprising peaks at three or more of 4.8, 9.7, 11.6, 11.9, 14.5, 17.2, and 29.1 degrees±0.2 degrees 2-theta, on the 2-theta scale with lambda=1.54 angstroms (Cu Kα).

Aspect 84. The pharmaceutically acceptable salt of fospropofol according to aspect 1, wherein said salt is the magnesium salt.

Aspect 85. The magnesium salt of aspect 84, wherein said salt is characterized by an X-ray powder diffraction pattern substantially as shown in FIG. 72.

Aspect 86. The magnesium salt of either aspect 84 or aspect 85, wherein said salt is characterized by an X-ray powder diffraction pattern comprising a peak at 4.5 degrees±0.2 degrees 2-theta, on the 2-theta scale with lambda=1.54 angstroms (Cu Kα).

Aspect 87. The magnesium salt of any one of aspects 84-86, wherein said salt is characterized by an X-ray powder diffraction pattern comprising peaks at two or more of 4.5, 9.1, 13.6, 20.8, and 27.9 degrees±0.2 degrees 2-theta, on the 2-theta scale with lambda=1.54 angstroms (Cu Kα).

Aspect 88. The magnesium salt of any one of aspects 84-87, wherein said salt is characterized by a DSC thermogram substantially as shown in FIG. 40, or by a TGA profile substantially as shown in FIG. 73.

Aspect 89. The magnesium salt of any one of aspects 84-88, wherein said salt is characterized by a differential scanning calorimetry (DSC) thermogram comprising an endothermic peak at about 129° C. when heated at a rate of 10° C./min.

Aspect 90. The pharmaceutically acceptable salt of fospropofol according to aspect 1, wherein said salt is the zinc salt.

Aspect 91. The zinc salt of aspect 90, wherein said salt is the Form II salt characterized by an X-ray powder diffraction pattern substantially as shown in FIG. 74.

Aspect 92. The zinc salt of either aspect 90 or aspect 91, wherein said salt is characterized by an X-ray powder diffraction pattern comprising a peak at 4.9 degrees±0.2 degrees 2-theta, on the 2-theta scale with lambda=1.54 angstroms (Cu Kα).

Aspect 93. The zinc salt of aspect 90, wherein said salt is the Form I salt characterized by an X-ray powder diffraction pattern substantially as shown in FIG. 75.

Aspect 94. The zinc salt of either aspect 90 or aspect 93, wherein said salt is characterized by an X-ray powder diffraction pattern comprising peaks at 8.1, 9.6, and 10.3 degrees±0.2 degrees 2-theta, on the 2-theta scale with lambda=1.54 angstroms (Cu Kα).

Aspect 95. The zinc salt of any one of aspects 90, 93, or 94, wherein said salt is characterized by an X-ray powder diffraction pattern comprising peaks at three or more of 5.1, 8.1, 9.6, 10.3, 11.6, 12.2, 18.2, 18.6, and 26.3 degrees±0.2 degrees 2-theta, on the 2-theta scale with lambda=1.54 angstroms (Cu Kα).

Aspect 96. The zinc salt of any one of aspects 90, or 93-95, wherein said salt is characterized by a DSC thermogram substantially as shown in FIG. 76, or by a TGA profile substantially as shown in FIG. 76.

Aspect 97. The zinc salt of any one of aspects 90, or 93-96, wherein said salt is characterized by a differential scanning calorimetry (DSC) thermogram comprising an endothermic peak at about 114° C. or about 210° C. when heated at a rate of 10° C./min.

Aspect 98. A pharmaceutical composition comprising the fospropofol salt according to any one of aspects 1-97, and a pharmaceutically acceptable excipient.

Aspect 99. A method of treating migraine in a patient in need thereof, comprising administering to said patient an effective amount of the fospropofol salt according to any one of aspects 1-97.

Aspect 100. The method of aspect 99 wherein said patient's migraine is refractory migraine.

Aspect 101. The method of any one of claim 99 or 100, wherein said effective amount of fospropofol salt is administered orally, perorally, subcutaneously, intramuscularly, intravenously, transmucosally, sublingually, buccally, transdermally, intraintestinally, rectally, or intrapulmonarily.

Acidified Pharmaceutical Dosage Forms

Aspect 1. A pharmaceutical dosage form for oral administration comprising fospropofol or a pharmaceutically acceptable salt thereof, a pharmaceutically acceptable acid.

Aspect 2. The pharmaceutical dosage form according to aspect 1 comprising fospropofol.

Aspect 3. The pharmaceutical dosage form according to aspect 1 comprising a pharmaceutically acceptable salt of fospropofol.

Aspect 4. The pharmaceutical dosage form according to aspect 3, wherein the pharmaceutically acceptable salt of fospropofol is fospropofol disodium.

Aspect 5. The pharmaceutical dosage form according to any one of the preceding aspects, wherein the pharmaceutically acceptable acid is on the FDA inactive ingredient database (ID) for approved drug products or generally recognized as safe (GRAS).

Aspect 6. The pharmaceutical dosage form according to any one of the preceding aspects, wherein the pharmaceutically acceptable acid is 1-hydroxy-2-naphthoic acid, 2,2-dichloroacetic acid, 2-hydroxethanesulfonic acid, 4-acetamidobenzoic acid, 4-aminosalicyclic acid, acetic acid, aceturic acid, Acid hydrolyzed proteins, Acid Modified Starch, Aconitic Acid, adipic acid, alginic acid, a-oxo-glutaric acid, benzenesulfonic acid, benzoic acid, butyric acid, camphor-10-sulfonic acid, camphoric acid, capric acid, caproic acid, caprylic acid, carbonic acid, Cholic acid, cinnamic acid, citric acid, cyclamic acid, D(−)-Lactic acid, Desoxycholic acid, D-glucaric acid, D-glucoheptonic acid, D-glucuronic acid, Di(tert-butyl)naphthalenedisulfonic acid, Di(tert-butyl)naphthalenesulfonic acid, DL-lactic acid, DL-mandelic acid, DL-tartaric acid, tartaric acid, dodecylsulfuric acid, Erythorbic acid (D-isoascorbic acid), ethane-1,2-disulfonic acid, ethanesulfonic acid, formic acid, fumaric acid, galactaric acid, gentisic acid, glutaric acid, glycerophosphoric acid, Glycocholic acid, glycolic acid, hexanedioic acid, hippuric acid, hydrobromic acid, Hydrochloric acid, Iron naphthenate, iron salts, iron salts, isobutyric acid, L(+)-lactic acid, L(+)-potassium acid tartrate, L(+)-tartaric acid, Lactic acid, lactobionic acid, L-ascorbic acid, ascorbic acid, L-aspartic acid, lauric acid, L-glutamic acid, L-Glutamic acid hydrochloride, Linoleic acid, L-Malic acid, L-pyroglutamic acid, L-tartaric acid, maleic acid, malic acid, malonic acid, methanesulfonic acid, monobasic potassium phosphate, monobasic sodium phosphate, naphthalene-1,5-disulfonic acid, naphthalene-2-sulfonic acid, naphthenic acids, Niacin (nicotinic acid), nicotinic acid, nitric acid, octanoic acid, oleic acid, orotic acid, oxalic acid, palmitic acid, pamoic acid, Pectin low acid, Pectinic acid, phosphoric acid, propanoic acid, Propionic acid, p-toluenesulfonic acid, pyruvic acid, saccharin, salicylic acid, sebacic acid, Sodium acid pyrophosphate, Sodium aluminum phosphate, sodium metabisulfite, Sorbic acid, stearic acid, succinic acid, sulfuric acid, tall oil fatty acids, Tannic acid (hydrolyzable gallotannins), Taurocholic acid, thiocyanic acid, Thiodipropionic acid, trifluoroacetic acid, undec-10-enoic acid, orange juice, apple juice, grapefruit juice, or a combination thereof or a combination thereof.

Aspect 7. The pharmaceutical dosage form according to any one of the preceding aspects, wherein the pharmaceutically acceptable acid is ascorbic acid, citric acid, malic acid, or tartaric acid.

Aspect 8. The pharmaceutical dosage form according to any one of the preceding aspects, wherein the pharmaceutically acceptable acid is ascorbic acid.

Aspect 9. The pharmaceutical dosage form according to any one of the preceding aspects, wherein the pharmaceutically acceptable acid is tartaric acid.

Aspect 10. The pharmaceutical dosage form according to any one of the preceding aspects, wherein the pharmaceutically acceptable acid is citric acid.

Aspect 11. The pharmaceutical dosage form according to any one of the preceding aspects, wherein the pharmaceutically acceptable acid is malic acid.

Aspect 12. The pharmaceutical dosage form according to any one of the preceding aspects, wherein dissolution of an amount of the dosage form containing a therapeutically effective amount of fospropofol, or a pharmaceutically acceptable salt thereof, in 300 mL of water at 25° C. results in a solution having a pH of 6.3 or less.

Aspect 13. The pharmaceutical dosage form according to any one of the preceding aspects, wherein dissolution of an amount of the dosage form containing a therapeutically effective amount of fospropofol, or a pharmaceutically acceptable salt thereof, in 300 mL of water at 25° C. results in a solution having a pH of 4.5 or less.

Aspect 14. The pharmaceutical dosage form according to any one of the preceding aspects, wherein dissolution of an amount of the dosage form containing a therapeutically effective amount of fospropofol, or a pharmaceutically acceptable salt thereof, in 300 mL of water at 25° C. results in a solution having a pH of 4.2 or less.

Aspect 15. The pharmaceutical dosage form according to any one of the preceding aspects, wherein dissolution of an amount of the dosage form containing a therapeutically effective amount of fospropofol, or a pharmaceutically acceptable salt thereof, in 300 mL of water at 25° C. results in a solution having a pH of 4.0 or less.

Aspect 16. The pharmaceutical dosage form according to any one of the preceding aspects, wherein dissolution of an amount of the dosage form containing a therapeutically effective amount of fospropofol, or a pharmaceutically acceptable salt thereof, in 300 mL of 0.1 N HCl at 37° C., results in at least 30% of the fospropofol or pharmaceutically acceptable salt thereof (on a fospropofol basis) in the dosage form being released from the dosage form within 60 minutes.

Aspect 17. The pharmaceutical dosage form according to aspect 16, wherein dissolution of an amount of the dosage form containing a therapeutically effective amount of fospropofol, or a pharmaceutically acceptable salt thereof, in 300 mL of 0.1 N HCl at 37° C. results in at least 30% of the fospropofol or pharmaceutically acceptable salt thereof (on a fospropofol basis) in the dosage form being released from the dosage form within 30 minutes.

Aspect 18. The pharmaceutical dosage form according to any one of the preceding aspects, wherein dissolution of an amount of the dosage form containing a therapeutically effective amount of fospropofol, or a pharmaceutically acceptable salt thereof, in 300 mL of 0.1 N HCl at 37° C. results in at least 50% of the fospropofol or pharmaceutically acceptable salt thereof(on a fospropofol basis) in the dosage form being released from the dosage form within 60 minutes.

Aspect 19. The pharmaceutical dosage form according to any one of the preceding aspects, wherein dissolution of an amount of the dosage form containing a therapeutically effective amount of fospropofol, or a pharmaceutically acceptable salt thereof, in 300 mL of 0.1 N HCl at 37° C. results in at least 50% of the fospropofol or pharmaceutically acceptable salt thereof(on a fospropofol basis) in the dosage form being released from the dosage form within 30 minutes.

Aspect 20. The pharmaceutical dosage form according to any one of the preceding aspects, wherein dissolution of an amount of the dosage form containing a therapeutically effective amount of fospropofol, or a pharmaceutically acceptable salt thereof, in 300 mL of 0.1 N HCl at 37° C. results in at least 90% of the fospropofol or pharmaceutically acceptable salt thereof(on a fospropofol basis) in the dosage form being released from the dosage form within 30 minutes.

Aspect 21. The pharmaceutical dosage form according to any one of the preceding aspects, wherein dissolution of an amount of the dosage form containing a therapeutically effective amount of fospropofol, or a pharmaceutically acceptable salt thereof, in 300 mL of 0.1 N HCl at 37° C. results in at least 90% of the fospropofol or pharmaceutically acceptable salt thereof(on a fospropofol basis) in the dosage form being released from the dosage form within 60 minutes.

Aspect 22. The pharmaceutical dosage form according to any one of the preceding aspects, wherein dissolution of an amount of the dosage form containing a therapeutically effective amount of fospropofol, or a pharmaceutically acceptable salt thereof, in 300 mL of 0.1 N HCl at 37° C. results in release of at least 90% of the fospropofol from the dosage form within 30 minutes.

Aspect 23. The pharmaceutical dosage form according to any one of the preceding aspects, wherein the mole ratio of fospropofol or a pharmaceutically acceptable salt thereof (on a fospropofol basis) to pharmaceutically acceptable acid is 3:1 or less.

Aspect 24. A method of administering fospropofol or a pharmaceutically acceptable salt thereof to a subject in need thereof, comprising orally administering to said subject a pharmaceutical dosage form according to any one of the preceding aspects.

Aspect 25. A method of administering fospropofol or a pharmaceutically acceptable salt thereof to a subject in need thereof, said method comprising orally administering fospropofol, or a pharmaceutically acceptable salt thereof, and a pharmaceutically acceptable acid, to the subject.

Aspect 26. The method of aspect 24 or aspect 25, wherein said fospropofol, or a pharmaceutically acceptable salt thereof, and said pharmaceutically acceptable acid are present in the same unit dosage form.

Aspect 27. The method of aspect 25, wherein all or a portion of said pharmaceutically acceptable acid is administered separately from the unit dosage form comprising said fospropofol, or a pharmaceutically acceptable salt thereof.

Aspect 28. The method according to any one of aspects 24 to 27, wherein said pharmaceutically acceptable acid is ascorbic acid, citric acid, malic acid, tartaric acid, succinic acid, fumaric acid, maleic acid, lactic acid, monobasic sodium phosphate, monobasic potassium phosphate, sodium metabisulfite, apple juice, orange juice, or grapefruit juice.

Aspect 29. The method according to aspect 28, wherein said pharmaceutically acceptable acid is ascorbic acid, citric acid, malic acid, or tartaric acid.

Aspect 30. The method according to aspect 29, wherein said pharmaceutically acceptable acid is ascorbic acid.

Aspect 31. The method according to aspect 29, wherein said pharmaceutically acceptable acid is citric acid.

Aspect 32. The method according to aspect 29, wherein said pharmaceutically acceptable acid is malic acid.

Aspect 33. The method according to aspect 29, wherein said pharmaceutically acceptable acid is tartaric acid.

Aspect 34. The method of any one of aspects 24 to 33, wherein said subject is experiencing hypochlorhydria or achlorhydria prior to the administration.

Aspect 35. The method according to aspect 34, wherein said subject has been administered a proton pump inhibitor (PPI) prior to the administration.

Aspect 36. The method of any one of aspects 24 to 35, wherein said administration results in a propofol Cmax that is greater than a propofol Cmax resulting from administering fospropofol, or a pharmaceutically acceptable salt thereof, without administration of the pharmaceutically acceptable acid.

Aspect 37. The method of aspect 36, wherein the propofol Cmax is at least 1.5 times greater than a propofol Cmax resulting from administering fospropofol, or a pharmaceutically acceptable salt thereof, without administration of the pharmaceutically acceptable acid.

Aspect 38. The method of aspect 36, wherein the propofol Cmax is at least 2 times greater than a propofol Cmax resulting from administering fospropofol, or a pharmaceutically acceptable salt thereof, without administration of the pharmaceutically acceptable acid.

Aspect 39. The method of aspect 36, wherein the propofol Cmax is at least 2.5 times greater than a propofol Cmax resulting from administering fospropofol, or a pharmaceutically acceptable salt thereof, without administration of the pharmaceutically acceptable acid.

Aspect 40. The method of aspect 36, wherein the propofol Cmax is at least 3 times greater than a propofol Cmax resulting from administering fospropofol, or a pharmaceutically acceptable salt thereof without administration of the pharmaceutically acceptable acid.

Aspect 41. The method of any one of aspects 24 to 40, wherein said administration results in a propofol $AUC_\infty$ that is greater than a propofol $AUC_\infty$ resulting from administering fospropofol, or a pharmaceutically acceptable salt thereof, without administration of the pharmaceutically acceptable acid.

Aspect 42. The method of aspect 41, wherein the propofol $AUC_\infty$ is at least 1.5 times greater than a propofol $AUC_\infty$ resulting from administering fospropofol, or a pharmaceutically acceptable salt thereof, without administration of the pharmaceutically acceptable acid.

Aspect 43. The method of aspect 41, wherein the propofol $AUC_\infty$ is at least 2 times greater than a propofol $AUC_\infty$ resulting from administering fospropofol, or a pharmaceutically acceptable salt thereof, without administration of the pharmaceutically acceptable acid.

Aspect 44. The method of aspect 41, wherein the propofol $AUC_\infty$ is at least 2.5 times greater than a propofol $AUC_\infty$ resulting from administering fospropofol, or a pharmaceutically acceptable salt thereof, without administration of the pharmaceutically acceptable acid.

Aspect 45. The method of aspect 41, wherein the propofol $AUC_\infty$ is at least 3 times greater than a propofol $AUC_\infty$ resulting from administering fospropofol, or a pharmaceutically acceptable salt thereof, without co-administration of the pharmaceutically acceptable acid.

Aspect 46. The method of any one of aspects 24 to 45, wherein said method is directed to treating a disease or disorder in a subject in need thereof.

Aspect 47. The method of aspect 46, wherein said method comprises orally administering to a subject the pharmaceutical dosage form of any one of aspects 1 to 23.

Aspect 48. The method of aspect 46, comprising orally administering fospropofol, or a pharmaceutically acceptable salt thereof, and a pharmaceutically acceptable acid, to a subject.

Aspect 49. The method of any one of aspects 46 to 48, wherein the disease or disorder is migraine, acute repetitive seizures, seizure clusters, neuropathic pain, postherpetic neuralgia, traumatic brain injury, Alzheimer's disease, epilepsy, anxiety, fragile X syndrome, post-traumatic stress disorder, lysosomal storage disorders (Niemann-Pick type C disease), depression (including post-partum depression), premenstrual dysphoric disorder, alcohol craving, or smoking cessation.

Aspect 50. The method of aspect 49, wherein the disease or disorder is migraine.

Methods of Using Acidified Pharmaceutical Dosage Forms

Aspect 1. A method of treating a disease or disorder in subject in need thereof, said method comprising orally administering to said subject a pharmaceutical dosage form comprising fospropofol, or a pharmaceutically acceptable salt thereof, and a pharmaceutically acceptable acid, wherein the administration results in a plasma fospropofol Cmax (fed) that is at least 30% of the corresponding plasma fospropofol Cmax (fasted).

Aspect 2. The method according to aspect 1, wherein the administration results in a plasma fospropofol Cmax (fed) that is at least 90% of the corresponding plasma fospropofol Cmax (fasted).

Aspect 3. The method according to aspect 1, wherein the pharmaceutically acceptable acid is ascorbic acid, citric acid, malic acid, or tartaric acid.

Aspect 4. The method according to aspect 1, wherein the pharmaceutically acceptable acid is ascorbic acid.

Aspect 5. The method according to aspect 1, wherein the pharmaceutically acceptable acid is tartaric acid.

Aspect 6. The method according to aspect 1, wherein the pharmaceutically acceptable acid is citric acid.

Aspect 7. The method according to aspect 1, wherein the pharmaceutically acceptable acid is malic acid.

Aspect 8. The method according to aspect 1, wherein said subject is a human.

Aspect 9. The method of aspect 1, wherein the disease or disorder is migraine, acute repetitive seizures, seizure clusters, neuropathic pain, postherpetic neuralgia, traumatic brain injury, Alzheimer's disease, epilepsy, anxiety, fragile X syndrome, post-traumatic stress disorder, lysosomal storage disorders (Niemann-Pick type C disease), depression (including post-partum depression), premenstrual dysphoric disorder, alcohol craving, smoking cessation, tremor, essential tremor, Parkinsonian tremor, orthostatic tremor, primary writing tremor, cerebellar tremor, rubral tremor, neuropathic tremor, or dystonic tremor.

Aspect 10. The method of aspect 1, wherein the disease or disorder is migraine.

Aspect 11. A method of treating a disease or disorder in subject in need thereof, said method comprising orally administering to said subject a pharmaceutical dosage form comprising fospropofol, or a pharmaceutically acceptable salt thereof, and a pharmaceutically acceptable acid, wherein the administration results in a plasma total fospropofol $AUC_\infty$ (fed) that is at least 40% of the corresponding plasma total fospropofol $AUC_\infty$ (fasted).

Aspect 12. The method according to aspect 11, wherein the administration results in a plasma total fospropofol $AUC_\infty$ (fed) that is at least 70% of the corresponding plasma total fospropofol $AUC_\infty$ (fasted).

Aspect 13. The method according to aspect 11, wherein the pharmaceutically acceptable acid is ascorbic acid, citric acid, malic acid, or tartaric acid.

Aspect 14. The method according to aspect 11, wherein the pharmaceutically acceptable acid is ascorbic acid.

Aspect 15. The method according to aspect 11, wherein the pharmaceutically acceptable acid is tartaric acid.

Aspect 16. The method according to aspect 11, wherein the pharmaceutically acceptable acid is citric acid.

Aspect 17. The method according to aspect 11, wherein the pharmaceutically acceptable acid is malic acid.

Aspect 18. The method according to aspect 11, wherein said subject is a human.

Aspect 19. The method of aspect 11, wherein the disease or disorder is migraine, acute repetitive seizures, seizure clusters, neuropathic pain, postherpetic neuralgia, traumatic brain injury, Alzheimer's disease, epilepsy, anxiety, fragile X syndrome, post-traumatic stress disorder, lysosomal storage disorders (Niemann-Pick type C disease), depression (including post-partum depression), premenstrual dysphoric disorder, alcohol craving, smoking cessation, tremor, essential tremor, Parkinsonian tremor, orthostatic tremor, primary writing tremor, cerebellar tremor, rubral tremor, neuropathic tremor, or dystonic tremor.

Aspect 20. The method of aspect 11, wherein the disease or disorder is migraine.

Acidified Composition Aspects

Aspect 1. A method of treating a disease or disorder in subject in need thereof, said method comprising orally administering to said subject a pharmaceutical dosage form comprising fospropofol disodium, and a pharmaceutically acceptable acid that is ascorbic acid, citric acid, malic acid, fumaric acid, or tartaric acid, wherein the mole ratio of fospropofol disodium to the pharmaceutically acceptable acid is 3:1 or less.

Aspect 2. The method according to aspect 1, wherein the pharmaceutically acceptable acid in said pharmaceutical dosage form is ascorbic acid.

Aspect 3. The method according to aspect 1, wherein the pharmaceutically acceptable acid in said pharmaceutical dosage form is tartaric acid.

Aspect 4. The method according to aspect 1, wherein the pharmaceutically acceptable acid in said pharmaceutical dosage form is citric acid.

Aspect 5. The method according to aspect 1, wherein the pharmaceutically acceptable acid in said pharmaceutical dosage form is malic acid.

Aspect 6. The method according to aspect 1, wherein the pharmaceutically acceptable acid in said pharmaceutical dosage form is fumaric acid.

Aspect 7. The method according to aspect 1, wherein said subject is a human.

Aspect 8. The method of aspect 1, wherein the disease or disorder is migraine, acute repetitive seizures, seizure clusters, neuropathic pain, postherpetic neuralgia, traumatic brain injury, Alzheimer's disease, epilepsy, anxiety, fragile X syndrome, post-traumatic stress disorder, lysosomal storage disorders (Niemann-Pick type C disease), depression (including post-partum depression), premenstrual dysphoric disorder, alcohol craving, or smoking cessation.

Aspect 9. The method of aspect 8, wherein the disease or disorder is migraine.

Aspect 10. The method of aspect 1, wherein said subject has or is suspected of having hypochlorhydria or achlorhydria prior to the administration of the pharmaceutical dosage form.

Aspect 11. The method according to aspect 10, wherein said subject has been administered a proton pump inhibitor (PPI) prior to the administration of the pharmaceutical dosage form.

Aspect 12. The method of aspect 1, wherein said administration of the pharmaceutical dosage form results in a propofol Cmax that is greater than a propofol Cmax resulting from administering fospropofol disodium without administration of a pharmaceutically acceptable acid.

Aspect 13. The method of aspect 12, wherein the propofol Cmax is at least 1.2 times greater than a propofol Cmax resulting from administering fospropofol disodium without administration of the pharmaceutically acceptable acid.

Aspect 14. The method of aspect 13, wherein the propofol Cmax is at least 3 times greater than a propofol Cmax resulting from administering fospropofol disodium without administration of the pharmaceutically acceptable acid.

Aspect 15. The method of aspect 1, wherein said administration of the pharmaceutical dosage form results in a propofol $AUC_\infty$ that is greater than a propofol $AUC_\infty$ resulting from administering fospropofol disodium without administration of a pharmaceutically acceptable acid.

Aspect 16. The method of aspect 15, wherein the propofol $AUC_\infty$ is at least 1.5 times greater than a propofol $AUC_\infty$ resulting from administering fospropofol disodium without administration of a pharmaceutically acceptable acid.

Aspect 17. The method of aspect 16, wherein the propofol $AUC_\infty$ is at least 3 times greater than a propofol $AUC_\infty$ resulting from administering fospropofol disodium without administration of a pharmaceutically acceptable acid.

Aspect 18. A method of treating a disease or disorder in subject in need thereof, said method comprising orally administering to said subject a pharmaceutical dosage form comprising fospropofol disodium, and a pharmaceutically acceptable acid that is ascorbic acid, citric acid, malic acid, fumaric acid, or tartaric acid, wherein dissolution of an amount of the dosage form containing 10-4800 mg (on a fospropofol basis) of fospropofol disodium, in 300 mL of water at 25° C., results in a solution having a pH of 4.5 or less.

Aspect 19. The method according to aspect 18, wherein the pharmaceutically acceptable acid in said pharmaceutical dosage form is ascorbic acid.

Aspect 20. The method according to aspect 18, wherein the pharmaceutically acceptable acid in said pharmaceutical dosage form is tartaric acid.

Aspect 21. The method according to aspect 18, wherein the pharmaceutically acceptable acid in said pharmaceutical dosage form is citric acid.

Aspect 22. The method according to aspect 18, wherein the pharmaceutically acceptable acid in said pharmaceutical dosage form is malic acid.

Aspect 23. The method according to aspect 18, wherein the pharmaceutically acceptable acid in said pharmaceutical dosage form is fumaric acid.

Aspect 24. The method according to aspect 18, wherein said subject is a human.

Aspect 25. The method of aspect 18, wherein the disease or disorder is migraine, acute repetitive seizures, seizure clusters, neuropathic pain, postherpetic neuralgia, traumatic brain injury, Alzheimer's disease, epilepsy, anxiety, fragile X syndrome, post-traumatic stress disorder, lysosomal storage disorders (Niemann-Pick type C disease), depression (including post-partum depression), premenstrual dysphoric disorder, alcohol craving, or smoking cessation.

Aspect 26. The method of aspect 18, wherein the disease or disorder is migraine.

Aspect 27. The method of aspect 18, wherein said subject has or is suspected of having hypochlorhydria or achlorhydria prior to the administration of the pharmaceutical dosage form.

Aspect 28. The method according to aspect 27, wherein said subject has been administered a proton pump inhibitor (PPI) prior to the administration of the pharmaceutical dosage form.

Aspect 29. The method of aspect 18, wherein said administration of the pharmaceutical dosage form results in a propofol Cmax that is greater than a propofol Cmax resulting from administering fospropofol disodium without administration of a pharmaceutically acceptable acid.

Aspect 30. The method of aspect 29, wherein the propofol Cmax is at least 1.2 times greater than a propofol Cmax resulting from administering fospropofol disodium without administration of the pharmaceutically acceptable acid.

Aspect 31. The method of aspect 30, wherein the propofol Cmax is at least 3 times greater than a propofol Cmax resulting from administering fospropofol disodium without administration of the pharmaceutically acceptable acid.

Aspect 32. The method of aspect 18, wherein said administration of the pharmaceutical dosage form results in a propofol $AUC_\infty$ that is greater than a propofol $AUC_\infty$ resulting from administering fospropofol disodium without administration of a pharmaceutically acceptable acid.

Aspect 33. The method of aspect 32, wherein the propofol $AUC_\infty$ is at least 1.5 times greater than a propofol $AUC_\infty$ resulting from administering fospropofol disodium without administration of a pharmaceutically acceptable acid.

Aspect 34. The method of aspect 33, wherein the propofol $AUC_\infty$ is at least 3 times greater than a propofol $AUC_\infty$ resulting from administering fospropofol disodium without administration of a pharmaceutically acceptable acid.

Aspect 35. A method of treating a disease or disorder in subject in need thereof, said method comprising orally administering to said subject a pharmaceutical dosage form comprising fospropofol disodium, and a pharmaceutically acceptable acid that is ascorbic acid, citric acid, malic acid, fumaric acid, or tartaric acid, wherein dissolution of an amount of the dosage form containing 10-4800 mg (on a fospropofol basis) of fospropofol disodium, in 300 mL of 0.1 N HCl at 37° C., results in release of at least 30% of the fospropofol from the dosage form within 30 minutes.

Aspect 36. The method according to aspect 35, wherein the pharmaceutically acceptable acid in said pharmaceutical dosage form is ascorbic acid.

Aspect 37. The method according to aspect 35, wherein the pharmaceutically acceptable acid in said pharmaceutical dosage form is tartaric acid.

Aspect 38. The method according to aspect 35, wherein the pharmaceutically acceptable acid in said pharmaceutical dosage form is citric acid.

Aspect 39. The method according to aspect 35, wherein the pharmaceutically acceptable acid in said pharmaceutical dosage form is malic acid.

Aspect 40. The method according to aspect 35, wherein the pharmaceutically acceptable acid in said pharmaceutical dosage form is fumaric acid.

Aspect 41. The method according to aspect 35, wherein said subject is a human.

Aspect 42. The method of aspect 35, wherein the disease or disorder is migraine, acute repetitive seizures, seizure clusters, neuropathic pain, postherpetic neuralgia, traumatic brain injury, Alzheimer's disease, epilepsy, anxiety, fragile X syndrome, post-traumatic stress disorder, lysosomal storage disorders (Niemann-Pick type C disease), depression (including post-partum depression), premenstrual dysphoric disorder, alcohol craving, or smoking cessation.

Aspect 43. The method of aspect 42, wherein the disease or disorder is migraine.

Aspect 44. The method of aspect 35, wherein said subject has or is suspected of having hypochlorhydria or achlorhydria prior to the administration of the pharmaceutical dosage form.

Aspect 45. The method according to aspect 44, wherein said subject has been administered a proton pump inhibitor (PPI) prior to the administration of the pharmaceutical dosage form.

Aspect 46. The method of aspect 35, wherein said administration of the pharmaceutical dosage form results in a propofol Cmax that is greater than a propofol Cmax resulting from administering fospropofol disodium without administration of a pharmaceutically acceptable acid.

Aspect 47. The method of aspect 46, wherein the propofol Cmax is at least 1.2 times greater than a propofol Cmax resulting from administering fospropofol disodium without administration of the pharmaceutically acceptable acid.

Aspect 48. The method of aspect 47, wherein the propofol Cmax is at least 3 times greater than a propofol Cmax resulting from administering fospropofol disodium without administration of the pharmaceutically acceptable acid.

Aspect 49. The method of aspect 35, wherein said administration of the pharmaceutical dosage form results in a propofol $AUC_\infty$ that is greater than a propofol $AUC_\infty$ resulting from administering fospropofol disodium without administration of a pharmaceutically acceptable acid.

Aspect 50. The method of aspect 49, wherein the propofol $AUC_\infty$ is at least 1.5 times greater than a propofol $AUC_\infty$ resulting from administering fospropofol disodium without administration of a pharmaceutically acceptable acid.

Aspect 51. The method of aspect 50, wherein the propofol $AUC_\infty$ is at least 3 times greater than a propofol $AUC_\infty$ resulting from administering fospropofol disodium without administration of a pharmaceutically acceptable acid.

Acidified Dosage Form Aspects

Aspect 1. A pharmaceutical dosage form for oral administration comprising fospropofol, or a pharmaceutically acceptable salt thereof, and a pharmaceutically acceptable acid wherein the mole ratio of fospropofol, or a pharmaceutically acceptable salt thereof, to the pharmaceutically acceptable acid is 3:1 or less.

Aspect 2. 2. The pharmaceutical dosage form according to aspect 1, wherein said pharmaceutical dosage form comprises fospropofol.

Aspect 3. 3. The pharmaceutical dosage form according to aspect 1, wherein said pharmaceutical dosage form comprises a pharmaceutically acceptable salt of fospropofol.

Aspect 4. 4. The pharmaceutical dosage form according to aspect 3, wherein said pharmaceutically acceptable salt of fospropofol is fospropofol disodium.

Aspect 5. 5. The pharmaceutical dosage form according to aspect 1, in the form of a tablet, capsule, or softgel.

Aspect 6. 6. The pharmaceutical dosage form according to aspect 1, wherein the mole ratio of fospropofol, or a pharmaceutically acceptable salt thereof, to the pharmaceutically acceptable acid is 2:1 or less.

Aspect 7. 7. The pharmaceutical dosage form according to aspect 1, wherein the mole ratio of fospropofol, or a pharmaceutically acceptable salt thereof, to the pharmaceutically acceptable acid is 1.5:1 or less.

Aspect 8. A method of treating a disease or disorder in subject in need thereof, said method comprising orally administering to said subject pharmaceutical dosage form according to aspect 1.

Aspect 9. The method according to aspect 8, wherein said subject is a human.

Aspect 10. The method of aspect 8, wherein the disease or disorder is migraine, acute repetitive seizures, seizure clusters, neuropathic pain, postherpetic neuralgia, traumatic brain injury, Alzheimer's disease, epilepsy, anxiety, fragile X syndrome, post-traumatic stress disorder, lysosomal storage disorders (Niemann-Pick type C disease), depression (including post-partum depression), premenstrual dysphoric disorder, alcohol craving, or smoking cessation.

Aspect 11. The method of aspect 10, wherein the disease or disorder is migraine.

Aspect 12. The method of aspect 8, wherein said subject has or is suspected of having hypochlorhydria or achlorhydria prior to the administration of the pharmaceutical dosage form.

Aspect 13. The method according to aspect 12, wherein said subject has been administered a proton pump inhibitor (PPI) prior to the administration of the pharmaceutical dosage form.

Aspect 14. The method of aspect 8, wherein said administration of the pharmaceutical dosage form results in a propofol Cmax that is greater than a propofol Cmax resulting from administering fospropofol, or a pharmaceutically acceptable salt thereof, without administration of a pharmaceutically acceptable acid.

Aspect 15. The method of aspect 14, wherein the propofol Cmax is at least 1.2 times greater than a propofol Cmax resulting from administering fospropofol, or a pharmaceutically acceptable salt thereof, without administration of the pharmaceutically acceptable acid.

Aspect 16. The method of aspect 15, wherein the propofol Cmax is at least 3 times greater than a propofol Cmax resulting from administering fospropofol, or a pharmaceutically acceptable salt thereof, without administration of the pharmaceutically acceptable acid.

Aspect 17. The method of aspect 8, wherein said administration of the pharmaceutical dosage form results in a propofol $AUC_\infty$ that is greater than a propofol $AUC_\infty$ resulting from administering fospropofol, or a pharmaceutically acceptable salt thereof, without administration of a pharmaceutically acceptable acid.

Aspect 18. The method of aspect 17, wherein the propofol $AUC_\infty$ is at least 1.5 times greater than a propofol $AUC_\infty$ resulting from administering fospropofol, or a pharmaceutically acceptable salt thereof, without administration of a pharmaceutically acceptable acid.

Aspect 19. The method of aspect 18, wherein the propofol $AUC_\infty$ is at least 3 times greater than a propofol $AUC_\infty$ resulting from administering fospropofol, or a pharmaceutically acceptable salt thereof, without administration of a pharmaceutically acceptable acid.

Acidified Composition Aspects II

Aspect 1. A pharmaceutical dosage form for oral administration comprising fospropofol disodium, and a pharmaceutically acceptable acid that is ascorbic acid, citric acid, malic acid, or tartaric acid.

Aspect 2. The pharmaceutical dosage form according to aspect 1, wherein the pharmaceutically acceptable acid is ascorbic acid.

Aspect 3. The pharmaceutical dosage form according to aspect 1, wherein the pharmaceutically acceptable acid is tartaric acid.

Aspect 4. The pharmaceutical dosage form according to aspect 1, wherein the pharmaceutically acceptable acid is citric acid.

Aspect 5. The pharmaceutical dosage form according to aspect 1, wherein the pharmaceutically acceptable acid is malic acid.

Aspect 6. The pharmaceutical dosage form according to aspect 1, in the form of a tablet, capsule, or softgel.

Aspect 7. The pharmaceutical dosage form according to aspect 1, wherein dissolution of an amount of the dosage form containing a therapeutically effective amount of fospropofol, or a pharmaceutically acceptable salt thereof, in 300 mL of water at 25° C., results in a solution having a pH of 4.5 or less.

Aspect 8. The pharmaceutical dosage form according to aspect 1, wherein dissolution of an amount of the dosage form containing a therapeutically effective amount of fospropofol, or a pharmaceutically acceptable salt thereof, in 300 mL of water at 25° C., results in a solution having a pH of 4.2 or less.

Aspect 9. The pharmaceutical dosage form according to aspect 1, wherein dissolution of an amount of the dosage form containing a therapeutically effective amount of fospropofol, or a pharmaceutically acceptable salt thereof, in 300 mL of water at 25° C. results, in a solution having a pH of 4.0 or less.

Aspect 10. The pharmaceutical dosage form according to aspect 1, wherein dissolution of an amount of the dosage form containing a therapeutically effective amount of fospropofol, or a pharmaceutically acceptable salt thereof, in 300 mL of 0.1 N HCl at 37° C., results in release of at least 30% of the fospropofol from the dosage form within 30 minutes.

Aspect 11. The pharmaceutical dosage form according to aspect 1, wherein the mole ratio of fospropofol, or a pharmaceutically acceptable salt thereof, to the pharmaceutically acceptable acid is 3:1 or less.

Aspect 12. A method of treating a disease or disorder in subject in need thereof, said method comprising orally administering to said subject a pharmaceutical dosage form according to aspect 1.

Aspect 13. The method according to aspect 12, wherein the pharmaceutically acceptable acid in said pharmaceutical dosage form according to aspect 1 is ascorbic acid.

Aspect 14. The method according to aspect 12, wherein the pharmaceutically acceptable acid in said pharmaceutical dosage form according to aspect 1 is tartaric acid.

Aspect 15. The method according to aspect 12, wherein the pharmaceutically acceptable acid in said pharmaceutical dosage form according to aspect 1 is citric acid.

Aspect 16. The method according to aspect 12, wherein the pharmaceutically acceptable acid in said pharmaceutical dosage form according to aspect 1 is malic acid.

Aspect 17. The method according to aspect 12, wherein said subject is a human.

Aspect 18. The method of aspect 12, wherein the disease or disorder is migraine, acute repetitive seizures, seizure clusters, neuropathic pain, postherpetic neuralgia, traumatic brain injury, Alzheimer's disease, epilepsy, anxiety, fragile X syndrome, post-traumatic stress disorder, lysosomal storage disorders (Niemann-Pick type C disease), depression (including post-partum depression), premenstrual dysphoric disorder, alcohol craving, or smoking cessation.

Aspect 19. The method of aspect 18, wherein the disease or disorder is migraine.

Aspect 20. The method of aspect 12, wherein said subject has or is suspected of having hypochlorhydria or achlorhydria prior to the administration of the pharmaceutical dosage form according to aspect 1.

Aspect 21. The method according to aspect 20, wherein said subject has been administered a proton pump inhibitor (PPI) prior to the administration of the pharmaceutical dosage form according to aspect 1.

Aspect 22. The method of aspect 12, wherein said administration of the pharmaceutical dosage form according to aspect 1 results in a propofol Cmax that is greater than a propofol Cmax resulting from administering fospropofol disodium without administration of a pharmaceutically acceptable acid.

Aspect 23. The method of aspect 22, wherein the propofol Cmax is at least 1.2 times greater than a propofol Cmax resulting from administering fospropofol disodium without administration of the pharmaceutically acceptable acid.

Aspect 24. The method of aspect 23, wherein the propofol Cmax is at least 3 times greater than a propofol Cmax resulting from administering fospropofol disodium without administration of the pharmaceutically acceptable acid.

Aspect 25. The method of aspect 12, wherein said administration of the pharmaceutical dosage form according to aspect 1 results in a propofol $AUC_\infty$ that is greater than a propofol $AUC_\infty$ resulting from administering fospropofol disodium without administration of a pharmaceutically acceptable acid.

Aspect 26. The method of aspect 25, wherein the propofol $AUC_\infty$ is at least 1.5 times greater than a propofol $AUC_\infty$ resulting from administering fospropofol disodium without administration of a pharmaceutically acceptable acid.

Aspect 27. The method of aspect 26, wherein the propofol $AUC_\infty$ is at least 3 times greater than a propofol $AUC_\infty$ resulting from administering fospropofol disodium without administration of a pharmaceutically acceptable acid.

What is claimed:

1. A method of treating migraine in a patient in need thereof, the method comprising orally administering a propofol prodrug, a pharmaceutically acceptable salt of a propofol prodrug, or mixtures thereof, to the patient in one or more doses, wherein the administration results in a Cmax of propofol of at least 50-500 ng/mL, wherein following the administration the patient is headache free, has experienced a reduction in headache pain, or is no longer experiencing a most bothersome symptom, and wherein the propofol prodrug is:
  sodium 2-(2-(2,6-diisopropylphenoxy)-2-oxoethoxy) acetate;
  (Azepan-1-ylcarbamoylmethyl)carbamic acid 2,6-diisopropylphenyl ester hydrochloride; (E)-3-(2,6-diisopropylphenoxy)acrylic acid;
  (O-[2-carboxyethyl]-propofol), (S)-2-amino-3-(2,6-diisopropylphenoxycarbonyloxy)-propanoic acid;
  (S)-2-amino-3-(2,6-diisopropylphenoxycarbonyloxy)-propanoic acid mesylate salt; (S)-2-amino-3-(2, 6-diisopropylphenoxycarbonyloxy)-propanoic acid hydrochloride;

{1-[3-(2, 6-diisopropylphenoxy)-3-oxo-2(R)-fluoro-1-propyl]}phosphate monoesterdipotassium salt;
{1-[4-(2,6-diisopropylphenoxy)-4-oxo-2(R)-trifluoromethyl-1-butyl]}phosphate monoester dilithium salt;
{1-[4-(2,6-diisopropylphenoxy)-4-oxo-3-(R)-trifluoromethyl-1-butyl]}phosphate monoester dilithium salt; {1-[4-(2,6-diisopropylphenoxy)-4-oxo-3-(R,S)-3-fluoro-1-butyl]} phosphate monoesterdipotassium salt;
{1-[4-(2,6-diisopropylphenoxy)-4-oxo-3-(S)-3-fluoro-1-butyl]} phosphate monoester disodium salt;
{1-[6-(2,6-diisopropylphenoxy)-6-oxo-5-(S)-difluoromethyl-1-hexyl]} phosphate di arginine salt;
1-((((2,6-diisopropyl phenoxy)carbonyl) oxy)methyl)-3-(dimethylcarbamoyl) pyridinium iodide;
1-((((2,6-diisopropylphenoxy)carbonyl) oxy)methyl)-3-(hydroxycarbamoyl) pyridin-1-ium iodide;
1-((((2,6-diisopropylphenoxy)carbonyl) oxy)methyl)-3-(methoxycarbonyl)pyridin-1-ium iodide;
1-((((2,6-diisopropylphenoxy)carbonyl) oxy)methyl)-3-(methoxycarbonyl)pyridin-1-ium methanesulfonate;
1-((((2,6-diisopropylphenoxy)carbonyl)oxy)methyl)-3-(methylcarbamoyl)pyridin-1-ium tetrafluoroborate;
1-((((2,6-diisopropylphenoxy)carbonyl)oxy)methyl)-3-(methylcarbamoyl)pyridin-1-ium nitrate;
1-((((2,6-diisopropylphenoxy)carbonyl)oxy)methyl)-3-(methylcarbamoyl)pyridin-1-ium chloride;
1-((((2,6-diisopropylphenoxy)carbonyl) oxy)methyl)-4-formyl-3-hydroxy-5-(hydroxymethyl)-2-methylpyridin-1-ium iodide;
1-(((2,6-diisopropylphenoxy)carbonyl)oxy)N-((((2,6-diisopropylphenoxy)carbonyl)oxy)methyl)-N,N-dimethyl-methanaminiumiodide;
1-(((2,6-diisopropylphenoxy)carbonyloxy)methyl)-3-(dimethylcarbamoyl)pyridinium mesylate;
1-(((2,6-diisopropylphenoxy)carbonyloxy) methyl)-3-(methylcarbamoyl)pyridinium mesylate;
1-(((2,6-diisopropylphenoxy)carbonyloxy)methyl)-3-(methylcarbamoyl)pyridiniumiodide;
1-((2',6'-diisopropylphenoxy)carbonylamino)ethyl-2,3,4,6-tetra-O-acetyl-β-D-glucopyrano side;
1-((2',6'diisopropylphenoxy) carbonylamino)ethyl-β-D-glucopyranoside;
1-((2',6'diisopropylphenoxy)carbonyloxy)ethyl-2,3,4,6-tetra-O-acetyl-13-D-glucopyranoside;
1-((2',6'diisopropylphenoxy)carbonyloxy)ethyl-2,3,4,6-tetra-O-acetyl-α-D-glucopyranoside;
1-((2',6'diisopropylphenoxy)carbonyloxy)ethyl-hepta-O-acetyl-13-D-maltose;
1-((2',6'diisopropylphenoxy)carbonyloxy)ethyl-α-D-glucopyranoside;
1-((2',6'-diisopropylphenoxy)carbonyloxy)ethyl-β-D-maltose;
1-((2',6'diisopropylphenoxy)carbonyloxy)ethyl-β-n-glucopyranoside;
1-((2',6'diisopropylphenoxy)carbonyloxy)propyl-2,3,4,6-tetra-O-acetyl-β-D-glucopyranoside;
1-((2',6'-diisopropylphenoxy)carbonyloxy)propyl-2,3,4,6-tetra-O-acetyl-α-D-glucopyranoside;
1-((2',6'-diisopropylphenoxy)carbonyloxy)propyl-hepta-O-acetyl-β-D-maltose;
1-((2',6'-diisopropylphenoxy)carbonyloxy)propyl-α-D-glucopyranoside;
1-((2',6'diisopropylphenoxy)carbonyloxy)propyl-β-D-glucopyranoside;
1-((2',6'diisopropylphenoxy)carbonyloxy)propyl-β-D-maltose;
1-Amino-2-[2,6-(diisopropyl)phenoxycarbonyloxy]ethane;
2-[2,6-(Diisopropyl)phenoxycarbonyloxy]ethyl (2S)-2-amino-3-hydroxypropionamide;
2-(((2,6-diisopropylphenoxy)carbonyl) oxy)-N((((2,6-diisopropylphenoxy)carbonyl)oxy)methyl)-N,N-dimethylethan-1-aminiumiodide;
2-(((2,6-diisopropylphenoxy)carbonyl)oxy)-N,N,N-trimethylethan-1-aminium iodide;
2-(((2,6-diisopropyl phenoxy)carbonyl)oxy)-N,N,N-trimethyl ethan-1-aminium methanesulfonate;
2-(2,6-diisopropyl phenoxy)-2-hydroxyethyl phosphate;
2-(2,6-diisopropylphenoxy)-3,4,5-trihydroxy tetrahydropyran-6-yl, dihydrogen phosphate;
2-(2,6-diisopropylphenxoy)-3,4,5-trihydroxytetrahydropyran-6-yl dihydrogen phosphate arginine;
2,6-(diisopropyl)phenyl 1-[((2S)-2-amino-(3R)-3-hydroxybutyryl)aminomethyl]-1-cyclohexane acetate;
2,6-(diisopropyl)phenyl 1-[((2S)-2-amino-3-hydroxypropionyl)aminomethyl]-1-cyclohexane acetate;
2,6-(diisopropyl)phenyl 1-[((2S)-2-amino-3-methylbutyryl)aminomethyl]-1-cyclohexane acetate;
2,6-(diisopropyl)phenyl 4-[(2S)-2,3-diaminopropionylamino]-3,3-dimethylbutanoate;
2,6-(diisopropyl)phenyl 4-[(2S)-2,6-diaminohexanoylamino]-3,3-dimethylbutanoate;
2,6-(Diisopropyl)phenyl 4-[(2S)-2-amino-(3R)-3-hydroxybutyryl]aminobutanoate;
2,6-(diisopropyl)phenyl 4-[(2S)-2-amino-(3R)-3-hydroxybutyryl]amino-3,3-dimethylbutanoate;
2,6-(diisopropyl)phenyl 4-[(2S)-2-amino-(3R)-3-hydroxylbutyryl]aminobutanoate;
2,6-(diisopropyl)phenyl 4-[(2S)-2-amino-(4-hydroxyphenyl)propionylamino]-3,3-dimethylbutanoate;
2,6-(Diisopropyl)phenyl 4-[(2S)-2-amino-(indol-3-yl)propionylamino]-3,3-dimethylbutanoate;
2,6-(Diisopropyl)phenyl 4-[(2S)-2-amino-3-carbamoylpropionylamino]butanoate;
2,6-(Diisopropyl)phenyl 4-[(2S)-2-amino-3-hydroxypropionylamino]butanoate;
2,6-(diisopropyl)phenyl 4-[(2S)-2-amino-3-carbamoylpropionylamino]-3,3-dimethylbutanoate;
2,6-(diisopropyl)phenyl 4-[(2S)-2-amino-3-carbamoylpropionylamino]butanoate;
2,6-(diisopropyl)phenyl 4-[(2S)-2-amino-3-carboxypropionylamino]-3,3-dimethylbutanoate;
2,6-(diisopropyl)phenyl 4-[(2S)-2-amino-3-hydroxypropionylamino]-3,3-dimethylbutanoate;
2,6-(diisopropyl)phenyl4-[(2S)-2-amino-3-hydroxypropionylamino]butanoate;
2,6-(Diisopropyl)phenyl 4-[(2S)-2-amino-3-hydroxypropionylamino]-3,3-dimethylbutanoate;
2,6-(diisopropyl)phenyl 4-[(2S)-2-amino-3-methylbutyrylamino]-3,3-dimethylbutanoate;
2,6-(diisopropyl)phenyl 4-[(2S)-2-amino-3-methylbutyrylamino]butanoate;
2,6-(diisopropyl)phenyl 4-[(2S)-2-amino-4-carboxybutyrylamino]-3,3-dimethylbutanoate;
2,6-(diisopropyl)phenyl 4-[(2S)-2-amino-4-carboxylbutyrylamino]butanoate;
2,6-(diisopropyl)phenyl 4-[(2S)-2-aminopropionylamino]-3,3-dimethylbutanoate;

2,6-(diisopropyl)phenyl4-[(2S)-pyrrolidin-2-ylcarbonylamino]-3,3-dimethylbutanoate;
2,6-(diisopropyl)phenyl 4-[(2S)-pyrrolidin-2-ylcarbonylamino]butanoate;
2,6-(Diisopropyl)phenyl 4-[(2S)-pyrrolidin-2-ylcarbonylaraino]-3,3-dimethylbutanoate;
2,6-(diisopropyl)phenyl 4-[aminomethylcarbonylamino]-3,3-dimethylbutanoate;
2,6-(Diisopropyl)phenyl 1-[((2S)-2-amino-(3R)-3-hydroxybutyryl)aminomethyl]-1-cyclohexane acetate;
2,6-(Diisopropyl)phenyl 1-[((2S)-2-amino-3-hydroxypropionyl)aminomethyl]1-cyclohexane acetate;
2,6-(Diisopropyl)phenyl 1-[((2S)-2-amino-3-methylbutyryl)aminomethyl]-1-cyclohexane acetate;
2,6-diisopropylphenyl 4-((2-(2-methylpyrazolidin-1-yl)ethyl)amino)-4-oxobutanoate;
2,6-diisopropylphenyl 4-((2-(4,5-dihydro-1H-pyrazol-1-yl)ethyl)amino)-4-oxobutanoate;
2,6-diisopropylphenyl 4-((2-(4-ethylpiperazin-1-yl)ethyl)amino)-4-oxobutanoate;
2,6-diisopropylphenyl 4-((2-(4-methylpiperazin-1-yl)ethyl)amino)-4-oxobutanoate; 2,6-diisopropylphenyl4-((2-morpholinoethyl)amino)-4-oxobutanoate;
2,6-Diisopropylphenyl 4-(2-(TertButoxycarbonylamino) Propanoyloxy)Butanoate;
2,6-Diisopropylphenyl4-(2-Aminoacetoxy) Butanoate Trifluoroacetic Acid Salt;
2,6-Diisopropylphenyl 4-(2-Aminopropanoyloxy)Butanoate Hydrochloride;
2,6-Diisopropyl phenyl 4-Hydroxybutanoate;
2,6-diisopropyl phenyl 4-oxo-4-((2-(piperazin-1-yl)ethyl)amino)butanoate;
2,6-diisopropyl phenyl 4-oxo-4-((2-(piperidin-1-yl)ethyl)amino)butanoate;
2,6-diisopropyl phenyl 4-oxo-4-((2-(pyrazolidin-1-yl)ethyl)amino)butanoate;
2,6-diisopropylphenyl 4-oxo-4-((2-(pyrrolidin-1-yl)ethyl)amino)butanoate;
2, 6-diisopropylphenyl 4-oxo-4-((2-thiomorpholinoethyl)amino)butanoate;
2-[2,6-(diisopropyl)phenoxycarbonylamino]ethyl (2S)-2-amino-3-carboxypropionamide;
2-[2,6-(diisopropyl)phenoxycarbonylamino]ethyl (2S)-2-amino-3-hydroxypropionamide;
2-[2,6-(diisopropyl)phenoxycarbonylamino]ethyl (2S)-2-amino-3-methylbutanoylamide;
2-[2,6-(diisopropyl)phenoxycarbonyloxy]ethyl (2S)-2,6-diaminohexanoylamide;
2-[2,6-(diisopropyl)phenoxycarbonyloxy]ethyl (2S)-2-amino-(4-hydroxyphenyl)propionamide;
2-[2,6-(Diisopropyl)phenoxycarbonyloxy]ethyl (2S)-2-amino(4-hydroxyphenyl)propionamide;
2-[2,6-(diisopropyl)phenoxycarbonyloxy]ethyl (2S)-2-amino-3-carbamoylpropionate;
2-[2,6-(diisopropyl)phenoxycarbonyloxy]ethyl (2S)-2-amino-3-carbamoylpropionamide;
2-[2,6-(Diisopropyl)phenoxycarbonyloxy]ethanol;
1-Amino-2-[2,6-(diisopropyl)phenoxycarbonyloxy]ethane;
2-[2,6-(diisopropyl)phenoxycarbonyloxy]ethyl (2S)-2-amino-3-hydroxypropionate;
2-[2,6-(diisopropyl)phenoxycarbonyloxy]ethyl (2S)-2-amino-3-hydroxypropionamide;
2-[2,6-(diisopropyl)phenoxycarbonyloxy]ethyl glycinamide;
2-amino-3-(2,6-diisopropylphenoxycarbonyloxy)-propanoic acid mesylate;
2-amino-3-methyl-3-(2,6-diisopropyl-phenoxycarbonyloxy)-propanoic acid;
3-(((((2,6-diisopropylphenoxy)carbonyl)oxy)methyl)carbamoyl)-1-methylpyridin-1-ium iodide;
3-((2,6-diisopropylphenoxy)carbonyl)-1-((((2,6-diisopropyl phenoxy)carbonyl)oxy) methyl)pyridin-1-ium methanesulfonate;
3-{[2-[2,6-Bis(isopropyl)phenoxycarbonyl]-benzoyl]amino}propanoic acid;
3-{[2-[2,6-Bis(isopropyl)phenoxycarbonyloxy]-benzoyl]amino}-propanoic acid;
3-carbamoyl-1-((((2,6-diisopropyl-phenoxy)carbonyl)oxy)methyl)pyridin-1-ium iodide;
3-carbamoyl-1-((((2,6-diisopropylphenoxy)carbonyloxy)methyl)pyridinium mesylate;
3-carboxy-1-((((2,6-diisopropylphenoxy)carbonyl)oxy)methyl)pyridin-1-ium iodide;
3-carboxy-1-((((2,6-diisopropylphenoxy) carbonyl)oxy)methyl)pyridin-1-ium methanesulfonate;
4-[(2S)-2-amino-(3R)-3-hydroxybutyryl]amino-3,3-dimethylbutanoate;
4-[(2S)-2-amino-3-carbamoylpropionylamino]-3,3-dimethylbutanoate;
4-[(2S)-2-amino-4-carboxybutyrylamino]-3,3-dimethylbutanoate;
4-[(2S)-2-aminopropionylamino]-3,3-dimethylbutanoate;
2,6-(Diisopropyl)phenyl;
4-[aminomethylcarbonylamino]-3,3-dimethylbutanoate;
2,6-(Diisopropyl)phenyl;
arginine2-(2,6-diisopropylphenoxy)-2-hydroxyethylphosphate;
arginine2-(2,6-diisopropylphenoxy)-3,4,5-trihydroxytetrahydropyran-6-yl dihydrogen phosphate;
Boc-Asp(OPropofol)-OBzl; Boc-Asp(OPropofol)-OH;
Boc-Glu(OPropofol)-OBzl;
Boe-Glu(OPropofol)-OH;
di[propofol 5-carboxyl-2(S)-fluorohexanoate] zinc salt;
di[propofol 5-carboxyl-2-(S)-fluorohexanoate] zinc salt;
di[propofol 7-carboxyl-2(R,S)-fluorocaprylate] calcium salt;
di[propofol 7-carboxyl-2-(R,S)fluorocaprylate] calcium salt;
disodium lauryl-imino-dipropionate2-(2,6-diisopropylphenoxy) tetrahydropyran-6-yl dihydrogen phosphate;
disodium lauryl-iminodipropionate-2-(2,6-diisopropyl phenoxy) tetrahydropyran-6-yl dihydrogen phosphate;
H-Abu-Asp(OPropofol)-OH;
H-Abu-Thr(γ-OC(O)OPropofol)-OH Hydrochloride;
H-Aib-OCH$_2$OPropofol;
H-Ala-Asn-OPropofol;
H-Ala-Asp(OCH$_2$OPropofol)-OH;
H-AlaAsp(OPropofol)-OH;
H-Ala-Cys(β-SC(O)OPropofol)-OH;
H-Ala-Glu(OPropofol)-OH;
H-Ala-OPropofol Hydrochloride;
H-Ala-Phe-OPropofol;
H-Ala-Ser(β-OC(O)OPropofol)-OH;
H-Ala-Thr(β-OC(O)OPropofol)-OH;
H-Ala-Thr(γ-OC(O)OPropofol)-OH Hydrochloride;
H-Ala-Tyr-OPropofol;
H-Arg-Asp(OPropofol)-OH;
H-Arg-Phe-OPropofol;

H-Arg Thr(γ-OC(O)OPropofol)-OH Tris-Hydrochloride;
H-Asn-Asp(OCH₂OPropofol)-OH;
H-Asn-Asp(OPropofol)-OH;
H-Asn-D-Thr(γ-OC(O)OPropofol)-OH;
H-Asn-Glu(OPropofol)-OH;
H-Asn-OPropofol Hydrochloride;
H-Asn-Thr(β-OC(O)OPropofol)-OH;
H-Asn-Thr(γ-OC(O)OPropofol)-OH Hydrochloride;
H-Asn-Tyr-OPropofol;
H-Asp(OCH₂OPropofol)-ArgOH;
H-Asp(OCH₂OPropofol)-Asp-OH;
H-Asp(OCH₂OPropofol)-Lys-OH;
H-Asp(OCH₂OPropofol)-OH;
H-Asp(OCH₂OPropofol)-Ser-OH;
H-Asp(OPropofol)-Ala-OH;
H-Asp(OPropofol)-Asp-OH;
H-Asp(OPropofol)-Gln-OH;
H-Asp(OPropofol)-Glu-OH;
H-Asp(OPropofol)-Gly-OH;
H-Asp(OPropofol)-Ile-OH;
H-Asp(OPropofol)-Leu-OH;
H-Asp(OPropofol)-Met-OH;
H-Asp(OPropofol)-OBzl;
H-Asp(OPropofol)-OH;
H-Asp(OPropofol)-O-Trityl;
H-Asp(OPropofol)-Phe-OH;
H-Asp(OPropofol)-Pro-OH;
HAsp(OPropofol)-Ser-OH;
H-Asp(OPropofol)-Val-OH;
H-Asp-Ala-OPropofol;
H-Asp-AsnOPropofol;
H-Asp-Asp(OCH₂OPropofol)-OH;
H-Asp-Asp(OPropofol)-OH;
H-AspOCH₂OPropofol;
H-Asp-Phe-OPropofol;
H-Asp-Ser(β-OC(O)OPropofol)-OH;
H-Asp-TyrOPropofol;
H-Cys-Asp(OPropofol)-OH;
H-Dap(β-NHC(O)OPropofol)-Ala-OH;
H-Dap-Ala-OPropofol;
H-Dap-Asn-OPropofol;
H-Dap-Thr(γ-OC(O)OPropofol)-OH Bis-Hydrochloride;
H-Dap-Tyr-OPropofol;
H-D-Asn-Thr(γ-OC(O)OPropofol)-OH;
H-D-LysThr(γ-OC(O)OPropofol)-OH Bis-Hydrochloride;
H-D-Ser-Thr(γ-OC(O)OPropofol-OH Hydrochloride;
H-Gln-Asn-OPropofol;
H-Gln-Asp(OCH₂OPropofol)-OH;
H-Gln-OPropofol Hydrochloride;
H-Gln-Phe-OPropofol;
H-Glu(OPropofol)-Ala-OH;
H-Glu(OPropofol)-ArgOH;
H-Glu(OPropofol)-Asp-OH;
H-Glu(OPropofol)-Gln-OH;
H-Glu(OPropofol)-Glu-OH;
H-Glu(OPropofol)-Gly-OH;
H-Glu(OPropofol)-Ile-OH;
H-Glu(OPropofol)-Leu-OH;
H-Glu(OPropofol)-Lys-OH;
H-Glu(OPropofol)-Met-OH;
H-Glu(OPropofol)-OBzl;
H-Glu(OPropofol)-OH;
H-Glu(OPropofol)-Phe-OH;
H-Glu(OPropofol)-Ser-OH;
H-Glu(OPropofol)-Val-OH;
H-Glu-Asp(OCH₂OPropofol)-OH;
H-Glu-Phe-OPropofol;
H-GluTyr-OPropofol;
H-Gly-Asn-OPropofol;
H-Gly-Asp(OCH₂OPropofol)-OH;
H-Gly-OPropofol Hydrochloride;
H-Gly-Phe-OPropofol;
H-Gly-Thr(γ-OC(O)OPropofol)-OH;
H-Gly-TyrOPropofol;
H-His-Asp(OCH₂OPropofol)-OH;
H-His-OPropofol;
H-His-Phe-OPropofol;
H-His-Thr(γ-OC(O)OPropofol)-OH Bis-Hydrochloride;
H-Leu-Asp(OPropofol)-OH;
H-Leu-D-Thr(γ-OC(O)OPropofol)-OH;
H-Leu-Glu(OPropofol)-OH;
H-Leu-Thr(γ-OC(O)OPropofol)OH Hydrochloride;
H-Lys-Asp(OPropofol)-OH;
H-Lys-Cys(β-SC(O)OPropofol)-OH;
H-Lys-Glu(OPropofol)-OH;
H-Lys-OPropofol Hydrochloride;
H-Lys-Ser(β-OC(O)OPropofol)-OH;
H-Lys-Thr(β-OC(O)OPropofol)-OH;
H-Lys-Thr(γ OC(O)OPropofol)-OH Bis-Hydrochloride;
H-Lys-Tyr-OPropofol;
H-Met-Asp(OPropofol)OH;
H-Met-OPropofol;
H-Met-Thr(γ-OC(O)OPropofol)-OH Hydrochloride;
H-NVal-Asp(OPropofol)-OH;
H-Orn-Asp(OPropofol)-OH;
H-Orn-Thr(γ-OC(O)OPropofol)-OH BisHydrochloride;
H-Phe-Asp(OPropofol)-OH;
H-Phe-OPropofol;
H-Pro-OPropofol Hydrochloride;
H-Pro-Phe-OPropofol;
H-Pro-Thr(γ-OC(O)OPropofol)-OH Hydrochloride;
H-Pro-Tyr-OPropofol;
H-Sar-Asp(OPropofol)-OH;
H-Ser-Asn-OPropofol;
H-SerAsp(OCH₂OPropofol)-OH;
H-Ser-Cys(β-SC(O)OPropofol)-OH;
H-Ser-D-Thr(γOC(O)OPropofol)-OH;
H-Ser-OPropofol;
H-Ser-Phe-OPropofol;
H-Ser-Ser(β-OC(O)OPropofol)-OH;
H-Ser-Thr(β-OC(O)OPropofol)-OH;
H-Ser-Thr(γ-OC(O)OPropofol)-OH Hydrochloride
H-Ser-Tyr-OPropofol;
H-ThrAsp(OCH₂OPropofol)-OH;
H-Thr-OPropofol Hydrochloride;
H-Thr-Phe-OPropofol;
H-Trp-Asp(OCH₂OPropofol)-OH;
H-Trp-Phe-OPropofol;
H-Tyr-Asn-OPropofol;
H-TyrAsp(OCH₂OPropofol)-OH;
H-Tyr-Asp(OPropofol)-OH;
H-Tyr-OPropofol Hydrochloride;
H-Tyr-Phe-OPropofol;
H-Tyr-Ser(β-OC(O)OPropofol)-OH;
H-Val-Ala-OPropofol;
H-Val-Asn-OPropofol;
H-Val-OCH₂OPropofol;
H-Val-OPropofol;

H-Val-Phe-OPropofol;
H-Val-Ser-OPropofol;
H-Val-Thr(β-OC(O)OPropofol)-OH;
H-Val-Thr(γ-OC(O)OPropofol)-OH Hydrochloride
H-Val-Tyr-OPropofol;
2,6-(Diisopropyl)phenyl hydroxybutyrate disodiumphosphate;
2,6-(Diisopropyl)phenyl hydroxyvaleratephosphate disodium salt;
H-[3-Ala-Asp(OPropofol)-OH;
H-[3-Ala-Thr(γ-OC(O)OPropofol)-OH Hydrochloride;
1-Amino-2-[2,6-(diisopropyl)phenoxycarbonyloxy]ethane;
N-(2-Dibutylaminoethyl)-succinamic acid 2,6-diisopropyl-phenyl ester;
N-(2-Dibutylaminoethyl)-succinamic acid 2,6-diisopropyl-phenyl ester hydrochloride;
N-(2-Diethylamino-ethyl)-succinamic acid 2,6-diisopropyl-phenyl ester Hydrochloride;
N-(2-Diethylammoethyl)-succinamic acid 2,6-diisopropylphenyl ester;
N-(2-Diisopropylaminoethyl)-succinamic acid 2,6-diisopropyl-phenyl ester;
N-(2-Diisopropylamino-ethyl)-succinamic acid 2,6-diisopropyl phenyl ester Hydrochloride;
N-(2-Dimethylamino-ethyl)-succinamic acid 2,6-diisopropyl-phenyl ester Hydrochloride;
N-(2-Dimethylaminoethyl)-succinamic acid 2,6-diisopropyl-phenyl ester;
N-(2-Morpholin-4-ylethyl)-succinamic acid 2,6-diisopropylphenyl ester;
N-(2-Morpholin-4-yl-ethyl)-succinamic acid 2,6-diisopropylphenyl ester Hydrochloride;
N-(2-Piperidin-1-yl-ethyl)-succinamic acid 2,6-diisopropylphenyl ester;
N-(2-Piperidin-1-yl-ethyl)-succinamic acid 2,6-diisopropylphenyl ester hydrochloride;
N-(2-Pyrrolidin-1-yl-ethyl)-succinamic acid 2,6-diisopropylphenyl ester;
N-(2-Pyrrolidin-1-yl-ethyl)-succinamic acid 2,6-diisopropylphenyl ester hydrochloride;
O-[t-butoxycarbonyl]-propofol);
propofol 2-carboxyl-2(S)fluoropropionate sodium salt;
propofol 3-(N,N-diethyl)amino-2-(R,S)-fluoropropionate hydrochloride;
propofol 3-(N-isopropyl)amino-2-(R,S)-2-monofluoromethylpropionate methanesulfonate;
propofol 3-(N-isopropyl)amino-2(R,S)-2-monofluoromethyl propionate methanesulfonate;
propofol 3-(pyrrolidin-1-yl)-2-(S)-trifluoromethyl propionate hydrochloride;
propofol 3-(pyrrolidin-1-yl)-2(S)-trifluoromethylpropionate hydrochloride;
propofol 3-carboxyl-2(R)-fluorobutyrate sodium salt;
propofol 3-N-isopropylamino-2-(R,S)-fluoropropionate hydrochloride;
propofol 3-N-methyl-N-cyclohexylamino-2-(R,S)fluoropropionate hydrochloride;
propofol 3-N-methyl-N-cyclohexylamino-2-(R,S)fluoropropionate hydrochloride;
propofol 3-phosphoryl-2-(R,S)-fluoropropionate zinc salt;
propofol 4-(aziridin-1-yl)-2-(S)-2-fluorobutyratehydrochloride;
propofol 4-(N,Ndimethyl)amino-2-(R)-2-trifluoromethylbutyrate hydrochloride;
propofol 4-(N,Ndimethyl)amino-2-(R)-fluorobutyrate hydrochloride;
propofol 4-(N,N-dimethyl)amino-2-(R)trifluoromethylbutyrate hydrochloride;
propofol 4-(N,N-dimethyl)amino-2-(R,S)fluorobutyrate hydrochloride;
propofol 4-(N-cyclopropyl-N-methyl)amino-2-(R)difluoromethylbutyratehydrochloride;
propofol 4-(N-methyl-N-benzyl)amino-2-(R,S)trifluoromethylbutyrate hydrochloride;
propofol 4-(N-methyl-N-ethyl)amino-2-(R,S)-2-fluorobutyratehydrochloride;
propofol 4-(N-methyl-N-isopropyl)amino-2-(R,S)fluorobutyrate methanesulfonate;
propofol 4-(pyrrolidin-1-yl)-2-(R)-2-fluorobutyrate hydrochloride;
propofol 4-carboxyl-2-(R)-2-trifluoromethylvalerate lithium salt;
propofol 4-carboxyl-2(R)-fluorobutyrate sodium salt;
propofol 4-carboxyl-2-(R,S)difluoromethylvalerate potassium salt;
propofol 4-carboxyl-2(R,S)-fluorovalerate sodium salt;
propofol 4-carboxyl-2-(S)-fluorovalerate potassium salt;
propofol 4-carboxyl-2-(S)fluorovalerate potassium salt;
propofol 4-carboxyl-2-(S)-trifluoromethylbutyrate ammonium salt;
propofol 4-N-(aziridin-1-yl)-2(S)-2-fluorobutyrate hydrochloride;
propofol 4-N-methyl-N-benzylamino-2-(R)-fluorobutyrate hydrochloride;
propofol 4-phosphoryl-2-(R)fluorobutyrate disodium salt;
propofol 4-phosphoryl-2-(R,S)-fluorobutyrate calcium salt;
propofol 5-(N-methyl-N-benzyl)amino-2-(S)-2-fluorovalerate hydrochloride;
propofol 5-carboxyl-2-(R,S)-difluoromethylvalerate potassium salt;
propofol 5-N-cyclopentylamino-2,2-difluorovalerate hydrochloride;
propofol 5-phosphoryl-2-(S)-fluorovalerate zinc salt;
propofol 6-(N,N-dimethyl)amino-2(R)-fluorovalerate hydrochloride;
Propofol Hemisuccinate;
propofol hydroxybutyrate;
propofol hydroxyvalerate;
propofol 8-(N,Ndimethyl)amino-2-(R)-fluorovaleratehydrochloride;
propofol-2-(R)-fluoropropionate monoester sodium salt;
propofol-2-(R,S)-fluorobutyratemonoester sodium salt;
propofol-2-(R,S)-fluoropentanoate monoester sodium salt;
(S)-2-amino-3-(2,6-diisopropylphenoxycarbonyloxy)-propanoic acid mesylate;
Sodium 4-(2,6-Diisopropyl phenoxy)-4-oxobuty 1 Phosphate;
2-(2,6-diisopropyl phenoxy)-tetrahydropyran-6-yl dihydrogen phosphate arginine;
tri[propofol 3-phosphoryl-2-(R,S)-2-monofluoromethylpropionate] dialuminum salt;
tri[propofol 8-carboxyl-2-(R,S)monofluoromethylpelargonate]aluminum salt; Succinic Acid Mono-Propofol Ester;
BOC-protected 1-deoxy-1-hydrazinoglucitol;

2-amino-3-methyl-3-(2,6-diisopropyl-phenoxycarbonyloxy)-propanoic acid;
2-amino-3-(2,6-diisopropylphenoxycarbonyloxy)-propanoic acid;
1-(2,6-diisopropyl phenoxy)ethyl dihydrogen phosphate;
Mono(propofol) phosphate;
Di(propofol) phosphate;
Carboxylic hemiesters of propofol;
hemisuccinate ester of propofol;
hemiglutarate ester of propofol;
hemiadipate ester of propofol;
(2',6'-Diisopropylphenyl4-(2-trimethylammoniumethyloxy) phosphonobutyrate);
(2',6'-Diisopropylphenyl3-ortho-(O-trimethylammonium ethylphosphonooxy)-1-propionate)
(4-(2,6-diisopropylphenoxy)-4-oxobutanoyl)glycine;
4-(4-(2,6-diisopropylphenoxy)-4-oxobutanamido)butanoic acid
HX0507;
HX0969w;
HX0892;
HX0891;
propofol methoxymethylphosphonic prodrug;
propofol hemiglutarate;
propofol hemiadipate;
monopropofol phosphate;
dipropofol phosphate;
1-(((2,6-diisopropylphenoxy)carbonyloxy)methyl)-3-(dimethylcarbamoyl)pyridinium mesylate;
1-(((2,6-diisopropylphenoxy)carbonyloxy)methyl)-3-(methylcarbamoyl)pyridinium mesylate;
3-carbamoyl-1-(((2,6-diisopropylphenoxy)carbonyloxy)methyl)pyridinium mesylate;
1-(((2,6-diisopropyl phenoxy)carbonyloxy)methyl)-3-(methylcarbamoyl)pyridinium iodide;
1-((((2,6-diisopropylphenoxy)carbonyl)oxy)methyl)-3-(dimethylcarbamoyl)pyridin-1-ium methanesulfonate;
1-((((2,6-diisopropylphenoxy)carbonyl)oxy)methyl)-3-(dimethylcarbamoyl)pyridin-1-ium iodide;
1-((((2,6-diisopropylphenoxy)carbonyl)oxy)methyl)-3-(methoxycarbonyl)pyridin-1-ium iodide;
3-carboxy-1-((((2,6-diisopropylphenoxy)carbonyl)oxy)methyl)pyridin-1-ium iodide;
2-(((2,6-diisopropylphenoxy)carbonyl)oxy)-N,N,N-trimethylethan-1-aminium iodide;
2-(((2,6-diisopropylphenoxy)carbonyl)oxy)-N,N-dimethylethan-1-aminium chloride;
1-((((2,6-diisopropylphenoxy)carbonyl)oxy)methyl)-3-(hydroxycarbamoyl)pyridin-1-ium iodide;
3-(((((2,6-diisopropylphenoxy)carbonyl)oxy)methyl)carbamoyl)-1-methylpyridin-1-ium iodide;
1-(((2,6-diisopropylphenoxy)carbonyl)oxy)-N-((((2,6-diisopropylphenoxy)carbonyl)oxy)methyl)-N,N-dimethylmethanaminiumiodide;
2-(((2,6-diisopropylphenoxy)carbonyl)oxy)-N-((((2,6-diisopropylphenoxy)carbonyl)oxy)methyl)N,N-dimethylethan-1-aminiumiodide;
1-((((2,6-diisopropylphenoxy)carbonyl)oxy)methyl)-4-formyl-3-hydroxy-5-(hydroxymethyl)-2-methylpyridin-1-ium iodide;
3-((2,6-diisopropylphenoxy)carbonyl)-1-((((2,6-diisopropylphenoxy)carbonyl)oxy)methyl)pyridin-1-ium methanesulfonate;
2-(((2,6-diisopropylphenoxy)carbonyl)oxy)-N,N,N-trimethylethan-1-aminium methanesulfonate;
3-carbamoyl-1-((((2,6-diisopropylphenoxy)carbonyl)oxy)methy)pyridin-1-ium bromide;
3-carbamoyl-1-((((2,6-diisopropylphenoxy)carbonyl)oxy)methyl)pyridin-1-ium chloride;
1-((((2,6-diisopropyl phenoxy)carbonyl)oxy)methyl)-3-(methylcarbamoyl)pyridin-1-ium tetrafluoroborate;
1-((((2,6-diisopropyl phenoxy)carbonyl)oxy)methyl)-3-(methylcarbamoyl)pyridin-1-ium nitrate;
1-((((2,6-diisopropylphenoxy)carbonyl)oxy)methyl)-3-(methylcarbamoyl)pyridin-1-ium chloride;
1-((((2,6-diisopropylphenoxy)carbonyl)oxy)methyl)-3-(methoxycarbonyl)pyridin-1-ium methanesulfonate; or
3-carboxy-1-((((2,6-diisopropyl phenoxy)carbonyl)oxy)methyl)pyridin-1-ium methanesulfonate.

2. The method of claim 1, wherein the administration results in a Cmax of propofol of at least 50 ng/mL.

3. The method of claim 1, wherein the administration results in a Cmax of propofol of at least 75 ng/mL.

4. The method of claim 1, wherein the administration results in a Cmax of propofol of at least 100 ng/mL.

5. The method of claim 1, wherein the administration results in a Cmax of propofol of at least 200 ng/mL.

6. The method of claim 1, wherein the administration results in a Cmax of propofol of at least 300 ng/mL.

7. The method of claim 1, wherein the administration results in a Cmax of propofol of at least 400 ng/mL.

8. The method of claim 1, wherein the administration results in a Cmax of propofol of at least 500 ng/mL.

9. A method of treating migraine in a patient in need thereof, the method comprising orally administering a propofol prodrug, a pharmaceutically acceptable salt of a propofol prodrug, or mixtures thereof, to the patient in one or more doses, wherein the administration results in an $AUC_{4hr}$ of propofol of no less than 100 ng hr/mL, and wherein following the administration the patient is headache free, has experienced a reduction in headache pain, or is no longer experiencing a most bothersome symptom, and
wherein the propofol prodrug is:
sodium 2-(2-(2,6-diisopropylphenoxy)-2-oxoethoxy)acetate;
(Azepan-1-ylcarbamoylmethyl)carbamic acid 2,6-diisopropylphenyl ester hydrochloride; (E)-3-(2,6-diisopropylphenoxy)acrylic acid;
(O-[2-carboxyethyl]-propofol), (S)-2-amino-3-(2,6-diisopropylphenoxycarbonyloxy)-propanoic acid;
(S)-2-amino-3-(2,6-diisopropylphenoxycarbonyloxy)-propanoic acid mesylate salt; (S)-2-amino-3-(2, 6-diisopropylphenoxycarbonyloxy)-propanoic acid hydrochloride;
{1-[3-(2, 6-diisopropylphenoxy)-3-oxo-2(R)-fluoro-1-propyl]}phosphate monoesterdipotassium salt;
{1-[4-(2,6-diisopropylphenoxy)-4-oxo-2(R)-trifluoromethyl-1-butyl]} phosphate monoester dilithium salt;
{1-[4-(2,6-diisopropylphenoxy)-4-oxo-3-(R)-3-trifluoromethyl-1-butyl]}phosphate monoester dilithium salt;
{1-[4-(2,6-diisopropylphenoxy)-4-oxo-3-(R,S)-3-fluoro-1-butyl]} phosphate monoesterdipotassium salt;
{1-[4-(2,6-diisopropylphenoxy)-4-oxo-3-(S)-3-fluoro-1-butyl]} phosphate monoester di sodium salt;
{1-[6-(2,6-diisopropylphenoxy)-6-oxo-5-(S)-difluoromethyl-1-hexyl]} phosphate di arginine salt;

1-((((2,6-diisopropyl phenoxy)carbonyl)oxy)methyl)-3-(dimethylcarbamoyl) pyridinium iodide;
1-((((2,6-diisopropylphenoxy)carbonyl) oxy)methyl)-3-(hydroxycarbamoyl) pyridin-1-ium iodide;
1-((((2,6-diisopropylphenoxy)carbonyl) oxy)methyl)-3-(methoxycarbonyl)pyridin-1-ium iodide;
1-((((2,6-diisopropylphenoxy)carbonyl) oxy)methyl)-3-(methoxycarbonyl)pyridin-1-ium methanesulfonate;
1-((((2,6-diisopropylphenoxy)carbonyl)oxy)methyl)-3-(methylcarbamoyl)pyridin-1-ium tetrafluoroborate;
1-((((2,6-diisopropylphenoxy)carbonyl)oxy)methyl)-3-(methylcarbamoyl)pyridin-1-ium nitrate;
1-((((2,6-diisopropylphenoxy)carbonyl)oxy)methyl)-3-(methylcarbamoyl)pyridin-1-ium chloride;
1-((((2,6-diisopropylphenoxy)carbonyl)oxy)methyl)-4-formyl-3-hydroxy-5-(hydroxymethyl)-2-methylpyridin-1-ium iodide;
1-(((2,6-diisopropylphenoxy)carbonyl)oxy)N-((((2,6-diisopropylphenoxy)carbonyl)oxy)methyl)-N,N-dimethyl-methanaminiumiodide;
1-(((2,6-diisopropylphenoxy)carbonyloxy)methyl)-3-(dimethylcarbamoyl)pyridinium mesylate;
1-(((2,6-diisopropylphenoxy)carbonyloxy) methyl)-3-(methylcarbamoyl)pyridinium mesylate;
1-(((2,6-diisopropylphenoxy)carbonyloxy)methyl)-3-(methylcarbamoyl)pyridiniumiodide;
1-((2',6'-diisopropylphenoxy)carbonylamino)ethyl-2,3,4,6-tetra-O-acetyl-β-D-glucopyrano side;
1-((2',6'diisopropylphenoxy) carbonylamino)ethyl-β-D-glucopyranoside;
1-((2',6'diisopropylphenoxy)carbonyloxy)ethyl-2,3,4,6-tetra-O-acetyl-β-D-glucopyranoside;
1-((2',6'diisopropylphenoxy)carbonyloxy)ethyl-2,3,4,6-tetra-O-acetyl-α-D-glucopyranoside;
1-((2',6'diisopropylphenoxy)carbonyloxy)ethyl-hepta-O-acetyl-β-D-maltose;
1-((2',6'diisopropylphenoxy)carbonyloxy)ethyl-α-D-glucopyranoside;
1-((2',6'-diisopropylphenoxy)carbonyloxy)ethyl-β-D-maltose;
1-((2',6'-diisopropylphenoxy)carbonyloxy)ethyl-β-n-glucopyranoside;
1-((2',6'diisopropylphenoxy)carbonyloxy)propyl-2,3,4,6-tetra-O-acetyl-β-D-glucopyranoside;
1-((2',6'-diisopropylphenoxy)carbonyloxy)propyl-2,3,4,6-tetra-O-acetyl-α-D-glucopyranoside;
1-((2',6'-diisopropylphenoxy)carbonyloxy)propyl-hepta-O-acetyl-β-D-maltose;
1-((2',6'-diisopropylphenoxy)carbonyloxy)propyl-α-D-glucopyranoside;
1-((2',6'diisopropylphenoxy)carbonyloxy)propyl-β-D-glucopyranoside;
1-((2',6'diisopropylphenoxy)carbonyloxy)propyl-β-D-maltose;
1-Amino-2-[2,6-(diisopropyl)phenoxycarbonyloxy]ethane;
2-[2,6-(Diisopropyl)phenoxycarbonyloxy]ethyl (2S)-2-amino-3-hydroxypropionamide;
2-(((2,6-diisopropylphenoxy)carbonyl) oxy)-N((((2,6-diisopropylphenoxy)carbonyl)oxy)methyl)-N,N-dimethylethan-1-aminiumiodide;
2-(((2,6-diisopropylphenoxy)carbonyl)oxy)-N,N,N-trimethylethan-1-aminium iodide;
2-(((2,6-diisopropyl phenoxy)carbonyl)oxy)-N,N,N-trimethyl ethan-1-aminium methanesulfonate;
2-(2,6-diisopropyl phenoxy)-2-hydroxyethyl phosphate;
2-(2,6-diisopropylphenoxy)-3,4,5-trihydroxy tetrahydropyran-6-yl, dihydrogen phosphate;
2-(2,6-diisopropylphenxoy)-3,4,5-trihydroxytetrahydropyran-6-yl dihydrogen phosphate arginine;
2,6-(diisopropyl)phenyl 1-[((2S)-2-amino-(3R)-3-hydroxybutyryl)aminomethyl]-1-cyclohexane acetate;
2,6-(diisopropyl)phenyl 1-[((2S)-2-amino-3-hydroxypropionyl)aminomethyl]-1-cyclohexane acetate;
2,6-(diisopropyl)phenyl 1-[((2S)-2-amino-3-methylbutyryl)aminomethyl]-1-cyclohexane acetate;
2,6-(diisopropyl)phenyl 4-[(2S)-2,3-diaminopropionylamino]-3,3-dimethylbutanoate;
2,6-(diisopropyl)phenyl 4-[(2S)-2,6-diaminohexanoylamino]-3,3-dimethylbutanoate;
2,6-(Diisopropyl)phenyl 4-[(2S)-2-amino-(3R)-3-hydroxylbutyryl]aminobutanoate;
2,6-(diisopropyl)phenyl 4-[(2S)-2-amino-(3R)-3-hydroxybutyryl]amino-3,3-dimethylbutanoate;
2,6-(diisopropyl)phenyl 4-[(2S)-2-amino-(3R)-3-hydroxylbutyryl]aminobutanoate;
2,6-(diisopropyl)phenyl 4-[(2S)-2-amino-(4-hydroxyphenyl)propionylamino]-3,3-dimethylbutanoate;
2,6-(Diisopropyl)phenyl 4-[(2S)-2-amino-(indol-3-yl)propionylamino]-3,3-dimethylbutanoate;
2,6-(Diisopropyl)phenyl 4-[(2S)-2-amino-3-carbamoylpropionylamino]butanoate;
2,6-(Diisopropyl)phenyl 4-[(2S)-2-amino-3-hydroxypropionylamino]butanoate;
2,6-(diisopropyl)phenyl 4-[(2S)-2-amino-3-carbamoylpropionylamino]-3,3-dimethylbutanoate;
2,6-(diisopropyl)phenyl 4-[(2S)-2-amino-3-carbamoylpropionylamino]butanoate;
2,6-(diisopropyl)phenyl 4-[(2S)-2-amino-3-carboxypropionylamino]-3,3-dimethylbutanoate;
2,6-(diisopropyl)phenyl 4-[(2S)-2-amino-3-hydroxypropionylamino]-3,3-dimethylbutanoate;
2,6-(diisopropyl)phenyl4-[(2S)-2-amino-3-hydroxypropionylamino]butanoate;
2,6-(Diisopropyl)phenyl 4-[(2S)-2-amino-3-hydroxypropionylamino]-3,3-dimethylbutanoate;
2,6-(diisopropyl)phenyl 4-[(2S)-2-amino-3-methylbutyrylamino]-3,3-dimethylbutanoate;
2,6-(diisopropyl)phenyl 4-[(2S)-2-amino-3-methylbutyrylamino]butanoate;
2,6-(diisopropyl)phenyl 4-[(2S)-2-amino-4-carboxybutyrylamino]-3,3-dimethylbutanoate;
2,6-(diisopropyl)phenyl 4-[(2S)-2-amino-4-carboxylbutyrylamino]butanoate;
2,6-(diisopropyl)phenyl 4-[(2S)-2-aminopropionylamino]-3,3-dimethylbutanoate;
2,6-(diisopropyl)phenyl4-[(2S)-pyrrolidin-2-ylcarbonylamino]-3,3-dimethylbutanoate;
2,6-(diisopropyl)phenyl 4-[(2S)-pyrrolidin-2-ylcarbonylamino]butanoate;
2,6-(Diisopropyl)phenyl 4-[(2S)-pyrrolidin-2-ylcarbonylaraino]-3,3-dimethylbutanoate;
2,6-(diisopropyl)phenyl 4-[aminomethylcarbonylamino]-3,3-dimethylbutanoate;
2,6-(Diisopropyl)phenyl 1-[((2S)-2-amino-(3R)-3-hydroxybutyryl)aminomethyl]-1-cyclohexane acetate;
2,6-(Diisopropyl)phenyl 1-[((2S)-2-amino-3-hydroxypropionyl)aminomethyl] 1-cyclohexane acetate;
2,6-(Diisopropyl)phenyl 1-[((2S)-2-amino-3-methylbutyryl)aminomethyl]-1-cyclohexane acetate;

2,6-diisopropylphenyl 4-((2-(2-methylpyrazolidin-1-yl)ethyl)amino)-4-oxobutanoate;
2,6-diisopropylphenyl 4-((2-(4,5-dihydro-1H-pyrazol-1-yl)ethyl)amino)-4-oxobutanoate;
2,6-diisopropylphenyl 4-((2-(4-ethylpiperazin-1-yl) ethyl)amino)-4-oxobutanoate;
2,6-diisopropylphenyl 4-((2-(4-methylpiperazin-1-yl) ethyl)amino)-4-oxobutanoate; 2,6-diisopropylphenyl4-((2-morpholinoethyl)amino)-4-oxobutanoate;
2,6-Diisopropylphenyl 4-(2-(TertButoxycarbonylamino) Propanoyloxy)Butanoate;
2,6-Diisopropylphenyl4-(2-Aminoacetoxy) Butanoate Trifluoroacetic Acid Salt;
2,6-Diisopropylphenyl 4-(2-Aminopropanoyloxy)Butanoate Hydrochloride;
2,6-Diisopropyl phenyl 4-Hydroxybutanoate;
2,6-diisopropyl phenyl 4-oxo-4-((2-(piperazin-1-yl) ethyl)amino)butanoate;
2,6-diisopropyl phenyl 4-oxo-4-((2-(piperidin-1-yl) ethyl)amino)butanoate;
2,6-diisopropyl phenyl 4-oxo-4-((2-(pyrazolidin-1-yl) ethyl)amino)butanoate;
2,6-diisopropylphenyl 4-oxo-4-((2-(pyrrolidin-1-yl) ethyl)amino)butanoate;
2, 6-diisopropylphenyl 4-oxo-4-((2-thiomorpholinoethyl)amino)butanoate;
2-[2,6-(diisopropyl)phenoxycarbonylamino]ethyl (2S)-2-amino-3-carboxypropionamide;
2-[2,6-(diisopropyl)phenoxycarbonylamino]ethyl (2S)-2-amino-3-hydroxypropionamide;
2-[2,6-(diisopropyl)phenoxycarbonylamino]ethyl (2S)-2-amino-3-methylbutanoylamide;
2-[2,6-(diisopropyl)phenoxycarbonyloxy]ethyl (2S)-2, 6-diaminohexanoylamide;
2-[2,6-(diisopropyl)phenoxycarbonyloxy]ethyl (2S)-2-amino-(4-hydroxyphenyl)propionamide;
2-[2,6-(Diisopropyl)phenoxycarbonyloxy]ethyl (2S)-2-amino(4-hydroxyphenyl)propionamide;
2-[2,6-(diisopropyl)phenoxycarbonyloxy]ethyl (2S)-2-amino-3-carbamoylpropionate;
2-[2,6-(diisopropyl)phenoxycarbonyloxy]ethyl (2S)-2-amino-3-carbamoylpropionamide;
2-[2,6-(Diisopropyl)phenoxycarbonyloxy]ethanol;
1-Amino-2-[2,6-(diisopropyl)phenoxycarbonyloxy] ethane;
2-[2,6-(diisopropyl)phenoxycarbonyloxy]ethyl (2S)-2-amino-3-hydroxypropionate;
2-[2,6-(diisopropyl)phenoxycarbonyloxy]ethyl (2S)-2-amino-3-hydroxypropionamide;
2-[2,6-(diisopropyl)phenoxycarbonyloxy]ethyl glycinamide;
2-amino-3-(2,6-diisopropylphenoxycarbonyloxy)-propanoic acid mesylate;
2-amino-3-methyl-3-(2,6-diisopropyl-phenoxycarbonyloxy)-propanoic acid;
3-(((((2,6-diisopropylphenoxy)carbonyl)oxy)methyl) carbamoyl)-1-methylpyridin-1-ium iodide;
3-((2,6-diisopropylphenoxy)carbonyl)-1-((((2,6-diisopropyl phenoxy)carbonyl)oxy) methyl)pyridin-1-ium methanesulfonate;
3-{[2-[2,6-Bis(isopropyl)phenoxycarbonyl]-benzoyl] amino}propanoic acid;
3-{[2-[2,6-Bis(isopropyl)phenoxycarbonyloxy]-benzoyl]amino}-propanoic acid;
3-carbamoyl-1-((((2,6-diisopropyl-phenoxy)carbonyl) oxy)methyl)pyridin-1-ium iodide;
3-carbamoyl-1-(((2,6-diisopropylphenoxy)carbonyloxy)methyl)pyridinium mesylate;
3-carboxy-1-((((2,6-diisopropylphenoxy)carbonyl) oxy)methyl)pyridin-1-ium iodide;
3-carboxy-1-((((2,6-diisopropylphenoxy) carbonyl) oxy)methyl)pyridin-1-ium methanesulfonate;
4-[(2S)-2-amino-(3R)-3-hydroxybutyryl]amino-3,3-dimethylbutanoate;
4-[(2S)-2-amino-3-carbamoylpropionylamino]-3,3-dimethylbutanoate;
4-[(2S)-2-amino-4-carboxybutyrylamino]-3,3-dimethylbutanoate;
4-[(2S)-2-aminopropionylamino]-3,3-dimethylbutanoate;
2,6-(Diisopropyl)phenyl;
4-[aminomethylcarbonylamino]-3,3-dimethylbutanoate;
2,6-(Diisopropyl)phenyl;
arginine2-(2,6-diisopropylphenoxy)-2-hydroxyethylphosphate;
arginine2-(2,6-diisopropylphenoxy)-3,4,5-trihydroxytetrahydropyran-6-yl dihydrogen phosphate;
Boc-Asp(OPropofol)-OBzl; Boc-Asp(OPropofol)-OH;
Boc-Glu(OPropofol)-OBzl;
Boe-Glu(OPropofol)-OH;
di[propofol 5-carboxyl-2(S)-fluorohexanoate] zinc salt;
di[propofol 5-carboxyl-2-(S)-fluorohexanoate] zinc salt;
di[propofol 7-carboxyl-2(R,S)-fluorocaprylate] calcium salt;
di[propofol 7-carboxyl-2-(R,S)fluorocaprylate] calcium salt;
disodium lauryl-imino-dipropionate2-(2,6-diisopropylphenoxy) tetrahydropyran-6-yl dihydrogen phosphate;
disodium lauryl-iminodipropionate-2-(2,6-diisopropyl phenoxy) tetrahydropyran-6-yl dihydrogen phosphate;
H-Abu-Asp(OPropofol)-OH;
H-Abu-Thr(γ-OC(O)OPropofol)-OH Hydrochloride;
H-Aib-OCH$_2$OPropofol;
H-Ala-Asn-OPropofol;
H-Ala-Asp(OCH$_2$OPropofol)-OH;
H-AlaAsp(OPropofol)-OH;
H-Ala-Cys(β-SC(O)OPropofol)-OH;
H-Ala-Glu(OPropofol)-OH;
H-Ala-OPropofol Hydrochloride;
H-Ala-Phe-OPropofol;
H-Ala-Ser(β-OC(O)OPropofol)-OH;
H-Ala-Thr(β-OC(O)OPropofol)-OH;
H-Ala-Thr(γ-OC(O)OPropofol)-OH Hydrochloride;
H-Ala-Tyr-OPropofol;
H-Arg-Asp(OPropofol)-OH;
H-Arg-Phe-OPropofol;
H-Arg-Thr(γ-OC(O)OPropofol)-OH Tris-Hydrochloride;
H-Asn-Asp(OCH$_2$OPropofol)-OH;
H-Asn-Asp(OPropofol)-OH;
H-Asn-D-Thr(γ-OC(O)OPropofol)-OH;
H-Asn-Glu(OPropofol)-OH;
H-Asn-OPropofol Hydrochloride;
H-Asn-Thr(β-OC(O)OPropofol)-OH;
H-Asn-Thr(γ-OC(O)OPropofol)-OH Hydrochloride;
H-Asn-Tyr-OPropofol;
H-Asp(OCH$_2$OPropofol)-ArgOH;
H-Asp(OCH$_2$OPropofol)-Asp-OH;
H-Asp(OCH$_2$OPropofol)-Lys-OH;

H-Asp(OCH₂OPropofol)-OH;
H-Asp(OCH₂OPropofol)-Ser-OH;
H-Asp(OPropofol)-Ala-OH;
H-Asp(OPropofol)-Asp-OH;
H-Asp(OPropofol)-Gln-OH;
H-Asp(OPropofol)-Glu-OH;
H-Asp(OPropofol)-Gly-OH;
H-Asp(OPropofol)-Ile-OH;
H-Asp(OPropofol)-Leu-OH;
H-Asp(OPropofol)-Met-OH;
H-Asp(OPropofol)-OBzl;
H-Asp(OPropofol)-OH;
H-Asp(OPropofol)-O-Trityl;
H-Asp(OPropofol)-Phe-OH;
H-Asp(OPropofol)-Pro-OH;
HAsp(OPropofol)-Ser-OH;
H-Asp(OPropofol)-Val-OH;
H-Asp-Ala-OPropofol;
H-Asp-AsnOPropofol;
H-Asp-Asp(OCH₂OPropofol)-OH;
H-Asp-Asp(OPropofol)-OH;
H-AspOCH₂OPropofol;
H-Asp-Phe-OPropofol;
H-Asp-Ser(β-OC(O)OPropofol)-OH;
H-Asp-TyrOPropofol;
H-Cys-Asp(OPropofol)-OH;
H-Dap(β-NHC(O)OPropofol)-Ala-OH;
H-Dap-Ala-OPropofol;
H-Dap-Asn-OPropofol;
H-Dap-Thr(γ-OC(O)OPropofol)-OH Bis-Hydrochloride;
H-Dap-Tyr-OPropofol;
H-D-Asn-Thr(γ-OC(O)OPropofol)-OH;
H-D-LysThr(γ-OC(O)OPropofol)-OH Bis-Hydrochloride;
H-D-Ser-Thr(γ-OC(O)OPropofol-OH Hydrochloride;
H-Gln-Asn-OPropofol;
H-Gln-Asp(OCH₂OPropofol)-OH;
H-Gln-OPropofol Hydrochloride;
H-Gln-Phe-OPropofol;
H-Glu(OPropofol)-Ala-OH;
H-Glu(OPropofol)-ArgOH;
H-Glu(OPropofol)-Asp-OH;
H-Glu(OPropofol)-Gln-OH;
H-Glu(OPropofol)-Glu-OH;
H-Glu(OPropofol)-Gly-OH;
H-Glu(OPropofol)-Ile-OH;
H-Glu(OPropofol)-Leu-OH;
H-Glu(OPropofol)-Lys-OH;
H-Glu(OPropofol)-Met-OH;
H-Glu(OPropofol)-OBzl;
H-Glu(OPropofol)-OH;
H-Glu(OPropofol)-Phe-OH;
H-Glu(OPropofol)-Ser-OH;
H-Glu(OPropofol)-Val-OH;
H-Glu-Asp(OCH₂OPropofol)-OH;
H-Glu-Phe-OPropofol;
H-GluTyr-OPropofol;
H-Gly-Asn-OPropofol;
H-Gly-Asp(OCH₂OPropofol)-OH;
H-Gly-OPropofol Hydrochloride;
H-Gly-Phe-OPropofol;
H-Gly-Thr(γ-OC(O)OPropofol)-OH;
H-Gly-TyrOPropofol;
H-His-Asp(OCH₂OPropofol)-OH;
H-His-OPropofol;
H-His-Phe-OPropofol;
H-His-Thr(γ-OC(O)OPropofol)-OH Bis-Hydrochloride;
H-Leu-Asp(OPropofol)-OH;
H-Leu-D-Thr(γ-OC(O)OPropofol)-OH;
H-Leu-Glu(OPropofol)-OH;
H-Leu-Thr(γ-OC(O)OPropofol)OH Hydrochloride;
H-Lys-Asp(OPropofol)-OH;
H-Lys-Cys(β-SC(O)OPropofol)-OH;
H-Lys-Glu(OPropofol)-OH;
H-Lys-OPropofol Hydrochloride;
H-Lys-Ser(β-OC(O)OPropofol)-OH;
H-Lys-Thr(β-OC(O)OPropofol)-OH;
H-Lys-Thr(γ OC(O)OPropofol)-OH Bis-Hydrochloride;
H-Lys-Tyr-OPropofol;
H-Met-Asp(OPropofol)OH;
H-Met-OPropofol;
H-Met-Thr(γ-OC(O)OPropofol)-OH Hydrochloride;
H-NVal-Asp(OPropofol)-OH;
H-Orn-Asp(OPropofol)-OH;
H-Orn-Thr(γ-OC(O)OPropofol)-OH BisHydrochloride;
H-Phe-Asp(OPropofol)-OH;
H-Phe-OPropofol;
H-Pro-OPropofol Hydrochloride;
H-Pro-Phe-OPropofol;
H-Pro-Thr(γ-OC(O)OPropofol)-OH Hydrochloride;
H-Pro-Tyr-OPropofol;
H-Sar-Asp(OPropofol)-OH;
H-Ser-Asn-OPropofol;
H-SerAsp(OCH₂OPropofol)-OH;
H-Ser-Cys(β-SC(O)OPropofol)-OH;
H-Ser-D-Thr(γOC(O)OPropofol)-OH;
H-Ser-OPropofol;
H-Ser-Phe-OPropofol;
H-Ser-Ser(β-OC(O)OPropofol)-OH;
H-Ser-Thr(β-OC(O)OPropofol)-OH;
H-Ser-Thr(γ-OC(O)OPropofol)-OH Hydrochloride
H-Ser-Tyr-OPropofol;
H-ThrAsp(OCH₂OPropofol)-OH;
H-Thr-OPropofol Hydrochloride;
H-Thr-Phe-OPropofol;
H-Trp-Asp(OCH₂OPropofol)-OH;
H-Trp-Phe-OPropofol;
H-Tyr-Asn-OPropofol;
H-TyrAsp(OCH₂OPropofol)-OH;
H-Tyr-Asp(OPropofol)-OH;
H-Tyr-OPropofol Hydrochloride;
H-Tyr-Phe-OPropofol;
H-Tyr-Ser(β-OC(O)OPropofol)-OH;
H-Val-Ala-OPropofol;
H-Val-Asn-OPropofol;
H-Val-OCH₂OPropofol;
H-Val-OPropofol;
H-Val-Phe-OPropofol;
H-Val-Ser-OPropofol;
H-Val-Thr(β-OC(O)OPropofol)-OH;
H-Val-Thr(γ-OC(O)OPropofol)-OH Hydrochloride
H-Val-Tyr-OPropofol;
2,6-(Diisopropyl)phenyl hydroxybutyrate disodiumphosphate;
2,6-(Diisopropyl)phenyl hydroxyvaleratephosphate disodium salt;
H-β-Ala-Asp(OPropofol)-OH;
H-β-Ala-Thr(γ-OC(O)OPropofol)-OH Hydrochloride;
1-Amino-2-[2,6-(diisopropyl)phenoxycarbonyloxy]ethane;

N-(2-Dibutylaminoethyl)-succinamic acid 2,6-diisopropyl-phenyl ester;
N-(2-Dibutylaminoethyl)-succinamic acid 2,6-diisopropyl-phenyl ester hydrochloride;
N-(2-Diethylamino-ethyl)-succinamic acid 2,6-diisopropyl-phenyl ester Hydrochloride;
N-(2-Diethylammoethyl)-succinamic acid 2,6-diisopropylphenyl ester;
N-(2-Diisopropylaminoethyl)-succinamic acid 2,6-diisopropyl-phenyl ester;
N-(2-Diisopropylamino-ethyl)-succinamic acid 2,6-diisopropyl phenyl ester Hydrochloride;
N-(2-Dimethylamino-ethyl)-succinamic acid 2,6-diisopropyl-phenyl ester Hydrochloride;
N-(2-Dimethylaminoethyl)-succinamic acid 2,6-diisopropyl-phenyl ester;
N-(2-Morpholin-4-ylethyl)-succinamic acid 2,6-diisopropylphenyl ester;
N-(2-Morpholin-4-yl-ethyl)-succinamic acid 2,6-diisopropylphenyl ester Hydrochloride;
N-(2-Piperidin-1-yl-ethyl)-succinamic acid 2,6-diisopropylphenyl ester;
N-(2-Piperidin-1-yl-ethyl)-succinamic acid 2,6-diisopropylphenyl ester hydrochloride;
N-(2-Pyrrolidin-1-yl-ethyl)-succinamic acid 2,6-diisopropylphenyl ester;
N-(2-Pyrrolidin-1-yl-ethyl)-succinamic acid 2,6-diisopropylphenyl ester hydrochloride;
O-[t-butoxycarbonyl]-propofol);
propofol 2-carboxyl-2(S)fluoropropionate sodium salt;
propofol 3-(N,N-diethyl)amino-2-(R,S)-fluoropropionate hydrochloride;
propofol 3-(N-isopropyl)amino-2-(R,S)-2-monofluoromethylpropionate methanesulfonate;
propofol 3-(N-isopropyl)amino-2(R,S)-2-monofluoromethyl propionate methanesulfonate;
propofol 3-(pyrrolidin-1-yl)-2-(S)-trifluoromethyl propionate hydrochloride;
propofol 3-(pyrrolidin-1-yl)-2(S)-trifluoromethylpropionate hydrochloride;
propofol 3-carboxyl-2(R)-fluorobutyrate sodium salt;
propofol 3-N-isopropylamino-2-(R,S)-fluoropropionate hydrochloride;
propofol 3-N-methyl-N-cyclohexylamino-2-(R,S)fluoropropionate hydrochloride;
propofol 3-N-methyl-N-cyclohexylamino-2-(R,S)fluoropropionate hydrochloride;
propofol 3-phosphoryl-2-(R,S)-fluoropropionate zinc salt;
propofol 4-(aziridin-1-yl)-2-(S)-2-fluorobutyratehydrochloride;
propofol 4-(N,Ndimethyl)amino-2-(R)-2-trifluoromethylbutyrate hydrochloride;
propofol 4-(N,Ndimethyl)amino-2-(R)-fluorobutyrate hydrochloride;
propofol 4-(N,N-dimethyl)amino-2-(R)trifluoromethylbutyrate hydrochloride;
propofol 4-(N,N-dimethyl)amino-2-(R,S)fluorobutyrate hydrochloride;
propofol 4-(N-cyclopropyl-N-methyl)amino-2-(R)difluoromethylbutyratehydrochloride;
propofol 4-(N-methyl-N-benzyl)amino-2-(R,S)trifluoromethylbutyrate hydrochloride;
propofol 4-(N-methyl-N-ethyl)amino-2-(R,S)-2-fluorobutyratehydrochloride propofol 4-(N-methyl-N-isopropyl)amino-2-(R,S)fluorobutyrate methanesulfonate;
propofol 4-(pyrrolidin-1-yl)-2-(R)-2-fluorobutyrate hydrochloride;
propofol 4-carboxyl-2-(R)-2-trifluoromethylvalerate lithium salt;
propofol 4-carboxyl-2(R)-fluorobutyrate sodium salt;
propofol 4-carboxyl-2-(R,S)difluoromethylvalerate potassium salt;
propofol 4-carboxyl-2(R,S)-fluorovalerate sodium salt;
propofol 4-carboxyl-2-(S)-fluorovalerate potassium salt;
propofol 4-carboxyl-2-(S)fluorovalerate potassium salt;
propofol 4-carboxyl-2-(S)-trifluoromethylbutyrate ammonium salt;
propofol 4-N-(aziridin-1-yl)-2(S)-2-fluorobutyrate hydrochloride;
propofol 4-N-methyl-N-benzylamino-2-(R)-fluorobutyrate hydrochloride;
propofol 4-phosphoryl-2-(R)fluorobutyrate disodium salt;
propofol 4-phosphoryl-2-(R,S)-fluorobutyrate calcium salt;
propofol 5-(N-methyl-N-benzyl)amino-2-(S)-2-fluorovalerate hydrochloride;
propofol 5-carboxyl-2-(R,S)-difluoromethylvalerate potassium salt;
propofol 5-N-cyclopentylamino-2,2-difluorovalerate hydrochloride;
propofol 5-phosphoryl-2-(S)-fluorovalerate zinc salt;
propofol 6-(N,N-dimethyl)amino-2(R)-fluorovalerate hydrochloride;
Propofol Hemisuccinate;
propofol hydroxybutyrate;
propofol hydroxyvalerate;
propofol 8-(N,Ndimethyl)amino-2-(R)-fluorovalerate-hydrochloride;
propofol-2-(R)-fluoropropionate monoester sodium salt;
propofol-2-(R,S)-fluorobutyratemonoester sodium salt;
propofol-2-(R,S)-fluoropentanoate monoester sodium salt;
(S)-2-amino-3-(2,6-diisopropylphenoxycarbonyloxy)-propanoic acid mesylate;
Sodium 4-(2,6-Diisopropyl phenoxy)-4-oxobuty 1 Phosphate;
2-(2,6-diisopropyl phenoxy)-tetrahydropyran-6-yl dihydrogen phosphate arginine;
tri[propofol 3-phosphoryl-2-(R,S)-2-monofluoromethylpropionate]dialuminum salt;
tri[propofol 8-carboxyl-2-(R,S)monofluoromethylpelargonate]aluminum salt; Succinic Acid Mono-Propofol Ester;
BOC-protected 1-deoxy-1-hydrazinoglucitol;
2-amino-3-methyl-3-(2,6-diisopropyl-phenoxycarbonyloxy)-propanoic acid;
2-amino-3-(2,6-diisopropylphenoxycarbonyloxy)-propanoic acid;
1-(2,6-diisopropyl phenoxy)ethyl dihydrogen phosphate;
Mono(propofol) phosphate;
Di(propofol) phosphate;
Carboxylic hemiesters of propofol;
hemisuccinate ester of propofol;
hemiglutarate ester of propofol;
hemiadipate ester of propofol;
(2', 6'-Diisopropylphenyl 4-(2-trimethylammoniumethyloxy) phosphonobutyrate);

(2', 6'-Diisopropylphenyl 3-ortho-(O-trimethylammonium ethylphosphonooxy)-1-propionate);
(4-(2,6-diisopropylphenoxy)-4-oxobutanoyl)glycine;
4-(4-(2,6-diisopropylphenoxy)-4-oxobutanamido)butanoic acid
HX0507;
HX0969w;
HX0892;
HX0891;
propofol methoxymethylphosphonic prodrug;
propofol hemiglutarate;
propofol hemiadipate;
monopropofol phosphate;
dipropofol phosphate;
1-((((2,6-diisopropylphenoxy)carbonyloxy)methyl)-3-(dimethylcarbamoyl)pyridinium mesylate;
1-((((2,6-diisopropylphenoxy)carbonyloxy)methyl)-3-(methylcarbamoyl)pyridinium mesylate;
3-carbamoyl-1-(((2,6-diisopropylphenoxy)carbonyloxy)methyl)pyridinium mesylate;
1-(((2,6-diisopropyl phenoxy)carbonyloxy)methyl)-3-(methylcarbamoyl)pyridinium iodide;
1-((((2,6-diisopropylphenoxy)carbonyl)oxy)methyl)-3-(dimethylcarbamoyl)pyridin-1-ium methanesulfonate;
1-((((2,6-diisopropylphenoxy)carbonyl)oxy)methyl)-3-(dimethylcarbamoyl)pyridin-1-ium iodide;
1-((((2,6-diisopropylphenoxy)carbonyl)oxy)methyl)-3-(methoxycarbonyl)pyridin-1-ium iodide;
3-carboxy-1-((((2,6-diisopropylphenoxy)carbonyl)oxy)methyl)pyridin-1-ium iodide;
2-(((2,6-diisopropylphenoxy)carbonyl)oxy)-N,N,N-trimethylethan-1-aminium iodide;
2-(((2,6-diisopropylphenoxy)carbonyl)oxy)-N,N-dimethylethan-1-aminium chloride;
1-((((2,6-diisopropylphenoxy)carbonyl)oxy)methyl)-3-(hydroxycarbamoyl)pyridin-1-ium iodide;
3-(((((2,6-diisopropylphenoxy)carbonyl)oxy)methyl)carbamoyl)-1-methylpyridin-1-ium iodide;
1-(((2,6-diisopropylphenoxy)carbonyl)oxy)-N-((((2,6-diisopropylphenoxy)carbonyl)oxy)methyl)-N,N-dimethylmethanaminiumiodide;
2-(((2,6-diisopropylphenoxy)carbonyl)oxy)-N-((((2,6-diisopropylphenoxy)carbonyl)oxy)methyl)N,N-dimethylethan-1-aminiumiodide;
1-((((2,6-diisopropylphenoxy)carbonyl)oxy)methyl)-4-formyl-3-hydroxy-5-(hydroxymethyl)-2-methylpyridin-1-ium iodide;
3-((2,6-diisopropylphenoxy)carbonyl)-1-((((2,6-diisopropylphenoxy)carbonyl)oxy)methyl)pyridin-1-ium methanesulfonate;
2-(((2,6-diisopropylphenoxy)carbonyl)oxy)-N,N,N-trimethylethan-1-aminium methanesulfonate;
3-carbamoyl-1-((((2,6-diisopropylphenoxy)carbonyl)oxy)methy)pyridin-1-ium bromide;
3-carbamoyl-1-((((2,6-diisopropylphenoxy)carbonyl)oxy)methyl)pyridin-1-ium chloride;
1-((((2,6-diisopropyl phenoxy)carbonyl)oxy)methyl)-3-(methylcarbamoyl)pyridin-1-ium tetrafluoroborate;
1-((((2,6-diisopropyl phenoxy)carbonyl)oxy)methyl)-3-(methylcarbamoyl)pyridin-1-ium nitrate;
1-((((2,6-diisopropylphenoxy)carbonyl)oxy)methyl)-3-(methylcarbamoyl)pyridin-1-ium chloride;
1-((((2,6-diisopropylphenoxy)carbonyl)oxy)methyl)-3-(methoxycarbonyl)pyridin-1-ium methanesulfonate; or
3-carboxy-1-((((2,6-diisopropyl phenoxy)carbonyl)oxy)methyl)pyridin-1-ium methanesulfonate.

10. The method of claim 9, the administration results in an $AUC_{4hr}$ of propofol of no less than 200 ng hr/mL.

11. The method of claim 9, wherein the administration results in an $AUC_{4hr}$ of propofol of no less than 300 ng hr/mL.

12. The method of claim 9, wherein the administration results in an $AUC_{4hr}$ of propofol of no less than 400 ng hr/mL.

13. The method of claim 9, wherein the administration results in an $AUC_{4hr}$ of propofol of no less than 500 ng hr/mL.

14. A method of treating migraine in a patient in need thereof, the method comprising orally administering a propofol prodrug, a pharmaceutically acceptable salt of a propofol prodrug, or mixtures thereof, to the patient in one or more doses, wherein the administration results in a Cmax of fospropofol no less than 2000 ng/mL, and wherein following the administration the patient is headache free, has experienced a reduction in headache pain, or is no longer experiencing a most bothersome symptom, and
    wherein the propofol prodrug is:
        sodium 2-(2-(2,6-diisopropylphenoxy)-2-oxoethoxy)acetate;
        (Azepan-1-ylcarbamoylmethyl)carbamic acid 2,6-diisopropylphenyl ester hydrochloride; (E)-3-(2,6-diisopropylphenoxy)acrylic acid;
        (O-[2-carboxyethyl]-propofol), (S)-2-amino-3-(2,6-diisopropylphenoxycarbonyloxy)-propanoic acid;
        (S)-2-amino-3-(2,6-diisopropylphenoxycarbonyloxy)-propanoic acid mesylate salt; (S)-2-amino-3-(2, 6-diisopropylphenoxycarbonyloxy)-propanoic acid hydrochloride;
        {1-[3-(2, 6-diisopropylphenoxy)-3-oxo-2(R)-fluoro-1-propyl]} phosphate monoesterdipotassium salt;
        {1-[4-(2,6-diisopropylphenoxy)-4-oxo-2(R)-trifluoromethyl-1-butyl]}phosphate monoester dilithium salt;
        {1-[4-(2,6-diisopropylphenoxy)-4-oxo-3-(R)-3-trifluoromethyl-1-butyl]}phosphate monoester dilithium salt;
        {1-[4-(2,6-diisopropylphenoxy)-4-oxo-3-(R,S)-3-fluoro-1-butyl]} phosphate monoesterdipotassium salt;
        {1-[4-(2,6-diisopropylphenoxy)-4-oxo-3-(S)-3-fluoro-1-butyl]} phosphate monoester di sodium salt;
        {1-[6-(2,6-diisopropylphenoxy)-6-oxo-5-(S)-difluoromethyl-1-hexyl]} phosphate di arginine salt;
        1-((((2,6-diisopropyl phenoxy)carbonyl) oxy)methyl)-3-(dimethylcarbamoyl) pyridinium iodide;
        1-((((2,6-diisopropylphenoxy)carbonyl) oxy)methyl)-3-(hydroxycarbamoyl) pyridin-1-ium iodide;
        1-((((2,6-diisopropylphenoxy)carbonyl) oxy)methyl)-3-(methoxycarbonyl)pyridin-1-ium iodide;
        1-((((2,6-diisopropylphenoxy)carbonyl) oxy)methyl)-3-(methoxycarbonyl)pyridin-1-ium methanesulfonate;
        1-((((2,6-diisopropylphenoxy)carbonyl)oxy)methyl)-3-(methylcarbamoyl)pyridin-1-ium tetrafluoroborate;
        1-((((2,6-diisopropylphenoxy)carbonyl)oxy)methyl)-3-(methylcarbamoyl)pyridin-1-ium nitrate;
        1-((((2,6-diisopropylphenoxy)carbonyl)oxy)methyl)-3-(methylcarbamoyl)pyridin-1-ium chloride;

1-((((2,6-diisopropylphenoxy)carbonyl) oxy)methyl)-4-formyl-3-hydroxy-5-(hydroxymethyl)-2-methylpyridin-1-ium iodide;
1-(((2,6-diisopropylphenoxy)carbonyl)oxy)N-((((2,6-diisopropylphenoxy)carbonyl)oxy)methyl)-N,N-dimethyl-methanaminiumiodide;
1-(((2,6-diisopropylphenoxy)carbonyloxy)methyl)-3-(dimethylcarbamoyl)pyridinium mesylate;
1-(((2,6-diisopropylphenoxy)carbonyloxy) methyl)-3-(methylcarbamoyl)pyridinium mesylate;
1-(((2,6-diisopropylphenoxy)carbonyloxy)methyl)-3-(methylcarbamoyl)pyridiniumiodide;
1-((2',6'-diisopropylphenoxy)carbonylamino)ethyl-2,3,4,6-tetra-O-acetyl-β-D-glucopyranoside;
1-((2',6'diisopropylphenoxy) carbonylamino)ethyl-β-D-glucopyranoside;
1-((2',6'diisopropylphenoxy)carbonyloxy)ethyl-2,3,4,6-tetra-O-acetyl-13-D-glucopyranoside;
1-((2',6'diisopropylphenoxy)carbonyloxy)ethyl-2,3,4,6-tetra-O-acetyl-α-D-glucopyranoside;
1-((2',6'diisopropylphenoxy)carbonyloxy)ethyl-hepta-O-acetyl-β-D-maltose;
1-((2',6'diisopropylphenoxy)carbonyloxy)ethyl-α-D-glucopyranoside;
1-((2',6'-diisopropylphenoxy)carbonyloxy)ethyl-β-D-maltose;
1-((2',6'diisopropylphenoxy)carbonyloxy)ethyl-β-n-glucopyranoside;
1-((2',6'diisopropylphenoxy)carbonyloxy)propyl-2,3,4,6-tetra-O-acetyl-β-D-glucopyranoside;
1-((2',6'-diisopropylphenoxy)carbonyloxy)propyl-2,3,4,6-tetra-O-acetyl-α-D-glucopyranoside;
1-((2',6'-diisopropylphenoxy)carbonyloxy)propyl-hepta-O-acetyl-β-D-maltose;
1-((2',6'-diisopropylphenoxy)carbonyloxy)propyl-α-D-glucopyranoside;
1-((2',6'diisopropylphenoxy)carbonyloxy)propyl-β-D-glucopyranoside;
1-((2',6'diisopropylphenoxy)carbonyloxy)propyl-β-D-maltose;
1-Amino-2-[2,6-(diisopropyl)phenoxycarbonyloxy]ethane;
2-[2,6-(Diisopropyl)phenoxycarbonyloxy]ethyl (2S)-2-amino-3-hydroxypropionamide;
2-(((2,6-diisopropylphenoxy)carbonyl) oxy)-N((((2,6-diisopropylphenoxy)carbonyl)oxy)methyl)-N,N-dimethylethan-1-aminiumiodide;
2-(((2,6-diisopropylphenoxy)carbonyl)oxy)-N,N,N-trimethylethan-1-aminium iodide;
2-(((2,6-diisopropyl phenoxy)carbonyl)oxy)-N,N,N-trimethyl ethan-1-aminium methanesulfonate;
2-(2,6-diisopropyl phenoxy)-2-hydroxyethyl phosphate;
2-(2,6-diisopropylphenoxy)-3,4,5-trihydroxy tetrahydropyran-6-yl, dihydrogen phosphate;
2-(2,6-diisopropylphenxoy)-3,4,5-trihydroxytetrahydropyran-6-yl dihydrogen phosphate arginine;
2,6-(diisopropyl)phenyl 1-[((2S)-2-amino-(3R)-3-hydroxybutyryl)aminomethyl]-1-cyclohexane acetate;
2,6-(diisopropyl)phenyl 1-[((2S)-2-amino-3-hydroxypropionyl)aminomethyl]-1-cyclohexane acetate;
2,6-(diisopropyl)phenyl 1-[((2S)-2-amino-3-methylbutyryl)aminomethyl]-1-cyclohexane acetate;
2,6-(diisopropyl)phenyl 4-[(2S)-2,3-diaminopropionylamino]-3,3-dimethylbutanoate;
2,6-(diisopropyl)phenyl 4-[(2S)-2,6-diaminohexanoylamino]-3,3-dimethylbutanoate;
2,6-(Diisopropyl)phenyl 4-[(2S)-2-amino-(3R)-3-hydroxylbutyryl]aminobutanoate;
2,6-(diisopropyl)phenyl 4-[(2S)-2-amino-(3R)-3-hydroxybutyryl]amino-3,3-dimethylbutanoate;
2,6-(diisopropyl)phenyl 4-[(2S)-2-amino-(3R)-3-hydroxylbutyryl]aminobutanoate;
2,6-(diisopropyl)phenyl 4-[(2S)-2-amino-(4-hydroxyphenyl)propionylamino]-3,3-dimethylbutanoate;
2,6-(Diisopropyl)phenyl 4-[(2S)-2-amino-(indol-3-yl)propionylamino]-3,3-dimethylbutanoate;
2,6-(Diisopropyl)phenyl 4-[(2S)-2-amino-3-carbamoylpropionylamino]butanoate;
2,6-(Diisopropyl)phenyl 4-[(2S)-2-amino-3-hydroxypropionylamino]butanoate;
2,6-(diisopropyl)phenyl 4-[(2S)-2-amino-3-carbamoylpropionylamino]-3,3-dimethylbutanoate;
2,6-(diisopropyl)phenyl 4-[(2S)-2-amino-3-carbamoylpropionylamino]butanoate;
2,6-(diisopropyl)phenyl 4-[(2S)-2-amino-3-carboxypropionylamino]-3,3-dimethylbutanoate;
2,6-(diisopropyl)phenyl 4-[(2S)-2-amino-3-hydroxypropionylamino]-3,3-dimethylbutanoate;
2,6-(diisopropyl)phenyl4-[(2S)-2-amino-3-hydroxypropionylamino]butanoate;
2,6-(Diisopropyl)phenyl 4-[(2S)-2-amino-3-hydroxypropionylamino]-3,3-dimethylbutanoate;
2,6-(diisopropyl)phenyl 4-[(2S)-2-amino-3-methylbutyrylamino]-3,3-dimethylbutanoate;
2,6-(diisopropyl)phenyl 4-[(2S)-2-amino-3-methylbutyrylamino]butanoate;
2,6-(diisopropyl)phenyl 4-[(2S)-2-amino-4-carboxybutyrylamino]-3,3-dimethylbutanoate;
2,6-(diisopropyl)phenyl 4-[(2S)-2-amino-4-carboxylbutyrylamino]butanoate;
2,6-(diisopropyl)phenyl 4-[(2S)-2-aminopropionylamino]-3,3-dimethylbutanoate;
2,6-(diisopropyl)phenyl4-[(2S)-pyrrolidin-2-ylcarbonylamino]-3,3-dimethylbutanoate;
2,6-(diisopropyl)phenyl 4-[(2S)-pyrrolidin-2-ylcarbonylamino]butanoate;
2,6-(Diisopropyl)phenyl 4-[(2S)-pyrrolidin-2-ylcarbonylaraino]-3,3-dimethylbutanoate;
2,6-(diisopropyl)phenyl 4-[aminomethylcarbonylamino]-3,3-dimethylbutanoate;
2,6-(Diisopropyl)phenyl 1-[((2S)-2-amino-(3R)-3-hydroxybutyryl)aminomethyl]-1-cyclohexane acetate;
2,6-(Diisopropyl)phenyl 1-[((2S)-2-amino-3-hydroxypropionyl)aminomethyl] 1-cyclohexane acetate;
2,6-(Diisopropyl)phenyl 1-[((2S)-2-amino-3-methylbutyryl)aminomethyl]-1-cyclohexane acetate;
2,6-diisopropylphenyl 4-((2-(2-methylpyrazolidin-1-yl)ethyl)amino)-4-oxobutanoate;
2,6-diisopropylphenyl 4-((2-(4,5-dihydro-1H-pyrazol-1-yl)ethyl)amino)-4-oxobutanoate;
2,6-diisopropylphenyl 4-((2-(4-ethylpiperazin-1-yl)ethyl)amino)-4-oxobutanoate;
2,6-diisopropylphenyl 4-((2-(4-methylpiperazin-1-yl)ethyl)amino)-4-oxobutanoate; 2,6-diisopropylphenyl4-((2-morpholinoethyl)amino)-4-oxobutanoate;
2,6-Diisopropylphenyl 4-(2-(TertButoxycarbonylamino) Propanoyloxy)Butanoate;
2,6-Diisopropylphenyl4-(2-Aminoacetoxy) Butanoate Trifluoroacetic Acid Salt;
2,6-Diisopropylphenyl 4-(2-Aminopropanoyloxy)Butanoate Hydrochloride;
2,6-Diisopropyl phenyl 4-Hydroxybutanoate;

2,6-diisopropyl phenyl 4-oxo-4-((2-(piperazin-1-yl)ethyl)amino)butanoate;
2,6-diisopropyl phenyl 4-oxo-4-((2-(piperidin-1-yl)ethyl)amino)butanoate;
2,6-diisopropyl phenyl 4-oxo-4-((2-(pyrazolidin-1-yl)ethyl)amino)butanoate;
2,6-diisopropylphenyl 4-oxo-4-((2-(pyrrolidin-1-yl)ethyl)amino)butanoate;
2,6-diisopropylphenyl 4-oxo-4-((2-thiomorpholino-ethyl)amino)butanoate;
2-[2,6-(diisopropyl)phenoxycarbonylamino]ethyl (2S)-2-amino-3-carboxypropionamide;
2-[2,6-(diisopropyl)phenoxycarbonylamino]ethyl (2S)-2-amino-3-hydroxypropionamide;
2-[2,6-(diisopropyl)phenoxycarbonylamino]ethyl (2S)-2-amino-3-methylbutanoylamide;
2-[2,6-(diisopropyl)phenoxycarbonyloxy]ethyl (2S)-2,6-diaminohexanoylamide;
2-[2,6-(diisopropyl)phenoxycarbonyloxy]ethyl (2S)-2-amino-(4-hydroxyphenyl)propionamide;
2-[2,6-(Diisopropyl)phenoxycarbonyloxy]ethyl (2S)-2-amino(4-hydroxyphenyl)propionamide;
2-[2,6-(diisopropyl)phenoxycarbonyloxy]ethyl (2S)-2-amino-3-carbamoylpropionate;
2-[2,6-(diisopropyl)phenoxycarbonyloxy]ethyl (2S)-2-amino-3-carbamoylpropionamide;
2-[2,6-(Diisopropyl)phenoxycarbonyloxy]ethanol;
1-Amino-2-[2,6-(diisopropyl)phenoxycarbonyloxy]ethane;
2-[2,6-(diisopropyl)phenoxycarbonyloxy]ethyl (2S)-2-amino-3-hydroxypropionate;
2-[2,6-(diisopropyl)phenoxycarbonyloxy]ethyl (2S)-2-amino-3-hydroxypropionamide;
2-[2,6-(diisopropyl)phenoxycarbonyloxy]ethyl glycinamide;
2-amino-3-(2,6-diisopropylphenoxycarbonyloxy)-propanoic acid mesylate;
2-amino-3-methyl-3-(2,6-diisopropyl-phenoxycarbonyloxy)-propanoic acid;
3-(((((2,6-diisopropylphenoxy)carbonyl)oxy)methyl)carbamoyl)-1-methylpyridin-1-ium iodide;
3-((2,6-diisopropylphenoxy)carbonyl)-1-((((2,6-diisopropyl phenoxy)carbonyl)oxy) methyl)pyridin-1-ium methanesulfonate;
3-{[2-[2,6-Bis(isopropyl)phenoxycarbonyl]-benzoyl]amino}propanoic acid;
3-{[2-[2,6-Bis(isopropyl)phenoxycarbonyloxy]-benzoyl]amino}-propanoic acid;
3-carbamoyl-1-((((2,6-diisopropyl-phenoxy)carbonyl)oxy)methyl)pyridin-1-ium iodide;
3-carbamoyl-1-(((2,6-diisopropylphenoxy)carbonyloxy)methyl)pyridinium mesylate;
3-carboxy-1-((((2,6-diisopropylphenoxy)carbonyl)oxy)methyl)pyridin-1-ium iodide;
3-carboxy-1-((((2,6-diisopropylphenoxy) carbonyl) oxy)methyl)pyridin-1-ium methanesulfonate;
4-[(2S)-2-amino-(3R)-3-hydroxybutyryl]amino-3,3-dimethylbutanoate;
4-[(2S)-2-amino-3-carbamoylpropionylamino]-3,3-dimethylbutanoate;
4-[(2S)-2-amino-4-carboxybutyrylamino]-3,3-dimethylbutanoate;
4-[(2S)-2-aminopropionylamino]-3,3-dimethylbutanoate;
2,6-(Diisopropyl)phenyl;
4-[aminomethylcarbonylamino]-3,3-dimethylbutanoate;
2,6-(Diisopropyl)phenyl;
arginine2-(2,6-diisopropylphenoxy)-2-hydroxyethylphosphate;
arginine2-(2,6-diisopropylphenoxy)-3,4,5-trihydroxytetrahydropyran-6-yl dihydrogen phosphate;
Boc-Asp(OPropofol)-OBzl; Boc-Asp(OPropofol)-OH;
Boc-Glu(OPropofol)-OBzl;
Boe-Glu(OPropofol)-OH;
di[propofol 5-carboxyl-2(S)-fluorohexanoate] zinc salt;
di[propofol 5-carboxyl-2-(S)-fluorohexanoate] zinc salt;
di[propofol 7-carboxyl-2(R,S)-fluorocaprylate] calcium salt;
di[propofol 7-carboxyl-2-(R,S)fluorocaprylate] calcium salt;
disodium lauryl-imino-dipropionate2-(2,6-diisopropylphenoxy) tetrahydropyran-6-yl dihydrogen phosphate;
disodium lauryl-iminodipropionate-2-(2,6-diisopropyl phenoxy) tetrahydropyran-6-yl dihydrogen phosphate;
H-Abu-Asp(OPropofol)-OH;
H-Abu-Thr(γ-OC(O)OPropofol)-OH Hydrochloride;
H-Aib-OCH$_2$OPropofol;
H-Ala-Asn-OPropofol;
H-Ala-Asp(OCH$_2$OPropofol)-OH;
H-AlaAsp(OPropofol)-OH;
H-Ala-Cys(β-SC(O)OPropofol)-OH;
H-Ala-Glu(OPropofol)-OH;
H-Ala-OPropofol Hydrochloride;
H-Ala-Phe-OPropofol;
H-Ala-Ser(β-OC(O)OPropofol)-OH;
H-Ala-Thr(β-OC(O)OPropofol)-OH;
H-Ala-Thr(γ-OC(O)OPropofol)-OH Hydrochloride;
H-Ala-Tyr-OPropofol;
H-Arg-Asp(OPropofol)-OH;
H-Arg-Phe-OPropofol;
H-Arg-Thr(γ-OC(O)OPropofol)-OH Tris-Hydrochloride;
H-Asn-Asp(OCH$_2$OPropofol)-OH;
H-Asn-Asp(OPropofol)-OH;
H-Asn-D-Thr(γ-OC(O)OPropofol)-OH;
H-Asn-Glu(OPropofol)-OH;
H-Asn-OPropofol Hydrochloride;
H-Asn-Thr(β-OC(O)OPropofol)-OH;
H-Asn-Thr(γ-OC(O)OPropofol)-OH Hydrochloride;
H-Asn-Tyr-OPropofol;
H-Asp(OCH$_2$OPropofol)-ArgOH;
H-Asp(OCH$_2$OPropofol)-Asp-OH;
H-Asp(OCH$_2$OPropofol)-Lys-OH;
H-Asp(OCH$_2$OPropofol)-OH;
H-Asp(OCH$_2$OPropofol)-Ser-OH;
H-Asp(OPropofol)-Ala-OH;
H-Asp(OPropofol)-Asp-OH;
H-Asp(OPropofol)-Gln-OH;
H-Asp(OPropofol)-Glu-OH;
H-Asp(OPropofol)-Gly-OH;
H-Asp(OPropofol)-Ile-OH;
H-Asp(OPropofol)-Leu-OH;
H-Asp(OPropofol)-Met-OH;
H-Asp(OPropofol)-OBzl;
H-Asp(OPropofol)-OH;
H-Asp(OPropofol)-O-Trityl;
H-Asp(OPropofol)-Phe-OH;
H-Asp(OPropofol)-Pro-OH;
HAsp(OPropofol)-Ser-OH;
H-Asp(OPropofol)-Val-OH;

H-Asp-Ala-OPropofol;
H-Asp-AsnOPropofol;
H-Asp-Asp(OCH$_2$OPropofol)-OH;
H-Asp-Asp(OPropofol)-OH;
H-AspOCH$_2$OPropofol;
H-Asp-Phe-OPropofol;
H-Asp-Ser(β-OC(O)OPropofol)-OH;
H-Asp-TyrOPropofol;
H-Cys-Asp(OPropofol)-OH;
H-Dap(β-NHC(O)OPropofol)-Ala-OH;
H-Dap-Ala-OPropofol;
H-Dap-Asn-OPropofol;
H-Dap-Thr(γ-OC(O)OPropofol)-OH Bis-Hydrochloride;
H-Dap-Tyr-OPropofol;
H-D-Asn-Thr(γ-OC(O)OPropofol)-OH;
H-D-LysThr(γ-OC(O)OPropofol)-OH Bis-Hydrochloride;
H-D-Ser-Thr(γ-OC(O)OPropofol-OH Hydrochloride;
H-Gln-Asn-OPropofol;
H-Gln-Asp(OCH$_2$OPropofol)-OH;
H-Gln-OPropofol Hydrochloride;
H-Gln-Phe-OPropofol;
H-Glu(OPropofol)-Ala-OH;
H-Glu(OPropofol)-ArgOH;
H-Glu(OPropofol)-Asp-OH;
H-Glu(OPropofol)-Gln-OH;
H-Glu(OPropofol)-Glu-OH;
H-Glu(OPropofol)-Gly-OH;
H-Glu(OPropofol)-Ile-OH;
H-Glu(OPropofol)-Leu-OH;
H-Glu(OPropofol)-Lys-OH;
H-Glu(OPropofol)-Met-OH;
H-Glu(OPropofol)-OBzl;
H-Glu(OPropofol)-OH;
H-Glu(OPropofol)-Phe-OH;
H-Glu(OPropofol)-Ser-OH;
H-Glu(OPropofol)-Val-OH;
H-Glu-Asp(OCH$_2$OPropofol)-OH;
H-Glu-Phe-OPropofol;
H-GluTyr-OPropofol;
H-Gly-Asn-OPropofol;
H-Gly-Asp(OCH$_2$OPropofol)-OH;
H-Gly-OPropofol Hydrochloride;
H-Gly-Phe-OPropofol;
H-Gly-Thr(γ-OC(O)OPropofol)-OH;
H-Gly-TyrOPropofol;
H-His-Asp(OCH$_2$OPropofol)-OH;
H-His-OPropofol;
H-His-Phe-OPropofol;
H-His-Thr(γ-OC(O)OPropofol)-OH Bis-Hydrochloride;
H-Leu-Asp(OPropofol)-OH;
H-Leu-D-Thr(γ-OC(O)OPropofol)-OH;
H-Leu-Glu(OPropofol)-OH;
H-Leu-Thr(γ-OC(O)OPropofol)OH Hydrochloride;
H-Lys-Asp(OPropofol)-OH;
H-Lys-Cys(β-SC(O)OPropofol)-OH;
H-Lys-Glu(OPropofol)-OH;
H-Lys-OPropofol Hydrochloride;
H-Lys-Ser(β-OC(O)OPropofol)-OH;
H-Lys-Thr(β-OC(O)OPropofol)-OH;
H-Lys-Thr(γ OC(O)OPropofol)-OH Bis-Hydrochloride;
H-Lys-Tyr-OPropofol;
H-Met-Asp(OPropofol)OH;
H-Met-OPropofol;
H-Met-Thr(γ-OC(O)OPropofol)-OH Hydrochloride;
H-NVal-Asp(OPropofol)-OH;
H-Orn-Asp(OPropofol)-OH;
H-Orn-Thr(γ-OC(O)OPropofol)-OH BisHydrochloride;
H-Phe-Asp(OPropofol)-OH;
H-Phe-OPropofol;
H-Pro-OPropofol Hydrochloride;
H-Pro-Phe-OPropofol;
H-Pro-Thr(γ-OC(O)OPropofol)-OH Hydrochloride;
H-Pro-Tyr-OPropofol;
H-Sar-Asp(OPropofol)-OH;
H-Ser-Asn-OPropofol;
H-SerAsp(OCH$_2$OPropofol)-OH;
H-Ser-Cys(β-SC(O)OPropofol)-OH;
H-Ser-D-Thr(γOC(O)OPropofol)-OH;
H-Ser-OPropofol;
H-Ser-Phe-OPropofol;
H-Ser-Ser(β-OC(O)OPropofol)-OH;
H-Ser-Thr(β-OC(O)OPropofol)-OH;
H-Ser-Thr(γ-OC(O)OPropofol)-OH Hydrochloride
H-Ser-Tyr-OPropofol;
H-ThrAsp(OCH$_2$OPropofol)-OH;
H-Thr-OPropofol Hydrochloride;
H-Thr-Phe-OPropofol;
H-Trp-Asp(OCH$_2$OPropofol)-OH;
H-Trp-Phe-OPropofol;
H-Tyr-Asn-OPropofol;
H-TyrAsp(OCH$_2$OPropofol)-OH;
H-Tyr-Asp(OPropofol)-OH;
H-Tyr-OPropofol Hydrochloride;
H-Tyr-Phe-OPropofol;
H-Tyr-Ser(β-OC(O)OPropofol)-OH;
H-Val-Ala-OPropofol;
H-Val-Asn-OPropofol;
H-Val-OCH$_2$OPropofol;
H-Val-OPropofol;
H-Val-Phe-OPropofol;
H-Val-Ser-OPropofol;
H-Val-Thr(β-OC(O)OPropofol)-OH;
H-Val-Thr(γ-OC(O)OPropofol)-OH Hydrochloride;
H-Val-Tyr-OPropofol;
2,6-(Diisopropyl)phenyl hydroxybutyrate disodiumphosphate;
2,6-(Diisopropyl)phenyl hydroxyvaleratephosphate disodium salt;
H-[3-Ala-Asp(OPropofol)-OH;
H-[3-Ala-Thr(γ-OC(O)OPropofol)-OH Hydrochloride;
1-Amino-2-[2,6-(diisopropyl)phenoxycarbonyloxy]ethane;
N-(2-Dibutylaminoethyl)-succinamic acid 2,6-diisopropyl-phenyl ester;
N-(2-Dibutylaminoethyl)-succinamic acid 2,6-diisopropyl-phenyl ester hydrochloride;
N-(2-Diethylamino-ethyl)-succinamic acid 2,6-diisopropyl-phenyl ester Hydrochloride;
N-(2-Diethylammoethyl)-succinamic acid 2,6-diisopropylphenyl ester;
N-(2-Diisopropylaminoethyl)-succinamic acid 2,6-diisopropyl-phenyl ester;
N-(2-Diisopropylamino-ethyl)-succinamic acid 2,6-diisopropyl phenyl ester Hydrochloride;
N-(2-Dimethylamino-ethyl)-succinamic acid 2,6-diisopropyl-phenyl ester Hydrochloride;
N-(2-Dimethylaminoethyl)-succinamic acid 2,6-diisopropyl-phenyl ester;

N-(2-Morpholin-4-ylethyl)-succinamic acid 2,6-diisopropylphenyl ester;
N-(2-Morpholin-4-yl-ethyl)-succinamic acid 2,6-diisopropylphenyl ester Hydrochloride;
N-(2-Piperidin-1-yl-ethyl)-succinamic acid 2,6-diisopropylphenyl ester;
N-(2-Piperidin-1-yl-ethyl)-succinamic acid 2,6-diisopropylphenyl ester hydrochloride;
N-(2-Pyrrolidin-1-yl-ethyl)-succinamic acid 2,6-diisopropylphenyl ester;
N-(2-Pyrrolidin-1-yl-ethyl)-succinamic acid 2,6-diisopropylphenyl ester hydrochloride;
O-[t-butoxycarbonyl]-propofol);
propofol 2-carboxyl-2(S)-fluoropropionate sodium salt;
propofol 3-(N,N-diethyl)amino-2-(R,S)-fluoropropionate hydrochloride;
propofol 3-(N-isopropyl)amino-2-(R,S)-2-monofluoromethylpropionate methanesulfonate;
propofol 3-(N-isopropyl)amino-2(R,S)-2-monofluoromethyl propionate methanesulfonate;
propofol 3-(pyrrolidin-1-yl)-2-(S)-trifluoromethyl propionate hydrochloride;
propofol 3-(pyrrolidin-1-yl)-2(S)-trifluoromethylpropionate hydrochloride;
propofol 3-carboxyl-2(R)-fluorobutyrate sodium salt;
propofol 3-N-isopropylamino-2-(R,S)-fluoropropionate hydrochloride;
propofol 3-N-methyl-N-cyclohexylamino-2-(R,S)fluoropropionate hydrochloride;
propofol 3-N-methyl-N-cyclohexylamino-2-(R,S)fluoropropionate hydrochloride;
propofol 3-phosphoryl-2-(R,S)-fluoropropionate zinc salt;
propofol 4-(aziridin-1-yl)-2-(S)-2-fluorobutyratehydrochloride;
propofol 4-(N,Ndimethyl)amino-2-(R)-2-trifluoromethylbutyrate hydrochloride;
propofol 4-(N,Ndimethyl)amino-2-(R)-fluorobutyrate hydrochloride;
propofol 4-(N,N-dimethyl)amino-2-(R)trifluoromethylbutyrate hydrochloride;
propofol 4-(N,N-dimethyl)amino-2-(R,S)fluorobutyrate hydrochloride;
propofol 4-(N-cyclopropyl-N-methyl)amino-2-(R)difluoromethylbutyratehydrochloride;
propofol 4-(N-methyl-N-benzyl)amino-2-(R,S)trifluoromethylbutyrate hydrochloride;
propofol 4-(N-methyl-N-ethyl)amino-2-(R,S)-2-fluorobutyratehydrochloride
propofol 4-(N-methyl-N-isopropyl)amino-2-(R,S)fluorobutyrate methanesulfonate;
propofol 4-(pyrrolidin-1-yl)-2-(R)-2-fluorobutyrate hydrochloride;
propofol 4-carboxyl-2-(R)-2-trifluoromethylvalerate lithium salt;
propofol 4-carboxyl-2(R)-fluorobutyrate sodium salt;
propofol 4-carboxyl-2-(R,S)difluoromethylvalerate potassium salt;
propofol 4-carboxyl-2(R,S)-fluorovalerate sodium salt;
propofol 4-carboxyl-2-(S)-fluorovalerate potassium salt;
propofol 4-carboxyl-2-(S)fluorovalerate potassium salt;
propofol 4-carboxyl-2-(S)-trifluoromethylbutyrate ammonium salt;
propofol 4-N-(aziridin-1-yl)-2(S)-2-fluorobutyrate hydrochloride;
propofol 4-N-methyl-N-benzylamino-2-(R)-fluorobutyrate hydrochloride;
propofol 4-phosphoryl-2-(R)fluorobutyrate disodium salt;
propofol 4-phosphoryl-2-(R,S)-fluorobutyrate calcium salt;
propofol 5-(N-methyl-N-benzyl)amino-2-(S)-2-fluorovalerate hydrochloride;
propofol 5-carboxyl-2-(R,S)-difluoromethylvalerate potassium salt;
propofol 5-N-cyclopentylamino-2,2-difluorovalerate hydrochloride;
propofol 5-phosphoryl-2-(S)-fluorovalerate zinc salt;
propofol 6-(N,N-dimethyl)amino-2(R)-fluorovalerate hydrochloride;
Propofol Hemisuccinate;
propofol hydroxybutyrate;
propofol hydroxyvalerate;
propofol 8-(N,Ndimethyl)amino-2-(R)-fluorovaleratehydrochloride;
propofol-2-(R)-fluoropropionate monoester sodium salt;
propofol-2-(R,S)-fluorobutyratemonoester sodium salt;
propofol-2-(R,S)-fluoropentanoate monoester sodium salt;
(S)-2-amino-3-(2,6-diisopropylphenoxycarbonyloxy)-propanoic acid mesylate;
Sodium 4-(2,6-Diisopropyl phenoxy)-4-oxobuty 1 Phosphate;
2-(2,6-diisopropyl phenoxy)-tetrahydropyran-6-yl dihydrogen phosphate arginine;
tri[propofol 3-phosphoryl-2-(R,S)-2-monofluoromethylpropionate] dialuminum salt;
tri[propofol 8-carboxyl-2-(R,S)monofluoromethylpelargonate]aluminum salt; Succinic Acid Mono-Propofol Ester;
BOC-protected 1-deoxy-1-hydrazinoglucitol;
2-amino-3-methyl-3-(2,6-diisopropyl-phenoxycarbonyloxy)-propanoic acid;
2-amino-3-(2,6-diisopropylphenoxycarbonyloxy)-propanoic acid;
1-(2,6-diisopropyl phenoxy)ethyl dihydrogen phosphate;
Mono(propofol) phosphate;
Di(propofol) phosphate;
Carboxylic hemiesters of propofol;
hemisuccinate ester of propofol;
hemiglutarate ester of propofol;
hemiadipate ester of propofol;
(2', 6'-Diisopropylphenyl 4-(2-trimethylammoniumethyloxy) phosphonobutyrate);
(2',6'-Diisopropylphenyl3-ortho-(O-trimethylammonium ethylphosphonooxy)-1-propionate);
(4-(2,6-diisopropylphenoxy)-4-oxobutanoyl)glycine;
4-(4-(2,6-diisopropylphenoxy)-4-oxobutanamido)butanoic acid
HX0507;
HX0969w;
HX0892;
HX0891;
propofol methoxymethylphosphonic prodrug;
propofol hemiglutarate;
propofol hemiadipate;
monopropofol phosphate;
dipropofol phosphate;

1-(((2,6-diisopropylphenoxy)carbonyloxy)methyl)-3-(dimethylcarbamoyl)pyridinium mesylate;
1-(((2,6-diisopropylphenoxy)carbonyloxy)methyl)-3-(methylcarbamoyl)pyridinium mesylate;
3-carbamoyl-1-(((2,6-diisopropylphenoxy)carbonyloxy)methyl)pyridinium mesylate;
1-(((2,6-diisopropyl phenoxy)carbonyloxy)methyl)-3-(methylcarbamoyl)pyridinium iodide;
1-((((2,6-diisopropylphenoxy)carbonyl)oxy)methyl)-3-(dimethylcarbamoyl)pyridin-1-ium methanesulfonate;
1-((((2,6-diisopropylphenoxy)carbonyl)oxy)methyl)-3-(dimethylcarbamoyl)pyridin-1-ium iodide;
1-((((2,6-diisopropylphenoxy)carbonyl)oxy)methyl)-3-(methoxycarbonyl)pyridin-1-ium iodide;
3-carboxy-1-((((2,6-diisopropylphenoxy)carbonyl)oxy)methyl)pyridin-1-ium iodide;
2-(((2,6-diisopropylphenoxy)carbonyl)oxy)-N,N,N-trimethylethan-1-aminium iodide;
2-(((2,6-diisopropylphenoxy)carbonyl)oxy)-N,N-dimethylethan-1-aminium chloride;
1-((((2,6-diisopropylphenoxy)carbonyl)oxy)methyl)-3-(hydroxycarbamoyl)pyridin-1-ium iodide;
3-(((((2,6-diisopropylphenoxy)carbonyl)oxy)methyl)carbamoyl)-1-methylpyridin-1-ium iodide;
1-(((2,6-diisopropylphenoxy)carbonyl)oxy)-N-((((2,6-diisopropylphenoxy)carbonyl)oxy)methyl)-N,N-dimethylmethanaminiumiodide;
2-(((2,6-diisopropylphenoxy)carbonyl)oxy)-N-((((2,6-diisopropylphenoxy)carbonyl)oxy)methyl)N,N-dimethylethan-1-aminiumiodide;
1-((((2,6-diisopropylphenoxy)carbonyl)oxy)methyl)-4-formyl-3-hydroxy-5-(hydroxymethyl)-2-methylpyridin-1-ium iodide;
3-((2,6-diisopropylphenoxy)carbonyl)-1-((((2,6-diisopropylphenoxy)carbonyl)oxy)methyl)pyridin-1-ium methanesulfonate;
2-(((2,6-diisopropylphenoxy)carbonyl)oxy)-N,N,N-trimethylethan-1-aminium methanesulfonate;
3-carbamoyl-1-(((((2,6-diisopropylphenoxy)carbonyl)oxy)methy)pyridin-1-ium bromide;
3-carbamoyl-1-(((((2,6-diisopropylphenoxy)carbonyl)oxy)methyl)pyridin-1-ium chloride;
1-(((((2,6-diisopropyl phenoxy)carbonyl)oxy)methyl)-3-(methylcarbamoyl)pyridin-1-ium tetrafluoroborate;
1-(((((2,6-diisopropyl phenoxy)carbonyl)oxy)methyl)-3-(methylcarbamoyl)pyridin-1-ium nitrate;
1-(((((2,6-diisopropylphenoxy)carbonyl)oxy)methyl)-3-(methylcarbamoyl)pyridin-1-ium chloride;
1-(((((2,6-diisopropylphenoxy)carbonyl)oxy)methyl)-3-(methoxycarbonyl)pyridin-1-ium methanesulfonate; or
3-carboxy-1-(((((2,6-diisopropyl phenoxy)carbonyl)oxy)methyl)pyridin-1-ium methanesulfonate.

15. The method of claim 14, wherein the administration results in a Cmax of fospropofol no less than 3000 ng/mL.

16. The method of claim 14, wherein the administration results in a Cmax of fospropofol no less than 4000 ng/mL.

17. The method of claim 14, wherein the administration results in a Cmax of fospropofol no less than 5000 ng/mL.

18. A method of treating migraine in a patient in need thereof, the method comprising orally administering a propofol prodrug, a pharmaceutically acceptable salt of a propofol prodrug, or mixtures thereof, to the patient in one or more doses, wherein the administration results in a $AUC_{4hr}$ of fospropofol of no less than 1000 ng hr/mL, and wherein following the administration the patient is headache free, has experienced a reduction in headache pain, or is no longer experiencing a most bothersome symptom, and
wherein the propofol prodrug is:
sodium 2-(2-(2,6-diisopropylphenoxy)-2-oxoethoxy)acetate;
(Azepan-1-ylcarbamoylmethyl)carbamic acid 2,6-diisopropylphenyl ester hydrochloride; (E)-3-(2,6-diisopropylphenoxy)acrylic acid;
(O-[2-carboxyethyl]-propofol), (S)-2-amino-3-(2,6-diisopropylphenoxycarbonyloxy)-propanoic acid;
(S)-2-amino-3-(2,6-diisopropylphenoxycarbonyloxy)-propanoic acid mesylate salt; (S)-2-amino-3-(2, 6-diisopropylphenoxycarbonyloxy)-propanoic acid hydrochloride;
{1-[3-(2, 6-diisopropylphenoxy)-3-oxo-2(R)-fluoro-1-propyl]} phosphate monoesterdipotassium salt;
{1-[4-(2,6-diisopropylphenoxy)-4-oxo-2(R)-trifluoromethyl-1-butyl]} phosphate monoester dilithium salt;
{1-[4-(2,6-diisopropylphenoxy)-4-oxo-3-(R)-3-trifluoromethyl-1-butyl]}phosphate monoester dilithium salt; {1-[4-(2,6-diisopropylphenoxy)-4-oxo-3-(R,S)-3-fluoro-1-butyl]}phosphate monoesterdipotassium salt; {1-[4-(2,6-diisopropylphenoxy)-4-oxo-3-(S)-3-fluoro-1-butyl]} phosphate monoester di sodium salt;
{1-[6-(2,6-diisopropylphenoxy)-6-oxo-5-(S)-difluoromethyl-1-hexyl]} phosphate di arginine salt;
1-(((((2,6-diisopropyl phenoxy)carbonyl) oxy)methyl)-3-(dimethylcarbamoyl) pyridinium iodide;
1-(((((2,6-diisopropylphenoxy)carbonyl) oxy)methyl)-3-(hydroxycarbamoyl) pyridin-1-ium iodide;
1-(((((2,6-diisopropylphenoxy)carbonyl) oxy)methyl)-3-(methoxycarbonyl)pyridin-1-ium iodide;
1-(((((2,6-diisopropylphenoxy)carbonyl) oxy)methyl)-3-(methoxycarbonyl)pyridin-1-ium methanesulfonate;
1-(((((2,6-diisopropylphenoxy)carbonyl)oxy)methyl)-3-(methylcarbamoyl)pyridin-1-ium tetrafluoroborate;
1-(((((2,6-diisopropylphenoxy)carbonyl)oxy)methyl)-3-(methylcarbamoyl)pyridin-1-ium nitrate;
1-(((((2,6-diisopropylphenoxy)carbonyl)oxy)methyl)-3-(methylcarbamoyl)pyridin-1-ium chloride;
1-(((((2,6-diisopropylphenoxy)carbonyl)oxy)methyl)-4-formyl-3-hydroxy-5-(hydroxymethyl)-2-methylpyridin-1-ium iodide;
1-(((2,6-diisopropylphenoxy)carbonyl)oxy)N-((((2,6-diisopropylphenoxy)carbonyl)oxy)methyl)-N,N-dimethyl-methanaminiumiodide;
1-(((2,6-diisopropylphenoxy)carbonyloxy)methyl)-3-(dimethylcarbamoyl)pyridinium mesylate;
1-(((2,6-diisopropylphenoxy)carbonyloxy) methyl)-3-(methylcarbamoyl)pyridinium mesylate;
1-(((2,6-diisopropylphenoxy)carbonyloxy)methyl)-3-(methylcarbamoyl)pyridiniumiodide;
1-((2',6'-diisopropylphenoxy)carbonylamino)ethyl-2,3,4,6-tetra-O-acetyl-β-D-glucopyrano side;
1-((2',6'diisopropylphenoxy) carbonylamino)ethyl-β-D-glucopyranoside;
1-((2',6'diisopropylphenoxy)carbonyloxy)ethyl-2,3,4,6-tetra-O-acetyl-β-D-glucopyranoside;
1-((2',6'diisopropylphenoxy)carbonyloxy)ethyl-2,3,4,6-tetra-O-acetyl-α-D-glucopyranoside;
1-((2',6'diisopropylphenoxy)carbonyloxy)ethyl-hepta-O-acetyl-β-D-maltose;

1-((2',6'diisopropylphenoxy)carbonyloxy)ethyl-α-D-glucopyranoside;
1-((2',6'-diisopropylphenoxy)carbonyloxy)ethyl-β-D-maltose;
1-((2',6'diisopropylphenoxy)carbonyloxy)ethyl-β-n-glucopyranoside;
1-((2',6'diisopropylphenoxy)carbonyloxy)propyl-2,3,4,6-tetra-O-acetyl-β-D-glucopyranoside;
1-((2',6'-diisopropylphenoxy)carbonyloxy)propyl-2,3,4,6-tetra-O-acetyl-α-D-glucopyranoside;
1-((2',6'-diisopropylphenoxy)carbonyloxy)propyl-hepta-O-acetyl-β-D-maltose;
1-((2',6'-diisopropylphenoxy)carbonyloxy)propyl-α-D-glucopyranoside;
1-((2',6'diisopropylphenoxy)carbonyloxy)propyl-β-D-glucopyranoside;
1-((2',6'diisopropylphenoxy)carbonyloxy)propyl-β-D-maltose;
1-Amino-2-[2,6-(diisopropyl)phenoxycarbonyloxy]ethane;
2-[2,6-(Diisopropyl)phenoxycarbonyloxy]ethyl (2S)-2-amino-3-hydroxypropionamide;
2-(((2,6-diisopropylphenoxy)carbonyl) oxy)-N((((2,6-diisopropylphenoxy)carbonyl)oxy)methyl)-N,N-dimethylethan-1-aminiumiodide;
2-(((2,6-diisopropylphenoxy)carbonyl)oxy)-N,N,N-trimethylethan-1-aminium iodide;
2-(((2,6-diisopropyl phenoxy)carbonyl)oxy)-N,N,N-trimethyl ethan-1-aminium methanesulfonate;
2-(2,6-diisopropyl phenoxy)-2-hydroxyethyl phosphate;
2-(2,6-diisopropylphenoxy)-3,4,5-trihydroxy tetrahydropyran-6-yl, dihydrogen phosphate;
2-(2,6-diisopropylphenoxy)-3,4,5-trihydroxytetrahydropyran-6-yl dihydrogen phosphate arginine;
2,6-(diisopropyl)phenyl 1-[((2S)-2-amino-(3R)-3-hydroxybutyryl)aminomethyl]-1-cyclohexane acetate;
2,6-(diisopropyl)phenyl 1-[((2S)-2-amino-3-hydroxypropionyl)aminomethyl]-1-cyclohexane acetate;
2,6-(diisopropyl)phenyl 1-[((2S)-2-amino-3-methylbutyryl)aminomethyl]-1-cyclohexane acetate;
2,6-(diisopropyl)phenyl 4-[(2S)-2,3-diaminopropionylamino]-3,3-dimethylbutanoate;
2,6-(diisopropyl)phenyl 4-[(2S)-2,6-diaminohexanoylamino]-3,3-dimethylbutanoate;
2,6-(Diisopropyl)phenyl 4-[(2S)-2-amino-(3R)-3-hydroxylbutyryl]aminobutanoate;
2,6-(diisopropyl)phenyl 4-[(2S)-2-amino-(3R)-3-hydroxybutyryl]amino-3,3-dimethylbutanoate;
2,6-(diisopropyl)phenyl 4-[(2S)-2-amino-(3R)-3-hydroxylbutryl]aminobutanoate;
2,6-(diisopropyl)phenyl 4-[(2S)-2-amino-(4-hydroxyphenyl)propionylamino]-3,3-dimethylbutanoate;
2,6-(Diisopropyl)phenyl 4-[(2S)-2-amino-(indol-3-yl)propionylamino]-3,3-dimethylbutanoate;
2,6-(Diisopropyl)phenyl 4-[(2S)-2-amino-3-carbamoylpropionylamino]butanoate;
2,6-(Diisopropyl)phenyl 4-[(2S)-2-amino-3-hydroxypropionylamino]butanoate;
2,6-(diisopropyl)phenyl 4-[(2S)-2-amino-3-carbamoyl-propionylamino]-3,3-dimethylbutanoate;
2,6-(diisopropyl)phenyl 4-[(2S)-2-amino-3-carbamoyl-propionylamino]butanoate;
2,6-(diisopropyl)phenyl 4-[(2S)-2-amino-3-carboxy-propionylamino]-3,3-dimethylbutanoate;
2,6-(diisopropyl)phenyl 4-[(2S)-2-amino-3-hydroxy-propionylamino]-3,3-dimethylbutanoate;
2,6-(diisopropyl)phenyl4-[(2S)-2-amino-3-hydroxy-propionylamino]butanoate;
2,6-(Diisopropyl)phenyl 4-[(2S)-2-amino-3-hydroxy-propionylamino]-3,3-dimethylbutanoate;
2,6-(diisopropyl)phenyl 4-[(2S)-2-amino-3-methylbutyrylamino]-3,3-dimethylbutanoate;
2,6-(diisopropyl)phenyl 4-[(2S)-2-amino-3-methylbutyrylamino]butanoate;
2,6-(diisopropyl)phenyl 4-[(2S)-2-amino-4-carboxybutyrylamino]-3,3-dimethylbutanoate;
2,6-(diisopropyl)phenyl 4-[(2S)-2-amino-4-carboxyl-butyrylamino]butanoate;
2,6-(diisopropyl)phenyl 4-[(2S)-2-aminopropionylamino]-3,3-dimethylbutanoate;
2,6-(diisopropyl)phenyl4-[(2S)-pyrrolidin-2-ylcarbonylamino]-3,3-dimethylbutanoate;
2,6-(diisopropyl)phenyl 4-[(2S)-pyrrolidin-2-ylcarbonylamino]butanoate;
2,6-(Diisopropyl)phenyl 4-[(2S)-pyrrolidin-2-ylcarbonylaraino]-3,3-dimethylbutanoate;
2,6-(diisopropyl)phenyl 4-[aminomethylcarbonylamino]-3,3-dimethylbutanoate;
2,6-(Diisopropyl)phenyl 1-[((2S)-2-amino-(3R)-3-hydroxybutyryl)aminomethyl]-1-cyclohexane acetate;
2,6-(Diisopropyl)phenyl 1-[((2S)-2-amino-3-hydroxypropionyl)aminomethyl] 1-cyclohexane acetate;
2,6-(Diisopropyl)phenyl 1-[((2S)-2-amino-3-methylbutyryl)aminomethyl]-1-cyclohexane acetate;
2,6-diisopropylphenyl 4-((2-(2-methylpyrazolidin-1-yl)ethyl)amino)-4-oxobutanoate;
2,6-diisopropylphenyl 4-((2-(4,5-dihydro-1H-pyrazol-1-yl)ethyl)amino)-4-oxobutanoate;
2,6-diisopropylphenyl 4-((2-(4-ethylpiperazin-1-yl)ethyl)amino)-4-oxobutanoate;
2,6-diisopropylphenyl 4-((2-(4-methylpiperazin-1-yl)ethyl)amino)-4-oxobutanoate; 2,6-diisopropylphenyl4-((2-morpholinoethyl)amino)-4-oxobutanoate;
2,6-Diisopropylphenyl 4-(2-(TertButoxycarbonylamino) Propanoyloxy)Butanoate;
2,6-Diisopropylphenyl4-(2-Aminoacetoxy) Butanoate Trifluoroacetic Acid Salt;
2,6-Diisopropylphenyl 4-(2-Aminopropanoyloxy)Butanoate Hydrochloride;
2,6-Diisopropyl phenyl 4-Hydroxybutanoate;
2,6-diisopropyl phenyl 4-oxo-4-((2-(piperazin-1-yl)ethyl)amino)butanoate;
2,6-diisopropyl phenyl 4-oxo-4-((2-(piperidin-1-yl)ethyl)amino)butanoate;
2,6-diisopropyl phenyl 4-oxo-4-((2-(pyrazolidin-1-yl)ethyl)amino)butanoate;
2,6-diisopropylphenyl 4-oxo-4-((2-(pyrrolidin-1-yl)ethyl)amino)butanoate;
2, 6-diisopropylphenyl 4-oxo-4-((2-thiomorpholinoethyl)amino)butanoate;
2-[2,6-(diisopropyl)phenoxycarbonylamino]ethyl (2S)-2-amino-3-carboxypropionamide;
2-[2,6-(diisopropyl)phenoxycarbonylamino]ethyl (2S)-2-amino-3-hydroxypropionamide;
2-[2,6-(diisopropyl)phenoxycarbonylamino]ethyl (2S)-2-amino-3-methylbutanoylamide;
2-[2,6-(diisopropyl)phenoxycarbonyloxy]ethyl (2S)-2,6-diaminohexanoylamide;
2-[2,6-(diisopropyl)phenoxycarbonyloxy]ethyl (2S)-2-amino-(4-hydroxyphenyl)propionamide;
2-[2,6-(Diisopropyl)phenoxycarbonyloxy]ethyl (2S)-2-amino(4-hydroxyphenyl)propionamide;

2-[2,6-(diisopropyl)phenoxycarbonyloxy]ethyl (2S)-2-amino-3-carbamoylpropionate;
2-[2,6-(diisopropyl)phenoxycarbonyloxy]ethyl (2S)-2-amino-3-carbamoylpropionamide;
2-[2,6-(Diisopropyl)phenoxycarbonyloxy]ethanol;
1-Amino-2-[2,6-(diisopropyl)phenoxycarbonyloxy]ethane;
2-[2,6-(diisopropyl)phenoxycarbonyloxy]ethyl (2S)-2-amino-3-hydroxypropionate;
2-[2,6-(diisopropyl)phenoxycarbonyloxy]ethyl (2S)-2-amino-3-hydroxypropionamide;
2-[2,6-(diisopropyl)phenoxycarbonyloxy]ethyl glycinamide;
2-amino-3-(2,6-diisopropylphenoxycarbonyloxy)-propanoic acid mesylate;
2-amino-3-methyl-3-(2,6-diisopropyl-phenoxycarbonyloxy)-propanoic acid;
3-(((((2,6-diisopropylphenoxy)carbonyl)oxy)methyl)carbamoyl)-1-methylpyridin-1-ium iodide;
3-((2,6-diisopropylphenoxy)carbonyl)-1-((((2,6-diisopropyl phenoxy)carbonyl)oxy) methyl)pyridin-1-ium methanesulfonate;
3-{[2-[2,6-Bis(isopropyl)phenoxycarbonyl]-benzoyl]amino}propanoic acid;
3-{[2-[2,6-Bis(isopropyl)phenoxycarbonyloxy]-benzoyl]amino}-propanoic acid;
3-carbamoyl-1-((((2,6-diisopropyl-phenoxy)carbonyl)oxy)methyl)pyridin-1-ium iodide;
3-carbamoyl-1-(((2,6-diisopropylphenoxy)carbonyloxy)methyl)pyridinium mesylate;
3-carboxy-1-((((2,6-diisopropylphenoxy)carbonyl)oxy)methyl)pyridin-1-ium iodide;
3-carboxy-1-((((2,6-diisopropylphenoxy) carbonyl)oxy)methyl)pyridin-1-ium methanesulfonate;
4-[(2S)-2-amino-(3R)-3-hydroxybutyryl]amino-3,3-dimethylbutanoate;
4-[(2S)-2-amino-3-carbamoylpropionylamino]-3,3-dimethylbutanoate;
4-[(2S)-2-amino-4-carboxybutyrylamino]-3,3-dimethylbutanoate;
4-[(2S)-2-aminopropionylamino]-3,3-dimethylbutanoate;
2,6-(Diisopropyl)phenyl;
4-[aminomethylcarbonylamino]-3,3-dimethylbutanoate;
2,6-(Diisopropyl)phenyl;
arginine2-(2,6-diisopropylphenoxy)-2-hydroxyethylphosphate;
arginine2-(2,6-diisopropylphenoxy)-3,4,5-trihydroxytetrahydropyran-6-yl dihydrogen phosphate;
Boc-Asp(OPropofol)-OBzl; Boc-Asp(OPropofol)-OH;
Boc-Glu(OPropofol)-OBzl;
Boe-Glu(OPropofol)-OH;
di[propofol 5-carboxyl-2(S)-fluorohexanoate] zinc salt;
di[propofol 5-carboxyl-2-(S)-fluorohexanoate] zinc salt;
di[propofol 7-carboxyl-2-(R,S)-fluorocaprylate] calcium salt;
di[propofol 7-carboxyl-2-(R,S)fluorocaprylate] calcium salt;
disodium lauryl-imino-dipropionate2-(2,6-diisopropylphenoxy) tetrahydropyran-6-yl dihydrogen phosphate;
disodium lauryl-iminodipropionate-2-(2,6-diisopropyl phenoxy) tetrahydropyran-6-yl dihydrogen phosphate;

H-Abu-Asp(OPropofol)-OH;
H-Abu-Thr(γ-OC(O)OPropofol)-OH Hydrochloride;
H-Aib-OCH₂OPropofol;
H-Ala-Asn-OPropofol;
H-Ala-Asp(OCH₂OPropofol)-OH;
H-AlaAsp(OPropofol)-OH;
H-Ala-Cys(β-SC(O)OPropofol)-OH;
H-Ala-Glu(OPropofol)-OH;
H-Ala-OPropofol Hydrochloride;
H-Ala-Phe-OPropofol;
H-Ala-Ser(β-OC(O)OPropofol)-OH;
H-Ala-Thr(β-OC(O)OPropofol)-OH;
H-Ala-Thr(γ-OC(O)OPropofol)-OH Hydrochloride;
H-Ala-Tyr-OPropofol;
H-Arg-Asp(OPropofol)-OH;
H-Arg-Phe-OPropofol;
H-Arg-Thr(γ-OC(O)OPropofol)-OH Tris-Hydrochloride;
H-Asn-Asp(OCH₂OPropofol)-OH;
H-Asn-Asp(OPropofol)-OH;
H-Asn-D-Thr(γ-OC(O)OPropofol)-OH;
H-Asn-Glu(OPropofol)-OH;
H-Asn-OPropofol Hydrochloride;
H-Asn-Thr(β-OC(O)OPropofol)-OH;
H-Asn-Thr(γ-OC(O)OPropofol)-OH Hydrochloride;
H-Asn-Tyr-OPropofol;
H-Asp(OCH₂OPropofol)-ArgOH;
H-Asp(OCH₂OPropofol)-Asp-OH;
H-Asp(OCH₂OPropofol)-Lys-OH;
H-Asp(OCH₂OPropofol)-OH;
H-Asp(OCH₂OPropofol)-Ser-OH;
H-Asp(OPropofol)-Ala-OH;
H-Asp(OPropofol)-Asp-OH;
H-Asp(OPropofol)-Gln-OH;
H-Asp(OPropofol)-Glu-OH;
H-Asp(OPropofol)-Gly-OH;
H-Asp(OPropofol)-Ile-OH;
H-Asp(OPropofol)-Leu-OH;
H-Asp(OPropofol)-Met-OH;
H-Asp(OPropofol)-OBzl;
H-Asp(OPropofol)-OH;
H-Asp(OPropofol)-O-Trityl;
H-Asp(OPropofol)-Phe-OH;
H-Asp(OPropofol)-Pro-OH;
HAsp(OPropofol)-Ser-OH;
H-Asp(OPropofol)-Val-OH;
H-Asp-Ala-OPropofol;
H-Asp-AsnOPropofol;
H-Asp-Asp(OCH₂OPropofol)-OH;
H-Asp-Asp(OPropofol)-OH;
H-AspOCH₂OPropofol;
H-Asp-Phe-OPropofol;
H-Asp-Ser(β-OC(O)OPropofol)-OH;
H-Asp-TyrOPropofol;
H-Cys-Asp(OPropofol)-OH;
H-Dap(β-NHC(O)OPropofol)-Ala-OH;
H-Dap-Ala-OPropofol;
H-Dap-Asn-OPropofol;
H-Dap-Thr(γ-OC(O)OPropofol)-OH Bis-Hydrochloride;
H-Dap-Tyr-OPropofol;
H-D-Asn-Thr(γ-OC(O)OPropofol)-OH;
H-D-LysThr(γ-OC(O)OPropofol)-OH Bis-Hydrochloride;
H-D-Ser-Thr(γ-OC(O)OPropofol-OH Hydrochloride;
H-Gln-Asn-OPropofol;
H-Gln-Asp(OCH₂OPropofol)-OH;
H-Gln-OPropofol Hydrochloride;

H-Gln-Phe-OPropofol;
H-Glu(OPropofol)-Ala-OH;
H-Glu(OPropofol)-ArgOH;
H-Glu(OPropofol)-Asp-OH;
H-Glu(OPropofol)-Gln-OH;
H-Glu(OPropofol)-Glu-OH;
H-Glu(OPropofol)-Gly-OH;
H-Glu(OPropofol)-Ile-OH;
H-Glu(OPropofol)-Leu-OH;
H-Glu(OPropofol)-Lys-OH;
H-Glu(OPropofol)-Met-OH;
H-Glu(OPropofol)-OBzl;
H-Glu(OPropofol)-OH;
H-Glu(OPropofol)-Phe-OH;
H-Glu(OPropofol)-Ser-OH;
H-Glu(OPropofol)-Val-OH;
H-Glu-Asp(OCH$_2$OPropofol)-OH;
H-Glu-Phe-OPropofol;
H-GluTyr-OPropofol;
H-Gly-Asn-OPropofol;
H-Gly-Asp(OCH$_2$OPropofol)-OH;
H-Gly-OPropofol Hydrochloride;
H-Gly-Phe-OPropofol;
H-Gly-Thr(γ-OC(O)OPropofol)-OH;
H-Gly-TyrOPropofol;
H-His-Asp(OCH$_2$OPropofol)-OH;
H-His-OPropofol;
H-His-Phe-OPropofol;
H-His-Thr(γ-OC(O)OPropofol)-OH Bis-Hydrochloride;
H-Leu-Asp(OPropofol)-OH;
H-Leu-D-Thr(γ-OC(O)OPropofol)-OH;
H-Leu-Glu(OPropofol)-OH;
H-Leu-Thr(γ-OC(O)OPropofol)OH Hydrochloride;
H-Lys-Asp(OPropofol)-OH;
H-Lys-Cys(β-SC(O)OPropofol)-OH;
H-Lys-Glu(OPropofol)-OH;
H-Lys-OPropofol Hydrochloride;
H-Lys-Ser(β-OC(O)OPropofol)-OH;
H-Lys-Thr(β-OC(O)OPropofol)-OH;
H-Lys-Thr(γ OC(O)OPropofol)-OH Bis-Hydrochloride;
H-Lys-Tyr-OPropofol;
H-Met-Asp(OPropofol)OH;
H-Met-OPropofol;
H-Met-Thr(γ-OC(O)OPropofol)-OH Hydrochloride;
H-NVal-Asp(OPropofol)-OH;
H-Orn-Asp(OPropofol)-OH;
H-Orn-Thr(γ-OC(O)OPropofol)-OH BisHydrochloride;
H-Phe-Asp(OPropofol)-OH;
H-Phe-OPropofol;
H-Pro-OPropofol Hydrochloride;
H-Pro-Phe-OPropofol;
H-Pro-Thr(γ-OC(O)OPropofol)-OH Hydrochloride;
H-Pro-Tyr-OPropofol;
H-Sar-Asp(OPropofol)-OH;
H-Ser-Asn-OPropofol;
H-SerAsp(OCH$_2$OPropofol)-OH;
H-Ser-Cys(β-SC(O)OPropofol)-OH;
H-Ser-D-Thr(γOC(O)OPropofol)-OH;
H-Ser-OPropofol;
H-Ser-Phe-OPropofol;
H-Ser-Ser(β-OC(O)OPropofol)-OH;
H-Ser-Thr(β-OC(O)OPropofol)-OH;
H-Ser-Thr(γ-OC(O)OPropofol)-OH Hydrochloride
H-Ser-Tyr-OPropofol;
H-ThrAsp(OCH$_2$OPropofol)-OH;
H-Thr-OPropofol Hydrochloride;
H-Thr-Phe-OPropofol;
H-Trp-Asp(OCH$_2$OPropofol)-OH;
H-Trp-Phe-OPropofol;
H-Tyr-Asn-OPropofol;
H-TyrAsp(OCH$_2$OPropofol)-OH;
H-Tyr-Asp(OPropofol)-OH;
H-Tyr-OPropofol Hydrochloride;
H-Tyr-Phe-OPropofol;
H-Tyr-Ser(β-OC(O)OPropofol)-OH;
H-Val-Ala-OPropofol;
H-Val-Asn-OPropofol;
H-Val-OCH$_2$OPropofol;
H-Val-OPropofol;
H-Val-Phe-OPropofol;
H-Val-Ser-OPropofol;
H-Val-Thr(β-OC(O)OPropofol)-OH;
H-Val-Thr(γ-OC(O)OPropofol)-OH Hydrochloride
H-Val-Tyr-OPropofol;
2,6-(Diisopropyl)phenyl hydroxybutyrate disodium-phosphate;
2,6-(Diisopropyl)phenyl hydroxyvaleratephosphate disodium salt;
H-[3-Ala-Asp(OPropofol)-OH;
H-[3-Ala-Thr(γ-OC(O)OPropofol)-OH Hydrochloride;
1-Amino-2-[2,6-(diisopropyl)phenoxycarbonyloxy]ethane;
N-(2-Dibutylaminoethyl)-succinamic acid 2,6-diisopropyl-phenyl ester;
N-(2-Dibutylaminoethyl)-succinamic acid 2,6-diisopropyl-phenyl ester hydrochloride;
N-(2-Diethylamino-ethyl)-succinamic acid 2,6-diisopropyl-phenyl ester Hydrochloride;
N-(2-Diethylammoethyl)-succinamic acid 2,6-diisopropylphenyl ester;
N-(2-Diisopropylaminoethyl)-succinamic acid 2,6-diisopropyl-phenyl ester;
N-(2-Diisopropylamino-ethyl)-succinamic acid 2,6-diisopropyl phenyl ester Hydrochloride;
N-(2-Dimethylamino-ethyl)-succinamic acid 2,6-diisopropyl-phenyl ester Hydrochloride;
N-(2-Dimethylaminoethyl)-succinamic acid 2,6-diisopropyl-phenyl ester;
N-(2-Morpholin-4-ylethyl)-succinamic acid 2,6-diisopropylphenyl ester;
N-(2-Morpholin-4-yl-ethyl)-succinamic acid 2,6-diisopropylphenyl ester Hydrochloride;
N-(2-Piperidin-1-yl-ethyl)-succinamic acid 2,6-diisopropylphenyl ester;
N-(2-Piperidin-1-yl-ethyl)-succinamic acid 2,6-diisopropylphenyl ester hydrochloride;
N-(2-Pyrrolidin-1-yl-ethyl)-succinamic acid 2,6-diisopropylphenyl ester;
N-(2-Pyrrolidin-1-yl-ethyl)-succinamic acid 2,6-diisopropylphenyl ester hydrochloride;
O-[t-butoxycarbonyl]-propofol);
propofol 2-carboxyl-2(S)fluoropropionate sodium salt;
propofol 3-(N,N-diethyl)amino-2-(R,S)-fluoropropionate hydrochloride;
propofol 3-(N-isopropyl)amino-2-(R,S)-2-monofluoromethylpropionate methanesulfonate;
propofol 3-(N-isopropyl)amino-2-(R,S)-2-monofluoromethyl propionate methanesulfonate;
propofol 3-(pyrrolidin-1-yl)-2-(S)-trifluoromethyl propionate hydrochloride;

propofol 3-(pyrrolidin-1-yl)-2(S)-trifluoromethylpropionate hydrochloride;
propofol 3-carboxyl-2(R)-fluorobutyrate sodium salt;
propofol 3-N-isopropylamino-2-(R,S)-fluoropropionate hydrochloride;
propofol 3-N-methyl-N-cyclohexylamino-2-(R,S)fluoropropionate hydrochloride;
propofol 3-N-methyl-N-cyclohexylamino-2-(R,S)fluoropropionate hydrochloride;
propofol 3-phosphoryl-2-(R,S)-fluoropropionate zinc salt;
propofol 4-(aziridin-1-yl)-2-(S)-2-fluorobutyratehydrochloride;
propofol 4-(N,Ndimethyl)amino-2-(R)-2-trifluoromethylbutyrate hydrochloride;
propofol 4-(N,Ndimethyl)amino-2-(R)-fluorobutyrate hydrochloride;
propofol 4-(N,N-dimethyl)amino-2-(R)trifluoromethylbutyrate hydrochloride;
propofol 4-(N,N-dimethyl)amino-2-(R,S)fluorobutyrate hydrochloride;
propofol 4-(N-cyclopropyl-N-methyl)amino-2-(R)difluoromethylbutyratehydrochloride;
propofol 4-(N-methyl-N-benzyl)amino-2-(R,S)trifluoromethylbutyrate hydrochloride;
propofol 4-(N-methyl-N-ethyl)amino-2-(R,S)-2-fluorobutyratehydrochloride;
propofol 4-(N-methyl-N-isopropyl)amino-2-(R,S)fluorobutyrate methanesulfonate;
propofol 4-(pyrrolidin-1-yl)-2-(R)-2-fluorobutyrate hydrochloride;
propofol 4-carboxyl-2-(R)-2-trifluoromethylvalerate lithium salt;
propofol 4-carboxyl-2(R)-fluorobutyrate sodium salt;
propofol 4-carboxyl-2-(R,S)difluoromethylvalerate potassium salt;
propofol 4-carboxyl-2(R,S)-fluorovalerate sodium salt;
propofol 4-carboxyl-2-(S)-fluorovalerate potassium salt;
propofol 4-carboxyl-2-(S)fluorovalerate potassium salt;
propofol 4-carboxyl-2-(S)-trifluoromethylbutyrate ammonium salt;
propofol 4-N-(aziridin-1-yl)-2(S)-2-fluorobutyrate hydrochloride;
propofol 4-N-methyl-N-benzylamino-2-(R)-fluorobutyrate hydrochloride;
propofol 4-phosphoryl-2-(R)fluorobutyrate disodium salt;
propofol 4-phosphoryl-2-(R,S)-fluorobutyrate calcium salt;
propofol 5-(N-methyl-N-benzyl)amino-2-(S)-2-fluorovalerate hydrochloride;
propofol 5-carboxyl-2-(R,S)-difluoromethylvalerate potassium salt;
propofol 5-N-cyclopentylamino-2,2-difluorovalerate hydrochloride;
propofol 5-phosphoryl-2-(S)-fluorovalerate zinc salt;
propofol 6-(N,N-dimethyl)amino-2(R)-fluorovalerate hydrochloride;
Propofol Hemisuccinate;
propofol hydroxybutyrate;
propofol hydroxyvalerate;
propofol 8-(N,Ndimethyl)amino-2-(R)-fluorovaleratehydrochloride;
propofol-2-(R)-fluoropropionate monoester sodium salt;
propofol-2-(R,S)-fluorobutyratemonoester sodium salt;
propofol-2-(R,S)-fluoropentanoate monoester sodium salt;
(S)-2-amino-3-(2,6-diisopropylphenoxycarbonyloxy)-propanoic acid mesylate;
Sodium 4-(2,6-Diisopropyl phenoxy)-4-oxobuty 1 Phosphate;
2-(2,6-diisopropyl phenoxy)-tetrahydropyran-6-yl dihydrogen phosphate arginine;
tri[propofol 3-phosphoryl-2-(R,S)-monofluoromethylpropionate] dialuminum salt;
tri[propofol 8-carboxyl-2-(R,S)monofluoromethylpelargonate]aluminum salt; Succinic Acid Mono-Propofol Ester;
BOC-protected 1-deoxy-1-hydrazinoglucitol;
2-amino-3-methyl-3-(2,6-diisopropyl-phenoxycarbonyloxy)-propanoic acid;
2-amino-3-(2,6-diisopropylphenoxycarbonyloxy)-propanoic acid;
1-(2,6-diisopropyl phenoxy)ethyl dihydrogen phosphate;
Mono(propofol) phosphate;
Di(propofol) phosphate;
Carboxylic hemiesters of propofol;
hemisuccinate ester of propofol;
hemiglutarate ester of propofol;
hemiadipate ester of propofol;
(2', 6'-Diisopropylphenyl 4-(2-trimethylammoniumethyloxy) phosphonobutyrate);
(2',6'-Diisopropylphenyl3-ortho-(O-trimethylammonium ethylphosphonooxy)-1-propionate);
(4-(2,6-diisopropylphenoxy)-4-oxobutanoyl)glycine;
4-(4-(2,6-diisopropylphenoxy)-4-oxobutanamido)butanoic acid
HX0507;
HX0969w;
HX0892;
HX0891;
propofol methoxymethylphosphonic prodrug;
propofol hemiglutarate;
propofol hemiadipate;
monopropofol phosphate;
dipropofol phosphate;
1-(((2,6-diisopropylphenoxy)carbonyloxy)methyl)-3-(dimethylcarbamoyl)pyridinium mesylate;
1-(((2,6-diisopropylphenoxy)carbonyloxy)methyl)-3-(methylcarbamoyl)pyridinium mesylate;
3-carbamoyl-1-(((2,6-diisopropylphenoxy)carbonyloxy)methyl)pyridinium mesylate;
1-(((2,6-diisopropyl phenoxy)carbonyloxy)methyl)-3-(methylcarbamoyl)pyridinium iodide;
1-((((2,6-diisopropylphenoxy)carbonyl)oxy)methyl)-3-(dimethylcarbamoyl)pyridin-1-ium methanesulfonate;
1-((((2,6-diisopropylphenoxy)carbonyl)oxy)methyl)-3-(dimethylcarbamoyl)pyridin-1-ium iodide;
1-((((2,6-diisopropylphenoxy)carbonyl)oxy)methyl)-3-(methoxycarbonyl)pyridin-1-ium iodide;
3-carboxy-1-((((2,6-diisopropylphenoxy)carbonyl)oxy)methyl)pyridin-1-ium iodide;
2-(((2,6-diisopropylphenoxy)carbonyl)oxy)-N,N,N-trimethylethan-1-aminium iodide;
2-(((2,6-diisopropylphenoxy)carbonyl)oxy)-N,N-dimethylethan-1-aminium chloride;
1-((((2,6-diisopropylphenoxy)carbonyl)oxy)methyl)-3-(hydroxycarbamoyl)pyridin-1-ium iodide;

3-(((((2,6-diisopropylphenoxy)carbonyl)oxy)methyl) carbamoyl)-1-methylpyridin-1-ium iodide;

1-(((2,6-diisopropylphenoxy)carbonyl)oxy)-N-((((2,6-diisopropylphenoxy)carbonyl)oxy)methyl)-N,N-dimethylmethanaminiumiodide;

2-(((2,6-diisopropylphenoxy)carbonyl)oxy)-N-((((2,6-diisopropylphenoxy)carbonyl)oxy)methyl)N,N-dimethylethan-1-aminiumiodide;

1-((((2,6-diisopropylphenoxy)carbonyl)oxy)methyl)-4-formyl-3-hydroxy-5-(hydroxymethyl)-2-methylpyridin-1-ium iodide;

3-((2,6-diisopropylphenoxy)carbonyl)-1-((((2,6-diisopropylphenoxy)carbonyl)oxy)methyl)pyridin-1-ium methanesulfonate;

2-(((2,6-diisopropylphenoxy)carbonyl)oxy)-N,N,N-trimethylethan-1-aminium methanesulfonate;

3-carbamoyl-1-((((2,6-diisopropylphenoxy)carbonyl)oxy)methy)pyridin-1-ium bromide;

3-carbamoyl-1-((((2,6-diisopropylphenoxy)carbonyl)oxy)methyl)pyridin-1-ium chloride;

1-((((2,6-diisopropyl phenoxy)carbonyl)oxy)methyl)-3-(methylcarbamoyl)pyridin-1-ium tetrafluoroborate;

1-((((2,6-diisopropyl phenoxy)carbonyl)oxy)methyl)-3-(methylcarbamoyl)pyridin-1-ium nitrate;

1-((((2,6-diisopropylphenoxy)carbonyl)oxy)methyl)-3-(methylcarbamoyl)pyridin-1-ium chloride;

1-((((2,6-diisopropylphenoxy)carbonyl)oxy)methyl)-3-(methoxycarbonyl)pyridin-1-ium methanesulfonate; or 3-carboxy-1-((((2,6-diisopropyl phenoxy)carbonyl)oxy)methyl)pyridin-1-ium methanesulfonate.

19. The method of claim 18, wherein the administration results in an $AUC_{4hr}$ of fospropofol of no less than 2000 ng hr/mL.

20. The method of claim 18, wherein the administration results in an $AUC_{4hr}$ of fospropofol of no less than 3000 ng hr/mL.

21. The method of claim 1, wherein 2 hours following the administration, the patient is headache free.

22. The method of claim 1, wherein 2 hours following the administration, the patient has experienced a reduction in headache pain.

23. The method of claim 1, wherein 2 hours following the administration, the patient is no longer experiencing a most bothersome symptom.

24. The method of claim 9, wherein 2 hours following the administration, the patient is headache free.

25. The method of claim 9, wherein 2 hours following the administration, the patient has experienced a reduction in headache pain.

26. The method of claim 9, wherein 2 hours following the administration, the patient is no longer experiencing a most bothersome symptom.

27. The method of claim 14, wherein 2 hours following the administration, the patient is headache free.

28. The method of claim 14, wherein 2 hours following the administration, the patient has experienced a reduction in headache pain.

29. The method of claim 14, wherein 2 hours following the administration, the patient is no longer experiencing a most bothersome symptom.

30. The method of claim 18, wherein 2 hours following the administration, the patient is headache free.

31. The method of claim 18, wherein 2 hours following the administration, the patient has experienced a reduction in headache pain.

32. The method of claim 18, wherein 2 hours following the administration, the patient is no longer experiencing a most bothersome symptom.

* * * * *